US009556187B2

(12) United States Patent
Hayashi et al.

(10) Patent No.: US 9,556,187 B2
(45) Date of Patent: Jan. 31, 2017

(54) SUBSTITUTED PYRROLO[3',2':5,6]PYRIDO[4,3-D] PYRIMIDINES AND JAK INHIBITORS COMPRISING THE SAME

(71) Applicant: NISSAN CHEMICAL INDUSTRIES, LTD., Tokyo (JP)

(72) Inventors: Keishi Hayashi, Funabashi (JP); Tsuneo Watanabe, Funabashi (JP); Koji Toyama, Funabashi (JP); Junji Kamon, Minamisaitama-gun (JP); Masataka Minami, Funabashi (JP); Miyuki Uni, Funabashi (JP); Mariko Nasu, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/873,897

(22) Filed: Oct. 2, 2015

(65) Prior Publication Data

US 2016/0102102 A1 Apr. 14, 2016

Related U.S. Application Data

(63) Continuation of application No. 14/238,507, filed as application No. PCT/JP2012/070876 on Aug. 10, 2012, now Pat. No. 9,216,999.

(30) Foreign Application Priority Data

| | | |
|---|---|---|
| Aug. 12, 2011 | (JP) | 2011-177270 |
| Aug. 12, 2011 | (JP) | 2011-177289 |
| Apr. 20, 2012 | (JP) | 2012-097073 |
| Apr. 27, 2012 | (JP) | 2012-103516 |
| Apr. 27, 2012 | (JP) | 2012-103517 |

(51) Int. Cl.

| | |
|---|---|
| ***A61K 31/519*** | (2006.01) |
| ***C07D 239/70*** | (2006.01) |
| ***C07D 487/14*** | (2006.01) |
| ***C07D 471/14*** | (2006.01) |
| ***C07D 498/14*** | (2006.01) |
| ***C07D 513/14*** | (2006.01) |

(52) U.S. Cl.

CPC .......... *C07D 487/14* (2013.01); *C07D 471/14* (2013.01); *C07D 498/14* (2013.01); *C07D 513/14* (2013.01)

(58) Field of Classification Search

CPC .... A61K 31/519; C07D 239/70; C07D 487/14

USPC .......................................... 514/267; 544/251

See application file for complete search history.

(56) References Cited

U.S. PATENT DOCUMENTS

| | | | |
|---|---|---|---|
| RE41,783 | E | 9/2010 | Blumenkopf et al. |
| 2001/0053782 | A1 | 12/2001 | Blumenkopf et al. |
| 2004/0053947 | A1 | 3/2004 | Blumenkopf et al. |
| 2005/0288313 | A1 | 12/2005 | Blumenkopf et al. |
| 2006/0241131 | A1 | 10/2006 | Blumenkopf et al. |
| 2007/0292430 | A1 | 12/2007 | Blumenkopf et al. |
| 2010/0035903 | A1 | 2/2010 | Blumenkopf et al. |
| 2010/0048552 | A1 | 2/2010 | Ren et al. |
| 2011/0311474 | A1 | 12/2011 | Wishart et al. |

FOREIGN PATENT DOCUMENTS

| | | |
|---|---|---|
| WO | 01 42246 | 6/2001 |
| WO | 2007 007919 | 1/2007 |
| WO | 2007 077949 | 7/2007 |
| WO | 2007 134259 | 11/2007 |
| WO | 2008 084861 | 7/2008 |
| WO | 2009 152133 | 12/2009 |
| WO | 2010/044885 | 4/2010 |

(Continued)

OTHER PUBLICATIONS

International Search Report Issued Jan. 4, 2013 in PCT/JP12/070876 Filed Aug. 10, 2012.

Written Opinion Issued Jan. 4, 2013 in PCT/JP12/070876 Filed Aug. 10, 2012.

O'Shea, J. J. et al., "Cytokine Signaling in 2002: New Surprises in the Jak/Stat Pathway" Cell. Press, vol. 109, pp. 121-131, Apr. 2002.

Ozaki, K. et al., "A Critical Role for IL-21 in Regulating Immunoglobulin Production" Science, vol. 298, pp. 1630-1634, Nov. 22, 2002.

Macchi, P. et al., "Mutations of Jak-3 gene in patients with autosomal severe combined immune deficiency (SCID)" Nature, vol. 377, pp. 65-68, Sep. 7, 1995.

Russell, S. M. et al., "Mutation of Jack3 in a Patient with SCID: Essential Role of Jak3 in Lymphoid Development" Science, vol. 270, pp. 797-800, Nov. 3, 1995.

(Continued)

*Primary Examiner* — Douglas M Willis

(74) *Attorney, Agent, or Firm* — Oblon, McClelland, Maier & Neustadt, L.L.P.

(57) ABSTRACT

This disclosure relates to novel tricyclic pyrimidine compounds and tricyclic pyridine compounds having JAK inhibitory activities. A tricyclic heterocyclic compound represented by the formula ($I^b$), wherein the rings $A^b$ and $B^b$, $X^b$, $Y^b$, $R^{1b}$, $R^{2b}$, $R^{3b}$, $L^{1b}$, $L^{2b}$, $L^{3b}$ and $n^b$ are as defined in the specification.

($I^b$)

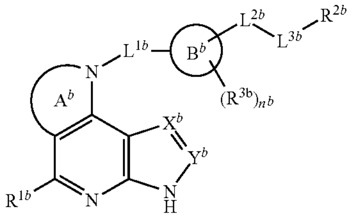

25 Claims, No Drawings

(56) References Cited

FOREIGN PATENT DOCUMENTS

| | | | |
|---|---|---|---|
| WO | 2010 119875 | | 10/2010 |
| WO | WO 2011/012540 | A1 | 2/2011 |
| WO | 2011 045702 | | 4/2011 |
| WO | 2011 068881 | | 6/2011 |
| WO | 2011 068899 | | 6/2011 |
| WO | 2011 075334 | | 6/2011 |
| WO | 2011 086053 | | 7/2011 |
| WO | 2012 085176 | | 6/2012 |
| WO | 2012 149280 | | 11/2012 |
| WO | 2013/024895 | | 2/2013 |

OTHER PUBLICATIONS

Murray, P. J., "The JAK-STAT Signaling Pathway: Input and Output Integration'" The Journal of Immunology, vol. 178, pp. 2623-2629, 2007.

Staerk, J. et al., "JAK2, the JAK2 V617F mutant and cytokine receptors" Pathology Biologie, vol. 55, pp. 88-91, 2007.

Yoo J. et al., "JAK2 V617F/C618R mutation in a patient with polycythemia vera: A case study and review of the literature" Cancer genetics and Cytogenetics, vol. 189, pp. 43-47, 2009.

Vainchenker W. et al., "JAKs in pathology: Role of Janus kinases in hematopoietic malignancies and immunodeficiencies" Seminars in Cell & Developmental Biology, vol. 19, pp. 385-393, 2008.

Kremer, J. M. et al., "The Safety and Efficacy of a Jak Inhibitor in Patients With Active Rheumatoid Arthritis" Arthritis & Rheumatism, vol. 60, No. 7, pp. 1895-1905, Jul. 2009.

Boy M. G., et al., "Double-Blind, Placebo-Controlled, Dose-Escalation Study to Evaluate the Pharmacologic Effect of CP690,550 in Patients With Psoriasis" Journal of Investigative Dermatology, vol. 129, pp. 2299-2302, doi:10.1038/jid.2009.25;, Feb. 19, 2009.

Changelian, P. S. et al., "Prevention of Organ Allograft Rejection by a Specific Janus Kinase 3 Inhibitor" Science, vol. 302, pp. 875-878, Oct. 31, 2003.

Kudlacz, E., et al., "The JAK-3 inhibitor CP-690550 is a potent anti-inflammatory agent in a murine model of pulmonary eosinophilia" European Journal of Pharmacology, vol. 582, pp. 154-161, 2008.

Jordan, V. C. Nature Reviews: Drug Discovery, 2, 2003, 205.

Vippagunta, et al. Advanced Drug Delivery Reviews, 48, 2001, 18.

SUBSTITUTED PYRROLO[3',2':5,6]PYRIDO[4,3-D] PYRIMIDINES AND JAK INHIBITORS COMPRISING THE SAME

CROSS-REFERENCE TO RELATED APPLICATIONS

This application is a Continuation of U.S. Non-Provisional application Ser. No. 14/238,507, which was filed on Feb. 12, 2014. Application Ser. No. 14/238,507 is a National Stage of PCT/JP2012/070876, which was filed on Aug. 10, 2012. This application is based upon and claims the benefit of priority to: Japanese Application No. 2011/177270, which was filed on Aug. 12, 2011; Japanese Application No. 2011-177289, which was filed on Aug. 12, 2011; Japanese Application No. 2012-097073, which was filed on Apr. 20, 2012; Japanese Application No. 2012-103516, which was filed on Apr. 27, 2012; and Japanese Application No. 2012-103517, which was filed on Apr. 27, 2012.

TECHNICAL FIELD

The present invention relates to novel tricyclic pyrimidine compounds and tricyclic pyridine compounds having JAK inhibitory activities.

BACKGROUND ART

The JAK (Janus kinase) family is a tyrosine kinase family consisting of four members, JAK1, JAK2, JAK3 and Tyk2 (Tyrosine kinase 2) and plays an important role in cytokine signaling.

While the kinases of this family, except for JAK3, are widely expressed in tissues, expression of JAK3 is restricted to immune cells. This is consistent with the fact that JAK3 plays an important role in various receptor-mediated signaling pathways such as IL (interleukin)-2, IL-4, IL-7, IL-9, IL-15 and IL-21 signaling by noncovalently associating with the common γ chain (Non-Patent Documents 1 and 2).

Lowered JAK3 protein levels or defects in the common γ chain gene observed in patients with an immunodeficiency called X-linked Severe Combined Immuno Deficiency (XS-CID) suggest that blocking of the JAK3 signaling pathway leads to immunosuppression (Non-Patent Documents 3 and 4). Animal experiments indicate the importance of JAK3 not only in maturation of B- and T-lymphocytes but also in maintenance of T-lymphocyte functions. Therefore, regulation of immune responses via this mechanism is a promising therapy for T-cell lymphoproliferative diseases such as organ transplant rejection and autoimmune diseases.

Analyses of JAK1 knockout mice and JAK1-deficient cells suggest involvement of JAK1 in various receptor-mediated signaling pathways such as IFN (Interferon)α, IFNβ, IFNγ, IL-2, IL-4, IL-6, IL-7 and IL-15 signaling (Non-Patent Document 5). Therefore, regulation of inflammatory responses via these signaling pathways is therapeutically promising for treatment of diseases involving macrophage and lymphocyte activation such as autoimmune diseases and acute and chronic organ transplant rejection.

Analyses of JAK2 knockout mice and JAK2-deficient cells suggest involvement of JAK2 in various receptor-mediated signaling pathways such as EPO (Erythropoietin) α, thrombopoietin, IFNγ, IL-3 and GM-CSF signaling (Non-Patent Documents 6, 7 and 8). These signaling pathways are supposed to mediate differentiation of erythrocyte or thrombocyte progenitor cells in bone marrow. Meanwhile, it is suggested that a substitution of phenylalanine-617 with valine in JAK2 is associated with myeloproliferative diseases (Non-Patent Document 6). Therefore, regulation of differentiation of myeloid progenitor cells via these signaling pathways is therapeutically promising for treatment of myeloproliferative diseases.

The JAK inhibitor CP-690,550 is reported to have improved the pathology of rheumatoid arthritis and psoriasis in clinical tests (Non-Patent Documents 9 and 10) and suppressed rejection in a monkey model of kidney transplantation and airway inflammation in a murine asthma model (Non-Patent Documents 11 and 12). From these findings, immunosuppression by JAK inhibitors is considered to be useful for prevention or treatment of organ transplant rejection and post-transplant graft-versus-host reaction, autoimmune diseases and allergic diseases. Although other compounds having JAK inhibitory action than CP-690,550 have been reported (Patent Documents 1 to 11), development of more of such compounds is demanded.

PRIOR ART DOCUMENT

Patent Document 1: WO01/42246
Patent Document 2: WO2008/084861
Patent Document 3: WO2010/119875
Patent Document 4: WO2011/045702
Patent Document 5: WO2011/068881
Patent Document 6: WO2011/075334
Patent Document 7: WO2007/007919
Patent Document 8: WO2007/077949
Patent Document 9: WO2009/152133
Patent Document 10: WO2011/086053
Patent Document 11: WO2011/068899
Non-Patent Document 1: Cell, 2002, 109, pp. S121-131
Non-Patent Document 2: Science, 2002, 298, pp., 1630-1634
Non-Patent Document 3: Nature, 1995, 377, pp. 65-68
Non-Patent Document 4: Science, 1995, 270, pp. 797-800
Non-Patent Document 5: J. Immunol., 2007, 178, pp. 2623-2629
Non-Patent Document 6: Pathol. Biol., 2007, 55, pp. 88-91
Non-Patent Document 7: Cancer Genet. Cytogenet., 2009, 189, pp. 43-47
Non-Patent Document 8: Semin. Cell. Dev. Biol., 2008, 19, pp. 385-393
Non-Patent Document 9: Arthritis Rheum., 2009, 60, pp. 1895-1905
Non-Patent Document 10: J. Invest. Dermatol., 2009, 129, pp. 2299-2302
Non-Patent Document 11: Science, 2003, 302, pp. 875-878
Non-Patent Document 12: Eur. J. Pharmacol., 2008, 582, pp. 154-161

DISCLOSURE OF THE INVENTION

Technical Problem

The object of the present invention is to provide novel drug compounds having excellent JAK inhibitory activities useful for prevention or treatment of autoimmune diseases, inflammatory diseases and allergic diseases.

Solution to Problems

As a result of their extensive research in search of new low-molecular-weight compounds having JAK inhibitory activities, the present inventors found that the compounds of the present invention have high inhibitory action and accomplished the present invention. Namely, the present invention provide:

(1) A compound represented by the formula ($I^a$):

($I^a$)

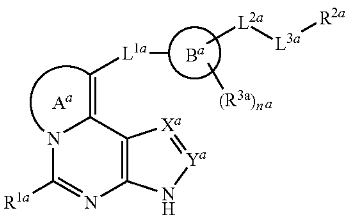

[wherein the ring $A^a$ is represented by the following formula ($II^a$-1) or the formula ($II^a$-2):

($II^a$)

($II^a$-1)

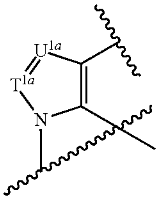

($II^a$-2)

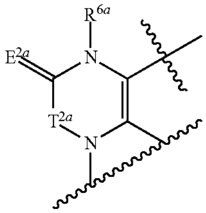

(wherein $T^{1a}$ is a nitrogen atom or $CR^{4a}$, $U^{1a}$ is a nitrogen atom or $CR^{5a}$, $T^{2a}$ is a single bond or $CR^{7a}R^{8a}$, and $E^{2a}$ is an oxygen atom or a sulfur atom), $X^a$ is a nitrogen atom or $CR^{9a}$, $Y^a$ is $CR^{10a}$, $R^{1a}$ is a hydrogen atom, a halogen atom, a $C_{1-6}$ alkyl group or a $C_{1-6}$ haloalkyl group, the ring $B^a$ is a $C_{3-11}$ cycloalkane, a $C_{3-11}$ cycloalkene (a ring-constituting methylene group of the $C_{3-11}$ cycloalkane and the $C_{3-11}$ cycloalkene may be replaced by a carbonyl group), a 3 to 14-membered non-aromatic heterocycle, a $C_{6-14}$ aromatic carbocycle or a 5 to 10-membered aromatic heterocycle, $L^{1a}$ is a single bond, a $C_{1-6}$ alkylene group, a $C_{2-6}$ alkenylene group or a $C_{2-6}$ alkynylene group (the $C_{1-6}$ alkylene group, the $C_{2-6}$ alkenylene group and the $C_{2-6}$ alkynylene group are unsubstituted or substituted with one or more identical or different substituents independently selected from the group consisting of halogen atoms, hydroxy groups, amino groups, cyano groups and nitro groups), $L^{2a}$ is a single bond, a $C_{1-6}$ alkylene group, a $C_{2-6}$ alkenylene group, a $C_{2-6}$ alkynylene group (the $C_{1-6}$ alkylene group, the $C_{2-6}$ alkenylene group and the $C_{2-6}$ alkynylene group are unsubstituted or substituted with one or more identical or different substituents independently selected from the group consisting of halogen atoms, hydroxy groups, amino groups, cyano groups and nitro groups), $=C(R^{15a})—$ (wherein $R^{15a}$ is a hydrogen atom or a cyano group, and the bond connecting the ring $B^a$ and $L^{2a}$ is a double bond) or $=C(R^{15a})—CH_2—$ (wherein $R^{15a}$ is a hydrogen atom or a cyano group, and the bond connecting the ring $B^a$ and $L^{2a}$ is a double bond), $L^{3a}$ is a single bond or represented by any of the following formulae ($III^a$-1) to ($III^a$-20) and the formula ($XIII^a$):

($III^a$)

($III^a$-1)

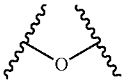

($III^a$-2)

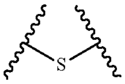

($III^a$-3)

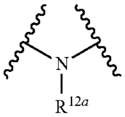

($III^a$-4)

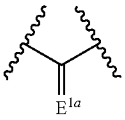

($III^a$-5)

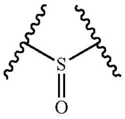

($III^a$-6)

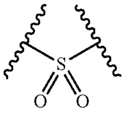

($III^a$-7)

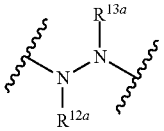

($III^a$-8)

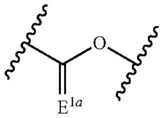

($III^a$-9)

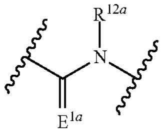

($III^a$-10)

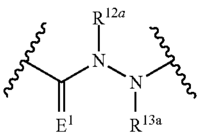

-continued (III$^a$-11)

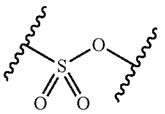

(III$^a$-12)

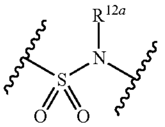

(III$^a$-13)

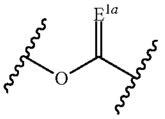

(III$^a$-14)

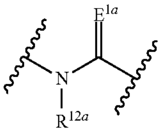

(III$^a$-15)

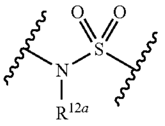

(III$^a$-16)

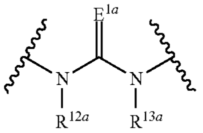

(III$^a$-17)

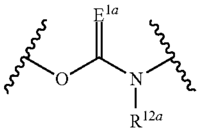

(III$^a$-18)

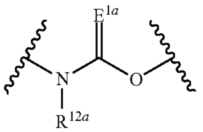

(III$^a$-19)

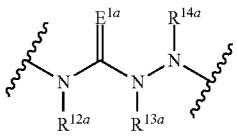

(III$^a$-20)

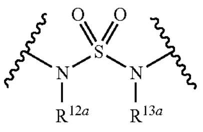

(XIII$^a$)

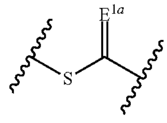

(wherein $E^{1a}$ is an oxygen atom, a sulfur atom or $NR^{11a}$), when $L^{3a}$ is a single bond, $R^{2a}$ is a hydrogen atom, a halogen atom, an azido group, a $C_{3-11}$ cycloalkyl group, a 3 to 14-membered non-aromatic heterocyclyl group, a $C_{6-14}$ aryl group, a 5 to 10-membered aromatic heterocyclyl group, a 8 to 14-membered partially saturated aromatic cyclic group or a 8 to 14-membered aromatic ring-condensed alicyclic hydrocarbon group (the $C_{3-11}$ cycloalkyl group, the 3 to 14-membered non-aromatic heterocyclyl group, the $C_{6-14}$ aryl group, the 5 to 10-membered aromatic heterocyclyl group, the 8 to 14-membered partially saturated aromatic cyclic group and the 8 to 14-membered aromatic ring-condensed alicyclic hydrocarbon group are unsubstituted or substituted with one or more identical or different substituents independently selected from the group consisting of the substituent set $V^{4a}$, substituent set $V^{9a}$ and $C_{1-6}$ alkyl groups (the $C_{1-6}$ alkyl groups are substituted with a $C_{1-6}$ alkoxycarbonylamino group (the $C_{1-6}$ alkoxycarbonylamino group is unsubstituted or substituted with one or more identical or different halogen atoms independently selected from the group consisting of fluorine atoms, chlorine atoms, bromine atoms and iodine atoms))), when $L^{3a}$ is not a single bond, $R^{2a}$ is a hydrogen atom, a $C_{1-6}$ alkyl group, a $C_{2-6}$ alkenyl group, a $C_{2-6}$ alkynyl group (the $C_{1-6}$ alkyl group the $C_{2-6}$ alkenyl group and the $C_{2-6}$ alkynyl group are unsubstituted or substituted with one or more identical or different substituents independently selected from the substituent set $V^{6a}$ and the substituent set $V^{9a}$), a $C_{3-11}$ cycloalkyl group, a 3 to 14-membered non-aromatic heterocyclyl group, a $C_{6-14}$ aryl group, a 5 to 10-membered aromatic heterocyclyl group, a 8 to 14-membered partially saturated aromatic cyclic group or a 8 to 14-membered aromatic ring-condensed alicyclic hydrocarbon group (the $C_{3-11}$ cycloalkyl group, the 3 to 14-membered non-aromatic heterocyclyl group, the $C_{6-14}$ aryl group, the 5 to 10-membered aromatic heterocyclyl group, the 8 to 14-membered partially saturated aromatic cyclic group and the 8 to 14-membered aromatic ring-condensed alicyclic hydrocarbon group are unsubstituted or substituted with one or more identical or different substituents independently selected from the substituent set $V^{4a}$ and the substituent set $V^{9a}$), $n^a$ is 0, 1 or 2, $R^{3a}$ is a hydroxy group, an amino group, a carboxy group, a carbamoyl group, a sulfamoyl group, a phosphono group, a phosphonooxy group, a sulfo group, a sulfoxy group, a tetrazolyl group, a halogen atom, a cyano group, a nitro group, a $C_{1-6}$ alkyl group, a $C_{1-6}$ haloalkyl group, a $C_{3-11}$ cycloalkyl group, a $C_{2-6}$ alkenyl group, a $C_{2-6}$ haloalkenyl group, a $C_{1-6}$ alkoxy group, a $C_{1-6}$ haloalkoxy group, a $C_{1-6}$ alkylthio group, a $C_{1-6}$ haloalkylthio group, a $C_{1-6}$ alkylcarbonyl group, a $C_{1-6}$ haloalkylcarbonyl group, a $C_{1-6}$ alkylsulfonyl group, a $C_{1-6}$ haloalkylsulfonyl group, a $C_{1-6}$ alkoxycarbonyl group, a mono-$C_{1-6}$ alkylamino group, a di-$C_{1-6}$ alkylamino group, a mono-$C_{1-6}$ alkylaminocarbonyl group, a di-$C_{1-6}$ alkylaminocarbonyl group or a $C_{1-6}$ alkylcarbonylamino group (when $n^a$ is 2, $R^{3a}$'s may be identical or different), each of $R^{4a}$, $R^{5a}$, $R^{7a}$ and $R^{8a}$ is independently a hydrogen atom, a hydroxy group, an amino group, a carboxy group, a carbamoyl group, a tetrazolyl group, a halogen atom, a cyano group, a $C_{1-6}$ alkyl group, a $C_{2-6}$ alkenyl group, a $C_{1-6}$ alkoxy group, a $C_{1-6}$ alkylthio group, a $C_{1-6}$ alkylcarbonyl group, a $C_{1-6}$ alkylsulfonyl group, a mono-$C_{1-6}$ alkylamino group, a di-$C_{1-6}$ alkylamino group (the $C_{1-6}$ alkyl group, the $C_{2-6}$ alkenyl group, the $C_{1-6}$ alkoxy group, the $C_{1-6}$ alkylthio group, the $C_{1-6}$ alkylcarbonyl group, the $C_{1-6}$ alkylsulfonyl group, the mono-$C_{1-6}$ alkylamino group and the di-$C_{1-6}$ alkylamino group are unsubstituted or substituted with one or more identical or different substituents independently selected from the substituent set $V^{3a}$), a $C_{1-6}$ alkoxycarbonyl group, a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{1a}$), $R^{6a}$ is a hydrogen atom, a $C_{1-6}$ alkyl group, a $C_{2-6}$ alkenyl group, a $C_{1-6}$ alkylcarbonyl group, a $C_{1-6}$ alkylsulfonyl group, a $C_{1-6}$ alkoxycarbonyl group, a mono-$C_{1-6}$ alkylaminocarbonyl group, a di-$C_{1-6}$ alkylaminocarbonyl group (the $C_{1-6}$ alkyl group, the $C_{2-6}$ alkenyl group, the $C_{1-6}$ alkylcarbonyl group, the $C_{1-6}$ alkylsulfonyl group, the $C_{1-6}$ alkoxycarbonyl group, the mono-$C_{1-6}$ alkylaminocarbonyl group and the di-$C_{1-6}$ alkylaminocarbonyl group are unsubstituted or substituted with one or more identical or different substituents independently selected from the substituent set $V^{3a}$), a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{1a}$), each of $R^{9a}$ and $R^{10a}$ is independently a hydrogen atom, a halogen atom, a cyano group, a carbamoyl group, a $C_{1-6}$ alkyl group, a $C_{1-6}$ haloalkyl group, a $C_{3-11}$ cycloalkyl group, a $C_{1-6}$ alkoxy group, a $C_{1-6}$ haloalkoxy group, a $C_{1-6}$ alkylthio group, a $C_{1-6}$ alkylcarbonyl group, a $C_{1-6}$ alkylsulfonyl group, a 3 to 11-membered non-aromatic heterocyclyl group, a $C_{6-14}$ aryl group or a 5 to 10-membered aromatic heterocyclyl group, $R^{11a}$ is a hydrogen atom, a hydroxy group, a cyano group, a nitro group, a $C_{1-6}$ alkyl group or a $C_{1-6}$ alkoxy group, each of $R^{12a}$, $R^{13a}$ and $R^{14a}$ is independently a hydrogen atom, a $C_{1-6}$ alkyl group, a $C_{1-6}$ haloalkyl group (the $C_{1-6}$ alkyl group and the $C_{1-6}$ haloalkyl group are unsubstituted or substituted with one or more identical or different substituents independently selected from the substituent set $V^{2a}$, the substituent set $V^{8a}$ and the substituent set $V^{9a}$), a $C_{3-11}$ cycloalkyl group, a 3 to 11-membered non-aromatic heterocyclyl group, a $C_{6-14}$ aryl group, a 5 to 10-membered aromatic heterocyclyl group, a 8 to 14-membered partially saturated aromatic cyclic group or a 8 to 14-membered aromatic ring-condensed alicyclic hydrocarbon group (the $C_{3-11}$ cycloalkyl group, the 3 to 11-membered non-aromatic heterocyclyl group, the $C_{6-14}$ aryl group, the 5 to 10-membered aromatic heterocyclyl group, the 8 to 14-membered partially saturated aromatic cyclic group and the 8 to 14-membered aromatic ring-condensed alicyclic hydrocarbon group are unsubstituted or substituted with one or more identical or different substituents independently selected from the substituent set $V^{4a}$ and the substituent set $V^{9a}$), the substituent set $V^{1a}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkyl groups, $C_{1-6}$ haloalkyl groups, $C_{3-11}$ cycloalkyl groups, $C_{2-6}$ alkenyl groups, $C_{2-6}$ haloalkenyl groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, $C_{1-6}$ alkoxycarbonyl groups, 3 to 11-membered non-aromatic heterocyclyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups and $C_{1-6}$ alkylcarbonylamino groups, the substituent set $V^{2a}$ consists of the groups in the substituent set $V^{1a}$ and $C_{6-14}$ aryl groups and 5 to 10-membered aromatic heterocyclyl groups (the $C_{6-14}$ aryl groups and 5 to 10-membered aromatic heterocyclyl groups are unsubstituted or substituted with one or more identical or different substituents independently selected from the substituent set $V^{1a}$), the substituent set $V^{3a}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{3-11}$ cycloalkyl groups, 3 to 11-membered non-aromatic heterocyclyl groups, $C_{6-14}$ aryl groups and 5 to 10-membered aromatic heterocyclyl groups (the $C_{3-11}$ cycloalkyl groups, the 3 to 11-membered non-aromatic heterocyclyl groups, the $C_{6-14}$ aryl groups and the 5 to 10-membered aromatic heterocyclyl groups are unsubstituted or substituted with one or more identical or different substituents independently selected from the substituent set $V^{1a}$), the substituent set $V^{4a}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkyl groups, $C_{2-6}$ alkenyl groups, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups (the $C_{1-6}$ alkyl groups, the $C_{2-6}$ alkenyl groups, the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups and the $C_{1-6}$ alkylcarbonylamino groups are unsubstituted or substituted with one or more identical or different substituents independently selected from the substituent set $V^{3a}$), $C_{3-11}$ cycloalkyl groups, 3 to 11-membered non-aromatic heterocyclyl groups, $C_{6-14}$ aryl groups and 5 to 10-membered aromatic heterocyclyl groups (the $C_{3-11}$ cycloalkyl groups, the 3 to 11-membered non-aromatic heterocyclyl groups, the $C_{6-14}$ aryl group and the 5 to 10-membered aromatic heterocyclyl groups are unsubstituted or substituted with one or more identical or different substituents independently selected from the substituent set $V^{1a}$), the substituent set $V^{5a}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{3-11}$ cycloalkyl groups, 3 to 11-membered non-aromatic heterocyclyl groups, $C_{6-14}$ aryl group and 5 to 10-membered aromatic heterocyclyl groups (the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups, the $C_{1-6}$ alkylcarbonylamino groups, the $C_{3-11}$ cycloalkyl groups, the 3 to 11-membered non-aromatic heterocyclyl groups, the $C_{6-14}$ aryl groups and the 5 to 10-membered aromatic heterocyclyl groups are unsubstituted or substituted with one or more identical or different substituents independently selected from the substituent set $V^{3a}$), the substituent set $V^{6a}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups (the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups and the $C_{1-6}$ alkylcarbonylamino groups are unsubstituted or substituted with one or more identical or different substituents independently selected from the substituent set $V^{3a}$), $C_{3-11}$ cycloalkyl groups, 3 to 11-membered non-aromatic heterocyclyl groups, $C_{6-14}$ aryl groups, 5 to 10-membered aromatic heterocyclyl groups, 8 to 14-membered partially saturated aromatic cyclic groups and 8 to 14-membered aromatic ring-condensed alicyclic hydrocarbon groups (the $C_{3-11}$ cycloalkyl groups, the 3 to 11-membered non-aromatic heterocyclyl groups, the $C_{6-14}$ aryl groups and the 5 to 10-membered aromatic heterocyclyl groups, the 8 to 14-membered partially saturated aromatic cyclic groups and the 8 to 14-membered aromatic ring-condensed alicyclic hydrocarbon groups are unsubstituted or substituted with one or more identical or different substituents independently selected from the substituent set $V^{4a}$ and the substituent set $V^{9a}$), the substituent set $V^{8a}$ consists of $C_{3-11}$ cycloalkyl groups, 3 to 11-membered non-aromatic heterocyclyl groups (the $C_{3-11}$ cycloalkyl groups and 3 to 11-membered non-aromatic heterocyclyl groups are substituted with one or more identical or different substituent independently selected from the substituent set $V^{2a}$), 8 to 14-membered partially saturated aromatic cyclic groups and 8 to 14-membered aromatic ring-condensed alicyclic hydrocarbon groups (the 8 to 14-membered partially saturated aromatic cyclic groups and the 8 to 14-membered aromatic ring-condensed alicyclic hydrocarbon groups are unsubstituted or substituted with one or more identical or different substituents independently selected from the substituent set $V^{2a}$), and the substituent set $V^{9a}$ consists of mono-$C_{1-6}$ alkylaminosulfonyl groups, di-$C_{1-6}$ alkylaminosulfonyl groups, $C_{1-6}$ alkylsulfonylamino groups, $C_{1-6}$ alkoxycarbonylamino groups (the mono-$C_{1-6}$ alkylaminosulfonyl groups, the di-$C_{1-6}$ alkylaminosulfonyl groups the $C_{1-6}$ alkylsulfonylamino groups and the $C_{1-6}$ alkoxycarbonylamino groups are unsubstituted or substituted with one or more identical or different substituents independently selected from the substituent set $V^{3a}$), $C_{3-6}$ cycloalkoxy groups, $C_{3-6}$ cycloalkylamino groups, $C_{3-6}$ cycloalkylthio groups, $C_{3-6}$ cycloalkylcarbonyl groups and $C_{3-6}$ cycloalkylsulfonyl groups (the $C_{3-6}$ cycloalkoxy groups, the $C_{3-6}$ cycloalkylamino groups, the $C_{3-6}$ cycloalkylthio groups, the $C_{3-6}$ cycloalkylcarbonyl groups and the $C_{3-6}$ cycloalkylsulfonyl groups are unsubstituted or substituted with one or more identical or different substituents independently selected from the substituent set $V^{2a}$)], a tautomer or a pharmaceutically acceptable salt of the compound or a solvate thereof.

(2) The compound according to (1), which is represented by the formula ($I^a$):

($I^a$)

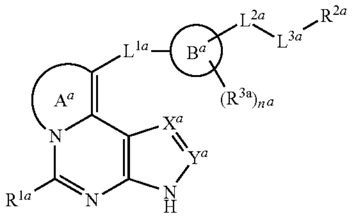

[wherein the ring $A^a$ is represented by the following formula ($II^a$-1) or the formula ($II^a$-2):

($II^a$)

($II^a$-1)

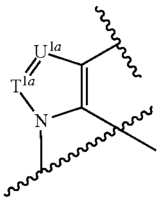

($II^a$-2)

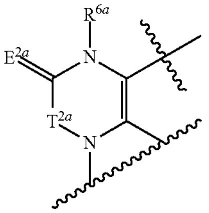

(wherein $T^{1a}$ is a nitrogen atom or $CR^{4a}$ $U^{1a}$ is a nitrogen atom or a $CR^{5a}$, $R^{2a}$ is a single bond or $CR^{7a}R^{8a}$, $E^{2a}$ is an oxygen atom or a sulfur atom), $X^a$ is a nitrogen atom or $CR^{9a}$, $Y^a$ is $CR^{10a}$, $R^{1a}$ is a hydrogen atom, a halogen atom, a $C_{1-6}$ alkyl group or a $C_{1-6}$ haloalkyl group, the ring $B^a$ is a $C_{3-11}$ cycloalkane, a $C_{3-11}$ cycloalkene, a 3 to 11-membered non-aromatic heterocycle, a $C_{6-14}$ aromatic carbocycle or a 5 to 10-membered aromatic heterocycle, $L^{1a}$ is a single bond, a $C_{1-6}$ alkylene group, a $C_{2-6}$ alkenylene group or a $C_{2-6}$ alkynylene group (the $C_{1-6}$ alkylene group, the $C_{2-6}$ alkenylene group and the $C_{2-6}$ alkynylene group are unsubstituted or substituted with one or more identical or different substituents independently selected from the group consisting of halogen atoms, hydroxy groups, amino groups, cyano groups and nitro groups), $L^{2a}$ is a single bond, a $C_{1-6}$ alkylene group, a $C_{2-6}$ alkenylene group or a $C_{2-6}$ alkynylene group (the $C_{1-6}$ alkylene group, the $C_{2-6}$ alkenylene group and the $C_{2-6}$ alkynylene group are unsubstituted or substituted with one or more identical or different substituents independently selected from the group consisting of halogen atoms, hydroxy groups, amino groups, cyano groups and nitro groups), $L^{3a}$ is a single bond or represented by any of the following formulae ($III^a$-1) to ($III^a$-20)

($III^a$)

($III^a$-1)

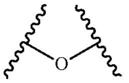

($III^a$-2)

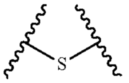

($III^a$-3)

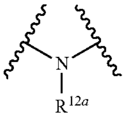

($III^a$-4)

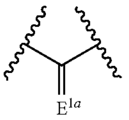

($III^a$-5)

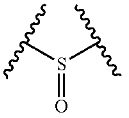

($III^a$-6)

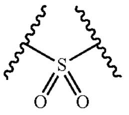

($III^a$-7)

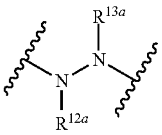

($III^a$-8)

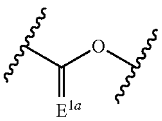

($III^a$-9)

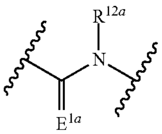

($III^a$-10)

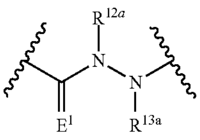

-continued ($III^a$-11)

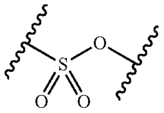

($III^a$-12)

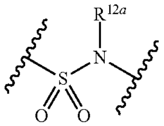

($III^a$-13)

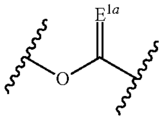

($III^a$-14)

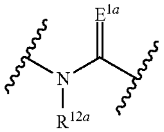

($III^a$-15)

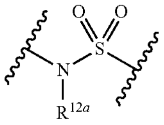

($III^a$-16)

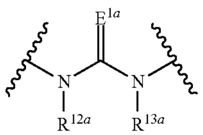

($III^a$-17)

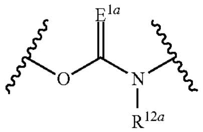

($III^a$-18)

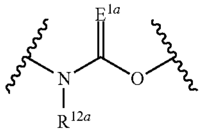

($III^a$-19)

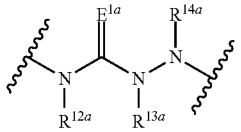

($III^a$-20)

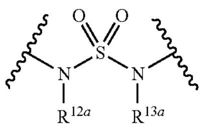

(wherein $E^{1a}$ is an oxygen atom, a sulfur atom or $NR^{11a}$), when $L^{3a}$ is a single bond, $R^{2a}$ is a hydrogen atom, a halogen atom, a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{4a}$), when $L^{3a}$ is not a single bond, $R^{2a}$ is a hydrogen atom, a $C_{1-6}$ alkyl group, a $C_{2-6}$ alkenyl group (the $C_{1-6}$ alkyl group and the $C_{2-6}$ alkenyl group are unsubstituted or substituted with one or more identical or different substituents independently selected from the substituent set $V^{5a}$), a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{4a}$), $n^a$ is 0, 1 or 2, $R^{3a}$ is a hydroxy group, an amino group, a carboxy group, a carbamoyl group, a sulfamoyl group, a phosphono group, a phosphonooxy group, a sulfo group, a sulfoxy group, a tetrazolyl group, a halogen atom, a cyano group, a nitro group, a $C_{1-6}$ alkyl group, a $C_{1-6}$ haloalkyl group, a $C_{3-11}$ cycloalkyl group, a $C_{2-6}$ alkenyl group, a $C_{2-6}$ haloalkenyl group, a $C_{1-6}$ alkoxy group, a $C_{1-6}$ haloalkoxy group, a $C_{1-6}$ alkylthio group, a $C_{1-6}$ haloalkylthio group, a $C_{1-6}$ alkylcarbonyl group, a $C_{1-6}$ haloalkylcarbonyl group, a $C_{1-6}$ alkylsulfonyl group, a $C_{1-6}$ haloalkylsulfonyl group, a $C_{1-6}$ alkoxycarbonyl group, a mono-$C_{1-6}$ alkylamino group, a di-$C_{1-6}$ alkylamino group, a mono-$C_{1-6}$ alkylaminocarbonyl group, a di-$C_{1-6}$ alkylaminocarbonyl group or a $C_{1-6}$ alkylcarbonylamino group (when $n^a$ is 2, $R^{3a}$'s may be identical or different), each of $R^{4a}$, $R^{5a}$, $R^{7a}$ and $R^{8a}$ is independently a hydrogen atom, a hydroxy group, an amino group, a carboxy group, a carbamoyl group, a tetrazolyl group, a halogen atom, a cyano group, a $C_{1-6}$ alkyl group, a $C_{2-6}$ alkenyl group, a $C_{1-6}$ alkoxy group, a $C_{1-6}$ alkylthio group, a $C_{1-6}$ alkylcarbonyl group, a $C_{1-6}$ alkylsulfonyl group, a mono-$C_{1-6}$ alkylamino group, a di-$C_{1-6}$ alkylamino group (the $C_{1-6}$ alkyl group, the $C_{2-6}$ alkenyl group, the $C_{1-6}$ alkoxy group, the $C_{1-6}$ alkylthio group, the $C_{1-6}$ alkylcarbonyl group, the $C_{1-6}$ alkylsulfonyl group, the mono-$C_{1-6}$ alkylamino group and the di-$C_{1-6}$ alkylamino group are unsubstituted or substituted with one or more identical or different substituents independently selected from the substituent set $V^{3a}$), a $C_{1-6}$ alkoxycarbonyl group, a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{1a}$), $R^{6a}$ is a hydrogen atom, a $C_{1-6}$ alkyl group, a $C_{2-6}$ alkenyl group, a $C_{1-6}$ alkylcarbonyl group, a $C_{1-6}$ alkylsulfonyl group, a $C_{1-6}$ alkoxycarbonyl group, a mono-$C_{1-6}$ alkylaminocarbonyl group, a di-$C_{1-6}$ alkylaminocarbonyl group (the $C_{1-6}$ alkyl group, the $C_{2-6}$ alkenyl group, the $C_{1-6}$ alkylcarbonyl group, the $C_{1-6}$ alkylsulfonyl group, the $C_{1-6}$ alkoxycarbonyl group, the mono-$C_{1-6}$ alkylaminocarbonyl group and the di-$C_{1-6}$ alkylaminocarbonyl group are unsubstituted or substituted with one or more identical or different substituents independently selected from the substituent set $V^{3a}$), a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{1a}$), each of $R^{9a}$ and $R^{10a}$ is independently a hydrogen atom, a halogen atom, a cyano group, a carbamoyl group, a $C_{1-6}$ alkyl group, a $C_{1-6}$ haloalkyl group, a $C_{3-11}$ cycloalkyl group, a $C_{1-6}$ alkoxy group, a $C_{1-6}$ haloalkoxy group, a $C_{1-6}$ alkylthio group, a $C_{1-6}$ alkylcarbonyl group, a $C_{1-6}$ alkylsulfonyl group, a 3 to 11-membered non-aromatic heterocyclyl group, a $C_{6-14}$ aryl group or a 5 to 10-membered aromatic heterocyclyl group, $R^{11a}$ is a hydrogen atom, a hydroxy group, a cyano group, a nitro group, a $C_{1-6}$ alkyl group or a $C_{1-6}$ alkoxy group, each of $R^{12a}$, $R^{13a}$ and $R^{14a}$ is independently a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or more identical or different substituents independently selected from the substituent set $V^{2a}$), the substituent set $V^{1a}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkyl groups, $C_{1-6}$ haloalkyl groups, $C_{3-11}$ cycloalkyl groups, $C_{2-6}$ alkenyl groups, $C_{2-6}$ haloalkenyl groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, $C_{1-6}$ alkoxycarbonyl groups, 3 to 11-membered non-aromatic heterocyclyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups and $C_{1-6}$ alkylcarbonylamino groups, the substituent set $V^{2a}$ consists of the groups in the substituent set $V^{1a}$, $C_{6-14}$ aryl groups and 5 to 10-membered aromatic heterocyclyl groups (the $C_{6-14}$ aryl group and the 5 to 10-membered aromatic heterocyclyl groups are unsubstituted or substituted with one or more identical or different substituents independently selected from the substituent set $V^{1a}$)

the substituent set $V^{3a}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{3-11}$ cycloalkyl groups, 3 to 11-membered non-aromatic heterocyclyl groups, $C_{6-14}$ aryl groups and 5 to 10-membered aromatic heterocyclyl groups (the $C_{3-11}$ cycloalkyl groups, the 3 to 11-membered non-aromatic heterocyclyl groups, the $C_{6-14}$ aryl groups and the 5 to 10-membered aromatic heterocyclyl groups are unsubstituted or substituted with one or more identical or different substituents independently selected from the substituent set $V^{1a}$), the substituent set $V^{4a}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkyl groups, $C_{2-6}$ alkenyl groups, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups (the $C_{1-6}$ alkyl groups, the $C_{2-6}$ alkenyl groups, the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups and the $C_{1-6}$ alkylcarbonylamino groups are unsubstituted or substituted with one or more identical or different substituents independently selected from the substituent set $V^{3a}$), $C_{3-11}$ cycloalkyl groups, 3 to 11-membered non-aromatic heterocyclyl groups, $C_{6-14}$ aryl groups and 5 to 10-membered aromatic heterocyclyl groups (the $C_{3-11}$ cycloalkyl groups, 3 to 11-membered non-aromatic heterocyclyl groups, $C_{6-14}$ aryl groups and 5 to 10-membered aromatic heterocyclyl groups are unsubstituted or substituted with one or more identical or different substituents independently selected from the substituent set $V^{1a}$), and the substituent set $V^{5a}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{3-11}$ cycloalkyl groups, 3 to 11-membered non-aromatic heterocyclyl groups, $C_{6-14}$ aryl groups and 5 to 10-membered aromatic heterocyclyl groups (the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups, the $C_{1-6}$ alkylcarbonylamino groups, the $C_{3-11}$ cycloalkyl groups, the 3 to 11-membered non-aromatic heterocyclyl groups, the $C_{6-14}$ aryl groups and the 5 to 10-membered aromatic heterocyclyl group are unsubstituted or substituted with one or more identical or different substituents independently selected from the substituent set $V^{3a}$)], a tautomer or a pharmaceutically acceptable salt of the compound or a solvate thereof.

(3) The compound according to (2), wherein $R^{1a}$ is a hydrogen atom, a tautomer or a pharmaceutically acceptable salt of the compound or a solvate thereof.

(4) The compound according to (2) or (3), wherein $Y^a$ is $CR^{10a}$ (wherein $R^{10a}$ is a hydrogen atom), a tautomer or a pharmaceutically acceptable salt of the compound or a solvate thereof.

(5) The compound according to any one of (2) to (4), wherein $X^a$ is a nitrogen atom or $CR^{9a}$ (wherein $R^{9a}$ is a hydrogen atom, a halogen atom, a cyano group, a $C_{1-3}$ alkyl group, a $C_{1-3}$ haloalkyl group or a $C_{3-6}$ cycloalkyl group), a tautomer or a pharmaceutically acceptable salt of the compound or a solvate thereof.

(6) The compound according to any one of (2) to (5), wherein the ring $A^a$ is represented by any of the following formulae ($IV^a$-1) to ($IV^a$-3):

($IV^a$)

($IV^a$-1)

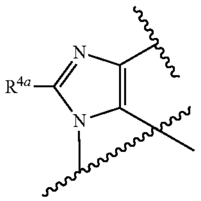

($IV^a$-2)

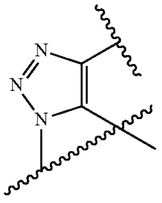

($IV^a$-3)

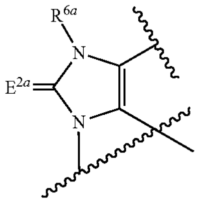

(wherein $E^{2a}$ is an oxygen atom or a sulfur atom), a tautomer or a pharmaceutically acceptable salt of the compound or a solvate thereof.

(7) The compound according to any one of (2) to (6), wherein $L^{1a}$ is a single bond, $L^{2a}$ is a single bond, a $C_{1-6}$ alkylene group or a $C_{2-6}$ alkenylene group (the $C_{1-6}$ alkylene group and the $C_{2-6}$ alkenylene group are unsubstituted or substituted with one or more identical or different substituents independently selected from the group consisting of halogen atoms, hydroxy groups, amino groups, cyano groups and nitro groups), the ring $B^a$ is a $C_{3-11}$ cycloalkane, a $C_{3-11}$ cycloalkene, a 3 to 11-membered non-aromatic heterocycle, a $C_{6-14}$ aromatic carbocycle or a 5 to 10-membered an aromatic heterocycle, $n^a$ is 0 or 1, $R^{3a}$ is a hydroxy group, an amino group, a carboxy group, a carbamoyl group, a tetrazolyl group, a halogen atom, a cyano group, a nitro group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkylsulfonyl group, $L^{3a}$ is a single bond, and $R^{2a}$ is a hydrogen atom, a halogen atom, a $C_{3-11}$ cycloalkyl group, a 3 to 11-membered non-aromatic heterocyclyl group, a phenyl group, a naphthyl group or a 5 to 10-membered aromatic heterocyclyl group (the $C_{3-11}$ cycloalkyl group, the 3 to 11-membered non-aromatic heterocyclyl group, the phenyl group, the naphthyl group and the 5 to 10-membered aromatic heterocyclyl group are unsubstituted or substituted with one or more identical or different substituents independently selected from the substituent set $V^{4a}$), a tautomer or a pharmaceutically acceptable salt of the compound or a solvate thereof.

(8) The compound according to any one of (2) to (6), wherein $L^{1a}$ is a single bond or a $C_{1-3}$ alkylene group, $L^{2a}$ is a single bond or a $C_{1-3}$ alkylene group (the $C_{1-3}$ alkylene group is unsubstituted or substituted with a cyano group or a $C_{1-3}$ haloalkyl group), the ring $B^a$ is a $C_{3-11}$ cycloalkane, a $C_{3-11}$ cycloalkene, a 3 to 11-membered non-aromatic heterocycle, benzene or a 5 to 6-membered aromatic heterocycle, $n^a$ is 0 or 1, $R^{3a}$ is a hydroxy group, an amino group, a carboxy group, a carbamoyl group, a tetrazolyl group, a halogen atom, a cyano group, a nitro group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkylsulfonyl group, $L^{3a}$ is a single bond, and $R^{2a}$ is a hydrogen atom, a halogen atom, a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the substituent set $V^{4a}$), a tautomer or a pharmaceutically acceptable salt of the compound or a solvate thereof.

(9) The compound according to (7), wherein the ring $B^a$ is a $C_{3-11}$ cycloalkane, a 4 to 7-membered non-aromatic heterocycle or benzene, $n^a$ is, 0 or 1, and $R^{3a}$ is a hydroxy group, a halogen atom, a cyano group or a $C_{1-3}$ alkyl group, a tautomer or a pharmaceutically acceptable salt of the compound or a solvate thereof.

(10) The compound according to (7) or (9), wherein $L^{2a}$ is a single bond, a $C_{1-6}$ alkylene group, a $C_{2-6}$ alkenylene group or a $C_{1-6}$ haloalkylene group (the $C_{1-6}$ alkylene group, the $C_{2-6}$ alkenylene group and the $C_{1-6}$ haloalkylene group are unsubstituted or substituted with one or two identical or different substituents independently selected from the group consisting of hydroxy groups and cyano groups), the ring $B^a$ is a $C_{3-11}$ cycloalkane or a 4 to 7-membered non-aromatic heterocycle, and $R^{2a}$ is a hydrogen atom, a halogen atom, a $C_{3-6}$ cycloalkyl group, a 3 to 11-membered non-aromatic heterocyclyl group, a phenyl group or a 5 to 10-membered aromatic heterocyclyl group (the $C_{3-6}$ cycloalkyl group, the 3 to 11-membered non-aromatic heterocyclyl group, the phenyl group and the 5 to 10-membered aromatic heterocyclyl group are unsubstituted or substituted with one or more identical or different substituents independently selected from the group consisting of hydroxy groups, amino groups, halogen atoms, cyano groups, nitro groups, carboxy groups, carbamoyl groups, sulfamoyl groups, $C_{1-6}$ alkyl groups, $C_{1-6}$ alkoxy groups, mono-$C_{1-6}$ alkylamino groups, di-$C_{1-6}$ alkylamino groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylaminocarbonyl groups, alkylaminocarbonyl groups, $C_{1-6}$ alkylcarbonylamino groups (the $C_{1-6}$ alkyl groups, the $C_{1-6}$ alkoxy groups, the mono-$C_{1-6}$ alkylamino groups, the di-$C_{1-6}$ alkylamino groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylaminocarbonyl groups, the di-$C_{1-6}$ alkylaminocarbonyl groups and the $C_{1-6}$ alkylcarbonylamino groups are unsubstituted or substituted with one or more identical or different substituents independently selected from the group consisting of halogen atoms, hydroxy groups, amino groups, cyano groups and $C_{1-3}$ alkoxy groups), $C_{3-6}$ cycloalkyl groups, 4 to 7-membered non-aromatic heterocyclyl groups, phenyl groups and 5 to 6-membered aromatic heterocyclyl groups (the $C_{3-6}$ cycloalkyl groups, the 4 to 7-membered non-aromatic heterocyclyl groups, the phenyl groups and the 5 to 6-membered aromatic heterocyclyl groups are unsubstituted or substituted with one or more identical or different substituents independently selected from the group consisting of hydroxy groups, halogen atoms, cyano groups, $C_{1-6}$ alkyl groups and $C_{1-6}$ haloalkyl groups)), a tautomer or a pharmaceutically acceptable salt of the compound or a solvate thereof.

(11) The compound according to (7) or (9), wherein $L^{2a}$ is a single bond, a $C_{1-3}$ alkylene group, a $C_{2-3}$ alkenylene group (the $C_{1-3}$ alkylene group and the $C_{2-3}$ alkenylene group are unsubstituted or substituted with one or two identical or different substituents independently selected from the group consisting of hydroxy groups and cyano groups) or a $C_{1-3}$ haloalkylene group, and $R^{2a}$ is a hydrogen atom or a halogen atom, a tautomer or a pharmaceutically acceptable salt of the compound or a solvate thereof.

(12) The compound according to any one of (7), (9) and (10), wherein the ring $B^a$ is a $C_{4-7}$ cycloalkane or a 4 to 7-membered non-aromatic heterocycle, and $R^{2a}$ is a 3 to 11-membered non-aromatic heterocyclyl group, a phenyl group or a 5 to 10-membered aromatic heterocyclyl group (the 3 to 11-membered non-aromatic heterocyclyl group, the phenyl group and the 5 to 10-membered aromatic heterocyclyl group are unsubstituted or substituted with one or more identical or different substituents independently selected from the group consisting of hydroxy groups, halogen atoms, cyano groups, carbamoyl groups, $C_{1-3}$ alkyl groups, $C_{1-3}$ alkoxy groups, mono-$C_{1-3}$ alkylamino groups, di-$C_{1-3}$ alkylamino groups (the $C_{1-3}$ alkyl groups, the $C_{1-3}$ alkoxy groups, the mono-$C_{1-3}$ alkylamino groups and the di-$C_{1-3}$ alkylamino groups are unsubstituted or substituted with a hydroxy group or a cyano group), $C_{1-3}$ haloalkyl groups, $C_{1-3}$ haloalkoxy groups, $C_{1-3}$ alkylthio groups, $C_{1-3}$ haloalkylthio groups, $C_{1-3}$ alkylsulfonyl groups, $C_{1-3}$ haloalkylsulfonyl groups, 4 to 7-membered non-aromatic heterocyclyl groups, phenyl groups and 5 to 6-membered aromatic heterocyclyl groups (the 4 to 7-membered non-aromatic heterocyclyl groups, the phenyl groups and the 5 to 6-membered aromatic heterocyclyl groups are unsubstituted or substituted with a substituent selected from the group consisting of a halogen atom, a $C_{1-3}$ alkyl group and a $C_{1-3}$ haloalkyl group)), a tautomer or a pharmaceutically acceptable salt of the compound or a solvate thereof.

(13) The compound according to any one of (7), (9) and (10), wherein the ring $B^a$ is a $C_{4-7}$ cycloalkane, and $R^{2a}$ is a 4 to 7-membered non-aromatic heterocyclyl group (the 4 to 7-membered non-aromatic heterocyclyl group is unsubstituted or substituted with one or two identical or different substituents independently selected from the group consisting of hydroxy groups, halogen atoms, cyano groups, carboxy groups, $C_{1-3}$ alkyl groups (the $C_{1-3}$ alkyl groups are unsubstituted or substituted with a hydroxy group or a cyano group), $C_{1-3}$ haloalkyl groups, $C_{1-3}$ alkoxy groups, di-$C_{1-3}$ alkylamino groups, mono-$C_{1-3}$ alkylaminocarbonyl groups, $C_{1-3}$ alkylsulfonyl group, $C_{1-3}$ alkylcarbonylamino groups (the $C_{1-3}$ alkoxy groups, the di-$C_{1-3}$ alkylamino groups, the mono-$C_{1-3}$ alkylaminocarbonyl groups, the $C_{1-3}$ alkylsulfonyl group and the $C_{1-3}$ alkylcarbonylamino groups are unsubstituted or substituted with one or more identical or different halogen atoms independently selected from the group consisting of fluorine atoms, chlorine atoms, bromine atoms and iodine atoms), 4 to 7-membered non-aromatic heterocyclyl groups and phenyl groups (the phenyl groups are unsubstituted or substituted with one or two identical or different substituents independently selected from the group consisting of halogen atoms, $C_{1-3}$ alkyl groups and $C_{1-3}$ haloalkyl groups)), a tautomer or a pharmaceutically acceptable salt of the compound or a solvate thereof.

(14) The compound according to any one of (2) to (6), wherein $L^{1a}$ is a single bond, $L^{2a}$ is a single bond, a $C_{1-6}$ alkylene group or a $C_{2-6}$ alkenylene group (the $C_{1-6}$ alkylene group and the $C_{2-6}$ alkenylene group are unsubstituted or substituted with one or more identical or different substituents independently selected from the group consisting of halogen atoms, hydroxy groups, amino groups, cyano groups and nitro groups), the ring $B^a$ is a $C_{3-11}$ cycloalkane, a $C_{3-11}$ cycloalkene, a 3 to 11-membered non-aromatic heterocycle, a $C_{6-14}$ aromatic carbocycle or a 5 to 10-membered aromatic heterocycle, $n^a$ is 0 or 1, $R^{3a}$ is a hydroxy group, an amino group, a carboxy group, a carbamoyl group, a halogen atom, a cyano group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkylsulfonyl group, $L^{3a}$ is represented by any of the following formulae ($XIV^a$-1) to ($XIV^a$-15):

($XIV^a$)

($XIV^a$-1)

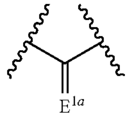

($XIV^a$-2)

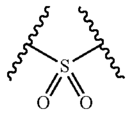

($XIV^a$-3)

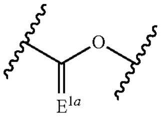

($XIV^a$-4)

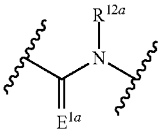

($XIV^a$-5)

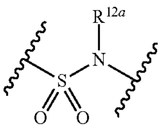

($XIV^a$-6)

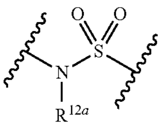

($XIV^a$-7)

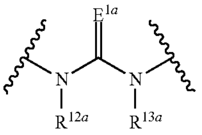

-continued ($XIV^a$-8)

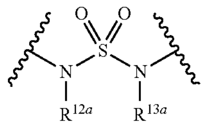

($XIV^a$-9)

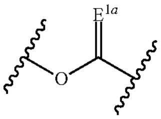

($XIV^a$-10)

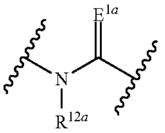

($XIV^a$-11)

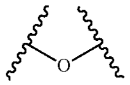

($XIV^a$-12)

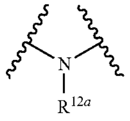

($XIV^a$-13)

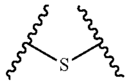

($XIV^a$-14

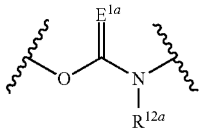

($XIV^a$-15)

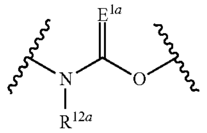

(wherein $E^{1a}$ is an oxygen atom, a sulfur atom or $NR^{11a}$ (wherein $R^{11a}$ is a hydroxy group or a $C_{1-3}$ alkoxy group), each of $R^{12a}$ and $R^{13a}$ is independently a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or more identical or different substituents independently selected from the group consisting of hydroxy groups, amino groups, cyano groups, $C_{3-11}$ cycloalkyl groups, $C_{1-6}$ alkoxy groups, $C_{1-6}$ haloalkoxy groups, $C_{1-6}$ alkylthio groups, $C_{1-6}$ alkylsulfonyl groups, $C_{1-6}$ haloalkylsulfonyl groups, $C_{1-6}$ alkoxycarbonyl groups, 3 to 11-membered non-aromatic heterocyclyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, phenyl groups and 5 to 10-membered aromatic heterocyclyl groups (the phenyl groups and the 5 to 10-membered aromatic heterocyclyl groups are unsubstituted or substituted with one or more identical or different substituents independently selected from the substituent set $V^{1a}$))), and $R^{2a}$ is a hydrogen atom, a $C_{1-6}$ alkyl group, a $C_{2-6}$ alkenyl group (the $C_{1-6}$ alkyl group and the $C_{2-6}$ alkenyl group are unsubstituted or substituted with one or more identical or different substituents independently selected from the substituent set $V^{5a}$), a $C_{3-11}$ cycloalkyl group, a 3 to 11-membered non-aromatic heterocyclyl group, a phenyl group, a naphthyl group or a 5 to 10-membered aromatic heterocyclyl group (the $C_{3-11}$ cycloalkyl group, the 3 to 11-membered non-aromatic heterocyclyl group, the phenyl group, the naphthyl group and the 5 to 10-membered aromatic heterocyclyl group are unsubstituted or substituted with one or more identical or different substituents independently selected from the substituent set $V^{4a}$), a tautomer or a pharmaceutically acceptable salt of the compound or a solvate thereof.

(15) The compound according to any one of (2) to (6), wherein $L^{1a}$ is a single bond or a $C_{1-3}$ alkylene group, $L^{2a}$ is a single bond or a $C_{1-3}$ alkylene group (the $C_{1-3}$ alkylene group is unsubstituted or substituted with a cyano group or a $C_{1-3}$ haloalkylene group), the ring $B^a$ is a $C_{3-11}$ cycloalkane, a $C_{3-11}$ cycloalkene, a 3 to 11-membered non-aromatic heterocycle, benzene or a 5 to 6-membered aromatic heterocycle, $n^a$ is 0 or 1

$R^{3a}$ is a hydroxy group, an amino group, a carbamoyl group, a halogen atom, a cyano group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkylsulfonyl group, $L^{3a}$ is represented by any of the following formulae ($V^a$-1) to ($V^a$-11):

($V^a$)

($V^a$-1)

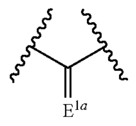

($V^a$-2)

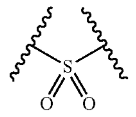

($V^a$-3)

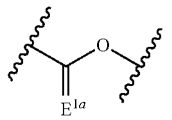

($V^a$-4)

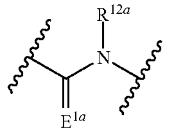

($V^a$-5)

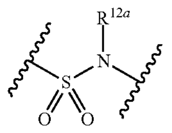

($V^a$-6)

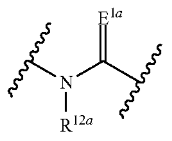

-continued ($V^a$-7)

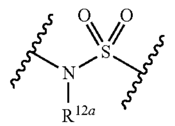

($V^a$-8)

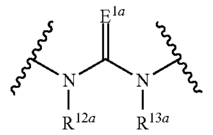

($V^a$-9)

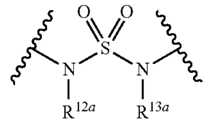

($V^a$-10)

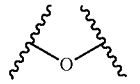

($V^a$-11)

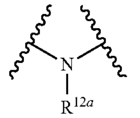

(wherein $E^{1a}$ is an oxygen atom, each of $R^{12a}$ and $R^{13a}$ is independently a hydrogen atom, a $C_{1-6}$ alkyl group or a $C_{1-6}$ haloalkyl group), and $R^{2a}$ is a hydrogen atom, a $C_{1-6}$ alkyl group (the $C_{1-6}$ alkyl group is unsubstituted or substituted with one or more identical or different substituents independently selected from the substituent set $V^{5a}$), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the substituent set $V^{1a}$), a tautomer or a pharmaceutically acceptable salt of the compound or a solvate thereof.

(16) The compound according to (14), wherein $L^{2a}$ is a single bond, a $C_{1-3}$ alkylene group, a $C_{2-3}$ alkenylene group (the $C_{1-3}$ alkylene group and the $C_{2-3}$ alkenylene group are unsubstituted or substituted with one or two identical or different substituents independently selected from the group consisting of hydroxy groups and cyano groups) or a $C_{1-3}$ haloalkylene group, the ring $B^a$ is a $C_{3-11}$ cycloalkane, a 4 to 7-membered non-aromatic heterocycle or benzene, $n^a$ is 0 or 1, $R^{3a}$ is a halogen atom, a cyano group or a $C_{1-3}$ alkyl group, and $L^{3a}$ is represented by any of the following formulae ($XV^a$-1) to ($XV^a$-12):

($XV^a$)

($XV^a$-1)

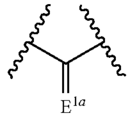

($XV^a$-2)

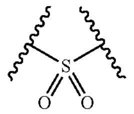

($XV^a$-3)

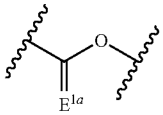

($XV^a$-4)

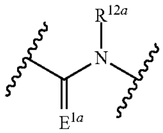

($XV^a$-5)

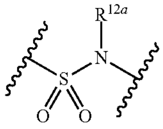

($XV^a$-6)

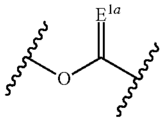

($XV^a$-7)

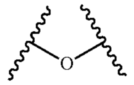

($XV^a$-8)

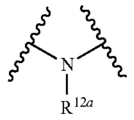

($XV^a$-9)

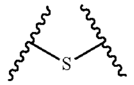

($XV^a$-10)

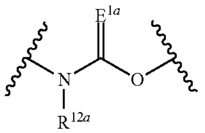

($XV^a$-11)

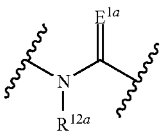

-continued ($XV^a$-12)

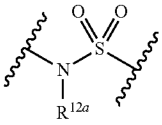

(wherein $E^{1a}$ is an oxygen atom or $NR^{11}$ (wherein $R^{11a}$ is a hydroxy group), and $R^{12a}$ is a hydrogen atom, a $C_{1-6}$ alkyl group or a $C_{1-6}$ haloalkyl group (the $C_{1-6}$ alkyl group and the $C_{1-6}$ haloalkyl group is unsubstituted or substituted with a substituent selected from the group consisting of a hydroxy group, a cyano group, a $C_{1-3}$ alkoxy group, a $C_{3-6}$ cycloalkyl group, a phenyl group and a 5 to 6-membered aromatic heterocyclyl group (the phenyl group and the 5 to 6-membered aromatic heterocyclyl group are unsubstituted or substituted with a substituent selected from the group consisting of a halogen atom, a cyano group, a $C_{1-3}$ alkyl group and a $C_{1-3}$ haloalkyl group))), a tautomer or a pharmaceutically acceptable salt of the compound or a solvate thereof.

(17) The compound according to (14) or (16), wherein $L^{2a}$ is a single bond or a $C_{1-3}$ alkylene group, the ring $B^a$ is a $C_{4-7}$ cycloalkane or a 4 to 7-membered non-aromatic heterocycle, and $R^{2a}$ is a hydrogen atom, a $C_{1-6}$ alkyl group, a $C_{1-6}$ haloalkyl group (the $C_{1-6}$ alkyl group and the $C_{1-6}$ haloalkyl group are unsubstituted or substituted with one or more identical or different substituents independently selected from the group consisting of cyano groups, hydroxy groups, $C_{1-6}$ alkoxy groups, mono-$C_{1-6}$ alkylaminocarbonyl groups, di-$C_{1-6}$ alkylaminocarbonyl groups (the mono-$C_{1-6}$ alkylaminocarbonyl groups and the di-$C_{1-6}$ alkylaminocarbonyl groups are unsubstituted or substituted with one or more identical or different halogen atoms independently selected from the group consisting of fluorine atoms, chlorine atoms, bromine atoms and iodine atoms), $C_{3-6}$ cycloalkyl groups, 4 to 7-membered non-aromatic heterocyclyl groups, phenyl groups or 5 to 10-membered aromatic heterocyclyl groups (the $C_{3-6}$ cycloalkyl groups, the 4 to 7-membered non-aromatic heterocyclyl groups, the phenyl groups and the 5 to 10-membered aromatic heterocyclyl groups are unsubstituted or substituted with identical or different one, two or three substituents independently selected from the group consisting of hydroxy groups, halogen atoms, cyano groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylsulfonyl groups, $C_{1-6}$ haloalkylsulfonyl groups, $C_{1-6}$ alkoxycarbonyl groups, 4 to 7-membered non-aromatic heterocyclyl groups and phenyl groups (the phenyl groups are unsubstituted or substituted with a halogen atom))), a $C_{3-11}$ cycloalkyl group, a 4 to 7-membered non-aromatic heterocyclyl group, a phenyl group, a naphthyl group or a 5 to 10-membered aromatic heterocyclyl group (the $C_{3-11}$ cycloalkyl group, the 4 to 7-membered non-aromatic heterocyclyl group, the phenyl group, the naphthyl group and the 5 to 10-membered aromatic heterocyclyl group are unsubstituted or substituted with one, two or three identical or different substituents independently selected from the group consisting of hydroxy groups, halogen atoms, cyano groups, $C_{1-6}$ alkyl groups (the $C_{1-6}$ alkyl groups are unsubstituted or substituted with one or more identical or different substituents independently selected from the group consisting of halogen atoms, cyano groups, hydroxy groups and $C_{1-3}$ alkoxy groups), $C_{1-6}$ alkoxy groups, $C_{1-6}$ haloalkoxy groups, $C_{1-6}$ alkylthio groups, $C_{1-6}$ haloalkylthio groups, $C_{1-6}$ alkylsulfonyl groups, $C_{1-6}$ haloalkylsulfonyl groups, $C_{1-6}$ alkoxycarbonyl groups (the $C_{1-6}$ alkoxycarbonyl groups are unsubstituted or substituted with one or more identical or different halogen atoms independently selected from the group consisting of fluorine atoms, chlorine atoms, bromine atoms and iodine atoms), 4 to 7-membered non-aromatic heterocyclyl groups and phenyl groups (the phenyl groups are unsubstituted or substituted with a halogen atom)), a tautomer or a pharmaceutically acceptable salt of the compound or a solvate thereof.

(18) The compound according to any one of (14), (16) and (17), wherein $L^{3a}$ is represented by any of the following formulae ($XXIII^a$-1) to ($XXIII^a$-7):

($XXIII^a$)

($XXIII^a$-1)

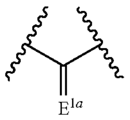

($XXIII^a$-2)

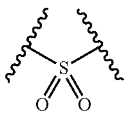

($XXIII^a$-3)

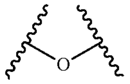

($XXIII^a$-4)

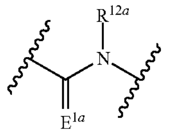

($XXIII^a$-5)

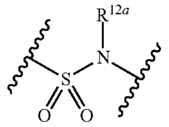

($XXIII^a$-6)

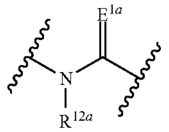

($XXIII^a$-7)

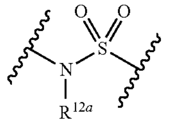

(wherein $E^{1a}$ is an oxygen atom, and $R^{12a}$ is a hydrogen atom, a $C_{1-3}$ alkyl group (the $C_{1-3}$ alkyl group is unsubstituted or substituted with a cyano group) or a $C_{1-3}$ haloalkyl group), and $R^{2a}$ is a $C_{1-6}$ alkyl group (the $C_{1-6}$ alkyl group is unsubstituted or substituted with a cyano group), a $C_{1-6}$ haloalkyl group, a $C_{3-6}$ cycloalkyl group, a 4 to 7-membered non-aromatic heterocyclyl group or a phenyl group (the 4 to 7-membered non-aromatic heterocyclyl group and the phenyl group are unsubstituted or substituted with a substituent selected from the group consisting of a halogen atom, a hydroxy group, a cyano group, a $C_{1-3}$ alkyl group and a $C_{1-3}$ haloalkyl group), a tautomer or a pharmaceutically acceptable salt of the compound or a solvate thereof.

(19) The compound according to any one of (14) and (16) to (18), wherein $L^{3a}$ is represented by any of the following formulae ($XXIV^a$-1) to ($XXIV^a$-4):

($XXIV^a$)

($XXIV^a$-1)

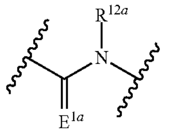

($XXIV^a$-2)

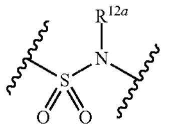

($XXIV^a$-3)

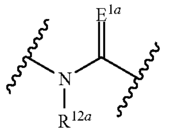

($XXIV^a$-4)

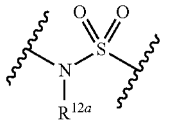

(wherein $E^{1a}$ is an oxygen atom, and $R^{12a}$ is a hydrogen atom, a $C_{1-3}$ alkyl group (the $C_{1-3}$ alkyl group is unsubstituted or substituted with a cyano group) or a $C_{1-3}$ haloalkyl group), and $R^{2a}$ is a $C_{1-3}$ alkyl group (the $C_{1-3}$ alkyl group is unsubstituted or substituted with a cyano group), a $C_{1-3}$ haloalkyl group or a $C_{3-6}$ cycloalkyl group, a tautomer or a pharmaceutically acceptable salt of the compound or a solvate thereof.

(20) The compound according to any one of (14), (16) and (17), wherein $L^{3a}$ is represented by the formula ($XVI^a$):

($XVI^a$)

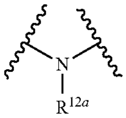

(wherein $R^{12a}$ is a hydrogen atom, a $C_{1-3}$ alkyl group (the $C_{1-3}$ alkyl group is unsubstituted or substituted with a substituent selected from the group consisting of a hydroxy group, a cyano group, a $C_{1-3}$ alkoxy group, a $C_{3-6}$ cycloalkyl group and a phenyl group) or a $C_{1-3}$ haloalkyl group), and $R^{2a}$ is a hydrogen atom, a $C_{1-6}$ alkyl group (the $C_{1-6}$ alkyl group is unsubstituted or substituted with one or two identical or different substituents independently selected from the group consisting of cyano groups, hydroxy groups, $C_{1-3}$ alkoxy groups, mono-$C_{1-3}$ alkylaminocarbonyl groups (the mono-$C_{1-3}$ alkylaminocarbonyl groups are unsubstituted or substituted with one or more identical or different halogen atoms independently selected from the group consisting of fluorine atoms, chlorine atoms, bromine atoms and iodine atoms), $C_{3-6}$ cycloalkyl groups, 4 to 7-membered non-aromatic heterocyclyl groups, phenyl groups and 5 to 6-membered aromatic heterocyclyl groups (the $C_{3-6}$ cycloalkyl groups, the 4 to 7-membered non-aromatic heterocyclyl groups, the phenyl groups and the 5 to 6-membered aromatic heterocyclyl groups are unsubstituted or substituted with one or two identical or different substituents independently selected from the group consisting of hydroxy groups, halogen atoms, cyano groups, $C_{1-3}$ alkoxy groups, $C_{1-3}$ haloalkoxy groups, $C_{1-3}$ alkylsulfonyl groups, $C_{1-6}$ alkoxy carbonyl groups and phenyl groups (the phenyl groups are unsubstituted or substituted with a halogen atom))), a $C_{1-6}$ haloalkyl group (the $C_{1-6}$ haloalkyl group is unsubstituted or substituted with one or two identical or different substituents independently selected from the group consisting of hydroxy groups, phenyl groups and 5 to 6-membered aromatic heterocyclyl groups (the phenyl groups and the 5 to 6-membered aromatic heterocyclyl groups are unsubstituted or substituted with one or two identical or different substituents independently selected from the group consisting of halogen atoms, $C_{1-3}$ alkoxy groups and $C_{1-3}$ alkylthio groups)), a $C_{3-11}$ cycloalkyl group, a 4 to 7-membered non-aromatic heterocyclyl group, a phenyl group or a 5 to 10-membered aromatic heterocyclyl group (the $C_{3-11}$ cycloalkyl group, the 4 to 7-membered non-aromatic heterocyclyl group, the phenyl group and the 5 to 10-membered aromatic heterocyclyl group are unsubstituted or substituted with one, two or three identical or different substituents independently selected from the group consisting of hydroxy groups, halogen atoms, cyano groups, $C_{1-3}$ alkyl groups (the $C_{1-3}$ alkyl groups are unsubstituted or substituted with a substituent selected from the group consisting of a hydroxy group, a cyano group and a $C_{1-3}$ alkoxy group), $C_{1-3}$ haloalkyl groups, $C_{1-3}$ alkoxy groups, $C_{1-3}$ haloalkoxy groups, $C_{1-3}$ alkylsulfonyl groups, $C_{1-3}$ haloalkylsulfonyl groups, $C_{1-6}$ alkoxycarbonyl groups, 4 to 7-membered non-aromatic heterocyclyl groups and phenyl groups (the phenyl groups are unsubstituted or substituted with a halogen atom)), a tautomer or a pharmaceutically acceptable salt of the compound or a solvate thereof.

(21) The compound according to any one of (2) to (12) and (14) to (19), wherein the ring $B^a$ is cyclohexane or piperidine, a tautomer or a pharmaceutically acceptable salt of the compound or a solvate thereof.

(22) The compound according to (13) or (20), wherein the ring $B^a$ is cyclohexane, a tautomer or a pharmaceutically acceptable salt of the compound or a solvate thereof.

(23) The compound according to any one of (5) to (22), wherein r is $CR^{9a}$ (wherein $R^{9a}$ is a hydrogen atom), a tautomer or a pharmaceutically acceptable salt of the compound or a solvate thereof.

(24) The compound according to any one of (6) to (23), wherein the ring $A^a$ is represented by any of the following formulae ($IV^a$-1) to ($IV^a$-3):

($IV^a$)

($IV^a$-1)

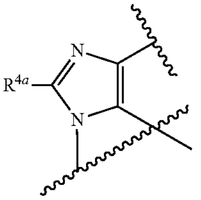

-continued ($IV^a$-2)

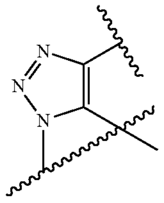

($IV^a$-3)

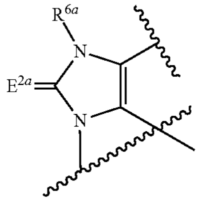

(wherein $E^{2a}$ is an oxygen atom or a sulfur atom, and each of $R^{4a}$ and $R^{ha}$ is independently a hydrogen atom or a $C_{1-3}$ alkyl group), a tautomer or a pharmaceutically acceptable salt of the compound or a solvate thereof.

(25) The compound according to any one of (8), (23) and (24), wherein $L^{1a}$ is a single bond, $L^{2a}$ is a single bond or a $C_{1-3}$ alkylene group, the ring $B^a$ is a $C_{4-7}$ cycloalkane, benzene or a 4 to 7-membered non-aromatic heterocycle, $n^a$ is 0, $L^{3a}$ is a single bond, and $R^{2a}$ is a hydrogen atom, a tautomer or a pharmaceutically acceptable salt of the compound or a solvate thereof.

(26) The compound according to any one of (15), (23) and (24), wherein $L^{1a}$ is a single bond, $L^{2a}$ is a single bond, the ring $B^a$ is a $C_{4-7}$ cycloalkane or a 4 to 7-membered non-aromatic heterocycle, $n^a$ is 0, $L^{3a}$ is represented by any of the following formulae ($VI^a$-1) to ($VI^a$-3):

($VI^a$)

($VI^a$-1)

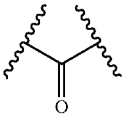

($VI^a$-2)

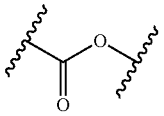

($VI^a$-3)

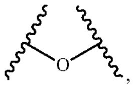, and $R^{2a}$ is a hydrogen atom or a $C_{1-3}$ alkyl group (the $C_{1-3}$ alkyl group is unsubstituted or substituted with a cyano group or a phenyl group), a tautomer or a pharmaceutically acceptable salt of the compound or a solvate thereof.

(27) The compound according to any one of (2) to (6), (8), (15), (25) and (26), wherein the ring $B^a$ is cyclohexane, benzene or piperidine, a tautomer or a pharmaceutically acceptable salt of the compound or a solvate thereof.

(28) The compound according to (1), wherein $R^{1a}$ is a hydrogen atom, $X^a$ is $CR^{9a}$ (wherein $R^{9a}$ is a hydrogen atom or a halogen atom), $Y^a$ is $CR^{10a}$ (wherein $R^{10a}$ is a hydrogen atom), the ring $A^a$ is represented by any of the following formulae ($IV^a$-1) to ($IV^a$-3):

($IV^a$)

($IV^a$-1)

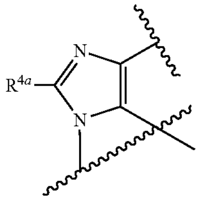

($IV^a$-2)

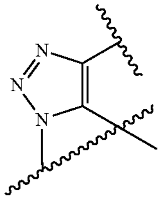

($IV^a$-3)

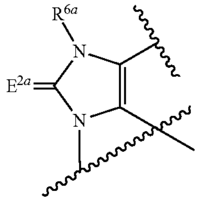

(wherein $E^{2a}$ is an oxygen atom or a sulfur atom, $R^{4a}$ is a hydrogen atom or a $C_{1-3}$ alkyl group, and $R^{6a}$ is a hydrogen atom), $L^{1a}$ is a single bond, the ring $B^a$ is a $C_{3-11}$ cycloalkane, a $C_{3-11}$ cycloalkene (a ring-constituting methylene group of the $C_{3-11}$ cycloalkane and the $C_{3-11}$ cycloalkene may be replaced by a carbonyl group), a 3 to 11-membered non-aromatic heterocycle, a $C_{6-14}$ aromatic carbocycle or a 5 to 10-membered aromatic heterocycle, $n^a$ is 0, 1 or 2, $R^{3a}$ is a hydroxy group, an amino group, a carboxy group, a carbamoyl group, a halogen atom, a cyano group, a $C_{1-3}$ alkyl group, a $C_{1-3}$ haloalkyl group or a $C_{1-3}$ alkoxy group (when $n^a$ is 2, $R^{3a}$'s may be identical or different), $L^{2a}$ is a single bond, a $C_{1-6}$ alkylene group, a $C_{2-6}$ alkenylene group (the $C_{1-6}$ alkylene group and the $C_{2-6}$ alkenylene group are unsubstituted or substituted with one or more identical or different substituents independently selected from the group consisting of halogen atoms, hydroxy groups, amino groups, cyano groups and nitro groups), $=C(R^{15a})—$ (wherein $R^{15a}$ is a hydrogen atom or a cyano group, and the bond connecting the ring $B^a$ and $L^{2a}$ is a double bond) or $=C(R^{15a})—CH_2—$ (wherein $R^{15a}$ is a hydrogen atom or a cyano group, and the bond connecting the ring $B^a$ and $L^{2a}$ is a double bond), $L^{3a}$ is a single bond or represented by any of the following formulae ($XIV^a$-1) to ($XIV^a$-15) and ($XIII^a$)

($XIV^a$)

($XIV^a$-1)

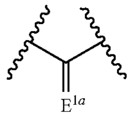

($XIV^a$-2)

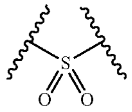

($XIV^a$-3)

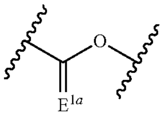

($XIV^a$-4)

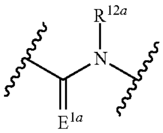

($XIV^a$-5)

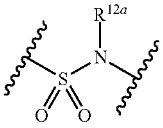

($XIV^a$-6)

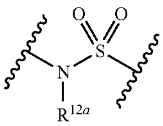

($XIV^a$-7)

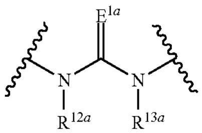

($XIV^a$-8)

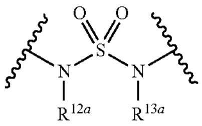

($XIV^a$-9)

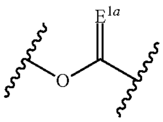

($XIV^a$-10)

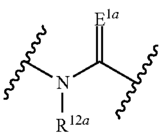

($XIV^a$-11)

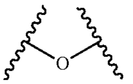

-continued (XIV$^a$-12)

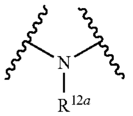

(XIV$^a$-13)

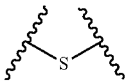

(XIV$^a$-14)

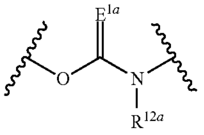

(XIV$^a$-15)

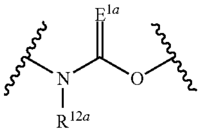

(XIII$^a$)

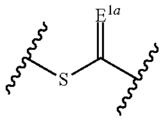

(wherein $E^{1a}$ is an oxygen atom), when $L^{3a}$ is a single bond, $R^{2a}$ is a hydrogen atom, a halogen atom, an azido group, a $C_{3-11}$ cycloalkyl group, a 3 to 11-membered non-aromatic heterocyclyl group, a $C_{6-14}$ aryl group, a 5 to 10-membered aromatic heterocyclyl group, a 8 to 11-membered partially saturated aromatic cyclic group or a 8 to 11-membered aromatic ring-condensed alicyclic hydrocarbon group (the $C_{3-11}$ cycloalkyl group, the 3 to 11-membered non-aromatic heterocyclyl group, the $C_{6-14}$ aryl group, the 5 to 10-membered aromatic heterocyclyl group, the 8 to 11-membered partially saturated aromatic cyclic group and the 8 to 11-membered aromatic ring-condensed alicyclic hydrocarbon group are unsubstituted or substituted with one or more identical or different substituents independently selected from the group consisting of the substituent set $V^{4a}$, the substituent set $V^{9a}$ and $C_{1-6}$ alkyl groups (the $C_{1-6}$ alkyl groups are substituted with a $C_{1-6}$ alkoxycarbonylamino group (the $C_{1-6}$ alkoxycarbonylamino group is unsubstituted or substituted with one or more identical or different halogen atoms independently selected from the group consisting of fluorine atoms, chlorine atoms, bromine atoms and iodine atoms))), when $L^{3a}$ is not a single bond, $R^{2a}$ is a hydrogen atom, a $C_{1-6}$ alkyl group, a $C_{2-6}$ alkenyl group, a $C_{2-6}$ alkynyl group (the $C_{1-6}$ alkyl group, the $C_{2-6}$ alkenyl group and the $C_{2-6}$ alkynyl group are unsubstituted or substituted with one or more identical or different substituents independently selected from the substituent set $V^{6a}$ and the substituent set $V^{9a}$), a $C_{3-11}$ cycloalkyl group, a 3 to 11-membered non-aromatic heterocyclyl group, a $C_{6-14}$ aryl group, a 5 to 10-membered aromatic heterocyclyl group, a 8 to 11-membered partially saturated aromatic cyclic group or a 8 to 11-membered aromatic ring-condensed alicyclic hydrocarbon group (the $C_{3-11}$ cycloalkyl group, the 3 to 11-membered non-aromatic heterocyclyl group, the $C_{6-14}$ aryl group, the 5 to 10-membered aromatic heterocyclyl group, the 8 to 11-membered partially saturated aromatic cyclic group and the 8 to 11-membered aromatic ring-condensed alicyclic hydrocarbon group are unsubstituted or substituted with one or more identical or different substituents independently selected from the substituent set $V^{4a}$ and the substituent set $V^{9a}$), and each of $R^{12a}$ and $R^{13a}$ is independently a hydrogen atom, a $C_{1-6}$ alkyl group, a $C_{1-6}$ haloalkyl group (the $C_{1-6}$ alkyl group and the $C_{1-6}$ haloalkyl group are unsubstituted or substituted with one or more identical or different substituents independently selected from the substituent set $V^{2a}$, the substituent set $V^{8a}$ and the substituent set $V^{9a}$), a $C_{3-11}$ cycloalkyl group, a 3 to 11-membered non-aromatic heterocyclyl group, a $C_{6-14}$ aryl group, a 5 to 10-membered aromatic heterocyclyl group or a 8 to 11-membered partially saturated aromatic cyclic group (the $C_{3-11}$ cycloalkyl group, the 3 to 11-membered non-aromatic heterocyclyl group, the $C_{6-14}$ aryl group, the 5 to 10-membered aromatic heterocyclyl group and the 8 to 11-membered partially saturated aromatic cyclic group are unsubstituted or substituted with one or more identical or different substituents independently selected from the substituent set $V^{4a}$ and the substituent set $V^{9a}$), a tautomer or a pharmaceutically acceptable salt of the compound or a solvate thereof.

(29) The compound according to (1) or (28), wherein $L^{2a}$ is a single bond, a $C_{1-6}$ alkylene group, a $C_{2-6}$ alkenylene group (the $C_{1-6}$ alkylene group and the $C_{2-6}$ alkenylene group are unsubstituted or substituted with one or two identical or different substituents independently selected from the group consisting of hydroxy groups and cyano groups) or a $C_{1-6}$ haloalkylene group, the ring $B^a$ is a $C_{4-7}$ cycloalkane (a ring-constituting methylene group of the $C_{4-7}$ cycloalkane may be replaced by a carbonyl group) or a 4 to 7-membered non-aromatic heterocycle, $n^a$ is 0, 1 or 2, $R^{3a}$ is a cyano group, a $C_{1-3}$ alkyl group or a halogen atom (when $n^a$ is 2, $R^{3a}$'s may be identical or different), a tautomer or a pharmaceutically acceptable salt of the compound or a solvate thereof.

(30) The compound according to any one of (1), (28) and (29), wherein $L^{3a}$ is a single bond, $R^{2a}$ is a hydrogen atom, a halogen atom, an azido group, a $C_{3-11}$ cycloalkyl group, a 3 to 11-membered non-aromatic heterocyclyl group, a phenyl group, a 5 to 10-membered aromatic heterocyclyl group or a 8 to 11-membered partially saturated aromatic cyclic group (the $C_{3-11}$ cycloalkyl group, the 3 to 11-membered non-aromatic heterocyclyl group, the phenyl group, the 5 to 10-membered aromatic heterocyclyl group and the 8 to 11-membered partially saturated aromatic cyclic group are unsubstituted or substituted with one or more identical or different substituents independently selected from the group consisting of the substituent set $V^{4a}$, the substituent set $V^{9a}$ and $C_{1-6}$ alkyl groups (the $C_{1-6}$ alkyl groups are substituted with a $C_{1-6}$ alkoxycarbonylamino group (the $C_{1-6}$ alkoxycarbonylamino group is unsubstituted or substituted with one or more identical or different halogen atoms independently selected from the group consisting of fluorine atoms, chlorine atoms, bromine atoms and iodine atoms))), a tautomer or a pharmaceutically acceptable salt of the compound or a solvate thereof.

(31) The compound according to (30), wherein $L^{2a}$ is a $C_{1-3}$ alkylene group, the ring $B^a$ is a 4 to 7-membered non-aromatic heterocycle, $L^{3a}$ is a single bond, $R^{2a}$ is a phenyl group or a 5 to 10-membered aromatic heterocyclyl group or a 8 to 11-membered partially saturated aromatic cyclic group (the phenyl group, the 5 to 10-membered aromatic heterocyclyl group and the 8 to 11-membered partially saturated aromatic cyclic group are unsubstituted or substituted with one, two or three identical or different substituents independently selected from the group consisting of hydroxy groups, halogen atoms, cyano groups, carbamoyl groups, $C_{1-6}$ alkyl groups, $C_{1-6}$ haloalkyl groups, $C_{1-6}$ alkoxy groups, $C_{1-6}$ haloalkoxy groups, di-$C_{1-6}$ alkylamino groups, $C_{1-6}$ alkylthio groups, $C_{1-6}$ haloalkylthio groups, $C_{1-6}$ alkylsulfonyl groups, 4 to 7-membered non-aromatic heterocyclyl groups and 5 to 6-membered aromatic heterocyclyl groups), a tautomer or a pharmaceutically acceptable salt of the compound or a solvate thereof.

(32) The compound according to any one of (28) to (30), wherein the ring $B^a$ is a $C_{4-7}$ cycloalkane, $L^{3a}$ is a single bond, $R^{2a}$ is a 3 to 11-membered non-aromatic heterocyclyl group (the 3 to 11-membered non-aromatic heterocyclyl group is unsubstituted or substituted with one or more identical or different substituents independently selected from the group consisting of hydroxy groups, amino groups, halogen atoms, cyano groups, carbamoyl groups, carboxy groups, $C_{1-6}$ alkyl groups (the $C_{1-6}$ alkyl groups are unsubstituted or substituted with one or more identical or different halogen atoms independently selected from the group consisting of fluorine atoms, chlorine atoms, bromine atoms and iodine atoms or with a substituent selected from the group consisting of a hydroxy group, a cyano group and a $C_{1-6}$ alkoxycarbonylamino group), $C_{1-3}$ alkoxy groups, mono-$C_{1-3}$ alkylaminocarbonyl groups, $C_{1-3}$ alkylcarbonylamino groups (the $C_{1-3}$ alkoxy groups, the mono-$C_{1-3}$ alkylaminocarbonyl groups, the $C_{1-3}$ alkylcarbonylamino groups are unsubstituted or substituted with one or more identical or different halogen atoms independently selected from the group consisting of fluorine atoms, chlorine atoms, bromine atoms and iodine atoms), di-$C_{1-3}$ alkylamino groups, $C_{1-3}$ alkylsulfonyl groups, di-$C_{1-3}$ alkylaminosulfonyl groups, $C_{1-6}$ alkoxycarbonylamino groups, 4 to 7-membered non-aromatic heterocyclyl groups and phenyl groups (the phenyl groups are unsubstituted or substituted with a halogen atom)), a tautomer or a pharmaceutically acceptable salt of the compound or a solvate thereof.

(33) The compound according to any one of (1), (28) and (29), wherein $L^{3a}$ is represented by any of the following formulae ($XV^a$-1) to ($XV^a$-12) and ($XIII^a$):

($XV^a$)

($XV^a$-1)

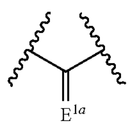

($XV^a$-2)

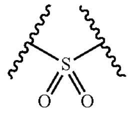

($XV^a$-3)

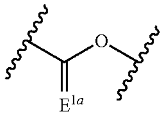

-continued ($XV^a$-4)

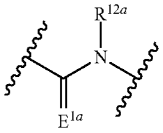

($XV^a$-5)

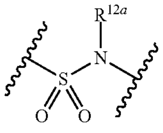

($XV^a$-6)

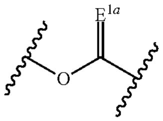

($XV^a$-7)

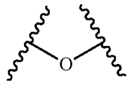

($XV^a$-8)

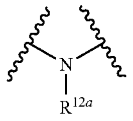

($XV^a$-9)

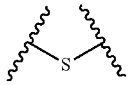

($XV^a$-10)

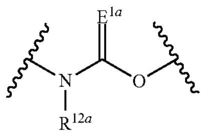

($XV^a$-11)

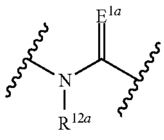

($XV^a$-12)

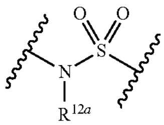

($XIII^a$)

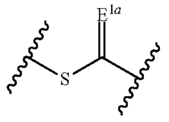

(wherein $E^{1a}$ is an oxygen atom, and $R^{12a}$ is a hydrogen atom, a $C_{1-6}$ alkyl group (the $C_{1-6}$ alkyl group is unsubstituted or substituted with a substituent selected from the group consisting of a hydroxy group, a cyano group, a $C_{1-3}$ alkoxy group, a $C_{3-6}$ cycloalkyl group, a phenyl group and a 5 to 6-membered aromatic heterocyclyl group (the phenyl group and the 5 to 6-membered aromatic heterocyclyl group are unsubstituted or substituted with a substituent selected from the group consisting of a halogen atom, a cyano group, a $C_{1-3}$ alkyl group and a $C_{1-3}$ haloalkyl group)), a $C_{1-6}$ haloalkyl group, a $C_{3-6}$ cycloalkyl group or a phenyl group (the phenyl group is unsubstituted or substituted with a halogen atom or a cyano group)), $R^{2a}$ is a hydrogen atom, a $C_{1-6}$ alkyl group (the $C_{1-6}$ alkyl group is unsubstituted or substituted with one or more identical or different substituents independently selected from the substituent set $V^{6a}$ and the substituent set $V^{9a}$), a $C_{2-6}$ alkynyl group, a $C_{3-11}$ cycloalkyl group, a 3 to 11-membered non-aromatic heterocyclyl group, a phenyl group, a 5 to 10-membered aromatic heterocyclyl group, a 8 to 11-membered partially saturated aromatic cyclic group or a 8 to 11-membered aromatic ring-condensed alicyclic hydrocarbon group (the $C_{3-11}$ cycloalkyl group, the 3 to 11-membered non-aromatic heterocyclyl group, the phenyl group, the 5 to 10-membered aromatic heterocyclyl group, the 8 to 11-membered partially saturated aromatic cyclic group and the 8 to 11-membered aromatic ring-condensed alicyclic hydrocarbon group are unsubstituted or substituted with one or more identical or different substituents independently selected from the substituent set $V^{4a}$ and the substituent set $V^{9a}$), a tautomer or a pharmaceutically acceptable salt of the compound or a solvate thereof.

(34) The compound according to (33), wherein the ring $B^a$ is a $C_{4-7}$ cycloalkane or a 4 to 7-membered non-aromatic heterocycle, $L^{3a}$ is represented by the following formulae ($XXV^a$-1) or ($XXV^a$-2):

($XXV^a$)

($XXV^a$-1)

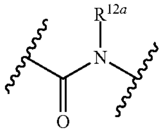

($XXV^a$-2)

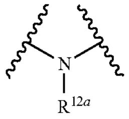

(wherein $R^{12a}$ is a hydrogen atom, a $C_{1-3}$ alkyl group (the $C_{1-3}$ alkyl group is unsubstituted or substituted with a substituent selected from the group consisting of a hydroxy group, a cyano group, a $C_{1-3}$ alkoxy group, a $C_{3-6}$ cycloalkyl group and a phenyl group), a $C_{1-3}$ haloalkyl group, a $C_{3-6}$ cycloalkyl group or a phenyl group (the phenyl group is unsubstituted or substituted with a halogen atom or a cyano group)), $R^{2a}$ is a hydrogen atom, a $C_{1-6}$ alkyl group, a $C_{1-6}$ haloalkyl group (the $C_{1-6}$ alkyl group and the $C_{1-6}$ haloalkyl group are unsubstituted or substituted with one or two identical or different substituents independently selected from the group consisting of hydroxy groups, cyano groups, $C_{1-3}$ alkoxy groups, $C_{1-3}$ alkylthio groups, $C_{1-3}$ alkylsulfonyl groups, mono-$C_{1-3}$ alkylaminocarbonyl groups, di-$C_{1-3}$ alkylaminocarbonyl groups (the mono-$C_{1-3}$ alkylaminocarbonyl groups and the di-$C_{1-3}$ alkylaminocarbonyl groups are unsubstituted or substituted with one or more identical or different halogen atoms independently selected from the group consisting of fluorine atoms, chlorine atoms, bromine atoms and iodine atoms), $C_{3-6}$ cycloalkyl groups, 4 to 7-membered non-aromatic heterocyclyl groups, phenyl groups and 5 to 6-membered aromatic heterocyclyl groups (the $C_{3-6}$ cycloalkyl groups, the 4 to 7-membered non-aromatic heterocyclyl groups, the phenyl groups and the 5 to 6-membered aromatic heterocyclyl groups are unsubstituted or substituted with one or two identical or different substituents independently selected from the group consisting of hydroxy groups, amino groups, halogen atoms, cyano groups, $C_{1-3}$ alkyl groups, $C_{1-3}$ haloalkyl groups, $C_{1-3}$ alkoxy groups, $C_{1-3}$ haloalkoxy groups, $C_{1-3}$ alkylthio groups, $C_{1-3}$ haloalkylthio groups, $C_{1-3}$ alkylsulfonyl groups, $C_{1-3}$ haloalkylsulfonyl groups, $C_{1-6}$ alkoxycarbonyl groups, mono-$C_{1-3}$ alkylamino groups, di-$C_{1-3}$ alkylamino groups, mono-$C_{1-3}$ alkylaminocarbonyl groups, di-$C_{1-3}$ alkylaminocarbonyl groups, $C_{1-3}$ alkylcarbonylamino group (the $C_{1-6}$ alkoxycarbonyl groups, the mono-$C_{1-3}$ alkylamino groups, the di-$C_{1-3}$ alkylamino groups, the mono-$C_{1-3}$ alkylaminocarbonyl groups, the di-$C_{1-3}$ alkylaminocarbonyl groups and the $C_{1-3}$ alkylcarbonylamino group are unsubstituted or substituted with one or more identical or different halogen atoms independently selected from the group consisting of fluorine atoms, chlorine atoms, bromine atoms and iodine atoms), 4 to 7-membered non-aromatic heterocyclyl groups, phenyl groups (the phenyl groups are unsubstituted or substituted with a halogen atom) and 5 to 6-membered aromatic heterocyclyl groups)), a $C_{2-6}$ alkynyl group, a $C_{3-6}$ cycloalkyl group, a 4 to 7-membered non-aromatic heterocyclyl group, a phenyl group, a 8 to 11-membered partially saturated aromatic cyclic group or a 8 to 11-membered aromatic ring-condensed alicyclic hydrocarbon group (the $C_{3-6}$ cycloalkyl group, the 4 to 7-membered non-aromatic heterocyclyl group, the phenyl group, the 8 to 11-membered partially saturated aromatic cyclic group and the 8 to 11-membered aromatic ring-condensed alicyclic hydrocarbon group are unsubstituted or substituted with one, two or three identical or different substituents independently selected from the group consisting of hydroxy groups, amino groups, halogen atoms, cyano groups, $C_{1-3}$ alkyl groups (the $C_{1-3}$ alkyl groups are unsubstituted or substituted with a substituent selected from the group consisting of a hydroxy group, a cyano group and a $C_{1-3}$ alkoxy group), $C_{1-3}$ haloalkyl groups, $C_{1-3}$ alkoxy groups, $C_{1-3}$ haloalkoxy groups, $C_{1-3}$ alkylthio groups, $C_{1-3}$ haloalkylthio groups, $C_{1-3}$ alkylsulfonyl groups, $C_{1-3}$ haloalkylsulfonyl groups, $C_{1-6}$ alkoxycarbonyl groups, mono-$C_{1-3}$ alkylamino groups, di-$C_{1-3}$ alkylamino groups, mono-$C_{1-3}$ alkylaminocarbonyl groups, di-$C_{1-3}$ alkylaminocarbonyl groups, $C_{1-3}$ alkylcarbonylamino groups (the $C_{1-6}$ alkoxycarbonyl groups, the mono-$C_{1-3}$ alkylamino groups, the di-$C_{1-3}$ alkylamino groups, the mono-$C_{1-3}$ alkylaminocarbonyl groups, the di-$C_{1-3}$ alkylaminocarbonyl groups and the $C_{1-3}$ alkylcarbonylamino group are unsubstituted or substituted with one or more identical or different halogen atoms independently selected from the group consisting of fluorine atoms, chlorine atoms, bromine atoms and iodine atoms), 4 to 7-membered non-aromatic heterocyclyl groups and phenyl groups (the phenyl groups are unsubstituted or substituted with a halogen atom)), a tautomer or a pharmaceutically acceptable salt of the compound or a solvate thereof.

(35) The compound according to (33), wherein the ring $B^a$ is a $C_{4-7}$ cycloalkane, $L^{3a}$ is represented by any of the following formulae ($XXVI^a$-1) to ($XXVI^a$-5):

($XXVI^a$)

($XXVI^a$-1)

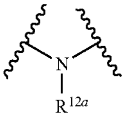

-continued (XXVI$^a$-2)

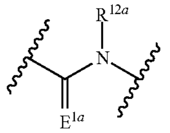

(XXVI$^a$-3)

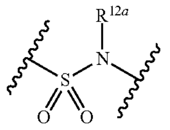

(XXVI$^a$-4)

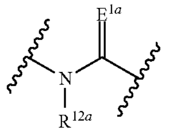

(XXVI$^a$-5)

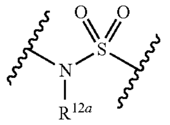

(wherein $E^{1a}$ is an oxygen atom, and $R^{12a}$ is a hydrogen atom, a $C_{1-3}$ alkyl group (the $C_{1-3}$ alkyl group is unsubstituted or substituted with a substituent selected from the group consisting of a hydroxy group, a cyano group, a $C_{1-3}$ alkoxy group, a $C_{3-6}$ cycloalkyl group, a phenyl group and a 5 to 6-membered aromatic heterocyclyl group (the 5 to 6-membered aromatic heterocyclyl group is unsubstituted or substituted with a $C_{1-3}$ alkyl group)), a $C_{1-3}$ haloalkyl group, a $C_{3-6}$ cycloalkyl group or a phenyl group (the phenyl group is unsubstituted or substituted with a halogen atom or a cyano group)), and $R^{2a}$ is a $C_{1-3}$ alkyl group (the $C_{1-3}$ alkyl group is unsubstituted or substituted with a cyano group), a $C_{1-3}$ haloalkyl group or a $C_{3-6}$ cycloalkyl group, a tautomer or a pharmaceutically acceptable salt of the compound or a solvate thereof.

(36) The compound according to (34) or (35), wherein $L^{3a}$ is represented by the formula (XVI$^a$):

(XVI$^a$)

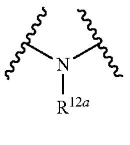

(wherein $R^{12a}$ is a hydrogen atom, a $C_{1-3}$ alkyl group (the $C_{1-3}$ alkyl group is unsubstituted or substituted with a substituent selected from the group consisting of a hydroxy group, a cyano group, a $C_{1-3}$ alkoxy group, a $C_{3-6}$ cycloalkyl group and a phenyl group), a $C_{1-3}$ haloalkyl group, a $C_{3-6}$ cycloalkyl group or a phenyl group (the phenyl group is unsubstituted or substituted with a halogen atom or a cyano group)), a tautomer or a pharmaceutically acceptable salt of the compound or a solvate thereof.

(37) The compound according to (33), wherein $L^{3a}$ is represented by the formula (XIII$^a$):

(XIII$^a$)

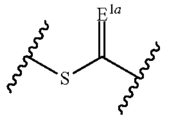

(wherein $E^{1a}$ is an oxygen atom),
$R^{2a}$ is a $C_{1-3}$ alkyl group, a tautomer or a pharmaceutically acceptable salt of the compound or a solvate thereof.

(38) The compound according to any one of (1) to (24), (28) to (30) and (32) to (37),
wherein $L^{2a}$ is a single bond or a $C_{1-3}$ alkylene group, a tautomer or a pharmaceutically acceptable salt of the compound or a solvate thereof.

(39) The compound according to (1) or (28), wherein $L^{1a}$ is a single bond,
the ring $B^a$ is a $C_{4-7}$ cycloalkane,
$L^{2a}$ is $=C(R^{15a})-$(wherein $R^{15a}$ is a hydrogen atom or a cyano group, and the bond connecting the ring $B^a$ and $L^{2a}$ is a double bond) or $=C(R^{15a})-CH_2-$ (wherein $R^{15a}$ is a hydrogen atom or a cyano group, and the bond connecting the ring $B^a$ and $L^{2a}$ is a double bond), and
when $L^{3a}$ is a single bond, $R^{2a}$ is a hydrogen atom, and
when $L^{3a}$ is the formula (X$^a$-2):

(X$^a$-2)

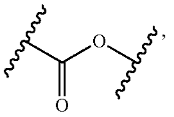

$R^{2a}$ is a $C_{1-3}$ alkyl group,
a tautomer or a pharmaceutically acceptable salt of the compound or a solvate thereof.

(40) The compound according to any one of (1) to (39), wherein $n^a$ is 0, a tautomer or a pharmaceutically acceptable salt of the compound or a solvate thereof.

(41) A compound represented by the formula (I$^b$):

(I$^b$)

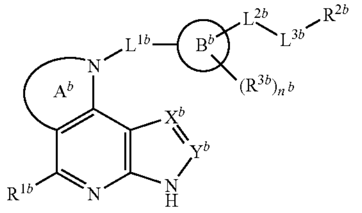

[wherein the ring $A^b$ is represented by the formula (II$^b$):

(II$^b$)

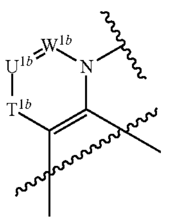

(wherein $T^{1b}$ is $CR^{4b}R^{5b}$, C(═O), C(═S), C(═$NR^{17b}$), a sulfur atom, S(═O) or $S(═O)_2$, $U^{1b}$ is a nitrogen atom or $CR^{6b}$, and $W^{1b}$ is a nitrogen atom or $CR^{8b}$), the formula ($III^b$):

($III^b$)

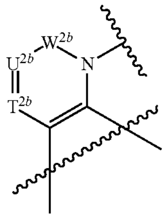

(wherein $T^{2b}$ is $CR^{4b}$, $U^{2b}$ is a nitrogen atom or $CR^{6b}$, and $W^{2b}$ is $CR^{8b}R^{9b}$, C(═O), C(═S), C(═$NR^{17b}$), $NR^{10b}$ an oxygen atom, a sulfur atom, S(═O) or $S(═O)_2$ (provided that when $U^{2b}$ is $CR^{6b}$, $W^{2b}$ is not C(═O))) or the formula ($IV^b$):

($IV^b$)

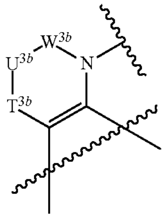

(wherein $T^{3b}$ is $CR^{4b}R^{5b}$, C(═O), C(═S), C(═$NR^{17b}$), a sulfur atom, S(═O) or $S(═O)_2$, $U^{3b}$ is $CR^{6b}R^{7b}$, C(═O), C(═S), C(═$NR^{17b}$), $NR^{10b}$, an oxygen atom, a sulfur atom, S(═O) or $S(═O)_2$, and $W^{3b}$ is $CR^{8b}R^{9b}$, C(═O), C(═S), C(═$NR^{17b}$), $NR^{11b}$, an oxygen atom, a sulfur atom, S(═O) or $S(═O)_2$ (provided that when $T^{3b}$ is $CR^{4b}R^{5b}$ and $U^{3b}$ is $CR^{6b}R^{7b}$, $W^{3b}$ is not $CR^{8b}R^{9b}$)), $X^b$ is a nitrogen atom or $CR^{16b}$, $Y^b$ is $CR^{16b}$, $R^{1b}$ is a hydrogen atom, a halogen atom, a $C_{1-6}$ alkyl group or a $C_{1-6}$ haloalkyl group, the ring $B^b$ is a $C_{3-11}$ cycloalkene, a $C_{3-11}$ cycloalkene, a 3 to 11-membered non-aromatic heterocycle, a $C_{6-14}$ aromatic carbocycle or a 5 to 10-membered aromatic heterocycle, $L^{1b}$ is a single bond, a $C_{1-6}$ alkylene group, a $C_{2-6}$ alkenylene group or a $C_{2-6}$ alkynylene group (the $C_{1-6}$ alkylene group, the $C_{2-6}$ alkenylene group and the $C_{2-6}$ alkynylene group are unsubstituted or substituted with one or more identical or different substituents independently selected from the group consisting of halogen atoms, hydroxy groups, amino groups, cyano groups and nitro groups), $L^{2b}$ is a single bond, a $C_{1-6}$ alkylene group, a $C_{2-6}$ alkenylene group or a $C_{2-6}$ alkynylene group (the $C_{1-6}$ alkylene group, the $C_{2-6}$ alkenylene group and the $C_{2-6}$ alkynylene group are unsubstituted or substituted with one or more identical or different substituents independently selected from the group consisting of halogen atoms, hydroxy groups, amino groups, cyano groups and nitro groups), $L^{3b}$ is a single bond or represented by any of the following formulae ($V^b$-1) to ($V^b$-20):

($V^b$)

($V^b$-1)

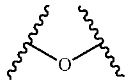

($V^b$-2)

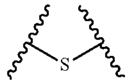

($V^b$-3)

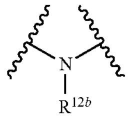

($V^b$-4)

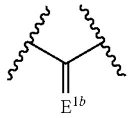

($V^b$-5)

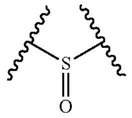

($V^b$-6)

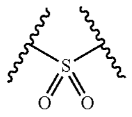

($V^b$-7)

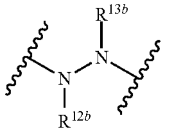

($V^b$-8)

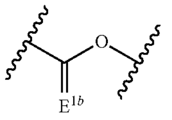

(Vb-9)

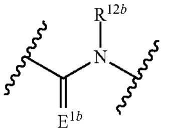

($V^b$-10)

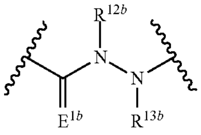

(Vb-11)

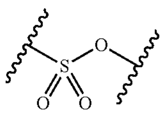

-continued ($V^b$-12)

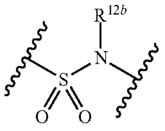

($V^b$-13)

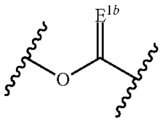

($V^b$-14)

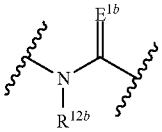

($V^b$-15)

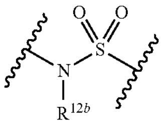

($V^b$-16)

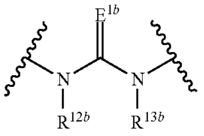

($V^b$-17)

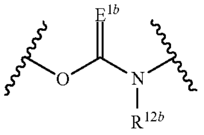

($V^b$-18)

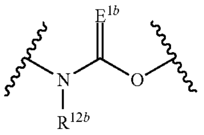

($V^b$-19)

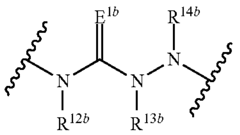

($V^b$-20)

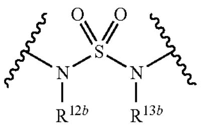

(wherein $E^{1b}$ is an oxygen atom, a sulfur atom or $NR^{18b}$), when $L^{3b}$ is a single bond, $R^{2b}$ is a hydrogen atom, a halogen atom, a $C_{3-11}$ cycloalkyl group, a 3 to 14-membered non-aromatic heterocyclyl group, a $C_{6-14}$ aryl group, a 5 to 10-membered aromatic heterocyclyl group, a 8 to 14-membered partially saturated aromatic cyclic group or a 8 to 14-membered aromatic ring-condensed alicyclic hydrocarbon group (the $C_{3-11}$ cycloalkyl group, the 3 to 14-membered non-aromatic heterocyclyl group, the $C_{6-14}$ aryl group, the 5 to 10-membered aromatic heterocyclyl group, the 8 to 14-membered partially saturated aromatic cyclic group and the 8 to 14-membered aromatic ring-condensed alicyclic hydrocarbon group are unsubstituted or substituted with one or more identical or different substituents independently selected from the substituent set $V^{4b}$ and the substituent set $V^{9b}$), when $L^{3b}$ is not a single bond, $R^{2b}$ is a hydrogen atom, a $C_{1-6}$ alkyl group, a $C_{2-6}$ alkenyl group (the $C_{1-6}$ alkyl group and the $C_{2-6}$ alkenyl group are unsubstituted or substituted with one or more identical or different substituents independently selected from the substituent set $V^{6b}$ and the substituent set $V^{9b}$), a $C_{3-11}$ cycloalkyl group, a 3 to 14-membered non-aromatic heterocyclyl group, a $C_{6-14}$ aryl group, a 5 to 10-membered aromatic heterocyclyl group, a 8 to 14-membered partially saturated aromatic cyclic group or a 8 to 14-membered aromatic ring-condensed alicyclic hydrocarbon group (the $C_{3-11}$ cycloalkyl group, the 3 to 14-membered non-aromatic heterocyclyl group, the $C_{6-14}$ aryl group, the 5 to 10-membered aromatic heterocyclyl group, the 8 to 14-membered partially saturated aromatic cyclic group and the 8 to 14-membered aromatic ring-condensed alicyclic hydrocarbon group are unsubstituted or substituted with one or more identical or different substituents independently selected from the substituent set $V^{4b}$ and substituent set $V^{9b}$), $n^b$ is 0, 1 or 2, $R^{3b}$ is a hydroxy group, an amino group, a carboxy group, a carbamoyl group, a sulfamoyl group, a phosphono group, a phosphonooxy group, a sulfo group, a sulfoxy group, a tetrazolyl group, a halogen atom, a cyano group, a nitro group, a $C_{1-6}$ alkyl group, a $C_{1-6}$ haloalkyl group, a $C_{3-11}$ cycloalkyl group, a $C_{2-6}$ alkenyl group, a $C_{2-6}$ haloalkenyl group, a $C_{1-6}$ alkoxy group, a $C_{1-6}$ haloalkoxy group, a $C_{1-6}$ alkylthio group, a $C_{1-6}$ haloalkylthio group, a $C_{1-6}$ alkylcarbonyl group, a $C_{1-6}$ haloalkylcarbonyl group, a $C_{1-6}$ alkylsulfonyl group, a $C_{1-6}$ haloalkylsulfonyl group, a $C_{1-6}$ alkoxycarbonyl group, a mono-$C_{1-6}$ alkylamino group, a di-$C_{1-6}$ alkylamino group, a mono-$C_{1-6}$ alkylaminocarbonyl group, a di-$C_{1-6}$ alkylaminocarbonyl group or a $C_{1-6}$ alkylcarbonylamino group (when $n^b$ is 2, $R^{3b}$'s may be identical or different), each of $R^{4b}$, $R^{5b}$, $R^{6b}$, $R^{7b}$, $R^{8b}$ and $R^{9b}$ is independently a hydrogen atom, a hydroxy group, an amino group, a carboxy group, a carbamoyl group, a tetrazolyl group, a halogen atom, a cyano group, a $C_{1-6}$ alkyl group, a $C_{2-6}$ alkenyl group, a $C_{1-6}$ alkoxy group, a $C_{1-6}$ alkylthio group, a $C_{1-6}$ alkylcarbonyl group, a $C_{1-6}$ alkylsulfonyl group, a mono-$C_{1-6}$ alkylamino group, a di-$C_{1-6}$ alkylamino group (the $C_{1-6}$ alkyl group, the $C_{2-6}$ alkenyl group, the $C_{1-6}$ alkoxy group, the $C_{1-6}$ alkylthio group, the $C_{1-6}$ alkylcarbonyl group, the $C_{1-6}$ alkylsulfonyl group, the mono-$C_{1-6}$ alkylamino group and the di-$C_{1-6}$ alkylamino group are unsubstituted or substituted with one or more identical or different substituents independently selected from the substituent set $V^{3b}$), a $C_{1-6}$ alkoxycarbonyl group, a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{1b}$), each of $R^{10b}$ and $R^{11b}$ is independently a hydrogen atom, a $C_{1-6}$ alkyl group, a $C_{2-6}$ alkenyl group, a $C_{1-6}$ alkylcarbonyl group, a $C_{1-6}$ alkylsulfonyl group, a $C_{1-6}$ alkoxycarbonyl group, a mono-$C_{1-6}$ alkylaminocarbonyl group, a di-$C_{1-6}$ alkylaminocarbonyl group (the $C_{1-6}$ alkyl group, the $C_{2-6}$ alkenyl group, the $C_{1-6}$ alkylcarbonyl group, the $C_{1-6}$ alkylsulfonyl group, the $C_{1-6}$ alkoxycarbonyl group, the mono- $C_{1-6}$ alkylaminocarbonyl group and the di-$C_{1-6}$ alkylaminocarbonyl group are unsubstituted or substituted with one or more identical or different substituents independently selected from the substituent set $V^{3b}$), a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{1b}$), each of $R^{12b}$, $R^{13b}$ and $R^{14b}$ is independently a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or more identical or different substituents independently selected from the substituent set $V^{3b}$, the substituent set $V^{8b}$ and the substituent set $V^{9b}$), each of $R^{15b}$ and $R^{16b}$ is independently a hydrogen atom, a halogen atom, a cyano group, a carbamoyl group, a $C_{1-6}$ alkyl group, a $C_{1-6}$ haloalkyl group, a $C_{3-11}$ cycloalkyl group, a $C_{1-6}$ alkoxy group, a $C_{1-6}$ haloalkoxy group, a $C_{1-6}$ alkylthio group, a $C_{1-6}$ alkylcarbonyl group, a $C_{1-6}$ alkylsulfonyl group, a 3 to 11-membered non-aromatic heterocyclyl group, a $C_{6-14}$ aryl group or a 5 to 10-membered aromatic heterocyclyl group, each of $R^{17b}$ and $R^{18b}$ is independently a hydrogen atom, a hydroxy group, a cyano group, a nitro group, a $C_{1-6}$ alkyl group or a $C_{1-6}$ alkoxy group, the substituent set $V^{1b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkyl groups, $C_{1-6}$ haloalkyl groups, $C_{3-11}$ cycloalkyl groups, $C_{2-6}$ alkenyl groups, $C_{2-6}$ haloalkenyl groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, $C_{1-6}$ alkoxycarbonyl groups, 3 to 11-membered non-aromatic heterocyclyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups and $C_{1-6}$ alkylcarbonylamino groups, the substituent set $V^{2b}$ consists of the groups in the substituent set $V^{1b}$, and $C_{6-14}$ aryl groups and 5 to 10-membered aromatic heterocyclyl groups (the $C_{6-14}$ aryl groups and the 5 to 10-membered aromatic heterocyclyl groups are unsubstituted or substituted with one or more identical or different substituents independently selected from the substituent set $V^{1b}$), the substituent set $V^{3b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{3-11}$ cycloalkyl groups, 3 to 11-membered non-aromatic heterocyclyl groups, $C_{6-14}$ aryl group and 5 to 10-membered aromatic heterocyclyl groups (the $C_{3-11}$ cycloalkyl groups, the 3 to 11-membered non-aromatic heterocyclyl groups, the $C_{6-14}$ aryl groups and the 5 to 10-membered aromatic heterocyclyl groups are unsubstituted or substituted with one or more identical or different substituents independently selected from the substituent set $V^{1b}$), the substituent set $V^{4b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkyl groups, $C_{2-6}$ alkenyl groups, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups (the $C_{1-6}$ alkyl groups, the $C_{2-6}$ alkenyl groups, the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups and the $C_{1-6}$ alkylcarbonylamino groups are unsubstituted or substituted with one or more identical or different substituents independently selected from the substituent set $V^{3b}$), $C_{3-11}$ cycloalkyl groups, 3 to 11-membered non-aromatic heterocyclyl groups, $C_{6-14}$ aryl groups and 5 to 10-membered aromatic heterocyclyl groups (the $C_{3-11}$ cycloalkyl groups, the 3 to 11-membered non-aromatic heterocyclyl groups, the $C_{6-14}$ aryl groups and the 5 to 10-membered aromatic heterocyclyl groups are unsubstituted or substituted with one or more identical or different substituents independently selected from the substituent set $V^{1b}$), the substituent set $V^{5b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{3-11}$ cycloalkyl groups, 3 to 11-membered non-aromatic heterocyclyl groups, $C_{6-14}$ aryl groups and 5 to 10-membered aromatic heterocyclyl groups (the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups, the $C_{1-6}$ alkylcarbonylamino groups, the $C_{3-11}$ cycloalkyl groups, the 3 to 11-membered non-aromatic heterocyclyl groups, the $C_{6-14}$ aryl groups and the 5 to 10-membered aromatic heterocyclyl groups are unsubstituted or substituted with one or more identical or different substituents independently selected from the substituent set $V^{3b}$), the substituent set $V^{6b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups (the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups and the $C_{1-6}$ alkylcarbonylamino groups are unsubstituted or substituted with one or more identical or different substituents independently selected from the substituent set $V^{3b}$), $C_{3-11}$ cycloalkyl groups, 3 to 11-membered non-aromatic heterocyclyl groups, $C_{6-14}$ aryl groups, 5 to 10-membered aromatic heterocyclyl groups, 8 to 14-membered partially saturated aromatic cyclic groups and 8 to 14-membered aromatic ring-condensed alicyclic hydrocarbon groups (the $C_{3-11}$ cycloalkyl groups, the 3 to 11-membered non-aromatic heterocyclyl groups, the $C_{6-14}$ aryl groups, the 5 to 10-membered aromatic heterocyclyl groups, the 8 to 14-membered partially saturated aromatic cyclic groups and the 8 to 14-membered aromatic ring-condensed alicyclic hydrocarbon groups are unsubstituted or substituted with one or more identical or different substituents independently selected from the substituent set $V^{4b}$ and the substituent set $V^{9b}$), and the substituent set $V^{8b}$ consists of 8 to 14-membered partially saturated aromatic cyclic groups and 8 to 14-membered aromatic ring-condensed alicyclic hydrocarbon groups (the 8 to 14-membered partially saturated aromatic cyclic groups and the 8 to 14-membered aromatic ring-condensed alicyclic hydrocarbon groups are unsubstituted or substituted with one or more identical or different substituents independently selected from the substituent set $V^{2b}$), the substituent set $V^{9b}$ consists of, mono-$C_{1-6}$ alkylaminosulfonyl groups, di-$C_{1-6}$ alkylaminosulfonyl groups, $C_{1-6}$ alkylsulfonylamino groups (the mono-$C_{1-6}$ alkylaminosulfonyl groups, di-$C_{1-6}$ alkylaminosulfonyl groups and $C_{1-6}$ alkylsulfonylamino groups are unsubstituted or substituted with one or more identical or different substituents independently selected from the substituent set $V^{3b}$), $C_{3-6}$ cycloalkoxy groups, $C_{3-6}$ cycloalkylamino groups, $C_{3-6}$ cycloalkylthio groups, $C_{3-6}$ cycloalkylcarbonyl groups and $C_{3-6}$ cycloalkylsulfonyl groups (the $C_{3-6}$ cycloalkoxy groups, the $C_{3-6}$ cycloalkylamino groups, the $C_{3-6}$ cycloalkylthio groups, the $C_{3-6}$ cycloalkylcarbonyl groups and the $C_{3-6}$ cycloalkylsulfonyl groups unsubstituted or substituted with one or more identical or different substituents independently selected from the substituent set $V^{2b}$)], a tautomer or a pharmaceutically acceptable salt of the compound or a solvate thereof.

(42) The compound according to (41), which is represented by the formula ($I^b$):

($I^b$)

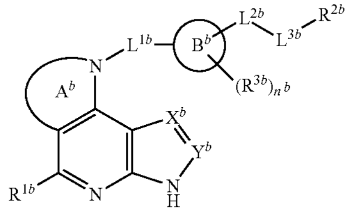

[wherein the ring $A^b$ is represented by the formula ($II^b$):

($II^b$)

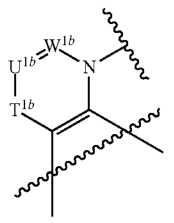

(wherein $T^{1b}$ is $CR^{4b}R^{5b}$, C(=O), C(=S), C(=$NR^{17b}$), a sulfur atom, S(=O) or $S(=O)_2$, $U^{1b}$ is a nitrogen atom or $CR^{6b}$, and $W^{1b}$ is a nitrogen atom or $CR^{8b}$), the formula ($III^b$):

($III^b$)

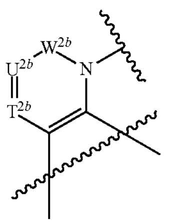

(wherein $T^{2b}$ is $CR^{4b}$, $U^{2b}$ is a nitrogen atom or $CR^{6b}$, and $W^{2b}$ is $CR^{8b}R^{9b}$, C(=O), C(=S), C(=$NR^{17b}$), $NR^{10b}$, an oxygen atom, a sulfur atom, S(=O) or $S(=O)_2$ (provided that when $U^{2b}$ is $CR^{6b}$, $W^{2b}$ is not C(=O))), or the formula ($IV^b$):

($IV^b$)

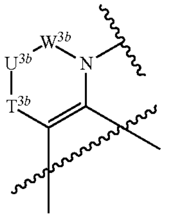

(wherein $T^{3b}$ is $CR^{4b}R^{5b}$, C(=O), C(=S), C(=$NR^{17b}$), a sulfur atom, S(=O) or $S(=O)_2$, $U^{3b}$ is $CR^{6b}R^{7b}$, C(=O), C(=S), C(=$NR^{17b}$), $NR^{10b}$, an oxygen atom, a sulfur atom, S(=O) or $S(=O)_2$, and $W^{3b}$ is $CR^{8b}R^{9b}$, C(=O), C(=$NR^{17b}$), $NR^{11b}$, an oxygen atom, a sulfur atom, S(=O) or $S(=O)_2$ (provided that when $T^{3b}$ is $CR^{4b}R^{5b}$ and $U^{3b}$ is $CR^{6b}R^{7b}$, $W^{3b}$ is not $CR^{8b}R^{9b}$)), $X^b$ is a nitrogen atom or $CR^{15b}$, $Y^b$ is $CR^{16b}$, $R^{1b}$ is a hydrogen atom, a halogen atom, a $C_{1-6}$ alkyl group or a $C_{1-6}$ haloalkyl group, the ring $B^b$ is a $C_{3-11}$ cycloalkane, a $C_{3-11}$ cycloalkene, a 3 to 11-membered non-aromatic heterocycle, a $C_{6-14}$ aromatic carbocycle or a 5 to 10-membered aromatic heterocycle, $L^{1b}$ is a single bond, a $C_{1-6}$ alkylene group, a $C_{2-6}$ alkenylene group or a $C_{2-6}$ alkynylene group (the $C_{1-6}$ alkylene group, the $C_{2-6}$ alkenylene group and the $C_{2-6}$ alkynylene group are unsubstituted or substituted with one or more identical or different substituents independently selected from the group consisting of halogen atoms, hydroxy groups, amino groups, cyano groups and nitro groups), $L^{2b}$ is a single bond, a $C_{1-6}$ alkylene group, a $C_{2-6}$ alkenylene group or a $C_{2-6}$ alkynylene group (the $C_{1-6}$ alkylene group, the $C_{2-6}$ alkenylene group and the $C_{2-6}$ alkynylene group are unsubstituted or substituted with one or more identical or different substituents independently selected from the group consisting of halogen atoms, hydroxy groups, amino groups, cyano groups and nitro groups), $L^{3b}$ is a single bond or represented by any of the following formulae ($V^b$-1) to ($V^b$-20):

($V^b$)

($V^b$-1)

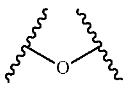

($V^b$-2)

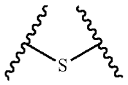

($V^b$-3)

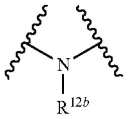

($V^b$-4)

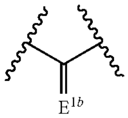

($V^b$-5)

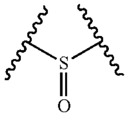

($V^b$-6)

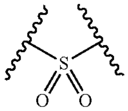

($V^b$-7)

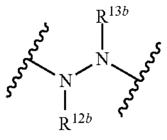

($V^b$-8)

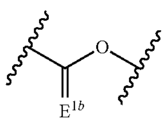

(Vb-9)

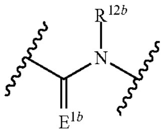

-continued ($V^b$-10)

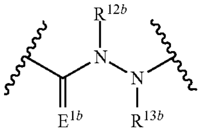

(Vb-11)

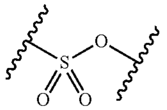

($V^b$-12)

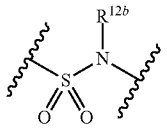

($V^b$-13)

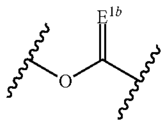

($V^b$-14)

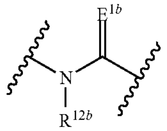

($V^b$-15)

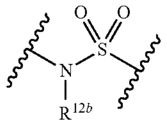

($V^b$-16)

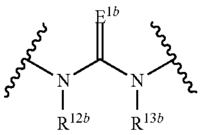

($V^b$-17)

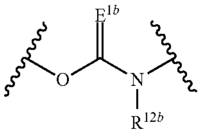

($V^b$-18)

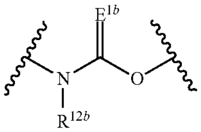

($V^b$-19)

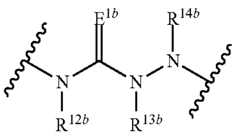

($V^b$-20)

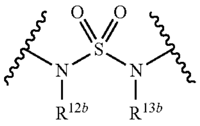

(wherein $E^{1b}$ is an oxygen atom, a sulfur atom or $NR^{18b}$), when $L^{3b}$ is a single bond, $R^{2b}$ is a hydrogen atom, a halogen atom, a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{4b}$), when $L^{3b}$ is not a single bond, $R^{2b}$ is a hydrogen atom, a $C_{1-6}$ alkyl group, a $C_{2-6}$ alkenyl group (the $C_{1-6}$ alkyl group and the $C_{2-6}$ alkenyl group are unsubstituted or substituted with one or more identical or different substituents independently selected from the substituent set $V^{5b}$), a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{4b}$), $n^b$ is 0, 1 or 2, $R^{3b}$ is a hydroxy group, an amino group, a carboxy group, a carbamoyl group, a sulfamoyl group, a phosphono group, a phosphonooxy group, a sulfo group, a sulfoxy group, a tetrazolyl group, a halogen atom, a cyano group, a nitro group, a $C_{1-6}$ alkyl group, a $C_{1-6}$ haloalkyl group, a $C_{3-11}$ cycloalkyl group, a $C_{2-6}$ alkenyl group, a $C_{2-6}$ haloalkenyl group, a $C_{1-6}$ alkoxy group, a $C_{1-6}$ haloalkoxy group, a $C_{1-6}$ alkylthio group, a $C_{1-6}$ haloalkylthio group, a $C_{1-6}$ alkylcarbonyl group, a $C_{1-6}$ haloalkylcarbonyl group, a $C_{1-6}$ alkylsulfonyl group, a $C_{1-6}$ haloalkylsulfonyl group, a $C_{1-6}$ alkoxycarbonyl group, a mono-$C_{1-6}$ alkylamino group, a di-$C_{1-6}$ alkylamino group, a mono-$C_{1-6}$ alkylaminocarbonyl group, a di-$C_{1-6}$ alkylaminocarbonyl group or a $C_{1-6}$ alkylcarbonylamino group (when $n^b$ is 2, $R^{3b}$'s may be identical or different), each of $R^{4b}$, $R^{5b}$, $R^{6b}$, $R^{7b}$, $R^{8b}$ and $R^{9b}$ is independently a hydrogen atom, a hydroxy group, an amino group, a carboxy group, a carbamoyl group, a tetrazolyl group, a halogen atom, a cyano group, a $C_{1-6}$ alkyl group, a $C_{2-6}$ alkenyl group, a $C_{1-6}$ alkoxy group, a $C_{1-6}$ alkylthio group, a $C_{1-6}$ alkylcarbonyl group, a $C_{1-6}$ alkylsulfonyl group, a mono-$C_{1-6}$ alkylamino group, a di-$C_{1-6}$ alkylamino group (the $C_{1-6}$ alkyl group, the $C_{2-6}$ alkenyl group, the $C_{1-6}$ alkoxy group, the $C_{1-6}$ alkylthio group, the $C_{1-6}$ alkylcarbonyl group, the $C_{1-6}$ alkylsulfonyl group, the mono-$C_{1-6}$ alkylamino group and the di-$C_{1-6}$ alkylamino group are unsubstituted or substituted with one or more identical or different substituents independently selected from the substituent set $V^{3b}$), a $C_{1-6}$ alkoxycarbonyl group, a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{1b}$), each of $R^{10b}$ and $R^{11b}$ is independently a hydrogen atom, a $C_{1-6}$ alkyl group, a $C_{2-6}$ alkenyl group, a $C_{1-6}$ alkylcarbonyl group, a $C_{1-6}$ alkylsulfonyl group, a $C_{1-6}$ alkoxycarbonyl group, a mono-$C_{1-6}$ alkylaminocarbonyl group, a di-$C_{1-6}$ alkylaminocarbonyl group (the $C_{1-6}$ alkyl group, the $C_{2-6}$ alkenyl group, the $C_{1-6}$ alkylcarbonyl group, the $C_{1-6}$ alkylsulfonyl group, the $C_{1-6}$ alkoxycarbonyl group, the mono-$C_{1-6}$ alkylaminocarbonyl group and the di-$C_{1-6}$ alkylaminocarbonyl group are unsubstituted or substituted with one or more identical or different substituents independently selected from the substituent set $V^{3b}$), a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{1b}$), each of $R^{12b}$, $R^{13b}$ and $R^{14b}$ is independently a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or more identical or different substituents independently selected from the substituent set $V^{3b}$), each of $R^{15b}$ and $R^{16b}$ is independently a hydrogen atom, a halogen atom, a cyano group, a carbamoyl group, a $C_{1-6}$ alkyl group, a $C_{1-6}$ haloalkyl group, a $C_{3-11}$ cycloalkyl group, a $C_{1-6}$ alkoxy group, a $C_{1-6}$ haloalkoxy group, a $C_{1-6}$ alkylthio group, a $C_{1-6}$ alkylcarbonyl group, a $C_{1-6}$ alkylsulfonyl group, a 3 to 11-membered non-aromatic heterocyclyl group, a $C_{6-14}$ aryl group or a 5 to 10-membered aromatic heterocyclyl group, each of $R^{17b}$ and $R^{18b}$ is independently a hydrogen atom, a hydroxy group, a cyano group, a nitro group, a $C_{1-6}$ alkyl group or a $C_{1-6}$ alkoxy group, the substituent set $V^{1b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkyl groups, $C_{1-6}$ haloalkyl groups, $C_{3-11}$ cycloalkyl groups, $C_{2-6}$ alkenyl groups, $C_{2-6}$ haloalkenyl groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, $C_{1-6}$ alkoxycarbonyl groups, 3 to 11-membered non-aromatic heterocyclyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups and $C_{1-6}$ alkylcarbonylamino groups, the substituent set $V^{2b}$ consists of the groups in the substituent set $V^{1b}$ and $C_{6-14}$ aryl groups and 5 to 10-membered aromatic heterocyclyl groups (the $C_{6-14}$ aryl groups and 5 to 10-membered aromatic heterocyclyl groups are unsubstituted or substituted with one or more identical or different substituents independently selected from the substituent set $V^{1b}$), the substituent set $V^{3b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{3-11}$ cycloalkyl groups, 3 to 11-membered non-aromatic heterocyclyl groups, $C_{6-14}$ aryl groups and 5 to 10-membered aromatic heterocyclyl groups (the $C_{3-11}$ cycloalkyl groups, the 3 to 11-membered non-aromatic heterocyclyl groups, the $C_{6-14}$ aryl groups and the 5 to 10-membered aromatic heterocyclyl groups are unsubstituted or substituted with one or more identical or different substituents independently selected from the substituent set $V^{1b}$), the substituent set $V^{4b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkyl groups, $C_{2-6}$ alkenyl groups, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups (the $C_{1-6}$ alkyl groups, the $C_{2-6}$ alkenyl groups, the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups and the $C_{1-6}$ alkylcarbonylamino groups are unsubstituted or substituted with one or more identical or different substituents independently selected from the substituent set $V^{3b}$), $C_{3-11}$ cycloalkyl groups, 3 to 11-membered non-aromatic heterocyclyl groups, $C_{6-14}$ aryl groups and 5 to 10-membered aromatic heterocyclyl groups (the $C_{3-11}$ cycloalkyl groups, the 3 to 11-membered non-aromatic heterocyclyl groups, the $C_{6-14}$ aryl groups and the 5 to 10-membered aromatic heterocyclyl groups are unsubstituted or substituted with one or more identical or different substituents independently selected from the substituent set $V^{1b}$), and the substituent set $V^{5b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{3-11}$ cycloalkyl groups, 3 to 11-membered non-aromatic heterocyclyl groups, $C_{6-14}$ aryl groups and 5 to 10-membered aromatic heterocyclyl groups (the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups, the $C_{1-6}$ alkylcarbonylamino groups, the $C_{3-11}$ cycloalkyl groups, the 3 to 11-membered non-aromatic heterocyclyl groups, the $C_{6-14}$ aryl groups and the 5 to 10-membered aromatic heterocyclyl groups are unsubstituted or substituted with one or more identical or different substituents independently selected from the substituent set $V^{3b}$)], a tautomer or a pharmaceutically acceptable salt of the compound or a solvate thereof.

(43) The compound according to (42), wherein $R^{1b}$ is a hydrogen atom, a tautomer or a pharmaceutically acceptable salt of the compound or a solvate thereof.

(44) The compound according to (42) or (43), wherein $X^b$ is a nitrogen atom or $CR^{15b}$ (wherein $R^{15b}$ is a hydrogen atom, a halogen atom, a cyano group, a $C_{1-3}$ alkyl group, a $C_{1-3}$ haloalkyl group or a $C_{3-6}$ cycloalkyl group), and $Y^b$ is $CR^{16b}$ (wherein $R^{16b}$ is a hydrogen atom), a tautomer or a pharmaceutically acceptable salt of the compound or a solvate thereof.

(45) The compound according to (44), wherein $X^b$ is a nitrogen atom or $CR^{15b}$ (wherein $R^{15b}$ is a hydrogen atom or a halogen atom), a tautomer or a pharmaceutically acceptable salt of the compound or a solvate thereof.

(46) The compound according to any one of (42) to (45), wherein the ring $A^b$ is represented by the formula ($II^b$):

($II^b$)

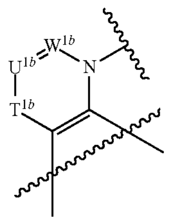

(wherein $T^{1b}$ is $CR^{4b}R^{5b}$, C(═O), C(═S) or $S(═O)_2$, $U^{1b}$ is a nitrogen atom or $CR^{6b}$, and $W^{1b}$ is $CR^{8b}$), the formula ($III^b$):

($III^b$)

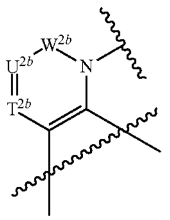

(wherein $T^{2b}$ is $CR^{4b}$, $U^{2b}$ is a nitrogen atom, and $W^{2b}$ is C(═O) or C(═S)) or the formula ($IV^b$):

($IV^b$)

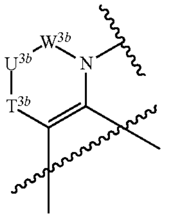

(wherein $T^{3b}$ is $CR^{4b}R^{5b}$, $U^{3b}$ is $NR^{10b}$ or an oxygen atom, and $W^{3b}$ is $CR^{8b}R^{9b}$, C(═O) or C(═S)), a tautomer or a pharmaceutically acceptable salt of the compound or a solvate thereof.

(47) The compound according to any one of (42) to (45), wherein the ring $A^b$ is represented by any of the following formulae ($XVIII^b$-1) to ($XVIII^b$-8):

($XVIII^b$)

($XVIII^b$-1)

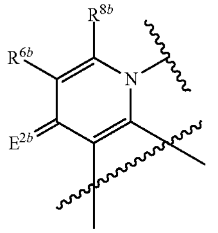

($XVIII^b$-2)

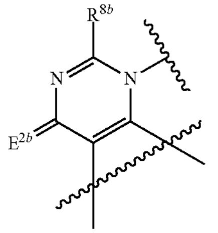

($XVIII^b$-3)

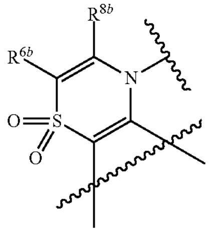

($XVIII^b$-4)

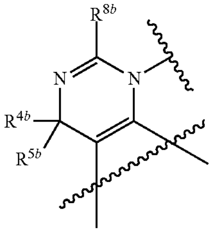

($XVIII^b$-5)

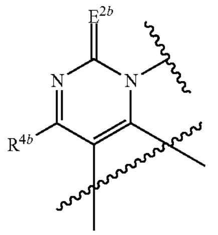

($XVIII^b$-6)

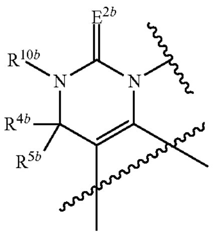

-continued ($XVIII^b$-7)

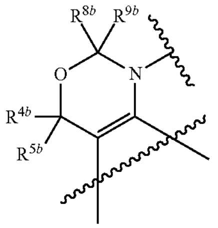

($XVIII^b$-8)

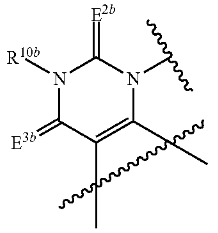

(wherein each of $E^{2b}$ and $E^{3b}$ is independently an oxygen atom or a sulfur atom, each of $R^{4b}$, $R^{5b}$, $R^{6b}$, $R^{8b}$ and $R^{9b}$ is independently a hydrogen atom, a halogen atom or a $C_{1-3}$ alkyl group, and $R^{10b}$ is a hydrogen atom or a $C_{1-3}$ alkyl group), a tautomer or a pharmaceutically acceptable salt of the compound or a solvate thereof.

(48) The compound according to any one of (42) to (47), wherein $L^{1b}$ is a single bond, $L^{2b}$ is a single bond, a $C_{1-6}$ alkylene group or a $C_{2-6}$ alkenylene group (the $C_{1-6}$ alkylene group and the $C_{2-6}$ alkenylene group are unsubstituted or substituted with one or more identical or different substituents independently selected from the group consisting of a halogen atoms, hydroxy groups, amino groups, cyano groups and nitro groups), the ring $B^b$ is a $C_{3-11}$ cycloalkane, a $C_{3-11}$ cycloalkene, a 3 to 11-membered non-aromatic heterocycle, a $C_{6-14}$ aromatic carbocycle or a 5 to 10-membered aromatic heterocycle, $n^b$ is, 0 or 1, $R^{3b}$ is a hydroxy group, an amino group, a halogen atom, a cyano group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkylsulfonyl group, $L^{3b}$ is a single bond, and $R^{2b}$ is a hydrogen atom, a halogen atom, a $C_{3-11}$ cycloalkyl group, a 3 to 11-membered non-aromatic heterocyclyl group, a phenyl group, a naphthyl group or a 5 to 10-membered aromatic heterocyclyl group (the $C_{3-11}$ cycloalkyl group, the 3 to 11-membered non-aromatic heterocyclyl group, the phenyl group, the naphthyl group and the 5 to 10-membered aromatic heterocyclyl group are unsubstituted or substituted with one or more identical or different substituents independently selected from the substituent set $V^{4b}$), a tautomer or a pharmaceutically acceptable salt of the compound or a solvate thereof.

(49) The compound according to any one of (42) to (47), wherein $L^{1b}$ is a single bond or a $C_{1-3}$ alkylene group, $L^{2b}$ is a single bond or a $C_{1-3}$ alkylene group (the $C_{1-3}$ alkylene group is unsubstituted or substituted with a cyano group or a $C_{1-3}$ haloalkyl group), the ring $B^b$ is a $C_{3-11}$ cycloalkane, a $C_{3-11}$ cycloalkene, a 3 to 11-membered non-aromatic heterocycle, benzene or a 5 to 6-membered aromatic heterocycle, $n^b$ is, 0 or 1, $R^{3b}$ is a hydroxy group, an amino group, a carboxy group, a carbamoyl group, a tetrazolyl group, a halogen atom, a cyano group, a nitro group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkylsulfonyl group, $L^{3b}$ is a single bond, and $R^{2b}$ is a hydrogen atom, a halogen atom, a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the substituent set $V^{4b}$), a tautomer or a pharmaceutically acceptable salt of the compound or a solvate thereof.

(50) The compound according to (48), wherein the ring $B^b$ is a $C_{3-11}$ cycloalkane or a 4 to 7-membered non-aromatic heterocycle, $n^b$ is 0 or 1, and $R^{3b}$ is a hydroxy group, a $C_{1-3}$ alkyl group or a $C_{1-3}$ alkoxy group, a tautomer or a pharmaceutically acceptable salt of the compound or a solvate thereof.

(51) The compound according to (48) or (50), wherein $L^{2b}$ is a single bond, a $C_{1-6}$ alkylene group, a $C_{2-6}$ alkenylene group or a $C_{1-6}$ haloalkylene group (the $C_{1-6}$ alkylene group, the $C_{2-6}$ alkenylene group and the $C_{1-6}$ haloalkylene group are unsubstituted or substituted with one or two identical or different substituents independently selected from the group consisting of hydroxy groups and cyano groups), a tautomer or a pharmaceutically acceptable salt of the compound or a solvate thereof.

(52) The compound according to any one of (48), (50) and (51), wherein $R^{2b}$ is a hydrogen atom, a $C_{3-6}$ cycloalkyl group, a 4 to 7-membered non-aromatic heterocyclyl group, a phenyl group or a 5 to 10-membered aromatic heterocyclyl group (the 4 to 7-membered non-aromatic heterocyclyl group, the phenyl group and the 5 to 10-membered aromatic heterocyclyl group are unsubstituted or substituted with one or more identical or different substituents independently selected from the group consisting of hydroxy groups, amino groups, carbamoyl groups, sulfamoyl groups, halogen atoms, cyano groups, nitro groups, $C_{1-6}$ alkyl groups, $C_{1-6}$ alkoxy groups, $C_{1-6}$ alkylthio groups, $C_{1-6}$ alkylsulfonyl groups, mono-$C_{1-6}$ alkylamino groups, di-$C_{1-6}$ alkylamino groups, $C_{1-6}$ alkoxycarbonyl groups, mono-$C_{1-6}$ alkylaminocarbonyl groups, di-$C_{1-6}$ alkylaminocarbonyl groups, $C_{1-6}$ alkylcarbonylamino groups (the $C_{1-6}$ alkyl groups, the $C_{1-6}$ alkoxy groups, the $C_{1-6}$ alkylthio groups, the $C_{1-6}$ alkylsulfonyl groups, the mono-$C_{1-6}$ alkylamino groups, the di-$C_{1-6}$ alkylamino groups, the $C_{1-6}$ alkoxycarbonyl groups, the mono-$C_{1-6}$ alkylaminocarbonyl groups, the di-$C_{1-6}$ alkylaminocarbonyl groups and the $C_{1-6}$ alkylcarbonylamino groups are unsubstituted or substituted with one or more identical or different halogen atoms independently selected from the group consisting of fluorine atoms, chlorine atoms, bromine atoms and iodine atoms or with a hydroxy group or a cyano group), $C_{3-6}$ cycloalkyl groups, 4 to 7-membered non-aromatic heterocyclyl groups, phenyl groups and 5 to 6-membered aromatic heterocyclyl groups), a tautomer or a pharmaceutically acceptable salt of the compound or a solvate thereof.

(53) The compound according to (52), wherein $R^{2b}$ is a hydrogen atom, a 4 to 7-membered non-aromatic heterocyclyl group, a phenyl group or a 5 to 10-membered aromatic heterocyclyl group (the 4 to 7-membered non-aromatic heterocyclyl group, the phenyl group and the 5 to 10-membered aromatic heterocyclyl group are unsubstituted or substituted with one or two identical or different substituents independently selected from the group consisting of hydroxy groups, halogen atoms, cyano groups, nitro groups, $C_{1-3}$ alkyl groups (the $C_{1-3}$ alkyl groups are unsubstituted or substituted with a cyano group), $C_{1-3}$ haloalkyl groups and $C_{1-6}$ alkoxycarbonyl groups), a tautomer or a pharmaceutically acceptable salt of the compound or a solvate thereof.

(54) The compound according to any one of (48) and (50) to (53), wherein $L^{2b}$ is a $C_{1-6}$ alkylene group, a $C_{2-3}$ alkenylene group (the $C_{1-6}$ alkylene group and the $C_{2-3}$ alkenylene group are unsubstituted or substituted with a cyano group) or $C_{1-6}$ haloalkylene group, and $R^{2b}$ is, a hydrogen atom, a tautomer or a pharmaceutically acceptable salt of the compound or a solvate thereof.

(55) The compound according to any one of (42) to (47), wherein $L^{1b}$ is a single bond, $L^{2b}$ is a single bond, a $C_{1-6}$ alkylene group or a $C_{2-6}$ alkenylene group (the $C_{1-6}$ alkylene group and the $C_{2-6}$ alkenylene group are unsubstituted or substituted with one or more identical or different substituents independently selected from the group consisting of halogen atoms, hydroxy groups, amino groups, cyano groups and nitro groups), the ring $B^b$ is a $C_{3-11}$ cycloalkane, a $C_{3-11}$ cycloalkene, a 3 to 11-membered non-aromatic heterocyclyl group, a $C_{6-14}$ aryl group or a 5 to 10-membered aromatic heterocycle, $n^b$ is 0 or 1, $R^{3b}$ is a hydroxy group, an amino group, a halogen atom, a cyano group, a $C_{1-3}$ alkyl group, a $C_{1-3}$ haloalkyl group, a $C_{3-6}$ cycloalkyl group, a $C_{1-3}$ alkoxy group or a $C_{1-3}$ haloalkoxy group, $L^{3b}$ is represented by any of the following formulae ($VI^b$-1) to ($VI^b$-11):

($VI^b$)

($VI^b$-1)

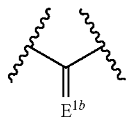

($VI^b$-2)

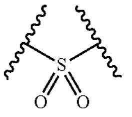

($VI^b$-3)

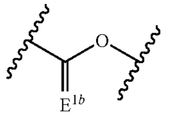

($VI^b$-4)

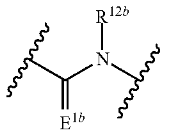

($VI^b$-5)

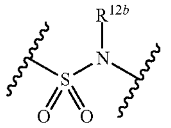

-continued (VI$^b$-6)

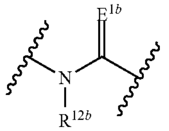

(VI$^b$-7)

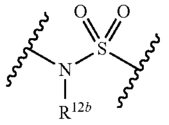

(VI$^b$-8)

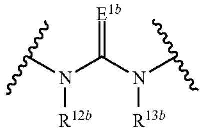

(VI$^b$-9)

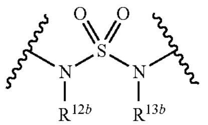

(VI$^b$-10)

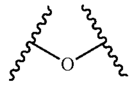

(VI$^b$-11)

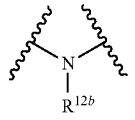

(wherein $E^{1b}$ is an oxygen atom or a sulfur atom, each of $R^{12b}$ and $R^{13b}$ is independently a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or more identical or different substituents independently selected from the group consisting of halogen atoms, cyano groups, hydroxy group, $C_{1-6}$ alkoxy groups, $C_{1-6}$ alkylthio groups, $C_{1-6}$ alkylsulfonyl groups, $C_{3-6}$ cycloalkyl groups, 4 to 7-membered non-aromatic heterocyclyl groups, phenyl groups and 5 to 6-membered aromatic heterocyclyl groups (the phenyl groups and the 5 to 6-membered aromatic heterocyclyl groups are unsubstituted or substituted with a substituent selected from the group consisting of a halogen atom, a cyano group, a $C_{1-3}$ alkyl group and a $C_{1-3}$ haloalkyl group))), and $R^{2b}$ is a hydrogen atom, a $C_{1-6}$ alkyl group (the $C_{1-6}$ alkyl group is unsubstituted or substituted with one or more identical or different substituents independently selected from the substituent set $V^{5b}$), a $C_{3-11}$ cycloalkyl group, a 3 to 11-membered non-aromatic heterocyclyl group, a phenyl group, a naphthyl group or a 5 to 10-membered aromatic heterocyclyl group (the $C_{3-11}$ cycloalkyl group, the 3 to 11-membered non-aromatic heterocyclyl group, the phenyl group, the naphthyl group and the 5 to 10-membered aromatic heterocyclyl group are unsubstituted or substituted with one or more identical or different substituents independently selected from the substituent set $V^{4b}$), a tautomer or a pharmaceutically acceptable salt of the compound or a solvate thereof.

(56) The compound according to any one of (42) to (47), wherein $L^{1b}$ is a single bond or a $C_{1-3}$ alkylene group, $L^{2b}$ is a single bond or a $C_{1-3}$ alkylene group (the $C_{1-3}$ alkylene group is unsubstituted or substituted with a cyano group or a $C_{1-3}$ haloalkyl group), the ring $B^b$ is a $C_{3-11}$ cycloalkane, a $C_{3-11}$ cycloalkene, a 3 to 11-membered non-aromatic heterocycle, benzene or a 5 to 6-membered aromatic heterocycle, $n^b$ is 0 or 1, $R^{3b}$ is a hydroxy group, an amino group, a carbamoyl group, a halogen atom, a cyano group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkylsulfonyl group, $L^{3b}$ is represented by any of the following formulae (VI$^b$-1) to (VI$^b$-11):

(VI$^b$)

(VI$^b$-1)

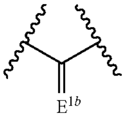

(VI$^b$-2)

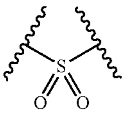

(VI$^b$-3)

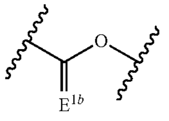

(VI$^b$-4)

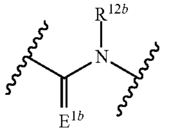

(VI$^b$-5)

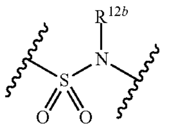

(VI$^b$-6)

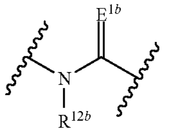

(VI$^b$-7)

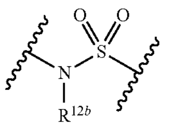

(VI$^b$-8)

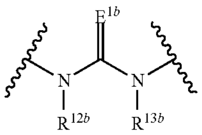

-continued (VI$^b$-9)

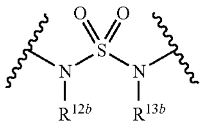

(VI$^b$-10)

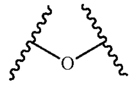

(VI$^b$-11)

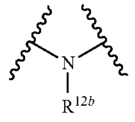

(wherein $E^{1b}$ is an oxygen atom, each of $R^{12b}$ and $R^{13b}$ is independently a hydrogen atom, a $C_{1-6}$ alkyl group or a $C_{1-6}$ haloalkyl group), and $R^{2b}$ is a hydrogen atom, a $C_{1-6}$ alkyl group (the $C_{1-6}$ alkyl group is unsubstituted or substituted with one or more identical or different substituents independently selected from the substituent set $V^{5b}$), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the substituent set $V^{1b}$), a tautomer or a pharmaceutically acceptable salt of the compound or a solvate thereof.

(57) The compound according to (55), wherein the ring $B^b$ is a $C_{3-11}$ cycloalkane or a 4 to 7-membered non-aromatic heterocycle, $L^{3b}$ is represented by any of the following formulae (XIX$^b$-1) to (XIX$^b$-7):

(XIX$^b$)

(XIX$^b$-1)

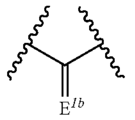

(XIX$^b$-2)

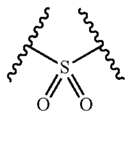

(XIX$^b$-3)

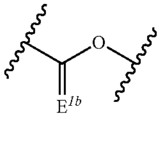

(XIX$^b$-4)

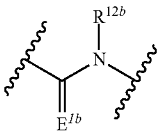

-continued (XIX$^b$-5)

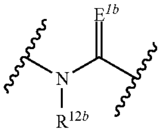

(XIX$^b$-6)

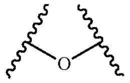

(XIX$^b$-7)

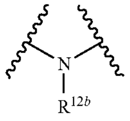

(wherein $E^{1b}$ is an oxygen atom, and $R^{12b}$ is a hydrogen atom, a $C_{1-6}$ alkyl group (the $C_{1-6}$ alkyl group is unsubstituted or substituted with one or more identical or different substituents independently selected from the group consisting of cyano groups, hydroxy groups, $C_{1-3}$ alkoxy groups, $C_{3-6}$ cycloalkyl groups and phenyl groups) or a $C_{1-6}$ haloalkyl group), and $R^{2b}$ is a hydrogen atom, a $C_{1-6}$ alkyl group, a $C_{1-6}$ haloalkyl group (the $C_{1-6}$ alkyl group and the $C_{1-6}$ haloalkyl group are unsubstituted or substituted with one or two identical or different substituents independently selected from the group consisting of hydroxy groups, cyano groups, $C_{1-3}$ alkoxy groups, $C_{1-3}$ alkylthio groups, $C_{1-3}$ alkylsulfonyl groups, $C_{3-6}$ cycloalkyl groups, 4 to 7-membered non-aromatic heterocyclyl groups, phenyl groups and 5 to 6-membered aromatic heterocyclyl groups (the $C_{3-6}$ cycloalkyl groups, the 4 to 7-membered non-aromatic heterocyclyl groups, the phenyl groups and the 5 to 6-membered aromatic heterocyclyl groups are unsubstituted or substituted with one or more identical or different substituents independently selected from the group consisting of halogen atoms, hydroxy groups, cyano groups, $C_{1-6}$ alkoxy groups, $C_{1-6}$ haloalkoxy groups and $C_{1-6}$ alkoxycarbonyl groups)), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the group consisting of halogen atoms, hydroxy groups, cyano groups, $C_{1-6}$ alkyl groups, $C_{1-6}$ haloalkyl groups, $C_{1-6}$ alkoxy groups, $C_{1-6}$ haloalkoxy groups and $C_{1-6}$ alkoxycarbonyl groups), a tautomer or a pharmaceutically acceptable salt of the compound or a solvate thereof.

(58) The compound according to (55) or (57), wherein $L^{3b}$ is represented by any of the following formulae (XX$^b$-1) to (XX$^b$-4):

(XX$^b$)

(XX$^b$-1)

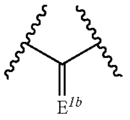

-continued (XX$^b$-2)

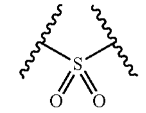

(XX$^b$-3)

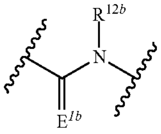

(XX$^b$-4)

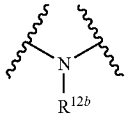

(wherein $E^{1b}$ is an oxygen atom, and $R^{12b}$ is a hydrogen atom, a $C_{1-3}$ alkyl group (the $C_{1-3}$ alkyl group is unsubstituted or substituted with a substituent selected from the group consisting of a cyano group, a hydroxy group, a $C_{1-3}$ alkoxy group, a $C_{3-6}$ cycloalkyl group and a phenyl group) or $C_{1-3}$ haloalkyl group)), and $R^{2b}$ is a hydrogen atom, a $C_{1-3}$ alkyl group, a $C_{1-3}$ haloalkyl group (the $C_{1-3}$ alkyl group and the $C_{1-3}$ haloalkyl group are unsubstituted or substituted with one or two identical or different substituent selected from the group consisting of hydroxy groups, cyano groups, $C_{1-3}$ alkoxy groups, $C_{3-6}$ cycloalkyl groups, 4 to 7-membered non-aromatic heterocyclyl groups, phenyl groups and 5 to 6-membered aromatic heterocyclyl groups (the $C_{3-6}$ cycloalkyl groups, the 4 to 7-membered non-aromatic heterocyclyl groups, the phenyl groups and the 5 to 6-membered aromatic heterocyclyl groups are unsubstituted or substituted with a hydroxy group or a halogen atom)), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or two identical or different substituents independently selected from the group consisting of hydroxy groups, halogen atoms, cyano groups, $C_{1-6}$ alkyl groups, $C_{1-3}$ haloalkyl groups and $C_{1-6}$ alkoxycarbonyl groups), a tautomer or a pharmaceutically acceptable salt of the compound or a solvate thereof.

(59) The compound according to any one of (48) to (53) or (55) to (58), wherein $L^{2b}$ is a single bond or a $C_{1-3}$ alkylene group, a tautomer or a pharmaceutically acceptable salt of the compound or a solvate thereof.

(60) The compound according to any one of (44) to (59), wherein $X^b$ is a nitrogen atom or $CR^{15b}$ (wherein $R^{15b}$ is a hydrogen atom), and $Y^b$ is $CR^{16b}$ (wherein $R^{16b}$ is a hydrogen atom), a tautomer or a pharmaceutically acceptable salt of the compound or a solvate thereof.

(61) The compound according to any one of (46) to (60), wherein the ring $A^b$ is represented by any of the following formulae (VII$^b$-1) to (VII$^b$-7):

(VII$^b$)

(VII$^b$-1)

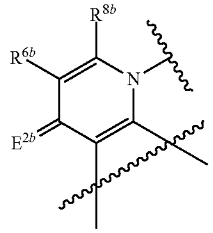

(VII$^b$-2)

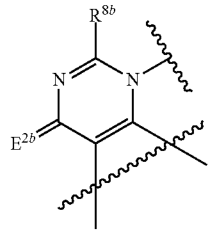

(VII$^b$-3)

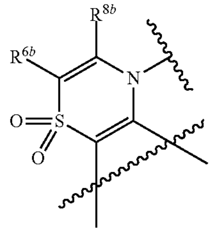

(VII$^b$-4)

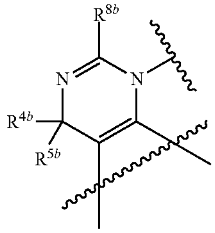

(VII$^b$-5)

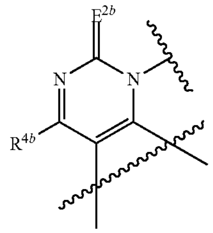

(VII$^b$-6)

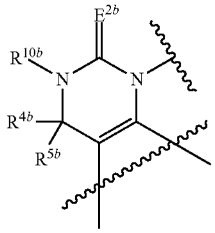

-continued (VII$^b$-7)

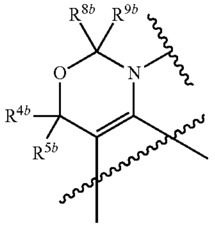

(wherein $E^{2b}$ is an oxygen atom, and each of $R^{4b}$, $R^{5b}$, $R^{6b}$, $R^{8b}$, $R^{9b}$ and $R^{10b}$ is independently a hydrogen atom or a $C_{1-3}$ alkyl group), a tautomer or a pharmaceutically acceptable salt of the compound or a solvate thereof.

(62) The compound according to any one of (46) to (60), wherein the ring $A^b$ is represented by any of the following formulae (XXXIII$^b$-1) to (XXXIII$^b$-3):

(XXXIII$^b$)

(XXXIII$^b$-1)

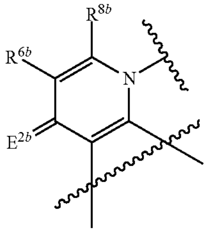

(XXXIII$^b$-2)

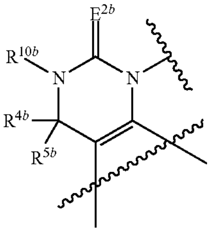

(XXXIII$^b$-3)

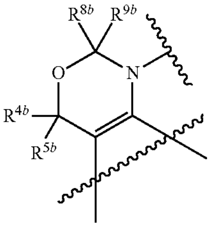

(wherein $E^{2b}$ is an oxygen atom, and each of $R^{4b}$, $R^{5b}$, $R^{8b}$, $R^{9b}$ and $R^{10b}$ are hydrogen atoms, and $R^{6b}$ is a hydrogen atom, a halogen atom or a $C_{1-3}$ alkyl group), a tautomer or a pharmaceutically acceptable salt of the compound or a solvate thereof.

(63) The compound according to any one of (49), (60) and (61), wherein $L^{1b}$ is a single bond, $L^{2b}$ is a $C_{1-3}$ alkylene group, the ring $B^b$ is a $C_{4-7}$ cycloalkane or a 4 to 7-membered non-aromatic heterocycle, $n^b$ is 0 or 1, $R^{3b}$ is a $C_{1-3}$ alkyl group, $L^{3b}$ is a single bond, and $R^{2b}$ is a hydrogen atom or a phenyl group (the phenyl group is unsubstituted or substituted with one or more identical or different halogen atoms independently selected from the group consisting of fluorine atoms, chlorine atoms, bromine atoms and iodine atoms), a tautomer or a pharmaceutically acceptable salt of the compound or a solvate thereof.

(64) The compound according to any one of (49), (60) and (61), wherein $L^{1b}$ is a single bond, $L^{2b}$ is a single bond, the ring $B^b$ is a $C_{4-7}$ cycloalkane or a 4 to 7-membered non-aromatic heterocycle, $n^b$ is 0, $L^{3b}$ is a single bond, and $R^{2b}$ is a hydrogen atom, a tautomer or a pharmaceutically acceptable salt of the compound or a solvate thereof.

(65) The compound according to any one of (56), (60) and (61), wherein $L^{1b}$ is a single bond, $L^{2b}$ is a single bond, the ring $B^b$ is a $C_{4-7}$ cycloalkane or a 4 to 7-membered non-aromatic heterocycle, $n^b$ is 0 or 1, $R^{3b}$ is a $C_{1-3}$ alkyl group, $L^{3b}$ is represented by any of the following formula (VIII$^b$-1) or (VIII$^b$-2):

(VIII$^b$)

(VIII$^b$-1)

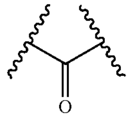

(VIII$^b$-2)

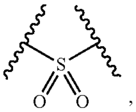

, and $R^{2b}$ is a $C_{1-6}$ alkyl group (the $C_{1-6}$ alkyl group is unsubstituted or substituted with a cyano group or a $C_{3-6}$ cycloalkyl group) or a $C_{1-3}$ haloalkyl group, a tautomer or a pharmaceutically acceptable salt of the compound or a solvate thereof.

(66) The compound according to any one of (42) to (65), wherein the ring $B^b$ is cyclohexane or piperidine, a tautomer or a pharmaceutically acceptable salt of the compound or a solvate thereof.

(67) The compound according to any one of (42) to (62), wherein the ring $B^b$ is a 4 to 7-membered non-aromatic heterocycle, a tautomer or a pharmaceutically acceptable salt of the compound or a solvate thereof.

(68) The compound according to (41), wherein $X^b$ is a nitrogen atom or $CR^{15b}$ (wherein $R^{15b}$ is a hydrogen atom or a halogen atom), $Y^b$ is $CR^{16b}$(wherein $R^{16b}$ is a hydrogen atom), $R^{1b}$ is a hydrogen atom, the ring $A^b$ is represented by any of the following formulae (XVIII$^b$-1) to (XVIII$^b$-8):

$(XVIII^b)$ $(XVIII^b\text{-}1)$

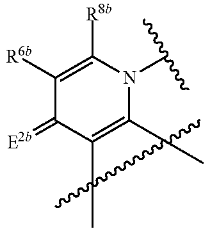

$(XVIII^b\text{-}2)$

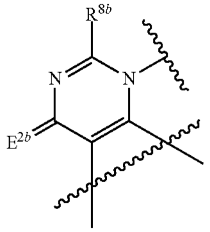

$(XVIII^b\text{-}3)$

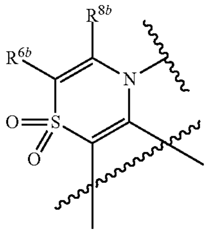

$(XVIII^b\text{-}4)$

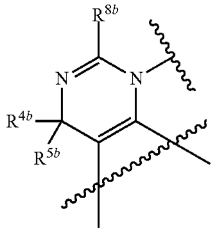

$(XVIII^b\text{-}5)$

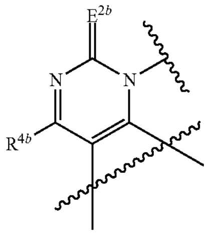

$(XVIII^b\text{-}6)$

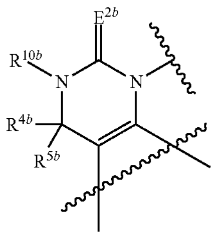

-continued $(XVIII^b\text{-}7)$

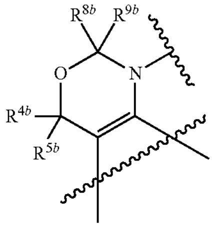

$(XVIII^b\text{-}8)$

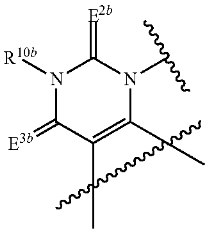

(wherein each of $E^{2b}$ and $E^{3b}$ is independently an oxygen atom or a sulfur atom, each of $R^{4b}$, $R^{5b}$, $R^{6b}$, $R^{8b}$ and $R^{9b}$ is independently a hydrogen atom, a halogen atom or a $C_{1-3}$ alkyl group, and $R^{10b}$ is a hydrogen atom, a $C_{1-6}$ alkyl group (the $C_{1-6}$ alkyl group is unsubstituted or substituted with one or more identical or different substituents independently selected from the substituent set $V^{3b}$), a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{1b}$)), the ring $B^b$ is a $C_{3-11}$ cycloalkane, a 3 to 11-membered non-aromatic heterocycle, a $C_{6-14}$ aromatic carbocycle or a 5 to 10-membered aromatic heterocycle, $L^{1b}$ is single bond or a $C_{1-3}$ alkylene group, $L^{2b}$ is a single bond, a $C_{1-6}$ alkylene group or a $C_{2-6}$ alkenylene group (the $C_{1-6}$ alkylene group and the $C_{2-6}$ alkenylene group are unsubstituted or substituted with one or more identical or different substituents independently selected from the group consisting of halogen atoms, hydroxy groups, amino groups, cyano groups and nitro groups), $n^b$ is 0 or 1, $R^{3b}$ is a hydroxy group, an amino group, a carboxy group, a carbamoyl group, a tetrazolyl group, a halogen atom, a cyano group, a nitro group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkylsulfonyl group, $L^{3b}$ is a single bond or represented by any of the following formulae $(XXII^b\text{-}1)$ to $(XXII^b\text{-}15)$:

$(XXII^b)$ $(XXII^b\text{-}1)$

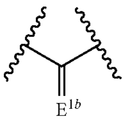

-continued (XXII$^b$-2)

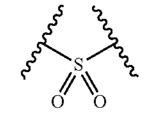

(XXII$^b$-3)

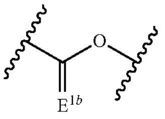

(XXII$^b$-4)

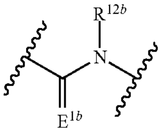

(XXII$^b$-5)

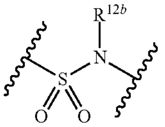

(XXII$^b$-6)

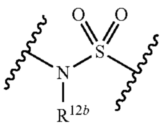

(XXII$^b$-7)

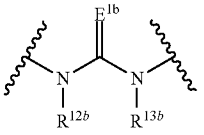

(XXII$^b$-8)

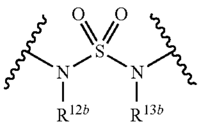

(XXII$^b$-9)

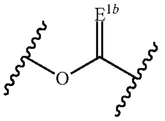

(XXII$^b$-10)

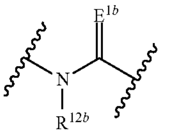

(XXII$^b$-11)

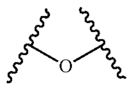

(XXII$^b$-12)

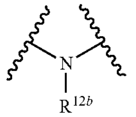

(XXII$^b$-13)

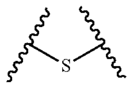

-continued (XXII$^b$-14)

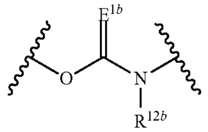

(XXII$^b$-15)

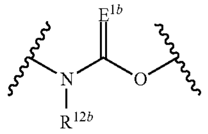

(wherein $E^{1b}$ is an oxygen atom or a sulfur atom, and each of $R^{12b}$ and $R^{13b}$ is independently a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or more identical or different substituents independently selected from the group consisting of halogen atoms, cyano groups, hydroxy groups, $C_{1-6}$ alkoxy groups, $C_{1-6}$ alkylthio groups, $C_{1-6}$ alkylsulfonyl groups, $C_{3-6}$ cycloalkyl groups, 4 to 7-membered non-aromatic heterocyclyl groups, phenyl groups and 5 to 6-membered aromatic heterocyclyl groups (the phenyl groups and 5 to 6-membered aromatic heterocyclyl groups are unsubstituted or substituted with a substituent selected from the group consisting of a halogen atom, a cyano group, a $C_{1-3}$ alkyl group and a $C_{1-3}$ haloalkyl group))), when $L^{3b}$ is a single bond, $R^{2b}$ is a hydrogen atom, a halogen atom, a $C_{3-11}$ cycloalkyl group, a 3 to 11-membered non-aromatic heterocyclyl group, a phenyl group, a naphthyl group, a 5 to 10-membered aromatic heterocyclyl group, a 8 to 11-membered partially saturated aromatic cyclic group or a 8 to 11-membered aromatic ring-condensed alicyclic hydrocarbon group (the $C_{3-11}$ cycloalkyl group, the 3 to 11-membered non-aromatic heterocyclyl group, the phenyl group, the naphthyl group, the 5 to 10-membered aromatic heterocyclyl group, the 8 to 11-membered partially saturated aromatic cyclic group and the 8 to 11-membered aromatic ring-condensed alicyclic hydrocarbon group are unsubstituted or substituted with one or more identical or different substituents independently selected from the substituent set $V^{4b}$ and the substituent set $V^{9b}$), when $L^{3b}$ is not a single bond, $R^{2b}$ is a hydrogen atom, a $C_{1-6}$ alkyl group, a $C_{2-6}$ alkenyl group (the $C_{1-6}$ alkyl group and the $C_{2-6}$ alkenyl group are unsubstituted or substituted with one or more identical or different substituents independently selected from the substituent set $V^{6b}$ and the substituent set $V^{9b}$), a $C_{3-11}$ cycloalkyl group, a 3 to 11-membered non-aromatic heterocyclyl group, a $C_{6-14}$ aryl group, a 5 to 10-membered aromatic heterocyclyl group, a 8 to 11-membered partially saturated aromatic cyclic group or a 8 to 11-membered aromatic ring-condensed alicyclic hydrocarbon group (the $C_{3-11}$ cycloalkyl group, the 3 to 11-membered non-aromatic heterocyclyl group, the $C_{6-14}$ aryl group, the 5 to 10-membered aromatic heterocyclyl group, the 8 to 11-membered partially saturated aromatic cyclic group or the 8 to 11-membered aromatic ring-condensed alicyclic hydrocarbon group are unsubstituted or substituted with one or more identical or different substituents independently selected from the substituent set $V^{4b}$ and the substituent set $V^{9b}$), a tautomer or a pharmaceutically acceptable salt of the compound or a solvate thereof.

(69) The compound according to (41) or (68), wherein the ring $A^b$ is represented by any of the following formulae (XXI$^b$-1) to (XXI$^b$-4):

(XXI$^b$)

(XXI$^b$-1)

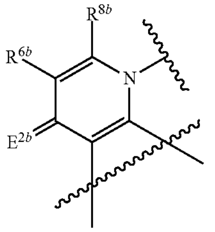

(XXI$^b$-2)

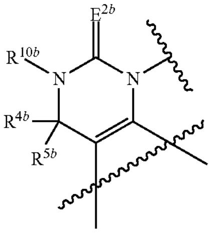

(XXI$^b$-3)

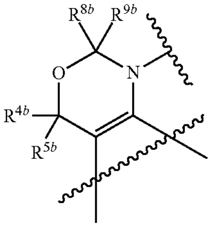

(XXI$^b$-4)

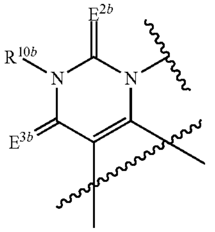

(wherein each of $E^{2b}$ and $E^{3b}$ is independently an oxygen atom or a sulfur atom, $R^{4b}$, $R^{5b}$, $R^{8b}$ and $R^{9b}$ are hydrogen atoms, $R^{6b}$ is a hydrogen atom, a halogen atom or a $C_{1-3}$ alkyl group, and $R^{10b}$ is a hydrogen atom, a $C_{1-6}$ alkyl group (the $C_{1-6}$ alkyl group is unsubstituted or substituted with one or two identical or different substituents independently selected from the group consisting of cyano groups, hydroxy groups, $C_{1-3}$ alkoxy groups, $C_{1-3}$ alkylthio groups, mono-$C_{1-3}$ alkylamino groups, di-$C_{1-3}$ alkylamino groups, mono-$C_{1-3}$ alkylaminocarbonyl groups, di-$C_{1-3}$ alkylaminocarbonyl groups, $C_{3-6}$ cycloalkyl groups, 4 to 7-membered non-aromatic heterocyclyl groups, phenyl groups and 5 to 6-membered aromatic heterocyclyl groups (the phenyl groups and the 5 to 6-membered aromatic heterocyclyl groups are unsubstituted or substituted with one or two identical or different substituents independently selected from the group consisting of halogen atoms, $C_{1-3}$ alkyl groups and $C_{1-3}$ haloalkyl groups)), a $C_{1-6}$ haloalkyl group, a $C_{3-6}$ cycloalkyl group or a 4 to 7-membered non-aromatic heterocyclyl group), a tautomer or a pharmaceutically acceptable salt of the compound or a solvate thereof.

(70) The compound according to any one of (41), (68) and (69), wherein the ring $A^b$ is represented by the following formulae (XXIX$^b$-1) or (XXIX$^b$-2):

(XXIX$^b$)

(XXIX$^b$-1)

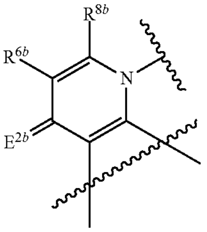

(XXIX$^b$-2)

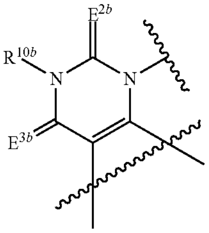

(wherein $E^{2b}$ and $E^{3b}$ are oxygen atoms, $R^{6b}$ is a hydrogen atom, a halogen atom or a $C_{1-3}$ alkyl group, $R^{8b}$ is a hydrogen atom, and $R^{10b}$ is a hydrogen atom, a $C_{1-6}$ alkyl group (the $C_{1-6}$ alkyl group is unsubstituted or substituted with one or two identical or different substituents independently selected from the group consisting of cyano groups, hydroxy groups, $C_{1-3}$ alkoxy groups, $C_{1-3}$ alkylthio groups, di-$C_{1-3}$ alkylamino groups, $C_{3-6}$ cycloalkyl groups and 4 to 7-membered non-aromatic heterocyclyl groups), a $C_{1-6}$ haloalkyl group, a $C_{3-6}$ cycloalkyl group or a 4 to 7-membered non-aromatic heterocyclyl group, a tautomer or a pharmaceutically acceptable salt of the compound or a solvate thereof.

(71) The compound according to any one of (41) and (68) to (71), wherein $L^{1b}$ is a single bond, $L^{2b}$ is a single bond, a $C_{1-6}$ alkylene group, a $C_{2-6}$ alkenylene group or a $C_{1-6}$ haloalkylene group (the $C_{1-6}$ alkylene group, the $C_{2-6}$ alkenylene group and the $C_{1-6}$ haloalkylene group are unsubstituted or substituted with a hydroxy group or a cyano group), the ring $B^b$ is a $C_{3-11}$ cycloalkane or a 4 to 7-membered non-aromatic heterocycle, $n^b$ is 0 or 1, and $R^{3b}$ is a hydroxy group, a $C_{1-3}$ alkyl group or a $C_{1-3}$ alkoxy group, a tautomer or a pharmaceutically acceptable salt of the compound or a solvate thereof.

(72) The compound according to any one of (41) and (68) to (70), wherein $L^{3b}$ is a single bond, and $R^{2b}$ is a hydrogen atom, a 4 to 7-membered non-aromatic heterocyclyl group, a phenyl group, a 5 to 10-membered aromatic heterocyclyl group or a 8 to 11-membered partially saturated aromatic cyclic group (the 4 to 7-membered non-aromatic heterocyclyl group, the phenyl group, the 5 to 10-membered aromatic heterocyclyl group and the 8 to 11-membered partially saturated aromatic cyclic group are unsubstituted or substituted with one or more identical or different substituents independently selected from the group consisting of hydroxy groups, amino groups, carbamoyl groups, sulfamoyl groups, halogen atoms, cyano groups, nitro groups, $C_{1-6}$ alkyl groups (the $C_{1-6}$ alkyl groups are unsubstituted or substituted with a cyano group), $C_{1-6}$ haloalkyl groups, $C_{3-11}$ cycloalkyl groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylsulfonyl groups, $C_{1-6}$ haloalkylsulfonyl groups, $C_{1-6}$ alkoxycarbonyl groups, 4 to 7-membered non-aromatic heterocyclyl groups, mono-$C_{1-6}$ alkylamino groups, di-$C_{1-6}$ alkylamino groups, phenyl groups, 5 to 6-membered aromatic heterocyclyl groups, mono-$C_{1-6}$ alkylaminosulfonyl groups and di-$C_{1-6}$ alkylaminosulfonyl groups), a tautomer or a pharmaceutically acceptable salt of the compound or a solvate thereof.

(73) The compound according to (72), wherein $R^{2b}$ is a hydrogen atom, a phenyl group, a 5 to 10-membered aromatic heterocyclyl group or a 8 to 11-membered partially saturated aromatic cyclic group (the phenyl group, the 5 to 10-membered aromatic heterocyclyl group and the 8 to 11-membered partially saturated aromatic cyclic group are unsubstituted or substituted with one, two or three identical or different substituents independently selected from the group consisting of halogen atoms, cyano groups, nitro groups, $C_{1-3}$ alkyl groups, $C_{1-3}$ haloalkyl groups and $C_{1-6}$ alkoxycarbonyl groups), a tautomer or a pharmaceutically acceptable salt of the compound or a solvate thereof.

(74) The compound according to (72), wherein $R^{2b}$ is a 4 to 7-membered non-aromatic heterocyclyl group (the 4 to 7-membered non-aromatic heterocyclyl group is unsubstituted or substituted with one or two identical or different substituents independently selected from the group consisting of hydroxy groups, halogen atoms, cyano groups, $C_{1-3}$ alkyl groups (the $C_{1-3}$ alkyl groups are unsubstituted or substituted with a cyano group) and $C_{1-3}$ haloalkyl groups), a tautomer or a pharmaceutically acceptable salt of the compound or a solvate thereof.

(75) The compound according to any one of (41) and (68) to (71), wherein $L^{3b}$ is represented by any of the following formulae ($XIX^b$-1) to ($XIX^b$-7):

($XIX^b$)

($XIX^b$-1)

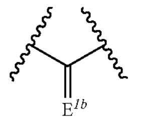

($XIX^b$-2)

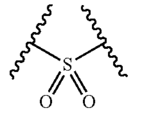

($XIX^b$-3)

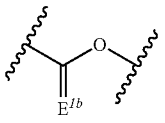

($XIX^b$-4)

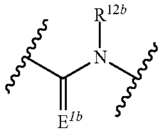

($XIX^b$-5)

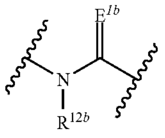

-continued ($XIX^b$-6)

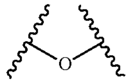

($XIX^b$-7)

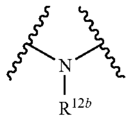

(wherein $E^{1b}$ is an oxygen atom, and $R^{12b}$ is a hydrogen atom or a $C_{1-6}$ alkyl group (the $C_{1-6}$ alkyl group is unsubstituted or substituted with one or more identical or different substituents independently selected from the group consisting of halogen atoms, cyano groups, hydroxy groups, $C_{1-3}$ alkoxy groups, $C_{3-6}$ cycloalkyl groups, 4 to 7-membered non-aromatic heterocyclyl groups, phenyl groups and 5 to 6-membered aromatic heterocyclyl groups)), and $R^{2b}$ is a hydrogen atom, a $C_{1-6}$ alkyl group, a $C_{1-6}$ haloalkyl group (the $C_{1-6}$ alkyl group and the $C_{1-6}$ haloalkyl group are unsubstituted or substituted with one or two identical or different substituents independently selected from the group consisting of cyano groups, hydroxy groups, $C_{1-6}$ alkoxy groups, $C_{1-6}$ alkylthio groups, $C_{1-6}$ alkylsulfonyl groups, $C_{3-6}$ cycloalkyl groups, 4 to 7-membered non-aromatic heterocyclyl groups, phenyl groups and 5 to 6-membered aromatic heterocyclyl groups (the $C_{3-6}$ cycloalkyl groups, the 4 to 7-membered non-aromatic heterocyclyl groups, the phenyl groups and the 5 to 6-membered aromatic heterocyclyl groups are unsubstituted or substituted with one, two or three identical or different substituents independently selected from the group consisting of the substituent set $V^{2b}$, mono-$C_{1-6}$ alkylaminosulfonyl groups and di-$C_{1-6}$ alkylaminosulfonyl groups)), a $C_{3-6}$ cycloalkyl group, a 4 to 7-membered non-aromatic heterocyclyl group, a phenyl group, a 5 to 6-membered aromatic heterocyclyl group or a 8 to 11-membered partially saturated aromatic cyclic group (the $C_{3-6}$ cycloalkyl group, the 4 to 7-membered non-aromatic heterocyclyl group, the phenyl group, the 5 to 6-membered aromatic heterocyclyl group and the 8 to 11-membered partially saturated aromatic cyclic group are unsubstituted or substituted with one, two or three identical or different substituents independently selected from the group consisting of the substituent set $V^{2b}$, mono-$C_{1-6}$ alkylaminosulfonyl groups and di-$C_{1-6}$ alkylaminosulfonyl groups), a tautomer or a pharmaceutically acceptable salt of the compound or a solvate thereof.

(76) The compound according to (75), wherein $L^{3b}$ is represented by any of the following formulae ($XXXI^b$-1) to ($XXXI^b$-5):

($XXXI^b$)

($XXXI^b$-1)

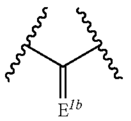

($XXXI^b$-2)

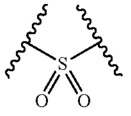

-continued (XXXI$^b$-3)

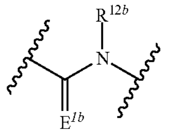

(XXXI$^b$-4)

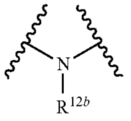

(XXXI$^b$-5)

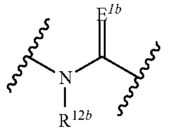

(wherein $E^{1b}$ is an oxygen atom, and $R^{12b}$ is a hydrogen atom, a $C_{1-3}$ alkyl group (the $C_{1-3}$ alkyl group is unsubstituted or substituted with a substituent selected from the group consisting of a cyano group, a hydroxy group, a $C_{1-3}$ alkoxy group, a $C_{3-6}$ cycloalkyl group and a phenyl group) or $C_{1-3}$ haloalkyl group), and $R^{2b}$ is a hydrogen atom, a $C_{1-6}$ alkyl group, a $C_{1-6}$ haloalkyl group (the $C_{1-6}$ alkyl group and the $C_{1-6}$ haloalkyl group are unsubstituted or substituted with one or two identical or different substituent selected from the group consisting of hydroxy groups, cyano groups, $C_{1-3}$ alkoxy groups, $C_{3-6}$ cycloalkyl groups, 4 to 7-membered non-aromatic heterocyclyl groups, phenyl groups and 5 to 6-membered aromatic heterocyclyl groups (the $C_{3-6}$ cycloalkyl groups, the 4 to 7-membered non-aromatic heterocyclyl groups, the phenyl groups and the 5 to 6-membered aromatic heterocyclyl groups are unsubstituted or substituted with a hydroxy group or a halogen atom)), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or two identical or different substituents independently selected from the group consisting of hydroxy groups, halogen atoms, cyano groups, $C_{1-3}$ alkyl groups, $C_{1-3}$ haloalkyl groups and $C_{1-6}$ alkoxycarbonyl groups), a tautomer or a pharmaceutically acceptable salt of the compound or a solvate thereof.

(77) The compound according to (75), wherein $L^{3b}$ is represented by the formula (XXXII$^b$):

(XXXII$^b$)

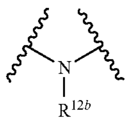

(wherein $R^{12b}$ is a hydrogen atom, a $C_{1-3}$ alkyl group (the $C_{1-3}$ alkyl group is unsubstituted or substituted with a substituent selected from the group consisting of a cyano group, a hydroxy group, a $C_{1-3}$ alkoxy group, a $C_{3-6}$ cycloalkyl group and a phenyl group) or a $C_{1-3}$ haloalkyl group), and $R^{2b}$ is a hydrogen atom, a $C_{1-3}$ alkyl group, a $C_{1-3}$ haloalkyl group (the $C_{1-3}$ alkyl group and the $C_{1-3}$ haloalkyl group are unsubstituted or substituted with one or two identical or different substituent selected from the group consisting of hydroxy groups, cyano groups, $C_{1-3}$ alkoxy groups, $C_{3-6}$ cycloalkyl groups (the $C_{3-6}$ cycloalkyl groups are unsubstituted or substituted with a hydroxy groups), 4 to 7-membered non-aromatic heterocyclyl groups, phenyl groups and 5 to 6-membered aromatic heterocyclyl groups), a $C_{3-6}$ cycloalkyl group or a 4 to 7-membered non-aromatic heterocyclyl group (the $C_{3-6}$ cycloalkyl group and the 4 to 7-membered non-aromatic heterocyclyl group are unsubstituted or substituted with one or two identical or different substituents independently selected from the group consisting of $C_{1-3}$ alkyl groups, $C_{1-3}$ haloalkyl groups and $C_{1-6}$ alkoxycarbonyl groups), a tautomer or a pharmaceutically acceptable salt of the compound or a solvate thereof.

(78) The compound according to any one of (41) or (68) to (77), wherein $L^{2b}$ is a single bond or a $C_{1-3}$ alkylene group, and the ring $B^b$ is cyclohexane or piperidine, a tautomer or a pharmaceutically acceptable salt of the compound or a solvate thereof.

(79) The compound according to any one of (41) to (78), wherein $n^b$ is 0 or 1, and $R^{3b}$ is a $C_{1-3}$ alkyl group, a tautomer or a pharmaceutically acceptable salt of the compound or a solvate thereof.

(80) A JAK inhibitor containing the compound as defined in any one of (1) to (79), a tautomer or a pharmaceutically acceptable salt of the compound or a solvate thereof, as an active ingredient.

(81) A preventive, therapeutic or improving agent for diseases against which inhibition of JAK is effective, which contains the JAK inhibitor as defined in (80).

(82) A therapeutic agent for articular rheumatism, which contains the JAK inhibitor as defined in (80).

(83) Medicament containing the compound as defined in any one of (1) to (79), a tautomer or a pharmaceutically acceptable salt of the compound or a solvate thereof, as an active ingredient.

The present invention has made it possible to provide novel tricyclic pyrimidine compounds and tricyclic pyridine compounds which have excellent JAK inhibitory action and are especially useful for prevention and treatment of autoimmune diseases, inflammatory diseases and allergic diseases.

Now, the present invention will be described in further detail.

In the present invention, "n-" denotes normal, "i-" denotes iso, "s-" or "sec" denotes secondary, "t-" or "tert-" denotes tertiary, "c-" denotes cyclo, "o-" denotes ortho, "m-" denotes meta, "p-" denotes para, "cis-" denotes a cis isomer, "trans-" denotes a trans isomer, "(E)-" denotes a E isomer, "(Z)-" denotes a Z isomer, "rac" and "racemate" denotes racemate, "diastereomixture" denotes a mixture of diastereomers, "Ph" denotes phenyl, "Py" denotes pyridyl, "Me" denotes methyl, "Et" denotes ethyl, "Pr" denotes propyl, "Bu" denotes butyl, "Boc" denotes tertiary-butoxycarbonyl, "Cbz" denotes benzyloxycarbonyl, "Ms" denotes methanesulfonyl, "Tf" denotes trifluoromethanesulfonyl, "Ts" denotes p-toluenesulfonyl, "SEM" denotes [2-(trimethylsilyl)ethoxy]methyl, "TIPS" denotes triisopropylsilyl, "TBDPS" denotes tertiary-butyldiphenylsilyl, and "TBS" denotes tertiary-butyldimethylsilyl.

First, the terms used herein for description of chemical structures will be explained.

A "halogen atom" is a fluorine atom, a chlorine atom, a bromine atom or an iodine atom.

A "$C_{1-3}$ alkyl group" is a methyl group, an ethyl group, a propyl group or an isopropyl group.

A "$C_{1-6}$ alkyl group" is a linear or branched alkyl group containing one to six carbon atoms and may, for example, be a methyl group, an ethyl group, a n-propyl group, an isopropyl group, a n-butyl group, an isobutyl group, a t-butyl group, a n-pentyl group, n-hexyl group or the like.

A "$C_{1-3}$ haloalkyl group" is a group derived from the above-mentioned $C_{1-3}$ alkyl group by replacing one or more hydrogen atom(s) at arbitrary position(s) by one or more identical or different halogen atoms selected from the group consisting of fluorine atoms, chlorine atoms, bromine atoms and iodine atoms.

A "$C_{1-6}$ haloalkyl group" is a group derived from the above-mentioned $C_{1-6}$ alkyl group by replacing one or more hydrogen atom(s) at arbitrary position(s) by one or more identical or different halogen atoms selected from the group consisting of fluorine atoms, chlorine atoms, bromine atoms and iodine atoms.

A "$C_{3-11}$ cycloalkane" is a monocyclic, fused, bridged or Spiro aliphatic hydrocarbon ring having 3 to 11 ring-constituting carbon atoms and may, for example, be cyclopropane, cyclobutane, cyclopentane, cyclohexane, cycloheptane, cyclooctane, adamantane, bicyclo[3.1.0]octane, bicyclo[2.2.1]heptane, spiro[5.5]undecane or the like.

A "$C_{3-11}$ cycloalkyl group" is a monovalent group derived from the above-mentioned "$C_{3-11}$ cycloalkane" by removing a hydrogen atom at an arbitrary position.

A "$C_{3-6}$ cycloalkane" is a ring having 3 to 6 ring-constituting carbon atoms among the above-mentioned "$C_{3-11}$ cycloalkane" and may, for example, be cyclopropane, cyclobutane, cyclopentane, cyclohexane or the like.

A "$C_{3-6}$ cycloalkyl group" is a group having 3 to 6 ring-constituting carbon atoms among the above-mentioned "$C_{3-11}$ cycloalkyl group", and may, for example, be a cyclopropyl group, a cyclobutyl group, a cyclopentyl group, a cyclohexyl group or the like.

A "$C_{4-7}$ cycloalkane" is a ring having 4 to 7 ring-constituting carbon atoms among the above-mentioned "$C_{3-11}$ cycloalkane" and may, for example, be cyclobutane, cyclopentane, cyclohexane, cycloheptane or the like.

A "$C_{3-11}$ cycloalkene" is a non-aromatic ring derived from replacing one or more bonds in the above-mentioned "$C_{3-11}$ cycloalkane" are replaced by double bond(s) and may, for example, be cyclopropene, cyclobutene, cyclopentene, cyclohexene, cyclohexa-1,3-diene, cyclohexa-1,4-diene, bicyclo[2.2.1]hepta-2,5-diene, spiro[2.5]oct-4-ene, 1,2,5,6-tetrahydronaphthalene or the like.

A "$C_{2-6}$ alkenyl group" is a linear or branched alkenyl group having at least one double bond and 2 to 6 carbon atoms and may, for example be an ethenyl(vinyl) group, a 1-propenyl group, a 2-propenyl(allyl) group, an isopropenyl group, a 1-butenyl group, a 2-butenyl group, a 3-butenyl (homoallyl) group, a 4-pentenyl group, a 5-hexenyl group or the like.

A "$C_{2-3}$ alkenyl group" is an ethenyl(vinyl) group, a 1-propenyl group, a 2-propenyl(allyl) group or an isopropenyl group.

A "$C_{2-6}$ haloalkenyl group" is a group derived from the above-mentioned "$C_{2-6}$ alkenyl group" by replacing one or more hydrogen atom(s) at arbitrary position(s) by one or more identical or different halogen atoms selected from the group consisting of fluorine atoms, chlorine atoms, bromine atoms and iodine atoms.

A "$C_{2-6}$ alkynyl group" is a linear or branched alkynyl group having at least one triple bond and 2 to 6 carbon atoms and may, for example be an ethynyl group, a 1-propynyl group, a 3-propynyl group, a 1-butynyl group, a 2-butynyl group, a 3-butynyl group, a 4-pentynyl group, a 5-hexynyl group, a 1,5-hexandiynyl group or the like.

A "$C_{1-6}$ alkoxy group" is a linear or branched alkoxy group having 1 to 6 carbon atoms and may, for example, be a methoxy group, an ethoxy group, a n-propoxy group, an isopropoxy group, a n-butoxy group, an isobutoxy group, a t-butoxy group, a n-pentyloxy group, a n-hexyloxy group or the like.

A "$C_{1-3}$ alkoxy group" is a methoxy group, an ethoxy group, a n-propoxy group or an i-propoxy group.

A "$C_{1-6}$ haloalkoxy group" is a group derived from the above-mentioned "$C_{1-6}$ alkoxy group" by replacing one or more hydrogen atom(s) at arbitrary position(s) by one or more identical or different halogen atoms selected from the group consisting of fluorine atoms, chlorine atoms, bromine atoms and iodine atoms.

A "$C_{1-3}$ haloalkoxy group" is a group derived from the above-mentioned "$C_{1-3}$ alkoxy group" by replacing one or more hydrogen atom(s) at arbitrary position(s) by one or more identical or different halogen atoms selected from the group consisting of fluorine atoms, chlorine atoms, bromine atoms and iodine atoms.

A "$C_{1-6}$ alkylene group" is a bivalent group derived from the above-mentioned "$C_{1-6}$ alkyl group" by removing a hydrogen atom at an arbitrary position and may, for example, be a methylene group, an ethylene group, a propane-1,3-diyl group, a propane-1,2-diyl group, a 2,2-dimethyl-propane-1,3-diyl group, a hexane-1,6-diyl group, or a 3-methylbutane-1,2-diyl group or the like.

A "$C_{1-3}$ alkylene group" is a methylene group, an ethylene group, a propane-1,3-diyl group or a propane-1,2-diyl group.

A "$C_{1-6}$ haloalkylene group" is a group derived from the above-mentioned "$C_{1-6}$ alkylene group" by replacing one or more hydrogen atom(s) at arbitrary position(s) by one or more identical or different halogen atoms selected from the group consisting of fluorine atoms, chlorine atoms, bromine atoms and iodine atoms.

A "$C_{1-3}$ haloalkylene group" is a group derived from the above-mentioned "$C_{1-3}$ alkylene group" by replacing one or more hydrogen atom(s) at arbitrary position(s) by one or more identical or different halogen atoms selected from the group consisting of fluorine atoms, chlorine atoms, bromine atoms and iodine atoms.

A "$C_{2-6}$ alkenylene group" is a bivalent group derived from the above-mentioned "$C_{2-6}$ alkenyl group" by removing a hydrogen atom at an arbitrary position and may, for example, be an ethenylene group, an ethene-1,1-diyl group, an ethane-1,2-diyl group, a propene-1,1-diyl group, a propene-1,2-diyl group, a propene-1,3-diyl group, a but-1-ene-1,4-diyl group, a but-1-ene-1,3-diyl group, a but-2-ene-1,4-diyl group, a but-1,3-diene-1,4-diyl group, a pent-2-ene-1,5-diyl group, a hex-3-ene-1,6-diyl group, a hexa-2,4-diene-1,6-diyl group or the like.

A "$C_{2-3}$ alkenylene group" is an ethene-1,1-diyl group, an ethane-1,2-diyl group, a propene-1,1-diyl group, a propene-1,2-diyl group, a propene-1,3-diyl group.

A "$C_{2-6}$ alkynylene group" is a linear or branched alkynylene group having at least one triple bond and 2 to 6 carbon atoms and may, for example, be an ethyn-1,2-diyl group, a propyn-1,2-diyl group, a but-1-yn-1,4-diyl group, a but-1-yn-1,3-diyl group, a but-2-yn-1,4-diyl group, a pent-2-yn-1,5-diyl group, a pent-2-yn-1,4-diyl group, a hex-3-yn-1,6-diyl group or the like.

A "$C_{6-14}$ aromatic carbocycle" is a monocyclic, bicyclic or tricyclic aromatic carbocycle having 6 to 14 carbon atoms as the sole ring-constituting atoms and may, for example, be benzene, pentalene, naphthalene, azulene, anthracene, phenanthrene or the like.

A "$C_{6-14}$ aryl group" is a monovalent group derived from the above-mentioned "$C_{6-14}$ aromatic carbocycle" by removing a hydrogen atom and may have the free valence at any position without particular restriction.

A "5 to 10-membered aromatic heterocycle" is a monocyclic or fused aromatic heterocyclyl group having 5 to 10 ring-constituting atoms including 1 to 5 hetero atoms (such as nitrogen atoms, oxygen atoms and sulfur atoms) and may, for example, be furan, thiophene, pyrrole, imidazole, triazole, tetrazole, thiazole, pyrazole, oxazole, isoxazole, isothiazole, thiadiazole, oxadiazole, pyridine, pyrazine, pyridazine, pyrimidine, triazine, purine, pteridine, quinoline, isoquinoline, naphthylidine, quinoxaline, cinnoline, quinazoline, phthalazine, imidazopyridine, imidazothiazole, imidazooxazole, benzothiazole, benzoxazole, benzimidazole, indole, isoindole, indazole, pyrrolopyridine, thienopyridine, furopyridine, benzothiadiazole, benzoxadiazole, pyridopyrimidine, benzofuran, benzothiophene, thienofuran or the like.

In the case of a "5 to 10-membered aromatic heterocycle" having a C═N double bond, it may be in the form of an N-oxide.

A "5 to 10-membered aromatic heterocyclyl group" is a monovalent group derived from the above-mentioned "5 to 10-membered aromatic heterocycle" by removing a hydrogen atom at an arbitrary position and may have the free valence at any position without particular restrictions.

A "5 to 6-membered aromatic heterocycle" is a monocyclic group having 5 to 6 ring-constituting atoms among the above-mentioned "5 to 10-membered aromatic heterocycles" and may, for example, be pyrrole, pyrazole, imidazole, triazole, tetrazole, pyridine, pyridazine, pyrimidine, pyrazine, triazine, furan, thiophene, thiazole, isothiazole, oxazole, isoxazole, oxadiazole, thiadiazole or the like.

A "5 to 6-membered aromatic heterocyclyl group" is a monovalent group derived from the above-mentioned "5 to 6-membered aromatic heterocycle" by removing a hydrogen atom at an arbitrary position and may have the free valence at any position without particular restrictions.

A "3 to 14-membered non-aromatic heterocycle" is a non-aromatic heterocycle:

1) which has 3 to 14 ring-constituting atoms,
2) the ring-constituting atoms of which contains 1 to 7 hetero atoms selected from nitrogen atoms, oxygen atoms or sulfur atoms,
3) which may have one or more carbonyl groups, one or more double or triple bonds in the ring system,
4) which may contain one or more sulfur atoms in the form of sulfinyl or sulfonyl groups as ring-constituting atoms, and
5) which may be a monocyclic ring, a fused ring (in the fused ring, a non-aromatic ring may be fused to non-aromatic ring(s) or to aromatic-ring(s)), a bridged ring or a spiro ring. It may, for example, be azetidine, pyrrolidine, piperidine, azepane, azocane, tetrahydrofuran, tetrahydropyran, morpholine, thiomorpholine, piperazine, thiazolidine, 1,4-dioxane, imidazoline, thiazoline, benzopyran, isochroman, chroman, indoline, isoindoline, azaindane, tetrahydroazanaphthalene, azachroman, tetrahydrobenzofuran, tetrahydrobenzothiophene, 2,3,4,5-tetrahydro-benzo[b]thiophene, 3,4-dihydro-2H-benzo[b][1,4]dioxepane, 6,7-dihydro-5H-cyclopenta[b]pyrazine, 5,6-dihydro-4H-cyclopenta[b]thiophene, 4,5,6,7-tetrahydrobenz[b]thiophene, 2,3-dihydroisoindol-1-one, 3,4-dihydro-2H-isoquinolin-1-one, 3,4-dihydro-2H-benzo[b]oxepin-5-one, 2,3,4,4a,9,9a-hexahydro-1H-carbazole, 1'H-spiro[cyclopropane-1,2-quinoxalin]-3'(4'H)-one, 10H-phenoxazine, [1,3]dioxolo[4,5-f]quinoline or the like.

A "3 to 14-membered non-aromatic heterocyclyl group" is a monovalent group derived from the above-mentioned "3 to 14-membered non-aromatic heterocycle" by removing a hydrogen atom at an arbitrary position. It may have the free valence at any position without particular restrictions, but in the case of an fused ring system consisting of a non-aromatic ring fused to an aromatic ring, it has the free valence in the non-aromatic ring.

A "3 to 11-membered non-aromatic heterocycle" is non-aromatic heterocycle:

1) which has 3 to 11 ring-constituting atoms
2) the ring-constituting atoms of which contains 1 to 5 hetero atoms selected from nitrogen atoms, oxygen atoms or sulfur atoms,
3) which may have one or more carbonyl groups, one or more double or triple bonds in the ring system,
4) which may contain one or more sulfur atoms in the form of sulfinyl or sulfonyl groups as ring-constituting atoms, and
5) which may be a monocyclic ring, a fused ring (in the fused ring, a non-aromatic ring may be fused to non-aromatic ring(s) or to aromatic-ring(s)), a bridged ring or a spiro ring. It may, for example, be azetidine, pyrrolidine, piperidine, azepane, azocane, tetrahydrofuran, tetrahydropyran, morpholine, thiomorpholine, piperazine, thiazolidine, 1,4-dioxane, imidazoline, thiazoline, benzopyran, isochroman, chroman, indoline, isoindoline, azaindane, tetrahydroazanaphthalene, azachroman, tetrahydrobenzofuran, tetrahydrobenzothiophene, 2,3,4,5-tetrahydro-benzo[b]thiophene, 3,4-dihydro-2H-benzo[b][1,4]oxepine, 6,7-dihydro-5H-cyclopenta[b]pyrazine, 5,6-dihydro-4H-cyclopenta[b]thiophene, 4,5,6,7-tetrahydrobenzo[b]thiophene, 2,3-dihydroisoindol-1-one, 3,4-dihydro2H-isoquinolin-1-one, 3,4-dihydro2H-benzo[b]oxepin-5-one or the like.

A 3 to 11-membered non-aromatic heterocyclyl group" is a monovalent group derived from the above-mentioned "3 to 11-membered non-aromatic heterocycle" by removing a hydrogen atom at an arbitrary position. It may have the free valence at any position without particular restrictions, but in the case of an fused ring system consisting of a non-aromatic ring fused to an aromatic ring, it has the free valence in the non-aromatic ring.

A "4 to 7-membered non-aromatic heterocycle" is a monocyclic non-aromatic heterocycle:

1) which has 4 to 7 ring-constituting atoms
2) the ring-constituting atoms of which contains 1 to 3 hetero atoms selected from nitrogen atoms, oxygen atoms and sulfur atoms,
3) which may have one or more carbonyl groups, one or more double or triple bonds in the ring system, and
4) which may contain one or more sulfur atoms in the form of sulfinyl or sulfonyl groups as ring-constituting atoms. It may, for example, be azetidine, pyrrolidine, pyrrolidinone, oxazolidine, isoxazolidine, thiazolidine, isothiazolidine, piperazine, piperazinone, piperidine, piperidinone, morpholine, thiomorpholine, azepine, diazepine, oxetane, tetrahydrofuran, 1,3-dioxorane, tetrahydropyran, 1,4-dioxane, oxepane, homomorpholine or the like.

A "4 to 7-membered non-aromatic heterocyclyl group" is a monovalent group derived from the above-mentioned "4 to 7-membered non-aromatic heterocycle" by removing a hydrogen atom at an arbitrary position and may have the free valence at any position without particular restrictions.

A "$C_{1-6}$ alkylthio group" is a group consisting of the above-mentioned "$C_{1-6}$ alkyl group" attached to a sulfur atom and may, for example, be a methylthio group, an ethylthio group, a n-propylthio group, an isopropylthio group, a n-butylthio group, an isobutylthio group, a t-butylthio group, a n-pentylthio group, a n-hexylthio group or the like.

A "$C_{1-3}$ alkylthio group" is a group consisting of the above-mentioned "$C_{1-3}$ alkyl group" attached to a sulfur atom and may, for example, be a methylthio group, an ethylthio group, a n-propylthio group or an isopropylthio group.

A "$C_{1-6}$ haloalkylthio group" is a group derived from the above-mentioned "$C_{1-6}$ alkylthio group" by replacing one or more hydrogen atom(s) at arbitrary position(s) by one or more identical or different halogen atoms selected from the group consisting of fluorine atoms, chlorine atoms, bromine atoms and iodine atoms.

A "$C_{1-3}$ haloalkylthio group" is a group derived from the above-mentioned "$C_{1-3}$ alkylthio group" by replacing one or more hydrogen atom(s) at arbitrary position(s) by one or more identical or different halogen atoms selected from the group consisting of fluorine atoms, chlorine atoms, bromine atoms and iodine atoms.

A "$C_{1-6}$ alkylsulfonyl group" is a group consisting of the above-mentioned "$C_{1-6}$ alkyl group" attached to a sulfonyl group and may, for example, be a methylsulfonyl group, an ethylsulfonyl group, a n-propylsulfonyl group, an isopropylsulfonyl group, a n-butylsulfonyl group, an isobutylsulfonyl group, a t-butylsulfonyl group, a n-pentylsulfonyl group, a n-hexylsulfonyl group or the like.

A "$C_{1-3}$ alkylsulfonyl group" is a group consisting of the above-mentioned "$C_{1-3}$ alkyl group" attached to a sulfonyl group and may, for example, be a methylsulfonyl group, an ethylsulfonyl group, a n-propylsulfonyl group or an isopropylsulfonyl group.

A "$C_{1-6}$ haloalkylsulfonyl group" is a group derived from the above-mentioned "$C_{1-6}$ alkylsulfonyl group" by replacing one or more hydrogen atom(s) at arbitrary position(s) by one or more identical or different halogen atoms selected from the group consisting of fluorine atoms, chlorine atoms, bromine atoms and iodine atoms.

A "$C_{1-3}$ haloalkylsulfonyl group" is a group derived from the above-mentioned "$C_{1-3}$ alkylsulfonyl group" by replacing one or more hydrogen atom(s) at arbitrary position(s) by one or more identical or different halogen atoms selected from the group consisting of fluorine atoms, chlorine atoms, bromine atoms and iodine atoms.

A "$C_{1-6}$ alkoxycarbonyl group" is a group consisting of the above-mentioned "$C_{1-6}$ alkoxy group" attached to a carbonyl group and may, for example, be a methoxycarbonyl group, an ethoxycarbonyl group, a n-propoxycarbonyl group, an isopropoxycarbonyl group, a n-butoxycarbonyl group, an isobutoxycarbonyl group, a t-butoxycarbonyl group, a n-pentyloxycarbonyl group, a n-hexyloxycarbonyl group or the like.

A "$C_{1-3}$ alkoxycarbonyl group" is a methoxycarbonyl group, an ethoxycarbonyl group, a n-propoxycarbonyl group or an isopropoxycarbonyl group.

A "mono-$C_{1-6}$ alkylamino group" is a group consisting of the above-mentioned "$C_{1-6}$ alkyl group" attached to an amino group and may, for example, be a methylamino group, an ethylamino group, a n-propylamino group, an isopropylamino group, a n-butylamino group, an isobutylamino group, a t-butylamino group, a n-pentylamino group, a n-hexylamino group or the like.

A "mono-$C_{1-3}$ alkylamino group" is a methylamino group, an ethylamino group, a n-propylamino group or an isopropylamino group.

A "di-$C_{1-6}$ alkylamino group" is a group consisting of an amino group attached to two identical or different "$C_{1-6}$ alkyl groups" such as those mentioned above and may, for example, be a dimethylamino group, a diethylamino group, a di-n-propylamino group, a diisopropylamino group, a di-n-butylamino group, a diisobutylamino group, a di-t-butylamino group, a di-n-pentylamino group, a di-n-hexylamino group, an N-ethyl-N-methylamino group, an N-methyl-N-n-propylamino group, an N-isopropyl-N-methylamino group, an N-n-butyl-N-methylamino group, an N-isobutyl-N-methylamino group, an N-t-butyl-N-methylamino group, an N-methyl-N-n-pentylamino group, N-n-hexyl-N-methylamino group, an N-ethyl-N-n-propylamino group, an N-ethyl-N-isopropylamino group, an N-n-butyl-N-ethylamino group, an N-ethyl-N-isobutylamino group, an N-t-butyl-N-ethylamino group, an N-ethyl-N-n-pentylamino group, an N-ethyl-N-n-hexylamino group or the like.

A "di-$C_{1-3}$ alkylamino group" is a dimethylamino group, a diethylamino group, a di-n-propylamino group, a diisopropylamino group, an N-ethyl-N-methylamino group, an N-methyl-N-n-propylamino group, an N-isopropyl-N-methylamino group, an N-ethyl-N-n-propylamino group or an N-ethyl-N-isopropylamino group.

A "$C_{1-6}$ alkylcarbonyl group" is a group consisting of the above-mentioned "$C_{1-6}$ alkyl group" attached to a carbonyl group and may, for example, be an acetyl group, a propionyl group, a butyryl group, an isobutyryl group, a pentanoyl group, a 3-methylbutanoyl group, a pivaloyl group, a hexanoyl group or a heptanoyl group.

A "$C_{1-3}$ alkylcarbonyl group" is an acetyl group, a propionyl group, a butyryl group or an isobutyryl group.

A "$C_{1-6}$ haloalkylcarbonyl group" is a group derived from the above-mentioned "$C_{1-6}$ alkylcarbonyl group" by replacing one or more hydrogen atom(s) at arbitrary position(s) by one or more identical or different halogen atoms selected from the group consisting of fluorine atoms, chlorine atoms, bromine atoms and iodine atoms.

A "$C_{1-3}$ haloalkylcarbonyl group" is a group derived from the above-mentioned "$C_{1-3}$ alkylcarbonyl group" by replacing one or more hydrogen atom(s) at arbitrary position(s) by one or more identical or different halogen atoms selected from the group consisting of fluorine atoms, chlorine atoms, bromine atoms and iodine atoms.

A "mono-$C_{1-6}$ alkylaminocarbonyl group" is a group consisting of the above-mentioned "mono-$C_{1-6}$ alkylamino group" attached to a carbonyl group and may, for example, be a methylaminocarbonyl group, an ethylaminocarbonyl group, a n-propylaminocarbonyl group, an isopropylaminocarbonyl group, a n-butylaminocarbonyl group, an isobutylaminocarbonyl group, a t-butylaminocarbonyl group, a n-pentylaminocarbonyl group, a n-hexylaminocarbonyl group or the like.

A "mono-$C_{1-3}$ alkylaminocarbonyl group" is a methylaminocarbonyl group, an ethylaminocarbonyl group, a n-propylaminocarbonyl group or an isopropylaminocarbonyl group.

A "di-$C_{1-6}$ alkylaminocarbonyl group" is a group consisting of the above-mentioned "di-$C_{1-6}$ alkylamino group" attached to a carbonyl group and may, for example, be a dimethylaminocarbonyl group, a diethylaminocarbonyl group, a di-n-propylaminocarbonyl group, a diisopropylaminocarbonyl group, a di-n-butylaminocarbonyl group, a diisobutylaminocarbonyl group, a di-t-butylaminocarbonyl group, a di-n-pentylaminocarbonyl group, a di-n-hexylaminocarbonyl group, an N-ethyl-N-methylaminocarbonyl group, an N-methyl-N-n-propylaminocarbonyl group, an N-isopropyl-N-methylaminocarbonyl group, an N-n-butyl-N-methylaminocarbonyl group, an N-isobutyl-N-methylaminocarbonyl group, an N-t-butyl-N-methylaminocarbonyl group, an N-methyl-N-n-pentylaminocarbonyl group, an N-n-hexyl-N-methylaminocarbonyl group, an N-ethyl-N-n-propylaminocarbonyl group, an N-ethyl-N-isopropylaminocarbonyl group, an N-n-butyl-N-ethylaminocarbonyl group, an N-ethyl-N-isobutylaminocarbonyl group, an N-t-butyl-N-ethylaminocarbonyl group, an N-ethyl-N-n-pentylaminocarbonyl group, an N-ethyl-N-n-hexylaminocarbonyl group or the like.

A "di-$C_{1-3}$ alkylaminocarbonyl group" is a dimethylaminocarbonyl group, a diethylaminocarbonyl group, a di-n-propylaminocarbonyl group, a diisopropylaminocarbonyl group, an N-ethyl-N-methylaminocarbonyl group, an N-methyl-N-n-propylaminocarbonyl group, an N-isopropyl-N-methylaminocarbonyl group, N-ethyl-N-n-propylaminocarbonyl group, or an N-ethyl-N-isopropylaminocarbonyl group.

A "$C_{1-6}$ alkylcarbonylamino group" is a group consisting of the above-mentioned "$C_{1-6}$ alkylcarbonyl group" attached to an amino group and may, for example, be a methylcarbonylamino group, an ethylcarbonylamino group, a n-propylcarbonylamino group, an isopropylcarbonylamino group, a n-butylcarbonylamino group, an isobutylcarbonylamino group, a t-butylcarbonylamino group, a n-pentylcarbonylamino group, a n-hexylcarbonylamino group or the like.

A "$C_{1-3}$ alkylcarbonylamino group" is a methylcarbonylamino group, an ethylcarbonylamino group, a n-propylcarbonylamino group or an isopropylcarbonylamino group.

A "mono-$C_{1-6}$ alkylaminosulfonyl group" is a group consisting of the above-mentioned "mono-$C_{1-6}$ alkylamino group" attached to a sulfonyl group and may, for example, be a methylaminosulfonyl group, an ethylaminosulfonyl group, a n-propylaminosulfonyl group, an isopropylaminosulfonyl group, a n-butylaminosulfonyl group, an isobutylaminosulfonyl group, a t-butylaminosulfonyl group, a n-pentylaminosulfonyl group, a n-hexylaminosulfonyl group or the like.

A "mono-$C_{1-3}$ alkylaminosulfonyl group" is a methylaminosulfonyl group, an ethylaminosulfonyl group, a n-propylaminosulfonyl group or an isopropylaminosulfonyl group.

A "di-$C_{1-6}$ alkylaminosulfonyl group" is a group consisting of the above-mentioned "di-$C_{1-6}$ alkylamino group" attached to a sulfonyl group and may, for example, be a dimethylaminosulfonyl group, a diethylaminosulfonyl group, a di-n-propylaminosulfonyl group, a diisopropylaminosulfonyl group, a di-n-butylaminosulfonyl group, a diisobutylaminosulfonyl group, a di-t-butylaminosulfonyl group, a di-n-pentylaminosulfonyl group, a di-n-hexylaminosulfonyl group, an N-ethyl-N-methylaminosulfonyl group, an N-methyl-N-n-propylaminosulfonyl group, an N-isopropyl-N-methylaminosulfonyl group, an N-n-butyl-N-methylaminosulfonyl group, an N-isobutyl-N-methylaminosulfonyl group, an N-t-butyl-N-methylaminosulfonyl group, an N-methyl-N-n-pentylaminosulfonyl group, N-n-hexyl-N-methylaminosulfonyl group, an N-ethyl-N-n-propylaminosulfonyl group, an N-ethyl-N-isopropylaminosulfonyl group, an N-n-butyl-N-ethylaminosulfonyl group, an N-ethyl-N-isobutylaminosulfonyl group, an N-t-butyl-N-ethylaminosulfonyl group, an N-ethyl-N-n-pentylaminosulfonyl group, an N-ethyl-N-n-hexylaminosulfonyl group or the like.

A "di-$C_{1-3}$ alkylaminosulfonyl group" is a dimethylaminosulfonyl group, a diethylaminosulfonyl group, a di-n-propylaminosulfonyl group, a diisopropylaminosulfonyl group, an N-ethyl-N-methylaminosulfonyl group, an N-methyl-N-n-propylaminosulfonyl group, an N-isopropyl-N-methylaminosulfonyl group, an N-ethyl-N-n-propylaminosulfonyl group, or an N-ethyl-N-isopropylaminosulfonyl group or an N-isopropyl-N-n-propylaminosulfonyl group.

A "$C_{1-6}$ alkylsulfonylamino group" is a group consisting of the above-mentioned "$C_{1-6}$ alkylsulfonyl group" attached to an amino group and may, for example, be a methylsulfonylamino group, an ethylsulfonylamino group, a n-propylsulfonylamino group, an isopropylsulfonylamino group, a n-butylsulfonylamino group, an isobutylsulfonylamino group, a t-butylsulfonylamino group, a n-pentylsulfonylamino group, a n-hexylsulfonylamino group or the like.

A "$C_{1-6}$ alkoxycarbonylamino group" is a group consisting of the above-mentioned "$C_{1-6}$ alkoxycarbonyl group" attached to an amino group and may, for example, be a methoxycarbonylamino group, an ethoxycarbonylamino group, a n-propoxycarbonylamino group, an isopropoxycarbonylamino group, a n-butoxycarbonylamino group, an isobutoxycarbonylamino group, a t-butoxycarbonylamino group, a n-pentyloxycarbonylamino group, a n-hexyloxycarbonylamino group or the like.

A "$C_{3-6}$ cycloalkoxy group" is a group consisting of the above-mentioned "$C_{3-6}$ cycloalkyl group" attached to an oxygen atom and may, for example, be a cyclopropoxy group, a cyclobutoxy group, a cyclopentyloxy group, a cyclohexyloxy group or the like.

A "$C_{3-6}$ cycloalkylamino group" is a group consisting of the above-mentioned "$C_{3-6}$ cycloalkyl group" attached to an amino group and may, for example, be a cyclopropylamino group, a cyclobutylamino group, a cyclopentylamino group, a cyclohexylamino group or the like.

A "di-$C_{3-6}$ cycloalkylamino group" is a group consisting of an amino group attached to two identical or different "$C_{3-6}$ cycloalkyl groups" such as those mentioned above and may, for example, be a dicyclopropylamino group, a dicyclobutylamino group, a dicylopentylamino group, a dicyclohexylamino group or the like.

A "$C_{3-6}$ cycloalkylthio group" is a group consisting of the "$C_{3-6}$ cycloalkyl group" attached to —S— and may, for example, be a cyclopropylthio group, a cyclobutylthio group, a cyclopentylthio group, a cyclohexylthio group or the like.

A "$C_{3-6}$ cycloalkylcarbonyl group" is a group consisting of the above-mentioned "$C_{3-6}$ cycloalkyl group" attached to a carbonyl group and may, for example, be a cyclopropylcarbonyl group, a cyclobutylcarbonyl group, a cyclopentylcarbonyl group, a cyclohexylcarbonyl group or the like.

A "$C_{3-6}$ cycloalkylsulfonyl group" is a group consisting of the above-mentioned "$C_{3-6}$ cycloalkyl group" attached to a sulfonyl group and may, for example, be a cyclopropylsulfonyl group, a cyclobutylsulfonyl group, a cyclopentylsulfonyl group, a cyclohexylsulfonyl group or the like.

A "8 to 14-membered aromatic ring-condensed alicyclic hydrocarbon" is a fused ring system:

1) which has 8 to 14 ring-constituting atoms,
2) all the ring-constituting atoms of which are carbon atoms,
3) which may have one or more carbonyl groups, one or more double or triple bonds in the ring system, and
4) which consists of non-aromatic ring(s) fused to aromatic-ring(s). It may, for example, be 1H-indene, 2,3-dihydroindene, 1H-inden-1-on, 1,2-dihydronaphthalene, 1,2,3,4-tetrahydronaphthalene, 3,4-dihydronaphthalen-1(2H)-on, 1,2,3,4-tetrahydro-1,4-methanonaphthalene, 1,2,3,4-tetrahydrophenanthrene, 2,3-dihydro-1H-phenalene, 9H-fluorene or the like.

A "8 to 14-membered aromatic ring-condensed alicyclic hydrocarbon group" is a monovalent group derived from the above-mentioned "8 to 14-membered aromatic ring-condensed alicyclic hydrocarbon" by removing a hydrogen atom at an arbitrary position. It may have the free valence at any position in the alicyclic carbocycle without particular restrictions.

It may, for example, be a 1H-inden-1-yl group, a 1H-inden-2-yl group, a 1H-inden-3-yl group, a 1,2,3,4-tetrahydronaphthalen-1-yl group, a 1,2,3,4-tetrahydronaphthalen-2-yl group, a 1,2,3,4-tetrahydronaphthalen-3-yl group, a 1,2,3,4-tetrahydronaphthalen-4-yl group, a 4-oxo-1,2,3,4-tetrahydronaphthalen-1-yl group, a 9H-fluoren-9-yl group or the like.

A "8 to 14-membered partially saturated aromatic cyclic group" is a group derived from 1) a bicyclic or tricyclic ring having 8 to 14 ring-constituting atoms and consisting of a non-aromatic ring fused to aromatic rings among the above-mentioned "3 to 14-membered non-aromatic heterocycle" or 2) the above-mentioned "8 to 14-membered aromatic ring-condensed alicyclic hydrocarbon" by removing a hydrogen atom at an arbitrary position. It may have the free valence at any position in the aromatic ring without particular restrictions.

It may, for example, be a 1H-inden-4-yl group, a 1H-inden-5-yl group, a 1H-inden-6-yl group, a 1H-inden-7-yl group, a 5,6,7,8-tetrahydronaphthalen-1-yl group, a 5,6,7,8-tetrahydronaphthalen-2-yl group, a 5,6,7,8-tetrahydronaphthalen-3-yl group, a 5,6,7,8-tetrahydronaphthalen-4-yl group, a 9H-fluorene2-yl group, an indolin-4-yl group, an indolin-5-yl group, an indolin-6-yl group, an indolin-7-yl group, a chroman-5-yl group, a chroman-6-yl group, a chroman-7-yl group, a chroman-8-yl group, a 4,5,6,7-tetrahydrobenzo[b]thiophen-3-yl group, a 2,3,4,4a,9,9a-hexahydro-1H-carbazol-5-yl group or the like.

A "8 to 11-membered aromatic ring-condensed alicyclic hydrocarbon" is a fused ring system:
1) which has 8 to 11 ring-constituting atoms,
2) all the ring-constituting atoms of which are carbon atoms,
3) which may have one or more carbonyl groups, one or more double or triple bonds in the ring system, and
4) which consists of an alicyclic hydrocarbon fused to a benzene ring, and it may, for example, be 1H-indene, 2,3-dihydroindene, 1H-inden-1-on, 1,2-dihydronaphthalene, 1,2,3,4-tetrahydronaphthalene, 3,4-dihydronaphthalen-1(2H)-one or the like.

A "8 to 11-membered aromatic ring-condensed alicyclic hydrocarbon group" is a group derived from the above-mentioned "8 to 11-membered aromatic ring-condensed alicyclic hydrocarbon" by removing a hydrogen atom at an arbitrary position. and may have the free valence at any position in the alicyclic carbocycle without particular restrictions.

It may, for example, be a 1H-inden-4-yl group, a 1H-inden-5-yl group, a 1H-inden-6-yl group, a 1H-inden-7-yl group, a 5,6,7,8-tetrahydronaphthalen-1-yl group, a 5,6,7,8-tetrahydronaphthalen-2-yl group, a 5,6,7,8-tetrahydronaphthalen-3-yl group, a 5,6,7,8-tetrahydronaphthalen-4-yl group or the like.

A "8 to 11-membered partially saturated aromatic cyclic group" is a group derived from 1) a partially saturated aromatic ring having 8 to 11 ring-constituting atoms and consisting of an aromatic ring fused to a non-aromatic ring or 2) the above-mentioned "8 to 11-membered aromatic ring-condensed alicyclic hydrocarbon group" by removing a hydrogen atom at an arbitrary position. and may have the free valence at any position in the aromatic ring without particular restrictions.

It may, for example, be a 1H-inden-4-yl group, a 1H-inden-5-yl group, a 1H-inden-6-yl group, a 1H-inden-7-yl group, a 5,6,7,8-tetrahydronaphthalen-1-yl group, a 5,6,7,8-tetrahydronaphthalen-2-yl group, a 5,6,7,8-tetrahydronaphthalen-3-yl group, a 5,6,7,8-tetrahydronaphthalen-4-yl group, an indolin-4-yl group, an indolin-5-yl group, an indolin-6-yl group, an indolin-7-yl group, a chroman-5-yl group, a chroman-6-yl group, a chroman-7-yl group, a chroman-8-yl group, 4,5,6,7-tetrahydrobenzo[b]thiophen-3-yl group or the like.

Now, the tricyclic pyrimidine compounds of the present invention represented by the formula ($I^a$) will be described.

First, how the ring $A^a$ is fused in the tricyclic pyrimidine compounds of the present invention will be described.

As is indicated in the formula ($I^a$), the ring $A^a$ is fused to the pyrimidine ring so as to have a carbon atom and a nitrogen atom in common and attached to $L^{1a}$ via a carbon atom in the ring $A^a$ in the formula ($I^a$).

($I^a$)

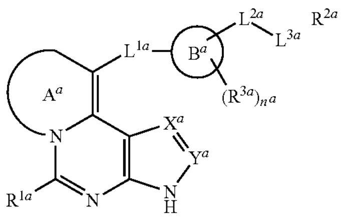

Therefore, when the ring $A^a$ is represented by the formula ($II^a$-1), ($II^a$-1)

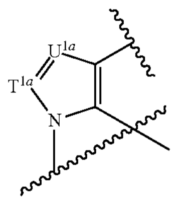

the molecule as a whole is represented by the formula ($I^a$)-2:

($I^a$)-2

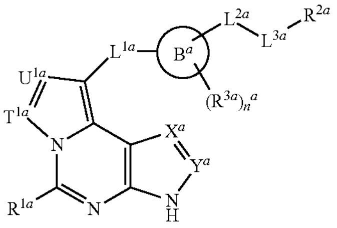

and when the ring $A^a$ is represented by the formula ($II^a$-2), ($II^a$-2)

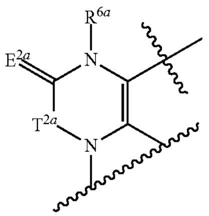

the molecule as a whole is represented by the formula ($I^a$)-3.

($I^a$)-3

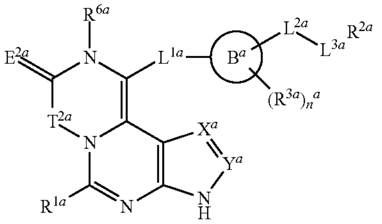

In the present invention, the formulae representing $L^{3a}$ indicate that the left ends of the formulae are bonded to $L^{2a}$, and the right ends of the formulae are bonded to $R^{2a}$.

In the present invention, $L^{1a}$, $L^{2a}$ and $R^{3a}$ may be bounded to the ring $B^a$ in the formula ($I^a$) at any positions of the ring $B^a$ without any particular restrictions.

Next, preferred structures of the respective substituents will be mentioned.

A preferred embodiment of the substituent $R^{1a}$ is a hydrogen atom or a halogen atom.

A more preferred embodiment of the substituent $R^{1a}$ is a hydrogen atom.

A preferred embodiment of the substituent $Y^a$ is $CR^{10a}$ (wherein $R^{10a}$ is a hydrogen atom, a halogen atom, a cyano group, a $C_{1-6}$ alkyl group, a $C_{1-6}$ haloalkyl group or a $C_{3-6}$ cycloalkyl group).

A more preferred embodiment of the substituent $Y^a$ is $CR^{10a}$ (wherein $R^{10a}$ is a hydrogen atom).

A preferred embodiment of the substituent $X^a$ is $CR^{9a}$ (wherein $R^{9a}$ is a hydrogen atom, a halogen atom, a cyano group, a $C_{1-6}$ alkyl group, a $C_{1-6}$ haloalkyl group or a $C_{3-6}$ cycloalkyl group) or a nitrogen atom.

A more preferred embodiment of the substituent $X^a$ is $CR^{9a}$ (wherein $R^{9a}$ is a hydrogen atom).

Another more preferred embodiment of the substituent $X^a$ is $CR^{9a}$ (wherein $R^{9a}$ is a halogen atom).

A preferred embodiment of the ring $A^a$ is represented by any of the following formulae ($VII^a$-1) to ($VII^a$-4):

($VII^a$)

($VII^a$-1)

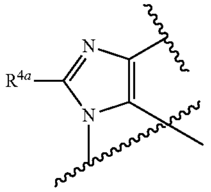

-continued ($VII^a$-2)

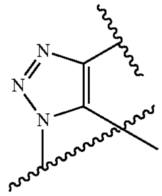

($VII^a$-3)

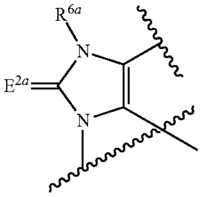

($VII^a$-4)

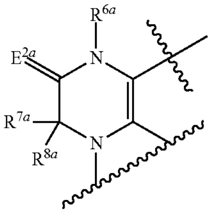

(wherein $E^{2a}$ is an oxygen atom or a sulfur atom, each of $R^{4a}$, $R^{7a}$ and $R^{8a}$ is independently a hydrogen atom, an amino group, a carbamoyl group, a halogen atom, a cyano group, a $C_{1-6}$ alkyl group, a $C_{1-6}$ alkoxy group, a $C_{1-6}$ alkylthio group, a $C_{1-6}$ alkylsulfonyl group (the $C_{1-6}$ alkyl group, the $C_{1-6}$ alkoxy group, the $C_{1-6}$ alkylthio group and the $C_{1-6}$ alkylsulfonyl group are unsubstituted or substituted with one or more identical or different substituents independently selected from the substituent set $V^{3a}$), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the substituent set $V^{1a}$), and $R^{ha}$ is a hydrogen atom, a $C_{1-6}$ alkyl group (the $C_{1-6}$ alkyl group is unsubstituted or substituted with one or more identical or different substituents independently selected from the substituent set $V^{3a}$), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the substituent set $V^{1a}$)).

A more preferred embodiment of the ring $A^a$ is represented by any of the following formulae ($IV^a$-1) to ($IV^a$-3):

($IV^a$)

($IV^a$-1)

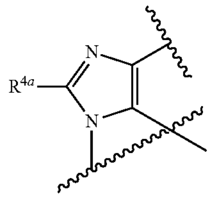

($IV^a$-2)

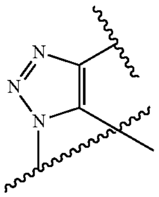

($IV^a$-3)

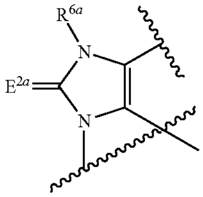

(wherein $E^{2a}$ is an oxygen atom or a sulfur atom, $R^{4a}$ is a hydrogen atom, a halogen atom, a $C_{1-3}$ alkyl group, a $C_{1-3}$ alkoxy group, a $C_{1-3}$ alkylthio group or a $C_{1-3}$ alkylsulfonyl group, and $R^{6a}$ is a hydrogen atom or a $C_{1-3}$ alkyl group).

A further preferred embodiment of the ring $A^a$ is represented by any of the following formulae ($VIII^a$-1) to ($VIII^a$-5).

($VIII^a$)

($VIII^a$-1)

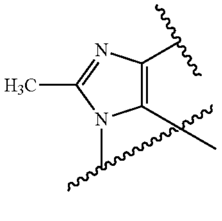

($VIII^a$-2)

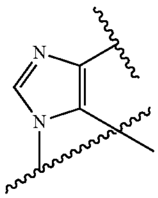

-continued ($VIII^a$-3)

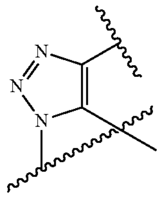

($VIII^a$-4)

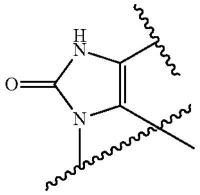

($VIII^a$-5)

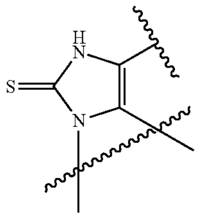

A particularly preferred embodiment of the ring $A^a$ is represented by the formula ($XXX^a$).

($XXX^a$)

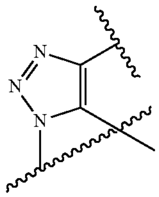

A preferred embodiment of the substituent $L^{1a}$ is a single bond or a $C_{1-3}$ alkylene group.

A more preferred embodiment of the substituent $L^{1a}$ is a single bond or a methylene group.

A further preferred embodiment of the substituent $L^{1a}$ is a single bond.

A preferred embodiment of the ring $B^a$ is a $C_{3-11}$ cycloalkane, a 3 to 11-membered non-aromatic heterocycle, a $C_{6-14}$ aromatic carbocycle or a 5 to 10-membered aromatic heterocycle.

Another preferred embodiment of the ring $B^a$ is a $C_{3-11}$ cycloalkane (a ring-constituting methylene group of the $C_{3-11}$ cycloalkane and the $C_{3-11}$ cycloalkene is replaced by a carbonyl group).

A more preferred embodiment of the ring Er is a $C_{4-7}$ cycloalkane, a 4 to 7-membered non-aromatic heterocycle, benzene or a 5 to 6-membered aromatic heterocycle.

Another more preferred embodiment of the ring Er is a $C_{4-7}$ cycloalkane (a ring-constituting methylene group of the $C_{4-7}$ cycloalkane is replaced by a carbonyl group).

Another more preferred embodiment of the ring $B^a$ is spiro[2,5]octane or adamantane.

A further preferred embodiment of the ring $B^a$ is azetidine, pyrrolidine, piperidine, azepane, cyclobutane, cyclopentane, cyclohexane, bicyclo[2.2.1]heptane, cycloheptane or benzene.

Another further preferred embodiment of the ring $B^a$ is cyclohexanone.

A particularly preferred embodiment of the ring $B^a$ is cyclohexane or piperidine.

A preferred embodiment of the substituent $L^{2a}$ is a single bond, a $C_{1-3}$ alkylene group or a $C_{1-3}$ haloalkylene group (the $C_{1-3}$ alkylene group and the $C_{1-3}$ haloalkylene group are substituted with a cyano group).

Another preferred embodiment of the substituent $L^{2a}$ is a $C_{1-3}$ alkylene group or a $C_{1-3}$ haloalkylene group (the $C_{1-3}$ alkylene group and the $C_{1-3}$ haloalkylene group are unsubstituted or substituted with a hydroxy group).

Another preferred embodiment of the substituent $L^{2a}$ is a $C_{2-3}$ alkenylene group (the $C_{2-3}$ alkenylene group is unsubstituted or substituted with a hydroxy group or a cyano group).

Another preferred embodiment of the substituent $L^{2a}$ is a $C_{1-3}$ alkylene group or a $C_{2-3}$ alkenylene group (the $C_{1-3}$ alkylene group and the $C_{2-3}$ alkenylene group are substituted with two cyano groups).

Another preferred embodiment of the substituent $L^{2a}$ is a $C_{1-6}$ alkylene group or a $C_{2-6}$ alkenylene group (the $C_{1-6}$ alkylene group and the $C_{2-6}$ alkenylene group are unsubstituted or substituted with one or two cyano groups) or a $C_{1-6}$ haloalkylene.

Another preferred embodiment of the substituent $L^{2a}$ is $=C(R^{15a})-$ (wherein $R^{15a}$ is a hydrogen atom or a cyano group, and the bond connecting the ring Er and $L^{2a}$ is a double bond) or $=C(R^{15a})-CH_2-$ (wherein $R^{15a}$ is a cyano group, and the bond connecting the ring $B^a$ and $L^{2a}$ is a double bond).

A more preferred embodiment of the substituent $L^{2a}$ is a single bond or a methylene group (the methylene group is unsubstituted or substituted with one or more identical or different halogen atoms independently selected from the group consisting of fluorine atoms, chlorine atoms, bromine atoms and iodine atoms or with a hydroxy group).

Another more preferred embodiment of the substituent $L^{2a}$ is an ethylene group (the ethylene group is unsubstituted or substituted with one or more identical or different halogen atoms independently selected from the group consisting of fluorine atoms, chlorine atoms, bromine atoms and iodine atoms or with a hydroxy group) or a propylene group.

Another more preferred embodiment of the substituent $L^{2a}$ is a $C_{1-3}$ alkylene group (the $C_{1-3}$ alkylene group is substituted with a cyano group).

Another more preferred embodiment of the substituent $L^{2a}$ is a $C_{1-3}$ alkylene group (the $C_{1-3}$ alkylene group is substituted with two cyano groups).

Another more preferred embodiment of the substituent $L^{2a}$ is a $C_{2-3}$ alkenylene group (the $C_{2-3}$ alkenylene group is substituted with a cyano group).

Another more preferred embodiment of the substituent $L^{2a}$ is a $C_{2-3}$ alkenylene group (the $C_{2-3}$ alkenylene group is substituted with two cyano groups).

A further preferred embodiment of the substituent $L^{2a}$ is a single bond or a methylene group.

Another further preferred embodiment of the substituent $L^{2a}$ is a $C_{1-3}$ alkylene group (the $C_{1-3}$ alkylene group is substituted with one or two cyano groups).

A preferred embodiment of the substituent $L^{3a}$ and the substituent $R^{2a}$ is such that $L^{3a}$ is a single bond, and $R^{2a}$ is a hydrogen atom, a halogen atom, a $C_{3-6}$ cycloalkyl group, a 3 to 11-membered non-aromatic heterocyclyl group, a phenyl group or a 5 to 10-membered aromatic heterocyclyl group (the $C_{3-6}$ cycloalkyl group, the 3 to 11-membered non-aromatic heterocyclyl group, the phenyl group and the 5 to 10-membered aromatic heterocyclyl group are unsubstituted or substituted with one or more identical or different substituents independently selected from the substituent set $V^{1a}$).

Another preferred embodiment of the substituent $L^{3a}$ and the substituent $R^{2a}$ is such that $L^{3a}$ is a single bond, and $R^{2a}$ is a hydrogen atom, a halogen atom, an azido group, a $C_{3-6}$ cycloalkyl group, a 3 to 11-membered non-aromatic heterocyclyl group, a phenyl group or a 5 to 10-membered aromatic heterocyclyl group (the $C_{3-6}$ cycloalkyl group, the 3 to 11-membered non-aromatic heterocyclyl group, the phenyl group and the 5 to 10-membered aromatic heterocyclyl group are unsubstituted or substituted with one or more identical or different substituents independently selected from the group consisting of the substituent set $V^{4a}$, the substituent set $V^{9a}$ and $C_{1-6}$ alkyl groups (the $C_{1-6}$ alkyl groups are substituted with a $C_{1-6}$ alkoxycarbonylamino group (the $C_{1-6}$ alkoxycarbonylamino group is unsubstituted or substituted with one or more identical or different halogen atoms independently selected from the group consisting of fluorine atoms, chlorine atoms, bromine atoms and iodine atoms))).

Another preferred embodiment of the substituent $L^{3a}$ and the substituent $R^{2a}$ is such that $L^{3a}$ is a single bond, and $R^{2a}$ is a 8 to 11-membered partially saturated aromatic cyclic group (the 8 to 11-membered partially saturated aromatic cyclic group is unsubstituted or substituted with one or more identical or different substituents independently selected from the substituent set $V^{1a}$).

Another preferred embodiment of the substituent $L^{3a}$ and the substituent $R^{2a}$ is such that $L^{3a}$ is represented by any of the following formulae ($V^a$-1) to ($V^a$-11):

($V^a$)

($V^a$-1)

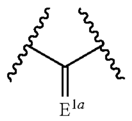

($V^a$-2)

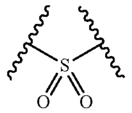

($V^a$-3)

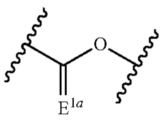

($V^a$-4)

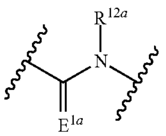

($V^a$-5)

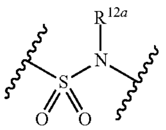

-continued (V$^a$-6)

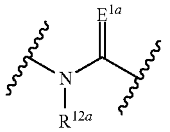

(V$^a$-7)

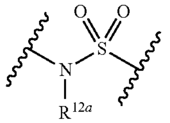

(V$^a$-8)

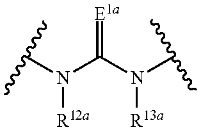

(V$^a$-9)

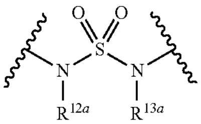

(V$^a$-10)

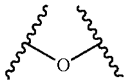

(V$^a$-11)

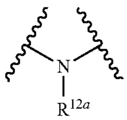

(wherein $E^{1a}$ is an oxygen atom or a sulfur atom, and each of $R^{12a}$ and $R^{13a}$ is independently a hydrogen atom, a $C_{1-6}$ alkyl group or a $C_{1-6}$ haloalkyl group), and $R^{2a}$ is a hydrogen atom, a $C_{1-6}$ alkyl group (the $C_{1-6}$ alkyl group is unsubstituted or substituted with one or more identical or different substituents independently selected from the substituent set $V^{5a}$), a $C_{2-6}$ alkenyl group, a $C_{3-6}$ cycloalkyl group, a 3 to 11-membered non-aromatic heterocyclyl group, a phenyl group or a 5 to 10-membered aromatic heterocyclyl group (the $C_{2-6}$ alkenyl group, the $C_{3-6}$ cycloalkyl group, the 3 to 11-membered non-aromatic heterocyclyl group, the phenyl group and the 5 to 10-membered aromatic heterocyclyl group are unsubstituted or substituted with one or more identical or different substituents independently selected from the substituent set $V^{4a}$).

Another preferred embodiment of the substituent $L^{3a}$ and the substituent $R^{2a}$ is such that $L^{3a}$ is represented by any of the following formulae (XIV$^a$-1) to (XIV$^a$-15) and (XIII$^a$):

(XIV$^a$)

(XIV$^a$-1)

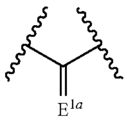

-continued (XIV$^a$-2)

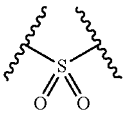

(XIV$^a$-3)

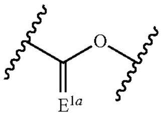

(XIV$^a$-4)

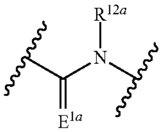

(XIV$^a$-5)

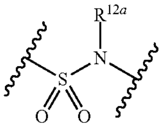

(XIVa-6)

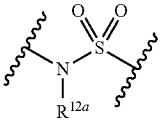

(XIVa-7)

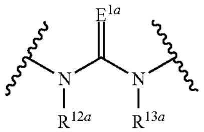

(XIVa-8)

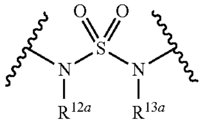

(XIVa-9)

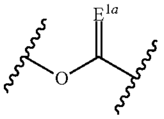

(XIV$^a$-10)

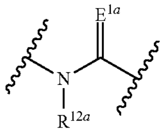

(XIV$^a$-11)

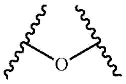

(XIV$^a$-12)

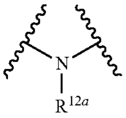

(XIV$^a$-13)

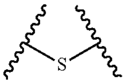

-continued (XIV$^a$-14)

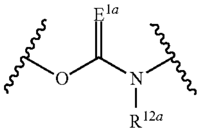

(XIV$^a$-15)

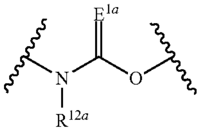

(XIII$^a$)

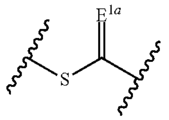

(wherein $E^{1a}$ is an oxygen atom, a sulfur atom or $NR^{11a}$ (wherein $R^{11a}$ is a hydroxy group), and each of $R^{12a}$ and $R^{13a}$ is independently a hydrogen atom, a $C_{1-6}$ alkyl group or a $C_{1-6}$ haloalkyl group), and $R^{2a}$ is a hydrogen atom, a $C_{1-6}$ alkyl group, a $C_{2-6}$ alkenyl group, a $C_{2-6}$ alkynyl group (the $C_{1-6}$ alkyl group, the $C_{2-6}$ alkenyl group and the $C_{2-6}$ alkynyl group are unsubstituted or substituted with one or more identical or different substituents independently selected from the substituent set $V^{6a}$ and the substituent set $V^{9a}$), a $C_{3-11}$ cycloalkyl group, a 3 to 11-membered non-aromatic heterocyclyl group, a phenyl group, a naphthyl group, a 5 to 10-membered aromatic heterocyclyl group, a 8 to 11-membered partially saturated aromatic cyclic group or a 8 to 11-membered aromatic ring-condensed alicyclic hydrocarbon group (the $C_{3-11}$ cycloalkyl group, the 3 to 11-membered non-aromatic heterocyclyl group, the phenyl group, the naphthyl group, the 5 to 10-membered aromatic heterocyclyl group, the 8 to 11-membered partially saturated aromatic cyclic group and the 8 to 11-membered aromatic ring-condensed alicyclic hydrocarbon group are unsubstituted or substituted with one or more identical or different substituents independently selected from the substituent set $V^{1a}$ and the substituent set $V^{9a}$).

Another preferred embodiment of the substituent $L^{3a}$ and the substituent $R^{2a}$ is such that $L^{3a}$ is represented by the formula ($X^a$-9):

($X^a$-9)

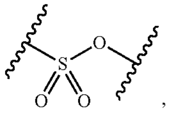

, and $R^{2a}$ is a hydrogen atom.

Another preferred embodiment of the substituent $L^{3a}$ and the substituent $R^{2a}$ is such that $L^{3a}$ is represented by any of the following formulae (XXVI$^a$-1) to (XXVI$^a$-5):

(XXVI$^a$)

(XXVI$^a$-1)

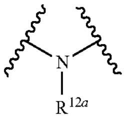

(XXVI$^a$-2)

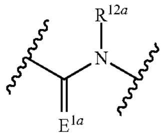

(XXVI$^a$-3)

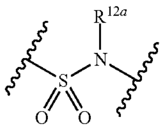

(XXVI$^a$-4)

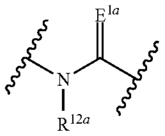

(XXVI$^a$-5)

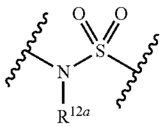

(wherein $E^{1a}$ is an oxygen atom or a sulfur atom, and $R^{12a}$ is a $C_{1-6}$ alkyl group or a $C_{1-6}$ haloalkyl group (the $C_{1-6}$ alkyl group and the $C_{1-6}$ haloalkyl group is substituted with one or two identical or different substituents independently selected from the group consisting of hydroxy groups, amino groups, carboxy groups, carbamoyl groups, sulfamoyl groups, halogen atoms, cyano groups, nitro groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{3-11}$ cycloalkyl groups, 3 to 11-membered non-aromatic heterocyclyl groups, $C_{6-14}$ aryl groups and 5 to 10-membered aromatic heterocyclyl groups (the $C_{3-11}$ cycloalkyl groups, the 3 to 11-membered non-aromatic heterocyclyl groups, the $C_{6-14}$ aryl groups and the 5 to 10-membered aromatic heterocyclyl groups are unsubstituted or substituted with one or more identical or different substituents independently selected from the substituent set $V^{1a}$)), a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted and substituted with one or more identical or different substituents independently selected from the substituent set $V^{1a}$)), and $R^{2a}$ is a $C_{1-6}$ alkyl group, a $C_{2-6}$ alkenyl group, a $C_{2-6}$ alkynyl group (the $C_{1-6}$ alkyl group, the $C_{2-6}$ alkenyl group and the $C_{2-6}$ alkynyl group are unsubstituted or substituted with one or more identical or different substituents independently selected from the substituent set $V^{6a}$ and the substituent set $V^{9a}$), a $C_{3-6}$ cycloalkyl group, a 3 to 11-membered non-aromatic heterocyclyl group, a phenyl group, a naphthyl group or a 5 to 10-membered aromatic heterocyclyl group (the $C_{3-6}$ cycloalkyl group, the 3 to 11-membered non-aromatic heterocyclyl group, the phenyl group, the naphthyl group and the 5 to 10-membered aromatic heterocyclyl group are unsubstituted or substituted with one or more identical or different substituents independently selected from the substituent set $V^{1a}$ and the substituent set $V^{9a}$).

A more preferred embodiment of the substituent $L^{3a}$ and the substituent $R^{2a}$ is such that $L^{3a}$ is a single bond, and $R^{2a}$ is a hydrogen atom, a halogen atom, a $C_{3-6}$ cycloalkyl group, a phenyl group or a 5 to 6-membered aromatic heterocyclyl group (the $C_{3-6}$ cycloalkyl group, the phenyl group and the 5 to 6-membered aromatic heterocyclyl group are unsubstituted or substituted with one or more identical or different substituents independently selected from the substituent set $V^{1a}$).

Another more preferred embodiment of the substituent $L^{3a}$ and the substituent $R^{2a}$ is such that $L^{3a}$ is a single bond, and $R^{2a}$ is a 3 to 11-membered non-aromatic heterocyclyl group (the 3 to 11-membered non-aromatic heterocyclyl group is unsubstituted or substituted with one or more identical or different substituents independently selected from the substituent set $V^{1a}$).

Another more preferred embodiment of the substituent $L^{3a}$ and the substituent $R^{2a}$ is such that $L^{3a}$ is a single bond, and $R^{2a}$ is a $C_{3-6}$ cycloalkyl group, a 3 to 11-membered non-aromatic heterocyclyl group, a phenyl group or a 5 to 6-membered aromatic heterocyclyl group (the $C_{3-6}$ cycloalkyl group, the 3 to 11-membered non-aromatic heterocyclyl group, the phenyl group and the 5 to 6-membered aromatic heterocyclyl group are substituted with identical or different one, two or three substituents independently selected from the group consisting of $C_{1-6}$ alkyl groups, $C_{1-6}$ alkoxy groups, $C_{1-6}$ alkylthio groups, $C_{1-6}$ alkylsulfonyl groups, $C_{1-6}$ alkylcarbonyl groups (the $C_{1-6}$ alkyl groups, the $C_{1-6}$ alkoxy groups, the $C_{1-6}$ alkylthio groups, the $C_{1-6}$ alkylsulfonyl groups and the $C_{1-6}$ alkylcarbonyl groups are substituted with a substituent selected from the group consisting of a hydroxy group, a cyano group, a $C_{1-6}$ alkoxy group and a $C_{1-6}$ alkoxycarbonylamino group), $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, (the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups and the $C_{1-6}$ alkylcarbonylamino groups are substituted with one or more identical or different halogen atoms independently selected from the group consisting of fluorine atoms, chlorine atoms, bromine atoms and iodine atoms or with a hydroxy group or a cyano group), mono-alkylaminosulfonyl groups, di-$C_{1-6}$ alkylaminosulfonyl groups, $C_{1-6}$ alkylsulfonylamino groups, $C_{1-6}$ alkoxycarbonylamino groups (the mono-$C_{1-6}$ alkylaminosulfonyl groups, the di-$C_{1-6}$ alkylaminosulfonyl groups, the $C_{1-6}$ alkylsulfonylamino groups and the $C_{1-6}$ alkoxycarbonylamino groups are unsubstituted or substituted with one or more identical or different halogen atoms independently selected from the group consisting of fluorine atoms, chlorine atoms, bromine atoms and iodine atoms), phenyl groups and 5 to 6-membered aromatic heterocyclyl groups (the phenyl groups and the 5 to 6-membered aromatic heterocyclyl groups are unsubstituted or substituted with one or two identical or different substituents independently selected from the substituent set $V^{1a}$)).

Another more preferred embodiment of the substituent $L^{3a}$ and the substituent $R^{2a}$ is such that $L^{3a}$ is a single bond, and $R^{2a}$ is a $C_{3-6}$ cycloalkyl group, a 3 to 11-membered non-aromatic heterocyclyl group, a phenyl group or a 5 to 6-membered aromatic heterocyclyl group (the $C_{3-6}$ cycloalkyl group, the 3 to 11-membered non-aromatic heterocyclyl group, the phenyl group and the 5 to 6-membered aromatic heterocyclyl group are substituted with a substituent selected from the group consisting of a $C_{1-6}$ alkyl group, a $C_{1-6}$ alkoxy group (the $C_{1-6}$ alkyl group and the $C_{1-6}$ alkoxy group are substituted with a hydroxy group or a cyano group), a mono-$C_{1-6}$ alkylamino group, a di-$C_{1-6}$ alkylamino group, a mono-$C_{1-6}$ alkylaminocarbonyl group, a $C_{1-6}$ alkylcarbonylamino group (the mono-$C_{1-6}$ alkylamino group, the di-$C_{1-6}$ alkylamino group, the mono-$C_{1-6}$ alkylaminocarbonyl group and the $C_{1-6}$ alkylcarbonylamino group are substituted with one or more identical or different substituents independently selected from the group consisting of halogen atoms, hydroxy groups and cyano groups), a phenyl group, a 5 to 6-membered aromatic heterocyclyl group (the phenyl group and the 5 to 6-membered aromatic heterocyclyl group are unsubstituted or substituted with one or two identical or different substituents independently selected from the group consisting of halogen atoms, cyano groups, $C_{1-6}$ alkyl groups and $C_{1-6}$ haloalkyl groups), a mono-$C_{1-6}$ alkylaminosulfonyl group, a di-$C_{1-6}$ alkylaminosulfonyl group, a $C_{1-6}$ alkylsulfonylamino group and a $C_{1-6}$ alkoxycarbonylamino group (the mono-$C_{1-6}$ alkylaminosulfonyl group, the di-$C_{1-6}$ alkylaminosulfonyl group, the $C_{1-6}$ alkylsulfonylamino group and the $C_{1-6}$ alkoxycarbonylamino group are unsubstituted or substituted with one or more identical or different halogen atoms independently selected from the group consisting of fluorine atoms, chlorine atoms, bromine atoms and iodine atoms) and with one or more identical or different substituents independently selected from the group consisting of hydroxy groups, halogen atoms, cyano groups, $C_{1-6}$ alkyl groups, $C_{1-6}$ haloalkyl groups, $C_{1-6}$ alkoxy groups, $C_{1-6}$ haloalkoxy groups, $C_{1-6}$ alkylsulfonyl groups and $C_{1-6}$ haloalkylsulfonyl groups).

Another more preferred embodiment of the substituent $L^{3a}$ and the substituent $R^{2a}$ is such that $L^{3a}$ is a single bond, and $R^{2a}$ is an azido group.

Another more preferred embodiment of the substituent $L^{3a}$ and the substituent $R^{2a}$ is such that $L^{3a}$ is a single bond, and $R^{2a}$ is a 8 to 11-membered partially saturated aromatic cyclic group (the 8 to 11-membered partially saturated aromatic cyclic group is unsubstituted or substituted with one or two identical or different halogen atoms independently selected from the group consisting of fluorine atoms, chlorine atoms, bromine atoms and iodine atoms).

Another more preferred embodiment of the substituent $L^{3a}$ and the substituent $R^{2a}$ is such that $L^{3a}$ is represented by any of the following formulae ($IX^a$-1) to ($IX^a$-9):

($IX^a$)

($IX^a$-1)

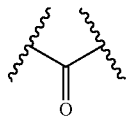

($IX^a$-2)

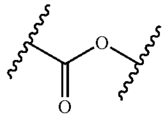

-continued ($IX^a$-3)

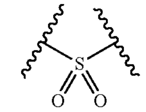

($IX^a$-4)

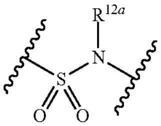

($IX^a$-5)

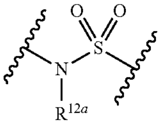

($IX^a$-6)

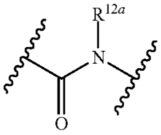

($IX^a$-7)

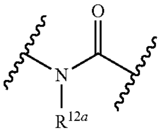

($IX^a$-8)

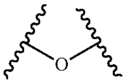

($IX^a$-9)

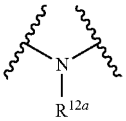

(wherein $R^{12a}$ is a hydrogen atom or a $C_{1-3}$ alkyl group), and $R^{2a}$ is a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or two identical or different substituents independently selected from the group consisting of hydroxy groups, amino groups, carbamoyl groups, sulfamoyl groups, tetrazolyl groups, cyano groups, nitro groups, $C_{3-6}$ cycloalkyl groups, $C_{1-3}$ alkoxy groups, $C_{1-6}$ haloalkoxy groups, $C_{1-3}$ alkylsulfonyl groups, $C_{1-3}$ haloalkylsulfonyl groups, 4 to 7-membered non-aromatic heterocyclyl groups, phenyl groups and 5 to 6-membered aromatic heterocyclyl groups).

Another more preferred embodiment of the substituent $L^{3a}$ and the substituent $R^{2a}$ is such that $L^{3a}$ is represented by any of the following formulae ($IX^a$-1) to ($IX^a$-9):

($IX^a$)

($IX^a$-1)

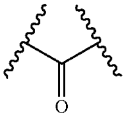

-continued ($IX^a$-2)

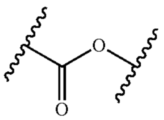

($IX^a$-3)

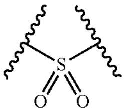

($IX^a$-4)

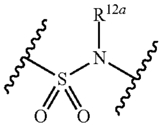

($IX^a$-5)

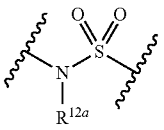

($IX^a$-6)

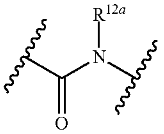

($IX^a$-7)

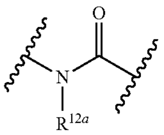

($IX^a$-8)

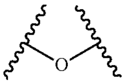

($IX^a$-9)

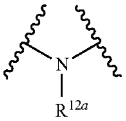

(wherein $R^{12a}$ is a hydrogen atom, a $C_{1-3}$ alkyl group or a $C_{1-3}$ haloalkyl group), and $R^{2a}$ is a hydrogen atom, a $C_{1-6}$ alkyl group, a $C_{1-6}$ haloalkyl group (the $C_{1-6}$ alkyl group and the $C_{1-6}$ haloalkyl group are unsubstituted or substituted with one, two or three identical or different substituents independently selected from the group consisting of hydroxy groups, amino groups, carbamoyl groups, sulfamoyl groups, cyano groups, nitro groups, $C_{1-6}$ alkoxy groups, $C_{1-6}$ haloalkoxy groups, $C_{1-6}$ alkylsulfonyl groups, $C_{1-6}$ haloalkylsulfonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups (the mono-$C_{1-6}$ alkylamino groups, the di-$C_{1-6}$ alkylamino groups, the mono-$C_{1-6}$ alkylaminocarbonyl groups and the di-$C_{1-6}$ alkylaminocarbonyl groups are unsubstituted or substituted with one or more identical or different halogen atoms independently selected from the group consisting of fluorine atoms, chlorine atoms, bromine atoms and iodine atoms), $C_{3-6}$ cycloalkyl groups, 3 to 11-membered non-aromatic heterocyclyl groups, phenyl groups and 5 to 10-membered aromatic heterocyclyl groups (the $C_{3-6}$ cycloalkyl groups, the 3 to 11-membered non-aromatic heterocyclyl groups, the phenyl groups and the 5 to 10-membered aromatic heterocyclyl groups are unsubstituted or substituted with identical or different one or more substituents independently selected from the group consisting of hydroxy groups, amino groups, halogen atoms, cyano groups, carbamoyl groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylsulfonyl groups, $C_{1-6}$ haloalkylsulfonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{1-6}$ alkoxycarbonyl groups (the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups, the $C_{1-6}$ alkylcarbonylamino groups and the $C_{1-6}$ alkoxycarbonyl groups are unsubstituted or substituted with one or more identical or different halogen atoms independently selected from the group consisting of fluorine atoms, chlorine atoms, bromine atoms and iodine atoms), 4 to 7-membered non-aromatic heterocyclyl groups, phenyl groups and 5 to 6-membered aromatic heterocyclyl groups)), a $C_{3-6}$ cycloalkyl group, a 3 to 11-membered non-aromatic heterocyclyl group, a phenyl group or a 5 to 10-membered aromatic heterocyclyl group (the $C_{3-6}$ cycloalkyl group, the 3 to 11-membered non-aromatic heterocyclyl group, the phenyl group and the 5 to 10-membered aromatic heterocyclyl group are unsubstituted or substituted with identical or different one or more substituents independently selected from the group consisting of hydroxy groups, amino groups, halogen atoms, cyano groups, carbamoyl groups, $C_{1-6}$ alkyl groups (the $C_{1-6}$ alkyl groups are unsubstituted or substituted with a substituent selected from the group consisting of a hydroxy group, a cyano group and a $C_{1-3}$ alkoxy group), $C_{1-6}$ haloalkyl groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylsulfonyl groups, $C_{1-6}$ haloalkylsulfonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{1-6}$ alkoxycarbonyl groups (the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups, the $C_{1-6}$ alkylcarbonylamino groups and the $C_{1-6}$ alkoxycarbonyl groups are unsubstituted or substituted with one or more identical or different halogen atoms independently selected from the group consisting of fluorine atoms, chlorine atoms, bromine atoms and iodine atoms), 4 to 7-membered non-aromatic heterocyclyl groups, phenyl groups and 5 to 6-membered aromatic heterocyclyl groups (the phenyl groups and the 5 to 6-membered aromatic heterocyclyl groups are unsubstituted or substituted with one or two identical or different substituents independently selected from the group consisting of halogen atoms, cyano groups and $C_{1-3}$ haloalkyl groups)).

Another more preferred embodiment of the substituent $L^{3a}$ and the substituent $R^{2a}$ is such that $L^{3a}$ is represented by any of the following formulae ($XVII^a$-1) to ($XVII^a$-3):

($XVII^a$)

($XVII^a$-1)

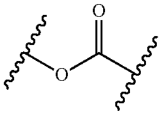

-continued ($XVII^a$-2)

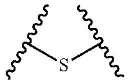

($XVII^a$-3)

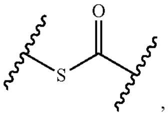

, and $R^{2a}$ is a hydrogen atom or a $C_{1-6}$ alkyl group.

Another more preferred embodiment of the substituent $L^{3a}$ and the substituent $R^{2a}$ is such that $L^{3a}$ is represented by the formula ($XVIII^a$):

($XVIII^a$)

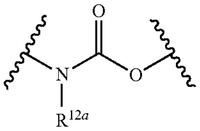

(wherein $R^{12a}$ is a hydrogen atom), and $R^{2a}$ is a $C_{1-6}$ alkyl group (the $C_{1-6}$ alkyl group is, unsubstituted or substituted with a phenyl group).

Another more preferred embodiment of the substituent $L^{3a}$ and the substituent $R^{2a}$ is such that $L^{3a}$ is represented by any of the following formulae ($IX^a$-1) to ($IX^a$-9):

($IX^a$)

($IX^a$-1)

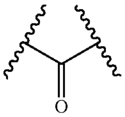

($IX^a$-2)

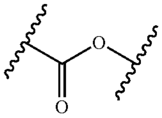

($IX^a$-3)

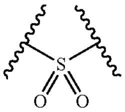

($IX^a$-4)

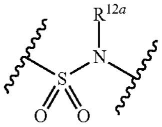

($IX^a$-5)

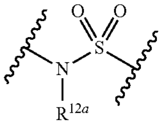

-continued (IX$^a$-6)

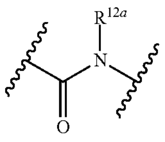

(IX$^a$-7)

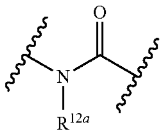

(IX$^a$-8)

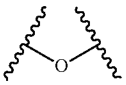

(IX$^a$-9)

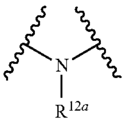

(wherein $R^{12a}$ is a hydrogen atom, a $C_{1-3}$ alkyl group or a $C_{1-3}$ haloalkyl group), and $R^{2a}$ is a $C_{1-6}$ alkyl group, a $C_{1-6}$ haloalkyl group (the $C_{1-6}$ alkyl group and the $C_{1-6}$ haloalkyl group are substituted with a substituent selected from the group consisting of a $C_{3-6}$ cycloalkyl group, a 3 to 11-membered non-aromatic heterocyclyl group, a phenyl group and a 5 to 10-membered aromatic heterocyclyl group (the $C_{3-6}$ cycloalkyl group, the 3 to 11-membered non-aromatic heterocyclyl group, the phenyl group and the 5 to 10-membered aromatic heterocyclyl group are substituted with one or two identical or different substituents independently selected from the group consisting of $C_{1-6}$ alkyl groups (the $C_{1-6}$ alkyl groups are unsubstituted or substituted with a hydroxy group or a cyano group) and $C_{1-6}$ haloalkyl groups)) or a $C_{2-6}$ alkynyl group.

Another more preferred embodiment of the substituent $L^{3a}$ and the substituent $R^{2a}$ is such that $L^{3a}$ is represented by any of the following formulae (IX$^a$-1) to (IX$^a$-9):

(IX$^a$)

(IX$^a$-1)

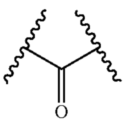

(IX$^a$-2)

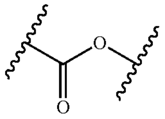

(IX$^a$-3)

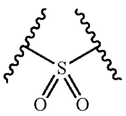

-continued (IX$^a$-4)

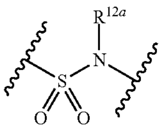

(IX$^a$-5)

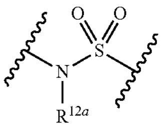

(IX$^a$-6)

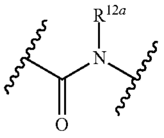

(IX$^a$-7)

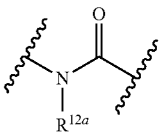

(IX$^a$-8)

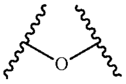

(IX$^a$-9)

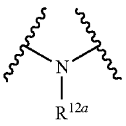

(wherein $R^{12a}$ is a hydrogen atom, a $C_{1-3}$ alkyl group or a $C_{1-3}$ haloalkyl group), and $R^{2a}$ is a $C_{1-6}$ alkyl group or a $C_{1-6}$ haloalkyl group (the $C_{1-6}$ alkyl group and the $C_{1-6}$ haloalkyl group are substituted with a substituent selected from the group consisting of a $C_{3-6}$ cycloalkyl group, a 3 to 11-membered non-aromatic heterocyclyl group, a phenyl group and a 5 to 10-membered aromatic heterocyclyl group (the $C_{3-6}$ cycloalkyl group, the 3 to 11-membered non-aromatic heterocyclyl group, the phenyl group and the 5 to 10-membered aromatic heterocyclyl group are substituted with one or two identical or different substituents independently selected from the group consisting of $C_{1-6}$ alkyl groups and $C_{1-6}$ haloalkyl groups and with one or two identical or different substituents independently selected from the group consisting of hydroxy groups, amino groups, halogen atoms, cyano groups, $C_{1-6}$ alkoxy groups, $C_{1-6}$ haloalkoxy groups, mono-$C_{1-6}$ alkylamino groups, di-$C_{1-6}$ alkylamino groups, $C_{1-6}$ alkylthio groups, $C_{1-6}$ haloalkylthio groups, $C_{1-6}$ alkylsulfonyl groups, $C_{1-6}$ haloalkylsulfonyl groups, $C_{3-6}$ cycloalkyl groups, 4 to 7-membered non-aromatic heterocyclyl groups, phenyl groups and 5 to 6-membered aromatic heterocyclyl groups)).

Another more preferred embodiment of the substituent $L^{3a}$ and the substituent $R^{2a}$ is such that $L^{3a}$ is represented by the formula (XVI$^a$):

(XVI$^a$)

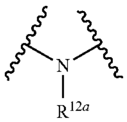

(wherein $R^{12a}$ is a hydrogen atom), and $R^{2a}$ is a 8 to 11-membered partially saturated aromatic cyclic group or a 8 to 11-membered aromatic ring-condensed alicyclic hydrocarbon group (the 8 to 11-membered partially saturated aromatic cyclic group and the 8 to 11-membered aromatic ring-condensed alicyclic hydrocarbon group are unsubstituted or substituted with one or more identical or different substituents independently selected from the group consisting of halogen atoms and hydroxy groups).

Another more preferred embodiment of the substituent $L^{3a}$ and the substituent $R^{2a}$ is such that $L^{3a}$ is represented by the formula ($X^a$-10):

($X^a$-10)

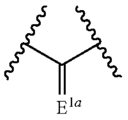

(wherein $E^{1a}$ is $NR^{11a}$ (wherein $R^{11a}$ is a hydroxy group)), and $R^{2a}$ is a hydrogen atom.

Another more preferred embodiment of the substituent $L^{3a}$ and the substituent $R^{2a}$ is such that $L^{3a}$ is represented by any of the following formulae (XXVI$^a$-1) to (XXVI$^a$-5):

(XXVI$^a$)

(XXVI$^a$-1)

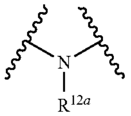

(XXVI$^a$-2)

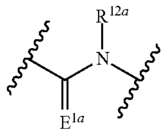

(XXVI$^a$-3)

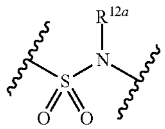

(XXVI$^a$-4)

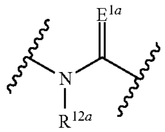

(XXVI$^a$-5)

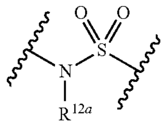

(wherein $E^{1a}$ is an oxygen atom, and $R^{12a}$ is a $C_{1-6}$ alkyl group (the $C_{1-6}$ alkyl group is substituted with a substituent selected from the group consisting of a hydroxy group, a cyano group, a $C_{1-3}$ alkoxy group, a $C_{3-6}$ cycloalkyl group, a 4 to 7-membered non-aromatic heterocyclyl group, a phenyl group and a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with a substituent selected from the group consisting of a hydroxy group, a halogen atom, a cyano group, a $C_{1-3}$ alkyl group, a $C_{1-3}$ haloalkyl group and a $C_{1-3}$ alkoxy group)), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or two identical or different substituents independently selected from the group consisting of hydroxy groups, halogen atoms, cyano groups, $C_{1-3}$ alkyl groups, $C_{1-3}$ haloalkyl groups and $C_{1-3}$ alkoxy groups)), and $R^{2a}$ is a $C_{1-6}$ alkyl group, a $C_{1-6}$ haloalkyl group (the $C_{1-6}$ alkyl group and the $C_{1-6}$ haloalkyl group are unsubstituted or substituted with one or two identical or different substituents independently selected from the group consisting of hydroxy groups, cyano groups, $C_{1-3}$ alkoxy groups, mono-$C_{1-6}$ alkylaminocarbonyl groups, (the mono-$C_{1-6}$ alkylaminocarbonyl groups are unsubstituted or substituted with one or more identical or different halogen atoms independently selected from the group consisting of fluorine atoms, chlorine atoms, bromine atoms and iodine atoms), $C_{3-6}$ cycloalkyl groups, 4 to 7-membered non-aromatic heterocyclyl groups, phenyl groups and 5 to 6-membered aromatic heterocyclyl groups (the $C_{3-6}$ cycloalkyl groups, the 4 to 7-membered non-aromatic heterocyclyl groups, the phenyl groups and the 5 to 6-membered aromatic heterocyclyl groups are unsubstituted or substituted with identical or different one or two substituents independently selected from the group consisting of hydroxy groups, halogen atoms, cyano groups, carbamoyl groups, $C_{1-6}$ alkyl groups, $C_{1-6}$ haloalkyl groups, $C_{1-6}$ alkoxy groups, $C_{1-6}$ haloalkoxy groups, mono-$C_{1-6}$ alkylamino groups and di-$C_{1-6}$ alkylamino groups)), a $C_{2-6}$ alkynyl group, a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one, two or three identical or different substituents independently selected from the group consisting of hydroxy groups, halogen atoms, cyano groups, carbamoyl groups, $C_{1-6}$ alkyl groups, $C_{1-6}$ haloalkyl groups, $C_{1-6}$ alkoxy groups, $C_{1-6}$ halo alkoxy groups, mono-$C_{1-6}$ alkylamino groups, di-$C_{1-6}$ alkylamino groups, phenyl groups and 5 to 6-membered aromatic heterocyclyl group).

A further preferred embodiment of the substituent $L^{3a}$ and the substituent $R^{2a}$ is such that $L^{3a}$ is a single bond, and $R^{2a}$ is a hydrogen atom, a halogen atom, a $C_{3-6}$ cycloalkyl group, a phenyl group or a 5 to 6-membered aromatic heterocyclyl group (the $C_{3-6}$ cycloalkyl group, the phenyl group and the 5 to 6-membered aromatic heterocyclyl group are unsubstituted or substituted with identical or different one, two or three substituents independently selected from the group consisting of hydroxy groups, amino groups, halogen atoms, cyano groups, nitro groups, carbamoyl groups, sulfamoyl groups, $C_{1-6}$ alkyl groups, $C_{1-6}$ haloalkyl groups, $C_{1-6}$ alkoxy groups, $C_{1-6}$ haloalkoxy groups, mono-$C_{1-6}$ alkylamino groups, di-$C_{1-6}$ alkylamino groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, carboxy groups, $C_{1-6}$ alkoxycarbonyl groups, mono-$C_{1-6}$ alkylaminocarbonyl groups, di-$C_{1-6}$ alkylaminocarbonyl groups, $C_{1-6}$ alkylcarbonylamino groups, $C_{3-6}$ cycloalkyl groups and 4 to 7-membered non-aromatic heterocyclyl groups).

Another further preferred embodiment of the substituent $L^{3a}$ and the substituent $R^{2a}$ is such that $L^{3a}$ is a single bond, and $R^{2a}$ is a 3 to 11-membered non-aromatic heterocyclyl group (the 3 to 11-membered non-aromatic heterocyclyl group is unsubstituted or substituted with one, two or three identical or different substituents independently selected from the group consisting of hydroxy groups, amino groups, halogen atoms, cyano groups, nitro groups, carbamoyl groups, sulfamoyl groups, $C_{1-6}$ alkyl groups, $C_{1-6}$ haloalkyl groups, $C_{1-6}$ alkoxy groups, $C_{1-6}$ haloalkoxy groups, mono-$C_{1-6}$ alkylamino groups, di-$C_{1-6}$ alkylamino groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, carboxy groups, $C_{1-6}$ alkoxycarbonyl groups, mono-$C_{1-6}$ alkylaminocarbonyl groups, di-$C_{1-6}$ alkylaminocarbonyl groups, $C_{1-6}$ alkylcarbonylamino groups, $C_{3-6}$ cycloalkyl groups and 4 to 7-membered non-aromatic heterocyclyl groups).

Another further preferred embodiment of the substituent $L^{3a}$ and the substituent $R^{2a}$ is such that $L^{3a}$ is a single bond, and $R^{2a}$ is a 4 to 7-membered non-aromatic heterocyclyl group, a phenyl group or a 5 to 6-membered aromatic heterocyclyl group (the 4 to 7-membered non-aromatic heterocyclyl group, the phenyl group and the 5 to 6-membered aromatic heterocyclyl group are substituted with a $C_{1-6}$ alkyl group, a $C_{1-6}$ alkoxy group (the $C_{1-6}$ alkyl group and the $C_{1-6}$ alkoxy group are substituted with a substituent selected from the group consisting of a hydroxy group, a cyano group and a $C_{1-6}$ alkoxycarbonylamino group), a mono-$C_{1-6}$ alkylamino group, a di-$C_{1-6}$ alkylamino group, a mono-$C_{1-6}$ alkylaminocarbonyl group, a $C_{1-6}$ alkylcarbonylamino group (the mono-$C_{1-6}$ alkylamino group, the di-$C_{1-6}$ alkylamino group, the mono-$C_{1-6}$ alkylaminocarbonyl group and the $C_{1-6}$ alkylcarbonylamino group are substituted with one or more identical or different halogen atoms independently selected from the group consisting of fluorine atoms, chlorine atoms, bromine atoms and iodine atoms or with a hydroxy group or a cyano group), a $C_{1-6}$ alkoxycarbonylamino group, a phenyl group and a 5 to 6-membered aromatic heterocyclyl group (the phenyl group and the 5 to 6-membered aromatic heterocyclyl group are unsubstituted or substituted with one or two identical or different substituents independently selected from the group consisting of halogen atoms, cyano groups, $C_{1-3}$ alkyl groups and $C_{1-3}$ haloalkyl groups)).

Another further preferred embodiment of the substituent $L^{3a}$ and the substituent $R^{2a}$ is such that $L^{3a}$ is a single bond, $R^{2a}$ is a 3 to 11-membered non-aromatic heterocyclyl group (the 3 to 11-membered non-aromatic heterocyclyl group is substituted with a di-$C_{1-3}$ alkylaminosulfonyl group).

Another further preferred embodiment of the substituent $L^{3a}$ and the substituent $R^{2a}$ is such that $L^{3a}$ is a single bond, $R^{2a}$ is a 4 to 7-membered non-aromatic heterocyclyl group (the 4 to 7-membered non-aromatic heterocyclyl group is substituted with a phenyl group (the phenyl group is unsubstituted or substituted with one or two identical or different substituents independently selected from the group consisting of halogen atoms, $C_{1-3}$ alkyl groups and $C_{1-3}$ haloalkyl groups) and with a substituent selected from the group consisting of a hydroxy group, a halogen atom, a cyano group, a $C_{1-3}$ alkyl group and a $C_{1-3}$ haloalkyl group).

Another further preferred embodiment of the substituent $L^{3a}$ and the substituent $R^{2a}$ is such that $L^{3a}$ is represented by any of the following formulae ($XX^a$-1) to ($XX^a$-3):

($XX^a$)

($XX^a$-1)

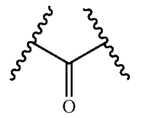

($XX^a$-2)

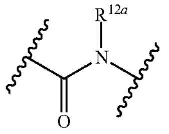

($XX^a$-3)

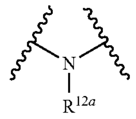

(wherein $R^{12a}$ is a hydrogen atom or a $C_{1-3}$ alkyl group), and $R^{2a}$ is a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or two identical or different substituents independently selected from the group consisting of hydroxy groups, cyano groups, $C_{1-3}$ alkoxy groups, $C_{3-6}$ cycloalkyl groups, 4 to 7-membered non-aromatic heterocyclyl groups, phenyl groups and 5 to 6-membered aromatic heterocyclyl groups).

Another further preferred embodiment of the substituent $L^{3a}$ and the substituent $R^{2a}$ is such that $L^{3a}$ is represented by any of the following formulae ($XXI^a$-1) to ($XXI^a$-3):

($XXI^a$)

($XXI^a$-1)

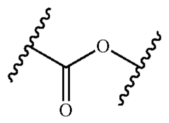

($XXI^a$-2)

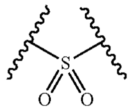

($XXI^a$-3)

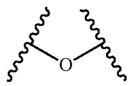

and $R^{2a}$ is a hydrogen atom or a $C_{1-6}$ alkyl group (the $C_{1-6}$ alkyl group is unsubstituted or substituted with a phenyl groups).

Another further preferred embodiment of the substituent $L^{3a}$ and the substituent $R^{2a}$ is such that $L^{3a}$ is represented by the formula ($X^a$-4):

($X^a$-4)

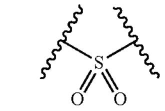

, and $R^{2a}$ is a $C_{1-3}$ haloalkyl group.

Another further preferred embodiment of the substituent $L^{3a}$ and the substituent $R^{2a}$ is such that $L^{3a}$ is represented by any of the following formulae ($XXVIII^a$-1) to ($XXVIII^a$-3):

($XXVIII^a$)

($XXVIII^a$-1)

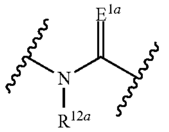

($XXVIII^a$-2)

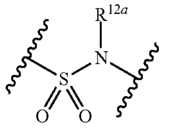

($XXVIII^a$-3)

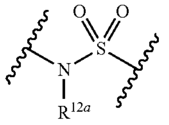

(wherein $E^{1a}$ is an oxygen atom, and $R^{12a}$ is a hydrogen atom or a $C_{1-3}$ alkyl group), and $R^{2a}$ is a $C_{1-6}$ alkyl group (the $C_{1-6}$ alkyl group is unsubstituted or substituted with a cyano group) or a $C_{1-6}$ haloalkyl group.

Another further preferred embodiment of the substituent $L^{3a}$ and the substituent $R^{2a}$ is such that $L^{3a}$ is represented by any of the following formulae ($XX^a$-1) to ($XX^a$-3):

($XX^a$)

($XX^a$-1)

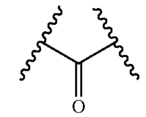

($XX^a$-2)

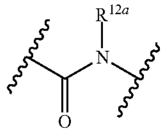

($XX^a$-3)

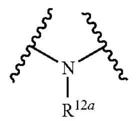

(wherein $R^{12a}$ is a hydrogen atom or a $C_{1-3}$ alkyl group), and $R^{2a}$ is a $C_{1-6}$ alkyl group or a $C_{1-6}$ haloalkyl group (the $C_{1-6}$ alkyl group and the $C_{1-6}$ haloalkyl group are substituted with a substituent selected from the group consisting of a mono-$C_{1-6}$ alkylaminocarbonyl group (the mono-$C_{1-6}$ alkylaminocarbonyl group is unsubstituted or substituted with one or more identical or different halogen atoms independently selected from the group consisting of fluorine atoms, chlorine atoms, bromine atoms and iodine atoms), a $C_{3-6}$ cycloalkyl group, a 4 to 7-membered non-aromatic heterocyclyl group, a phenyl group and a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are substituted with one or two identical or different substituents independently selected from the group consisting of hydroxy groups, amino groups, halogen atoms, cyano groups, carbamoyl groups, $C_{1-6}$ alkoxy groups, $C_{1-6}$ haloalkoxy groups, mono-$C_{1-6}$ alkylamino groups, di-$C_{1-6}$ alkylamino groups, $C_{1-6}$ alkylthio groups, $C_{1-6}$ haloalkylthio groups, $C_{1-6}$ alkylsulfonyl groups, $C_{1-6}$ haloalkylsulfonyl groups, $C_{1-6}$ alkoxycarbonyl groups and phenyl groups (the phenyl groups are unsubstituted or substituted with one or two identical or different substituents independently selected from the group consisting of halogen atoms and $C_{1-3}$ haloalkyl groups))).

Another further preferred embodiment of the substituent $L^{3a}$ and the substituent $R^{2a}$ is such that $L^{3a}$ is represented by any of the following formulae ($XX^a$-1) to ($XX^a$-3):

($XX^a$)

($XX^a$-1)

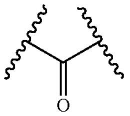

($XX^a$-2)

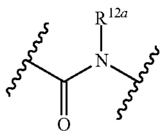

($XX^a$-3)

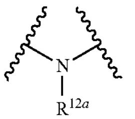

(wherein $R^{12a}$ is a hydrogen atom or a $C_{1-3}$ alkyl group), and $R^{2a}$ is a $C_{1-6}$ alkyl group or a $C_{1-6}$ haloalkyl group (the $C_{1-6}$ alkyl group and the $C_{1-6}$ haloalkyl group are substituted with a substituent selected from the group consisting of a $C_{3-6}$ cycloalkyl group, a 4 to 7-membered non-aromatic heterocyclyl group, a phenyl group and a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are substituted with one or two identical or different substituents independently selected from the group consisting of hydroxy groups, amino groups, halogen atoms, cyano groups, carbamoyl groups, $C_{1-6}$ alkoxy groups, $C_{1-6}$ haloalkoxy groups, mono-$C_{1-6}$ alkylamino groups, di-$C_{1-6}$ alkylamino groups, $C_{1-6}$ alkylthio groups, $C_{1-6}$ haloalkylthio groups, $C_{1-6}$ alkylsulfonyl groups, $C_{1-6}$ haloalkylsulfonyl groups and 4 to 7-membered non-aromatic heterocyclyl groups) and with a substituent selected from the group consisting of a hydroxy group and a cyano group).

Another further preferred embodiment of the substituent $L^{3a}$ and the substituent $R^{2a}$ is such that $L^{3a}$ is represented by any of the following formulae ($XXVII^{a}$-1) to ($XXVII^{a}$-5):

($XXVII^{a}$)

($XXVII^{a}$-1)

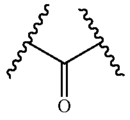

($XXVII^{a}$-2)

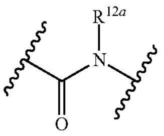

($XXVII^{a}$-3)

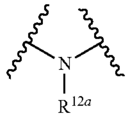

($XXVII^{a}$-4)

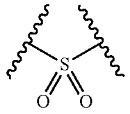

($XXVII^{a}$-5)

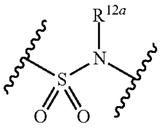

(wherein $R^{12a}$ is a hydrogen atom or a $C_{1-3}$ alkyl group), and $R^{2a}$ is a $C_{3-6}$ cycloalkyl group, a 3 to 11-membered non-aromatic heterocyclyl group, a phenyl group or a 5 to 10-membered aromatic heterocyclyl group (the $C_{3-6}$ cycloalkyl group, the 3 to 11-membered non-aromatic heterocyclyl group, the phenyl group and the 5 to 10-membered aromatic heterocyclyl group are unsubstituted or substituted with one or two identical or different substituents independently selected from the group consisting of hydroxy groups, amino groups, halogen atoms, cyano groups, carbamoyl groups, $C_{1-6}$ alkyl groups (the $C_{1-6}$ alkyl groups are unsubstituted or substituted with a substituent selected from the group consisting of a hydroxy group, a cyano group and a $C_1$ alkoxy group), $C_{1-6}$ haloalkyl groups, $C_{1-6}$ alkoxy groups, $C_{1-6}$ haloalkoxy groups, mono-$C_{1-6}$ alkylamino groups, di-$C_{1-6}$ alkylamino groups, $C_{1-6}$ alkylthio groups, $C_{1-6}$ haloalkylthio groups, $C_{1-6}$ alkylsulfonyl groups, $C_{1-6}$ haloalkylsulfonyl groups, $C_{1-6}$ alkoxycarbonyl groups, 4 to 7-membered non-aromatic heterocyclyl groups, phenyl groups and 5 to 6-membered aromatic heterocyclyl groups (the phenyl groups and the 5 to 6-membered aromatic heterocyclyl groups are unsubstituted or substituted with a halogen atom)).

Another further preferred embodiment of the substituent $L^{3a}$ and the substituent $R^{2a}$ is such that $L^{3a}$ is represented by any of the following formulae ($XXVI^{a}$-1) to ($XXVI^{a}$-5):

($XXVI^{a}$)

($XXVI^{a}$-1)

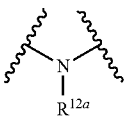

($XXVI^{a}$-2)

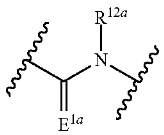

($XXVI^{a}$-3)

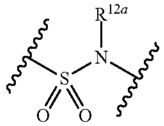

($XXVI^{a}$-4)

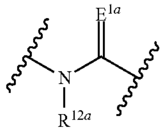

($XXVI^{a}$-5)

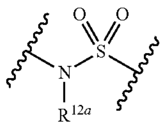

(wherein $E^{1a}$ is an oxygen atom, and $R^{12a}$ is a $C_{1-6}$ haloalkyl group), and $R^{2a}$ is a $C_{1-6}$ alkyl group (the $C_{1-6}$ alkyl group is unsubstituted or substituted with a substituent selected from the group consisting of a hydroxy group, a cyano group, a $C_{1-3}$ alkoxy group, a $C_{3-6}$ cycloalkyl group and a phenyl group) or a $C_{1-6}$ haloalkyl group.

Another further preferred embodiment of the substituent $L^{3a}$ and the substituent $R^{2a}$ is such that $L^{3a}$ is represented by the formula ($X^{a}$-5):

($X^{a}$-5)

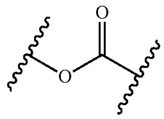

, and $R^{2a}$ is a $C_{1-3}$ alkyl group.

Another further preferred embodiment of the substituent $L^{3a}$ and the substituent $R^{2a}$ is such that $L^{3a}$ is represented by the formula ($X^{a}$-6):

($X^{a}$-6)

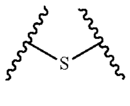

, and $R^{2a}$ is a hydrogen atom.

Another further preferred embodiment of the substituent $L^{3a}$ and the substituent $R^{2a}$ is such that $L^{3a}$ is represented by the formula ($XVIII^{a}$):

(XVIII$^a$)

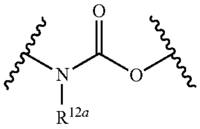

(wherein $R^{12a}$ is a hydrogen atom), and $R^{2a}$ is a $C_{1-6}$ alkyl group or a $C_{1-3}$ alkyl group (the $C_{1-3}$ alkyl group is substituted with a phenyl group).

Another further preferred embodiment of the substituent $L^{3a}$ and the substituent $R^{2a}$ is such that $L^{3a}$ is represented by the formula ($X^a$-8):

($X^a$-8)

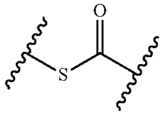

, and $R^{2a}$ is a $C_{1-3}$ alkyl group.

Another further preferred embodiment of the substituent $L^{3a}$ and the substituent $R^{2a}$ is such that $L^{3a}$ is represented by any of the following formulae ($XX^a$-1) to ($XX^a$-3):

($XX^a$)

($XX^a$-1)

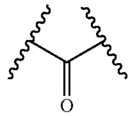

($XX^a$-2)

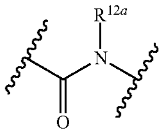

($XX^a$-3)

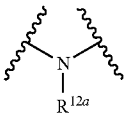

(wherein $R^{12a}$ is a hydrogen atom or a $C_{1-3}$ alkyl group), and $R^{2a}$ is a $C_{1-3}$ alkyl group (the $C_{1-3}$ alkyl group is substituted with a substituent selected from the group consisting of a $C_{3-6}$ cycloalkyl group, a 4 to 7-membered non-aromatic heterocyclyl group, a phenyl group and a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are substituted with a $C_{1-3}$ alkyl group or a $C_{1-3}$ haloalkyl group)) or a $C_{2-6}$ alkynyl group.

Another further preferred embodiment of the substituent $L^{3a}$ and the substituent $R^{2a}$ is such that $L^{3a}$ is represented by any of the following formulae ($XX^a$-1) to ($XX^a$-3):

($XX^a$)

($XX^a$-1)

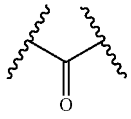

($XX^a$-2)

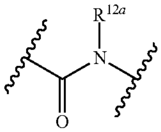

($XX^a$-3)

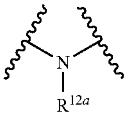

(wherein $R^{12a}$ is a hydrogen atom or a $C_{1-3}$ alkyl group), and $R^{2a}$ is a $C_{1-3}$ alkyl group (the $C_{1-3}$ alkyl group is substituted with a substituent selected from the group consisting of a phenyl group and a 5 to 6-membered aromatic heterocyclyl group (the phenyl group and the 5 to 6-membered aromatic heterocyclyl group are substituted with a $C_{1-3}$ alkyl group or a $C_{1-3}$ haloalkyl group and with a substituent selected from the group consisting of a halogen atom, a cyano group, a $C_{1-3}$ alkoxy group, a $C_{1-3}$ haloalkoxy group and a $C_{1-3}$ alkylsulfonyl group)).

Another further preferred embodiment of the substituent $L^{3a}$ and the substituent $R^{2a}$ is such that $L^{3a}$ is represented by the formula ($XVI^a$):

($XVI^a$)

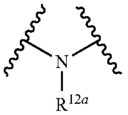

(wherein $R^{12a}$ is a hydrogen atom), and $R^{2a}$ is a 8 to 11-membered partially saturated aromatic cyclic group or a 8 to 11-membered aromatic ring-condensed alicyclic hydrocarbon group (the 8 to 11-membered partially saturated aromatic cyclic group and the 8 to 11-membered aromatic ring-condensed alicyclic hydrocarbon group are unsubstituted or substituted with one or two identical or different substituents independently selected from the group consisting of halogen atoms and hydroxy groups).

Another further preferred embodiment of the substituent $L^{3a}$ and the substituent $R^{2a}$ is such that $L^{3a}$ is represented by any of the following formulae ($XXVI^a$-1) to ($XXVI^a$-5):

($XXVI^a$)

($XXVI^a$-1)

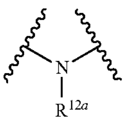

-continued (XXVI$^a$-2)

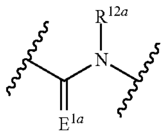

(XXVI$^a$-3)

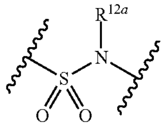

(XXVI$^a$-4)

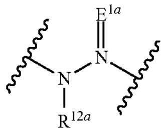

(XXVI$^a$-5)

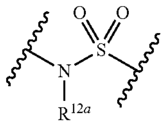

(wherein $E^{1a}$ is an oxygen atom, and $R^{12a}$ is a $C_{1-3}$ alkyl group (the $C_{1-3}$ alkyl group is substituted with a substituent selected from the group consisting of a cyano group, a hydroxy group, a $C_{1-3}$ alkoxy group, a $C_{3-6}$ cycloalkyl group, a phenyl group and a 5 to 6-membered aromatic heterocyclyl group (the 5 to 6-membered aromatic heterocyclyl group is unsubstituted or substituted with a $C_{1-3}$ alkyl group)), a $C_{3-6}$ cycloalkyl group or a phenyl group (the phenyl group is unsubstituted or substituted with a halogen or a cyano group)), and $R^{2a}$ is a $C_{1-3}$ alkyl group, a $C_{1-3}$ haloalkyl group (the $C_{1-3}$ alkyl group and the $C_{1-3}$ haloalkyl group are unsubstituted or substituted with one or two identical or different substituents independently selected from the group consisting of hydroxy groups, cyano groups, $C_{1-3}$ alkoxy groups, $C_{3-6}$ cycloalkyl groups, phenyl groups and 5 to 6-membered aromatic heterocyclyl groups).

A particularly preferred embodiment of the substituent $L^{3a}$ and the substituent $R^{2a}$ is such that $L^{3a}$ is a single bond, and $R^{2a}$ is a hydrogen atom or a halogen atom.

Another particularly preferred embodiment of the substituent $L^{3a}$ and the substituent $R^{2a}$ is such that $L^{3a}$ is a single bond, and $R^{2a}$ is a $C_{3-6}$ cycloalkyl group (the $C_{3-6}$ cycloalkyl group is unsubstituted or substituted with a $C_{1-3}$ haloalkyl group).

Another particularly preferred embodiment of the substituent $L^{3a}$ and the substituent $R^{2a}$ is such that $L^{3a}$ is a single bond, and $R^{2a}$ is a phenyl group or a 5 to 6-membered aromatic heterocyclyl group (the phenyl group and the 5 to 6-membered aromatic heterocyclyl group are unsubstituted or substituted with one, two or three identical or different substituents independently selected from the group consisting of halogen atoms, cyano groups, carbamoyl groups, $C_{1-3}$ alkyl groups, $C_{1-3}$ alkoxy groups, $C_{1-3}$ alkylthio groups, $C_{1-3}$ alkylsulfonyl groups, $C_{1-3}$ haloalkyl groups, $C_{1-3}$ haloalkoxy groups, $C_{1-3}$ haloalkylthio groups and 4 to 7-membered non-aromatic heterocyclyl groups).

Another particularly preferred embodiment of the substituent $L^{3a}$ and the substituent $R^{2a}$ is such that $L^{3a}$ is a single bond, and $R^{2a}$ is a 4 to 7-membered non-aromatic heterocyclyl group (the 4 to 7-membered non-aromatic heterocyclyl group is unsubstituted or substituted with one or two identical or different substituents independently selected from the group consisting of cyano groups, halogen atoms, $C_{1-3}$ alkyl groups, $C_{1-3}$ haloalkyl groups, hydroxy groups, di-$C_{1-3}$ alkylamino groups, carboxy groups, carbamoyl groups, $C_{1-3}$ haloalkoxy groups, $C_{1-3}$ alkylcarbonylamino groups and 4 to 7-membered non-aromatic heterocyclyl groups).

Another particularly preferred embodiment of the substituent $L^{3a}$ and the substituent $R^{2a}$ is such that $L^{3a}$ is a single bond, and $R^{2a}$ is a phenyl group (the phenyl group is substituted with a substituent selected from the group consisting of a $C_{1-3}$ alkoxy group, a di-$C_{1-3}$ alkylamino group (the $C_{1-3}$ alkoxy group and the di-$C_{1-3}$ alkylamino group are substituted with a hydroxy group or a cyano group) and a 5 to 6-membered aromatic heterocyclyl group).

Another particularly preferred embodiment of the substituent $L^{3a}$ and the substituent $R^{2a}$ is such that $L^{3a}$ is a single bond, and $R^{2a}$ is a 5 to 6-membered aromatic heterocyclyl group (the 5 to 6-membered aromatic heterocyclyl group is substituted with a $C_{1-3}$ alkyl group (the $C_{1-3}$ alkyl group is substituted with a hydroxy group).

Another particularly preferred embodiment of the substituent $L^{3a}$ and the substituent $R^{2a}$ is such that $L^{3a}$ is a single bond, and $R^{2a}$ is a 4 to 7-membered non-aromatic heterocyclyl group (the 4 to 7-membered non-aromatic heterocyclyl group is substituted with a substituent selected from the group consisting of a $C_{1-6}$ alkyl group (the $C_{1-6}$ alkyl group is substituted with a substituent selected from the group consisting of a hydroxy group, a cyano group and a $C_{1-6}$ alkoxycarbonylamino group), a mono-$C_{1-3}$ alkylaminocarbonyl group, a $C_{1-3}$ alkylcarbonylamino group (the mono-$C_{1-3}$ alkylaminocarbonyl group and the $C_{1-3}$ alkylcarbonylamino group are substituted with one or more identical or different halogen atoms independently selected from the group consisting of fluorine atoms, chlorine atoms, bromine atoms and iodine atoms) and a $C_{1-6}$ alkoxycarbonylamino group).

Another particularly preferred embodiment of the substituent $L^{3a}$ and the substituent $R^{2a}$ is such that $L^{3a}$ is a single bond, and $R^{2a}$ is a 4 to 7-membered non-aromatic heterocyclyl group (the 4 to 7-membered non-aromatic heterocyclyl group is substituted with a phenyl group (the phenyl group is unsubstituted or substituted with one or two identical or different substituents independently selected from the group consisting of halogen atoms and $C_{1-3}$ haloalkyl groups) and with a hydroxy group or a cyano group).

Another particularly preferred embodiment of the substituent $L^{3a}$ and the substituent $R^{2a}$ is such that $L^{3a}$ is represented by the formula ($X^a$-1):

($X^a$-1)

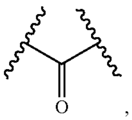

, and $R^{2a}$ is a methyl group (the methyl group is unsubstituted or substituted with a cyano group).

Another particularly preferred embodiment of the substituent $L^{3a}$ and the substituent $R^{2a}$ is such that $L^{3a}$ is represented by the formula ($X^a$-1):

($X^a$-1)

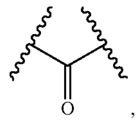

, and $R^{2a}$ is a hydrogen atom or a $C_{1-3}$ haloalkyl group.

Another particularly preferred embodiment of the substituent $L^{3a}$ and the substituent $R^{2a}$ is such that $L^{3a}$ is represented by the formula ($X^a$-1):

($X^a$-1)

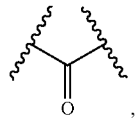

, and $R^{2a}$ is a 4 to 7-membered non-aromatic heterocyclyl group or a phenyl group (the 4 to 7-membered non-aromatic heterocyclyl group and the phenyl group are unsubstituted or substituted with a substituent selected from the group consisting of a hydroxy group, a cyano group, a halogen atom and a $C_{1-3}$ haloalkyl group).

Another particularly preferred embodiment of the substituent $L^{3a}$ and the substituent $R^{2a}$ is such that $L^{3a}$ is represented by the formula ($X^a$-7):

($X^a$-7)

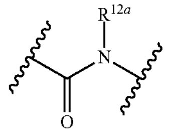

(wherein $R^{12a}$ is a hydrogen atom), and $R^{2a}$ is a hydrogen atom, a $C_{1-3}$ alkyl group or a $C_{1-3}$ haloalkyl group (the $C_{1-3}$ alkyl group and the a $C_{1-3}$ haloalkyl group are unsubstituted or substituted with one or two identical or different substituents independently selected from the group consisting of hydroxy groups, cyano groups and phenyl groups).

Another particularly preferred embodiment of the substituent $L^{3a}$ and the substituent $R^{2a}$ is such that $L^{3a}$ is represented by the formula ($X^a$-7):

($X^a$-7)

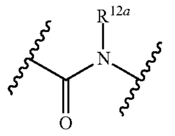

(wherein $R^{12a}$ is a hydrogen atom), and $R^{2a}$ is a $C_{1-3}$ alkyl group (the $C_{1-3}$ alkyl group is substituted with a phenyl group (the phenyl group is substituted with a halogen atom or a cyano group)).

Another particularly preferred embodiment of the substituent $L^{3a}$ and the substituent $R^{2a}$ is such that $L^{3a}$ is represented by the formula ($X^a$-7):

($X^a$-7)

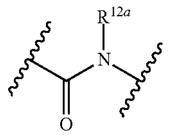

(wherein $R^{12a}$ is a hydrogen atom), and $R^{2a}$ is a $C_{1-3}$ haloalkyl group (the $C_{1-3}$ haloalkyl group is substituted with a phenyl group (the phenyl group is substituted with a halogen atom) and with a hydroxy group).

Another particularly preferred embodiment of the substituent $L^{3a}$ and the substituent $R^{2a}$ is such that $L^{3a}$ is represented by the formula ($X^a$-7):

($X^a$-7)

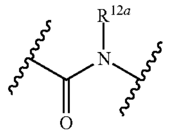

(wherein $R^{12a}$ is a hydrogen atom), and $R^{2a}$ is a $C_{3-6}$ cycloalkyl group, a phenyl group or a 5 to 6-membered aromatic heterocyclyl group (the $C_{3-6}$ cycloalkyl group, the phenyl group and the 5 to 6-membered aromatic heterocyclyl group are unsubstituted or substituted with a substituent selected from the group consisting of a $C_{1-3}$ alkyl group, a $C_{1-3}$ haloalkyl group and a halogen atom).

Another particularly preferred embodiment of the substituent $L^{3a}$ and the substituent $R^{2a}$ is such that $L^{3a}$ is represented by the formula ($XVI^a$):

($XVI^a$)

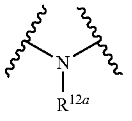

(wherein $R^{12a}$ is a hydrogen atom or a $C_{1-3}$ alkyl group), and $R^{2a}$ is a hydrogen atom, a $C_{1-6}$ alkyl group (the $C_{1-6}$ alkyl group is unsubstituted or substituted with a substituent selected from the group consisting of a hydroxy group, a cyano group, a $C_{1-3}$ alkoxy group, a $C_{3-6}$ cycloalkyl group, a 4 to 7-membered non-aromatic heterocyclyl group, a phenyl group and a 5 to 6-membered aromatic heterocyclyl group) or a $C_{1-6}$ haloalkyl group (the $C_{1-6}$ haloalkyl group is unsubstituted or substituted with a hydroxy group).

Another particularly preferred embodiment of the substituent $L^{3a}$ and the substituent $R^{2a}$ is such that $L^{3a}$ is represented by the formula ($XVI^a$):

($XVI^a$)

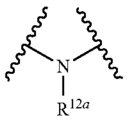

(wherein $R^{12a}$ is a $C_{1-3}$ haloalkyl group), and $R^{2a}$ is a $C_{1-3}$ alkyl group (the $C_{1-3}$ alkyl group is substituted with a $C_{3-6}$ cycloalkyl group).

Another particularly preferred embodiment of the substituent $L^{3a}$ and the substituent $R^{2a}$ is such that $L^{3a}$ is represented by the formula ($XVI^a$):

($XVI^a$)

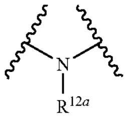

(wherein $R^{12a}$ is a hydrogen atom), and $R^{2a}$ is a $C_{1-3}$ alkyl group or a $C_{1-3}$ haloalkyl group (the $C_{1-3}$ alkyl group and the $C_{1-3}$ haloalkyl group are substituted with a hydroxy group and with a phenyl group or a 5 to 6-membered aromatic heterocyclyl group).

Another particularly preferred embodiment of the substituent $L^{3a}$ and the substituent $R^{2a}$ is such that $L^{3a}$ is represented by the formula ($XVI^a$):

($XVI^a$)

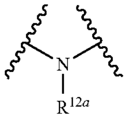

(wherein $R^{12a}$ is a hydrogen atom or a $C_{1-3}$ alkyl group), and $R^{2a}$ is a $C_{1-6}$ alkyl group (the $C_{1-6}$ alkyl group is substituted with a phenyl group or a 5 to 6-membered aromatic heterocyclyl group (the phenyl group and the 5 to 6-membered aromatic heterocyclyl group are substituted with one or two identical or different substituents independently selected from the group consisting of halogen atoms, cyano groups, $C_{1-3}$ alkoxy groups, $C_{1-3}$ haloalkoxy groups and $C_{1-3}$ alkylsulfonyl groups)).

Another particularly preferred embodiment of the substituent $L^{2a}$ and the substituent $R^{2a}$ is such that $L^{3a}$ is represented by the formula ($XVI^a$):

($XVI^a$)

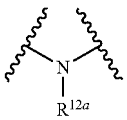

(wherein $R^{12a}$ is a hydrogen atom), and $R^{2a}$ is a $C_{1-6}$ alkyl group (the $C_{1-6}$ alkyl group is substituted with a $C_{3-6}$ cycloalkyl group or a 4 to 7-membered non-aromatic heterocyclyl group (the $C_{3-6}$ cycloalkyl group and the 4 to 7-membered non-aromatic heterocyclyl group are substituted with a substituent selected from the group consisting of a hydroxy group, a $C_{1-6}$ alkoxycarbonyl group and a phenyl group (the phenyl group is unsubstituted or substituted with a halogen atom))).

Another particularly preferred embodiment of the substituent $L^{3a}$ and the substituent $R^{2a}$ is such that $L^{3a}$ is represented by the formula ($XVI^a$):

($XVI^a$)

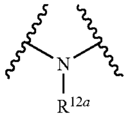

(wherein $R^{12a}$ is a hydrogen atom), and $R^{2a}$ is a $C_{1-3}$ alkyl group or a $C_{1-3}$ haloalkyl group (the $C_{1-3}$ alkyl group and the $C_{1-3}$ haloalkyl group are substituted with a phenyl group or a 5 to 6-membered aromatic heterocyclyl group (the phenyl group and the 5 to 6-membered aromatic heterocyclyl group are substituted with one or two identical or different substituents independently selected from the group consisting of halogen atoms, $C_{1-3}$ alkoxy groups, $C_{1-3}$ haloalkoxy groups and $C_{1-3}$ alkylthio groups) and with a hydroxy group).

Another particularly preferred embodiment of the substituent $L^{3a}$ and the substituent $R^{2a}$ is such that $L^{3a}$ is represented by the formula ($XVI^a$):

($XVI^a$)

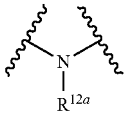

(wherein $R^{12a}$ is a hydrogen atom or a $C_{1-3}$ alkyl group), and $R^{2a}$ is a $C_{3-6}$ cycloalkyl group, a 4 to 7-membered non-aromatic heterocyclyl group (the $C_{3-6}$ cycloalkyl group and the 4 to 7-membered non-aromatic heterocyclyl group are unsubstituted or substituted with one or two identical or different substituents independently selected from the group consisting of hydroxy groups, $C_{1-3}$ alkyl groups (the $C_{1-3}$ alkyl groups are unsubstituted or substituted with a substituent selected from the group consisting of a hydroxy group, a cyano group and a $C_{1-3}$ alkoxy group), $C_{1-3}$ haloalkyl groups, $C_{1-6}$ alkoxycarbonyl groups and phenyl groups (the phenyl groups are unsubstituted or substituted with a halogen atom), a phenyl group or a 5 to 10-membered aromatic heterocyclyl group (the phenyl group and the 5 to 10-membered aromatic heterocyclyl group are unsubstituted or substituted with identical or different one, two or three substituents independently selected from the group consisting of halogen atoms, cyano groups, $C_{1-3}$ alkyl groups, $C_{1-3}$ haloalkyl groups, $C_{1-3}$ alkoxy groups, $C_{1-3}$ haloalkoxy groups, $C_{1-3}$ haloalkylsulfonyl groups and 4 to 7-membered non-aromatic heterocyclyl groups).

Another particularly preferred embodiment of the substituent $L^{3a}$ and the substituent $R^{2a}$ is such that $L^{3a}$ is represented by the formula ($X^a$-2):

($X^a$-2)

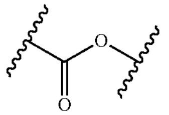, and $R^{2a}$ is a methyl group (the methyl group is unsubstituted or substituted with a phenyl group).

Another particularly preferred embodiment of the substituent $L^{3a}$ and the substituent $R^{2a}$ is such that $L^{3a}$ is represented by the formula ($X^a$-2):

(X$^a$-2)

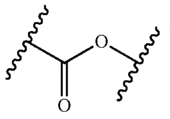, and $R^{2a}$ is a hydrogen atom or a t-butyl group.

Another particularly preferred embodiment of the substituent $L^{3a}$ and the substituent $R^{2a}$ is such that $L^{3a}$ is represented by the formula (X$^a$-3):

(X$^a$-3)

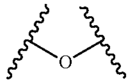, and $R^{2a}$ is a hydrogen atom.

Another particularly preferred embodiment of the substituent $L^{3a}$ and the substituent $R^{2a}$ is such that $L^{3a}$ is represented by the formula (X$^a$-3):

(X$^a$-3)

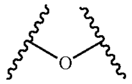, and $R^{2a}$ is a $C_{1-3}$ alkyl group.

Another particularly preferred embodiment of the substituent $L^{3a}$ and the substituent $R^{2a}$ is such that $L^{3a}$ is represented by the formula (X$^a$-4):

(X$^a$-4)

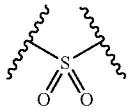, and $R^{2a}$ is a $C_{1-3}$ alkyl group.

Another particularly preferred embodiment of the substituent $L^{3a}$ and the substituent $R^{2a}$ is such that $L^{3a}$ is represented by the formula (X$^a$-4):

(X$^a$-4)

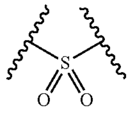, and $R^{2a}$ is a $C_{3-6}$ cycloalkyl group or a phenyl group (the phenyl group is unsubstituted or substituted with a halogen atom).

Another particularly preferred embodiment of the substituent $L^{3a}$ and the substituent $R^{2a}$ is such that $L^{3a}$ is represented by the formula (X$^a$-11):

(X$^a$-11)

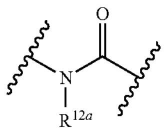

(wherein $R^{12a}$ is a hydrogen atom or a $C_{1-3}$ alkyl group), and $R^{2a}$ is a $C_{1-3}$ alkyl group (the $C_{1-3}$ alkyl group is unsubstituted or substituted with a cyano group) or a $C_{1-3}$ haloalkyl group.

Another particularly preferred embodiment of the substituent $L^{3a}$ and the substituent $R^{2a}$ is such that $L^{3a}$ is represented by the formula (X$^a$-11):

(X$^a$-11)

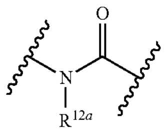

(wherein $R^{12a}$ is a $C_{1-3}$ haloalkyl group), and $R^{2a}$ is a $C_{1-3}$ alkyl group (the $C_{1-3}$ alkyl group is unsubstituted or substituted with a cyano group) or a $C_{1-3}$ haloalkyl group.

Another particularly preferred embodiment of the substituent $L^{3a}$ and the substituent $R^{2a}$ is such that $L^{3a}$ is represented by the formula (X$^a$-12):

(X$^a$-12)

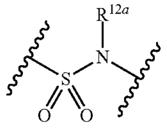

(wherein $R^{12a}$ is a hydrogen atom or a $C_{1-3}$ alkyl group), and $R^{2a}$ is a $C_{1-3}$ alkyl group (the $C_{1-3}$ alkyl group is unsubstituted or substituted with a cyano group) or a $C_{1-3}$ haloalkyl group.

Another particularly preferred embodiment of the substituent $L^{3a}$ and the substituent $R^{2a}$ is such that $L^{3a}$ is represented by the formula (X$^a$-12):

(X$^a$-12)

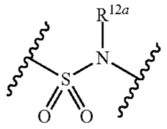

(wherein $R^{12a}$ is a hydrogen atom), and $R^{2a}$ is a $C_{3-6}$ cycloalkyl group.

Another particularly preferred embodiment of the substituent $L^{3a}$ and the substituent $R^{2a}$ is such that $L^{3a}$ is represented by the formula (X$^a$-13):

(X$^a$-13)

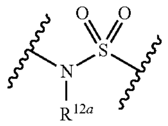

(wherein $R^{12a}$ is a hydrogen atom), and $R^{2a}$ is a $C_{1-3}$ alkyl group.

Another particularly preferred embodiment of the substituent $L^{3a}$ and the substituent $R^{2a}$ is such that $L^{3a}$ is represented by the formula (X$^a$-5):

(X$^a$-5)

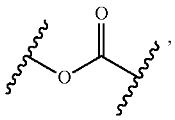

, and $R^{2a}$ is a methyl group.

Another particularly preferred embodiment of the substituent $L^{3a}$ and the substituent $R^{2a}$ is such that $L^{3a}$ is represented by the formula (XVIII$^a$):

(XVIII$^a$)

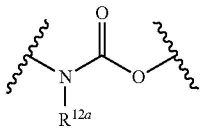

(wherein $R^{12a}$ is a hydrogen atom), and $R^{2a}$ is a methyl group (the methyl group is substituted with a phenyl group) or a t-butyl group.

Another particularly preferred embodiment of the substituent $L^{3a}$ and the substituent $R^{2a}$ is such that $L^{3a}$ is represented by the formula (X$^a$-8):

(X$^a$-8)

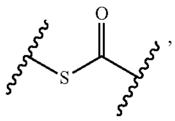

, and $R^{2a}$ is a methyl group.

Another particularly preferred embodiment of the substituent $L^{3a}$ and the substituent $R^{2a}$ is such that $L^{3a}$ is represented by the formula (X$^a$-7):

(X$^a$-7)

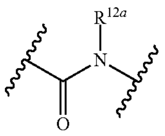

(wherein $R^{12a}$ is a hydrogen atom), and $R^{2a}$ is a $C_{1-3}$ alkyl group (the $C_{1-3}$ alkyl group is substituted with a 5 to 6-membered aromatic heterocyclyl group (the 5 to 6-membered aromatic heterocyclyl group is substituted with a $C_{1-3}$ alkyl group)).

Another particularly preferred embodiment of the substituent $L^{3a}$ and the substituent $R^{2a}$ is such that $L^{3a}$ is represented by the formula (XVI$^a$):

(XVI$^a$)

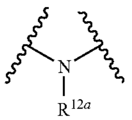

(wherein $R^{12a}$ is a hydrogen atom), and $R^{2a}$ is a $C_{1-3}$ alkyl group (the $C_{1-3}$ alkyl group is substituted with a phenyl group or a 5 to 6-membered aromatic heterocyclyl group (the phenyl group and the 5 to 6-membered aromatic heterocyclyl group are substituted with a $C_{1-3}$ alkyl group or a $C_{1-3}$ haloalkyl group)) or a $C_{2-6}$ alkynyl group.

Another particularly preferred embodiment of the substituent $L^{3a}$ and the substituent $R^{2a}$ is such that $L^{3a}$ is represented by the formula (XVI$^a$):

(XVI$^a$)

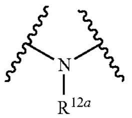

(wherein $R^{12a}$ is a hydrogen atom), and $R^{2a}$ is a $C_{1-3}$ alkyl group (the $C_{1-3}$ alkyl group is substituted with a phenyl group or a 5 to 6-membered aromatic heterocyclyl group (the phenyl group and the 5 to 6-membered aromatic heterocyclyl group are substituted with a $C_{1-3}$ alkyl group or a $C_{1-3}$ haloalkyl group and with a halogen atom)).

Another particularly preferred embodiment of the substituent $L^{3a}$ and the substituent $R^{2a}$ is such that $L^{3a}$ is represented by the formula (X$^a$-11):

(X$^a$-11)

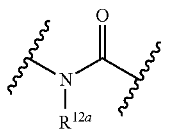

(wherein $R^{12a}$ is a $C_{1-3}$ alkyl group (the $C_{1-3}$ alkyl group is substituted with a cyano group or a 5 to 6-membered aromatic heterocyclyl group (the 5 to 6-membered aromatic heterocyclyl group is unsubstituted or substituted with a $C_{1-3}$ alkyl group)) or a $C_{3-6}$ cycloalkyl group), and $R^{2a}$ is a $C_{1-3}$ alkyl group (the $C_{1-3}$ alkyl group is unsubstituted or substituted with a cyano group) or a $C_{1-3}$ haloalkyl group.

Another particularly preferred embodiment of the substituent $L^{3a}$ and the substituent $R^{2a}$ is such that $L^{3a}$ is represented by the formula (XVI$^a$):

(XVI$^a$)

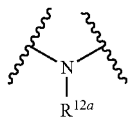

(wherein $R^{12a}$ is a $C_{1-3}$ alkyl group (the $C_{1-3}$ alkyl group is substituted with a substituent selected from the group consisting of a cyano group, a hydroxy group, a $C_{1-3}$ alkoxy group, a $C_{3-6}$ cycloalkyl group and a phenyl group), a $C_{3-6}$ cycloalkyl group or a phenyl group), and $R^{2a}$ is a $C_{1-3}$ alkyl group (the $C_{1-3}$ alkyl group is substituted with a substituent selected from the group consisting of a cyano group, a hydroxy group, a $C_{1-3}$ alkoxy group, a $C_{3-6}$ cycloalkyl group and a phenyl group).

A preferred embodiment of $n^a$ and the substituent $R^{3a}$ is such that $n^a$ is 0, 1 or 2, and $R^{3a}$ is a hydroxy group, an amino group, a halogen atom, a cyano group, a $C_{1-3}$ alkyl group, a $C_{1-3}$ haloalkyl group, a $C_{1-3}$ alkoxy group or a $C_{1-3}$ haloalkoxy group (when $n^a$ is 2, $R^{3a}$ 's may be identical or different).

Another preferred embodiment of $n^a$ and the substituent $R^{3a}$ is such that $n^a$ is 0, 1 or 2, and $R^{3a}$ is a carbamoyl group, a carboxy group, a $C_{1-3}$ haloalkylcarbonyl group, a $C_{1-6}$ alkoxycarbonyl group, a mono-$C_{1-3}$ alkylamino group, di-$C_{1-3}$ alkylamino group, mono-$C_{1-3}$ alkylaminocarbonyl group, a di-$C_{1-3}$ alkylaminocarbonyl group or a $C_{1-3}$ alkylcarbonylamino group (when $n^a$ is 2, $R^{3a}$ 's may be identical or different).

A more preferred embodiment of $n^a$ and the substituent $R^{3a}$ is such that $n^a$ is 0 or 1, and $R^{3a}$ is a $C_{1-3}$ alkyl group.

Another more preferred embodiment of $n^a$ and the substituent $R^{3a}$ is such that $n^a$ is 0 or 1, and $R^{3a}$ is a halogen atom.

Another more preferred embodiment of $n^a$ and the substituent $R^{1a}$ is such that $n^a$ is 0 or 1, and $R^{3a}$ is a cyano group.

Another more preferred embodiment of $n^a$ and the substituent $R^{3a}$ is such that $n^a$ is 0 or 1, and $R^{3a}$ is a hydroxy group.

Another more preferred embodiment of $n^a$ and the substituent $R^{3a}$ is such that $n^a$ is 2, and $R^{3a}$ is a halogen atom or a $C_{1-3}$ alkyl group ($R^{3a}$ 's may be identical or different).

As favorable tricyclic pyrimidine compounds of the present invention for use as JAK inhibitors and as preventive, therapeutic and/or improving agent for diseases against which inhibition of JAK is effective, the following compounds may be mentioned.

1$^a$) Compounds represented by the formula (I$^a$):

(I$^a$)

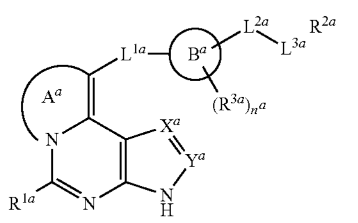

[wherein $R^{1a}$ is a hydrogen atom or a halogen atom, $X^a$ is $CR^{9a}$ (wherein $R^{9a}$ is a hydrogen atom, a halogen atom, a cyano group, a $C_{1-6}$ alkyl group, a $C_{1-6}$ haloalkyl group or a $C_{3-6}$ cycloalkyl group) or a nitrogen atom, $Y^a$ is $CR^{10a}$ (wherein $R^{10a}$ is a hydrogen atom), the ring $A^a$ is represented by the following formula (II$^a$-1) or (II$^a$-2):

(II$^a$)

(II$^a$-1)

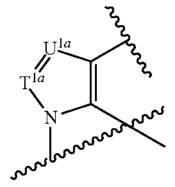

(II$^a$-2)

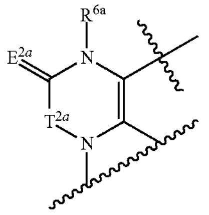

(wherein $T^{1a}$ is a nitrogen atom or $CR^{4a}$, $U^{1a}$ is a nitrogen atom or $CR^{5a}$, $T^{2a}$ is a single bond, and $E^{2a}$ is an oxygen atom or a sulfur atom), the ring $B^a$ is a $C_{3-11}$ cycloalkane, a $C_{3-11}$ cycloalkene (a ring-constituting methylene group of the $C_{3-11}$ cycloalkane and the $C_{3-11}$ cycloalkene may be replaced by a carbonyl group), a 3 to 11-membered non-aromatic heterocycle, a $C_{6-14}$ aromatic carbocycle or a 5 to 10-membered aromatic heterocycle, $L^{1a}$ is a single bond or a $C_{1-6}$ alkylene group, $L^{2a}$ is a single bond, a $C_{1-6}$ alkylene group, a $C_{2-6}$ alkenylene group (the $C_{1-6}$ alkylene group and the $C_{2-6}$ alkenylene group are unsubstituted or substituted with one or more identical or different substituents independently selected from the group consisting of halogen atoms, hydroxy groups, amino groups and cyano groups), $=C(R^{15a})-$ (wherein $R^{15a}$ is a hydrogen atom or a cyano group, and the bond connecting the ring $B^a$ and $L^{2a}$ is a double bond) or $=C(R^{15a})-CH_2-$ (wherein $R^{15a}$ is a hydrogen atom or a cyano group, and the bond connecting the ring $B^a$ and $L^{2a}$ is a double bond), $L^{3a}$ is a single bond or represented by any of the following formulae (XIV$^a$-1) to (XIV$^a$-15) or (XIII$^a$):

(XIV$^a$)

(XIV$^a$-1)

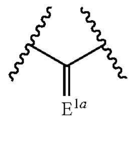

(XIV$^a$-2)

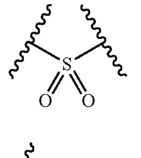

(XIV$^a$-3)

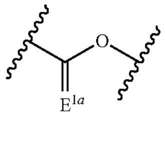

-continued (XIV$^a$-4)

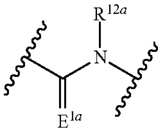

(XIV$^a$-5)

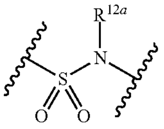

(XIVa-6)

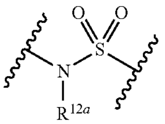

(XIVa-7)

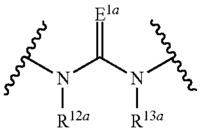

(XIVa-8)

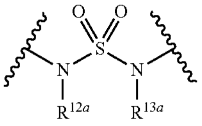

(XIVa-9)

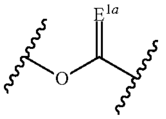

(XIV$^a$-10)

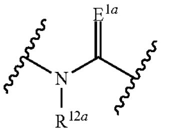

(XIV$^a$-11)

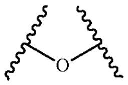

(XIV$^a$-12)

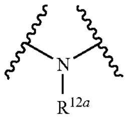

(XIV$^a$-13)

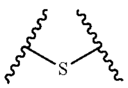

(XIV$^a$-14)

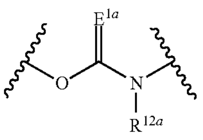

(XIV$^a$-15)

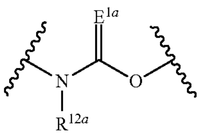

-continued (XIII$^a$)

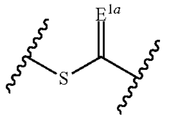

(wherein $E^{1a}$ is an oxygen atom or a sulfur atom), when $L^{3a}$ is a single bond, $R^{2a}$ is a hydrogen atom, a halogen atom, an azido group, a $C_{3-11}$ cycloalkyl group, a 3 to 11-membered non-aromatic heterocyclyl group, a $C_{6-14}$ aryl group, a 5 to 10-membered aromatic heterocyclyl group, a 8 to 11-membered partially saturated aromatic cyclic group or a 8 to 11-membered aromatic ring-condensed alicyclic hydrocarbon group (the $C_{3-11}$ cycloalkyl group, the 3 to 11-membered non-aromatic heterocyclyl group, the $C_{6-14}$ aryl group, the 5 to 10-membered aromatic heterocyclyl group, the 8 to 11-membered partially saturated aromatic cyclic group and the 8 to 11-membered aromatic ring-condensed alicyclic hydrocarbon group are unsubstituted or substituted with one or more identical or different substituents independently selected from the group consisting of the substituent set $V^{4a}$, the substituent set $V^{9a}$ and $C_{1-6}$ alkyl groups (the $C_{1-6}$ alkyl groups are substituted with a $C_{1-6}$ alkoxycarbonylamino group (the $C_{1-6}$ alkoxycarbonylamino group is unsubstituted or substituted with one or more identical or different halogen atoms independently selected from the group consisting of fluorine atoms, chlorine atoms, bromine atoms and iodine atoms)), when $L^{3a}$ is not a single bond, $R^{2a}$ is a hydrogen atom, a $C_{1-6}$ alkyl group, a $C_{2-6}$ alkenyl group, a $C_{2-6}$ alkynyl group (the $C_{1-6}$ alkyl group, the $C_{2-6}$ alkenyl group and the $C_{2-6}$ alkynyl group are unsubstituted or substituted with one or more identical or different substituents independently selected from the substituent set $V^{6a}$ and the substituent set $V^{9a}$), a $C_{3-11}$ cycloalkyl group, a 3 to 11-membered non-aromatic heterocyclyl group, a $C_{6-14}$ aryl group, a 5 to 10-membered aromatic heterocyclyl group, a 8 to 11-membered partially saturated aromatic cyclic group or a 8 to 11-membered aromatic ring-condensed alicyclic hydrocarbon group (the $C_{3-11}$ cycloalkyl group, the 3 to 11-membered non-aromatic heterocyclyl group, the $C_{6-14}$ aryl group, the 5 to 10-membered aromatic heterocyclyl group, the 8 to 11-membered partially saturated aromatic cyclic group and the 8 to 11-membered aromatic ring-condensed alicyclic hydrocarbon group are unsubstituted or substituted with one or more identical or different substituents independently selected from the substituent set $V^{4a}$ and the substituent set $V^{9a}$), $n^a$ is 0, 1 or 2, $R^{3a}$ is a hydroxy group, an amino group, a carboxy group, a carbamoyl group, a sulfamoyl group, a phosphono group, a phosphonooxy group, a sulfo group, a sulfoxy group, a tetrazolyl group, a halogen atom, a cyano group, a nitro group, a $C_{1-6}$ alkyl group, a $C_{1-6}$ haloalkyl group, a $C_{3-11}$ cycloalkyl group, a $C_{2-6}$ alkenyl group, a $C_{2-6}$ haloalkenyl group, a $C_{1-6}$ alkoxy group, a $C_{1-6}$ haloalkoxy group, a $C_{1-6}$ alkylthio group, a $C_{1-6}$ haloalkylthio group, a $C_{1-6}$ alkylcarbonyl group, a $C_{1-6}$ haloalkylcarbonyl group, a $C_{1-6}$ alkylsulfonyl group, a $C_{1-6}$ haloalkylsulfonyl group, a $C_{1-6}$ alkoxycarbonyl group, a mono-$C_{1-6}$ alkylamino group, a di-$C_{1-6}$ alkylamino group, a mono-$C_{1-6}$ alkylaminocarbonyl group, a di-$C_{1-6}$ alkylaminocarbonyl group or a $C_{1-6}$ alkylcarbonylamino group (when $n^a$ is 2, $R^{3a}$'s may be identical or different), each of $R^{4a}$ and $R^{5a}$ is independently a hydrogen atom, a hydroxy group, an amino group, a carboxy group, a carbamoyl group, a tetrazolyl group, a halogen atom, a cyano group, a $C_{1-6}$ alkyl group, a $C_{2-6}$ alkenyl group, a $C_{1-6}$ alkoxy group, a $C_{1-6}$ alkylthio group, a $C_{1-6}$ alkylcarbonyl group, a $C_{1-6}$ alkylsulfonyl group, a mono-$C_{1-6}$ alkylamino group, a di-$C_{1-6}$ alkylamino group (the $C_{1-6}$ alkyl group, the $C_{2-6}$ alkenyl group, the $C_{1-6}$ alkoxy group, the $C_{1-6}$ alkylthio group, the $C_{1-6}$ alkylcarbonyl group, the $C_{1-6}$ alkylsulfonyl group, the mono-$C_{1-6}$ alkylamino group and the di-$C_{1-6}$ alkylamino group are unsubstituted or substituted with one or more identical or different substituents independently selected from the substituent set $V^{3a}$), a $C_{1-6}$ alkoxycarbonyl group, a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{1a}$), $R^{6a}$ is a hydrogen atom, a $C_{1-6}$ alkyl group (the $C_{1-6}$ alkyl group is unsubstituted or substituted with one or more identical or different substituents independently selected from the substituent set $V^{3a}$), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the substituent set $V^{1a}$), each of $R^{12a}$ and $R^{13a}$ is independently a hydrogen atom, a $C_{1-6}$ alkyl group, a $C_{1-6}$ haloalkyl group (the $C_{1-6}$ alkyl group and the $C_{1-6}$ haloalkyl group are unsubstituted or substituted with one or more identical or different substituents independently selected from the substituent set $V^{2a}$, the substituent set $V^{8a}$ and the substituent set $V^{9a}$), a $C_{3-11}$ cycloalkyl group, a 3 to 11-membered non-aromatic heterocyclyl group, a $C_{6-14}$ aryl group, a 5 to 10-membered aromatic heterocyclyl group, a 8 to 14-membered partially saturated aromatic cyclic group or a 8 to 14-membered aromatic ring-condensed alicyclic hydrocarbon group (the $C_{3-11}$ cycloalkyl group, the 3 to 11-membered non-aromatic heterocyclyl group, $C_{6-14}$ aryl group, the 5 to 10-membered aromatic heterocyclyl group, the 8 to 14-membered partially saturated aromatic cyclic group and the 8 to 14-membered aromatic ring-condensed alicyclic hydrocarbon group are unsubstituted or substituted with one or more identical or different substituents independently selected from the substituent set $V^{1a}$ or the substituent set $V^{9a}$)], tautomers or pharmaceutically acceptable salts of the compounds or solvates thereof.

$2^a$) The compounds according to $1^a$), wherein $R^{1a}$ is a hydrogen atom or a halogen atom, $X^a$ is $CR^{9a}$ (wherein $R^{9a}$ is a hydrogen atom, a halogen atom, a cyano group, a $C_{1-6}$ alkyl group, a $C_{1-6}$ haloalkyl group or a $C_{3-6}$ cycloalkyl group) or a nitrogen atom, $Y^a$ is $CR^{10a}$ (wherein $R^{10a}$ is a hydrogen atom), the ring $A^a$ is represented by the following formula ($II^a$-1) or ($II^a$-2):

($II^a$)

($II^a$-1)

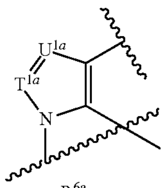

($II^a$-2)

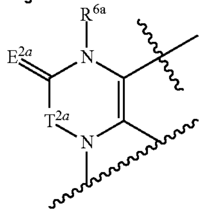

(wherein $T^{1a}$ is a nitrogen atom or $CR^{4a}$, $U^{1a}$ is a nitrogen atom or $CR^{5a}$, $T^{2a}$ is a single bond, $E^{2a}$ is an oxygen atom or a sulfur atom, and $R^{6a}$ is a hydrogen atom, a $C_{1-6}$ alkyl group (the $C_{1-6}$ alkyl group is unsubstituted or substituted with one or more identical or different substituents independently selected from the substituent set $V^{3a}$), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the substituent set $V^{1a}$)), $L^{1a}$ is a single bond or a $C_{1-3}$ alkylene group, $L^{2a}$ is a single bond, a $C_{1-6}$ alkylene group or a $C_{1-6}$ haloalkylene group (the $C_{1-6}$ alkylene group and the $C_{1-6}$ haloalkylene group are unsubstituted or substituted with a hydroxy group or a cyano group), the ring $B^a$ is a $C_{3-11}$ cycloalkane, a $C_{3-11}$ cycloalkene, a 3 to 11-membered non-aromatic heterocycle, a $C_{6-14}$ aromatic carbocycle or a 5 to 10-membered aromatic heterocycle, $n^a$ is 0 or 1, $R^{3a}$ is a hydroxy group, an amino group, a carboxy group, a carbamoyl group, a tetrazolyl group, a halogen atom, a cyano group, a nitro group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkylsulfonyl group, and $L^{3a}$ is a single bond, and $R^{2a}$ is a hydrogen atom, a halogen atom, a $C_{3-6}$ cycloalkyl group, a 3 to 11-membered non-aromatic heterocyclyl group, a phenyl group or a 5 to 6-membered aromatic heterocyclyl group (the $C_{3-6}$ cycloalkyl group, the 3 to 11-membered non-aromatic heterocyclyl group, the phenyl group and the 5 to 6-membered aromatic heterocyclyl group are unsubstituted or substituted with one or more identical or different substituents independently selected from the substituent set $V^{4a}$), or $L^{3a}$ is represented by any of the following formulae ($V^a$-1) to ($V^a$-11):

($V^a$)

($V^a$-1)

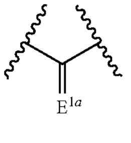

-continued ($V^a$-2)

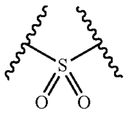

($V^a$-3)

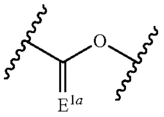

($V^a$-4)

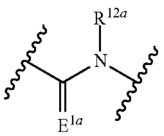

($V^a$-5)

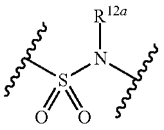

($V^a$-6)

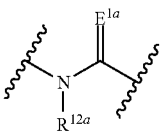

($V^a$-7)

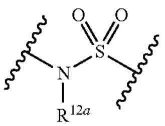

($V^a$-8)

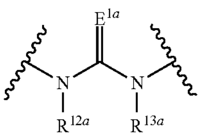

($V^a$-9)

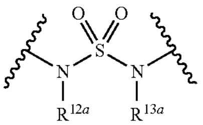

($V^a$-10)

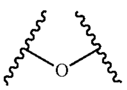

($V^a$-11)

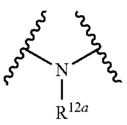

(wherein $E^{1a}$ is an oxygen atom, and each of $R^{12a}$ and $R^{13a}$ is independently a hydrogen atom or a $C_{1-6}$ alkyl group), and $R^{2a}$ is a hydrogen atom, a $C_{1-6}$ alkyl group (the $C_{1-6}$ alkyl group is unsubstituted or substituted with one or more identical or different substituents independently selected from the substituent set $V^{5a}$), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the substituent set $V^{4a}$), and each of $R^{4a}$ and $R^{5a}$ is independently a hydrogen atom, an amino group, a carbamoyl group, a halogen atom, a cyano group, a $C_{1-6}$ alkyl group, a $C_{1-6}$ haloalkyl group, a $C_{3-6}$ cycloalkyl group, a $C_{1-6}$ alkoxy group, a $C_{1-6}$ haloalkoxy group, a $C_{1-6}$ alkylsulfonyl group, a 4 to 7-membered non-aromatic heterocyclyl group, a phenyl group or a 5 to 6-membered aromatic heterocyclyl group, tautomers or pharmaceutically acceptable salts of the compounds or solvates thereof.

$3^a$) The compounds according to $2^a$), wherein $R^{1a}$ is a hydrogen atom, tautomers or pharmaceutically acceptable salts of the compounds or solvates thereof.

$4^a$) The compounds according to $2^a$) or $3^a$), wherein $Y^a$ is $CR^{10a}$ (wherein $R^{10a}$ is a hydrogen atom), tautomers or pharmaceutically acceptable salts of the compounds or solvates thereof.

$5^a$) The compounds according to any one of $2^a$) to $4^a$), wherein $X^a$ is a nitrogen atom or $CR^{9a}$ (wherein $R^{9a}$ is a hydrogen atom, a halogen atom or a cyano group), tautomers or pharmaceutically acceptable salts of the compounds or solvates thereof.

$6^a$) The compounds according to any one of $2^a$) to $5^a$), wherein $X^a$ is $CR^{9a}$ (wherein $R^{9a}$ is a hydrogen atom), tautomers or pharmaceutically acceptable salts of the compounds or solvates thereof.

$7^a$) The compounds according to any one of $2^a$) to $6^a$), wherein the ring $A^a$ is represented by any of the following formulae ($IV^a$-1) to ($IV^a$-3):

($IV^a$)

($IV^a$-1)

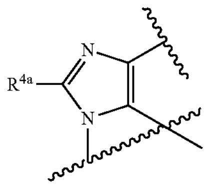

($IV^a$-2)

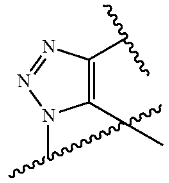

($IV^a$-3)

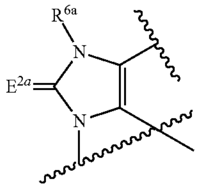

(wherein $E^{2a}$ is an oxygen atom or a sulfur atom, $R^{4a}$ is a hydrogen atom, an amino group, a carbamoyl group, a halogen atom, a cyano group, a $C_{1-6}$ alkyl group, a $C_{1-6}$ haloalkyl group, a $C_{3-6}$ cycloalkyl group, a $C_{1-6}$ alkoxy group, a $C_{1-6}$ haloalkoxy group, a $C_{1-6}$ alkylsulfonyl group, a 4 to 7-membered non-aromatic heterocyclyl group, a phenyl group or a 5 to 6-membered aromatic heterocyclyl group, and $R^{ha}$ is a hydrogen atom, a $C_{1-6}$ alkyl group, a $C_{1-6}$ haloalkyl group, a $C_{3-6}$ cycloalkyl group, a 4 to 7-membered non-aromatic heterocyclyl group, a phenyl group or a 5 to 6-membered aromatic heterocyclyl group), tautomers or pharmaceutically acceptable salts of the compounds or solvates thereof.

$8^a$) The compounds according to any one of $2^a$) to $7^a$), wherein the ring $A^a$ is represented by any of the following formulae ($VIII^a$-1) to ($VIII^a$-5):

($VIII^a$)

($VIII^a$-1)

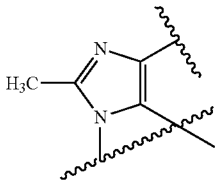

($VIII^a$-2)

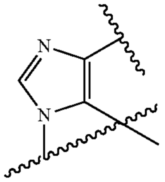

($VIII^a$-3)

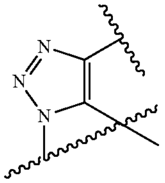

($VIII^a$-4)

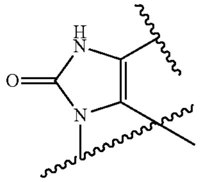

($VIII^a$-5)

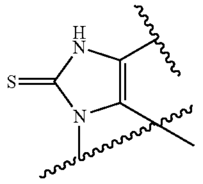

tautomers or pharmaceutically acceptable salts of the compounds or solvates thereof.

$9^a$) The compounds according to any one of $2^a$) to $8^a$), wherein $L^{1a}$ is a single bond, tautomers or pharmaceutically acceptable salts of the compounds or solvates thereof.

$10^a$) The compounds according to any one of $2^a$) to $9^a$), wherein $L^{2a}$ is a single bond or a $C_{1-3}$ alkylene group (the $C_{1-3}$ alkylene group is unsubstituted or substituted with a cyano group) or a $C_{1-3}$ haloalkylene group, tautomers or pharmaceutically acceptable salts of the compounds or solvates thereof.

$11^a$) The compounds according to any one of $2^a$) to $9^a$), wherein $L^{2a}$ is a single bond or a methylene group, tautomers or pharmaceutically acceptable salts of the compounds or solvates thereof.

$12^a$) The compounds according to any one of $2^a$) to $11^a$), wherein the ring $B^a$ is a $C_{4-7}$ cycloalkane, benzene or a 4 to 7-membered non-aromatic heterocycle, tautomers or pharmaceutically acceptable salts of the compounds or solvates thereof.

$13^a$) The compounds according to any one of $2^a$) to $11^a$), wherein the ring $B^a$ is cyclohexane, benzene or piperidine, tautomers or pharmaceutically acceptable salts of the compounds or solvates thereof.

$14^a$) The compounds according to any one of $2^a$) to $11^a$), wherein the ring $B^a$ is spiro[2,5]octane or adamantane, tautomers or pharmaceutically acceptable salts of the compounds or solvates thereof.

$15^a$) The compounds according to any one of $2^a$) to $11^a$), wherein the ring $B^a$ is cyclohexane, tautomers or pharmaceutically acceptable salts of the compounds or solvates thereof.

$16^a$) The compounds according to any one of $2^a$) to $15^a$), wherein $n^a$ is 0 or 1, and $R^{3a}$ is a methyl group, tautomers or pharmaceutically acceptable salts of the compounds or solvates thereof.

$17^a$) The compounds according to any one of $2^a$) to $15^a$), wherein $n^a$ is 0 or 1, and $R^{3a}$ is a halogen atom, tautomers or pharmaceutically acceptable salts of the compounds or solvates thereof.

$18^a$) The compounds according to any one of $2^a$) to $15^a$), wherein $n^a$ is 0 or 1, and $R^{3a}$ is a cyano group, tautomers or pharmaceutically acceptable salts of the compounds or solvates thereof.

$19^a$) The compounds according to any one of $2^a$) to $15^a$), wherein $n^a$ is 0 or 1, and $R^{3a}$ is a hydroxy group, tautomers or pharmaceutically acceptable salts of the compounds or solvates thereof.

$20^a$) The compounds according to any one of $2^a$) to $15^a$), wherein $n^a$ is 0, tautomers or pharmaceutically acceptable salts of the compounds or solvates thereof.

$21^a$) The compounds according to any one of $2^a$) to $20^a$), wherein $L^{3a}$ is a single bond, and $R^{2a}$ is a hydrogen atom, tautomers or pharmaceutically acceptable salts of the compounds or solvates thereof.

$22^a$) The compounds according to any one of $2^a$) to $20^a$), wherein $L^{3a}$ is a single bond, and $R^{2a}$ is a halogen atom, tautomers or pharmaceutically acceptable salts of the compounds or solvates thereof.

$23^a$) The compounds according to any one of $2^a$) to $20^a$), wherein $L^{3a}$ is a single bond, and $R^{2a}$ is a $C_{3-6}$ cycloalkyl group or a 3 to 11-membered non-aromatic heterocyclyl group (the $C_{3-6}$ cycloalkyl group and the 3 to 11-membered non-aromatic heterocyclyl group are unsubstituted or substituted with one or more identical or different substituents independently selected from the group consisting of hydroxy groups, cyano groups, halogen atoms, carboxy groups, carbamoyl groups, $C_{1-6}$ alkyl groups (the $C_{1-6}$ alkyl groups are unsubstituted or substituted with a hydroxy group or a cyano group), $C_{1-6}$ haloalkyl groups, $C_{1-6}$ haloalkoxy groups, di-$C_{1-6}$ alkylamino groups, $C_{1-6}$ alkylsulfonyl groups, mono-$C_{1-6}$ alkylaminocarbonyl groups, $C_{1-6}$ alkylcarbonylamino groups (the mono-$C_{1-6}$ alkylaminocarbonyl groups and the $C_{1-6}$ alkylcarbonylamino groups are unsubstituted or substituted with one or more identical or different halogen atoms independently selected from the group consisting of fluorine atoms, chlorine atoms, bromine atoms and iodine atoms), 4 to 7-membered non-aromatic heterocyclyl groups and phenyl groups (the phenyl groups are unsubstituted or substituted with one or two identical or different substituents independently selected from the group consisting of halogen atoms and $C_{1-6}$ haloalkyl groups)), tautomers or pharmaceutically acceptable salts of the compounds or solvates thereof.

24[a]) The compounds according to 23[a]), wherein $L^{3a}$ is a single bond, and $R^{2a}$ is a cyclohexyl group or a cyclopentyl group (the cyclohexyl group and the cyclopentyl group are unsubstituted or substituted with a $C_{1-3}$ alkyl group or a $C_{1-3}$ haloalkyl group), tautomers or pharmaceutically acceptable salts of the compounds or solvates thereof.

25[a]) The compounds according to 23[a]), wherein $L^{3a}$ is a single bond, and $R^{2a}$ is an azetidinyl group, a pyrrolidinyl group, a piperidinyl group, a morpholinyl group, a 1,1-dioxothiomorpholino group, a thiazolidinyl group, a piperadinyl group, an oxopiperadinyl group or a indolinyl group (the azetidinyl group, the pyrrolidinyl group, the piperidinyl group, the morpholinyl group, the 1,1-dioxothiomorpholino group, the thiazolidinyl group, the piperadinyl group, the oxopiperadinyl group and the indolinyl group are unsubstituted or substituted with one or two identical or different substituents independently selected from the group consisting of hydroxy groups, cyano groups, halogen atoms, carboxy groups, carbamoyl groups, $C_{1-6}$ alkyl groups (the $C_{1-6}$ alkyl groups are unsubstituted or substituted with a hydroxy group or a cyano group), $C_{1-6}$ haloalkyl groups, $C_{1-6}$ haloalkoxy groups, di-$C_{1-6}$ alkylamino groups, $C_{1-6}$ alkylsulfonyl groups, mono-$C_{1-6}$ alkylaminocarbonyl groups, $C_{1-6}$ alkylcarbonylamino groups (the mono-$C_{1-6}$ alkylaminocarbonyl groups and the $C_{1-6}$ alkylcarbonylamino groups are unsubstituted or substituted with one or more identical or different halogen atoms independently selected from the group consisting of fluorine atoms, chlorine atoms, bromine atoms and iodine atoms), 4 to 7-membered non-aromatic heterocyclyl groups and phenyl groups (the phenyl groups are unsubstituted or substituted with one or two identical or different substituents independently selected from the group consisting of halogen atoms and $C_{1-6}$ haloalkyl groups)), tautomers or pharmaceutically acceptable salts of the compounds or solvates thereof.

26[a]) The compounds according to any one of 2[a]) to 20[a]), wherein $L^{3a}$ is a single bond, and $R^{2a}$ is a phenyl group or a 5 to 10-membered aromatic heterocyclyl group (the phenyl group and the 5 to 10-membered aromatic heterocyclyl group are unsubstituted or substituted with one or more identical or different substituents independently selected from the group consisting of halogen atoms, cyano groups, carbamoyl groups, $C_{1-6}$ alkyl groups, $C_{1-6}$ alkoxy groups, di-$C_{1-3}$ alkylamino groups (the $C_{1-6}$ alkyl groups, the $C_{1-6}$ alkoxy groups and the di-$C_{1-3}$ alkylamino groups are unsubstituted or substituted with a hydroxy group or a cyano group), $C_{1-6}$ alkylthio groups, $C_{1-6}$ alkylsulfonyl groups, $C_{1-6}$ haloalkyl groups, $C_{1-6}$ haloalkoxy groups, $C_{1-6}$ haloalkylthio groups, 4 to 7-membered non-aromatic heterocyclyl groups and 5 to 6-membered aromatic heterocyclyl groups), tautomers or pharmaceutically acceptable salts of the compounds or solvates thereof.

27[a]) The compounds according to any one of 2[a]) to 20[a]), wherein $L^{3a}$ is a single bond, and $R^{2a}$ is a phenyl group or a 5 to 6-membered aromatic heterocyclyl group (the phenyl group and the 5 to 6-membered aromatic heterocyclyl group are unsubstituted or substituted with one, two or three identical or different substituents independently selected from the group consisting of halogen atoms, hydroxy groups, cyano groups, $C_{1-6}$ alkyl groups, $C_{1-6}$ alkoxy groups, $C_{1-6}$ alkylthio groups, mono-$C_{1-3}$ alkylamino groups, alkylamino groups, $C_{1-6}$ alkylsulfonyl groups (the $C_{1-6}$ alkyl group, the $C_{1-6}$ alkoxy group, the $C_{1-6}$ alkylthio group, the mono-$C_{1-3}$ alkylamino group, the di-$C_{1-3}$ alkylamino group and the $C_{1-6}$ alkylsulfonyl group are unsubstituted or substituted with a hydroxy group or a cyano group), $C_{1-6}$ haloalkyl groups, $C_{1-6}$ haloalkoxy groups, $C_{1-6}$ haloalkylthio groups and $C_{1-6}$ haloalkylsulfonyl groups), tautomers or pharmaceutically acceptable salts of the compounds or solvates thereof.

28[a]) The compounds according to 27[a]), wherein $L^{3a}$ is a single bond, and $R^{2a}$ is a phenyl group (the phenyl group is unsubstituted or substituted with one, two or three identical or different substituents independently selected from the group consisting of halogen atoms, cyano groups, $C_{1-3}$ alkyl groups, $C_{1-3}$ alkoxy groups (the $C_{1-3}$ alkoxy group is unsubstituted or substituted with a hydroxy group or a cyano group), $C_{1-3}$ alkylthio groups, $C_1$ alkylsulfonyl groups, $C_{1-3}$ haloalkyl groups, $C_{1-3}$ haloalkoxy groups, $C_{1-3}$ haloalkylthio groups, di-$C_{1-3}$ alkylamino groups (the di-$C_{1-3}$ alkylamino groups are unsubstituted or substituted with a cyano group), carbamoyl groups and 5 to 6-membered aromatic heterocyclyl groups), tautomers or pharmaceutically acceptable salts of the compounds or solvates thereof.

29[a]) The compounds according to 27[a]), wherein $L^{3a}$ is a single bond, and $R^{2a}$ is a furanyl group, a thienyl group, a pyrazolyl group, an isoxazolyl group, a thiazolyl group, a thiadiazolyl group, an indazolyl group, a quinoxalinyl group, an oxazolyl group, a benzothiazolyl group, a triazolyl group or a pyridinyl group (the furanyl group, the thienyl group, the pyrazolyl group, the isoxazolyl group, the thiazolyl group, the thiadiazolyl group, the indazolyl group, the quinoxalinyl group, the oxazolyl group, the benzothiazolyl group, the triazolyl group and the pyridinyl group are unsubstituted or substituted with identical or different one, two or three substituents independently selected from the group consisting of halogen atoms, cyano groups, $C_{1-3}$ alkyl groups (the $C_{1-3}$ alkyl groups are unsubstituted or substituted with a hydroxy group), $C_{1-3}$ haloalkyl groups, hydroxy groups, $C_{1-3}$ alkoxy groups, 4 to 7-membered non-aromatic heterocyclyl group and $C_{1-3}$ haloalkoxy groups), tautomers or pharmaceutically acceptable salts of the compounds or solvates thereof.

30[a]) The compounds according to any one of 2[a]) to 20[a]), wherein $L^{3a}$ is represented by the following formula ($XI^a$-11 or ($XI^a$-2):

($XI^a$)

($XI^a$-1)

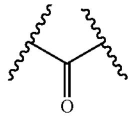

($XI^a$-2)

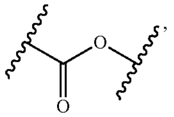

and $R^{2a}$ is a methyl group (the methyl group is unsubstituted or substituted with a cyano groups or a phenyl group), tautomers or pharmaceutically acceptable salts of the compounds or solvates thereof.

31[a]) The compounds according to any one of 2[a]) to 20[a]), wherein $L^{3a}$ is represented by the formula ($X^a$-1):

($X^a$-1)

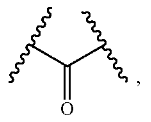

and $R^{2a}$ is a hydrogen atom, a $C_{1-3}$ alkyl group (the $C_{1-3}$ alkyl group is unsubstituted or substituted with a cyano group), a $C_{1-3}$ haloalkyl group, a 4 to 7-membered non-aromatic heterocyclyl group or a phenyl group (the 4 to 7-membered non-aromatic heterocyclyl group and the phenyl group are unsubstituted or substituted with a substituent selected from the group consisting of a hydroxy group, a halogen atom, a $C_{1-3}$ alkyl group and a $C_{1-3}$ haloalkyl group), tautomers or pharmaceutically acceptable salts of the compounds or solvates thereof.

32[a]) The compounds according to any one of 2[a]) to 20[a]), wherein $L^{3a}$ is represented by the formula ($X^a$-10):

($X^a$-10)

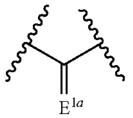

(wherein $E^{1a}$ is $NR^{11a}$ (wherein $R^{11a}$ is a hydroxy group)), and $R^{2a}$ is a hydrogen atom, tautomers or pharmaceutically acceptable salts of the compounds or solvates thereof.

33[a]) The compounds according to any one of 2[a]) to 20[a]), wherein $L^{3a}$ is represented by the formula ($X^a$-2):

($X^a$-2)

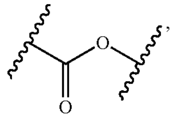

and $R^{2a}$ is a $C_{1-6}$ alkyl group (the $C_{1-6}$ alkyl group is unsubstituted or substituted with a phenyl group), tautomers or pharmaceutically acceptable salts of the compounds or solvates thereof.

34[a]) The compounds according to any one of 2[a]) to 20[a]), wherein $L^{3a}$ is represented by the formula ($X^a$-3):

($X^a$-3)

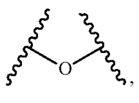

and $R^{2a}$ is a hydrogen atom, tautomers or pharmaceutically acceptable salts of the compounds or solvates thereof.

35[a]) The compounds according to any one of 2[a]) to 20[a]), wherein $L^{3a}$ is represented by the formula ($X^a$-3):

($X^a$-3)

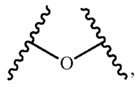

and $R^{2a}$ is a $C_{1-3}$ alkyl group, tautomers or pharmaceutically acceptable salts of the compounds or solvates thereof.

36[a]) The compounds according to any one of 2[a]) to 20[a]), wherein $L^{3a}$ is represented by the formula ($X^a$-4):

($X^a$-4)

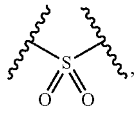

and $R^{2a}$ is a $C_{1-3}$ alkyl group, a $C_{1-3}$ haloalkyl group, a $C_{3-6}$ cycloalkyl group or a phenyl group (the phenyl group is unsubstituted or substituted with a halogen atom), tautomers or pharmaceutically acceptable salts of the compounds or solvates thereof.

37[a]) The compounds according to any one of 2[a]) to 20[a]), wherein $L^{3a}$ is represented by the formula ($X^a$-7):

($X$-$7^a$)

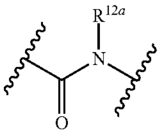

(wherein $R^{12a}$ is a hydrogen atom), and $R^{2a}$ is a hydrogen atom, a $C_{1-6}$ alkyl group, a 6 haloalkyl group (the $C_{1-6}$ alkyl group and the $C_{1-6}$ haloalkyl group are unsubstituted or substituted with one or two identical or different substituents independently selected from the group consisting of hydroxy groups, cyano groups and phenyl groups (the phenyl groups are unsubstituted or substituted with a halogen atom or a cyano group)), a $C_{3-6}$ cycloalkyl group, a phenyl group or a 5 to 6-membered aromatic heterocyclyl group (the $C_{3-6}$ cycloalkyl group, the phenyl group and the 5 to 6-membered aromatic heterocyclyl group are unsubstituted or substituted with a substituent selected from the group consisting of a $C_{1-3}$ alkyl group, a $C_{1-3}$ haloalkyl group and a halogen atom), tautomers or pharmaceutically acceptable salts of the compounds or solvates thereof.

38[a]) The compounds according to any one of 2[a]) to 20[a]), wherein $L^{3a}$ is represented by the formula ($XVI^a$)

($XVI^a$)

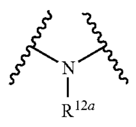

(wherein $R^{12a}$ is a hydrogen atom, a $C_{1-6}$ alkyl group or $C_{1-6}$ haloalkyl group), and $R^{2a}$ is a hydrogen atom, a $C_{1-6}$ alkyl group, a $C_{1-6}$ haloalkyl group (the $C_{1-6}$ alkyl group and the $C_{1-6}$ haloalkyl group are unsubstituted or substituted with a substituent selected from the group consisting of a hydroxy group, a cyano group, a $C_{1-3}$ alkoxy group, mono-$C_{1-3}$ alkylaminocarbonyl group (the mono-$C_{1-3}$ alkylaminocarbonyl group is unsubstituted or substituted with one or more identical or different halogen atoms independently selected from the group consisting of fluorine atoms, chlorine atoms, bromine atoms and iodine atoms), a $C_{3-6}$ cycloalkyl group, a 4 to 7-membered non-aromatic heterocyclyl group, a phenyl group and a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or two identical or different substituents independently selected from the group consisting of halogen atoms, cyano groups, hydroxy groups, $C_{1-3}$ alkoxy groups, $C_{1-3}$ haloalkoxy groups, $C_{1-3}$ haloalkylsulfonyl groups, $C_{1-6}$ alkoxycarbonyl groups, 4 to 7-membered non-aromatic heterocyclyl groups and phenyl groups (the phenyl groups are unsubstituted or substituted with a halogen atom))), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or two identical or different substituents independently selected from the group consisting of hydroxy groups, halogen atoms, cyano groups, $C_{1-3}$ alkyl groups (the $C_{1-3}$ alkyl groups are unsubstituted or substituted with a substituent selected from the group consisting of a hydroxy group, a cyano group and a $C_{1-3}$ alkoxy group), $C_{1-3}$ haloalkyl groups, $C_{1-3}$ alkoxy groups, $C_{1-3}$ haloalkoxy groups, $C_{1-3}$ haloalkylsulfonyl groups, 4 to 7-membered non-aromatic heterocyclyl groups and phenyl groups (the phenyl groups are unsubstituted or substituted with a halogen atom)), tautomers or pharmaceutically acceptable salts of the compounds or solvates thereof.

39$^a$) The compounds according to any one of 2$^a$) to 20$^a$), wherein $L^{3a}$ is represented by the formula (XVI$^a$):

(XVI$^a$)

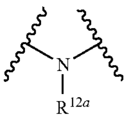

(wherein $R^{12a}$ is a hydrogen atom or a $C_{1-3}$ alkyl group), and $R^{2a}$ is a hydrogen atom, a $C_{1-6}$ alkyl group or a $C_{1-6}$ haloalkyl group (the $C_{1-6}$ alkyl group and the $C_{1-6}$ haloalkyl group are substituted with a substituent selected from the group consisting of a hydroxy group and a cyano group and with a substituent selected from the group consisting of a phenyl group and a 5 to 6-membered aromatic heterocyclyl group (the phenyl group and the 5 to 6-membered aromatic heterocyclyl group are unsubstituted or substituted with one or two identical or different substituents independently selected from the group consisting of halogen atoms, cyano groups, $C_{1-3}$ alkoxy groups and $C_{1-3}$ alkylthio groups)), tautomers or pharmaceutically acceptable salts of the compounds or solvates thereof.

40$^a$) The compounds according to any one of 2$^a$) to 20$^a$), wherein $L^{3a}$ is represented by the formula (X$^a$-11):

(X$^a$-11)

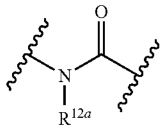

(wherein $R^{12a}$ is a hydrogen atom, a $C_{1-3}$ alkyl group or a $C_{1-3}$ haloalkyl group), and $R^{2a}$ is a $C_{1-6}$ alkyl group (the $C_{1-6}$ alkyl group is unsubstituted or substituted with a cyano group) or a $C_{1-6}$ haloalkyl group, tautomers or pharmaceutically acceptable salts of the compounds or solvates thereof.

41$^a$) The compounds according to any one of 2$^a$) to 20$^a$), wherein $L^{3a}$ is represented by the formula (X$^a$-12):

(X$^a$-12)

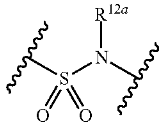

(wherein $R^{12a}$ is a hydrogen atom or a $C_{1-3}$ alkyl group), and $R^{2a}$ is a $C_{1-6}$ alkyl group (the $C_{1-6}$ alkyl group is unsubstituted or substituted with a cyano group), a $C_{1-6}$ haloalkyl group or a $C_{3-6}$ cycloalkyl group, tautomers or pharmaceutically acceptable salts of the compounds or solvates thereof.

42$^a$) The compounds according to any one of 2$^a$) to 20$^a$), wherein $L^{3a}$ is represented by the formula (X$^a$-13):

(X$^a$-13)

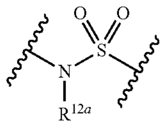

(wherein $R^{12a}$ is a hydrogen atom), and $R^{2a}$ is a $C_{1-6}$ alkyl group, tautomers or pharmaceutically acceptable salts of the compounds or solvates thereof.

43$^a$) The compounds according to 1$^a$), wherein $R^{1a}$ is a hydrogen atom, $X^a$ is $CR^{9a}$ (wherein $R^{9a}$ is a hydrogen atom), $Y^a$ is $CR^{10a}$ (wherein $R^{10a}$ is a hydrogen atom), the ring $A^a$ is represented by any of the following formulae (VIII$^a$-1) to (VIII$^a$-5):

(VIII$^a$)

(VIII$^a$-1)

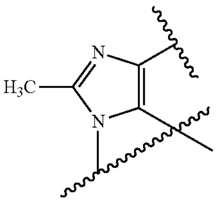

-continued (VIII$^a$-2)

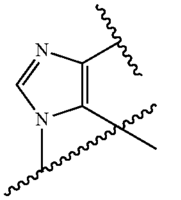

(VIII$^a$-3)

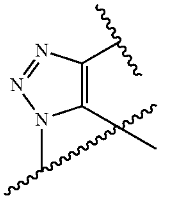

(VIII$^a$-4)

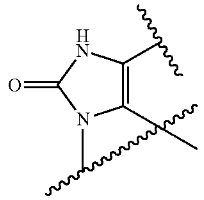

(VIII$^a$-5)

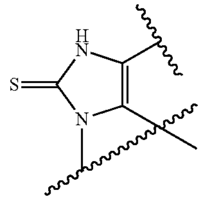

$L^{1a}$ is a single bond, the ring $B^a$ is a $C_{4-7}$ cycloalkane, (a ring-constituting methylene group of the $C_{4-7}$ cycloalkane may be replaced by a carbonyl group) or a 4 to 7-membered non-aromatic heterocycle, $n^a$ is 0 or 1, $R^{3a}$ is a hydroxy group, a cyano group, a halogen atom or a $C_{1-3}$ alkyl group, $L^{2a}$ is a single bond, a $C_{1-6}$ alkylene group (the $C_{1-6}$ alkylene group is unsubstituted or substituted with one or two identical or different substituents independently selected from the group consisting of hydroxy groups and cyano groups), a $C_{1-6}$ haloalkylene group, a $C_{2-6}$ alkenylene group (the $C_{1-6}$ haloalkylene group and the $C_{2-6}$ alkenylene group are unsubstituted or substituted with one or two cyano groups), $=C(R^{15a})-$(wherein $R^{15a}$ is a hydrogen atom or a cyano group, and the bond connecting the ring $B^a$ and $L^{2a}$ is a double bond) or $=C(R^{15a})-CH_2-$ (wherein $R^{15a}$ is a hydrogen atom or a cyano group, and the bond connecting the ring $B^a$ and $L^{2a}$ is a double bond), tautomers or pharmaceutically acceptable salts of the compounds or solvates thereof.

$44^a$) The compounds according to $43^a$), wherein the ring $B^a$ is cyclohexane or piperidine, tautomers or pharmaceutically acceptable salts of the compounds or solvates thereof.

$45^a$) The compounds according to $43^a$), wherein $L^{2a}$ is a single bond, a $C_{1-3}$ alkylene, a $C_{2-3}$ alkenylene group (the $C_{1-3}$ alkylene group and the $C_{2-3}$ alkenylene group are unsubstituted or substituted with one or two cyano groups) or a $C_{1-3}$ haloalkylene group, tautomers or pharmaceutically acceptable salts of the compounds or solvates thereof.

$46^a$) The compounds according to $43^a$), wherein $n^a$ is 0, tautomers or pharmaceutically acceptable salts of the compounds or solvates thereof.

$47^a$) The compounds according to any one of $1^a$) or $43^a$) to $46^a$), wherein $L^{3a}$ is a single bond, $R^{2a}$ is a hydrogen atom, a halogen atom, an azido group, a 3 to 11-membered non-aromatic heterocyclyl group, a phenyl group, a 5 to 10-membered aromatic heterocyclyl group or a 8 to 11-membered partially saturated aromatic cyclic group (the 3 to 11-membered non-aromatic heterocyclyl group, the phenyl group, the 5 to 10-membered aromatic heterocyclyl group and the 8 to 11-membered partially saturated aromatic cyclic group are unsubstituted or substituted with one, two or three identical or different substituents independently selected from the group consisting of hydroxy groups, amino groups, halogen atoms, cyano groups, nitro groups, carbamoyl groups, sulfamoyl groups, $C_{1-6}$ alkyl groups, $C_{1-6}$ haloalkyl groups, $C_{1-6}$ alkoxy groups, $C_{1-6}$ haloalkoxy groups, mono-$C_{1-6}$ alkylamino groups, di-$C_{1-6}$ alkylamino groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, mono-$C_{1-6}$ alkylaminosulfonyl groups, di-$C_{1-6}$ alkylaminosulfonyl groups, $C_{1-6}$ alkoxycarbonyl groups, mono-$C_{1-6}$ alkylaminocarbonyl groups, di-$C_{1-6}$ alkylaminocarbonyl groups, $C_{1-6}$ alkylcarbonylamino groups, $C_{1-6}$ alkoxycarbonylamino groups (the $C_{1-6}$ alkoxycarbonyl groups, the mono-$C_{1-6}$ alkylaminocarbonyl groups, the di-$C_{1-6}$ alkylaminocarbonyl groups, the $C_{1-6}$ alkylcarbonylamino groups and the $C_{1-6}$ alkoxycarbonylamino groups are unsubstituted or substituted with one or more identical or different halogen atoms independently selected from the group consisting of fluorine atoms, chlorine atoms, bromine atoms and iodine atoms), $C_{3-6}$ cycloalkyl groups, 4 to 7-membered non-aromatic heterocyclyl groups, phenyl groups and 5 to 6-membered aromatic heterocyclyl groups), tautomers or pharmaceutically acceptable salts of the compounds or solvates thereof.

$48^a$) The compounds according to any one of $1^a$) or $43^a$) to $46^a$), wherein $R^{2a}$ is a 3 to 11-membered non-aromatic heterocyclyl group (the 3 to 11-membered non-aromatic heterocyclyl group is unsubstituted or substituted with one or two identical or different substituents independently selected from the group consisting of cyano groups, halogen atoms, hydroxy groups, amino groups, carbamoyl groups, sulfamoyl groups, $C_{1-3}$ alkyl groups (the $C_{1-3}$ alkyl groups are unsubstituted or substituted with a substituent selected from the group consisting of a cyano group, a hydroxy group and a $C_{1-6}$ alkoxycarbonylamino group), $C_{1-3}$ haloalkyl groups, $C_{1-3}$ alkoxy groups, mono-$C_{1-3}$ alkylamino groups, di-$C_{1-3}$ alkylamino groups, $C_{1-3}$ alkylsulfonyl groups, mono-$C_{1-3}$ alkylaminocarbonyl groups, di-$C_{1-3}$ alkylaminocarbonyl groups, mono-$C_{1-3}$ alkylaminosulfonyl groups, di-$C_{1-3}$ alkylaminosulfonyl groups, $C_{1-3}$ alkylcarbonylamino groups and $C_{1-6}$ alkoxycarbonylamino groups (the $C_{1-3}$ alkoxy groups, the mono-$C_{1-3}$ alkylamino groups, the di-$C_{1-3}$ alkylamino groups, the $C_{1-3}$ alkylsulfonyl groups, the mono-$C_{1-3}$ alkylaminocarbonyl groups, the di-$C_{1-3}$ alkylaminocarbonyl groups, the mono-$C_{1-3}$ alkylaminosulfonyl groups, the di-$C_{1-3}$ alkylaminosulfonyl groups, the $C_{1-3}$ alkylcarbonylamino groups and the $C_{1-6}$ alkoxycarbonylamino groups are unsubstituted or substituted with one or more identical or different halogen atoms independently selected from the group consisting of fluorine atoms, chlorine atoms, bromine atoms and iodine atoms or with a cyano group)), tautomers or pharmaceutically acceptable salts of the compounds or solvates thereof.

$49^a$) The compounds according to any one of $1^a$) or $43^a$) to $46^a$), wherein $L^{3a}$ is represented by the formulae ($XVI^a$):

($XVI^a$)

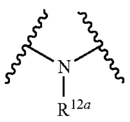

(wherein $R^{12a}$ is a hydrogen atom, a $C_{1-3}$ alkyl group (the $C_{1-3}$ alkyl group is unsubstituted or substituted with a substituent selected from the group consisting of a hydroxy group, a cyano group, a $C_{1-3}$ alkoxy group, a $C_{3-6}$ cycloalkyl group and a phenyl group), a $C_{1-3}$ haloalkyl group, a $C_{3-6}$ cycloalkyl group or a phenyl group (the phenyl group is unsubstituted or substituted with a halogen atom or a cyano group)), and $R^{2a}$ is a hydrogen atom, a $C_{1-6}$ alkyl group (the $C_{1-6}$ alkyl group is unsubstituted or substituted with a substituent selected from the group consisting of a hydroxy group, a cyano group, a $C_{1-3}$ alkoxy group, a mono-$C_{1-3}$ alkylaminocarbonyl group (the $C_{1-3}$ alkoxy group and the mono-$C_{1-3}$ alkylaminocarbonyl group are unsubstituted or substituted with one or more identical or different halogen atoms independently selected from the group consisting of fluorine atoms, chlorine atoms, bromine atoms and iodine atoms), a $C_{3-6}$ cycloalkyl group, a 3 to 11-membered non-aromatic heterocyclyl group, a phenyl group and a 5 to 10-membered aromatic heterocyclyl group (the $C_{3-6}$ cycloalkyl group, the 3 to 11-membered non-aromatic heterocyclyl group, the phenyl group and the 5 to 10-membered aromatic heterocyclyl group are unsubstituted or substituted with one or two identical or different substituents independently selected from the group consisting of halogen atoms, cyano groups, $C_{1-3}$ alkyl groups, $C_{1-3}$ haloalkyl groups, $C_{1-3}$ alkoxy groups, $C_{1-3}$ haloalkoxy groups, $C_{1-3}$ alkylthio groups, $C_{1-3}$ haloalkylthio groups, $C_{1-3}$ haloalkylsulfonyl groups and 4 to 7-membered non-aromatic heterocyclyl groups)), a $C_{1-6}$ haloalkyl group, a $C_{2-6}$ alkynyl group, a $C_{3-6}$ cycloalkyl group, a 3 to 11-membered non-aromatic heterocyclyl group, a phenyl group, a naphthyl group, a 5 to 10-membered aromatic heterocyclyl group, a 8 to 11-membered partially saturated aromatic cyclic group or a 8 to 11-membered aromatic ring-condensed alicyclic hydrocarbon group (the $C_{3-6}$ cycloalkyl group, the 3 to 11-membered non-aromatic heterocyclyl group, the phenyl group, the naphthyl group, the 5 to 10-membered aromatic heterocyclyl group, the 8 to 11-membered partially saturated aromatic cyclic group and the 8 to 11-membered aromatic ring-condensed alicyclic hydrocarbon group are unsubstituted or substituted with one or two identical or different substituents independently selected from the group consisting of hydroxy groups, halogen atoms, cyano groups, $C_{1-3}$ alkyl groups, $C_{1-3}$ haloalkyl groups, $C_{1-3}$ alkoxy groups, $C_{1-3}$ haloalkoxy groups, $C_{1-3}$ alkylthio groups, $C_{1-3}$ haloalkylthio groups, $C_{1-3}$ haloalkylsulfonyl groups and 4 to 7-membered non-aromatic heterocyclyl groups), tautomers or pharmaceutically acceptable salts of the compounds or solvates thereof.

$50^a$) The compounds according to any one of $1^a$) or $43^a$) to $46^a$), wherein $L^{3a}$ is represented by any of the following formulae ($XX^a$-1) to ($XX^a$-3):

($XX^a$)

($XX^a$-1)

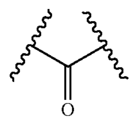

($XX^a$-2)

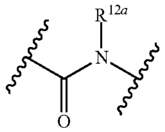

($XX^a$-3)

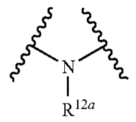

(wherein $R^{12a}$ is a hydrogen atom, a $C_{1-3}$ alkyl group (the $C_{1-3}$ alkyl group is unsubstituted or substituted with a cyano group) or a $C_{1-3}$ haloalkyl group), and $R^{2a}$ is a hydrogen atom, a $C_{1-3}$ alkyl group or a $C_{1-3}$ haloalkyl group (the $C_{1-3}$ alkyl group and the $C_{1-3}$ haloalkyl group are substituted with a substituent selected from the group consisting of a hydroxy group and a cyano group and with a substituent selected from the group consisting of a 3 to 11-membered non-aromatic heterocyclyl group, a phenyl group and a 5 to 10-membered aromatic heterocyclyl group (the 3 to 11-membered non-aromatic heterocyclyl group, the phenyl group and the 5 to 10-membered aromatic heterocyclyl group are unsubstituted or substituted with one or two identical or different substituents independently selected from the group consisting of halogen atoms, cyano groups, $C_{1-3}$ alkyl groups, $C_{1-3}$ haloalkyl groups, $C_{1-3}$ alkoxy groups and $C_{1-3}$ alkylthio groups)), tautomers or pharmaceutically acceptable salts of the compounds or solvates thereof.

$51^a$) The compounds according to any one of $1^a$) or $43^a$) to $46^a$), wherein $L^{3a}$ is represented by any of the following formulae ($XXVI^a$-1) to ($XXVI^a$-5):

($XXVI^a$)

($XXVI^a$-1)

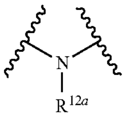

($XXVI^a$-2)

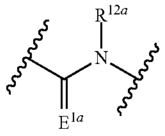

($XXVI^a$-3)

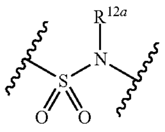

($XXVI^a$-4)

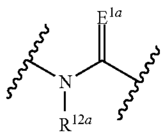

-continued (XXVI$^a$-5)

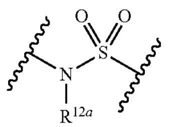

(wherein $E^{1a}$ is an oxygen atom, $R^{12a}$ is a $C_{1-6}$ alkyl group (the $C_{1-6}$ alkyl group is unsubstituted or substituted with a substituent selected from the group consisting of a cyano group, a hydroxy group, a $C_{1-3}$ alkoxy group, a $C_{3-6}$ cycloalkyl group and a phenyl group), a $C_{1-6}$ haloalkyl group, a $C_{3-6}$ cycloalkyl group or a phenyl group (the phenyl group is unsubstituted or substituted with a halogen atom or a cyano group)), and $R^{2a}$ is a $C_{1-6}$ alkyl group (the $C_{1-6}$ alkyl group is unsubstituted or substituted with a substituent selected from the group consisting of a cyano group, a hydroxy group, a $C_{1-3}$ alkoxy group, a $C_{3-6}$ cycloalkyl group and a phenyl group), a $C_{1-6}$ haloalkyl group, a $C_{3-6}$ cycloalkyl group or a phenyl group (the phenyl group is unsubstituted or substituted with a halogen atom)), tautomers or pharmaceutically acceptable salts of the compounds or solvates thereof.

52$^a$) The compounds according to any one of any one of 1$^a$) or 43$^a$) to 46$^a$), wherein $L^{3a}$ is represented by the formula (X$^a$-11):

(X$^a$-11)

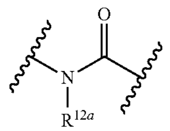

(wherein $R^{12a}$ is a hydrogen atom, a $C_{1-3}$ alkyl group (the $C_{1-3}$ alkyl group is unsubstituted or substituted with a cyano group or a 5 to 6-membered aromatic heterocyclyl group (the 5 to 6-membered aromatic heterocyclyl group is unsubstituted or substituted with a $C_{1-3}$ alkyl group)), a $C_{1-3}$ haloalkyl group or a $C_{3-6}$ cycloalkyl group), and $R^{2a}$ is a $C_{1-3}$ alkyl group (the $C_{1-3}$ alkyl group is unsubstituted or substituted with a cyano group) or a $C_{1-3}$ haloalkyl group, tautomers or pharmaceutically acceptable salts of the compounds or solvates thereof.

53$^a$) The compounds according to any one of 1$^a$) or 43$^a$) to 46$^a$), wherein $L^{3a}$ is represented by the formula (X$^a$-5):

(X$^a$-5)

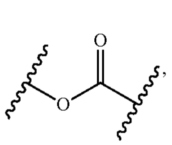

and $R^{2a}$ is a $C_{1-3}$ alkyl group, tautomers or pharmaceutically acceptable salts of the compounds or solvates thereof.

54$^a$) The compounds according to any one of 1$^a$) or 43$^a$) to 46$^a$), wherein $L^{3a}$ is represented by the formula (X$^a$-6):

(X$^a$-6)

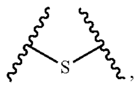

and $R^{2a}$ is a hydrogen atom, tautomers or pharmaceutically acceptable salts of the compounds or solvates thereof.

55$^a$) The compounds according to any one of 1$^a$) or 43$^a$) to 46$^a$), wherein $L^{3a}$ is represented by the formula (XVIII$^a$):

(XVIII$^a$)

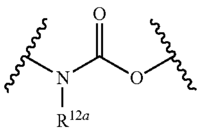

(wherein $R^{12a}$ is a hydrogen atom), and $R^{2a}$ is a $C_{1-6}$ alkyl group (the $C_{1-6}$ alkyl group is unsubstituted or substituted with a phenyl group), tautomers or pharmaceutically acceptable salts of the compounds or solvates thereof.

56$^a$) The compounds according to any one of 1$^a$) or 43$^a$) to 46$^a$), wherein $L^{3a}$ is represented by the formula (X$^a$-8):

(X$^a$-8)

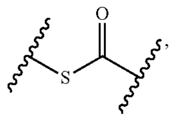

and $R^{2a}$ is a $C_{1-3}$ alkyl group, tautomers or pharmaceutically acceptable salts of the compounds or solvates thereof.

57$^a$) The compounds according to any one of 1$^a$), 2$^a$) or 43$^a$) to 56$^a$), which is represented by the following formula (XXII$^a$-1) or (XXII$^a$-2):

(XXII$^a$)

(XXII$^a$-1)

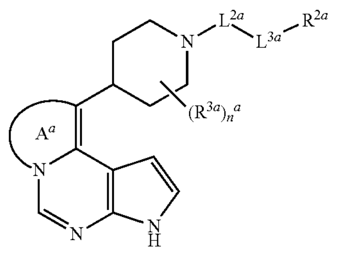

(XXII$^a$-2)

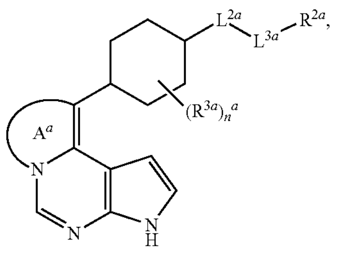

tautomers or pharmaceutically acceptable salts of the compounds or solvates thereof.

$58^{a}$) Compounds represented by the formula ($XII^{a}$):

($XII^{a}$)

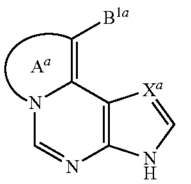

wherein $X^{a}$ is $CR^{9a}$ (wherein $R^{9a}$ is a hydrogen atom, a halogen atom or a cyano group), and the rings $A^{a}$ and $B^{1a}$ are any of the following combinations shown in $Table^{a}$ 1, tautomers or pharmaceutically acceptable salts of the compounds or solvates thereof.

The symbols in $Table^{a}$ 1 denote the following substituents.

A1 = 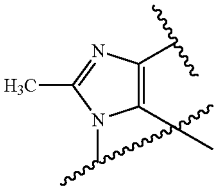 A2 = 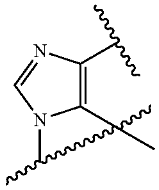

A3 = 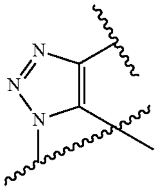 A4 = 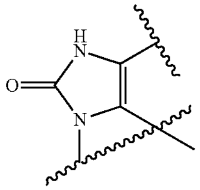

A5 = 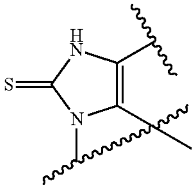 A6 = 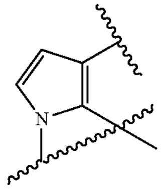

A7 = 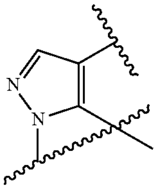 A8 = 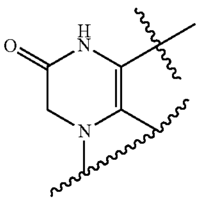

$B^{1}1$ = 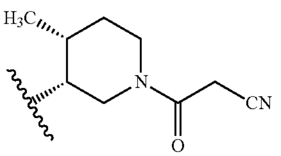

$B^{1}2$ = 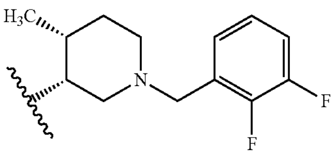

-continued $B^{1}3$ = 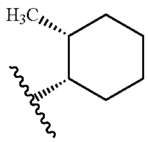 $B^{1}4$ = 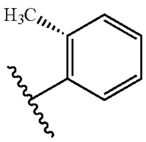

$B^{1}5$ = 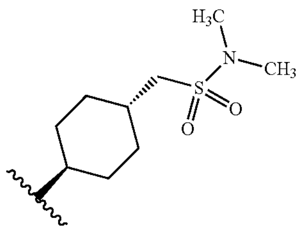

$B^{1}6$ = 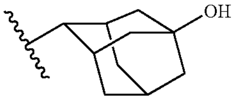

$B^{1}7$ = 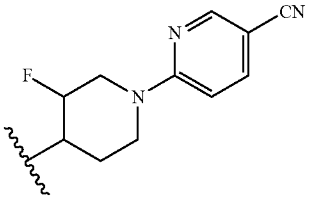

$B^{1}8$ = 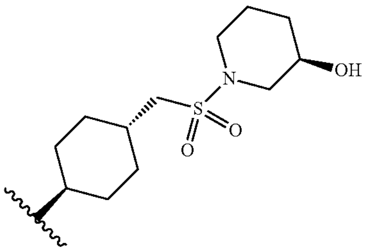

$TABLE^{a}$ 1

| $A^{a}$ | $B^{1a}$ | $A^{a}$ | $B^{1a}$ | $A^{a}$ | $B^{1a}$ | $A^{a}$ | $B^{1a}$ |
|---|---|---|---|---|---|---|---|
| A 1 | $B^{1}1$ | A 1 | $B^{1}3$ | A 1 | $B^{1}5$ | A 1 | $B^{1}7$ |
| A 2 | $B^{1}1$ | A 2 | $B^{1}3$ | A 2 | $B^{1}5$ | A 2 | $B^{1}7$ |
| A 3 | $B^{1}1$ | A 3 | $B^{1}3$ | A 3 | $B^{1}5$ | A 3 | $B^{1}7$ |
| A 4 | $B^{1}1$ | A 4 | $B^{1}3$ | A 4 | $B^{1}5$ | A 4 | $B^{1}7$ |
| A 5 | $B^{1}1$ | A 5 | $B^{1}3$ | A 5 | $B^{1}5$ | A 5 | $B^{1}7$ |
| A 6 | $B^{1}1$ | A 6 | $B^{1}3$ | A 6 | $B^{1}5$ | A 6 | $B^{1}7$ |
| A 7 | $B^{1}1$ | A 7 | $B^{1}3$ | A 7 | $B^{1}5$ | A 7 | $B^{1}7$ |
| A 8 | $B^{1}1$ | A 8 | $B^{1}3$ | A 8 | $B^{1}5$ | A 8 | $B^{1}7$ |
| A 1 | $B^{1}2$ | A 1 | $B^{1}4$ | A 1 | $B^{1}6$ | A 1 | $B^{1}8$ |
| A 2 | $B^{1}2$ | A 2 | $B^{1}4$ | A 2 | $B^{1}6$ | A 2 | $B^{1}8$ |
| A 3 | $B^{1}2$ | A 3 | $B^{1}4$ | A 3 | $B^{1}6$ | A 3 | $B^{1}8$ |
| A 4 | $B^{1}2$ | A 4 | $B^{1}4$ | A 4 | $B^{1}6$ | A 4 | $B^{1}8$ |
| A 5 | $B^{1}2$ | A 5 | $B^{1}4$ | A 5 | $B^{1}6$ | A 5 | $B^{1}8$ |
| A 6 | $B^{1}2$ | A 6 | $B^{1}4$ | A 6 | $B^{1}6$ | A 6 | $B^{1}8$ |
| A 7 | $B^{1}2$ | A 7 | $B^{1}4$ | A 7 | $B^{1}6$ | A 7 | $B^{1}8$ |
| A 8 | $B^{1}2$ | A 8 | $B^{1}4$ | A 8 | $B^{1}6$ | A 8 | $B^{1}8$ |

$59^a$) Compounds represented by the formula ($XII^a$-1):

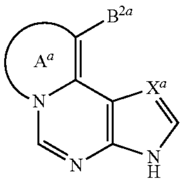

($XII^a$-1)

wherein $X^a$ is $CR^{9a}$ (wherein $R^{9a}$ is a hydrogen atom, a halogen atom or a cyano group), and the rings $A^a$ and $B^{2a}$ are any of the following combinations shown in $Table^a$ 2, tautomers or pharmaceutically acceptable salts of the compounds or solvates thereof.

The symbols in $Table^a$ 2 denote the following substituents.

A1 = 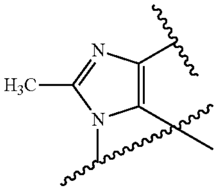

A2 = 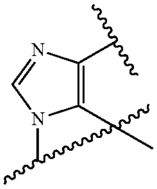

A3 = 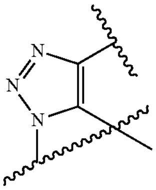

A4 = 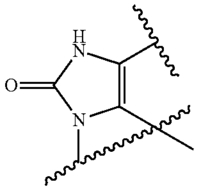

A5 = 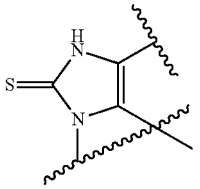

A6 = 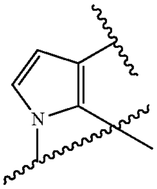

A7 = 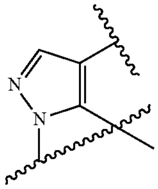

A8 = 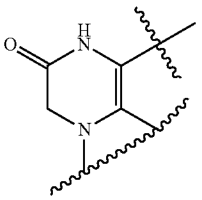

$B^21$ = 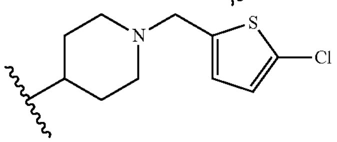

$B^22$ = 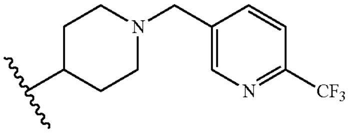

$B^23$ = 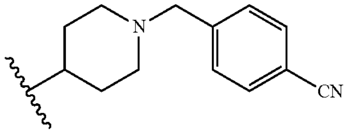

-continued $B^24$ = 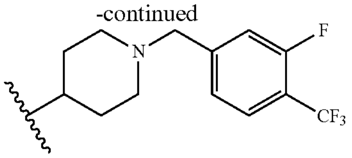

$B^25$ = 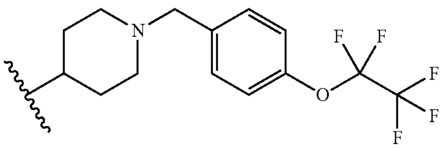

$B^26$ = 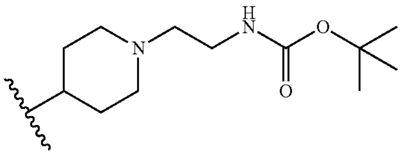

$B^27$ = 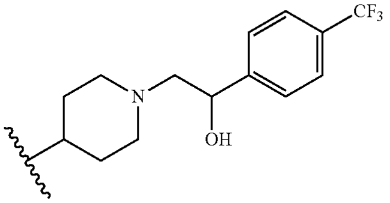

$B^28$ = 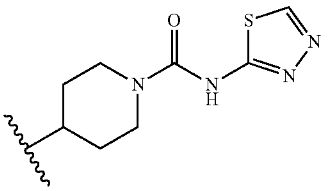

$TABLE^a$ 2

| $A^a$ | $B^{2a}$ | $A^a$ | $B^{2a}$ | $A^a$ | $B^{2a}$ | $A^a$ | $B^{2a}$ |
|---|---|---|---|---|---|---|---|
| A 1 | $B^2$ 1 | A 1 | $B^2$ 3 | A 1 | $B^2$ 5 | A 1 | $B^2$ 7 |
| A 2 | $B^2$ 1 | A 2 | $B^2$ 3 | A 2 | $B^2$ 5 | A 2 | $B^2$ 7 |
| A 3 | $B^2$ 1 | A 3 | $B^2$ 3 | A 3 | $B^2$ 5 | A 3 | $B^2$ 7 |
| A 4 | $B^2$ 1 | A 4 | $B^2$ 3 | A 4 | $B^2$ 5 | A 4 | $B^2$ 7 |
| A 5 | $B^2$ 1 | A 5 | $B^2$ 3 | A 5 | $B^2$ 5 | A 5 | $B^2$ 7 |
| A 6 | $B^2$ 1 | A 6 | $B^2$ 3 | A 6 | $B^2$ 5 | A 6 | $B^2$ 7 |
| A 7 | $B^2$ 1 | A 7 | $B^2$ 3 | A 7 | $B^2$ 5 | A 7 | $B^2$ 7 |
| A 8 | $B^2$ 1 | A 8 | $B^2$ 3 | A 8 | $B^2$ 5 | A 8 | $B^2$ 7 |
| A 1 | $B^2$ 2 | A 1 | $B^2$ 4 | A 1 | $B^2$ 6 | A 1 | $B^2$ 8 |
| A 2 | $B^2$ 2 | A 2 | $B^2$ 4 | A 2 | $B^2$ 6 | A 2 | $B^2$ 8 |
| A 3 | $B^2$ 2 | A 3 | $B^2$ 4 | A 3 | $B^2$ 6 | A 3 | $B^2$ 8 |
| A 4 | $B^2$ 2 | A 4 | $B^2$ 4 | A 4 | $B^2$ 6 | A 4 | $B^2$ 8 |
| A 5 | $B^2$ 2 | A 5 | $B^2$ 4 | A 5 | $B^2$ 6 | A 5 | $B^2$ 8 |
| A 6 | $B^2$ 2 | A 6 | $B^2$ 4 | A 6 | $B^2$ 6 | A 6 | $B^2$ 8 |
| A 7 | $B^2$ 2 | A 7 | $B^2$ 4 | A 7 | $B^2$ 6 | A 7 | $B^2$ 8 |
| A 8 | $B^2$ 2 | A 8 | $B^2$ 4 | A 8 | $B^2$ 6 | A 8 | $B^2$ 8 |

$60^a$) Compounds represented by the formula ($XII^a$-2):

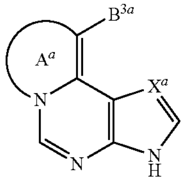

($XII^a$-2)

wherein $X^a$ is $CR^{9a}$ (wherein $R^{9a}$ is a hydrogen atom, a halogen atom or a cyano group), and the rings $A^a$ and $B^{3a}$ are any of the following combinations shown in Table$^a$ 3, tautomers or pharmaceutically acceptable salts of the compounds or solvates thereof.

The symbols in Table$^a$ 3 denote the following substituents.

A1 = 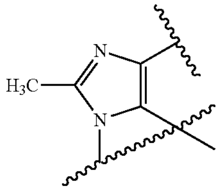

A2 = 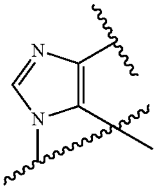

A3 = 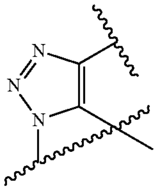

A4 = 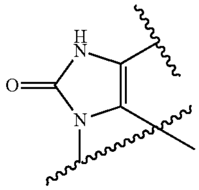

A5 = 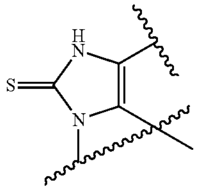

A6 = 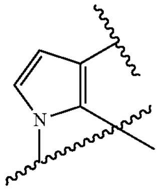

A7 = 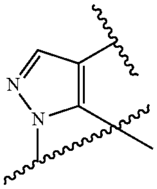

A8 = 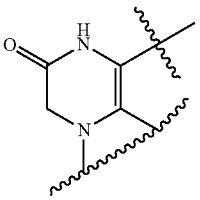

$B^31$ = 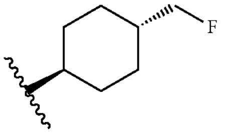

$B^32$ = 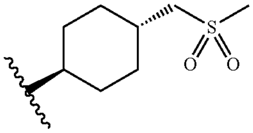

$B^33$ = 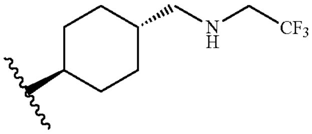

$B^34$ = 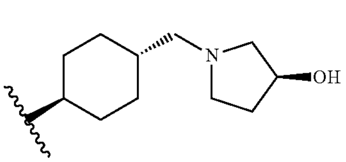

$B^35$ = 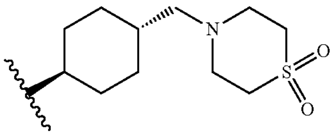

-continued $B^36$ = 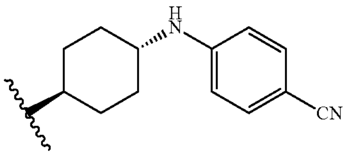

$B^37$ = 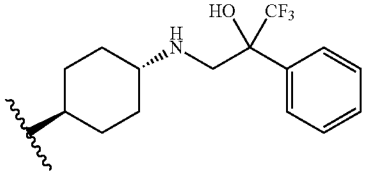

$B^38$ = 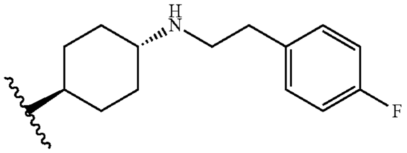

TABLE$^a$ 3

| $A^a$ | $B^{3a}$ | $A^a$ | $B^{3a}$ | $A^a$ | $B^{3a}$ | $A^a$ | $B^{3a}$ |
|---|---|---|---|---|---|---|---|
| A 1 | $B^3$ 1 | A 1 | $B^3$ 3 | A 1 | $B^3$ 5 | A 1 | $B^3$ 7 |
| A 2 | $B^3$ 1 | A 2 | $B^3$ 3 | A 2 | $B^3$ 5 | A 2 | $B^3$ 7 |
| A 3 | $B^3$ 1 | A 3 | $B^3$ 3 | A 3 | $B^3$ 5 | A 3 | $B^3$ 7 |
| A 4 | $B^3$ 1 | A 4 | $B^3$ 3 | A 4 | $B^3$ 5 | A 4 | $B^3$ 7 |
| A 5 | $B^3$ 1 | A 5 | $B^3$ 3 | A 5 | $B^3$ 5 | A 5 | $B^3$ 7 |
| A 6 | $B^3$ 1 | A 6 | $B^3$ 3 | A 6 | $B^3$ 5 | A 6 | $B^3$ 7 |
| A 7 | $B^3$ 1 | A 7 | $B^3$ 3 | A 7 | $B^3$ 5 | A 7 | $B^3$ 7 |
| A 8 | $B^3$ 1 | A 8 | $B^3$ 3 | A 8 | $B^3$ 5 | A 8 | $B^3$ 7 |
| A 1 | $B^3$ 2 | A 1 | $B^3$ 4 | A 1 | $B^3$ 6 | A 1 | $B^3$ 8 |
| A 2 | $B^3$ 2 | A 2 | $B^3$ 4 | A 2 | $B^3$ 6 | A 2 | $B^3$ 8 |
| A 3 | $B^3$ 2 | A 3 | $B^3$ 4 | A 3 | $B^3$ 6 | A 3 | $B^3$ 8 |
| A 4 | $B^3$ 2 | A 4 | $B^3$ 4 | A 4 | $B^3$ 6 | A 4 | $B^3$ 8 |
| A 5 | $B^3$ 2 | A 5 | $B^3$ 4 | A 5 | $B^3$ 6 | A 5 | $B^3$ 8 |
| A 6 | $B^3$ 2 | A 6 | $B^3$ 4 | A 6 | $B^3$ 6 | A 6 | $B^3$ 8 |
| A 7 | $B^3$ 2 | A 7 | $B^3$ 4 | A 7 | $B^3$ 6 | A 7 | $B^3$ 8 |
| A 8 | $B^3$ 2 | A 8 | $B^3$ 4 | A 8 | $B^3$ 6 | A 8 | $B^3$ 8 |

61$^a$) Compounds represented by the formula (XII$^a$-3):

(XII$^a$-3)

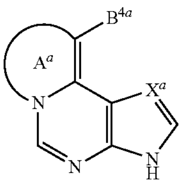

wherein $X^a$ is $CR^{9a}$ (wherein $R^{9a}$ is a hydrogen atom, a halogen atom or a cyano group), the rings $A^a$ and $B^{4a}$ are any of the following combinations shown in Table 4, tautomers or pharmaceutically acceptable salts of the compounds or solvates thereof.

The symbols in Table$^a$ 4 denote the following substituents.

A1 = 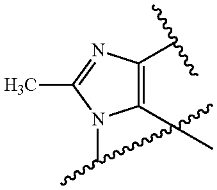

A2 = 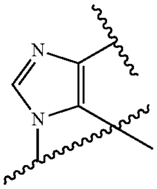

A3 = 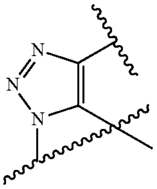

A4 = 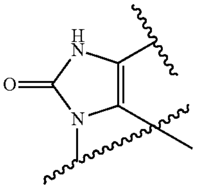

A5 = 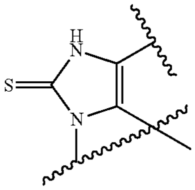

A6 = 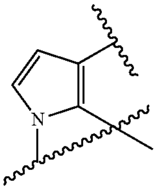

A7 = 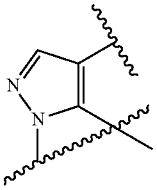

A8 = 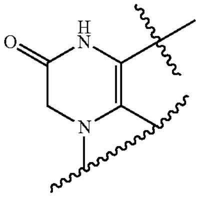

$B^41$ = 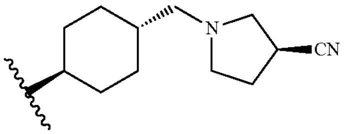

$B^42$ = 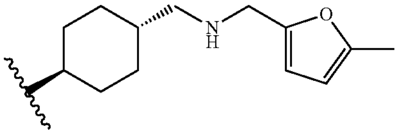

$B^43$ = 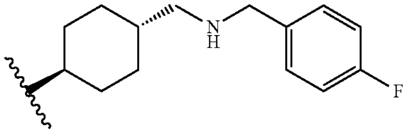

$B^44$ = 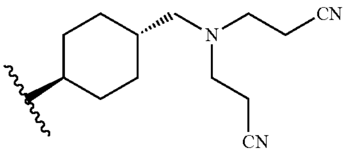

$B^45$ = 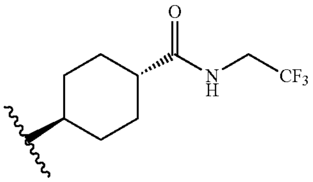

$B^46$ = 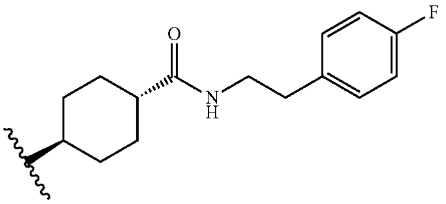

-continued $B^47$ = 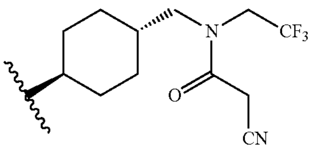

$B^48$ = 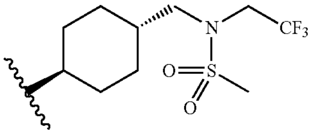

TABLE$^a$ 4

| $A^a$ | $B^{4a}$ | $A^a$ | $B^{4a}$ | $A^a$ | $B^{4a}$ | $A^a$ | $B^{4a}$ |
|---|---|---|---|---|---|---|---|
| A1 | $B^41$ | A1 | $B^43$ | A1 | $B^45$ | A1 | $B^47$ |
| A2 | $B^41$ | A2 | $B^43$ | A2 | $B^45$ | A2 | $B^47$ |
| A3 | $B^41$ | A3 | $B^43$ | A3 | $B^45$ | A3 | $B^47$ |
| A4 | $B^41$ | A4 | $B^43$ | A4 | $B^45$ | A4 | $B^47$ |
| A5 | $B^41$ | A5 | $B^43$ | A5 | $B^45$ | A5 | $B^47$ |
| A6 | $B^41$ | A6 | $B^43$ | A6 | $B^45$ | A6 | $B^47$ |
| A7 | $B^41$ | A7 | $B^43$ | A7 | $B^45$ | A7 | $B^47$ |
| A8 | $B^41$ | A8 | $B^43$ | A8 | $B^45$ | A8 | $B^47$ |
| A1 | $B^42$ | A1 | $B^44$ | A1 | $B^46$ | A1 | $B^48$ |
| A2 | $B^42$ | A2 | $B^44$ | A2 | $B^46$ | A2 | $B^48$ |
| A3 | $B^42$ | A3 | $B^44$ | A3 | $B^46$ | A3 | $B^48$ |
| A4 | $B^42$ | A4 | $B^44$ | A4 | $B^46$ | A4 | $B^48$ |
| A5 | $B^42$ | A5 | $B^44$ | A5 | $B^46$ | A5 | $B^48$ |
| A6 | $B^42$ | A6 | $B^44$ | A6 | $B^46$ | A6 | $B^48$ |
| A7 | $B^42$ | A7 | $B^44$ | A7 | $B^46$ | A7 | $B^48$ |
| A8 | $B^42$ | A8 | $B^44$ | A8 | $B^46$ | A8 | $B^48$ |

62$^a$) The compounds with the combinations of substituents as defined in any of 58$^a$) to 61$^a$), wherein $X^a$ is converted to a nitrogen atom, tautomers or pharmaceutically acceptable salts of the compounds or solvates thereof.

Next, the tricyclic pyridine compounds of the present invention represented by the formula ($I^b$) will be described.

First, how the ring $A^b$ is fused in the tricyclic pyridine compounds of the present invention will be described.

As is indicated in the formula ($I^b$), the ring $A^b$ is fused to the pyridine ring so as to have two carbon atoms in common and attached to $L^{1b}$ via a nitrogen atom in the ring $A^b$ in the formula ($I^b$).

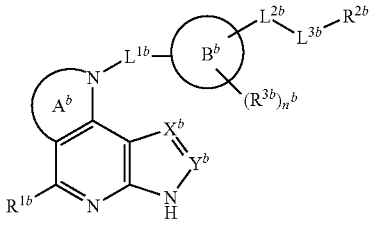

($I^b$)

Therefore, when the ring $A^b$ is represented by the formula ($II^b$), ($II^b$)

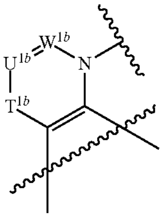

the molecule of the compounds as a whole is represented by the formula ($I^b$)-2, ($I^b$)-2

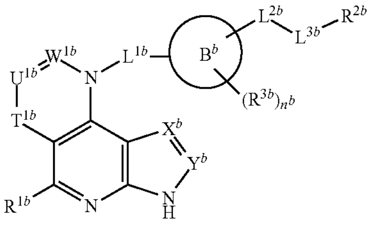

and when the ring $A^b$ is represented by the formula ($III^b$), ($III^b$)

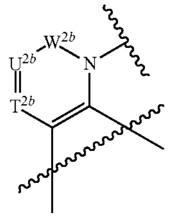

the molecule as a whole is represented by the formula ($I^b$)-3.

($I^b$)-3

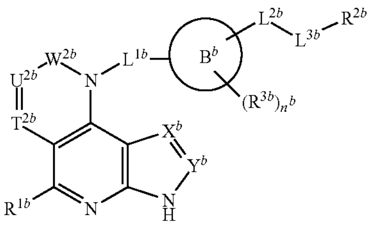

and when the ring $A^b$ is represented by the formula ($IV^b$), ($IV^b$)

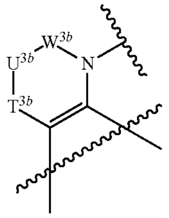

the molecule as a whole is represented by the formula ($I^b$)-4.

($I^b$)-4

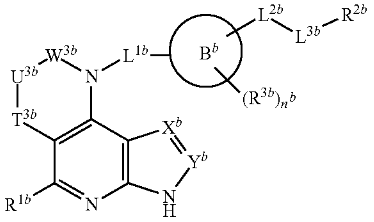

In the present invention, the formulae representing $L^{3b}$ indicate that the left ends of the formulae are bonded to $L^{2b}$, and the right ends of the formulae are bonded to $R^{2b}$.

In the present invention, $L^{1b}$, $L^{2b}$ and $R^{3b}$ may be bounded to the ring $B^b$ in the formula ($I^b$) at any positions of the ring $B^a$ without any particular restrictions.

Next, preferred structures of the respective substituents will be mentioned.

A preferred embodiment of the substituent $R^{1b}$ is a hydrogen atom or a halogen atom.

A more preferred embodiment of the substituent $R^{1b}$ is a hydrogen atom.

A preferred embodiment of the substituent $X^b$ is a nitrogen atom or $CR^{15b}$ (wherein $R^{15b}$ is a hydrogen atom, a halogen atom, a cyano group, a $C_{1-6}$ alkyl group, a $C_{1-6}$ haloalkyl group or a $C_{3-6}$ cycloalkyl group).

A more preferred embodiment of the substituent $X^b$ is a nitrogen atom or $CR^{15b}$ (wherein $R^{15b}$ is a hydrogen atom).

Another more preferred embodiment of the substituent $X^b$ is $CR^{15b}$ (wherein $R^{15b}$ is a halogen atom).

A further preferred embodiment of the substituent $X^b$ is $CR^{15b}$ (wherein $R^{16b}$ is a hydrogen atom).

A preferred embodiment of the substituent $Y^b$ is $CR^{16b}$ (wherein $R^{16b}$ is a hydrogen atom).

A preferred embodiment of the ring $A^b$ is represented by the following formula ($IX^b$-1) or ($IX^b$-2):

($IX^b$)

($IX^b$-1)

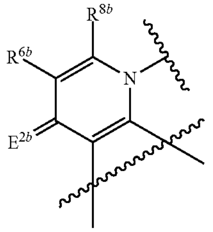

-continued $(IX^b\text{-}2)$

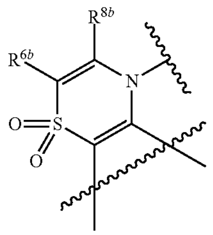

(wherein $E^{2b}$ is an oxygen atom, a sulfur atom or $NR^{17b}$, and each of $R^{6b}$ and $R^{8b}$ is independently a hydrogen atom, an amino group, a carbamoyl group, a halogen atom, a cyano group, a $C_{1-6}$ alkyl group, a $C_{1-6}$ alkoxy group, a $C_{1-6}$ alkylsulfonyl group (the $C_{1-6}$ alkyl group, the $C_{1-6}$ alkoxy group and the $C_{1-6}$ alkylsulfonyl group are unsubstituted or substituted with one or more identical or different substituents independently selected from the substituent set $V^{3b}$), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the substituent set $V^{1b}$)).

Another preferred embodiment of the ring $A^b$ is represented by any of the following formulae $(X^b\text{-}1)$ to $(X^b\text{-}10)$:

$(X^b)$ $(X^b\text{-}1)$

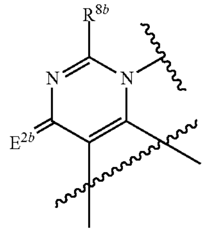

$(X^b\text{-}2)$

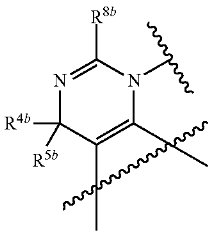

$(X^b\text{-}3)$

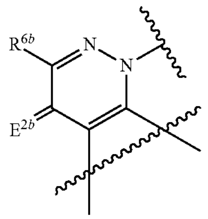

-continued $(X^b\text{-}4)$

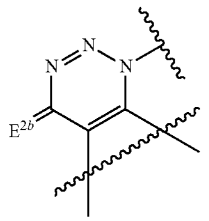

$(X^b\text{-}5)$

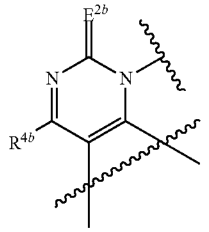

$(X^b\text{-}6)$

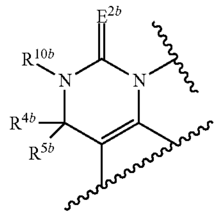

$(X^b\text{-}7)$

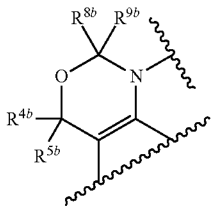

$(X^b\text{-}8)$

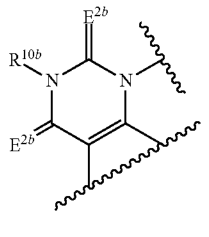

$(X^b\text{-}9)$

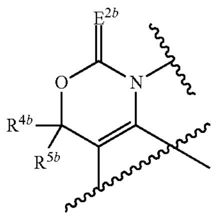

-continued (X$^b$-10)

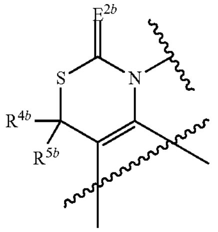

(wherein $E^{2b}$ is an oxygen atom, a sulfur atom or $NR^{17b}$, and each of $R^{4b}$, $R^{5b}$, $R^{6b}$, $R^{8b}$ and $R^{9b}$ is independently a hydrogen atom, an amino group, a carbamoyl group, a halogen atom, a cyano group, a $C_{1-6}$ alkyl group, a $C_{1-6}$ alkoxy group, a $C_{1-6}$ alkylcarbonyl group, a $C_{1-6}$ alkylsulfonyl group (the $C_{1-6}$ alkyl group, the $C_{1-6}$ alkoxy group, the $C_{1-6}$ alkylcarbonyl group and the $C_{1-6}$ alkylsulfonyl group are unsubstituted or substituted with one or more identical or different substituents independently selected from the substituent set $V^{3b}$), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the substituent set $V^{1b}$), and $R^{10b}$ is a hydrogen atom, a $C_{1-6}$ alkyl group (the $C_{1-6}$ alkyl group is unsubstituted or substituted with one or more identical or different substituents independently selected from substituent set $V^{3b}$), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the substituent set $V^{1b}$)).

A more preferred embodiment of the ring $A^b$ is represented by the following formula (IX$^b$-1) or (IX$^b$-2):

(IX$^b$)

(IX$^b$-1)

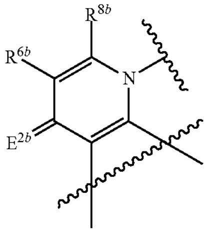

(IX$^b$-2)

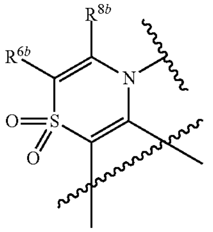

(wherein $E^{2b}$ is an oxygen atom, each of $R^{6b}$ and $R^{8b}$ is independently a hydrogen atom, a halogen atom or a $C_{1-3}$ alkyl group).

Another more preferred embodiment of the ring $A^b$ is represented by any of the following formulae (XXIII$^b$-1) to (XXIII$^b$-5):

(XXIII$^b$)

(XXIII$^b$-1)

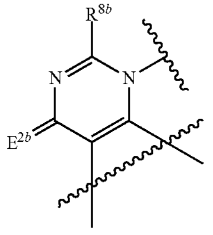

(XXIII$^b$-2)

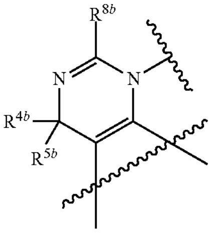

(XXIII$^b$-3)

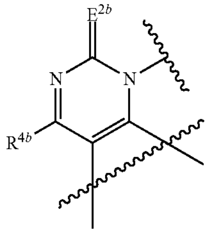

(XXIII$^b$-4)

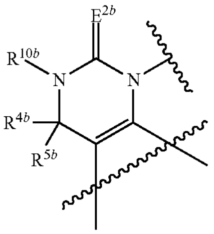

(XXIII$^b$-5)

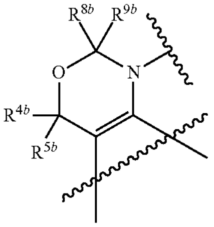

(wherein $E^{2b}$ is an oxygen atom, each of $R^{4b}$, $R^{5b}$, $R^{8b}$ and $R^{9b}$ is independently a hydrogen atom, a halogen atom or a $C_{1-3}$ alkyl group, and $R^{10b}$ is a hydrogen atom or a $C_{1-3}$ alkyl group).

Another more preferred embodiment of the ring $A^b$ is represented by the formula is represented by the formula (XXIV$^b$):

(XXIV$^b$)

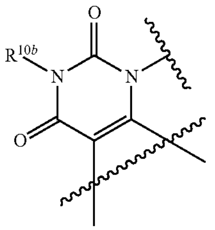

(wherein $R^{10b}$ is a hydrogen atom or a $C_{1-3}$ alkyl group).

Another more preferred embodiment of the ring $A^b$ is represented by the formula is represented by the formula (XXIV$^b$):

(XXIV$^b$)

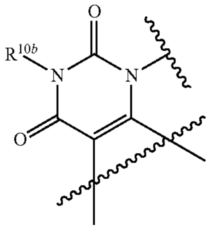

(wherein $R^{10b}$ is a $C_{1-6}$ alkyl group (the $C_{1-6}$ alkyl group is unsubstituted or substituted with one or two identical or different substituents independently selected from the group consisting of cyano groups, hydroxy groups, $C_{1-3}$ alkoxy groups, $C_{1-3}$ alkylthio groups, di-$C_{1-3}$ alkylamino groups, di-$C_{1-3}$ alkylaminocarbonyl groups, $C_{3-6}$ cycloalkyl groups, 4 to 7-membered non-aromatic heterocyclyl groups, phenyl groups, and 5 to 6-membered aromatic heterocyclyl groups (the phenyl groups and the 5 to 6-membered aromatic heterocyclyl groups are unsubstituted or substituted with one or two identical or different substituents independently selected from the group consisting of halogen atoms, $C_{1-3}$ alkyl groups and $C_{1-3}$ haloalkyl groups)), a $C_{1-6}$ haloalkyl group, a $C_{3-6}$ cycloalkyl group or a 4 to 7-membered non-aromatic heterocyclyl group).

Another more preferred embodiment of the ring $A^b$ is represented by the formula is represented by the formula (XIV$^b$):

(XIV$^b$)

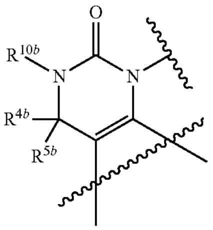

(wherein each of $R^{4b}$ and $R^{5b}$ is independently a hydrogen atom or a $C_{1-3}$ alkyl group, and $R^{10b}$ is a $C_{1-6}$ alkyl group (the $C_{1-6}$ alkyl group is unsubstituted or substituted with one or two identical or different substituents independently selected from the group consisting of cyano groups, hydroxy groups, $C_{1-3}$ alkoxy groups, $C_{1-3}$ alkylthio groups, alkylamino groups, di-$C_{1-3}$ alkylaminocarbonyl groups, $C_{3-6}$ cycloalkyl groups, 4 to 7-membered non-aromatic heterocyclyl groups), a $C_{1-6}$ haloalkyl group, a $C_{3-6}$ cycloalkyl group or a 4 to 7-membered non-aromatic heterocyclyl group).

A further preferred embodiment of the ring $A^b$ is represented by the formula (XI$^b$):

(XI$^b$)

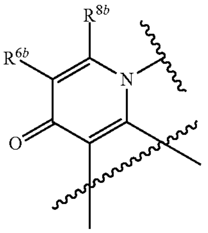

(wherein each of $R^{6b}$ and $R^{8b}$ is independently a hydrogen atom, a halogen atom or a $C_{1-3}$ alkyl group).

Another further preferred embodiment of the ring $A^b$ is represented by the formula (XII$^b$):

(XII$^b$)

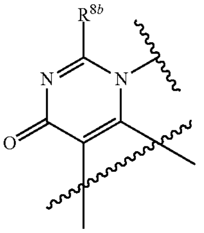

(wherein $R^{8b}$ is a hydrogen atom, a halogen atom or a $C_{1-3}$ alkyl group).

Another further preferred embodiment of the ring $A^b$ is represented by the formula (XIII$^b$):

(XIII$^b$)

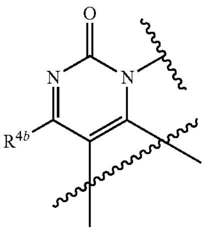

(wherein $R^{4b}$ is a hydrogen atom, a halogen atom or a $C_{1-3}$ alkyl group).

Another further preferred embodiment of the ring $A^b$ is represented by the formula ($XIV^b$):

($XIV^b$)

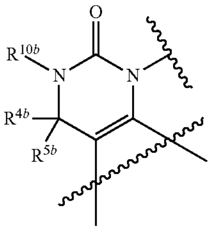

(wherein each of $R^{4b}$, $R^{5b}$ and $R^{10b}$ is independently a hydrogen atom or a $C_{1-3}$ alkyl group).

Another further preferred embodiment of the ring $A^b$ is represented by the formula ($XXIV^b$):

($XXIV^b$)

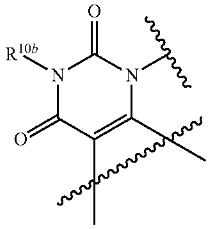

(wherein $R^{10b}$ is a hydrogen atom).

Another further preferred embodiment of the ring $A^b$ is represented by the formula ($XXIV^b$):

($XXIV^b$)

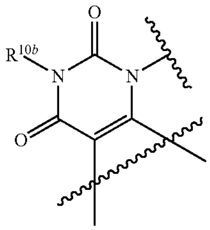

(wherein $R^{10b}$ is a $C_{1-6}$ alkyl group (the $C_{1-6}$ alkyl group is unsubstituted or substituted with one or two identical or different substituents independently selected from the group consisting of cyano groups, hydroxy groups, $C_{1-3}$ alkoxy groups, $C_{1-3}$ alkylthio groups, di-$C_{1-3}$ alkylamino groups and 4 to 7-membered non-aromatic heterocyclyl groups), a $C_{1-6}$ haloalkyl group, a $C_{3-6}$ cycloalkyl group or a 4 to 7-membered non-aromatic heterocyclyl group).

A particularly preferred embodiment of the $A^b$ is represented by the formula ($XI^b$):

($XI^b$)

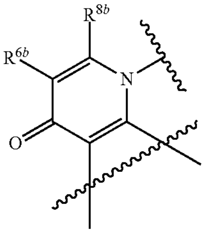

(wherein $R^{6b}$ is a hydrogen atom, a halogen atom or a $C_{1-3}$ alkyl group, and $R^{8b}$ is a hydrogen atom).

Another particularly preferred embodiment of the $A^b$ is represented by the formula ($XII^b$):

($XII^b$)

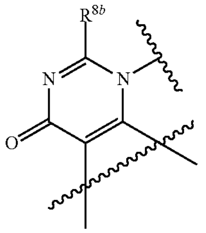

(wherein $R^{8b}$ is a hydrogen atom).

Another particularly preferred embodiment of the $A^b$ is represented by the formula ($XIII^b$):

($XIII^b$)

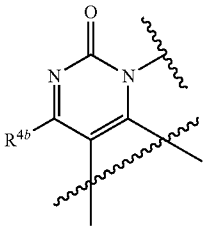

(wherein $R^{4b}$ is a hydrogen atom).

Another particularly preferred embodiment of the $A^b$ is represented by the formula ($XIV^b$):

($XIV^b$)

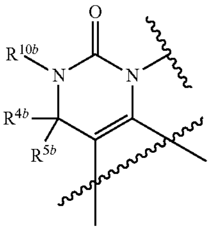

(wherein each of $R^{4b}$, $R^{5b}$ and $R^{10b}$ is a hydrogen atom).

A preferred embodiment of the substituent $L^{1b}$ is a single bond or a $C_{1-3}$ alkylene group.

A more preferred embodiment of the substituent $L^{1b}$ is a single bond or a methylene group.

A further preferred embodiment of the substituent $L^{1b}$ is a single bond.

A preferred embodiment of the ring $B^b$ is a $C_{3-11}$ cycloalkane, a 3 to 11-membered non-aromatic heterocycle, benzene or a 5 to 10-membered aromatic heterocycle.

A more preferred embodiment of the $B^b$ is a $C_{4-7}$ cycloalkane, a 4 to 7-membered non-aromatic heterocycle or a 5 to 6-membered aromatic heterocycle.

Another more preferred embodiment of the $B^b$ is adamantane.

A further preferred embodiment of the ring $B^b$ is a $C_{4-7}$ cycloalkane or a 4 to 7-membered non-aromatic heterocycle.

A particularly preferred embodiment of the ring $B^b$ is cyclohexane or piperidine.

A preferred embodiment of the substituent $L^{2b}$ is a single bond, a $C_{1-3}$ alkylene group or a $C_{1-3}$ haloalkylene group (the $C_{1-3}$ alkylene group and the $C_{1-3}$ haloalkylene group are substituted with a cyano group).

Another preferred embodiment of the substituent $L^{2b}$ is a $C_{1-3}$ alkylene group, a $C_{1-3}$ haloalkylene group (the $C_{1-3}$ alkylene group and the $C_{1-3}$ haloalkylene group are unsubstituted or substituted with a hydroxy group) or a $C_{2-6}$ alkenylene group (the $C_{2-6}$ alkenylene group is unsubstituted or substituted with a cyano group).

Another preferred embodiment of the substituent $L^{2b}$ is a $C_{1-6}$ alkylene group (the $C_{1-6}$ alkylene group is unsubstituted or substituted with one or two cyano groups) or a $C_{1-6}$ haloalkylene group.

A more preferred embodiment of the substituent $L^{2b}$ is a single bond or a $C_{1-3}$ alkylene group.

Another more preferred embodiment of the substituent $L^{2b}$ is a $C_{1-3}$ alkylene group. (the $C_{1-3}$ alkylene group is substituted with a cyano group) or a $C_{1-3}$ haloalkylene group.

Another more preferred embodiment of the substituent $L^{2b}$ is a $C_{2-3}$ alkenylene group (the $C_{2-3}$ alkenylene group is substituted with a cyano group).

A further preferred embodiment of the substituent $L^{2b}$ is a single bond or a methylene group.

A preferred embodiment of the substituent $L^{3b}$ and the substituent $R^{2b}$ is such that $L^{3b}$ is a single bond, and $R^{2b}$ is a hydrogen atom, a halogen atom, a $C_{3-6}$ cycloalkyl group, a 3 to 11-membered non-aromatic heterocyclyl group, a phenyl group or a 5 to 10-membered aromatic heterocyclyl group (the $C_{3-6}$ cycloalkyl group, the 3 to 11-membered non-aromatic heterocyclyl group, the phenyl group and the 5 to 10-membered aromatic heterocyclyl group are unsubstituted or substituted with one or more identical or different substituents independently selected from the substituent set $V^{1b}$).

Another preferred embodiment of the substituent $L^{3b}$ and the substituent $R^{2b}$ is such that $L^{3b}$ is a single bond, and $R^{2b}$ is a hydrogen atom, a halogen atom, a $C_{3-11}$ cycloalkyl group, a 3 to 11-membered non-aromatic heterocyclyl group, a phenyl group, a naphthyl group, a 5 to 10-membered aromatic heterocyclyl group or a 8 to 11-membered partially saturated aromatic cyclic group (the $C_{3-11}$ cycloalkyl group, the 3 to 11-membered non-aromatic heterocyclyl group, the phenyl group, the naphthyl group, the 5 to 10-membered aromatic heterocyclyl group and the 8 to 11-membered partially saturated aromatic cyclic group are unsubstituted or substituted with one or more identical or different substituents independently selected from the substituent set $V^{4b}$ and the substituent set $V^{9b}$).

Another preferred embodiment of the substituent $L^{3b}$ and the substituent $R^{2b}$ is such that $L^{3b}$ is represented by any of the following formulae ($VI^b$-1) to ($VI^b$-11):

($VI^b$)

($VI^b$-1)

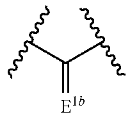

($VI^b$-2)

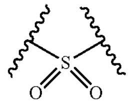

($VI^b$-3)

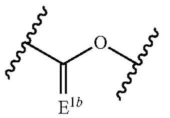

($VI^b$-4)

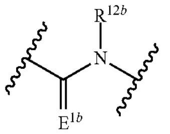

($VI^b$-5)

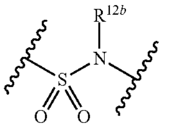

($VI^b$-6)

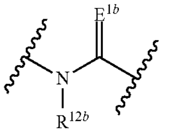

($VI^b$-7)

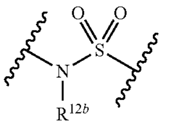

($VI^b$-8)

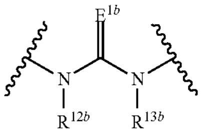

($VI^b$-9)

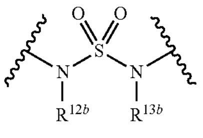

($VI^b$-10)

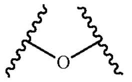

($VI^b$-11)

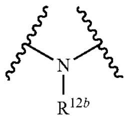

(wherein $E^{1b}$ is an oxygen atom or a sulfur atom, and each of $R^{12b}$ and $R^{13b}$ is independently a hydrogen atom, a $C_{1-6}$ alkyl group or a $C_{1-6}$ haloalkyl group), and $R^{2b}$ is a hydrogen atom, a $C_{1-6}$ alkyl group (the $C_{1-6}$ alkyl group is unsubstituted or substituted with one or more identical or different substituents independently selected from the substituent set $V^{5b}$), a $C_{2-6}$ alkenyl group, a $C_{3-6}$ cycloalkyl group, a 3 to 11-membered non-aromatic heterocyclyl group, a phenyl group or a 5 to 10-membered aromatic heterocyclyl group (the $C_{2-6}$ alkenyl group, the $C_{3-6}$ cycloalkyl group, the 3 to 11-membered non-aromatic heterocyclyl group, the phenyl group and the 5 to 10-membered aromatic heterocyclyl group are unsubstituted or substituted with one or more identical or different substituents independently selected from the substituent set $V^{4b}$).

Another preferred embodiment of the substituent $L^{3b}$ and the substituent $R^{2b}$ is such that $L^{3b}$ is represented by any of the following formulae ($VI^b$-1) to ($VI^b$-11):

($VI^b$)

($VI^b$-1)

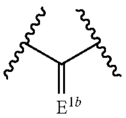

($VI^b$-2)

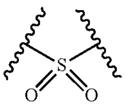

($VI^b$-3)

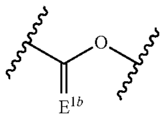

($VI^b$-4)

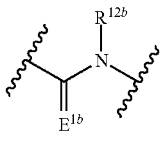

($VI^b$-5)

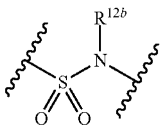

($VI^b$-6)

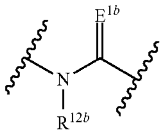

($VI^b$-7)

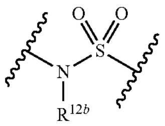

($VI^b$-8)

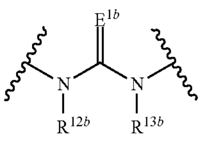

-continued ($VI^b$-9)

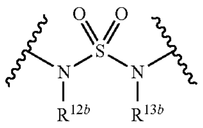

($VI^b$-10)

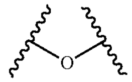

($VI^b$-11)

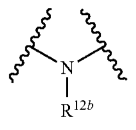

(wherein $E^{1b}$ is an oxygen atom or a sulfur atom, and each of $R^{12b}$ and $R^{13b}$ is independently a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or two identical or different substituents independently selected from the group consisting of cyano groups, hydroxy groups, $C_{1-6}$ alkoxy groups, $C_{3-6}$ cycloalkyl groups, 4 to 7-membered non-aromatic heterocyclyl groups, phenyl groups and 5 to 6-membered aromatic heterocyclyl groups)), and $R^{2b}$ is a hydrogen atom, a $C_{1-6}$ alkyl group, a $C_{2-6}$ alkenyl group (the $C_{1-6}$ alkyl group and the $C_{2-6}$ alkenyl group are unsubstituted or substituted with one or more identical or different substituents independently selected from the substituent set $V^{6b}$ and the substituent set $V^{9b}$), a $C_{3-6}$ cycloalkyl group, a 3 to 11-membered non-aromatic heterocyclyl group, a phenyl group, a 5 to 10-membered aromatic heterocyclyl group or a 8 to 11-membered partially saturated aromatic cyclic group (the $C_{3-6}$ cycloalkyl group, the 3 to 11-membered non-aromatic heterocyclyl group, the phenyl group, the 5 to 10-membered aromatic heterocyclyl group and the 8 to 11-membered partially saturated aromatic cyclic group are unsubstituted or substituted with one or more identical or different substituents independently selected from the substituent set $V^{4b}$ and the substituent set $V^{9b}$).

A more preferred embodiment of the substituent $L^{3b}$ and the substituent $R^{2b}$ is such that $L^{3b}$ is a single bond, and $R^{2b}$ is a hydrogen atom, a halogen atom, a $C_{3-6}$ cycloalkyl group, a phenyl group or a 5 to 6-membered aromatic heterocyclyl group (the $C_{3-6}$ cycloalkyl group, the phenyl group and the 5 to 6-membered aromatic heterocyclyl group are unsubstituted or substituted with one or more identical or different substituents independently selected from the substituent set $V^{1b}$).

Another more preferred embodiment of the substituent $L^{3b}$ and the substituent $R^{2b}$ is such that $L^{3b}$ is a single bond, and $R^{2b}$ is a hydrogen atom, a halogen atom, a $C_{3-6}$ cycloalkyl group, a 4 to 7-membered non-aromatic heterocyclyl group, a phenyl group or a 5 to 10-membered aromatic heterocyclyl group (the $C_{3-6}$ cycloalkyl group, the 4 to 7-membered non-aromatic heterocyclyl group, the phenyl group and the 5 to 10-membered aromatic heterocyclyl group are unsubstituted or substituted with one or more identical or different substituents independently selected from the substituent set $V^{1b}$).

Another more preferred embodiment of the substituent $L^{3b}$ and the substituent $R^{2b}$ is such that $L^{3b}$ is a single bond, and $R^{2b}$ is a 4 to 7-membered non-aromatic heterocyclyl group, a phenyl group or a 5 to 6-membered aromatic heterocyclyl group (the 4 to 7-membered non-aromatic heterocyclyl group, the phenyl group and the 5 to 6-membered aromatic heterocyclyl group are unsubstituted or substituted with one or two identical or different substituents independently selected from the group consisting of $C_{1-6}$ alkyl groups, $C_{1-6}$ alkoxy groups (the $C_{1-6}$ alkyl group and the $C_{1-6}$ alkoxy group are substituted with a hydroxy group or a cyano group), mono-$C_{1-6}$ alkylamino groups, di-$C_{1-6}$ alkylamino groups, the mono-$C_{1-6}$ alkylaminocarbonyl groups, the di-$C_{1-6}$ alkylaminocarbonyl groups, $C_{1-6}$ alkylcarbonylamino groups (the mono-$C_{1-6}$ alkylamino group, the di-$C_{1-6}$ alkylamino group, mono-$C_{1-6}$ alkylaminocarbonyl groups, di-$C_{1-6}$ alkylaminocarbonyl groups and the $C_{1-6}$ alkylcarbonylamino groups are substituted with one or more identical or different halogen atoms independently selected from the group consisting of fluorine atoms, chlorine atoms, bromine atoms and iodine atoms), phenyl groups, 5 to 6-membered aromatic heterocyclyl groups (the phenyl group and the 5 to 6-membered aromatic heterocyclyl group are unsubstituted or substituted with one or two identical or different substituents independently selected from the group consisting of halogen atoms, cyano atoms and $C_{1-6}$ haloalkyl groups)).

Another more preferred embodiment of the substituent $L^{3b}$ and the substituent $R^{2b}$ is such that $L^{3b}$ is a single bond, and $R^{2b}$ is a 8 to 11-membered partially saturated aromatic cyclic group (the 8 to 11-membered partially saturated aromatic cyclic group is unsubstituted or substituted with one or more identical or different substituents independently selected from the group consisting of hydroxy groups, amino groups, halogen atoms, cyano groups, nitro groups, carbamoyl groups, sulfamoyl groups, $C_{1-6}$ alkyl groups, $C_{1-6}$ haloalkyl groups, $C_{1-6}$ alkoxy groups, $C_{1-6}$ haloalkoxy groups, mono-$C_{1-6}$ alkylamino groups, di-$C_{1-6}$ alkylamino groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups and $C_{1-6}$ alkoxycarbonyl groups).

Another more preferred embodiment of the substituent $L^{3b}$ and the substituent $R^{2b}$ is such that $L^{3b}$ is represented by any of the following formulae ($XV^b$-1) to ($XV^b$-9):

($XV^b$)

($XV^b$-1)

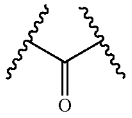

($XV^b$-2)

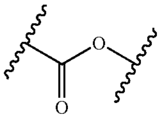

($XV^b$-3)

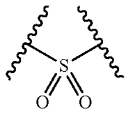

($XV^b$-4)

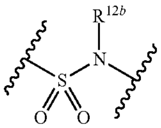

-continued ($XV^b$-5)

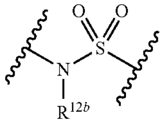

($XV^b$-6)

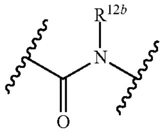

($XV^b$-7)

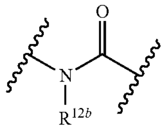

($XV^b$-8)

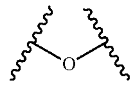

($XV^b$-9)

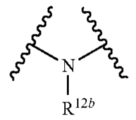

(wherein $R^{12b}$ is a hydrogen atom or a $C_{1-6}$ alkyl group), and $R^{2b}$ is a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or two identical or different substituents independently selected from the group consisting of hydroxy groups, amino groups, carbamoyl groups, sulfamoyl groups, tetrazolyl groups, cyano groups, nitro groups, $C_{3-6}$ cycloalkyl groups, $C_{1-3}$ alkoxy groups, $C_{1-6}$ haloalkoxy groups, $C_{1-3}$ alkylsulfonyl groups, $C_{1-3}$ haloalkylsulfonyl groups, 4 to 7-membered non-aromatic heterocyclyl groups, phenyl groups and 5 to 6-membered aromatic heterocyclyl groups).

Another more preferred embodiment of the substituent $L^{3b}$ and the substituent $R^{2b}$ is such that $L^{3b}$ is represented by any of the following formulae ($XV^b$-1) to ($XV^b$-9):

($XV^b$)

($XV^b$-1)

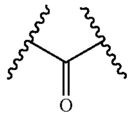

($XV^b$-2)

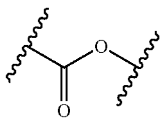

($XV^b$-3)

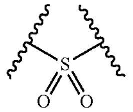

-continued (XV$^b$-4)

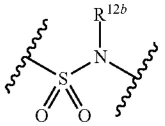

(XV$^b$-5)

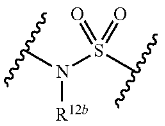

(XV$^b$-6)

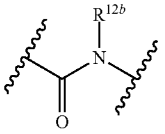

(XV$^b$-7)

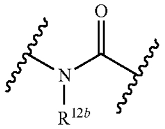

(XV$^b$-8)

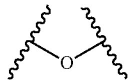

(XV$^b$-9)

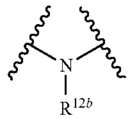

(wherein $R^{12b}$ is a hydrogen atom, a $C_{1-6}$ alkyl group or a $C_{1-6}$ haloalkyl group), and $R^{2b}$ is a $C_{1-6}$ alkyl group (the $C_{1-6}$ alkyl group is substituted with a substituent selected from the group consisting of a $C_{3-6}$ cycloalkyl group, a 4 to 7-membered non-aromatic heterocyclyl group, a phenyl group and a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group is substituted with one or two identical or different substituents independently selected from the group consisting of hydroxy groups, halogen atoms and cyano groups)), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or two identical or different substituents independently selected from the group consisting of hydroxy groups, halogen atoms, cyano groups, $C_{1-3}$ alkyl groups, $C_{1-3}$ haloalkyl groups and $C_{1-6}$ alkoxycarbonyl groups).

Another more preferred embodiment of the substituent $L^{3b}$ and the substituent $R^{2b}$ is such that $L^{3b}$ is represented by any of the following formulae (XXXIV$^b$-1) to (XXXIV$^b$-3):

(XXXIV$^b$)

(XXXIV$^b$-1)

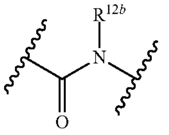

(XXXIV$^b$-2)

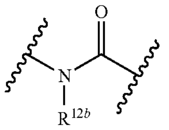

(XXXIV$^b$-3)

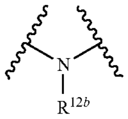

(wherein $R^{12b}$ is a $C_{1-6}$ alkyl group (the $C_{1-6}$ alkyl group is substituted with a substituent selected from the group consisting of a cyano group, a hydroxy group and a phenyl group)), and $R^{2b}$ is a $C_{1-6}$ alkyl group (the $C_{1-6}$ alkyl group is unsubstituted or substituted with a substituent selected from the group consisting of a hydroxy group, a cyano group and a phenyl group) or a $C_{1-6}$ haloalkyl group.

A further preferred embodiment of the substituent $L^{3b}$ and the $R^{2b}$ is such that $L^{3b}$ is a single bond, and $R^{2b}$ is a hydrogen atom, a phenyl group (the phenyl group is unsubstituted or substituted with one or more identical or different substituents independently selected from the group consisting of halogen atoms, hydroxy groups, cyano groups, $C_{1-3}$ alkyl groups, $C_{1-3}$ haloalkyl groups, $C_{1-3}$ alkoxy groups and $C_{1-3}$ haloalkoxy groups).

Another further preferred embodiment of the substituent $L^{3b}$ and the $R^{2b}$ is such that $L^{3b}$ is a single bond, and $R^{2b}$ is a hydrogen atom, a $C_{3-6}$ cycloalkyl group, a phenyl group or a 5 to 6-membered aromatic heterocyclyl group (the phenyl group and the 5 to 6-membered aromatic heterocyclyl group are unsubstituted or substituted with one or more identical or different substituents independently selected from the group consisting of halogen atoms, cyano groups, nitro groups, $C_{1-3}$ alkyl groups, $C_{1-3}$ haloalkyl groups and $C_{1-3}$ alkoxycarbonyl groups).

Another further preferred embodiment of the substituent $L^{3b}$ and the $R^{2b}$ is such that $L^{3b}$ is a single bond, and $R^{2b}$ is an indolinyl group.

Another further preferred embodiment of the substituent $L^{3b}$ and the $R^{2b}$ is such that $L^{3b}$ is a single bond, and $R^{2b}$ is a 4 to 7-membered non-aromatic heterocyclyl group (the 4 to 7-membered non-aromatic heterocyclyl group is unsubstituted or substituted with one or more identical or different substituents independently selected from the group consisting of hydroxy groups, halogen atoms, cyano groups, $C_{1-6}$ alkyl groups, $C_{1-6}$ haloalkyl groups, $C_{1-6}$ alkoxy groups, $C_{1-6}$ haloalkoxy groups and $C_{1-6}$ alkoxycarbonyl groups).

Another further preferred embodiment of the substituent $L^{3b}$ and the $R^{2b}$ is such that $L^{3b}$ is a single bond, and $R^{2b}$ is a 4 to 7-membered non-aromatic heterocyclyl group (the 4 to 7-membered non-aromatic heterocyclyl group is substituted with a $C_{1-6}$ alkyl groups (the $C_{1-6}$ alkyl group is substituted with a cyano group)).

Another further preferred embodiment of the substituent $L^{3b}$ and the $R^{2b}$ is such that $L^{3b}$ is a single bond, and $R^{2b}$ is a 8 to 11-membered partially saturated aromatic cyclic group (the 8 to 11-membered partially saturated aromatic cyclic group is unsubstituted or substituted with one or more identical or different halogen atoms independently selected from the group consisting of fluorine atoms, chlorine atoms, bromine atoms and iodine atoms).

Another further preferred embodiment of the substituent $L^{3b}$ and the $R^{2b}$ is such that $L^{3b}$ is represented by the following formula ($VIII^b$-1) or ($VIII^b$-2):

($VIII^b$)

($VIII^b$-1)

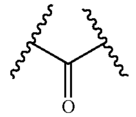

($VIII^b$-2)

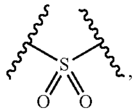

and $R^{2b}$ is a $C_{1-6}$ alkyl group or a $C_{1-3}$ haloalkyl group (the $C_{1-6}$ alkyl group and the $C_{1-3}$ haloalkyl group are unsubstituted or substituted with a cyano group or a $C_{3-6}$ cycloalkyl group).

Another further preferred embodiment of the substituent $L^{3b}$ and the $R^{2b}$ is such that $L^{3b}$ is represented by the following formula ($VIII^b$-1) or ($VIII^b$-2):

($VIII^b$)

($VIII^b$-1)

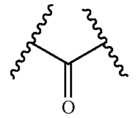

($VIII^b$-2)

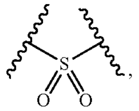

and $R^{2b}$ is a $C_{1-3}$ alkyl group (the $C_{1-3}$ alkyl group is substituted with a phenyl group).

Another further preferred embodiment of the substituent $L^{3b}$ and the $R^{2b}$ is such that $L^{3b}$ is represented by the following formula ($VIII^b$-1) or ($VIII^b$-2):

($VIII^b$)

($VIII^b$-1)

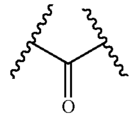

($VIII^b$-2)

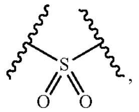

and $R^{2b}$ is a $C_{1-3}$ alkyl group (the $C_{1-3}$ alkyl group is substituted with a phenyl group (the phenyl group is substituted with a halogen atom)), a $C_{3-6}$ cycloalkyl group, a phenyl group or a 5 to 6-membered aromatic heterocyclyl group (the $C_{3-6}$ cycloalkyl group, the phenyl group and the 5 to 6-membered aromatic heterocyclyl group are unsubstituted or substituted with one or two identical or different substituents independently selected from the group consisting of halogen atoms, cyano groups, $C_{1-6}$ alkyl groups and $C_{1-3}$ haloalkyl groups).

Another further preferred embodiment of the substituent $L^{3b}$ and the $R^{2b}$ is such that $L^{3b}$ is represented by the formula ($XXV^b$):

($XXV^b$)

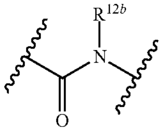

(wherein $R^{12b}$ is a hydrogen atom), and $R^{2b}$ is a phenyl group or a 5 to 6-membered aromatic heterocyclyl group (the phenyl group and the 5 to 6-membered aromatic heterocyclyl group are unsubstituted or substituted with a substituent selected from the group consisting of a $C_{1-3}$ alkyl group and a $C_{1-3}$ haloalkyl group).

Another further preferred embodiment of the substituent $L^{3b}$ and the $R^{2b}$ is such that $L^{3b}$ is represented by the formula ($XXVI^b$):

($XXVI^b$)

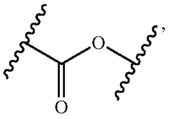

and $R^{2b}$ is a $C_{1-6}$ alkyl group (the $C_{1-6}$ alkyl group is unsubstituted or substituted with a phenyl group).

Another further preferred embodiment of the substituent $L^{3b}$ and the $R^{2b}$ is such that $L^{3b}$ is represented by the formula ($XXVII^b$):

($XXVII^b$)

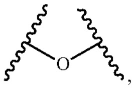

and $R^{2b}$ is a hydrogen atom or a $C_{1-3}$ alkyl group.

Another further preferred embodiment of the substituent $L^{3b}$ and the $R^{2b}$ is such that $L^{3b}$ is represented by the formula ($XXXV^b$):

($XXXV^b$)

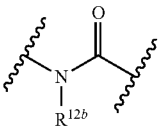

(wherein $R^{12b}$ is a $C_{1-3}$ haloalkyl group), and $R^{2b}$ is a $C_{1-6}$ alkyl group (the $C_{1-6}$ alkyl group is unsubstituted or substituted with a cyano group) or a $C_{1-6}$ haloalkyl group.

Another further preferred embodiment of the substituent $L^{3b}$ and the $R^{2b}$ is such that $L^{3b}$ is represented by the formula (XXXII$^b$):

(XXXII$^b$)

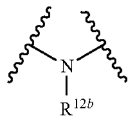

(wherein $R^{12b}$ is a hydrogen atom or a $C_{1-3}$ alkyl group), and $R^{2b}$ is a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or two identical or different substituents independently selected from the group consisting of hydroxy groups, cyano groups, $C_{1-3}$ alkoxy groups, $C_{3-6}$ cycloalkyl groups, 4 to 7-membered non-aromatic heterocyclyl groups, phenyl groups and 5 to 6-membered aromatic heterocyclyl groups).

Another further preferred embodiment of the substituent $L^{3b}$ and the $R^{2b}$ is such that $L^{3b}$ is represented by the formula (XXXII$^b$):

(XXXII$^b$)

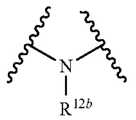

(wherein $R^{12b}$ is a $C_{1-3}$ haloalkyl group), and $R^{2b}$ is a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or two identical or different substituents independently selected from the group consisting of hydroxy groups, cyano groups, $C_{1-3}$ alkoxy groups, $C_{3-6}$ cycloalkyl groups, 4 to 7-membered non-aromatic heterocyclyl groups, phenyl groups and 5 to 6-membered aromatic heterocyclyl groups).

Another further preferred embodiment of the substituent $L^{3b}$ and the $R^{2b}$ is such that $L^{3b}$ is represented by the formula (XXXII$^b$):

(XXXII$^b$)

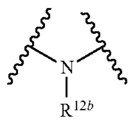

(wherein $R^{12b}$ is a hydrogen atom or a $C_{1-3}$ alkyl group), and $R^{2b}$ is a $C_{1-6}$ alkyl group (the $C_{1-6}$ alkyl group is substituted with a $C_{3-6}$ cycloalkyl group (the $C_{3-6}$ cycloalkyl group is substituted with a hydroxy group)), a $C_{3-6}$ cycloalkyl group, a 4 to 7-membered non-aromatic heterocyclyl group, a phenyl group or a 5 to 6-membered aromatic heterocyclyl group (the $C_{3-6}$ cycloalkyl group, the 4 to 7-membered non-aromatic heterocyclyl group, the phenyl group and the 5 to 6-membered aromatic heterocyclyl group are unsubstituted or substituted with one or two identical or different substituents independently selected from the group consisting of $C_{1-3}$ alkyl groups, $C_{1-3}$ haloalkyl groups and $C_{1-6}$ alkoxycarbonyl groups).

Another further preferred embodiment of the substituent $L^{3b}$ and the $R^{2b}$ is such that $L^{3b}$ is represented by the formula (XXXII$^b$):

(XXXII$^b$)

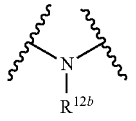

(wherein $R^{12b}$ is a $C_{1-3}$ alkyl group (the $C_{1-3}$ alkyl group is substituted with a substituent selected from the group consisting of a cyano group, a hydroxy group and a phenyl group)), and $R^{2b}$ is a $C_{1-6}$ alkyl group (the $C_{1-6}$ alkyl group is unsubstituted or substituted with a substituent selected from the group consisting of a hydroxy group, a cyano group and a phenyl group) or a $C_{1-6}$ haloalkyl group.

A particularly preferred embodiment of the substituent $L^{3b}$ and the $R^{2b}$ is such that $L^{3b}$ is a single bond, and $R^{2b}$ is a hydrogen atom or a phenyl group (the phenyl group is unsubstituted or substituted with one or more identical or different halogen atoms selected from the group consisting of fluorine atoms, chlorine atoms, bromine atoms and iodine atoms).

Another particularly preferred embodiment of the substituent $L^{3b}$ and the $R^{2b}$ is such that $L^{3b}$ is a single bond, and $R^{2b}$ is a phenyl group (the phenyl group is unsubstituted or substituted with one or two identical or different substituents independently selected from the group consisting of halogen atoms, cyano groups and $C_{1-3}$ haloalkyl groups).

Another particularly preferred embodiment of the substituent $L^{3b}$ and the $R^{2b}$ is such that $L^{3b}$ is a single bond, and $R^{2b}$ is a 5 to 6-membered aromatic heterocyclyl group (the 5 to 6-membered aromatic heterocyclyl group is unsubstituted or substituted with a substituent selected from the group consisting of a halogen atom, a cyano group, a nitro group, a $C_{1-3}$ alkyl group, a $C_{1-3}$ haloalkyl group and a $C_{1-3}$ alkoxycarbonyl group).

Another particularly preferred embodiment of the substituent $L^{3b}$ and the $R^{2b}$ is such that $L^{3b}$ is a single bond, and $R^{2b}$ is a $C_{3-6}$ cycloalkyl group.

Another particularly preferred embodiment of the substituent $L^{3b}$ and the $R^{2b}$ is such that $L^{3b}$ is a single bond, and $R^{2b}$ is a 4 to 7-membered non-aromatic heterocyclyl group (the 4 to 7-membered non-aromatic heterocyclyl group is unsubstituted or substituted with one or two identical or different substituents independently selected from the group consisting of hydroxy groups, halogen atoms, cyano groups, $C_{1-3}$ alkyl groups and $C_{1-3}$ haloalkyl groups).

Another particularly preferred embodiment of the substituent $L^{3b}$ and the $R^{2b}$ is such that $L^{3b}$ is represented by the following formula (VIII$^b$-1) or (VIII$^b$-2):

(VIII$^b$)

(VIII$^b$-1)

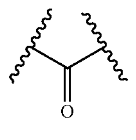

-continued (VIII$^b$-2)

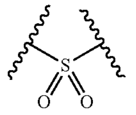

and $R^{2b}$ is a methyl group (the methyl group is unsubstituted or substituted with a cyano group, a cyclopropyl group or a trifluoromethyl group) or an isobutyl group.

Another particularly preferred embodiment of the substituent $L^{3b}$ and the $R^{2b}$ is such that $L^{3b}$ is represented by the following formula (VIII$^b$-1) or (VIII$^b$-2):

(VIII$^b$)

(VIII$^b$-1)

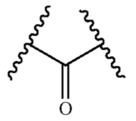

(VIII$^b$-2)

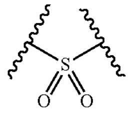

and $R^{2b}$ is a phenyl group (the phenyl group is unsubstituted or substituted with a substituent selected from the group consisting of a halogen atom, a cyano group and a $C_{1-3}$ haloalkyl group) or a 5 to 6-membered aromatic heterocyclyl group (the 5 to 6-membered aromatic heterocyclyl group is unsubstituted or substituted with a halogen atom).

Another particularly preferred embodiment of the substituent $L^{3b}$ and the $R^{2b}$ is such that $L^{3b}$ is represented by the formula (XXXII$^b$):

(XXXII$^b$)

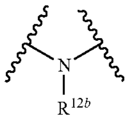

(wherein $R^{12b}$ is a hydrogen atom), and $R^{2b}$ is a $C_{3-6}$ cycloalkyl group or a 4 to 7-membered non-aromatic heterocyclyl group (the $C_{3-6}$ cycloalkyl group and the 4 to 7-membered non-aromatic heterocyclyl group are unsubstituted or substituted with one or two identical or different substituents independently selected from the group consisting of $C_{1-3}$ alkyl groups, $C_{1-3}$ haloalkyl groups and $C_{1-6}$ alkoxycarbonyl groups).

A preferred embodiment of $n^b$ and the substituent $R^{3b}$ is such that $n^b$ is 0, 1 or 2, and $R^{3b}$ is a hydroxy group, an amino group, a halogen atom, a cyano group, a $C_{1-3}$ alkyl group, a $C_{1-3}$ haloalkyl group, a $C_{1-3}$ alkoxy group or a $C_{1-3}$ haloalkoxy group (when $n^b$ is 2, $R^{3b}$'s may be identical or different).

A more preferred embodiment of $n^b$ and the substituent $R^{3b}$ is such that $n^b$ is 0 or 1, and $R^{3b}$ is a $C_{1-3}$ alkyl group.

As favorable tricyclic pyridine compounds of the present invention for use as JAK inhibitors and as preventive, therapeutic and/or improving agent for diseases against which inhibition of JAK is effective, the following compound may be mentioned.

$1^b$) Compounds represented by the formula (I$^b$):

(I$^b$)

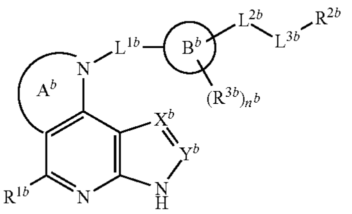

[wherein $R^{1b}$ is a hydrogen atom or a halogen atom,
$X^b$ is a nitrogen atom or $CR^{15b}$ (wherein $R^{15b}$ is a hydrogen atom, a halogen atom, a cyano group, a $C_{1-6}$ alkyl group, a $C_{1-6}$ haloalkyl group or a $C_{3-6}$ cycloalkyl group),
$Y^b$ is $CR^{16b}$ (wherein $R^{16b}$ is a hydrogen atom),
the ring $A^b$ is represented by the formula (II$^b$):

(II$^b$)

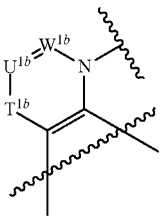

(wherein $T^{1b}$ is $CR^{4b}R^{5b}$, C(=O), C(=S), C(=$NR^{17b}$), a sulfur atom, S(=O) or S(=O)$_2$, $U^{1b}$ is a nitrogen atom or $CR^{6b}$, and $W^{1b}$ is a nitrogen atom or $CR^{8b}$), the formula (III$^b$):

(III$^b$)

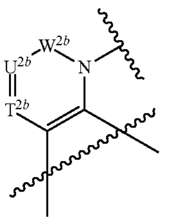

(wherein $T^{2b}$ is $CR^{4b}$, $U^{2b}$ is a nitrogen atom or $CR^{6b}$, and $W^{2b}$ is $CR^{8b}R^{9b}$, C(=O), C(=S), C(=$NR^{17b}$), $NR^{10b}$ an oxygen atom, a sulfur atom, S(=O) or S(=O)$_2$ (provided that when $U^{2b}$ is $CR^{6b}$, $W^{2b}$ is not C(=O))) or the formula (IV$^b$):

(IV$^b$)

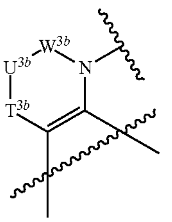

(wherein $T^{3b}$ is $CR^{4b}R^{5b}$, C(=O), C(=S), C(=$NR^{17b}$), a sulfur atom, S(=O) or S(=O)$_2$, $U^{3b}$ is $CR^{6b}R^{7b}$, C(=O), C(═S), C(═$NR^{17b}$), $NR^{19b}$, an oxygen atom, a sulfur atom, S(═O) or S(═$O)_2$, and $W^{3b}$ is $CR^{8b}R^{9b}$, C(═O), C(═S), C(═$NR^{17b}$), $NR^{11b}$, an oxygen atom, a sulfur atom, S(═O) or S(═$O)_2$ (provided that when $T^{3b}$ is $CR^{4b}R^{5b}$, and $U^{3b}$ is $CR^{6b}R^{7b}$, $W^{3b}$ is not $CR^{8b}R^{9b}$)), $L^{1b}$ is a single bond or a $C_{1-3}$ alkylene group, $L^{2b}$ is a single bond, a $C_{1-6}$ alkylene group, a $C_{2-6}$ alkenylene group or a $C_{2-6}$ alkynylene group (the $C_{1-6}$ alkylene group, the $C_{2-6}$ alkenylene group and the $C_{2-6}$ alkynylene group are unsubstituted or substituted with one or more identical or different substituents independently selected from the group consisting of halogen atoms, hydroxy groups, amino groups, cyano groups and nitro groups), the ring $B^b$ is a $C_{3-11}$ cycloalkane, a $C_{3-11}$ cycloalkene, a 3 to 11-membered non-aromatic heterocycle, a $C_{6-14}$ aromatic carbocycle or a 5 to 10-membered aromatic heterocycle, $n^b$ is 0 or 1, $R^{3b}$ is a hydroxy group, an amino group, a carboxy group, a carbamoyl group, a tetrazolyl group, a halogen atom, a cyano group, a nitro group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkylsulfonyl group, and $L^{3b}$ is a single bond or represented by any of the following formulae ($XXII^b$-1) to ($XXII^b$-15):

($XXII^b$)

($XXII^b$-1)

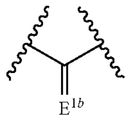

($XXII^b$-2)

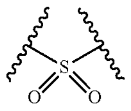

($XXII^b$-3)

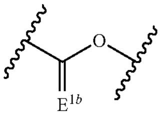

($XXII^b$-4)

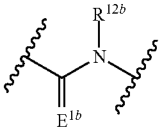

($XXII^b$-5)

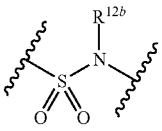

(XXII$b$-6)

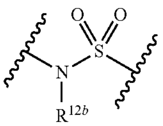

(XXII$b$-7)

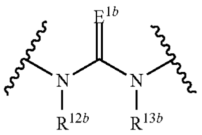

-continued ($XXII^b$-8)

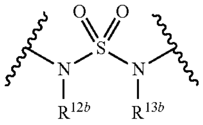

($XXII^b$-9)

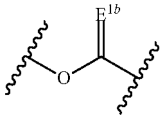

($XXII^b$-10)

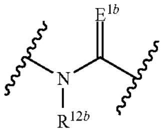

($XXII^b$-11)

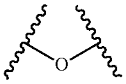

($XXII^b$-12)

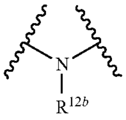

($XXII^b$-13)

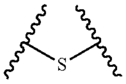

($XXII^b$-14)

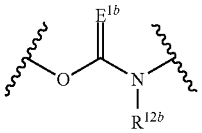

($XXII^b$-15)

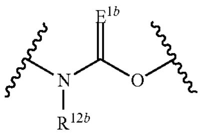

(wherein $E^{1b}$ is an oxygen atom or a sulfur atom), when $L^{3b}$ is a single bond, $R^{2b}$ is a hydrogen atom, a halogen atom, a $C_{3-11}$ cycloalkyl group, a 3 to 11-membered non-aromatic heterocyclyl group, a $C_{6-14}$ aryl group, a 5 to 10-membered aromatic heterocyclyl group, a 8 to 11-membered partially saturated aromatic cyclic group or a 8 to 11-membered aromatic ring-condensed alicyclic hydrocarbon group (the $C_{3-11}$ cycloalkyl group, the 3 to 11-membered non-aromatic heterocyclyl group, the $C_{6-14}$ aryl group, the 5 to 10-membered aromatic heterocyclyl group, the 8 to 11-membered partially saturated aromatic cyclic group and the 8 to 11-membered aromatic ring-condensed alicyclic hydrocarbon group are unsubstituted or substituted with one or more identical or different substituents independently selected from the substituent set $V^{4b}$ and the substituent set $V^{9b}$), when $L^{3b}$ is not a single bond, $R^{2b}$ is a hydrogen atom, a $C_{1-6}$ alkyl group, a $C_{2-6}$ alkenyl group (the $C_{1-6}$ alkyl group and the $C_{2-6}$ alkenyl group are unsubstituted or substituted with one or more identical or different substituents independently selected from the substituent set $V^{6b}$ and the substituent set $V^{9b}$), a $C_{3-11}$ cycloalkyl group, a 3 to 11-membered non-aromatic heterocyclyl group, a $C_{6-14}$ aryl group, a 5 to 10-membered aromatic heterocyclyl group, a 8 to 11-membered partially saturated aromatic cyclic group or a 8 to 11-membered aromatic ring-condensed alicyclic hydrocarbon group (the $C_{3-11}$ cycloalkyl group, the 3 to 11-membered non-aromatic heterocyclyl group, the $C_{6-14}$ aryl group, the 5 to 10-membered aromatic heterocyclyl group, the 8 to 11-membered partially saturated aromatic cyclic group and the 8 to 11-membered aromatic ring-condensed alicyclic hydrocarbon group are unsubstituted or substituted with one or more identical or different substituents independently selected from the substituent set $V^{4b}$ and the substituent set $V^{9b}$), $n^b$ is 0, 1 or 2, $R^{3b}$ is a hydroxy group, an amino group, a carboxy group, a carbamoyl group, a sulfamoyl group, a phosphono group, a phosphonooxy group, a sulfo group, a sulfoxy group, a tetrazolyl group, a halogen atom, a cyano group, a nitro group, a $C_{1-6}$ alkyl group, a $C_{1-6}$ haloalkyl group, a $C_{3-11}$ cycloalkyl group, a $C_{2-6}$ alkenyl group, a $C_{2-6}$ haloalkenyl group, a $C_{1-6}$ alkoxy group, a $C_{1-6}$ haloalkoxy group, a $C_{1-6}$ alkylthio group, a $C_{1-6}$ haloalkylthio group, a $C_{1-6}$ alkylcarbonyl group, a $C_{1-6}$ haloalkylcarbonyl group, a $C_{1-6}$ alkylsulfonyl group, a $C_{1-6}$ haloalkylsulfonyl group, a $C_{1-6}$ alkoxycarbonyl group, a mono-$C_{1-6}$ alkylamino group, a di-$C_{1-6}$ alkylamino group, a mono-$C_{1-6}$ alkylaminocarbonyl group, a di-$C_{1-6}$ alkylaminocarbonyl group or a $C_{1-6}$ alkylcarbonylamino group (when $n^b$ is 2, $R^{3b}$'s may be identical or different), each of $R^{4b}$, $R^{5b}$, $R^{6b}$, $R^{7b}$, $R^{8b}$ and $R^{9b}$ is independently a hydrogen atom, a hydroxy group, an amino group, a carboxy group, a carbamoyl group, a tetrazolyl group, a halogen atom, a cyano group, a $C_{1-6}$ alkyl group, a $C_{2-6}$ alkenyl group, a $C_{1-6}$ alkoxy group, a $C_{1-6}$ alkylthio group, a $C_{1-6}$ alkylcarbonyl group, a $C_{1-6}$ alkylsulfonyl group, a mono-$C_{1-6}$ alkylamino group, a di-$C_{1-6}$ alkylamino group (the $C_{1-6}$ alkyl group, the $C_{2-6}$ alkenyl group, the $C_{1-6}$ alkoxy group, the $C_{1-6}$ alkylthio group, the $C_{1-6}$ alkylcarbonyl group, the $C_{1-6}$ alkylsulfonyl group, the mono-$C_{1-6}$ alkylamino group and the di-$C_{1-6}$ alkylamino group are unsubstituted or substituted with one or more identical or different substituents independently selected from the substituent set $V^{3b}$), a $C_{1-6}$ alkoxycarbonyl group, a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{1b}$), each of $R^{10b}$ and $R^{11b}$ is independently a hydrogen atom, a $C_{1-6}$ alkyl group, a $C_{2-6}$ alkenyl group, a $C_{1-6}$ alkylcarbonyl group, a $C_{1-6}$ alkylsulfonyl group, a $C_{1-6}$ alkoxycarbonyl group, a mono-$C_{1-6}$ alkylaminocarbonyl group, a di-$C_{1-6}$ alkylaminocarbonyl group (the $C_{1-6}$ alkyl group, the $C_{2-6}$ alkenyl group, the $C_{1-6}$ alkylcarbonyl group, the $C_{1-6}$ alkylsulfonyl group, the $C_{1-6}$ alkoxycarbonyl group, the mono-$C_{1-6}$ alkylaminocarbonyl group and the di-$C_{1-6}$ alkylaminocarbonyl group are unsubstituted or substituted with one or more identical or different substituents independently selected from the substituent set $V^{3b}$), a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{1b}$), each of $R^{12b}$ and $R^{13b}$ is independently a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or more identical or different substituents independently selected from the substituent set $V^{3b}$, the substituent set $V^{8b}$ and the substituent set $V^{9b}$), and $R^{17b}$ is a hydrogen atom, a hydroxy group, a cyano group, a nitro group, a $C_{1-6}$ alkyl group or a $C_{1-6}$ alkoxy group], tautomers or pharmaceutically acceptable salts of the compounds or solvates thereof.

$2^b$) The compounds according to $1^b$), wherein $R^{1b}$ is a hydrogen atom or a halogen atom, $X^b$ is a nitrogen atom or $CR^{15b}$ (wherein $R^{15b}$ is a hydrogen atom, a halogen atom, a cyano group, a $C_{1-6}$ alkyl group, a $C_{1-6}$ haloalkyl group or a $C_{3-6}$ cycloalkyl group), $Y^b$ is $CR^{16b}$ (wherein $R^{18b}$ is a hydrogen atom), the ring $A^b$ is represented by the formula ($II^b$):

($II^b$)

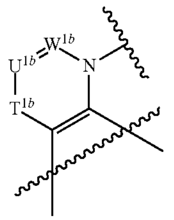

(wherein $T^{1b}$ is $CR^{4b}R^{5b}$, C(=O), C(=S), C(=$NR^{17b}$), a sulfur atom, S(=O) or S(=O)$_2$, $U^{1b}$ is a nitrogen atom or $CR^{6b}$, and $W^{1b}$ is a nitrogen atom or $CR^{8b}$), the formula ($III^b$):

($III^b$)

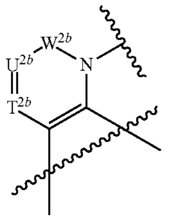

(wherein $T^{2b}$ is $CR^{4b}$, $U^{2b}$ is a nitrogen atom or $CR^{6b}$, and $W^{2b}$ is $CR^{8b}R^{9b}$, C(=O), C(=S), C(=$NR^{17b}$), $NR^{10b}$, an oxygen atom, a sulfur atom, S(=O) or S(=O)$_2$ (provided that when $U^{2b}$ is $CR^{6b}$, $W^{2b}$ is not C(=O))) or the formula ($IV^b$):

($IV^b$)

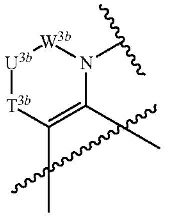

(wherein $T^{3b}$ is $CR^{4b}R^{5b}$, C(=O), C(=S), C(=$NR^{17b}$), a sulfur atom, S(=O) or S(=O)$_2$, $U^{3b}$ is $CR^{6b}R^{7b}$, C(=O), C(=S), C(=NR$^{17b}$), NR$^{10b}$, an oxygen atom, a sulfur atom, S(=O) or S(=O)$_2$, and W$^{3b}$ is CR$^{8b}$R$^{9b}$, C(=O), C(=S), C(=NR$^{17b}$), NR$^{11b}$, an oxygen atom, a sulfur atom, S(=O) or S(=O)$_2$ (provided that when T$^{3b}$ is CR$^{4b}$R$^{5b}$, and U$^{3b}$ is CR$^{8b}$R$^{7b}$, W$^{3b}$ is not CR$^{8b}$R$^{9b}$)), L$^{1b}$ is a single bond or a C$_{1-3}$ alkylene group, L$^{2b}$ is a single bond, a C$_{1-6}$ alkylene group or a C$_{1-6}$ haloalkylene group (the C$_{1-6}$ alkylene group and the C$_{1-6}$ haloalkylene group are unsubstituted or substituted with one or more hydroxy groups or one or more cyano groups), the ring B$^{b}$ is a C$_{3-11}$ cycloalkane, a C$_{3-11}$ cycloalkene, a 3 to 11-membered non-aromatic heterocycle, a C$_{6-14}$ aromatic carbocycle or a 5 to 10-membered aromatic heterocycle, n$^{b}$ is 0 or 1, R$^{3b}$ is a hydroxy group, an amino group, a carboxy group, a carbamoyl group, a tetrazolyl group, a halogen atom, a cyano group, a nitro group, a C$_{1-3}$ alkyl group, a C$_{1-3}$ haloalkyl group, a C$_{3-6}$ cycloalkyl group, a C$_{1-3}$ alkoxy group, a C$_{1-3}$ haloalkoxy group or a C$_{1-3}$ alkylsulfonyl group, L$^{3b}$ is a single bond, and R$^{2b}$ is a hydrogen atom, a halogen atom, a C$_{3-6}$ cycloalkyl group, a 3 to 11-membered non-aromatic heterocyclyl group, a phenyl group or a 5 to 6-membered aromatic heterocyclyl group (the C$_{3-6}$ cycloalkyl group, the 3 to 11-membered non-aromatic heterocyclyl group, the phenyl group and the 5 to 6-membered aromatic heterocyclyl group are unsubstituted or substituted with one or more identical or different substituents independently selected from the substituent set V$^{4b}$), or L$^{3b}$ is represented by any of the following formulae (VI$^{b}$-1) to (VI$^{b}$-11):

(VI$^{b}$)

(VI$^{b}$-1)

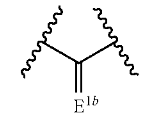

(VI$^{b}$-2)

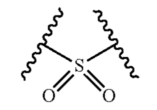

(VI$^{b}$-3)

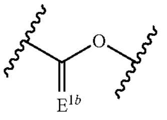

(VI$^{b}$-4)

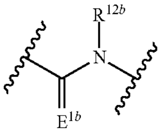

(VI$^{b}$-5)

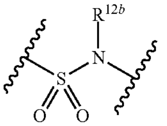

-continued (VI$^{b}$-6)

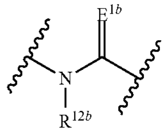

(VI$^{b}$-7)

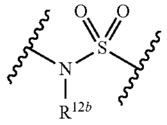

(VI$^{b}$-8)

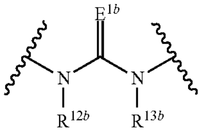

(VI$^{b}$-9)

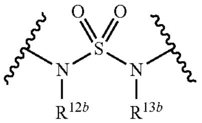

(VI$^{b}$-10)

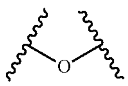

(VI$^{b}$-11)

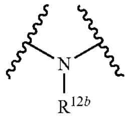

(wherein E$^{1b}$ is an oxygen atom, and each of R$^{12b}$ and R$^{13b}$ is independently a hydrogen atom or a C$_{1-6}$ alkyl group), and R$^{2b}$ is a hydrogen atom, a C$_{1-6}$ alkyl group (the C$_{1-6}$ alkyl group is unsubstituted or substituted with one or more identical or different substituents independently selected from the substituent set V$^{5b}$), a C$_{3-6}$ cycloalkyl group, a 4 to 7-membered non-aromatic heterocyclyl group, a phenyl group or a 5 to 6-membered aromatic heterocyclyl group (the C$_{3-6}$ cycloalkyl group, the 4 to 7-membered non-aromatic heterocyclyl group, the phenyl group and the 5 to 6-membered aromatic heterocyclyl group are unsubstituted or substituted with one or more identical or different substituents independently selected from the substituent set V$^{4b}$), each of R$^{4b}$, R$^{5b}$, R$^{6b}$, R$^{7b}$, R$^{8b}$ and R$^{9b}$ is independently a hydrogen atom, an amino group, a carbamoyl group, a halogen atom, a cyano group, a C$_{1-6}$ alkyl group, a C$_{1-6}$ haloalkyl group, a C$_{1-6}$ alkoxy group, a C$_{1-6}$ haloalkoxy group, a C$_{1-6}$ alkylsulfonyl group, a C$_{3-6}$ cycloalkyl group, a 4 to 7-membered non-aromatic heterocyclyl group, a phenyl group or a 5 to 6-membered aromatic heterocyclyl group (the phenyl group and the 5 to 6-membered aromatic heterocyclyl group are unsubstituted or substituted with one or more identical or different substituents independently selected from the substituent set V$^{1b}$), each of R$^{10b}$ and R$^{11b}$ is independently a hydrogen atom, a C$_{1-6}$ alkyl group, a C$_{1-6}$ haloalkyl group, a C$_{3-6}$ cycloalkyl group, a C$_{1-6}$ alkoxy group, a C$_{1-6}$ haloalkoxy group, a C$_{1-6}$ alkylsulfonyl group, a 4 to 7-membered non-aromatic heterocyclyl group, a phenyl group or a 5 to 6-membered aromatic heterocyclyl group (the phenyl group and the 5 to 6-membered aromatic heterocyclyl group are unsubstituted or substituted with one or more identical or different substituents independently selected from the substituent set $V^{1b}$), and $R^{17b}$ is a hydrogen atom, a hydroxy group, a cyano group, a nitro group, a $C_{1-6}$ alkyl group or a $C_{1-6}$ alkoxy group, tautomers or pharmaceutically acceptable salts of the compounds or solvates thereof.

$3^b$) The compounds according to $1^b$) or $2^b$), wherein $R^{1b}$ is a hydrogen atom, tautomers or pharmaceutically acceptable salts of the compounds or solvates thereof.

$4^b$) The compounds according to any one of $1^b$) to $3^b$), wherein $X^b$ is a nitrogen atom or a $CR^{15b}$ (wherein $R^{15b}$ is a hydrogen atom, a halogen atom or a cyano group) or a nitrogen atom, tautomers or pharmaceutically acceptable salts of the compounds or solvates thereof.

$5^b$) The compounds according to any one of $1^b$) to $4^b$), wherein $X^b$ is a nitrogen atom or $CR^{15b}$ (wherein $R^{15b}$ is a hydrogen atom), tautomers or pharmaceutically acceptable salts of the compounds or solvates thereof.

$6^b$) The compounds according to any one of $1^b$) to $5^b$), wherein $Y^b$ is $CR^{16b}$ (wherein $R^{16b}$ is a hydrogen atom), tautomers or pharmaceutically acceptable salts of the compounds or solvates thereof.

$7^b$) The compounds according to any one of $1^b$) to $6^b$), wherein the ring $A^b$ is represented by any of the following formulae ($VII^b$-1) to ($VII^b$-7):

($VII^b$)

($VII^b$-1)

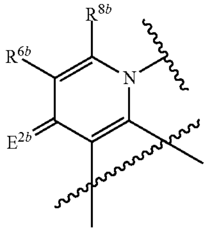

($VII^b$-2)

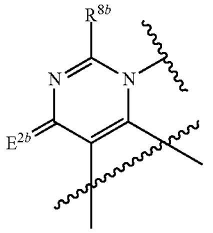

($VII^b$-3)

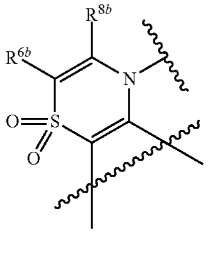

-continued ($VII^b$-4)

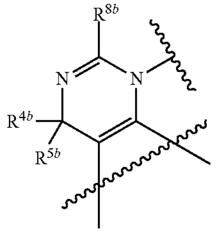

($VII^b$-5)

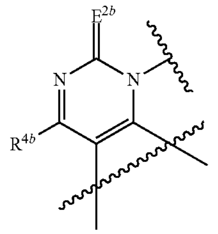

($VII^b$-6)

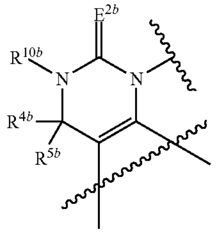

($VII^b$-7)

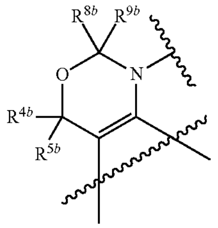

(wherein $E^{2b}$ is an oxygen atom or a sulfur atom, each of each of $R^{4b}$, $R^{5b}$, $R^{6b}$, $R^{8b}$ and $R^{9b}$ is independently a hydrogen atom, an amino group, a carbamoyl group, a halogen atom, a cyano group, a $C_{1-6}$ alkyl group, a $C_{1-6}$ haloalkyl group, a $C_{3-6}$ cycloalkyl group, a $C_{1-6}$ alkoxy group, a $C_{1-6}$ haloalkoxy group, a $C_{1-6}$ alkylsulfonyl group, a 4 to 7-membered non-aromatic heterocyclyl group, a phenyl group or a 5 to 6-membered aromatic heterocyclyl group, and $R^{10b}$ is a hydrogen atom, a $C_{1-6}$ alkyl group, a $C_{1-6}$ haloalkyl group, a $C_{3-6}$ cycloalkyl group, a $C_{1-6}$ alkoxy group, a $C_{1-6}$ haloalkoxy group, a $C_{1-6}$ alkylsulfonyl group, a 4 to 7-membered non-aromatic heterocyclyl group, a phenyl group or a 5 to 6-membered aromatic heterocyclyl group), tautomers or pharmaceutically acceptable salts of the compounds or solvates thereof.

$8^b$) The compounds according to any one of $1^b$) to $6^b$), wherein the ring $A^b$ is represented by the formula ($XXVIII^b$):

(XXVIII$^b$)

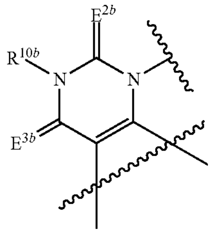

(wherein each of $E^{2b}$ and $E^{3b}$ is independently, an oxygen atom or a sulfur atom, and $R^{10b}$ is a hydrogen atom, a $C_{1-6}$ alkyl group (the $C_{1-6}$ alkyl group is unsubstituted or substituted with one or two identical or different substituents independently selected from the group consisting of cyano groups, hydroxy groups, $C_{1-3}$ alkoxy groups, $C_{1-3}$ alkylthio groups, di-$C_{1-3}$ alkylamino groups, di-$C_{1-3}$ alkylaminocarbonyl groups, $C_{3-6}$ cycloalkyl groups and 4 to 7-membered non-aromatic heterocyclyl groups), a $C_{1-6}$ haloalkyl group, a $C_{3-6}$ cycloalkyl group or a 4 to 7-membered non-aromatic heterocyclyl group), tautomers or pharmaceutically acceptable salts of the compounds or solvates thereof.

9$^b$) The compounds according to any one of 1$^b$) to 7$^b$), wherein the ring $A^b$ is represented by any of the following formulae (XVI$^b$-1) to (XVI$^b$-7):

(XVI$^b$)

(XVI$^b$-1)

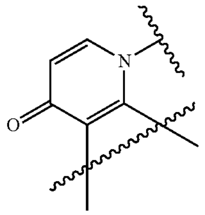

(XVI$^b$-2)

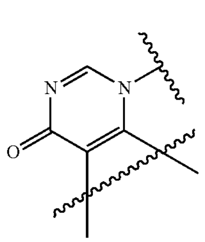

(XVI$^b$-3)

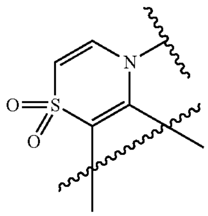

-continued (XVI$^b$-4)

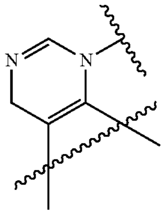

(XVI$^b$-5)

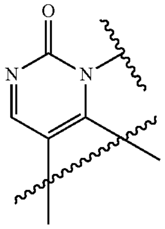

(XVI$^b$-6)

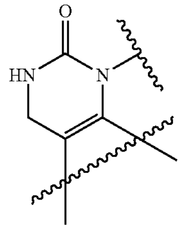

(XVI$^b$-7)

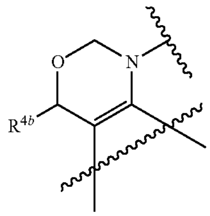

(wherein $R^{4b}$ is a hydrogen atom or a methyl group), tautomers or pharmaceutically acceptable salts of the compounds or solvates thereof.

10$^b$) The compounds according to any one of 1$^b$) to 6$^b$), wherein the ring $A^b$ is represented by any of the following formula (XXIX$^b$-1) or (XXIX$^b$-2)

(XXIX$^b$)

(XXIX$^b$-1)

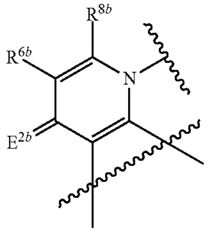

-continued (XXIX$^b$-2)

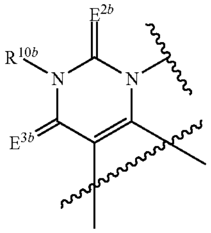

(wherein $E^{2b}$ and $E^{3b}$ are oxygen atoms, $R^{6b}$ is a hydrogen atom, a halogen atom or a $C_{1-3}$ alkyl group, and $R^{8b}$ and $R^{10b}$ are hydrogen atoms), tautomers or pharmaceutically acceptable salts of the compounds or solvates thereof.

$11^b$) The compounds according to any one of $1^b$) to $10^b$), wherein $L^{1b}$ is a single bond, tautomers or pharmaceutically acceptable salts of the compounds or solvates thereof.

$12^b$) The compounds according to any one of $1^b$) to $11^b$), wherein $L^{2b}$ is a single bond or a $C_{1-6}$ alkylene group, a $C_{1-6}$ alkenylene group (the $C_{1-6}$ alkylene group and the $C_{1-6}$ alkenylene group are unsubstituted or substituted with a cyano group) or a $C_{1-6}$ haloalkylene group, tautomers or pharmaceutically acceptable salts of the compounds or solvates thereof.

$13^b$) The compounds according to any one of $1^b$) to $11^b$), wherein $L^{2b}$ is a single bond or a $C_{1-3}$ alkylene group, tautomers or pharmaceutically acceptable salts of the compounds or solvates thereof.

$14^b$) The compounds according to any one of $1^b$) to $11^b$), wherein $L^{2b}$ is a single bond or a methylene group, tautomers or pharmaceutically acceptable salts of the compounds or solvates thereof.

$15^b$) The compounds according to any one of $1^b$) to $14^b$), wherein the ring $B^b$ is a $C_{4-7}$ cycloalkane or a 4 to 7-membered non-aromatic heterocycle, tautomers or pharmaceutically acceptable salts of the compounds or solvates thereof.

$16^b$) The compounds according to any one of $1^b$) to $14^b$), wherein the ring $B^b$ is cyclohexane or piperidine, tautomers or pharmaceutically acceptable salts of the compounds or solvates thereof.

$17^b$) The compounds according to any one of $1^b$) to $16^b$), wherein $n^b$ is, 0 or 1, and $R^{3b}$ is a methyl group, tautomers or pharmaceutically acceptable salts of the compounds or solvates thereof.

$18^b$) The compounds according to any one of $1^b$) to $17^b$), wherein $L^{3b}$ is a single bond, and $R^{2b}$ is a hydrogen atom, a $C_{3-6}$ cycloalkyl group, a 4 to 7-membered non-aromatic heterocyclyl group, a phenyl group or a 5 to 10-membered aromatic heterocyclyl group (the $C_{3-11}$ cycloalkyl group, the 4 to 7-membered non-aromatic heterocyclyl group, the phenyl group and the 5 to 10-membered aromatic heterocyclyl group are unsubstituted or substituted with one or more identical or different substituents independently selected from the substituent set $V^{1b}$), tautomers or pharmaceutically acceptable salts of the compounds or solvates thereof.

$19^b$) The compounds according to any one of $1^b$) to $17^b$), wherein $L^{3b}$ is a single bond, and $R^{2b}$ is a hydrogen atom, a 4 to 7-membered non-aromatic heterocyclyl group, a phenyl group or a 5 to 6-membered aromatic heterocyclyl group (the 4 to 7-membered non-aromatic heterocyclyl group, the phenyl group and the 5 to 6-membered aromatic heterocyclyl group are unsubstituted or substituted with one or two identical or different substituents independently selected from the group consisting of hydroxy groups, halogen atoms, cyano groups, nitro groups, $C_{1-6}$ alkyl groups, $C_{1-6}$ alkoxy groups and $C_{1-6}$ alkoxycarbonyl groups (the $C_{1-6}$ alkyl groups, the $C_{1-6}$ alkoxy groups and the $C_{1-6}$ alkoxycarbonyl groups are unsubstituted or substituted with one or more identical or different substituents independently selected from the group consisting of halogen atoms and cyano groups)), tautomers or pharmaceutically acceptable salts of the compounds or solvates thereof.

$20^b$) The compounds according to any one of $1^b$) to $17^b$), wherein $L^{3b}$ is a single bond, and $R^{2b}$ is a hydrogen atom or a phenyl group (the phenyl group is unsubstituted or substituted with one or two halogen atoms), tautomers or pharmaceutically acceptable salts of the compounds or solvates thereof.

$21^b$) The compounds according to any one of $1^b$) to $17^b$), wherein $L^{3b}$ is a single bond, and $R^{2b}$ is a $C_{3-6}$ cycloalkyl group, tautomers or pharmaceutically acceptable salts of the compounds or solvates thereof.

$22^b$) The compounds according to any one of $1^b$) to $17^b$), wherein $L^{3b}$ is a single bond, and $R^{2b}$ is a 4 to 7-membered non-aromatic heterocyclyl group (the 4 to 7-membered non-aromatic heterocyclyl group is unsubstituted or substituted with one or more identical or different substituents independently selected from the group consisting of hydroxy groups, halogen atoms, cyano groups, $C_{1-6}$ alkyl groups (the $C_{1-6}$ alkyl groups are unsubstituted or substituted with a cyano group), $C_{1-6}$ haloalkyl groups, $C_{1-6}$ alkoxy groups, $C_{1-6}$ haloalkoxy groups and $C_{1-6}$ alkoxycarbonyl groups), tautomers or pharmaceutically acceptable salts of the compounds or solvates thereof.

$23^b$) The compounds according to any one of $1^b$) to $17^b$), wherein $L^{3b}$ is represented by any of the following formulae (XIX$^b$-1) to (XIX$^b$-7):

(XIX$^b$)

(XIX$^b$-1)

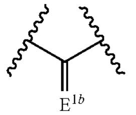

(XIX$^b$-2)

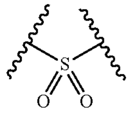

(XIX$^b$-3)

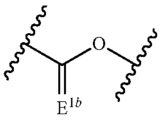

(XIX-$^b$4)

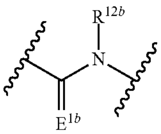

(XIX$^b$-5)

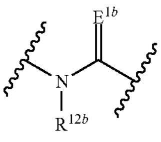

-continued (XIX$^b$-6)

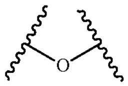

(XIX$^b$-7)

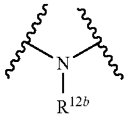

(wherein $E^{1b}$ is an oxygen atom, and $R^{12b}$ is a hydrogen atom or a $C_{1-3}$ alkyl group), and $R^{2b}$ is a hydrogen atom, a $C_{1-6}$ alkyl group, a $C_{1-6}$ haloalkyl group (the $C_{1-6}$ alkyl group and the $C_{1-6}$ haloalkyl group are unsubstituted or substituted with a substituent selected from the group consisting of a cyano group, a hydroxy group, a $C_{3-6}$ cycloalkyl group, a phenyl group and a 5 to 6-membered aromatic heterocyclyl group (the $C_{3-6}$ cycloalkyl group, the phenyl group and the 5 to 6-membered aromatic heterocyclyl group are unsubstituted or substituted with one or two identical or different substituents independently selected from the group consisting of halogen atoms, cyano groups, $C_{1-3}$ alkoxy groups, $C_{1-3}$ haloalkoxy groups, $C_{1-3}$ alkylsulfonyl groups and $C_{1-3}$ haloalkylsulfonyl groups)), a $C_{3-6}$ cycloalkyl group, a phenyl group or a 5 to 6-membered aromatic heterocyclyl group (the $C_{3-6}$ cycloalkyl group, the phenyl group and the 5 to 6-membered aromatic heterocyclyl group are unsubstituted or substituted with one or two identical or different substituents independently selected from the group consisting of halogen atoms, cyano groups, $C_{1-6}$ alkyl groups, $C_{1-3}$ haloalkyl groups, $C_{1-3}$ alkoxy groups, $C_{1-3}$ haloalkoxy groups, $C_{1-3}$ alkylsulfonyl groups and $C_{1-3}$ haloalkylsulfonyl groups), tautomers or pharmaceutically acceptable salts of the compounds or solvates thereof.

24$^b$) The compounds according to any one of 1$^b$) to 17$^b$), wherein $L^{3b}$ is represented by the following formula (VIII$^b$-1) or (VIII$^b$-2):

(VIII$^b$)

(VIII$^b$-1)

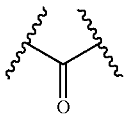

(VIII$^b$-2)

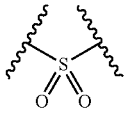

and $R^{2b}$ is a $C_{1-6}$ alkyl group (the $C_{1-6}$ alkyl group is unsubstituted or substituted with a substituent selected from the group consisting of a cyano group, a $C_{3-6}$ cycloalkyl group, a phenyl group and a 5 to 6-membered aromatic heterocyclyl group (the phenyl group, the 5 to 6-membered aromatic heterocyclyl group are unsubstituted or substituted with one or two identical or different substituents independently selected from the group consisting of halogen atoms and cyano groups)) or a $C_{1-3}$ haloalkyl group, tautomers or pharmaceutically acceptable salts of the compounds or solvates thereof.

25$^b$) The compounds according to any one of 1$^b$) to 17$^b$), wherein $L^{3b}$ is represented by the following formula (VIII$^b$-1) or (VIII$^b$-2):

(VIII$^b$)

(VIII$^b$-1)

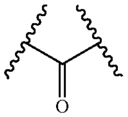

(VIII$^b$-2)

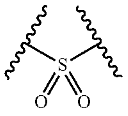

and $R^{2b}$ is a methyl group (the methyl group is unsubstituted or substituted with a cyano groups, a cyclopropyl groups or a trifluoromethyl groups) or an isobutyl group, tautomers or pharmaceutically acceptable salts of the compounds or solvates thereof.

26$^b$) The compounds according to any one of 1$^b$) to 17$^b$), wherein $L^{3b}$ is represented by the formula (XXVI$^b$):

(XXVI$^b$)

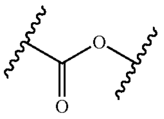

and $R^{2b}$ is a $C_{1-6}$ alkyl group (the $C_{1-6}$ alkyl group is unsubstituted or substituted with a cyano group or a phenyl group), tautomers or pharmaceutically acceptable salts of the compounds or solvates thereof.

27$^b$) The compounds according to any one of 1$^b$) to 17$^b$), wherein $L^{3b}$ is represented by the formula (XXV$^b$):

(XXV$^b$)

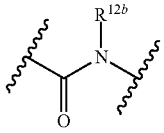

(wherein $R^{12b}$ is a hydrogen atom), and $R^{2b}$ is a phenyl group or a 5 to 6-membered aromatic heterocyclyl group (the phenyl group and the 5 to 6-membered aromatic heterocyclyl group are unsubstituted or substituted with a $C_{1-3}$ alkyl group or a $C_{1-3}$ haloalkyl group), tautomers or pharmaceutically acceptable salts of the compounds or solvates thereof.

28$^b$) The compounds according to any one of 1$^b$) to 17$^b$), wherein $L^{3b}$ is represented by the formula (XXVII$^b$):

(XXVII$^b$)

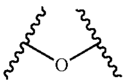

and $R^{2b}$ is a hydrogen atom or a $C_{1-3}$ alkyl group, tautomers or pharmaceutically acceptable salts of the compounds or solvates thereof.

$29^b$) The compounds according to any one of $1^b$) to $17^b$), wherein $L^{3b}$ is represented by the formula ($XXXII^b$):

($XXXII^b$)

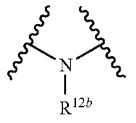

(wherein $R^{12b}$ is a hydrogen atom, a $C_{1-3}$ alkyl group (the $C_{1-3}$ alkyl group is unsubstituted or substituted with a substituent selected from the group consisting of a cyano group, a hydroxy group, a $C_{1-3}$ alkoxy group, a $C_{3-6}$ cycloalkyl group and a phenyl group) or a $C_{1-3}$ haloalkyl group), and $R^{2b}$ is a hydrogen atom, a $C_{1-3}$ alkyl group, a $C_{1-3}$ haloalkyl group (the $C_{1-3}$ alkyl group and the $C_{1-3}$ haloalkyl group are unsubstituted or substituted with one or two identical or different substituents independently selected from the group consisting of hydroxy groups, cyano groups, $C_{1-3}$ alkoxy groups, $C_{3-6}$ cycloalkyl groups, 4 to 7-membered non-aromatic heterocyclyl groups, phenyl groups and 5 to 6-membered aromatic heterocyclyl groups (the $C_{3-6}$ cycloalkyl groups, the 4 to 7-membered non-aromatic heterocyclyl groups, the phenyl groups and the 5 to 6-membered aromatic heterocyclyl groups are unsubstituted or substituted with a substituent selected from the group consisting of a hydroxy group, a halogen atom and a cyano group)), a $C_{3-6}$ cycloalkyl group or a 4 to 7-membered non-aromatic heterocyclyl group (the $C_{3-6}$ cycloalkyl group and the 4 to 7-membered non-aromatic heterocyclyl group are unsubstituted or substituted with one or two identical or different substituents independently selected from the group consisting of halogen atoms, cyano groups, $C_{1-3}$ alkyl groups, $C_{1-3}$ haloalkyl groups and $C_{1-6}$ alkoxycarbonyl groups), tautomers or pharmaceutically acceptable salts of the compounds or solvates thereof.

$30^b$) The compounds according to any one of $1^b$) to $17^b$), wherein $L^{3b}$ is represented by the formula ($XXXV^b$):

($XXXV^b$)

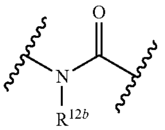

(wherein $R^{12b}$ is a hydrogen atom, a $C_{1-3}$ alkyl group or a $C_{1-3}$ haloalkyl group), and $R^{2b}$ is a $C_{1-6}$ alkyl group (the $C_{1-6}$ alkyl group is unsubstituted or substituted with a cyano group) or a $C_{1-6}$ haloalkyl group, tautomers or pharmaceutically acceptable salts of the compounds or solvates thereof.

$31^b$) The compounds according to $1^b$), wherein $X^b$ is a nitrogen atom or $CR^{15b}$ (wherein $R^{15b}$ is a hydrogen atom or a halogen atom), $Y^b$ is $CR^{16b}$ (wherein $R^{16b}$ is a hydrogen atom), $R^{1b}$ is a hydrogen atom, the ring $A^b$ is represented by any of the following formulae ($XVIII^b$-1) to ($XVIII^b$-8):

($XVIII^b$)

($XVIII^b$-1)

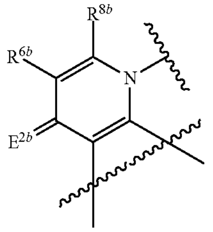

($XVIII^b$-2)

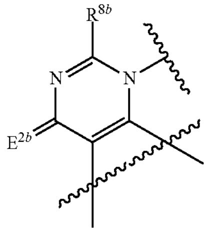

($XVIII^b$-3)

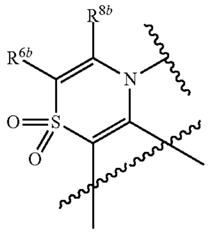

($XVIII^b$-4)

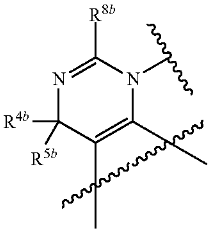

($XVIII^b$-5)

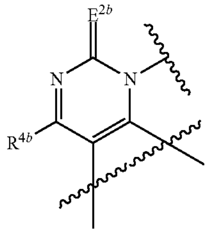

($XVIII^b$-6)

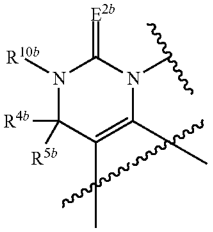

-continued (XVIII$^b$-7)

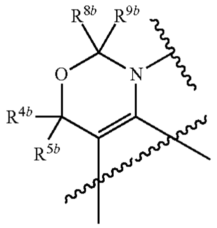

(XVIII$^b$-8)

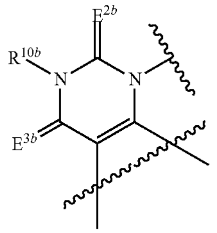

(wherein each of $E^{2b}$ and $E^{3b}$ is independently an oxygen atom or a sulfur atom, and each of $R^{4b}$, $R^{5b}$, $R^{6b}$, $R^{8b}$ and $R^{9b}$ is independently a hydrogen atom or a $C_{1-3}$ alkyl group, and $R^{10b}$ is a hydrogen atom, a $C_{1-6}$ alkyl group (the $C_{1-6}$ alkyl group is unsubstituted or substituted with one or two identical or different substituents independently selected from the group consisting of cyano groups, hydroxy groups, $C_{1-3}$ alkoxy groups, di-$C_{1-3}$ alkylamino groups, $C_{3-6}$ cycloalkyl groups, 4 to 7-membered non-aromatic heterocyclyl groups, phenyl groups and 5 to 6-membered aromatic heterocyclyl groups (the phenyl group and the 5 to 6-membered aromatic heterocyclyl groups are unsubstituted or substituted with one or two identical or different substituents independently selected from the group consisting of halogen atoms, $C_{1-3}$ alkyl groups and $C_{1-3}$ haloalkyl groups)), a $C_{1-6}$ haloalkyl group, a $C_{3-6}$ cycloalkyl group, a 4 to 7-membered non-aromatic heterocyclyl group, a phenyl group or a 5 to 6-membered aromatic heterocyclyl group), the ring $B^b$ is a $C_{3-11}$ cycloalkane, a 3 to 11-membered non-aromatic heterocycle, a $C_{6-14}$ aromatic carbocycle or a 5 to 10-membered aromatic heterocycle, $L^{1b}$ is a single bond or a $C_{1-3}$ alkylene group, $L^{2b}$ is a single bond, a $C_{1-6}$ alkylene group or a $C_{2-6}$ alkenylene group (the $C_{1-6}$ alkylene group and the $C_{2-6}$ alkenylene group are unsubstituted or substituted with one or more identical or different substituents independently selected from the group consisting of halogen atoms, hydroxy groups, amino groups, cyano groups and nitro groups), $n^b$ is 0 or 1, $R^{3b}$ is a hydroxy group, an amino group, a carboxy group, a carbamoyl group, a tetrazolyl group, a halogen atom, a cyano group, a nitro group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkylsulfonyl group, $L^{3b}$ is a simile bond or is represented by any of the following formulae (VI$^b$-1) to (VI$^b$-11)

(VI$^b$)

(VI$^b$-1)

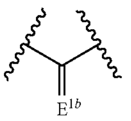

(VI$^b$-2)

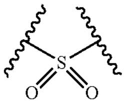

(VI$^b$-3)

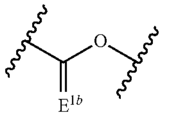

(VI$^b$-4)

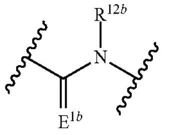

(VI$^b$-5)

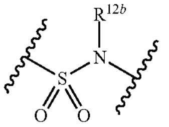

(VI$^b$-6)

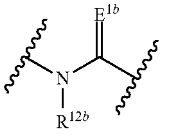

(VI$^b$-7)

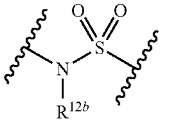

(VI$^b$-8)

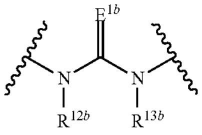

(VI$^b$-9)

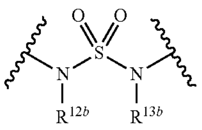

(VI$^b$-10)

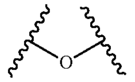

(VI$^b$-11)

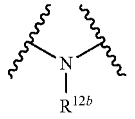

(wherein $E^{1b}$ is an oxygen atom or a sulfur atom, and each of $R^{12b}$ and $R^{13b}$ is independently a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or two identical or different substituents independently selected from the group consisting of cyano groups, hydroxy groups, $C_{1-6}$ alkoxy groups, $C_{3-6}$ cycloalkyl groups, 4 to 7-membered non-aromatic heterocyclyl groups, phenyl groups and 5 to 6-membered aromatic heterocyclyl groups)), and when $L^{3b}$ is a single bond, $R^{2b}$ is a hydrogen atom, a halogen atom, a $C_{3-11}$ cycloalkyl group, a 3 to 11-membered non-aromatic heterocyclyl group, a phenyl group, a naphthyl group, a 5 to 10-membered aromatic heterocyclyl group, a 8 to 11-membered partially saturated aromatic cyclic group or a 8 to 11-membered aromatic ring-condensed alicyclic hydrocarbon group (the $C_{3-11}$ cycloalkyl group, the 3 to 11-membered non-aromatic heterocyclyl group, the phenyl group, the naphthyl group, the 5 to 10-membered aromatic heterocyclyl group, the 8 to 11-membered partially saturated aromatic cyclic group and the 8 to 11-membered aromatic ring-condensed alicyclic hydrocarbon group are unsubstituted or substituted with one or more identical or different substituents independently selected from the substituent set $V^{4b}$ and the substituent set $V^{9b}$), and when $L^{3b}$ is not a single bond, $R^{2b}$ is a hydrogen atom, a $C_{1-6}$ alkyl group, a $C_{2-6}$ alkenyl group (the $C_{1-6}$ alkyl group and the $C_{2-6}$ alkenyl group are unsubstituted or substituted with one or more identical or different substituents independently selected from the substituent set $V^{6b}$ and the substituent set $V^{9b}$), a $C_{3-11}$ cycloalkyl group, a 3 to 11-membered non-aromatic heterocyclyl group, a $C_{6-14}$ aryl group, a 5 to 10-membered aromatic heterocyclyl group, a 8 to 11-membered partially saturated aromatic cyclic group or a 8 to 11-membered aromatic ring-condensed alicyclic hydrocarbon group (the $C_{3-11}$ cycloalkyl group, the 3 to 11-membered non-aromatic heterocyclyl group, the $C_{6-14}$ aryl group, the 5 to 10-membered aromatic heterocyclyl group, the 8 to 11-membered partially saturated aromatic cyclic group and the 8 to 11-membered aromatic ring-condensed alicyclic hydrocarbon group are unsubstituted or substituted with one or more identical or different substituents independently selected from the substituent set $V^{4b}$ and the substituent set $V^{9b}$), tautomers or pharmaceutically acceptable salts of the compounds or solvates thereof.

32$^{b}$) The compounds according to 1$^{b}$) or 31$^{b}$), wherein the ring $A^b$ is represented by any of the following formulae (XXI$^{b}$-1) to (XXI$^{b}$-4):

(XXI$^{b}$)

(XXI$^{b}$-1)

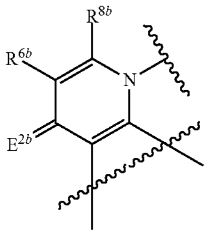

(XXI$^{b}$-2)

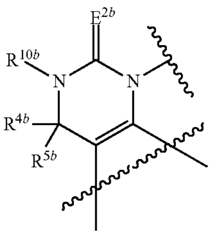

-continued (XXI$^{b}$-3)

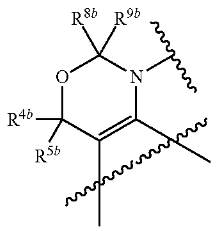

(XXI$^{b}$-4)

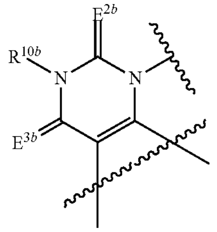

(wherein $E^{2b}$ and $E^{3b}$ are oxygen atoms, $R^{4b}$, $R^{5b}$, $R^{8b}$ and $R^{9b}$ are hydrogen atoms, and $R^{6b}$ is a hydrogen atom, a halogen atom or a $C_{1-3}$ alkyl group, and $R^{10b}$ is a hydrogen atom, a $C_{1-6}$ alkyl group (the $C_{1-6}$ alkyl group is unsubstituted or substituted with one or two identical or different substituents independently selected from the group consisting of cyano groups, hydroxy groups, $C_{1-3}$ alkoxy groups, $C_{1-3}$ alkylthio groups, di-$C_{1-3}$ alkylamino groups, di-$C_{1-3}$ alkylaminocarbonyl groups, $C_{3-6}$ cycloalkyl groups and 4 to 7-membered non-aromatic heterocyclyl groups), a $C_{1-6}$ haloalkyl group, a $C_{3-6}$ cycloalkyl group or a 4 to 7-membered non-aromatic heterocyclyl group), tautomers or pharmaceutically acceptable salts of the compounds or solvates thereof.

33$^{b}$) The compounds according to 1$^{b}$), 31$^{b}$) or 32$^{b}$), wherein $L^{1b}$ is a single bond, $L^{2b}$ is a single bond, a $C_{1-6}$ alkylene group (the $C_{1-6}$ alkylene group is unsubstituted or substituted with a hydroxy group or a cyano group) or a $C_{1-6}$ haloalkylene group, the ring $B^b$ is a $C_{4-7}$ cycloalkane or a 4 to 7-membered non-aromatic heterocycle, $n^b$ is 0 or 1, and $R^{3b}$ is a $C_{1-3}$ alkyl group, tautomers or pharmaceutically acceptable salts of the compounds or solvates thereof.

34$^{b}$) The compounds according to any one of 1$^{b}$) and 31$^{b}$) to 33$^{b}$), wherein $L^{3b}$ is a single bond, and $R^{2b}$ is a hydrogen atom, a 4 to 7-membered non-aromatic heterocyclyl group, a phenyl group, a 5 to 10-membered aromatic heterocyclyl group or a 8 to 11-membered partially saturated aromatic cyclic group (the 4 to 7-membered non-aromatic heterocyclyl group, the phenyl group, the 5 to 10-membered aromatic heterocyclyl group and the 8 to 11-membered partially saturated aromatic cyclic group are unsubstituted or substituted with one or more identical or different substituents independently selected from the group consisting of hydroxy groups, amino groups, carbamoyl groups, sulfamoyl groups, halogen atoms, cyano groups, nitro groups, $C_{1-6}$ alkyl groups (the $C_{1-6}$ alkyl groups are unsubstituted or substituted with a cyano group), $C_{1-6}$ haloalkyl groups, $C_{3-11}$ cycloalkyl group, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylsulfonyl groups, $C_{1-6}$ haloalkylsulfonyl groups, $C_{1-6}$ alkoxycarbonyl groups, 4 to 7-membered non-aromatic heterocyclyl groups, mono-$C_{1-6}$ alkylamino groups, di-$C_{1-6}$ alkylamino groups, phenyl groups and 5 to 6-membered aromatic heterocyclyl groups), tautomers or pharmaceutically acceptable salts of the compounds or solvates thereof.

$35^b$) The compounds according to any one of $1^b$) and $31^b$) to $33^b$), wherein $L^{3b}$ is a single bond, and $R^{2b}$ is a 8 to 11-membered partially saturated aromatic cyclic group (the 8 to 11-membered partially saturated aromatic cyclic group is unsubstituted or substituted with one or more identical or different halogen atoms independently selected from the group consisting of fluorine atoms, chlorine atoms, bromine atoms and iodine atoms), tautomers or pharmaceutically acceptable salts of the compounds or solvates thereof.

$36^b$) The compounds according to $34^b$) or $35^b$), wherein $L^{2b}$ is a $C_{1-3}$ alkylene group, and the ring $B^b$ is cyclohexane or piperidine, tautomers or pharmaceutically acceptable salts of the compounds or solvates thereof.

$37^b$) The compounds according to any one of $1^b$) and $31^b$) to $33^b$), wherein $L^{3b}$ is represented by any of the following formulae ($XIX^b$-1) to ($XIX^b$-7):

($XIX^b$)

($XIX^b$-1)

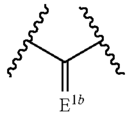

($XIX^b$-2)

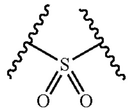

($XIX^b$-3)

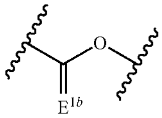

(XIX-$^b$4)

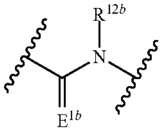

($XIX^b$-5)

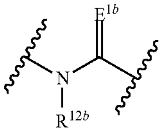

($XIX^b$-6)

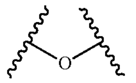

($XIX^b$-7)

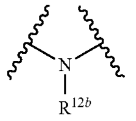

(wherein $E^{1b}$ is an oxygen atom, and $R^{12b}$ is a hydrogen atom, a $C_{1-6}$ alkyl group (the $C_{1-6}$ alkyl group is unsubstituted or substituted with one or two identical or different substituents independently selected from the group consisting of cyano groups, hydroxy groups, $C_{1-3}$ alkoxy groups, $C_{3-6}$ cycloalkyl groups and phenyl groups) or a $C_{1-6}$ haloalkyl groups), and $R^{2b}$ is a hydrogen atom, a $C_{1-6}$ alkyl group, a $C_{1-6}$ haloalkyl group (the $C_{1-6}$ alkyl group and the $C_{1-6}$ haloalkyl group are unsubstituted or substituted with one or two identical or different substituents independently selected from the group consisting of cyano groups, hydroxy groups, $C_{3-6}$ cycloalkyl groups, 4 to 7-membered non-aromatic heterocyclyl groups, phenyl groups, 5 to 6-membered aromatic heterocyclyl groups and 8 to 11-membered partially saturated aromatic cyclic groups (the $C_{3-6}$ cycloalkyl groups, the 4 to 7-membered non-aromatic heterocyclyl groups, the phenyl groups, the 5 to 6-membered aromatic heterocyclyl groups and the 8 to 11-membered partially saturated aromatic cyclic group are unsubstituted or substituted with one or two identical or different substituents independently selected from the group consisting of hydroxy groups, amino groups, halogen atoms, cyano groups, $C_{1-6}$ alkyl groups, $C_{1-3}$ haloalkyl groups, $C_{1-3}$ alkoxy groups, $C_{1-3}$ haloalkoxy groups, $C_{1-3}$ alkylsulfonyl groups, $C_{1-3}$ haloalkylsulfonyl groups, 4 to 7-membered non-aromatic heterocyclyl group, phenyl groups, 5 to 6-membered aromatic heterocyclyl groups (the phenyl group and the 5 to 6-membered aromatic heterocyclyl group are unsubstituted or substituted with one or two identical or different substituents independently selected from the substituent set $V^{1b}$), mono-$C_{1-6}$ alkylaminosulfonyl groups, di-$C_{1-6}$ alkylaminosulfonyl groups and $C_{1-6}$ alkylsulfonylamino groups)), a $C_{3-6}$ cycloalkyl group, a 4 to 7-membered non-aromatic heterocyclyl group, a phenyl group, a 5 to 6-membered aromatic heterocyclyl group or a 8 to 11-membered partially saturated aromatic cyclic group (the $C_{3-6}$ cycloalkyl group, the 4 to 7-membered non-aromatic heterocyclyl group, the phenyl group, the 5 to 6-membered aromatic heterocyclyl group and the 8 to 11-membered partially saturated aromatic cyclic group are unsubstituted or substituted with one or two identical or different substituents independently selected from the group consisting of hydroxy groups, amino groups, halogen atoms, cyano groups, $C_{1-6}$ alkyl groups, $C_{1-3}$ haloalkyl groups, $C_{1-3}$ alkoxy groups, $C_{1-3}$ haloalkoxy groups, $C_{1-3}$ alkylsulfonyl groups, $C_{1-3}$ haloalkylsulfonyl groups, 4 to 7-membered non-aromatic heterocyclyl groups, phenyl groups, 5 to 6-membered aromatic heterocyclyl groups (the phenyl groups and the 5 to 6-membered aromatic heterocyclyl groups are unsubstituted or substituted with one or more identical or different substituents independently selected from the substituent set $V^{1b}$), mono-$C_{1-6}$ alkylaminosulfonyl groups, di-$C_{1-6}$ alkylaminosulfonyl groups and $C_{1-6}$ alkylsulfonylamino groups), tautomers or pharmaceutically acceptable salts of the compounds or solvates thereof.

$38^b$) The compounds according to any one of $1^b$), $31^b$) to $33^b$) and $37^b$), wherein $L^{3b}$ is represented by any of the following formulae ($XXX^b$-1) to ($XXX^b$-3):

($XXX^b$)

($XXX^b$-1)

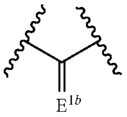

($XXX^b$-2)

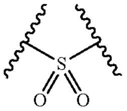

-continued (XXX$^{b}$-3)

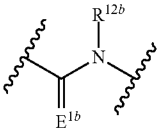

(wherein $E^{1b}$ is an oxygen atom, and $R^{12b}$ is a hydrogen atom), and $R^{2b}$ is a $C_{1-6}$ alkyl group (the $C_{1-6}$ alkyl group is unsubstituted or substituted with a substituent selected from the group consisting of a cyano group, a $C_{3-6}$ cycloalkyl group, a phenyl group and a 5 to 6-membered aromatic heterocyclyl group (the phenyl group and the 5 to 6-membered aromatic heterocyclyl group are unsubstituted or substituted with one or two identical or different substituents independently selected from the group consisting of halogen atoms, cyano groups, $C_{1-6}$ alkyl groups and $C_{1-3}$ haloalkyl groups)), a $C_{1-3}$ haloalkyl group, a $C_{3-6}$ cycloalkyl group, a phenyl group or a 5 to 6-membered aromatic heterocyclyl group (the phenyl group and the 5 to 6-membered aromatic heterocyclyl group are unsubstituted or substituted with one or two identical or different substituents independently selected from the group consisting of halogen atoms, cyano groups, $C_{1-3}$ alkyl groups and $C_{1-3}$ haloalkyl groups), tautomers or pharmaceutically acceptable salts of the compounds or solvates thereof.

39$^{b}$) The compounds according to any one of 1$^{b}$) and 31$^{b}$) to 33$^{b}$), wherein $L^{3b}$ is represented by the formula (XXXII$^{b}$):

(XXXII$^{b}$)

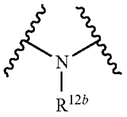

(wherein $R^{12b}$ is a hydrogen atom, a $C_{1-3}$ alkyl group (the $C_{1-3}$ alkyl group is unsubstituted or substituted with a substituent selected from the group consisting of a cyano group, a hydroxy group, a $C_{1-3}$ alkoxy group, a $C_{3-6}$ cycloalkyl group and a phenyl group) or a $C_{1-3}$ haloalkyl group), and $R^{2b}$ is a hydrogen atom, a $C_{1-3}$ alkyl group, a $C_{1-3}$ haloalkyl group (the $C_{1-3}$ alkyl group and the $C_{1-3}$ haloalkyl group are unsubstituted or substituted with one or two identical or different substituents independently selected from the group consisting of hydroxy groups, cyano groups, $C_{1-3}$ alkoxy groups, $C_{3-6}$ cycloalkyl groups, 4 to 7-membered non-aromatic heterocyclyl groups, phenyl groups and 5 to 6-membered aromatic heterocyclyl groups (the $C_{3-6}$ cycloalkyl groups, the 4 to 7-membered non-aromatic heterocyclyl groups, the phenyl groups and the 5 to 6-membered aromatic heterocyclyl groups are unsubstituted or substituted with a substituent selected from the group consisting of a hydroxy group, a halogen atom, a cyano group and a $C_{1-3}$ haloalkyl group)), a $C_{3-6}$ cycloalkyl group or a 4 to 7-membered non-aromatic heterocyclyl group (the $C_{3-6}$ cycloalkyl group and the 4 to 7-membered non-aromatic heterocyclyl group are unsubstituted or substituted with one or two identical or different substituents independently selected from the group consisting of halogen atoms, cyano groups, $C_{1-3}$ alkyl groups, $C_{1-3}$ haloalkyl groups and $C_{1-6}$ alkoxycarbonyl groups), tautomers or pharmaceutically acceptable salts of the compounds or solvates thereof.

40$^{b}$) The compounds according to any one of 1$^{b}$) and 31$^{b}$) to 33$^{b}$), wherein $L^{3b}$ is represented by the following formula (XXXVI$^{b}$-1) or (XXXVI$^{b}$-2):

(XXXVI$^{b}$)

(XXXVI$^{b}$-1)

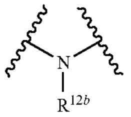

(XXXVI$^{b}$-2)

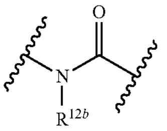

(wherein $R^{12b}$ is a hydrogen atom, a $C_{1-3}$ alkyl group (the $C_{1-3}$ alkyl group is unsubstituted or substituted with a substituent selected from the group consisting of a cyano group, a hydroxy group, a $C_{1-3}$ alkoxy group, a $C_{3-6}$ cycloalkyl group and a phenyl group) or a $C_{1-3}$ haloalkyl group), and $R^{2b}$ is a hydrogen atom, a $C_{1-3}$ alkyl group, a $C_{1-3}$ haloalkyl group (the $C_{1-3}$ alkyl group and the $C_{1-3}$ haloalkyl group are unsubstituted or substituted with one or two identical or different substituents independently selected from the group consisting of hydroxy groups, cyano groups, $C_{1-3}$ alkoxy groups, $C_{3-6}$ cycloalkyl groups, 4 to 7-membered non-aromatic heterocyclyl groups, phenyl groups and 5 to 6-membered aromatic heterocyclyl groups), a $C_{3-6}$ cycloalkyl group or a 4 to 7-membered non-aromatic heterocyclyl group, tautomers or pharmaceutically acceptable salts of the compounds or solvates thereof.

41$^{b}$) The compounds according to 37$^{b}$) or 40$^{b}$), wherein $L^{2b}$ is a single bond or a $C_{1-3}$ alkylene group, and the ring $B^{b}$ is a cyclohexane or piperidine, tautomers or pharmaceutically acceptable salts of the compounds or solvates thereof.

42$^{b}$) Compounds represented by the formula (XVII$^{b}$):

(XVII$^{b}$)

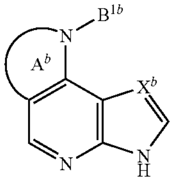

wherein $X^{b}$ is $CR^{15b}$ (wherein $R^{15b}$ is a hydrogen atom, a halogen atom or a cyano group), and the rings $A^{b}$ and $B^{1b}$ are any of the following combinations shown in Table$^{b}$ 1, tautomers or pharmaceutically acceptable salts of the compounds or solvates thereof.

The symbols in Table$^b$ 1 denote the following substituents.

A1 = 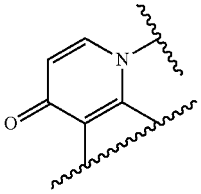
A2 = 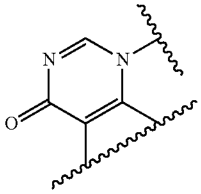
A3 = 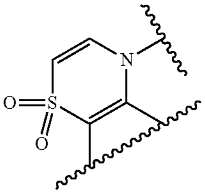
A4 = 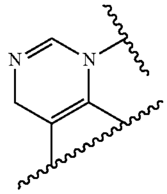
A5 = 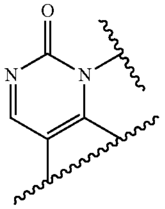
A6 = 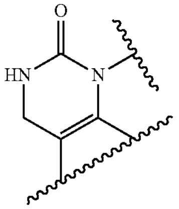
A7 = 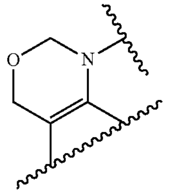
A8 = 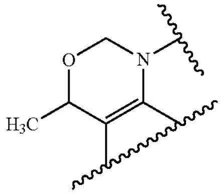
$B^1 1$ = 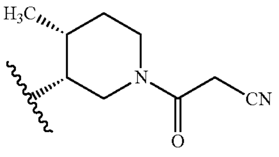
$B^1 2$ = 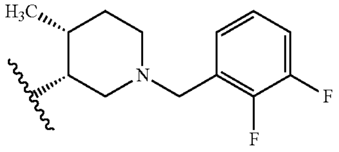
$B^1 3$ = 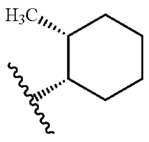
$B^1 4$ = 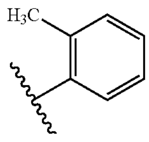
$B^1 5$ = 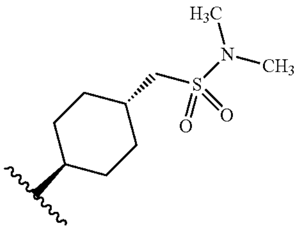
$B^1 6$ = 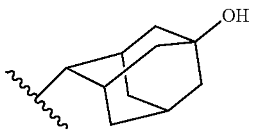

-continued $B^1 7$ = 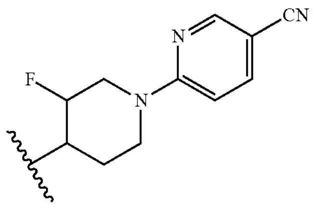

$B^1 8$ = 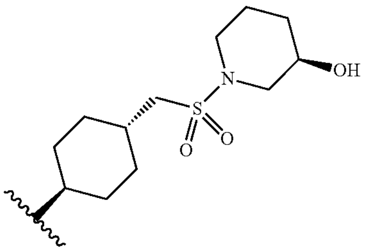

TABLE$^b$ 1

| $A^b$ | $B^{1b}$ | $A^b$ | $B^{1b}$ | $A^b$ | $B^{1b}$ | $A^b$ | $B^{1b}$ |
|---|---|---|---|---|---|---|---|
| A 1 | $B^1 1$ | A 1 | $B^1 3$ | A 1 | $B^1 5$ | A 1 | $B^1 7$ |
| A 2 | $B^1 1$ | A 2 | $B^1 3$ | A 2 | $B^1 5$ | A 2 | $B^1 7$ |
| A 3 | $B^1 1$ | A 3 | $B^1 3$ | A 3 | $B^1 5$ | A 3 | $B^1 7$ |
| A 4 | $B^1 1$ | A 4 | $B^1 3$ | A 4 | $B^1 5$ | A 4 | $B^1 7$ |
| A 5 | $B^1 1$ | A 5 | $B^1 3$ | A 5 | $B^1 5$ | A 5 | $B^1 7$ |
| A 6 | $B^1 1$ | A 6 | $B^1 3$ | A 6 | $B^1 5$ | A 6 | $B^1 7$ |
| A 7 | $B^1 1$ | A 7 | $B^1 3$ | A 7 | $B^1 5$ | A 7 | $B^1 7$ |
| A 8 | $B^1 1$ | A 8 | $B^1 3$ | A 8 | $B^1 5$ | A 8 | $B^1 7$ |
| A 1 | $B^1 2$ | A 1 | $B^1 4$ | A 1 | $B^1 6$ | A 1 | $B^1 8$ |
| A 2 | $B^1 2$ | A 2 | $B^1 4$ | A 2 | $B^1 6$ | A 2 | $B^1 8$ |
| A 3 | $B^1 2$ | A 3 | $B^1 4$ | A 3 | $B^1 6$ | A 3 | $B^1 8$ |
| A 4 | $B^1 2$ | A 4 | $B^1 4$ | A 4 | $B^1 6$ | A 4 | $B^1 8$ |
| A 5 | $B^1 2$ | A 5 | $B^1 4$ | A 5 | $B^1 6$ | A 5 | $B^1 8$ |
| A 6 | $B^1 2$ | A 6 | $B^1 4$ | A 6 | $B^1 6$ | A 6 | $B^1 8$ |
| A 7 | $B^1 2$ | A 7 | $B^1 4$ | A 7 | $B^1 6$ | A 7 | $B^1 8$ |
| A 8 | $B^1 2$ | A 8 | $B^1 4$ | A 8 | $B^1 6$ | A 8 | $B^1 8$ |

43$^b$) Compounds represented by the formula (XVII$^b$-1):

(XVII$^b$-1)

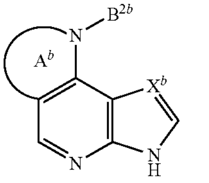

wherein $X^b$ is $CR^{15b}$ (wherein $R^{15b}$ is a hydrogen atom, a halogen atom or a cyano group), and the rings $A^b$ and $B^{2b}$ are any of the following combinations shown in Table$^b$ 2, tautomers or pharmaceutically acceptable salts of the compounds or solvates thereof.

The symbols in Table$^b$ 2 denote the following substituents.

A1 = 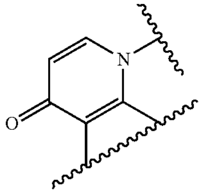

A2 = 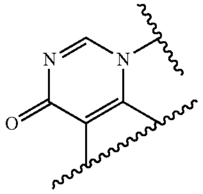

A3 = 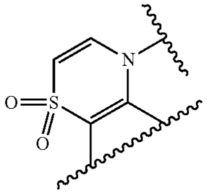

A4 = 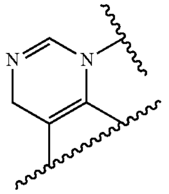

A5 = 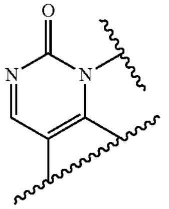

A6 = 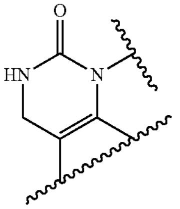

A7 = 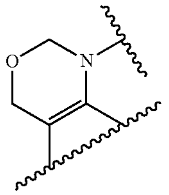

A9 = 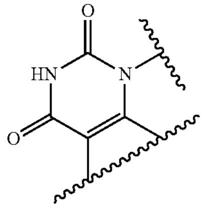

B$^2$1 = 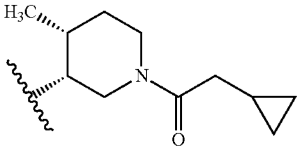

B$^2$2 = 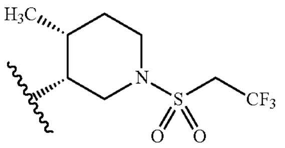

B$^2$3 = 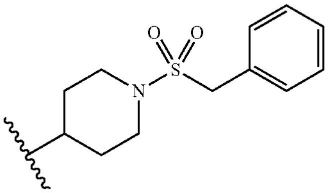

B$^2$4 = 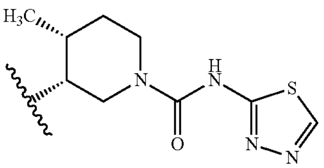

B$^2$5 = 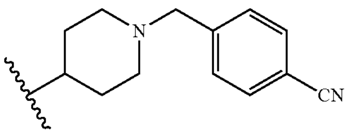

-continued

B$^2$6 = 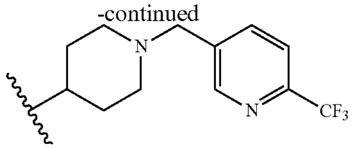

B$^2$7 = 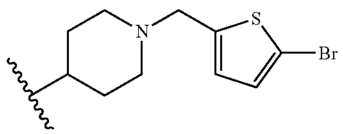

B$^2$8 = 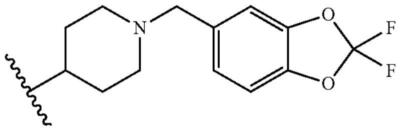

TABLE$^a$ 2

| A$^b$ | B$^{2b}$ | A$^b$ | B$^{2b}$ | A$^b$ | B$^{2b}$ | A$^b$ | B$^{2b}$ |
|---|---|---|---|---|---|---|---|
| A1 | B$^2$1 | A1 | B$^2$3 | A1 | B$^2$5 | A1 | B$^2$7 |
| A2 | B$^2$1 | A2 | B$^2$3 | A2 | B$^2$5 | A2 | B$^2$7 |
| A3 | B$^2$1 | A3 | B$^2$3 | A3 | B$^2$5 | A3 | B$^2$7 |
| A4 | B$^2$1 | A4 | B$^2$3 | A4 | B$^2$5 | A4 | B$^2$7 |
| A5 | B$^2$1 | A5 | B$^2$3 | A5 | B$^2$5 | A5 | B$^2$7 |
| A6 | B$^2$1 | A6 | B$^2$3 | A6 | B$^2$5 | A6 | B$^2$7 |
| A7 | B$^2$1 | A7 | B$^2$3 | A7 | B$^2$5 | A7 | B$^2$7 |
| A9 | B$^2$1 | A9 | B$^2$3 | A9 | B$^2$5 | A9 | B$^2$7 |
| A1 | B$^2$2 | A1 | B$^2$4 | A1 | B$^2$6 | A1 | B$^2$8 |
| A2 | B$^2$2 | A2 | B$^2$4 | A2 | B$^2$6 | A2 | B$^2$8 |
| A3 | B$^2$2 | A3 | B$^2$4 | A3 | B$^2$6 | A3 | B$^2$8 |
| A4 | B$^2$2 | A4 | B$^2$4 | A4 | B$^2$6 | A4 | B$^2$8 |
| A5 | B$^2$2 | A5 | B$^2$4 | A5 | B$^2$6 | A5 | B$^2$8 |
| A6 | B$^2$2 | A6 | B$^2$4 | A6 | B$^2$6 | A6 | B$^2$8 |
| A7 | B$^2$2 | A7 | B$^2$4 | A7 | B$^2$6 | A7 | B$^2$8 |
| A9 | B$^2$2 | A9 | B$^2$4 | A9 | B$^2$6 | A9 | B$^2$8 |

44$^b$) The compounds with the combinations of substituents as defined in 42$^b$) or 43$^b$), wherein X$^b$ is converted to a nitrogen atom, tautomers or pharmaceutically acceptable salts of the compounds or solvates thereof.

The compounds of the present invention can be synthesized by the processes mentioned later, but the production of the compounds of the present invention is not restricted to these general examples.

The compounds of the present invention can usually be purified by column chromatography, thin layer chromatography, high performance liquid chromatography (HPLC) or high performance liquid chromatography-mass spectrometry (LC-MS) and, if necessary, they may be obtained with high purity by recrystallization or washing with solvents.

In general, in the production of the compounds of the present invention, any solvents that are stable and inert under the reaction conditions and do not hinder the reactions may be used without any particular restrictions, and for example, sulfoxide solvents (such as dimethyl sulfoxide), amide solvents (such as N,N-dimethylformamide or N,N-dimethylacetamide), ether solvents (such as diethyl ether, 1,2-dimethoxyethane, tetrahydrofuran, 1,4-dioxane or cyclopentyl methyl ether), halogenated solvents (such as dichloromethane, chloroform or 1,2-dichloroethane), nitrile solvents (such as acetonitrile or propionitrile), aromatic hydrocarbon solvents (such as benzene or toluene), aliphatic hydrocarbon solvents (such as hexane or heptane), ester solvents (such as ethyl acetate), alcohol solvents (such as methanol, ethanol, 1-propanol, 2-propanol or ethylene glycol) and water may be mentioned. The reactions may be carried out in an arbitrary mixture of solvents mentioned above or in the absence of a solvent.

In general, in the production of the compounds of the present invention, the reaction temperature is chosen appropriately within the range of from −78° C. to the boiling point of the solvent used for the reaction, and the production of the compounds of the present invention may be carried out at ordinary pressure or under pressure or with microwave irradiation.

As acids generally used in the production of the compounds of the present invention, for example, organic acids (such as acetic acid, trifluoroacetic acid or p-toluenesulfonic acid) and inorganic acids (such as sulfuric acid or hydrochloric acid) may be mentioned.

As bases generally used in the production of the compounds of the present invention, for example, organic metal compounds (such as n-butyllithium, s-butyllithium, lithiumdiisopropylamide or isopropylmagnesium bromide), organic bases (such as triethylamine, N,N-diisopropylethylamine or N,N-dimethylaminopyridine) and inorganic bases (such as sodium carbonate, potassium carbonate, cesium carbonate, sodium hydroxide, potassium hydroxide or sodium hydride) may be mentioned.

General processes for production of the compounds of the present invention are shown below, and the formulae of the intermediate and the end product in each step therein conceptually cover their protected derivatives, too. Herein, protected derivatives are defined as compounds which can be converted to the desired product, if necessary, through hydrolysis, reduction, oxidation, alkylation or the like and include compounds protected with chemically acceptable protective groups.

Protection and deprotection may be carried out by generally known protection and deprotection reactions (for example, by referring to Protective Groups in Organic Synthesis, Fourth edition, T. W. Greene, John Wiley & Sons Inc. (2006)).

Hydrolysis, reduction and oxidation may be carried out by generally known functional group conversions (for example, by referring to Comprehensive Organic Transformations, Second Edition, R. C. Larock, Wiley-VCH (1999)).

First, processes for producing the tricyclic pyrimidine compounds represented by the formula ($I^a$) will be described.

Among the tricyclic pyrimidine compounds represented by the formula ($I^a$), the compounds (1a)-3 can be produced, for example, through the following scheme (1a) (wherein $R^{PR}$ is a hydrogen atom or a protective group such as a Ts group, a TIPS group or a SEM group, and the other symbols are the same as defined above).

(1a)

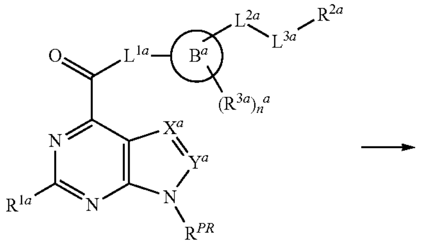

(1a)-1

-continued

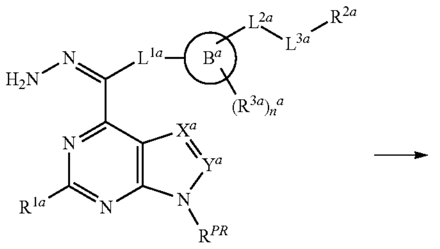

(1a)-2

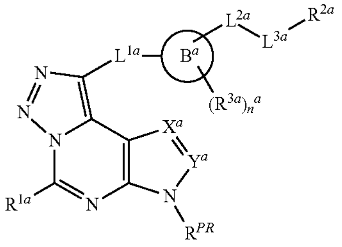

(1a)-3

A compound (1a)-1 can be converted to a compound (1a)-2 by using an equivalent or excessive amount of hydrazine or its equivalent in an appropriate solvent or in the absence of solvent at room temperature to a refluxing temperature.

A compound (1a)-2 can be converted to a compound (1a)-3 by using an equivalent or excessive amount of an oxidizing agent such as manganese dioxide or iodobenzenediacetate in an appropriate solvent or in the absence of solvent at room temperature to a refluxing temperature. The presence of an acid or a base is sometimes effective for smooth progress of the reaction.

A compound (1a)-3 can also be obtained by using a compound (1a)-1 and an equivalent or excessive amount of tosylhydrazine or its equivalent in an appropriate solvent or in the absence of solvent at room temperature to a refluxing temperature. The presence of a base is sometimes effective for smooth progress of the reaction.

A compound (1a)-3 having a protective group as $R^{PR}$ can be converted to a compound (1a)-3 having a hydrogen atom as $R^{PR}$ by deprotection.

Among the compounds represented by the formula ($I^a$), the compounds (2a)-2, (2a)-3 and (2a)-4 can be produced, for example, through the following scheme (2a) (wherein $E^{2a}$ is an oxygen atom or a sulfur atom, $R^{PR}$ is a hydrogen atom or a protective group such as a Ts group, a TIPS group or a SEM group, and the other symbols are the same as defined above).

(2a)

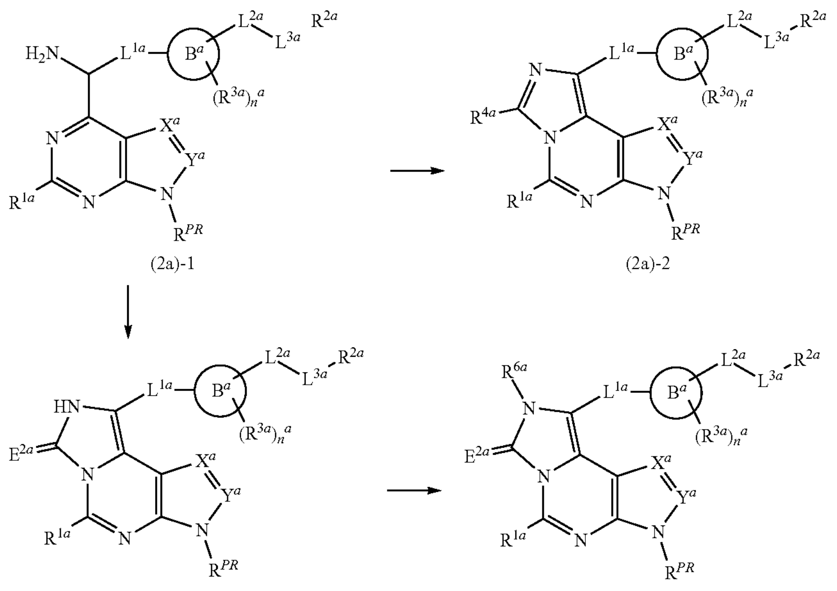

(2a)-1 (2a)-2

(2a)-3 (2a)-4

A compound (2a)-1 can be converted to a compound (2a)-2 by using an equivalent or excessive amount of $R^{4a}CHO$, $R^{4a}CO_2R^Q$, $R^{4a}C(OR^Q)_3$, $R^{4a}CONR^Q_2$ or $R^{4a}C(OR^Q)_2NR^Q_2$ (wherein $R^Q$ is a hydrogen atom or a $C_{1-6}$ alkyl group) in an appropriate solvent or in the absence of solvent at room temperature to a refluxing temperature. Microwave irradiation or the presence of an acid or a base is sometimes effective for smooth progress of the reaction.

A compound (2a)-1 can be converted to a compound (2a)-3 by using an equivalent or excessive amount of phosgene, phosgene dimer, phosgene trimer, 1,1'-carbonyldiimidazole, dimethyl carbonate, carbon disulfide or 1,1'-thiocarbonyldiimidazole in an appropriate solvent or in the absence of solvent at room temperature to a refluxing temperature. The presence of an acid or a base is sometimes effective for smooth progress of the reaction.

A compound (2a)-3 can be converted to a compound (2a)-4 by using equivalent or excessive amounts of $R^{6a}$—$R^L$ (wherein $R^L$ is a leaving group such as a halogen atom, a methanesulfonyloxy group or a p-toluenesulfonyloxy group) and a base such as potassium carbonate or sodium hydride in an appropriate solvent or in the absence of solvent at room temperature to a refluxing temperature.

A compound (2a)-3 or (2a)-4 having an oxygen atom as $E^{2a}$ can be converted to a compound (2a)-3 or (2a)-4 having a sulfur atom as $E^{2a}$ by using an equivalent or excessive amount of a thiocarbonylation reagent such as phosphorus pentasulfide or Lawesson's reagent in an appropriate solvent or in the absence of solvent at −78° C. to a refluxing temperature.

Compounds (2a)-2, (2a)-3 and (2a)-4 having a protective group as $R^{PR}$ can be converted to compounds (2a)-2, (2a)-3 and (2a)-4 having a hydrogen atom as $R^{PR}$ by deprotection.

Synthesis of Starting Materials 1a

The compounds (3a)-3 and (3a)-6 can be produced, for example, through the following scheme (3a) (wherein $X^A$ is a chlorine atom, a bromine atom or an iodine atom, each of $R^X$ and $R^Y$ is independently a $C_{1-6}$ alkyl group, and $R^{PR}$ is a hydrogen atom or a protective group such as a Ts group, a TIPS group or a SEM group, and the other symbols are the same as defined above).

(3a)

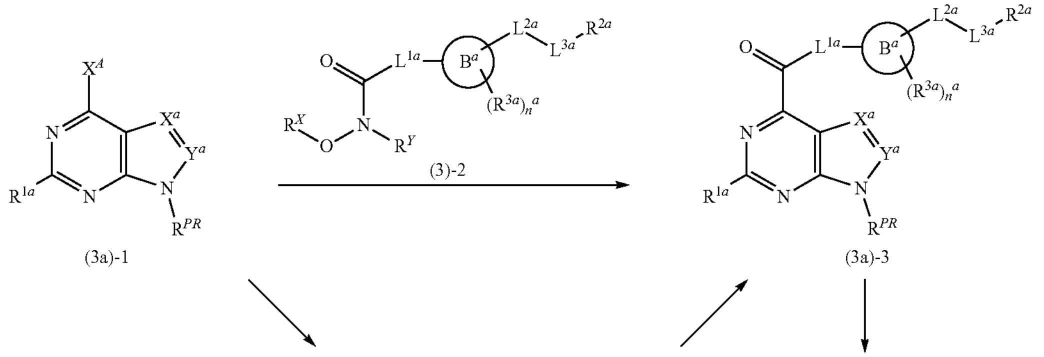

(3)-2

(3a)-1 (3a)-3

-continued

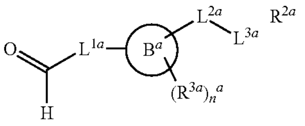

(3a)-4

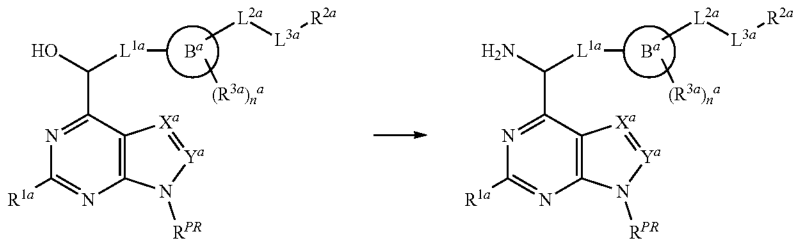

(3a)-5 (3a)-6

A compound (3a)-1 can be converted to a compound (3a)-3 by a metal-halogen exchange reaction using an equivalent or excessive amount of an organic metal reagent such as isopropylmagnesium chloride, 2,6-dimethylphenylmagnesium bromide or n-butyllithium in an appropriate solvent at −78° C. to room temperature followed by treatment with an equivalent or excessive amount of a compound (3a)-2 in an appropriate solvent at −78° C. to room temperature.

A compound (3a)-1 can be converted to a compound (3a)-5 by a metal-halogen exchange reaction using an equivalent or excessive amount of an organic metal reagent such as isopropylmagnesium chloride, 2,6-dimethylphenylmagnesium bromide or n-butyllithium in an appropriate solvent at −78° C. to room temperature followed by treatment with an equivalent or excessive amount of a compound (3a)-4 in an appropriate solvent at −78° C. to room temperature.

A compound (3a)-5 can be converted to a compound (3a)-3 by using an equivalent or excessive amount of an oxidizing agent such as manganese dioxide or 1,1,1-triacetoxy-1,1-dihydro-1,2-benziodoxol-3(1H)-one (Dess-Martin reagent) in an appropriate solvent at −78° C. to a refluxing temperature.

A compound (3a)-3 can be converted to a compound (3a)-6 by using equivalent or excessive amounts of an amine reagent such as ammonium acetate or hydroxylamine and a reducing agent such as sodium triacetoxyborohydride or zinc in an appropriate solvent or in the absence of solvent at −78° C. to a refluxing temperature.

A compound (3a)-5 can be converted to a compound (3a)-6 by carrying out a reaction using equivalent or excessive amounts of phthalimide, a Mitsunobu reagent and a phosphine reagent in an appropriate solvent or in the absence of solvent at −78° C. to a refluxing temperature, followed by deprotection. As a Mitsunobu reagent, diethyl azodicarboxylate, diisopropyl azodicarboxylate or the like may be mentioned, and as a phosphine reagent, triphenylphosphine, tributylphosphine or the like may be mentioned.

A compound (3a)-1 having a chlorine atom as $X^A$ can be converted to a compound (3a)-1 having a bromine or iodine atom as $X^A$ by using an equivalent or excessive amount of hydrobromic acid or hydroiodic acid in an appropriate solvent or in the absence of solvent at 0° C. to a refluxing temperature.

Compounds (3a)-3 and (3a)-6 having a protective group as $R^{PR}$ can be converted to compounds (3a)-3 and (3a)-6 having a hydrogen atom as $R^{PR}$ by deprotection.

Synthesis of Starting Materials 2a

The compounds (4a)-2 can be produced, for example, through the following scheme (4a) (wherein each of $R^X$ and $R^Y$ is independently a $C_{1-6}$ alkyl group, and the other symbols are the same as defined above).

(4a)

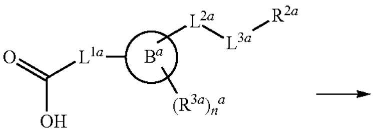

(4a)-1

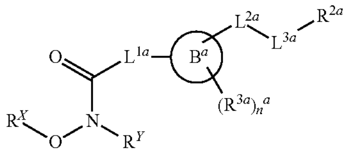

(4a)-2

A compound (4a)-1 can be converted to a compound (4a)-2 by using equivalent or excessive amounts of $R^YNH(OR^X)$ and a condensation agent such as dicyclohexylcarbodiimide or 1-ethyl-3-(3-dimethylaminopropyl)carbodiimide hydrochloride in an appropriate solvent or in the absence of solvent at 0° C. to a refluxing temperature. The presence of an acid or a base is sometimes effective for smooth progress of the reaction.

Among the compounds represented by the formula ($I^a$), the compounds (5a)-3, (5a)-4, (5a)-5 and (5a)-6 can be produced, for example, through the following scheme (5a) (wherein m is 0,1,2 or 3, $R^{PR}$ is a hydrogen atom or a protective group such as a Ts group, a TIPS group or a SEM group, $R^{PR2}$ is a protective group such as a Boc group or a Cbz group, $E^{3a}$ is an oxygen atom or a sulfur atom, and the other symbols are the same as defined above).

(5a)

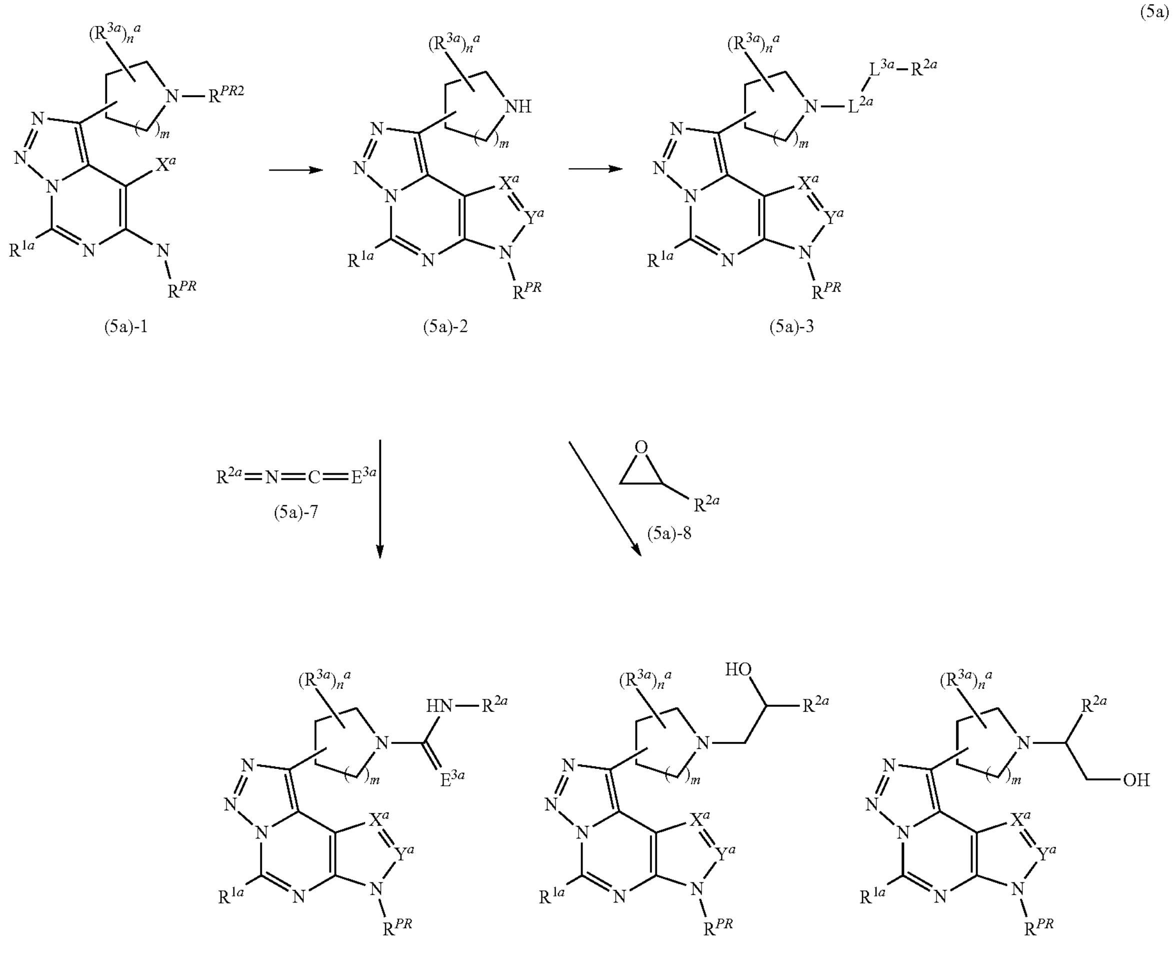

(5a)-1 (5a)-2 (5a)-3 (5a)-7 (5a)-8 (5a)-4 (5a)-5 (5a)-6

A compound (5a)-1 among the compounds (1a)-3 can be converted to a compound (5a)-2 by deprotection.

A compound (5a)-2 can be converted to a compound (5a)-3 by using equivalent or excessive amounts of an electrophilic reagent represented by $R^{2a}L^{3a}L^{2a}$-$R^L$ (wherein $R^L$ is a leaving group such as a halogen atom, a methanesulfonyloxy group, a p-toluenesulfonyloxy group) such as an alkyl halide, a methanesulfonate ester, an acid halide, a sulfonyl chloride, a chloroformate and a base such as triethylamine in an appropriate solvent or in the absence of solvent at −78° C. to a refluxing temperature.

A compound (5a)-2 can be converted to a compound (5a)-3 by using equivalent or excessive amounts of $R^{2a}$—CHO and a reducing agent such as 2-picoline borane or sodium triacetoxyborohydride in an appropriate solvent or in the absence of solvent at room temperature to a refluxing temperature.

A compound (5a)-2 can be converted to a compound (5a)-4 by using equivalent or excessive amounts of a compound (5a)-7 and a base such as potassium carbonate or triethylamine in an appropriate solvent or in the absence of solvent at −78° C. to a refluxing temperature.

A compound (5a)-2 can be converted to a compound (5a)-5 or/and (5a)-6 by using equivalent or excessive amounts of a compound (5a)-8, a base such as triethylamine and an acid catalyst such as ytterbium (III) trifluoromethanesulfonate in an appropriate solvent or in the absence of solvent at −78° C. to a refluxing temperature.

Compounds (5a)-3, (5a)-4, (5a)-5 and (5a)-6 having a protective group as $R^{PR}$ can be converted to compounds (5a)-3, (5a)-4, (5a)-5 and (5a)-6 having a hydrogen atom as $R^{PR}$ by deprotection.

Among the compounds represented by the formula ($I^a$), the compounds (6a)-3, (6a)-4 and (6a)-5 can be produced, for example, through the following scheme (6a) (wherein m is 0,1,2 or 3, $R^{PR}$ is a hydrogen atom or a protective group such as a Ts group, a TIPS group or a SEM group, $R^{PR3}$ is a protective group such as a benzyl group or an acetyl group, and the other symbols are the same as defined above).

(6a)

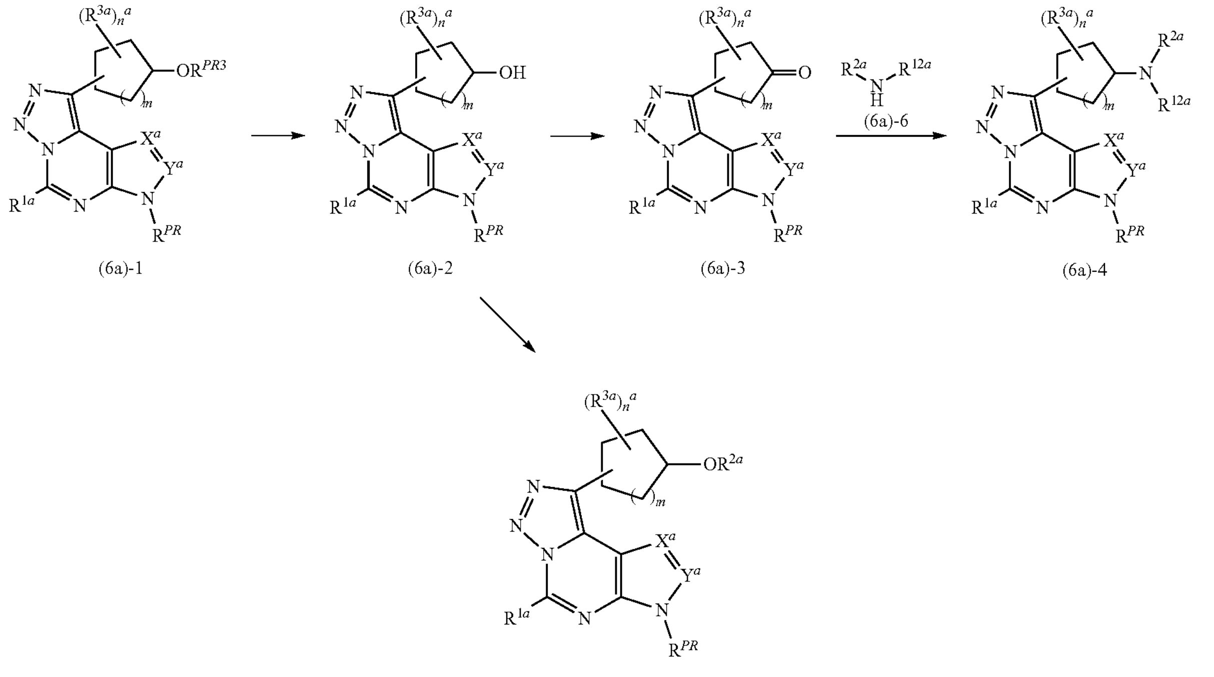

(6a)-1 (6a)-2 (6a)-3 (6a)-4

(6a)-5

A compound (6a)-1 among the compounds (1a)-3 is converted to a compound (6a)-2 by deprotection.

A compound (6a)-2 can be converted to a compound (6a)-3 by using an equivalent or excessive amount of an oxidizing agent such as 2-iodoxybenzoic acid or pyridinium chlorochromate in an appropriate solvent or in the absence of solvent at −78° C. to a refluxing temperature.

A compound (6a)-3 can be converted to a compound (6a)-4 by using equivalent or excessive amounts of a compound (6a)-6 and a reducing agent such as 2-picoline borane or sodium triacetoxyborohydride in an appropriate solvent or in the absence of solvent at room temperature to a refluxing temperature.

A compound (6a)-2 can be converted to a compound (6a)-5 by using equivalent or excessive amounts of an acidic alcohol represented by $R^{2a}$—OH such as phenol, a Mitsunobu reagent and a phosphine reagent in an appropriate solvent or in the absence of solvent at −78° C. to a refluxing temperature. As a Mitsunobu reagent, diethyl azodicarboxylate, diisopropyl azodicarboxylate or the like may be mentioned, and as a phosphine reagent, triphenylphosphine, tributylphosphine or the like may be mentioned.

Compounds (6a)-3, (6a)-4 and (6a)-5 having a protective group as $R^{PR}$ can be converted to compounds (6a)-3, (6a)-4 and (6a)-5 having a hydrogen atom as $R^{PR}$ by deprotection.

Among the compounds represented by the formula ($I^a$), the compounds (7a)-3, (7a)-4, (7a)-5, (7a)-6, (7a)-7, (7a)-8 and (7a)-9 can be produced, for example, through the following scheme (7a) (wherein m is 0,1,2 or 3, $R^{PR}$ is a hydrogen atom or a protective group such as a Ts group, a TIPS group or a SEM group, $R^{PR3}$ is a protective group such as a benzyl group or an acetyl group, $R^Z$ is a hydrogen atom or a $C_{1-6}$ alkyl group, $X^b$ is a halogen atom, and the other symbols are the same as defined above).

(7a)

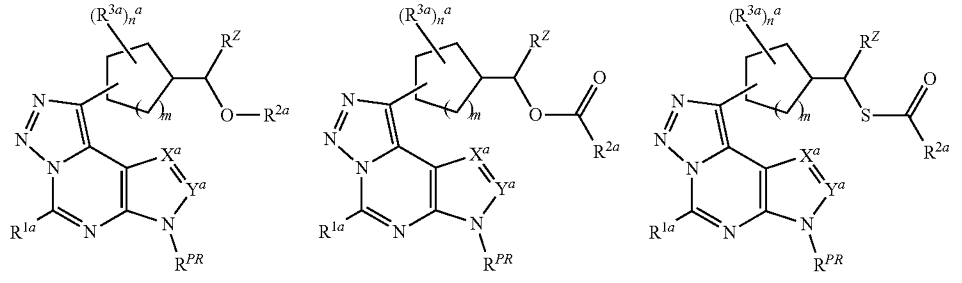

(7a)-7 (7a)-8 (7a)-9

-continued

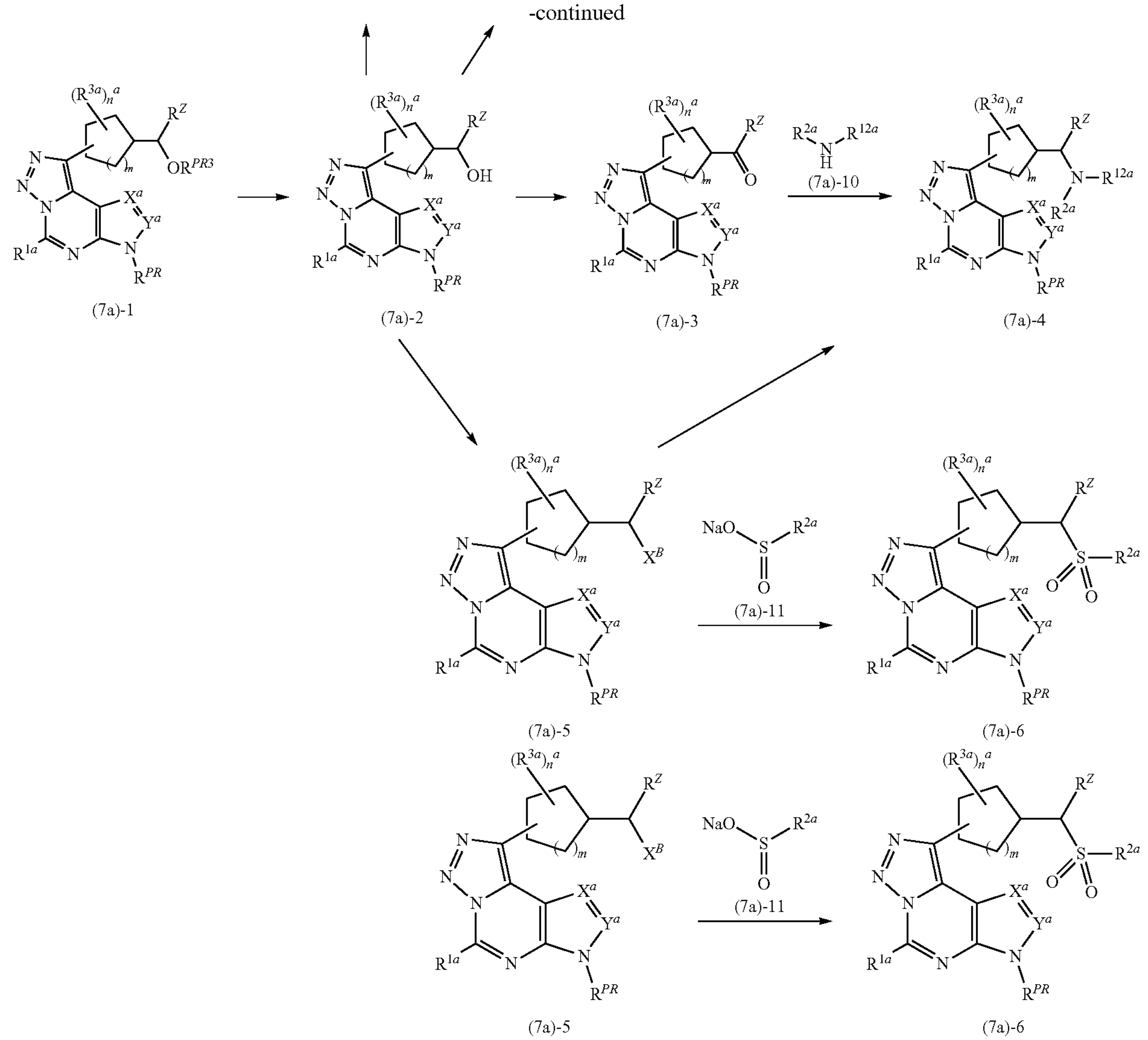

A compound (7a)-1 among the compounds (1a)-3 can be converted to a compound (7a)-2 by deprotection.

A compound (7a)-2 can be converted to a compound (7a)-3 by using an equivalent or excessive amount of an oxidizing agent such as 2-iodoxybenzoic acid or pyridinium chlorochromate in an appropriate solvent or in the absence of solvent at −78° C. to a refluxing temperature.

A compound (7a)-3 can be converted to a compound (7a)-4 by using equivalent or excessive amounts of a compound (7a)-10 and a reducing agent such as 2-picoline borane or sodium triacetoxyborohydride in an appropriate solvent or in the absence of solvent at room temperature to a refluxing temperature.

A compound (7a)-5 can be converted to a compound (7a)-4 by using an equivalent or excessive amount of a compound (7a)-10 in an appropriate solvent or in the absence of solvent at −78° C. to a refluxing temperature. The presence of a base is sometimes effective for smooth progress of the reaction.

A compound (7a)-2 can be converted to a compound (7a)-5 by using equivalent or excessive amounts of a halogenating agent and a phosphine reagent in an appropriate solvent or in the absence of solvent at −78° C. to a refluxing temperature. As a halogenating agent, N-bromosuccinimide, N,N-diethylaminosulfur trifluoride or the like may be mentioned, and as a phosphine reagent, triphenylphosphine, tributylphosphine or the like may be mentioned.

A compound (7a)-5 can be converted to a compound (7a)-6 by using an equivalent or excessive amount of a compound (7a)-11 in an appropriate solvent or in the absence of solvent at room temperature to a refluxing temperature. The presence of an acid or a base is sometimes effective for smooth progress of the reaction.

A compound (7a)-2 can be converted to a compound (7a)-7 by using equivalent or excessive amounts of an electrophilic reagent represented by $R^{2a}$—$R^L$($R^L$ is a leaving group such as a halogen atom, a methanesulfonyloxy group or a p-toluenesulfonyloxy group) such as an alkyl halide, a methanesulfonyl ester or an acid halide and a base such as potassium carbonate or sodium hydroxide in an appropriate solvent or in the absence of solvent at −78° C. to a refluxing temperature.

A compound (7a)-2 can be converted to a compound (7a)-7 by using equivalent or excessive amounts of an acidic alcohol represented by $R^{2a}$—OH such as phenol, a Mitsunobu reagent and a phosphine reagent in an appropriate solvent or in the absence of solvent at −78° C. to a refluxing temperature. As a Mitsunobu reagent, diethyl azodicarboxylate, diisopropyl azodicarboxylate or the like may be mentioned, and as a phosphine reagent, triphenylphosphine, tributylphosphine or the like may be mentioned.

A compound (7a)-2 can be converted to a compound (7a)-8 or (7a)-9 by using equivalent or excessive amounts of $R^{2a}C({=}O)OH$ or $R^{2a}(C{=}O)SH$, a Mitsunobu reagent and a phosphine reagent in an appropriate solvent or in the absence of solvent at −78° C. to a refluxing temperature. As $R^{2a}C({=}O)OH$, acetic acid or the like may be mentioned, as $R^{2a}(C{=}O)SH$, thioacetic acid or the like may be mentioned. As a Mitsunobu reagent, diethyl azodicarboxylate, diisopropyl azodicarboxylate or the like may be mentioned, and as a phosphine reagent, triphenylphosphine, tributylphosphine or the like may be mentioned.

Compounds (7a)-3, (7a)-4, (7a)-5, (7a)-6, (7a)-7, (7a)-8 and (7a)-9 having a protective group as $R^{PR}$ can be converted to compounds (7a)-3, (7a)-4, (7a)-5, (7a)-6, (7a)-7, (7a)-8 and (7a)-9 having a hydrogen atom as $R^{PR}$ by deprotection.

Among the compounds represented by the formula ($I^a$), the compounds (8a)-2 and (8a)-3 can be produced, for example, through the following scheme (8a) (wherein m is 0, 1, 2 or 3, $R^{PR}$ is a hydrogen atom or a protective group such as a Ts group, a TIPS group or a SEM group, and the other symbols are the same as defined above).

(8a)

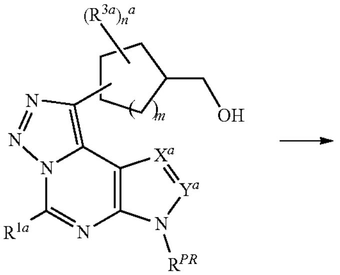

(8a)-1

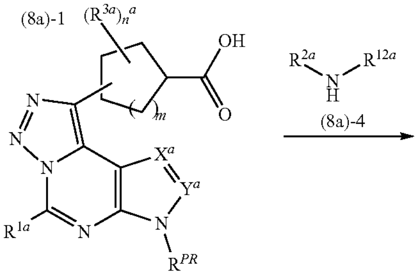

(8a)-4

(8a)-2

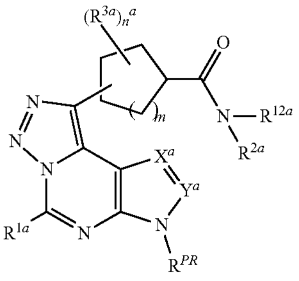

(8a)-3

A compound (8a)-1 among the compounds (7a)-2 can be converted to a compound (8a)-2 by using an equivalent or excessive amount of an oxidizing agent such as Jones reagent in an appropriate solvent or in the absence of solvent at −78° C. to a refluxing temperature.

A compound (8a)-2 can be converted to a compound (8a)-3 by using equivalent or excessive amounts of a compound (8a)-4 and a condensation agent such as N,N'-dicyclohexylcarbodiimide or 1-ethyl-3-(3-dimethylaminopropyl)carbodiimide hydrochloride in an appropriate solvent or in the absence of solvent at 0° C. to a refluxing temperature. The presence of an acid or a base is sometimes effective for smooth progress of the reaction.

Compounds (8a)-2 and (8a)-3 having a protective group as $R^{PR}$ can be converted to compounds (8a)-2 and (8a)-3 having a hydrogen atom as $R^{PR}$ by deprotection.

Among the compounds represented by the formula ($I^a$), the compounds (9a)-2 and (9a)-3 can be produced, for example, through the following scheme (9a) (wherein m is 0, 1, 2 or 3, $R^{PR}$ is a hydrogen atom or a protective group such as a Ts group, a TIPS group or a SEM group, $R^Z$ is a hydrogen atom or a $C_{1-6}$ alkyl group, and the other symbols are the same as defined above).

(9a)

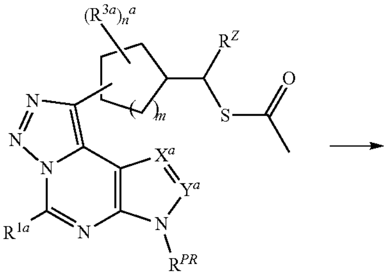

(9a)-1

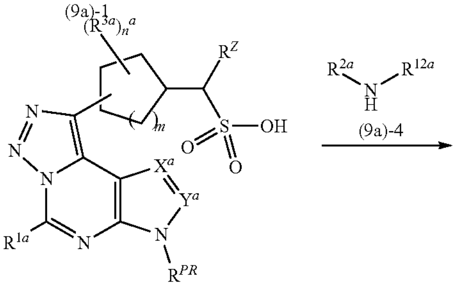

(9a)-4

(9a)-2

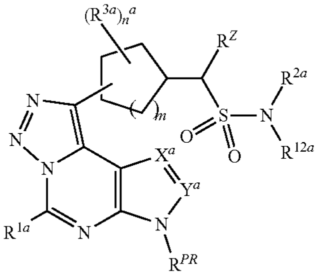

(9a)-3

A compound (9a)-1 among the compounds (7a)-9 can be converted to a compound (9a)-2 by using an equivalent or excessive amount of an oxidizing agent such as hydrogen peroxide in an appropriate solvent or in the absence of solvent at −78° C. to a refluxing temperature. The presence of an acid catalyst such as ammonium molybdate tetrahydrate is sometimes effective for smooth progress of the reaction.

A compound (9a)-2 can be converted to a compound (9a)-3 by using equivalent or excessive amounts of a compound (9a)-4 and a halogenating agent such as thionyl chloride or phosphorus oxychloride in an appropriate solvent or in the absence of solvent at 0° C. to a refluxing temperature. The presence of a base such as triethylamine is sometimes effective for smooth progress of the reaction.

Compounds (9a)-2 and (9a)-3 having a protective group as $R^{PR}$ can be converted to compounds (9a)-2 and (9a)-3 having a hydrogen atom as $R^{PR}$ by deprotection.

Among the compounds represented by the formula ($I^a$), the compounds (10a)-2 and (10a)-3 can be produced, for example, through the following scheme (10a) (wherein m is 0, 1, 2 or 3, $R^{PR}$ is a hydrogen atom or a protective group such as a Ts group, a TIPS group or a SEM group, $R^7$ is a hydrogen atom or a $C_{1-6}$ alkyl group, and the other symbols are the same as defined above).

(10a)

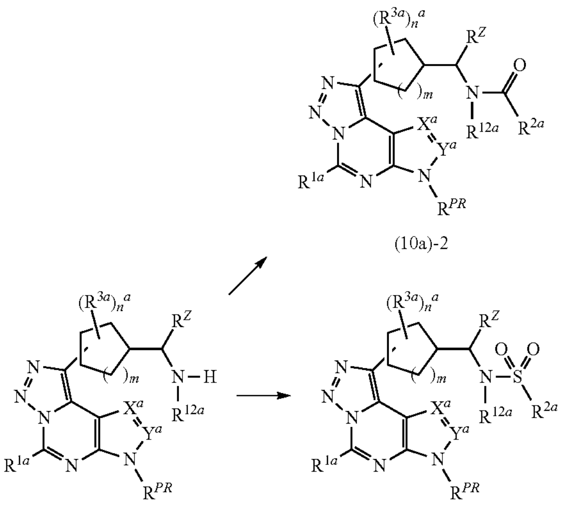

(10a)-2

(10a)-1

(10a)-3

A compound (10a)-1 among the compounds (7a)-4 can be converted to a compound (10a)-2 by using an equivalent or excessive amount of an acid halide in an appropriate solvent or in the absence of solvent at −78° C. to a refluxing temperature. The presence of a base is sometimes effective for smooth progress of the reaction.

A compound (10a)-1 among the compounds (7a)-4 can be converted to a compound (10a)-3 by using an equivalent or excessive amount of a sulfonyl halide in an appropriate solvent or in the absence of solvent at −78° C. to a refluxing temperature. The presence of a base is sometimes effective for smooth progress of the reaction.

Compounds (10a)-2 and (10a)-3 having a protective group as $R^{PR}$ can be converted to compounds (10a)-2 and (10a)-3 having a hydrogen atom as $R^{PR}$ by deprotection.

Among the compounds represented by the formula ($I^a$), the compounds (11a)-2, (11a)-3, (11a)-4, (11a)-5, (11a)-6, (11a)-7, (11a)-8 and (11a)-9 can be produced, for example, through the following scheme (11a) (wherein m is 0, 1, 2 or 3, $R^{PR}$ is a hydrogen atom or a protective group such as a Ts group, a TIPS group or a SEM group, $R^Z$ is a hydrogen atom or a $C_{1-6}$ alkyl group, $R^{Z1}$ is a $C_{1-6}$ alkyl group, and the other symbols are the same as defined above).

(11a)

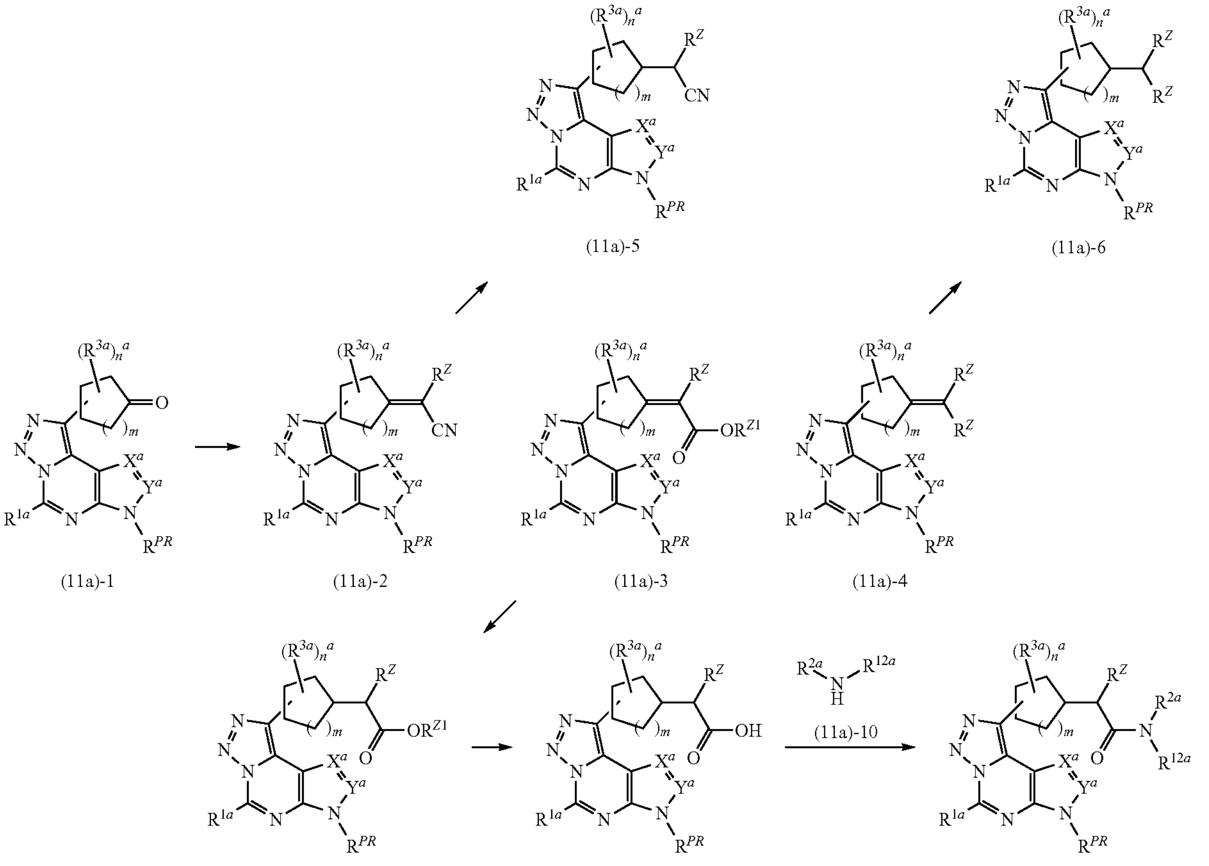

(11a)-5

(11a)-6

(11a)-1

(11a)-2

(11a)-3

(11a)-4

(11a)-10

(11a)-7

(11a)-8

(11a)-9

A compound (11a)-1 can be converted to a compound (11a)-2, (11a)-3 or (11a)-4 by using an equivalent or excessive amounts of a phosphonium ylide such as a Homer-Wadsworth-Emmons reagent and a base such as sodium hydride in an appropriate solvent or in the absence of solvent at −78° C. to a refluxing temperature.

A compound (11a)-2, (11a)-4 or (11a)-3 can be converted to a compound (11a)-5, (11a)-6 or (11a)-7 respectively by using an equivalent or excessive amount of a metal catalyst such as palladium-carbon catalyst under a hydrogen atmosphere in an appropriate solvent at −78° C. to a refluxing temperature.

A compounds (11a)-7 can be converted to a compounds (11a)-8 by deprotection.

A compound (11a)-8 can be converted to a compound (11a)-9 by using equivalent or excessive amounts of a compound (11a)-10 and a condensation agent such as N,N'-dicyclohexylcarbodiimide or 1-ethyl-3-(3-dimethylaminopropyl)carbodiimide hydrochloride in an appropriate solvent or in the absence of solvent at 0° C. to a refluxing temperature. The presence of an acid or a base is sometimes effective for smooth progress of the reaction.

Compounds (11a)-2, (11a)-3, (11a)-4, (11a)-5, (11a)-6, (11a)-7, (11a)-8 and (11a)-9 having a protective group as $R^{PR}$ can be converted to compounds (11a)-2, (11a)-3, (11a)-4, (11a)-5, (11a)-6, (11a)-7, (11a)-8 and (11a)-9 having a hydrogen atom as $R^{PR}$ by deprotection.

Among the compounds represented by the formula ($I^a$), the compounds (12a)-2, (12a)-3, (12a)-4 and (12a)-5 can be produced, for example, through the following scheme (12a) (wherein m is 0, 1, 2 or 3, $R^{PR}$ is a hydrogen atom or a protective group such as a Ts group, a TIPS group or a SEM group, $R^Z$ is a hydrogen atom or a $C_{1-6}$ alkyl group, and the other symbols are the same as defined above).

A compound (12a)-1 among the compounds (7a)-3 can be converted to a compound (12a)-2 by using equivalent or excessive amounts of a phosphonium ylide such as a Horner-Wadsworth-Emmons reagent and a base such as sodium hydride in an appropriate solvent or in the absence of solvent at −78° C. to a refluxing temperature.

A compound (12a)-2 can be converted to a compound (12a)-3 by using an equivalent or excessive amount of a metal catalyst such as palladium-carbon catalyst under a hydrogen atmosphere in an appropriate solvent at −78° C. to a refluxing temperature.

A compound (12a)-1 can be converted to a compound (12a)-4 by using equivalent or excessive amounts of malononitrile and a base such as piperidine in an appropriate solvent or in the absence of solvent at −78° C. to a refluxing temperature.

A compound (12a)-4 can be converted to a compound (12a)-5 by using an equivalent or excessive amount of a metal catalyst such as palladium-carbon catalyst under a hydrogen atmosphere in an appropriate solvent at −78° C. to a refluxing temperature.

Compounds (12a)-2, (12a)-3, (12a)-4 and (12a)-5 having a protective group as $R^{PR}$ can be converted to compounds (12a)-2, (12a)-3, (12a)-4 and (12a)-5 having a hydrogen atom as $R^{PR}$ by deprotection.

Next, processes for producing the tricyclic pyridine compounds represented by the formula ($I^b$) will be described.

Among the tricyclic pyridine compounds represented by the formula ($I^b$), the compounds (1b)-2 can be produced, for example, through the following scheme (1b) (wherein $R^{PR}$ is a hydrogen atom or a protective group such as a Ts group, a TIPS group or a SEM group, and the other symbols are the same as defined above).

(12a)

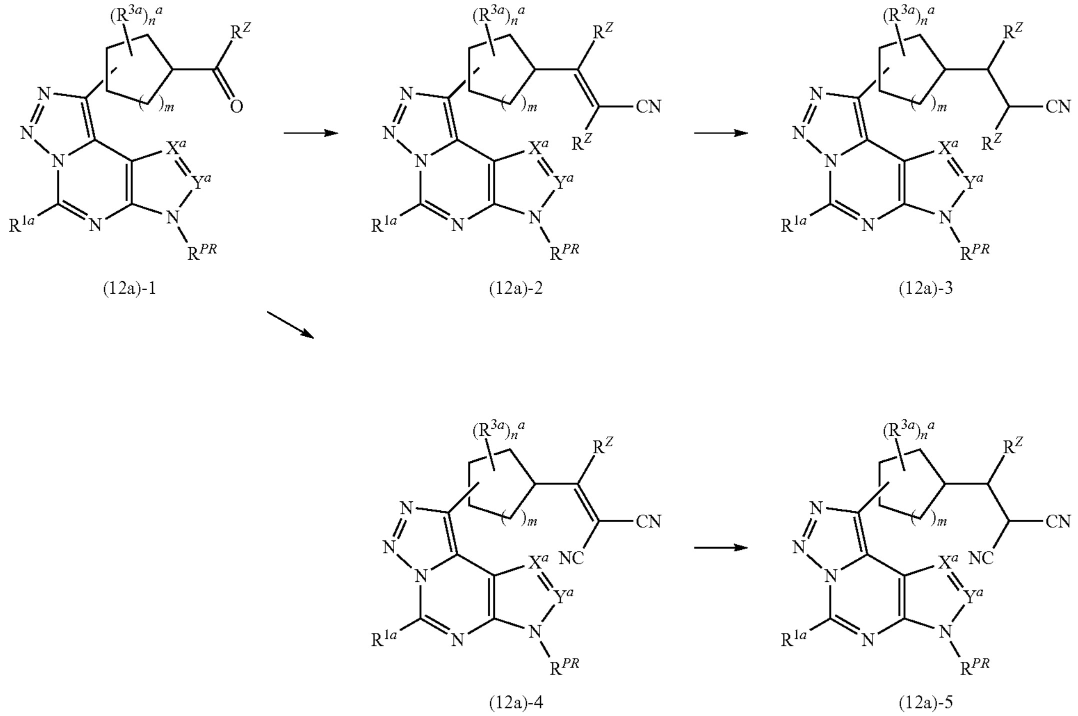
(12a)-1 (12a)-2 (12a)-3 (12a)-4 (12a)-5

(1b)

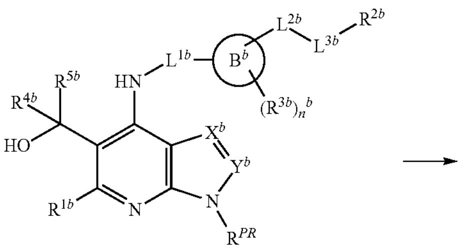

(1b)-1

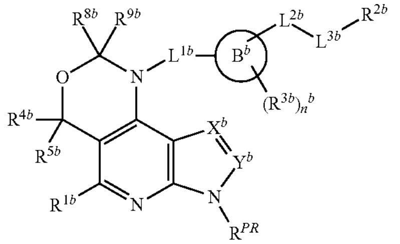

(1b)-2

A compound (1b)-2 can be obtained by cyclization of a compound (1b)-1.

A compound (1b)-1 can be converted to a compound (1b)-2 by using an equivalent or excessive amount of $R^{8b}C(=O)R^{9b}$ or $R^{8b}C(OR^{Q})_2R^{9b}$ (wherein $R^{Q}$ is a hydrogen atom or a $C_{1-6}$ alkyl group) in an appropriate solvent or in the absence of solvent at room temperature to a refluxing temperature. Microwave irradiation or the presence of an acid catalyst such as acetic acid, trifluoroacetic acid, hydrochloric acid, sulfuric acid or p-toluenesulfonic acid is sometimes effective for smooth progress of the reaction.

A compound (1b)-2 having a protective group as $R^{PR}$ can be converted to a compound having a hydrogen atom as $R^{PR}$ by deprotection.

Among the compounds represented by the formula ($I^b$), the compounds (2b)-2 and (3b)-2 can be produced, for example, through the following schemes (2b) and (3b) (wherein $Y^A$ is an oxygen atom or a sulfur atom, $R^{PR}$ is a hydrogen atom or a protective group such as a Ts group, a TIPS group or a SEM group, and the other symbols are the same as defined above).

(2b)

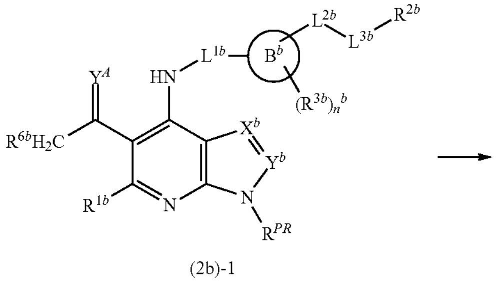

(2b)-1

-continued

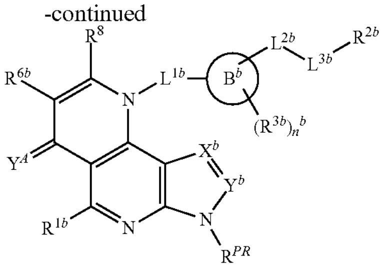

(2b)-2

(3b)

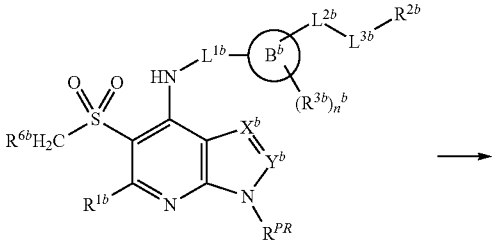

(3b)-1

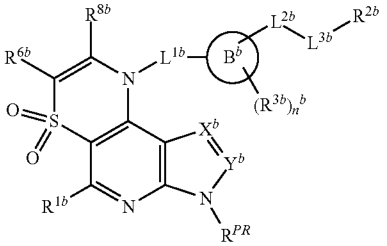

(3b)-2

A compound (2b)-2 can be obtained by cyclization of a compound (2b)-1.

A compound (2b)-1 can be converted to a compound (2b)-2 by using an equivalent or excessive amount of $R^{8b}CHO$, $R^{8b}CO_2R^{Q}$, $R^{8b}C(OR^{Q})_3$, $R^{8b}CONR^{Q}_2$ or $R^{8b}C(OR^{Q})_2NR^{Q}_2$ (wherein $R^{Q}$ is a hydrogen atom or a $C_{1-6}$ alkyl group) in an appropriate solvent or in the absence of solvent at room temperature to a refluxing temperature. Microwave irradiation or the presence of an acid or a base is sometimes effective for smooth progress of the reaction.

A compound (2b)-2 having an oxygen atom as $Y^A$ can be converted to a compound (2b)-2 having a sulfur atom as $Y^A$ by using an equivalent or excessive amount of a thiocarbonylation agent such as phosphorus pentasulfide or Lawesson's reagent in an appropriate solvent or in the absence of solvent at −78° C. to a refluxing temperature.

A compound (2b)-2 having a protective group as $R^{PR}$ can be converted to a compound having a hydrogen atom as $R^{PR}$ by deprotection.

A compound (3b)-2 can be obtained by cyclization of a compound (3b)-1 like the synthesis of a compound (2b)-2.

A compound (3b)-2 having a protective group as $R^{PR}$ can be converted to a compound having a hydrogen atom as $R^{PR}$ by deprotection.

Among the compounds represented by the formula ($I^b$), the compounds (4b)-2, (4b)-3 and (4b)-4 can be produced, for example, through the following scheme (4b) (wherein $Y^A$ is an oxygen atom or a sulfur atom, $R^{PR}$ is a hydrogen atom or a protective group such as a Ts group, a TIPS group or a SEM group, and the other symbols are the same as defined above).

(4b)

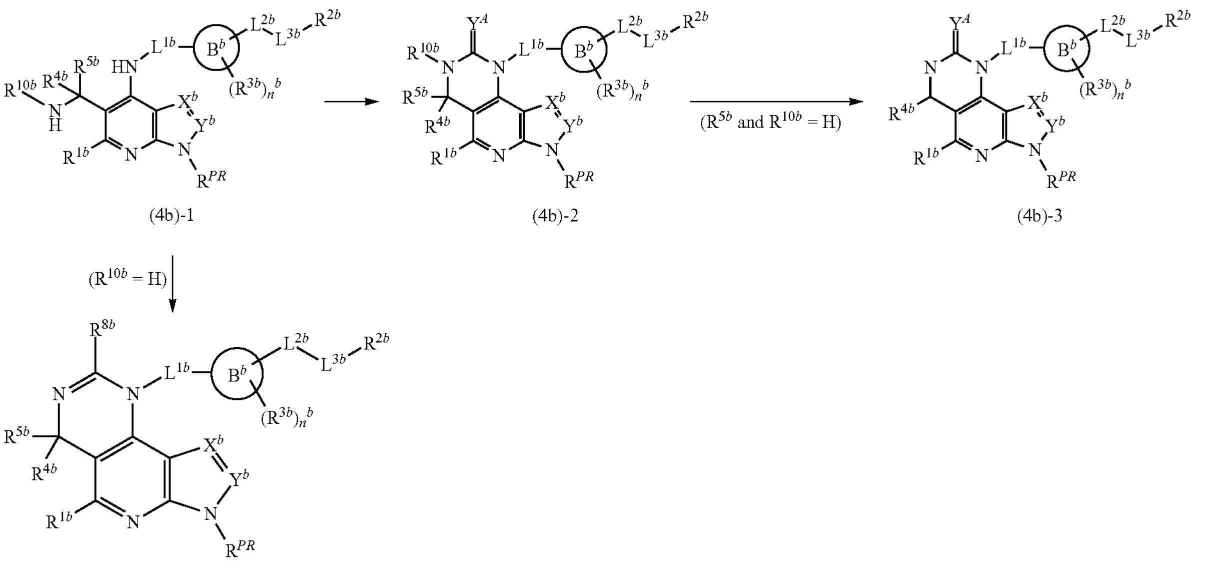

(4b)-1 (4b)-2 (4b)-3

(4b)-4

A compound (4b)-2 can be obtained by cyclization of a compound (4b)-1.

A compound (4b)-1 can be converted to a compound (4b)-2 by using an equivalent or excessive amount of phosgene, phosgene dimmer, phosgene trimer, 1,1'-carbonyldiimidazole, dimethyl carbonate, 1,1'-thiocarbonyldiimidazole, carbon disulfide or the like in an appropriate solvent at room temperature to a refluxing temperature. The presence of an acid or a base is sometimes effective for smooth progress of the reaction.

A compound (4b)-2 having hydrogen atoms as $R^{5b}$ and $R^{10b}$ can be converted to a compound (4b)-3 by using a catalyst such as palladium-carbon or manganese dioxide in an appropriate solvent at room temperature to a refluxing temperature.

A compound (4b)-2 or (4b)-3 having an oxygen atom as $Y^A$ can be converted to a compound (4b)-2 or (4b)-3 having a sulfur atom as $Y^A$ by using a thiocarbonylation agent such as phosphorus pentasulfide or Lawesson's reagent in an appropriate solvent or in the absence of solvent at −78° C. to a refluxing temperature.

A compound (4b)-2 or (4b)-3 having a protective group as $R^{PR}$ can be converted to a compound having a hydrogen atom as $R^{PR}$ by deprotection.

A compound (4b)-1 having a hydrogen atom as $R^{10b}$ can be converted to a compound (4b)-4 by cyclization.

A compound (4b)-1 can be converted to a compound (4b)-4 by using an equivalent or excessive amount of $R^{8b}CHO$, $R^{8b}CO_2R^Q$, $R^{8b}C(OR^Q)_3$, $R^{8b}CONR^Q_2$ or $R^{8b}C(OR^Q)_2NR^Q_2$ (wherein $R^Q$ is a hydrogen atom or $C_{1-6}$ alkyl group) in an appropriate solvent or in the absence of solvent at room temperature to a refluxing temperature. Microwave irradiation or the presence of an acid or a base is sometimes effective for smooth progress of the reaction.

A compound (4b)-4 having a protective group as $R^{PR}$ can be converted to a compound having a hydrogen atom as $R^{PR}$ by deprotection.

Among the compounds represented by the formula ($I^b$), the compounds (5b)-2 can be produced, for example, through the following scheme (5b) (wherein $Y^A$ is an oxygen atom or a sulfur atom, $R^{PR}$ is a hydrogen atom or a protective group such as a Ts group, a TIPS group or a SEM group, and the other symbols are the same as defined above).

(5b)

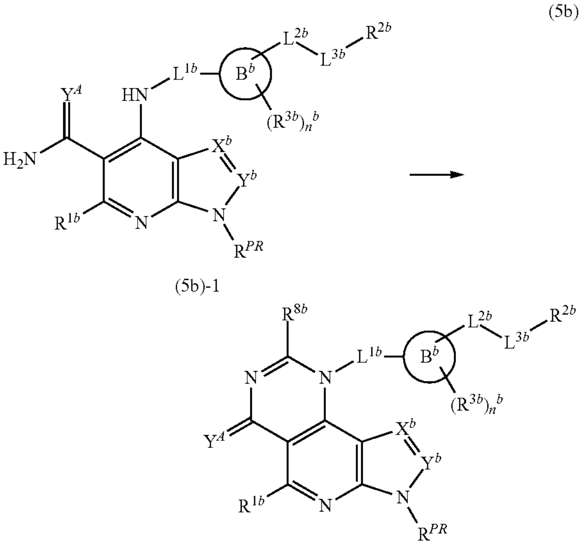

(5b)-1

(5b)-2

A compound (5b)-2 can be obtained by cyclization of a compound (5b)-1.

A compound (5b)-1 can be converted to a compound (5b)-2 by using an equivalent or excessive amount of $R^{8b}CHO$, $R^{8b}CO_2R^Q$, $R^{8b}C(OR^Q)_3$, $R^{8b}CONR^Q_2$ or $R^{8b}C(OR^Q)_2NR^Q_2$ (wherein $R^Q$ is a hydrogen atom or a $C_{1-6}$ alkyl group) in an appropriate solvent or in the absence of solvent at room temperature to a refluxing temperature. Microwave irradiation or the presence of an acid or a base is sometimes effective for smooth progress of the reaction.

A compound (5b)-2 having an oxygen atom as $Y^A$ can be converted to a compound having a sulfur atom as $Y^A$ by using an equivalent or excessive amount of a thiocarbonylation agent such as phosphorus pentasulfide or Lawesson's reagent in an appropriate solvent or in the absence of solvent at −78° C. to a refluxing temperature.

A compound (5b)-2 having a protective group as $R^{PR}$ can be converted to a compound having a hydrogen atom as $R^{PR}$ by deprotection.

Among the compounds represented by the formula ($I^b$), the compounds (6b)-2 and (6b)-3 can be produced, for example, through the following scheme (6b) (wherein $X^b$ is a bromine atom or an iodine atom, $R^{PR}$ is a hydrogen atom or a protective group such as a Ts group, a TIPS group or a SEM group, and the other symbols are the same as defined above).

(6b)

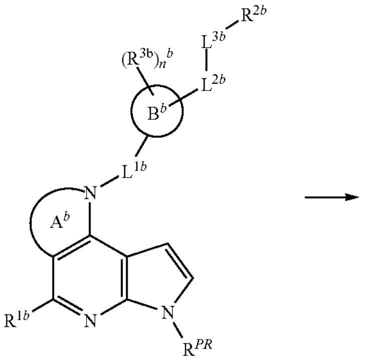

(6b)-1

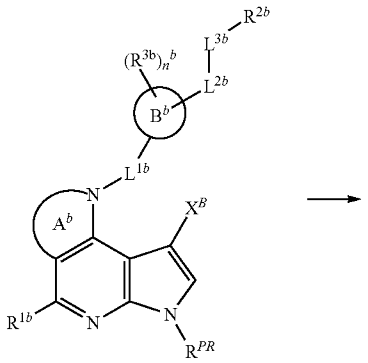

(6b)-2

-continued

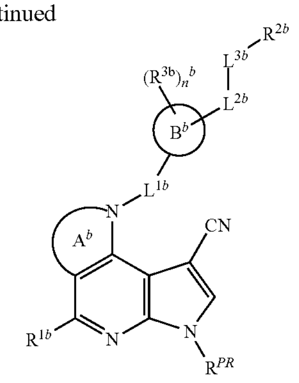

(6b)-3

A compound (6b)-3 can be obtained by bromination or iodination of a compound (6b)-1 followed by cyanization of the resulting compound (6b)-2.

A compound (6b)-1 can be converted to a compound (6b)-2 by using an equivalent or excessive amount of a halogenating agent such as bromine, iodine, N-bromosuccinimide or N-iodosuccinimide in an appropriate solvent or in the absence of solvent at −78° C. to a refluxing temperature.

A compound (6b)-2 can be converted to a compound (6b)-3 by using an equivalent or excessive amount of a metal cyanide such as copper cyanide or zinc cyanide in the presence of a palladium catalyst such as tetrakis(triphenylphosphine)palladium(0) or bis(triphenylphosphine)palladium(II) dichloride in an appropriate solvent or in the absence of solvent at room temperature to a refluxing temperature.

A compound (6b)-2 or (6b)-3 having a protective group as $R^{PR}$ can be converted to a compound having a hydrogen atom as $R^{PR}$ by deprotection.

Synthesis of Starting Materials 1b

The compounds (7b)-2 can be produced, for example, through the following scheme (7b) (wherein $R^L$ is a leaving group such as a chlorine atom, a methanesulfonyloxy group or a p-toluenesulfonyloxy group, $R^{PR}$ is a hydrogen atom or a protective group such as a Ts group, a TIPS group or a SEM group, and the other symbols are the same as defined above).

(7b)

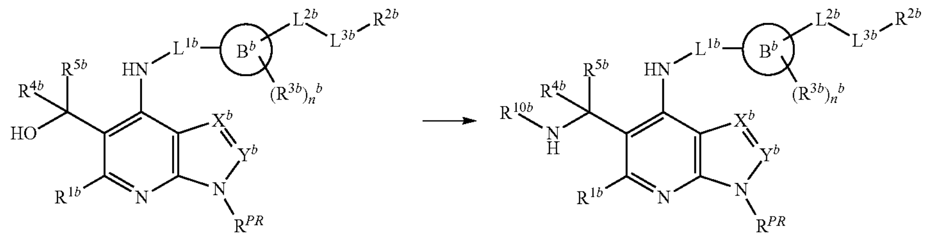

(7b)-1 (7b)-2

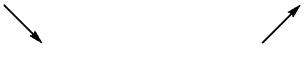

-continued

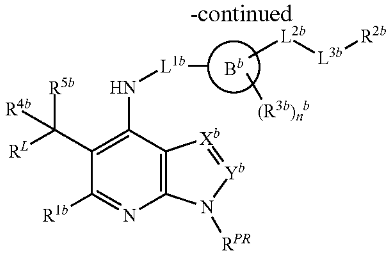

(7b)-3

A compound (7b)-2 can be obtained by a Mitsunobu reaction of a compound (7b)-1 with $R^{10b}R^{PR1}$ NH (wherein $R^{PR1}$ is a protective group suited for a Mitsunobu reaction such as a methanesulfonyl group or a p-toluenesulfonyl group) following by deprotection.

A compound (7b)-1 can be converted to a compound (7b)-2 by using equivalent or excessive amounts of $R^{10b}R^{PR1}$NH, a Mitsunobu reagent and a phosphine reagent in an appropriate solvent or in the absence of solvent at −78° C. to a refluxing temperature, followed by deprotection. As a Mitsunobu reagent, diethyl azodicarboxylate, diisopropyl azodicarboxylate or the like may be mentioned, and as a phosphine reagent, triphenylphosphine, tributylphosphine or the like may be mentioned. A compound (7b)-2 having a hydrogen atom as $R^{10b}$ can be obtained by a similar reaction using phthalimide instead of $R^{10b}R^{PR1}$ NH followed by deprotection.

A compound (7b)-2 can be obtained by conversion of a compound (7b)-1 to a compound (7b)-3 having a leaving group $R^L$ followed by a substitution reaction using $R^{10b}NH_2$.

A compound (7b)-1 can be converted to a compound (7b)-3 by using an equivalent or excessive amount of phosphorus oxychloride, thionyl chloride, methanesulfonyl chloride, p-toluenesulfonyl chloride or the like in an appropriate solvent or in the absence of solvent at −78° C. to a refluxing temperature. The presence of a base is sometimes effective for smooth progress of the reaction.

A compound (7b)-3 can be converted to a compound (7b)-2 by using an equivalent or excessive amount of $R^{10b}NH_2$ in an appropriate solvent or in the absence of solvent at −78° C. to a refluxing temperature. Microwave irradiation or the presence of a base is sometimes effective for smooth progress of the reaction.

Synthesis of Starting Materials 2b

The compounds (8b)-3 can be produced, for example, through the following scheme (8b) (wherein $R^{PR}$ is a hydrogen atom or a protective group such as a Ts group, a TIPS group or a SEM group, and the other symbols are the same as defined above).

(8b)

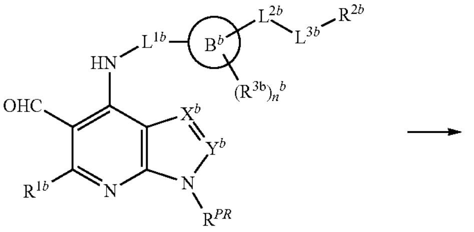

(8b)-1

-continued

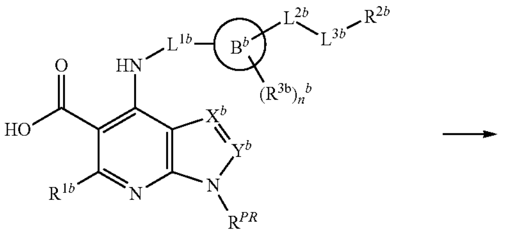

(8b)-2

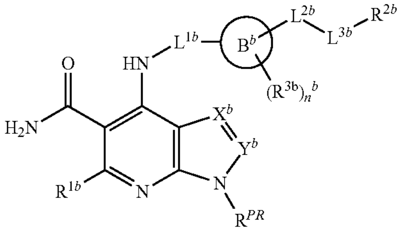

(8b)-3

A compound (8b)-3 can be obtained by oxidation of a compound (8b)-1 followed by condensation of the resulting compound (8b)-2.

A compound (8b)-1 can be converted to a compound (8b)-2 by using an equivalent or excessive amount of a oxidizing agent such as potassium permanganate or sodium chlorite in an appropriate solvent or in the absence of solvent at room temperature to a refluxing temperature.

A compound (8b)-2 can be converted to a compound (8b)-3 by using equivalent or excessive amounts of ammonia-methanol or its equivalent and a condensation agent such as N,N'-dicyclohexylcarbodiimide or 1-ethyl-3-(3-dimethylaminopropyl)carbodiimide hydrochloride in an appropriate solvent or in the absence of solvent at 0° C. to a refluxing temperature. The presence of a catalyst such as N-hydroxybenzotriazole or a base is sometimes effective for smooth progress of the reaction.

Synthesis of Staring Materials 3b

The compounds (9b)-2 and (9b)-3 can be produced, for example, through the following scheme (9b) (wherein $R^{PR}$ is a hydrogen atom or a protective group such as a Ts group, a TIPS group or a SEM group, and the other symbols are the same as defined above).

(9b)

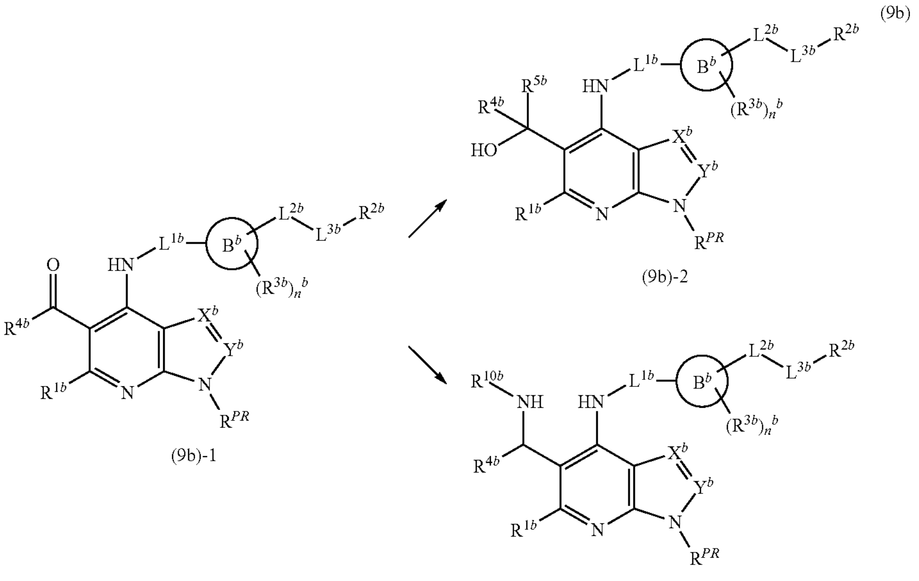

(9b)-1 (9b)-2 (9b)-3

A compound (9b)-2 can be obtained by an addition reaction of a compound (9b)-1.

A compound (9b)-1 can be converted to a compound (9b)-2 by using an equivalent or excessive amount of an addition reaction reagent in a solvent inert to the reaction at −78° C. to a refluxing temperature. As an addition reaction reagent, a hydride reducing agent such as sodium borohydride or diisobutylaluminum hydride or a metal reagent such as methyllithium or phenylmagnesium bromide may be mentioned.

A compound (9b)-3 can be obtained by reductive N-alkylation of a compound (9b)-1 through formation of an imine.

A compound (9b)-1 can be converted to a compound (9b)-3 by using equivalent or excessive amounts of $R^{10b}NH_2$ and a hydride reducing agent such as sodium cyanoborohydride or sodium triacetoxyborohydride in an appropriate solvent or in the absence of solvent at 0° C. to a refluxing temperature. Microwave irradiation or the presence of an acid is sometimes effective for smooth progress of the reaction. A compound having a hydrogen atom as $R^{10b}$ can be obtained by using hydroxylamine or its equivalent instead of $R^{10b}NH_2$ and lithium aluminum hydride, zinc or a hydrogen atmosphere containing palladium-carbon as a reducing agent.

Synthesis of Starting Materials 4b

The compounds (10b)-3, (11b)-3 and (12b)-3 can be produced, for example, through the following schemes (10b), (11b) and (12b) (wherein $R^{PR}$ is a hydrogen atom or a protective group such as a Ts group, a TIPS group or a SEM group, and the other symbols are the same as defined above).

(10b)

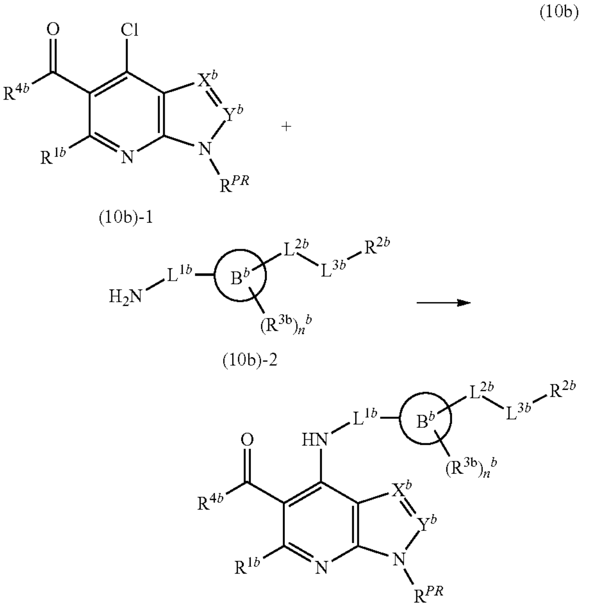

(10b)-1 (10b)-2 (10b)-3

(11b)

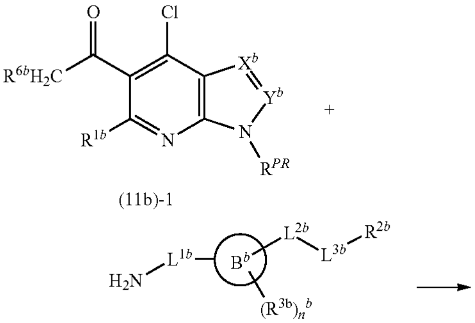

(11b)-1 (11b)-2

-continued

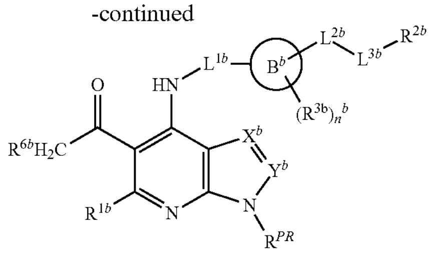

(11b)-3

(12b)

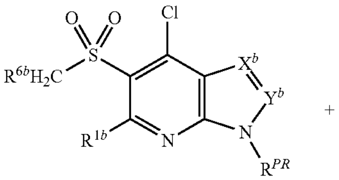

(12b)-1

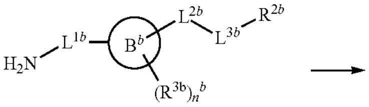

(12b)-2

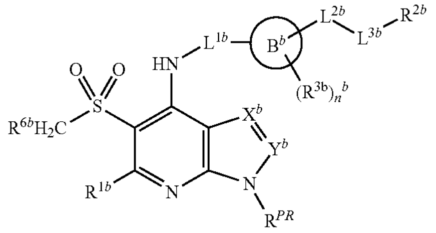

(12b)-3

A compound (10b)-1 can be converted to a compound (10b)-3 by using an equivalent or excessive amount of an amine derivative (10b)-2 in an appropriate solvent or in the absence of solvent at room temperature to a refluxing temperature. The substituent reaction is preferred to be carried out under microwave irradiation or sometimes in the presence of a base or may be carried out under the reaction conditions used for the Buchwald-Hartwig reaction (for example, by referring to Advanced Synthesis & Catalysis, 2004, 346, pp. 1599-1626). It is possible to appropriately combine tris(dibenzylideneacetone)dipalladium (0), tetrakis (triphenylphosphine)palladium(0), palladium (II) acetate or the like with 4,5-bis(diphenylphosphino)-9,9-dimethylxanthene (Xantphos), 2-dicyclohexylphosphino-2',6'-dimethoxybiphenyl (SPhos), 2-dicyclohexylphosphino-2',4',6'-triisopropylbiphenyl (XPhos) or the like, without particular restrictions.

Compounds (11b)-3 and (12b)-3 can be obtained by using a compound (11b)-1 and an amine derivative (11b)-2 or a compound (12b)-1 and an amine derivative (12b)-2, like a compound (10b)-3.

Synthesis of Starting Materials 5b

The compounds (13b)-4 can be produced, for example, through the following scheme (13b) (wherein $R^{PR}$ is a hydrogen atom or a protective group such as a Ts group, a TIPS group or a SEM group, $R^{Q}$ is a hydrogen atom or a $C_{1-6}$ alkyl group, and the other symbols are the same as defined above).

(13b)

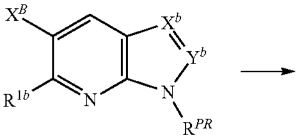

(13b)-1

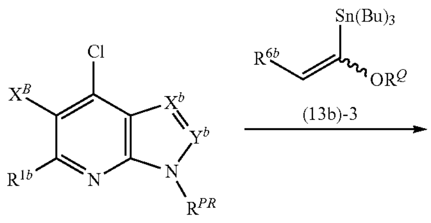

(13b)-2

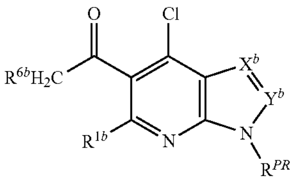

(13b)-4

A compound (13b)-4 can be obtained by the Stille reaction of compounds (13b)-2 and (13b)-3 (for example, by referring Bulletin of the Chemical Society of Japan, 1987, 60, pp. 767-768).

A compound (13b)-2 can be converted to a compound (13b)-4 by using an equivalent or excessive amount of a compound (13b)-3 in the presence of a palladium catalyst such as tetrakis(triphenylphosphine)palladium (0), bis(triphenylphosphine)palladium (II) dichloride or bis(acetonitrile) palladium (II) dichloride in an appropriate solvent or in the absence of solvent at room temperature to a refluxing temperature. The presence of an acid or a base is sometimes effective for smooth progress of the reaction.

A compound (13b)-2 can be obtained by oxidization of a compound (13b)-1 followed by a reaction of the resulting N-oxide derivative with a chlorination agent.

A compound (13b)-1 can be converted to a compound (13b)-2 by oxidation with an equivalent or excessive amount of an oxidizing agent such as m-chloroperbenzoic acid, peracetic acid or aqueous hydrogen peroxide in an appropriate solvent or in the absence of solvent at 0° C. to a refluxing temperature, followed by a reaction of the resulting N-oxide derivative with an equivalent or excessive amount of a chlorination agent such as phosphorus oxychloride or methanesulfonyl chloride in an appropriate solvent or in the absence of solvent at room temperature to a refluxing temperature.

Synthesis of Starting Materials 6b

The compounds (14b)-3 and (14b)-5 can be produced, for example, through the following scheme (14b) (wherein $R^{PR}$ is a hydrogen atom or a protective group such as a Ts group, a TIPS group or a SEM group, and the other symbols are the same as defined above).

(14b)

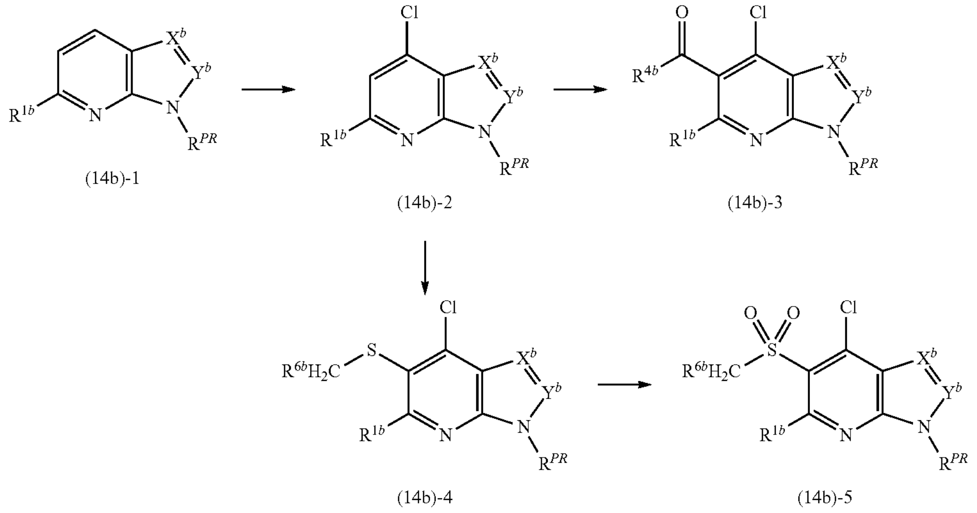

(14b)-1 (14b)-2 (14b)-3 (14b)-4 (14b)-5

Compounds (14b)-3 and (14b)-4 can be obtained by coupling of an anion formed from a compound (14b)-2.

A compound (14b)-2 can be converted to a compound (14b)-3 by lithiation using an equivalent or excessive amount of an organic metal reagent such as n-butyllithium or s-butyllithium in an appropriate solvent or in the absence of solvent at −78° C. to room temperature followed by coupling with an electrophilic reagent such as N,N-dimethylformamide, $R^{4b}CO_2R^Q$, $R^{4b}CONR^Q_2$ or $R^{4b}C(O)N(OR^Q)R^Q$ (wherein $R^Q$ is a hydrogen atom or a $C_{1-6}$ alkyl group).

A compound (14b)-2 can be converted to a compound (14b)-4 by lithiation using an equivalent or excessive amount of an organic metal reagent such as n-butyllithium or s-butyllithium in an appropriate solvent or in the absence of solvent at −78° C. to room temperature followed by coupling with an electrophilic reagent such as $(R^{6b}CH_2S)_2$.

A compound (14b)-4 can be converted to a compound (14b)-5 by using an equivalent or excessive amount of an oxidizing agent such as m-chloroperbenzoic acid, peracetic acid or aqueous hydrogen peroxide in an appropriate solvent or in the absence of solvent at 0° C. to a refluxing temperature.

A compound (14b)-1 can be converted to a compound (14b)-2 by oxidation with an equivalent or excessive amount of an oxidizing agent such as m-chloroperbenzoic acid, peracetic acid or aqueous hydrogen peroxide in an appropriate solvent or in the absence of solvent at 0° C. to a refluxing temperature, followed by a reaction of the resulting N-oxide derivative with an equivalent or excessive amount of a chlorination agent such as phosphorus oxychloride or methanesulfonyl chloride in an appropriate solvent or in the absence of solvent at room temperature to a refluxing temperature.

Synthesis of Starting Materials 7b

The compounds (15b)-4 can be produced, for example, through the following scheme (15b) (wherein $R^{PR}$ is a hydrogen atom or a protective group such as a Ts group, a TIPS group or a SEM group).

(15b)

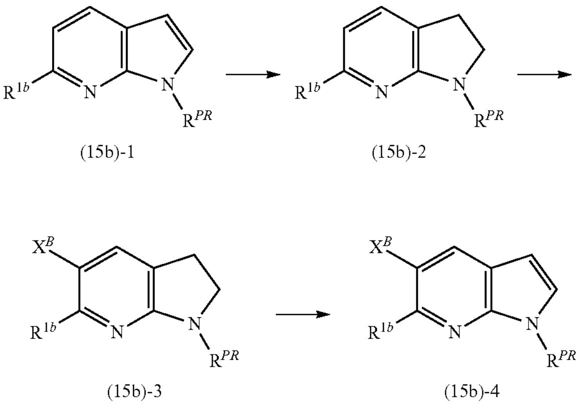

(15b)-1 (15b)-2 (15b)-3 (15b)-4

A compound (15b)-4 can be obtained by bromination or iodination of a compound (15b)-2 followed by dehydrogenation of the resulting compound (15b)-3.

A compound (15b)-3 can be converted to a compound (15b)-4 by using a catalyst such as palladium-carbon or manganese dioxide in an appropriate solvent or in the absence of solvent at room temperature to a refluxing temperature.

A compound (15b)-2 can be converted to a compound (15b)-3 by using an equivalent or excessive amount of a halogenating agent such as bromine, N-bromosuccinimide, iodine or N-iodosuccinimide in an appropriate solvent or in the absence of solvent at 0° C. to a refluxing temperature.

A compound (15b)-1 can be converted to a compound (15b)-2 in the presence of a palladium-carbon catalyst under a hydrogen atmosphere in an appropriate solvent or in the absence of solvent at room temperature to a refluxing temperature.

Synthesis of Starting Materials 8b

The compounds (16b)-2 can be produced, for example, through the following scheme (16b).

(16b)

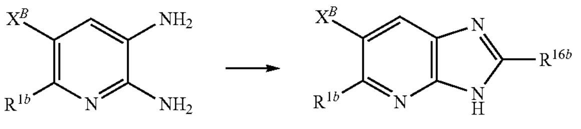

(16b)-1 (16b)-2

A compound (16b)-1 can be converted to a compound (16b)-2 by using an equivalent or excessive amount of $R^{16b}CO_2R^Q$ or $R^{16b}C(OR^Q)_3$ (wherein $R^Q$ is a hydrogen atom or a $C_{1-6}$ alkyl group) in an appropriate solvent or in the absence of solvent at room temperature to a refluxing temperature.

For synthesis of 7-azaindole or 1-deazapurine, the following general methods may be referred to.

As general methods for synthesis of 7-azaindole, those disclosed in Current Organic Chemistry, 2001, 5, pp. 471-506 are known.

As general methods for synthesis of 1-deazapurine, those disclosed in Shin-pen Hetero-kan Kagoubutsu Ouyou-hen (Kodansha, 2004) pp. 233-251 are known.

Synthesis of Starting Materials 9b (17b)

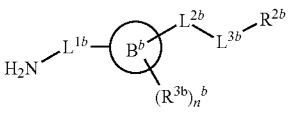

(17b)-1

The amine compounds (17b)-1 can be produced from the corresponding nitrile compounds, acid amide compounds, oxime compounds, halogen compounds, ketone compounds, aldehyde compounds, alcohol compounds, boron compounds, epoxide compounds, acid imide compounds and carbamate compounds (for example, by referring to Jikken Kagaku Koza vol. 20 Yuki Gosei II, edited by the Chemical Society of Japan, published by MARUZEN Co., Ltd., 1992; Bioorganic & Medicinal Chemistry, 13, 4022, 2005, Kuramochi T. et al.; Journal of Medicinal Chemistry, 50, 149, 2007; Journal of Organic Chemistry, 46, 4296, 1981; Journal of Organic Chemistry, 44, 2081, 1979; Acta Chemica Scandinavica, 19, 1741, 1965; and Organic Letters, 5, 4497, 2003).

Among the compounds represented by the formula ($I^b$), the compounds (18b)-2 and (18b)-3 can be produced, for example, through the following scheme (18b) (wherein $R^{PR}$ is a hydrogen atom or a protective group such as a Ts group, a TIPS group or a SEM group, and the other symbols are the same as defined above).

(18b)

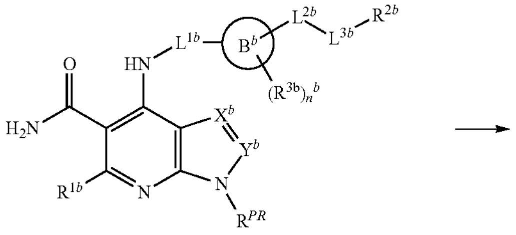

(18b)-1

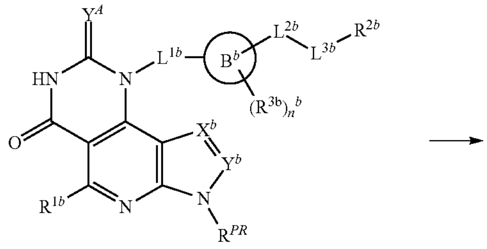

(18b)-2

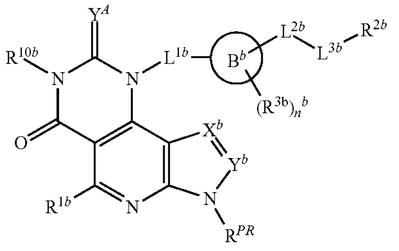

(18b)-3

A compound (18b)-3 can be obtained by cyclization of a compound (18b)-1 followed by a substitution reaction of the resulting compound (18b)-2.

A compound (18b)-1 can be converted to a compound (18b)-2 by using an equivalent or excessive amount of phosgene, phosgene dimer, phosgene trimer, 1,1'-carbonyldiimidazole, dimethyl carbonate, 1,1'-thiocarbonyldiimidazole, carbon disulfide or the like in an appropriate solvent or in the absence of solvent at room temperature to a refluxing temperature. The presence of an acid or a base or microwave irradiation is sometimes effective for smooth progress of the reaction.

A compound (18b)-2 can be converted to a compound (18b)-3 by using an equivalent or excessive amount of an electrophilic reagent represented by $R^{10b}$-$R^L$ (wherein $R^L$ is a leaving group such as a chlorine atom, a methanesulfonyloxy group or a p-toluenesulfonyloxy group) such as an alkyl halide, an alkyl mesylate or an aryl halide in the presence of a base such as triethylamine in an appropriate solvent or in the absence of solvent at room temperature to a refluxing temperature. Microwave irradiation is sometimes effective for smooth progress of the reaction. A compound (18b)-2 can also be converted to a compound (18b)-3 by using equivalent or excessive amounts of a primary or secondary alcohol, a Mitsunobu reagent and a phosphine reagent in an appropriate solvent or in the absence of solvent at −78° C. to a refluxing temperature. As a Mitsunobu reagent, diethyl azodicarboxylate, diisopropyl azodicarboxylate or the like may be mentioned, and as a phosphine reagent, triphenylphosphine, tributylphosphine or the like may be mentioned.

A compound (18b)-2 or (18b)-3 having an oxygen atom as $Y^A$ can be converted to a compound (18b)-2 or (18b)-3 having a sulfur atom as $Y^A$ by using an equivalent or excessive amount of a thiocarbonylation agent such as phosphorus pentasulfide or Lawesson's reagent in an appropriate solvent or in the absence of solvent at −78° C. to a refluxing temperature.

A compound (18b)-2 or (18)-3 having a protective group as $R^{PR}$ can be converted to a compound having a hydrogen atom as $R^{PR}$ by deprotection.

Among the compounds represented by the formula ($I^b$), the compounds (19b)-2 and (19b)-3 can be produced, for example, through the following scheme (19b) (wherein $R^{PR}$ is a hydrogen atom or a protective group such as a Ts group, a TIPS group or a SEM group, $R^{PR2}$ is a benzyl type protective group such as a benzyl group or a benzyloxycarbonyl group, m is 0~3, and the other symbols are the same as defined above).

(19b)

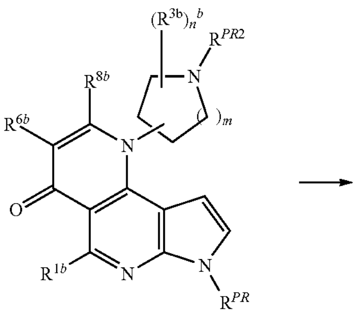

(19b)-1

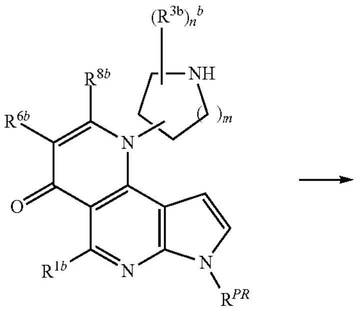

(19b)-2

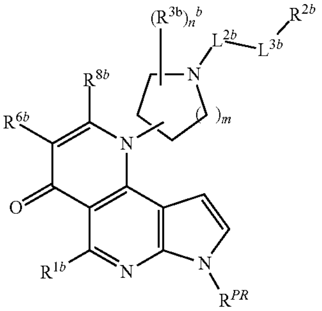

(19b)-3

A compound (19b)-3 can be obtained by deprotection of the $R^{PR2}$ in a compound (19b)-1 among the compounds (2b)-2 followed by a substitution reaction of the resulting compound (19b)-2.

A compound (19b)-1 having a benzyl type protective group as $R^{PR2}$ can be converted to a compound (19b)-2 by using a catalytic amount of palladium-carbon under a hydrogen atmosphere in an appropriate solvent at room temperature to a refluxing temperature. The presence of an acid is sometimes effective for smooth progress of the reaction.

A compound (19b)-2 can be converted to a compound (19b)-3 by using equivalent or excessive amounts of an electrophilic reagent represented by $R^{2b}L^{3b}L^{2b}$-$R^L$ (wherein $R^L$ is a leaving group such as a halogen atom, a methanesulfonyloxy group or a p-toluenesulfonyloxy group) such as an alkyl halide, an acid chloride, a sulfonyl chloride, a chloroformate ester, an isocyanate or an isothiocyanate and a base such as triethylamine in an appropriate solvent or in the absence of solvent at −78° C. to a refluxing temperature. A compound (19b)-2 can also be converted to a compound (19b)-3 by using an equivalent or excessive amount of an aldehyde or a ketone in the presence of a hydride reducing agent such as sodium cyanoborohydride or 2-picoline borane in an appropriate solvent or in the absence of solvent at 0° C. to a refluxing temperature. Microwave irradiation or the presence of an acid is sometimes effective for smooth progress of the reaction.

A compound (19b)-3 having a protective group as $R^{PR}$ can be converted to a compound having a hydrogen atom as $R^{PR}$ by deprotection.

Among the compounds represented by the formula ($I^b$), the compounds (20b)-2 and (20b)-3 can be produced, for example, through the following scheme (20b) (wherein $R^{PR}$ is a hydrogen atom or a protective group such as a Ts group, a TIPS group or a SEM group, $R^{PR2}$ is a benzyl type protective group such as a benzyl group or a benzyloxycarbonyl group, m is 0, 1, 2 or 3 and the other symbols are the same as defined above).

(20b)

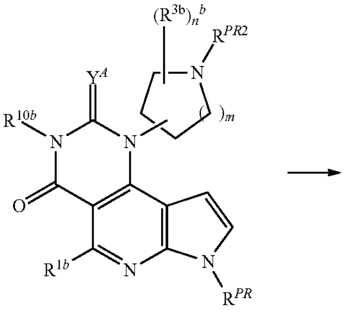

(20b)-1

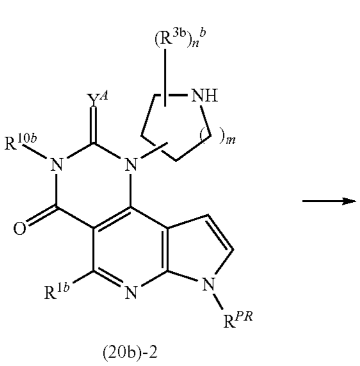

(20b)-2

-continued

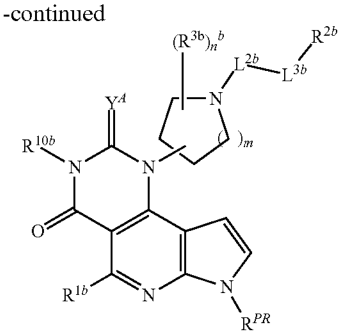

(20b)-3

A compound (20b)-3 can be obtained by deprotection of the $R^{PR2}$ in a compound (20b)-1 among the compounds (18b)-3 followed by a substitution reaction of the resulting compound (20b)-2.

A compound (20b)-1 having a benzyl type protective group as $R^{PR2}$ can be converted to a compound (20b)-2 by using a catalytic amount of palladium-carbon under a hydrogen atmosphere in an appropriate solvent at room temperature to a refluxing temperature. The presence of an acid is sometimes effective for smooth progress of the reaction.

A compound (20b)-2 can be converted to a compound (20b)-3 by using equivalent or excessive amounts of an electrophilic reagent represented by $R^{2b}L^{3b}L^{2b}$-$R^L$ (wherein $R^L$ is a leaving group such as a halogen atom, a methanesulfonyloxy group or a p-toluenesulfonyloxy group) such as an alkyl halide, an acid chloride, sulfonyl chloride, a chloroformate, an isocyanate or an isothiocyanate and a base such as triethylamine in an appropriate solvent or in the absence of solvent at −78° C. to a refluxing temperature. A compound (20b)-2 can also be converted to a compound (20b)-3 by using an equivalent or excessive amount of an aldehyde or a ketone in the presence of a reducing agent such as sodium cyanoborohydride or 2-picoline borane in an appropriate solvent or in the absence of solvent at 0° C. to a refluxing temperature. Microwave irradiation or the presence of an acid is sometimes effective for smooth progress of the reaction.

A compound (20b)-3 having a protective group as $R^{PR}$ can be converted to a compound having a hydrogen atom as $R^{PR}$ by deprotection.

Among the compounds represented by the formula ($I^b$), the compounds (21 b)-2, (21b)-3 and (21b)-4 can be produced, for example, through the following scheme (21b) (wherein $R^{PR}$ is a hydrogen atom or a protective group such as a Ts group, a TIPS group or a SEM group, $R^{PR5}$ is a protective group such as a benzyl group or an acetyl group, $R^Z$ is a hydrogen atom or a $C_{1-6}$ alkyl group, m is 0, 1, 2 or 3, and the other symbols are the same as defined above).

(21b)

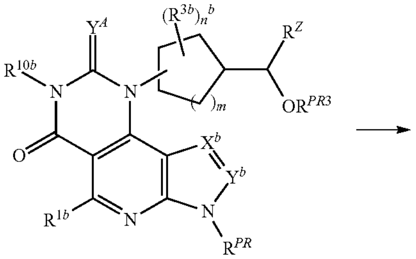

(21b)-1

-continued

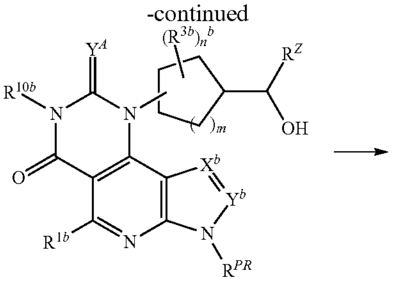

(21b)-2

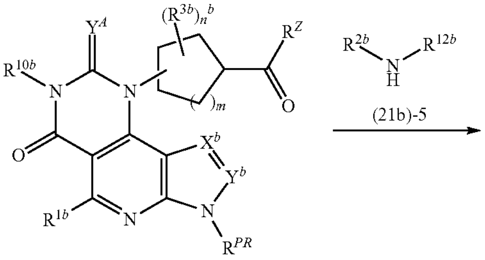

(21b)-3

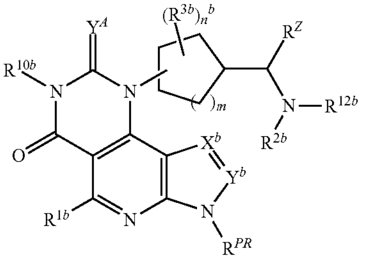

(21b)-4

A compound (21b)-1 among the compounds (18b)-3 is converted to a compound (21b)-2 by deprotection.

A compound (21 b)-2 can be converted to a compound (21 b)-3 by oxidation with an equivalent or excessive amount of an oxidizing agent such as 2-iodoxybenzoic acid or pyridinium chlorochromate in an appropriate solvent or in the absence of solvent at −78° C. to a refluxing temperature.

A compound (21b)-3 can be converted to a compound (21b)-4 by using equivalent or excessive amounts of a compound (21 b)-5 and a reducing agent such as 2-picoline borane or sodium triacetoxyborohydride in an appropriate solvent or in the absence of solvent at room temperature to a refluxing temperature.

Compounds (21b)-3 and (21b)-4 having a protective group as $R^{PR}$ can be converted to compounds (21 b)-3 and (21 b)-4 having a hydrogen atom as $R^{PR}$ by deprotection.

In the present invention, the tricyclic pyrimidine compounds of the present invention represented by the formula ($I^a$) and the tricyclic pyridine compounds of the present invention represented by the formula ($I^b$) may be present in the form of tautomers or geometrical isomers which undergo endocyclic or exocyclic isomerization, mixtures of tautomers or geometric isomers or mixtures of thereof. When the compounds of the present invention have an asymmetric center, whether or not resulting from an isomerization, the compounds of the present invention may be in the form of resolved optical isomers or in the form of mixtures containing them in certain ratios. Further, when the compounds of the present invention have two or more asymmetric centers, the compounds of the present invention can be in the form of diastereomers due to optical isomerism about them. The compounds of the present invention may be in the form of a mixture of all these isomers in certain ratios. For example, diastereomer can be separated by techniques well known to those skilled in the art such as fractional crystallization, and optical isomers can be obtained by techniques well known in the field of organic chemistry for this purpose.

The tricyclic pyrimidine compounds of the present invention represented by the formula ($I^a$) and the tricyclic pyridine compounds of the present invention represented by the formula ($I^b$) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol, 1-propanol and 2-propanol, and the present invention covers any of these forms.

The present invention covers pharmaceutically acceptable salts of the compounds of the present invention represented by the formulae ($I^a$) and ($I^b$).

The compounds of the present invention represented by the formulae ($I^a$) and ($I^b$) may be converted to pharmaceutically acceptable salts or may be liberated from the resulting salts, if necessary. The pharmaceutically acceptable salts of the present invention may be, for example, salts with alkali metals (such as lithium, sodium and potassium), alkaline earth metals (such as magnesium and calcium), ammonium, organic bases, amino acids, inorganic acids (such as hydrochloric acid, hydrobromic acid, phosphoric acid and sulfuric acid) and organic acids (such as acetic acid, citric acid, maleic acid, fumaric acid, tartaric acid, benzenesulfonic acid, methanesulfonic acid and p-toluenesulfonic acid).

The present invention covers prodrugs of the compounds of the present invention represented by the formulae ($I^a$) and ($I^b$).

Prodrugs are derivatives of medicinal compounds having chemically or metabolically degradable groups and give pharmacologically active medicinal compounds upon solvolysis or under physiological conditions in vivo. Methods for selecting or producing appropriate prodrugs are disclosed in, for example, Design of Prodrugs (Elsevier, Amsterdam 1985). In the present invention, in the case of a compound having a hydroxy group, prodrugs like acyloxy derivatives obtained by reacting the compound with appropriate acyl halides, appropriate acid anhydrides or appropriate haloalkoxycarbonyl compounds may, for example, be mentioned. Structures particularly preferred as prodrugs include $-OCOC_2H_5$, $-OCO(t-Bu)$, $-OCOC_{15}H_{31}$, $-OCO(m-CO_2Na-Ph)$, $-OCOCH_2CH_2CO_2Na$, $-OCOCH(NH_2)CH_3$, $-OCOCH_2N(CH_3)_2$, $-O-CH_2OC(=O)CH_3$ or the like. In the case of a compound having an amino group, prodrugs obtained by reacting the compound having an amino group with appropriate acid halides, appropriate mixed acid anhydrides or haloalkoxycarbonyl compounds may, for example, be mentioned. Structures particularly preferred as prodrugs include $-NHCO(CH_2)_{20}OCH_3$, $-NHCOCH(NH_2)CH_3$, $-NH-CH_2O(C=O)CH_3$ or the like.

The JAK inhibitors and the preventive, therapeutic and/or improving agents for diseases against which inhibition of JAK is effective are those mentioned below among the tricyclic pyrimidine compounds and the tricyclic pyridine compounds of the present invention.

1) JAK inhibitors containing the compounds as defined in any one of $1^a$) to $62^a$) and $1^b$) to $44^b$), tautomers or pharmaceutically acceptable salts of the compounds or solvates thereof, as an active ingredient.

2) Preventive, therapeutic or improving agents for diseases against which inhibition of JAK is effective, which contains the JAK inhibitors as defined in 1) as an active ingredient.

3) Therapeutic agents for rheumatoid arthritis, which contain the JAK inhibitors as defined in 1) as an active ingredient.

4) Medicaments containing the compound as defined in any one of $1^a$) to $62^a$) and $1^b$) to $44^b$), tautomers or pharmaceutically acceptable salts of the compounds or solvates thereof, as an active ingredient.

The preventive, therapeutic and improving agents for diseases against which inhibition of JAK is effective which contain the JAK inhibitors of the present invention, as an active ingredient may usually be administered as oral medicines such as tablets, capsules, powder, granules, pills and syrup, as rectal medicines, percutaneous medicines or injections. The agents of the present invention may be administered as a single therapeutic agent or as a mixture with other therapeutic agents. Though they may be administered as they are, they are usually administered in the form of medical compositions. These pharmaceutical preparations can be obtained by adding pharmacologically and pharmaceutically acceptable additives by conventional methods. Namely, for oral medicines, ordinary additives such as excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the agents of the present invention for administration to human is usually about from 0.1 to 1000 mg/body/day in the case of oral drugs or rectal administration and about from 0.05 mg to 500 mg/body/day in the case of injections, though it depends on the age and conditions of the patient. The above-mentioned ranges are mere examples, and the dose should be determined from the conditions of the patient.

The present invention is used when it is expected to improve pathology of diseases associated with JAK1, JAK2 and JAK3 separately or in combination. Among these diseases, JAK3-associated diseases are, in addition to rheumatoid arthritis, inflammatory or proliferative dermatoses such as psoriasis, atopic dermatitis, contact dermatitis, eczematoid dermatitis, seborrheic dermatitis, lichen planus, pemphigus, pemphigoid, epidermolysis bullosa, hives, angioedema, angiitis, erythema, dermal eosinophilia, lupus erythematosus, acne, alopecia areata, immune dermatoses, reversible airway obstruction, mucitis and angitis. Among these diseases, JAK3- and JAK1-associated diseases are, in addition to rheumatoid arthritis, asthma, atopic dermatitis, Alzheimer disease, atherosclerosis, cancer, leukemia, rejection of organ or tissue grafts (such as heart, kidney, liver, bone marrow, skin, horn, lung, pancreas, islet, small intestine, extremities, muscles, nerves, intervertebral disks, trachea, myoblasts and cartilage), graft-versus-host reaction after bone marrow transplantation and autoimmune diseases such as rheumatic disease, systemic lupus erythematosus (SLE), Hashimoto's disease, multiple sclerosis, myasthenia gravis, type I diabetes and diabetic complications. Among these diseases, JAK2-associated diseases include, for example, myeloproliferative disorders.

As an application of the present invention, treatment and prevention of the above-mentioned diseases may be mentioned, but there is no restriction.

Compounds of the present invention are administered either alone or in combination with one or more additional agents such as immunomodulators, antiinflammatory agents or antirheumatic drugs. The additional agents may be cyclosporin A, tacrolimus, leflunomide, deoxyspergualin, mycophenolate, azathioprine, etanercept (e.g. Enbrel®), infliximab (e.g. Remicade®), adalimumab (e.g. Humira®), certolizumab pegol (e.g. Cimzia®), Golimumab (e.g. Simponi®), Anakinra (e.g. Kineret®), rituximab (e.g. Rituxan®), Tocilizumab (e.g. Actemra®), methotrexate, aspirin, acetaminophen, ibuprofen, naproxen, piroxicam, and antiinflammatory steroids (e.g. prednisolone or dexamethasone), but are not restricted thereto.

Now, the present invention will be described in further detail with reference to Reference Synthetic Examples, Synthetic Examples, Assay Examples and Formulation examples. However, it should be understood that the present invention is by no means restricted by these specific Examples. In the Examples, "NMR" denotes nuclear magnetic resonance, "LC/MS" denotes high performance liquid chromatography-mass spectrometry, "v/v" means volume ratio. In the tables, "Rf" denotes Reference Synthetic Example, "Ex" denotes Synthetic Example, "Structure" denotes chemical structural formula, "diastereomixture" denotes a diastereomeric mixture, "racemate" denotes a racemic mixture, "cis/trans mixture" denotes a cis- and trans-isomeric mixture, and "E/Z mixture" denotes a E- and Z-isomeric mixture, and "Data" denotes physical property data, "condition" denotes measurement condition, "retention time" denotes retention time in LC/MS, "Compound Name" denotes compound name of the synthesized compound, "Morphology" denotes morphology of a synthesized compound, "Yield" denotes yield of a synthesized compound, "quant" denotes quantitative, "min" denotes minute.

In the Examples herein, "rac-" or "racemate" used in texts or tables for a compound having more than one asymmetric center means that the compound is in the form of a racemic mixture of the specified absolute configuration and its enantiomer.

The $^1$H-NMR data show chemical shifts δ (unit: ppm) (splitting pattern, value of integral) measured at 300 MHz (with JNM-ECP300, manufactured by JEOL Ltd or JNM-ECX300, manufactured by JEOL Ltd) using tetramethylsilane as an internal standard. "s" denotes "singlet", "d" denotes "doublet", "t" denotes "triplet", "q" denotes "quartet", "quint" denotes quintet, "sextet" denotes sextet, "septet" denotes septet, "dd" denotes doublet of doublets, "dt" denotes doublet of triplets, "td" denotes triplet of doublets, "dq" denotes doublet of quartets, "qd" denotes quartet of doublets, "tt" denotes triplet of triplets, "ddd" denotes doublet of doublet of doublets, "m" denotes multiplet, "br" denotes broad, "J" denotes coupling constant, "$CDCl_3$" denotes deuterated chloroform, "$CD_3OD$" denotes deuterated methanol, and "DMSO-$d_6$" denotes deuterated dimethyl sulfoxide.

For purification by silica gel column chromatography, Hi Flash column manufactured by Yamazen Corporation, a silica gel 60 manufactured by Merck & Co., Inc. or PSQ60B manufactured by Fuji Silysia Chemical Ltd. was used unless otherwise noted.

For purification by silica gel thin layer chromatography, PLC plate manufactured by Merck & Co., Inc. was used unless otherwise noted.

As a microwave reactor, Initiator sixty manufactured by Biotage was used.

LC/MS spectra were measured by using ESI (electrospray ionization). "$ESI^+$" denotes ESI-positive mode, and "$ESI^-$" denotes ESI-negative mode.

LC/MS condition 1
Instrument: Waters Alliance-ZQ
Column: Waters SunFire C18(3.5 μm, 2.1×20 mm)
Column Temp.: 40° C.
Eluents: Liquid A: 0.1% aqueous formic acid
Liquid B: 0.1% formic acid in acetonitrile
Elution: A mixture of Liquids A and B was flown at 0.4 m L/min while the mixing ratio was linearly changed from 90/10 (v/v) to 15/85 (v/v) over the first 3 minutes, and then the flow rate was linearly changed to 0.5 m L/min for 2 minutes at a constant mixing ratio of 15/85 (v/v). Then, the mixing ratio was linearly changed to 90/10 (v/v) over 0.5 minute and maintained at 90/10 (v/v) for 2.5 minutes.

LC/MS condition 2
Instrument: Waters Alliance-ZQ
Column: Waters SunFire C18(3.5 μm, 2.1×20 mm)
Column Temp.: 40° C.
Eluents: Liquid A: 0.2% aqueous formic acid
Liquid B: acetonitrile
Elution: A mixture of Liquids A and B was flown at 0.4 mL/min while the mixing ratio was linearly changed from 90/10 (v/v) to 15/85 (v/v) over the first 3 minutes, and then the flow rate was linearly changed to 0.5 m L/min over 2 minutes at a constant mixing ratio of 15/85 (v/v). Then, the mixing ratio was linearly changed to 95/5 (v/v) over 0.5 minute and maintained at 95/5 (v/v) for 1.5 minutes.

LC/MS condition 3
Instrument: Thermo LTQ XL
Column: Waters AQUITY UPLC BEH C18(1.7 μm, 2.1×50 mm)
Column Temp.: 40° C.
Eluents: Liquid A: 0.1% aqueous formic acid
Liquid B: 0.1% formic acid in acetonitrile
Elution: A mixture of Liquids A and B was flown at 0.6 mL/min at a mixing ratio of 90/10 (v/v) for the first 0.5 minutes, and then the mixing ratio was linearly changed to 10/90 (v/v) over 2.5 minutes and then maintained at 10/90 (v/v) for 0.7 minute. The mixing ratio and the flow rate were linearly changed to 90/10 (v/v) and 0.8 mL/min, respectively, over 0.1 minute, maintained constant for 1 minute and linearly changed to 90/10 (v/v) and 0.6 mL/min, respectively, over 0.1 minute.

Reference Synthetic Example[a] 1

4-Iodo-7H-pyrrolo[2,3-d]pyrimidine

Hydroiodic acid (55 wt %, 100 g) was mixed with 4-chloro-7H-pyrrolo[2,3-d]pyrimidine (manufactured by Tokyo Chemical Industry Co., Ltd., 10.6 g, 69.0 mmol) under cooling with ice and stirred at 0° C. for 1 hour and then at room temperature for one day. The precipitated solid was collected by filtration and washed with water. The residue was suspended in water, neutralized with 1 M aqueous sodium hydroxide and filtered. The yellow solid was washed with water and dried under reduced pressure to give the title compound as a yellow solid (16.2 g, yield 96%, including 10% 4-chloro-7H-pyrrolo[2,3-d]pyrimidine as the starting compound).

Reference Synthetic Example[a] 2

4-Iodo-7-(triisopropylsilyl)-7H-pyrrolo[2,3-d]pyrimidine

4-Iodo-7H-pyrrolo[2,3-d]pyrimidine (352 mg, 1.44 mmol) in tetrahydrofuran (15 mL) cooled to 0° C. was mixed with sodium hydride (55 wt % dispersion in mineral oil, 75.5 mg, 1.73 mmol) and chlorotriisopropylsilane (0.37 mL, 1.7 mmol) and stirred at room temperature for 45 minutes. After addition of water, the reaction mixture was extracted with ethyl acetate, and the organic layer was dried over anhydrous sodium sulfate and concentrated under reduced pressure. The residue was purified by silica gel column chromatography (hexane/ethyl acetate=100/1 (v/v)) to give the title compound as a pale yellow oil (431 mg, yield 74%).

Reference Synthetic Example[a] 3

Cyclohexyl[7-(triisopropylsilyl)-7H-pyrrolo[2,3-d]pyrimidin-4-yl]methanol n-Butyllithium (1.6 M solution in hexane, 0.23 mL, 0.380 mmol) was gradually added dropwise to 4-iodo-7-(triisopropylsilyl)-7H-pyrrolo[2,3-d]pyrimidine (126 mg, 0.310 mmol) in tetrahydrofuran (1.5 mL) cooled to −78° C., and the reaction mixture was stirred at −78° C. for 30 minutes. After addition of cyclohexanecarbaldehyde (42 μL, 0.35 mmol) in tetrahydrofuran (1.5 mL), the reaction mixture was gradually warmed from −78° C. to room temperature and stirred for one day. After addition of saturated aqueous ammonium chloride, the reaction mixture was extracted with ethyl acetate, and the organic layer was dried over anhydrous sodium sulfate and concentrated under reduced pressure. The residue was purified by silica gel column chromatography (Hi Flash column amino type manufactured by Yamazen Corporation: hexane/ethyl acetate=10/1→7/1→4/1 (v/v)) to give the title compound as a colorless oil (65.5 mg, yield 55%).

Reference Synthetic Example[a] 4

Cyclohexyl[7-(triisopropylsilyl)-7H-pyrrolo[2,3-d]pyrimidin-4-yl]methanone

Cyclohexyl[7-(triisopropylsilyl)-7H-pyrrolo[2,3-d]pyrimidin-4-yl]methanol (211 mg, 0.540 mmol) in dichloromethane (7 mL) was stirred with 1,1,1-triacetoxy-1,1-dihydro-1,2-benziodoxol-3(1H)-one (347 mg, 0.820 mmol) at room temperature for 2.5 hours. After addition of a mixture (1/1 (v/v)) of saturated aqueous sodium hydrogen carbonate and saturated aqueous sodium thiosulfate, the reaction mixture was extracted with ethyl acetate, and the organic layer was dried over anhydrous sodium sulfate and concentrated under reduced pressure. The residue was purified by silica gel column chromatography (hexane/ethyl acetate=30/1 (v/v)) to give the title compound as a colorless solid (117 mg, yield 55%).

Reference Synthetic Example[a] 5

Cyclohexyl(7H-pyrrolo[2,3-d]pyrimidin-4-yl)methanone

Cyclohexyl[7-(triisopropylsilyl)-7H-pyrrolo[2,3-d]pyrimidin-4-yl]methanone (22.4 mg, 58.0 μmol) was stirred with hydrogen chloride-methanol solution (10 wt %, 2.0 mL) at room temperature for 15 minutes. The reaction mixture was concentrated under reduced pressure, and the residue was purified by silica gel column chromatography (Hi Flash column amino type manufactured by Yamazen Corporation: chloroform/methanol=10/1 (v/v)) to give the title compound as a pale yellow oil (9.2 mg, yield 69%).

Reference Synthetic Example[a] 6

Cyclohexyl(7-{[2-(trimethylsilyl)ethoxy]methyl}-7H-pyrrolo[2,3-d]pyrimidin-4-yl)methanone Cyclohexyl(7H-pyrrolo[2,3-d]pyrimidin-4-yl)methanone (50.0 mg, 0.218 mmol) in N,N-dimethylformamide (1 mL) was mixed with sodium hydride (60 wt % dispersion in mineral oil, 9.6 mg, 0.24 mmol) and [2-(chloromethoxy)ethyl]trimethylsilane (42.5 μL, 0.240 mmol) under cooling with ice and stirred for 30 minutes while the temperature was gradually raised to room temperature. Separately, cyclohexyl(7H-pyrrolo[2,3-d]pyrimidin-4-yl)methanone (500 mg, 2.18 mmol) in N,N-dimethylformamide (5 mL) was mixed with sodium hydride (60 wt % dispersion in mineral oil, 96 mg, 2.4 mmol) and (chloromethoxy)ethyl]trimethylsilane (425 μL, 2.40 mmol) under cooling with ice and stirred for 30 minutes while the temperature was gradually raised to room temperature. After addition of water, the reaction solution and the previously obtained reaction solution were extracted with ethyl acetate, respectively, and the organic layers were washed with saturated aqueous sodium chloride, dried over anhydrous magnesium sulfate and concentrated under reduced pressure. The resulting residues were combined and purified by silica gel column chromatography (hexane/ethyl acetate=5/1 (v/v)) to give the title compound as a pale yellow oil (850 mg, yield 99%).

Reference Synthetic Example[a] 7

Cyclohexyl(7-{[2-(trimethylsilyl)ethoxy]methyl}-7H-pyrrolo[2,3-d]pyrimidin-4-yl)methanamine Cyclohexyl(7-{[2-(trimethylsilyl)ethoxy]methyl}-7H-pyrrolo[2,3-d]pyrimidin-4-yl)methanone (406 mg, 1.13 mmol) in methanol (10 ml) was stirred with hydroxylamine hydrochloride (395 mg, 5.66 mmol) for 4 hours. After addition of water, the reaction mixture was extracted with ethyl acetate, and the organic layer was dried over anhydrous sodium sulfate and concentrated under reduced pressure. The resulting residue was dissolved in ethanol (3.0 mL), mixed with ammonium acetate (105 mg, 1.36 mmol), water (3 mL) and aqueous ammonia (5 mL) and refluxed with zinc powder (600 mg, 9.17 mmol) for 4 hours. The reaction mixture was allowed to cool to room temperature and filtered, and the filtrate was concentrated under reduced pressure. The residue was purified by silica gel column chromatography (Hi Flash column amino type manufactured by Yamazen Corporation: chloroform/methanol=20/1 (v/v)) to give the title compound as a yellow oil (390 mg, yield 79%).

Reference Synthetic Example[a] 8

1-Cyclohexyl-7-{[2-(trimethylsilyl)ethoxy]methyl}-7H-imidazo[1,5-c]pyrrolo[3,2-e]pyrimidine Cyclohexyl(7-{[2-(trimethylsilyl)ethoxy]methyl}-7H-pyrrolo[2,3-d]pyrimidin-4-yl)methanamine (10 mg. 0.028 mmol) in N,N-dimethylformamide dimethyl acetal (0.7 mL) was stirred at 170° C. for 30 minutes under microwave irradiation. The reaction mixture was allowed to cool to room temperature and concentrated under reduced pressure, and the resulting residue was dissolved in 1,3-dimethylimidazolidin-2-one (1.0 mL) and stirred at 230° C. for 1.5 hours under microwave irradiation. Separately, cyclohexyl(7-{[2-(trimethylsilyl)ethoxy]methyl}-7H-pyrrolo[2,3-d]pyrimidin-4-ylmethanamine (89 mg, 0.25 mmol) in N,N-dimethylformamide dimethyl acetal (1 mL) was stirred at 170° C. for 30 minutes under microwave irradiation. The reaction mixture was allowed to cool to room temperature and concentrated under reduced pressure, and the resulting residue was dissolved in 1,3-dimethylimidazolidin-2-one (4.5 mL) and stirred at 230° C. for 1.5 hours under microwave irradiation. The reaction mixture and the previously obtained reaction mixture were combined, diluted with ethyl acetate, acidified with 1 M hydrochloric acid and washed with saturated aqueous ammonium chloride and saturated aqueous sodium chloride, and the organic layer was dried over anhydrous sodium sulfate and concentrated under reduced pressure. The residue was purified by silica gel thin layer chromatography (hexane/ethyl acetate=2/1→1/1→1/2 (v/v)) to give the title compound as a pale yellow oil (31.4 mg, yield 30%).

Reference Synthetic Example[a] 9

N-Methoxy-N,2-dimethylbenzamide

2-Methylbenzoic acid (1.00 g, 7.34 mmol) and 1-(3-dimethylaminopropyl)-3-ethylcarbodiimide hydrochloride (1.69 g, 8.81 mmol) in chloroform (10 mL) stirred with N,N-diisopropylethylamine (1.50 mL, 8.81 mmol) for 10 minutes under cooling with ice and then stirred with N,O-dimethylhydroxylamine hydrochloride (860 mg, 8.81 mmol) and N,N-diisopropylethylamine (1.50 mL, 8.81 mmol) for one day while the temperature was gradually raised to room temperature. After addition of water, the reaction mixture was extracted with chloroform, and the organic layer was washed with saturated aqueous sodium chloride, dried over anhydrous magnesium sulfate and concentrated under reduced pressure. The residue was purified by silica gel column chromatography (hexane/ethyl acetate=1/1 (v/v)) to give the title compound as a pale yellow oil (658 mg, yield 50%).

Reference Synthetic Example[a] 10

(7H-Pyrrolo[2,3-d]pyrimidin-4-yl)(o-tolyl)methanone

Isopropylmagnesium chloride (2.0 M solution in tetrahydrofuran, 1.05 mL, 2.10 mmol) was gradually added dropwise to 4-iodo-7H-pyrrolo[2,3-d]pyrimidine (245 mg, 1.00 mmol) obtained in Reference Synthetic Example[a] 1 in tetrahydrofuran (5 mL) cooled to −78° C., and the resulting reaction mixture was stirred at −78° C. for 15 minutes. The reaction mixture was warmed to room temperature and stirred with (2,6-dimethylphenyl)magnesium bromide (1.0 M solution in tetrahydrofuran, 1.1 mL, 1.1 mmol) and N-methoxy-N,2-dimethylbenzamide (180 mg, 1.00 mmol) in tetrahydrofuran (4 mL) at room temperature for one day. After addition of saturated aqueous ammonium chloride, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (hexane/ethyl acetate=2/1→>1/1 (v/v)) to give the title compound as a pale yellow solid (162 mg, yield 68%).

Reference Synthetic Example[a] 11

N-Methoxy-N-methylcyclohexanecarboxamide

The reactions in Reference Synthetic Example[a] 9 were carried out in substantially the same manners except that cyclohexanecarboxylic acid was used instead of 2-methylbenzoic acid to give the title compound as a colorless oil (2.14 g, yield 46%).

Reference Synthetic Example[a] 12

Cyclohexyl(7H-pyrrolo[2,3-d]pyrimidin-4-yl)methanone

The reactions in Reference Synthetic Example[a] 10 were carried out in substantially the same manners except that N-methoxy-N-methylcyclohexanecarboxamide was used instead of N-methoxy-N,2-dimethylbenzamide to give the title compound as a pale yellow solid (1.26 g, yield 67%).

Reference Synthetic Example[a] 13

N-Methoxy-N,2-dimethylcyclohexanecarboxamide

The reactions in Reference Synthetic Example[a] 9 were carried out in substantially the same manners except that 2-methylcyclohexanecarboxylic acid was used instead of 2-methylbenzoic acid to give the title compound as a colorless oil (623 mg, yield 48%).

Reference Synthetic Example[a] 14

(2-Methylcyclohexyl)(7H-pyrrolo[2,3-d]pyrimidin-4-yl)methanone

The reactions in Reference Synthetic Example[a] 10 were carried out in substantially the same manners except that N-methoxy-N,2-dimethylcyclohexanecarboxamide was used instead of N-methoxy-N,2-dimethylbenzamide to give the title compound as a colorless solid (165 mg, yield 68%).

Reference Synthetic Example[a] 15

4-Iodo-7-{[2-(trimethylsilyl)ethoxy]methyl}-7H-pyrrolo[2,3-d]pyrimidine

4-Iodo-7H-pyrrolo[2,3-d]pyrimidine (90 mg, 0.037 mmol) obtained in Reference Synthetic Example[a] 1 in N,N-dimethylformamide (4 mL) was stirred with sodium hydride (55 wt % dispersion in mineral oil, 19.2 mg, 0.0440 mmol) and [2-(chloromethoxy)ethyl]trimethylsilane (77.9 μL, 0.0440 mmol) at room temperature for one day. After addition of saturated aqueous sodium chloride, the reaction mixture was extracted with ethyl acetate, and the organic layer was dried over anhydrous sodium sulfate and concentrated under reduced pressure. The residue was purified by silica gel column chromatography (hexane/ethyl acetate=10/1→4/1 (v/v)) to give the title compound as a colorless oil (115 mg, yield 83%).

Reference Synthetic Example[a] 16

Benzyl 3-(hydroxymethyl)piperidine-1-carboxylate

3-Piperidinemethanol (3.59 g, 31.2 mmol) in 1,4-dioxane (8 mL) was mixed with potassium carbonate (4.55 g, 33.0 mmol), 1 M aqueous sodium hydroxide (2 mL) and benzyl chloroformate (5.20 mL, 36.4 mmol) under cooling with ice and stirred at room temperature for one day. After addition of water, the reaction mixture was extracted with ethyl acetate, and the organic layer was washed with saturated aqueous potassium hydrogen sulfate and saturated aqueous sodium chloride, dried over anhydrous magnesium sulfate and concentrated under reduced pressure. The resulting residue was purified by silica gel column chromatography (hexane/ethyl acetate=1/1 (v/v)) to give the title compound as a colorless oil (6.41 g, yield 83%).

Reference Synthetic Example[a] 17

Benzyl 3-[methoxy(methyl)carbamoyl]piperidine-1-carboxylate

Benzyl 3-(hydroxymethyl)piperidine-1-carboxylate (2.0 g, 8.0 mmol) in dichloromethane (50 mL) was stirred with 1,1,1-triacetoxy-1,1-dihydro-1,2-benziodoxol-3(1H)-one (5.1 g, 12 mmol) at room temperature for 2.5 hours. After addition of a mixture (1/1(v/v)) of saturated aqueous sodium hydrogen carbonate and saturated aqueous sodium thiosulfate, the reaction mixture was extracted with ethyl acetate, and the organic layer was dried over anhydrous sodium sulfate and concentrated under reduced pressure. The resulting residue was dissolved in t-butanol (25 mL), mixed with sodium dihydrogen phosphate (2.89 g, 24.1 mmol), water (25 mL) and 2-methyl-2-butene (25 mL, 241 mmol), then stirred with sodium chlorite (3.62 g, 40.1 mmol) at 0° C. for 1 hour and then stirred at room temperature for 1 hour. After addition of saturated aqueous sodium thiosulfate, the reaction mixture was extracted with ethyl acetate, and the organic layer was dried over anhydrous sodium sulfate and concentrated under reduced pressure. The resulting residue was dissolved in N,N-dimethylformamide (60 mL) and mixed with N,O-dimethylhydroxylamine hydrochloride (1.02 g, 10.4 mmol) and O-(7-azabenzotriazol-1-yl)-N,N,N',N'-tetramethyluronium hexafluorophosphate (4.0 g, 10.4 mmol) and then stirred with triethylamine (1.5 mL, 10 mmol) at room temperature for 2.5 hours. After addition of water, the reaction mixture was extracted with ethyl acetate, and the organic layer was dried over anhydrous sodium sulfate and concentrated under reduced pressure. The residue was purified by silica gel column chromatography (hexane/ethyl acetate=3/1→1/1 (v/v)) to give the title compound as a pale yellow oil (1.44 mg, yield 59% (three steps)).

Reference Synthetic Example[a] 18

Benzyl 3-(7-{[2-(trimethylsilyl)ethoxy]methyl}-7H-pyrrolo[2,3-d]pyrimidine-4-carbonyl)piperidine-1-carboxylate Isopropylmagnesium chloride (2.0 M solution in tetrahydrofuran, 0.4 mL, 0.80 mmol) was gradually added dropwise to 4-iodo-7-{[2-(trimethylsilyl)ethoxy]methyl}-7H-pyrrolo[2,3-d]pyrimidine (200 mg, 0.530 mmol) obtained in Reference Synthetic Example[a] 15 in tetrahydrofuran (3 mL) cooled to −78° C., and the resulting reaction mixture was stirred at −78° C. for 15 minutes. The reaction mixture was warmed to room temperature and stirred with (2,6-dimethylphenyl)magnesium bromide (1.0 M solution in tetrahydrofuran, 0.8 mL, 0.80 mmol) and benzyl 3-[methoxy(methyl)carbamoyl]piperidine-1-carboxylate (245 mg, 0.800 mmol) in tetrahydrofuran (3.0 mL) at room temperature for 2.5 hours. After addition of saturated aqueous ammonium chloride, the reaction mixture was extracted with ethyl acetate, and the organic layer was dried over anhydrous sodium sulfate and concentrated under reduced pressure. The residue was purified by silica gel column chromatography (hexane/ethyl acetate=4/1→2/1→1/1 (v/v)) to give the title compound as a yellow oil (107 mg, yield 41%).

Reference Synthetic Example[a] 19

Benzyl 3-[amino(7-{[2-(trimethylsilyl)ethoxy]methyl}-7H-pyrrolo[2,3-d]pyrimidin-4-yl)methyl]piperidine-1-carboxylate The reactions in Reference Synthetic Example[a] 7 were carried out in substantially the same manners except that 3-(7-{[2-(trimethylsilyl)ethoxy]methyl}-7H-pyrrolo[2,3-d]pyrimidine-4-carbonyl)piperidine-1-carboxylate (253 mg, 0.510 mmol) was used instead of cyclohexyl(7-{[2-(trimethylsilyl)ethoxy]methyl}-7H-pyrrolo[2,3-d]pyrimidin-4-yl)methanone to give the title compound as a pale blue oil (183 mg, yield 72%).

Reference Synthetic Example[a] 20

Benzyl 3-(7-{[2-(trimethylsilyl)ethoxy]methyl}-7H-imidazo[1,5-c]pyrrolo[3,2-e]pyrimidin-1-yl)piperidine-1-carboxylate Benzyl 3-[amino(7-{[2-(trimethylsilyl)ethoxy]methyl}-7H-pyrrolo[2,3-d]pyrimidin-4-yl)methyl]piperidine-1-carboxylate (63 mg, 0.13 mmol) in N,N-dimethylformamide dimethyl acetal (1 mL) was stirred at 170° C. for 30 minutes under microwave irradiation. The reaction mixture was allowed to cool to room temperature and concentrated under reduced pressure, and the resulting residue was dissolved in 1,3-dimethylimidazolidin-2-one (1 mL) and stirred at 230° C. for 1.5 hours under microwave irradiation. The reaction mixture was allowed to cool to room temperature, diluted with ethyl acetate and washed with saturated aqueous ammonium chloride and saturated aqueous sodium chloride, and the organic layer was dried over anhydrous sodium sulfate and concentrated under reduced pressure. The concentrate was purified by silica gel thin layer chromatography (hexane/ethyl acetate=1/1→1/2 (v/v)) to give a brown oil containing the title compound (45.2 mg). The resulting mixture was used for the next step.

Reference Synthetic Example[a] 21 trans-4-(Hydroxymethyl)-N-methoxy-N-methylcyclohexanecarboxamide

The reactions in Reference Synthetic Example[a] 9 were carried out in substantially the same manners except that trans-4-(hydroxylmethyl)cyclohexanecarboxylic acid (manufactured by Tokyo Chemical Industry Co., Ltd.) was used instead of 2-methylbenzoic acid to give the title compound as a colorless oil (515 mg, yield 41%).

Reference Synthetic Example[a] 22 trans-4-[(tert-Butyldiphenylsilyloxy)methyl]-N-methoxy-N-methylcyclohexanecarboxamide trans-4-(Hydroxymethyl)-N-methoxy-N-methylcyclohexanecarboxamide (403 mg, 2.00 mmol) in N,N-dimethylformamide (4 mL) was mixed with tert-butylchlorodiphenylsilane (514 μL, 2.00 mmol) and 1H-imidazole (136 mg, 2.00 mmol) under cooling with ice and stirred for one day while the temperature was gradually raised to room temperature. After addition of water, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (hexane/ethyl acetate=8/1 (v/v)) to give the title compound as a colorless oil (536 mg, yield 61%).

Reference Synthetic Example[a] 23

{trans-4-[(tert-Butyldiphenylsilyloxy)methyl]cyclohexyl}(7H-pyrrolo[2,3-d]pyrimidin-4-yl)methanone The reactions in Reference Synthetic Example[a] 10 were carried out in substantially the same manners except that trans-4-[(tert-butyldiphenylsilyloxy)methyl]-N-methoxy-N-methylcyclohexanecarboxamide was used instead of N-methoxy-N,2-dimethylbenzamide to give the title compound as a yellow oil (111 mg, yield 59%).

Reference Synthetic Example[a] 24

1-{trans-4-[(tert-Butyldiphenylsilyloxy)methyl]cyclohexyl}-7H-pyrrolo[3,2-e][1,2,3]triazolo[1,5-c]pyrimidine The reactions in Synthetic Example[a] 5 were carried out in substantially the same manners except that {trans-4-[(tert-butyldiphenylsilyloxy)methyl]cyclohexyl}(7H-pyrrolo[2,3-d]pyrimidin-4-yl)methanone obtained in Reference Synthetic Example[a] 23 was used instead of (7H-pyrrolo[2,3-d]pyrimidin-4-yl)(o-tolyl)methanone to give the title compound as a pale yellow solid (50.6 mg, yield 46%).

Reference Synthetic Example[a] 25

3-Methyl 1-tert-butyl 4-methylpiperidine-1,3-dicarboxylate

4-Methylpyridine-3-carboxylic acid (1.13 g, 6.48 mmol) in methanol (20 mL) was refluxed with concentrated sulfuric acid (4.0 mL) for 2 days under heating. The reaction mixture was concentrated under reduced pressure, gradually adjusted to pH 8 or above with saturated aqueous sodium hydrogen carbonate and extracted with ethyl acetate twice. The resulting organic layer was washed with water and saturated aqueous sodium chloride, dried over anhydrous magnesium sulfate and concentrated under reduced pressure to give a red oil (0.89 g). The reactions were carried out with 4-methylpyridine-3-carboxylic acid (1.77 g, 10.2 mmol) to give a red oil (1.37 g).

The red oil (2.26 g) obtained above was dissolved in ethyl acetate (35 mL) was stirred with active carbon (400 mg) at room temperature for 30 minutes. The mixture was filtered, and the filtrate was concentrated under reduced pressure. The resulting residue was dissolved in acetic acid (35 mL) and stirred with platinum(IV) oxide (162 mg) under a hydrogen atmosphere at 0.5 MPa for 3 days. The reaction mixture was filtered, and the filtrate was concentrated under reduced pressure. The resulting residue was dissolved in acetonitrile (50 mL) and water (40 mL) and stirred with sodium hydrogen carbonate (5.00 g, 59.5 mmol) and tert-butyl bicarbonate (5.10 g, 23.4 mmol) for one day. The reaction mixture was extracted with diethyl ether twice, and the organic layer was washed with 1 M hydrochloric acid and saturated aqueous magnesium chloride, dried over anhydrous magnesium sulfate and concentrated under reduced pressure. The resulting residue was purified by silica gel column chromatography (hexane/ethyl acetate=1/1 (v/v)) to give the title compound as a colorless oil (4.33 g, yield 90% (three steps)).

Reference Synthetic Example[a] 26 tert-Butyl 3-[methoxy(methyl)carbamoyl]-4-methylpiperidine-1-carboxylate

Diisobutylaluminum hydride (1.0 M solution in toluene, 23.4 mL, 23.7 mmol) was added dropwise to 3-methyl 1-tert-butyl 4-methylpiperidine-1,3-dicarboxylate (2.43 g, 9.46 mmol) in tetrahydrofuran (60 mL) cooled to −78° C., and the resulting reaction mixture was stirred at −78° C. for 1 hour and at room temperature for 2 hours, then stirred with methanol and Celite at room temperature for 30 minutes and filtered. The filtrate was concentrated under reduced pressure. The resulting residue was roughly purified by silica gel column chromatography (hexane/ethyl acetate=4/1→2/1→1/1 (v/v)) to give a colorless oil (1.62 g). The crude product (1.02 g) was dissolved in dichloromethane (30 m L) and stirred with 1,1,1-triacetoxy-1,1-dihydro-1,2-benziodoxol-3(1H)-one (2.83 g, 6.67 mmol) at room temperature for 1.5 hours. After addition of a mixture (1/1 (v/v)) of saturated aqueous sodium hydrogen carbonate and saturated aqueous sodium thiosulfate, the reaction mixture was extracted with ethyl acetate, and the organic layer was dried over anhydrous sodium sulfate and concentrated under reduced pressure. The resulting residue was dissolved in t-butanol (12 mL), mixed with sodium dihydrogen phosphate (1.33 g, 11.1 mmol), water (12 mL) and 2-methyl-2-butene (12 mL, 111 mmol) and stirred with sodium chlorite (1.68 g, 18.6 mmol) under cooling with ice for 30 minutes and then at room temperature 1 hour. After addition of saturated aqueous sodium thiosulfate, the reaction mixture was extracted with ethyl acetate, and the organic layer was dried over anhydrous sodium sulfate and concentrated under reduced pressure. The resulting residue was dissolved in N,N-dimethylformamide (30 mL), mixed with N,O-dimethylhydroxylamine hydrochloride (396 mg, 4.06 mmol) and O-(7-azabenzotriazol-1-yl)-N,N,N',N'-tetramethyluronium hexafluorophosphate (2.00 g, 5.41 mmol) and stirred with N,N-diisopropylethylamine (1.50 mL, 8.45 mmol) at room temperature for one day. After addition of water, the reaction solution was extracted with ethyl acetate, and the organic layer was dried over anhydrous sodium sulfate and concentrated under reduced pressure. The residue was purified by silica gel column chromatography (hexane/ethyl acetate=4/

1→2/1 (v/v)) to give the title compound as a pale yellow oil (644 mg, yield 38% (four steps)).

Reference Synthetic Example[a] 27 tert-Butyl 4-methyl-3-(7H-pyrrolo[2,3-d]pyrimidine-4-carbonyl)piperidine-1-carboxylate The reactions in Reference Synthetic Example[a] 10 were carried out in substantially the same manners except that tert-butyl 3-[methoxy(methyl)carbamoyl]-4-methylpiperidine-1-carboxylate was used instead of N-methoxy-N,2-dimethylbenzamide to give the title compound as a pale yellow solid (53.8 mg, yield 73%).

Reference Synthetic Example[a] 28 tert-Butyl 3-[methoxy(methyl)carbamoyl]piperidine-1-carboxylate

The reactions in Reference Synthetic Example[a] 9 were carried out in substantially the same manners except that 1-(tert-butoxycarbonyl)piperidine-3-carboxylate was used instead of 2-methylbenzoic acid to give the title compound as a colorless oil (1.68 g, yield 57%).

Reference Synthetic Example[a] 29 tert-Butyl 3-(7H-pyrrolo[2,3-d]pyrimidine-4-carbonyl)piperidine-1-carboxylate

The reactions in Reference Synthetic Example[a] 10 were carried out in substantially the same manners except that tert-butyl 3-[methoxy(methyl)carbamoyl]piperidine-1-carboxylate was used instead of N-methoxy-N,2-dimethylbenzamide to give the title compound as a pale yellow solid (1.19 g, yield 68%).

Reference Synthetic Example[a] 30

1-[(Benzyloxy)carbonyl]piperidine-3-carboxylic acid

Nipecotic acid (3.93 g, 30.4 mmol) and sodium carbonate (5.10 g, 48.1 mmol) in water (40 mL) was mixed with benzyl chloroformate (5.20 mL, 36.4 mmol) under cooling with ice and stirred at room temperature for one day. After addition of water and 1 M aqueous sodium hydroxide, the reaction mixture was allowed to separate by adding diethyl ether. The aqueous layer was adjusted to pH 1 with concentrated hydrochloric acid and extracted with ethyl acetate. The resulting organic layer was washed with saturated aqueous sodium chloride, dried over anhydrous magnesium sulfate and concentrated under reduced pressure to give the title compound as a pale yellow oil (5.86 g, yield 73%).

Reference Synthetic Example[a] 31

Benzyl 3-[methoxy(methyl)carbamoyl]piperidine-1-carboxylate

1-[(Benzyloxy)carbonyl]piperidine-3-carboxylic acid (5.86 g, 22.3 mmol) and N,O-dimethylhydroxylamine hydrochloride (3.55 g, 36.4 mmol) in tetrahydrofuran (60 mL) was stirred with triethylamine (5.50 mL, 39.5 mmol), 1-hydroxybenzotriazole (1.17 g, 8.66 mmol) and 1-(3-dimethylaminopropyl)-3-ethylcarbodiimide hydrochloride (7.18 g, 37.4 mmol) at room temperature for one day. After addition of water, the reaction solution was extracted with ethyl acetate, and the organic layer was washed with saturated aqueous sodium chloride, dried over anhydrous magnesium sulfate and concentrated under reduced pressure. The residue was purified by silica gel column chromatography (hexane/ethyl acetate=1/1 (v/v)) to give the title compound as a colorless oil (5.95 g, yield 87%).

Reference Synthetic Example[a] 32

Benzyl 3-(7H-pyrrolo[2,3-d]pyrimidine-4-carbonyl)piperidine-1-carboxylate

The reactions in Reference Synthetic Example[a] 10 were carried out in substantially the same manners except that benzyl 3-[methoxy(methyl)carbamoyl]piperidine-1-carboxylate was used instead of N-methoxy-N,2-dimethylbenzamide to give the title compound as a pale yellow solid (3.56 g, yield 53%).

Reference Synthetic Example[a] 33

1-Benzylpiperidine-3-carboxylic acid

Nipecotic acid (1.31 g, 10.2 mmol), benzaldehyde (1.12 g, 10.6 mmol) and 5% palladium-carbon (0.18 g) in methanol (10 mL) was stirred at room temperature for one day under a hydrogen atmosphere. The reaction mixture was filtered, and the filtrate was concentrated under reduced pressure. The resulting residue was dissolved in methanol (50 mL) was stirred with benzaldehyde (4.40 g, 41.5 mmol) and 5% palladium-carbon (0.118 g) at room temperature for one day. The reaction mixture was filtered, and the filtrated was concentrated under reduced pressure. The resulting residue was purified by silica gel column chromatography (chloroform/methanol=10/1→5/1 (v/v)) to give the title compound as a colorless oil (1.41 g, yield 63%).

Reference Synthetic Example[a] 34

1-Benzyl-N-methoxy-N-methylpiperidine-3-carboxamide

1-Benzylpiperidine-3-carboxylic acid (318 mg, 1.45 mmol) and N,O-dimethylhydroxylamine hydrochloride (287 mg, 2.94 mmol) in tetrahydrofuran (5 mL) was stirred with triethylamine (283 μL, 2.03 mmol), 1-hydroxybenzotriazole (101 mg, 0.747 mmol) and 1-(3-dimethylaminopropyl)-3-ethylcarbodiimide hydrochloride (560 mg, 2.92 mmol) at room temperature for one day. After addition of water, the reaction mixture was extracted with ethyl acetate, and the organic layer was washed with saturated aqueous sodium chloride, dried over anhydrous magnesium sulfate and concentrated under reduced pressure. The residues was purified by silica gel column chromatography (hexane/ethyl acetate=1/1 (v/v)) to give the title compound as a colorless oil (272 mg, yield 71%).

Reference Synthetic Example[a] 35

(1-Benzylpiperidin-3-yl)(7H-pyrrolo[2,3-d]pyrimidin-4-yl)methanone

The reactions in Reference Synthetic Example[a] 10 were carried out in substantially the same manners except that 1-benzyl-N-methoxy-N-methylpiperidine-3-carboxamide was used instead of N-methoxy-N,2-dimethylbenzamide to give the title compound as a yellow amorphous (121 mg, yield 91%).

Reference Synthetic Example[a] 36

Phenyl 1,3,4-thiadiazol-2-ylcarbamate 1,3,4-Thiadiazol-2-amine (253 mg, 2.50 mmol) in dimethylacetamide (3 mL) was stirred with phenyl chloroformate (392 μL, 3.13. mmol) at room temperature for one day. After addition of water, the precipitated solid was collected by filtration, washed with water and hexane and dried under reduced pressure to give the title compound as a colorless solid (418 mg, yield 76%).

Reference Synthetic Example[a] 37

Phenyl(3-methylisothiazol-5-yl)carbamate

3-Methythiazol-5-amine (156 mg, 1.04 mmol) in pyridine (1.2 mL) was mixed with phenyl chloroformate (260 μL, 2.07 mmol) under cooling with ice and stirred at room temperature for 3 hours. The reaction mixture was concentrated under reduced pressure, and after addition of water, extracted with chloroform twice, and the organic layer was concentrated under reduced pressure. The resulting residue was purified by silica gel column chromatography (hexane/ethyl acetate=1/1 (v/v)) to give the title compound as a pale yellow solid (173 mg, yield 71%).

Reference Synthetic Example[a] 38 tert-Butyl 4-[methoxy(methyl)carbamoyl]piperidine-1-carboxylate

The reactions in Reference Synthetic Example[a] 9 were carried out in substantially the same manners except that 1-(tert-butoxycarbonyl)piperidine-carboxylic acid was used instead of 2-methylbenzoic acid to give the title compound as a colorless oil (763 mg, yield 64%).

Reference Synthetic Example[a] 39 tert-Butyl 4-(7H-pyrrolo[2,3-d]pyrimidine-4-carbonyl)piperidine-1-carboxylate

The reactions in Reference Synthetic Example[a] 10 were carried out in substantially the same manners except that tert-butyl 4-[methoxy(methyl)carbamoyl]piperidine-1-carboxylate was used instead of N-methoxy-N,2-dimethylbenzamide to give the title compound as a pale yellow amorphous (486 mg, yield 74%).

Reference Synthetic Example[a] 40

N-Methoxy-N-methylpiperidine-4-carboxamide hydrochloride tert-Butyl 4-[methoxy(methyl)carbamoyl]piperidine-1-carboxylate (1.00 g, 3.67 mmol) obtained in Reference Synthetic Example[a] 38 in 1,4-dioxane (10 mL) was stirred with 4 M hydrogen chloride-1,4-dioxane solution (8 mL) at room temperature for one day. The solid precipitated in the reaction mixture was collected by filtration to give the title compound as a colorless solid (650 mg, yield 85%).

Reference Synthetic Example[a] 41

N-Methoxy-N-methyl-1-(2,2,2-trifluoroethyl)piperidine-4-carboxamide

N-Methoxy-N-methylpiperidine-4-carboxamide hydrochloride (600 mg, 2.88 mmol) in water (5 mL) was adjusted to pH 10 with 1 M aqueous sodium hydroxide and extracted with 1-butanol. The organic layer was dried over anhydrous sodium sulfate and concentrated under reduced pressure to give a colorless solid. The resulting solid (200 mg, 1.16 mmol) was dissolved in N,N-dimethylformamide (4 mL) and stirred with potassium carbonate (481 mg, 3.48 mmol) and 2,2,2-trifluoroethyl trifluoromethanesulfonate (335 μL, 2.32 mmol) at room temperature for one day. After addition of water and saturated aqueous sodium chloride, the reaction mixture was extracted with ethyl acetate. The organic layer was dried over anhydrous sodium sulfate and concentrated under reduced pressure. The resulting residue was purified by silica gel column chromatography (methanol/chloroform=1/19→1/9 (v/v)) to give the title compound as a colorless oil (190 mg, yield 26%).

Reference Synthetic Example[a] 42

(7H-Pyrrolo[2,3-d]pyrimidin-4-yl)[1-(2,2,2-trifluoroethyl)piperidin-4-yl]methanone The reactions in Reference Synthetic Example[a] 10 were carried out in substantially the same manners except that N-methoxy-N-methyl-1-(2,2,2-trifluoroethyl)piperidine-4-carboxamide was used instead of N-methoxy-N,2-dimethylbenzamide to give the title compound as a colorless solid (100 mg, yield 43%).

Reference Synthetic Example[a] 43

Benzyl 4-[methoxy(methyl)carbamoyl]piperidine-1-carboxylate

Benzyl chloroformate (1.64 mL, 11.6 mmol) was gradually added dropwise to piperidine-4-carboxylic acid (1.00 g, 7.74 mmol) and sodium carbonate (1.64 g, 15.5 mmol) in water (20 mL) under cooling with ice, and the resulting reaction mixture was stirred for 2 hours. After addition of 1 M aqueous sodium hydroxide, the reaction mixture was allowed to separate by adding ethyl acetate. The resulting aqueous layer was adjusted to pH 4 with 1 M hydrochloric acid and extracted with ethyl acetate, and the organic layer was dried over anhydrous sodium sulfate and concentrated under reduced pressure to give a colorless oil. The oil was dissolved in chloroform (30 mL) and stirred with N,O-dimethylhydroxylamine hydrochloride (1.50 g, 15.4 mmol), 1-(3-dimethylaminopropyl)-3-ethylcarbodiimide hydrochloride (3.00 g, 15.4 mmol), 1-hydroxybenzotriazole (2.00 g, 15.4 mmol) and triethylamine (3.2 mL, 23.1 mmol) at room temperature for 3 days. After addition of water and saturated aqueous ammonium chloride, the reaction mixture was extracted with chloroform, and the organic layer was dried over anhydrous sodium sulfate and concentrated under reduced pressure. The residue was purified by silica gel column chromatography (hexane/ethyl acetate=1/1 (v/v)) to give the title compound as a colorless oil (1.57 g, yield 66%).

Reference Synthetic Example[a] 44

Benzyl 4-(7H-pyrrolo[2,3-d]pyrimidine-4-carbonyl) piperidine-1-carboxylate

The reactions in Reference Synthetic Example[a] 10 were carried out in substantially the same manners except that benzyl 4-[methoxy(methyl)carbamoyl]piperidine-1-carboxylate was used instead of N-methoxy-N,2-dimethylbenzamide to give the title compound as a yellow oil (1.40 g, yield 78%).

Reference Synthetic Example[a] 45 tert-Butyl {trans-4-[methoxy(methyl)carbamoyl] cyclohexyl}carbamate trans-4-Aminocyclohexanecarboxylic acid (500 mg, 3.49 mmol) in water (10 mL) was stirred with di-tert-butyl bicarbonate (1.50 g, 6.98 mmol) and sodium hydroxide (280 mg, 6.98 mmol) at room temperature for 2 hours. The reaction mixture was washed with ethyl acetate, and the aqueous layer was adjusted to pH 3 with 1 M hydrochloric acid and extracted with ethyl acetate. The organic layer was dried over anhydrous sodium sulfate and concentrated under reduced pressure to give a colorless oil. The oil was dissolved in chloroform (10 mL) and stirred with N,O-dimethylhydroxylamine hydrochloride (683 mg, 7.00 mmol), 1-(3-dimethylaminopropyl)-3-ethylcarbodiimide hydrochloride (1.34 g, 7.00 mmol), 1-hydroxybenzotriazole (946 mg, 7.00 mmol) and triethylamine (1.50 mL, 10.5 mmol) at room temperature for one day. After addition of water and saturated aqueous sodium chloride, the reaction mixture was extracted with chloroform, and the organic layer was dried over anhydrous sodium sulfate, and concentrated under reduced pressure. The residue was purified by silica gel column chromatography (hexane/ethyl acetate=2/1→1/1 (v/v)) to give the title compound as a colorless solid (513 mg, yield 51%).

Reference Synthetic Example[a] 46 tert-Butyl [trans-4-(7H-pyrrolo[2,3-d]pyrimidine-4-carbonyl)cyclohexyl]carbamate The reactions in Reference Synthetic Example[a] 10 were carried out in substantially the same manners except that tert-butyl {trans-4-[methoxy(methyl)carbamoyl] cyclohexyl}carbamate was used instead of N-methoxy-N,2-dimethylbenzamide to give the title compound as a colorless solid (52.0 mg, yield 8.4%).

Reference Synthetic Example[a] 47

Benzyl {trans-4-[methoxy(methyl)carbamoyl] cyclohexyl}carbamate

Benzyl chloroformate (885 μL, 6.30 mmol) was gradually added dropwise to trans-4-aminocyclohexanecarboxylic acid (600 mg, 4.20 mmol) and sodium carbonate (891 mg, 8.40 mmol) in water (12 mL) under cooling with ice, and the reaction mixture was stirred for one day. After addition of 1 M aqueous sodium hydroxide and ethyl acetate, the insoluble solid was collected by filtration to give a colorless solid. The solid was dissolved in chloroform (10 mL) and stirred with N,O-dimethylhydroxylamine hydrochloride (416 mg, 4.27 mmol), 1-(3-dimethylaminopropyl)-3-ethylcarbodiimide hydrochloride (819 mg, 4.27 mmol), 1-hydroxybenzotriazole (577 mg, 4.27 mmol) and triethylamine (892 μL, 6.40 mmol) at room temperature for one day. After addition of water and saturated aqueous sodium chloride, the reaction mixture was extracted with chloroform, and the organic layer was dried over anhydrous sodium sulfate and concentrated under reduced pressure. The resulting residue was purified by silica gel column chromatography (hexane/ethyl acetate=2/1 (v/v)) to give the title compound as a colorless solid (350 mg, yield 26%).

Reference Synthetic Example[a] 48

Benzyl [trans-4-(7H-pyrrolo[2,3-d]pyrimidine-4-carbonyl)cyclohexyl]carbamate

The reactions in Reference Synthetic Example[a] 10 were carried out in substantially the same manners except that benzyl {trans-4-[methoxy(methyl)carbamoyl] cyclohexyl}carbamate was used instead of N-methoxy-N,2-dimethylbenzamide to give the title compound as a colorless solid (33.0 mg, yield 9.0%).

Reference Synthetic Example[a] 49 trans-N-Methoxy-4-(methoxymethyl)-N-methylcyclohexanecarboxamide trans-4-(Hydroxymethyl)-N-methoxy-N-methylcyclohexanecarboxamide (200 mg, 0.994 mmol) obtained in Reference Synthetic Example[a] 21 in N,N-dimethylformamide (2 mL) was mixed with sodium hydride (55 wt % dispersion in mineral oil, 52.0 mg, 1.19 mmol) and methyl iodide (74.0 μL, 1.19 mmol) under cooling with ice and stirred for 1 hour while the temperature was gradually raised to room temperature. After addition of water, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (ethyl acetate/hexane=1/2→1/1 (v/v)) to give the title compound as a colorless oil (197 mg, yield 92%).

Reference Synthetic Example[a] 50

[trans-4-(Methoxymethyl)cyclohexyl](7H-pyrrolo[2,3-d]pyrimidin-4-yl)methanone

The reactions in Reference Synthetic Example[a] 10 were carried out in substantially the same manners except that trans-N-methoxy-4-(methoxymethyl)-N-methylcyclohexanecarboxamide was used instead of N-methoxy-N,2-dimethylbenzamide to give the title compound as an ivory solid (153 mg, yield 70%).

Reference Synthetic Example[a] 51 trans-4-Hydroxy-N-methoxy-N-methylcyclohexanecarboxamide

The reactions in Reference Synthetic Example[a] 9 were carried out in substantially the same manners except that trans-4-hydroxycyclohexanecarboxylic acid was used instead of 2-methylbenzoic acid to give the title compound as a colorless oil (1.89 g, yield 48%).

Reference Synthetic Example[a] 52 trans-N,4-Dimethoxy-N-methylcyclohexanecarboxamide trans-4-Hydroxy-N-methoxy-N-methylcyclohexanecarboxamide (536 mg, 2.86 mmol) in N,N-dimethylformamide (5 mL) was mixed with sodium hydride (55 wt % dispersion in mineral oil, 150 mg, 3.44 mmol) and methyl iodide (214 μL, 3.44 mmol) under cooling with ice and stirred for 3 hours while the temperature was gradually raised to room temperature. After addition of water, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (ethyl acetate/hexane=1/2→1/1 (v/v)) to give the title compound as a colorless oil (556 mg, yield 97%).

Reference Synthetic Example[a] 53

(trans-4-Methoxycyclohexyl)(7H-pyrrolo[2,3-d]pyrimidin-4-yl)methanone

The reactions in Reference Synthetic Example[a] 10 were carried out in substantially the same manners except that trans-N,4-dimethoxy-N-methylcyclohexanecarboxamide was used instead of N-methoxy-N,2-dimethylbenzamide to give the title compound as an ivory solid (178 mg, yield 69%).

Reference Synthetic Examples[a] 54 to 60

The reactions in Reference Synthetic Example[a] 9 were carried out in substantially the same manners except that 4,4-difluoroxyclohexanecarboxylic acid, bicycle[2.2.1]heptane-2-carboxylic acid, cycloheptanecarboxylic acid, cyclobutanecarboxylic acid, cyclopentanecarboxylic acid, trans-4-(trifluoromethyl)cyclohexanecarboxylic acid or cis-4-(trifluoromethyl)cyclohexanecarboxylic acid was used instead of 2-methylbenzoic acid to give the compounds of Reference Synthetic Examples[a] 54 to 60. The names, morphologies and yields of the compounds synthesized are shown in Table[a] 5.

TABLE[a] 5

| Rf | Compound Name | Morphology | Yield |
|---|---|---|---|
| 54 | 4,4-difluoro-N-methoxy-N-methylcyclohexanecarboxamide | colorless oil | 63% |
| 55 | N-methoxy-N-methylbicyclo[2.2.1]heptane-2-carboxamide | colorless oil | 47% |
| 56 | N-methoxy-N-methylcycloheptanecarboxamide | colorless oil | 49% |
| 57 | N-methoxy-N-methylcyclobutanecarboxamide | colorless oil | 57% |
| 58 | N-methoxy-N-methylcyclopentanecarboxamide | colorless oil | 45% |
| 59 | trans-N-methoxy-N-methyl-4-(trifluoromethyl)cyclohexanecarboxamide | colorless solid | 82% |
| 60 | cis N methoxy N methyl 4 (trifluoromethyl)cyclohexanecarboxamide | colorless oil | 72% |

Reference Synthetic Examples[a] 61 to 67

The reactions in Reference Synthetic Example[a] 10 were carried out in substantially the same manners except that the compounds obtained in Reference Synthetic Examples[a] 54 to 60 were used instead of N-methoxy-N,2-dimethylbenzamide to give the compounds of Reference Synthetic Examples[a] 61 to 67. The names, morphologies and yields of the compounds synthesized are shown in Table[a] 6.

TABLE[a] 6

| Rf | Compound Name | Morphology | Yield |
|---|---|---|---|
| 61 | (4,4 difluorocyclohexyl) (7H-pyrrolo[2,3-d]pyrimidin-4-yl)methanone | yellow solid | 44% |
| 62 | bicyclo[2.2.1]heptan-2-yl(7H-pyrrolo[2,3-d]pyrimidin-4-yl)methanone | pale yellow solid | 66% |
| 63 | cycloheptyl(7H-pyrrolo[2,3-d]pyrimidin-4-yl)methanone | pale yellow solid | 76% |
| 64 | cyclobutyl(7H-pyrrolo[2,3-d]pyrimidin-4-yl)methanone | pale yellow solid | 38% |
| 65 | cyclopentyl(7H-pyrrolo[2,3-d]pyrimidin-4-yl)methanone | pale yellow solid | 73% |
| 66 | (7H-pyrrolo[2,3-d]pyrimidin-4-yl)[trans-4-(trifluoromethyl)cyclohexyl]methanone | milky solid | 65% |
| 67 | (7H-pyrrolo[2,3-d]pyrimidin-4-yl[cis-4-(trifluoromethyl)cyclohexyl]methanone | milky solid | 53% |

Reference Synthetic Example[a] 68

[trans-4-(tert-Butyldiphenylsilyl)oxy]-N-methoxyl-N-methylcyclohexanecarboxamide trans-4-Hydroxy-N-methoxy-N-methylcyclohexanecarboxamide (1.35 g, 7.21 mmol) obtained in Reference Synthetic Example[a] 51 in N,N-dimethylformamide (48 mL) was stirred with imidazole (598 mg, 8.65 mmol) and tert-butylchlorodiphenylsilane (2.07 mL, 7.93 mmol) for 4 hours under cooling with ice. After addition of water, the reaction mixture was extracted with ethyl acetate, and the organic layer was washed with saturated aqueous sodium chloride, dried over anhydrous sodium sulfate and concentrated under reduced pressure. The residue was purified by silica gel column chromatography (hexane/ethyl acetate=15/1→7/1→3/1 (v/v)) to give the title compound as a colorless oil (1.52 g, yield 50%).

Reference Synthetic Example[a] 69

{trans-4-[(tert-Butyldiphenylsilyl)oxy]cyclohexyl}(7H-pyrrolo[2,3-d]pyrimidin-4-yl)methanone The reactions in Reference Synthetic Example[a] 10 were carried out in substantially the same manners except that trans-4-[(tert-butyldiphenylsilyl)oxy]-N-methoxy-N-methylcyclohexanecarboxamide was used instead of N-methoxy-N,2-dimethylbenzamide to give the title compound as a yellow amorphous (1.34 g, yield 78%).

Reference Synthetic Example[a] 70

1-{4-[(tert-Butyldiphenylsilyl)oxy]cyclohexyl}-7H-pyrrolo[3,2-e][1,2,3]triazolo[1,5-c]pyrimidine The reactions in Synthetic Example[a] 5 were carried out in substantially the same manners except that {trans-4-[(tert-butyldiphenylsilyl)oxy]cyclohexyl}(7H-pyrrolo[2,3-d]pyrimidin-4-yl)methanone was used instead of (7H-pyrrolo[2,3-d]pyrimidin-4-yl)(o-tolyl)methanone to give the title compound as a pale yellow solid (838 mg, yield 61%).

Reference Synthetic Example[a] 71

4-Hydroxy-N-methoxy-N-methylcyclohexanecarboxamide

4-Hydroxycyclohexanecarboxylic acid (10.0 g, 69.4 mmol) and N,O-dimethylhydroxylamine hydrochloride (8.80 g, 90.2 mmol) in dichloromethane (500 mL) was stirred with 1-(3-dimethylaminopropyl)-3-ethylcarbodiimide hydrochloride (17.3 g, 90.2 mmol), 1-hydroxybenzotriazole (12.2 g, 90.2 mmol) and N,N-diisopropylethylamine (24.2 mL, 139 mmol) at room temperature for one day. After addition of water, the reaction mixture was extracted with chloroform, and the organic layer was washed with saturated aqueous sodium chloride, dried over anhydrous sodium sulfate and concentrated under reduced pressure. The residue was purified by silica gel column chromatography (hexane/ethyl acetate=1/1 (v/v)→ethyl acetate) to give the title compound as a yellow oil (9.07 g, yield 70%).

Reference Synthetic Example[a] 72

4-[(tert-Butyldimethylsilyl)oxy]-N-methoxy-N-methylcyclohexanecarboxamide

4-Hydroxy-N-methoxy-N-methylcyclohexanecarboxamide (7.34 g, 39.2 mmol) in N,N-dimethylformamide (200 mL) was stirred with imidazole (4.80 g, 70.6 mmol) and tert-butylchlorodimethylsilane (7.70 g, 51.0 mmol) at room temperature for one day. After addition of water, the reaction mixture was extracted with ethyl acetate, and the organic layer was washed with saturated aqueous sodium chloride, dried over anhydrous sodium sulfate and concentrated under reduced pressure. The residue was purified by silica gel column chromatography (hexane/ethyl acetate=25/1→4/1 (v/v)) to give the title compound as a colorless oil (8.68 g, yield 73%).

Reference Synthetic Example[a] 73

{4-[(tert-Butyldimethylsilyl)oxy]cyclohexyl}(7H-pyrrolo[2,3-d]pyrimidin-4-yl)methanone The reactions in Reference Synthetic Example[a] 10 were carried out in substantially the same manners except that 4-[(tert-butyldimethylsilyl)oxy]-N-methoxy-N-methylcyclohexanecarboxamide was used instead of N-methoxy-N, 2-dimethylbenzamide to give the title compound as a pale yellow solid (7.14 g, yield 69%).

Reference Synthetic Example[a] 74

1-{4-[(tert-Butyldimethylsilyl)oxy]cyclohexyl}-7H-pyrrolo[3,2-e][1,2,3]triazolo[,1,5-c]pyrimidine The reactions in Synthetic Example[a] 5 were carried out in substantially the same manners except that {4-[(tert-butyldiphenylsilyl)oxy]cyclohexyl}(7H-pyrrolo[2,3-d]pyrimidin-4-yl)methanone was used instead of (7H-pyrrolo[2,3-d]pyrimidin-4-yl)(o-tolyl)methanone to give the title compound as a pale yellow solid (5.20 g, yield 70%).

Reference Synthetic Example[a] 75

4-(7H-Pyrrolo[3,2-e][1,2,3]triazolo[1,5-c]pyrimidin-1-yl)cyclohexanol

1-{4-[(tert-Butyldimethylsilyl)oxy]cyclohexyl}-7H-pyrrolo[3,2-e][1,2,3]triazolo[1,5-c]pyrimidine (500 mg, 1.35 mmol) in a mixture of dichloromethane (5 mL) and methanol (5 mL) was stirred with pyridinium p-toluenesulfonate (338 mg, 1.35 mmol) at 60° C. for 3 hours. The reaction mixture was concentrated under reduced pressure, and the residue was purified by silica gel column chromatography (hexane/ethyl acetate=4/1→1/1 (v/v)→ethyl acetate) to give the title compound as a colorless solid (259 mg, yield 75%).

Reference Synthetic Example[a] 76

Benzyl 4-(7-{[2-(trimethylsilyl)ethoxy]methyl}-7H-pyrrolo[2,3-d]pyrimidine-4-carbonyl)piperidine-1-carboxylate The reactions in Reference Synthetic Example[a] 18 were carried out in substantially the same manners except that benzyl 4-[methoxy(methyl)carbamoyl]piperidine-1-carboxylate obtained in Reference Synthetic Example[a] 43 was used instead of benzyl 3-[methoxy(methyl)carbamoyl]piperidine-1-carboxylate to give the title compound as a yellow oil (49.6 mg, yield 71%).

Reference Synthetic Example[a] 77

Benzyl 4-[amino(7-{[2-(trimethylsilyl)ethoxy]methyl}-7H-pyrrolo[2,3-d]pyrimidin-4-yl)methyl]piperidine-1-carboxylate The reactions in Reference Synthetic Example[a] 7 were carried out in substantially the same manners except that benzyl 4-(7-{[2-(trimethylsilyl)ethoxy]methyl}-7H-pyrrolo[2,3-d]pyrimidine-4-carbonyl)piperidine-1-carboxylate was used instead of cyclohexyl(7-{[2-(trimethylsilyl)ethoxy]methyl}-7H-pyrrolo[2,3-d]pyrimidin-4-yl)methanone to give the title compound as a colorless oil (33.2 mg, yield 67%).

Reference Synthetic Example[a] 78

Benzyl 4-(7-{[2-(trimethylsilyl)ethoxy]methyl}-7H-imidazo[1,5-c]pyrrolo[3,2-e]pyrimidin-1-yl)piperidine-1-carboxylate The reactions in Reference Synthetic Example[a] 20 were carried out in substantially the same manners except that benzyl 4-[amino(7-{[2-(trimethylsilyl)ethoxy]methyl}-7H-pyrrolo[2,3-d]pyrimidin-4-yl)methyl]piperidine-1-carboxylate was used instead of benzyl 3-[amino(7-{[2-(trimethylsilyl)ethoxy]methyl}-7H-pyrrolo[2,3-d]pyrimidin-4-yl)methyl]piperidine-1-carboxylate to give a brown oily mixture containing the title compound (16.0 mg). The resulting mixture was used for the next step without purification.

Reference Synthetic Example[a] 79

Benzyl 4-[amino(7H-pyrrolo[2,3-d]pyrimidin-4-yl)methyl]piperidine-1-carboxylate

Benzyl 4-(7H-pyrrolo[2,3-d]pyrimidine-4-carbonyl)piperidine-1-carboxylate (50.0 mg, 0.137 mmol) obtained in Reference Synthetic Example[a] 44 in methanol (1 mL) was stirred with aqueous hydroxylamine (300 μL) at 75° C. for 4 hours and allowed to cool to room temperature. After addition of water and saturated aqueous ammonium chloride, the reaction mixture was extracted with chloroform. The organic layer was dried over anhydrous sodium sulfate and concentrated under reduced pressure to give a colorless oil. The oil was dissolved in methanol (3 mL), stirred with zinc powder (45.0 mg, 0.685 mmol) and acetic acid (24.0 μL, 0.411 mmol) at 75° C. for 3 hours and allowed to cool to room temperature. After addition of water and saturated aqueous sodium hydrogen carbonate, the reaction mixture was extracted with chloroform. The organic layer was dried over anhydrous sodium sulfate and concentrated under reduced pressure to give the title compound as a yellow oil (50.0 mg, yield 99%).

Reference Synthetic Example[a] 80

Piperidin-4-yl(7H-pyrrolo[2,3-d]pyrimidin-4-yl) methanone hydrochloride tert-Butyl 4-(7H-pyrrolo[2,3-d]pyrimidine-4-carbonyl)piperidine-1-carboxylate (840 mg, 2.54 mmol) obtained in Reference Synthetic Example[a] 39 in 1,4-dioxane (3 mL) was stirred with 4 M hydrogen chloride-1,4-dioxane (3 mL) at room temperature for one day. The resulting solid was collected by filtration to give the title compound as a brown solid (677 mg, yield 99%).

Reference Synthetic Example[a] 81

(7H-Pyrrolo[2,3-d]pyrimidin-4-yl){1-[4-(trifluoromethyl)benzyl]piperidin-4-yl}methanone Piperidin-4-yl(7H-pyrrolo[2,3-d]pyrimidin-4-yl)methanone hydrochloride (60.0 mg, 0.224 mmol) in acetonitrile (3 mL) was stirred with 4-(trifluoromethyl)benzyl bromide (70.0 mg, 0.292 mmol) and N,N-diisopropylethylamine (144 μL, 0.784 mmol) at 60° C. for 2 hours and allowed to cool to room temperature. After addition of water and saturated aqueous ammonium chloride, the reaction mixture was extracted with ethyl acetate. The organic layer was dried over anhydrous sodium sulfate and concentrated under reduced pressure. The residue was purified by silica gel column chromatography (hexane/ethyl acetate=1/1 (v/v)) to give the title compound as a pale yellow solid (65.0 mg, yield 75%).

Reference Synthetic Example[a] 82

(7H-Pyrrolo[2,3-d]pyrimidin-4-yl){1-[4-(trifluoromethyl)benzyl]piperidin-4-yl}methanamine The reactions in Reference Synthetic Example[a] 79 were carried out in substantially the same manners except that (7H-pyrrolo[2,3-d]pyrimidin-4-yl){1-[4-(trifluoromethyl) benzyl]piperidin-4-yl}methanone was used instead of benzyl 4-(7H-pyrrolo[2,3-d]pyrimidine-4-carbonyl)piperidine-1-carboxylate to give the title compound as a colorless solid (65.0 mg, yield 99%).

Reference Synthetic Example[a] 83

Benzyl 3-[methoxy(methyl)carbamoyl]azetidine-1-carboxylate

The reactions in Reference Synthetic Example[a] 43 were carried out in substantially the same manners except that azetidine-3-carboxylic acid was used instead of piperidine-4-carboxylic acid to give the title compound as a colorless oil (1.18 g, yield 21%).

Reference Synthetic Example[a] 84

Benzyl 3-(7H-pyrrolo[2,3-d]pyrimidine-4-carbonyl) azetidine-1-carboxylate

The reactions in Reference Synthetic Example[a] 10 were carried out in substantially the same manners except that benzyl 3-[methoxy(methyl)carbamoyl]azetidine-1-carboxylate was used instead of N-methoxy-N,2-dimethylbenzamide to give the title compound as a yellow solid (656 mg, yield 46%).

Reference Synthetic Example[a] 85

4-(Hydroxymethyl)-N-methoxy-N-methylbenzamide 4-(Hydroxymethyl)benzoic acid (3.00 g, 19.7 mmol) and N,O-dimethylhydroxylamine hydrochloride (2.31 g, 23.7 mmol) in chloroform (30 mL) was stirred with 1-(3-dimethylaminopropyl)-3-ethylcarbodiimide hydrochloride (4.54 g, 23.7 mmol), 1-hydroxybenzotriazole (3.20 g, 23.7 mmol) and N,N-diisopropylethylamine (8.04 mL, 47.3 mmol) at room temperature for one day. After addition of water, the reaction mixture was extracted with ethyl acetate, and the organic layer was washed with saturated aqueous sodium chloride, dried over anhydrous sodium sulfate and concentrated under reduced pressure to give a mixture containing the title compound as a colorless oil (4.20 g). The resulting mixture was used for the next step.

Reference Synthetic Example[a] 86

4-{[(tert-Butyldimethylsilyl)oxy]methyl}-N-methoxy-N-methylbenzamide 4-(Hydroxymethyl)-N-methoxy-N-methylbenzamide (4.20 g) obtained in Reference Synthetic Example[a] 85 in N,N-dimethylformamide (10 mL) was stirred with imidazole (4.00 g, 59.2 mmol) and tert-butylchlorodimethylsilane (3.60 g, 23.7 mmol) at room temperature for one day. After addition of water, the reaction mixture was extracted with ethyl acetate, and the organic layer was washed with saturated aqueous sodium chloride, dried over anhydrous sodium sulfate and concentrated under reduced pressure. The residue was purified by silica gel column chromatography (hexane/ethyl acetate=5/1→3/1 (v/v)) to give the title compound as a colorless oil (5.45 g, yield 89% (two steps)).

Reference Synthetic Example[a] 87

(4-{[(tert-Butyldimethylsilyl)oxy]methyl}phenyl) (7H-pyrrolo[2,3-d]pyrimidin-4-yl)methanone The reactions in Reference Synthetic Example[a] 10 were carried out in substantially the same manners except that 4-{[(tert-butyldimethylsilyl)oxy]methyl}-N-methoxy-N-methylbenzamide was used instead of N-methoxy-N,2-dimethylbenzamide to give the title compound as a pale yellow solid (4.40 g, yield 68%).

Reference Synthetic Example[a] 88

1-(4-{[(tert-Butyldimethylsilyl)oxy]methyl}phenyl)-7H-pyrrolo[3,2-e][1,2,3]triazolo[1,5-c]pyrimidine The reactions in Synthetic Example[a] 5 were carried out in substantially the same manners except that (4-{[(tert-butyldimethylsilyl)oxy]methyl}phenyl)(7H-pyrrolo[2,3-d]pyrimidin-4-yl)methanone was used instead of (7H-pyrrolo[2,3-d]pyrimidin-4-yl)(o-tolyl)methanone to give the title compound as a colorless solid (3.58 g, yield 79%).

Reference Synthetic Example[a] 89 cis-4-(Hydroxymethyl)-N-methoxy-N-methylcyclohexanecarboxamide

The reactions in Reference Synthetic Example[a] 85 were carried out in substantially the same manners except that cis-4-(hydroxymethyl)cyclohexanecarboxylic acid was used instead of 4-(hydroxymethyl)benzoic acid to give a mixture containing the title compound as a colorless oil (3.17 g). The resulting mixture was used for the next step.

Reference Synthetic Example[a] 90 cis-4-{[(tert-Butyldimethylsilyl)oxy]methyl}-N-methoxy-N-methylcyclohexanecarboxamide The reactions in Reference Synthetic Example[a] 86 were carried out in substantially the same manners except that cis-4-(hydroxymethyl)-N-methoxy-N-methylcyclohexanecarboxamide obtained in Reference Synthetic Example[a] 89 was used instead of 4-(hydroxymethyl)-N-methoxy-N-methylbenzamide to give the title compound as a colorless oil (5.3 g, yield 89% (two steps)).

Reference Synthetic Example[a] 91

(cis-4-{[(tert-Butyldimethylsilyl)oxy]methyl}cyclohexyl)(7H-pyrrolo[2,3-d]pyrimidin-4-yl)methanone The reactions in Reference Synthetic Example[a] 10 were carried out in substantially the same manners except that cis-4-{[(tert-butyldimethylsilyl)oxy]methyl}-N-methoxy-N-methylcyclohexanecarboxamide was used instead of N-methoxy-N,2-dimethylbenzamide to give the title compound as a pale yellow solid (4.50 g, yield 72%).

Reference Synthetic Example[a] 92

1-(trans-4-{[(tert-Butyldimethylsilyl)oxy]methyl}cyclohexyl)-7H-pyrrolo[3,2-e][1,2,3]triazolo[1,5-c]pyrimidine The reactions in Synthetic Example[a] 5 were carried out in substantially the same manners except that (cis-4-{[(tert-Butyldimethylsilyl)oxy]methyl}cyclohexyl)(7H-pyrrolo[2,3-d]pyrimidin-4-yl)methanone was used instead of (7H-pyrrolo[2,3-d]pyrimidin-4-yl)(o-tolyl)methanone to give the title compound as a pale yellow solid (3.49 g, yield 75%). (although the cis-isomer was used as the starting material, only the trans-isomer of the title compound was obtained.)

Reference Synthetic Example[a] 93

5-(Bromomethyl)thiophene-2-carbonitrile

5-Methylthiophene-2-carbonitrile (500 mg, 4.06 mmol) in carbon tetrachloride (10 mL) was stirred with N-bromosuccinimide (867 mg, 4.87 mmol) and 2,2'-azobis(isobutyronitrile) (133 mg, 0.810 mmol) at 60° C. for 4.5 hours and allowed to cool to room temperature. After addition of saturated aqueous sodium thiosulfate, the reaction mixture was extracted with chloroform, and the organic layer was dried over anhydrous sodium sulfate and concentrated under reduced pressure. The residue was purified by silica gel column chromatography (hexane/ethyl acetate=2/1→1/1 (v/v)) to give the title compound as a yellow oil (186 mg, yield 23%).

Reference Synthetic Example[a] 94

4-{[4-(7H-pyrrolo[2,3-d]pyrimidine-4-carbonyl)piperidin-1-yl]methyl}benzonitrile The reactions in Reference Synthetic Example[a] 81 were carried out in substantially the same manners except that 4-(bromomethyl)benzonitrile was used instead of 4-(trifluoromethyl)benzyl bromide to give the title compound as a pale yellow solid (150.9 mg, yield 65%).

Reference Synthetic Example[a] 95

4-{[4-(7-{[2-(Trimethylsilyl)ethoxy]methyl}-7H-pyrrolo[2,3-d]pyrimidine-4-carbonyl)piperidin-1-yl]methyl}benzonitrile The reactions in Reference Synthetic Example[a] 15 were carried out in substantially the same manners except that 4-{[4-(7H-pyrrolo[2,3-d]pyrimidine-4-carbonyl)piperidin-1-yl]methyl}benzonitrile was used instead of 4-iodo-7H-pyrrolo[2,3-d]pyrimidine to give the title compound as a yellow oil (124.1 mg, yield 75%).

Reference Synthetic Example[a] 96

4-({4-[Amino(7-{[2-(trimethylsilyl)ethoxy]methyl}-7H-pyrrolo[2,3-d]pyrimidin-4-yl)methyl]piperidin-1-yl}methyl)benzonitrile The reactions in Reference Synthetic Example[a] 7 were carried out in substantially the same manners except that 4-({4-[amino(7-{[2-(trimethylsilyl)ethoxy]methyl}-7H-pyrrolo[2,3-d]pyrimidin-4-yl)methyl]piperidin-1-yl}methyl)benzonitrile was used instead of cyclohexyl(7-{[2-(trimethylsilyl)ethoxy]methyl}-7H-pyrrolo[2,3-d]pyrimidin-4-yl)methanone to give the title compound as a yellow oil (42.9 mg, yield 34%).

Reference Synthetic Example[a] 97

4-{[4-(7-{[2-(trimethylsilyl)ethoxy]methyl}-7H-imidazo[1,5-c]pyrrolo[3,2-e]pyrimidin-1-yl)piperidin-1-yl]methyl}benzonitrile The reactions in Reference Synthetic Example[a] 20 were carried out in substantially the same manners except that 4-({4-[amino(7-{[2-(trimethylsilyl)ethoxy]methyl}-7H-pyrrolo[2,3-d]pyrimidin-4-yl)methyl]piperidin-1-yl}methyl)benzonitrile was used instead of benzyl 3-[amino(7-{[2-(trimethylsilyl)ethoxy]methyl}-7H-pyrrolo[2,3-d]pyrimidin-4-yl)methyl]piperidine-1-carboxylate to give a brown oil containing the title compound (37.4 mg). The resulting mixture was used for the next step.

Reference Synthetic Example[a] 98

Benzyl 3-[methoxy(methyl)carbamoyl]pyrrolidine-1-carboxylate

Triethylamine (1.68 mL, 12.0 mmol) was added dropwise to 1-[(benzyloxy)carbonyl]pyrrolidine-3-carboxylic acid (1.00 g, 4.01 mmol), N,O-dimethylhydroxylamine hydrochloride (782 mg, 8.02 mmol), 1-(3-dimethylaminopropyl)-3-ethylcarbodiimide hydrochloride (1.54 g, 8.02 mmol) and 1-hydroxybenzotriazole (1.08 g, 8.02 mmol) in chloroform (20 mL), and the reaction mixture was stirred at room temperature for 16 hours. After addition of water, the reaction mixture was extracted with chloroform, and the organic layer was dried over anhydrous sodium sulfate and concentrated under reduced pressure. The residue was purified by silica gel column chromatography (hexane/ethyl acetate=1/1→3/7 (v/v)) to give the title compound as a yellow oil (1.11 g, yield 95%).

Reference Synthetic Example[a] 99

Benzyl 3-(7H-pyrrolo[2,3-d]pyrimidine-4-carbonyl)pyrrolidine-1-carboxylate

The reactions in Reference Synthetic Example[a] 10 were carried out in substantially the same manners except that benzyl 3-[methoxy(methyl)carbamoyl]pyrrolidine-1-carboxylate was used instead of N-methoxy-N,2-dimethylbenzamide to give a pale yellow solid containing the title compound (216 mg). The resulting mixture was used for the next step.

Reference Synthetic Example[a] 100

3-Amino-2-(4-chlorophenyl)-1,1,1-trifluoropropan-2-ol 1-(4-Chlorophenyl)-2,2,2-trifluoroethanone (2.00 g, 9.59 mmol) in nitromethane (10 mL) was stirred with potassium carbonate (1.32 g, 9.59 mmol) at room temperature for 1 hour. After addition of water, the reaction mixture was extracted with ethyl acetate, and the organic layer was dried over anhydrous magnesium sulfate and concentrated under reduced pressure. The resulting residue (pale yellow amorphous, 3.3 g) was dissolved in ethanol (52 mL), then 6 M hydrochloric acid was added dropwise under cooling with ice, and zinc powder (3.13 g, 48.0 mmol) was gradually added. The reaction mixture was stirred for one day while the temperature was gradually raised to room temperature, and filtered through Celite. The filtrate was concentrated under reduced pressure. The residue was mixed with 28 wt % aqueous ammonia and extracted with chloroform, and the organic layer was dried over anhydrous magnesium sulfate and concentrated under reduced pressure. The residue was purified by silica gel column chromatography (hexane/ethyl acetate=3/1→1/1 (v/v)) to give the title compound as a colorless solid (609 mg, yield 26%).

Reference Synthetic Example[a] 101

3-Amino-1,1,1-trifluoro-2-phenylpropan-2-ol

The reactions in Reference Synthetic Example[a] 100 were carried out in substantially the same manners except that 2,2,2-trifluoro-1-phenylethanone was used instead of 1-(4-chlorophenyl)-2,2,2-trifluoroethanone to give the title compound as a colorless solid (54 mg, yield 46%).

Reference Synthetic Example[a] 102

3-Amino-1,1,1-trifluoro-2-(4-fluorophenyl)propan-2-ol n-Butyllithium (2.66 M solution in hexane, 12.4 mL, 33.0 mmol) was added dropwise to 1-bromo-4-fluorobenzene (5.25 g, 30.0 mmol) in tetrahydrofuran (50 mL) cooled to −78° C., and the reaction mixture was stirred at −78° C. for 30 minutes, mixed with ethyl 2,2,2-trifluoroacetate (4.64 mL, 45 mmol) at −78° C. and then stirred for another 30 minutes while the temperature was gradually raised to room temperature. The reaction mixture was stirred with nitromethane (3.25 mL, 60 mmol) at room temperature for 30 minutes. The resulting reaction mixture was added to 1 M hydrochloric acid (50 mL) and extracted with ethyl acetate. The organic layer was dried over anhydrous sodium sulfate and concentrated under reduced pressure. The residue was purified by silica gel column chromatography (hexane/ethyl acetate=5/1 (v/v/)) to give a colorless oil. The colorless oil was dissolved in ethanol (25 mL) and stirred with 10% palladium-carbon (1 g) at room temperature for one day under a hydrogen atmosphere. The reaction mixture was filtered through Celite, and the filtrate was concentrated under reduced pressure to give the title compound as a colorless solid (4.52 g, yield 68% (three steps)).

Reference Synthetic Example[a] 103

2-[4-(Trifluoromethyl)phenyl]oxirane

Trimethylsulfonium iodide (4.08 g, 20.0 mmol) in dimethyl sulfoxide (15 mL) was stirred with sodium hydride (55 wt % dispersion in mineral oil, 873 mg, 20.0 mmol) at room temperature for 1 hour and then with 4-(trifluoromethyl)styrene (2.96 g, 17.0 mmol) in dimethyl sulfoxide (10 mL) at room temperature for 2 hours. After addition of water, the reaction mixture was extracted with ethyl acetate, and the organic layer was dried over anhydrous sodium sulfate and concentrated under reduced pressure. The residue was purified by silica gel column chromatography (hexane/ethyl acetate=9/1 (v/v)) to give the title compound as a colorless oil (2.59 g, yield 81%).

Reference Synthetic Example[a] 104

1-(Piperidin-4-yl)-7H-pyrrolo[3,2-e][1,2,3]triazolo[1,5-c]pyrimidine acetate

5% Palladium-carbon (0.87 g) was added to benzyl 4-(7H-pyrrolo[3,2-e][1,2,3]triazolo[1,5-c]pyrimidin-1-yl)piperidine-1-carboxylate (4.88 g, 13.0 mmol) obtained in Synthetic Example[a] 26 in a mixture of acetic acid (60 mL), water (6 mL) and ethanol (10 mL), and after then the reaction system was flushed with hydrogen, the reaction mixture was stirred at room temperature for one day and then filtered. The filtrate was concentrated, and the resulting yellow solid was washed with ethanol to give the title compound as a colorless solid (3.30 g, yield 84%).

Reference Synthetic Example[a] 105

2-(4-Formylphenoxy)acetonitrile

4-Hydroxybenzaldehyde (244 mg, 2.00 mmol) in N,N-dimethylformamide (5 mL) was mixed with sodium hydride (60 wt % dispersion in liquid paraffin, 120 mg, 3.00 mmol) and chloroacetonitrile (189 μL, 3.00 mmol) under cooling with ice and then stirred at 50° C. for 3 hours. The reaction mixture was allowed to cool to room temperature and mixed with saturated aqueous ammonium chloride and extracted with ethyl acetate. The organic layer was washed with 1M aqueous sodium hydroxide, dried over anhydrous sodium sulfate and concentrated under reduced pressure to give the title compound as a brown oil (128 mg, yield 40%).

Reference Synthetic Example[a] 106

4-(Bromomethyl)benzamide 4-(Bromomethyl)benzoic acid (300 mg, 1.40 mmol) in ethyl acetate (5 mL) was stirred with thionyl chloride (249 μL, 3.50 mmol) at 75° C. for 9 hours. The reaction mixture was allowed to cool to room temperature and concentrated under reduced pressure. The residue was dissolved in dichloromethane (5 mL) and stirred with 28% ammonia aqueous solution (380 μL, 5.60 mmol) under cooling with ice for 80 minutes. The reaction mixture was mixed with water, and the precipitate was collected by filtration, washed with dichloromethane to give the title compound as a colorless solid (274 mg, yield 91%).

Reference Synthetic Example[a] 107

5-(Bromomethyl)-2-(trifluoromethyl)benzonitrile

5-Methyl-2-(trifluoromethyl)benzonitrile (200 mg, 1.08 mmol) in 1,2-dichloroethane (3 mL) was stirred with N-bromosuccinimide (192 mg, 1.08 mmol) and azobisisobutyronitrile (36.1 mg, 0.22 mmol) at 80° C. for 2 hours. The reaction mixture allowed to cool to room temperature and was concentrated under reduced pressure. The residue was purified by silica gel column chromatography (hexane→ethyl acetate/hexane=1/3 (v/v)) to give the title compound as a colorless solid (140 mg, yield 49%).

Reference Synthetic Example[a] 108

4-(Bromomethyl)phthalonitrile

The reactions in Reference Synthetic Example[a] 107 were carried out in substantially the same manners except that 4-methylphthalonitrile was used instead of 5-methyl-2-(trifluoromethyl)benzonitrile to give the title compound as a colorless solid (163 mg, yield 52%).

Reference Synthetic Example[a] 109

4-(Bromomethyl)-2-(trifluoromethyl)benzonitrile

The reactions in Reference Synthetic Example[a] 107 were carried out in substantially the same manners except that 4-methyl-2-(trifluoromethyl)benzonitrile was used instead of 5-methyl-2-(trifluoromethyl)benzonitrile to give the title compound as a colorless solid (177 mg, yield 62%).

Reference Synthetic Example[a] 110 tert-Butyl 4-cyanophenethylcarbamate 2-(4-Bromophenyl)ethylamine (2.00 g, 10.0 mmol) in tetrahydrofuran (5 mL) was mixed with Di-tert-butyl dicarbonate (2.20 g, 10.0 mmol) under cooling with ice and then stirred at room temperature for one day. After addition of water, the reaction mixture was extracted with ethyl acetate. The organic layer was dried over anhydrous sodium sulfate and concentrated under reduced pressure. The resulting residue (900 mg) was dissolved in N,N-dimethylformamide (30 mL) and mixed with zinc cyanide (705 mg, 60.0 mmol) and tetrakis(triphenylphosphine)palladium(0) (347 mg, 0.300 mmol), and the reaction mixture was stirred at 150° C. for 20 minutes under microwave irradiation. The resulting reaction mixture was allowed to cool to room temperature, mixed with saturated aqueous ammonium chloride and extracted with ethyl acetate. The organic layer was dried over anhydrous sodium sulfate and concentrated under reduced pressure. The residue was purified by silica gel column chromatography (hexane/ethyl acetate=10/1→4/1 (v/v)) to give the title compound as a pale yellow solid (305 mg, yield 41%).

Reference Synthetic Example[a] 111

4-(2-Aminoethyl)benzonitrile tert-Butyl 4-cyanophenethylcarbamate (305 mg, 1.24 mmol) in dichloromethane (4 mL) was mixed with trifluoroacetic acid (3.50 mL, 47.1 mmol) under cooling with ice and then stirred at room temperature for 30 minutes. The reaction mixture was concentrated under reduced pressure, mixed with saturated aqueous potassium carbonate and extracted with ethyl acetate. The organic layer was washed with saturated aqueous sodium chloride, dried over anhydrous sodium sulfate and concentrated under reduced pressure to give the title compound as a pale orange solid (72.5 mg, yield 40%).

Reference Synthetic Example[a] 112 tert-Butyl 3-oxoazetidine-1-carboxylate tert-Butyl 3-hydroxyazetidine-1-carboxylate (4.02 g, 23.2 mmol) in dichloromethane (305 mL) was mixed with Dess-Martin Periodinane (9.55 g, 22.5 mmol) under cooling with ice and then stirred at room temperature for 3 hours. After addition of 10% aqueous sodium thiosulfate and saturated aqueous sodium hydrogen carbonate under cooling with ice, the reaction mixture was extracted with chloroform, and the organic layer was washed with saturated aqueous sodium chloride, dried over anhydrous magnesium sulfate and concentrated under reduced pressure. The residue was purified by silica gel column chromatography (hexane/ethyl acetate=2/1 (v/v)) to give the title compound as a colorless solid (3.39 g, yield 85%).

Reference Synthetic Example[a] 113 tert-Butyl 3-hydroxy-3-methylazetidine-1-carboxylate

Methylmagnesium bromide-tetrahydrofuran solution (1.12 M, 3.90 mL, 4.38 mmol) was added dropwise to tert-butyl 3-oxoazetidine-1-carboxylate (500 mg, 2.92 mmol) in tetrahydrofuran (5 mL) under cooling with ice and stirred for 90 minutes. After addition of saturated aqueous ammonium chloride, the reaction mixture was extracted with ethyl acetate, and the organic layer was dried over anhydrous sodium sulfate and concentrated under reduced pressure. The residue was purified by silica gel column chromatography (hexane/ethyl acetate=2/1→1/1 (v/v)) to give the title compound as a colorless solid (224 mg, yield 41%).

Reference Synthetic Example[a] 114

3-Methylazetidin-3-ol hydrochloride tert-Butyl 3-hydroxy-3-methylazetidine-1-carboxylate (224 mg, 1.20 mmol) in ethyl acetate (1 mL) was mixed with 4 M hydrogen chloride-1,4-dioxane solution (3.0 mL) under cooling with ice and then stirred at room temperature for 1 hour. The reaction mixture was concentrated under reduced pressure to give a mixture containing the title compound (colorless oil, 162 mg). The mixture was used for the next step without further purification.

Reference Synthetic Example[a] 115

3-(Trifluoromethyl)azetidin-3-ol hydrochloride tert-Butyl 3-oxoazetidine-1-carboxylate (500 mg, 2.92 mmol) obtained in Reference Synthetic Example[a] 112 and (trifluoromethyl)trimethylsilane (0.648 mL, 4.38 mmol) in tetrahydrofuran (10 mL) were mixed with tetrabutylammonium fluoride-tetrahydrofuran solution (1 M, 0.291 mL, 0.291 mmol) under cooling with ice and then stirred at room temperature for 1 hour. After addition of saturated aqueous ammonium chloride, the reaction mixture was extracted with diethyl ether, and the organic layer was dried over anhydrous magnesium sulfate and concentrated under reduced pressure. The residue was mixed with ethyl acetate (5 mL) and 1M aqueous citric acid (5 mL) and stirred at room temperature for 1 hour. After addition of water, the reaction mixture was extracted with diethyl ether. The organic layer was dried over anhydrous magnesium sulfate and concentrated under reduced pressure. The resulting residue was dissolved in ethyl acetate (1.0 mL), mixed with 4 M hydrogen chloride-1,4-dioxane solution (4 mL) under cooling with ice and then stirred at room temperature for 22 hours. The reaction mixture was concentrated under reduced pressure, and the precipitate was washed with ethyl acetate to give the title compound as a white solid (340 mg, yield 66% (2 steps)).

Reference Synthetic Example[a] 116 tert-Butyl 3-(2,2,2-trifluoroethoxy)azetidine-1-carboxylate

Sodium hydride (55 wt % dispersion in liquid paraffin, 151 mg, 3.46 mmol) in N,N-dimethylformamide (5 mL) was mixed with tert-butyl 3-hydroxyazetidine-1-carboxylate (500 mg, 2.89 mmol) in N,N-dimethylformamide (3 mL) under cooling with ice and stirred for 30 minutes, and the resulting reaction mixture was mixed with 2,2,2-trifluoroethyl trifluoromethanesulfonate (0.499 mL, 3.46 mmol) under cooling with ice and then stirred at room temperature for 5 hours. After addition of water, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (hexane/ethyl acetate=3/1→1/1 (v/v)) to give the title compound as a colorless solid (350 mg, yield 48%).

Reference Synthetic Example[a] 117

3-(2,2,2-Trifluoroethoxy)azetidine hydrochloride tert-Butyl 3-(2,2,2-trifluoroethoxy)azetidine-1-carboxylate (350 mg, 1.37 mmol) in ethyl acetate (1.0 mL) was mixed with 4 M hydrogen chloride-1,4-dioxane solution (3.0 mL) under cooling with ice and then stirred at room temperature for 2 hours. The reaction mixture was concentrated to give a mixture containing the title compound as a colorless oil (224 mg). The mixture was used for next step without further purification.

Reference Synthetic Example[a] 118

3-Amino-1,1,1-trifluoro-2-(pyridin-3-yl)propan-2-ol

Isopropylmagnesium chloride-lithium chloride complex-tetrahydrofuran solution (1.3 M, 20.7 mL, 27.0 mmol) was added dropwise to 5-bromo-2-chloropyridine (5.20 g, 27.0 mmol) in tetrahydrofuran (40 mL) under cooling with ice, and the reaction mixture was stirred for 30 minutes and then mixed with ethyl 2,2,2-trifluoroacetate (11.5 g, 81.0 mmol) under cooling with ice and stirred at room temperature for 10 minutes. After addition of 1M hydrochloric acid, the reaction mixture was extracted with ethyl acetate, and the organic layer was dried over anhydrous sodium sulfate and concentrated under reduced pressure to give a yellow oil. The yellow oil was dissolved in nitromethane (30 mL) and stirred with potassium carbonate (3.73 g, 27.0 mmol) at room temperature for 30 minutes. The reaction mixture was added to 1M hydrochloric acid and extracted with ethyl acetate, and the organic layer was dried over anhydrous sodium sulfate and concentrated under reduced pressure. The residue was purified by silica gel column chromatography (hexane/ethyl acetate=3/1 (v/v)) to give a yellow oil. The yellow oil was dissolved in tetrahydrofuran (20 mL), mixed with 10% palladium-carbon (600 mg) and triethylamine (2.60 mL, 18.7 mmol) and then stirred at room temperature for one day under a hydrogen atmosphere. The reaction mixture was filtered, and the filtrate was concentrated under reduced pressure. The residue was purified by silica gel column chromatography (ethyl acetate→ethyl acetate/methanol/triethylamine=9/1/1 (v/v/v)) to give the title compound as a colorless solid (913 mg, yield 31% (4 steps)).

Reference Synthetic Example[a] 119

3-Amino-1,1,1-trifluoro-2-[4-(methylthio)phenyl]propan-2-ol

The reactions in Reference Synthetic Example[a] 102 were carried out in substantially the same manners except that (4-bromomethyl)(methyl)sulfane was used instead of 1-bromo-4-fluorobenzene to give the title compound as a colorless solid (2.61 g, yield 64%).

Reference Synthetic Example[a] 120

3-Amino-1,1,1-trifluoro-2-(6-methoxypyridin-3-yl)propan-2-ol

The reactions in Reference Synthetic Example[a] 102 were carried out in substantially the same manners except that 5-bromo-2-methoxypyridine was used instead of 1-bromo-4-fluorobenzene to give the title compound as a colorless solid (1.52 g, yield 76%).

Reference Synthetic Example[a] 121

3-Amino-1,1,1-trifluoro-2-(4-methoxyphenyl)propan-2-ol

The reactions in Reference Synthetic Example[a] 100 were carried out in substantially the same manners except that 2,2,2-trifluoro-1-(4-methoxyphenyl)etanone was used instead of 1-(4-Chlorophenyl)-2,2,2-trifluoroethanone to give the title compound as a colorless solid (823 mg, yield 36%).

Reference Synthetic Example[a] 122

3-Amino-2-(3,4-dimethoxyphenyl)-1,1,1-trifluoro-propan-2-ol

The reactions in Synthetic Example[a] 100 were carried out in substantially the same manners except that 1-(3,4-dimethoxyphenyl)-2,2,2-trifluoroethanone was used instead of 1-(4-Chlorophenyl)-2,2,2-trifluoroethanone to give the title compound as a colorless solid (532 mg, yield 39%).

Reference Synthetic Example[a] 123

Ethyl(E)-3-(4-fluorophenyl)acrylate

4-Fluorobenzaldehyde (9.61 g, 80.0 mmol) in tetrahydrofuran (120 mL) was mixed with ethyl 2-(diethoxyphosphoryl) acetate (17.9 g, 80.0 mmol) under cooling with ice, and then sodium ethoxide-ethanol solution (21 wt %, 44.8 mL, 120 mmol) was added dropwise to the reaction mixture under cooling with ice, and the resulting reaction mixture was stirred at room temperature for 2 hours. After addition of water, the reaction mixture was extracted with ethyl acetate, and the organic layer dried over anhydrous sodium sulfate and concentrated under reduced pressure. The residue was purified by silica gel column chromatography (hexane/ethyl acetate=20/1→10/1 (v/v)) to give the title compound as a colorless oil (14.1 g, yield 91%).

Reference Synthetic Example[a] 124 trans-Ethyl 2-(4-fluorophenyl)cyclopropanecarboxylate

Trimethylsulfoxonium iodide (7.92 g, 36.0 mmol) in dimethyl sulfoxide (40 mL) was mixed with sodium hydride (55 wt % dispersion in mineral oil, 1.57 g, 36.0 mmol) under cooling with ice, stirred at room temperature for 1 hour and then stirred with (E)-ethyl 3-(4-fluorophenyl)acrylate (5.83 g, 30.0 mmol) for 18 hours. After addition of water, the reaction mixture was extracted with ethyl acetate, and the organic layer was dried over anhydrous sodium sulfate and concentrated under reduced pressure. The residue was purified by silica gel column chromatography (hexane/ethyl acetate=10/1) to give the title compound as a colorless oil (793 mg, yield 13%).

Reference Synthetic Example[a] 125

2-{[trans-2-(4-Fluorophenyl)cyclopropyl] methyl}isoindoline-1,3-dione trans-Ethyl 2-(4-Fluorophenyl)cyclopropane-1-carboxylate (793 mg, 4.57 mmol) in tetrahydrofuran (7 mL) was stirred with lithium aluminium hydride (173 mg, 4.57 mmol) under cooling with ice for 10 minutes. After addition of 1 M aqueous sodium hydroxide, the reaction mixture was extracted with ethyl acetate, and the organic layer was dried over anhydrous sodium sulfate and concentrated under reduced pressure. The resulting residue was dissolved in tetrahydrofuran (10 mL), mixed with triphenylphosphine (999 mg, 3.81 mmol), isoindoline-1,3-dione (560 mg, 3.81 mmol) and azodicarboxylic acid diisopropyl ester-toluene solution (1.9 M, 2.00 mL, 3.81 mmol) under cooling with ice, and the reaction mixture was stirred at room temperature for 1 hour and concentrated under reduced pressure. The residue was purified by silica gel column chromatography (hexane/ethyl acetate=5/1 (v/v)) to give the title compound as a colorless solid (975 mg, yield 87% (2 steps)).

Reference Synthetic Example[a] 126

[trans-2-(4-Fluorophenyl)cyclopropyl]methanamine

2-{[trans-2-(4-Fluorophenyl)cyclopropyl] methyl}isoindoline-1,3-dione (974 mg, 3.30 mmol) in ethanol (50 mL) was stirred with hydrazine monohydrate (825 mg, 16.5 mmol) at 100° C. for 30 minutes. The reaction mixture was concentrated to give the title compound as a colorless oil (360 mg, yield 66%).

Reference Synthetic Example[a] 127

4-Aminoadamantan-1-ol

Concentrated sulfuric acid (35 mL) was mixed with concentrated nitric acid (4.5 mL) and 2-adamantylamine (5.10 g, 4.57 mmol) under cooling with ice, and the reaction mixture was stirred at room temperature for 2 hours. The reaction mixture was added to ice water and adjusted to pH 10 with 7.5 M aqueous sodium hydroxide. After addition of water, the reaction mixture was extracted with chloroform, and the organic layer was dried over anhydrous magnesium sulfate and concentrated under reduced pressure to give the title compound as a yellow solid (2.79 g, yield 61%).

Reference Synthetic Example[a] 128

128a: Benzyl [(1R,2s,3S,5s,7s)-5-hydroxyadamantan-2-yl]carbamate

128b: Benzyl [(1R,2r,3S,5s,7s)-5-hydroxyadamantan-2-yl]carbamate

4-Aminoadamantan-1-ol (2.57 g, 15.4 mmol) in tetrahydrofuran (25 mL) was mixed with benzyl chloroformate (2.30 mL, 16.1 mmol) and 1 M aqueous sodium hydroxide (16.0 mL, 16.0 mmol) under cooling with ice and then stirred at room temperature for one day. After addition of 10% aqueous potassium hydrogen sulfate, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (hexane/ethyl acetate=1/2 (v/v)) to give benzyl [(1R,2S3S,5S,7S)-5-hydroxyadamantan-2-yl] carbamate (Reference Synthetic Example[a] 128a; yellow oil, 1.72 g, yield 37%) in a more polar fraction and benzyl [(1R,2R,3S,5S,7S)-5-hydroxyadamantan-2-yl]carbamate (Reference Synthetic Example[a] 128b; yellow oil, 2.24 g, yield 48%) in a less polar fraction.

Reference Synthetic Example[a] 129

(1s,3R,4s,5S,7s)-4-Aminoadamantan-1-ol

Benzyl [(1R,2s,3S,5s,7s)-5-hydroxyadamantan-2-yl]carbamate (318 mg, 1.05 mmol) obtained in Reference Synthetic Example[a] 128a and 5% palladium-carbon (63 mg) in methanol (2 mL) were stirred at room temperature for one day under a hydrogen atmosphere. The reaction mixture was filtered, and the filtrate was concentrated under reduced pressure to give the title compound as a colorless solid (144 mg, yield 82%).

Reference Synthetic Example[a] 130

(1s,3R,4r,5S,7s)-4-Aminoadamantan-1-ol

Benzyl [(1R,2r,3S,5s,7s)-5-hydroxyadamantan-2-yl]carbamate (2.24 g, 7.46 mmol) obtained in Reference Synthetic Example[a] 128b and 5% palladium-carbon (700 mg) in methanol (30 mL) were stirred at room temperature for one day under a hydrogen atmosphere. The reaction mixture was filtered, and the filtrate was concentrated under reduced pressure to give the title compound as a colorless solid (1.29 g, quantitative yield).

Reference Synthetic Example[a] 131

2-Bromo-2,2-difluoroethanamine hydrochloride

Borane tetrahydrofuran complex-tetrahydrofuran solution (1.06 M, 12.0 mL, 12.6 mmol) was added dropwise to 2-bromo-2,2-difluoroacetamide (2.00 g, 11.5 mmol) in tetrahydrofuran (20 mL) under cooling with ice, and the resulting reaction mixture was stirred at room temperature for 5 hours. After addition of ethanol (10 mL) and concentrated hydrochloric acid (7 mL), the reaction mixture was concentrated under reduced pressure. The precipitate was collected by filtration to give the title compound as a colorless solid (1.60 g, yield 71%).

Reference Synthetic Example[a] 132

4-Cyanophenethyl 4-methylbenzenesulfonate 4-(2-Hydroxyethyl)benzonitrile (200 mg, 1.35 mmol) in tetrahydrofuran (4 mL) was mixed with 4-methylbenzene-1-sulfonyl chloride (389 mg, 2.04 mmol) and triethylamine (569 μL, 4.08 mmol) and stirred at room temperature for 1 day. After addition of water, the reaction mixture was extracted with ethyl acetate. The organic layer was dried over anhydrous sodium sulfate and concentrated under reduced pressure. The residue was purified by silica gel column chromatography (hexane/ethyl acetate=9/1→3/1→1/1 (v/v)) to give the title compound as a colorless solid (174 mg, yield 43%).

Reference Synthetic Example[a] 133

4-{[(tert-Butyldimethylsilyl)oxy]methyl}-N-methoxy-N-methylcyclohexanecarboxamide 4-(Hydroxymethyl)cyclohexanecarboxic acid (25.0 g, 158 mmol) and N,O-dimethylhydroxylamine hydrochloride (23.1 g, 237 mmol) in chloroform (100 mL) were mixed with 1-(3-Dimethylaminopropyl)-3-ethylcarbodiimide hydrochloride (36.4 g, 190 mmol), 1-hydroxybenzotriazole (5.00 g, 37.0 mmol) and N,N-diisopropylethylamine (41.3 mL, 237 mmol) and stirred at room temperature for 1 day. After addition of water, the reaction mixture was extracted with ethyl acetate. The organic layer was washed with saturated sodium chloride, dried over anhydrous sodium sulfate and concentrated under reduced pressure. The residue was dissolved in N,N-dimethylformamide (100 mL) and mixed with imidazole (21.5 g, 316 mmol) and tert-butylchlorodimethylsilane (26.2 g, 174 mmol). The reaction mixture was stirred at room temperature for 1 day. After addition of water, the reaction mixture was extracted with ethyl acetate. The organic layer was washed with saturated sodium chloride, dried over anhydrous sodium sulfate and concentrated under reduced pressure. The residue was purified by silica gel column chromatography (hexane/ethyl acetate=5/1→3/1 (v/v)) to give the title compound as a colorless oil (32.4 g, yield 65%).

Reference Synthetic Example[a] 134

(4-{[(tert-Butyldimethylsilyl)oxy]methyl}cyclohexyl)(7H-pyrrolo[2,3-d]pyrimidin-4-yl)methanone Isopropylmagnesium chloride-lithium chloride complex-tetrahydrofuran solution (1.3 M, 39.2 mL, 51.0 mmol) was added dropwise to 4-iodo-7H-pyrrolo[2,3-d]pyrimidine (5.00 g, 20.4 mmol) obtained in Reference Synthetic Example[a] 1 in tetrahydrofuran (50 mL) at −50° C., and stirred at −50° C. for 1 hour. The reaction mixture was mixed with 4-{[(tert-butyldimethylsilyl)oxy]methyl}-N-methoxy-N-methylcyclohexanecarboxamide (6.44 g, 20.4 mmol) in tetrahydrofuran (30 mL) at −50° C. and then stirred at room temperature for 23 hours. After addition of saturated aqueous ammonium chloride, the reaction mixture was extracted with ethyl acetate. The organic layer was washed with saturated sodium chloride, dried over anhydrous sodium sulfate and concentrated under reduced pressure. The residue was purified by silica gel column chromatography (hexane/ethyl acetate=3/1 (v/v)) to give the title compound as a colorless oil (5.14 g, yield 67%).

Reference Synthetic Example[a] 135

135a: 1-(cis-4-{[(tert-Butyldimethylsilyl)oxy]methyl}cyclohexyl)-7H-pyrrolo[3,2-e][1,2,3]triazolo[1,5-c]pyrimidine 135b: 1-(trans-4-{[(tert-Butyldimethylsilyl)oxy]methyl}cyclohexyl)-7H-pyrrolo[3,2-e][1,2,3]triazolo[1,5-c]pyrimidine (4-{[(tert-Butyldimethylsilyl)oxy]methyl}cyclohexyl)(7H-pyrrolo[2,3-d]pyrimidin-4-yl)methanone (9.23 g, 24.7 mmol) in methanol (200 mL) was mixed with hydrazine monohydrate (38.0 mL, 618 mmol) and then stirred at 80° C. for 3 hours. The reaction mixture was allowed to cool to room temperature and mixed with ethyl acetate, washed with water and saturated sodium chloride. The organic layer was dried over anhydrous sodium sulfate and concentrated under reduced pressure. The residue was dissolved in chloroform (240 mL) and mixed with manganese(IV) oxide (10.7 g, 124 mmol). The reaction mixture was stirred at 70° C. for 1 day. The reaction mixture was filtered, and the filtrate was concentrated under reduced pressure. The residue was purified by silica gel chromatography (hexane/ethyl acetate=3/1 (v/v)) to give 1-(cis-4-{[(tert-butyldimethylsilyl)oxy]methyl)}cyclohexyl)-7H-pyrrolo[3,2-e][1,2,3]triazolo[1,5-c]pyrimidine (Reference Synthetic Example[a] 135a; pale yellow solid, 670 mg, yield 7%) in a less polar fraction and 1-(trans-4-{[(tert-butyldimethylsilyl)oxy]methyl)}cyclohexyl)-7H-pyrrolo[3,2-e][1,2,3]triazolo[1,5- c]pyrimidine (Reference Synthetic Example[a] 135b, pale yellow solid, 5.02 g, yield 52%) in a more polar fraction.

Reference Synthetic Example[a] 136

Cyclopropylamine hydrochloride

Cyclopropylamine (0.600 mL, 8.76 mmol) was mixed with 1 M hydrogen chloride-diethylether solution (10 mL) under cooling with ice and stirred for 2 hours. The reaction mixture was concentrated under reduced pressure, and the precipitate was washed with diethyl ether to give the title compound as a colorless solid (686 mg, yield 84%).

Reference Synthetic Example[a] 137 tert-Butyl 3-(dimethylamino)azetidine-1-carboxylate tert-Butyl 3-oxoazetidine-1-carboxylate (300 mg, 1.75 mmol) obtained in Reference Synthetic Example[a] 112 in methanol (15 mL) was mixed with acetic acid (1.0 mL), dimethylamine-tetrahydrofuran solution (2.0M, 1.31 mL, 2.63 mmol) and 2-picoline borane (280 mg, 2.63 mmol). The reaction mixture was stirred at room temperature for 1 day. After addition of 1M aqueous hydrogen chloride, the reaction mixture was extracted with ethyl acetate. The aqueous layer was adjusted to pH 10 with 1 M aqueous sodium hydroxide and extracted with ethyl acetate. The organic layer was dried over anhydrous sodium sulfate and concentrated under reduced pressure to give the title compound as a colorless solid (134 mg, yield 90%).

Reference Synthetic Example[a] 138 tert-Butyl 3-[ethyl(methyl)amino]azetidine-1-carboxylate

The reactions in Reference Synthetic Example[a] 137 were carried out in substantially the same manners except that N-methylethanamine hydrochloride was used instead of dimethylamine-tetrahydrofuran solution to give the title compound as a colorless solid (121 mg, yield 46%).

Reference Synthetic Example[a] 139 tert-Butyl 3-(cyanomethylene)azetidine-1-carboxylate

Potassium tert-butoxide (2.03 g, 21.1 mmol) in tetrahydrofuran (20 mL) was mixed with diethyl cyanomethylphosphonate (3.54 g, 20.0 mmol) in tetrahydrofuran (20 mL) under cooling with ice and stirred for 30 minutes. The reaction mixture was mixed with tert-butyl 3-oxoazetidine-1-carboxylate (2.96 g, 17.3 mmol) obtained in Reference Synthetic Example[a] 112 in tetrahydrofuran (20 mL) under cooling with ice and then stirred at room temperature for 1 day. After addition of water, the reaction mixture was extracted with ethyl acetate. The organic layer was washed with saturated sodium chloride, dried over anhydrous magnesium sulfate and concentrated under reduced pressure. The residue was purified by silica gel column chromatography (hexane/ethyl acetate=3/1 (v/v)) to give the title compound as a colorless solid (1.93 g, yield 58%).

Reference Synthetic Example[a] 140

3-Hydroxy-N-methoxy-N-methyladamantane-1-carboxamide

3-Hydroxyadamantane-1-carboxylic acid (500 mg, 2.55 mmol) in dichloromethane (15 mL) was mixed with 1-(3-dimethylaminopropyl)-3-ethylcarbodiimide hydrochloride (587 mg, 3.06 mmol), 1-hydroxybenzotriazole (103 mg, 0.765 mmol), N,O-dimethylhydroxylamine hydrochloride (298 mg, 3.06 mmol) and N,N-diisopropylethylamine (1.06 mL, 6.12 mmol) and then stirred at 40° C. for 1 hours. The reaction mixture was stirred with 4-dimethylaminopyridine (779 mg, 6.38 mmol) at 40° C. for 1 hours. After addition of saturated aqueous ammonium chloride, the reaction mixture was extracted with chloroform. The organic layer was washed with 1M hydrochloric acid and saturated aqueous sodium chloride, dried over anhydrous sodium sulfate and concentrated under reduced pressure to give the title compound as a yellow oil (248 mg, yield 41%).

Reference Synthetic Example[a] 141

3-Hydroxyadamantan-1-yl)(7H-pyrrolo[2,3-d]pyrimidin-4-yl)methanone

Isopropylmagnesium chloride-tetrahydrofuran solution (2.0 M, 0.518 mL, 1.035 mmol) was gradually added dropwise to 4-iodo-7H-pyrrolo[2,3-d]pyrimidine (56.4 mg, 0.230 mmol) in tetrahydrofuran (1 mL) cooled to −78° C., and the resulting reaction mixture was stirred at −78° C. for 15 minutes. The reaction mixture was mixed with (2,6-dimethylphenyl)magnesium bromide-tetrahydrofuran solution (1.0 M, 0.575 mL, 0.575 mmol) and 3-hydroxy-N-methoxy-N-methyladamantane-1-carboxamide (55.1 mg, 0.23 mmol) in tetrahydrofuran (1 mL) and then stirred at room temperature for 1 day. After addition of saturated aqueous ammonium chloride, the reaction mixture was extracted with ethyl acetate. The organic layer was washed with water and saturated aqueous sodium chloride, dried over anhydrous sodium sulfate and concentrated under reduced pressure. The residue was purified by silica gel thin layer chromatography (ethyl acetate) to give the title compound as a pale yellow solid (22.5 mg, yield 33%).

Synthetic Example[a] 1

1-Cyclohexyl-3-methyl-7H-imidazo[1,5-c]pyrrolo[3,2-e]pyrimidine

Cyclohexyl[7-(triisopropylsilyl)-7H-pyrrolo[2,3-d]pyrimidin-4-yl]methanone (48.2 mg, 0.120 mmol) obtained in Reference Synthetic Example[a] 4 in acetic acid (1.2 mL) was stirred with ammonium acetate (46.2 mg, 0.600 mmol) and acetaldehyde (purity 90%, 15 μl, 0.24 mmol) at 110° C. for 2.5 hours, and the reaction mixture was allowed to cool to room temperature, basified with saturated aqueous sodium hydrogen carbonate and extracted with ethyl acetate. The organic layer was dried over anhydrous sodium sulfate and concentrated under reduced pressure. The residue was purified by silica gel thin layer chromatography (NH-PLC05 plate manufactured by Fuji Silysia Chemical Ltd.: ethyl acetate) and further purified under the same conditions to give the title compound as a brown solid (12.4 mg, yield 41%).

Synthetic Example[a] 2

1-Cyclohexyl-7H-imidazo[1,5-c]pyrrolo[3,2-e]pyrimidine

Cyclohexyl[7-(triisopropylsilyl)-7H-pyrrolo[2,3-d]pyrimidin-4-yl]methanone (52.5 mg, 0.136 mmol) obtained in Reference Synthetic Example[a] 4 in formamide (2 mL) was stirred with formic acid (0.4 mL) at 170° C. for 2 hours. The reaction mixture was allowed to cool to room temperature, and after dropwise addition of water, basified with 10 M aqueous sodium hydroxide and extracted with ethyl acetate. The organic layer was dried over anhydrous sodium sulfate and concentrated under reduced pressure. The residue was stirred with phosphorus oxychloride (2 mL) at 110° C. for 4 hours. The reaction mixture was allowed to cool to room temperature, and after dropwise addition of water, basified with 10 M aqueous sodium hydroxide and extracted with ethyl acetate. The organic layer was dried over anhydrous sodium sulfate and concentrated under reduced pressure. The residue was purified by silica gel column chromatography (Hi Flash column amino type manufactured by Yamazen Corporation: chloroform/methanol=7/1 (v/v)) and further purified by silica gel thin layer chromatography (NH-PLC05 plate manufactured by Fuji Silysia Chemical Ltd.: ethyl acetate) to give the title compound as a brown solid (2.29 mg. yield 7%).

Synthetic Example[a] 3

Benzyl 3-(7H-imidazo[1,5-c]pyrrolo[3,2-e]pyrimidin-1-yl)piperidine-1-carboxylate Benzyl 3-(7-{[2-(trimethylsilyl)ethoxy]methyl}-7H-imidazo[1,5-c]pyrrolo[3,2-e]pyrimidin-1-yl)piperidine-1-carboxylate obtained in Reference Synthetic Example[a] 20 in dichloromethane (1 mL) was stirred with trifluoroacetic acid (0.5 mL) at room temperature for 1.5 hours. The reaction mixture was concentrated under reduced pressure and azeotropically distilled with toluene. The resulting residue was dissolved in a mixture of dichloromethane (1 mL) and methanol (0.5 mL) and stirred with ethylenediamine (50 μL, 0.75 mmol) and 1 M aqueous sodium hydroxide (0.5 mL, 0.5 mmol) at room temperature for one day. The reaction mixture was diluted with ethyl acetate and washed with saturated aqueous ammonium chloride and saturated aqueous sodium chloride, and the organic layer was dried over anhydrous sodium sulfate and concentrated under reduced pressure. The residue was purified by silica gel column chromatography (Hi Flash column amino type manufactured by Yamazen Corporation: chloroform/methanol=10/1→5/1 (v/v)) to give the title compound as a pale yellow oil (17.3 mg, yield 52%).

Synthetic Example[a] 4

3-[3-(7H-Imidazo[1,5-c]pyrrolo[3,2-e]pyrimidin-1-yl)piperidin-1-yl]-3-oxopropanenitrile Benzyl 3-(7H-imidazo[1,5-c]pyrrolo[3,2-e]pyrimidin-1-yl)piperidine-1-carboxylate (13.3 mg, 0.0354 mmol) and 10% palladium hydroxide-carbon (small amount) in ethanol (1.5 mL) was stirred at room temperature for 2.5 hours under a hydrogen atmosphere. The reaction mixture was filtered, and the filtrate was concentrated under reduced pressure. The resulting residue was dissolved in N,N-dimethylformamide (1 mL) and stirred with 2-cyanoacetic acid (5.0 mg, 0.054 mmol), O-(7-azabenzotriazol-1-yl)-N,N,N',N'-tetramethyluronium hexafluorophosphate (27.5 mg, 0.0722 mmol) and N,N-diisopropylethylamine (19.0 μL, 0.11 mmol) at room temperature for one day. After addition of water, the reaction mixture was extracted with ethyl acetate, and the organic layer was dried over anhydrous sodium sulfate and concentrated under reduced pressure. The residue was purified by silica gel thin layer chromatography (NH-PLC05 plate manufactured by Fuji Silysia Chemical Ltd.: chloroform/methanol=15/1 (v/v)) to give the title compound as a pale yellow oil (1.02 mg, yield 11%).

Synthetic Example[a] 5

1-o-Tolyl-7H-pyrrolo[3,2-e][1,2,3]triazolo[1,5-c]pyrimidine (7H-Pyrrolo[2,3-d]pyrimidin-4-yl)(o-tolyl)methanone (50.0 mg, 0.211 mmol) obtained in Reference Synthetic Example[a] 10 in methanol (1 ml) was stirred with hydrazine monohydrate (295 μL, 9.48 mmol) at 75° C. for 7 hours. After addition of water and 1 M aqueous sodium hydroxide, the reaction mixture was extracted with chloroform, and the organic layer was dried over anhydrous magnesium sulfate and concentrated under reduced pressure. The resulting residue (pale yellow amorphous, 60.3 mg) was dissolved in chloroform (4 mL) and stirred with manganese dioxide (91.6 mg, 1.05 mmol) at 75° C. for 6 hours. The reaction mixture was filtered, and the filtrate was concentrated under reduced pressure. The residue was purified by silica gel column chromatography (hexane/ethyl acetate=4/1→1/1 (v/v)) to give the title compound as a white solid (21.5 mg, yield 41%).

Synthetic Example[a] 6

1-Cyclohexyl-7H-pyrrolo[3,2-e][1,2,3]triazolo[1,5-c]pyrimidine

The reactions in Synthetic Example[a] 5 were carried out in substantially the same manners except that cyclohexyl(7H-pyrrolo[2,3-d]pyrimidin-4-yl)methanone obtained in Reference Synthetic Example[a] 12 was used instead of (7H-pyrrolo[2,3-d]pyrimidin-4-yl)(o-tolyl)methanone to give the title compound as a pale yellow solid (76.6 mg, yield 73%).

Synthetic Example[a] 7

1-(2-Methylcyclohexyl)-7H-pyrrolo[3,2-e][1,2,3]triazolo[1,5-c]pyrimidine

The reactions in Synthetic Example[a] 5 were carried out in substantially the same manners except that (2-methylcyclohexyl)(7H-pyrrolo[2,3-d]pyrimidin-4-yl)methanone obtained in Reference Synthetic Example[a] 14 was used instead of (7H-pyrrolo[2,3-d]pyrimidin-4-yl)(o-tolyl)methanone to give the title compound as a pale yellow amorphous (16.9 mg, yield 32%).

Synthetic Example[a] 8

1-Cyclohexyl-2H-imidazo[1,5-c]pyrrolo[3,2-e]pyrimidine-3(7H)-thione

Cyclohexyl(7H-pyrrolo[2,3-d]pyrimidin-4-yl)methanone (50 mg, 0.22 mmol) obtained in Reference Synthetic Example[a] 12 in methanol (1 mL) was stirred with hydroxylamine (50 wt % aq., 735 μL, 12.0 mmol) at 75° C. for 6 hours. After addition of water and 1 M aqueous sodium hydroxide, the reaction mixture was extracted with chloroform, and the organic layer was dried over anhydrous magnesium sulfate and concentrated under reduced pressure. The resulting residue (colorless oil, 53.0 mg) was dissolved in methanol (3 mL) and stirred with zinc (128 mg, 1.96 mmol) and acetic acid (37.5 μL, 0.654 mmol) at 75° C. for 7 hours, and the reaction mixture was filtered. Chloroform and saturated aqueous sodium hydrogen carbonate were added to the filtrate, and the precipitate was separated by filtration. The filtrate was extracted with chloroform, and the organic layer was dried over anhydrous magnesium sulfate and concentrated under reduced pressure. The resulting residue (pale yellow oil, 23.7 mg) was dissolved in methanol (1 mL) and stirred with carbon disulfide (62.0 μL, 1.03 mmol) and triethylamine (43.0 μL, 0.309 mmol) at 75° C. for 2 hours. The reaction mixture was concentrated under reduced pressure, and the residue was purified by silica gel column chromatography (Hi Flash column amino type manufactured by Yamazen Corporation: chloroform/methanol=10/1 (v/v)) to give the title compound as a yellow solid (22.6 mg, yield 38%).

Synthetic Example[a] 9

1-Cyclohexyl-2H-imidazo[1,5-c]pyrrolo[3,2-e]pyrimidin-3(7H)-one

Cyclohexyl(7H-pyrrolo[2,3-d]pyrimidin-4-yl)methanone (100 mg, 0.436 mmol) obtained in Reference Synthetic Example[a] 12 in methanol (2 mL) was stirred with hydroxylamine (50 wt % aq., 1.34 mL, 21.8 mmol) at 75° C. for 5 hours. After addition of water and 1 M aqueous sodium hydroxide, the reaction mixture was extracted with chloroform. The organic layer was washed with saturated aqueous sodium chloride, dried over anhydrous magnesium sulfate and concentrated under reduced pressure. The resulting residue (colorless oil, 110 mg) was dissolved in methanol (3 mL) and stirred with zinc (258 mg, 3.93 mmol) and acetic acid (75.0 μL, 1.31 mmol) at 70° C. for 7.5 hours, and the reaction mixture was filtered. Chloroform and saturated aqueous sodium hydrogen carbonate were added to the filtrate, and the precipitate was separated by filtration. The filtrate was extracted with dichloromethane, and the organic layer was dried over anhydrous magnesium sulfate and concentrated under reduced pressure. The resulting residue (pale yellow amorphous, 57.5 mg) was dissolved in chloroform (1 mL) and stirred with triphosgene (29.6 mg, 0.0999 mmol) at room temperature for 3 hours. After addition of methanol, the reaction mixture was purified by silica gel column chromatography (Hi Flash column amino type manufactured by Yamazen Corporation: chloroform/methanol=10/1 (v/v)) to give the title compound as a yellow solid (6.0 mg, yield 5.4%).

Synthetic Example[a] 10

[trans-4-(7H-Pyrrolo[3,2-e][1,2,3]triazolo[1,5-c]pyrimidin-1-yl)cyclohexyl]methanol 1-{trans-4-[(tert-Butyldiphenylsilyloxy)methyl]cyclohexyl}-7H-pyrrolo[3,2-e][1,2,3]triazolo[1,5-c]pyrimidine (48.0 mg, 0.0942 mmol) obtained in Reference Synthetic Example[a] 24 in tetrahydrofuran (3 mL) was cooled with ice and stirred with tetrabutylammonium fluoride (1.0 M solution in tetrahydrofuran, 104 μL, 0.104 mmol) for 4 hours while the temperature was gradually raised to room temperature. After addition of water, the reaction solution was extracted with ethyl acetate, and the organic layer was washed with saturated aqueous sodium chloride, dried over anhydrous magnesium sulfate and concentrated under reduced pressure. The residue was purified by silica gel column chromatography (chloroform/methanol=10/1 (v/v)) to give the title compound as a pale yellow solid (25.3 mg, yield 99%).

Synthetic Example[a] 11 tert-Butyl 4-methyl-3-(7H-pyrrolo[3,2-e][1,2,3]triazolo[1,5-c]pyrimidin-1-yl)piperidine-1-carboxylate The reactions in Synthetic Example[a] 5 were carried out in substantially the same manners except that tert-butyl 4-methyl-3-(7H-pyrrolo[2,3-d]pyrimidine-4-carbonyl)piperidine-1-carboxylate obtained in Reference Synthetic Example[a] 27 was used instead of (7H-pyrrolo[2,3-d]pyrimidin-4-yl)(o-tolyl)methanone to give the title compound as a pale yellow solid (1.0 mg, yield 1.3%).

Synthetic Example[a] 12

3-[4-Methyl-3-(7H-pyrrolo[3,2-e][1,2,3]triazolo[1,5-c]pyrimidin-1-yl)piperidin-1-yl]-3-oxopropanenitrile tert-Butyl 4-methyl-3-(7H-pyrrolo[3,2-e][1,2,3]triazolo[1,5-c]pyrimidin-1-yl)piperidine-1-carboxylate (5.6 mg, 0.016 mmol) in 4 M hydrogen chloride-1,4-dioxane solution (1.0 mL) was stirred under cooling with ice for 1 hour and concentrated under reduced pressure. The residue was dissolved in N,N-dimethylformamide (1 mL) and mixed with 2-cyanoacetic acid (2.7 mg, 0.0314 mmol) and O-(7-azabenzotriazol-1-yl)-N,N,N,'N'-tetramethyluronium hexafluorophosphate (11.9 mg, 0.0314 mmol) and then with N,N-diisopylethylamine (0.0082 mL, 0.0471 mmol) and stirred at room temperature for 2 hours. After addition of water, the reaction mixture was extracted with ethyl acetate, and the organic layer was dried over anhydrous sodium sulfate and concentrated under reduced pressure. The residue was purified by silica gel thin layer chromatography (NH-PLC05 plate manufactured by Fuji Silysia Chemical Ltd.: chloroform/methanol=15/1 (v/v)) and further purified by silica gel thin layer chromatography (ethyl acetate) to give the title compound as a pale yellow solid (0.62 mg, yield 12%).

Synthetic Example[a] 13 tert-Butyl 3-(7H-pyrrolo[3,2-e][1,2,3]triazolo[1,5-c]pyrimidin-1-yl)piperidine-1-carboxylate The reactions in Synthetic Example[a] 5 were carried out in substantially the same manners except that tert-butyl 3-(7H-pyrrolo[2,3-d]pyrimidine-4-carbonyl)piperidine-1-carboxylate obtained in Reference Synthetic Example[a] 29 was used instead of (7H-pyrrolo[2,3-d]pyrimidin-4-yl)(o-tolyl)methanone to give the title compound as a pale yellow oil (48.2 mg, yield 47%).

Synthetic Example[a] 14

Benzyl 3-(7H-pyrrolo[3,2-e][1,2,3]triazolo[,1,5-c]pyrimidin-1-yl)piperidine-1-carboxylate The reactions in Synthetic Example[a] 5 were carried out in substantially the same manners except that benzyl 3-(7H- pyrrolo[2,3-d]pyrimidine-4-carbonyl)piperidine-1-carboxylate obtained in Reference Synthetic Example[a] 32 was used instead of (7H-pyrrolo[2,3-d]pyrimidin-4-yl)(o-tolyl)methanone to give the title compound as a pale yellow solid (185 mg, yield 85%).

Synthetic Example[a] 15

1-(Piperidin-3-yl)-7H-pyrrolo[3,2-e][1,2,3]triazolo[1,5-c]pyrimidine

Benzyl 3-(7H-pyrrolo[3,2-e][1,2,3]triazolo[1,5-c]pyrimidin-1-yl)piperidine-1-carboxylate (25.0 mg, 0.0664 mmol) in ethanol was stirred with 5% palladium-carbon (10 mg) under a hydrogen atmosphere at 50° C. for 2.5 hours. The reaction mixture was filtered, and the filtrate was concentrated under reduced pressure to give the title compound as a light brown solid (16.1 mg, yield quantitative).

Synthetic Example[a] 16

1-(1-Benzylpiperidin-3-yl)-7H-pyrrolo[3,2-e][1,2,3]triazolo[1,5-c]pyrimidine

The reactions in Synthetic Example[a] 5 were carried out in substantially the same manners except that (1-benzylpiperidin-3-yl)(7H-pyrrolo[2,3-d]pyrimidin-4-yl)methanone obtained in Reference Synthetic Example[a] 35 was used instead of (7H-pyrrolo[2,3-d]pyrimidin-4-yl)(o-tolyl)methanone to give the title compound as a pale yellow solid (2.6 mg, yield 2.5%).

Synthetic Example[a] 17

1-[3-(7H-Pyrrolo[3,2-e][1,2,3]triazolo[1,5-c]pyrimidin-1-yl)piperidin-1-yl]-3,3,3-trifluoropropan-1-one 1-(Piperidin-3-yl)-7H-pyrrolo[3,2-e][1,2,3]triazolo[1,5-c]pyrimidine (20.0 mg., 0.0825 mmol) obtained in Synthetic Example[a] 15 in N,N-dimethylformamide (1.5 mL) was mixed with 3,3,3-trifluoropropanoic acid (8.6 μL, 0.099 mmol) and O-(7-azabenzotriazol-1-yl)-N,N,N',N'-tetramethyluronium hexafluorophosphate (62.7 mg, 0.165 mmol) and then with N,N-diisopropylethylamine (0.0431 ml, 0.248 mmol) and stirred at room temperature for one day. After addition of water, the reaction mixture was extracted with ethyl acetate, and the organic layer was dried over anhydrous sodium sulfate and concentrated under reduced pressure. The residue was purified by silica gel column chromatography (hexane/ethyl acetate=1/1→1/2 (v/v)→ethyl acetate) to give the title compound as a colorless solid (7.3 mg, yield 25%).

Synthetic Example[a] 18

1-[1-(Pyridin-3-ylmethyl)piperidin-3-yl]-7H-pyrrolo[3,2-e][1,2,3]triazolo[1,5-c]pyrimidine 1-(Piperidin-3-yl)-7H-pyrrolo[3,2-e][1,2,3]triazolo[1,5-c]pyrimidine (21.9 mg, 0.0903 mmol) obtained in Synthetic Example[a] 15 in methanol (1.5 mL) was stirred with 3-pyridinecarboxyaldehyde (12.7 μL, 0.135 mmol) at 50° C. for 1.5 hours, then with a small amount of acetic acid at room temperature for 2 hours and with sodium triacetoxyborohydride (28.6 mg, 0.135 mmol) at room temperature for one day. After addition of water, the reaction mixture was extracted with chloroform, and the organic layer was dried over anhydrous sodium sulfate and concentrated under reduced pressure. The residue was purified by silica gel column chromatography (Hi Flash column amino type manufactured by Yamazen Corporation: chloroform/methanol=15/1 (v/v)) and then by silica gel thin layer chromatography (NH-PLC05 plate manufactured by Fuji Silysia Chemical Ltd.: ethyl acetate) to give the title compound as a colorless solid (5.8 mg, yield 19%).

Synthetic Example[a] 19

5-{[3-(7H-Pyrrolo[3,2-e][1,2,3]triazolo[1,5-c]pyrimidin-1-yl)-piperidin-1-yl]methyl}thiazole The reactions in Synthetic Example[a] 18 were carried out in substantially the same manners except that thiazole-5-carbaldehyde was used instead of 3-pyridinecarboxyaldehyde to give the title compound as a colorless solid (3.4 mg, yield 12%).

Synthetic Example[a] 20

3-(7H-Pyrrolo[3,2-e][1,2,3]triazolo[1,5-c]pyrimidin-1-yl)-N-(1,3,4-thiadiazol-2-yl)piperidine-1-carboxamide 1-(Piperidin-3-yl)-7H-pyrrolo[3,2-e][1,2,3]triazolo[1,5-c]pyrimidine (22.1 mg, 0.0912 mmol) obtained in Synthetic Example[a] 15 in tetrahydrofuran (1.5 mL) was stirred with phenyl 1,3,4-thiadiazol-2-ylcarbamate (24.1 mg, 0.109 mmol) obtained in Reference Synthetic Example[a] 36 and triethylamine (0.0191 mg, 0.137 mmol) at 60° C. for 1.5 hours and then stirred at room temperature for one day. The precipitate in the reaction mixture was washed with ethyl acetate, methanol and tetrahydrofuran, and the solid was dried under reduced pressure to give the title compound as a light brown solid (2.4 mg, yield 7%).

Synthetic Example[a] 21

N-(3-Methylisothiazol-5-yl)-3-(7H-pyrrolo[3,2-e][1,2,3]triazolo[1,5-c]pyrimidin-1-yl)piperidine-1-carboxamide 1-(Piperidin-3-yl)-7H-pyrrolo[3,2-e][1,2,3]triazolo[1,5-c]pyrimidine (23.2 mg., 0.0957 mmol) obtained in Synthetic Example[a] 15 in tetrahydrofuran (1.5 mL) was stirred with phenyl (3-methylisothiazol-5-yl)carbamate (26.9 mg, 0.115 mmol) obtained in Reference Synthetic Example[a] 37 and triethylamine (0.0201 mL, 0.144 mmol) at 60° C. for 1.5 hours. After addition of water, the reaction mixture was extracted with ethyl acetate, and the organic layer was dried over anhydrous sodium sulfate and concentrated under reduced pressure. The residue was purified by silica gel column chromatography (Hi Flash column amino type manufactured by Yamazen Corporation: chloroform/methanol=7/1 (v/v)), and the resulting solid was washed with ethyl acetate, methanol and tetrahydrofuran to give the title compound as a light brown solid (3.0 mg, yield 8.3%).

Synthetic Example[a] 22

4-{[3-(7H-Pyrrolo[3,2-e][1,2,3]triazolo[1,5-c]pyrimidin-1-yl)piperidin-1-yl]methyl}benzonitrile 1-(Piperidin-3-yl)-7H-pyrrolo[3,2-e][1,2,3]triazolo[1,5-c]pyrimidine (29.4 mg., 0.121 mmol) obtained in Synthetic Example[a] 15 in acetonitrile (1.5 mL) was stirred with 4-(bromomethyl)benzonitrile (31.0 mg, 0.168 mmol) and N,N-diisopropylethylamine (0.0317 mL, 0.182 mmol) at 60° C. for 2 hours. The reaction mixture was purified by silica gel column chromatography (Hi Flash column amino type manufactured by Yamazen Corporation: hexane/ethyl acetate=1/1 (v/v)→ethyl acetate) to give the title compound as a colorless solid (24.9 mg, yield 58%).

Synthetic Example[a] 23

1-{1-[4-(Trifluoromethyl)benzyl]piperidin-3-yl}-7H-pyrrolo[3,2-e][1,2,3]triazolo[1,5-c]pyrimidine The reactions in Synthetic Example[a] 22 were carried out in substantially the same manners except that 1-(bromomethyl)-4-(trifluoromethyl)benzene was used instead of 4-(bromomethyl)benzonitrile to give the title compound as a light brown solid (30.9 mg, yield 68%).

Synthetic Example[a] 24 tert-Butyl 4-(7H-pyrrolo[3,2-e][1,2,3]triazolo[1,5-c]pyrimidin-1-yl)piperidine-1-carboxylate The reactions in Synthetic Example[a] 5 were carried out in substantially the same manners except that tert-butyl 4-(7H-pyrrolo[2,3-d]pyrimidin-4-carbonyl)piperidine-1-carboxylate obtained in Reference Synthetic Example[a] 39 was used instead of (7H-pyrrolo[2,3-d]pyrimidin-4-yl)(o-tolyl)methanone to give the title compound as a pale yellow solid (157 mg, yield 69%).

Synthetic Example[a] 25

1-[1-(2,2,2-Trifluoroethyl)piperidin-4-yl]-7H-pyrrolo[3,2-e][1,2,3]triazolo[1,5-c]pyrimidine The reactions in Synthetic Example[a] 5 were carried out in substantially the same manners except that (7H-pyrrolo[2,3-d]pyrimidin-4-yl)[1-(2,2,2-trifluoroethyl)piperidin-4-yl]methanone obtained in Reference Synthetic Example[a] 42 was used instead of (7H-pyrrolo[2,3-d]pyrimidin-4-yl)(o-tolyl)methanone to give the title compound as a pale yellow solid (6.6 mg, yield 12%).

Synthetic Example[a] 26

Benzyl 4-(7H-pyrrolo[3,2-e][1,2,3]triazolo[,1,5-c]pyrimidin-1-yl)piperidine-1-carboxylate The reactions in Synthetic Example[a] 5 were carried out in substantially the same manners except that benzyl 4-(7H-pyrrolo[2,3-d]pyrimidine-4-carbonyl)piperidine-1-carboxylate obtained in Reference Synthetic Example[a] 44 was used instead of (7H-pyrrolo[2,3-d]pyrimidin-4-yl)(o-tolyl)methanone to give the title compound as a colorless solid (49.6 mg, yield 34%).

Synthetic Example[a] 27

1-(Piperidin-4-yl)-7H-pyrrolo[3,2-e][1,2,3]triazolo[1,5-c]pyrimidine

5% Palladium-carbon (10.0 mg) was added to benzyl 4-(7H-pyrrolo[3,2-e][1,2,3]triazolo[1,5-c]pyrimidin-1-yl)piperidine-1-carboxylate (30.0 mg, 0.0800 mmol) in methanol (2 mL) under an argon atmosphere, and after the reaction system was flushed with hydrogen, the reaction mixture was stirred at room temperature for 6 hours and then filtered. The filtrate was concentrated under reduced pressure. The resulting yellow solid was washed with methanol and collected by filtration to give the title compound as a pale yellow solid (5.0 mg, yield 26%).

Synthetic Example[a] 28

1-[1-(Pyridin-3-ylmethyl)piperidin-4-yl]-7H-pyrrolo[3,2-e][1,2,3]triazolo[1,5-c]pyrimidine 1-(Piperidin-4-yl)-7H-pyrrolo[3,2-e][1,2,3]triazolo[1,5-c]pyrimidine (11.0 mg, 0.0450 mmol) in a mixture of methanol (1 mL) and tetrahydrofuran (1 mL) was stirred with 3-pyridinecarboxyaldehyde (5.0 μL, 0.054 mmol), acetic acid (33 μL) and sodium cyanoborohydride (4.3 mg, 0.068 mmol) at room temperature for one day. The reaction mixture was stirred with sodium triacetoxyborohydride (10.0 mg, 0.047 mmol) for another 2 hours. The resulting reaction mixture was purified by silica gel thin layer chromatography (methanol/chloroform=1/9 (v/v)) twice to give the title compound as a colorless solid (1.4 mg, yield 9.3%).

Synthetic Example[a] 29

1-[4-(7H-Pyrrolo[3,2-e][1,2,3]triazolo[1,5-c]pyrimidin-1-yl)piperidin-1-yl]-3,3,3-trifluoropropan-1-one 1-(Piperidin-4-yl)-7H-pyrrolo[3,2-e][1,2,3]triazolo[1,5-c]pyrimidine acetate (30.0 mg, 0.0992 mmol) obtained in Reference Synthetic Example[a] 104 in N,N-dimethylformamide (1 mL) was stirred with 3,3,3-trifluoropropionic acid (14.0 μL, 0.161 mmol), 1-(3-dimethylaminopropyl)-3-ethylcarbodiimide hydrochloride (48.0 mg, 0.248 mmol), 1-hydroxybenzotriazole (34.0 mg, 0.248 mmol) and triethylamine (43.0 μL, 0.310 mmol) at room temperature for 3 hours and then with water (1 mL) for another 1 day. After addition of water, the reaction mixture was extracted with ethyl acetate, and the organic layer was dried over anhydrous sodium sulfate and concentrated under reduced pressure. The residue was purified by silica gel column chromatography (hexane/ethyl acetate=2/1 (v/v)) to give the title compound as a colorless solid (11.7 mg, yield 34%).

Synthetic Example[a] 30

4-(7H-Pyrrolo[3,2-e][1,2,3]triazolo[1,5-c]pyrimidin-1-yl)-N-(1,3,4-thiadiazol-2-yl)piperidine-1-carboxamide 1-(Piperidin-4-yl)-7H-pyrrolo[3,2-e][1,2,3]triazolo[1,5-c]pyrimidine acetate (25.0 mg, 0.0827 mmol) obtained in Reference Synthetic Example[a] 104 in tetrahydrofuran (1 mL) was stirred with phenyl 1,3,4-thiadiazol-2-ylcarbamate (27.0 mg, 0.124 mmol) obtained in Reference Synthetic Example[a] 36 and triethylamine (22.0 μL, 0.155 mmol) at room temperature for 2 hours. Water and ethyl acetate were added to the reaction mixture, and the insolubles were collected by filtration. The resulting solid was washed with methanol, chloroform, acetonitrile and ethanol to give the title compound as a colorless solid (19.3 mg, yield 63%).

Synthetic Example[a] 31

N-(3-Methylisothiazol-5-yl)-4-(7H-pyrrolo[3,2-e][1,2,3]triazolo[1,5-c]pyrimidin-1-yl)piperidine-1-carboxamide The reactions Synthetic Example[a] 30 were carried out in substantially the same manners except that phenyl (3-methylisothiazol-5-yl)carbamate obtained in Reference Synthetic Example[a] 37 was used instead of phenyl 1,3,4-thiadiazol-2-ylcarbamate to give the title compound as a pale yellow solid (17.6 mg, yield 56%).

Synthetic Example[a] 32

1-(1-Benzylpiperidin-4-yl)-7H-pyrrolo[3,2-e][1,2,3]triazolo[1,5-c]pyrimidine 1-(Piperidin-4-yl)-7H-pyrrolo[3,2-e][1,2,3]triazolo[1,5-c]pyrimidine acetate (20.0 mg, 0.0662 mmol) obtained in Reference Synthetic Example[a] 104 in acetonitrile (1 mL) was stirred with benzyl bromide (15.0 μL, 0.124 mmol) and N,N-diisopropylethylamine (28.0 μL, 0.166 mmol) at 60° C. for 2 hours. The reaction mixture was purified by silica gel column chromatography (methanol/chloroform=1/30→1/25 (v/v)), and the resulting solid was washed with isopropyl ether to give the title compound as a colorless solid (2.92 mg, yield 13%).

Synthetic Examples[a] 33 to 43

The reactions in Synthetic Example[a] 32 were carried out in substantially the same manners except that 4-(trifluoromethyl)benzyl bromide, 4-cyanobenzyl bromide, 3-cyanobenzyl bromide, 4-(chloromethyl)-3,5-dimethylisoxazole, 4-(trifluoromethoxy)benzyl bromide, 4-(trifluoromethylthio)benzyl bromide, 3-(trifluoromethyl)benzyl bromide, 4-(bromomethyl)-3-fluorobenzonitrile, 1-bromo-4-(bromomethyl)benzene, 1-(2-bromoethyl)-4-(trifluoromethyl)benzene or 4-fluorobenzyl bromide was used instead of benzyl bromide to give the compounds of Synthetic Examples[a] 33 to 43. The names, morphologies and yields of the synthesized compounds are shown in Table[a] 7.

TABLE[a] 7

| Ex | Compound Name | Morphology | Yield |
|---|---|---|---|
| 33 | 1-{1-[4-(trifluoromethyl)benzyl]piperidin-4-yl}-7H-pyrrolo[3,2-e][1,2,3]triazolo[1,5-c]pyrimidine | colorless solid | 64% |
| 34 | 4-{[4-(7H-pyrrolo[3,2-e][1,2,3]triazolo[1,5-c]pyrimidin-1-yl)piperidin-1-yl]methyl)} benzonitrile | pale yellow solid | 38% |
| 35 | 3-{[4-(7H-pyrrolo[3,2-e][1,2,3]triazolo[1,5-c]pyrimidin-1-yl)piperidin-1-yl]methyl} benzonitrile | colorless solid | 37% |
| 36 | 4-{[4-(7H-pyrrolo[3,2-e][1,2,3]triazolo[1,5-c]pyrimidin-1-yl)piperidin-1-yl]methyl}-3,5-dimethylisoxazole | colorless solid | 38% |
| 37 | 1-{1-[4-(trifluoromethoxy)benzyl]piperidin-4-yl}-7H-pyrrolo[3,2-e][1,2,3]triazolo[1,5-c]pyrimidine | colorless solid | 33% |
| 38 | 1-(1-{4-[(trifluoromethyl)thio]benzyl}piperidin-4-yl)-7H-pyrrolo[3,2-e][1,2,3]triazolo[1,5-c]pyrimidine | colorless solid | 28% |
| 39 | 1-{1-[3-(trifluoromethyl)benzyl]piperidin-4-yl}-7H-pyrrolo[3,2-e][1,2,3]triazolo[1,5-c]pyrimidine | colorless solid | 35% |
| 40 | 4-{[4-(7H-pyrrolo[3,2-e][1,2,3]triazolo[1,5-c]pyrimidin-1-yl) piperidin-1-yl]methyl}-3-fluorobenzonitrile | colorless solid | 45% |
| 41 | 1-[1-(4-bromobenzyl)piperidin-4-yl]-7H-pyrrolo [3,2-e][1,2,3]triazolo[1,5-c]pyrimidine | colorless solid | 64% |
| 42 | 1-{1-[4-(trifluoromethyl)phenethyl]piperidin-4-yl}-7H-pyrrolo[3,2-e][1,2,3]triazolo[1,5-c]pyrimidine hydrochloride | colorless solid | 33% |
| 43 | 1-[1-(4-fluorobenzyl)piperidin-4-yl]-7H-pyrrolo [3,2-e][1,2,3]triazolo[1,5-c]pyrimidine | colorless solid | 2.0% |

Synthetic Example[a] 44

5-{[4-(7H-Pyrrolo[3,2-e][1,2,3]triazolo[1,5-c]pyrimidin-1-yl)piperidin-1-yl]methyl}thiazole 1-(Piperidin-4-yl)-7H-pyrrolo[3,2-e][1,2,3]triazolo[1,5-c]pyrimidine acetate (20.0 mg, 0.0662 mmol) obtained in Reference Synthetic Example[a] 104 in methanol (1 mL) was stirred with thiazole-5-carbaldehyde (11.0 μL, 0.124 mmol), acetic acid (100 μL) and 2-picoline borane (13.0 mg, 0.124 mmol) at room temperature for one day. The reaction mixture was purified by silica gel column chromatography (methanol/chloroform=1/30→1/25→1/20 (v/v)). The resulting solid was washed with isopropyl ether to give the title compound as a colorless solid (9.05 mg, yield 40%).

Synthetic Examples[a] 45 to 55

The reactions in Synthetic Example 44 were carried out in substantially the same manners except that 3-phenylpropionaldehyde, 3-fluoro-4-methoxybenzaldehyde, 3,5-bis(trifluoromethyl)benzaldehyde, 2-formylthiazole, 5-chlorothiophene-2-carboxaldehyde, cyclohexanecarboxaldehyde, cyclopentanone, 6-(trifluoromethyl)-3-pyridinecarboxaldehyde, 3,5-difluoro-4-formylbenzonitrile, 4-chlorobenzaldehyde or 3-fluorobenzaldehyde was used instead of thiazole-5-carbaldehyde to give the compounds of Synthetic Examples[a] 45 to 55. The names, morphologies and yields of the compounds synthesized are shown in Table[a] 8.

TABLE[a] 8

| Ex | Compound Name | Morphology | Yield |
|---|---|---|---|
| 45 | 1-[1-(3-phenylpropyl)piperidin-4-yl]-7H-pyrrolo[3,2-e][1,2,3]triazolo[1,5-c]pyrimidine | colorless solid | 35% |
| 46 | 1-[1-(3-fluoro-4-methoxybenzyl)piperidin-4-yl]-7H-pyrrolo[3,2-e][1,2,3]triazolo[1,5-c]pyrimidine | colorless solid | 62% |
| 47 | 1-{1-[3,5-bis(trifluoromethyl)benzyl]piperidin-4-yl}-7H-pyrrolo[3,2-e][1,2,3]triazolo[1,5-c]pyrimidine | colorless solid | 31% |
| 48 | 2-{[4-(7H-pyrrolo[3,2-e][1,2,3]triazolo[1,5-c]pyrimidin-1-yl)piperidin-1-yl]methyl}thiazole | colorless solid | 61% |
| 49 | 1-{1-[(5-chlorothiophen-2-yl)methyl]piperidin-4-yl}-7H-pyrrolo[3,2-e][1,2,3]triazolo[1, 5-c]pyrimidine | colorless solid | 27% |
| 50 | 1-[1-(cyclohexylmethyl)piperidin-4-yl]-7H-pyrrolo[3,2-e][1,2,3]triazolo[1,5-c]pyrimidine | colorless solid | 41% |
| 51 | 1-(1-cyclopentylpiperidin-4-yl)-7H-pyrrolo[3,2-e][1,2,3]triazolo[1,5-c]pyrimidine | colorless solid | 63% |
| 52 | 1-(1-{[6-(trifluoromethyl)pyridin-3-yl]methyl}piperidin-4-yl)-7H-pyrrolo[3,2-e][1, 2,3]triazolo[1,5-c]pyrimidine | colorless solid | 55% |
| 53 | 4-{[4-(7H-pyrrolo[3,2-e][1,2,3]triazolo[1,5-c]pyrimidin-1-yl)piperidin-1-yl]methyl}-3,5-difluorobenzonitrile | colorless solid | 5.0% |
| 54 | 1-[1-(4-chlorobenzyl)piperidin-4-yl]-7H-pyrrolo[3,2-e][1,2,3]triazolo[1,5-c]pyrimidine | colorless solid | 24% |
| 55 | 1-[1-(3-fluorobenzyl)piperidin-4-yl]-7H-pyrrolo[3,2-e][1,2,3]triazolo[1,5-c]pyrimidine | colorless solid | 33% |

Synthetic Example[a] 56

1-{1-[4-(Trifluoromethyl)cyclohexyl]piperidin-4-yl}-7H-pyrrolo[3,2-e][1,2,3]triazolo[1,5-c]pyrimidine The reactions in Synthetic Example[a] 44 were carried out in substantially the same manners except that 4-(trifluoromethyl)cyclohexanone was used instead of thiazole-5-carbaldehyde to give an isomer mixture as a pale yellow solid. The isomer mixture was purified by silica gel thin layer chromatography (methanol/chloroform=1/9 (v/v)) to give the two isomers of the title compound in a less polar fraction (Synthetic Example[a] 56a; pale yellow solid, 5.6 mg, yield 22%) and in a more polar fraction (Synthetic Example[a] 56b; pale yellow solid, 4.9 mg, yield 19%).

Synthetic Example[a] 57

4-(7H-Pyrrolo[3,2-e][1,2,3]triazolo[1,5-c]pyrimidin-1-yl)-N-[3-(trifluoromethyl)phenyl]piperidine-1-carboxamide 1-(Piperidin-4-yl)-7H-pyrrolo[3,2-e][1,2,3]triazolo[1,5-c]pyrimidine acetate (20.0 mg, 0.0662 mmol) obtained in Reference Synthetic Example[a] 104 in tetrahydrofuran (1 mL) was stirred with 3-(trifluoromethyl)phenyl isocyanate (14.0 μL, 0.0990 mmol) and triethylamine (14.0 μL, 0.0990 mmol) at room temperature for 3 days. The reaction mixture was purified by silica gel thin layer chromatography (methanol/chloroform=1/9 (v/v)) to give the title compound as a light gray solid (7.5 mg, yield 27%).

Synthetic Example[a] 58

[4-(7H-Pyrrolo[3,2-e][1,2,3]triazolo[,1,5-c]pyrimidin-1-yl)piperidin-1-yl][4-(trifluoromethyl)phenyl]methanone 1-(Piperidin-4-yl)-7H-pyrrolo[3,2-e][1,2,3]triazolo[1,5-c]pyrimidine acetate (20.0 mg, 0.0662 mmol) obtained in Reference Synthetic Example[a] 104 in N,N-dimethylformamide (1 mL) was stirred with 4-(trifluoromethyl)benzoyl chloride (14.8 μL, 0.100 mmol) and triethylamine (13.9 μL, 0.100 mmol) under cooling with ice for 80 minutes. After addition of water, the reaction mixture was extracted with chloroform, and the organic layer was dried over anhydrous sodium sulfate and concentrated under reduced pressure. The residue was purified by silica gel thin layer chromatography (methanol/chloroform=1/19 (v/v)) to give the title compound as a colorless oil (16.3 mg, yield 59%).

Synthetic Example[a] 59 tert-Butyl [trans-4-(7H-pyrrolo[3,2-e][1,2,3]triazolo[1,5-c]pyrimidin-1-yl)cyclohexyl]carbamate The reactions in Synthetic Example[a] 5 were carried out in substantially the same manners except that tert-butyl [trans-4-(7H-pyrrolo[2,3-d]pyrimidine-4-carbonyl)cyclohexyl] carbamate obtained in Reference Synthetic Example[a] 46 was used instead of (7H-pyrrolo[2,3-d]pyrimidin-4-yl)(o-tolyl)methanone to give the title compound as a colorless solid (4.7 mg, yield 15%).

Synthetic Example[a] 60

Benzyl [trans-4-(7H-pyrrolo[3,2-e][1,2,3]triazolo[1,5-c]pyrimidin-1-yl)cyclohexyl]carbamate The reactions in Synthetic Example[a] 5 were carried out in substantially the same manners except that benzyl [trans-4-(7H-pyrrolo[2,3-d]pyrimidine-4-carbonyl)cyclohexyl]carbamate obtained in Reference Synthetic Example[a] 48 was used instead of (7H-pyrrolo[2,3-d]pyrimidin-4-yl)(o-tolyl)methanone to give the title compound as a colorless solid (10.0 mg, yield 29%).

Synthetic Example[a] 61 trans-4-(7H-Pyrrolo[3,2-e][1,2,3]triazolo[,1,5-c]pyrimidin-1-yl)cyclohexanamine

5% Palladium-carbon (5.00 mg) was added to benzyl [trans-4-(7H-pyrrolo[3,2-e][1,2,3]triazolo[1,5-c]pyrimidin-1-yl)cyclohexyl]carbamate (7.00 mg, 0.0180 mmol) in a mixture of ethanol (1 mL) and chloroform (1 mL) under an argon atmosphere, and after the reaction system was flushed with hydrogen, the reaction mixture was stirred at room temperature for one day and then filtered. The filtrate was concentrated under reduced pressure. The resulting residue was purified by silica gel thin layer chromatography (NH-PLC05 plate manufactured by Fuji Silysia Chemical Ltd.: methanol/chloroform=1/19 (v/v)) to give the title compound as a colorless solid (0.35 mg, yield 8.0%).

Synthetic Example[a] 62

1-[trans-4-(Methoxymethyl)cyclohexyl]-7H-pyrrolo[3,2-e][1,2,3]triazolo[1,5-c]pyrimidine The reactions in Synthetic Example[a] 5 were carried out in substantially the same manners except that [trans-4-

(methoxymethyl)cyclohexyl](7H-pyrrolo[2,3-d]pyrimidin-4-yl)methanone obtained in Reference Synthetic Example[a] 50 was used instead of (7H-pyrrolo[2,3-d]pyrimidin-4-yl)(o-tolyl)methanone to give the title compound as a colorless solid (52.4 mg, yield 63%).

Synthetic Example[a] 63

1-[trans-4-Methoxycyclohexyl]-7H-pyrrolo[3,2-e][1,2,3]triazolo[1,5-c]pyrimidine

The reactions in Synthetic Example[a] 5 were carried out in substantially the same manners except that (trans-4-methoxycyclohexyl)(7H-pyrrolo[2,3-d]pyrimidin-4-yl)methanone obtained in Reference Synthetic Example[a] 53 was used instead of (7H-pyrrolo[2,3-d]pyrimidin-4-yl)(o-tolyl)methanone to give the title compound as a pale yellow solid (7.80 mg, yield 7.6%).

Synthetic Examples[a] 64 to 69

The reactions in Synthetic Example[a] 5 were carried out in substantially the same manners except that the compounds obtained in Reference Synthetic Examples[a] 61 to 66 were used instead of (7H-pyrrolo[2,3-d]pyrimidin-4-yl)(o-tolyl)methanone to give the title compounds of Synthetic Examples[a] 64 to 69. The names, morphologies and yields of the compounds synthesized are shown in Table[a] 9.

TABLE[a] 9

| Ex | Compound Name | Morphology | Yield |
|---|---|---|---|
| 64 | 1-(4,4-difluorocyclohexyl)-7H-pyrrolo[3,2-e][1,2,3]triazolo[1,5-c]pyrimidine | pale cream solid | 51% |
| 65 | 1-(bicyclo[2.2.1]heptan-2-yl)-7H-pyrrol[3,2-e][1,2,3]triazolo[1,5-e]pyrimidine | colorless solid | 47% |
| 66 | 1-cycloheptyl-7H-1-pyrrolo[3,2-e][1,2,3]triazolo[1,5-c]pyrimidine | colorless solid | 49% |
| 67 | 1-cyclobutyl-7H-pyrrolo[3,2-e][1,2,3]triazolo[1,5-c]pyrimidine | colorless solid | 56% |
| 68 | 1-cyclopentyl-7H-pyrrolo[3,2-e][1,2,3]triazolo[1,5-c]pyrimidine | yellow amorphous | 10% |
| 69 | 1-[trans-4-(trifluoromethyl)cyclohexyl]-7H-pyrrolo[3,2-e][1,2,3]triazolo[1,5-c]pyrimidine | colorless solid | 12% |

Synthetic Example[a] 70

1-[trans-4-(Trifluoromethyl)cyclohexyl]-7H-pyrrolo[3,2-e][1,2,3]triazolo[1,5-c]pyrimidine The reactions in Synthetic Example[a] 5 were carried out in substantially the same manners except that (7H-pyrrolo[2,3-d]pyrimidin-4-yl)[cis-4-(trifluoromethyl)cyclohexyl]methanone obtained in Reference Synthetic Example[a] 67 was used instead of (7H-pyrrolo[2,3-d]pyrimidin-4-yl)(o-tolyl)methanone to give the title compound as a colorless solid (12.0 mg, yield 23%). (although the cis-isomer was used as the starting material, only the trans-isomer of the title compound was obtained.)

Synthetic Example[a] 71

S-{[trans-4-(7H-Pyrrolo[3,2-e][1,2,3]triazolo[1,5-c]pyrimidin-1-yl)cyclohexyl]methyl}ethanethioate Triphenylphosphine (58.0 mg, 0.221 mmol) in tetrahydrofuran (1 mL) was mixed with diisopropyl azodicarboxylate (116 μL, 0.428 mmol) and [trans-4-(7H-pyrrolo[3,2-e][1,2,3]triazolo[1,5-c]pyrimidin-1-yl)cyclohexyl]methanol (30.0 mg, 0.111 mmol) obtained in Synthetic Example[a] 10 and thioacetic acid (16.0 μL, 0.225 mmol) under cooling with ice, and stirred for 30 minutes while the temperature was gradually raised to room temperature. After addition of water, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (ethyl acetate/hexane=1/10→1/3 (v/v)) to give the title compound as a colorless solid (22.4 mg, yield 62%).

Synthetic Example[a] 72

[trans-4-(7H-Pyrrolo[3,2-e][1,2,3]triazolo[1,5-c]pyrimidin-1-yl)cyclohexyl]methyl acetate The reactions in Synthetic Example[a] 71 were carried out in substantially the same manners except that acetic acid was used instead of thioacetic acid to give the title compound as a colorless solid (18.3 mg, yield 53%).

Synthetic Example[a] 73

1-[trans-4-(Fluoromethyl)cyclohexyl]-7H-pyrrolo[3,2-e][1,2,3]triazolo[1,5-c]pyrimidine

[trans-4-(7H-Pyrrolo[3,2-e][1,2,3]triazolo[1,5-c]pyrimidin-1-yl)cyclohexyl]methanol (30.0 mg, 0.111 mmol) obtained in Synthetic Example[a] 10 suspended in dichloromethane (3 mL) was mixed with N,N-diethylaminosulfur trifluoride (16.1 μL, 0.122 mmol) under cooling with ice and stirred for 30 minutes while the temperature was gradually raised to room temperature. After addition of water, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (ethyl acetate/hexane=1/5→1/3 (v/v)) to give the title compound as a colorless solid (6.7 mg, yield 22%).

Synthetic Example[a] 74

1-[trans-4-(Bromomethyl)cyclohexyl]-7H-pyrrolo[3,2-e][1,2,3]triazolo[1,5-c]pyrimidine

[trans-4-(7H-Pyrrolo[3,2-e][1,2,3]triazolo[1,5-c]pyrimidin-1-yl)cyclohexyl]methanol (50.0 mg, 0.184 mmol) obtained in Synthetic Example[a] 10 in dichloromethane (3 mL) was mixed with triphenylphosphine (58.0 mg, 0.221 mmol) and N-bromosuccinimide (39.0 mg, 0.221 mmol) under cooling with ice and stirred for 19 hours while the temperature was gradually raised to room temperature. The reaction mixture was purified by silica gel column chromatography (ethyl acetate/hexane=1/1 (v/v)) to give the title compound as a colorless solid (27.4 mg, yield 44%).

Synthetic Example[a] 75

1-[trans-4-(Chloromethyl)cyclohexyl]-7H-pyrrolo[3,2-e][1,2,3]triazolo[1,5-c]pyrimidine The reactions in Synthetic Example[a] 74 were carried out in substantially the same manners except that N-chlorosuccinimide was used instead of N-bromosuccinimide to give the title compound as a colorless solid (1.25 mg, yield 2%).

Synthetic Example[a] 76

[trans-4-(7H-Pyrrolo[3,2-e][1,2,3]triazolo[1,5-c]pyrimidin-1-yl)cyclohexyl]methanethiol S-{[trans-4-(7H-Pyrrolo[3,2-e][1,2,3]triazolo[1,5-c]pyrimidin-1-yl)cyclohexyl]methyl}ethanethioate (30.0 mg, 0.0911 mmol) obtained in Synthetic Example[a] 71 in methanol (2 mL) was stirred with sodium methoxide (28 wt % solution in methanol, 10 μL) at room temperature for 30 minutes. The solid precipitated in the reaction solution was removed by filtration and washed with methanol. The filtrate and the washings were mixed with water, and the precipitated solid was collected by filtration and dried under reduced pressure to give the title compound as a colorless solid (12.9 mg, yield 49%).

Synthetic Example[a] 77

1-{trans-4-[(Methylsulfonyl)methyl]cyclohexyl}-7H-pyrrolo[3,2-e][1,2,3]triazolo[1,5-c]pyrimidine 1-[trans-4-(Bromomethyl)cyclohexyl]-7H-pyrrolo[3,2-e][1,2,3]triazolo[1,5-c]pyrimidine (27.3 mg, 0.0817 mmol) obtained in Synthetic Example[a] 74 in N,N-dimethylformamide (2 mL) was stirred with sodium methanesulfinate (10.8 mg, 0.106 mmol) at room temperature for 30 minutes and then at 65° C. for 1.5 hours. The reaction mixture was allowed to cool to room temperature and stirred with sodium methanesulfinate (21.7 mg, 0.212 mmol) at 65° C. for 7.5 hours. After addition of water, the reaction mixture was extracted with ethyl acetate, and the organic layer was washed with saturated aqueous sodium chloride, dried over anhydrous magnesium sulfate and concentrated under reduced pressure. The residues was purified by silica gel column chromatography (ethyl acetate/hexane=1/1 (v/v)) to give the title compound as a colorless solid (5.3 mg, yield 25%).

Synthetic Example[a] 78 trans-4-(7H-Pyrrolo[3,2-e][1,2,3]triazolo[1,5-c]pyrimidin-1-yl)cyclohexanecarbaldehyde

[trans-4-(7H-Pyrrolo[3,2-e][1,2,3]triazolo[1,5-c]pyrimidin-1-yl)cyclohexyl]methanol (50.0 mg, 0.184 mmol) obtained in Synthetic Example[a] 10 in a mixture of toluene (1 mL) and dimethyl sulfoxide (200 μL) was stirred with 2-iodoxybenzoic acid (62.0 mg, 0.221 mmol) at room temperature for 30 minutes and at 50° C. for 3 hours. After addition of saturated aqueous sodium hydrogen carbonate, the reaction mixture was extracted with ethyl acetate. The organic layer was washed with saturated aqueous sodium chloride, dried over anhydrous magnesium sulfate and concentrated under reduced pressure. The residues was purified by silica gel column chromatography (ethyl acetate/hexane=1/1 (v/v)) to give the title compound as a colorless solid (38.0 mg, yield 77%).

Synthetic Example[a] 79

1-[trans-4-(Difluoromethyl)cyclohexyl]-7H-pyrrolo[3,2-e][1,2,3]triazolo[1,5-c]pyrimidine The reactions in Synthetic Example[a] 73 were carried out in substantially the same manners except that trans-4-(7H-pyrrolo[3,2-e][1,2,3]triazolo[1,5-c]pyrimidin-1-yl)cyclohexanecarbaldehyde was used instead of [trans-4-(7H-pyrrolo[3,2-e][1,2,3]triazolo[1,5-c]pyrimidin-1-yl)cyclohexyl]methanol to give the title compound as a colorless solid (21.1 mg, yield 65%).

Synthetic Example[a] 80 trans-4-(7H-Pyrrolo[3,2-e][1,2,3]triazolo[1,5-c]pyrimidin-1-yl)cyclohexanecarboxylic acid trans-4-(7H-Pyrrolo[3,2-e][1,2,3]triazolo[1,5-c]pyrimidin-1-yl)cyclohexanecarbaldehyde (25.8 mg, 0.0958 mmol) obtained in Synthetic Example[a] 78 in t-butanol (0.31 mL) was mixed with sodium dihydrogen phosphate (34.4 mg, 0.287 mmol), water (0.31 mL) and 2-methyl-2-butene (0.31 mL, 2.87 mmol) and then with sodium chlorite (43.3 mg, 0.479 mmol) and stirred at room temperature for 2 hours. After addition of saturated aqueous sodium thiosulfate, the reaction mixture was extracted with ethyl acetate, and the organic layer was dried over anhydrous sodium sulfate and concentrated under reduced pressure. The residue was purified by silica gel column chromatography (chloroform/methanol=10/1→4/1→2/1 (v/v)) to give the title compound as a colorless solid (14.7 mg, yield 54%).

Synthetic Example[a] 81 trans-4-(7H-Pyrrolo[3,2-e][1,2,3]triazolo[1,5-c]pyrimidin-1-yl)cyclohexanol

1-{4-[(tert-Butyldiphenylsilyl)oxy]cyclohexyl}-7H-pyrrolo[3,2-e][1,2,3]triazolo[1,5-c]pyrimidine (400 mg, 0.807 mmol) obtained in Reference Synthetic Example[a] 70 in tetrahydrofuran (8 mL) was mixed with tetrabutylammonium fluoride (1 M solution in tetrahydrofuran, 0.97 mL, 0.986 mmol) under cooling with ice and stirred at room temperature for 2 hours and then at 40° C. for 1.5 hours. The reaction solution was stirred with tetrabutylammonium fluoride (1 M solution in tetrahydrofuran, 0.458 mL, 0.484 mmol) at 40° C. for 1 hour. After addition of water, the reaction solution was extracted with chloroform, and the organic layer was washed with saturated aqueous sodium chloride, dried over anhydrous sodium sulfate and concentrated under reduced pressure. The residue was purified by silica gel column chromatography (ethyl acetate→chloroform/methanol=10/1 (v/v)) to give the title compound as a colorless solid (78.1 mg, yield 37%).

Synthetic Example[a] 82

4-(7H-Pyrrolo[3,2-e][1,2,3]triazolo[1,5-c]pyrimidin-1-yl)cyclohexanone

The reactions in Synthetic Example[a] 78 were carried out in substantially the same manners except that trans-4-(7H-pyrrolo[3,2-e][1,2,3]triazolo[1,5-c]pyrimidin-1-yl)cyclohexanol was used instead of [trans-4-(7H-pyrrolo[3,2-e][1,2,3]triazolo[1,5-c]pyrimidin-1-yl)cyclohexyl]methanol to give the title compound as a pale yellow solid (27.1 mg, yield 35%).

Synthetic Example[a] 83 cis-4-(7H-Pyrrolo[3,2-e][1,2,3]triazolo[1,5-c]pyrimidin-1-yl)cyclohexanol

1-{4-[(tert-Butyldimethylsilyl)oxy]cyclohexyl}-7H-pyrrolo[3,2-e][1,2,3]triazolo[1,5-c]pyrimidine (1.18 g, 3.16 mmol) obtained in Reference Synthetic Example[a] 74 in tetrahydrofuran (10 mL) was stirred with tetrabutylammonium fluoride (1 M solution in tetrahydrofuran, 3.8 mL, 3.79 mmol) at room temperature for 15 hours and then with tetrabutylammonium fluoride (1 M solution in tetrahydrofuran, 7.6 mL, 7.58 mmol) at 60° C. for 8 hours and then allowed to cool to room temperature. After addition of water, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (ethyl acetate/hexane=1/1 (v/v)→ethyl acetate) to give a less polar fraction (colorless solid, 237 mg) and a more polar fraction (colorless solid, 438 mg). The less polar fraction was stirred with tetrabutylammonium fluoride (1 M solution in tetrahydrofuran, 440 μL) at room temperature for 4 days. After addition of water, the reaction solution was extracted with ethyl acetate, and the organic layer was washed with saturated aqueous sodium chloride, dried over anhydrous magnesium sulfate and concentrated under reduced pressure. The concentrate was purified by silica gel column chromatography (hexane/ethyl acetate=1/1 (v/v)→ethyl acetate) to give the title compound as a colorless solid (66.4 mg, yield 14%).

Synthetic Example[a] 84

Benzyl 4-(7H-imidazo[1,5-c]pyrrolo[3,2-e]pyrimidin-1-yl)piperidine-1-carboxylate The reactions in Synthetic Example[a] 3 were carried out in substantially the same manners except that benzyl 4-(7-{[2-(trimethylsilyl)ethoxy]methyl}-7H-imidazo[1,5-c]pyrrolo[3,2-e]pyrimidin-1-yl)piperidine-1-carboxylate obtained in Reference Synthetic Example[a] 78 was used instead of benzyl 3-(7-{[2-(trimethylsilyl)ethoxy]methyl}-7H-imidazo[1,5-c]pyrrolo[3,2-e]pyrimidin-1-yl)piperidine-1-carboxylate to give the title compound as a yellow solid (4.6 mg, yield 2%).

Synthetic Example[a] 85

Benzyl 4-(3-thioxo-3,7-dihydro-2H-imidazo[1,5-c]pyrrolo[3,2-e]pyrimidin-1-yl)piperidine-1-carboxylate Benzyl 4-[amino(7H-pyrrolo[2,3-d]pyrimidin-4-yl)methyl]piperidine-1-carboxylate (50.0 mg, 0.137 mmol) obtained in Reference Synthetic Example[a] 79 in methanol (1 mL) was stirred with carbon disulfide (81.0 μL, 1.35 mmol) and triethylamine (56.0 μL, 0.405 mmol) at 75° C. for 1.5 hours. The reaction mixture was allowed to cool to room temperature, and the precipitated solid was collected by filtration and washed with methanol to give the title compound as a yellow solid (28.0 mg, yield 51%).

Synthetic Example[a] 86

1-{1-[4-(Trifluoromethyl)benzyl]piperidin-4-yl}-2H-imidazo[1,5-c]pyrrolo[3,2-e]pyrimidine-3-(7H)-thione The reactions in Synthetic Example[a] 85 were carried out in substantially the same manners except that (7H-pyrrolo[2,3-d]pyrimidin-4-yl){1-[4-(trifluoromethyl)benzyl]piperidin-4-yl}methanamine obtained in Reference Synthetic Example[a] 82 was used instead of benzyl 4-[amino(7H-pyrrolo[2,3-d]pyrimidin-4-yl)methyl]piperidine-1-carboxylate to give the title compound as a yellow solid (2.6 mg, yield 4%).

Synthetic Example[a] 87

Benzyl 3-(7H-pyrrolo[3,2-e][1,2,3]triazolo[1,5-c]pyrimidin-1-yl)azetidine-1-carboxylate The reactions in Synthetic Example[a] 5 were carried out in substantially the same manners except that benzyl 3-(7H-pyrrolo[2,3-d]pyrimidine-4-carbonyl)azetidine-1-carboxylate obtained in Reference Synthetic Example[a] 84 was used instead of (7H-pyrrolo[2,3-d]pyrimidin-4-yl)(o-tolyl)methanone to give the title compound as a yellow solid (186 mg, yield 60%).

Synthetic Example[a] 88

4-{[trans-4-(7H-Pyrrolo[3,2-e][1,2,3]triazolo[1,5-c]pyrimidin-1-yl)cyclohexyl]methyl}thiomorpholine 1,1-dioxide trans-4-(7H-Pyrrolo[3,2-e][1,2,3]triazolo[1,5-c]pyrimidin-1-yl)cyclohexanecarbaldehyde (30.0 mg, 0.111 mmol) obtained in Synthetic Example[a] 78 in a mixture of methanol (2 mL) and acetic acid (200 μL) was stirred with thiomorpholine 1,1-dioxide (22.6 mg, 0.167 mmol) at room temperature for 1 hour, and then with 2-picoline borane (17.9 mg, 0.167 mmol) at room temperature for another 3 hours. After addition of water, the reaction mixture was extracted with ethyl acetate, and the organic layer was washed with saturated aqueous sodium chloride, dried over anhydrous magnesium sulfate and concentrated under reduced pressure. A mixture of ethyl acetate (1 mL), hexane (1 mL) and chloroform (100 μL) was added to the residue, and the precipitated solid was collected by filtration to give the title compound as a colorless solid (28.3 mg, yield 65%).

Synthetic Examples[a] 89 to 120

The reactions in Synthetic Example[a] 88 were carried out in substantially the same manners except that piperidin-4-carbonitrile, 3-aminopropanenitrile, morpholine, 4-aminobenzonitrile, 4-(aminomethyl)benzonitrile hydrochloride, (S)-3-fluoropyrrolidine, (R)-3-fluoropyrrolidine, 3,3-dimethylazetidine hydrochloride, 4,4-difluoropiperidine hydrochloride, [4-(trifluoromethyl)phenyl]methanamine, 4-(trifluoromethyl)aniline, 4-fluoroaniline, (4-fluorophenyl)methanamine, 4-fluoro-N-methylaniline, 4-amino-3-methylbenzonitrile, 2-methyl-4-(trifluoromethoxy)aniline, 4-amino-2-(trifluoromethyl)benzonitrile, (5-methylthiophen-2-yl)methanamine hydrochloride, 2-fluoroethanamine hydrochloride, 4-(methylamino)benzonitrile, 1-(3,4-difluorophenyl)ethanamine, [4-(trifluoromethoxy)phenyl]methanamine, 2-(4-fluorophenyl)ethanamine, [4-fluoro-3-(trifluoromethyl)phenyl]methanamine, [4-(methylsulfonyl)phenyl]methanamine, 4-(trifluoromethoxy)aniline, 2-chloro-4-(triluforomethoxy)aniline, 2-amino-5-fluorobenzonitrile, 4-fluoro-2-(trifluoromethyl)aniline, 4-morpholinoaniline, (S)-pyrrolidin-3-ol hydrochloride or (S)-(tetrahydrofuran-2-yl)methanamine was used instead of thiomorpholine 1,1-dioxide to give the compounds of Synthetic Examples[a] 89 to 120. The names, morphologies and yields of the compounds synthesized are shown in Tables[a] 10 to 12.

TABLE[a] 10

| Ex | Compound Name | Morphology | Yield |
|---|---|---|---|
| 89 | 1-{[trans-4-(7H-pyrrolo[3,2-e][1,2,3]triazolo[1,5-c]pyrimidin-1-yl)cyclohexyl]methyl}piperidine-4-carbonitrile | colorless solid | 83% |
| 90 | 3-({[trans-4-(7H-pyrrolo[3,2-e][1,2,3]triazolo[1,5-c]pyrimidin-1-yl)cyclohexyl]methyl}amino)propanenitrile | colorless solid | 74% |
| 91 | 4-{[trans-4-(7H-pyrrolo[3,2-e][1,2,3]triazolo[1,5-c]pyrimidin-1-yl)cyclohexyl]methyl}morpholine | colorless solid | 73% |
| 92 | 4-({[trans-4-(7H-pyrrolo[3,2-e][1,2,3]triazolo[1,5-c]pyrimidin-1-yl)cyclohexyl]methyl}amino)benzonitrile | colorless solid | 57% |
| 93 | 4-[({[trans-4-(7H-pyrrolo[3,2-e][1,2,3]triazolo[1,5-c]pyrimidin-1-yl)cyclohexyl]methyl}amino)methyl]benzonitrile | colorless solid | 64% |
| 94 | 1-(trans-4-{[(S)-3-fluoropyrrolidin-1-yl]methyl}cyclohexyl)-7H-pyrrolo[3,2-e][1,2,3]triazolo[1,5-c]pyrimidine | colorless solid | 80% |
| 95 | 1-(trans-4-{[(R)-3-fluoropyrrolidin-1-yl]methyl}cyclohexyl)-7H-pyrrolo[3,2-e][1,2,3]triazolo[1,5-c]pyrimidine | colorless solid | 63% |
| 96 | 1-{trans-4-[(3,3-dimethylazetidin-1-yl)methyl]cyclohexyl}-7H-pyrrolo[3,2-e][1,2,3]triazolo[1,5-c]pyrimidine | colorless solid | 37% |
| 97 | 1-{trans-4-[(4,4-difluoropiperidin-1-yl)methyl]cyclohexyl}-7H-pyrrolo[3,2-e][1,2,3]triazolo[1,5-c]pyrimidine | colorless solid | 64% |
| 98 | 1-[trans-4-(7H-pyrrolo[3,2-e][1,2,3]triazolo[1,5-c]pyrimidin-1-yl)cyclohexyl]-N-[4-(trifluoromethyl)benzyl]methanamine | colorless solid | 59% |
| 99 | N-{[trans-4-(7H-pyrrolo[3,2-e][1,2,3]triazolo[1,5-c]pyrimidin-1-yl)cyclohexyl]methyl}-4-(trifluoromethyl)aniline | colorless solid | 63% |
| 100 | N-{[trans-4-(7H-pyrrolo[3,2-e][1,2,3]triazolo[1,5-c]pyrimidin-1-yl)cyclohexyl]methyl}-4-fluoroaniline | colorless solid | 31% |
| 101 | 1-[trans-4-(7H-pyrrolo[3,2-e][1,2,3]triazolo[1,5-c]pyrimidin-1-yl)cyclohexyl]-N-(4-fluorobenzyl)methanamine | colorless solid | 67% |
| 102 | N-{[trans-4-(7H-pyrrolo[3,2-e][1,2,3]triazolo[1,5-c]pyrimidin-1-yl)cyclohexyl]methyl}-4-fluoro-N-methylaniline | colorless solid | 78% |
| 103 | 4-({[trans-4-(7H-pyrrolo[3,2-e][1,2,3]triazolo[1,5-c]pyrimidin-1-yl)cyclohexyl]methyl}amino)-3-methylbenzonitrile | colorless solid | 82% |

TABLE[a] 11

| Ex | Compound Name | Morphology | Yield |
|---|---|---|---|
| 104 | N-{[trans-4-(7H-pyrrolo[3,2-e][1,2,3]triazolo[1,5-c]pyrimidin-1-yl)cyclohexyl]methyl}-2-methyl-4-(trifluoromethoxy)aniline | colorless solid | 66% |
| 105 | 4-({[trans-4-(7H-pyrrolo[3,2-e][1,2,3]triazolo[1,5-c]pyrimidin-1-yl)cyclohexyl]methyl}amino)-2-(trifluoromethyl)benzonitrile | colorless solid | 61% |
| 106 | 1 [trans 4 (7H pyrrolo[3,2 e][1,2,3]triazolo[1,5-c]pyrimidin-1-yl)cyclohexyl]-N-[(5-methylthiophen-2-yl)methyl]methanamine | colorless solid | 49% |
| 107 | N-{[trans-4-(7H-pyrrolo[3,2-e][1,2,3]triazolo[1,5-c]pyrimidin-1-yl)cyclohexyl]methyl}-2-fluoroethanamine | colorless solid | 19% |
| 108 | 4-({[trans-4-(7H-pyrrolo[3,2-e][1,2,3]triazolo[1,5-c]pyrimidin-1-yl)cyclohexyl]methyl}(methyl)amino)benzonitrile | colorless solid | 36% |
| 109 | N-{[trans-4-(7H-pyrrolo[3,2-e][1,2,3]triazolo[1,5-c]pyrimidin-1-yl)cyclohexyl]methyl}-1-(3,4-difluorophenyl)ethanamine | colorless solid | 8.1% |
| 110 | 1 [trans 4 (7H pyrrolo[3,2 e][1,2,3]triazolo[1,5-c]pyrimidin-1-yl)cyclohexyl]-N-[4-(trifluoromethoxy)benzyl]methanamine | colorless solid | 16% |
| 111 | N-{[trans-4-(7H-pyrrolo[3,2-e][1,2,3]triazolo[1,5-c]pyrimidin-1-yl)cyclohexyl]methyl}-2-(4-fluorophonyl)ethanamine | pale purple solid | 12% |
| 112 | 1-[trans-4-(7H-pyrrolo[3,2-e][1,2,3]triazolo[1,5-c]pyrimidin-1-yl)cyclohexyl]-N-[4-fluoro-3-(trifluoromethyl)benzyl]methanamine | colorless solid | 5.1% |
| 113 | 1-[trans-4-(7H-pyrrolo[3,2-e][1,2,3]triazolo[1,5-c]pyrimidin-1-yl)cyclohexyl]-N-[4-(methylsulfonyl)benzyl]methanamine | colorless solid | 5.0% |

TABLE[a] 11-continued

| Ex | Compound Name | Morphology | Yield |
|---|---|---|---|
| 114 | N-{[trans-4-(7H-pyrrolo[3,2-e][1,2,3]triazolo[1,5-c]pyrimidin-1-yl)cyclohexyl]methyl}-4-(trifluoromethoxy)aniline | colorless solid | 69% |
| 115 | N-{[trans-4-(7H-pyrrolo[3,2-e][1,2,3]triazolo[1,5-c]pyrimidin-1-yl)cyclohexyl]methyl}-2-chloro-4-(trifluoromethoxy)aniline | colorless solid | 77% |
| 116 | 2-({[trans-4-(7H-pyrrolo[3,2-e][1,2,3]triazolo[1,5-c]pyrimidin-1-yl)cyclohexyl]methyl}amino)-5-fluorobenzonitrile | colorless solid | 59% |

TABLE[a] 12

| Ex | Compound Name | Morphology | Yield |
|---|---|---|---|
| 117 | N-{[trans-4-(7H-pyrrolo[3,2-e][1,2,3]triazolo[1,5-c]pyrimidin-1-yl)cyclohexyl]methyl}-4-fluoro-2-(trifluoromethyl)aniline | colorless solid | 63% |
| 118 | N-{[trans-4-(7H-pyrrolo[3,2-e][1,2,3]triazolo[1,5-c]pyrimidin-1-yl)cyclohexyl]methyl}-4-morpholinoaniline | colorless solid | 58% |
| 119 | (S)-1-{[trans-4-(7H-pyrrolo[3,2-e][1,2,3]triazolo[1,5-c]pyrimidin-1-yl)cyclohexyl]methyl}pyrrolidin-3-ol | pale yellow solid | 45% |
| 120 | 1-[trans-4-(7H-pyrrolo[3,2-e][1,2,3]triazolo[1,5-c]pyrimidin-1-yl)cyclohexyl]-N-{[(S)-tetrahydrofuran-2-yl]methyl}methanamine | colorless solid | 33% |

Synthetic Example[a] 121

4-{[4-(7H-Pyrrolo[3,2-e][1,2,3]triazolo[1,5-c]pyrimidin-1-yl)cyclohexyl]amino}benzonitrile 4-(7H-Pyrrolo[3,2-e][1,2,3]triazolo[1,5-c]pyrimidin-1-yl)cyclohexanone (21.5 mg, 0.0842 mmol) obtained in Synthetic Example[a] 82 in a mixture of methanol (1 mL) and acetic acid (0.1 mL) was stirred with 4-aminobenzonitrile (15.0 mg, 0.126 mmol) and 2-picoline borane (13.5 mg, 0.126 mmol) at room temperature for one day. The reaction mixture was concentrated under reduced pressure, and the residue was purified by silica gel thin layer chromatography (NH-PLC05 plate manufactured by Fuji Silysia Chemical Ltd.: ethyl acetate) to give cis/trans mixture of the title compound as a pale yellow solid (17.1 mg, yield 57%).

Synthetic Examples[a] 122 to 133

The reactions in Synthetic Example[a] 121 were carried out in substantially the same manners except that 2-(pyridin-4-yl)ethanamine, 2-phenylethanamine, morpholine, 2-[3-(trifluoromethyl)phenyl]ethanamine, 2-morpholinoethanamine, piperidine-4-carbonitrile, 4-(trifluoromethyl)aniline, 4-amino-3-fluorobenzonitrile, 4-fluoro-N-methylaniline, 4-fluoroaniline, 4-amino-3-methylbenzonitrile or 2-methyl-4-(trifluoromethoxy)aniline was used instead of 4-aminobenzonitrile to give the compounds of Synthetic Examples[a] 122 to 133. The names, morphologies and yields of the compounds synthesized are shown in Table[a] 13.

TABLE[a] 13

| Ex | Compound Name | Morphology | Yield |
|---|---|---|---|
| 122 | N-[2-(pyridin-4-yl)ethyl]-4-(7H-pyrrolo[3,2-e][1,2,3]triazolo[1,5-c]pyrimidin-1-yl)cyclohexanamine | colorless solid | 49% |
| 123 | N-phenethyl-4-(7H-pyrrolo[3,2-e][1,2,3]triazolo[1,5-c]pyrimidin-1-yl)cyclohexanamine | colorless solid | 33% |
| 124 | 4-[4-(7H-pyrrolo[3,2-e][1,2,3]triazolo[1,5-c]pyrimidin-1-yl)cyclohexyl]morpholine | pale brown solid | 28% |
| 125 | 4-(7H-pyrrolo[3,2-e][1,2,3]triazolo[1,5-c]pyrimidin-1-yl)-N-[3-(trifluoromethyl)phenethyl]cyclohexanamine | colorless oil | 2.2% |
| 126 | N-(2-morpholinoethyl)-4-(7H-pyrrolo[3,2-e][1,2,3]triazolo[1,5-c]pyrimidin-1-yl)cyclohexanamine | gray amorphous | 59% |
| 127 | 1-[4-(7H-pyrrolo[3,2-e][1,2,3]triazolo[1,5-c]pyrimidin-1-yl)cyclohexyl]piperidine-4-carbonitrile | colorless solid | 67% |
| 128 | N-[4-(7H-pyrrolo[3,2-e][1,2,3]triazolo[1,5-c]pyrimidin-1-yl)cyclohexyl]-4-(trifluoromethyl)aniline | pale yellow solid | 71% |
| 129 | 4-{[4-(7H-pyrrolo[3,2-e][1,2,3]triazolo[1,5-c]pyrimidin-1-yl)cyclohexyl]amino}-3-fluorobenzonitrile | colorless solid | 8.8% |
| 130 | N-[4-(7H-pyrrolo[3,2-e][1,2,3]triazolo[1,5-c]pyrimidin-1-yl)cyclohexyl]-4-fluoro-N-methylaniline | colorless solid | 63% |
| 131 | N-[4-(7H-pyrrolo[3,2-e][1,2,3]triazolo[1,5-c]pyrimidin-1-yl)cyclohexyl]-4-fluoroaniline | colorless solid | 59% |
| 132 | 4-{[4-(7H-pyrrolo[3,2-e][1,2,3]triazolo[1,5-c]pyrimidin-1-yl)cyclohexyl]amino}-3-methylbenzonitrile | colorless solid | 23% |

TABLE[a] 13-continued

| Ex | Compound Name | Morphology | Yield |
|---|---|---|---|
| 133 | N-[4-(7H-pyrrolo[3,2-e][1,2,3]triazolo[1,5-c]pyrimidin-1-yl)cyclohexyl]-2-methyl-4-(trifluoromethoxy)aniline | colorless solid | 22% |

Synthetic Example[a] 134

134a: 4-{[cis-4-(7H-Pyrrolo[3,2-e][1,2,3]triazolo[1,5-c]pyrimidin-1-yl)cyclohexyl]amino}benzonitrile

134b: 4-{[(trans-4-(7H-Pyrrolo[3,2-e][1,2,3]triazolo[1,5-c]pyrimidin-1-yl)cyclohexyl]amino}benzonitrile 4-{[4-(7H-Pyrrolo[3,2-e][1,2,3]triazolo[1,5-c]pyrimidin-1-yl)cyclohexyl]amino}benzonitrile (16.5 mg, 0.462 mmol) obtained in Synthetic Example[a] 121 was resolved by silica gel thin layer chromatography (hexane/ethyl acetate=1/2 (v/v)) into 4-{[cis-4-(7H-Pyrrolo[3,2-e][1,2,3]triazolo[1,5-c]pyrimidin-1-yl)cyclohexyl]amino}benzonitrile (Synthetic Example[a] 134a; pale yellow solid, 7.3 mg, yield 44%) in a less polar fraction and into 4-{[trans-4-(7H-Pyrrolo[3,2-e][1,2,3]triazolo[1,5-c]pyrimidin-1-yl)cyclohexyl]amino}benzonitrile (Synthetic Example[a] 134b, pale yellow solid, 3.0 mg, yield 18%) in a more polar fraction.

Synthetic Example[a] 135

135a: cis-N-Phenethyl-4-(7H-pyrrolo[3,2-e][1,2,3]triazolo[1,5-c]pyrimidin-1-yl)cyclohexanamine

135b: trans-N-Phenethyl-4-(7H-pyrrolo[3,2-e][1,2,3]triazolo[,1,5-c]pyrimidin-1-yl)cyclohexanamine The reactions in Synthetic Example[a] 134 were carried out in substantially the same manners except that N-phenethyl-4-(7H-pyrrolo[3,2-e][1,2,3]triazolo[1,5-c]pyrimidin-1-yl)cyclohexanamine obtained in Synthetic Example[a] 123 was used instead of 4-{[4-(7H-pyrrolo[3,2-e][1,2,3]triazolo[1,5-c]pyrimidin-1-yl)cyclohexyl]amino}benzonitrile to give cis-N-phenethyl-4-(7H-pyrrolo[3,2-e][1,2,3]triazolo[1,5-c]pyrimidin-1-yl)cyclohexanamine (Synthetic Example[a] 135a, colorless solid, 3.22 mg, yield 16%) in a less polar fraction and trans-N-phenethyl-4-(7H-pyrrolo[3,2-e][1,2,3]triazolo[1,5-c]pyrimidin-1-yl)cyclohexanamine (Synthetic Example[a] 135b, colorless solid, 2.52 mg, yield 11%) in a more polar fraction.

Synthetic Example[a] 136

136a: cis-N-(3-Phenylpropyl)-4-(7H-pyrrolo[3,2-e][1,2,3]triazolo[1,5-c]pyrimidin-1-yl)cyclohexanamine

136b: trans-N-(3-Phenylpropyl)-4-(7H-pyrrolo[3,2-e][1,2,3]triazolo[,1,5-c]pyrimidin-1-yl)cyclohexanamine 4-(7H-Pyrrolo[3,2-e][1,2,3]triazolo[1,5-c]pyrimidin-1-yl)cyclohexanone (30.0 mg, 0.118 mmol) obtained in Synthetic Example[a] 82 in a mixture of methanol (1.5 ml) and acetic acid (0.15 mL) was mixed with 3-phenylpropan-1-amine (25.0 μL, 0.176 mmol) at room temperature and stirred at 40° C. for 30 minutes. The reaction mixture was allowed to cool to room temperature and stirred with 2-picoline borane (19.0 mg, 0.176 mmol) at room temperature for one day. After addition of 1 M hydrochloric acid and ethyl acetate, the aqueous layer was separated, and after addition of 1 M aqueous sodium hydroxide, extracted with ethyl acetate. The organic layer was dried over anhydrous sodium sulfate and concentrated under reduced pressure, and the residue was purified by silica gel chromatography (Hi Flash amino silica gel column manufactured by Yamazen Corporation: ethyl acetate/hexane=1/1 (v/v)→ethyl acetate) to give cis-N-(3-phenylpropyl)-4-(7H-pyrrolo[3,2-e][1,2,3]triazolo[1,5-c]pyrimidin-1-yl)cyclohexanamine (Synthetic Example[a] 136a; colorless oil, 6.00 mg, yield 13%) in a less polar fraction and trans-N-(3-phenylpropyl)-4-(7H-pyrrolo[3,2-e][1,2,3]triazolo[1,5-c]pyrimidin-1-yl)cyclohexanamine (Synthetic Example[a] 136b; colorless solid, 2.52 mg, yield 5.7%) in a more polar fraction.

Synthetic Examples[a] 137 to 139

The reactions in Synthetic Example[a] 136 were carried out in substantially the same manners except that 4-(aminomethyl)benzonitrile, [4-(trifluoromethyl)phenyl]methanamine or morpholin-4-amine was used instead of 3-phenylpropan-1-amine to give the compounds of Synthetic Examples[a] 137a to 139a in less polar fractions and the compounds of Synthetic Examples[a] 137b to 139b in more polar fractions. The names, morphologies and yields of the compounds synthesized are shown in Table[a] 14.

TABLE[a] 14

| Ex | Compound Name | Morphology | Yield |
|---|---|---|---|
| 137a | 4-({[cis-4-(7H-pyrrolo[3,2-e][1,2,3]triazolo[1,5 c]pyrimidin 1 yl)cyclohexyl]amino}methyl)benzonitrile | colorless solid | 39% |
| 137b | 4-({[trans-4-(7H-pyrrolo[3,2-e][1,2,3]triazolo[1,5-c]pyrimidin-1-yl)cyclohexyl]amino}methyl)benzonitrile | colorless solid | 40% |
| 138a | cis-4-(7H-pyrrolo[3,2-e][1,2,3]triazolo[1,5-c]pyrimidin-1-yl)-N-[4-(trifluoromethyl)benzyl]cyclohexanamine | colorless solid | 51% |
| 138b | trans-4-(7H-pyrrolo[3,2-e][1,2,3]triazolo[1,5-c]pyrimidin-1-yl)-N-[4-(trifluoromethyl)benzyl]cyclohexanamine | colorless solid | 30% |
| 139a | N-[cis-4-(7H-pyrrolo[3,2-e][1,2,3]triazolo[1,5-c]pyrimidin-1-yl)cyclohexyl]morpholin-4-amine | Pale yellow solid | 21% |

TABLE[a] 14-continued

| Ex | Compound Name | Morphology | Yield |
|---|---|---|---|
| 139b | N-[trans-4-(7H-pyrrolo[3,2-e][1,2,3]triazolo[1,5-c]pyrimidin-1-yl)cyclohexyl]morpholin-4-amine | Pale yellow solid | 17% |

Synthetic Example[a] 140

[4-(7H-Pyrrolo[3,2-e][1,2,3]triazolo[1,5-c]pyrimidin-1-yl)phenyl]methanol 1-(4-{[(tert-Butyldimethylsilyl)oxy]methyl}phenyl)-7H-pyrrolo[3,2-e][1,2,3]triazolo[1,5-c]pyrimidine (3.58 g, 9.43 mmol) obtained in Reference Synthetic Example[a] 88 in a mixture of dichloromethane (20 mL) and methanol (50 mL) was stirred with pyridinium p-toluenesulfonate (1.18 g, 4.72 mmol) at 60° C. for 8 hours. The reaction mixture was concentrated under reduced pressure, and the residue was purified by silica gel column chromatography (hexane/ethyl acetate=1/1 (v/v)→ethyl acetate→ethyl acetate/methanol=1/1 (v/v)) to give the title compound as an ivory solid (831 mg, yield 33%).

Synthetic Example[a] 141

[trans-4-(7H-Pyrrolo[3,2-e][1,2,3]triazolo[1,5-c]pyrimidin-1-yl)cyclohexyl]methanol The reactions in Synthetic Example[a] 140 were carried out in substantially the same manners except that 1-(trans-4-{[(tert-butyldimethylsilyl)oxy]methyl}cyclohexyl)-7H-pyrrolo[3,2-e][1,2,3]triazolo[1,5-c]pyrimidine obtained in Reference Synthetic Example[a] 92 was used instead of 1-(4-{[(tert-butyldimethylsilyl)oxy]methyl}phenyl)-7H-pyrrolo[3,2-e][1,2,3]triazolo[1,5-c]pyrimidine to give the title compound as a pale yellow solid (2.05 g, yield 78%). (alternative to Synthetic Example[a] 10).

Synthetic Examples[a] 142 to 144

The reactions in Synthetic Example[a] 32 were carried out in substantially the same manners except that 1-(bromomethyl)-2-fluorobenzene, 2-(bromomethyl)-5-(trifluoromethyl)furan or 5-(bromomethyl)thiophene-2-carbonitrile (Reference Synthetic Example[a] 93) was used instead of benzyl bromide to give the compounds of Synthetic Examples[a] 142 to 144. The names, morphologies and yields of the compounds synthesized are shown in Table[a] 15.

TABLE[a] 15

| Ex | Compound Name | Morphology | Yield |
|---|---|---|---|
| 142 | 1-[1-(2-fluorobenzyl)piperidin-4-yl]-7H-pyrrolo[3,2-e][1,2,3]triazolo[1,5-c]pyrimidine | colorless solid | 11% |
| 143 | 1-(1-{[5-(trifluoromethyl)furan-2-yl]methyl}piperidin-4-yl)-7H-pyrrolo[3,2-e][1, 2,3]triazolo[1,5-c]pyrimidine | colorless solid | 4.0% |
| 144 | 5-{[4-(7H-pyrrolo[3,2-e][1,2,3]triazolo[1,5-c]pyrimidin-1-yl)piperidin-1-yl]methyl}thiophone-2-carbonitrile | colorless solid | 15% |

Synthetic Examples[a] 145 to 171

The reactions in Synthetic Example[a] 44 were carried out in substantially the same manners except that 6-fluoronicotinaldehyde, furan-2-carbaldehyde, 5-iodofuran-2-carbaldehyde, thiophene-2-carbaldehyde, 5-bromofuran-2-carbaldehyde, 2-chlorothiazole-5-carbaldehyde, 1H-pyrazole-5-carbaldehyde, 1,2,3-thiadiazole-4-carbaldehyde, 2-bromothiazole-5-carbaldehyde, 4-fluoro-3-(trifluoromethyl)benzaldehyde, 4-chloro-3-(trifluoromethyl)benzaldehyde, 4-(methylsulfonyl)benzaldehyde, 2-fluoro-4-(trifluoromethyl)benzaldehyde, 4-chloro-2-fluorobenzaldehyde, 4-chloro-3-fluorobenzaldehyde, 2-chloroisonicotinaldehyde, 3-fluoroisonicotinaldehyde, 5-fluoropyridine-2-carbaldehyde, 3-chloroisonicotinaldehyde, 2,4-difluorobenzaldehyde, 2-chloro-4-fluorobenzaldehyde, 3,4-difluorobenzaldehyde, 3-fluoro-4-(trifluoromethyl)benzaldehyde, 4-(2-hydroxyethoxy)benzaldehyde, 4-(1,1,2,2-tetrafluoroethoxy)benzaldehyde, 6-methoxynicotinaldehyde or tert-butyl(2-oxoethyl)carbamate was used instead of thiazole-5-carbaldehyde to give the compounds of Synthetic Examples[a] 145 to 171. The names, morphologies and yields of the compounds synthesized are shown in Tables[a] 16 and 17.

TABLE[a] 16

| Ex | Compound Name | Morphology | Yield |
|---|---|---|---|
| 145 | 1-{1-[(6-fluoropyridin-3-yl)methyl]piperidin-4-yl}-7H-pyrrolo[3,2-e][1,2,3]triazolo[1, 5-c]pyrimidine | colorless solid | 66% |
| 146 | 1-[1-(furan-9-ylmethyl)piperidin-4-yl]-7H-pyrrolo[3,2-e][1,2,3]triazolo[1,5-c]pyrimidine | colorless solid | 7.0% |
| 147 | 1-{1-[(5-iodofuran-2-yl)methyl]piperidin-4-yl}-7H-pyrrolo[3,2-e][1,2,3]triazolo[1,5-c]pyrimidine | colorless solid | 66% |
| 148 | 1-[1-(thiophen-2-ylmethyl)piperidin-4-yl]-7H-pyrrolo[3,2-e][1,2,3]-triazolo[1,5-c]pyrimidine | colorless solid | 49% |
| 149 | 1-{1-[(5-bromofuran-2-yl)methyl]piperidin-4-yl}-7H-pyrrolo[3,2-e][1,2,3]triazolo[1, 5-c]pyrimidine | colorless solid | 56% |
| 150 | 5-{[4-(7H-pyrrolo[3,2-e][1,2,3]triazolo[1,5-c]pyrimidin-1-yl)piperidin-1-yl]methyl}-2-chlorothiazole | colorless solid | 62% |
| 151 | 1-{1-[(1H-pyrazol-5-yl)methyl]piperidin-4-yl}-7H-pyrrolo[3,2-e][1,2,3]triazolo[1,5-c]pyrimidine | colorless solid | 17% |
| 152 | 4-{[4-(7H-pyrrolo[3,2-e][1,2,3]triazolo[1,5-c]pyrimidin-1-yl)piperidin-1-yl]methyl}-1,2,3-thiadiazole | colorless solid | 45% |
| 153 | 5-{[4-(7H-pyrrolo[3,2-e][1,2,3]triazolo[1,5-c]pyrimidin-1-yl)piperidin-1-yl]methyl}-2-bromothiazole | colorless solid | 58% |
| 154 | 1-{1-[4-fluoro-3-(trifluoromethyl)benzyl]piperidin-4-yl}-7H-pyrrolo[3,2-e][1, 2,3]triazolo[1,5-c]pyrimidine | colorless solid | 27% |
| 155 | 1-{1-[4-chloro-3-(trifluoromethyl)benzyl]piperidin-4-yl}-7H-pyrrolo[3,2-e][1, 2,3]triazolo[1,5-c]pyrimidine | colorless solid | 9.0% |
| 156 | 1-{1-[4-(methylsulfonyl)benzyl]piperidin-4-yl}-7H-pyrrolo[3,2-e][1,2,3]triazolo[1,5-c]pyrimidine | colorless solid | 21% |
| 157 | 1-{1-[2-fluoro-4-(trifluoromethyl)benzyl]piperidin-4-yl}-7H-pyrrolo[3,2-e][1, 2,3]triazolo[1,5- | colorless solid | 8.0% |

TABLE[a] 16-continued

| Ex | Compound Name | Morphology | Yield |
|---|---|---|---|
| | c]pyrimidine | | |
| 158 | 1-[1-(4-chloro-2-fluorobenzyl)piperidin-4-yl]-7H-pyrrolo[3,2-e][1,2,3]triazolo[1,5-c]pyrimidine | colorless solid | 50% |
| 159 | 1-[1-(4-chloro-3-fluorobenzyl)piperidin-4-yl]-7H-pyrrolo[3,2-e][1,2,3]triazolo[1,5-c]pyrimidine | colorless solid | 44% |
| 160 | 1-{1-[(2-chloropyridin-4-yl)methyl]piperidin-4-yl}-7H-pyrrolo[3,2-e][1,2,3]triazolo[1, 5-c]pyrimidine | colorless solid | 39% |

TABLE[a] 17

| Ex | Compound Name | Morphology | Yield |
|---|---|---|---|
| 161 | 1-{1-[(3-fluoropyridin-4-yl)methyl]piperidin-4-yl}-7H-pyrrolo[3,2-e][1,2,3]triazolo[1, 5-c]pyrimidine | colorless solid | 22% |
| 162 | 1-{1-[(5-fluoropyridin-2-yl)methyl]piperidin-4-yl}-7H-pyrrolo[3,2-e][1,2,3]triazolo[1, 5-c]pyrimidine | colorless solid | 39% |
| 163 | 1-{1-[(3-chloropyridin-4-yl)methyl]piperidin-4-yl}-7H-pyrrolo[3,2-e][1,2,3]triazolo[1,5-c]pyrimidine | colorless solid | 33% |
| 164 | 1-[1-(2,4-difluorobenzyl)piperidin-4-yl]-7H-pyrrolo[3,2-e][1,2,3]triazolo[1,5-c]pyrimidine | pink solid | 17% |
| 165 | 1-[1-(2-chloro-4-fluorobenzyl)piperidin-4-yl]-7H-pyrrolo[3,2-e][1,2,3]triazolo[1,5-c]pyrimidine | colorless solid | 18% |
| 166 | 1-[1-(3,4-difluorobenzyl)piperidin-4-yl]-7H-pyrrolo[3,2-e][1,2,3]triazolo[1,5-c]pyrimidine | colorless solid | 30% |
| 167 | 1-{1-[3-fluoro-4-(trifluoromethyl)benzyl]piperidin-4-yl}-7H-pyrrolo[3,2-e][1,2,3]triazolo[1,5-c]pyrimidine | colorless solid | 15% |
| 168 | 2-(4-{[4-(7H-pyrrolo[3,2-e][1,2,3]triazolo[1,5-c]pyrimidin-1-yl)piperidin-1-yl]methyl}phenoxy)ethanol | colorless solid | 7.0% |

TABLE[a] 17-continued

| Ex | Compound Name | Morphology | Yield |
|---|---|---|---|
| 169 | 1-{1-[4-(1,1,2,2-tetrafluoroethoxy)benzyl]piperidin-4-yl}-7H-pyrrolo[3,2-e][1,2,3]triazolo[1,5-c]pyrimidine | colorless solid | 11% |
| 170 | 1-{1-[(6-methoxypyridin-3-yl)methyl]piperidin-4-yl}-7H-pyrrolo[3,2-e][1,2,3]triazolo[1,5-c]pyrimidine | colorless solid | 15% |
| 171 | tert-butyl {2-[4-(7H-pyrrolo[3,2-e][1,2,3]triazolo[1,5-c]pyrimidin-1-yl)piperidin-1-yl]ethyl}carbamate | pale yellow amorphous | 75% |

Synthetic Examples[a] 172 to 193

The reactions in Synthetic Example[a] 88 were carried out in substantially the same manners except that 3-amino-1,1,1-trifluoro-2-phenylpropan-2-ol (Reference Synthetic Example[a] 101), 4-[(trifluoromethyl)sulfonyl]aniline, 2-phenylethanamine, 2-(trifluoromethyl)-1H-benzo[d]imidazol-6-amine, 4-chloroaniline, (4-chlorophenyl)methanamine, 2-(4-chlorophenyl)ethanamine, 5-fluoroindoline, 3,3'-azanediyldipropanenitrile, (S)—N,N-dimethylpyrrolidin-3-amine, (5-methylfuran-2-yl)methanamine, (5-methylpyrazin-2-yl)methanamine, (S)-1-aminopropan-2-ol, (R)-1-aminopropan-2-ol, 2-amino-1-phenylethanol, (S)-pyrrolidine-3-carbonitrile hydrochloride, 2,2,2-trifluoroethanamine, 5-(methylsulfonyl)indoline, N,N-dimethylindoline-5-sulfonamide, 1-(2-aminoethyl) imidazolidin-2-on, 2-(1H-imidazol-4-yl)ethanamine dihydrochloride or phenylmethanamine was used instead of thiomorpholine 1,1-dioxide to give the compounds of Synthetic Examples[a] 172 to 193. The names, morphologies and yields of the compounds synthesized are shown in Tables[a] 18 and 19.

TABLE[a] 18

| Ex | Compound Name | Morphology | Yield |
|---|---|---|---|
| 172 | 3-({[trans-4-(7H-pyrrolo[3,2-e][1,2,3]triazolo[1,5-c]pyrimidin-1-yl)cyclohexyl]methyl}amino)-1,1,1-trifluoro-2-phenylpropan-2-ol | colorless solid | 31% |
| 173 | N-{[trans-4-(7H-pyrrolo[3,2-e][1,2,3]triazolo[1,5-c]pyrimidin-1-yl)cyclohexyl]methyl}-4-[(trifluoromethyl)sulfonyl]aniline | colorless solid | 10% |
| 174 | N-{[trans-4-(7H-pyrrolo[3,2-e][1,2,3]triazolo[1,5-c]pyrimidin-1-yl)cyclohexyl]methyl}-2-phenylethanamine | colorless solid | 97% |
| 175 | N-{[trans-4-(7H-pyrrolo[3,2-e][1,2,3]triazolo[1,5-c]pyrimidin-1-yl)cyclohexyl]methyl}-2-(trifluoromethyl)-1H-benzo[d]imidazol-5-amine | colorless solid | 15% |
| 176 | N-{[trans-4-(7H-pyrrolo[3,2-e][1,2,3]triazolo[1,5-c]pyrimidin-1-yl)cyclohexyl]methyl}-4-chloroaniline | colorless solid | 52% |
| 177 | 1-[trans-4-(7H-pyrrolo[3,2-e][1,2,3]triazolo[1,5-c]pyrimidin-1-yl)cyclohexyl]-N-(4-chlorobenzyl)methanamine | colorless solid | 37% |
| 178 | N-{[trans-4-(7H-pyrrolo[3,2c][1,2,3]triazolo[1,5 c]pyrimidin 1 yl)cyclohexyl]methyl}-2-(4-chlorophenyl)ethanamine | pale purple solid | 86% |
| 179 | 1-[trans-4-((5-fluoroindolin-1-yl)methyl)cyclohexyl]-7H-pyrrolo[3,2-e][1,2,3]triazolo[1,5-c]pyrimidine | colorless solid | 83% |
| 180 | 3,3'-({[trans-4-(7H-pyrrolo[3,2-c][1,2,3]triazolo[1,5-c]pyrimidin-1-yl)cyclohexyl]methyl}azanediyl)dipropanenitrile | colorless solid | 74% |

TABLE[a] 18-continued

| Ex | Compound Name | Morphology | Yield |
|---|---|---|---|
| 181 | (S)-1-{[trans-4-(7H-pyrrolo[3,2-e][1,2,3]triazolo[1,5-c]pyrimidin-1-yl)cyclohexyl]methyl}-N,N-dimethylpyrrolidin-3-amine | colorless solid | 71% |
| 182 | 1-[trans-4-(7H-pyrrolo[3,2-e][1,2,3]triazolo[1,5-c]pyrimidin-1-yl)cyclohexyl]-N-[(5-methylfuran-2-yl)methyl]methanamine | pale yellow solid | 44% |
| 183 | 1-[trans-4-(7H-pyrrolo[3,2-e][1,2,3]triazolo[1,5-c]pyrimidin-1-yl)cyclohexyl]-N-[(5-methylpyrazin-2-yl)methyl]methanamine | colorless solid | 55% |
| 184 | (S)-1-({[trans-4-(7H-pyrrolo[3,2-e][1,2,3]triazolo[1,5-c]pyrimidin-1-yl)cyclohexyl]methyl}amino)propan-2-ol | colorless solid | 21% |
| 185 | (R)-1-({[trans-4-(7H-pyrrolo[3,2-e][1,2,3]triazolo[1,5-c]pyrimidin-1-yl)cyclohexyl]methyl}amino)propan-2-ol | colorless solid | 20% |

TABLE[a] 19

| Ex | Compound Name | Morphology | Yield |
|---|---|---|---|
| 186 | 2-({[trans-4-(7H-pyrrolo[3,2-e][1,2,3]triazolo[1,5-c]pyrimidin-1-yl)cyclohexyl]methyl]amino)-1-phenylethanol | colorless solid | 24% |
| 187 | (S)-1-{[trans-4-(7H-pyrrolo[3,2-e][1,2,triazolo[1,5-c]pyrimidin-1-yl)cyclohexyl]methyl}pyrrolidine-3-carbonitrile | colorless solid | 71% |
| 188 | N-{[trans-4-(7H-pyrrolo[3,2-e][1,2,3]triazolo[1,5-c]pyrimidin-1-yl)cyclohexyl]methyl}-2,2,2-trifluoroethanamine | colorless solid | 48% |
| 189 | 1-(trans-4-{[5-(methylsulfonyl)indolin-1-yl]methyl}cyclohexyl)-7H-pyrrolo[3,2-e][1,2,3]triazolo[1,5-c]pyrimidine | colorless solid | 57% |
| 190 | 1-{[trans-4-(7H-pyrrolo[3,2-e][1,2,3]triazolo[1,5-c]pyrimidin-1-yl)cyclohexyl]methyl}-N,N-dimethylindoline-5-sulfonamide | colorless solid | 72% |
| 191 | 1-[2-({[trans-4-(7H-pyrrolo[3,2-e][1,2,3]triazolo[1,5-c]pyrimidin-1-yl)cyclohexyl]methyl}amino)ethyl]imidazolidin-2-one | colorless solid | 33% |
| 192 | N-{[trans-4-(7H-pyrrolo[3,2-e][1,2,3]triazolo[1,5-c]pyrimidin-1-yl)cyclohexyl]methyl}-2-(1H-imidazol-4-yl)ethanamine hydrochloride | colorless solid | 56% |
| 193 | 1-[trans-4-(7H-Pyrrolo[3,2-e][1,2,3]triazolo[1,5-c]pyrimidin-1-yl)cyclohexyl]-N-benzylmethanamine | colorless solid | 84% |

Synthetic Examples[a] 194 to 197

The reactions in Synthetic Example[a] 136 were carried out in substantially the same manners except that phenylmethanamine, (4-fluorophenyl)methanamine, 3-amino-1,1,1-trifluoro-2-phenylpropan-2-ol (Reference Synthetic Example[a] 101) or (4-chlorophenyl)methanamine was used instead of 3-phenylpropan-1-amine to give the compounds of Synthetic Examples[a] 194a to 197a in less polar fractions and the compounds of Synthetic Examples[a] 194b to 197b in more polar fractions. The names, morphologies and yields of the compounds synthesized are shown in Table[a] 20.

TABLE[a] 20

| Ex | Compound Name | Morphology | Yield |
|---|---|---|---|
| 194a | cis-N-benzyl-4-(7H-pyrrolo[3,2-e][1,2,3]triazolo[1,5-c]pyrimidin-1-yl)cyclohexanamine | colorless solid | 44% |
| 194b | trans-N-benzyl-4-(7H-pyrrolo[3,2-e][1,2,3]triazolo[1,5-c]pyrimidin-1-yl)cyclohexanamine | colorless solid | 37% |

TABLE[a] 20-continued

| Ex | Compound Name | Morphology | Yield |
|---|---|---|---|
| 195a | cis-N-(4-fluorobenzyl)-4-(7H-pyrrolo[3,2-e][1,2,3]triazolo[1,5-c]pyrimidin-1-yl)cyclohexanamine | colorless solid | 30% |
| 195b | trans-N-(4-fluorobenzyl)-4-(7H-pyrrolo[3,2-e][1,2,3]triazolo[1,5-c]pyrimidin-1-yl)cyclohexanamine | colorless solid | 24% |
| 196a | 3-{[cis-4-(7H-pyrrolo[3,2-e-][1,2,3]triazolo[1,5-c]pyrimidin-1-yl)cyclohexyl]amino}-1,1,1-trifluoro-2-phenylpropan 2 ol | colorless solid | 34% |
| 196b | 3-{[trans-4-(7H-pyrrolo[3,2-e][1,2,3]triazolo[1,5-c]pyrimidin-1-yl)cyclohexyl]amino}-1,1,1-trifluoro-2-phenylpropan-2-ol | colorless solid | 39% |
| 197a | cis-N-(4-chlorobenzyl)-4-(7H-pyrrolo[3,2-e][1,2,3]triazolo[1,5-c]pyrimidin-1-yl)cyclohexanamine | colorless solid | 15% |
| 197b | trans-N-(4-chlorobenzyl)-4-(7H-pyrrolo[3,2-e][1,2,3]triazolo[1,5-c]pyrimidin-1-yl)cyclohexanamine | colorless solid | 24% |

Synthetic Examples[a] 198 to 204

The reactions in Synthetic Example[a] 136 were carried out in substantially the same manners except that 2-(4-chlorophenyl)ethanamine, 3-amino-2-(4-chlorophenyl)-1,1,1-trifluoropropan-2-ol (Reference Synthetic Example[a] 100), 3-amino-1,1,1-trifluoro-2-(4-fluorophenyl)propan-2-ol (Reference Synthetic Example[a] 102), 2-(4-fluorophenyl) ethanamine, 2-amino-1-phenylethanol, (S)-2-amino-1-phenylethanol or (R)-2-amino-1-phenylethanol was used instead of 3-phenylpropan-1-amine to give the compounds of Synthetic Examples[a] 198 b to 204b in more polar fractions. The names, morphologies and yields of the compounds synthesized are shown in Table[a] 21.

TABLE[a] 21

| Ex | Compound Name | Morphology | Yield |
|---|---|---|---|
| 198b | trans-N-(4-chlorophenethyl)-4-(7H-pyrrolo[3, 2-e][1,2,3]triazolo[1,5-c]pyrimidin-1-yl)cyclohexanamine | colorless solid | 17% |
| 199b | 3-((trans-4-(7H-pyrrolo[3,2-e][1,2,3]triazolo[1, 5-c]pyrimidin-1-yl)cyclohexyl)amino)-2-(4-chlorophenyl)-1,1,1-trifluoropropan-2-ol | pale green solid | 37% |
| 200b | 3-{[trans-4-(7H-pyrrolo[3,2-e][1,2,3]triazolo[1, 5-c]pyrimidin-1-yl)cyclohexyl]amino}-1,1,1-trifluoro-2-(4-fluorophenyl)propan-2-ol | pale green solid | 42% |
| 201b | trans-N-(4-fluorophenethyl)-4-(7H-pyrrolo[3, 2-e][1,2,3]triazolo[1,5-c]pyrimidin-1-yl)cyclolhexnamine | colorless solid | 24% |
| 202b | 2-{[trans-4-(7H-pyrrolo[3,2-e][1,2,3]triazolo[1, 5-c]pyrimidin-1-yl)cyclohexyl]amino}-1-phenylethanol | colorless solid | 8.0% |
| 203b | (S)-2-{[trans-4-(7H-pyrrolo[3,2-e][1, 2,3]triazolo[1,5-c]pyrimidin-1-yl)cyclohexyl]amino}-1-phenylethanol | pale yellow solid | 26% |
| 204b | (R)-2-{[trans-4-(7H-pyrrolo[3,2-e][1, 2,3]triazolo[1,5-c]pyrimidin-1-yl)cyclohexyl]amino}-1-phenylethanol | colorless solid | 9.0% |

Synthetic Example[a] 205

N-[4-(7H-Pyrrolo[3,2-e][1,2,3]triazolo[1,5-c]pyrimidin-1-yl)cyclohexyl]-4-chloroaniline The reactions in Synthetic Example[a] 121 were carried out in substantially the same manners except that 4-chloroaniline was used instead of 4-aminobenzonitrile to give the title compound as a colorless solid (10.2 mg, yield 28%).

Synthetic Example[a] 206 trans-N-(4-Fluorophenyl)-4-(7H-pyrrolo[3,2-e][1,2,3]triazolo[,1,5-c]pyrimidin-1-yl)cyclohexanecarboxamide trans-4-(7H-Pyrrolo[3,2-e][1,2,3]triazolo[1,5-c]pyrimidin-1-yl)cyclohexanecarboxylic acid (19.5 mg, 0.0683 mmol) obtained in Synthetic Example[a] 80 in N,N-dimethylformamide (1.5 mL) was mixed with 4-fluoroaniline (0.0977 mL, 0.102 mmol) and O-(7-azabenzotriazol-1-yl)-N,N,N',N'-tetramethyluronium hexafluorophosphate (38.8 mg, 0.102 mmol) and then with N,N-diisopropylethylamine (0.0238 mL, 0.137 mmol) and stirred at room temperature for 3 hours. After addition of water, the reaction mixture was extracted with ethyl acetate, and the organic layer was washed with saturated aqueous sodium chloride, dried over anhydrous sodium sulfate and concentrated under reduced pressure. The residue was purified by silica gel thin layer chromatography (NH-PLC05 plate manufactured by Fuji Silysia Chemical Ltd.: ethyl acetate). The resulting solid was washed with methanol to give the title compound as a colorless solid (6.45 mg, yield 25%).

Synthetic Examples[a] 207 to 209

The reactions in Synthetic Example[a] 206 were carried out in substantially the same manners except that (4-fluorophenyl)methanamine, 2-(4-fluorophenyl)ethanamine or (S)-3-fluoropyrrolidine was used instead of 4-fluoroaniline to give the compounds of Synthetic Examples[a] 207 to 209. The names, morphologies and yields of the compounds synthesized are shown in Table[a] 22.

TABLE[a] 22

| Ex | Compound Name | Morphology | Yield |
|---|---|---|---|
| 207 | trans-N-(4-fluorobenzyl)-4-(7H-pyrrolo[3, 2-c][1,2,3]triazolo[1,5-c]pyrimidin-1-yl)cyclohexanecarboxamide | colorless solid | 56% |
| 208 | trans-N-(4-fluorophenethyl)-4-(7H-, pyrrolo[32-e][1,2,3]triazolo[1,5-c]pyrimidin-1-yl)cyclohexanecarboxamide | colorless solid | 48% |
| 209 | [trans-4-(7H-pyrrolo[3,2-e][1,2,3]triazolo[1,5-c]pyrimidin-1-yl)cyclohexyl][(S)-3-fluoropyrrolidin-1-yl]methanone | colorless solid | 31% |

Synthetic Example[a] 210

4-{[4-(7H-Imidazo[1,5-c]pyrrolo[3,2-e]pyrimidin-1-yl)piperidin-1-yl]methyl}benzonitrile The reactions in Synthetic Example[a] 3 were carried out in substantially the same manners except that 4-{[4-(7-{[2-(trimethylsilyl)ethoxy]methyl}-7H-imidazo[1,5-c]pyrrolo[3,2-e]pyrimidin-1-yl)piperidin-1-yl]methyl}benzonitrile obtained in Reference Synthetic Example[a] 97 was used instead of benzyl 3-(7-{[2-(trimethylsilyl)ethoxy]methyl}-

7H-imidazo[1,5-c]pyrrolo[3,2-e]pyrimidin-1-yl)piperidine-1-carboxylate to give the title compound as a brown solid (1.3 mg, yield 4%).

Synthetic Example[a] 211

Benzyl 3-(7H-pyrrolo[3,2-e][1,2,3]triazolo[1,5-c]pyrimidin-1-yl)pyrrolidine-1-carboxylate The reactions in Synthetic Example[a] 5 were carried out in substantially the same manners except that benzyl 3-(7H-pyrrolo[2,3-d]pyrimidine-4-carbonyl)pyrrolidine-1-carboxylate obtained in Reference Synthetic Example[a] 99 was used instead of (7H-pyrrolo[2,3-d]pyrimidin-4-yl)(o-tolyl)methanone to give the title compound as a colorless solid (27.4 mg, yield 2%).

Synthetic Example[a] 212

2-[4-(7H-Pyrrolo[3,2-e][1,2,3]triazolo[1,5-c]pyrimidin-1-yl)piperidin-1-yl]-1-[4-(trifluoromethyl)phenyl]ethanol 1-(Piperidin-4-yl)-7H-pyrrolo[3,2-e][1,2,3]triazolo[1,5-c]pyrimidine acetate (33.1 mg, 0.110 mmol) obtained in Reference Synthetic Example[a] 104 in ethanol (3 mL) was stirred with water (0.5 mL), triethylamine (0.1 mL), ytterbium (III) trifluoromethanesulfonate (12.7 mg, 0.0237 mmol) and 2-[4-(trifluoromethyl)phenyl]oxirane (47.0 mg, 0.250 mmol) obtained in Reference Synthetic Example[a] 103 at 80° C. for 3 hours. After addition of water, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (methanol/chloroform, =1/20 (v/v)). The resulting solid was washed with hexane/ethyl acetate to give the title compound as a red solid (19.7 mg, yield 42%).

Synthetic Examples[a] 213 to 226

The reactions in Synthetic Example[a] 44 were carried out in substantially the same manners except that 2-(4-formylphenoxy)acetonitrile (Reference Synthetic Example[a] 105), 6-chloronicotinaldehyde, (E)-3-(furan-2-yl)acrylaldehyde, 1-methyl-1H-pyrrole-2-carbaldehyde, 3-chloro-1H-indazole-5-carbaldehyde, quinoxaline-6-carbaldehyde, oxazole-4-carbaldehyde, 4-(difluoromethoxy)benzaldehyde, 4-(1H-imidazole-1-yl)benzaldehyde, 2-fluoro-4-formylbenzonitrile, 2-fluoro-5-formylbenzonitrile, 2,6-difluoro-4-(trifluoromethyl)benzaldehyde, 3-oxo-3,4-dihydro-2H-benzo[b][1,4]oxazine-6-carbaldehyde or 4-[(2-cyanoethyl)methylamino]benzaldehyde was used instead of thiazole-5-carbaldehyde to give the compounds of Synthetic Examples[a] 213 to 226. The names, morphologies and yields of the synthesized compounds are shown in Table[a] 23.

TABLE[a] 23

| Ex | Compound Name | Morphology | Yield |
|---|---|---|---|
| 213 | 2-(4-{[4-(7H-pyrrolo[3,2-e][1,2,3]triazolo[1,5-c]pyrimidin-1-yl)piperidin-1-yl]methyl}phenoxy)acetonitrile | colorless solid | 15% |
| 214 | 1-{1-[(6-chloropyridin-3-yl)methyl]piperidin-4-yl}-7H-pyrrolo[3,2-e][1,2,3]triazolo[1,5-c]pyrimidine | colorless solid | 8% |
| 215 | (E)-1-{1-[3-(furan-2-yl)allyl]piperidin-4-yl}-7H-pyrrolo[3,2-e][1,2,3]triazolo[1,5-c]pyrimidine | colorless solid | 33% |
| 216 | 1-(1-methylpiperidin-4-yl)-7H-pyrrolo[3,2-e][1,2,3]triazolo[1,5-c]pyrimidine | yellow solid | 27% |
| 217 | 1-{1-[(3-chloro-1H-indazol-5-yl)methyl]piperidin-4-yl}-7H-pyrrolo[3,2-e][1,2,3]triazolo[1,5-c]pyrimidine | colorless solid | 4.0% |
| 218 | 1-[1-(quinoxalin-6-ylmethyl)piperidin-4-yl]-7H-pyrrolo[3,2-e][1,2,3]triazolo[1,5-c]pyrimidine | colorless solid | 42% |
| 219 | 4-{[4-(7H-pyrrolo[3,2-e][1,2,3]triazolo[1,5-c]pyrimidin-1-yl)piperidin-1-yl]methyl}oxazole | colorless solid | 23% |
| 220 | 1-{1-[4-(difluoromethoxy)benzyl]piperidin-4-yl}-7H-pyrrolo[3,2-e][1,2,3]triazolo[1,5-c]pyrimidine | colorless solid | 21% |
| 221 | 1-{1-[4-(1H-imidazol-1-yl)benzyl]piperidin-4-yl}-7H-pyrrolo[3,2-e][1,2,3]triazolo[1,5-c]pyrimidine | yellow solid | 64% |
| 222 | 4-{[4-(7H-pyrrolo[3,2-e][1,2,3]triazolo[1,5-c]pyrimidin-1-yl)piperidin-1-yl]methyl}-2-fluorobenzonitrile | colorless solid | 44% |
| 223 | 5-{[4-(7H-pyrrolo[3,2-e][1,2,3]triazolo[1,5-c]pyrimidin-1-yl)piperidin-1-yl]methyl}-2-fluorobenzonitrile | colorless solid | 61% |
| 224 | 1-{1-[2,6-difluoro-4-(trifluoromethyl)benzyl]piperidin-4-yl}-7H-pyrrolo[3,2-e][1,2,3]triazolo[1,5-c]pyrimidine | colorless solid | 26% |
| 225 | 6-{[4-(7H-pyrrolo[3,2-c][1,2,3]triazolo[1,5-c]pyrimidin-1-yl)piperidin-1-yl]methyl}-2H-benzo[b][1,4]oxazin-3(4H)-one | colorless solid | 12% |

TABLE[a] 23-continued

| Ex | Compound Name | Morphology | Yield |
|---|---|---|---|
| 226 | 3-[(4-{[4-(7H-pyrrolo[3,2-e][1,2,3]triazolo[1,5-c]pyrimidin-1-yl)piperidin-1-yl]methyl}phenyl)(methyl)amino]propanenitrile | colorless solid | 5.0% |

Synthetic Example[a] 227

1-{1-[(2,2-Difluorobenzo[d][1,3]dioxol-5-yl)methyl]piperidin-4-yl}-7H-pyrrolo[3,2-e][1,2,3]triazolo[1,5-c]pyrimidine 1-(Piperidin-4-yl)-7H-pyrrolo[3,2-e][1,2,3]triazolo[1,5-c]pyrimidine acetate (20.0 mg, 0.0660 mmol) obtained in Reference Synthetic Example[a] 104 in methanol (1 mL) was mixed with 2,2-difluorobenzo[d][1,3]dioxole-5-carbaldehyde (20.0 μL, 0.0990 mmol), nicotinic acid (12.3 mg, 0.0990 mmol), and 2-picoline borane (10.7 mg, 0.0990 mmol) and stirred at room temperature for 1 day. After addition of 1M aqueous sodium hydroxide, the reaction mixture was extracted with chloroform. The organic layer was dried over anhydrous sodium sulfate and concentrated under reduced pressure. The residue was purified by silica gel thin layer chromatography (methanol/chloroform=1/10 (v/v)) to give the title compound as a colorless solid (13.1 mg, yield 48%).

Synthetic Examples[a] 228 to 239

The reactions in Synthetic Example[a] 227 were carried out in substantially the same manners except that 5-chlorofuran-2-carbaldehyde, 2,2-difluorobenzo[d][1,3]dioxol-4-carbaldehyde, 3-oxo-2-phenylpropanenitrile, 2,6-dichloronicotinaldehyde, benzo[d]thiazole-2-carbaldehyde, 4,5-dibromothiophene-2-carbaldehyde, 2-morpholinothiazole-5-carbaldehyde, 2-(4-chlorophenyl)-3-oxopropanenitrile, 5-methylthiophene-2-carbaldehyde, 4-bromothiophene-2-carbaldehyde, 5-bromothiophene-2-carbaldehyde or isonicotinaldehyde was used instead of 2,2-difluorobenzo[d][1,3]dioxole-5-carbaldehyde to give the compounds of Synthetic Examples[a] 228 to 239. The names, morphologies and yields of the synthesized compounds are shown in Table[a] 24.

TABLE[a] 24

| Ex | Compound Name | Morphology | Yield |
|---|---|---|---|
| 228 | 1-{1-[(5-chlorofuran-2-yl)methyl]piperidin-4-yl}-7H-pyrrolo[3,2-e][1,2,3]triazolo[1,5-c]pyrimidine | colorless solid | 41% |
| 229 | 1-{1-[(2,2-difluorobenzo[d][1,3]dioxol-4-yl)methyl]piperidin-4-yl}-7H-pyrrolo[3,2-e][1,2,3]triazolo[1,5-c]pyrimidine | colorless solid | 26% |
| 230 | (Z)-3-[4-(7H-pyrrolo[3,2-e][1,2,3]triazolo[1,5-c]pyrimidin-1-yl)piperidin-1-yl]-2-phenylacrylonitrile | colorless solid | 22% |
| 231 | 1-{1-[(2,6-dichloropyridin-3-yl)methyl]piperidin-4-yl}-7H-pyrrolo[3,2-e][1,2,3]triazolo[1,5-c]pyrimidine | colorless solid | 29% |
| 232 | 2-{[4-(7H-pyrrolo[3,2-e][1,2,3]triazolo[1,5-c]pyrimidin-1-yl)piperidin-1-yl]methyl}benzo[d]thiazole | colorless solid | 13% |
| 233 | 1-{1-[(4,5-dibromothiophen-2-yl)methyl]piperidin-4-yl}-7H-pyrrolo[3,2-e][1,2,3]triazolo[1,5-c]pyrimidine | colorless solid | 40% |
| 234 | 4-(5-{[4-(7H-pyrrolo[3,2-e][1,2,3]triazolo[1,5-c]pyrimidin-1-yl)piperidin-1-yl]methyl}thiazol-2-yl)morpholine | colorless solid | 13% |
| 235 | (Z)-3-[4-(7H-pyrrolo[3,2-e][1,2,3]triazolo[1,5-c]pyrimidin-1-yl)piperidin-1-yl]-2-(4-chlorophenyl)acrylonitrile | pale purple solid | 5.0% |
| 236 | 1-{1-[(5-methylthiophen-2-yl)methyl]piperidin-4-yl}-7H-pyrrolo[3,2-e][1,2,3]triazolo[1,5-c]pyrimidine | pale orange solid | 27% |
| 237 | 1-{1-[(4-bromothiophen-2-yl)methyl]piperidin-4-yl}-7H-pyrrolo[3,2-e][1,2,3]triazolo[1,5-c]pyrimidine | colorless solid | 8.0% |
| 238 | 1-{1-[(5-bromothiophen-2-yl)methyl]piperidin-4-yl}-7H-pyrrolo[3,2-e][1,2,3]triazolo[1,5-c]pyrimidine | colorless solid | 41% |
| 239 | 1-[1-(pyridin-4-ylmethyl)piperidin-4-yl]-7H-pyrrolo[3,2-e][1,2,3]triazolo[1,5-c]pyrimidine | colorless solid | 39% |

Synthetic Examples[a] 240 to 246

The reactions in Synthetic Example[a] 32 were carried out in substantially the same manners except that 4-(chloromethyl)thiazole hydrochloride, 4-(bromomethyl)benzamide (Reference Synthetic Example[a] 106), 4-(bromomethyl) phthalonitrile (Reference Synthetic Example[a] 108), 5-(bromomethyl)-2-(trifluoromethyl)benzonitrile (Reference Synthetic Example[a] 107), 4-(bromomethyl)-2-(trifluoromethyl) benzonitrile (Reference Synthetic Example[a] 109), (1-bromoethyl)benzene or 2-chloroacetonitrile was used instead of benzylbromide to give the compounds of Synthetic Examples[a] 240 to 246. The names, morphologies and yields of the synthesized compounds are shown in Table[a] 25.

TABLE[a] 25

| Ex | Compound Name | Morphology | Yield |
|---|---|---|---|
| 240 | 4-{[4-(7H-pyrrolo[3,2-e][1,2,3]triazolo[1,5-c]pyrimidin-1-yl)piperidin-1-yl]methyl}thiazole | colorless solid | 21% |
| 241 | 4-{[4-(7H-pyrrolo[3,2-e][1,2,3]triazolo[1,5-c]pyrimidin-1-yl)piperidin-1-yl]methyl}benzamide | colorless solid | 24% |
| 242 | 4-{[4-(7H-pyrrolo[3,2-e][1,2,3]triazolo[1,5-c]pyrimidin-1-yl)piperidin-1-yl]methyl}phthalonitrile | colorless solid | 71% |
| 243 | 5-{[4-(7H-pyrrolo[3,2-e][1,2,3]triazolo[1,5-c]pyrimidin-1-yl)piperidin-1-yl]methyl}-2-(trifluoromethyl)benzonitrile | colorless solid | 77% |
| 244 | 4-{[4-(7H-pyrrolo[3,2-e][1,2,3]triazolo[1,5-c]pyrimidin-1-yl)piperidin-1-yl]methyl}-2-(trifluoromethyl)benzonitrile | colorless solid | 68% |
| 245 | 1-[1-(1-phenylethyl)piperidin-4-yl]-7H-pyrrolo[3,2-e][1,2,3]triazolo[1,5-c]pyrimidine | pale purple solid | 6.0% |
| 246 | 2-[4-(7H-pyrrolo[3,2-e][1,2,3]triazolo[1,5-c]pyrimidin-1-yl)piperidin-1-yl]acetonitrile | pale purple solid | 35% |

Synthetic Examples[a] 247 to 345

The reactions in Synthetic Example[a] 88 were carried out in substantially the same manners except that 4-amino-2-chlorobenzonitrile, 4-amino-1-naphthonitrile, 3,4-difluoroaniline, 3,4,5-trifluoroaniline, 4-fluoro-3-(trifluoromethyl) aniline, 5-amino-2-fluorobenzonitrile, 3-aminodihydrothiophen-2(3H)-one hydrochloride, thiazolidine, 2,2-difluoroethaneamine, 3,3,3-trifluoropropane-1-amine, 3-hydroxyazetidine hydrochloride, 4-(trifluoromethyl)piperidine hydrochloride, 2-aminoacetonitrile hydrochloride, piperazin-2-one, piperidine-4-carboxamide, 4-aminophthalonitrile, 5-amino-2-chlorobenzonitrile, 2-(4-aminophenyl)acetonitrile, (R)-pyrrolidine-2-yl methanol, (S)-pyrrolidine-2-yl methanol, (R)-pyrrolidin-3-ol, 2-(benzylamino)ethanol, 2-bromo-2,2-difluoroethaneamine hydrochloride (Reference Synthetic Example[a] 131), (4-methoxyphenyl)methanamine, piperidin-4-ol, 2-aminoethanol, 7-amino-2H-benzo[b][1,4]oxazine-3(4H)-one, 6-amino-2H-benzo[b][1,4]oxazine-3(4H)-one, 2,2-difluorobenzo[d][1,3] dioxol-5-amine, (R)-2-amino-1-phenylethanol, (S)-2-amino-1-phenylethanol, azetidine-3-carboxylic acid, 3-aminodihydrofuran-2(3H)-one hydrobromide, cyclopropylamine, azetidine-3-carbonitrile hydrochloride, 4-(2-aminoethyl)benzonitrile (Reference Synthetic Example[a] 111), cyclobutanamine, cyclopentanamine, cyclopropylmethanamine, azetidine hydrochloride, pyrrolidine, (R)-4-aminoisoxazolidin-3-one, (R)-(tetrahydrofuran-2-yl)methanamine, 2,2-dimethylcyclopropanamine hydrochloride, 2-methylcyclopropanamine, 1-(trifluoromethyl)cyclopropanamine, 1-(methoxymethyl)cyclopropanamine hydrochloride, oxetan-3-amine, 1-methylcyclopropanamine hydrochloride, dimethylamine hydrochloride, 2-(methylamino)ethanol, 2,2'-azanediyl diethanol, (R)-tert-butyl pyrrolidin-3-ylcarbamate, 3-(phenylamino)propanenitrile, (R)-pyrrolidine-3-carbonitrile hydrochloride, 3-(methylamino) propanenitrile, (1s,3R,4r,5S,7s)-4-aminoadamantan-1-ol (Reference Synthetic Example[a] 129), (1s,3R,4s,5S,7s)-4-aminoadamantan-1-ol (Reference Synthetic Example[a] 130), trans-4-aminocyclohexanol, 2-(cyclohexylamino)ethanol, tert-butyl(S)-pyrrolidin-3-ylcarbamate, 3-(4-chlorophenyl) oxetan-3-amine hydrochloride, 4-[4-chloro-3-(trifluoromethyl)phenyl]piperidin-4-ol, 4-phenylpiperidine-4-carbonitrile hydrochloride, 2-(piperidin-4-yl)propan-2-ol, cis-2-(aminomethyl)cyclohexanol hydrochloride, 1-(aminomethyl)cyclohexanol hydrochloride, 3-(piperazin-1-yl)propanenitrile, 2-(piperazin-1-yl)ethanol, bicyclo [1.1.1]pentan-1-amine hydrochloride, 1,1,1,3,3,3-hexafluoropropan-2-amine, (R)—N-(pyrrolidin-3-yl)acetamide, (S)—N-(pyrrolidin-3-yl)acetamide, (R)-2,2,2-trifluoro-N-(pyrrolidin-3-yl)acetamide hydrochloride, (S)-2,2,2-trifluoro-N-(pyrrolidin-3-yl)acetamide hydrochloride, 3-(4-fluorophenyl)oxetan-3-amine hydrochloride, 1-(4-fluorophenyl)cyclopropanamine hydrochloride, 1-(4-fluorophenyl)cyclobutanamine hydrochloride, 2-methoxy-N-methylethanamine, bis(2-methoxyethyl)amine, (1-aminocyclopropyl)methanol hydrochloride, 3,3-difluoropyrrolidine hydrochloride, methanamine hydrochloride, ethanamine hydrochloride, propan-2-amine, 2-methylpropan-2-amine, prop-2-yn-1-amine, 4-(piperidin-4-yl)morpholine, tert-butyl 4-(aminomethyl)piperidine-1-carboxylate, tert-butyl(piperidin-4-ylmethyl)carbamate, tert-butyl (S)-3-aminopyrrolidine-1-carboxylate, 3-fluoroazetidine hydrochloride, 3,3-difluoroazetidine hydrochloride, (R)—N,N-dimethylpyrrolidin-3-amine, 2-amino-N-(2,2,2-trifluoroethyl)acetamide hydrochloride, 2,2,3,3,3-pentafluoropropan-1-amine, 3-amino-1,1,1-trifluoropropan-2-ol, thietan-3-amine hydrobromide or 1-(ethylsulfonyl)piperazine was used instead of thiomorpholine 1,1-dioxide to give the compounds of Synthetic Examples[a] 247 to 345. The names, morphologies and yields of the synthesized compounds are shown in Tables[a] 26 to 33.

TABLE[a] 26

| Ex | Compound Name | Morphology | Yield |
|---|---|---|---|
| 247 | 4-({[trans-4-(7H-pyrrolo[3,2-e][1,2,3]triazolo[1,5-c]pyrimidin-1-yl)cyclohexyl]methyl}amino)-2-chlorobenzonitrile | colorless solid | 79% |
| 248 | 4-({[trans-4-(7H-pyrrolo[3,2-e][1,2,3]triazolo[1,5-c]pyrimidin-1-yl)cyclohexyl]methyl}amino)-1-naphthonitrile | pale pink solid | 56% |
| 249 | N-{[trans-4-(7H-pyrrolo[3,2-e][1,2,3]triazolo[1,5-c]pyrimidin-1-yl)cyclohexyl]methyl}-3,4-difluoroaniline | colorless solid | 47% |
| 250 | N-{[trans-4-(7H-pyrrolo[3,2-e][1,2,3]triazolo[1,5-c]pyrimidin-1-yl)cyclohexyl]methyl}-3,4,5-trifluoroaniline | colorless solid | 65% |
| 251 | N-{[trans-4-(7H-pyrrolo[3,2-e][1,2,3]triazolo[1,5-c]pyrimidin-1-yl)cyclohexyl]methyl}-4-fluoro-3-(trifluoromethyl)aniline | colorless solid | 47% |
| 252 | 5-({[trans-4-(7H-pyrrolo[3,2-e][1,2,3]triazolo[1,5-c]pyrimidin-1-yl)cyclohexyl]methyl}amino)-2-fluorobenzonitrile | colorless solid | 69% |
| 253 | 3-({[trans-4-(7H-pyrrolo[3,2-e][1,2,3]triazolo[1,5-c]pyrimidin-1-yl)cyclohexyl]methyl}amino)dihydrothiophen-2(3H)-one | colorless solid | 73% |
| 254 | 3-{[trans-4-(7H-pyrrolo[3,2-e][1,2,3]triazolo[1,5-c]pyrimidin-1-yl)cyclohexyl]methyl}thiazolidine | pale pink solid | 21% |
| 255 | N-{[trans-4-(7H-pyrrolo[3,2-e][1,2,3]triazolo[1,5-c]pyrimidin-1-yl)cyclohexyl]methyl}-2,2-difluoroethanamine | pale purple solid | 62% |
| 256 | N-{[trans-4-(7H-pyrrolo[3,2-e][1,2,3]triazolo[1,5-c]pyrimidin-1-yl)cyclohexyl]methyl}-3,3,3-trifluoropropan-1-amine | colorless solid | 66% |
| 257 | 1-{[trans-4-(7H-pyrrolo[3,2-e][1,2,3]triazolo[1,5-c]pyrimidin-1-yl)cyclohexyl]methyl}azetidin-3-ol | colorless solid | 37% |
| 258 | 1-(trans-4-{[4-(trifluoromethyl)piperidin-1-yl]methyl}cyclohexyl)-7H-pyrrolo[3,2-e][1,2,3]triazolo[1,5-c]pyrimidine | colorless solid | 94% |
| 259 | 2-({[trans-4-(7H-pyrrolo[3,2-e][1,2,3]triazolo[1,5-c]pyrimidin-1-yl)cyclohexyl]methyl}amino)acetonitrile | colorless solid | 27% |
| 260 | 4-{[trans-4-(7H-pyrrolo[3,2-e][1,2,3]triazolo[1,5-c]pyrimidin-1-yl)cyclohexyl]methyl}piperazin-2-one | colorless solid | 52% |

TABLE[a] 27

| Ex | Compound Name | Morphology | Yield |
|---|---|---|---|
| 261 | 1-{[trans-4-(7H-pyrrolo[3,2-e][1,2,3]triazolo[1,5-c]pyrimidin-1-yl)cyclohexyl]methyl}piperidine-4-carboxamide | colorless solid | 8.0% |
| 262 | 4-({[trans-4-(7H-pyrrolo[3,2-e][1,2,3]triazolo[1,5-c]pyrimidin-1-yl)cyclohexyl]methyl}amino)phthalonitrile | colorless solid | 54% |
| 263 | 5-({[trans-4-(7H-pyrrolo[3,2-e][1,2,3]triazolo[1,5-c]pyrimidin-1-yl)cyclohexyl]methyl}amino)-2-chlorobenzonitrile | colorless solid | 75% |
| 264 | 2-[4-({[trans-4-(7H-pyrrolo[3,2-c][1,2,3]triazolo[1,5-c]pyrimidin-1-yl)cyclohexyl]methyl}amino)phenyl]acetonitrile | colorless solid | 54% |
| 265 | ((R)-1-{[trans-4-(7H-pyrrolo[3,2-e][1,2,3]triazolo[1,5-c]pyrimidin-1-yl)cyclohexyl]methyl}pyrrolidin-2-yl)methanol | colorless solid | 71% |
| 266 | ((S)-1-{[trans-4-(7H-pyrrolo[3,2-e][1,2,3]triazolo[1,5-c]pyrimidin-1-yl)cyclohexyl]methyl}pyrrolidin-2-yl)methanol | colorless solid | 87% |
| 267 | (R)-1-{[trans-4-(7H-pyrrolo[3,2-c][1,2,3]triazolo[1,5-c]pyrimidin-1-yl)cyclohexyl]methyl}pyrrolidin-3-ol | colorless solid | 68% |
| 268 | 2-({[trans-4-(7H-pyrrolo[3,2-e][1,2,3]triazolo[1,5-c]pyrimidin-1-yl)cyclohexyl]methyl}(benzyl)amino)ethanol | colorless solid | 62% |
| 269 | N-{[trans-4-(7H-pyrrolo[3,2-e][1,2,3]triazolo[1,5-c]pyrimidin-1-yl)cyclohexyl]methyl}-2-bromo-2,2-difluoroethanamine | colorless solid | 42% |
| 270 | 1-[trans-4-(7H-pyrrolo[3,2-e][1,2,3]triazolo[1,5-c]pyrimidin-1-yl)cyclohexyl]-N-(4-methoxybenzyl)methanamine | colorless solid | 30% |

TABLE[a] 27-continued

| Ex | Compound Name | Morphology | Yield |
|---|---|---|---|
| 271 | 1-{[trans-4-(7H-pyrrolo[3,2-e][1,2,3]triazolo[1, 5-c]pyrimidin-1-yl)cyclohexyl]methyl}piperidin-4-ol | colorless solid | 54% |
| 272 | 2-({[trans-4-(7H-pyrrolo[3,2-e][1,2,3]triazolo[1, 5-c]pyrimidin-1-yl)cyclohexyl]methyl}amino)ethanol | colorless solid | 34% |
| 273 | 7-({[trans-4-(7H-pyrrolo[3,2-e][1,2,3]triazolo[1, 5-c]pyrimidin-1-yl)cyclohexyl]methyl}amino)-2H-benzo[b][1,4]oxazin-3(4H)-one | colorless solid | 80% |

TABLE[a] 28

| Ex | Compound Name | Morphology | Yield |
|---|---|---|---|
| 274 | 6-({[trans-4-(7H-pyrrolo[3,2-e][1,2,3]triazolo[1, 5-c]pyrimidin-1-yl)cyclohexyl]methyl}amino)-2H-benzo[b][1,4]oxazin-3(4H)-one | pale pink solid | 98% |
| 275 | N-{[trans-4-(7H-pyrrolo[3,2-e][1,2,3]triazolo[1, 5-c]pyrimidin-1-yl)cyclohexyl]methyl}-2,2-difluorobenzo[d][1,3]dioxol-5-amine | colorless solid | 63% |
| 276 | (R)-2-({[trans-4-(7H-pyrrolo[3,2-e][1, 2,3]triazolo[1,5-c]pyrimidin-1-yl)cyclohexyl]methyl}amino)-1-phenylethanol | colorless solid | 50% |
| 277 | (S)-2-({[trans-4-(7H-pyrrolo[3,2-e][1, 2,3]triazolo[1,5-c]pyrimidin-1-yl)cyclohexyl]methyl}amino)-1-phenylethanol | colorless solid | 73% |
| 278 | 1-{[trans-4-(7H-pyrrolo[3,2-e][1,2,3]triazolo[1, 5-c]pyrimidin-1-yl)cyclohexyl]methyl}azetidine-3-carboxylic acid | colorless solid | 90% |
| 279 | 3-({[trans-4-(7H-pyrrolo[3,2-e][1,2,3]triazolo[1, 5-c]pyrimidin-1-yl)cyclohexyl]methyl}amino)dihydrofuran-2(3H)-one | colorless solid | quant. |
| 280 | N-{[trans-4-(7H-pyrrolo[3,2-c][1,2,3]triazolo[1, 5-c]pyrimidin-1-yl)cyclohexyl]methyl}cyclopropanamine | colorless solid | 34% |
| 281 | 1-{[trans-4-(7H-pyrrolo[3,2-e][1,2,3]triazolo[1, 5-c]pyrimidin-1-yl)cyclohexyl]methyl}azetidine-3-carbonitrile | colorless solid | 46% |
| 282 | 4-[2-({[trans-4-(7H-pyrrolo[3,2-e][1, 2,3]triazolo[1,5-c]pyrimidin-1-yl)cyclohexyl]methyl}amino)ethyl]benzonitrile | colorless solid | 54% |
| 283 | N-{[trans-4-(7H-pyrrolo[3,2-e][1,2,3]triazolo[1, 5-c]pyrimidin-1-yl)cyclohexyl]methyl}cyclobutanamine | colorless solid | 70% |
| 284 | N-{[trans-4-(7H-pyrrolo[3,2-e][1,2,3]triazolo[1, 5-c]pyrimidin-1-yl)cyclohexyl]methyl}cyclopentanamine | colorless solid | 63% |
| 285 | 1-[trans-4-(7H-pyrrolo[3,2-e][1,2,3]triazolo[1, 5-c]pyrimidin-1-yl)cyclohexyl]-N-(cyclopropylmethyl)methanamine | colorless solid | 53% |
| 286 | 1-[trans-4-(azetidin-1-ylmethyl)cyclohexyl]-7H-pyrrolo[3,2-e][1,2,3]triazolo[1, 5-c]pyrimidine | colorless solid | 60% |

TABLE[a] 29

| Ex | Compound Name | Morphology | Yield |
|---|---|---|---|
| 287 | 1-[trans-4-(pyrrolidin-1-ylmethyl)cyclohexyl]-7H-pyrrolo[3,2-e][1,2,3]triazolo[1, 5-c]pyrimidine | colorless solid | 64% |
| 288 | (R)-4-({[trans-4-(7H-pyrrolo[3,2-e][1, 2,3]triazolo[1,5-c]pyrimidin-1-yl)cyclohexyl]methyl}amino)isoxazolidin-3-one | colorless solid | 78% |
| 289 | 1-[trans-4-(7H-pyrrolo[3,2-e][1,2,3]triazolo[1, 5-c]pyrimidin-1-yl)cyclohexyl]-N-{[(R)-tetrahydrofuran-2-yl]methyl}methanamine | colorless solid | 46% |
| 290 | N-{[trans-4-(7H-pyrrolo[3,2-e][1,2,3]triazolo[1, 5-c]pyrimidin-1-yl)cyclohexyl]methy}-2,2-dimethylcyclopropanamine | colorless solid | 44% |
| 291 | N-{[trans-4-(7H-pyrrolo[3,2-e][1,2,3]triazolo[1, 5-c]pyrimidin-1-yl)cyclohexyl]methyl}-2-methylcyclopropanamine | colorless solid | 53% |

TABLE[a] 29-continued

| Ex | Compound Name | Morphology | Yield |
|---|---|---|---|
| 292 | N-{[trans-4-(7H-pyrrolo[3,2-e][1,2,3]triazolo[1,5-c]pyrimidin-1-yl)cyclohexyl]methyl}-1-(trifluoromethyl)cyclopropanamine | colorless solid | 60% |
| 293 | N-{[trans-4-(7H-pyrrolo[3,2-e][1,2,3]triazolo[1,5-c]pyrimidin-1-yl)cyclohexyl]methyl}-1-(methoxymethyl)cyclopropanamine | colorless solid | 52% |
| 294 | N-{[trans-4-(7H-pyrrolo[3,2-e][1,2,3]triazolo[1,5-c]pyrimidin-1-yl)cyclohexyl]methyl}oxetan-3-amine | colorless solid | 40% |
| 295 | N-{[trans-4-(7H-pyrrolo[3,2-e][1,2,3]triazolo[1,5-c]pyrimidin-1-yl)cyclohexyl]methyl}-1-methylcyclopropanamine | colorless solid | 25% |
| 296 | 1-[trans-4-(7H-pyrrolo[3,2-e][1,2,3]triazolo[1,5-c]pyrimidin-1-yl)cyclohexyl]-N,N-dimethylmethanamine | colorless solid | 43% |
| 297 | 2-({[trans-4-(7H-pyrrolo[3,2-e][1,2,3]triazolo[1,5-c]pyrimidin-1-yl)cyclohexyl]methyl}(methyl)amino)ethanol | colorless solid | 57% |
| 298 | 2,2'-({[trans-4-(7H-pyrrolo[3,2-e][1,2,3]triazolo[1,5-c]pyrimidin-1-yl)cyclohexyl]methyl}azanediyl)diethanol | colorless solid | 43% |
| 299 | tert-butyl ((R)-1-{[trans-4-(7H-pyrrolo[3,2-e][1,2,3]triazolo[1,5-c]pyrimidin-1-yl)cyclohexyl]methyl}pyrrolidin-3-yl)carbamate | colorless solid | 64% |

TABLE[a] 30

| Ex | Compound Name | Morphology | Yield |
|---|---|---|---|
| 300 | 3-({[trans-4-(7H-pyrrolo[3,2-e][1,2,3]triazolo[1,5-c]pyrimidin-1-yl)cyclohexyl]methyl}(phenyl)amino)propanenitrile | colorless solid | 72% |
| 301 | (R)-1-{[trans-4-(7H-pyrrolo[3,2-e][1,2,3]triazolo[1,5-c]pyrimidin-1-yl)cyclohexyl]methyl}pyrrolidine-3-carbonitrile | colorless solid | 58% |
| 302 | 3-({[trans-4-(7H-pyrrolo[3,2-e][1,2,3]triazolo[1,5-c]pyrimidin-1-yl)cyclohexyl]methyl}(methyl)amino)propanenitrile | colorless solid | 42% |
| 303 | (1S,3R,4r,5S,7S)-4-({[trans-4-(7H-pyrrolo[3,2-e][1,2,3]triazolo[1,5-c]pyrimidin-1-yl)cyclohexyl]methyl}amino)adamantan-1-ol | colorless solid | 61% |
| 304 | (1S,3R,4s,5S,7S)-4-({[trans-4-(7H-pyrrolo[3,2-e][1,2,3]triazolo[1,5-c]pyrimidin-1-yl)cyclohexyl]methyl}amino)adamantan-1-ol | colorless solid | 53% |
| 305 | trans-4-({[trans-4-(7H-pyrrolo[3,2-e][1,2,3]triazolo[1,5-c]pyrimidin-1-yl)cyclohexyl]methyl}amino)cyclohexanol | colorless solid | 35% |
| 306 | 2-({[trans-4-(7H-pyrrolo[3,2-e][1,2,3]triazolo[1,5-c]pyrimidin-1-yl)cyclohexyl]methyl}(cyclohexyl)amino)ethanol | colorless solid | 40% |
| 307 | tert-butyl ((S)-1-{[trans-4-(7H-pyrrolo[3,2-e][1,2,3]triazolo[1,5-c]pyrimidin-1-yl)cyclohexyl]methyl}pyrrolidin-3-yl)carbamate | colorless solid | 69% |
| 308 | N-{[trans-4-(7H-pyrrolo[3,2-e][1,2,3]triazolo[1,5-c]pyrimidin-1-yl)cyclohexyl]methyl}-3-(4-chlorophenyl)oxetan-3-amine | colorless solid | 72% |
| 309 | 1-{[trans-4-(7H-pyrrolo[3,2-e][1,2,3]triazolo[1,5-c]pyrimidin-1-yl)cyclohexyl]methyl}-4-[4-chloro-3-(trifluoromethyl)phenyl]piperidin-4-ol | colorless solid | 54% |
| 310 | 1-{[trans-4-(7H-pyrrolo[3,2-e][1,2,3]triazolo[1,5-c]pyrimidin-1-yl)cyclohexyl]methyl}-4-phenylpiperidine-4-carbonitrile | colorless solid | 56% |
| 311 | 2-(1-{[trans-4-(7H-pyrrolo[3,2-e][1,2,3]triazolo[1,5-c]pyrimidin-1-yl)cyclohexyl]methyl}piperidin-4-yl)propan-2-ol | colorless solid | 59% |

TABLE[a] 31

| Ex | Compound Name | Morphology | Yield |
|---|---|---|---|
| 312 | cis-2-[({[trans-4-(7H-pyrrolo[3,2-e][1,2,3]triazolo[1,5-c]pyrimidin-1-yl)cyclohexyl]methyl}amino)methyl]cyclohexanol | colorless solid | 14% |
| 313 | 1-[({[trans-4-(7H-pyrrolo[3,2-e][1,2,3]triazolo[1,5-c]pyrimidin-1-yl)cyclohexyl]methyl}amino)methyl]cyclohexanol | colorless solid | 47% |

TABLE[a] 31-continued

| Ex | Compound Name | Morphology | Yield |
|---|---|---|---|
| 314 | 3-(4-{[trans-4-(7H-pyrrolo[3,2-e][1,2,3]triazolo[1,5-c]pyrimidin-1-yl)cyclohexyl]methyl}piperazin-1-yl)propanenitrile | colorless solid | 35% |
| 315 | 2-(4-{[trans-4-(7H-pyrrolo[3,2-e][1,2,3]triazolo[1,5-c]pyrimidin-1-yl)cyclohexyl]methyl}piperazin-1-yl)ethanol | colorless solid | 35% |
| 316 | N-{[trans-4-(7H-pyrrolo[3,2-e][1,2,3]triazolo[1,5-c]pyrimidin-1-yl)cyclohexyl]methyl}bicyclo[1.1.1]pentan-1-amine | colorless solid | 44% |
| 317 | N-{[trans-4-(7H-pyrrolo[3,2-e][1,2,3]triazolo[1,5-c]pyrimidin-1-yl)cyclohexyl]methyl}-1,1,1,3,3,3-hexafluoropropan-2-amine | colorless solid | 77% |
| 318 | N-((R)-1-{[trans-4-(7H-pyrrolo[3,2-e][1,2,3]triazolo[1,5-c]pyrimidin-1-yl)cyclohexyl]methyl}pyrrolidin-3-yl)acetamide | colorless solid | 48% |
| 319 | N-((S)-1-{[trans-4-(7H-pyrrolo[3,2-e][1,2,3]triazolo[1,5-c]pyrimidin-1-yl)cyclohexyl]methyl}pyrrolidin-3-yl)acetamide | colorless solid | 29% |
| 320 | N-((R)-1-{[trans-4-(7H-pyrrolo[3,2-e][1,2,3]triazolo[1,5-c]pyrimidin-1-yl)cyclohexyl]methyl}pyrrolidin-3-yl)-2,2,2-trifluoroacetamide | colorless solid | 49% |
| 321 | N-((S)-1-{[trans-4-(7H-pyrrolo[3,2-e][1,2,3]triazolo[1,5-c]pyrimidin-1-yl)cyclohexyl]methyl}pyrrolidin-3-yl)-2,2,2-trifluoroacetamide | colorless solid | 48% |
| 322 | N-{[trans-4-(7H-pyrrolo[3,2-e][1,2,3]triazolo[1,5-c]pyrimidin-1-yl)cyclohexyl]methyl}-3-(4-fluorophenyl)oxetan-3-amine | colorless solid | 52% |
| 323 | N-{[trans-4-(7H-pyrrolo[3,2-e][1,2,3]triazolo[1,5-c]pyrimidin-1-yl)cyclohexyl]methyl}-1-(4-fluorophenyl)cyclopropanamine | colorless solid | 39% |

TABLE[a] 32

| Ex | Compound Name | Morphology | Yield |
|---|---|---|---|
| 324 | N-{[trans-4-(7H-pyrrolo[3,2-e][1,2,3]triazolo[1,5-c]pyrimidin-1-yl)cyclohexyl]methyl}-1-(4-fluorophenyl)cyclobutanamine | colorless solid | 39% |
| 325 | N-{[trans-4-(7H-pyrrolo[3,2-e][1,2,3]triazolo[1,5-c]pyrimidin-1-yl)cyclohexyl]methyl}-2-methoxy-N-methylethanamine | colorless solid | 71% |
| 326 | N-{[trans-4-(7H-pyrrolo[3,2-e][1,2,3]triazolo[1,5-c]pyrimidin-1-yl)cyclohexyl]methyl}-2-methoxy-N-(2-methoxyethyl)ethanamine | colorless solid | 76% |
| 327 | [1-({[trans-4-(7H-pyrrolo[3,2-e][1,2,3]triazolo[1,5-c]pyrimidin-1-yl)cyclohexyl]methyl}amino)cyclopropyl]methanol | colorless solid | 58% |
| 328 | 1-{trans-4-[(3,3-difluoropyrrolidin-1-yl)methyl]cyclohexyl}-7H-pyrrolo[3,2-e][1,2,3]triazolo[1,5-c]pyrimidine | colorless solid | 26% |
| 329 | 1-[trans-4-(7H-pyrrolo[3,2-e][1,2,3]triazolo[1,5-c]pyrimidin-1-yl)cyclohexyl]-N-methylmethanamine | colorless solid | 26% |
| 330 | N-{[trans-4-(7H-pyrrolo[3,2-e][1,2,3]triazolo[1,5-c]pyrimidin-1-yl)cyclohexyl]methyl}ethanamine | colorless solid | 58% |
| 331 | N-{[trans-4-(7H-pyrrolo[3,2-e][1,2,3]triazolo[1,5-c]pyrimidin-1-yl)cyclohexyl]methyl}propan-2-amine | colorless solid | 55% |
| 332 | N-{[trans-4-(7H-pyrrolo[3,2-e][1,2,3]triazolo[1,5-c]pyrimidin-1-yl)cyclohexyl]methyl}-2-methylpropan-2-amine | colorless solid | 34% |
| 333 | N-{[trans-4-(7H-pyrrolo[3,2-e][1,2,3]triazolo[1,5-c]pyrimidin-1-yl)cyclohexyl]methyl}prop-2-yn-1-amine | colorless solid | 62% |
| 334 | 4-(1-{[trans-4-(7H-pyrrolo[3,2-e][1,2,3]triazolo[1,5-c]pyrimidin-1-yl)cyclohexyl]methyl}piperidin-4-yl)morpholine | colorless solid | 44% |
| 335 | tert-butyl 4-[({[trans-4-(7H-pyrrolo[3,2-e][1,2,3]triazolo[1,5-c]pyrimidin-1-yl)cyclohexyl]methyl}amino)methyl]piperidine-1-carboxylate | colorless solid | 17% |

TABLE[a] 32-continued

| Ex | Compound Name | Morphology | Yield |
|---|---|---|---|
| 336 | tert-butyl [(1-{[trans-4-(7H-pyrrolo[3,2-e][1,2,3]triazolo[1,5-c]pyrimidin-1-yl)cyclohexyl]methyl}piperidin-4-yl)methyl]carbamate | colorless solid | 3.0% |

TABLE[a] 33

| Ex | Compound Name | Morphology | Yield |
|---|---|---|---|
| 337 | (S)-tert-butyl 3-({[trans-4-(7H-pyrrolo[3,2-e][1,2,3]triazolo[1,5-c]pyrimidin-1-yl)cyclohexyl]methyl}amino)pyrrolidine-1-carboxylate | colorless solid | 10% |
| 338 | 1-{trans-4-[(3-fluoroazetidin-1-yl)methyl]cyclohexyl}-7H-pyrrolo[3,2-e][1,2,3]triazolo[1,5-c]pyrimidine | colorless solid | 33% |
| 339 | 1-{trans-4-[(3,3-difluoroazetidin-1-yl)methyl]cyclohexyl}-7H-pyrrolo[3,2-e][1,2,3]triazolo[1,5-c]pyrimidine | colorless solid | 35% |
| 340 | (R)-1-{[trans-4-(7H-pyrrolo[3,2-e][1,2,3]triazolo[1,5-c]pyrimidin-1-yl)cyclohexyl]methyl}-N,N-dimethylpyrrolidin-3-amine | colorless solid | 87% |
| 341 | 2-({[trans-4-(7H-pyrrolo[3,2-e][1,2,3]triazolo[1,5-c]pyrimidin-1-yl)cyclohexyl]methyl}amino)-N-(2,2,2-trifluoroethyl)acetamide | colorless solid | 63% |
| 342 | N-{[trans-4-(7H-pyrrolo[3,2-e][1,2,3]triazolo[1,5-c]pyrimidin-1-yl)cyclohexyl]methyl}-2,2,3,3,3-pentafluoropropan-1-amine | colorless solid | 74% |
| 343 | 3-({[trans-4-(7H-pyrrolo[3,2-e][1,2,3]triazolo[1,5-c]pyrimidin-1-yl)cyclohexyl]methyl}amino)-1,1,1-trifluoropropan-2-ol | colorless solid | 66% |
| 344 | N-{[trans-4-(7H-pyrrolo[3,2-e][1,2,3]triazolo[1,5-c]pyrimidin-1-yl)cyclohexyl]methyl}thietan-3-amine | colorless solid | 58% |
| 345 | 1-(trans-4-{[4-(ethylsulfonyl)piperazin-1-yl]methyl}cyclohexyl)-7H-pyrrolo[3,2-e][1,2,3]triazolo[1,5-c]pyrimidine | colorless solid | 71% |

Synthetic Example[a] 346 trans-4-(7H-Pyrrolo[3,2-e][1,2,3]triazolo[1,5-c]pyrimidin-1-yl)-N-(3,3,3-trifluoro-2-hydroxy-2-phenylpropyl)cyclohexanecarboxamide trans-4-(7H-Pyrrolo[3,2-e][1,2,3]triazolo[1,5-c]pyrimidin-1-yl)cyclohexanecarboxylic acid (10.0 mg, 0.0350 mmol) obtained in Synthetic Example[a] 80 in N,N-dimethylformamide (1 mL) was mixed with 1-(3-dimethylaminopropyl)-3-ethylcarbodiimide hydrochloride (8.10 mg, 0.0420 mmol), 1-hydroxybenzotriazole (4.70 mg, 0.0350 mmol) and 3-amino-1,1,1-trifluoro-2-phenylpropan-2-ol (7.20 mg, 0.0350 mmol) obtained in Reference Synthetic Example[a] 101 and stirred at room temperature for one day. After addition of saturated aqueous ammonium chloride, the reaction mixture was extracted with ethyl acetate, The organic layer was dried over anhydrous sodium sulfate and concentrated under reduced pressure. The residue was purified by silica gel thin layer chromatography (ethyl acetate/hexane=1/1(v/v)) to give the title compound as a colorless solid (5.80 mg, yield 35%).

Synthetic Example[a] 347 trans-4-(7H-Pyrrolo[3,2-e][1,2,3]triazolo[1,5-c]pyrimidin-1-yl)-N-[3,3,3-trifluoro-2-(4-fluorophenyl)-2-hydroxypropyl]cyclohexanecarboxamide The reactions in Synthetic Example[a] 346 were carried out in substantially the same manners except that 3-amino-1,1,1-trifluoro-2-(4-fluorophenyl)propan-2-ol obtained in Reference Synthetic Example[a] 102 was used instead of 3-amino-1,1,1-trifluoro-2-phenylpropan-2-ol to give the title compound as a colorless solid (7.37 mg, yield 43%).

Synthetic Example[a] 348 to 363

The reactions in Synthetic Example[a] 206 were carried out in substantially the same manners except that ammonium chloride, 5-methylfurfurylamine, 4-(aminomethyl)benzonitrile hydrochloride, 2-phenylglycinonitrile hydrochloride, 2-(4-chlorophenyl)ethylamine, (S)-2-amino-1-phenylethanol, 2,2,2-trifluoroethylamine hydrochloride, 2-aminoacetonitrile hydrochloride, 3-aminopropionitrile, (S)-pyrrolidine-3-carbonitrile, (S)-pyrrolidine-3-ol, cyclopropylamine, 2-aminoethanol, 3-hydroxyazetidine hydrochloride, 4-(2-aminoethyl)benzonitrile or azetidine-3-carbonitrile hydrochloride was used instead of 4-fluoroaniline to give the compounds of Synthetic Examples[a] 348 to 363. The names, morphologies and yields of the synthesized compounds are shown in Tables[a] 34 to 35.

TABLE[a] 34

| Ex | Compound Name | Morphology | Yield |
|---|---|---|---|
| 348 | trans-4-(7H-pyrrolo[3,2-e][1,2,3]triazolo[1,5-c]pyrimidin-1-yl)cyclohexanecarboxamide | colorless solid | 87% |
| 349 | trans-N-[(5-methylfuran-2-yl)methyl]-4-(7H-pyrrolo[3,2-e][1,2,3]triazolo[1,5-c]pyrimidin-1-yl)cyclohexanecarboxamide | colorless solid | 69% |
| 350 | trans-N-(4-cyanobenzyl)-4-(7H-pyrrolo[3,2-e][1,2,3]triazolo[1,5-c]pyrimidin-1-yl)cyclohexanecarboxamide | colorless solid | 57% |
| 351 | trans-N-[cyano(phenyl)methyl]-4-(7H-pyrrolo[3,2-e][1,2,3]triazolo[1,5-c]-pyrimidin-1-yl)cyclohexanecarboxamide | colorless solid | 58% |
| 352 | trans-N-(4-chlorophenethyl)-4-(7H-pyrrolo[3,2-e][1,2,3]triazolo[1,5-c]-pyrimidin-1-yl)cyclohexanecarboxamide | pale yellow solid | 68% |
| 353 | trans-N-[(S)-2-hydroxy-2-phenylethyl]-4-(7H-pyrrolo[3,2-e][1,2,3]triazolo[1,5-c]pyrimidin-1-yl)cyclohexanecarboamide | colorless solid | 40% |

TABLE[a] 35

| Ex | Compound Name | Morphology | Yield |
|---|---|---|---|
| 354 | trans-4-(7H-pyrrolo[3,2-e][1,2,3]triazolo[1,5-c]pyrimidin-1-yl)-N-(2,2,2-trifluoroethyl)-cyclohexanecarboxamide | colorless solid | 54% |
| 355 | trans-N-(cyanomethyl)-4-(7H-pyrrolo[3,2-e][1,2,3]triazolo[1,5-c]pyrimidin-1-yl)cyclohexanecarboxamide | pale brown solid | 27% |
| 356 | trans-N-(2-cyanoethyl)-4-(7H-pyrrolo[3,2-e][1,2,3]triazolo[1,5-c]pyrimidin-1-yl)cyclohexanecarboxamide | colorless solid | 29% |
| 357 | (S)-1-[trans-4-(7H-pyrrolo[3,2-e][1,2,3]triazolo[1,5-c]pyrimidin-1-yl)-cyclohexanecarbonyl]-pyrrolidine-3-carbonitrile | colorless solid | 17% |
| 358 | [trans-4-(7H-pyrrolo[3,2-e][1,2,3]triazolo[1,5-c]pyrimidin-1-yl)cyclohexyl][(S)-3-hydroxypyrrolidin-1-yl]methanone | colorless solid | 18% |
| 359 | trans-N-cyclopropyl-4-(7H-pyrrolo[3,2-c][1,2,3]triazolo[1,5-c]pyrimidin-1-yl)cyclohexanecarboxamide | pale yellow solid | 33% |
| 360 | trans-N-(2-hydroxyethyl)-4-(7H-pyrrolo[3,2-e][1,2,3]triazolo[1,5-c]pyrimidin-1-yl)cyclohexanecarboxamide | pale brown solid | 15% |
| 361 | [trans-4-(7H-pyrrolo[3,2-e][1,2,3]triazolo[1,5-c]pyrimidin-1-yl)cyclohexyl](3-hydroxyazetidin-1-yl)methanone | colorless solid | 87% |
| 362 | trans-N-(4-cyanophenethyl)-4-(7H-pyrrolo[3,2-e][1,2,3]triazolo[1,5-c]pyrimidin-1-yl)cyclohexanecarboxamide | colorless solid | 12% |
| 363 | 1-[trans-4-(7H-pyrrolo[3,2-e][1,2,3]triazolo-[1,5-c]pyrimidin-1-yl)cyclohexanecarbonyl]-azetidine-3-carbonitrile | colorless solid | 20% |

Synthetic Examples[a] 364 to 366

The reactions in Synthetic Example[a] 77 were carried out in substantially the same manners except that sodium benzene sulfinate, sodium 4-fluorobenzenesulfinate or sodium cyclopropanesulfinate was used instead of sodium methanesulfinate to give the compounds of Synthetic Examples[a] 364 to 366. The names, morphologies and yields of the synthesized compounds are shown in Table[a] 36.

TABLE[A] 36

| Ex | Compound Name | Morphology | Yield |
|---|---|---|---|
| 364 | 1-{trans-4-[(phenylsulfonyl)methyl]-cyclohexyl-}-7H-pyrrolo[3,2-e][1,2,3]-triazolo[1,5-c]pyrimidine | colorless solid | 30% |
| 365 | 1-(trans-4-{[(4-fluorophenyl)sulfonyl]-methyl}cyclohexyl)-7H-pyrrolo[3,2-c][1,2,3]triazolo[1,5-c]pyrimidine | colorless solid | 36% |
| 366 | 1-{trans-4-[(cyclopropylsulfonyl)methyl]-cyclohexyl}-7H-pyrrolo[3,2-e][1,2,3]triazolo[1,5-c]pyrimidine | colorless solid | 30% |

Synthetic Example[a] 367

1-[trans-4-(Iodomethyl)cyclohexyl]-7H-pyrrolo[3,2-e][1,2,3]triazolo[1,5-c]pyrimidine 2,3-Dichloro-5,6-dicyano-p-benzoquinone (50.0 mg, 0.221 mmol) and triphenylphosphine (58.0 mg, 0.221 mmol) in dichloromethane (3 mL) were mixed with tetrabutylammonium iodide (81.7 mg, 0.221 mmol) and [trans-4-(7H-pyrrolo[3,2-e][1,2,3]triazolo[1,5-c]pyrimidin-1-yl)cyclohexyl]methanol (50.0 mg, 0.184 mmol) obtained in Synthetic Example[a] 10 and then was stirred at 40° C. for 8 hours. After addition of water, the reaction mixture was extracted with ethyl acetate. The organic layer was dried over anhydrous sodium sulfate and concentrated under reduced pressure. The residue was purified by silica gel column chromatography (hexane/ethyl acetate=1/1→3/2 (v/v)) to give the title compound as a colorless solid (51.9 mg, yield 74%).

Synthetic Example[a] 368

1-(trans-4-{[(Trifluoromethyl)sulfonyl]methyl}cyclohexyl)-7H-pyrrolo[3,2-e][1,2,3]triazolo[1,5-c]pyrimidine 1-[trans-4-(Iodomethyl)cyclohexyl]-7H-pyrrolo[3,2-e][1,2,3]triazolo[1,5-c]pyrimidine (50.0 mg, 0.131 mmol) and sodium trifluoromethylsulfinate (205 mg, 1.31 mmol) in N,N-dimethylformamide (3 mL) were stirred at 100° C. for 26 hours. After addition of water, the reaction mixture was extracted with ethyl acetate. The organic layer washed with saturated aqueous sodium hydrogen carbonate, saturated aqueous ammonium chloride and saturated aqueous sodium chloride, dried over anhydrous sodium sulfate and concentrated under reduced pressure. The residue was purified by silica gel column chromatography (hexane/ethyl acetate=3/2→1/1(v/v)) and preparative HPLC (Waters XBridge Prep C18 μm ODS, 19×100 mm, acetonitrile/0.1% aqueous formic acid solution=20/80→80/20(v/v)) to give the title compound as a colorless solid (6.30 mg, yield 12%).

Synthetic Example[a] 369

1-[trans-4-(Azidomethyl)cyclohexyl]-7H-pyrrolo[3,2-e][1,2,3]triazolo[,1,5-c]pyrimidine 1-[trans-4-(Bromomethyl)cyclohexyl]-7H-pyrrolo[3,2-e][1,2,3]triazolo[1,5-c]pyrimidine (50.0 mg, 0.150 mmol) obtained in Synthetic Example[a] 74 in tetrahydrofurane (2 mL) was mixed with trimethylsilylazide (39.0 μL, 0.299 mmol) and tetrabutylammonium fluoride-tetrahydrofuran solution (1 M, 299 μL, 0.299 mmol) and then stirred at 50° C. for 3 hours. After addition of water, the reaction mixture was extracted with ethyl acetate. The organic layer was washed with saturated aqueous sodium chloride, dried over anhydrous sodium sulfate and concentrated under reduced pressure. The residue was washed with ethyl acetate/hexane (1/5 (v/v)) to give the title compound as a colorless solid (30.6 mg, yield 69%).

Synthetic Example[a] 370

2-(1-{[trans-4-(7H-Pyrrolo[3,2-e][1,2,3]triazolo[1,5-c]pyrimidin-1-yl)cyclohexyl]methyl}-1H-1,2,3-triazol-4-yl)propan-2-ol 1-[trans-4-(Azidomethyl)cyclohexyl]-7H-pyrrolo[3,2-e][1,2,3]triazolo[1,5-c]pyrimidine (30.0 mg, 0.101 mmol) and 2-methyl-3-butyn-2-ol (12.0 μL, 0.122 mmol) in dichloromethane (3 mL) were mixed with copper(II) sulfate (24.0 mg, 0.152 mmol) and sodium ascorbate (60.0 mg, 0.304 mmol) and then stirred at 80° C. for 2 hours. After addition of water, the reaction mixture was extracted with ethyl acetate. The organic layer was washed with saturated aqueous sodium hydrogen carbonate, dried over anhydrous sodium sulfate and concentrated under reduced pressure. The residue was purified by silica gel column chromatography (hexane/ethyl acetate=4/1→0/1→ethyl acetate/methanol=20/1 (v/v)) to give the title compound as a colorless solid (13.2 mg, yield 34%).

Synthetic Example[a] 371

[trans-4-(7H-Pyrrolo[3,2-e][1,2,3]triazolo[1,5-c]pyrimidin-1-yl)cyclohexyl]methanamine 1-[trans-4-(Azidomethyl)cyclohexyl]-7H-pyrrolo[3,2-e][1,2,3]triazolo[1,5-c]pyrimidine (127 mg, 0.427 mmol) obtained in Synthetic Example[a] 369 and 5% palladium-carbon (12.7 mg) in methanol (3 mL) and dichloromethane (3 mL) were stirred at room temperature for 4 hours under a hydrogen atmosphere. The reaction mixture was filtered, and the filtrate was concentrated under reduced pressure. The residue was purified by silica gel column chromatography (ethyl acetate/methanol=1/0→10/1 (v/v/) to give the title compound as a colorless solid (95.0 mg, yield 82%).

Synthetic Example[a] 372

N-{[trans-4-(7H-Pyrrolo[3,2-e][1,2,3]triazolo[1,5-c]pyrimidin-1-yl)cyclohexyl]methyl}-2-cyanoacetamide

[trans-4-(7H-Pyrrolo[3,2-e][1,2,3]triazolo[1,5-c]pyrimidin-1-yl)cyclohexyl]methanamine (40.0 mg, 0.148 mmol), 2-cyanoacetic acid (15.0 mg, 0.178 mmol) and O-(7-azabenzotriazol-1-yl)-N,N,N',N'-tetramethyluronium hexafluorophosphate (68.0 mg, 0.178 mmol) in N,N-dimethylformamide (2 mL) were mixed with N,N-diisopropylethylamine (57.0 μL, 0.326 mmol) and stirred at room temperature for 16 hours. After addition of water, the reaction mixture was extracted with ethyl acetate. The organic layer was washed with saturated aqueous sodium hydrogen carbonate, dried over anhydrous sodium sulfate and concentrated under reduced pressure. The residue was purified by silica gel column chromatography (hexane/acetone=1/1→2/3 (v/v)) to give the title compound as a colorless solid (11.4 mg, yield 23%).

Synthetic Example[a] 373

N-{[trans-4-(7H-Pyrrolo[3,2-e][1,2,3]triazolo[1,5-c]pyrimidin-1-yl)cyclohexyl]methyl}-3,3,3-trifluoropropanamide The reactions in Synthetic Example[a] 372 were carried out in substantially the same manners except that 3,3,3-trifluoropropanoic acid was used instead of 2-cyanoacetic acid to give the title compound as a colorless solid (5.00 mg, yield 12%).

Synthetic Example[a] 374

1-{1-[(3-Chloro-5-methyl-1-(2,2,2-trifluoroethyl)-1H-pyrazol-4-yl)methyl]piperidin-4-yl}-7H-pyrrolo[3,2-e][1,2,3]triazolo[1,5-c]pyrimidine 3-Chloro-5-methyl-1H-pyrazole-4-carbaldehyde (100 mg, 0.692 mmol) in N,N-dimethylformamide (2 mL) was mixed with potassium carbonate (287 mg, 2.08 mmol) and 2,2,2-trifluoroethyl trifluoromethanesulfonate (200 μL, 1.38 mmol) and stirred at room temperature for 1 day. After addition of saturated aqueous ammonium chloride, the reaction mixture was extracted with chloroform. The organic layer was dried over anhydrous sodium sulfate and concentrated under reduced pressure. The residue and 1-(piperidin-4-yl)-7H-pyrrolo[3,2-e][1,2,3]triazolo[1,5-c]pyrimidine acetate (20.0 mg, 0.0660 mmol) obtained in Reference Synthetic Example[a] 104 were dissolved in methanol (1 mL) and mixed with nicotinic acid (12.3 mg, 0.0990 mmol) and 2-picoline borane (10.7 mg, 0.0990 mmol). The reaction mixture was stirred at room temperature for 1 day. After addition of 1 M aqueous sodium hydroxide, the reaction mixture was extracted with chloroform. The organic layer was dried over anhydrous sodium sulfate and concentrated under reduced pressure. The residue was purified by silica gel thin layer chromatography (methanol/chloroform=1/10 (v/v)) to give the title compound as a colorless solid (2.35 mg, yield 8%).

Synthetic Example[a] 375

4-{2-[4-(7H-Pyrrolo[3,2-e][1,2,3]triazolo[1,5-c]pyrimidin-1-yl)piperidin-1-yl]ethyl}benzonitrile The reactions in Synthetic Example[a] 32 were carried out in substantially the same manners except that 4-cyanophenethyl 4-methylbenzenesulfonate (Reference Synthetic Example[a] 132) was used instead of benzyl bromide to give the title compound as a colorless solid (7.03 mg, yield 29%).

Synthetic Example[a] 376

4-[4-(7H-Pyrrolo[3,2-e][1,2,3]triazolo[1,5-c]pyrimidin-1-yl)piperidin-1-yl]benzonitrile 1-(Piperidin-4-yl)-7H-pyrrolo[3,2-e][1,2,3]triazolo[1,5-c]pyrimidine acetate (30.0 mg, 0.0992 mmol) obtained in Reference Synthetic Example[a] 104 in N,N-dimethylformamide (1 mL) was mixed with 4-fluorobenzonitrile (18.0 mg, 0.149 mmol) and potassium carbonate (27.4 mg, 0.198 mmol) and then stirred at 80° C. for 31 hours. After addition of water, the reaction mixture was extracted with chloroform. The organic layer was dried over anhydrous sodium sulfate and concentrated under reduced pressure. The residue was purified by silica gel thin layer chromatography (methanol/chloroform=1/19 (v/v)) to give the title compound as a colorless solid (0.520 mg, yield 2%).

Synthetic Example[a] 377

4-{[4-(9-Chloro-7H-pyrrolo[3,2-e][1,2,3]triazolo[1,5-c]pyrimidin-1-yl)piperidin-1-yl]methyl}benzonitrile 4-{[4-(7H-Pyrrolo[3,2-e][1,2,3]triazolo[1,5-c]pyrimidin-1-yl)piperidin-1-yl]methyl}benzonitrile (20.0 mg, 0.0660 mmol) obtained in Synthetic Example[a] 34 in N,N-dimethylformamide (1 mL) was mixed with N-chlorosuccinimide (10.7 mg, 0.0990 mmol) and stirred at room temperature for 1 day. After addition of 1M aqueous sodium hydroxide, the reaction mixture was extracted with chloroform. The organic layer was dried over anhydrous sodium sulfate and concentrated under reduced pressure. The residue was purified by silica gel thin layer chromatography (methanol/chloroform=1/10 (v/v)) to give the title compound as a colorless solid (13.1 mg, yield 48%).

Synthetic Examples[a] 378 to 380

The reactions in Synthetic Example[a] 121 were carried out in substantially the same manners except that (1R,2S)-1-amino-2,3-dihydro-1H-inden-2-ol, (1S,2R)-1-amino-2,3-dihydro-1H-inden-2-ol or 3,3'-azanediyldipropanenitrile was used instead of 4-aminobenzonitrile to give cis/trans mixture of the compounds of Synthetic Examples[a] 378 to 380. The names, morphologies and yields of the compounds synthesized are shown in Table[a] 37.

TABLE[A] 37

| Ex | Compound Name | Morphology | Yield |
|---|---|---|---|
| 378 | (1R,2S)-1-{[4-(7H-pyrrolo[3,2-e][1,2,3]triazolo[1,5-c]pyrimidin-1-yl)-cyclohexyl]amino}-2,3-dihydro-1H-inden-2-ol | pale yellow solid | 63% |
| 379 | (1S,2R)-1-{[4-(7H-pyrrolo[3,2-e][1,2,3]triazolo[1,5-c]pyrimidin-1-yl)-cyclohexyl]amino}-2,3-dihydro-1H-inden-2-ol | pale yellow solid | 78% |
| 380 | 3,3'-{[4-(7H-pyrrolo[3,2-e][1,2,3]triazolo[1,5-c]pyrimidin-1-yl)cyclohexyl]azanediyl}-dipropanenitrile | colorless solid | 22% |

Synthetic Examples[a] 381 to 384

The reactions in Synthetic Example[a] 136 were carried out in substantially the same manners except that 4-fluoroaniline, 2-bromo-2,2-difluoroethanamine hydrochloride (Reference Synthetic Example[a] 131), 2,2,3,3,3-pentafluoropropylamine or 2-amino-N-(2,2,2-trifluoroethyl)acetamide was used instead of 3-phenylpropan-1-amine to give the compounds of Synthetic Examples[a] 381a to 384a in less polar fractions and the compounds of Synthetic Examples[a] 381 b to 384b in more polar fractions. The names, morphologies and yields of the compounds synthesized are shown in Table[a] 38.

TABLE[a] 38

| Ex | Compound Name | Morphology | Yield |
|---|---|---|---|
| 381a | N-[cis-4-(7H-pyrrolo[3,2-e][1,2,3]triazolo[1,5-c]pyrimidin-1-yl)cyclohexyl]-4-fluoroaniline | pale yellow solid | 11% |
| 381b | N-[trans-4-(7H-pyrrolo[3,2-e][1,2,3]triazolo[1,5-c]pyrimidin-1-yl)cyclohexyl]-4-fluoroaniline | pale yellow solid | 13% |
| 382a | cis-N-(2-bromo-2,2-difluoroethyl)-4-(7H-pyrrolo[3,2-e][1,2,3]triazolo[1,5-c]pyrimidin-1-yl)cyclohexanamine | colorless solid | 1.0% |
| 382b | trans-N-(2-bromo-2,2-difluoroethyl)-4-(7H-pyrrolo[3,2-e][1,2,3]triazolo[1,5-c]pyrimidin-1-yl)cyclohexanamine | colorless solid | 4.0% |
| 383a | cis-N-(2,2,3,3,3-pentafluoropropyl)-4-(7H-pyrrolo[3,2-e][1,2,3]triazolo[1,5-c]pyrimidin-1-yl)cyclohexanamine | colorless solid | 12% |
| 383b | trans-N-(2,2,3,3,3-pentafluoropropyl)-4-(7H-pyrrolo[3,2-e][1,2,3]triazolo[1,5-c]pyrimidin-1-yl)cyclohexanamine | colorless solid | 29% |
| 384a | 2-{[cis-4-(7H-pyrrolo[3,2-e][1,2,3]triazolo[1,5-c]pyrimidin-1-yl)cyclohexyl]amino}-N-(2,2,2-trifluoroethyl)acetamide | colorless solid | 11% |
| 384b | 2-{[trans-4-(7H-pyrrolo[3,2-e][1,2,3]triazolo[1,5-c]pyrimidin-1-yl)cyclohexyl]amino}-N-(2,2,2-trifluoroethyl)acetamide | colorless solid | 27% |

Synthetic Examples[a] 385 to 400

The reactions in Synthetic Example[a] 136 were carried out in substantially the same manners except that 3-amino-1,1,1-trifluoro-2-(pyridin-3-yl)propan-2-ol, 3-amino-1,1,1-trifluoro-2-[4-(methylthio)phenyl]propan-2-ol, 3-amino-1,1,1-trifluoro-2-(6-methoxypyridin-3-yl)propan-2-ol, 3-amino-1,1,1-trifluoro-2-(4-methoxyphenyl)propan-2-ol, [trans-2-(4-fluorophenyl)cyclopropyl]methanamine, 3-amino-2-(3,4-dimethoxyphenyl)-1,1,1-trifluoropropan-2-ol, 4-(2-aminoethyl)benzonitrile, cyclopropylamine, 2-aminoacetonitrile hydrochloride, 3-aminopropanenitrile, 2,2,2-trifluoroethanamine hydrochloride, cyclopropylmethanamine, dimethylamine (2M solution in tetrahydrofuran), methanamine (2M solution in methanol), 2,2-difluoroethanamine or 1,1,1,3,3,3,-hexafluoropropan-2-amine was used instead of 3-phenylpropan-1-amine to give the compounds of Synthetic Examples[a] 385b to 400b in more polar fractions. The names, morphologies and yields of the compounds synthesized are shown in Tables[a] 39 to 40.

TABLE[a] 39

| Ex | Compound Name | Morphology | Yield |
|---|---|---|---|
| 385b | 3-{[trans-4-(7H-pyrrolo[3,2-e][1,2,3]triazolo[1,5-c]pyrimidin-1-yl)cyclohexyl]amino}-1,1,1-trifluoro-2-(pyridin-3-yl)propan-2-ol | colorless solid | 30% |
| 386b | 3-{[trans-4-(7H-pyrrolo[3,2-e][1,2,3]triazolo[1,5-c]pyrimidin-1-yl)cyclohexyl]amino}-1,1,1-trifluoro-2-[4-(methylthio)phenyl]propan-2-ol | colorless solid | 31% |

TABLE[a] 39-continued

| Ex | Compound Name | Morphology | Yield |
|---|---|---|---|
| 387b | 3-{[trans-4-(7H-pyrrolo[3,2-e][1,2,3]triazolo[1,5-c]pyrimidin-1-yl)cyclohexyl]amino}-1,1,1-trifluoro-2-(6-methoxypyridin-3-yl)propan-2-ol | colorless solid | 26% |
| 388b | 3-{[trans-4-(7H-pyrrolo[3,2-e][1,2,3]triazolo[1,5-c]pyrimidin-1-yl)cyclohexyl]amino}-1,1,1-trifluoro-2-(4-methoxyphenyl)propan-2-ol | colorless solid | 38% |
| 389b | trans-N-{[trans-2-(4-fluorophenyl)cyclopropyl]methyl}-4-(7H-pyrrolo[3,2-e][1,2,3]triazolo[1,5-c]pyrimidin-1-yl)cyclohexanamine | colorless solid | 16% |
| 390b | 3-{[trans-4-(7H-pyrrolo[3,2-e][1,2,3]triazolo[1,5-c]pyrimidin-1-yl)cyclohexyl]amino}-2-(3,4-dimethoxyphenyl)-1,1,1-trifluoropropan-2-ol | colorless solid | 12% |
| 391b | 4-(2-{[trans-4-(7H-pyrrolo[3,2-e][1,2,3]triazolo[1,5-c]pyrimidin-1-yl)cyclohexyl]amino}ethyl)benzonitrile | colorless solid | 12% |
| 392b | trans-N-cyclopropyl-4-(7H-pyrrolo[3,2-e][1,2,3]triazolo[1,5-c]pyrimidin-1-yl)cyclohexanamine | colorless solid | 26% |
| 393b | 2-{[trans-4-(7H-pyrrolo[3,2-e][1,2,3]triazolo[1,5-c]pyrimidin-1-yl)cyclohexyl]amino}acetonitrile | pale yellow solid | 15% |
| 394b | 3-{[trans-4-(7H-pyrrolo[3,2-e][1,2,3]triazolo[1,5-c]pyrimidin-1-yl)cyclohexyl]amino}propanenitrile | pale yellow solid | 8.0% |
| 395b | trans-4-(7H-pyrrolo[3,2-e][1,2,3]triazolo[1,5-c]pyrimidin-1-yl)-N-(2,2,2-trifluoroethyl)cyclohexanamine | colorless solid | 15% |
| 396b | trans-N-(cyclopropylmethyl)-4-(7H-pyrrolo[3,2-e][1,2,3]triazolo[1,5-c]pyrimidin-1-yl)cyclohexanamine | pale brown solid | 40% |
| 397b | trans-N,N-dimethyl-4-(7H-pyrrolo[3,2-e][1,2,3]triazolo[1,5-c]pyrimidin-1-yl)cyclohexanamine | pale yellow solid | 27% |

TABLE[a] 40

| Ex | Compound Name | Morphology | Yield |
|---|---|---|---|
| 398b | trans-N-methyl-4-(7H-pyrrolo[3,2-e][1,2,3]triazolo[1,5-c]pyrimidin-1-yl)cyclohexanamine | colorless solid | 19% |
| 399b | trans-N-(2,2-difluoroethyl)-4-(7H-pyrrolo[3,2-e][1,2,3]triazolo[1,5-c]pyrimidin-1-yl)cyclohexanamine | pale yellow solid | 20% |
| 400b | trans-N-(1,1,1,3,3,3-hexafluoropropan-2-yl)-4-(7H-pyrrolo[3,2-e][1,2,3]triazolo[1,5-c]pyrimidin-1-yl)cyclohexanamine | colorless solid | 7.0% |

Synthetic Example[a] 401

[cis-4-(7H-Pyrrolo[3,2-e][1,2,3]triazolo[1,5-c]pyrimidin-1-yl)cyclohexyl]methanol The reactions in Synthetic Example[a] 141 were carried out in substantially the same manners except that 1-(cis-4-{[(tert-butyldimethylsilyl)oxy]methyl}cyclohexyl)-7H-pyrrolo[3,2-e][1,2,3]triazolo[1,5-c]pyrimidine (Reference Synthetic Example[a] 135a) was used instead of 1-(trans-4-{[(tert-butyldimethylsilyl)oxy]methyl}cyclohexyl)-7H-pyrrolo[3,2-e][1,2,3]triazolo[1,5-c]pyrimidine to give the title compound as a pale pink solid (297 mg, yield 57%).

Synthetic Example[a] 402 cis-4-(7H-Pyrrolo[3,2-e][1,2,3]triazolo[1,5-c]pyrimidin-1-yl)cyclohexanecarbaldehyde The reactions in Synthetic Example[a] 78 were carried out in substantially the same manners except that [cis-4-(7H-pyrrolo[3,2-e][1,2,3]triazolo[1,5-c]pyrimidin-1-yl)cyclohexyl]methanol was used instead of [trans-4-(7H-pyrrolo[3,2-e][1,2,3]triazolo[1,5-c]pyrimidin-1-yl)cyclohexyl]methanol to give the title compound as a colorless solid (192 mg, yield 88%).

Synthetic Example[a] 403

1-{[cis-4-(7H-Pyrrolo[3,2-e][1,2,3]triazolo[1,5-c]pyrimidin-1-yl)cyclohexyl]methyl}azetidin-3-ol cis-4-(7H-Pyrrolo[3,2-e][1,2,3]triazolo[1,5-c]pyrimidin-1-yl)cyclohexanecarbaldehyde (30.0 mg, 0.111 mmol) in methanol (2 mL), tetrahydrofuran (1 mL) and acetic acid (100 μL) was mixed with 3-hydroxyazetidine hydrochloride (41.3 mg, 0.334 mmol) and stirred at room temperature for 1 hour. The reaction mixture was mixed with 2-picoline borane (23.8 mg, 0.334 mmol) and stirred at room temperature for 14 hours. After addition of water, the reaction mixture was extracted with ethyl acetate. The aqueous layer was adjusted to pH 10 with 1 M aqueous sodium hydroxide, and extracted with ethyl acetate. The organic layer was dried over anhydrous sodium sulfate and concentrated under reduced pressure. The residue was washed with hexane/ethyl acetate (5/1 (v/v)) to give the title compound as a colorless solid (7.40 mg, yield 31%).

Synthetic Examples[a] 404 to 406

The reactions in Synthetic Example[a] 403 were carried out in substantially the same manners except that (S)-pyrrolidin-3-ol hydrochloride, (R)-pyrrolidin-3-ol hydrochloride or cyclopropylamine hydrochloride (Reference Synthetic Example[a] 136) was used instead of 3-hydroxyazetidine hydrochloride to give the compounds of Synthetic Examples[a] 404 to 406. The names, morphologies and yields of the compounds synthesized are shown in Table[a] 41.

TABLE[a] 41

| Ex | Compound Name | Morphology | Yield |
|---|---|---|---|
| 404 | (S)-1-{[cis-4-(7H-pyrrolo[3,2-e][1,2,3]triazolo[1,5-c]pyrimidin-1-yl)cyclohexyl]methyl}pyrrolidin-3-ol | colorless solid | 96% |
| 405 | (R)-1-{[cis-4-(7H-pyrrolo[3,2-e][1,2,3]triazolo[1,5-c]pyrimidin-1-yl)cyclohexyl]methyl}pyrrolidin-3-ol | colorless solid | 55% |
| 406 | N-{[cis-4-(7H-pyrrolo[3,2-e][1,2,3]triazolo[1,5-c]pyrimidin-1-yl)cyclohexyl]methyl}cyclopropanamine | colorless solid | 16% |

Synthetic Example[a] 407

N-{[trans-4-(7H-Pyrrolo[3,2-e][1,2,3]triazolo[1,5-c]pyrimidin-1-yl)cyclohexyl]methyl}-2-cyano-N-(2,2,2-trifluoroethyl)acetamide N-{[trans-4-(7H-Pyrrolo[3,2-e][1,2,3]triazolo[1,5-c]pyrimidin-1-yl)cyclohexyl]methyl}-2,2,2-trifluoroethanamine (20.0 mg, 0.0567 mmol) obtained in Synthetic Example[a] 188 in N,N-dimethylformamide (1 mL) was mixed with 2-cyanoacetic acid (9.60 mg, 0.113 mmol) and O-(7-azabenzotriazol-1-yl)-N,N,N',N'-tetramethyluronium hexafluorophosphate (45.0 mg, 0.113 mmol) and stirred with N,N-diisopropylethylamine (0.0346 mL, 0.198 mmol) at room temperature for 2 hours. After addition of water, the reaction mixture was extracted with ethyl acetate. The organic layer was washed with saturated aqueous sodium chloride, dried over anhydrous sodium sulfate and concentrated under reduced pressure. The residue was purified by silica gel column chromatography (hexane/ethyl acetate=1/1→6/1 (v/v)) to give the title compound as a colorless solid (23.6 mg, yield 99%).

Synthetic Examples[a] 408 to 410

The reactions in Synthetic Example[a] 407 were carried out in substantially the same manners except that 2-({[trans-4-(7H-pyrrolo[3,2-e][1,2,3]triazolo[1,5-c]pyrimidin-1-yl)cyclohexyl]methyl}amino)acetonitrile (Synthetic Example[a] 259), N-{[trans-4-(7H-pyrrolo[3,2-e][1,2,3]triazolo[1,5-c]pyrimidin-1-yl)cyclohexyl]methyl}cyclopropanamine (Synthetic Example[a] 280) or 1-[trans-4-(7H-pyrrolo[3,2-e][1,2,3]triazolo[1,5-c]pyrimidin-1-yl)cyclohexyl]-N-[(5-methylfuran-2-yl)methyl]methanamine (Synthetic Example[a] 182) was used instead of N-{[trans-4-(7H-pyrrolo[3,2-e][1,2,3]triazolo[1,5-c]pyrimidin-1-yl)cyclohexyl]methyl}-2,2,2-trifluoroethanamine to give the compounds of Synthetic Examples[a] 408 to 410. The names, morphologies and yields of the compounds synthesized are shown in Table[a] 42.

TABLE[a] 42

| Ex | Compound Name | Morphology | Yield |
|---|---|---|---|
| 408 | N-{[trans-4-(7H-pyrrolo[3,2-e][1,2,3]triazolo[1,5-c]pyrimidin-1-yl)cyclohexyl]methyl}-2-cyano-N-(cyanomethyl)acetamide | colorless solid | 53% |
| 409 | N-{[trans-4-(7H-pyrrolo[3,2-e][1,2,3]triazolo[1,5-c]pyrimidin-1-yl)cyclohexyl]methyl}-2-cyano-N-cyclopropylacetamide | colorless solid | 93% |

TABLE[a] 42-continued

| Ex | Compound Name | Morphology | Yield |
|---|---|---|---|
| 410 | N-{[trans-4-(7H-pyrrolo[3,2-e][1,2,3]triazolo[1,5-c]pyrimidin-1-yl)cyclohexyl]methyl}-2-cyano-N-[(5-methylfuran-2-yl)methyl]acetamide | gray solid | 83% |

Synthetic Example[a] 411

N-{[trans-4-(7H-Pyrrolo[3,2-e][1,2,3]triazolo[1,5-c]pyrimidin-1-yl)cyclohexyl]methyl}-3,3,3-trifluoro-N-(2,2,2-trifluoroethyl)propanamide The reactions in Synthetic Example[a] 407 were carried out in substantially the same manners except that 3,3,3-trifluoropropionic acid was used instead of 2-cyanoacetic acid to give the title compound as a colorless solid (8.80 mg, yield 33%).

Synthetic Example[a] 412

N-{[trans-4-(7H-Pyrrolo[3,2-e][1,2,3]triazolo[1,5-c]pyrimidin-1-yl)cyclohexyl]methyl}-N-(cyanomethyl)-3,3,3-trifluoropropanamide The reactions in Synthetic Example[a] 411 were carried out in substantially the same manners except that 2-({[trans-4-(7H-pyrrolo[3,2-e][1,2,3]triazolo[1,5-c]pyrimidin-1-yl)cyclohexyl]methyl}amino)acetonitrile (Synthetic Example[a] 259) was used instead of N-{[trans-4-(7H-pyrrolo[3,2-e][1,2,3]triazolo[1,5-c]pyrimidin-1-yl)cyclohexyl]methyl}-2,2,2-trifluoroethanamine to give the title compound as a colorless solid (6.40 mg, yield 64%).

Synthetic Example[a] 413 trans-N-(Cyclopropylmethyl)-4-(7H-pyrrolo[3,2-e][1,2,3]triazolo[1,5-c]pyrimidin-1-yl)-N-(2,2,2-trifluoroethyl)cyclohexanamine trans-4-(7H-Pyrrolo[3,2-e][1,2,3]triazolo[1,5-c]pyrimidin-1-yl)-N-(2,2,2-trifluoroethyl)cyclohexanamine (5.00 mg, 0.0148 mmol) obtained in Synthetic Example[a] 395 in methanol (1 mL) and acetic acid (0.1 mL) was mixed with cyclopropanecarbaldehyde (1.60 μL, 0.0222 mmol) and 2-picoline borane (2.30 mg, 0.0222 mmol) and stirred at room temperature for 1 day. After addition of 1 M aqueous sodium hydroxide, the reaction mixture was extracted with ethyl acetate. The organic layer was dried over anhydrous sodium sulfate and concentrated under reduced pressure. The residue was purified by silica gel column chromatography (ethyl acetate/hexane=1/3→1/1 (v/v)) to give the title compound as a colorless solid (4.00 mg, yield 70%).

Synthetic Examples[a] 414 and 415

The reactions in Synthetic Example[a] 413 were carried out in substantially the same manners except that 2-({[trans-4-(7H-pyrrolo[3,2-e][1,2,3]triazolo[1,5-c]pyrimidin-1-yl)cyclohexyl]methyl}amino)acetonitrile (Synthetic Example[a] 259) or N-{[trans-4-(7H-pyrrolo[3,2-e][1,2,3]triazolo[1,5-c]pyrimidin-1-yl)cyclohexyl]methyl}-2,2,2-trifluoroethanamine (Synthetic Example[a] 188) was used instead of trans-4-(7H-pyrrolo[3,2-e][1,2,3]triazolo[1,5-c]pyrimidin-1-yl)-N-(2,2,2-trifluoroethyl)cyclohexanamine to give the compounds of Synthetic Examples[a] 414 and 415. The names, morphologies and yields of the compounds synthesized are shown in Table[a] 43.

TABLE[a] 43

| Ex | Compound Name | Morphology | Yield |
|---|---|---|---|
| 414 | 2-({[trans-4-(7H-pyrrolo[3,2-e][1,2,3]triazolo[1,5-c]pyrimidin-1-yl)cyclohexyl]methyl}(cyclopropylmethyl)amino)acetonitrile | colorless solid | 73% |
| 415 | N-{[trans-4-(7H-pyrrolo[3,2-e][1,2,3]triazolo[1, 5-c]pyrimidin-1-yl)cyclohexyl]methyl}-N-(cyclopropylmethyl)-2,2,2-trifluoroethanamine | colorless solid | 78% |

Synthetic Example[a] 416

[trans-4-(7H-Pyrrolo[3,2-e][1,2,3]triazolo[1,5-c]pyrimidin-1-yl)cyclohexyl]methanesulfonic acid S-[trans-4-(7H-Pyrrolo[3,2-e][1,2,3]triazolo[1,5-c]pyrimidin-1-yl)cyclohexyl]methyl ethanethioate (127 mg, 0.390 mmol) obtained in Synthetic Example[a] 71 in methanol (4 mL) was mixed with ammonium molybdate tetrahydrate (145 mg, 0.117 mmol) and hydrogen peroxide solution (0.63 mL, 7.80 mmol) and stirred at room temperature for 1 day. The reaction mixture was mixed with saturated aqueous sodium thiosulfate, concentrated under reduced pressure and purified by silica gel column chromatography (ethyl acetate/methanol=4/1→1/1 (v/v)). The resulting solid was mixed with water and extracted with n-butanol. The organic layer was dried over anhydrous sodium sulfate and concentrated under reduced pressure to give the title compound as a pale yellow solid (39.8 mg, yield 28%).

Synthetic Example[a] 417

1-[trans-4-(7H-Pyrrolo[3,2-e][1,2,3]triazolo[1,5-c]pyrimidin-1-yl)cyclohexyl]-N-cyclopropylmethanesulfonamide

[trans-4-(7H-Pyrrolo[3,2-e][1,2,3]triazolo[1,5-c]pyrimidin-1-yl)cyclohexyl]methanesulfonic acid (17.8 mg, 0.0530 mmol) in dichloromethane (1.5 mL) and N,N-dimethylformamide (1.8 mL) was stirred with thionyl chloride (0.00770 mL, 0.106 mmol) at room temperature for 1 hour. The reaction mixture was concentrated under reduced pressure. The residue was dissolved in dichloromethane (1.0 mL) and mixed with N,N-diisopropylethylamine (0.0923 mL, 0.530 mmol) and cyclopropylamine (0.0148 mL, 0.212 mmol) under cooling with ice and then stirred at room temperature for 1 day. After addition of water, the reaction mixture was extracted with ethyl acetate. The organic layer was washed with saturated aqueous sodium chloride, dried over anhydrous sodium sulfate and concentrated under reduced pressure. The residue was purified by silica gel column chromatography (ethyl hexane/acetate=4/1→1/1→1/3 (v/v)) to give the title compound as a brown solid (1.50 mg, yield 7.5%).

Synthetic Examples[a] 418 to 420

The reactions in Synthetic Example[a] 417 were carried out in substantially the same manners except that dimethylamine hydrochloride, 2-aminoacetonitrile hydrochloride or 2,2,2-trifluoroethanamine hydrochloride was used instead of cyclopropylamine to give the compounds of Synthetic Examples[a] 418 to 420. The names, morphologies and yields of the compounds synthesized are shown in Table[a] 44.

TABLE[a] 44

| Ex | Compound Name | Morphology | Yield |
|---|---|---|---|
| 418 | 1-[trans-4-(7H-pyrrolo[3,2-e][1,2,3]triazolo[1,5-c]pyrimidin-1-yl)cyclohexyl]-N,N-dimethylmethanesulfonamide | colorless solid | 15% |
| 419 | 1-[trans-4-(7H-pyrrolo[3,2-e][1,2,3]triazolo[1,5-c]pyrimidin-1-yl)cyclohexyl]-N-(cyanomethyl)methanesulfonamide | yellow solid | 12% |
| 420 | 1-[trans-4-(7H-pyrrolo[3,2-e][1,2,3]triazolo[1,5-c]pyrimidin-1-yl)cyclohexyl]-N-(2,2,2-trifluoroethyl)methanesulfonamide | pale yellow solid | 5.0% |

Synthetic Example[a] 421

1-(trans-4-{[3-(2,2,2-Trifluoroethoxy)azetidin-1-yl]methyl}cyclohexyl)-7H-pyrrolo[3,2-e][1,2,3]triazolo[1,5-c]pyrimidine tert-Butyl 3-(2,2,2-trifluoroethoxy)azetidine-1-carboxylate (350 mg, 1.37 mmol) obtained in Reference Synthetic Example[a] 116 in ethyl acetate (1 mL) was mixed with 4 M hydrogen chloride-1,4-dioxane solution (3 mL) under cooling with ice and then stirred at room temperature for 2 hours. The reaction mixture was concentrated to give a colorless oil (224 mg). The resulting colorless oil (64.0 mg) was dissolved in methanol (2 mL), tetrahydrofuran (1 mL) and acetic acid (100 μL) and stirred with trans-4-(7H-pyrrolo[3,2-e][1,2,3]triazolo[1,5-c]pyrimidin-1-yl)cyclohexanecarbaldehyde (30.0 mg, 0.111 mmol) obtained in Synthetic Example[a] 78 at room temperature for 1 hour. The reaction mixture was mixed with 2-picoline borane (23.8 mg, 0.334 mmol) and stirred at room temperature for 14 hours. After addition of water, the reaction mixture was extracted with ethyl acetate. The aqueous layer was adjusted to pH 10 with 1 M aqueous sodium hydroxide, and extracted with ethyl acetate. The organic layer was dried over anhydrous sodium sulfate and concentrated under reduced pressure. The residue was washed with hexane/ethyl acetate (5/1 (v/v)) to give the title compound as a light purple solid (14.9 mg, yield 33%).

Synthetic Examples[a] 422 to 424

The reactions in Synthetic Example[a] 421 were carried out in substantially the same manners except that tert-butyl 3-hydroxy-3-methylazetidine-1-carboxylate (Reference Synthetic Example[a] 113), tert-butyl 3-(dimethylamino)azetidine-1-carboxylate (Reference Synthetic Example[a] 137) or tert-butyl 3-[ethyl(methyl)amino]azetidine-1-carboxylate (Reference Synthetic Example[a] 138) was used instead of tert-butyl 3-(2,2,2-trifluoroethoxy)azetidine-1-carboxylate to give the compounds of Synthetic Examples[a] 422 to 424. The names, morphologies and yields of the compounds synthesized are shown in Table[a] 45.

TABLE[a] 45

| Ex | Compound Name | Morphology | Yield |
|---|---|---|---|
| 422 | 1-{[trans-4-(7H-pyrrolo[3,2-c][1,2,3]triazolo[1,5-c]pyrimidin-1- | colorless solid | 21% |

TABLE[a] 45-continued

| Ex | Compound Name | Morphology | Yield |
|---|---|---|---|
| | yl)cyclohexyl]methyl}-3-methylazetidin-3-ol | | |
| 423 | 1-{[trans-4-(7H-pyrrolo[3,2-e][1,2,3]triazolo[1,5-c]pyrimidin-1-yl)cyclohexyl]methyl}-N,N-dimethylazetidin-3-amine | colorless solid | 25% |
| 424 | 1-{[trans-4-(7H-pyrrolo[3,2-e][1,2,3]triazolo[1,5-c]pyrimidin-1-yl)cyclohexyl]methyl}-N-ethyl-N-methylazetidin-3-amine | colorless solid | 34% |

Synthetic Example[a] 425

1-{[trans-4-(7H-Pyrrolo[3,2-e][1,2,3]triazolo[1,5-c]pyrimidin-1-yl)cyclohexyl]methyl}-3-(trifluoromethyl)azetidin-3-ol The reactions in Synthetic Example[a] 88 were carried out in substantially the same manners except that 3-(trifluoromethyl)azetidin-3-ol hydrochloride (Reference Synthetic Example[a] 115) was used instead of thiomorpholine 1,1-dioxide to give the title compound as a colorless solid (11.9 mg, yield 27%).

Synthetic Example[a] 426

1-{[trans-4-(7H-Pyrrolo[3,2-e][1,2,3]triazolo[1,5-c]pyrimidin-1-yl)cyclohexyl]methyl}-N-(2,2,2-trifluoroethyl)azetidine-3-carboxamide 1-{[trans-4-(7H-Pyrrolo[3,2-e][1,2,3]triazolo[1,5-c]pyrimidin-1-yl)cyclohexyl]methyl}azetidine-3-carboxylic acid (40.0 mg, 0.113 mmol) obtained in Synthetic Example[a] 278 and 2,2,2-trifluoroethanamine hydrochloride (19.9 mg, 0.147 mmol) in N,N-dimethylformamide (2 mL) were mixed with N,N-diisopropylethylamine (74.9 μL, 0.440 mmol) and (1-cyano-2-ethoxy-2-oxoethylidenaminooxy)dimethylamino-morpholino-carbenium hexafluorophosphate (62.8 mg, 0.147 mmol) and stirred at room temperature for 1 day. After addition of saturated aqueous sodium hydrogen carbonate, the reaction mixture was extracted with ethyl acetate. The organic layer was dried over anhydrous magnesium sulfate and concentrated under reduced pressure. The residue was washed with hexane/chloroform (3/1 (v/v)) to give the title compound as a pale yellow solid (5.40 mg, yield 11%).

Synthetic Example[a] 427

N-{[trans-4-(7H-Pyrrolo[3,2-e][1,2,3]triazolo[1,5-c]pyrimidin-1-yl)cyclohexyl]methyl}methanesulfonamide

[trans-4-(7H-Pyrrolo[3,2-e][1,2,3]triazolo[1,5-c]pyrimidin-1-yl)cyclohexyl]methanamine (20.0 mg, 0.0740 mmol) obtained in Synthetic Example[a] 371 in dichloromethane (2 mL) was mixed with methanesulfonyl chloride (13.8 μL, 0.0814 mmol) under cooling with ice and then stirred at room temperature for 65 hours. After addition of water, the reaction mixture was extracted with ethyl acetate. The aqueous layer was washed with 1 M hydrochloric acid and saturated aqueous ammonium chloride, dried over anhydrous sodium sulfate and concentrated under reduced pressure. The residue was washed with chloroform/hexane (1/5 (v/v)) to give the title compound as a colorless solid (6.00 mg, yield 23%).

Synthetic Example[a] 428 tert-Butyl 3-({[trans-4-(7H-pyrrolo[3,2-e][1,2,3]triazolo[1,5-c]pyrimidin-1-yl)cyclohexyl]methyl}amino)-3-(cyanomethyl)azetidine-1-carboxylate

[trans-4-(7H-Pyrrolo[3,2-e][1,2,3]triazolo[1,5-c]pyrimidin-1-yl)cyclohexyl]methanamine (11.2 mg, 0.0414 mmol) obtained in Synthetic Example[a] 371 and tert-butyl 3-(cyanomethylene)azetidine-1-carboxylate (10.4 mg, 0.0535 mmol) obtained in Reference Synthetic Example[a] 139 in acetonitrile (2 mL) were mixed with 1,8-diazabicyclo[5.4.0]undec-7-ene (12.0 μL, 0.0535 mmol) and stirred at room temperature for 1 day. After addition of water, the reaction mixture was extracted with ethyl acetate. The organic layer was washed with saturated aqueous sodium chloride, dried over anhydrous sodium sulfate and concentrated under reduced pressure. The residue was purified by silica gel column chromatography (NH-silica gel manufactured by Fuji Silysia Chemical Ltd.; chloroform/methanol=20/1 (v/v)) to give the title compound as a pale yellow solid (14.2 mg, yield 74%).

Synthetic Example[a] 429

4-(7H-Pyrrolo[3,2-e][1,2,3]triazolo[1,5-c]pyrimidin-1-yl)cyclohexanecarbaldehyde oxime

[trans-4-(7H-Pyrrolo[3,2-e][1,2,3]triazolo[1,5-c]pyrimidin-1-yl)cyclohexylcarbaldehyde (60.0 mg, 0.223 mmol) obtained in Synthetic Example[a] 78 in methanol (1 mL) and water (1 mL) was mixed with hydroxylamine hydrochloride (31.0 mg, 0.446 mmol) and sodium hydrogen carbonate (37.4 mg, 0.446 mmol) and then stirred at 50° C. for 5 hours. The reaction mixture was filtered, and the resulting solid washed with water, water/methanol (10/1 (v/v)) and hexane to give the title compound as a colorless solid (44.6 mg, yield 70%).

Synthetic Example[a] 430 trans-4-(7H-Pyrrolo[3,2-e][1,2,3]triazolo[1,5-c]pyrimidin-1-yl)cyclohexanecarbonitrile trans-4-(7H-Pyrrolo[3,2-e][1,2,3]triazolo[1,5-c]pyrimidin-1-yl)cyclohexanecarbaldehyde oxime (37.4 mg, 0.132 mmol) in dichloromethane (3 mL) was mixed with trifluoromethanesulfonic anhydride (24.0 μL, 0.145 mmol) and 1,8-diazabicyclo[5.4.0]undec-7-ene (43.0 μL, 0.289 mmol) and stirred at room temperature for 18 hours. After addition of water, the reaction mixture was extracted with ethyl acetate. The organic layer was washed with saturated aqueous sodium hydrogen carbonate, dried over anhydrous magnesium sulfate and concentrated under reduced pressure. The residue was purified by silica gel column chromatography (hexane/ethyl acetate=3/2 (v/v)) and washed with hexane/ethyl acetate (5/1 (v/v)) to give the title compound as a colorless solid (20.7 mg, yield 59%).

Synthetic Example[a] 431

2-{[trans-4-(7H-Pyrrolo[3,2-e][1,2,3]triazolo[1,5-c]pyrimidin-1-yl)cyclohexyl]methylene}malononitrile trans-4-(7H-Pyrrolo[3,2-e][1,2,3]triazolo[1,5-c]pyrimidin-1-yl)cyclohexylcarbaldehyde (50.0 mg, 0.186 mmol) obtained in Synthetic Example[a] 78 and malononitrile (24.5 mg, 0.371 mmol) were mixed with acetic acid (3 mL), piperidine (18.3 μL, 0.186 mmol) and dichloromethane (2 mL) under cooling with ice and stirred for 1 hours. The reaction mixture was mixed anhydrous sodium sulfate and then stirred room temperature for 17 hours. After addition of water, the reaction mixture was extracted with ethyl acetate. The organic layer was washed with saturated aqueous sodium hydrogen carbonate, dried over anhydrous sodium sulfate and concentrated under reduced pressure. The residue was purified by silica gel column chromatography (hexane/acetone=2/1→3/2 (v/v)) to give the title compound as a colorless solid (36.3 mg, yield 62%).

Synthetic Example[a] 432

2-{[trans-4-(7H-Pyrrolo[3,2-e][1,2,3]triazolo[1,5-c]pyrimidin-1-yl)cyclohexyl]methyl}malononitrile 2-{[trans-4-(7H-Pyrrolo[3,2-e][1,2,3]triazolo[1,5-c]pyrimidin-1-yl)cyclohexyl]methylene}malononitrile (25.8 mg, 0.0812 mmol) in tetrahydrofuran (3 mL) was mixed with diethyl 1,4-dihydro-2,6-dimethylpyridine-3,5-dicarboxylate (30.8 mg, 0.122 mmol) and stirred at room temperature for 1 hours. After addition of water, the reaction mixture was extracted with ethyl acetate. The organic layer was washed with saturated aqueous ammonium chloride, dried over anhydrous sodium sulfate and concentrated under reduced pressure. The residue was purified by silica gel column chromatography (hexane/ethyl acetate=1/1→1/2→0/1 (v/v)) to give the title compound as a colorless solid (14.2 mg, yield 55%).

Synthetic Example[a] 433

1-(4-Methylenecyclohexyl)-7H-pyrrolo[3,2-e][1,2,3]triazolo[1,5-c]pyrimidine

1-[trans-4-(Iodomethyl)cyclohexyl]-7H-pyrrolo[3,2-e][1,2,3]triazolo[1,5-c]pyrimidine (15.0 mg, 0.0393 mmol) obtained in Synthetic Example[a] 367 in tetrahydrofuran (1 mL) was mixed with (trifluoromethyl)trimethylsilane (7.60 μL, 0.0512 mmol) and tetrabutylammonium fluoride tetrahydrofuran solution (1 M, 51.2 μL, 0.0512 mmol) under cooling with ice and then stirred at room temperature for 2 days. The reaction mixture was mixed with water, and the precipitate was collected by filtration. The resulting residue was purified by silica gel thin layer chromatography (ethyl acetate/hexane=1/1 (v/v)) to give the title compound as a colorless solid (3.80 mg, yield 38%).

Synthetic Example[a] 434

2-[4-(7H-Pyrrolo[3,2-e][1,2,3]triazolo[1,5-c]pyrimidin-1-yl)cyclohexylidene]acetonitrile Diethyl(cyanomethyl)phosphonate (37.0 μL, 0.235 mmol) in tetrahydrofuran (1 mL) was mixed with sodium hydride (55 wt % dispersion in mineral oil, 10.0 mg, 0.235 mmol) under cooling with ice and then stirred for 30 minutes. The reaction mixture was mixed with 4-(7H-pyrrolo[3,2-e][1,2,3]triazolo[1,5-c]pyrimidin-1-yl)cyclohexanone (20.0 mg, 0.0783 mmol) obtained in Synthetic Example[a] 82 and then stirred at room temperature for 30 minutes. After addition of water, the reaction mixture was extracted with ethyl acetate. The organic layer was washed with saturated aqueous sodium chloride, dried over anhydrous magnesium sulfate and concentrated under reduced pressure. The residue was purified by silica gel column chromatography (ethyl acetate/hexane=1/2→1/1→1/0 (v/v)) to give the title compound as a colorless solid (20.0 mg, yield 92%).

Synthetic Example[a] 435

435a: 2-[cis-4-(7H-Pyrrolo[3,2-e][1,2,3]triazolo[1,5-c]pyrimidin-1-yl)cyclohexyl]acetonitrile 435b: 2-[trans-4-(7H-Pyrrolo[3,2-e][1,2,3]triazolo[1,5-c]pyrimidin-1-yl)cyclohexyl]acetonitrile 2-[4-(7H-Pyrrolo[3,2-e][1,2,3]triazolo[1,5-c]pyrimidin-1-yl)cyclohexylidene]acetonitrile (20.0 g, 0.0720 mmol) in tetrahydrofuran (10 mL) were stirred with 5% palladium-carbon (10 mg) at room temperature for 4 hours under a hydrogen atmosphere. The reaction mixture was filtered, and the filtrate was concentrated under reduced pressure. The residue was purified by silica gel thin layer chromatography (hexane/ethyl acetate=1/1 (v/v)) to give 2-[cis-4-(7H-pyrrolo[3,2-e][1,2,3]triazolo[1,5-c]pyrimidin-1-yl)cyclohexyl]acetonitrile (Synthetic Example[a] 435a; colorless solid, 1.30 mg, yield 6%) in a less polar fraction and 2-[trans-4-(7H-pyrrolo[3,2-e][1,2,3]triazolo[1,5-c]pyrimidin-1-yl)cyclohexyl]acetonitrile (Synthetic Example[a] 435b; colorless solid, 3.40 mg, yield 17%) in a more polar fraction.

Synthetic Examples[a] 436 and 437

The reactions in Synthetic Example[a] 434 were carried out in substantially the same manners except that ethyl 2-(diethoxyphosphoryl) acetate or diethyl(1-cyanoethyl)phosphonate was used instead of diethyl(cyanomethyl)phosphonate to give the compounds of Synthetic Examples[a] 436 and 437. The names, morphologies and yields of the compounds synthesized are shown in Table[a] 46.

TABLE[a] 46

| Ex | Compound Name | Morphology | Yield |
|---|---|---|---|
| 436 | ethyl 2-[4-(7H-pyrrolo[3,2-c][1,2,3]triazolo[1,5-c]pyrimidin-1-yl)cyclohexylidene]acetate | colorless solid | 94% |
| 437 | 2-[4-(7H-pyrrolo[3,2-e][1,2,3]triazolo[1,5-c]pyrimidin-1-yl)cyclohexylidene]propanenitrile | colorless solid | 41% |

Synthetic Example[a] 438

Ethyl 2-[4-(7H-pyrrolo[3,2-e][1,2,3]triazolo[1,5-c]pyrimidin-1-yl)cyclohexyl]acetate The reactions in Synthetic Example[a] 435 were carried out in substantially the same manners except that ethyl 2-[4-(7H-pyrrolo[3,2-e][1,2,3]triazolo[1,5-c]pyrimidin-1-yl)cyclohexylidene]acetate obtained in Synthetic Example[a] 436 was used instead of 2-[4-(7H-pyrrolo[3,2-e][1,2,3]triazolo

[1,5-c]pyrimidin-1-yl)cyclohexylidene]acetonitrile to give the title compound as a colorless solid (cis/trans mixture; 29.0 mg, yield 51%).

Synthetic Example[a] 439

439a: 2-[cis-4-(7H-Pyrrolo[3,2-e][1,2,3]triazolo[1,5-c]pyrimidin-1-yl)cyclohexyl]propanenitrile 439b: 2-[trans-4-(7H-Pyrrolo[3,2-e][1,2,3]triazolo[1,5-c]pyrimidin-1-yl)cyclohexyl]propanenitrile The reactions in Synthetic Example[a] 435 were carried out in substantially the same manners except that 2-[4-(7H-pyrrolo[3,2-e][1,2,3]triazolo[1,5-c]pyrimidin-1-yl)cyclohexylidene]propanenitrile obtained in Synthetic Example[a] 437 was used instead of 2-[4-(7H-pyrrolo[3,2-e][1,2,3]triazolo[1,5-c]pyrimidin-1-yl)cyclohexylidene]acetonitrile to give 2-[cis-4-(7H-pyrrolo[3,2-e][1,2,3]triazolo[1,5-c]pyrimidin-1-yl)cyclohexyl]propanenitrile (Synthetic Example[a] 439a; colorless solid, 0.750 mg, yield 7%) in a less polar fraction and 2-[trans-4-(7H-pyrrolo[3,2-e][1,2,3]triazolo[1,5-c]pyrimidin-1-yl)cyclohexyl]propanenitrile (Synthetic Example[a] 439 b; colorless solid, 2.00 mg, yield 19%) in a more polar fraction.

Synthetic Example[a] 440

(E)-3-[trans-4-(7H-Pyrrolo[3,2-e][1,2,3]triazolo[1,5-c]pyrimidin-1-yl)cyclohexyl]acrylonitrile The reactions in Synthetic Example[a] 434 were carried out in substantially the same manners except that trans-4-(7H-pyrrolo[3,2-e][1,2,3]triazolo[1,5-c]pyrimidin-1-yl)cyclohexanecarbaldehyde (30.0 mg, 0.111 mmol) obtained in Synthetic Example[a] 78 was used instead of 4-(7H-pyrrolo[3,2-e][1,2,3]triazolo[1,5-c]pyrimidin-1-yl)cyclohexanone to give the title compound as a colorless solid (3.60 mg, yield 7%).

Synthetic Example[a] 441

3-[trans-4-(7H-Pyrrolo[3,2-e][1,2,3]triazolo[1,5-c]pyrimidin-1-yl)cyclohexyl]propanenitrile The reactions in Synthetic Example[a] 438 were carried out in substantially the same manners except that (E)-3-[trans-4-(7H-pyrrolo[3,2-e][1,2,3]triazolo[1,5-c]pyrimidin-1-yl)cyclohexyl]acrylonitrile obtained in Synthetic Example[a] 440 was used instead of ethyl 2-[4-(7H-pyrrolo[3,2-e][1,2,3]triazolo[1,5-c]pyrimidin-1-yl)cyclohexylidene]acetate to give the title compound as a colorless solid (7.30 mg, yield 72%).

Synthetic Example[a] 442

442a: 2-[cis-4-(7H-Pyrrolo[3,2-e][1,2,3]triazolo[1,5-c]pyrimidin-1-yl)cyclohexyl]-N-2,2,2-trifluoroethylacetamide 442b: 2-[trans-4-(7H-Pyrrolo[3,2-e][1,2,3]triazolo[1,5-c]pyrimidin-1-yl)cyclohexyl]-N-2,2,2-trifluoroethylacetamide Ethyl 2-[4-(7H-pyrrolo[3,2-e][1,2,3]triazolo[1,5-c]pyrimidin-1-yl)cyclohexyl]acetate (10.0 mg, 0.0305 mmol) obtained in Synthetic Example[a] 438 in tetrahydrofuran (1 mL) was mixed with ethanol (0.5 mL), water (0.25 mL) and 1 M aqueous lithium hydroxide (60 μL, 0.0611 mmol) and stirred at room temperature for 4 hours. The reaction mixture was mixed with 1 M hydrochloric acid and concentrated under reduced pressure. The residue was dissolved in N,N-dimethylformamide (2 mL) and stirred with O-(7-azabenzotriazol-1-yl)-N,N,N',N'-tetramethyluronium hexafluorophosphate (23.2 mg, 0.0610 mmol), N,N-diisopropylethylamine (21.0 μL, 0.122 mmol) and 2,2,2-trifluoroethanamine hydrochloride (8.30 mg, 0.0610 mmol) at room temperature for 13 hours. After addition of saturated aqueous ammonium chloride, the reaction mixture was extracted with ethyl acetate. The organic layer was washed with saturated aqueous sodium chloride, dried over anhydrous magnesium sulfate and concentrated under reduced pressure. The residue was purified by silica gel thin layer chromatography (ethyl acetate) to give 2-[cis-4-(7H-pyrrolo[3,2-e][1,2,3]triazolo[1,5-c]pyrimidin-1-yl)cyclohexyl]-N-(2,2,2-trifluoroethyl)acetamide (Synthetic Example[a] 442a; colorless solid, 5.80 mg, yield 50%) in a less polar fraction and 2-[trans-4-(7H-Pyrrolo[3,2-e][1,2,3]triazolo[1,5-c]pyrimidin-1-yl)cyclohexyl]-N-(2,2,2-trifluoroethyl)acetamide (Synthetic Example[a] 442b; colorless solid, 3.10 mg, yield 27%) in a more polar fraction.

Synthetic Example[a] 443

443a: 2-[cis-4-(7H-Pyrrolo[3,2-e][1,2,3]triazolo[1,5-c]pyrimidin-1-yl)cyclohexyl]-N-(cyanomethyl)acetamide 443b: 2-[trans-4-(7H-Pyrrolo[3,2-e][1,2,3]triazolo[1,5-c]pyrimidin-1-yl)cyclohexyl]-N-(cyanomethyl)acetamide The reactions in Synthetic Example[a] 442 were carried out in substantially the same manners except that 2-aminoacetonitrile hydrochloride was used instead of 2,2,2-trifluoroethanamine hydrochloride to give 2-[cis-4-(7H-pyrrolo[3,2-e][1,2,3]triazolo[1,5-c]pyrimidin-1-yl)cyclohexyl]-N-(cyanomethyl)acetamide (Synthetic Example[a] 443a; pale brown solid, 7.00 mg, yield 47%) in a less polar fraction and 2-[trans-4-(7H-pyrrolo[3,2-e][1,2,3]triazolo[1,5-c]pyrimidin-1-yl)cyclohexyl]-N-(cyanomethyl)acetamide (Synthetic Example[a] 443b; pale brown solid, 3.80 mg, yield 25%) in a more polar fraction.

Synthetic Example[a] 444

6-(7H-Pyrrolo[3,2-e][1,2,3]triazolo[1,5-c]pyrimidin-1-yl)spiro[2.5]octane-1-carbonitrile Trimethylsulfonium iodide (59.0 μL, 0.269 mmol) in dimethyl sulfoxide (1 mL) was stirred with sodium hydride (55 wt % dispersion in mineral oil, 12.0 mg, 0.269 mmol) at room temperature for 30 minutes. The reaction mixture was mixed with 2-[4-(7H-pyrrolo[3,2-e][1,2,3]triazolo[1,5-c]pyrimidin-1-yl)cyclohexylidene]acetonitrile (15.0 mg, 0.0539 mmol) obtained in Synthetic Example[a] 434 and then stirred at room temperature for 15 hours. After addition of water, the reaction mixture was extracted with ethyl acetate. The organic layer was washed with saturated aqueous sodium chloride, dried over anhydrous magnesium sulfate and concentrated under reduced pressure. The residue was purified by silica gel column chromatography (ethyl acetate/hexane=1/1 (v/v)) to give the title compound as a colorless solid (5.80 mg, yield 37%).

Synthetic Example[a] 445

3-(7H-Pyrrolo[3,2-e][1,2,3]triazolo[1,5-c]pyrimidin-1-yl)adamantan-1-ol (3-Hydroxyadamantan-1-yl)(7H-pyrrolo[2,3-d]pyrimidin-4-yl)methanone (22.5 mg, 0.0757 mmol) obtained in Reference Synthetic Example[a] 141 in methanol (1.5 mL) was mixed with hydrazine hydrate (0.141 mL, 2.27 mmol) and then stirred at 80° C. for 2 hours. The reaction mixture was mixed with hydrazine hydrate (0.118 mL, 1.89 mmol) and acetic acid (1 drop) and stirred at 80° C. for 2 hours. The reaction mixture was mixed with ethyl acetate, washed with water and saturated sodium chloride. The organic layer was dried over anhydrous sodium sulfate and concentrated under reduced pressure. The residue was dissolved in chloroform (1.5 mL) and mixed with manganese(IV) oxide (32.9 mg, 0.379 mmol). The reaction mixture was stirred at 70° C. for 6 hours. The reaction mixture was filtered, and the filtrate was concentrated under reduced pressure. The residue was purified by silica gel thin layer chromatography (ethyl acetate) and further by silica gel thin layer chromatography (NH-PLC05 plate manufactured by Fuji Silysia Chemical Ltd.: ethyl acetate/hexane=15/1) to give the title compound as a colorless solid (3.30 mg, yield 14%).

The structural formulae of the compounds obtained the Reference Synthetic Examples[a] and Synthetic Examples[a] are shown below in Tables[a] 47 to 80. The physical property data on the compounds obtained the Reference Synthetic Examples[a] and Synthetic Examples[a] are shown below in Tables[a] 81 to 151.

TABLE[a] 47

| Rf | Structure |
|---|---|
| 1 | 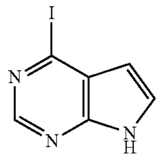 |
| 2 | 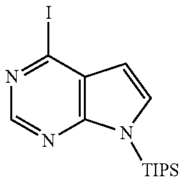 |
| 3 | 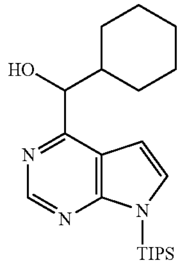 racemate |

TABLE[a] 47-continued

| Rf | Structure |
|---|---|
| 4 | 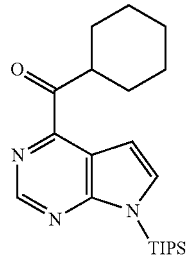 |
| 5 | 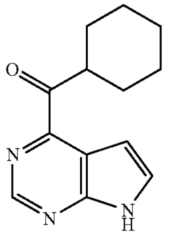 [SMILES: O=C(c1ncnc2[nH]ccc12)C1CCCCC1] |
| 6 | 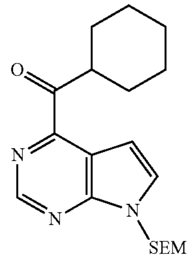 [SMILES: C[Si](C)(C)CCOCn1ccc2c(C(=O)C3CCCCC3)ncnc21] |
| 7 | 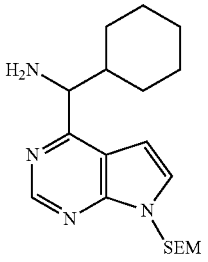 racemate |
| 8 | 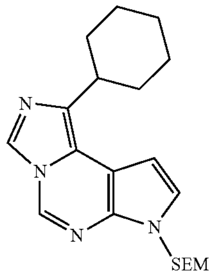 [SMILES: C[Si](C)(C)CCOCn1ccc2c1ncn1cnc(C3CCCCC3)c21] |
| 9 | 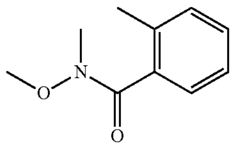 |

TABLE[a] 47-continued
| Rf | Structure |
|---|---|
| 10 | 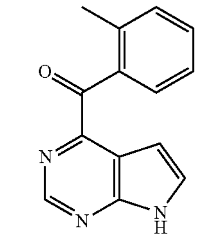 [SMILES: Cc1ccccc1C(=O)c1ncnc2[nH]ccc12] |
| 11 | 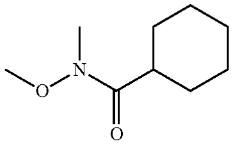 |
| 12 | 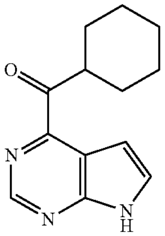 [SMILES: O=C(c1ncnc2[nH]ccc12)C1CCCCC1] |
| 13 | 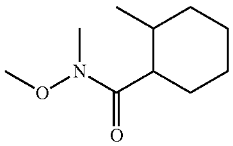 diastereomixture |
| 14 | 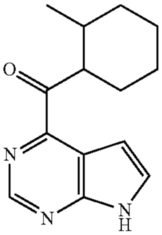 diastereomixture |
| 15 | 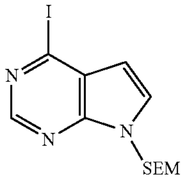 [SMILES: C[Si](C)(C)CCOCn1ccc2c(I)ncnc21] |
| 16 | 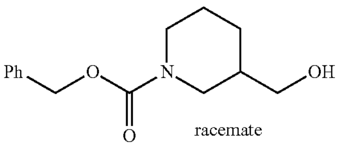 [SMILES: O=C(OCc1ccccc1)N1CCCC(CO)C1] racemate |
TABLE[a] 47-continued
| Rf | Structure |
|---|---|
| 17 | 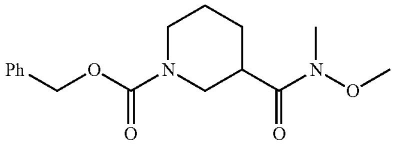 racemate |
| 18 | 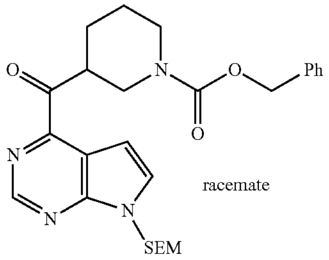 [SMILES: C[Si](C)(C)CCOCn1ccc2c(C(=O)C3CCCN(C(=O)OCc4ccccc4)C3)ncnc21] racemate |
| 19 | 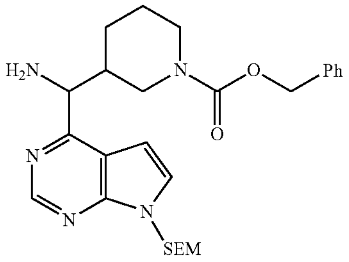 diastereomixture |
| 20 | 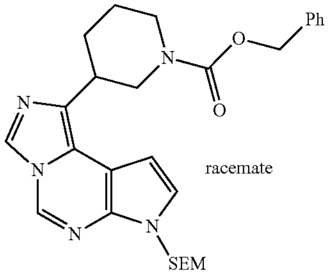 [SMILES: C[Si](C)(C)CCOCn1ccc2c1ncn1cnc(C3CCCN(C(=O)OCc4ccccc4)C3)c21] racemate |
| 21 | 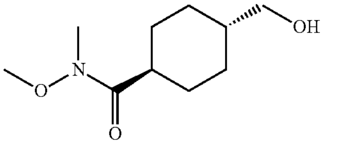 |
| 22 | 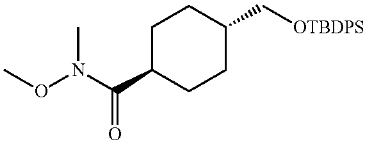 |
| 23 | 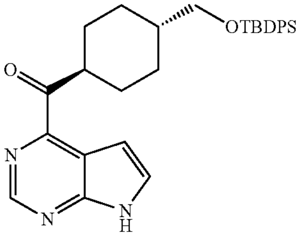 |

TABLE[a] 47-continued
| Rf | Structure |
|---|---|
| 24 | 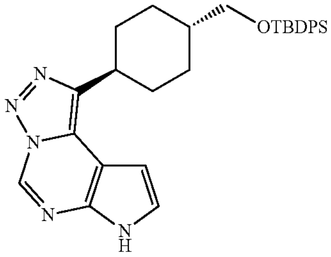 |
TABLE[a] 48
| Rf | Structure |
|---|---|
| 25 | 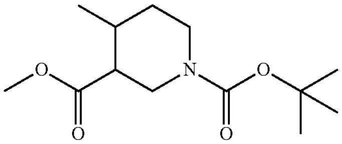 diastereomixture |
| 26 | 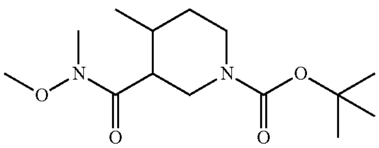 diastereomixture |
| 27 | 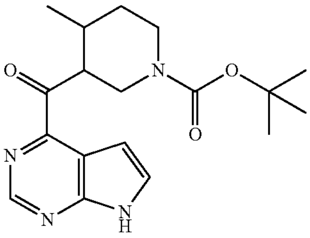 diastereomixture |
| 28 | 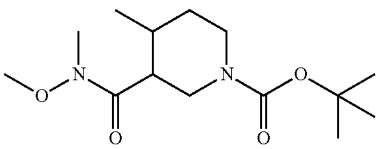 racemate |
| 29 | 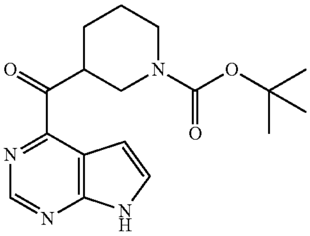 racemate |
TABLE[a] 48-continued
| Rf | Structure |
|---|---|
| 30 | 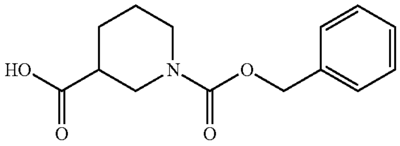 racemate |
| 31 | 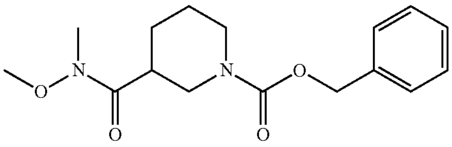 racemate |
| 32 | 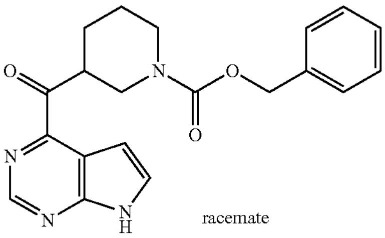 [SMILES: O=C(c1ncnc2[nH]ccc12)C1CCCN(C(=O)OCc2ccccc2)C1] racemate |
| 33 | 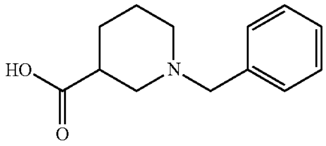 racemate |
| 34 | 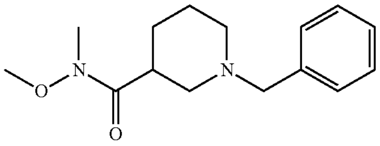 racemate |
| 35 | 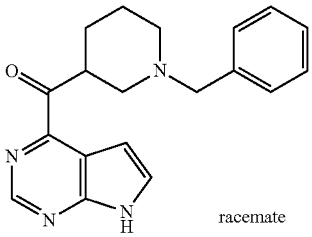 [SMILES: O=C(c1ncnc2[nH]ccc12)C1CCCN(Cc2ccccc2)C1] racemate |
| 36 | 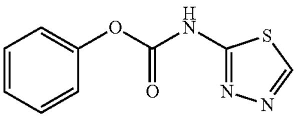 [SMILES: O=C(Nc1nncs1)Oc1ccccc1] |
| 37 | 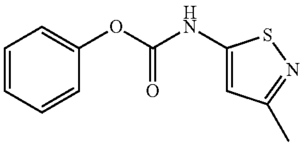 [SMILES: Cc1cc(NC(=O)Oc2ccccc2)sn1] |

TABLE[a] 48-continued
| Rf | Structure |
|---|---|
| 38 | 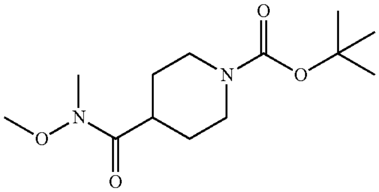 [SMILES: CON(C)C(=O)C1CCN(C(=O)OC(C)(C)C)CC1] |
| 39 | 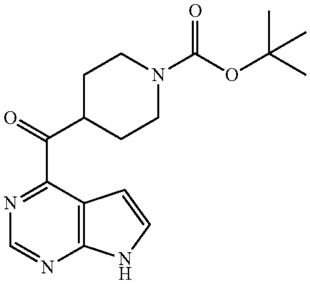 [SMILES: CC(C)(C)OC(=O)N1CCC(C(=O)c2ncnc3[nH]ccc23)CC1] |
| 40 | 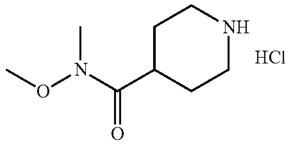 |
| 41 | 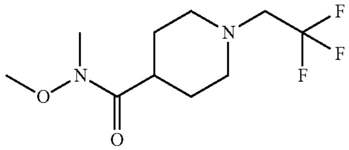 [SMILES: CON(C)C(=O)C1CCN(CC(F)(F)F)CC1] |
| 42 | 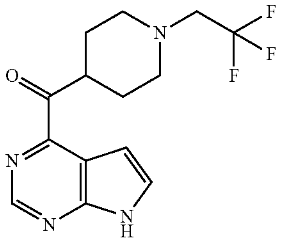 [SMILES: O=C(c1ncnc2[nH]ccc12)C1CCN(CC(F)(F)F)CC1] |
| 43 | 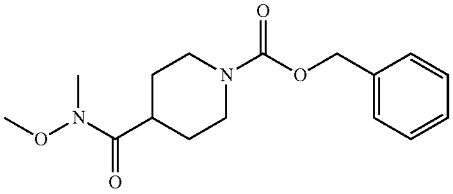 [SMILES: CON(C)C(=O)C1CCN(C(=O)OCc2ccccc2)CC1] |
| 44 | 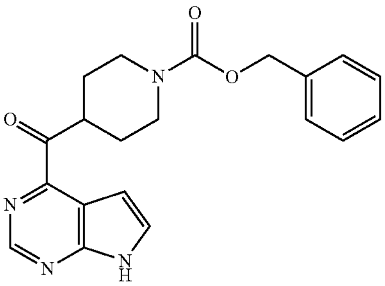 [SMILES: O=C(c1ncnc2[nH]ccc12)C1CCN(C(=O)OCc2ccccc2)CC1] |
| 45 | 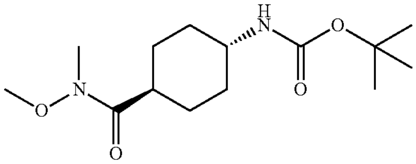 [SMILES: CON(C)C(=O)[C@H]1CC[C@H](NC(=O)OC(C)(C)C)CC1] |
TABLE[a] 49
| Rf | Structure |
|---|---|
| 46 | 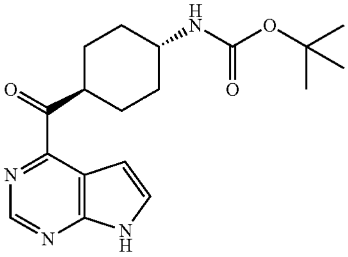 [SMILES: CC(C)(C)OC(=O)N[C@H]1CC[C@H](C(=O)c2ncnc3[nH]ccc23)CC1] |
| 47 | 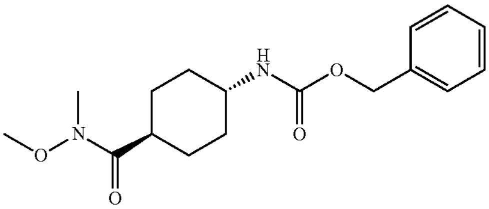 [SMILES: CON(C)C(=O)[C@H]1CC[C@H](NC(=O)OCc2ccccc2)CC1] |
| 48 | 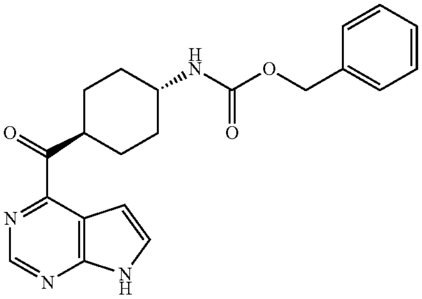 [SMILES: O=C(N[C@H]1CC[C@H](C(=O)c2ncnc3[nH]ccc23)CC1)OCc1ccccc1] |
| 49 | 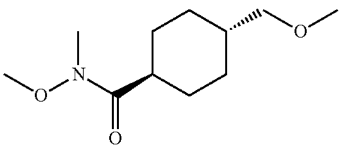 |
| 50 | 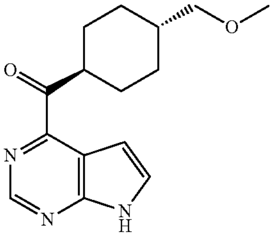 [SMILES: COC[C@H]1CC[C@H](C(=O)c2ncnc3[nH]ccc23)CC1] |

TABLE[a] 49-continued
| Rf | Structure |
|---|---|
| 51 | 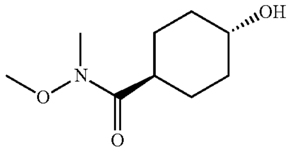 |
| 52 | 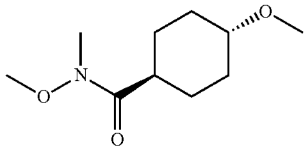 |
| 53 | 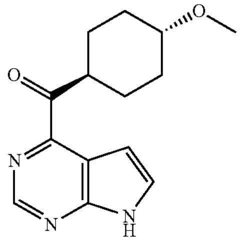 [SMILES: CO[C@H]1CC[C@H](C(=O)c2ncnc3[nH]ccc23)CC1] |
| 54 | 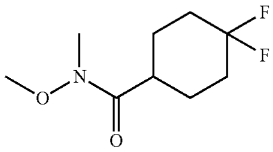 |
| 55 | 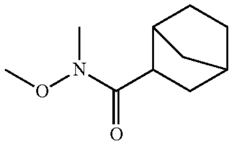 diastereomixture |
| 56 | 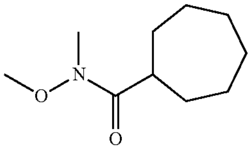 |
| 57 | 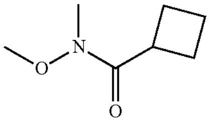 |
| 58 | 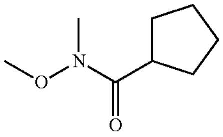 |
| 59 | 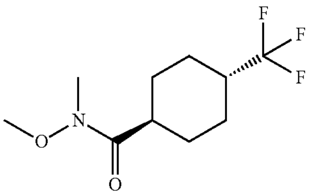 [SMILES: CON(C)C(=O)[C@H]1CC[C@H](C(F)(F)F)CC1] |
TABLE[a] 49-continued
| Rf | Structure |
|---|---|
| 60 | 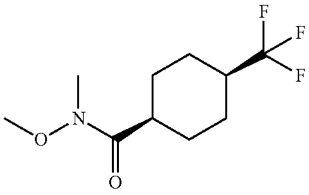 [SMILES: CON(C)C(=O)[C@H]1CC[C@@H](C(F)(F)F)CC1] |
| 61 | 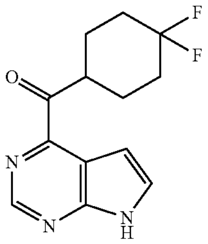 [SMILES: O=C(c1ncnc2[nH]ccc12)C1CCC(F)(F)CC1] |
| 62 | 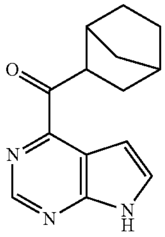 diastereomixture |
| 63 | 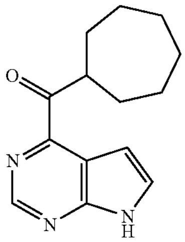 [SMILES: O=C(c1ncnc2[nH]ccc12)C1CCCCCC1] |
| 64 | 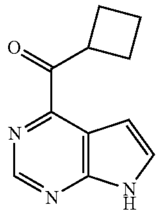 [SMILES: O=C(c1ncnc2[nH]ccc12)C1CCC1] |
| 65 | 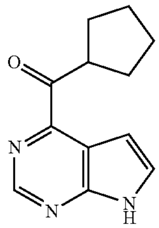 [SMILES: O=C(c1ncnc2[nH]ccc12)C1CCCC1] |

TABLE[a] 49-continued
| Rf | Structure |
|---|---|
| 66 | 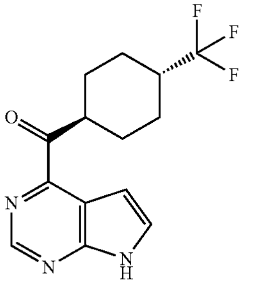 [SMILES: O=C(c1ncnc2[nH]ccc12)[C@H]1CC[C@H](C(F)(F)F)CC1] |
| 67 | 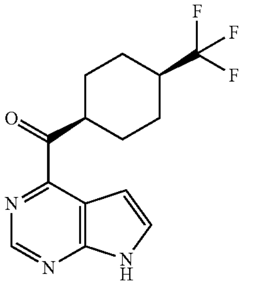 [SMILES: O=C(c1ncnc2[nH]ccc12)[C@H]1CC[C@@H](C(F)(F)F)CC1] |
| 68 | 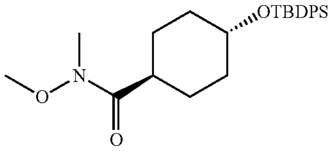 |
| 69 | 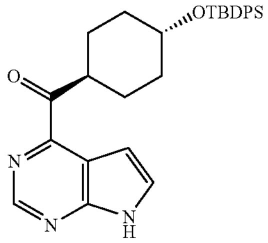 |
TABLE[a] 50
| Rf | Structure |
|---|---|
| 70 | 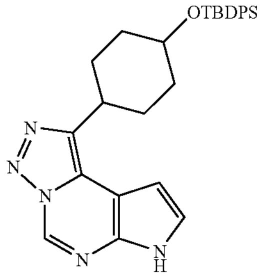 cis/trans mixture |
TABLE[a] 50-continued
| Rf | Structure |
|---|---|
| 71 | 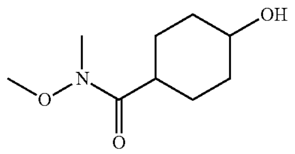 cis/trans mixture |
| 72 | 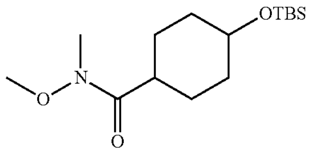 cis/trans mixture |
| 73 | 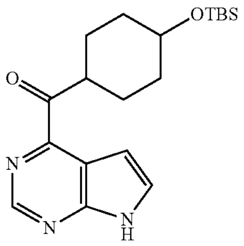 cis/trans mixture |
| 74 | 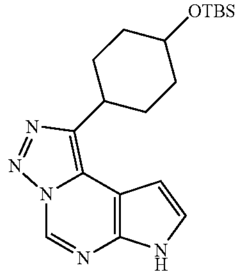 cis/trans mixture |
| 75 | 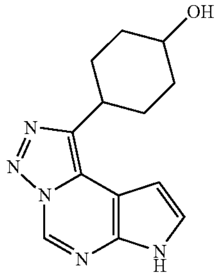 cis/trans mixture |

TABLE[a] 50-continued
| Rf | Structure |
|---|---|
| 76 | 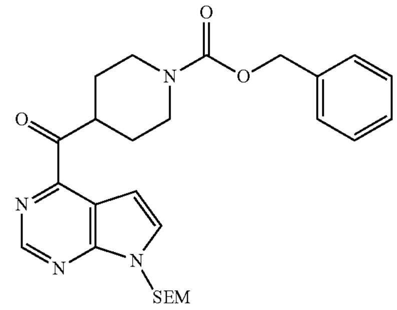 [SMILES: C[Si](C)(C)CCOCn1ccc2c(C(=O)C3CCN(C(=O)OCc4ccccc4)CC3)ncnc21] |
| 77 | 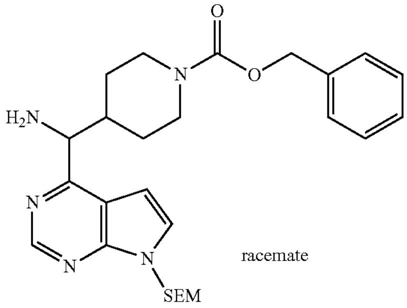 [SMILES: C[Si](C)(C)CCOCn1ccc2c(C(N)C3CCN(C(=O)OCc4ccccc4)CC3)ncnc21] racemate |
| 78 | 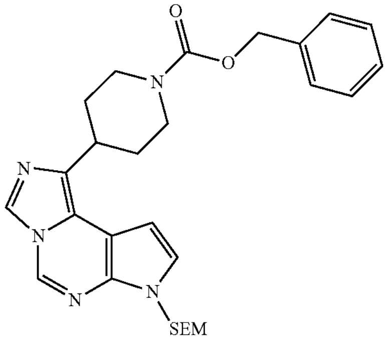 [SMILES: C[Si](C)(C)CCOCn1ccc2c1ncn1cnc(C3CCN(C(=O)OCc4ccccc4)CC3)c21] |
| 79 | 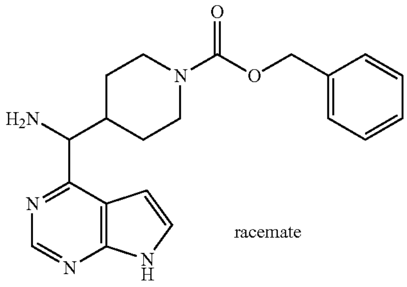 [SMILES: NC(c1ncnc2[nH]ccc12)C1CCN(C(=O)OCc2ccccc2)CC1] racemate |
| 80 | 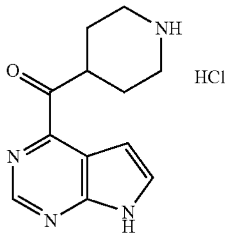 [SMILES: O=C(c1ncnc2[nH]ccc12)C1CCNCC1 ; Cl] HCl |
| 81 | 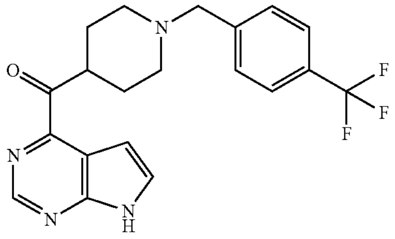 [SMILES: O=C(c1ncnc2[nH]ccc12)C1CCN(Cc2ccc(C(F)(F)F)cc2)CC1] |
| 82 | 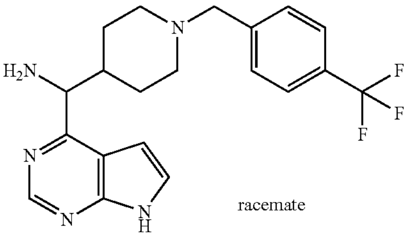 [SMILES: NC(c1ncnc2[nH]ccc12)C1CCN(Cc2ccc(C(F)(F)F)cc2)CC1] racemate |
| 83 | 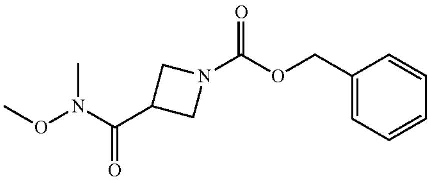 [SMILES: CON(C)C(=O)C1CN(C(=O)OCc2ccccc2)C1] |
| 84 | 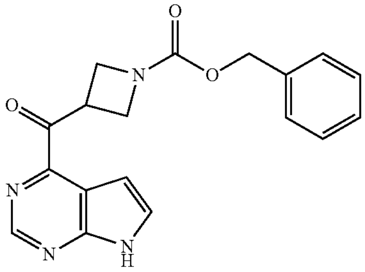 [SMILES: O=C(c1ncnc2[nH]ccc12)C1CN(C(=O)OCc2ccccc2)C1] |
| 85 | 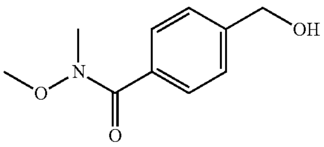 |
| 86 | 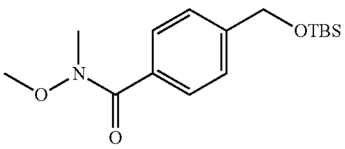 [SMILES: CON(C)C(=O)c1ccc(CO[Si](C)(C)C(C)(C)C)cc1] |
| 87 | 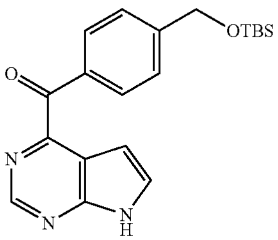 [SMILES: CC(C)(C)[Si](C)(C)OCc1ccc(C(=O)c2ncnc3[nH]ccc23)cc1] |

TABLE[a] 51
| Rf | Structure |
|---|---|
| 88 | 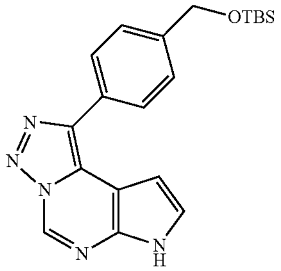 [SMILES: CC(C)(C)[Si](C)(C)OCc1ccc(-c2nnn3cnc4[nH]ccc4c23)cc1] |
| 89 | 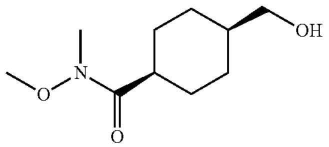 |
| 90 | 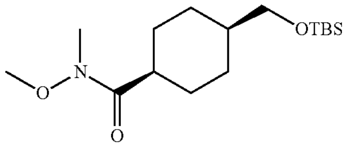 [SMILES: CON(C)C(=O)[C@H]1CC[C@@H](CO[Si](C)(C)C(C)(C)C)CC1] |
| 91 | 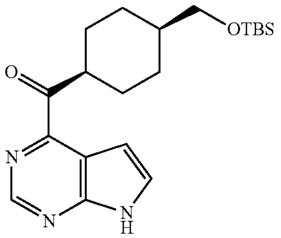 [SMILES: CC(C)(C)[Si](C)(C)OC[C@H]1CC[C@@H](C(=O)c2ncnc3[nH]ccc23)CC1] |
| 92 | 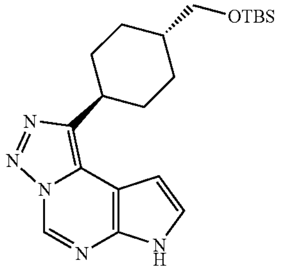 [SMILES: CC(C)(C)[Si](C)(C)OC[C@H]1CC[C@H](c2nnn3cnc4[nH]ccc4c23)CC1] |
| 93 | 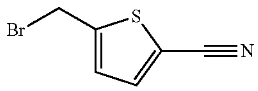 |
| 94 | 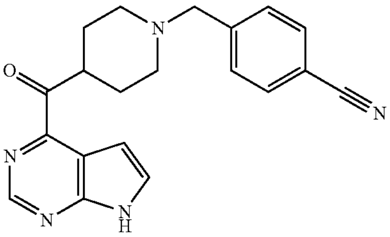 [SMILES: N#Cc1ccc(CN2CCC(C(=O)c3ncnc4[nH]ccc34)CC2)cc1] |
TABLE[a] 51-continued
| Rf | Structure |
|---|---|
| 95 | 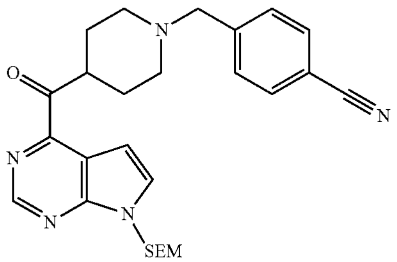 [SMILES: C[Si](C)(C)CCOCn1ccc2c(C(=O)C3CCN(Cc4ccc(C#N)cc4)CC3)ncnc21] |
| 96 | 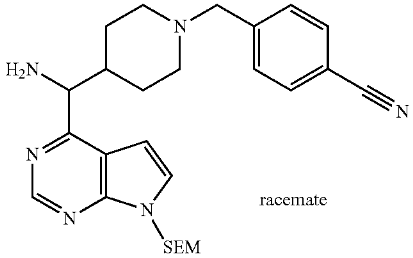 [SMILES: C[Si](C)(C)CCOCn1ccc2c(C(N)C3CCN(Cc4ccc(C#N)cc4)CC3)ncnc21] racemate |
| 97 | 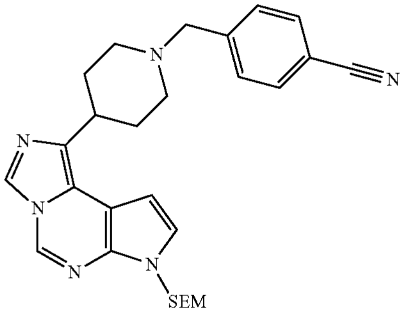 [SMILES: C[Si](C)(C)CCOCn1ccc2c1ncn1cnc(C3CCN(Cc4ccc(C#N)cc4)CC3)c21] |
| 98 | 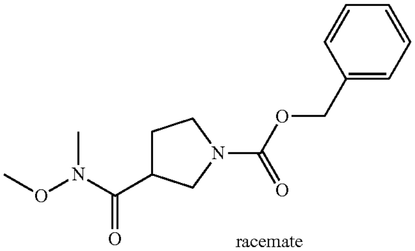 [SMILES: CON(C)C(=O)C1CCN(C(=O)OCc2ccccc2)C1] racemate |
| 99 | 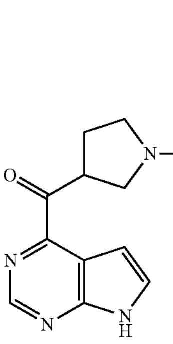 racemate |

TABLE[a] 51-continued
| Rf | Structure |
|---|---|
| 100 | 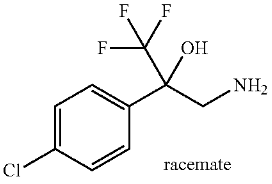 [SMILES: NCC(O)(c1ccc(Cl)cc1)C(F)(F)F] racemate |
| 101 | 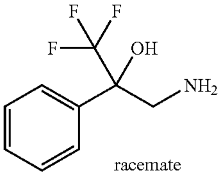 [SMILES: NCC(O)(c1ccccc1)C(F)(F)F] racemate |
| 102 | 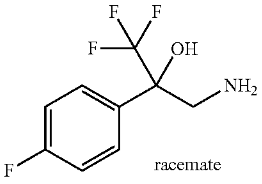 [SMILES: NCC(O)(c1ccc(F)cc1)C(F)(F)F] racemate |
| 103 | 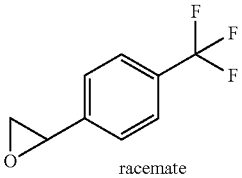 [SMILES: FC(F)(F)c1ccc(C2CO2)cc1] racemate |
| 104 | 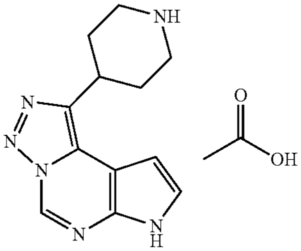 |
TABLE[a] 52
| Rf | Structure |
|---|---|
| 105 | 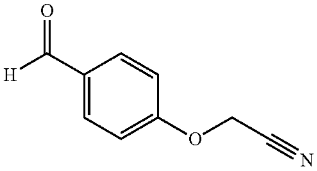 [SMILES: N#CCOc1ccc(C=O)cc1] |
| 106 | 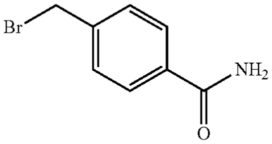 [SMILES: NC(=O)c1ccc(CBr)cc1] |
TABLE[a] 52-continued
| Rf | Structure |
|---|---|
| 107 | 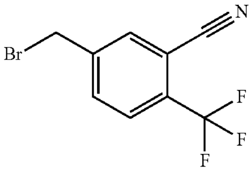 [SMILES: N#Cc1cc(CBr)ccc1C(F)(F)F] |
| 108 | 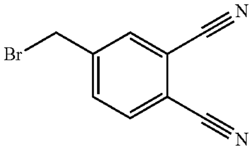 [SMILES: N#Cc1ccc(CBr)cc1C#N] |
| 109 | 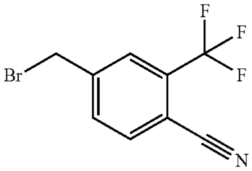 [SMILES: N#Cc1ccc(CBr)cc1C(F)(F)F] |
| 110 | 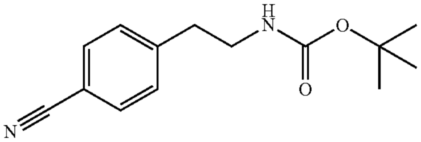 [SMILES: CC(C)(C)OC(=O)NCCc1ccc(C#N)cc1] |
| 111 | 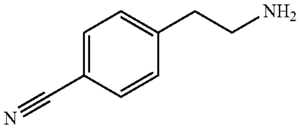 [SMILES: N#Cc1ccc(CCN)cc1] |
| 112 | 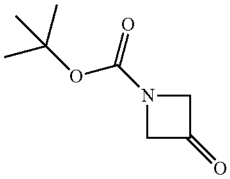 |
| 113 | 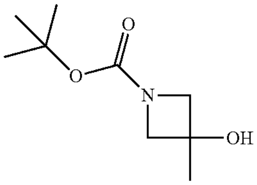 |
| 114 | 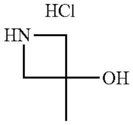 |
| 115 | 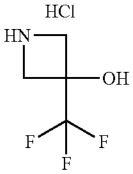 |

TABLE[a] 52-continued
| Rf | Structure |
|---|---|
| 116 | 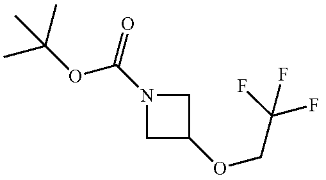 [SMILES: CC(C)(C)OC(=O)N1CC(OCC(F)(F)F)C1] |
| 117 | 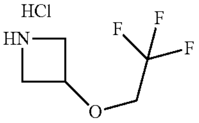 |
| 118 | 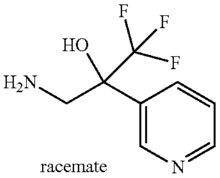 [SMILES: NCC(O)(c1cccnc1)C(F)(F)F] racemate |
| 119 | 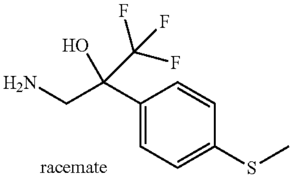 [SMILES: CSc1ccc(C(O)(CN)C(F)(F)F)cc1] racemate |
| 120 | 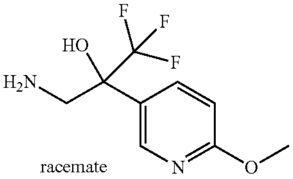 [SMILES: COc1ccc(C(O)(CN)C(F)(F)F)cn1] racemate |
| 121 | 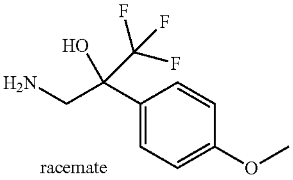 [SMILES: COc1ccc(C(O)(CN)C(F)(F)F)cc1] racemate |
| 122 | 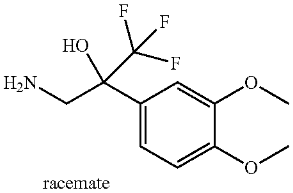 [SMILES: COc1ccc(C(O)(CN)C(F)(F)F)cc1OC] racemate |
| 123 | 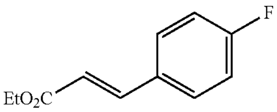 |
| 124 | 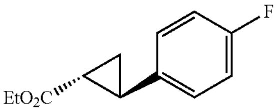 diastereomixture |
| 125 | 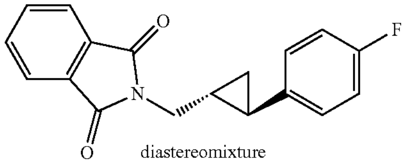 [SMILES: O=C1c2ccccc2C(=O)N1C[C@@H]1C[C@H]1c1ccc(F)cc1] diastereomixture |
| 126 | 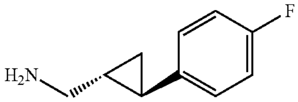 diastereomixture |
| 127 | 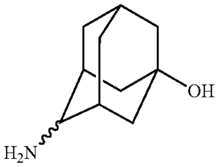 racemate |
| 128a | 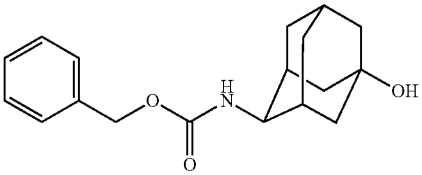 [SMILES: O=C(NC1C2CC3CC1CC(O)(C3)C2)OCc1ccccc1] |
| 128b | 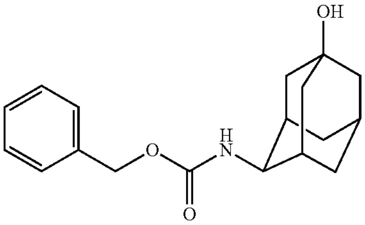 [SMILES: O=C(NC1C2CC3CC1CC(O)(C3)C2)OCc1ccccc1] |
| 129 | 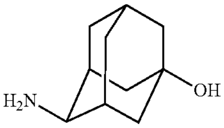 |
| 130 | 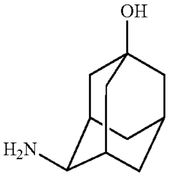 |
| 131 | 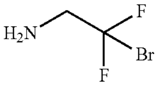 HCl |
| 132 | 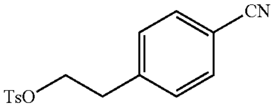 [SMILES: Cc1ccc(S(=O)(=O)OCCc2ccc(C#N)cc2)cc1] |

TABLE[a] 52-continued
| Rf | Structure |
|---|---|
| 133 | 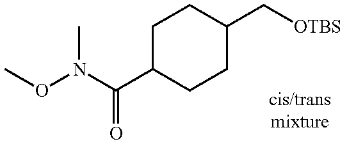 [SMILES: CON(C)C(=O)C1CCC(CO[Si](C)(C)C(C)(C)C)CC1] cis/trans mixture |
TABLE[a] 53
| Rf | Structure |
|---|---|
| 134 | 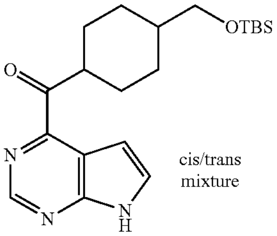 [SMILES: CC(C)(C)[Si](C)(C)OCC1CCC(C(=O)c2ncnc3[nH]ccc23)CC1] cis/trans mixture |
| 135a | 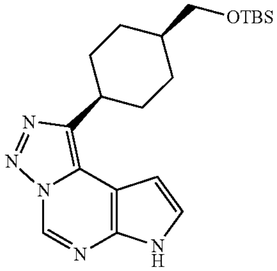 [SMILES: CC(C)(C)[Si](C)(C)OC[C@H]1CC[C@@H](c2nnn3cnc4[nH]ccc4c23)CC1] |
| 135b | 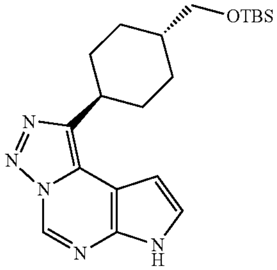 [SMILES: CC(C)(C)[Si](C)(C)OC[C@H]1CC[C@H](c2nnn3cnc4[nH]ccc4c23)CC1] |
| 136 | 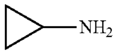 HCl |
| 137 | 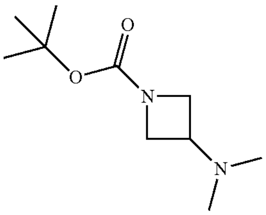 |
TABLE[a] 53-continued
| Rf | Structure |
|---|---|
| 138 | 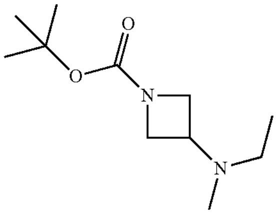 |
| 139 | 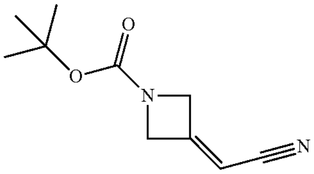 |
| 140 | 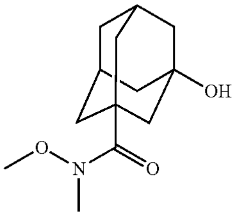 [SMILES: CON(C)C(=O)C12CC3CC(CC(O)(C3)C1)C2] |
| 141 | 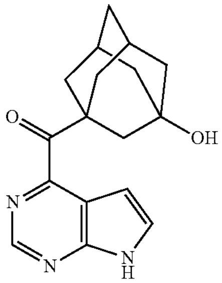 [SMILES: O=C(c1ncnc2[nH]ccc12)C12CC3CC(CC(O)(C3)C1)C2] |
TABLE[a] 54
| Ex | Structure |
|---|---|
| 1 | 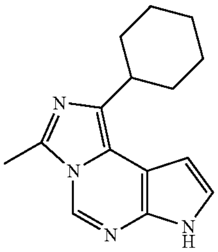 [SMILES: Cc1nc(C2CCCCC2)c2c3cc[nH]c3ncn12] |
| 2 | 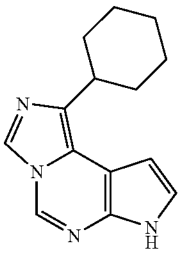 [SMILES: c1cc2c(ncn3cnc(C4CCCCC4)c23)[nH]1] |

TABLE[a] 54-continued
| Ex | Structure |
|---|---|
| 3 | 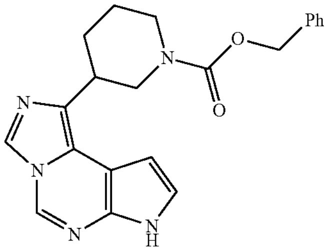 [SMILES: O=C(OCc1ccccc1)N1CCCC(c2ncn3cnc4[nH]ccc4c23)C1] racemate |
| 4 | 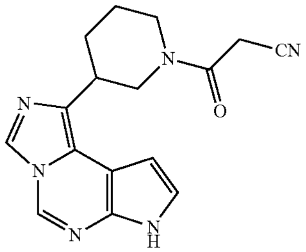 [SMILES: N#CCC(=O)N1CCCC(c2ncn3cnc4[nH]ccc4c23)C1] racemate |
| 5 | 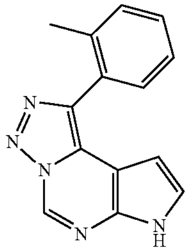 [SMILES: Cc1ccccc1-c1nnn2cnc3[nH]ccc3c12] |
| 6 | 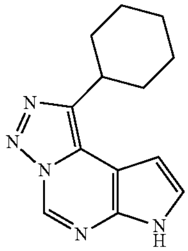 [SMILES: c1cc2c(ncn3nnc(C4CCCCC4)c23)[nH]1] |
| 7 | 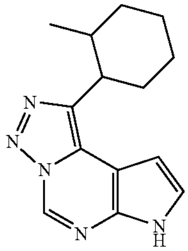 [SMILES: CC1CCCCC1c1nnn2cnc3[nH]ccc3c12] diastereomixture |
| 8 | 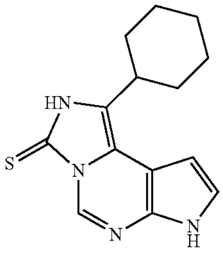 [SMILES: S=c1[nH]c(C2CCCCC2)c2c3cc[nH]c3ncn12] |
| 9 | 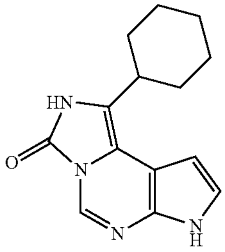 [SMILES: O=c1[nH]c(C2CCCCC2)c2c3cc[nH]c3ncn12] |
| 10 | 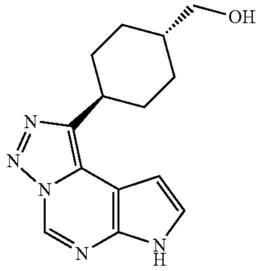 [SMILES: OC[C@H]1CC[C@H](c2nnn3cnc4[nH]ccc4c23)CC1] |
TABLE[a] 55
| Ex | Structure |
|---|---|
| 11 | 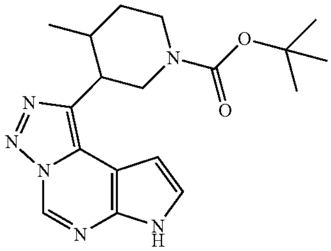 [SMILES: CC1CCN(C(=O)OC(C)(C)C)CC1c1nnn2cnc3[nH]ccc3c12] diastereomixture |
| 12 | 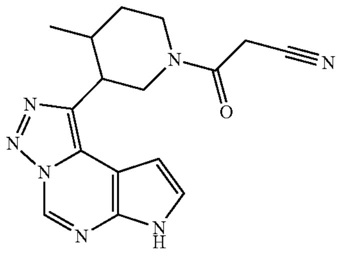 [SMILES: CC1CCN(C(=O)CC#N)CC1c1nnn2cnc3[nH]ccc3c12] diastereomixture |

TABLE[a] 55-continued
| Ex | Structure |
|---|---|
| 13 | 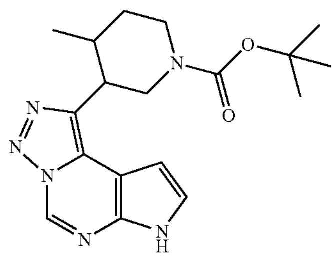 [SMILES: CC1CCN(C(=O)OC(C)(C)C)CC1c1nnn2cnc3[nH]ccc3c12] racemate |
| 14 | 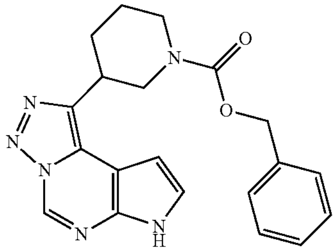 [SMILES: O=C(OCc1ccccc1)N1CCCC(c2nnn3cnc4[nH]ccc4c23)C1] racemate |
| 15 | 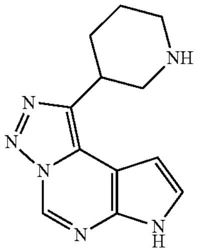 [SMILES: c1cc2c(ncn3nnc(C4CCCNC4)c23)[nH]1] racemate |
| 16 | 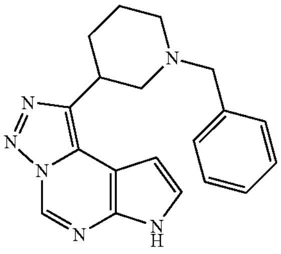 [SMILES: c1ccc(CN2CCCC(c3nnn4cnc5[nH]ccc5c34)C2)cc1] racemate |
| 17 | 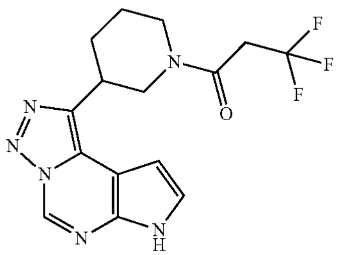 [SMILES: O=C(CC(F)(F)F)N1CCCC(c2nnn3cnc4[nH]ccc4c23)C1] racemate |
| 18 | 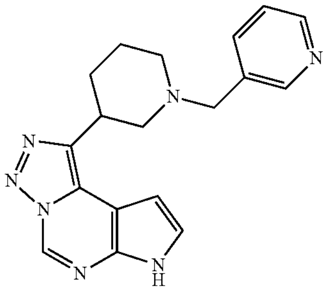 [SMILES: c1cncc(CN2CCCC(c3nnn4cnc5[nH]ccc5c34)C2)c1] racemate |
| 19 | 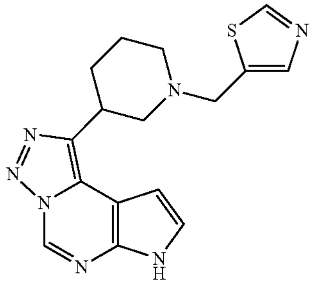 [SMILES: c1cc2c(ncn3nnc(C4CCCN(Cc5cncs5)C4)c23)[nH]1] racemate |
| 20 | 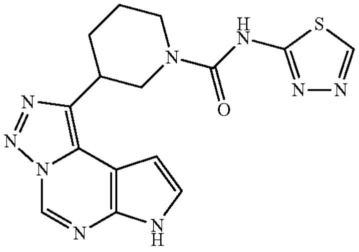 [SMILES: O=C(Nc1nncs1)N1CCCC(c2nnn3cnc4[nH]ccc4c23)C1] racemate |
| 21 | 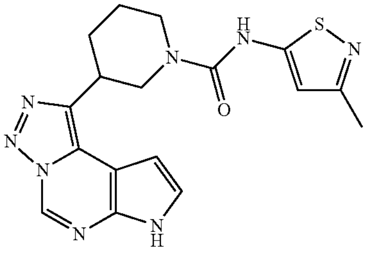 [SMILES: Cc1cc(NC(=O)N2CCCC(c3nnn4cnc5[nH]ccc5c34)C2)sn1] racemate |
| 22 | 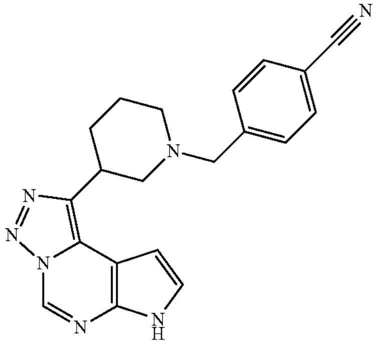 [SMILES: N#Cc1ccc(CN2CCCC(c3nnn4cnc5[nH]ccc5c34)C2)cc1] racemate |

TABLE[a] 55-continued
| Ex | Structure |
| --- | --- |
| 23 | 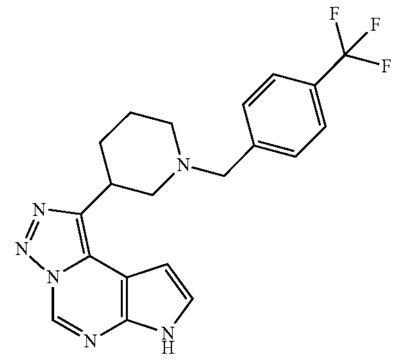 [SMILES: FC(F)(F)c1ccc(CN2CCCC(c3nnn4cnc5[nH]ccc5c34)C2)cc1] racemate |
| 24 | 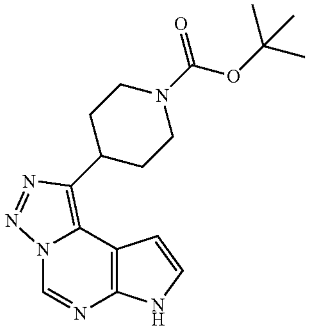 [SMILES: CC(C)(C)OC(=O)N1CCC(c2nnn3cnc4[nH]ccc4c23)CC1] |
| 25 | 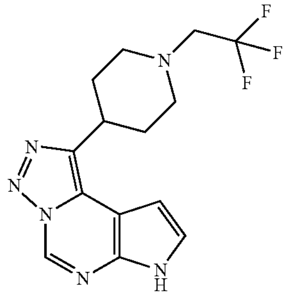 [SMILES: FC(F)(F)CN1CCC(c2nnn3cnc4[nH]ccc4c23)CC1] |
| 26 | 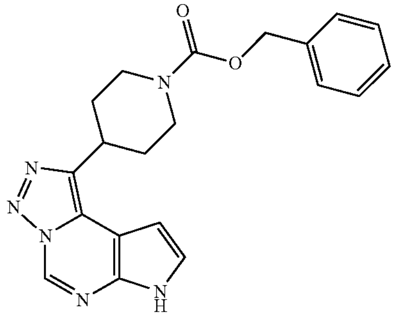 [SMILES: O=C(OCc1ccccc1)N1CCC(c2nnn3cnc4[nH]ccc4c23)CC1] |
| 27 | 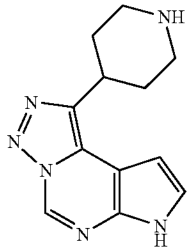 [SMILES: c1cc2c(ncn3nnc(C4CCNCC4)c23)[nH]1] |
| 28 | 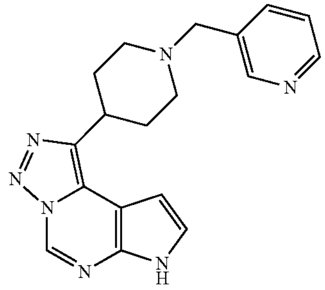 [SMILES: c1cncc(CN2CCC(c3nnn4cnc5[nH]ccc5c34)CC2)c1] |
TABLE[a] 56
| Ex | Structure |
| --- | --- |
| 29 | 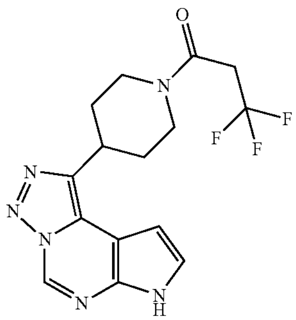 [SMILES: O=C(CC(F)(F)F)N1CCC(c2nnn3cnc4[nH]ccc4c23)CC1] |
| 30 | 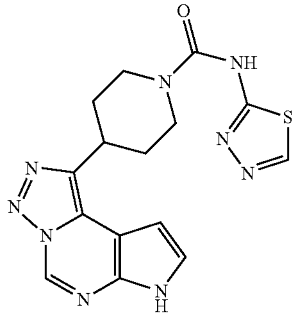 [SMILES: O=C(Nc1nncs1)N1CCC(c2nnn3cnc4[nH]ccc4c23)CC1] |

TABLE[a] 56-continued
| Ex | Structure |
| --- | --- |
| 31 | 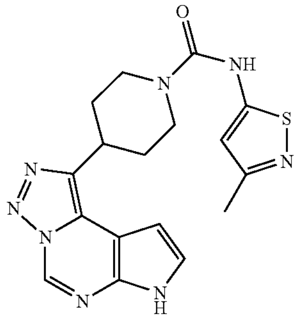 [SMILES: Cc1cc(NC(=O)N2CCC(c3nnn4cnc5[nH]ccc5c34)CC2)sn1] |
| 32 | 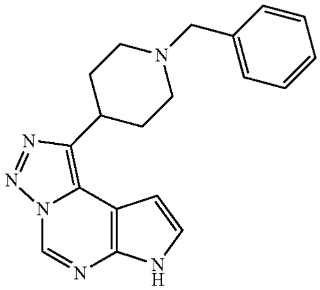 [SMILES: c1ccc(CN2CCC(c3nnn4cnc5[nH]ccc5c34)CC2)cc1] |
| 33 | 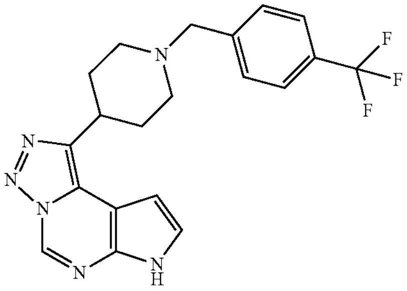 [SMILES: FC(F)(F)c1ccc(CN2CCC(c3nnn4cnc5[nH]ccc5c34)CC2)cc1] |
| 34 | 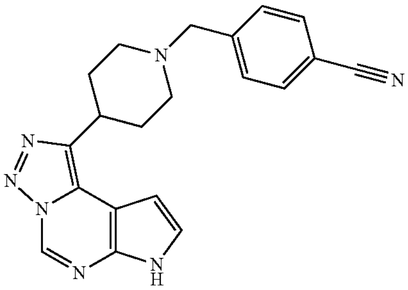 [SMILES: N#Cc1ccc(CN2CCC(c3nnn4cnc5[nH]ccc5c34)CC2)cc1] |
| 35 | 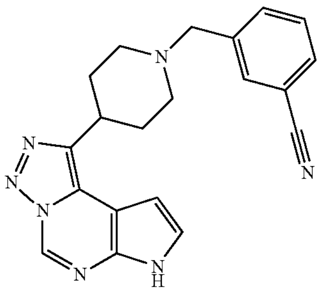 [SMILES: N#Cc1cccc(CN2CCC(c3nnn4cnc5[nH]ccc5c34)CC2)c1] |
TABLE[a] 56-continued
| Ex | Structure |
| --- | --- |
| 36 | 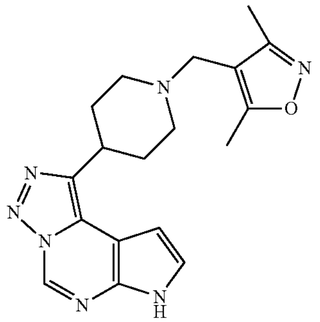 [SMILES: Cc1noc(C)c1CN1CCC(c2nnn3cnc4[nH]ccc4c23)CC1] |
| 37 | 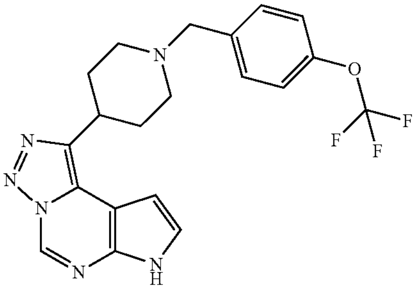 [SMILES: FC(F)(F)Oc1ccc(CN2CCC(c3nnn4cnc5[nH]ccc5c34)CC2)cc1] |
| 38 | 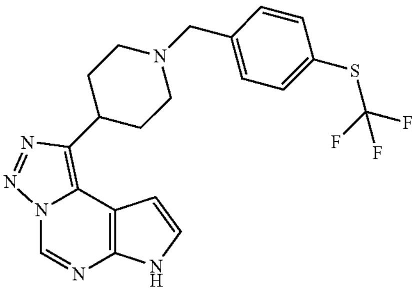 |
| 39 | 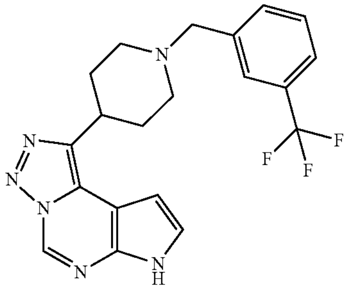 [SMILES: FC(F)(F)c1cccc(CN2CCC(c3nnn4cnc5[nH]ccc5c34)CC2)c1] |
| 40 | 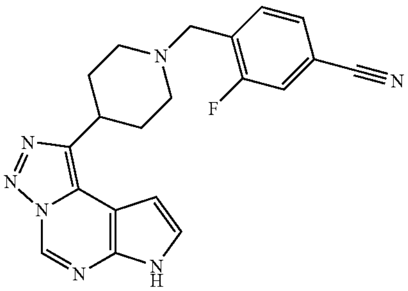 [SMILES: N#Cc1ccc(CN2CCC(c3nnn4cnc5[nH]ccc5c34)CC2)c(F)c1] |

TABLE[a] 56-continued
| Ex | Structure |
|---|---|
| 41 | 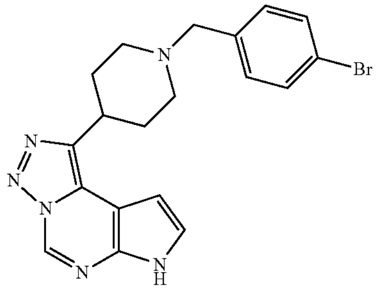 [SMILES: Brc1ccc(CN2CCC(c3nnn4cnc5[nH]ccc5c34)CC2)cc1] |
| 42 | 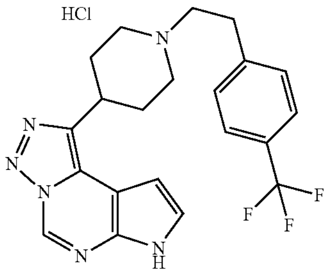 [SMILES: FC(F)(F)c1ccc(CCN2CCC(c3nnn4cnc5[nH]ccc5c34)CC2)cc1 ; Cl] |
| 43 | 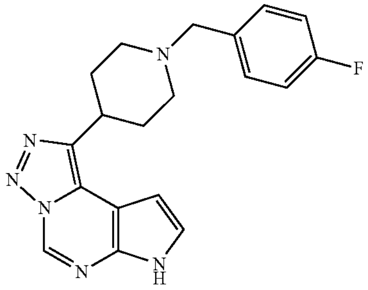 [SMILES: Fc1ccc(CN2CCC(c3nnn4cnc5[nH]ccc5c34)CC2)cc1] |
| 44 | 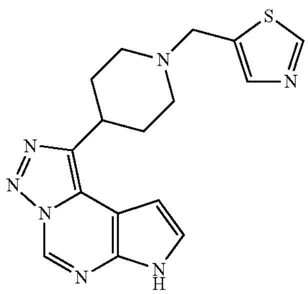 [SMILES: c1cc2c(ncn3nnc(C4CCN(Cc5cncs5)CC4)c23)[nH]1] |
| 45 | 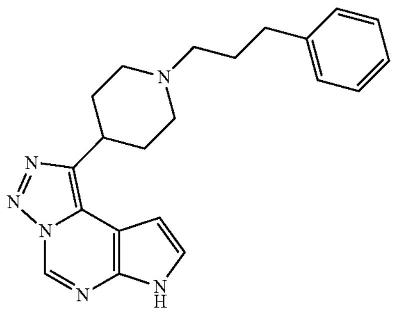 [SMILES: c1ccc(CCCN2CCC(c3nnn4cnc5[nH]ccc5c34)CC2)cc1] |
| 46 | 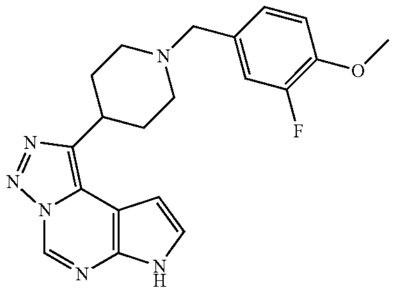 [SMILES: COc1ccc(CN2CCC(c3nnn4cnc5[nH]ccc5c34)CC2)cc1F] |
TABLE[a] 57
| Ex | Structure |
|---|---|
| 47 | 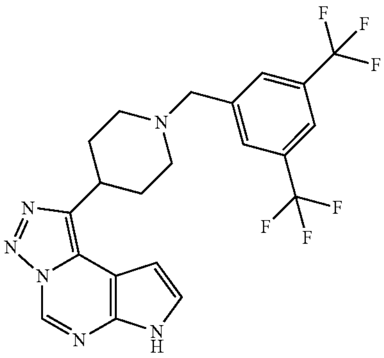 [SMILES: FC(F)(F)c1cc(CN2CCC(c3nnn4cnc5[nH]ccc5c34)CC2)cc(C(F)(F)F)c1] |
| 48 | 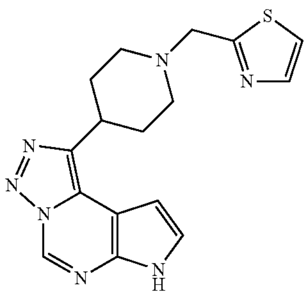 |
| 49 | 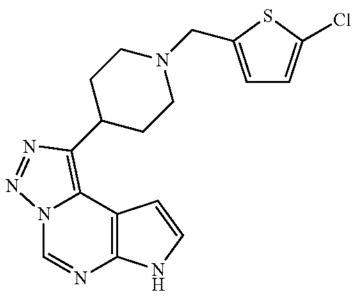 [SMILES: Clc1ccc(CN2CCC(c3nnn4cnc5[nH]ccc5c34)CC2)s1] |

TABLE[a] 57-continued
| Ex | Structure |
|---|---|
| 50 | 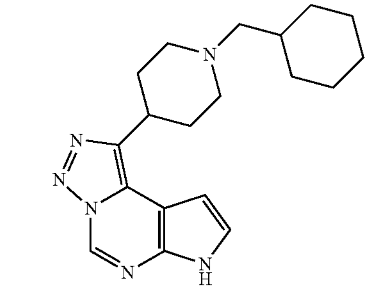 [SMILES: c1cc2c(ncn3nnc(C4CCN(CC5CCCCC5)CC4)c23)[nH]1] |
| 51 | 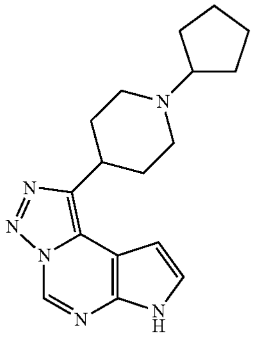 [SMILES: c1cc2c(ncn3nnc(C4CCN(C5CCCC5)CC4)c23)[nH]1] |
| 52 | 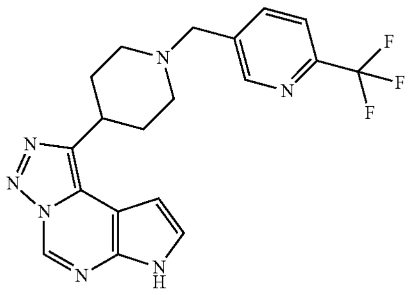 [SMILES: FC(F)(F)c1ccc(CN2CCC(c3nnn4cnc5[nH]ccc5c34)CC2)cn1] |
| 53 | 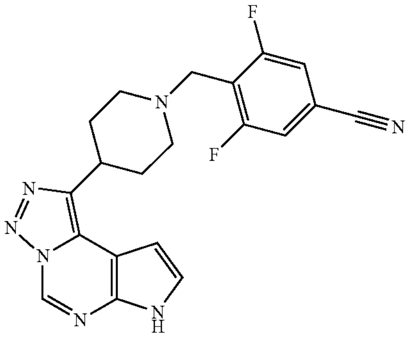 [SMILES: N#Cc1cc(F)c(CN2CCC(c3nnn4cnc5[nH]ccc5c34)CC2)c(F)c1] |
| 54 | 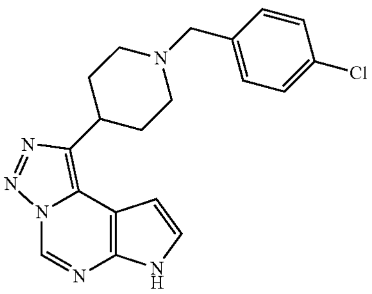 [SMILES: Clc1ccc(CN2CCC(c3nnn4cnc5[nH]ccc5c34)CC2)cc1] |
| 55 | 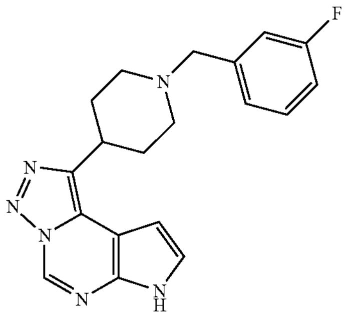 [SMILES: Fc1cccc(CN2CCC(c3nnn4cnc5[nH]ccc5c34)CC2)c1] |
| 56a | 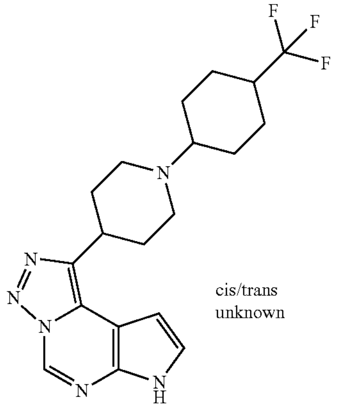 [SMILES: FC(F)(F)C1CCC(N2CCC(c3nnn4cnc5[nH]ccc5c34)CC2)CC1] cis/trans unknown<br>less polar fraction |
| 56b | 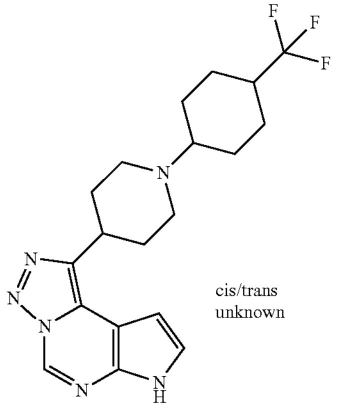 [SMILES: FC(F)(F)C1CCC(N2CCC(c3nnn4cnc5[nH]ccc5c34)CC2)CC1] cis/trans unknown<br>less polar fraction |
| 57 | 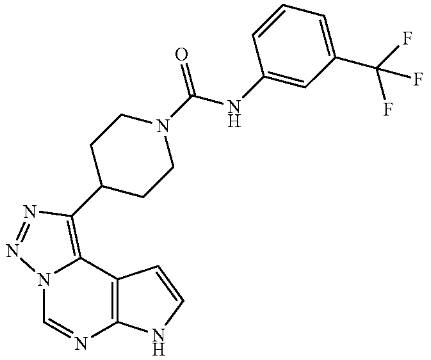 [SMILES: O=C(Nc1cccc(C(F)(F)F)c1)N1CCC(c2nnn3cnc4[nH]ccc4c23)CC1] |

TABLE[a] 57-continued
| Ex | Structure |
|---|---|
| 58 | 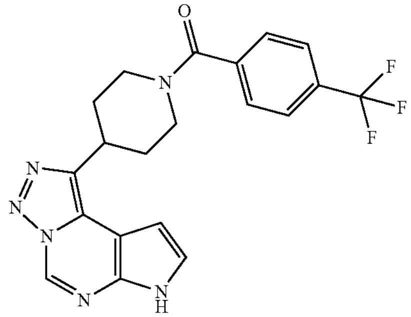 [SMILES: O=C(c1ccc(C(F)(F)F)cc1)N1CCC(c2nnn3cnc4[nH]ccc4c23)CC1] |
| 59 | 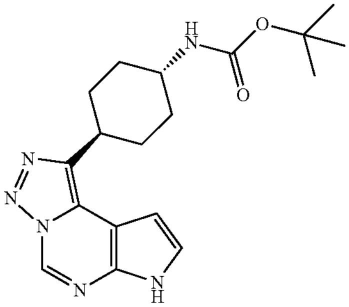 [SMILES: CC(C)(C)OC(=O)N[C@H]1CC[C@H](c2nnn3cnc4[nH]ccc4c23)CC1] |
| 60 | 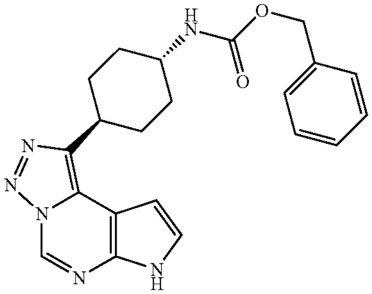 [SMILES: O=C(N[C@H]1CC[C@H](c2nnn3cnc4[nH]ccc4c23)CC1)OCc1ccccc1] |
| 61 | 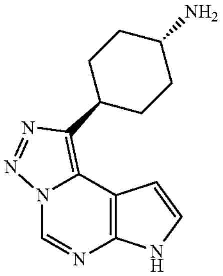 [SMILES: N[C@H]1CC[C@H](c2nnn3cnc4[nH]ccc4c23)CC1] |
| 62 | 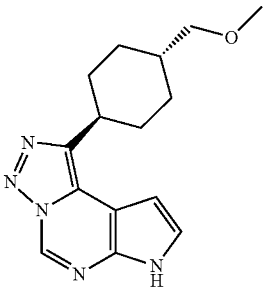 [SMILES: COC[C@H]1CC[C@H](c2nnn3cnc4[nH]ccc4c23)CC1] |
| 63 | 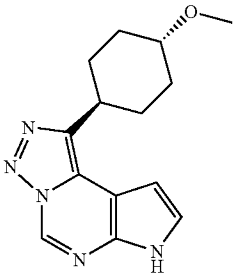 [SMILES: CO[C@H]1CC[C@H](c2nnn3cnc4[nH]ccc4c23)CC1] |
TABLE[a] 58
| Ex | Structure |
|---|---|
| 64 | 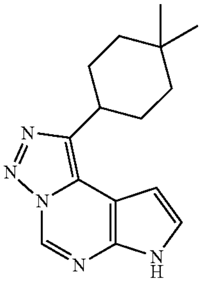 [SMILES: CC1(C)CCC(c2nnn3cnc4[nH]ccc4c23)CC1] |
| 65 | 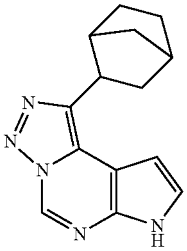 [SMILES: c1cc2c(ncn3nnc(C4CC5CCC4C5)c23)[nH]1] diastereomixture |
| 66 | 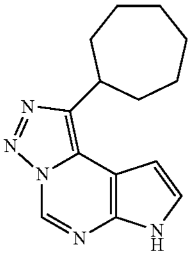 [SMILES: c1cc2c(ncn3nnc(C4CCCCCC4)c23)[nH]1] |
| 67 | 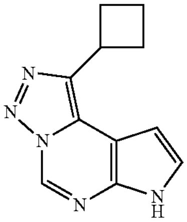 [SMILES: c1cc2c(ncn3nnc(C4CCC4)c23)[nH]1] |

TABLE[a] 58-continued
| Ex | Structure |
|---|---|
| 68 | 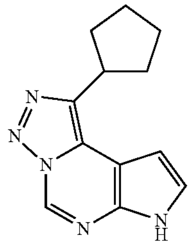 [SMILES: c1cc2c(ncn3nnc(C4CCCC4)c23)[nH]1] |
| 69 | 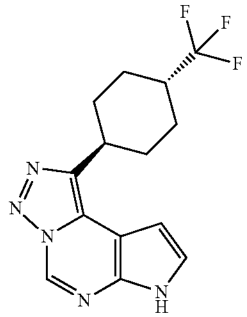 [SMILES: FC(F)(F)[C@H]1CC[C@H](c2nnn3cnc4[nH]ccc4c23)CC1] |
| 70 | 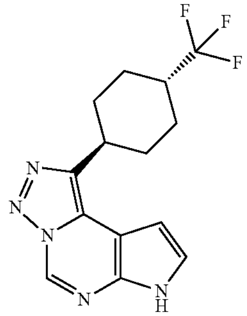 [SMILES: FC(F)(F)[C@H]1CC[C@H](c2nnn3cnc4[nH]ccc4c23)CC1] |
| 71 | 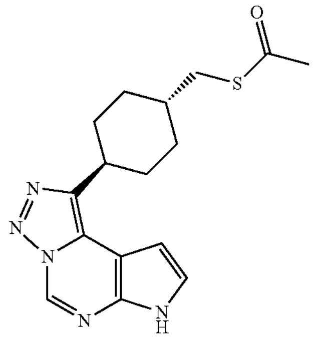 [SMILES: CC(=O)SC[C@H]1CC[C@H](c2nnn3cnc4[nH]ccc4c23)CC1] |
| 72 | 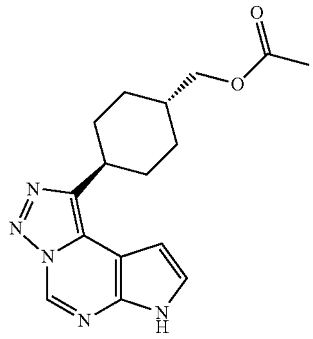 [SMILES: CC(=O)OC[C@H]1CC[C@H](c2nnn3cnc4[nH]ccc4c23)CC1] |
TABLE[a] 58-continued
| Ex | Structure |
|---|---|
| 73 | 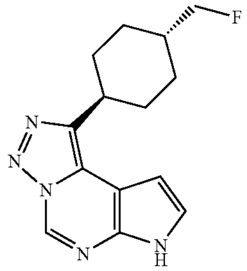 [SMILES: FC[C@H]1CC[C@H](c2nnn3cnc4[nH]ccc4c23)CC1] |
| 74 | 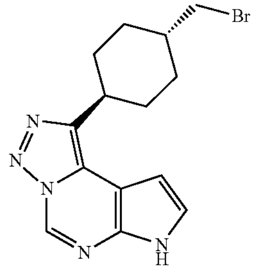 [SMILES: BrC[C@H]1CC[C@H](c2nnn3cnc4[nH]ccc4c23)CC1] |
| 75 | 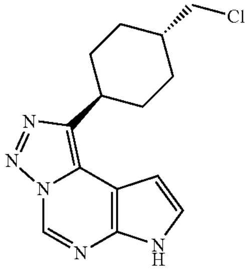 [SMILES: ClC[C@H]1CC[C@H](c2nnn3cnc4[nH]ccc4c23)CC1] |
| 76 | 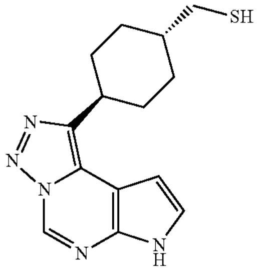 |
| 77 | 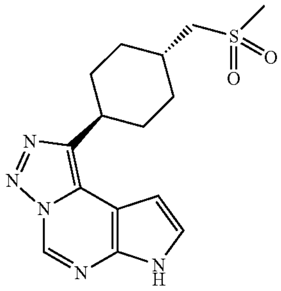 [SMILES: CS(=O)(=O)C[C@H]1CC[C@H](c2nnn3cnc4[nH]ccc4c23)CC1] |

TABLE[a] 58-continued
| Ex | Structure |
|---|---|
| 78 | 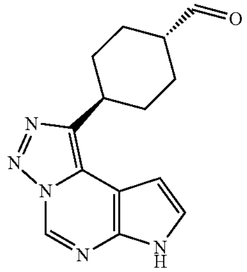 [SMILES: O=C[C@H]1CC[C@H](c2nnn3cnc4[nH]ccc4c23)CC1] |
| 79 | 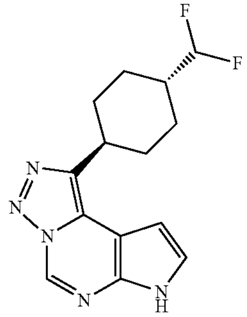 [SMILES: FC(F)[C@H]1CC[C@H](c2nnn3cnc4[nH]ccc4c23)CC1] |
| 80 | 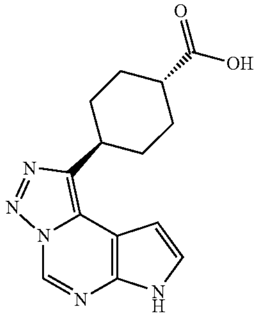 [SMILES: O=C(O)[C@H]1CC[C@H](c2nnn3cnc4[nH]ccc4c23)CC1] |
| 81 | 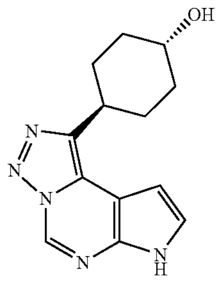 [SMILES: O[C@H]1CC[C@H](c2nnn3cnc4[nH]ccc4c23)CC1] |
TABLE[a] 59
| Ex | Structure |
|---|---|
| 82 | 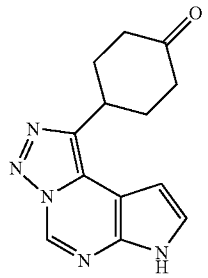 [SMILES: O=C1CCC(c2nnn3cnc4[nH]ccc4c23)CC1] |
| 83 | 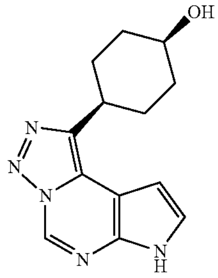 [SMILES: O[C@H]1CC[C@@H](c2nnn3cnc4[nH]ccc4c23)CC1] |
| 84 | 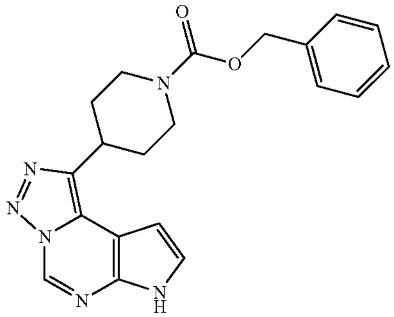 [SMILES: O=C(OCc1ccccc1)N1CCC(c2nnn3cnc4[nH]ccc4c23)CC1] |
| 85 | 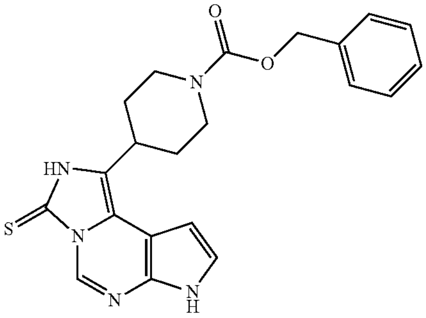 [SMILES: O=C(OCc1ccccc1)N1CCC(c2[nH]c(=S)n3cnc4[nH]ccc4c23)CC1] |
| 86 | 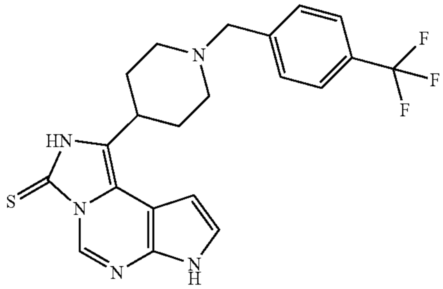 [SMILES: FC(F)(F)c1ccc(CN2CCC(c3[nH]c(=S)n4cnc5[nH]ccc5c34)CC2)cc1] |

TABLE[a] 59-continued
| Ex | Structure |
|---|---|
| 87 | 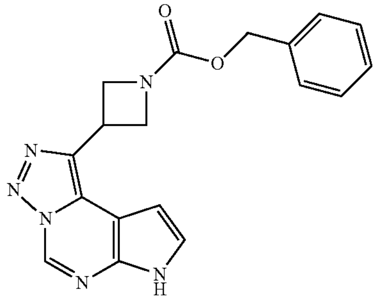 [SMILES: O=C(OCc1ccccc1)N1CC(c2nnn3cnc4[nH]ccc4c23)C1] |
| 88 | 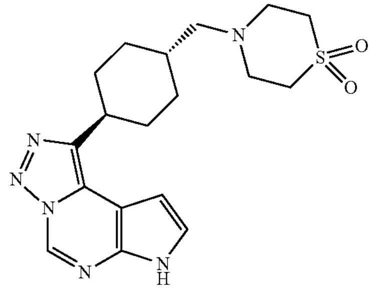 [SMILES: O=S1(=O)CCN(C[C@H]2CC[C@H](c3nnn4cnc5[nH]ccc5c34)CC2)CC1] |
| 89 | 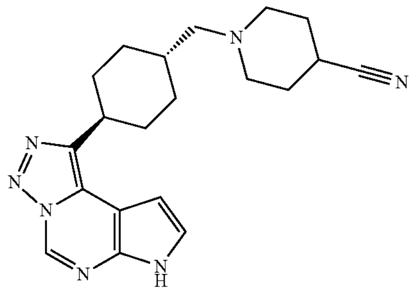 [SMILES: N#CC1CCN(C[C@H]2CC[C@H](c3nnn4cnc5[nH]ccc5c34)CC2)CC1] |
| 90 | 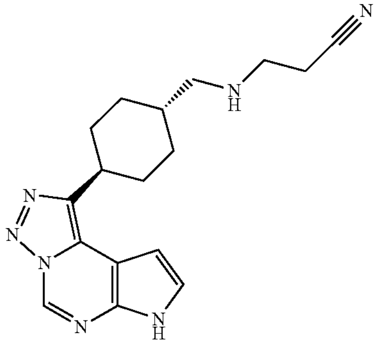 [SMILES: N#CCCNC[C@H]1CC[C@H](c2nnn3cnc4[nH]ccc4c23)CC1] |
| 91 | 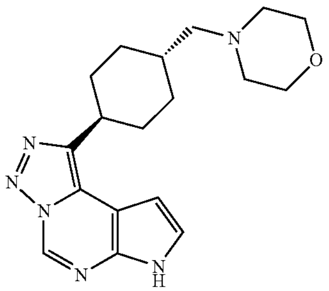 [SMILES: c1cc2c(ncn3nnc([C@H]4CC[C@H](CN5CCOCC5)CC4)c23)[nH]1] |
| 92 | 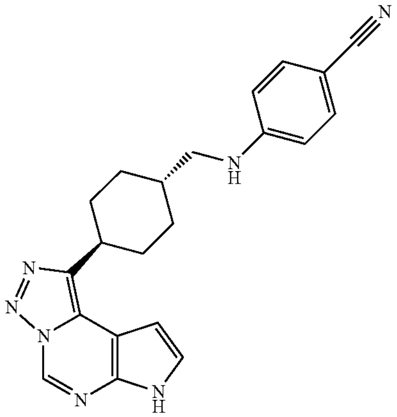 [SMILES: N#Cc1ccc(NC[C@H]2CC[C@H](c3nnn4cnc5[nH]ccc5c34)CC2)cc1] |
| 93 | 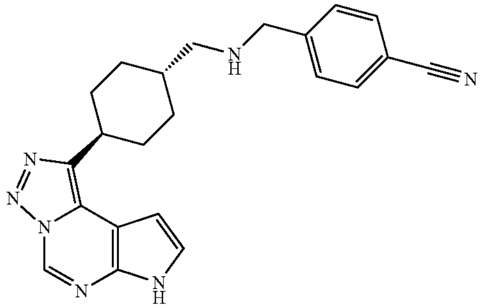 [SMILES: N#Cc1ccc(CNC[C@H]2CC[C@H](c3nnn4cnc5[nH]ccc5c34)CC2)cc1] |
| 94 | 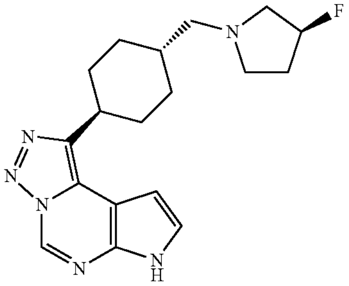 [SMILES: F[C@H]1CCN(C[C@H]2CC[C@H](c3nnn4cnc5[nH]ccc5c34)CC2)C1] |
| 95 | 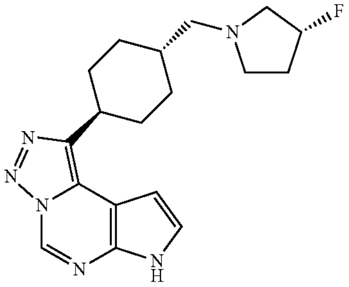 [SMILES: F[C@@H]1CCN(C[C@H]2CC[C@H](c3nnn4cnc5[nH]ccc5c34)CC2)C1] |
| 96 | 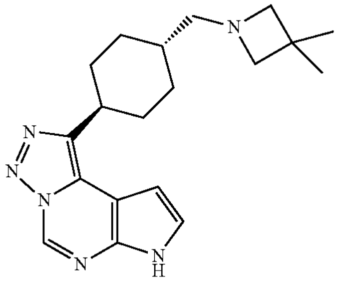 [SMILES: CC1(C)CN(C[C@H]2CC[C@H](c3nnn4cnc5[nH]ccc5c34)CC2)C1] |

TABLE[a] 59-continued
| Ex | Structure |
|---|---|
| 97 | 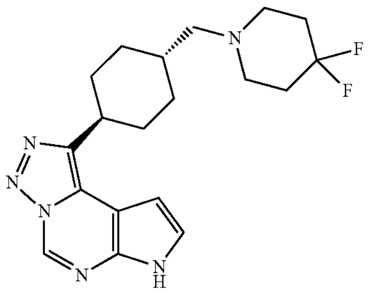 [SMILES: FC1(F)CCN(C[C@H]2CC[C@H](c3nnn4cnc5[nH]ccc5c34)CC2)CC1] |
| 98 | 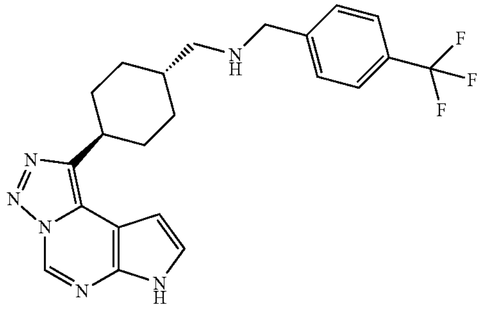 [SMILES: FC(F)(F)c1ccc(CNC[C@H]2CC[C@H](c3nnn4cnc5[nH]ccc5c34)CC2)cc1] |
| 99 | 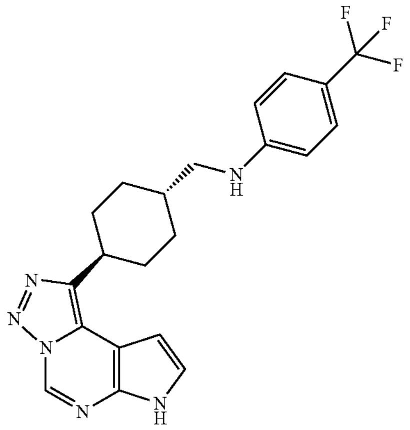 [SMILES: FC(F)(F)c1ccc(NC[C@H]2CC[C@H](c3nnn4cnc5[nH]ccc5c34)CC2)cc1] |
TABLE[a] 60
| Ex | Structure |
|---|---|
| 100 | 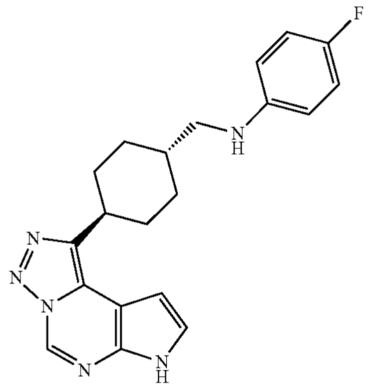 [SMILES: Fc1ccc(NC[C@H]2CC[C@H](c3nnn4cnc5[nH]ccc5c34)CC2)cc1] |
TABLE[a] 60-continued
| Ex | Structure |
|---|---|
| 101 | 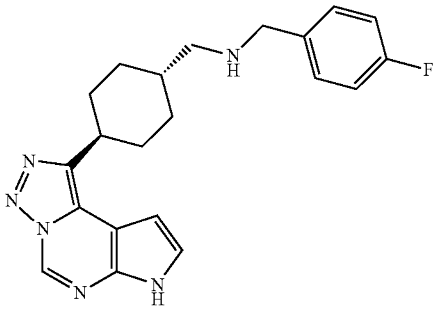 [SMILES: Fc1ccc(CNC[C@H]2CC[C@H](c3nnn4cnc5[nH]ccc5c34)CC2)cc1] |
| 102 | 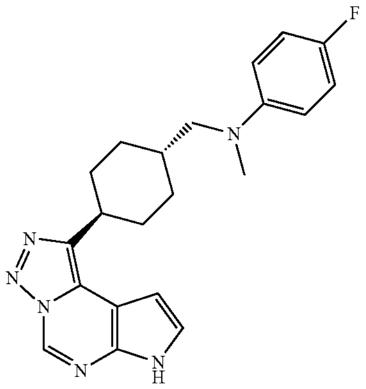 [SMILES: CN(C[C@H]1CC[C@H](c2nnn3cnc4[nH]ccc4c23)CC1)c1ccc(F)cc1] |
| 103 | 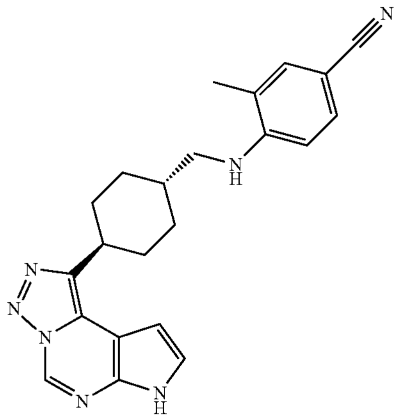 [SMILES: Cc1cc(C#N)ccc1NC[C@H]1CC[C@H](c2nnn3cnc4[nH]ccc4c23)CC1] |
| 104 | 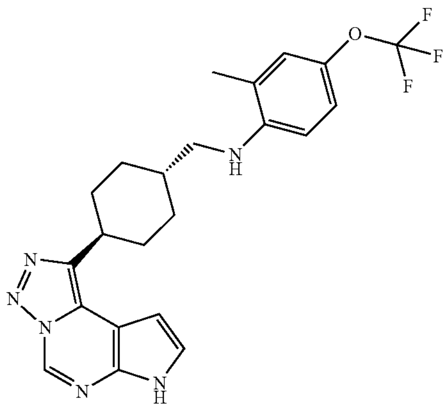 [SMILES: Cc1cc(OC(F)(F)F)ccc1NC[C@H]1CC[C@H](c2nnn3cnc4[nH]ccc4c23)CC1] |

TABLE[a] 60-continued
| Ex | Structure |
|---|---|
| 105 | 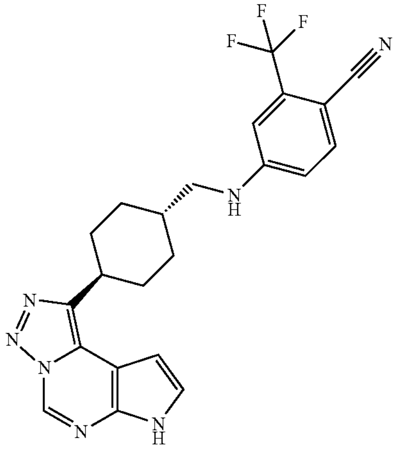 [SMILES: N#Cc1ccc(NC[C@H]2CC[C@H](c3nnn4cnc5[nH]ccc5c34)CC2)cc1C(F)(F)F] |
| 106 | 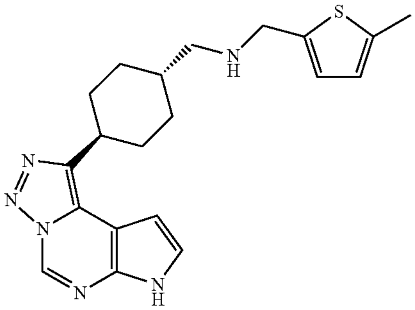 [SMILES: Cc1ccc(CNC[C@H]2CC[C@H](c3nnn4cnc5[nH]ccc5c34)CC2)s1] |
| 107 | 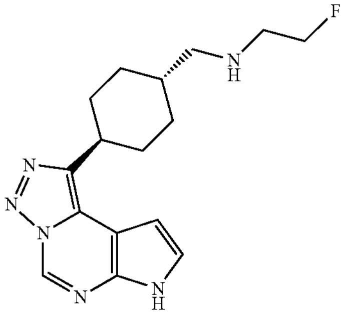 [SMILES: FCCNC[C@H]1CC[C@H](c2nnn3cnc4[nH]ccc4c23)CC1] |
| 108 | 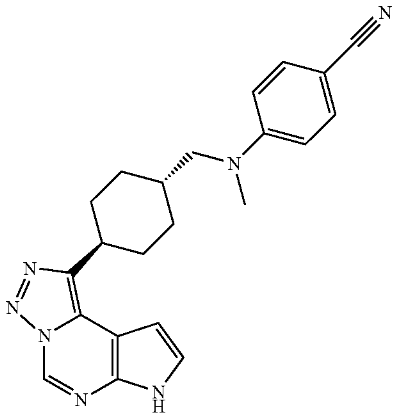 [SMILES: CN(C[C@H]1CC[C@H](c2nnn3cnc4[nH]ccc4c23)CC1)c1ccc(C#N)cc1] |
TABLE[a] 60-continued
| Ex | Structure |
|---|---|
| 109 | 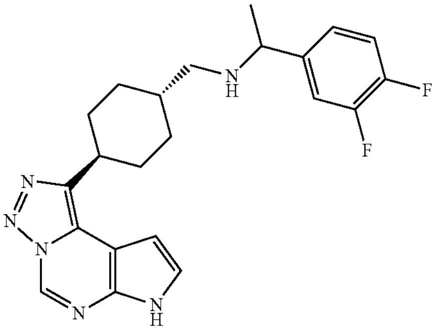 [SMILES: CC(NC[C@H]1CC[C@H](c2nnn3cnc4[nH]ccc4c23)CC1)c1ccc(F)c(F)c1]<br>racemate |
| 110 | 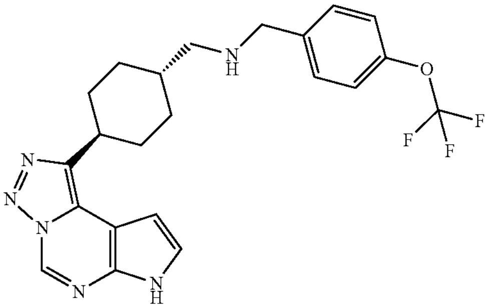 [SMILES: FC(F)(F)Oc1ccc(CNC[C@H]2CC[C@H](c3nnn4cnc5[nH]ccc5c34)CC2)cc1] |
| 111 | 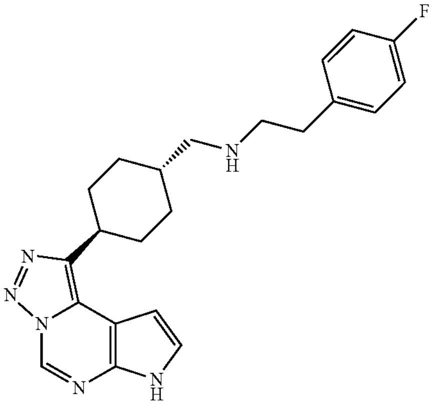 [SMILES: Fc1ccc(CCNC[C@H]2CC[C@H](c3nnn4cnc5[nH]ccc5c34)CC2)cc1] |
| 112 | 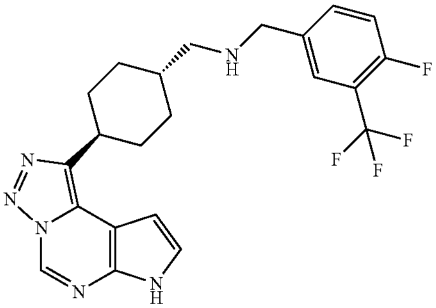 [SMILES: Fc1ccc(CNC[C@H]2CC[C@H](c3nnn4cnc5[nH]ccc5c34)CC2)cc1C(F)(F)F] |

TABLE[a] 60-continued
| Ex | Structure |
|---|---|
| 113 | 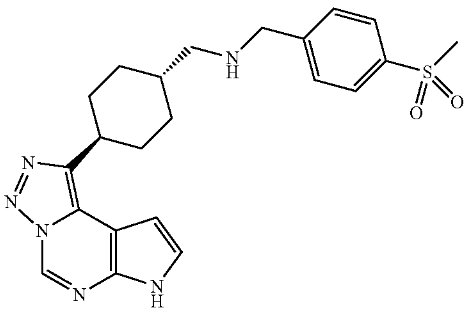 [SMILES: CS(=O)(=O)c1ccc(CNC[C@H]2CC[C@H](c3nnn4cnc5[nH]ccc5c34)CC2)cc1] |
| 114 | 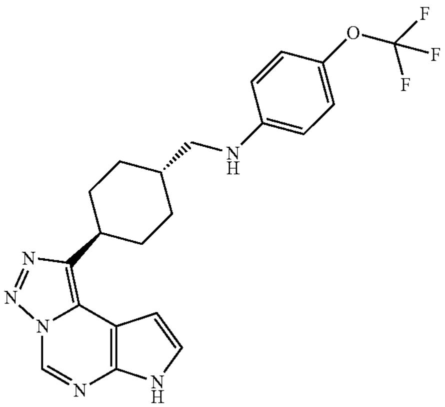 [SMILES: FC(F)(F)Oc1ccc(NC[C@H]2CC[C@H](c3nnn4cnc5[nH]ccc5c34)CC2)cc1] |
| 115 | 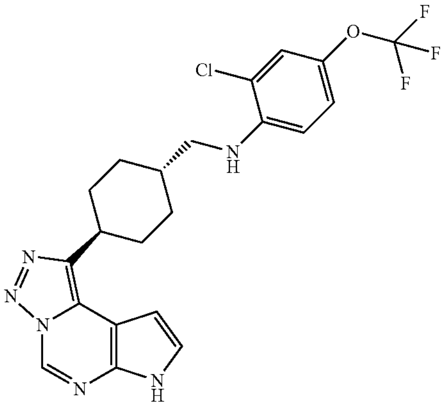 [SMILES: FC(F)(F)Oc1ccc(NC[C@H]2CC[C@H](c3nnn4cnc5[nH]ccc5c34)CC2)c(Cl)c1] |
| 116 | 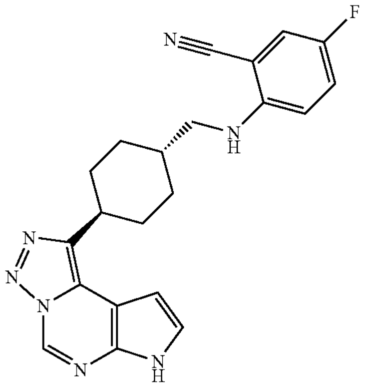 [SMILES: N#Cc1cc(F)ccc1NC[C@H]1CC[C@H](c2nnn3cnc4[nH]ccc4c23)CC1] |
| 117 | 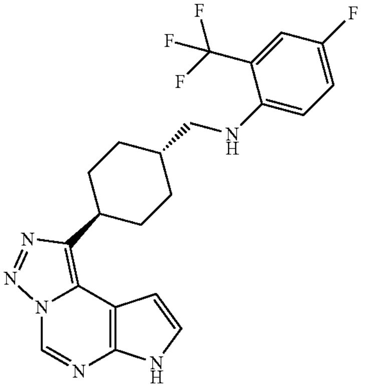 [SMILES: Fc1ccc(NC[C@H]2CC[C@H](c3nnn4cnc5[nH]ccc5c34)CC2)c(C(F)(F)F)c1] |
TABLE[a] 61
| Ex | Structure |
|---|---|
| 118 | 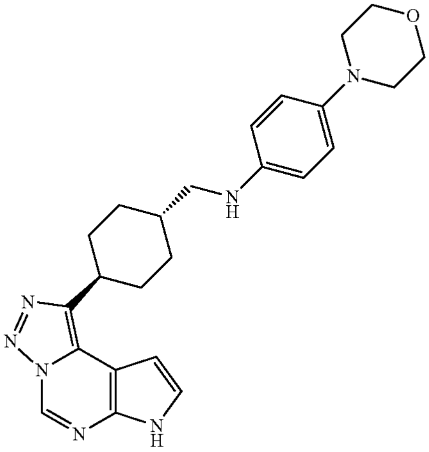 [SMILES: c1cc2c(ncn3nnc([C@H]4CC[C@H](CNc5ccc(N6CCOCC6)cc5)CC4)c23)[nH]1] |
| 119 | 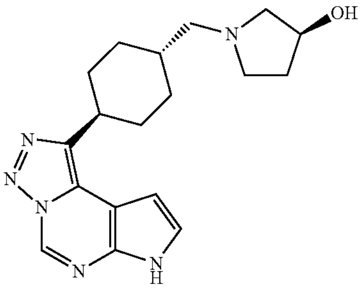 [SMILES: O[C@H]1CCN(C[C@H]2CC[C@H](c3nnn4cnc5[nH]ccc5c34)CC2)C1] |
| 120 | 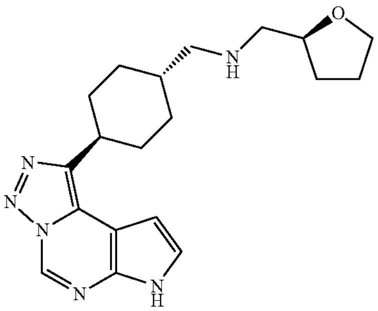 [SMILES: c1cc2c(ncn3nnc([C@H]4CC[C@H](CNC[C@@H]5CCCO5)CC4)c23)[nH]1] |

TABLE[a] 61-continued
| Ex | Structure |
|---|---|
| 121 | 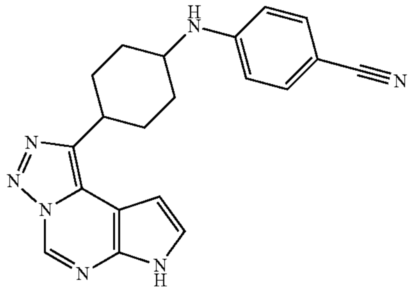 [SMILES: N#Cc1ccc(NC2CCC(c3nnn4cnc5[nH]ccc5c34)CC2)cc1] cis/trans mixture |
| 122 | 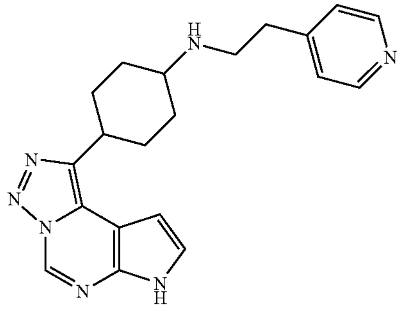 [SMILES: c1cc(CCNC2CCC(c3nnn4cnc5[nH]ccc5c34)CC2)ccn1] cis/trans mixture |
| 123 | 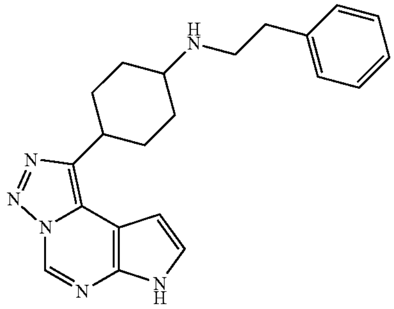 [SMILES: c1ccc(CCNC2CCC(c3nnn4cnc5[nH]ccc5c34)CC2)cc1] cis/trans mixture |
| 124 | 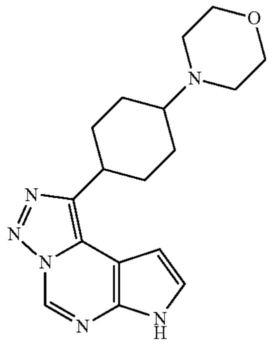 [SMILES: c1cc2c(ncn3nnc(C4CCC(N5CCOCC5)CC4)c23)[nH]1] cis/trans mixture |
| 125 | 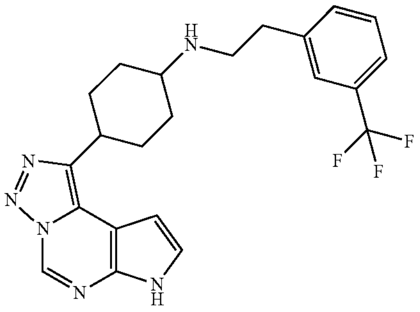 [SMILES: FC(F)(F)c1cccc(CCNC2CCC(c3nnn4cnc5[nH]ccc5c34)CC2)c1] cis/trans mixture |
| 126 | 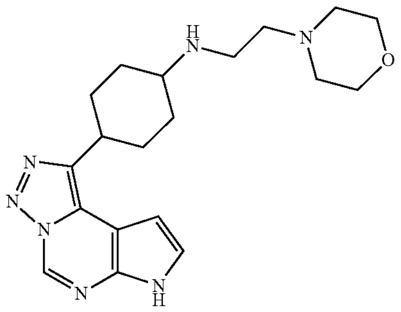 [SMILES: c1cc2c(ncn3nnc(C4CCC(NCCN5CCOCC5)CC4)c23)[nH]1] cis/trans mixture |
| 127 | 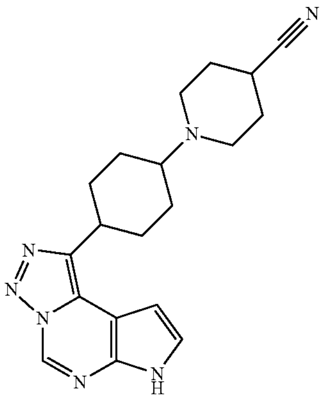 [SMILES: N#CC1CCN(C2CCC(c3nnn4cnc5[nH]ccc5c34)CC2)CC1] cis/trans mixture |
| 128 | 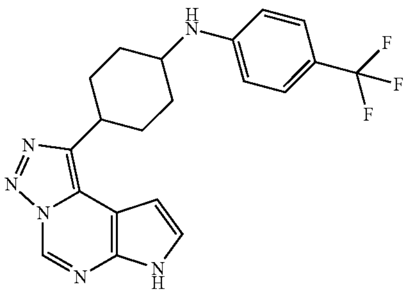 [SMILES: FC(F)(F)c1ccc(NC2CCC(c3nnn4cnc5[nH]ccc5c34)CC2)cc1] cis/trans mixture |

TABLE[a] 61-continued
| Ex | Structure |
|---|---|
| 129 | 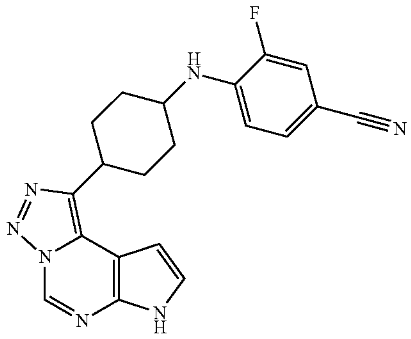 [SMILES: N#Cc1ccc(NC2CCC(c3nnn4cnc5[nH]ccc5c34)CC2)c(F)c1]<br>cis/trans mixture |
| 130 | 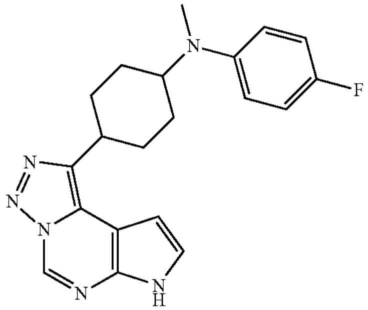 [SMILES: CN(c1ccc(F)cc1)C1CCC(c2nnn3cnc4[nH]ccc4c23)CC1]<br>cis/trans mixture |
| 131 | 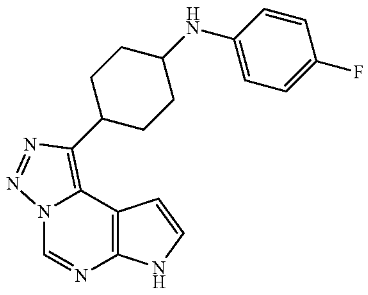 [SMILES: Fc1ccc(NC2CCC(c3nnn4cnc5[nH]ccc5c34)CC2)cc1]<br>cis/trans mixture |
| 132 | 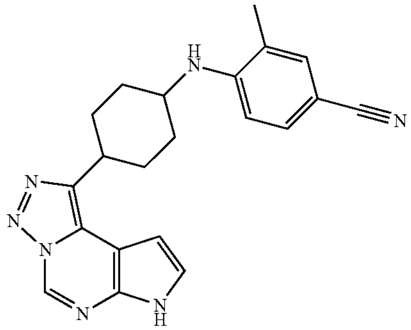 [SMILES: Cc1cc(C#N)ccc1NC1CCC(c2nnn3cnc4[nH]ccc4c23)CC1]<br>cis/trans mixture |
| 133 | 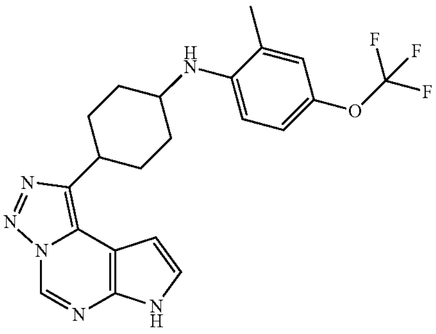 [SMILES: Cc1cc(OC(F)(F)F)ccc1NC1CCC(c2nnn3cnc4[nH]ccc4c23)CC1]<br>cis/trans mixture |
| 134a | 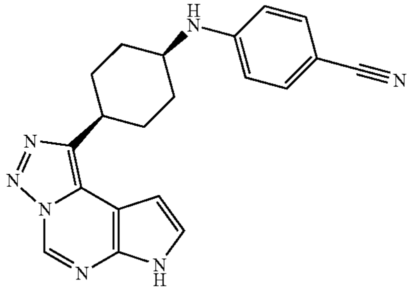 [SMILES: N#Cc1ccc(N[C@H]2CC[C@@H](c3nnn4cnc5[nH]ccc5c34)CC2)cc1] |
| 134b | 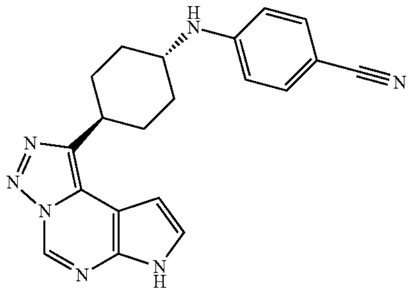 [SMILES: N#Cc1ccc(N[C@H]2CC[C@H](c3nnn4cnc5[nH]ccc5c34)CC2)cc1] |
TABLE[a] 62
| Ex | Structure |
|---|---|
| 135a | 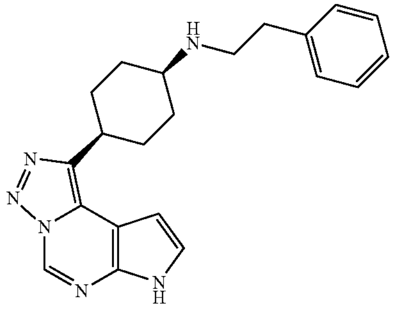 [SMILES: c1ccc(CCN[C@H]2CC[C@@H](c3nnn4cnc5[nH]ccc5c34)CC2)cc1] |

TABLE[a] 62-continued
| Ex | Structure |
|---|---|
| 135b | 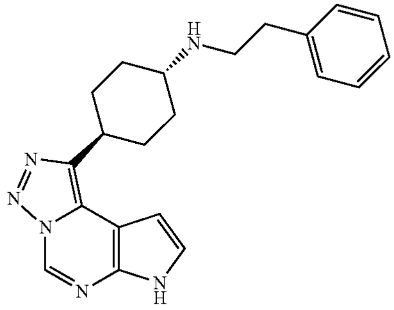 [SMILES: c1ccc(CCN[C@H]2CC[C@H](c3nnn4cnc5[nH]ccc5c34)CC2)cc1] |
| 136a | 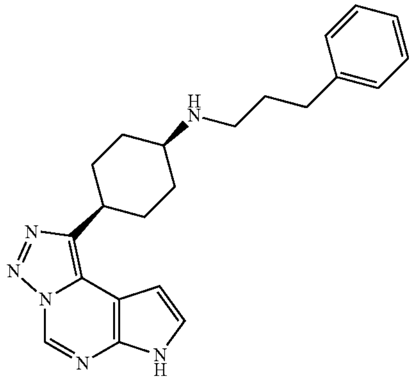 [SMILES: c1ccc(CCCN[C@H]2CC[C@@H](c3nnn4cnc5[nH]ccc5c34)CC2)cc1] |
| 136b | 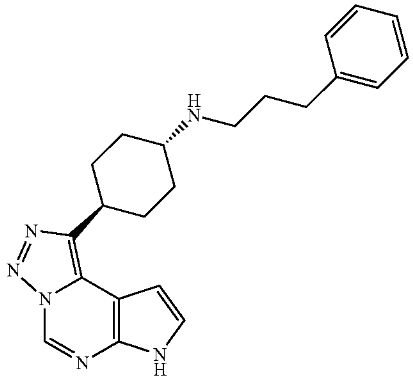 [SMILES: c1ccc(CCCN[C@H]2CC[C@H](c3nnn4cnc5[nH]ccc5c34)CC2)cc1] |
| 137a | 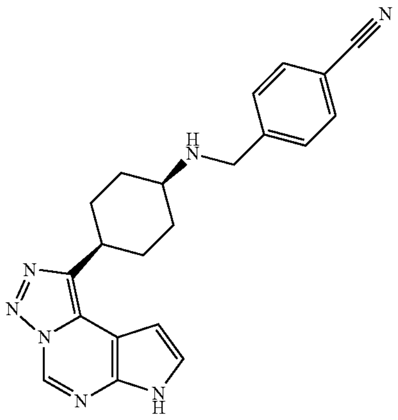 [SMILES: N#Cc1ccc(CN[C@H]2CC[C@@H](c3nnn4cnc5[nH]ccc5c34)CC2)cc1] |
| 137b | 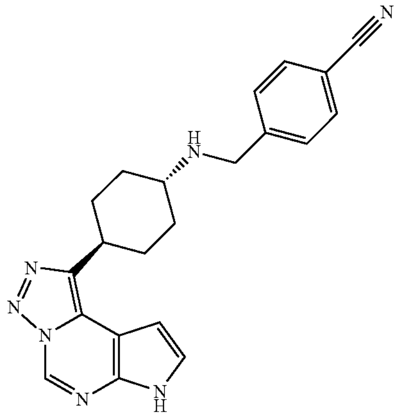 [SMILES: N#Cc1ccc(CN[C@H]2CC[C@H](c3nnn4cnc5[nH]ccc5c34)CC2)cc1] |
| 138a | 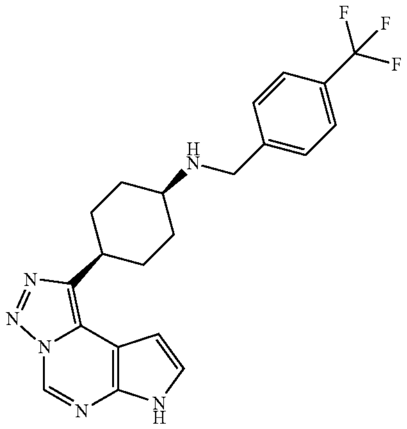 [SMILES: FC(F)(F)c1ccc(CN[C@H]2CC[C@@H](c3nnn4cnc5[nH]ccc5c34)CC2)cc1] |
| 138b | 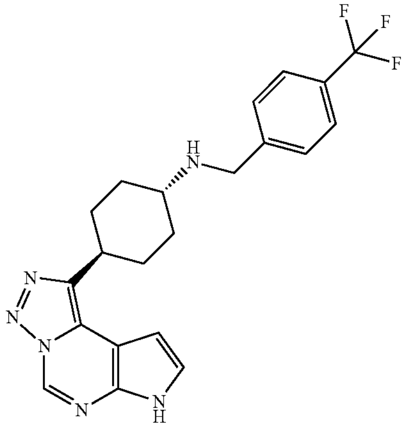 [SMILES: FC(F)(F)c1ccc(CN[C@H]2CC[C@H](c3nnn4cnc5[nH]ccc5c34)CC2)cc1] |
| 139a | 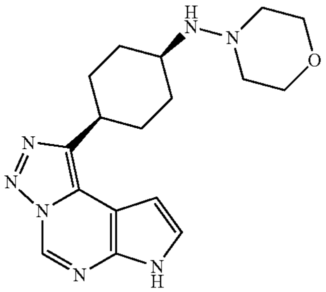 [SMILES: c1cc2c(ncn3nnc([C@H]4CC[C@@H](NN5CCOCC5)CC4)c23)[nH]1] |

TABLE[a] 62-continued
| Ex | Structure |
| --- | --- |
| 139b | 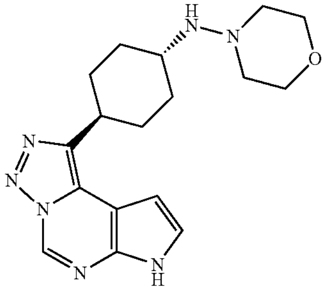 [SMILES: c1cc2c(ncn3nnc([C@H]4CC[C@H](NN5CCOCC5)CC4)c23)[nH]1] |
| 140 | 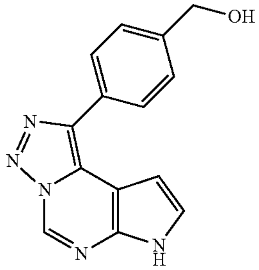 [SMILES: OCc1ccc(-c2nnn3cnc4[nH]ccc4c23)cc1] |
| 141 | 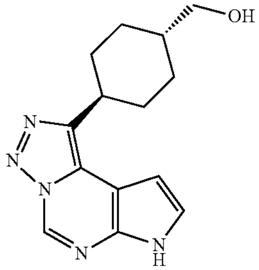 [SMILES: OC[C@H]1CC[C@H](c2nnn3cnc4[nH]ccc4c23)CC1] |
| 142 | 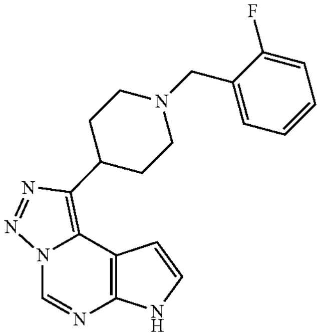 [SMILES: Fc1ccccc1CN1CCC(c2nnn3cnc4[nH]ccc4c23)CC1] |
| 143 | 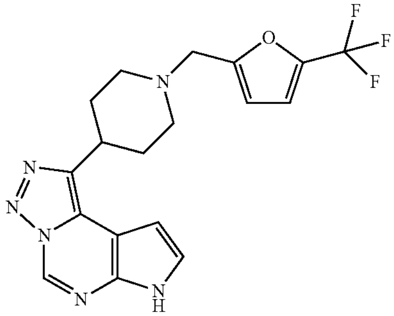 [SMILES: FC(F)(F)c1ccc(CN2CCC(c3nnn4cnc5[nH]ccc5c34)CC2)o1] |
TABLE[a] 62-continued
| Ex | Structure |
| --- | --- |
| 144 | 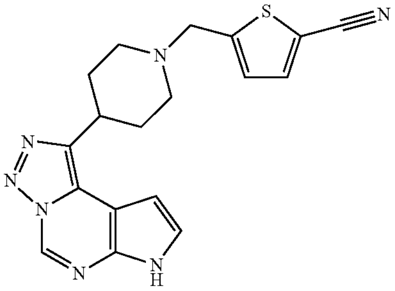 [SMILES: N#Cc1ccc(CN2CCC(c3nnn4cnc5[nH]ccc5c34)CC2)s1] |
| 145 | 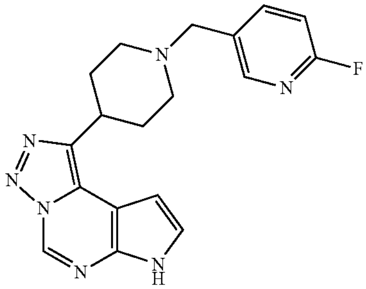 [SMILES: Fc1ccc(CN2CCC(c3nnn4cnc5[nH]ccc5c34)CC2)cn1] |
| 146 | 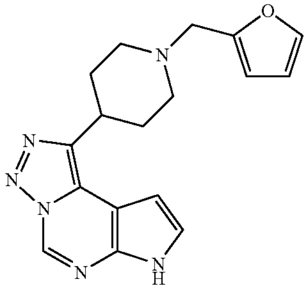 [SMILES: c1coc(CN2CCC(c3nnn4cnc5[nH]ccc5c34)CC2)c1] |
| 147 | 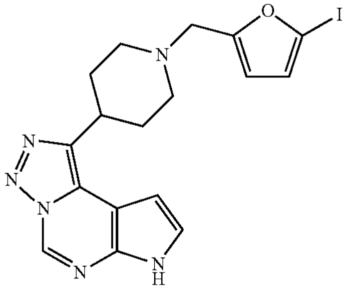 [SMILES: Ic1ccc(CN2CCC(c3nnn4cnc5[nH]ccc5c34)CC2)o1] |
TABLE[a] 63
| Ex | Structure |
| --- | --- |
| 148 | 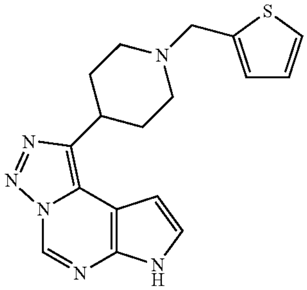 [SMILES: c1csc(CN2CCC(c3nnn4cnc5[nH]ccc5c34)CC2)c1] |

TABLE[a] 63-continued
| Ex | Structure |
| --- | --- |
| 149 | 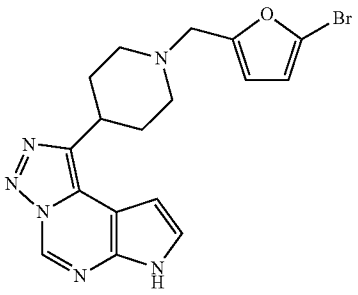 |
| 150 | 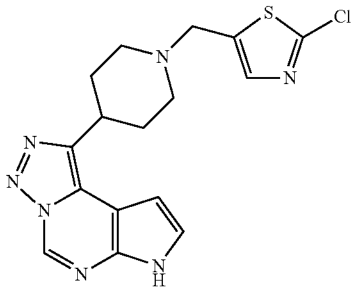 [SMILES: Clc1ncc(CN2CCC(c3nnn4cnc5[nH]ccc5c34)CC2)s1] |
| 151 | 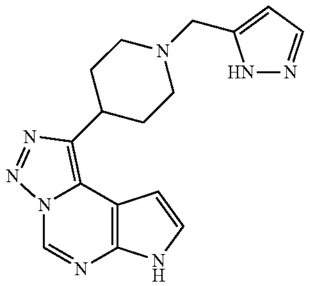 [SMILES: c1cc(CN2CCC(c3nnn4cnc5[nH]ccc5c34)CC2)[nH]n1] |
| 152 | 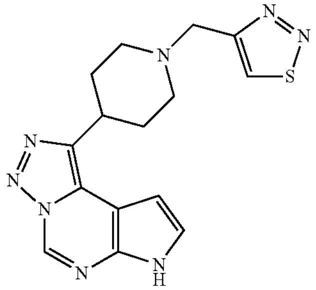 [SMILES: c1cc2c(ncn3nnc(C4CCN(Cc5csnn5)CC4)c23)[nH]1] |
| 153 | 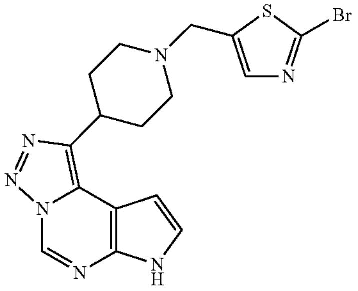 [SMILES: Brc1ncc(CN2CCC(c3nnn4cnc5[nH]ccc5c34)CC2)s1] |
TABLE[a] 63-continued
| Ex | Structure |
| --- | --- |
| 154 | 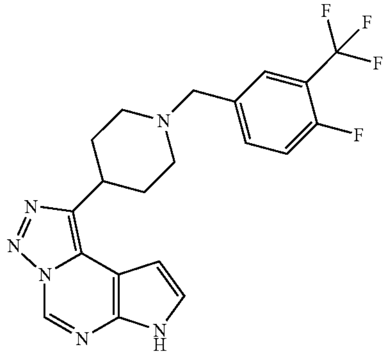 [SMILES: Fc1ccc(CN2CCC(c3nnn4cnc5[nH]ccc5c34)CC2)cc1C(F)(F)F] |
| 155 | 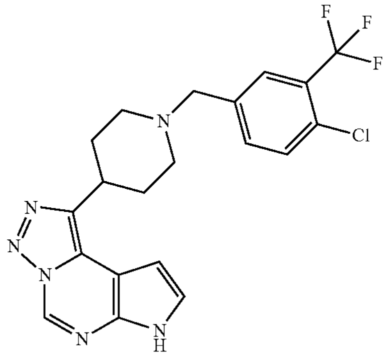 [SMILES: FC(F)(F)c1cc(CN2CCC(c3nnn4cnc5[nH]ccc5c34)CC2)ccc1Cl] |
| 156 | 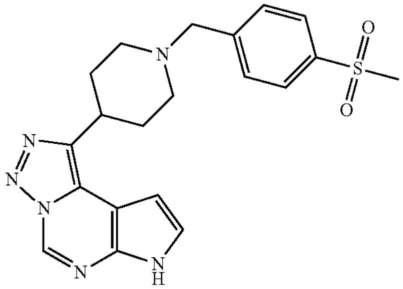 [SMILES: CS(=O)(=O)c1ccc(CN2CCC(c3nnn4cnc5[nH]ccc5c34)CC2)cc1] |
| 157 | 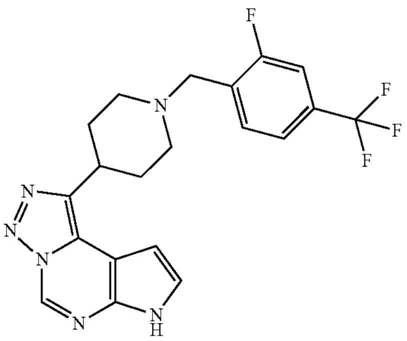 [SMILES: Fc1cc(C(F)(F)F)ccc1CN1CCC(c2nnn3cnc4[nH]ccc4c23)CC1] |

TABLE[a] 63-continued
| Ex | Structure |
|---|---|
| 158 | 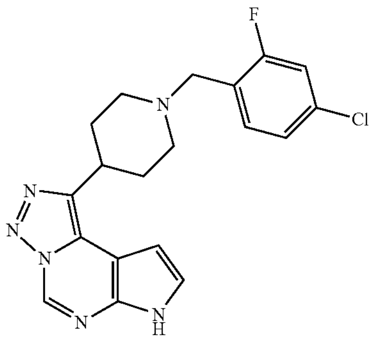 [SMILES: Fc1cc(Cl)ccc1CN1CCC(c2nnn3cnc4[nH]ccc4c23)CC1] |
| 159 | 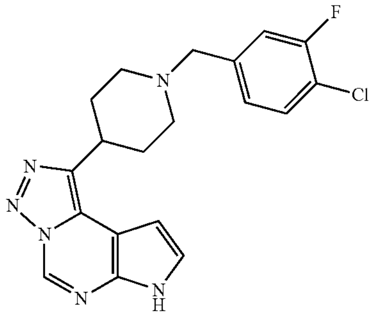 [SMILES: Fc1cc(CN2CCC(c3nnn4cnc5[nH]ccc5c34)CC2)ccc1Cl] |
| 160 | 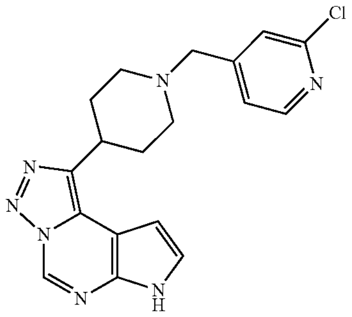 [SMILES: Clc1cc(CN2CCC(c3nnn4cnc5[nH]ccc5c34)CC2)ccn1] |
| 161 | 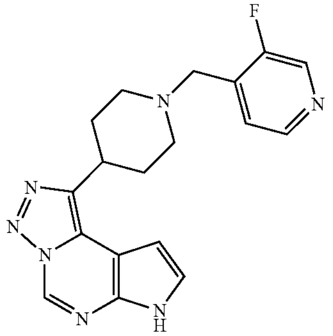 |
TABLE[a] 63-continued
| Ex | Structure |
|---|---|
| 162 | 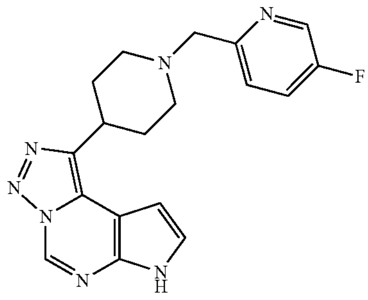 [SMILES: Fc1ccc(CN2CCC(c3nnn4cnc5[nH]ccc5c34)CC2)nc1] |
| 163 | 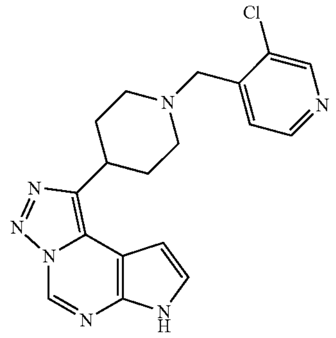 [SMILES: Clc1cnccc1CN1CCC(c2nnn3cnc4[nH]ccc4c23)CC1] |
| 164 | 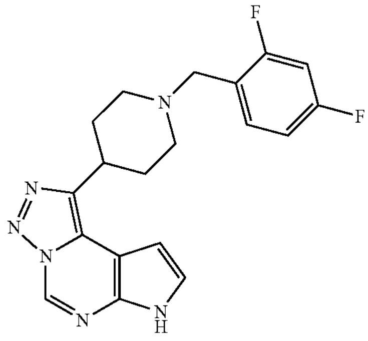 [SMILES: Fc1ccc(CN2CCC(c3nnn4cnc5[nH]ccc5c34)CC2)c(F)c1] |
| 165 | 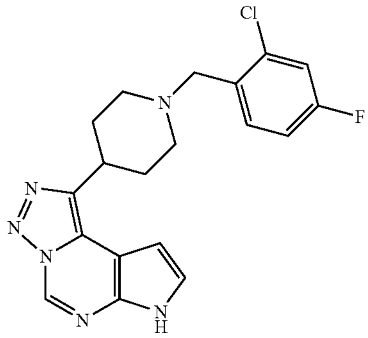 |

TABLE[a] 64
| Ex | Structure |
|---|---|
| 166 | 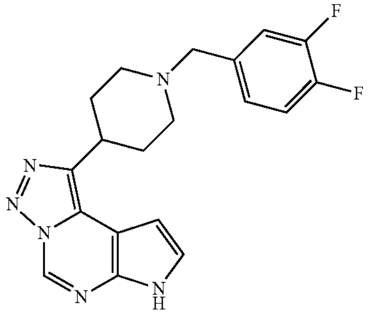 [SMILES: Fc1ccc(CN2CCC(c3nnn4cnc5[nH]ccc5c34)CC2)cc1F] |
| 167 | 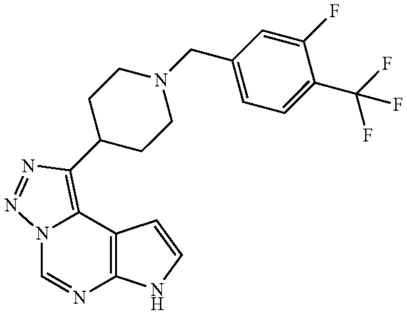 [SMILES: Fc1cc(CN2CCC(c3nnn4cnc5[nH]ccc5c34)CC2)ccc1C(F)(F)F] |
| 168 | 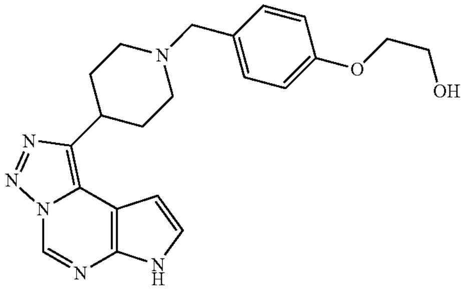 [SMILES: OCCOc1ccc(CN2CCC(c3nnn4cnc5[nH]ccc5c34)CC2)cc1] |
| 169 | 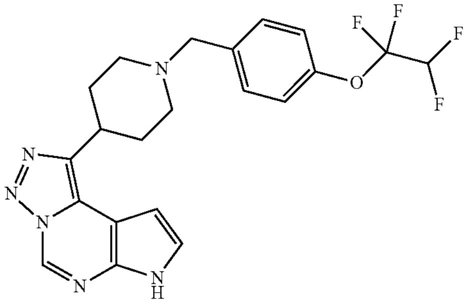 [SMILES: FC(F)C(F)(F)Oc1ccc(CN2CCC(c3nnn4cnc5[nH]ccc5c34)CC2)cc1] |
| 170 | 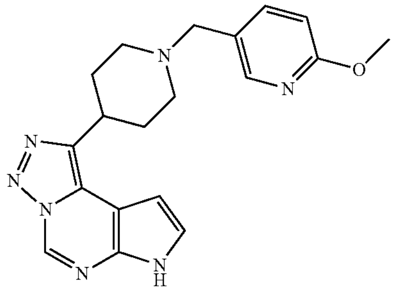 [SMILES: COc1ccc(CN2CCC(c3nnn4cnc5[nH]ccc5c34)CC2)cn1] |
TABLE[a] 64-continued
| Ex | Structure |
|---|---|
| 171 | 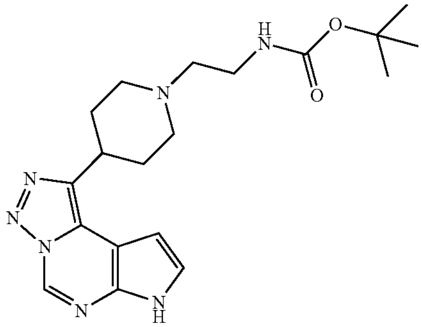 [SMILES: CC(C)(C)OC(=O)NCCN1CCC(c2nnn3cnc4[nH]ccc4c23)CC1] |
| 172 | 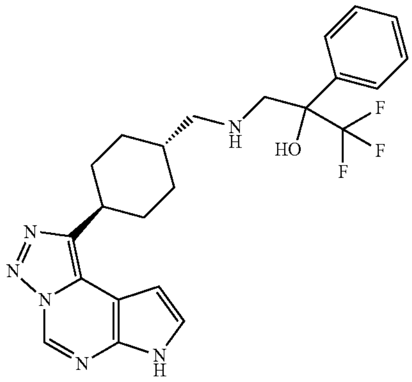 [SMILES: OC(CNC[C@H]1CC[C@H](c2nnn3cnc4[nH]ccc4c23)CC1)(c1ccccc1)C(F)(F)F] racemate |
| 173 | 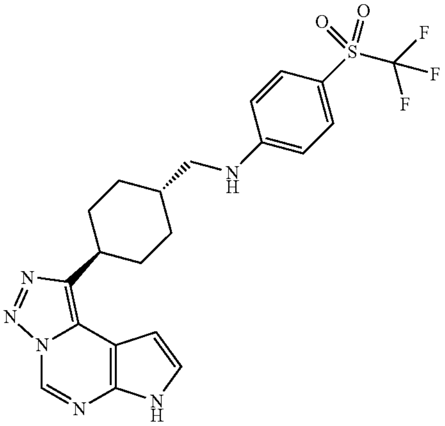 [SMILES: O=S(=O)(c1ccc(NC[C@H]2CC[C@H](c3nnn4cnc5[nH]ccc5c34)CC2)cc1)C(F)(F)F] |
| 174 | 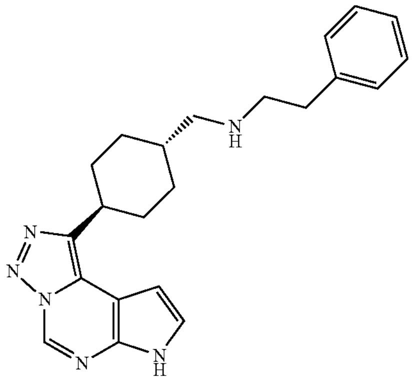 [SMILES: c1ccc(CCNC[C@H]2CC[C@H](c3nnn4cnc5[nH]ccc5c34)CC2)cc1] |

TABLE[a] 64-continued
| Ex | Structure |
|---|---|
| 175 | 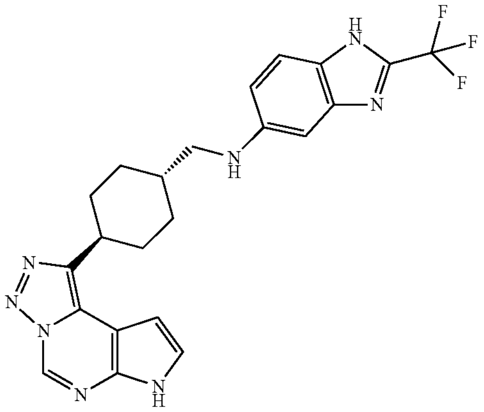 [SMILES: FC(F)(F)c1nc2cc(NC[C@H]3CC[C@H](c4nnn5cnc6[nH]ccc6c45)CC3)ccc2[nH]1] |
| 176 | 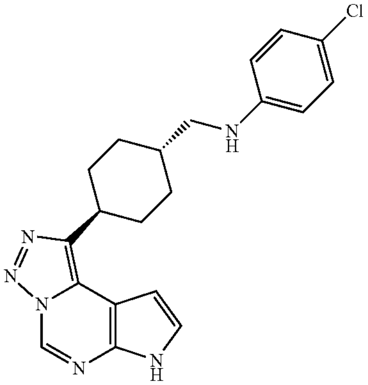 [SMILES: Clc1ccc(NC[C@H]2CC[C@H](c3nnn4cnc5[nH]ccc5c34)CC2)cc1] |
| 177 | 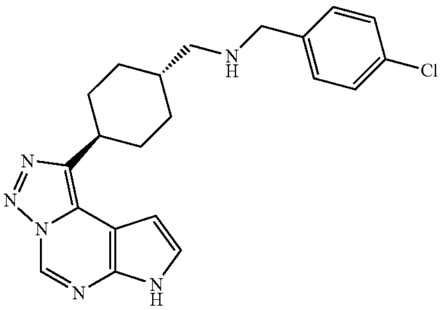 [SMILES: Clc1ccc(CNC[C@H]2CC[C@H](c3nnn4cnc5[nH]ccc5c34)CC2)cc1] |
| 178 | 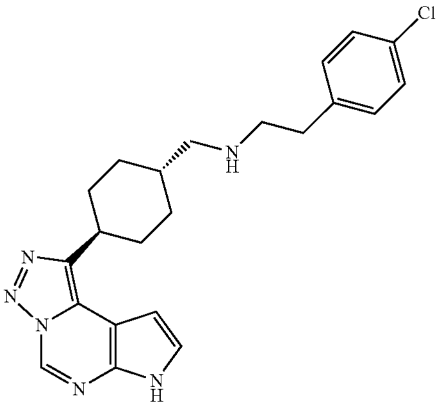 [SMILES: Clc1ccc(CCNC[C@H]2CC[C@H](c3nnn4cnc5[nH]ccc5c34)CC2)cc1] |
TABLE[a] 64-continued
| Ex | Structure |
|---|---|
| 179 | 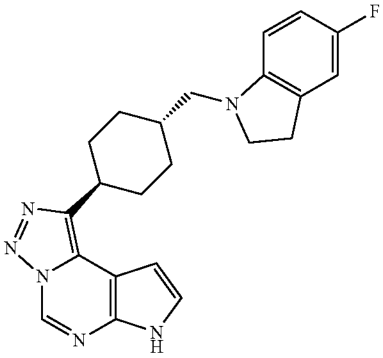 [SMILES: Fc1ccc2c(c1)CCN2C[C@H]1CC[C@H](c2nnn3cnc4[nH]ccc4c23)CC1] |
| 180 | 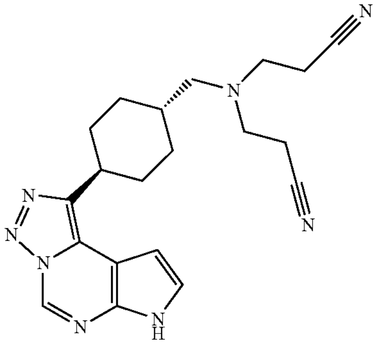 [SMILES: N#CCCN(CCC#N)C[C@H]1CC[C@H](c2nnn3cnc4[nH]ccc4c23)CC1] |
| 181 | 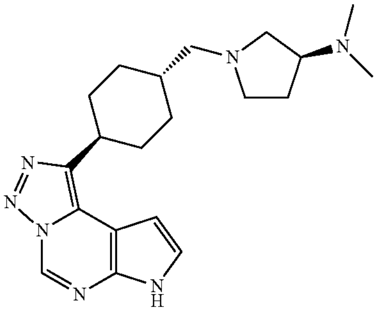 [SMILES: CN(C)[C@H]1CCN(C[C@H]2CC[C@H](c3nnn4cnc5[nH]ccc5c34)CC2)C1] |
| 182 | 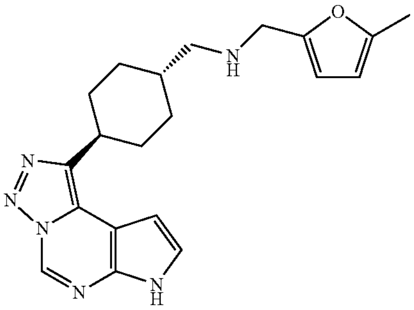 [SMILES: Cc1ccc(CNC[C@H]2CC[C@H](c3nnn4cnc5[nH]ccc5c34)CC2)o1] |

TABLE[a] 64-continued
| Ex | Structure |
|---|---|
| 183 | 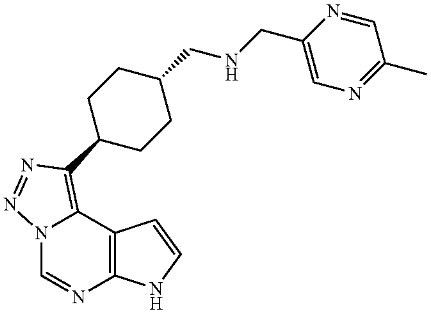 [SMILES: Cc1cnc(CNC[C@H]2CC[C@H](c3nnn4cnc5[nH]ccc5c34)CC2)cn1] |
TABLE[a] 65
| Ex | Structure |
|---|---|
| 184 | 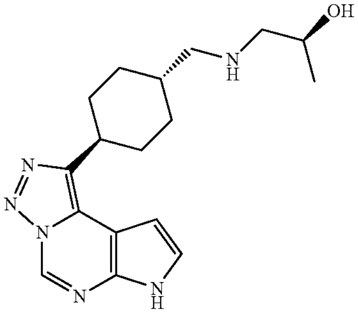 [SMILES: C[C@H](O)CNC[C@H]1CC[C@H](c2nnn3cnc4[nH]ccc4c23)CC1] |
| 185 | 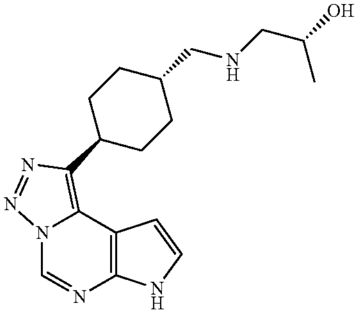 [SMILES: C[C@@H](O)CNC[C@H]1CC[C@H](c2nnn3cnc4[nH]ccc4c23)CC1] |
| 186 | 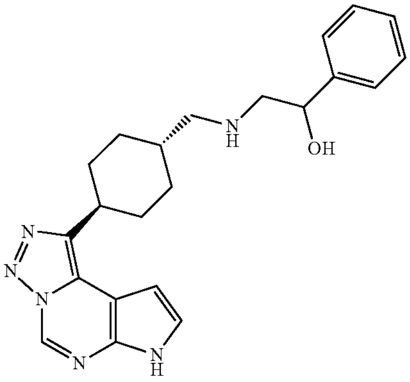 [SMILES: OC(CNC[C@H]1CC[C@H](c2nnn3cnc4[nH]ccc4c23)CC1)c1ccccc1]<br>racemate |
TABLE[a] 65-continued
| Ex | Structure |
|---|---|
| 187 | 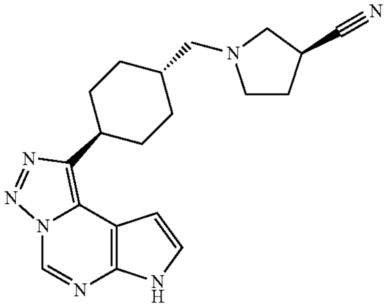 [SMILES: N#C[C@H]1CCN(C[C@H]2CC[C@H](c3nnn4cnc5[nH]ccc5c34)CC2)C1] |
| 188 | 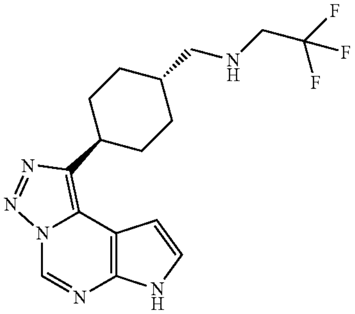 [SMILES: FC(F)(F)CNC[C@H]1CC[C@H](c2nnn3cnc4[nH]ccc4c23)CC1] |
| 189 | 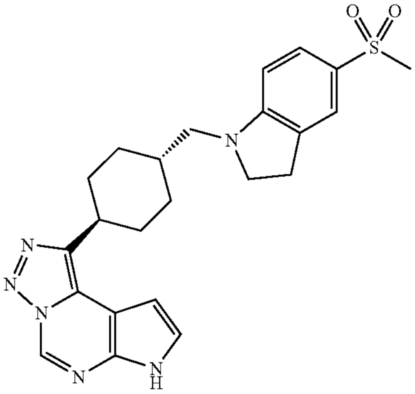 [SMILES: CS(=O)(=O)c1ccc2c(c1)CCN2C[C@H]1CC[C@H](c2nnn3cnc4[nH]ccc4c23)CC1] |
| 190 | 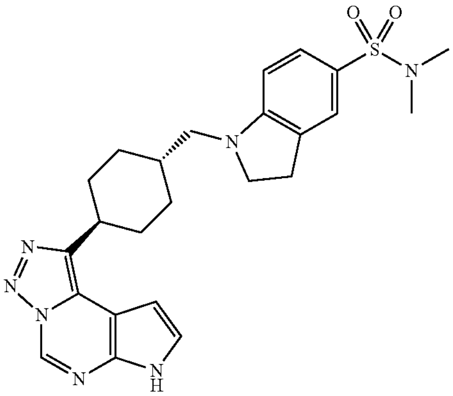 [SMILES: CN(C)S(=O)(=O)c1ccc2c(c1)CCN2C[C@H]1CC[C@H](c2nnn3cnc4[nH]ccc4c23)CC1] |

TABLE[a] 65-continued
| Ex | Structure |
| --- | --- |
| 191 | 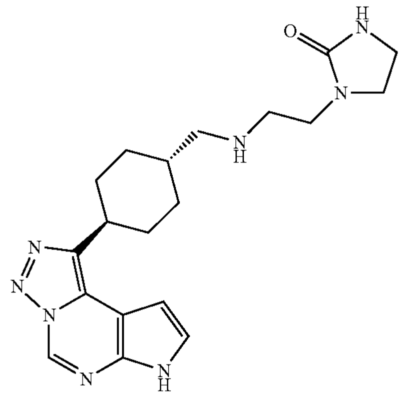 [SMILES: O=C1NCCN1CCNC[C@H]1CC[C@H](c2nnn3cnc4[nH]ccc4c23)CC1] |
| 192 | 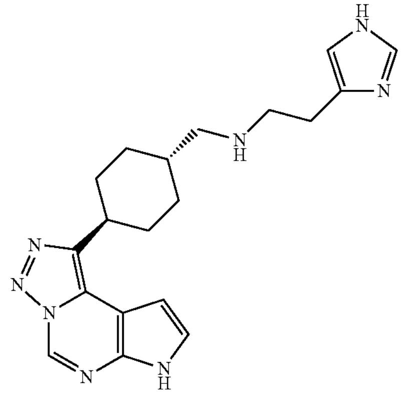 [SMILES: c1nc(CCNC[C@H]2CC[C@H](c3nnn4cnc5[nH]ccc5c34)CC2)c[nH]1] |
| 193 | 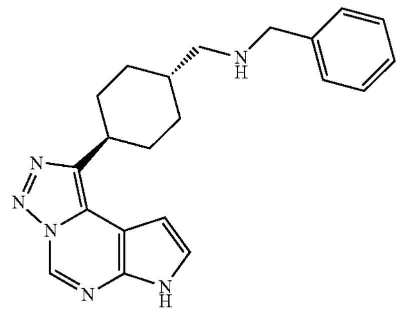 [SMILES: c1ccc(CNC[C@H]2CC[C@H](c3nnn4cnc5[nH]ccc5c34)CC2)cc1] |
| 194a | 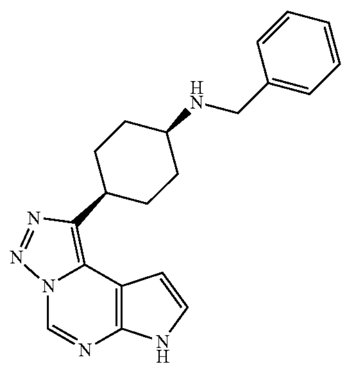 [SMILES: c1ccc(CN[C@H]2CC[C@@H](c3nnn4cnc5[nH]ccc5c34)CC2)cc1] |
TABLE[a] 65-continued
| Ex | Structure |
| --- | --- |
| 194b | 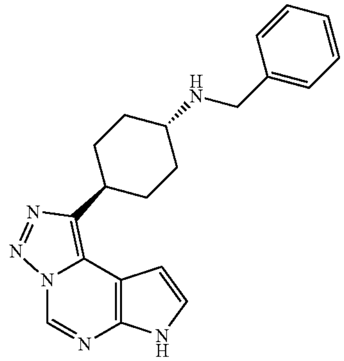 [SMILES: c1ccc(CN[C@H]2CC[C@H](c3nnn4cnc5[nH]ccc5c34)CC2)cc1] |
| 195a | 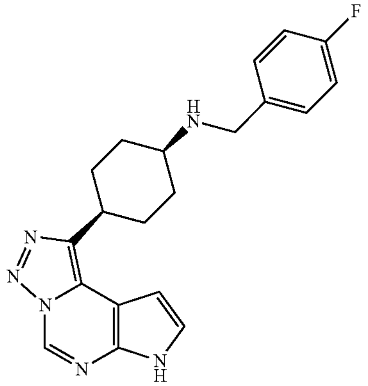 [SMILES: Fc1ccc(CN[C@H]2CC[C@@H](c3nnn4cnc5[nH]ccc5c34)CC2)cc1] |
| 195b | 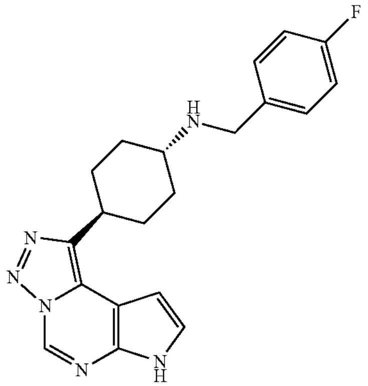 [SMILES: Fc1ccc(CN[C@H]2CC[C@H](c3nnn4cnc5[nH]ccc5c34)CC2)cc1] |
| 196a | 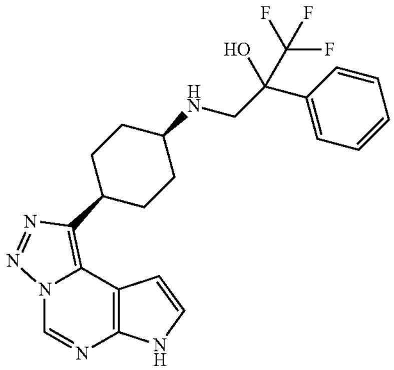 [SMILES: OC(CN[C@H]1CC[C@@H](c2nnn3cnc4[nH]ccc4c23)CC1)(c1ccccc1)C(F)(F)F] racemate |

TABLE[a] 65-continued
| Ex | Structure |
| --- | --- |
| 196b | 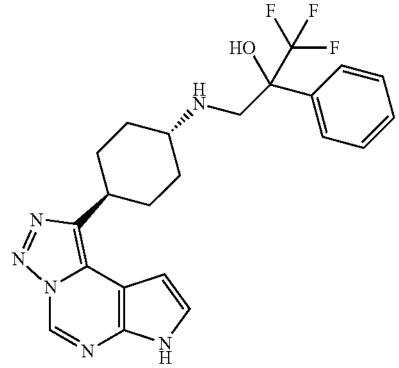 [SMILES: OC(CN[C@H]1CC[C@H](c2nnn3cnc4[nH]ccc4c23)CC1)(c1ccccc1)C(F)(F)F]<br>racemate |
| 197a | 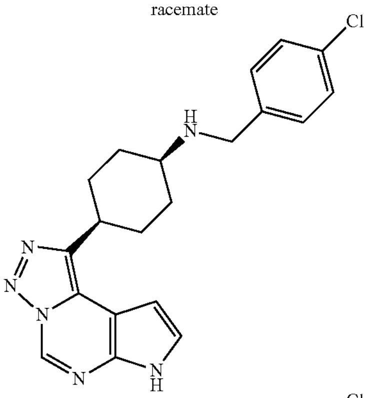 |
| 197b | 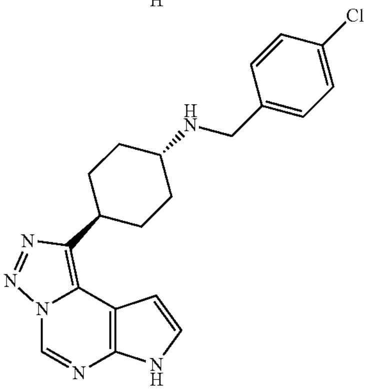 |
TABLE[a] 66
| Ex | Structure |
| --- | --- |
| 198b | 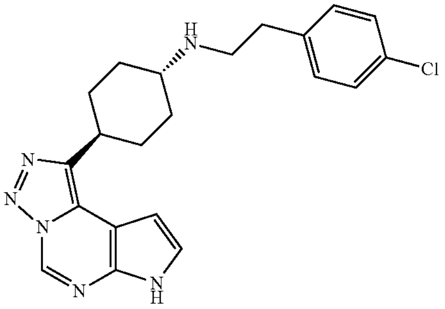 [SMILES: Clc1ccc(CCN[C@H]2CC[C@H](c3nnn4cnc5[nH]ccc5c34)CC2)cc1] |
TABLE[a] 66-continued
| Ex | Structure |
| --- | --- |
| 199b | 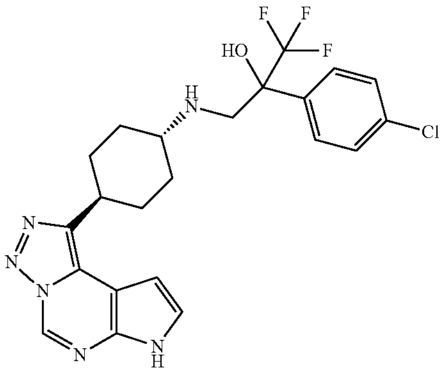 [SMILES: OC(CN[C@H]1CC[C@H](c2nnn3cnc4[nH]ccc4c23)CC1)(c1ccc(Cl)cc1)C(F)(F)F]<br>racemate |
| 200b | 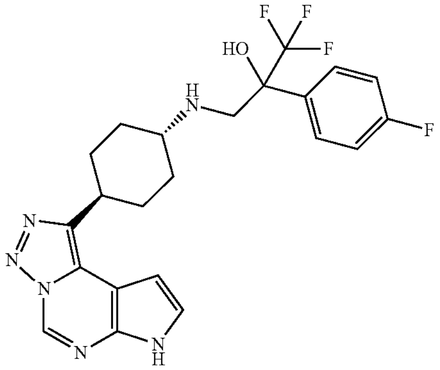 [SMILES: OC(CN[C@H]1CC[C@H](c2nnn3cnc4[nH]ccc4c23)CC1)(c1ccc(F)cc1)C(F)(F)F]<br>racemate |
| 201b | 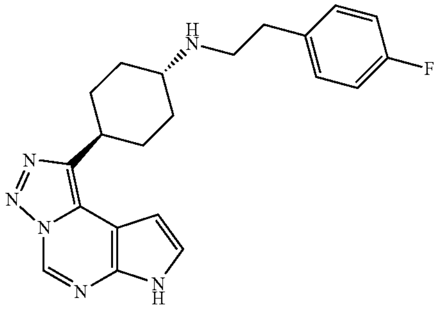 [SMILES: Fc1ccc(CCN[C@H]2CC[C@H](c3nnn4cnc5[nH]ccc5c34)CC2)cc1] |
| 202b | 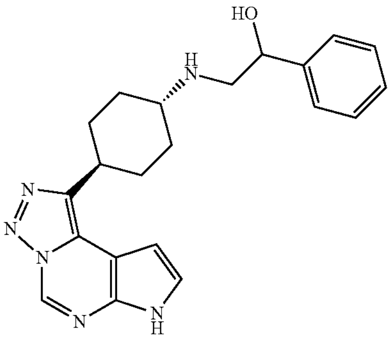<br>racemate |

TABLE[a] 66-continued
| Ex | Structure |
|---|---|
| 203b | 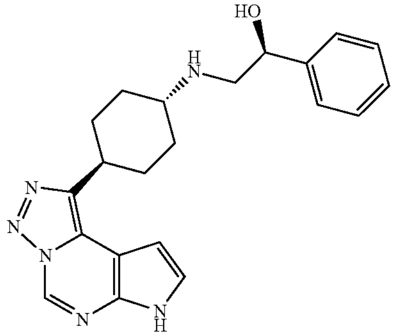 [SMILES: O[C@H](CN[C@H]1CC[C@H](c2nnn3cnc4[nH]ccc4c23)CC1)c1ccccc1] |
| 204b | 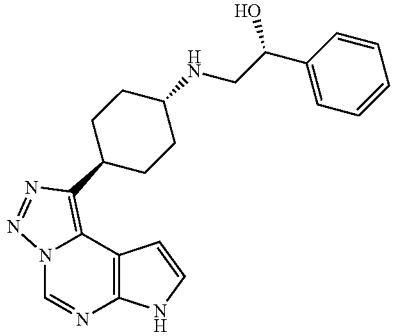 [SMILES: O[C@@H](CN[C@H]1CC[C@H](c2nnn3cnc4[nH]ccc4c23)CC1)c1ccccc1] |
| 205 | 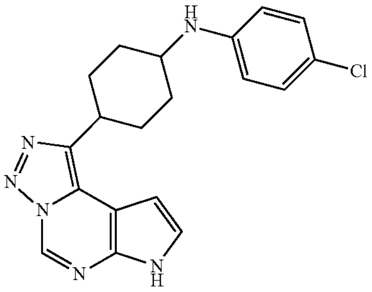 [SMILES: Clc1ccc(NC2CCC(c3nnn4cnc5[nH]ccc5c34)CC2)cc1] cis/trans mixture |
| 206 | 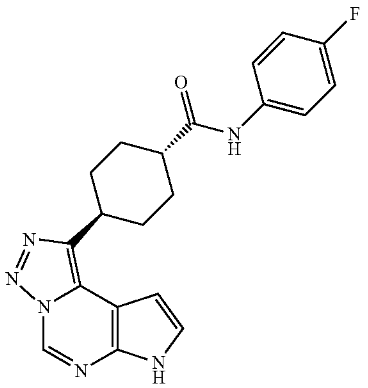 [SMILES: O=C(Nc1ccc(F)cc1)[C@H]1CC[C@H](c2nnn3cnc4[nH]ccc4c23)CC1] |
| 207 | 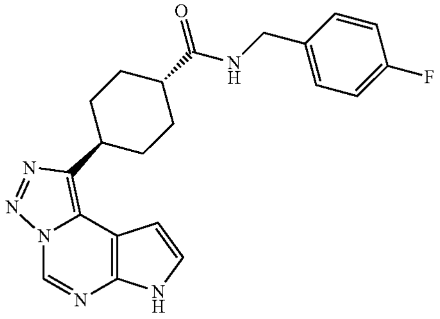 [SMILES: O=C(NCc1ccc(F)cc1)[C@H]1CC[C@H](c2nnn3cnc4[nH]ccc4c23)CC1] |
| 208 | 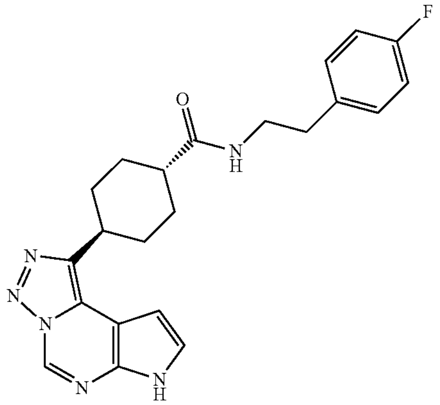 [SMILES: O=C(NCCc1ccc(F)cc1)[C@H]1CC[C@H](c2nnn3cnc4[nH]ccc4c23)CC1] |
| 209 | 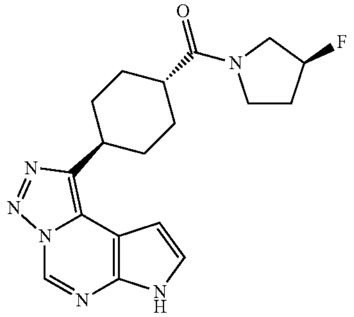 [SMILES: O=C([C@H]1CC[C@H](c2nnn3cnc4[nH]ccc4c23)CC1)N1CC[C@H](F)C1] |
| 210 | 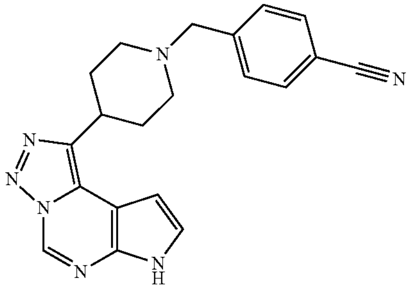 [SMILES: N#Cc1ccc(CN2CCC(c3nnn4cnc5[nH]ccc5c34)CC2)cc1] |

TABLE[a] 66-continued
| Ex | Structure |
|---|---|
| 211 | 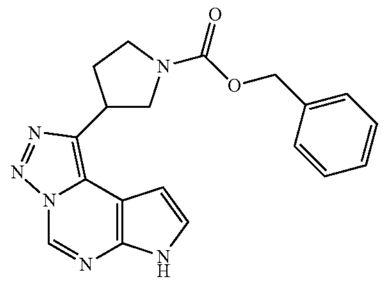 [SMILES: O=C(OCc1ccccc1)N1CCC(c2nnn3cnc4[nH]ccc4c23)C1] racemate |
| 212 | 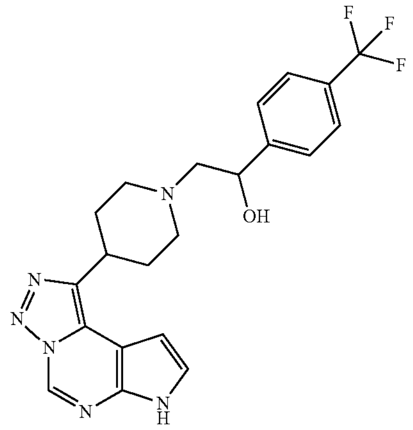 [SMILES: OC(CN1CCC(c2nnn3cnc4[nH]ccc4c23)CC1)c1ccc(C(F)(F)F)cc1] racemate |
TABLE[a] 67
| Ex | Structure |
|---|---|
| 213 | 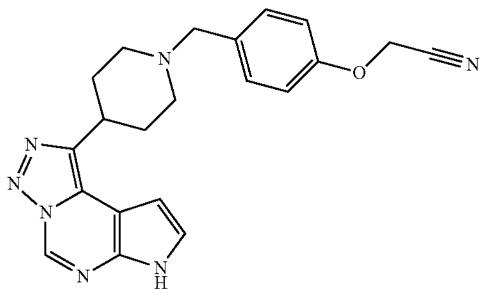 [SMILES: N#CCOc1ccc(CN2CCC(c3nnn4cnc5[nH]ccc5c34)CC2)cc1] |
| 214 | 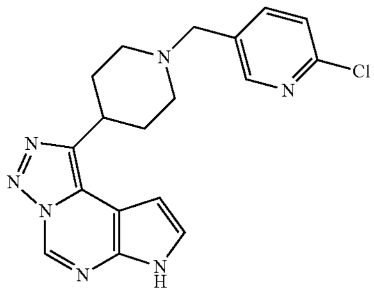 [SMILES: Clc1ccc(CN2CCC(c3nnn4cnc5[nH]ccc5c34)CC2)cn1] |
TABLE[a] 67-continued
| Ex | Structure |
|---|---|
| 215 | 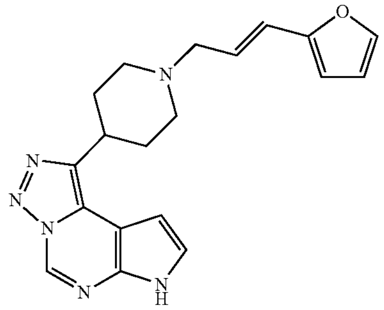 [SMILES: C(=C\c1ccco1)/CN1CCC(c2nnn3cnc4[nH]ccc4c23)CC1] |
| 216 | 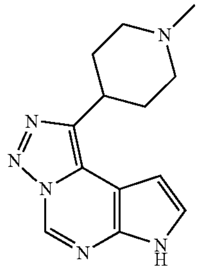 [SMILES: CN1CCC(c2nnn3cnc4[nH]ccc4c23)CC1] |
| 217 | 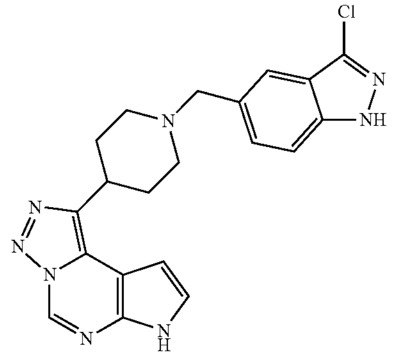 [SMILES: Clc1n[nH]c2ccc(CN3CCC(c4nnn5cnc6[nH]ccc6c45)CC3)cc12] |
| 218 | 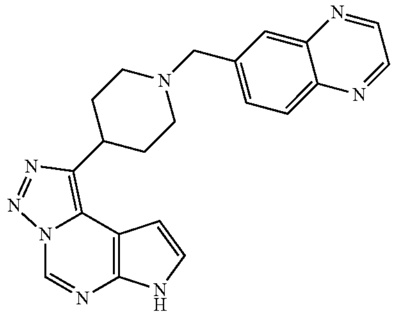 [SMILES: c1cnc2cc(CN3CCC(c4nnn5cnc6[nH]ccc6c45)CC3)ccc2n1] |
| 219 | 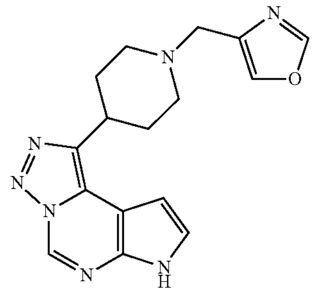 |

TABLE[a] 67-continued
| Ex | Structure |
|---|---|
| 220 | 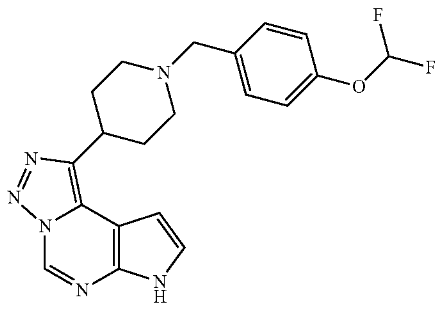 [SMILES: FC(F)Oc1ccc(CN2CCC(c3nnn4cnc5[nH]ccc5c34)CC2)cc1] |
| 221 | 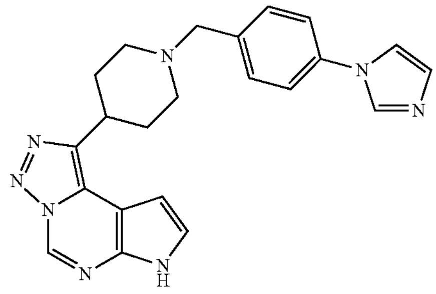 [SMILES: c1cn(-c2ccc(CN3CCC(c4nnn5cnc6[nH]ccc6c45)CC3)cc2)cn1] |
| 222 | 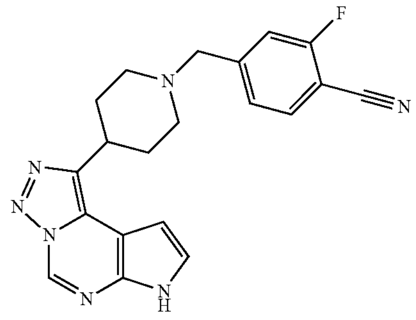 [SMILES: N#Cc1ccc(CN2CCC(c3nnn4cnc5[nH]ccc5c34)CC2)cc1F] |
| 223 | 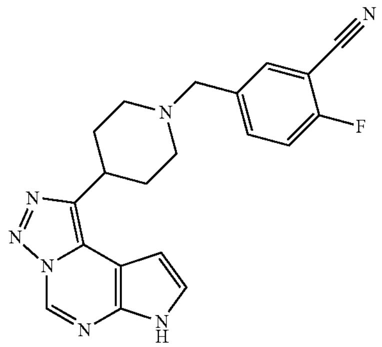 [SMILES: N#Cc1cc(CN2CCC(c3nnn4cnc5[nH]ccc5c34)CC2)ccc1F] |
| 224 | 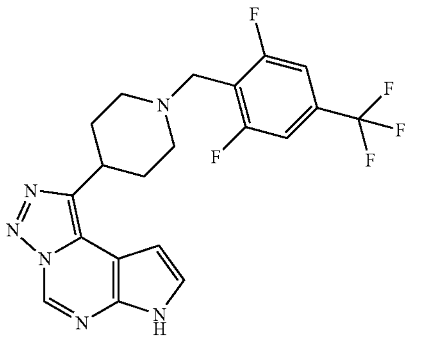 [SMILES: Fc1cc(C(F)(F)F)cc(F)c1CN1CCC(c2nnn3cnc4[nH]ccc4c23)CC1] |
TABLE[a] 67-continued
| Ex | Structure |
|---|---|
| 225 | 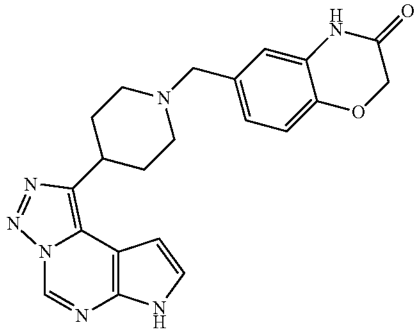 [SMILES: O=C1COc2ccc(CN3CCC(c4nnn5cnc6[nH]ccc6c45)CC3)cc2N1] |
| 226 | 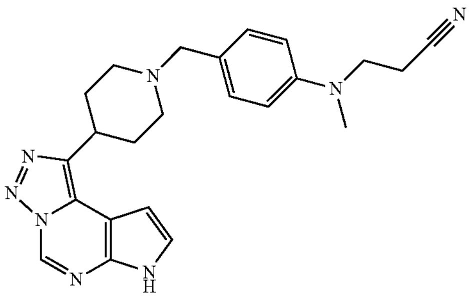 [SMILES: CN(CCC#N)c1ccc(CN2CCC(c3nnn4cnc5[nH]ccc5c34)CC2)cc1] |
| 227 | 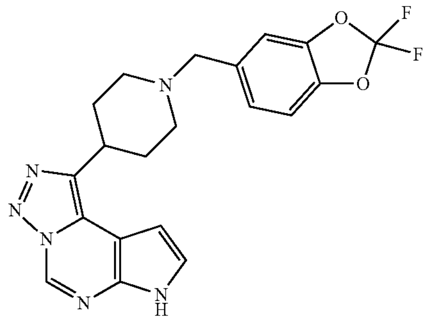 [SMILES: FC1(F)Oc2ccc(CN3CCC(c4nnn5cnc6[nH]ccc6c45)CC3)cc2O1] |
| 228 | 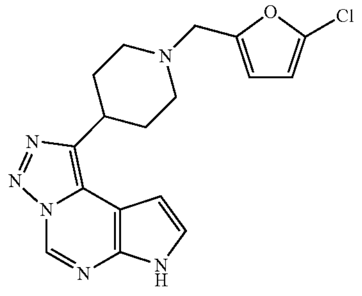 [SMILES: Clc1ccc(CN2CCC(c3nnn4cnc5[nH]ccc5c34)CC2)o1] |

TABLE[a] 67-continued
| Ex | Structure |
| --- | --- |
| 229 | 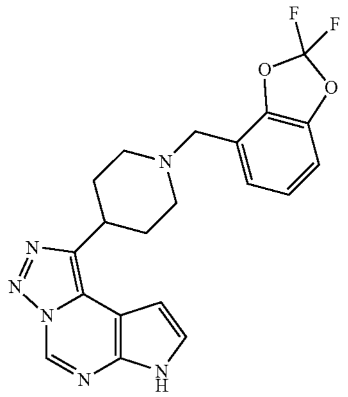 [SMILES: FC1(F)Oc2cccc(CN3CCC(c4nnn5cnc6[nH]ccc6c45)CC3)c2O1] |
| 230 | 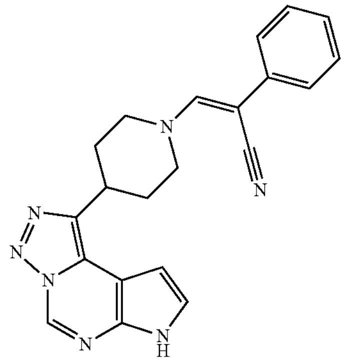 [SMILES: N#C/C(=C\N1CCC(c2nnn3cnc4[nH]ccc4c23)CC1)c1ccccc1] |
TABLE[a] 68
| Ex | Structure |
| --- | --- |
| 231 | 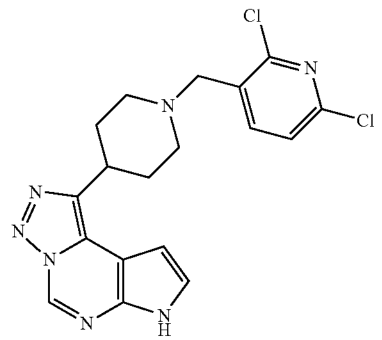 [SMILES: Clc1ccc(CN2CCC(c3nnn4cnc5[nH]ccc5c34)CC2)c(Cl)n1] |
| 232 | 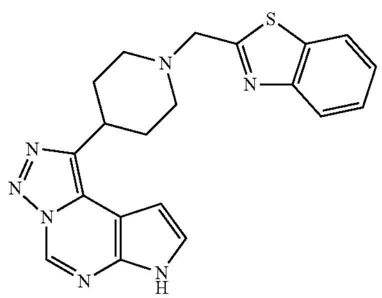 [SMILES: c1ccc2sc(CN3CCC(c4nnn5cnc6[nH]ccc6c45)CC3)nc2c1] |
TABLE[a] 68-continued
| Ex | Structure |
| --- | --- |
| 233 | 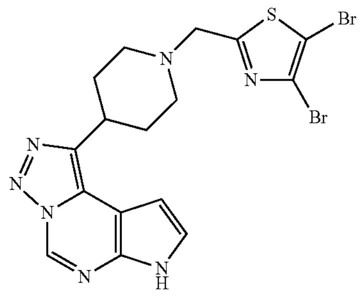 [SMILES: Brc1nc(CN2CCC(c3nnn4cnc5[nH]ccc5c34)CC2)sc1Br] |
| 234 | 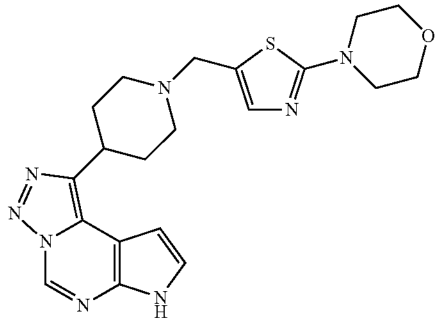 [SMILES: c1cc2c(ncn3nnc(C4CCN(Cc5cnc(N6CCOCC6)s5)CC4)c23)[nH]1] |
| 235 | 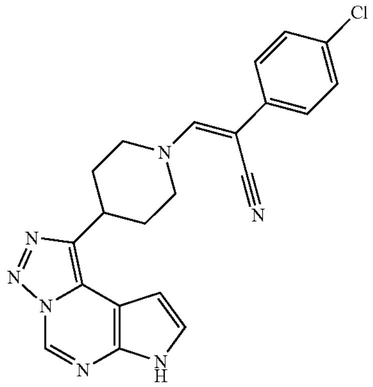 [SMILES: N#C/C(=C\N1CCC(c2nnn3cnc4[nH]ccc4c23)CC1)c1ccc(Cl)cc1] |
| 236 | 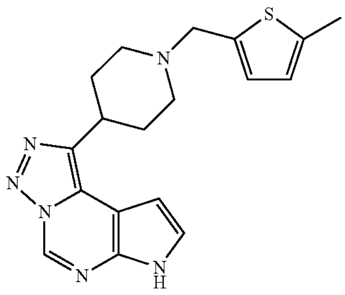 [SMILES: Cc1ccc(CN2CCC(c3nnn4cnc5[nH]ccc5c34)CC2)s1] |
| 237 | 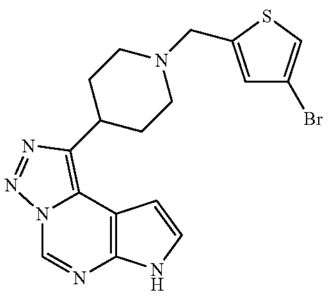 [SMILES: Brc1csc(CN2CCC(c3nnn4cnc5[nH]ccc5c34)CC2)c1] |

TABLE[a] 68-continued
| Ex | Structure |
| --- | --- |
| 238 | 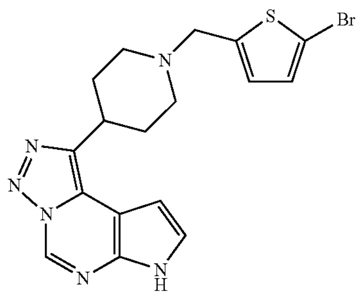 [SMILES: Brc1ccc(CN2CCC(c3nnn4cnc5[nH]ccc5c34)CC2)s1] |
| 239 | 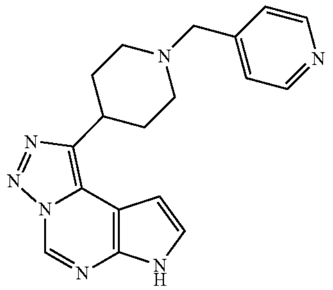 [SMILES: c1cc(CN2CCC(c3nnn4cnc5[nH]ccc5c34)CC2)ccn1] |
| 240 | 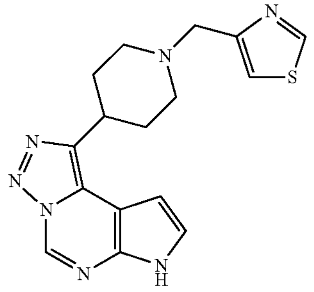 [SMILES: c1cc2c(ncn3nnc(C4CCN(Cc5cscn5)CC4)c23)[nH]1] |
| 241 | 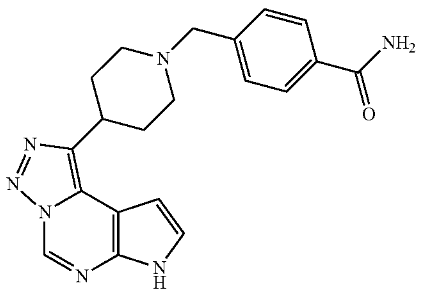 [SMILES: NC(=O)c1ccc(CN2CCC(c3nnn4cnc5[nH]ccc5c34)CC2)cc1] |
| 242 | 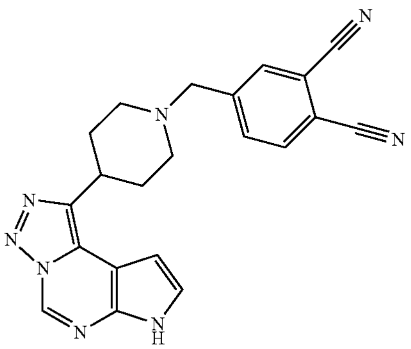 [SMILES: N#Cc1ccc(CN2CCC(c3nnn4cnc5[nH]ccc5c34)CC2)cc1C#N] |
TABLE[a] 68-continued
| Ex | Structure |
| --- | --- |
| 243 | 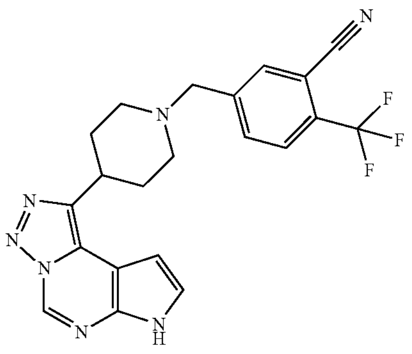 [SMILES: N#Cc1cc(CN2CCC(c3nnn4cnc5[nH]ccc5c34)CC2)ccc1C(F)(F)F] |
| 244 | 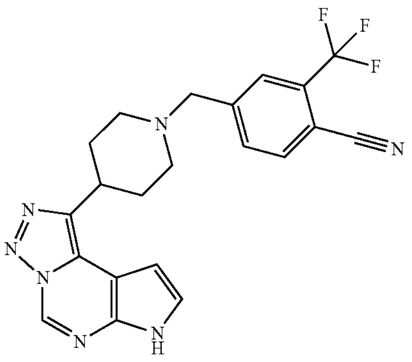 [SMILES: N#Cc1ccc(CN2CCC(c3nnn4cnc5[nH]ccc5c34)CC2)cc1C(F)(F)F] |
| 245 | 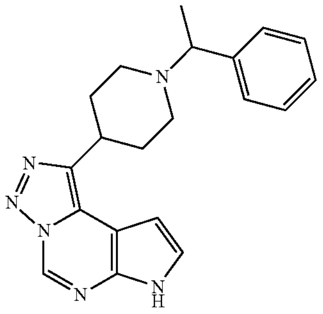 [SMILES: CC(c1ccccc1)N1CCC(c2nnn3cnc4[nH]ccc4c23)CC1]<br>racemate |
| 246 | 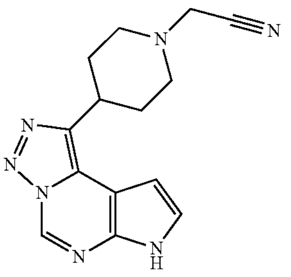 [SMILES: N#CCN1CCC(c2nnn3cnc4[nH]ccc4c23)CC1] |

TABLE[a] 68-continued
| Ex | Structure |
|---|---|
| 247 | 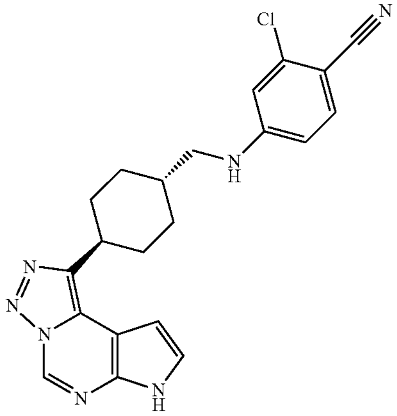 [SMILES: N#Cc1ccc(NC[C@H]2CC[C@H](c3nnn4cnc5[nH]ccc5c34)CC2)cc1Cl] |
| 248 | 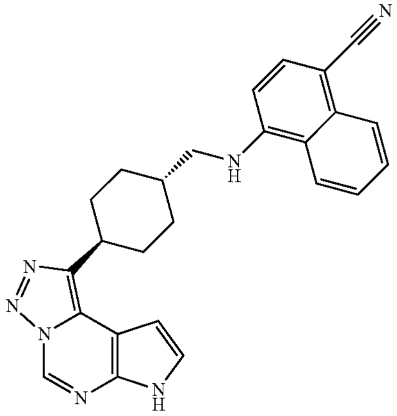 [SMILES: N#Cc1ccc(NC[C@H]2CC[C@H](c3nnn4cnc5[nH]ccc5c34)CC2)c2ccccc12] |
TABLE[a] 69
| Ex | Structure |
|---|---|
| 249 | 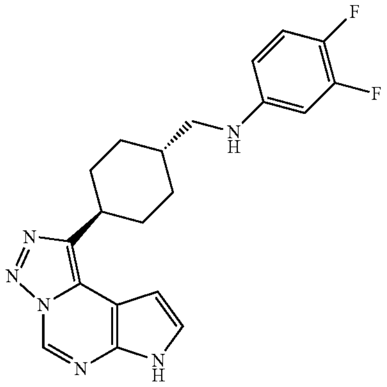 [SMILES: Fc1ccc(NC[C@H]2CC[C@H](c3nnn4cnc5[nH]ccc5c34)CC2)cc1F] |
TABLE[a] 69-continued
| Ex | Structure |
|---|---|
| 250 | 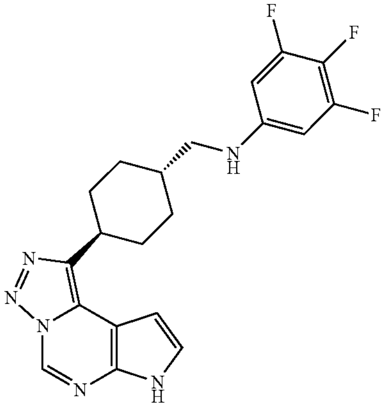 [SMILES: Fc1cc(NC[C@H]2CC[C@H](c3nnn4cnc5[nH]ccc5c34)CC2)cc(F)c1F] |
| 251 | 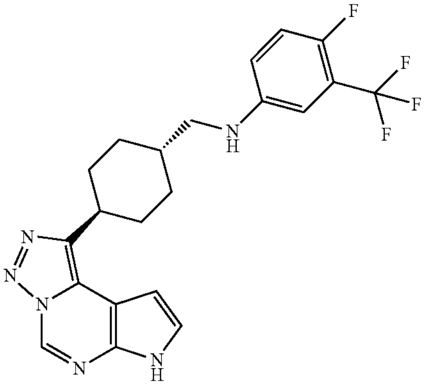 [SMILES: Fc1ccc(NC[C@H]2CC[C@H](c3nnn4cnc5[nH]ccc5c34)CC2)cc1C(F)(F)F] |
| 252 | 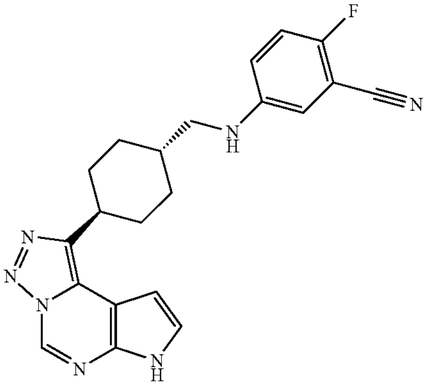 [SMILES: N#Cc1cc(NC[C@H]2CC[C@H](c3nnn4cnc5[nH]ccc5c34)CC2)ccc1F] |
| 253 | 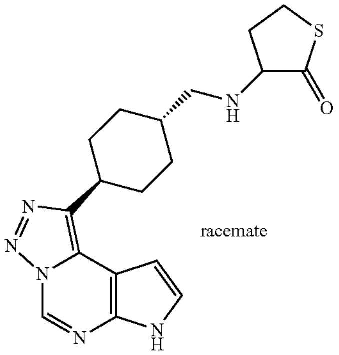 [SMILES: O=C1SCCC1NC[C@H]1CC[C@H](c2nnn3cnc4[nH]ccc4c23)CC1] racemate |

TABLE[a] 69-continued
| Ex | Structure |
|---|---|
| 254 | 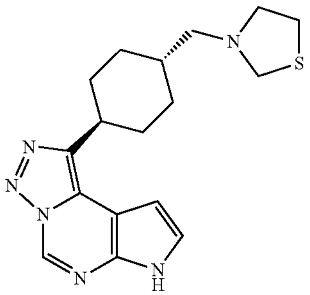 [SMILES: c1cc2c(ncn3nnc([C@H]4CC[C@H](CN5CCSC5)CC4)c23)[nH]1] |
| 255 | 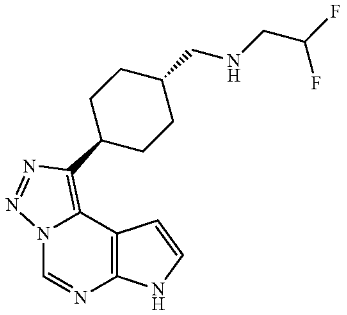 [SMILES: FC(F)CNC[C@H]1CC[C@H](c2nnn3cnc4[nH]ccc4c23)CC1] |
| 256 | 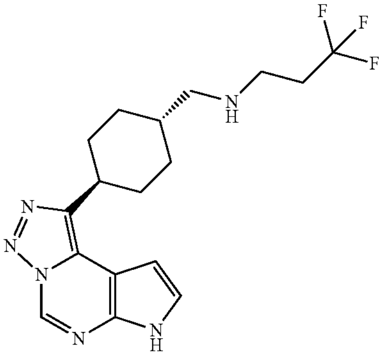 [SMILES: FC(F)(F)CCNC[C@H]1CC[C@H](c2nnn3cnc4[nH]ccc4c23)CC1] |
| 257 | 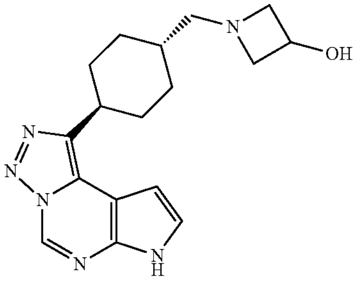 [SMILES: OC1CN(C[C@H]2CC[C@H](c3nnn4cnc5[nH]ccc5c34)CC2)C1] |
| 258 | 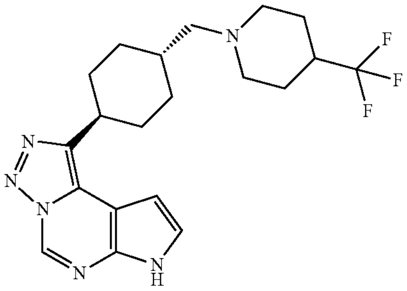 [SMILES: FC(F)(F)C1CCN(C[C@H]2CC[C@H](c3nnn4cnc5[nH]ccc5c34)CC2)CC1] |
TABLE[a] 69-continued
| Ex | Structure |
|---|---|
| 259 | 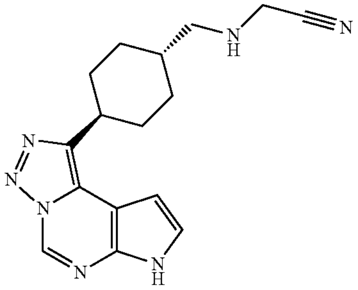 [SMILES: N#CCNC[C@H]1CC[C@H](c2nnn3cnc4[nH]ccc4c23)CC1] |
| 260 | 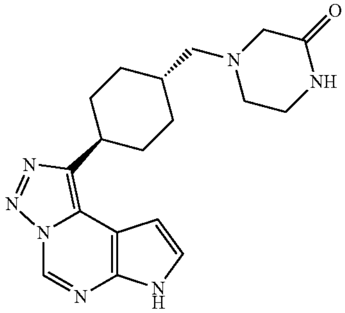 [SMILES: O=C1CN(C[C@H]2CC[C@H](c3nnn4cnc5[nH]ccc5c34)CC2)CCN1] |
| 261 | 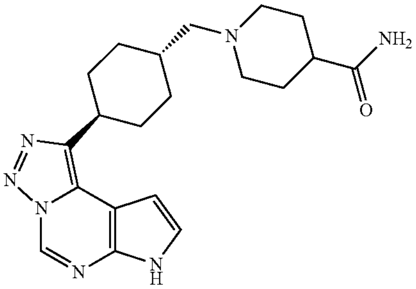 [SMILES: NC(=O)C1CCN(C[C@H]2CC[C@H](c3nnn4cnc5[nH]ccc5c34)CC2)CC1] |
| 262 | 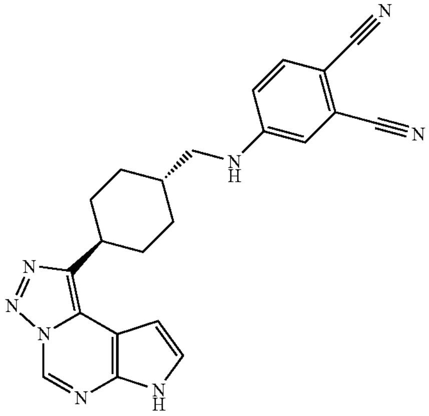 [SMILES: N#Cc1ccc(NC[C@H]2CC[C@H](c3nnn4cnc5[nH]ccc5c34)CC2)cc1C#N] |

TABLE[a] 69-continued
| Ex | Structure |
|---|---|
| 263 | 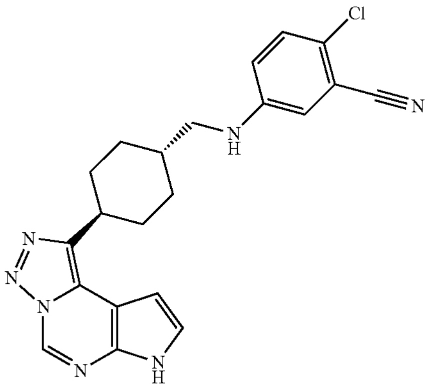 |
| 264 | 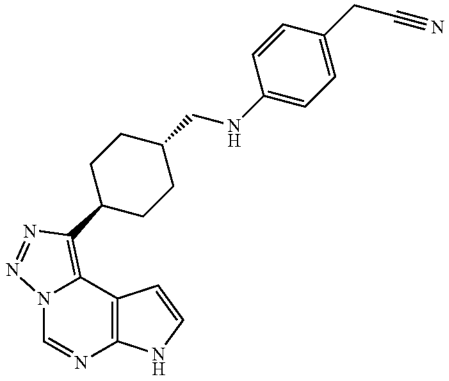 [SMILES: N#CCc1ccc(NC[C@H]2CC[C@H](c3nnn4cnc5[nH]ccc5c34)CC2)cc1] |
| 265 | 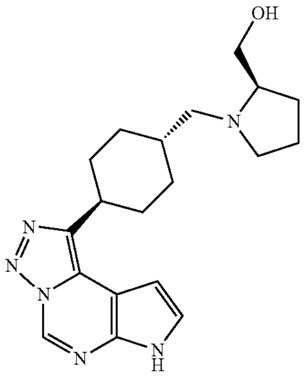 [SMILES: OC[C@H]1CCCN1C[C@H]1CC[C@H](c2nnn3cnc4[nH]ccc4c23)CC1] |
| 266 | 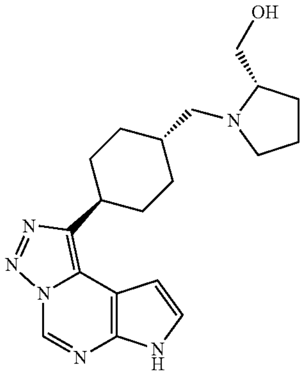 [SMILES: OC[C@@H]1CCCN1C[C@H]1CC[C@H](c2nnn3cnc4[nH]ccc4c23)CC1] |
TABLE[a] 70
| Ex | Structure |
|---|---|
| 267 | 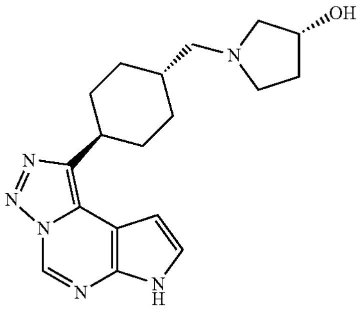 [SMILES: O[C@@H]1CCN(C[C@H]2CC[C@H](c3nnn4cnc5[nH]ccc5c34)CC2)C1] |
| 268 | 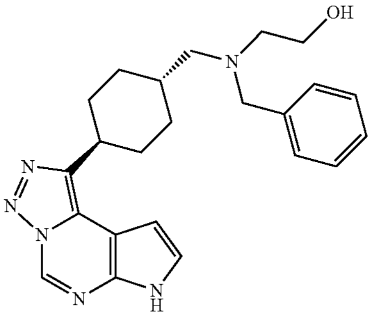 [SMILES: OCCN(Cc1ccccc1)C[C@H]1CC[C@H](c2nnn3cnc4[nH]ccc4c23)CC1] |
| 269 | 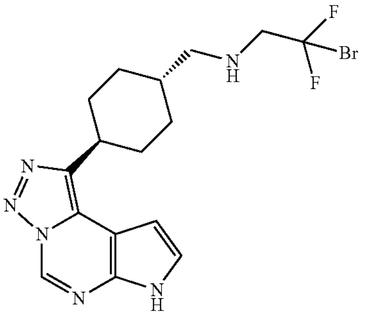 [SMILES: FC(F)(Br)CNC[C@H]1CC[C@H](c2nnn3cnc4[nH]ccc4c23)CC1] |
| 270 | 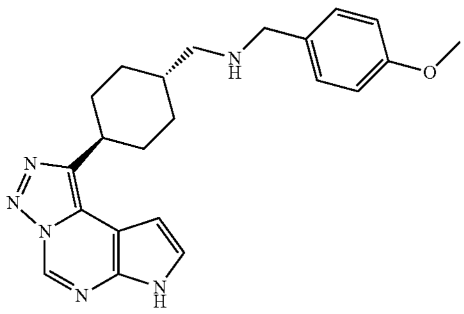 [SMILES: COc1ccc(CNC[C@H]2CC[C@H](c3nnn4cnc5[nH]ccc5c34)CC2)cc1] |
| 271 | 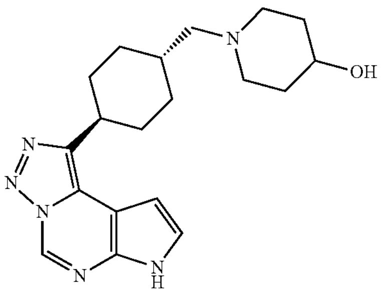 [SMILES: OC1CCN(C[C@H]2CC[C@H](c3nnn4cnc5[nH]ccc5c34)CC2)CC1] |

TABLE[a] 70-continued
| Ex | Structure |
|---|---|
| 272 | 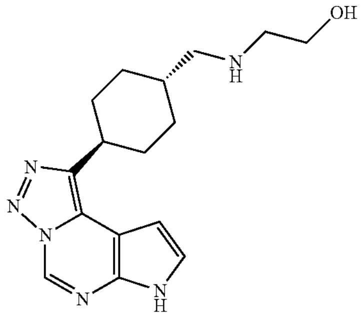 [SMILES: OCCNC[C@H]1CC[C@H](c2nnn3cnc4[nH]ccc4c23)CC1] |
| 273 | 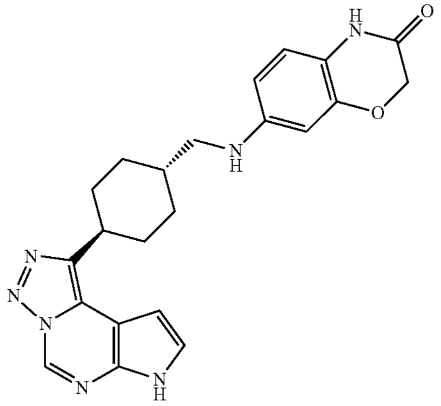 [SMILES: O=C1COc2cc(NC[C@H]3CC[C@H](c4nnn5cnc6[nH]ccc6c45)CC3)ccc2N1] |
| 274 | 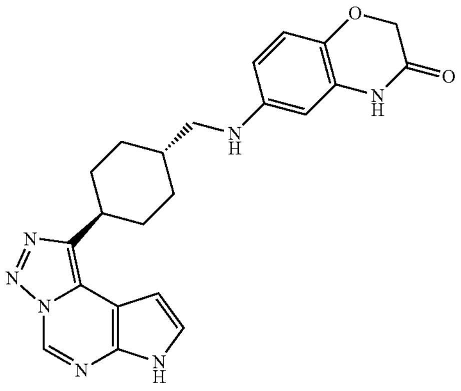 [SMILES: O=C1COc2ccc(NC[C@H]3CC[C@H](c4nnn5cnc6[nH]ccc6c45)CC3)cc2N1] |
| 275 | 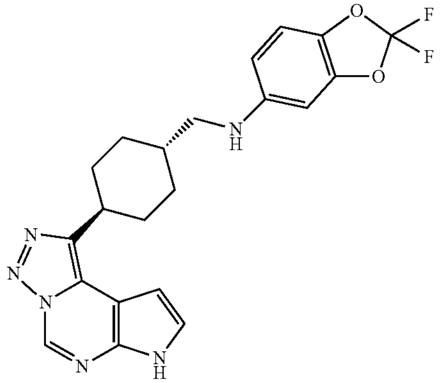 [SMILES: FC1(F)Oc2ccc(NC[C@H]3CC[C@H](c4nnn5cnc6[nH]ccc6c45)CC3)cc2O1] |
| 276 | 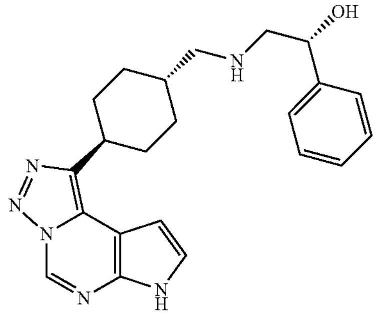 [SMILES: O[C@@H](CNC[C@H]1CC[C@H](c2nnn3cnc4[nH]ccc4c23)CC1)c1ccccc1] |
| 277 | 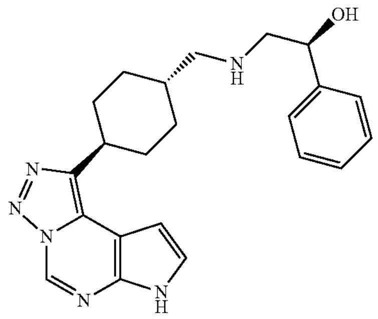 [SMILES: O[C@H](CNC[C@H]1CC[C@H](c2nnn3cnc4[nH]ccc4c23)CC1)c1ccccc1] |
| 278 | 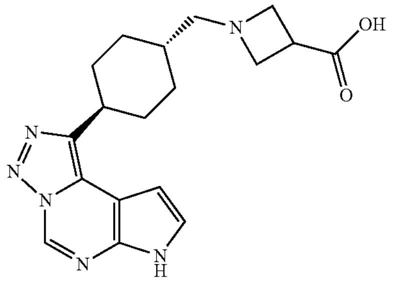 [SMILES: O=C(O)C1CN(C[C@H]2CC[C@H](c3nnn4cnc5[nH]ccc5c34)CC2)C1] |
| 279 | 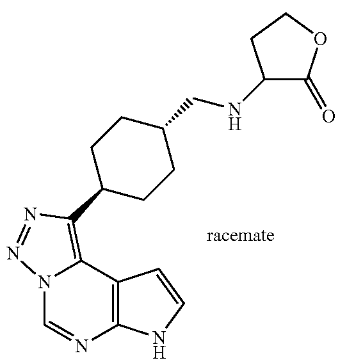 [SMILES: O=C1OCCC1NC[C@H]1CC[C@H](c2nnn3cnc4[nH]ccc4c23)CC1] racemate |

TABLE[a] 70-continued
| Ex | Structure |
| --- | --- |
| 280 | 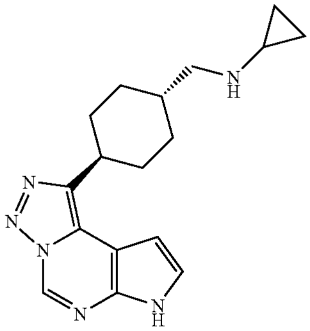 [SMILES: c1cc2c(ncn3nnc([C@H]4CC[C@H](CNC5CC5)CC4)c23)[nH]1] |
| 281 | 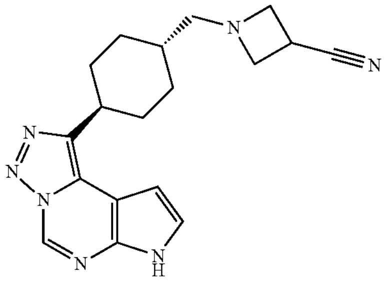 [SMILES: N#CC1CN(C[C@H]2CC[C@H](c3nnn4cnc5[nH]ccc5c34)CC2)C1] |
| 282 | 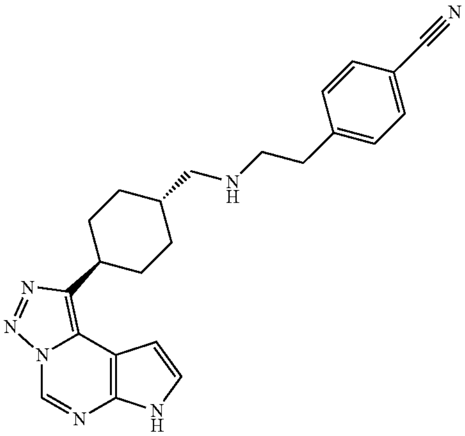 [SMILES: N#Cc1ccc(CCNC[C@H]2CC[C@H](c3nnn4cnc5[nH]ccc5c34)CC2)cc1] |
| 283 | 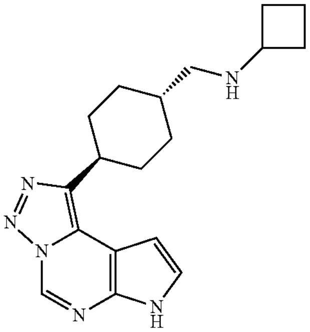 [SMILES: c1cc2c(ncn3nnc([C@H]4CC[C@H](CNC5CCC5)CC4)c23)[nH]1] |
| 284 | 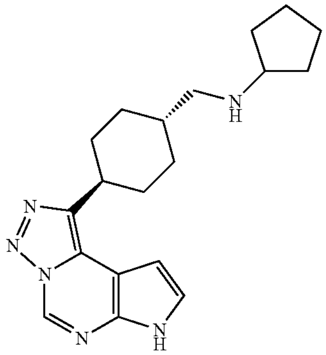 [SMILES: c1cc2c(ncn3nnc([C@H]4CC[C@H](CNC5CCCC5)CC4)c23)[nH]1] |
TABLE[a] 71
| Ex | Structure |
| --- | --- |
| 285 | 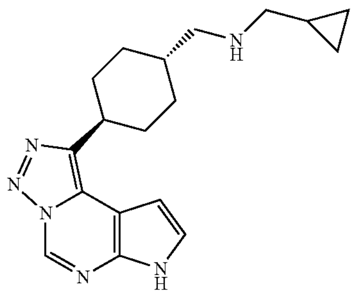 [SMILES: c1cc2c(ncn3nnc([C@H]4CC[C@H](CNCC5CC5)CC4)c23)[nH]1] |
| 286 | 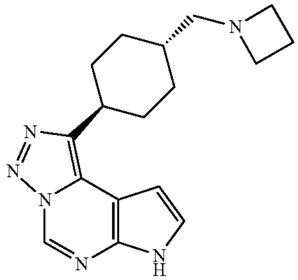 [SMILES: c1cc2c(ncn3nnc([C@H]4CC[C@H](CN5CCC5)CC4)c23)[nH]1] |
| 287 | 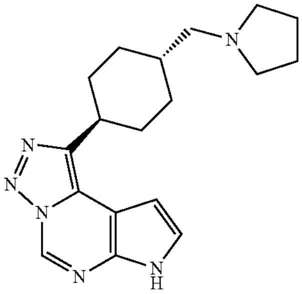 [SMILES: c1cc2c(ncn3nnc([C@H]4CC[C@H](CN5CCCC5)CC4)c23)[nH]1] |

TABLE[a] 71-continued
| Ex | Structure |
|---|---|
| 288 | 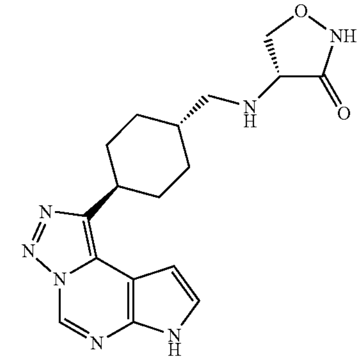 [SMILES: O=C1NOC[C@H]1NC[C@H]1CC[C@H](c2nnn3cnc4[nH]ccc4c23)CC1] |
| 289 | 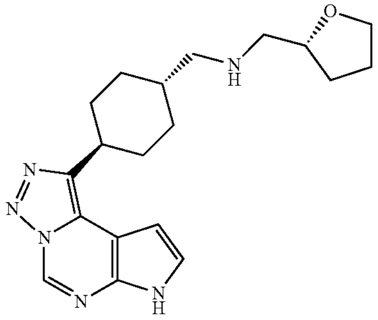 [SMILES: c1cc2c(ncn3nnc([C@H]4CC[C@H](CNC[C@H]5CCCO5)CC4)c23)[nH]1] |
| 290 | 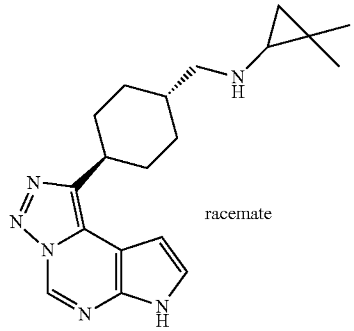 [SMILES: CC1(C)CC1NC[C@H]1CC[C@H](c2nnn3cnc4[nH]ccc4c23)CC1] racemate |
| 291 | 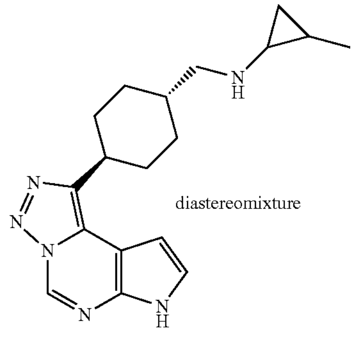 [SMILES: CC1CC1NC[C@H]1CC[C@H](c2nnn3cnc4[nH]ccc4c23)CC1] diastereomixture |
| 292 | 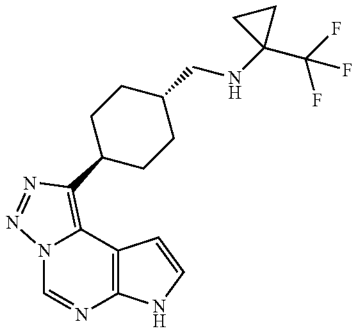 [SMILES: FC(F)(F)C1(NC[C@H]2CC[C@H](c3nnn4cnc5[nH]ccc5c34)CC2)CC1] |
| 293 | 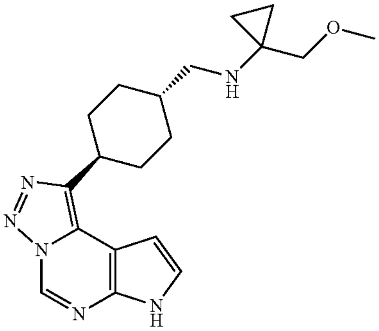 [SMILES: COCC1(NC[C@H]2CC[C@H](c3nnn4cnc5[nH]ccc5c34)CC2)CC1] |
| 294 | 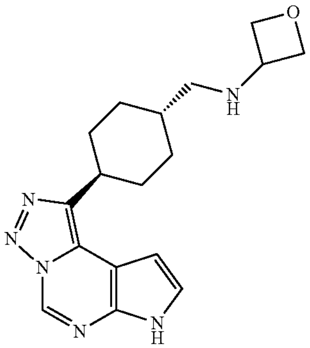 [SMILES: c1cc2c(ncn3nnc([C@H]4CC[C@H](CNC5COC5)CC4)c23)[nH]1] |
| 295 | 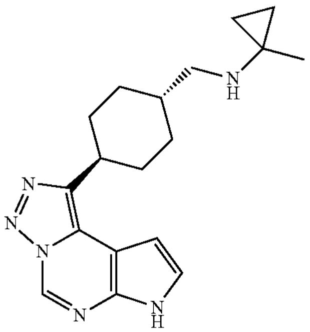 [SMILES: CC1(NC[C@H]2CC[C@H](c3nnn4cnc5[nH]ccc5c34)CC2)CC1] |

TABLE[a] 71-continued
| Ex | Structure |
|---|---|
| 296 | 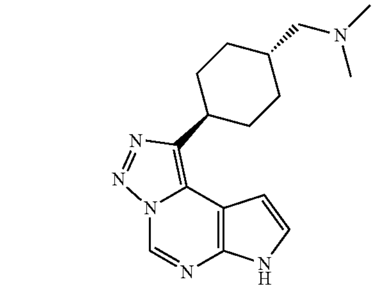 [SMILES: CN(C)C[C@H]1CC[C@H](c2nnn3cnc4[nH]ccc4c23)CC1] |
| 297 | 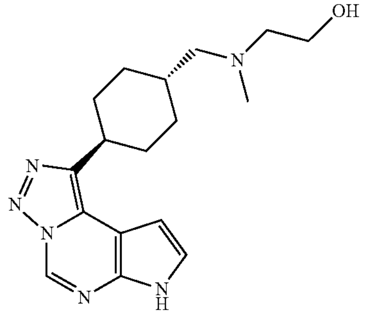 [SMILES: CN(CCO)C[C@H]1CC[C@H](c2nnn3cnc4[nH]ccc4c23)CC1] |
| 298 | 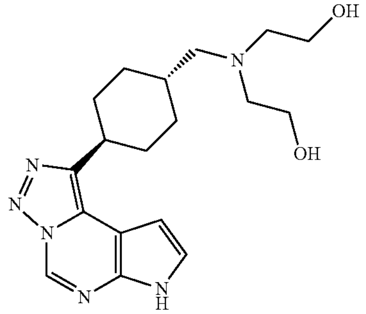 [SMILES: OCCN(CCO)C[C@H]1CC[C@H](c2nnn3cnc4[nH]ccc4c23)CC1] |
| 299 | 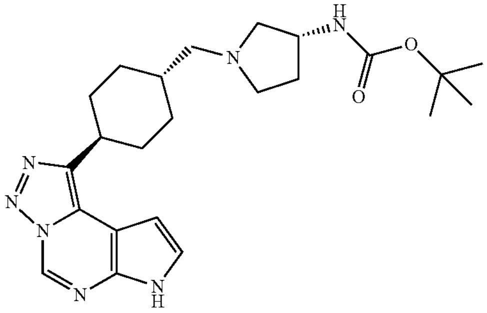 [SMILES: CC(C)(C)OC(=O)N[C@@H]1CCN(C[C@H]2CC[C@H](c3nnn4cnc5[nH]ccc5c34)CC2)C1] |
| 300 | 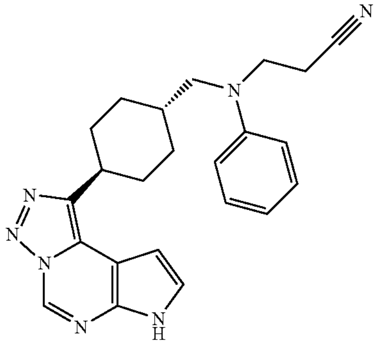 [SMILES: N#CCCN(C[C@H]1CC[C@H](c2nnn3cnc4[nH]ccc4c23)CC1)c1ccccc1] |
| 301 | 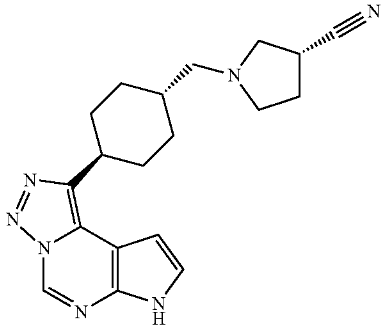 [SMILES: N#C[C@@H]1CCN(C[C@H]2CC[C@H](c3nnn4cnc5[nH]ccc5c34)CC2)C1] |
| 302 | 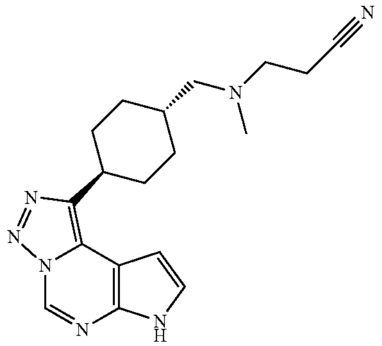 [SMILES: CN(CCC#N)C[C@H]1CC[C@H](c2nnn3cnc4[nH]ccc4c23)CC1] |
TABLE[a] 72
| Ex | Structure |
|---|---|
| 303 | 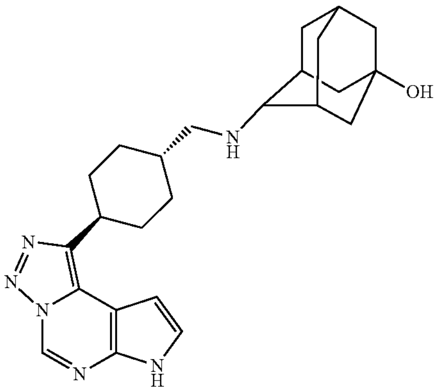 [SMILES: OC12CC3CC(C1)C(NC[C@H]1CC[C@H](c4nnn5cnc6[nH]ccc6c45)CC1)C(C3)C2] |

TABLE[a] 72-continued
| Ex | Structure |
|---|---|
| 304 | 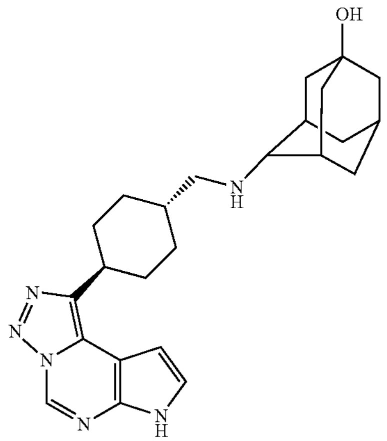 [SMILES: OC12CC3CC(C1)C(NC[C@H]1CC[C@H](c4nnn5cnc6[nH]ccc6c45)CC1)C(C3)C2] |
| 305 | 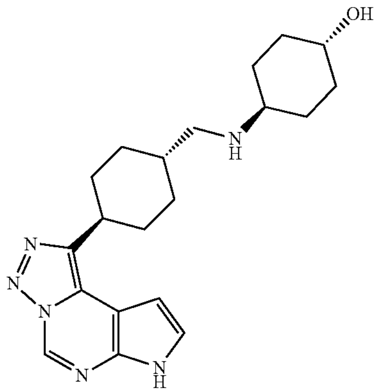 [SMILES: O[C@H]1CC[C@H](NC[C@H]2CC[C@H](c3nnn4cnc5[nH]ccc5c34)CC2)CC1] |
| 306 | 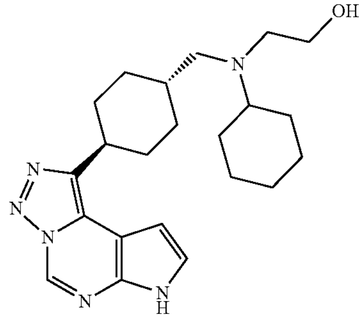 [SMILES: OCCN(C[C@H]1CC[C@H](c2nnn3cnc4[nH]ccc4c23)CC1)C1CCCCC1] |
| 307 | 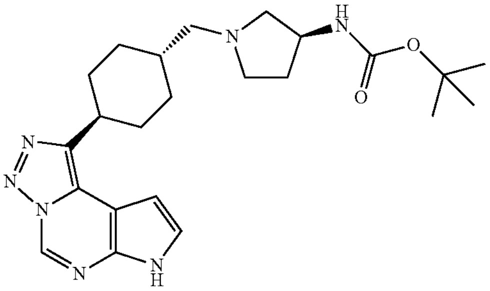 [SMILES: CC(C)(C)OC(=O)N[C@H]1CCN(C[C@H]2CC[C@H](c3nnn4cnc5[nH]ccc5c34)CC2)C1] |
TABLE[a] 72-continued
| Ex | Structure |
|---|---|
| 308 | 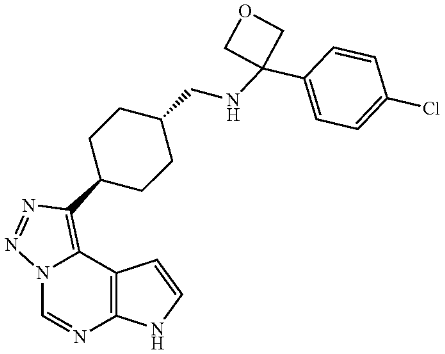 [SMILES: Clc1ccc(C2(NC[C@H]3CC[C@H](c4nnn5cnc6[nH]ccc6c45)CC3)COC2)cc1] |
| 309 | 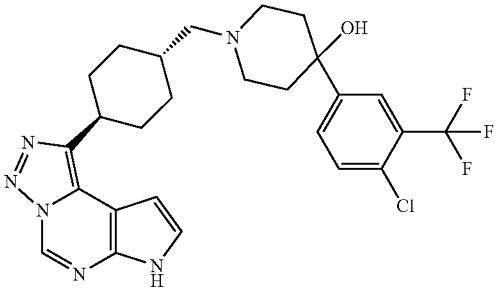 [SMILES: OC1(c2ccc(Cl)c(C(F)(F)F)c2)CCN(C[C@H]2CC[C@H](c3nnn4cnc5[nH]ccc5c34)CC2)CC1] |
| 310 | 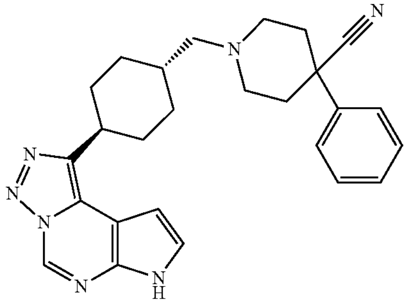 [SMILES: N#CC1(c2ccccc2)CCN(C[C@H]2CC[C@H](c3nnn4cnc5[nH]ccc5c34)CC2)CC1] |
| 311 | 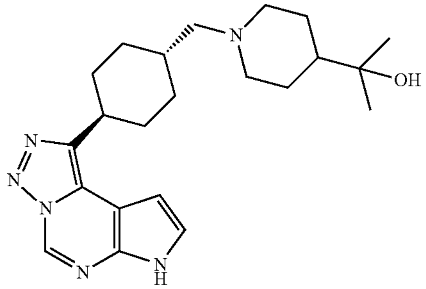 [SMILES: CC(C)(O)C1CCN(C[C@H]2CC[C@H](c3nnn4cnc5[nH]ccc5c34)CC2)CC1] |
| 312 | 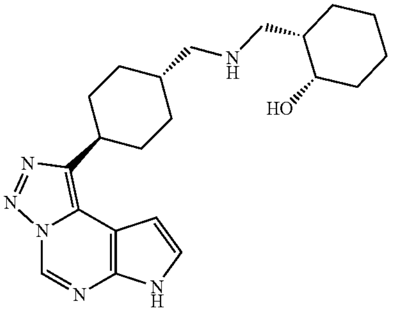 [SMILES: O[C@H]1CCCC[C@H]1CNC[C@H]1CC[C@H](c2nnn3cnc4[nH]ccc4c23)CC1] |

TABLE[a] 72-continued
| Ex | Structure |
|---|---|
| 313 | 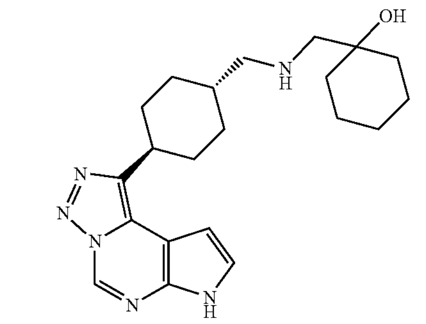 [SMILES: OC1(CNC[C@H]2CC[C@H](c3nnn4cnc5[nH]ccc5c34)CC2)CCCCC1] |
| 314 | 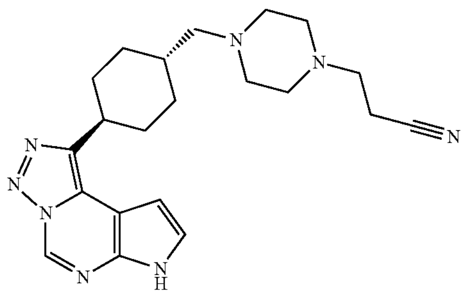 [SMILES: N#CCCN1CCN(C[C@H]2CC[C@H](c3nnn4cnc5[nH]ccc5c34)CC2)CC1] |
| 315 | 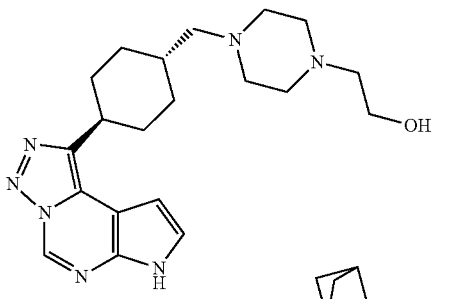 |
| 316 | 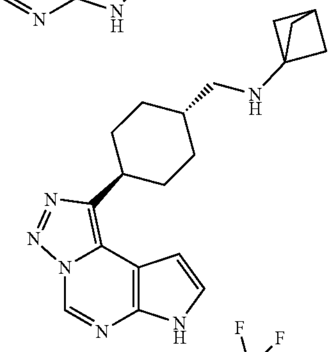 |
| 317 | 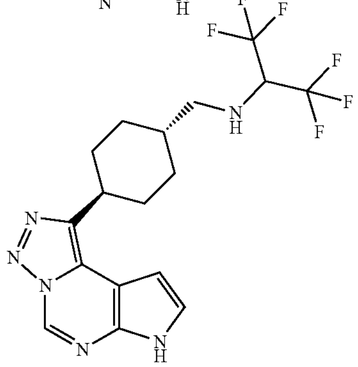 |
TABLE[a] 72-continued
| Ex | Structure |
|---|---|
| 318 | 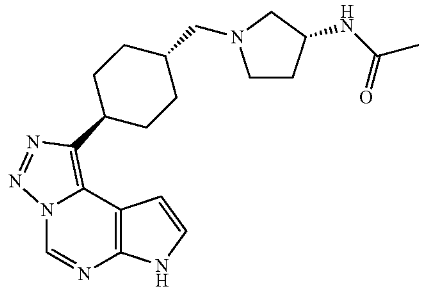 [SMILES: CC(=O)N[C@@H]1CCN(C[C@H]2CC[C@H](c3nnn4cnc5[nH]ccc5c34)CC2)C1] |
| 319 | 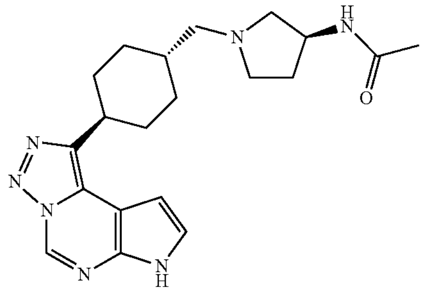 [SMILES: CC(=O)N[C@H]1CCN(C[C@H]2CC[C@H](c3nnn4cnc5[nH]ccc5c34)CC2)C1] |
| 320 | 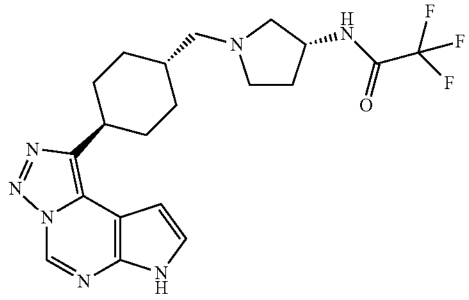 [SMILES: O=C(N[C@@H]1CCN(C[C@H]2CC[C@H](c3nnn4cnc5[nH]ccc5c34)CC2)C1)C(F)(F)F] |
TABLE[a] 73
| Ex | Structure |
|---|---|
| 321 | 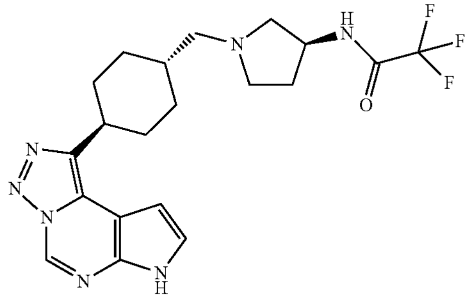 [SMILES: O=C(N[C@H]1CCN(C[C@H]2CC[C@H](c3nnn4cnc5[nH]ccc5c34)CC2)C1)C(F)(F)F] |

TABLE[a] 73-continued
| Ex | Structure |
|---|---|
| 322 | 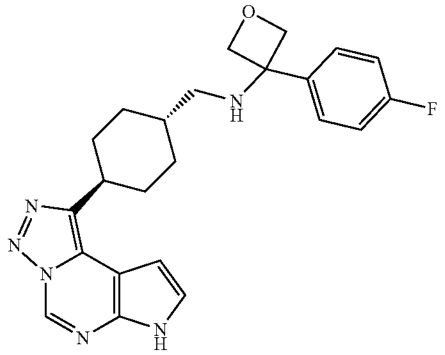 [SMILES: Fc1ccc(C2(NC[C@H]3CC[C@H](c4nnn5cnc6[nH]ccc6c45)CC3)COC2)cc1] |
| 323 | 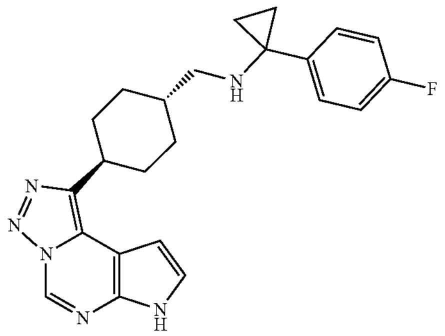 [SMILES: Fc1ccc(C2(NC[C@H]3CC[C@H](c4nnn5cnc6[nH]ccc6c45)CC3)CC2)cc1] |
| 324 | 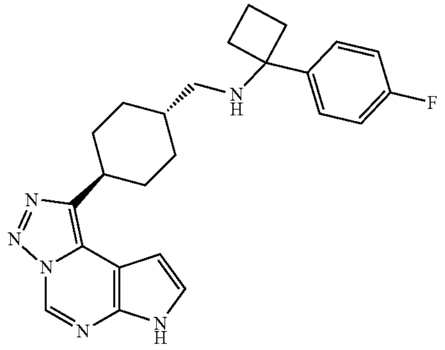 [SMILES: Fc1ccc(C2(NC[C@H]3CC[C@H](c4nnn5cnc6[nH]ccc6c45)CC3)CCC2)cc1] |
| 325 | 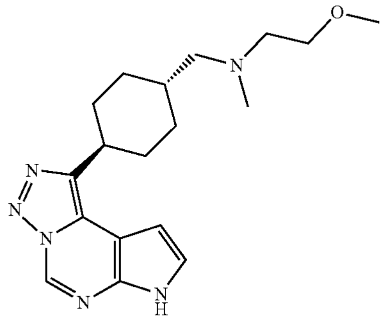 [SMILES: COCCN(C)C[C@H]1CC[C@H](c2nnn3cnc4[nH]ccc4c23)CC1] |
TABLE[a] 73-continued
| Ex | Structure |
|---|---|
| 326 | 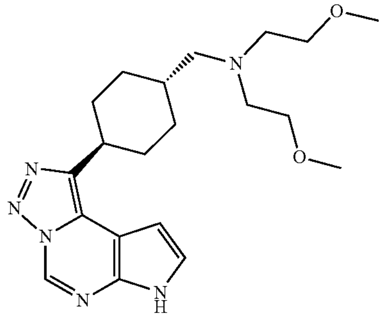 [SMILES: COCCN(CCOC)C[C@H]1CC[C@H](c2nnn3cnc4[nH]ccc4c23)CC1] |
| 327 | 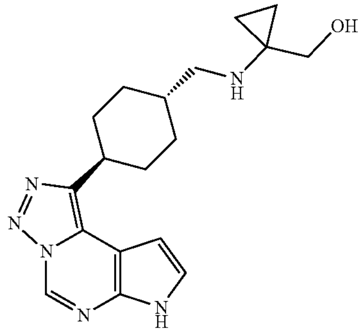 [SMILES: OCC1(NC[C@H]2CC[C@H](c3nnn4cnc5[nH]ccc5c34)CC2)CC1] |
| 328 | 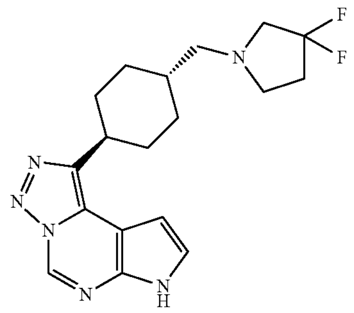 [SMILES: FC1(F)CCN(C[C@H]2CC[C@H](c3nnn4cnc5[nH]ccc5c34)CC2)C1] |
| 329 | 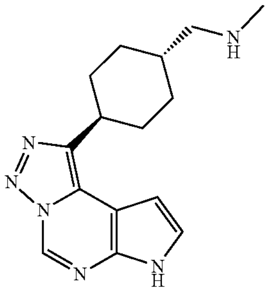 [SMILES: CNC[C@H]1CC[C@H](c2nnn3cnc4[nH]ccc4c23)CC1] |
| 330 | 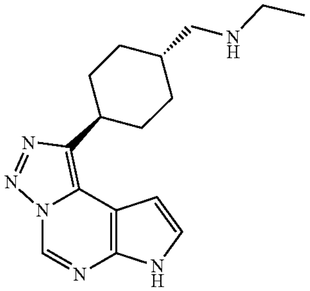 [SMILES: CCNC[C@H]1CC[C@H](c2nnn3cnc4[nH]ccc4c23)CC1] |

TABLE[a] 73-continued
| Ex | Structure |
|---|---|
| 331 | 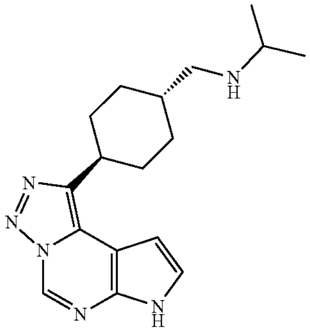 [SMILES: CC(C)NC[C@H]1CC[C@H](c2nnn3cnc4[nH]ccc4c23)CC1] |
| 332 | 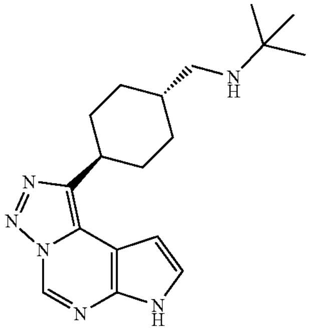 [SMILES: CC(C)(C)NC[C@H]1CC[C@H](c2nnn3cnc4[nH]ccc4c23)CC1] |
| 333 | 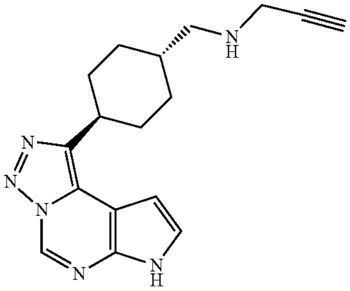 [SMILES: C#CCNC[C@H]1CC[C@H](c2nnn3cnc4[nH]ccc4c23)CC1] |
| 334 | 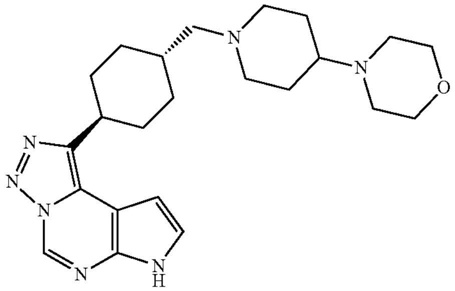 [SMILES: c1cc2c(ncn3nnc([C@H]4CC[C@H](CN5CCC(N6CCOCC6)CC5)CC4)c23)[nH]1] |
| 335 | 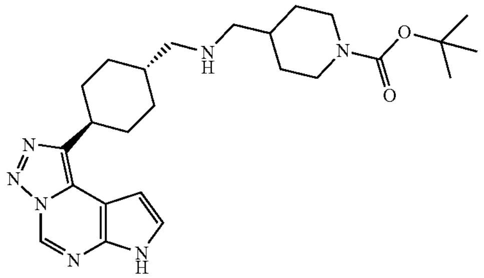 [SMILES: CC(C)(C)OC(=O)N1CCC(CNC[C@H]2CC[C@H](c3nnn4cnc5[nH]ccc5c34)CC2)CC1] |
TABLE[a] 73-continued
| Ex | Structure |
|---|---|
| 336 | 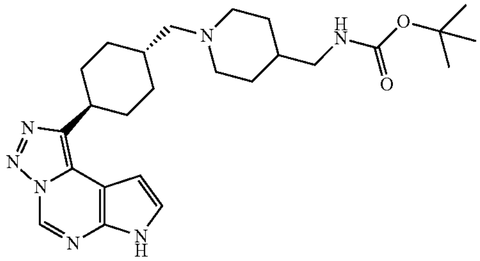 [SMILES: CC(C)(C)OC(=O)NCC1CCN(C[C@H]2CC[C@H](c3nnn4cnc5[nH]ccc5c34)CC2)CC1] |
| 337 | 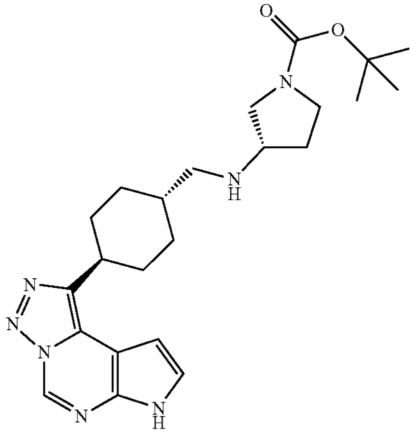 [SMILES: CC(C)(C)OC(=O)N1CC[C@H](NC[C@H]2CC[C@H](c3nnn4cnc5[nH]ccc5c34)CC2)C1] |
| 338 | 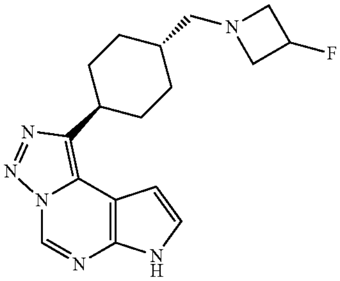 [SMILES: FC1CN(C[C@H]2CC[C@H](c3nnn4cnc5[nH]ccc5c34)CC2)C1] |
TABLE[a] 74
| Ex | Structure |
|---|---|
| 339 | 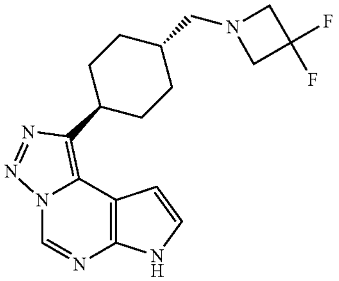 [SMILES: FC1(F)CN(C[C@H]2CC[C@H](c3nnn4cnc5[nH]ccc5c34)CC2)C1] |

TABLE[a] 74-continued
| Ex | Structure |
|---|---|
| 340 | 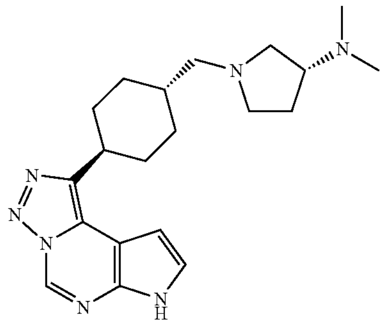 [SMILES: CN(C)[C@@H]1CCN(C[C@H]2CC[C@H](c3nnn4cnc5[nH]ccc5c34)CC2)C1] |
| 341 | 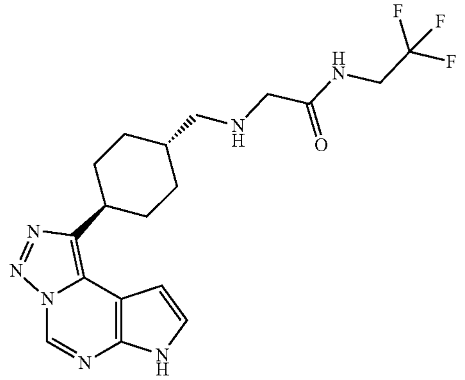 [SMILES: O=C(CNC[C@H]1CC[C@H](c2nnn3cnc4[nH]ccc4c23)CC1)NCC(F)(F)F] |
| 342 | 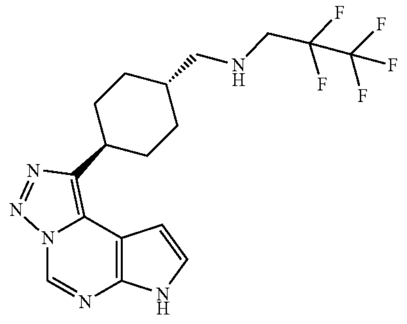 [SMILES: FC(F)(F)C(F)(F)CNC[C@H]1CC[C@H](c2nnn3cnc4[nH]ccc4c23)CC1] |
| 343 | 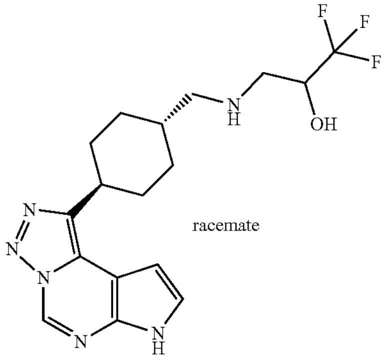 [SMILES: OC(CNC[C@H]1CC[C@H](c2nnn3cnc4[nH]ccc4c23)CC1)C(F)(F)F] racemate |
TABLE[a] 74-continued
| Ex | Structure |
|---|---|
| 344 | 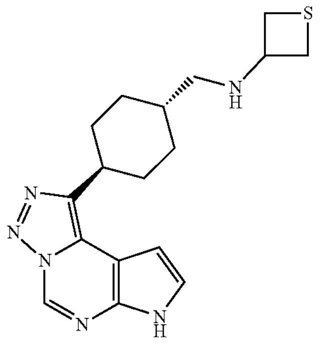 [SMILES: c1cc2c(ncn3nnc([C@H]4CC[C@H](CNC5CSC5)CC4)c23)[nH]1] |
| 345 | 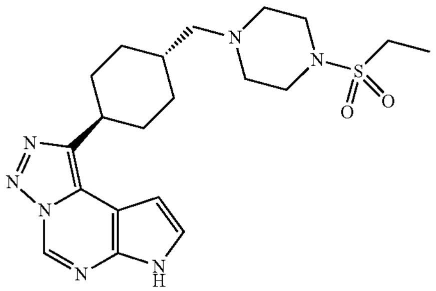 [SMILES: CCS(=O)(=O)N1CCN(C[C@H]2CC[C@H](c3nnn4cnc5[nH]ccc5c34)CC2)CC1] |
| 346 | 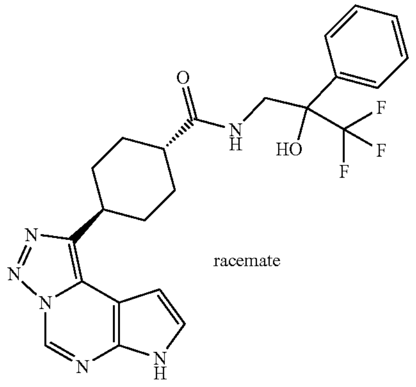 [SMILES: O=C(NCC(O)(c1ccccc1)C(F)(F)F)[C@H]1CC[C@H](c2nnn3cnc4[nH]ccc4c23)CC1] racemate |
| 347 | 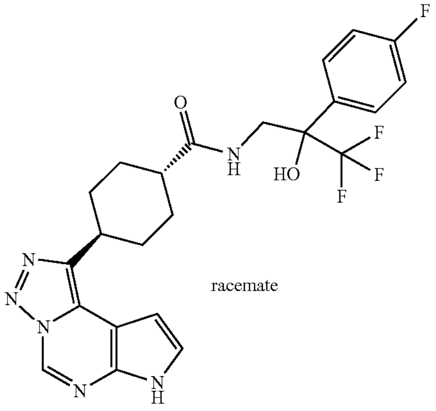 [SMILES: O=C(NCC(O)(c1ccc(F)cc1)C(F)(F)F)[C@H]1CC[C@H](c2nnn3cnc4[nH]ccc4c23)CC1] racemate |

TABLE[a] 74-continued
| Ex | Structure |
|---|---|
| 348 | 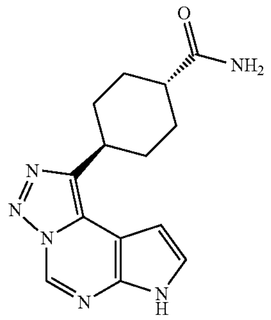 [SMILES: NC(=O)[C@H]1CC[C@H](c2nnn3cnc4[nH]ccc4c23)CC1] |
| 349 | 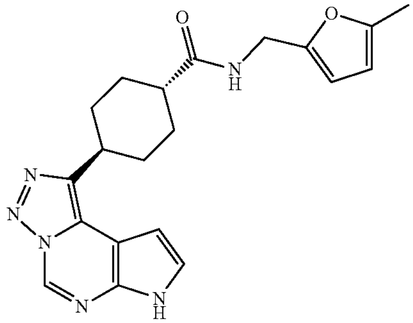 [SMILES: Cc1ccc(CNC(=O)[C@H]2CC[C@H](c3nnn4cnc5[nH]ccc5c34)CC2)o1] |
| 350 | 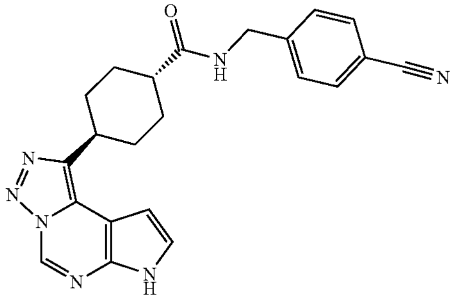 [SMILES: N#Cc1ccc(CNC(=O)[C@H]2CC[C@H](c3nnn4cnc5[nH]ccc5c34)CC2)cc1] |
| 351 | 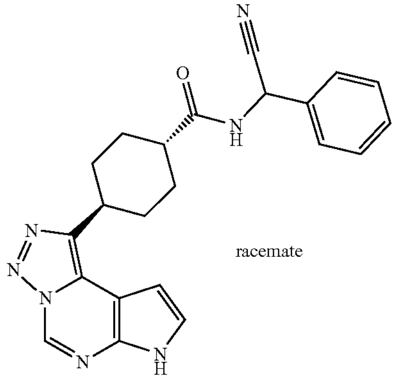 [SMILES: N#CC(NC(=O)[C@H]1CC[C@H](c2nnn3cnc4[nH]ccc4c23)CC1)c1ccccc1] racemate |
TABLE[a] 74-continued
| Ex | Structure |
|---|---|
| 352 | 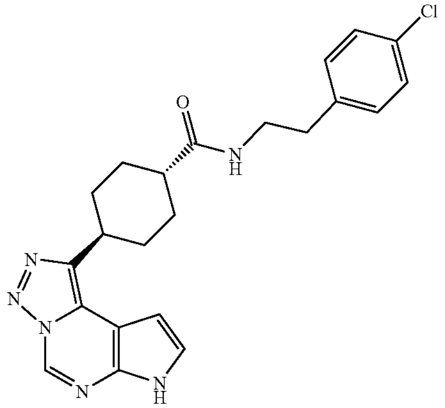 [SMILES: O=C(NCCc1ccc(Cl)cc1)[C@H]1CC[C@H](c2nnn3cnc4[nH]ccc4c23)CC1] |
| 353 | 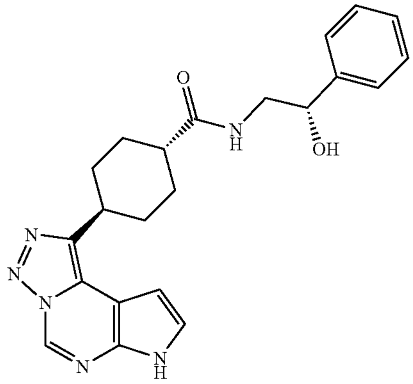 [SMILES: O=C(NC[C@@H](O)c1ccccc1)[C@H]1CC[C@H](c2nnn3cnc4[nH]ccc4c23)CC1] |
| 354 | 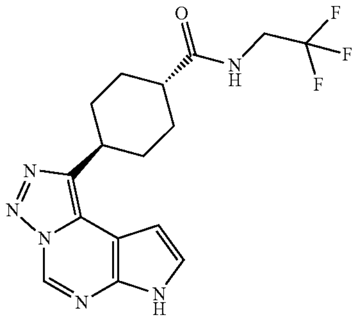 [SMILES: O=C(NCC(F)(F)F)[C@H]1CC[C@H](c2nnn3cnc4[nH]ccc4c23)CC1] |
| 355 | 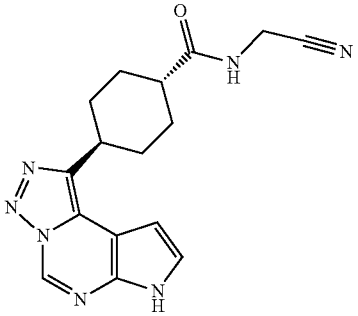 [SMILES: N#CCNC(=O)[C@H]1CC[C@H](c2nnn3cnc4[nH]ccc4c23)CC1] |

TABLE[a] 74-continued
| Ex | Structure |
|---|---|
| 356 | 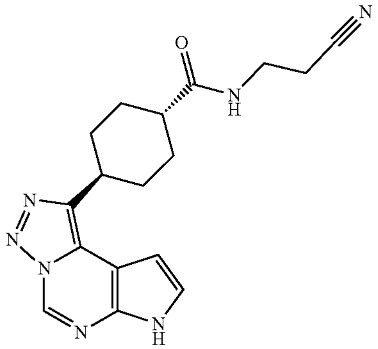 [SMILES: N#CCCNC(=O)[C@H]1CC[C@H](c2nnn3cnc4[nH]ccc4c23)CC1] |
TABLE[a] 75
| Ex | Structure |
|---|---|
| 357 | 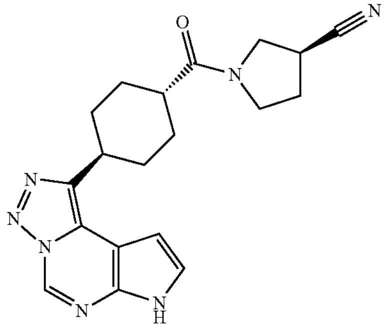 [SMILES: N#C[C@H]1CCN(C(=O)[C@H]2CC[C@H](c3nnn4cnc5[nH]ccc5c34)CC2)C1] |
| 358 | 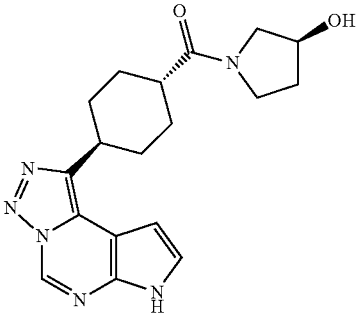 [SMILES: O=C([C@H]1CC[C@H](c2nnn3cnc4[nH]ccc4c23)CC1)N1CC[C@H](O)C1] |
| 359 | 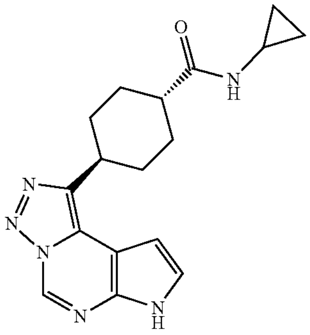 [SMILES: O=C(NC1CC1)[C@H]1CC[C@H](c2nnn3cnc4[nH]ccc4c23)CC1] |
TABLE[a] 75-continued
| Ex | Structure |
|---|---|
| 360 | 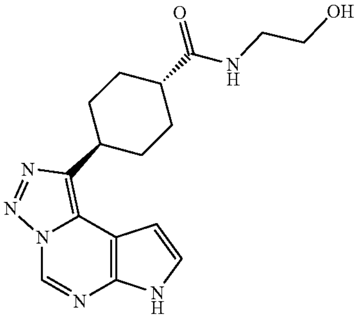 [SMILES: O=C(NCCO)[C@H]1CC[C@H](c2nnn3cnc4[nH]ccc4c23)CC1] |
| 361 | 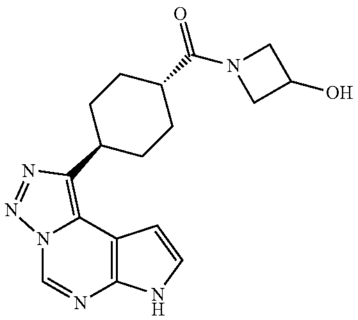 [SMILES: O=C([C@H]1CC[C@H](c2nnn3cnc4[nH]ccc4c23)CC1)N1CC(O)C1] |
| 362 | 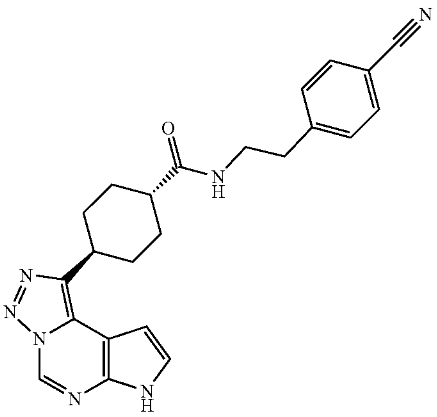 [SMILES: N#Cc1ccc(CCNC(=O)[C@H]2CC[C@H](c3nnn4cnc5[nH]ccc5c34)CC2)cc1] |
| 363 | 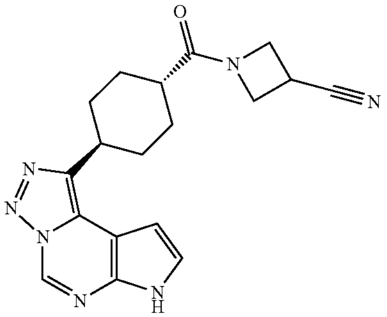 [SMILES: N#CC1CN(C(=O)[C@H]2CC[C@H](c3nnn4cnc5[nH]ccc5c34)CC2)C1] |

TABLE[a] 75-continued
| Ex | Structure |
|---|---|
| 364 | 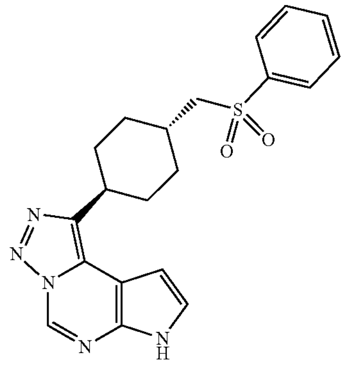 [SMILES: O=S(=O)(C[C@H]1CC[C@H](c2nnn3cnc4[nH]ccc4c23)CC1)c1ccccc1] |
| 365 | 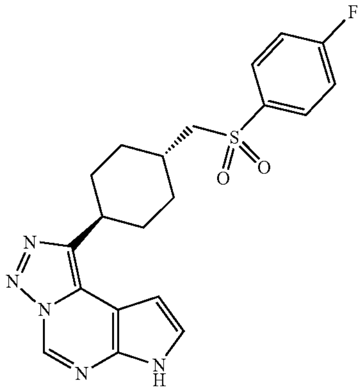 [SMILES: O=S(=O)(C[C@H]1CC[C@H](c2nnn3cnc4[nH]ccc4c23)CC1)c1ccc(F)cc1] |
| 366 | 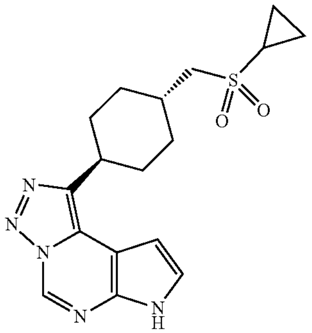 [SMILES: O=S(=O)(C[C@H]1CC[C@H](c2nnn3cnc4[nH]ccc4c23)CC1)C1CC1] |
| 367 | 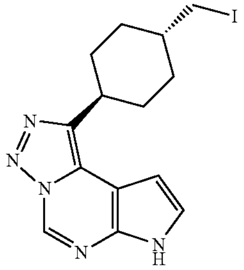 [SMILES: IC[C@H]1CC[C@H](c2nnn3cnc4[nH]ccc4c23)CC1] |
| 368 | 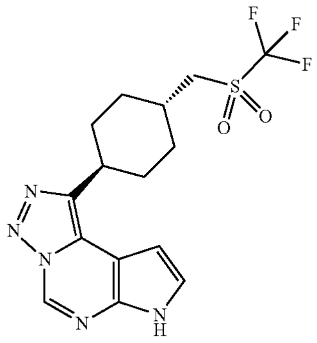 [SMILES: O=S(=O)(C[C@H]1CC[C@H](c2nnn3cnc4[nH]ccc4c23)CC1)C(F)(F)F] |
| 369 | 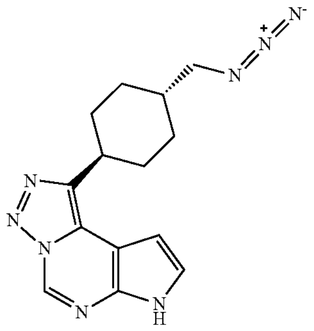 [SMILES: [N-]=[N+]=NC[C@H]1CC[C@H](c2nnn3cnc4[nH]ccc4c23)CC1] |
| 370 | 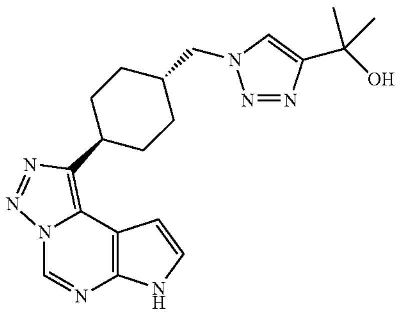 [SMILES: CC(C)(O)c1cn(C[C@H]2CC[C@H](c3nnn4cnc5[nH]ccc5c34)CC2)nn1] |
| 371 | 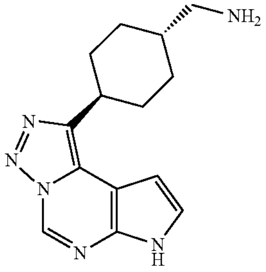 [SMILES: NC[C@H]1CC[C@H](c2nnn3cnc4[nH]ccc4c23)CC1] |

TABLE[a] 75-continued
| Ex | Structure |
| --- | --- |
| 372 | 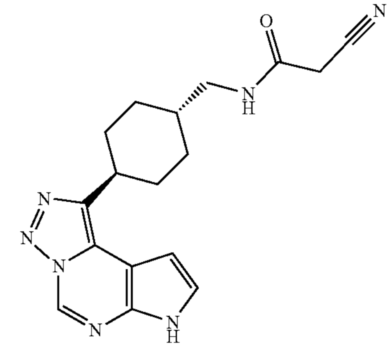 [SMILES: N#CCC(=O)NC[C@H]1CC[C@H](c2nnn3cnc4[nH]ccc4c23)CC1] |
| 373 | 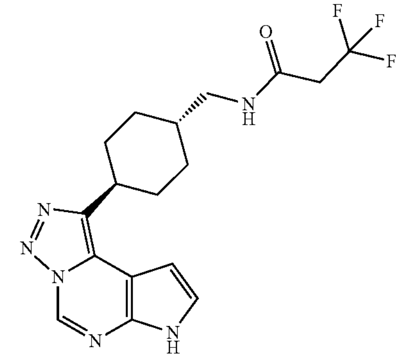 [SMILES: O=C(CC(F)(F)F)NC[C@H]1CC[C@H](c2nnn3cnc4[nH]ccc4c23)CC1] |
| 374 | 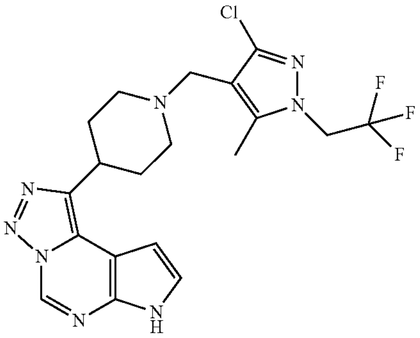 [SMILES: Cc1c(CN2CCC(c3nnn4cnc5[nH]ccc5c34)CC2)c(Cl)nn1CC(F)(F)F] |
TABLE[a] 76
| Ex | Structure |
| --- | --- |
| 375 | 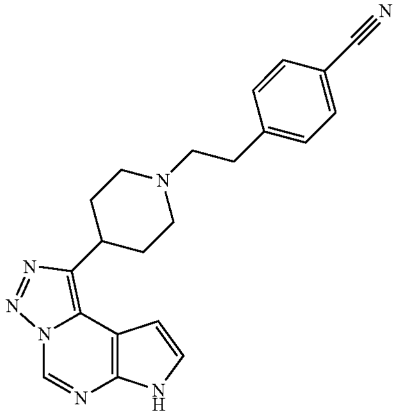 [SMILES: N#Cc1ccc(CCN2CCC(c3nnn4cnc5[nH]ccc5c34)CC2)cc1] |
TABLE[a] 76-continued
| Ex | Structure |
| --- | --- |
| 376 | 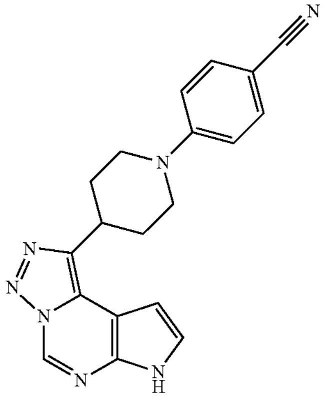 [SMILES: N#Cc1ccc(N2CCC(c3nnn4cnc5[nH]ccc5c34)CC2)cc1] |
| 377 | 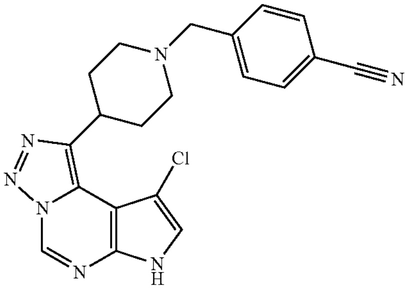 [SMILES: N#Cc1ccc(CN2CCC(c3nnn4cnc5[nH]cc(Cl)c5c34)CC2)cc1] |
| 378 | 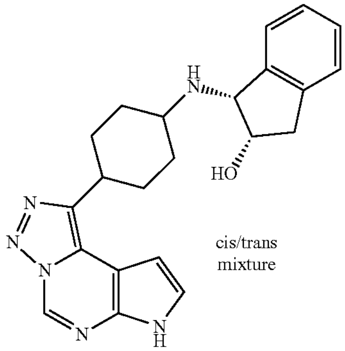 [SMILES: O[C@H]1Cc2ccccc2[C@H]1NC1CCC(c2nnn3cnc4[nH]ccc4c23)CC1] cis/trans mixture |
| 379 | 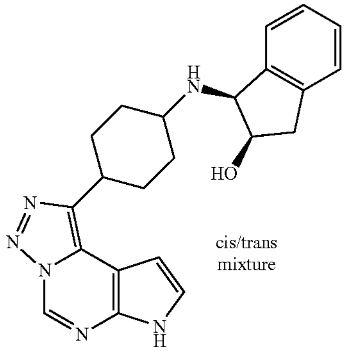 [SMILES: O[C@@H]1Cc2ccccc2[C@@H]1NC1CCC(c2nnn3cnc4[nH]ccc4c23)CC1] cis/trans mixture |

TABLE[a] 76-continued
| Ex | Structure |
|---|---|
| 380 | 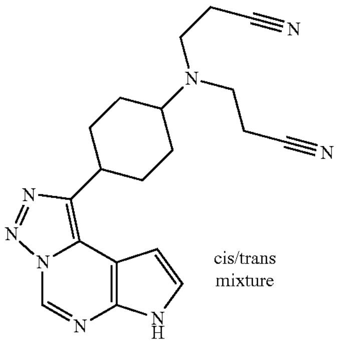 [SMILES: N#CCCN(CCC#N)C1CCC(c2nnn3cnc4[nH]ccc4c23)CC1] cis/trans mixture |
| 381a | 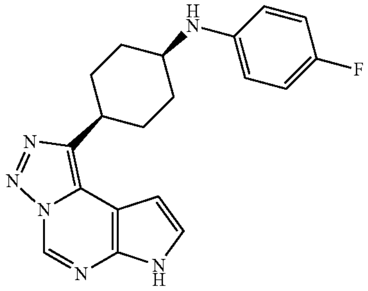 [SMILES: Fc1ccc(N[C@H]2CC[C@@H](c3nnn4cnc5[nH]ccc5c34)CC2)cc1] |
| 381b | 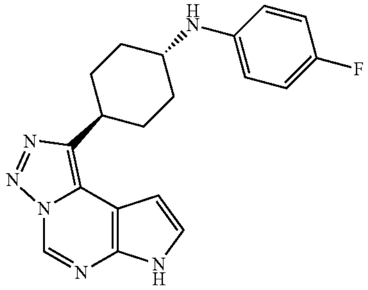 [SMILES: Fc1ccc(N[C@H]2CC[C@H](c3nnn4cnc5[nH]ccc5c34)CC2)cc1] |
| 382a | 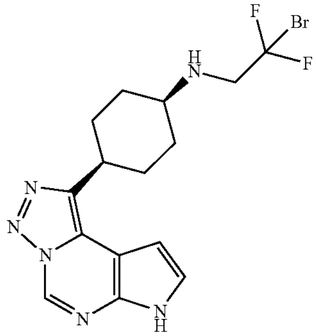 [SMILES: FC(F)(Br)CN[C@H]1CC[C@@H](c2nnn3cnc4[nH]ccc4c23)CC1] |
TABLE[a] 76-continued
| Ex | Structure |
|---|---|
| 382b | 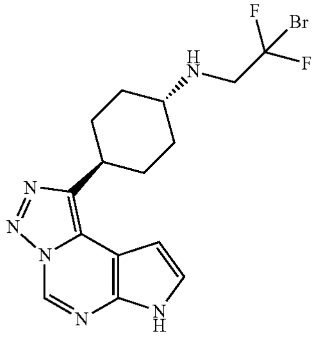 [SMILES: FC(F)(Br)CN[C@H]1CC[C@H](c2nnn3cnc4[nH]ccc4c23)CC1] |
| 383a | 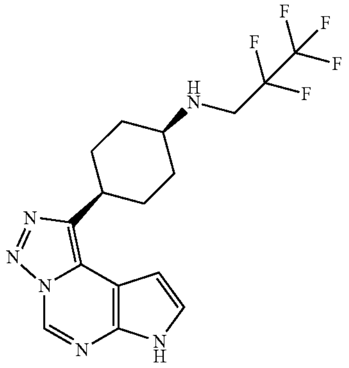 [SMILES: FC(F)(F)C(F)(F)CN[C@H]1CC[C@@H](c2nnn3cnc4[nH]ccc4c23)CC1] |
| 383b | 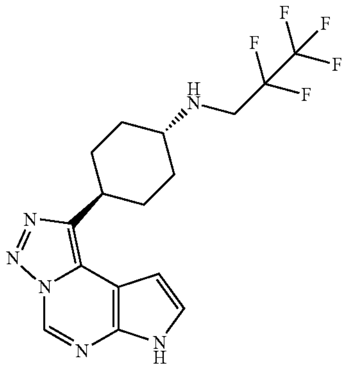 [SMILES: FC(F)(F)C(F)(F)CN[C@H]1CC[C@H](c2nnn3cnc4[nH]ccc4c23)CC1] |
| 384a | 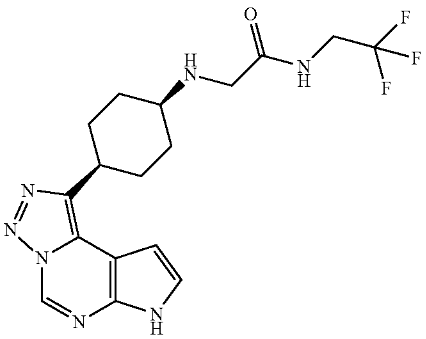 [SMILES: O=C(CN[C@H]1CC[C@@H](c2nnn3cnc4[nH]ccc4c23)CC1)NCC(F)(F)F] |

TABLE[a] 76-continued
| Ex | Structure |
|---|---|
| 384b | 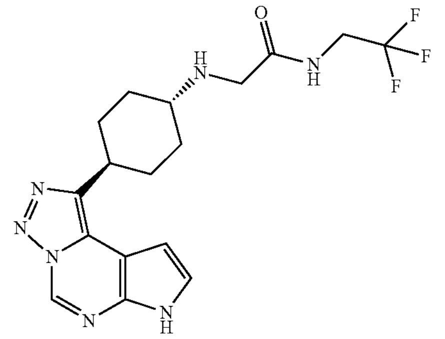 [SMILES: O=C(CN[C@H]1CC[C@H](c2nnn3cnc4[nH]ccc4c23)CC1)NCC(F)(F)F] |
| 385b | 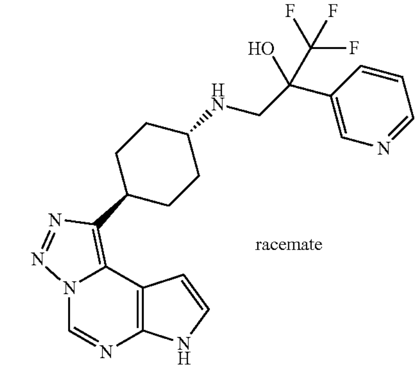 [SMILES: OC(CN[C@H]1CC[C@H](c2nnn3cnc4[nH]ccc4c23)CC1)(c1cccnc1)C(F)(F)F] racemate |
| 386b | 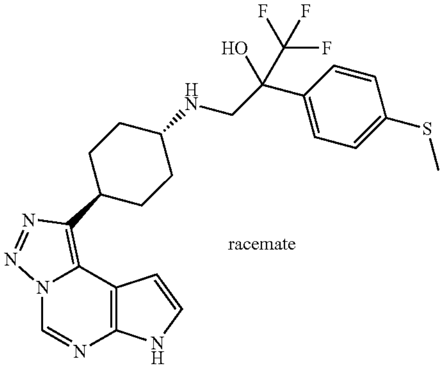 [SMILES: CSc1ccc(C(O)(CN[C@H]2CC[C@H](c3nnn4cnc5[nH]ccc5c34)CC2)C(F)(F)F)cc1] racemate |
| 387b | 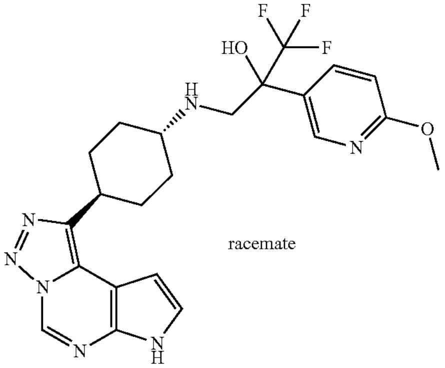 [SMILES: COc1ccc(C(O)(CN[C@H]2CC[C@H](c3nnn4cnc5[nH]ccc5c34)CC2)C(F)(F)F)cn1] racemate |
| 388b | 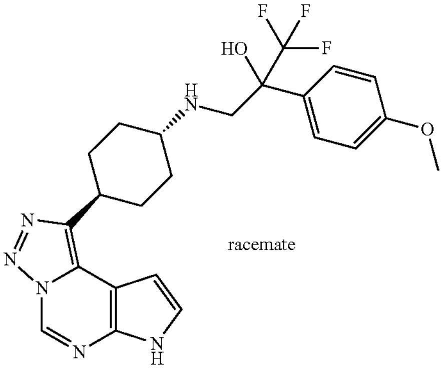 [SMILES: COc1ccc(C(O)(CN[C@H]2CC[C@H](c3nnn4cnc5[nH]ccc5c34)CC2)C(F)(F)F)cc1] racemate |
TABLE[a] 77
| Ex | Structure |
|---|---|
| 389b | 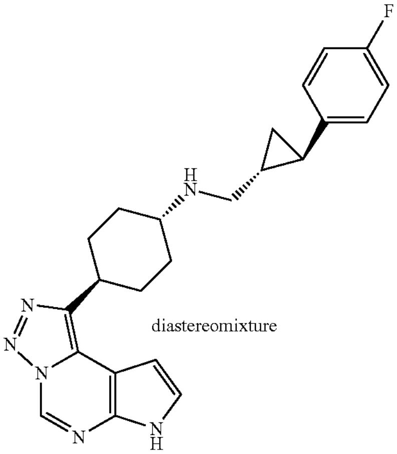 [SMILES: Fc1ccc([C@@H]2C[C@H]2CN[C@H]2CC[C@H](c3nnn4cnc5[nH]ccc5c34)CC2)cc1] diastereomixture |
| 390b | 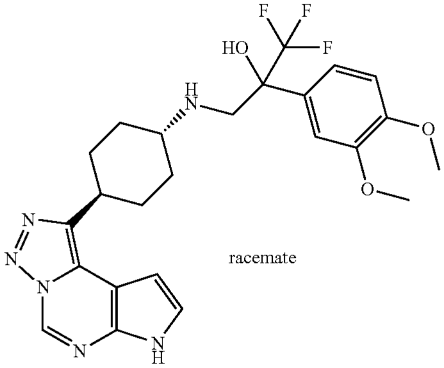 [SMILES: COc1ccc(C(O)(CN[C@H]2CC[C@H](c3nnn4cnc5[nH]ccc5c34)CC2)C(F)(F)F)cc1OC] racemate |

TABLE[a] 77-continued
| Ex | Structure |
| --- | --- |
| 391b | 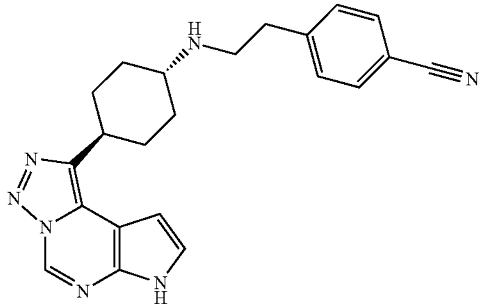 [SMILES: N#Cc1ccc(CCN[C@H]2CC[C@H](c3nnn4cnc5[nH]ccc5c34)CC2)cc1] |
| 392b | 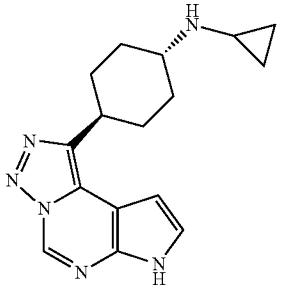 [SMILES: c1cc2c(ncn3nnc([C@H]4CC[C@H](NC5CC5)CC4)c23)[nH]1] |
| 393b | 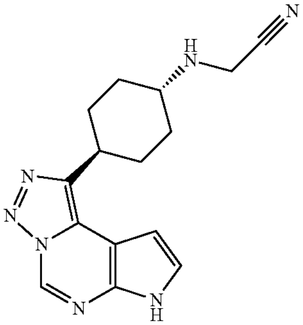 [SMILES: N#CCN[C@H]1CC[C@H](c2nnn3cnc4[nH]ccc4c23)CC1] |
| 394b | 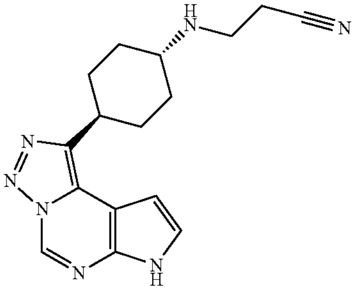 [SMILES: N#CCCN[C@H]1CC[C@H](c2nnn3cnc4[nH]ccc4c23)CC1] |
| 395b | 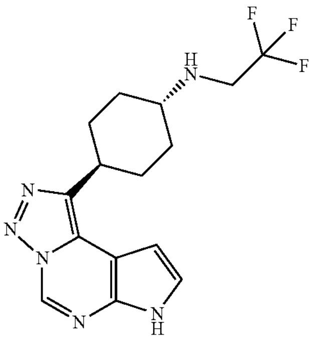 [SMILES: FC(F)(F)CN[C@H]1CC[C@H](c2nnn3cnc4[nH]ccc4c23)CC1] |
| 396b | 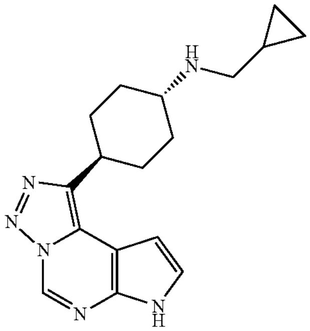 [SMILES: c1cc2c(ncn3nnc([C@H]4CC[C@H](NCC5CC5)CC4)c23)[nH]1] |
| 397b | 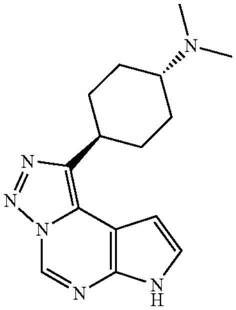 [SMILES: CN(C)[C@H]1CC[C@H](c2nnn3cnc4[nH]ccc4c23)CC1] |
| 398b | 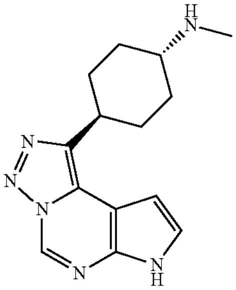 [SMILES: CN[C@H]1CC[C@H](c2nnn3cnc4[nH]ccc4c23)CC1] |
| 399b | 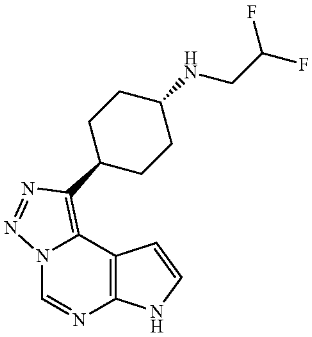 [SMILES: FC(F)CN[C@H]1CC[C@H](c2nnn3cnc4[nH]ccc4c23)CC1] |

TABLE[a] 77-continued
| Ex | Structure |
| --- | --- |
| 400b | 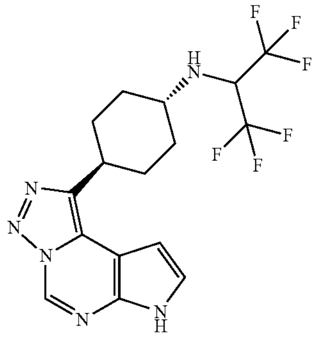 [SMILES: FC(F)(F)C(N[C@H]1CC[C@H](c2nnn3cnc4[nH]ccc4c23)CC1)C(F)(F)F] |
| 401 | 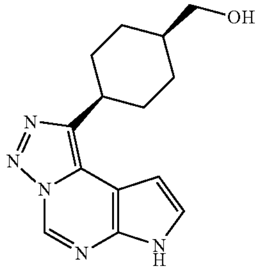 [SMILES: OC[C@H]1CC[C@@H](c2nnn3cnc4[nH]ccc4c23)CC1] |
| 402 | 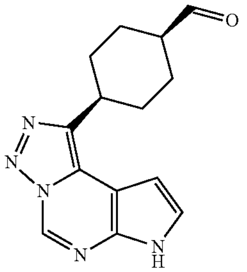 [SMILES: O=C[C@H]1CC[C@@H](c2nnn3cnc4[nH]ccc4c23)CC1] |
| 403 | 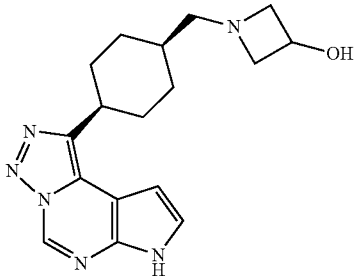 [SMILES: OC1CN(C[C@H]2CC[C@@H](c3nnn4cnc5[nH]ccc5c34)CC2)C1] |
| 404 | 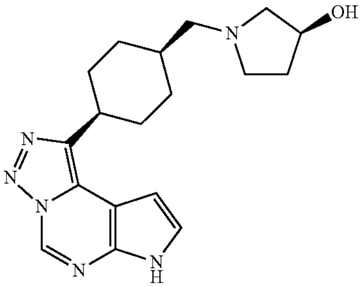 [SMILES: O[C@H]1CCN(C[C@H]2CC[C@@H](c3nnn4cnc5[nH]ccc5c34)CC2)C1] |
TABLE[a] 77-continued
| Ex | Structure |
| --- | --- |
| 405 | 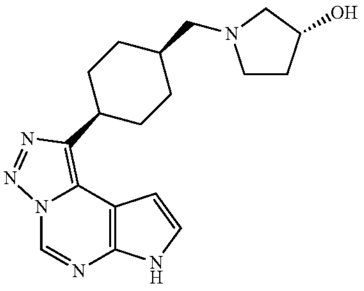 [SMILES: O[C@@H]1CCN(C[C@H]2CC[C@@H](c3nnn4cnc5[nH]ccc5c34)CC2)C1] |
| 406 | 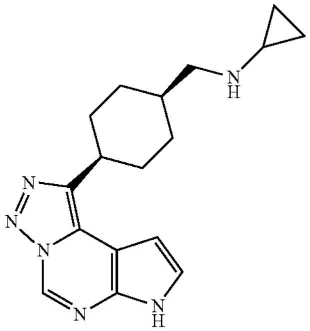 [SMILES: c1cc2c(ncn3nnc([C@H]4CC[C@@H](CNC5CC5)CC4)c23)[nH]1] |
TABLE[a] 78
| Ex | Structure |
| --- | --- |
| 407 | 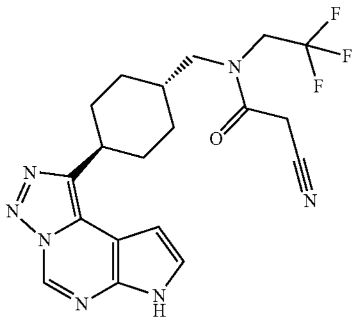 [SMILES: N#CCC(=O)N(CC(F)(F)F)C[C@H]1CC[C@H](c2nnn3cnc4[nH]ccc4c23)CC1] |
| 408 | 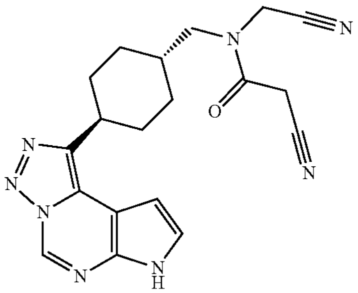 [SMILES: N#CCC(=O)N(CC#N)C[C@H]1CC[C@H](c2nnn3cnc4[nH]ccc4c23)CC1] |

TABLE[a] 78-continued
| Ex | Structure |
|---|---|
| 409 | 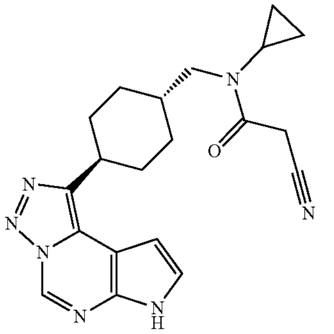 [SMILES: N#CCC(=O)N(C[C@H]1CC[C@H](c2nnn3cnc4[nH]ccc4c23)CC1)C1CC1] |
| 410 | 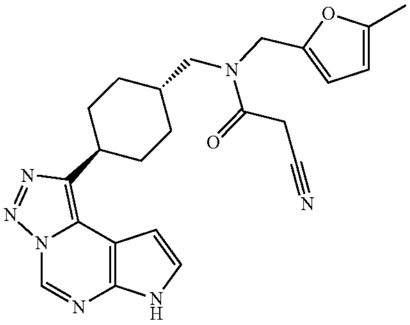 [SMILES: Cc1ccc(CN(C[C@H]2CC[C@H](c3nnn4cnc5[nH]ccc5c34)CC2)C(=O)CC#N)o1] |
| 411 | 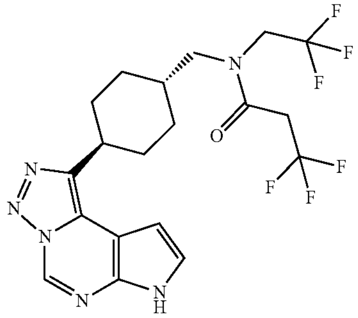 [SMILES: O=C(CC(F)(F)F)N(CC(F)(F)F)C[C@H]1CC[C@H](c2nnn3cnc4[nH]ccc4c23)CC1] |
| 412 | 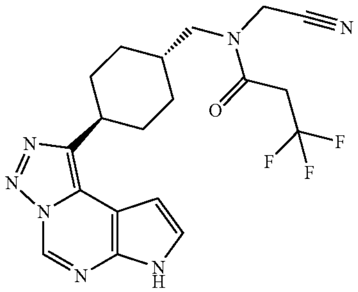 [SMILES: N#CCN(C[C@H]1CC[C@H](c2nnn3cnc4[nH]ccc4c23)CC1)C(=O)CC(F)(F)F] |
TABLE[a] 78-continued
| Ex | Structure |
|---|---|
| 413 | 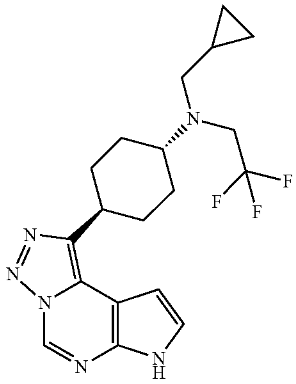 [SMILES: FC(F)(F)CN(CC1CC1)[C@H]1CC[C@H](c2nnn3cnc4[nH]ccc4c23)CC1] |
| 414 | 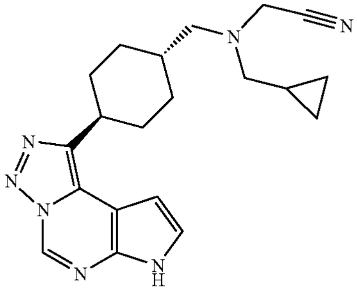 [SMILES: N#CCN(CC1CC1)C[C@H]1CC[C@H](c2nnn3cnc4[nH]ccc4c23)CC1] |
| 415 | 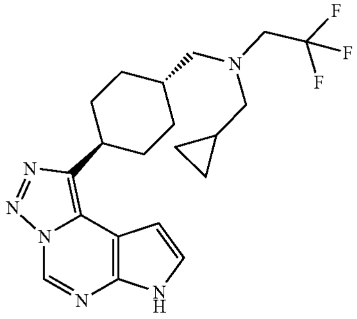 [SMILES: FC(F)(F)CN(CC1CC1)C[C@H]1CC[C@H](c2nnn3cnc4[nH]ccc4c23)CC1] |
| 416 | 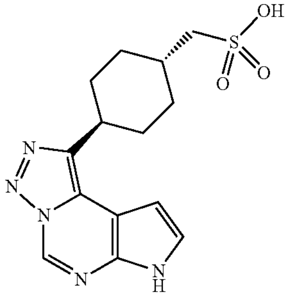 [SMILES: O=S(=O)(O)C[C@H]1CC[C@H](c2nnn3cnc4[nH]ccc4c23)CC1] |

TABLE[a] 78-continued
| Ex | Structure |
|---|---|
| 417 | 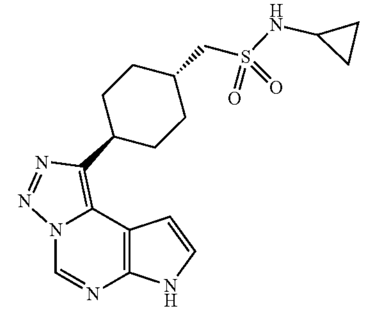 [SMILES: O=S(=O)(C[C@H]1CC[C@H](c2nnn3cnc4[nH]ccc4c23)CC1)NC1CC1] |
| 418 | 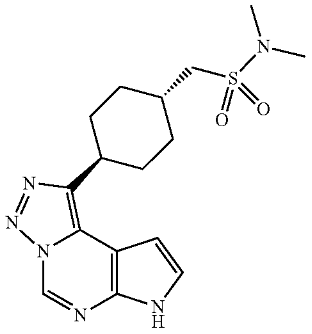 [SMILES: CN(C)S(=O)(=O)C[C@H]1CC[C@H](c2nnn3cnc4[nH]ccc4c23)CC1] |
| 419 | 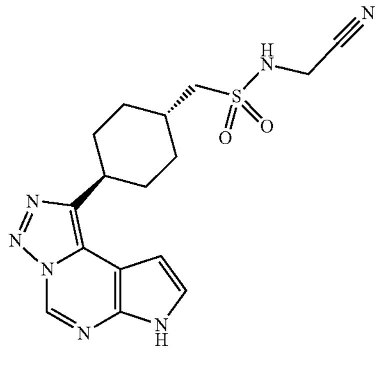 [SMILES: N#CCNS(=O)(=O)C[C@H]1CC[C@H](c2nnn3cnc4[nH]ccc4c23)CC1] |
| 420 | 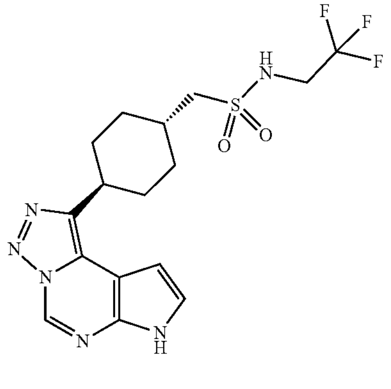 [SMILES: O=S(=O)(C[C@H]1CC[C@H](c2nnn3cnc4[nH]ccc4c23)CC1)NCC(F)(F)F] |
| 421 | 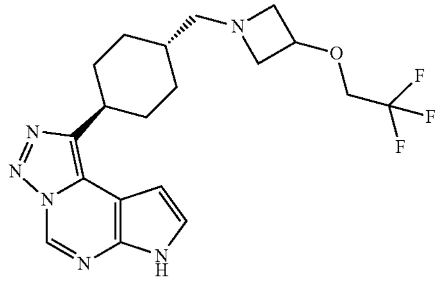 [SMILES: FC(F)(F)COC1CN(C[C@H]2CC[C@H](c3nnn4cnc5[nH]ccc5c34)CC2)C1] |
| 422 | 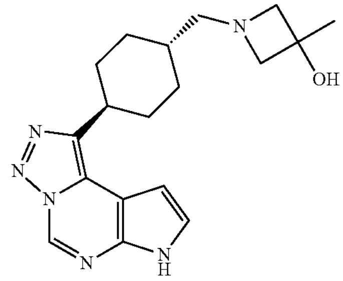 [SMILES: CC1(O)CN(C[C@H]2CC[C@H](c3nnn4cnc5[nH]ccc5c34)CC2)C1] |
| 423 | 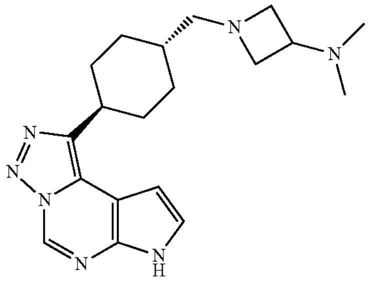 [SMILES: CN(C)C1CN(C[C@H]2CC[C@H](c3nnn4cnc5[nH]ccc5c34)CC2)C1] |
| 424 | 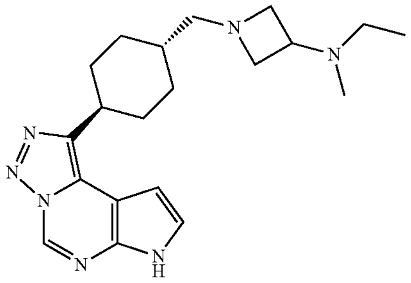 [SMILES: CCN(C)C1CN(C[C@H]2CC[C@H](c3nnn4cnc5[nH]ccc5c34)CC2)C1] |
TABLE[a] 79
| Ex | Structure |
|---|---|
| 425 | 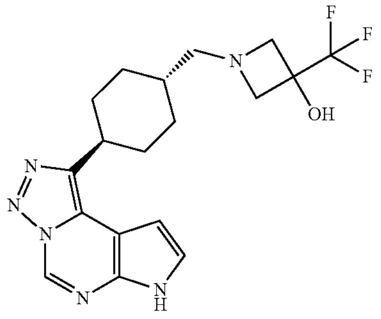 [SMILES: OC1(C(F)(F)F)CN(C[C@H]2CC[C@H](c3nnn4cnc5[nH]ccc5c34)CC2)C1] |

| Ex | Structure |
|---|---|
| 426 | 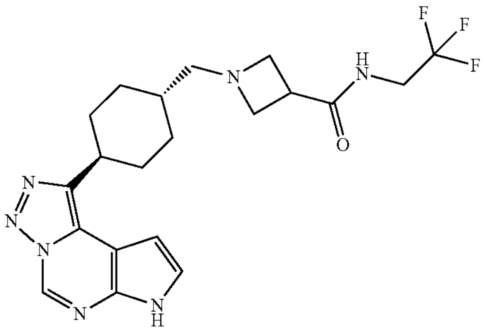 [SMILES: O=C(NCC(F)(F)F)C1CN(C[C@H]2CC[C@H](c3nnn4cnc5[nH]ccc5c34)CC2)C1] |
| 427 | 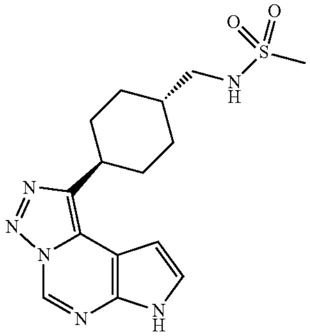 [SMILES: CS(=O)(=O)NC[C@H]1CC[C@H](c2nnn3cnc4[nH]ccc4c23)CC1] |
| 428 | 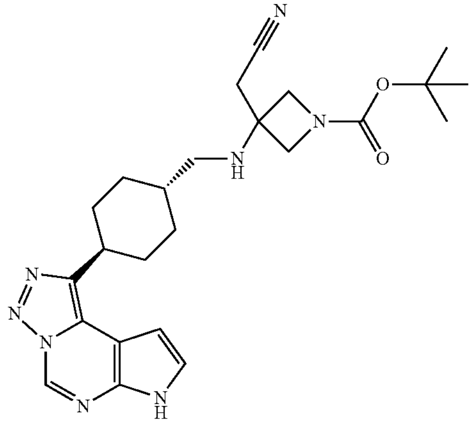 [SMILES: CC(C)(C)OC(=O)N1CC(CC#N)(NC[C@H]2CC[C@H](c3nnn4cnc5[nH]ccc5c34)CC2)C1] |
| 429 | 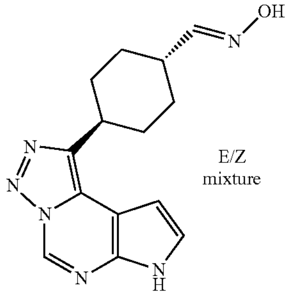 [SMILES: O/N=C/[C@H]1CC[C@H](c2nnn3cnc4[nH]ccc4c23)CC1] E/Z mixture |
| Ex | Structure |
|---|---|
| 430 | 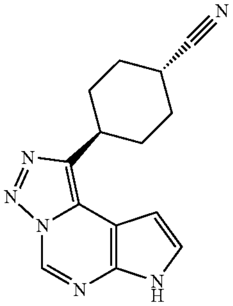 [SMILES: N#C[C@H]1CC[C@H](c2nnn3cnc4[nH]ccc4c23)CC1] |
| 431 | 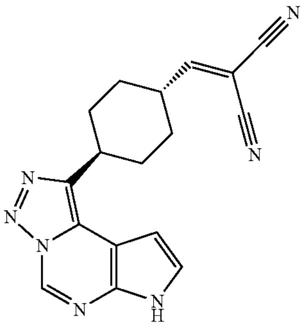 [SMILES: N#CC(C#N)=C[C@H]1CC[C@H](c2nnn3cnc4[nH]ccc4c23)CC1] |
| 432 | 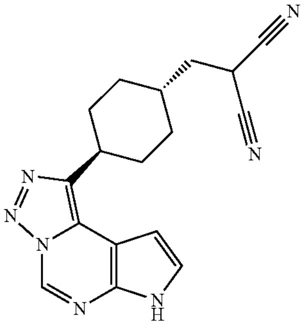 [SMILES: N#CC(C#N)C[C@H]1CC[C@H](c2nnn3cnc4[nH]ccc4c23)CC1] |
| 433 | 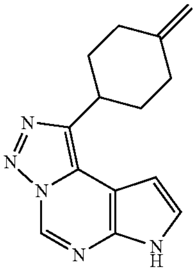 [SMILES: C=C1CCC(c2nnn3cnc4[nH]ccc4c23)CC1] |
| 434 | 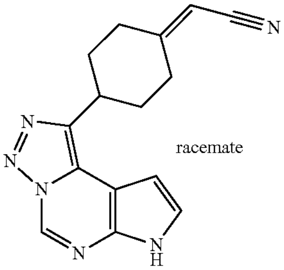 [SMILES: N#CC=C1CCC(c2nnn3cnc4[nH]ccc4c23)CC1] racemate |

TABLE[a] 79-continued
| Ex | Structure |
|---|---|
| 435a | 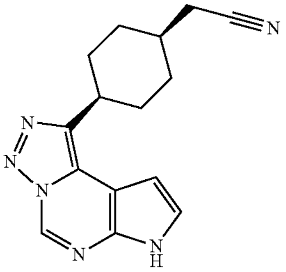 [SMILES: N#CC[C@H]1CC[C@@H](c2nnn3cnc4[nH]ccc4c23)CC1] |
| 435b | 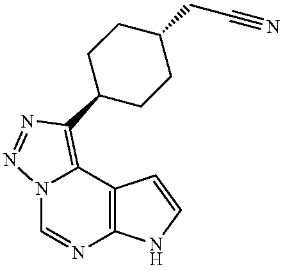 [SMILES: N#CC[C@H]1CC[C@H](c2nnn3cnc4[nH]ccc4c23)CC1] |
| 436 | 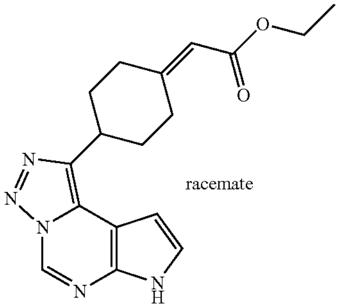 [SMILES: CCOC(=O)C=C1CCC(c2nnn3cnc4[nH]ccc4c23)CC1] racemate |
| 437 | 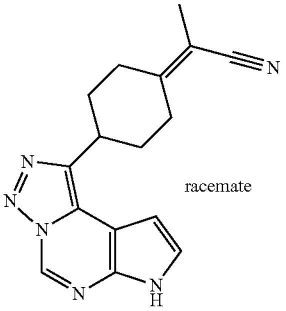 [SMILES: CC(C#N)=C1CCC(c2nnn3cnc4[nH]ccc4c23)CC1] racemate |
| 438 | 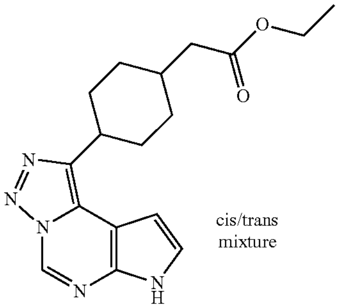 [SMILES: CCOC(=O)CC1CCC(c2nnn3cnc4[nH]ccc4c23)CC1] cis/trans mixture |
| 439a | 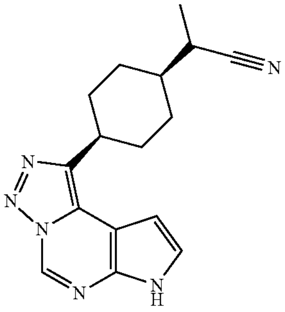 [SMILES: CC(C#N)[C@H]1CC[C@@H](c2nnn3cnc4[nH]ccc4c23)CC1] |
| 439b | 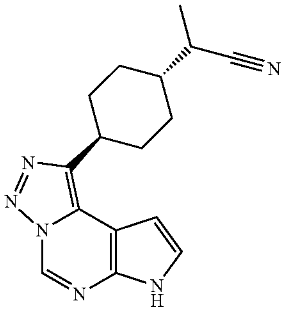 [SMILES: CC(C#N)[C@H]1CC[C@H](c2nnn3cnc4[nH]ccc4c23)CC1] |
| 440 | 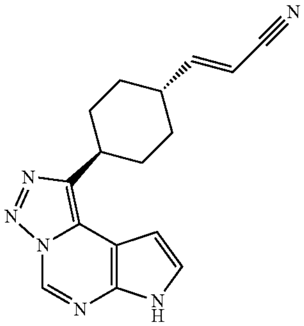 [SMILES: N#C/C=C/[C@H]1CC[C@H](c2nnn3cnc4[nH]ccc4c23)CC1] |
TABLE[a] 80
| Ex | Structure |
|---|---|
| 441 | 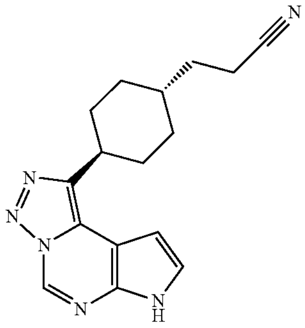 [SMILES: N#CCC[C@H]1CC[C@H](c2nnn3cnc4[nH]ccc4c23)CC1] |

TABLE[a] 80-continued

| Ex | Structure |
|---|---|
| 442a | 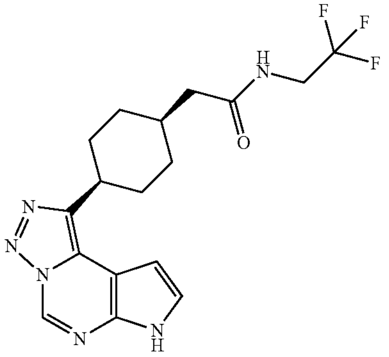 [SMILES: O=C(C[C@H]1CC[C@@H](c2nnn3cnc4[nH]ccc4c23)CC1)NCC(F)(F)F] |
| 442b | 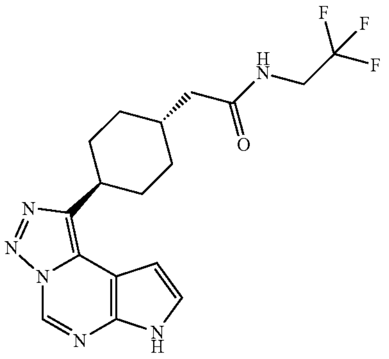 [SMILES: O=C(C[C@H]1CC[C@H](c2nnn3cnc4[nH]ccc4c23)CC1)NCC(F)(F)F] |
| 443a | 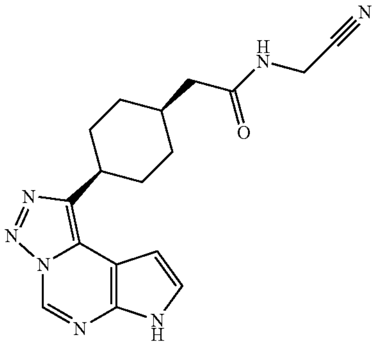 [SMILES: N#CCNC(=O)C[C@H]1CC[C@@H](c2nnn3cnc4[nH]ccc4c23)CC1] |
| 443b | 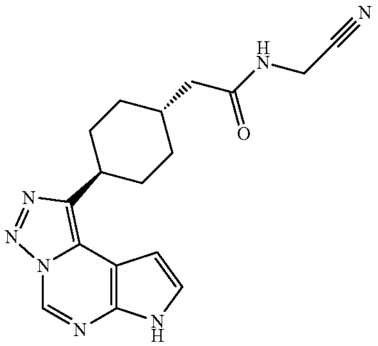 [SMILES: N#CCNC(=O)C[C@H]1CC[C@H](c2nnn3cnc4[nH]ccc4c23)CC1] |

TABLE[a] 80-continued

| Ex | Structure |
|---|---|
| 444 | 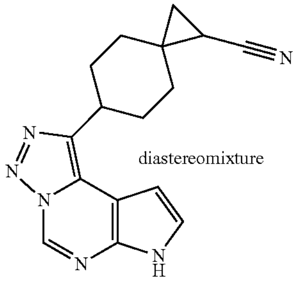 [SMILES: N#CC1CC12CCC(c1nnn3cnc4[nH]ccc4c13)CC2] diastereomixture |
| 445 | 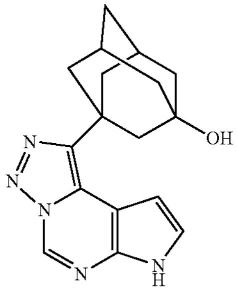 [SMILES: OC12CC3CC(C1)CC(c1nnn4cnc5[nH]ccc5c14)(C3)C2] |

TABLE[a] 81

| Rf | Data |
|---|---|
| 1 | $^1$H-NMR (DMSO-$d_6$) δ: 6.63 (d, J = 2.6 Hz, 1H), 7.67 (t, J = 2.6 Hz, 1H), 8.44 (s, 1H).<br>LC/MS: condition 1, retention time = 2.61 min<br>LC/MS ($ESI^+$) m/z; 246 $[M + H]^+$<br>LC/MS ($ESI^-$) m/z; 244 $[M - H]^-$ |
| 2 | $^1$H-NMR ($CDCl_3$) δ: 1.11 (d, J = 7.2 Hz, 18H), 1.79-1.89 (m, 3H), 6.46 (d, J = 3.3 Hz, 1H), 7.31 (d, J = 3.6 Hz, 1H), 8.47 (s, 1H).<br>LC/MS: condition 1, retention time = 5.97 min<br>LC/MS ($ESI^+$) m/z; 402 $[M + H]^+$ |
| 3 | LC/MS: condition 1, retention time = 4.91 min<br>LC/MS ($ESI^+$) m/z; 388 $[M + H]^+$ |
| 4 | LC/MS: condition 1, retention time = 4.05 min<br>LC/MS ($ESI^+$) m/z; 230 $[M - TIPS]^+$ |
| 5 | $^1$H-NMR ($CD_3OD$) δ: 1.46 (dd, J = 18.8, 9.5 Hz, 4H), 1.70-2.00 (m, 6H), 3.90-4.00 (m, 1H), 7.08 (d, J = 3.6 Hz, 1H), 7.63 (d, J = 3.6 Hz, 1H), 8.88 (s, 1H).<br>LC/MS: condition 1, retention time = 4.02 min<br>LC/MS ($ESI^+$) m/z; 230 $[M + H]^+$<br>LC/MS ($ESI^-$) m/z; 228 $[M - H]^-$ |
| 6 | $^1$H-NMR ($CDCl_3$) δ: −0.06 (s, 9H), 0.81-0.97 (m, 2H), 1.19-1.60 (m, 5H), 1.69-2.07 (m, 5H), 3.45-3.58 (m, 2H), 3.86-4.03 (m, 1H), 5.68 (s, 2H), 7.18-7.26 (m, 1H), 7.51 (d, J = 3.6 Hz, 1H), 9.01 (s, 1H).<br>LC/MS: condition 1, retention time = 5.59 min<br>LC/MS ($ESI^+$) m/z; 360 $[M + H]^+$ |
| 7 | LC/MS: condition 1, retention time = 3.39 min<br>LC/MS ($ESI^+$) m/z; 361 $[M + H]^+$ |
| 8 | LC/MS: condition 1, retention time = 4.54 min<br>LC/MS ($ESI^+$) m/z; 371 $[M + 1]^+$ |
| 9 | $^1$H-NMR ($CDCl_3$) δ: 2.34 (s, 3H), 3.30 (s, 3H), 3.53 (br s, 3H), 7.12-7.22 (m, 3H), 7.27-7.39 (m, 1H).<br>LC/MS: condition 1, retention time = 2.94 min<br>LC/MS ($ESI^+$) m/z; 180 $[M + H]^+$ |
| 10 | $^1$H-NMR ($CDCl_3$) δ: 2.46 (s, 3H), 7.02-7.10 (m, 1H), 7.21-7.39 (m, 2H), 7.40-7.48 (m, 1H), 7.50-7.58 (m, 2H), 9.01 (s, 1H), 9.49 (br s, 1H).<br>LC/MS: condition 1, retention time = 3.59 min<br>LC/MS ($ESI^+$) m/z; 238 $[M + H]^+$<br>LC/MS ($ESI^-$) m/z; 236 $[M - H]^-$ |
| 11 | $^1$H-NMR ($CDCl_3$) δ: 1.15-1.58 (m, 5H), 1.61-1.90 (m, 5H), 2.58-2.78 (m, 1H), 3.17 (s, 3H), 3.69 (s, 3H).<br>LC/MS: condition 1, retention time = 3.47 min<br>LC/MS ($ESI^+$) m/z; 172 $[M + H]^+$ |

TABLE[a] 81-continued

| Rf | Data |
|---|---|
| 12 | $^1$H-NMR ($CDCl_3$) δ: 1.19-1.60 (m, 5H), 1.68-2.10 (m, 5H), 3.85-4.07 (m, 1H), 7.19-7.25 (m, 1H), 7.45-7.58 (m, 1H), 9.00 (s, 1H), 9.43 (br s, 1H). LC/MS: condition 1, retention time = 4.05 min LC/MS ($ESI^+$) m/z; 230 $[M + H]^+$ LC/MS ($ESI^-$) m/z; 228 $[M - H]^-$ |

TABLE[a] 82

| Rf | Data |
|---|---|
| 13 | $^1$H-NMR ($CDCl_3$) δ: 0.91 (s, 1.5H), 0.94 (s, 1.5H), 1.21-1.91 (m, 8H), 2.00-2.19 (m, 1H), 2.80-2.94 (m, 1H), 3.17 (s, 3H), 3.68 (s, 3H). LC/MS: condition 1, retention time = 3.84 min LC/MS ($ESI^+$) m/z; 186 $[M + H]^+$ |
| 14 | $^1$H-NMR ($CDCl_3$) δ: 0.77-0.86 (m, 3H), 1.20-2.00 (m, 8H), 2.31-2.50 (m, 1H), 4.10-4.20 (m, 1H), 7.17-7.22 (m, 1H), 7.43-7.52 (m, 1H), 8.98 (s, 1H), 9.18 (br s, 1H). LC/MS: condition 1, retention time = 4.22 min LC/MS ($ESI^+$) m/z; 244 $[M + H]^+$ LC/MS ($ESI^-$) m/z; 242 $[M - H]^-$ |
| 15 | LC/MS: condition 2, retention time = 4.17 min LC/MS ($ESI^+$) m/z; 376 $[M + H]^+$ |
| 16 | $^1$H-NMR ($CDCl_3$) δ: 1.10-1.90 (m, 5H), 2.73-3.20 (m, 2H), 3.50 (t, J = 6.0 Hz, 2H), 3.65-4.15 (m, 2H), 5.13 (br s, 2H), 7.22-7.41 (m, 5H). |
| 17 | LC/MS: condition 1, retention time = 3.89 min LC/MS ($ESI^+$) m/z; 307 $[M + H]^+$ |
| 18 | LC/MS: condition 1, retention time = 5.34 min LC/MS ($ESI^+$) m/z; 495 $[M + H]^+$ |
| 19 | LC/MS: condition 2, retention time = 3.77 min LC/MS ($ESI^+$) m/z; 496 $[M + H]^+$ |
| 20 | LC/MS: condition 1, retention time = 4.87 min LC/MS ($ESI^+$) m/z; 506 $[M + H]^+$ |
| 21 | $^1$H-NMR ($CDCl_3$) δ: 0.93-1.13 (m, 2H), 1.20-1.32 (m, 1H), 1.44-1.65 (m, 2H), 1.78-1.93 (m, 4H), 2.56-2.74 (m, 1H), 3.18 (s, 3H), 3.48 (t, J = 6.0 Hz, 2H), 3.69 (s, 3H). LC/MS: condition 1, retention time = 1.22 min LC/MS ($ESI^+$) m/z; 202 $[M + H]^+$ |
| 22 | $^1$H-NMR ($CDCl_3$) δ: 1.05 (s, 9H), 1.40-1.68 (m, 5H), 1.72-1.95 (m, 4H), 2.51-2.73 (m, 1H), 3.18 (s, 3H), 3.47 (d, J = 6.3 Hz, 2H), 3.69 (s, 3H), 7.28-7.48 (m, 6H), 7.53-7.72 (m, 4H). LC/MS: condition 1, retention time = 5.67 min LC/MS ($ESI^+$) m/z; 440 $[M + H]^+$ |
| 23 | $^1$H-NMR ($CDCl_3$) δ: 1.07 (s, 9H), 1.42-1.68 (m, 5H), 1.87-2.00 (m, 3H), 2.01-2.13 (m, 1H), 3.53 (d, J = 6.0 Hz, 2H), 3.81-4.00 (m, 1H), 7.20-7.27 (m, 1H), 7.30-7.43 (m, 6H), 7.45-7.53 (m, 1H), 7.59-7.73 (m, 4H), 9.01 (d, J = 4.5 Hz, 1H), 9.07 (br s, 1H). LC/MS: condition 1, retention time = 5.94 min LC/MS ($ESI^+$) m/z; 498 $[M + H]^+$ |
| 24 | $^1$H-NMR ($CDCl_3$) δ: 1.09 (s, 9H), 1.17-1.37 (m, 2H), 1.68-1.82 (m, 1H), 1.83-2.21 (m, 6H), 3.07-3.22 (m, 1H), 3.58 (d, J = 6.3 Hz, 2H), 6.75-6.85 (m, 1H), 7.25-7.32 (m, 1H), 7.33-7.50 (m, 6H), 7.62-7.78 (m, 4H), 9.01 (br s, 1H), 9.21 (s, 1H). LC/MS: condition 1, retention time = 5.67 min LC/MS ($ESI^+$) m/z; 510 $[M + H]^+$ LC/MS ($ESI^-$) m/z; 508 $[M - H]^-$ |

TABLE[a] 83

| Rf | Data |
|---|---|
| 25 | $^1$H-NMR ($CDCl_3$) δ: 0.90-0.98 (m, 3H), 1.45 (s, 9H), 1.30-1.90 (m, 4H), 2.05-2.30 (m, 1H), 2.50-2.85 (m, 1H), 3.30-3.50 (m, 1H), 3.50-4.20 (m, 4H). |
| 26 | $^1$H-NMR ($CDCl_3$) δ: 0.87-1.01 (m, 3H), 1.41-1.47 (m, 9H), 1.54-1.79 (m, 4H), 2.80 (s, 2H), 2.89 (q, J = 6.3 Hz, 1H), 3.15-3.22 (m, 3H), 3.56 (br s, 1H), 3.68-3.73 (m, 3H). |

TABLE[a] 83-continued

| Rf | Data |
|---|---|
| | LC/MS: condition 1, retention time = 3.97 min LC/MS ($ESI^+$) m/z; 231 $[M - {}^tBu]^+$ |
| 27 | LC/MS: condition 1, retention time = 4.12 min LC/MS ($ESI^+$) m/z; 345 $[M + H]^+$ LC/MS ($ESI^-$) m/z; 343 $[M - H]^-$ |
| 28 | $^1$H-NMR ($CDCl_3$) δ: 1.46 (s, 9H), 1.48-1.56 (m, 1H), 1.58-1.76 (m, 2H), 1.88-1.97 (m, 1H), 2.63-2.95 (m, 3H), 3.19 (s, 3H), 3.73 (s, 3H), 4.03-4.22 (m, 2H). LC/MS: condition 1, retention time = 3.60 min LC/MS ($ESI^+$) m/z; 273 $[M - {}^tBu]^+$ |
| 29 | LC/MS: condition 1, retention time = 3.87 min LC/MS ($ESI^+$) m/z; 275 $[M - {}^tBu]^+$ LC/MS ($ESI^-$) m/z; 329 $[M - H]^-$ |
| 30 | LC/MS: condition 1, retention time = 2.88 min LC/MS ($ESI^+$) m/z; 222 $[M + H]^+$ |
| 31 | LC/MS: condition 1, retention time = 3.52 min LC/MS ($ESI^+$) m/z; 235 $[M + H]^+$ LC/MS ($ESI^-$) m/z; 233 $[M - H]^-$ |
| 32 | $^1$H-NMR ($CDCl_3$) δ: 1.65-1.75 (m, 2H), 1.80-1.87 (m, 1H), 2.16-2.23 (m, 1H), 2.91-3.02 (m, 1H), 3.22 (br s, 1H), 4.08-4.19 (m, 2H), 4.38 (br s, 1H), 5.10-5.18 (m, 2H), 7.21 (dd, J = 3.6, 2.0 Hz, 1H), 7.28-7.39 (m, 5H), 7.51 (dd, J = 4.0, 2.3 Hz, 1H), 8.95 (br s, 1H), 9.42 (br s, 1H). LC/MS: condition 1, retention time = 3.90 min LC/MS ($ESI^+$) m/z; 365 $[M + H]^+$ LC/MS ($ESI^-$) m/z; 363 $[M - H]^-$ |
| 33 | $^1$H-NMR ($CDCl_3$) δ: 1.35-1.80 (m, 3H), 2.00-2.15 (m, 1H), 2.40-2.59 (m, 1H), 2.93 (ddd, J = 13.0, 10.7, 3.0 Hz, 1H), 2.95-3.26 (m, 1H), 3.92-4.02 (m, 1H), 4.02-4.35 (m, 1H), 5.11 (d, J = 12.4 Hz, 1H), 5.16 (d, J = 12.4 Hz, 1H), 7.27-7.34 (m, 5H). LC/MS: condition 1, retention time = 3.52 min LC/MS ($ESI^+$) m/z; 264 $[M + H]^+$ LC/MS ($ESI^-$) m/z; 262 $[M - H]^-$ |
| 34 | $^1$H-NMR ($CDCl_3$) δ: 1.40-1.81 (m, 3H), 1.87-2.00 (m, 1H), 2.68-3.05 (m, 3H), 3.16 (s, 3H), 3.59-3.70 (m, 3H), 4.05-4.34 (m, 2H), 5.11 (d, J = 12.7 Hz, 1H), 5.16 (d, J = 12.7 Hz, 1H), 7.28-7.39 (m, 5H). LC/MS: condition 1, retention time = 3.70 min LC/MS ($ESI^+$) m/z; 307 $[M + H]^+$ |
| 35 | LC/MS: condition 1, retention time = 0.77 min LC/MS ($ESI^+$) m/z; 321 $[M + H]^+$ |

TABLE[a] 84

| Rf | Data |
|---|---|
| 36 | $^1$H-NMR ($CDCl_3$) δ: 1.16-1.40 (m, 3H), 1.61-1.82 (m, 1H), 1.85-2.09 (m, 4H), 2.10-2.26 (m, 2H), 3.09-3.25 (m, 1H), 3.58 (t, J = 6.0 Hz, 2H), 6.74-6.85 (m, 1H), 7.20-7.32 (m, 1H), 9.04 (br s, 1H), 9.22 (s, 1H). LC/MS: condition 1, retention time = 2.99 min LC/MS ($ESI^+$) m/z; 272 $[M + H]^+$ LC/MS ($ESI^-$) m/z; 270 $[M - H]^-$ |
| 37 | $^1$H-NMR ($CDCl_3$) δ: 0.93-1.13 (m, 2H), 1.20-1.32 (m, 1H), 1.44-1.65 (m, 2H), 1.78-1.93 (m, 4H), 2.56-2.74 (m, 1H), 3.18 (s, 3H), 3.48 (t, J = 6.0 Hz, 2H), 3.69 (s, 3H). LC/MS: condition 1, retention time = 1.22 min LC/MS ($ESI^+$) m/z; 202 $[M + H]^+$ |
| 38 | $^1$H-NMR ($CDCl_3$) δ: 1.46 (s, 9H), 1.60-1.81 (m, 4H), 2.65-2.90 (m, 3H), 3.18 (s, 3H), 3.71 (s, 3H), 4.00-4.30 (m, 2H). LC/MS: condition 1, retention time = 3.66 min LC/MS ($ESI^+$) m/z; 273 $[M + H]^+$ |
| 39 | $^1$H-NMR ($CDCl_3$) δ: 1.40-1.53 (m, 9H), 1.55-1.82 (m, 2H), 1.87-2.10 (m, 2H), 2.80-3.10 (m, 2H), 4.00-4.37 (m, 3H), 7.15-7.30 (m, 1H), 7.46-7.59 (m, 1H), 8.90-9.08 (m, 1H), 9.53 (br s, 1H). LC/MS: condition 1, retention time = 3.87 min LC/MS ($ESI^+$) m/z; 331 $[M + H]^+$ LC/MS ($ESI^-$) m/z; 329 $[M - H]^-$ |
| 40 | $^1$H-NMR (DMSO-$d_6$) δ: 1.63-1.89 (m, 4H), 2.82-3.04 (m, 3H), 3.10 (s, 3H), 3.18-3.31 (m, 2H), 3.69 (s, 3H), 8.73 (br s, 1H), 9.07 (br s, 1H). LC/MS: condition 1, retention time = 0.50 min LC/MS ($ESI^+$) m/z; 173 $[M + H]^+$ |

TABLE[a] 84-continued

| Rf | Data |
|---|---|
| 41 | $^1$H-NMR ($CDCl_3$) δ: 1.65-1.92 (m, 4H), 2.38-2.51 (m, 2H), 2.57-2.72 (m, 1H), 2.92-3.06 (m, 4H), 3.18 (s, 3H), 3.70 (s, 3H). LC/MS: condition 1, retention time = 0.74 min LC/MS ($ESI^+$) m/z; 255 $[M + H]^+$ |
| 42 | $^1$H-NMR ($CDCl_3$) δ: 1.78-2.05 (m, 4H), 2.56-2.68 (m, 2H), 2.87-3.12 (m, 4H), 3.87-4.00 (m, 1H), 7.22-7.25 (m, 1H), 7.26 (s, 1H), 7.50-7.56 (m, 1H), 8.99 (s, 1H), 9.74 (br s, 1H). LC/MS: condition 1, retention time = 2.75 min LC/MS ($ESI^+$) m/z; 313 $[M + H]^+$ |
| 43 | $^1$H-NMR ($CDCl_3$) δ: 1.64-1.82 (m, 4H), 2.76-2.95 (m, 3H), 3.18 (s, 3H), 3.71 (s, 3H), 4.12-4.30 (m, 2H), 5.13 (s, 2H), 7.25-7.39 (m, 5H). LC/MS: condition 1, retention time = 3.65 min LC/MS ($ESI^+$) m/z; 307 $[M + H]^+$ |
| 44 | $^1$H-NMR ($CDCl_3$) δ: 1.60-1.82 (m, 3H), 1.92-2.09 (m, 2H), 2.95-3.15 (m, 2H), 4.18-4.38 (m, 2H), 5.15 (s, 2H), 7.20-7.25 (m, 1H), 7.25-7.40 (m, 5H), 7.50-7.55 (m, 1H), 8.99 (s, 1H), 9.44-9.71 (m, 1H). LC/MS: condition 1, retention time = 3.90 min LC/MS ($ESI^+$) m/z; 365 $[M + H]^+$ |

TABLE[a] 85

| Rf | Data |
|---|---|
| 45 | $^1$H-NMR ($CDCl_3$) δ: 1.02-1.25 (m, 2H), 1.44 (s, 9H), 1.52-1.71 (m, 2H), 1.78-1.89 (m, 2H), 2.02-2.15 (m, 2H), 2.52-2.68 (m, 1H), 3.17 (s, 3H), 3.35-3.50 (m, 1H), 3.69 (s, 3H), 4.28-4.43 (m, 1H). |
| 46 | $^1$H-NMR ($CDCl_3$) δ: 1.26-1.41 (m, 2H), 1.46 (s, 9H), 1.52-1.80 (m, 3H), 2.00-2.20 (m, 3H), 3.49 (br s, 1H), 3.82-3.99 (m, 1H), 4.46 (br s, 1H), 7.19-7.25 (m, 1H), 7.46-7.55 (m, 1H), 9.00 (s, 1H), 9.44-9.85 (m, 1H). LC/MS: condition 1, retention time = 3.84 min LC/MS ($ESI^+$) m/z; 345 $[M + H]^+$ LC/MS ($ESI^-$) m/z; 343 $[M - H]^-$ |
| 47 | LC/MS: condition 1, retention time = 2.01 min LC/MS ($ESI^+$) m/z; 321 $[M + H]^+$ |
| 48 | LC/MS: condition 1, retention time = 2.18 min LC/MS ($ESI^+$) m/z; 379 $[M + H]^+$ LC/MS ($ESI^-$) m/z; 377 $[M - H]^-$ |
| 49 | $^1$H-NMR ($CDCl_3$) δ: 0.94-1.13 (m, 2H), 1.42-1.71 (m, 4H), 1.75-1.93 (m, 4H), 2.55-2.73 (m, 1H), 3.10-3.26 (m, 4H), 3.32 (s, 3H), 3.68 (s, 3H). LC/MS: condition 1, retention time = 3.19 min LC/MS ($ESI^+$) m/z; 216 $[M + H]^+$ |
| 50 | $^1$H-NMR ($CDCl_3$) δ: 1.10-1.30 (m, 2H), 1.41-1.78 (m, 3H), 1.86-2.12 (m, 4H), 3.25 (d, J = 6.3 Hz, 2H), 3.35 (s, 3H), 3.85-4.02 (m, 1H), 7.15-7.30 (m, 1H), 7.45-7.55 (m, 1H), 9.00 (s, 1H), 9.46 (br s, 1H). LC/MS: condition 1, retention time = 3.65 min LC/MS ($ESI^+$) m/z; 274 $[M + H]^+$ LC/MS ($ESI^-$) m/z; 272 $[M - H]^-$ |
| 51 | $^1$H-NMR ($CDCl_3$) δ: 1.20-1.41 (m, 1H), 1.48-1.70 (m, 4H), 1.77-1.92 (m, 2H), 2.00-2.13 (m, 1H), 2.50-2.73 (m, 1H), 3.18 (s, 3H), 3.55-3.78 (m, 1H), 3.70 (s, 3H). LC/MS: condition 1, retention time = 0.60 min LC/MS ($ESI^+$) m/z; 189 $[M + H]^+$ |
| 52 | $^1$H-NMR ($CDCl_3$) δ: 1.22 (qd, J = 13.8, 2.7 Hz, 2H), 1.55 (qd, J = 13.8, 2.7 Hz, 2H), 1.86 (m, 2H), 2.15 (m, 2H), 2.64 (m, 1H), 3.14 (m, 1H), 3.17 (s, 3H), 3.36 (s, 3H), 3.70 (s, 3H). LC/MS: condition 1, retention time = 1.77 min LC/MS ($ESI^+$) m/z; 202 $[M + H]^+$ |
| 53 | $^1$H-NMR ($CDCl_3$) δ: 1.50 (m, 4H), 2.15 (m, 4H), 3.21 (tt, J = 10.5, 3.9 Hz, 1H), 3.40 (s, 3H), 3.95 (tt, J = 11.4, 3.6 Hz, 1H), 7.23 (dd, J = 3.3, 2.1 Hz, 1H), 7.56 (t, J = 2.4 Hz, 1H), 9.03 (s, 1H), 10.9 (br s, 1H). LC/MS: condition 1, retention time = 3.35 min LC/MS ($ESI^+$) m/z; 260 $[M + H]^+$ LC/MS ($ESI^-$) m/z; 258 $[M - H]^-$ |

TABLE[a] 86

| Rf | Data |
|---|---|
| 54 | $^1$H-NMR ($CDCl_3$) δ: 1.60-1.95 (m, 6H), 2.10-2.30 (m, 2H), 2.64-2.83 (m, 1H), 3.18 (s, 3H), 3.71 (s, 3H). LC/MS: condition 1, retention time = 3.05 min LC/MS ($ESI^+$) m/z; 208 $[M + H]^+$ |
| 55 | LC/MS: condition 1, retention time = 3.60 min LC/MS ($ESI^+$) m/z; 184 $[M + H]^+$ |
| 56 | $^1$H-NMR ($CDCl_3$) δ: 1.35-1.88 (m, 12H), 2.73-2.90 (m, 1H), 3.17 (s, 3H), 3.69 (s, 3H). LC/MS: condition 1, retention time = 3.81 min LC/MS ($ESI^+$) m/z; 186 $[M + H]^+$ |
| 57 | $^1$H-NMR ($CDCl_3$) δ: 1.96 (m, 2H), 2.13 (m, 2H), 2.33 (m, 2H), 3.17 (s, 3H), 3.48 (m, 1H), 3.65 (s, 3H). LC/MS: condition 1, retention time = 1.85 min LC/MS ($ESI^+$) m/z; 144 $[M + H]^+$ |
| 58 | $^1$H-NMR ($CDCl_3$) δ: 1.57 (m, 2H), 1.78 (m, 6H), 3.10 (m, 1H), 3.19 (s, 3H), 3.69 (s, 3H). LC/MS: condition 1, retention time = 2.94 min LC/MS ($ESI^+$) m/z; 158 $[M + H]^+$ |
| 59 | $^1$H-NMR ($CDCl_3$) δ: 1.28-1.64 (m, 4H), 1.83-2.19 (m, 5H), 2.57-2.76 (m, 1H), 3.18 (s, 3H), 3.70 (s, 3H). LC/MS: condition 1, retention time = 3.74 min LC/MS ($ESI^+$) m/z; 240 $[M + H]^+$ |
| 60 | $^1$H-NMR ($CDCl_3$) δ: 1.45-1.80 (m, 4H), 1.82-2.20 (m, 5H), 2.81-2.99 (m, 1H), 3.17 (s, 3H), 3.68 (s, 3H). LC/MS: condition 1, retention time = 3.77 min LC/MS ($ESI^+$) m/z; 240 $[M + H]^+$ |
| 61 | $^1$H-NMR ($CDCl_3$) δ: 1.75-2.35 (m, 8H), 3.94-4.13 (m, 1H), 7.20-7.30 (m, 1H), 7.46-7.58 (m, 1H), 8.99 (s, 1H), 9.13 (br s, 1H). LC/MS: condition 1, retention time = 3.69 min LC/MS ($ESI^+$) m/z; 266 $[M + H]^+$ LC/MS ($ESI^-$) m/z; 264 $[M - H]^-$ |
| 62 | $^1$H-NMR ($CDCl_3$) δ: 1.16-1.74 (m, 7H), 1.96 (ddd, J = 12.9, 5.1, 3.3 Hz, 1H), 2.36 (br s, 1H), 2.86 (br s, 1H), 4.31 (m, 1H), 7.24 (m, 1H), 7.51 (m, 1H), 9.01 (s, 1H), 9.75 (br s, 1H). LC/MS: condition 1, retention time = 3.92 min LC/MS ($ESI^+$) m/z; 242 $[M + H]^+$ LC/MS ($ESI^-$) m/z; 240 $[M - H]^-$ |
| 63 | $^1$H-NMR ($CDCl_3$) δ: 1.60-1.82 (m, 10H), 2.03 (m, 2H), 4.16 (tt, J = 8.7, 4.5 Hz, 1H), 7.24 (m, 1H), 7.57 (m, 1H), 9.03 (s, 1H), 11.18 (br s, 1H). LC/MS: condition 1, retention time = 4.11 min LC/MS ($ESI^+$) m/z; 244 $[M + H]^+$ LC/MS ($ESI^-$) m/z; 242 $[M - H]^-$ |

TABLE[a] 87

| Rf | Data |
|---|---|
| 64 | $^1$H-NMR ($CDCl_3$) δ: 1.95 (m, 1H), 2.14 (m, 1H), 2.38 (m, 4H), 4.60 (quint, J = 8.4 Hz, 1H), 7.28 (m, 1H), 7.52 (m, 1H), 8.97 (s, 1H). LC/MS: condition 1, retention time = 3.22 min LC/MS ($ESI^+$) m/z; 202 $[M + H]^+$ LC/MS ($ESI^-$) m/z; 200 $[M - H]^-$ |
| 65 | $^1$H-NMR ($CDCl_3$) δ: 1.76 (m, 4H), 1.91 (m, 2H), 2.03 (m, 2H), 4.36 (m, 1H), 7.26 (m, 1H), 7.55 (m, 1H), 9.03 (s, 1H), 10.43 (br s, 1H). LC/MS: condition 1, retention time = 3.64 min LC/MS ($ESI^+$) m/z; 216 $[M + H]^+$ |
| 66 | $^1$H-NMR (DMSO-$d_6$) δ: 1.30-1.60 (m, 4H), 1.90-2.13 (m, 4H), 2.20-2.45 (m, 1H), 3.80-4.00 (m, 1H), 6.91-7.05 (m, 1H), 7.75-7.90 (m, 1H), 8.96 (s, 1H), 12.47 (br s, 1H). LC/MS: condition 1, retention time = 4.07 min LC/MS ($ESI^+$) m/z; 298 $[M + H]^+$ LC/MS ($ESI^-$) m/z; 296 $[M - H]^-$ |
| 67 | $^1$H-NMR (DMSO-$d_6$) δ: 1.50-1.88 (m, 6H), 1.95-2.11 (m, 2H), 2.30-2.45 (m, 1H), 4.05-4.20 (m, 1H), 6.90-7.05 (m, 1H), 7.75-7.90 (m, 1H), 8.93 (s, 1H), 12.46 (br s, 1H). LC/MS: condition 1, retention time = 4.00 min LC/MS ($ESI^+$) m/z; 298 $[M + H]^+$ LC/MS ($ESI^-$) m/z; 296 $[M - H]^-$ |
| 68 | $^1$H-NMR ($CDCl_3$) δ: 1.05 (s, 9H), 1.38 (dq, J = 10.9, 3.0 Hz, 4H), 1.65-1.74 (m, 2H), 1.86-1.95 (m, 2H), 2.53-2.65 (m, 1H), 3.13 (s, |

TABLE[a] 87-continued

| Rf | Data |
|---|---|
| | 3H), 3.56-3.64 (m, 1H), 3.67 (s, 3H), 7.32-7.45 (m, 6H), 7.64-7.69 (m, 4H).<br>LC/MS: condition 1, retention time = 5.45 min<br>LC/MS ($ESI^+$) m/z; 426 $[M + H]^+$ |
| 69 | $^1$H-NMR ($CDCl_3$) δ: 1.07 (s, 9H), 1.30-1.45 (m, 2H), 1.52-1.67 (m, 2H), 1.89-2.00 (m, 4H), 3.60-3.71 (m, 1H), 3.89 (tt, J = 12.2, 3.0 Hz, 1H), 7.17 (dd, J = 3.6, 2.0 Hz, 1H), 7.33-7.49 (m, 7H), 7.65-7.72 (m, 4H), 8.99 (s, 1H), 9.11 (br s, 1H).<br>LC/MS: condition 1, retention time = 5.64 min<br>LC/MS ($ESI^+$) m/z; 484 $[M + H]^+$<br>LC/MS ($ESI^-$) m/z; 482 $[M - H]^-$ |
| 70 | $^1$H-NMR ($CDCl_3$) δ: 1.09 (s, 5H), 1.15 (s, 4H), 1.53-1.97 (m, 5H), 1.98-2.08 (m, 2H), 2.49 (dq, J = 12.6, 3.0 Hz, 1H), 3.11 (tt, J = 11.2, 3.3 Hz, 0.6H), 3.25 (tt, J = 12.2, 3.3 Hz, 0.4H), 3.75-3.85 (m, 0.6H), 4.13-4.18 (m, 0.4H), 6.71 (dd, J = 3.3, 2.0 Hz, 0.6H), 7.01 (dd, J = 3.0, 2.3 Hz, 0.4H), 7.16 (t, J = 3.3 Hz, 0.6H), 7.21-7.28 (m, 0.4H), 7.34-7.47 (m, 6H), 7.69-7.75 (m, 4H), 9.04 (br s, 1H), 9.18 (s, 0.6H), 9.24 (s, 0.4H).<br>LC/MS: condition 1, retention time = 5.32, 5.39 min (cis/trans mixture)<br>LC/MS ($ESI^+$) m/z; 496 $[M + H]^+$<br>LC/MS ($ESI^-$) m/z; 494 $[M - H]^-$ |

TABLE[a] 88

| Rf | Data |
|---|---|
| 71 | $^1$H-NMR ($CDCl_3$) δ: 1.31-1.46 (m, 1H), 1.54-1.67 (m, 4H), 1.81-1.99 (m, 3H), 2.02-2.10 (m, 1H), 2.57-2.79 (m, 1H), 3.18 (d, J = 1.3 Hz, 3H), 3.70 (d, J = 1.7 Hz, 3H), 3.98-4.04 (m, 1H).<br>LC/MS: condition 1, retention time = 0.86 min (cis/trans mixture)<br>LC/MS ($ESI^+$) m/z; 188 $[M + H]^+$ |
| 72 | $^1$H-NMR ($CDCl_3$) δ: 0.03-0.05 (m, 6H), 0.85 (s, 4H), 0.86 (s, 5H), 1.27-1.52 (m, 4H), 1.67-1.82 (m, 2H), 1.93 (td, J = 11.9, 3.3 Hz, 2H), 2.53-2.66 (m, 1H), 3.14 (s, 3H), 3.66 (s, 3H), 3.94-3.98 (m, 1H).<br>LC/MS: condition 1, retention time = 4.83, 5.00 min (cis/trans mixture)<br>LC/MS ($ESI^+$) m/z; 302 $[M + H]^+$ |
| 73 | $^1$H-NMR ($CDCl_3$) δ: 0.05 (s, 4H), 0.08 (s, 2H), 0.90 (s, 9H), 1.49-1.83 (m, 6H), 1.93-2.08 (m, 2H), 3.59-3.69 (m, 0.3H), 3.93 (tt, J = 11.2, 3.0 Hz, 1H), 4.02-4.07 (m, 0.7H), 7.20-7.26 (m, 1H), 7.52 (dd, J = 4.3, 2.3 Hz, 1H), 9.01 (s, 0.7H), 9.02 (s, 0.3H), 9.78 (br s, 1H).<br>LC/MS: condition 1, retention time = 5.07, 5.14 min (cis/trans mixture)<br>LC/MS ($ESI^+$) m/z; 360 $[M + H]^+$<br>LC/MS ($ESI^-$) m/z; 358 $[M - H]^-$ |
| 74 | $^1$H-NMR ($CDCl_3$) δ: 0.11 (s, 3H), 0.14 (s, 3H), 0.93 (s, 4.5H), 0.98 (s, 4.5H), 1.50-1.81 (m, 3H), 1.83-2.17 (m, 4H), 2.37 (dq, J = 12.9, 4.0 Hz, 1H), 3.15 (tt, J = 11.9, 4.0 Hz, 0.5H), 3.29 (tt, J = 12.6, 4.0 Hz, 0.5H), 3.72-3.84 (m, 0.5H), 4.17 (br s, 0.5H), 6.77 (dd, J = 3.6, 2.0 Hz, 0.5H), 7.12 (dd, J = 3.6, 2.0 Hz, 0.5H), 7.24-7.27 (m, 0.5H), 7.30 (t, J = 3.3 Hz, 0.5H), 9.13 (br s, 1H), 9.22 (s, 0.5H), 9.23 (s, 0.5H).<br>LC/MS: condition 1, retention time = 4.88, 4.97 min (cis/trans mixture)<br>LC/MS ($ESI^+$) m/z; 372 $[M + H]^+$<br>LC/MS ($ESI^-$) m/z; 370 $[M - H]^-$ |
| 75 | $^1$H-NMR (DMSO-$d_6$) δ: 1.35-1.51 (m, 1H), 1.59-1.71 (m, 1H), 1.71-1.86 (m, 2H), 1.92-2.03 (m, 3H), 3.10 (dt, J = 12.9, 3.6 Hz, 0.7H), 3.18 (dt, J = 15.2, 3.0 Hz, 0.3H), 3.51-3.63 (m, 0.7H), 3.92-3.99 (m, 0.3H), 4.51 (d, J = 2.6 Hz, 0.3H), 4.61 (d, J = 4.3 Hz, 0.7H), 6.82 (dd, J = 3.3, 1.7 Hz, 0.7H), 6.97 (dd, J = 3.3, 1.7 Hz, 0.3H), 7.48 (t, J = 3.0 Hz, 1H), 9.51 (s, 0.7H), 9.51 (s, 0.3H), 12.51 (br s, 1H). |
| 76 | $^1$H-NMR ($CDCl_3$) δ: −0.04 (s, 9H), 0.94 (t, J = 8.1 Hz, 2H), 1.73 (qd, J = 12.4, 3.8 Hz, 2H), 2.00 (br s, 2H), 3.01 (t, J = 12.2 Hz, 2H), 3.55 (t, J = 8.0 Hz, 2H), 4.16 (tt, J = 11.4, 3.6 Hz, 2H), 4.29 (br s, 2H), 5.12 (s, 2H), 5.71 (s, 2H), 7.26 (d, J = 3.6Hz, 1H), 7.31-7.40 (m, 5H), 7.57 (d, J = 3.6Hz, 1H), 9.03 (s, 1H).<br>LC/MS: condition 3, retention time = 3.29 min<br>LC/MS ($ESI^+$) m/z; 495 $[M + H]^+$ |

TABLE[a] 89

| Rf | Data |
|---|---|
| 77 | $^1$H-NMR ($CDCl_3$) δ: −0.07 (s, 9H), 0.91 (t, J = 8.3 Hz, 2H), 1.27-1.38 (m, 3H), 1.97-2.02 (m, 2H), 2.70-2.74 (m, 2H), 3.53 (t, J = 8.3 Hz, 2H), 4.02-4.23 (m, 3H), 5.10 (s, 2H), 5.64 (d, J = 2.4Hz, 2H), 6.61 (d, J = 3.3Hz, 1H), 7.26-7.33 (m, 6H), 8.85 (s, 1H).<br>LC/MS: condition 3, retention time = 2.26 min<br>LC/MS ($ESI^+$) m/z; 496 $[M + H]^+$ |
| 78 | LC/MS: condition 3, retention time = 3.05 min<br>LC/MS ($ESI^+$) m/z; 506 $[M + H]^+$ |
| 79 | LC/MS: condition 3, retention time = 1.55 min<br>LC/MS ($ESI^+$) m/z; 366 $[M + H]^+$ |
| 80 | LC/MS: condition 3, retention time = 0.70 min<br>LC/MS ($ESI^+$) m/z; 231 $[M + H]^+$ |
| 81 | LC/MS: condition 3, retention time = 1.63 min<br>LC/MS ($ESI^+$) m/z; 389 $[M + H]^+$<br>LC/MS ($ESI^-$) m/z; 387 $[M - H]^-$ |
| 82 | LC/MS: condition 3, retention time = 1.08 min<br>LC/MS ($ESI^+$) m/z; 390 $[M + H]^+$ |
| 83 | $^1$H-NMR ($CDCl_3$) δ: 3.20 (s, 3H), 3.65 (s, 3H), 3.68-3.70 (m, 1H), 4.14 (t, J = 8.7 Hz, 2H), 4.22 (d, J = 6.0 Hz, 2H), 5.09 (s, 2H), 7.30-7.36 (m, 5H).<br>LC/MS: condition 3, retention time = 1.88 min<br>LC/MS ($ESI^+$) m/z; 279 $[M + H]^+$ |
| 84 | $^1$H-NMR ($CDCl_3$) δ: 4.31-4.41 (m, 4H), 4.62-4.69 (m, 2H), 5.11 (s, |

TABLE[a] 89-continued

| Rf | Data |
|---|---|
| | 2H), 7.27-7.36 (m, 6H), 7.55 (dd, J = 3.6, 2.4 Hz, 1H), 8.95 (s, 1H), 9.18 (br s, 1H). LC/MS: condition 3, retention time = 2.09 min LC/MS ($ESI^+$) m/z; 337 $[M + H]^+$ |
| 85 | $^1$H-NMR ($CDCl_3$) δ: 1.88 (br s, 1H). 3.35 (s, 3H), 3.55 (s, 3H), 4.74 (s, 2H), 7.39 (d, J = 8.1 Hz, 2H), 7.67 (d, J = 8.1 Hz, 2H). LC/MS: condition 1, retention time = 0.84 min LC/MS ($ESI^+$) m/z; 196 $[M + H]^+$ |
| 86 | $^1$H-NMR ($CDCl_3$) δ: 0.11 (s, 6H), 0.95 (s, 9H), 3.35 (s, 3H), 3.55 (s, 3H), 4.77 (s, 2H), 7.35 (d, J = 8.1 Hz, 2H), 7.65 (d, J = 8.1 Hz, 2H). LC/MS: condition 1, retention time = 4.73 min LC/MS ($ESI^+$) m/z; 310 $[M + H]^+$ |
| 87 | $^1$H-NMR ($CDCl_3$) δ: 0.12 (s, 6H), 0.96 (s, 9H), 4.83 (s, 2H), 7.00 (dd, J = 3.9, 2.1 Hz, 1H), 7.47 (d, J = 8.1 Hz, 2H), 7.49 (m, 1H), 8.14 (d, J = 8.1 Hz, 2H), 9.04 (s, 1H), 9.59 (br s, 1H). LC/MS: condition 1, retention time = 4.80 min LC/MS ($ESI^+$) m/z; 368 $[M + H]^+$ LC/MS ($ESI^-$) m/z; 366 $[M - H]^-$ |
| 88 | $^1$H-NMR ($CDCl_3$) δ: 0.15 (s, 6H), 0.98 (s, 9H), 4.84 (s, 2H), 6.97 (dd, J = 3.3, 2.1 Hz, 1H), 7.27 (dd, J = 6.0, 3.3 Hz, 1H), 7.50 (d, J = 8.4 Hz, 2H), 7.98 (d, J = 8.4 Hz, 2H), 9.22 (br s, 1H), 9.30 (s, 1H). LC/MS: condition 1, retention time = 4.93 min LC/MS ($ESI^+$) m/z; 380 $[M + H]^+$ |

TABLE[a] 90

| Rf | Data |
|---|---|
| 89 | $^1$H-NMR ($CDCl_3$) δ: 1.58 (m, 4H), 1.73 (m, 5H), 2.80 (tt, J = 8.4, 3.6 Hz, 1H), 3.17 (s, 3H), 3.62 (m, 2H), 3.69 (s, 3H). LC/MS: condition 1, retention time = 1.42 min LC/MS ($ESI^+$) m/z; 202 $[M + H]^+$ |
| 90 | $^1$H-NMR ($CDCl_3$) δ: 0.04 (s, 6H), 0.89 (s, 9H), 1.55 (m, 4H), 1.69 (m, 5H), 2.80 (tt, J = 7.8, 4.2 Hz, 1H), 3.17 (s, 3H), 3.58 (d, J = 10.5 Hz, 2H), 3.68 (s, 3H). LC/MS: condition 1, retention time = 5.08 min LC/MS ($ESI^+$) m/z; 316 $[M + H]^+$ |
| 91 | $^1$H-NMR ($CDCl_3$) δ: 0.06 (s, 6H), 0.90 (s, 9H), 1.71 (m, 7H), 1.90 (m, 2H), 3.53 (d, J = 6.9 Hz, 2H), 4.07 (m, 1H), 7.20 (dd, J = 3.3 2.1 Hz, 1H), 7.50 (t, J = 3.3 Hz, 1H), 8.98 (s, 1H), 9.42 (br s, 1H). LC/MS: condition 1, retention time = 5.19 min LC/MS ($ESI^+$) m/z; 374 $[M + H]^+$ LC/MS ($ESI^-$) m/z; 372 $[M - H]^-$ |
| 92 | $^1$H-NMR ($CDCl_3$) δ: 0.08 (s, 6H), 0.93 (s, 9H), 1.22 (m, 2H), 1.70 (m, 1H), 1.90-2.05 (m, 4H), 2.15 (m, 2H), 3.16 (m, 1H), 3.51 (d, J = 6.6 Hz, 2H), 6.08 Hz (m, 1H), 7.27 (m, 1H), 9.16 (br s, 1H), 9.22 (s, 1H). LC/MS: condition 1, retention time = 5.09 min LC/MS ($ESI^+$) m/z; 428 $[M + H]^+$ LC/MS ($ESI^-$) nn/z; 426 $[M - H]^-$ |
| 93 | LC/MS: condition 1, retention time = 3.62 min LC/MS ($ESI^+$) m/z; 202, 204 $[M + H]^+$ |
| 94 | $^1$H-NMR ($CDCl_3$) δ: 1.83-2.04 (m, 4H), 2.25 (td, J = 11.6, 2.5 Hz, 2H), 2.93 (d, J = 11.7 Hz, 2H), 3.59 (s, 2H), 3.92-3.99 (m, 1H), 7.24 (dd, J = 3.6, 2.1 Hz, 1H), 7.47 (d, J = 8.1 Hz, 2H), 7.50 (dd, J = 3.6, 2.4 Hz, 1H), 7.61 (d, J = 8.1 Hz, 2H), 8.98 (s, 1H), 9.04 (br s, 1H). LC/MS: condition 3, retention time = 1.25 min LC/MS ($ESI^+$) m/z; 346 $[M + H]^+$ |
| 95 | $^1$H-NMR ($CDCl_3$) δ: −0.06 (s, 9H), 0.91 (t, J = 8.3 Hz, 2H), 1.78-2.04 (m, 4H), 2.25 (td, J = 11.6, 2.8 Hz, 2H), 2.93 (d, J = 11.7 Hz, 2H), 3.53 (t, J = 8.3 Hz, 2H), 3.60 (s, 2H), 3.95 (tt, J = 11.4, 3.9 Hz, 1H), 5.68 (s, 2H), 7.23 (d, J = 3.3 Hz, 1H), 7.47 (d, J = 8.1 Hz, 2H), 7.53 (d, J = 3.6 Hz, 1H), 7.61 (d, J = 8.7 Hz, 2H), 8.99 (s, 1H). LC/MS: condition 3, retention time = 2.19 min LC/MS ($ESI^+$) m/z; 476 $[M + H]^+$ |
| 96 | $^1$H-NMR ($CDCl_3$) δ: −0.07 (s, 9H), 0.90 (t, J = 8.1 Hz, 2H), 1.23 (d, J = 14.4 Hz, 1H), 1.31-1.53 (m, 2H), 1.78-2.01 (m, 6H), 2.73 (d, J = 10.5 Hz, 1H), 2.89 (d, J = 11.4 Hz, 1H), 3.49 (s, 2H), 3.54 (t, J = 8.1 Hz, 2H), 4.05 (d, J = 7.5 Hz, 1H), 5.65 (d, J = 2.1 Hz, 2H), 6.63 (d, J = 3.6 Hz, 1H), 7.32 (d, J = 3.6 Hz, 1H), 7.41 (d, J = 8.1 Hz, 2H), 7.57 (d, J = 8.1 Hz, 2H), 8.86 (s, 1H). LC/MS: condition 3, retention time = 1.64 min LC/MS ($ESI^+$) m/z; 477 $[M + H]^+$ |
| 97 | LC/MS: condition 3, retention time = 2.15 min LC/MS ($ESI^+$) m/z; 487 $[M + H]^+$ |

TABLE[a] 91

| Rf | Data |
|---|---|
| 98 | $^1$H-NMR ($CDCl_3$) δ: 2.05-2.20 (m, 2H), 3.20 (s, 3H), 3.39-3.80 (m, 8H), 5.14 (s, 2H), 7.28-7.39 (m, 5H).<br>LC/MS: condition 3, retention time = 2.02 min<br>LC/MS ($ESI^+$) m/z; 293 $[M + H]^+$ |
| 99 | LC/MS: condition 3, retention time = 2.13 min<br>LC/MS ($ESI^+$) m/z; 351 $[M + H]^+$<br>LC/MS ($ESI^-$) m/z; 349 $[M - H]^-$ |
| 100 | $^1$H-NMR ($CDCl_3$) δ: 2.74 (br s, 2H), 2.96 (d, J = 12.0 Hz, 1H), 3.54 (d, J = 12.0 Hz, 1H), 7.35 (d, J = 9.0 Hz, 2H), 7.50 (d, J = 9.0 Hz, 2H).<br>LC/MS: condition 1, retention time = 0.78 min<br>LC/MS ($ESI^+$) m/z; 240, 242 $[M + H]^+$ |
| 101 | $^1$H-NMR ($CDCl_3$) δ: 2.69 (br s, 1H), 3.02 (d, J = 13.2 Hz, 1H), 3.52 (d, J = 13.2 Hz, 1H), 7.38 (m, 3H), 7.57 (m, 2H).<br>LC/MS: condition 1, retention time = 0.55 min<br>LC/MS ($ESI^+$) m/z; 206 $[M + H]^+$ |
| 102 | $^1$H-NMR ($CDCl_3$) δ: 2.97 (d, J = 12.9 Hz, 1H), 3.57 (d, J = 13.2 Hz, 1H), 7.08 (m, 2H), 7.55 (m, 2H).<br>LC/MS: condition 1, retention time = 0.56 min<br>LC/MS ($ESI^+$) m/z; 224 $[M + H]^+$ |
| 103 | $^1$H-NMR ($CDCl_3$) δ: 2.77 (ddd, J = 5.5, 2.5, 1.2 Hz, 1H), 3.19 (ddd, J = 5.5, 4.0, 1.1 Hz, 1H), 3.92 (dd, J = 4.0, 2.5 Hz, 1H), 7.40 (d, J = 8.3 Hz, 2H), 7.61 (d, J = 8.3 Hz, 2H). |
| 104 | $^1$H-NMR ($CD_3OD$) δ: 1.91 (s, 3H), 2.20-2.33 (m, 4H), 3.20-3.30 (m, 2H), 3.50-3.69 (m, 3H), 6.95 (d, J = 3.3 Hz, 1H), 7.43 (d, J = 3.3 Hz, 1H), 9.34 (s, 1H).<br>LC/MS: condition 1, retention time = 2.15 min<br>LC/MS ($ESI^+$) m/z; 243 $[M + H]^+$<br>LC/MS ($ESI^-$) m/z; 241 $[M - H]^-$ |

TABLE[a] 92

| Rf | Data |
|---|---|
| 105 | $^1$H-NMR ($CDCl_3$) δ: 4.87 (s, 2H), 7.11 (d, J = 8.9 Hz, 2H), 7.92 (d, J = 8.9 Hz, 2H), 9.95 (s, 1H). |
| 106 | $^1$H-NMR (DMSO-$d_6$) δ: 4.72 (s, 2H), 7.38 (br s, 1H), 7.50 (d, J = 8.1 Hz, 2H), 7.83 (d, J = 8.1 Hz, 2H), 7.97 (br s, 1H).<br>LC/MS: condition 3, retention time = 1.48 min<br>LC/MS ($ESI^+$) m/z; 213, 215 $[M + H]^+$ |
| 107 | $^1$H-NMR ($CDCl_3$) δ: 4.49 (s, 2H), 7.73-7.81 (m, 2H), 7.87 (s, 1H). |
| 108 | $^1$H-NMR ($CDCl_3$) δ: 4.48 (s, 2H), 7.74-7.84 (m, 3H). |
| 109 | $^1$H-NMR ($CDCl_3$) δ: 4.50 (s, 2H), 7.70 (d, J = 8.7 Hz, 1H), 7.81-7.84 (m, 2H). |
| 110 | $^1$H-NMR ($CDCl_3$) δ: 1.43 (s, 9H), 2.87 (t, J = 6.9 Hz, 2H), 3.39 (q, J = 6.9 Hz, 2H), 4.54 (br s, 1H), 7.31 (d, J = 8.6 Hz, 2H), 7.58-7.62 (m, 2H). |
| 111 | $^1$H-NMR ($CDCl_3$) δ: 2.83 (q, J = 6.9 Hz, 2H), 2.97-3.04 (m, 2H), 7.27-7.37 (m, 2H), 7.58-7.65 (m, 2H). |
| 112 | $^1$H-NMR ($CDCl_3$) δ: 1.48 (s, 9H), 4.70 (s, 4H). |
| 113 | $^1$H-NMR ($CDCl_3$) δ: 1.44 (s, 9H), 1.52 (s, 3H), 1.99 (s, 1H), 3.82 (d, J = 8.9 Hz, 2H), 3.86 (d, J = 8.9 Hz, 2H). |
| 115 | $^1$H-NMR ($CDCl_3$) δ: 4.06 (d, J = 12.5 Hz, 2H), 4.23 (d, J = 12.5 Hz, 2H), 7.96 (s, 1H), 9.76 (br s, 2H). |
| 116 | $^1$H-NMR ($CDCl_3$) δ: 1.44 (s, 9H), 3.77 (d, J = 8.6 Hz, 1H), 3.85 (d, J = 8.6 Hz, 1H) 3.85-3.92 (m, 2H), 4.06-4.15 (m, 2H), 4.30-4.40 (m, 1H). |
| 118 | $^1$H-NMR ($CDCl_3$) δ: 3.01 (d, J = 13.2 Hz, 1H), 3.62 (d, J = 13.2 Hz, 1H), 7.35 (m, 1H), 7.93 (m, 1H), 8.60 (m, 1H), 8.78 (s, 1H).<br>LC/MS: condition 3, retention time = 0.39 min<br>LC/MS ($ESI^+$) m/z; 207 $[M + H]^+$ |
| 119 | $^1$H-NMR ($CDCl_3$) δ: 2.49 (s, 3H), 2.98 (d, J = 13.2 Hz, 1H), 3.52 (d, J = 13.2 Hz, 1H), 7.25 (d, J = 8.1 Hz, 2H), 7.48 (d, J = 8.1 Hz, 2H).<br>LC/MS: condition 3, retention time = 1.44 min<br>LC/MS ($ESI^+$) m/z; 252 $[M + H]^+$ |
| 120 | $^1$H-NMR ($CDCl_3$) δ: 2.98 (d, J = 13.2 Hz, 1H), 3.55 (d, J = 13.2 Hz, 1H), 3.94 (s, 3H) 6.76 (d, J = 8.7 Hz, 1H), 7.77 (dd, J = 8.1, 2.4 Hz, 1H, 8.31 (d, J = 2.4 Hz, 1H).<br>LC/MS: condition 3, retention time = 0.54 min<br>LC/MS ($ESI^+$) m/z; 237 $[M + H]^+$ |
| 121 | $^1$H-NMR ($CDCl_3$) δ: 3.02 (d, J = 13.5 Hz, 1H), 3.37 (d, J = 13.5 Hz, 1H), 3.77 (s, 3H), 6.88 (d, J = 9.0 Hz, 2H), 7.45 (d, J = 9.0 Hz, 2H). |

TABLE[a] 93

| Rf | Data |
|---|---|
| 122 | $^1$H-NMR ($CDCl_3$) δ: 3.02 (d, J = 12.9 Hz, 1H), 3.50 (d, J = 13.5 Hz, 1H), 3.88 (s, 3H), 3.91 (s, 3H), 6.86 (d, J = 8.7 Hz, 1H), 7.04 (m, 1H), 7.17 (d, J = 1.8 Hz, 1H). |
| 123 | $^1$H-NMR ($CDCl_3$) δ: 1.34 (t, J = 7.2 Hz, 3H), 4.26 (q, J = 7.2 Hz, 2H), 6.35 (d, J = 15.9 Hz, 1H), 7.07 (m, 2H), 7.51 (m, 2H), 7.64 (d, J = 15.9 Hz, 1H).<br>LC/MS: condition 1, retention time = 4.17 min<br>LC/MS ($ESI^+$) m/z; 195 $[M + H]^+$ |
| 124 | $^1$H-NMR ($CDCl_3$) δ: 1.28 (m, 4H), 1.57 (m, 1H), 1.84 (m, 1H), 2.50 (m, 1H), 4.17 (q, J = 7.2 Hz, 2H), 6.96 (m, 2H), 7.07 (m, 2H). |
| 125 | LC/MS: condition 1, retention time = 4.42 min<br>LC/MS ($ESI^+$) m/z; 296 $[M + H]^+$ |
| 126 | $^1$H-NMR ($CDCl_3$) δ: 0.85 (m, 2H), 1.22 (m, 1H), 1.71 (m, 3H), 2.72 (m, 2H), 6.89-7.05 (m, 4H). |
| 127 | LC/MS: condition 1, retention time = 0.33 min<br>LC/MS ($ESI^+$) m/z; 168 $[M + H]^+$ |
| 128a | $^1$H-NMR ($CDCl_3$) δ: 1.52-1.80 (m, 9H), 2.05-2.25 (m, 3H), 3.60-3.75 (m, 1H), 4.90-5.15 (m, 1H), 5.10 (s, 2H), 7.25-7.45 (m, 5H).<br>LC/MS: condition 1, retention time = 3.63 min<br>LC/MS ($ESI^+$) m/z; 302 $[M + H]^+$ |
| 128b | $^1$H-NMR ($CDCl_3$) δ: 1.41-1.53 (m, 3H), 1.53-1.91 (m, 7H), 2.01-2.25 (m, 3H), 3.73-3.86 (m, 1H), 4.98-5.02 (m, 1H), 5.10 (s, 2H), 7.28-7.43 (m, 5H).<br>LC/MS: condition 1, retention time = 3.63 min<br>LC/MS ($ESI^+$) m/z; 302 $[M + H]^+$ |
| 129 | $^1$H-NMR (DMSO-$d_6$) δ: 1.20 (d, J = 12.3 Hz, 2H), 1.57 (m, 5H), 1.72 (s, 1H), 1.92-1.96 (m, 5H), 2.83 (s, 1H), 4.26 (br s, 1H). |

TABLE[a] 93-continued

| Rf | Data |
|---|---|
| | LC/MS: condition 1, retention time = 0.33 min<br>LC/MS ($ESI^+$) m/z; 168 $[M+H]^+$ |
| 130 | $^1$H-NMR (DMSO-$d_6$) δ: 1.27 (d, J = 12.7 Hz, 2H), 1.41-1.63 (m, 6H), 1.76-2.02 (m, 5H), 2.75-2.80 (br s, 1H).<br>LC/MS: condition 1, retention time = 0.33 min<br>LC/MS ($ESI^+$) m/z; 168 $[M+H]^+$ |
| 131 | $^1$H-NMR ($CD_3OD$) δ: 4.03 (dd, J = 13.5, 12.9 Hz, 2H). |
| 132 | LC/MS: condition 1, retention time = 4.18 min<br>LC/MS ($ESI^+$) m/z; 302 $[M+H]^+$ |
| 133 | $^1$H-NMR ($CDCl_3$) δ: 0.04 (s, 9H), 0.89 (s, 6H), 1.52-1.57 (m, 5H), 1.63-1.72 (m, 5H), 3.17 (s, 3H), 3.55 (d, J = 6.9 Hz, 2H), 3.68 (s, 3H). |
| 134 | $^1$H-NMR ($CDCl_3$) δ: −0.04 (s, 6H), 0.85 (s, 9H), 1.43-1.77 (m, 8H), 1.80-1.94 (m, 2H), 3.49 (d, J = 6.9 Hz, 2H), 7.16 (dd, J = 3.6, 2.1 Hz, 1H), 7.16 (dd, J = 3.6, 2.7 Hz, 1H), 8.95 (s, 1H), 9.16 (br s, 1H). |

TABLE[a] 94

| Rf | Data |
|---|---|
| 135a | $^1$H-NMR ($CDCl_3$) δ: −0.06 (s, 6H), 0.83 (s, 9H), 1.61-2.15 (m, 9H), 3.29-3.37 (m, 1H), 3.56 (d, J = 6.6 Hz, 2H), 6.72 (dd, J = 3.3 2.1 Hz, 1H), 7.22 (t, J = 3.3 Hz, 1H), ), 9.04 (s, 2H), 9.17 (br s, 1H).<br>LC/MS: condition 3, retention time = 3.22 min<br>LC/MS ($ESI^+$) m/z; 386 $[M+H]^+$<br>LC/MS ($ESI^-$) m/z; 384 $[M-H]^-$ |
| 135b | $^1$H-NMR ($CDCl_3$) δ: 0.08 (s, 6H), 0.93 (s, 9H), 1.20 (qd, J = 12.2, 3.6 Hz, 2H), 1.76-1.61 (m, 1H), 2.05-1.84 (m, 4H), 2.19-2.09 (m, 2H), 3.16 (tt, J = 12.2, 3.6 Hz, 1H), 3.52 (d, J = 6.3 Hz, 2H), 6.81 (dd, J = 3.3, 2.0 Hz, 1H), 7.29 (t, J = 3.3 Hz, 1H), 9.21 (br s, 1H), 9.23 (s, 1H).<br>LC/MS: condition 3, retention time = 3.20 min<br>LC/MS ($ESI^+$) m/z; 386 $[M+H]^+$<br>LC/MS ($ESI^-$) m/z; 384 $[M-H]^-$ |
| 137 | LC/MS: condition 1, retention time = 0.32 min<br>LC/MS ($ESI^+$) m/z; 201 $[M+H]^+$ |
| 138 | LC/MS: condition 1, retention time = 0.34 min<br>LC/MS ($ESI^+$) m/z; 215 $[M+H]^+$ |
| 139 | $^1$H-NMR ($CDCl_3$) δ: 1.46 (s, 9H), 4.58-4.65 (m, 2H), 4.68-4.74 (m, 2H), 5.36-5.41 (m, 1H).<br>LC/MS: condition 1, retention time = 3.44 min<br>LC/MS ($ESI^+$) m/z; 195 $[M+H]^+$ |
| 140 | $^1$H-NMR ($CDCl_3$) δ: 1.56-1.75 (m, 6H), 1.82-1.96 (m, 6H), 2.22-2.28 (m, 2H), 3.17 (s, 3H), 3.68 (s, 3H).<br>LC/MS: condition 3, retention time = 2.84 min<br>LC/MS ($ESI^+$) m/z; 240 $[M+H]^+$ |
| 141 | $^1$H-NMR ($CDCl_3$) δ: 1.50-1.97 (m, 8H), 2.10-2.27 (m, 6H), 2.33-2.38 (m, 2H), 6.96-6.99 (m, 1H), 7.43-7.47 (m, 1H), 8.93 (s, 1H), 9.25 (br s, 1H).<br>LC/MS: condition 3, retention time = 3.17 min<br>LC/MS ($ESI^+$) m/z; 298 $[M+H]^+$<br>LC/MS ($ESI^-$) m/z; 296 $[M-H]^-$ |

TABLE[a] 95

| Ex | Data |
|---|---|
| 1 | $^1$H-NMR ($CDCl_3$) δ: 1.41-1.52 (m, 3H), 1.77-1.91 (m, 7H), 2.72 (s, 3H), 2.97-3.05 (m, 1H), 6.64 (d, J = 2.3 Hz, 1H), 7.06 (d, J = 2.6 Hz, 1H), 8.29 (s, 1H), 8.80 (br s, 1H).<br>LC/MS: condition 1, retention time = 1.96 min<br>LC/MS ($ESI^+$) m/z; 255 $[M+H]^+$ |
| 2 | $^1$H-NMR ($CDCl_3$)<br>δ: 1.39-1.53 (m, 3H), 1.77-1.95 (m, 7H), 2.95-3.11 (m, 1H), 6.60 (d, J = 3.3 Hz, 1H), 7.12 (d, J = 3.0 Hz, 1H), 8.28 (s, 1H), 8.69 (s, 1H).<br>LC/MS: condition 1, retention time = 2.84 min<br>LC/MS ($ESI^+$) m/z; 241 $[M+H]^+$ |
| 3 | LC/MS: condition 1, retention time = 3.56 min<br>LC/MS ($ESI^+$) m/z; 376 $[M+H]^+$ |
| 4 | LC/MS: condition 1, retention time = 0.96 min<br>LC/MS ($ESI^+$) m/z; 309 $[M+H]^+$ |
| 5 | $^1$H-NMR ($CDCl_3$) δ: 2.46 (s, 3H), 6.60 (dd, J = 3.3, 2.4 Hz, 1H), 7.18-7.23 (m, 1H), 7.28-7.43 (m, 3H), 7.54-7.63 (m, 1H), 9.04 (br s, 1H), 9.32 (s, 1H).<br>LC/MS: condition 1, retention time = 3.87 min<br>LC/MS ($ESI^+$) m/z; 250 $[M+H]^+$<br>LC/MS ($ESI^-$) m/z; 248 $[M-H]^-$ |
| 6 | $^1$H-NMR ($CDCl_3$) δ: 1.31-1.69 (m, 3H), 1.72-1.86 (m, 2H), 1.87-2.01 (m, 3H), 2.02-2.16 (m, 2H), 3.07-3.29 (m, 1H), 6.81 (dd, J = 3.3, 2.1 Hz, 1H), 7.29 (t, J = 3.0 Hz, 1H), 9.23 (s, 1H), 9.33 (br s, 1H).<br>LC/MS: condition 1, retention time = 3.92 min<br>LC/MS ($ESI^+$) m/z; 242 $[M+H]^+$<br>LC/MS ($ESI^-$) m/z; 240 $[M-H]^-$ |
| 7 | LC/MS: condition 1, retention time = 4.12 min<br>LC/MS ($ESI^+$) m/z; 256 $[M+H]^+$<br>LC/MS ($ESI^-$) m/z; 254 $[M-H]^-$ |
| 8 | $^1$H-NMR (DMSO-$d_6$) δ: 1.15-1.55 (m, 3H), 1.60-1.92 (m, 7H), 2.85-3.10 (m, 1H), 6.57 (s, 1H), 7.17 (t, J = 3.0 Hz, 1H), 8.64 (s, 1H), 12.04 (s, 1H), 12.96 (br s, 1H).<br>LC/MS: condition 1, retention time = 3.79 min<br>LC/MS ($ESI^+$) m/z; 273 $[M+H]^+$<br>LC/MS ($ESI^-$) m/z; 271 $[M-H]^-$ |
| 9 | $^1$H-NMR (DMSO-$d_6$) δ: 1.07-1.64 (m, 5H), 1.65-1.89 (m, 5H), 2.67-2.84 (m, 1H), 6.33 (s, 1H), 6.93 (d, J = 2.7 Hz, 1H), 8.01 (d, J = 1.2 Hz, 1H), 10.76 (s, 1H), 11.63 (s, 1H).<br>LC/MS: condition 1, retention time = 3.62 min<br>LC/MS ($ESI^+$) m/z; 257 $[M+H]^+$ |
| 10 | $^1$H-NMR ($CDCl_3$) δ: 1.16-1.40 (m, 3H), 1.61-1.82 (m, 1H), 1.85-2.09 (m, 4H), 2.10-2.26 (m, 2H), 3.09-3.25 (m, 1H), 3.58 (t, J = 6.0 Hz, 2H), 6.74-6.85 |

TABLE[a] 95-continued

| Ex | Data |
|---|---|
| | (m, 1H), 7.20-7.32 (m, 1H), 9.04 (br s, 1H), 9.22 (s, 1H).<br>LC/MS: condition 1, retention time = 2.99 min<br>LC/MS (ESI$^+$) m/z; 272 [M + H]$^+$<br>LC/MS (ESI$^-$) m/z; 270 [M − H]$^-$ |

TABLE[a] 96

| Ex | Data |
|---|---|
| 11 | $^1$H-NMR ($CDCl_3$) δ: 0.86 (d, J = 6.5 Hz, 3H), 1.48 (br s, 9H), 1.87 (d, J = 12.3 Hz, 1H), 2.04-2.11 (m, 1H), 2.23-2.39 (m, 2H), 2.92 (td, J = 11.0, 4.5 Hz, 2H), 3.17 (t, J = 11.0 Hz, 1H), 3.48 (d, J = 7.0 Hz, 1H), 7.24-7.32 (m, 2H), 9.18 (br s, 1H), 9.22 (s, 1H).<br>LC/MS: condition 1, retention time = 4.05 min<br>LC/MS (ESI$^+$) m/z; 301 [M − $^t$Bu]$^+$<br>LC/MS (ESI$^-$) m/z; 355 [M − H]$^-$ |
| 12 | LC/MS: condition 1, retention time = 3.09 min<br>LC/MS (ESI$^+$) m/z; 324 [M + H]$^+$ |
| 13 | $^1$H-NMR ($CDCl_3$) δ: 1.18-1.29 (m, 1H), 1.49 (s, 9H), 1.63-1.77 (m, 1H), 1.90 (dt, J = 13.9, 3.0 Hz, 1H), 2.09-2.33 (m, 2H), 2.87 (t, J = 13.2 Hz, 1H), 3.30 (tt, J = 11.6, 4.3 Hz, 1H), 4.23 (br s, 1H), 4.44 (br s, 1H), 6.92 (br s, 1H), 7.31 (t, J = 3.3 Hz, 1H), 9.23 (s, 1H), 9.27 (br s, 1H).<br>LC/MS: condition 1, retention time = 3.79 min<br>LC/MS (ESI$^+$) m/z; 287 [M − $^t$Bu]$^+$<br>LC/MS (ESI$^-$) m/z; 341 [M − H]$^-$ |
| 14 | $^1$H-NMR ($CDCl_3$) δ: 1.68-1.80 (m, 1H), 1.93 (d, J = 13.5 Hz, 1H), 2.14-2.37 (m, 2H), 2.95 (br s, 1H), 3.07-3.22 (m, 1H), 3.26-3.38 (m, 1H), 4.33 (br s, 1H), 4.55 (br s, 1H), 5.20 (d, J = 5.9 Hz, 2H), 6.95-7.17 (m, 1H), 7.28-7.43 (m, 6H), 9.22 (s, 1H), 9.39 (br s, 1H).<br>LC/MS: condition 1, retention time = 3.84 min<br>LC/MS (ESI$^+$) m/z; 377 [M + H]$^+$<br>LC/MS (ESI$^-$) m/z; 375 [M − H]$^-$ |
| 15 | $^1$H-NMR ($CD_3OD$) δ: 1.71-1.93 (m, 3H), 2.01-2.24 (m, 2H), 2.70-2.81 (m, 1H), 2.94-3.17 (m, 2H), 3.37-3.47 (m, 1H), 6.91 (d, J = 3.3 Hz, 1H), 7.41 (d, J = 3.0 Hz, 1H), 9.32 (s, 1H).<br>LC/MS: condition 1, retention time = 0.35 min<br>LC/MS (ESI$^+$) m/z; 243 [M + H]$^+$<br>LC/MS (ESI$^-$) m/z; 241 [M − H]$^-$ |
| 16 | LC/MS: condition 1, retention time = 0.40 min<br>LC/MS (ESI$^+$) m/z; 333 [M + H]$^+$ |
| 17 | LC/MS: condition 1, retention time = 3.25 min<br>LC/MS (ESI$^+$) m/z; 353 [M + H]$^+$<br>LC/MS (ESI$^-$) m/z; 351 [M − H]$^-$ |
| 18 | $^1$H-NMR ($CDCl_3$) δ: 1.23-1.35 (m, 4H), 1.85-1.96 (m, 2H), 2.20 (m, 1H), 2.50 (t, J = 11.6 Hz, 1H), 3.01 (d, J = 10.9 Hz, 1H), 3.16 (d, J = 10.9 Hz, 1H), 3.41-3.53 (m, 1H), 6.71 (dd, J = 3.3, 2.0 Hz, 1H), 7.22-7.31 (m, 2H), 7.70 (d, J = 7.6 Hz, 1H), 8.50 (dd, J = 4.6, 2.0 Hz, 1H), 8.60 (d, J = 2.0 Hz, 1H), 9.21 (s, 1H), 9.32 (br s, 1H).<br>LC/MS: condition 1, retention time = 0.35 min<br>LC/MS (ESI$^+$) m/z; 334 [M + H]$^+$<br>LC/MS (ESI$^-$) m/z; 332 [M − H]$^-$ |

TABLE[a] 97

| Ex | Data |
|---|---|
| 19 | $^1$H-NMR ($CDCl_3$) δ: 1.23-1.29 (m, 1H), 1.85-1.96 (m, 3H), 2.13-2.27 (m, 2H), 2.49 (t, J = 11.2 Hz, 1H), 3.05 (d, J = 10.2 Hz, 1H), 3.20 (d, J = 10.9 Hz, 1H), 3.41-3.53 (m, 1H), 6.75 (dd, J = 3.3, 2.0 Hz, 1H), 7.23-7.29 (m, 1H), 8.74 (s, 1H), 9.19 (br s, 1H), 9.21 (s, 1H).<br>LC/MS: condition 1, retention time = 0.35 min<br>LC/MS (ESI$^+$) m/z; 340 [M + H]$^+$<br>LC/MS (ESI$^-$) m/z; 338 [M − H]$^-$ |
| 20 | $^1$H-NMR (DMSO-$d_6$) δ: 1.62-1.79 (t, J = 12.6 Hz, 1H), 1.81-1.92 (m, 1H), 1.95-2.11 (m, 1H), 2.12-2.24 (m, 1H), 3.07 (t, J = 12.6 Hz, 1H), 3.21 (m, 1H), 4.37 (d, J = 12.6 Hz, 1H), 4.57 (d, J = 11.6 Hz, 1H), 6.99 (s, 1H), 7.53 (s, 1H), 8.95 (br s, 1H), 9.56-9.60 (m, 1H), 12.59 (s, 1H).<br>LC/MS: condition 1, retention time = 2.94 min<br>LC/MS (ESI$^+$) m/z; 370 [M + H]$^+$<br>LC/MS (ESI$^-$) m/z; 368 [M − H]$^-$ |

TABLE[a] 97-continued

| Ex | Data |
|---|---|
| 21 | $^1$H-NMR (DMSO-$d_6$) δ: 1.64-1.79 (m, 1H), 1.82-2.06 (m, 2H), 2.13-2.22 (m, 1H), 2.25 (s, 3H), 3.07 (t, J = 12.2 Hz, 1H), 4.22 (d, J = 13.2 Hz, 1H), 4.43 (d, J = 12.9 Hz, 1H), 6.59 (s, 1H), 6.98 (d, J = 2.6 Hz, 1H), 7.53 (d, J = 3.3 Hz, 1H), 9.57 (s, 1H), 10.46 (br s, 1H), 12.58 (br s, 1H).<br>LC/MS: condition 1, retention time = 2.90 min<br>LC/MS (ESI$^+$) m/z; 383 $[M + H]^+$<br>LC/MS (ESI$^-$) m/z; 381 $[M - H]^-$ |
| 22 | $^1$H-NMR ($CDCl_3$) δ: 1.26 (t, J = 7.3 Hz, 1H), 1.86-2.01 (m, 2H), 2.15-2.27 (m, 2H), 2.47 (t, J = 11.2 Hz, 1H), 2.98 (d, J = 11.2 Hz, 1H), 3.11 (dt, J = 11.2, 1.7 Hz, 1H), 3.40-3.51 (m, 1H), 3.57 (d, J = 13.9 Hz, 1H), 3.69 (d, J = 13.9 Hz, 1H), 6.66 (dd, J = 3.3, 2.0 Hz, 1H), 7.25-7.28 (m, 1H), 7.49 (d, J = 8.3 Hz, 2H), 7.60 (d, J = 7.9 Hz, 2H), 9.17 (br s, 1H), 9.21 (s, 1H).<br>LC/MS: condition 1, retention time = 0.59 min<br>LC/MS (ESI$^+$) m/z; 358 $[M + H]^+$<br>LC/MS (ESI$^-$) m/z; 356 $[M - H]^-$ |
| 23 | $^1$H-NMR ($CDCl_3$) δ: 1.23-1.32 (m, 1H), 1.81-1.98 (m, 2H), 2.15-2.27 (m, 2H), 2.42 (t, J = 11.2 Hz, 1H), 3.01 (d, J = 10.9 Hz, 1H), 3.15 (d, J = 10.6 Hz, 1H), 3.45 (td, J = 11.6, 3.0 Hz, 1H), 3.56 (d, J = 13.2 Hz, 1H), 3.71 (d, J = 13.2 Hz, 1H), 6.58-6.62 (m, 1H), 7.20-7.24 (m, 1H), 7.48 (d, J = 7.9 Hz, 2H), 7.56 (d, J = 7.9 Hz, 2H), 9.21 (s, 2H).<br>LC/MS: condition 1, retention time = 2.49 min<br>LC/MS (ESI$^+$) m/z; 401 $[M + H]^+$<br>LC/MS (ESI$^-$) m/z; 399 $[M - H]^-$ |
| 24 | $^1$H-NMR ($CDCl_3$) δ: 1.51 (s, 9H), 1.95-2.20 (m, 4H), 2.85-3.10 (m, 2H), 3.29-3.48 (m, 1H), 4.15-4.42 (m, 2H), 6.71-6.80 (m, 1H), 7.27-7.35 (m, 1H), 9.23 (s, 1H), 9.27 (br s, 1H).<br>LC/MS: condition 1, retention time = 3.94 min<br>LC/MS (ESI$^+$) m/z; 343 $[M - {}^tBu]^+$<br>LC/MS (ESI$^-$) m/z; 341 $[M - H]^-$ |

TABLE[a] 98

| Ex | Data |
|---|---|
| 25 | $^1$H-NMR ($CDCl_3$) δ: 1.99-2.10 (m, 2H), 2.39 (dq, J = 11.7, 3.9 Hz, 2H), 2.65 (dt, J = 11.7, 2.4 Hz, 2H), 3.09 (q, J = 9.6 Hz, 2H), 3.11-3.29 (m, 3H), 6.85 (dd, J = 2.5, 0.9 Hz, 1H), 7.31 (dd, J = 3.0, 0.9 Hz, 1H), 9.11 (br s, 1H), 9.23 (s, 1H).<br>LC/MS: condition 1, retention time = 2.30 min<br>LC/MS (ESI$^+$) m/z; 325 $[M + H]^+$<br>LC/MS (ESI$^-$) m/z; 323 $[M - H]^-$ |
| 26 | $^1$H-NMR ($CDCl_3$) δ: 2.00-2.15 (m, 4H), 3.01-3.18 (m, 2H), 3.32-3.45 (m, 1H), 4.30-4.44 (m, 2H), 5.19 (s, 2H), 6.70-6.76 (m, 1H), 7.25-7.43 (m, 6H), 9.18 (br s, 1H), 9.22 (s, 1H).<br>LC/MS: condition 1, retention time = 3.79 min<br>LC/MS (ESI$^+$) m/z; 377 $[M + H]^+$<br>LC/MS (ESI$^-$) m/z; 375 $[M - H]^-$ |
| 27 | $^1$H-NMR ($CD_3OD$) δ: 2.05-2.15 (m, 4H), 2.90-3.13 (m, 2H), 3.38-3.50 (m, 1H), 6.93 (d, J = 3.3 Hz, 1H), 7.40 (d, J = 3.3 Hz, 1H), 9.31 (s, 1H).<br>LC/MS: condition 1, retention time = 0.44 min<br>LC/MS (ESI$^+$) m/z; 243 $[M + H]^+$<br>LC/MS (ESI$^-$) m/z; 241 $[M - H]^-$ |
| 28 | $^1$H-NMR ($CDCl_3$) δ: 1.95-2.12 (m, 2H), 2.12-2.31 (m, 4H), 2.99-3.12 (m, 2H), 3.17-3.31 (m, 1H), 3.61 (s, 2H), 6.85 (d, J = 2.4 Hz, 1H), 7.23-7.35 (m, 2H), 7.74 (d, J = 7.8 Hz, 1H), 8.52 (dd, J = 4.5, 1.2 Hz, 1H), 8.62 (d, J = 2.1 Hz, 1H), 9.22 (s, 1H), 9.39 (br s, 1H).<br>LC/MS: condition 3, retention time = 0.52 min<br>LC/MS (ESI$^+$) m/z; 334 $[M + H]^+$<br>LC/MS (ESI$^-$) m/z; 332 $[M - H]^-$ |
| 29 | $^1$H-NMR (DMSO-$d_6$) δ: 1.64-1.82 (m, 1H), 1.86-2.04 (m, 3H), 2.85-3.00 (m, 1H), 3.30-3.39 (m, 1H), 3.45-3.60 (m, 1H), 3.61-3.84 (m, 2H), 3.92-4.05 (m, 1H), 4.43-4.55 (m, 1H), 6.82-6.90 (m, 1H), 7.49-7.53 (m, 1H), 9.53 (s, 1H), 12.51 (br s, 1H).<br>LC/MS: condition 3, retention time = 1.62 min<br>LC/MS (ESI$^+$) m/z; 353 $[M + H]^+$<br>LC/MS (ESI$^-$) m/z; 351 $[M - H]^-$ |
| 30 | $^1$H-NMR (DMSO-$d_6$) δ: 1.70-2.10 (m, 4H), 3.09-3.26 (m, 2H), 3.43-3.65 (m, 1H), 4.14-4.50 (m, 2H), 6.85 (s, 1H), 7.49 (s, 1H), 9.00 (br s, 1H), 9.53 (s, 1H), 11.34 (br s, 1H), 12.54 (br s, 1H).<br>LC/MS: condition 3, retention time = 1.40 min<br>LC/MS (ESI$^+$) m/z; 370 $[M + H]^+$<br>LC/MS (ESI$^-$) m/z; 368 $[M - H]^-$ |
| 31 | $^1$H-NMR (DMSO-$d_6$) δ: 1.70-2.10 (m, 4H), 2.27 (s, 3H), 3.10-3.26 (m, 2H), 3.43-3.64 (m, 1H), 4.15-4.41 (m, 2H), 6.63 (s, 1H), 6.83-6.89 (m, 1H), 7.45-7.52 (m, 1H), 9.54 (s, 1H), 10.48 (s, 1H), 12.55 (br s, 1H).<br>LC/MS: condition 3, retention time = 1.43 min<br>LC/MS (ESI$^+$) m/z; 383 $[M + H]^+$<br>LC/MS (ESI$^-$) m/z; 381 $[M - H]^-$ |

TABLE[a] 99

| Ex | Data |
|---|---|
| 32 | $^1$H-NMR (DMSO-$d_6$) δ: 1.85-2.08 (m, 4H), 2.13-2.30 (m, 2H), 2.90-3.03 (m, 2H), 3.11-3.25 (m, 1H), 3.55 (s, 2H), 6.81 (s, 1H), 7.20-7.40 (m, 5H), 7.49 (s, 1H), 9.52 (s, 1H), 12.53 (br s, 1H).<br>LC/MS: condition 3, retention time = 1.31 min<br>LC/MS (ESI$^+$) m/z; 333 $[M + H]^+$ |
| 33 | $^1$H-NMR (DMSO-$d_6$) δ: 1.87-2.11 (m, 4H), 2.18-2.31 (m, 2H), 2.88-3.02 (m, 2H), 3.12-3.26 (m, 1H), 3.65 (s, 2H), 6.83 (s, 1H), 7.49 (m, 1H), 7.60 (d, J = 8.3 Hz, 2H), 7.71 (d, J = 8.3 Hz, 2H), 9.52 (s, 1H), 12.53 (br s, 1H).<br>LC/MS: condition 3, retention time = 1.63 min<br>LC/MS (ESI$^+$) m/z; 401 $[M + H]^+$ |
| 34 | $^1$H-NMR (DMSO-$d_6$) δ: 1.85-2.10 (m, 4H), 2.19-2.33 (m, 2H), 2.87-3.00 (m, 2H), 3.10-3.26 (m, 1H), 3.65 (s, 2H), 6.82 (d, J = 3.0 Hz, 1H), 7.49 (d, J = 3.0 Hz, 1H), 7.58 (d, J = 8.2 Hz, 2H), 7.81 (d, J = 8.2 Hz, 2H), 9.52 (s, 1H), 12.53 (br s, 1H).<br>LC/MS: condition 3, retention time = 1.23 min<br>LC/MS (ESI$^+$) m/z; 358 $[M + H]^+$<br>LC/MS (ESI$^-$) m/z; 356 $[M - H]^-$ |
| 35 | $^1$H-NMR (DMSO-$d_6$) δ: 1.85-2.10 (m, 4H), 2.18-2.31 (m, 2H), 2.87-2.99 (m, 2H), 3.13-3.23 (m, 1H), 3.62 (s, 2H), 6.83 (s, 1H), 7.49 (s, 1H), 7.57 (t, J = 7.8 Hz, 1H), 7.67-7.77 (m, 2H), 7.94 (s, 1H), 9.52 (s, 1H), 12.53 (br s, 1H).<br>LC/MS: condition 3, retention time = 1.24 min |

TABLE[a] 99-continued

| Ex | Data |
|---|---|
| | LC/MS ($ESI^+$) m/z; 358 $[M + H]^+$<br>LC/MS ($ESI^-$) m/z; 356 $[M - H]^-$ |
| 36 | $^1$H-NMR (DMSO-$d_6$) δ: 1.85-2.05 (m, 4H), 2.10-2.30 (m, 2H), 2.24 (s, 3H), 2.36 (s, 3H), 2.85-2.99 (m, 2H), 3.10-3.27 (m, 1H), 6.79 (d, J = 3.2 Hz, 1H), 7.49 (d, J = 3.2 Hz, 1H), 9.52 (s, 1H), 12.53 (br s, 1H).<br>LC/MS: condition 3, retention time = 1.07 min<br>LC/MS ($ESI^+$) m/z; 352 $[M + H]^+$<br>LC/MS ($ESI^-$) m/z; 350 $[M - H]^-$ |
| 37 | $^1$H-NMR (DMSO-$d_6$) δ: 1.86-2.08 (m, 4H), 2.16-2.29 (m, 2H), 2.88-3.00 (m, 2H), 3.10-3.25 (m, 1H), 3.58 (s, 2H), 6.82 (d, J = 3.0 Hz, 1H), 7.34 (d, J = 8.4 Hz, 2H), 7.46-7.55 (m, 3H), 9.53 (s, 1H), 12.54 (br s, 1H).<br>LC/MS: condition 3, retention time = 1.69 min<br>LC/MS ($ESI^+$) m/z; 417 $[M + H]^+$<br>LC/MS ($ESI^-$) m/z; 415 $[M - H]^-$ |
| 38 | $^1$H-NMR (DMSO-$d_6$) δ: 1.87-2.06 (m, 4H), 2.16-2.30 (m, 2H), 2.90-3.03 (m, 2H), 3.12-3.25 (m, 1H), 3.63 (s, 2H), 6.80-6.85 (m, 1H), 7.49-7.53 (m, 1H), 7.55 (d, J = 7.8 Hz, 2H), 7.70 (d, J = 7.8 Hz, 2H), 9.53 (s, 1H), 12.54 (br s, 1H).<br>LC/MS: condition 3, retention time = 1.78 min<br>LC/MS ($ESI^+$) m/z; 433 $[M + H]^+$<br>LC/MS ($ESI^-$) m/z; 431 $[M - H]^-$ |

TABLE[a] 100

| Ex | Data |
|---|---|
| 39 | $^1$H-NMR (DMSO-$d_6$) δ: 1.85-2.15 (m, 4H), 2.20-2.38 (m, 2H), 2.88-3.08 (m, 2H), 3.12-3.27 (m, 1H), 3.66 (s, 2H), 6.82 (d, J = 3.0 Hz, 1H), 7.49 (s, 1H), 7.52-7.80 (m, 4H), 9.52 (s, 1H), 12.53 (br s, 1H).<br>LC/MS: condition 3, retention time = 1.60 min<br>LC/MS ($ESI^+$) m/z; 401 $[M + H]^+$<br>LC/MS ($ESI^-$) m/z; 399 $[M - H]^-$ |
| 40 | $^1$H-NMR (DMSO-$d_6$) δ: 1.95-2.09 (m, 4H), 2.27-2.33 (m, 2H), 2.96 (d, J = 11.4 Hz, 2H), 3.15-3.20 (m, 1H), 3.69 (s, 2H), 6.82 (dd, J = 3.2, 1.4 Hz, 1H), 7.50 (t, J = 2.9 Hz, 1H), 7.72 (d, J = 4.2 Hz, 2H), 7.84 (d, J = 9.9 Hz, 1H), 9.53 (s, 1H), 12.54 (br s, 1H).<br>LC/MS: condition 3, retention time = 1.28 min<br>LC/MS ($ESI^+$) m/z; 376 $[M + H]^+$<br>LC/MS ($ESI^-$) m/z; 374 $[M - H]^-$ |
| 41 | $^1$H-NMR (DMSO-$d_6$) δ: 1.85-2.05 (m, 4H), 2.14-2.30 (m, 2H), 2.86-3.00 (m, 2H), 3.10-3.25 (m, 1H), 3.53 (s, 2H), 6.79-6.86 (m, 1H), 7.33 (d, J = 8.3 Hz, 2H), 7.44-7.52 (m, 1H), 7.53 (d, J = 8.3 Hz, 2H), 9.52 (s, 1H), 12.53 (br s, 1H).<br>LC/MS: condition 3, retention time = 1.58 min<br>LC/MS ($ESI^+$) m/z; 411, 413 $[M + H]^+$ |
| 42 | $^1$H-NMR (DMSO-$d_6$) δ: 2.15-2.37 (m, 4H), 3.16-3.30 (m, 3H), 3.36-3.50 (m, 3H), 3.50-3.73 (m, 1H), 3.79-3.82 (m, 2H), 7.07 (br s, 1H), 7.53-7.62 (m, 3H), 7.70-7.79 (m, 2H), 9.57 (s, 1H), 9.75-9.98 (br s, 1H), 12.61 (br s, 1H).<br>LC/MS: condition 3, retention time = 1.79 min<br>LC/MS ($ESI^+$) m/z; 415 $[M + H]^+$<br>LC/MS ($ESI^-$) m/z; 413 $[M - H]^-$ |
| 43 | $^1$H-NMR (DMSO-$d_6$) δ: 1.94-2.06 (m, 4H), 2.20 (td, J = 10.8, 3.3 Hz, 2H), 2.94 (d, J = 11.7 Hz, 2H), 3.18 (septet, J = 5.2 Hz, 1H), 3.54 (s, 2H), 6.82 (d, J = 3.3 Hz, 1H), 7.16 (tt, J = 9.2, 2.5 Hz, 2H), 7.40 (dd, J = 8.4, 5.7 Hz, 2H), 7.50 (d, J = 3.3 Hz, 1H), 9.52 (s, 1H), 12.53 (br s, 1H).<br>LC/MS: condition 3, retention time = 1.49 min<br>LC/MS ($ESI^+$) m/z; 351 $[M + H]^+$<br>LC/MS ($ESI^-$) m/z; 349 $[M - H]^-$ |
| 44 | $^1$H-NMR (DMSO-$d_6$) δ: 1.86-2.08 (m, 4H), 2.20-2.35 (m, 2H), 2.92-3.06 (m, 2H), 3.10-3.25 (m, 1H), 3.84 (s, 2H), 6.82 (d, J = 3.3 Hz, 1H), 7.49 (d, J = 3.3 Hz, 1H), 7.80 (s, 1H), 9.03 (s, 1H), 9.52 (s, 1H), 12.53 (br s, 1H).<br>LC/MS: condition 3, retention time = 0.62 min<br>LC/MS ($ESI^+$) m/z; 340 $[M + H]^+$<br>LC/MS ($ESI^-$) m/z; 338 $[M - H]^-$ |
| 45 | $^1$H-NMR (DMSO-$d_6$) δ: 1.73-1.88 (m, 2H), 1.88-2.12 (m, 4H), 2.14-2.32 (m, 2H), 2.33-2.50 (m, 2H), 2.59-2.71 (m, 2H), 2.98-3.13 (m, 2H), 3.14-3.25 (m, 1H), 6.82 (s, 1H), 7.10-7.36 (m, 5H), 7.49 (s, 1H), 9.52 (s, 1H), 12.53 (br s, 1H).<br>LC/MS: condition 3, retention time = 1.55 min<br>LC/MS ($ESI^+$) m/z; 361 $[M + H]^+$<br>LC/MS ($ESI^-$) m/z; 359 $[M - H]^-$ |

TABLE[a] 101

| Ex | Data |
|---|---|
| 46 | $^1$H-NMR (DMSO-$d_6$) δ: 1.91-2.05 (m, 4H), 2.16-2.23 (m, 2H), 2.94 (d, J = 11.4 Hz, 2H), 3.14-3.21 (m, 1H), 3.50 (s, 2H), 3.83 (s, 3H), 6.82 (t, J = 2.4 Hz, 1H), 7.12-7.20 (m, 3H), 7.50 (t, J = 2.7 Hz, 1H), 9.53 (s, 1H), 12.54 (br s, 1H).<br>LC/MS: condition 3, retention time = 1.39 min<br>LC/MS ($ESI^+$) m/z; 381 $[M + H]^+$ |
| 47 | $^1$H-NMR (DMSO-$d_6$) δ: 1.85-2.09 (m, 4H), 2.22-2.39 (m, 2H), 2.88-3.03 (m, 2H), 3.12-3.25 (m, 1H), 3.78 (s, 2H), 6.84 (d, J = 2.8 Hz, 1H), 7.49 (d, J = 2.8 Hz, 1H), 8.00 (s, 1H), 8.07 (s, 2H), 9.52 (s, 1H), 12.55 (br s, 1H).<br>LC/MS: condition 3, retention time = 1.84 min<br>LC/MS ($ESI^+$) m/z; 469 $[M + H]^+$<br>LC/MS ($ESI^-$) m/z; 467 $[M - H]^-$ |
| 48 | $^1$H-NMR (DMSO-$d_6$) δ: 1.88-2.13 (m, 4H), 2.32-2.46 (m, 2H), 2.97-3.10 (m, 2H), 3.14-3.27 (m, 1H), 3.91 (s, 2H), 6.85 (d, J = 3.0 Hz, 1H), 7.51 (d, J = 3.0 Hz, 1H), 7.67 (d, J = 3.3 Hz, 1H), 7.72 (d, J = 3.3 Hz, 1H), 9.52 (s, 1H), 12.55 (br s, 1H).<br>LC/MS: condition 3, retention time = 0.91 min<br>LC/MS ($ESI^+$) m/z; 340 $[M + H]^+$<br>LC/MS ($ESI^-$) m/z; 338 $[M - H]^-$ |
| 49 | $^1$H-NMR (DMSO-$d_6$) δ: 1.87-2.07 (m, 4H), 2.18-2.34 (m, 2H), 2.94-3.08 (m, 2H), 3.12-3.34 (m, 1H), 3.71 (s, 2H), 6.82 (d, J = 3.3 Hz, 1H), 6.87 (d, J = 3.3 Hz, 1H), 6.96 (d, J = 3.6 Hz, 1H), 7.50 (d, J = 3.6 Hz, 1H), 9.52 (s, 1H), 12.55 (br s, 1H).<br>LC/MS: condition 3, retention time = 1.49 min<br>LC/MS ($ESI^+$) m/z; 373, 375 $[M + H]^+$<br>LC/MS ($ESI^-$) m/z; 371, 373 $[M - H]^-$ |
| 50 | $^1$H-NMR (DMSO-$d_6$) δ: 0.78-0.98 (m, 2H), 1.12-1.32 (m, 3H), 1.59-1.72 (m, 2H), 1.72-1.85 (m, 2H), 1.85-2.04 (m, 4H), 2.04-2.23 (m, 3H), 2.67-2.78 (m, 2H), 2.88-3.05 (m, 3H), 3.08-3.21 (m, 1H), 6.79 (s, 1H), 7.49 (s, 1H), 9.52 (s, 1H), 12.52 (br s, 1H). |

TABLE[a] 101-continued

| Ex | Data |
|---|---|
| | LC/MS: condition 3, retention time = 1.51 min<br>LC/MS ($ESI^+$) m/z; 339 $[M + H]^+$<br>LC/MS ($ESI^-$) m/z; 337 $[M - H]^-$ |
| 51 | $^1$H-NMR (DMSO-$d_6$) δ: 1.32-1.70 (m, 6H), 1.77-2.05 (m, 6H), 2.06-2.30 (m, 2H), 3.04-3.23 (m, 3H), 6.80 (d, J = 3.0 Hz, 1H), 7.49 (s, 1H), 9.52 (s, 1H), 12.53 (br s, 1H).<br>LC/MS: condition 3, retention time = 1.18 min<br>LC/MS ($ESI^+$) m/z; 311 $[M + H]^+$ |
| 52 | $^1$H-NMR (DMSO-$d_6$) δ: 1.86-2.10 (m, 4H), 2.23-2.35 (m, 2H), 2.90-3.03 (m, 2H), 3.14-3.27 (m, 1H), 3.71 (s, 2H), 6.83 (d, J = 3.3 Hz, 1H), 7.49 (d, J = 3.3 Hz, 1H), 7.89 (d, J = 8.1 Hz, 1H), 8.07 (d, J = 9.3 Hz, 1H), 8.75 (s, 1H), 9.52 (s, 1H), 12.53 (br s, 1H).<br>LC/MS: condition 3, retention time = 1.40 min<br>LC/MS ($ESI^+$) m/z; 402 $[M + H]^+$<br>LC/MS ($ESI^-$) m/z; 400 $[M - H]^-$ |

TABLE[a] 102

| Ex | Data |
|---|---|
| 53 | $^1$H-NMR (DMSO-$d_6$) δ: 1.90-1.97 (m, 4H), 2.26-2.34 (m, 2H), 2.93-2.97 (m, 2H), 3.13 (quint, J = 6.2 Hz, 1H), 3.72 (s, 2H), 6.80 (dd, J = 2.9 Hz, 1.7 Hz, 1H), 7.47 (t, J = 2.9 Hz, 1H), 7.81 (s, 1H), 7.84 (s, 1H), 9.51 (s, 1H), 12.51 (br s, 1H).<br>LC/MS: condition 3, retention time = 1.26 min<br>LC/MS ($ESI^+$) m/z; 394 $[M + H]^+$ |
| 54 | $^1$H-NMR (DMSO-$d_6$) δ: 1.95-2.02 (m, 4H), 2.18-2.24 (m, 2H), 2.94 (d, J = 11.4 Hz, 2H), 3.55 (s, 2H), 6.79 (d, J = 3.0 Hz, 1H), 7.40 (s, 4H), 7.48 (d, J = 3.0 Hz, 1H), 9.48 (s, 1H).<br>LC/MS: condition 3, retention time = 1.75 min<br>LC/MS ($ESI^+$) m/z; 367, 369 $[M + H]^+$<br>LC/MS ($ESI^-$) m/z; 365, 367 $[M - H]^-$ |
| 55 | $^1$H-NMR (DMSO-$d_6$) δ: 1.95-2.03 (m, 4H), 2.19-2.27 (m, 2H), 2.95 (d, J = 12.0 Hz, 2H), 3.58 (s, 2H), 6.80 (d, J = 2.7 Hz, 1H), 7.05-7.22 (m, 3H), 7.35-7.42 (m, 1H), 7.48 (d, J = 3.3 Hz, 1H), 9.49 (s, 1H).<br>LC/MS: condition 3, retention time = 1.61 min<br>LC/MS ($ESI^+$) m/z; 351 $[M + H]^+$ |
| 56a | $^1$H-NMR (DMSO-$d_6$) δ: 1.20-1.52 (m, 4H), 1.86-2.10 (m, 8H), 2.16-2.41 (m, 3H), 2.63-2.80 (m, 1H), 2.88-3.24 (m, 3H), 6.84 (br s, 1H), 7.46-7.53 (m, 1H), 9.52 (s, 1H), 12.53 (br s, 1H).<br>LC/MS: condition 3, retention time = 1.57 min<br>LC/MS ($ESI^+$) m/z; 393 $[M + H]^+$<br>LC/MS ($ESI^-$) m/z; 391 $[M - H]^-$ |
| 56b | $^1$H-NMR (DMSO-$d_6$) δ: 1.40-1.66 (m, 4H), 1.66-1.85 (m, 2H), 1.92-2.18 (m, 8H), 2.34-2.40 (m, 1H), 2.65-2.77 (m, 1H), 3.08-3.28 (m, 3H), 6.78-6.84 (m, 1H), 7.45-7.56 (m, 1H), 9.52 (s, 1H), 12.53 (br s, 1H).<br>LC/MS: condition 3, retention time = 1.53 min<br>LC/MS ($ESI^+$) m/z; 393 $[M + H]^+$<br>LC/MS ($ESI^-$) m/z; 391 $[M - H]^-$ |
| 57 | $^1$H-NMR (DMSO-$d_6$) δ: 1.83-2.10 (m, 4H), 3.06-3.22 (m, 2H), 3.43-3.60 (m, 1H), 4.20-4.35 (m, 2H), 6.86 (d, J = 3.3 Hz, 1H), 7.26 (d, J = 8.1 Hz, 1H), 7.42-7.53 (m, 2H), 7.79 (d, J = 8.1 Hz, 1H), 7.97 (s, 1H), 8.94 (s, 1H), 9.54 (s, 1H), 12.57 (br s, 1H).<br>LC/MS: condition 3, retention time = 2.14 min<br>LC/MS ($ESI^+$) m/z; 430 $[M + H]^+$<br>LC/MS ($ESI^-$) m/z; 428 $[M - H]^-$ |
| 58 | $^1$H-NMR (DMSO-$d_6$) δ: 1.93-2.07 (m, 4H), 3.17 (br s, 1H), 3.56-3.62 (m, 2H), 4.58 (br s, 1H), 6.86 (d, J = 3.0 Hz, 1H), 7.50 (d, J = 3.0 Hz, 1H), 7.68 (d, J = 8.1 Hz, 2H), 7.85 (d, J = 8.4 Hz, 2H), 9.50 (s, 1H).<br>LC/MS: condition 3, retention time = 2.13 min<br>LC/MS ($ESI^+$) m/z; 415 $[M + H]^+$<br>LC/MS ($ESI^-$) m/z; 413 $[M - H]^-$ |

TABLE[a] 103

| Ex | Data |
|---|---|
| 59 | $^1$H-NMR ($CDCl_3$) δ: 1.20-1.42 (m, 4H), 1.48 (s, 9H), 1.92-2.30 (m, 5H), 3.10-3.25 (m, 1H), 3.63 (br s, 1H), 4.47 (br s, 1H), 6.79 (dd, J = 3.3, 1.8 Hz, 1H), 7.29 (dd, J = 3.3, 1.8 Hz, 1H), 9.22 (s, 1H).<br>LC/MS: condition 1, retention time = 3.74 min |

TABLE[a] 103-continued

| Ex | Data |
|---|---|
| | LC/MS ($ESI^+$) m/z; 357 $[M + H]^+$<br>LC/MS ($ESI^-$) m/z; 355 $[M - H]^-$ |
| 60 | $^1$H-NMR (DMSO-$d_6$) δ: 1.18 (d, J = 6.6 Hz, 1H), 1.38-1.57 (m, 2H), 1.71-1.90 (m, 2H), 1.91-2.10 (m, 4H), 3.05-3.20 (m, 1H), |

TABLE[a] 103-continued

| Ex | Data |
|---|---|
| | 3.37-3.54 (m, 1H), 5.03 (s, 2H), 6.81 (d, J = 3.3 Hz, 1H), 7.26-7.42 (m, 5H), 7.48 (d, J = 3.3 Hz, 1H), 9.51 (s, 1H), 12.51 (br s, 1H). LC/MS: condition 3, retention time = 2.10 min LC/MS (ESI$^+$) m/z; 391 [M + H]$^+$ |
| 61 | LC/MS: condition 3, retention time = 0.50 min LC/MS (ESI$^+$) m/z; 257 [M + H]$^+$ |
| 62 | $^1$H-NMR ($CDCl_3$) δ: 1.15-1.35 (m, 2H), 1.70-1.85 (m, 1H), 1.86-2.07 (m, 4H), 2.08-2.23 (m, 2H), 3.09-3.25 (m, 1H), 3.30 (d, J = 6.3 Hz, 2H), 3.38 (s, 3H), 6.73-6.83 (m, 1H), 7.21-7.33 (m, 1H), 9.02 (br s, 1H), 9.21 (s, 1H). LC/MS: condition 1, retention time = 3.57 min LC/MS (ESI$^+$) m/z; 286 [M + H]$^+$ LC/MS (ESI$^-$) m/z; 284 [M − H]$^-$ |
| 63 | $^1$H-NMR ($CDCl_3$) δ: 1.46, (m, 2H), 1.95 (m, 2H), 2.24 (m, 4H), 3.18 (tt, J = 12.0, 3.3 Hz, 1H), 3.34 (tt, J = 10.8, 3.9 Hz, 1H), 3.43 (s, 3H), 6.79 (m, 1H),, 7.30 (m, 1H), 9.22 (s, 1H), 9.31 (br s, 1H) LC/MS: condition 1, retention time = 3.13 min LC/MS (ESI$^+$) m/z; 272 [M + H]$^+$ LC/MS (ESI$^-$) m/z; 270 [M − H]$^-$ |
| 64 | $^1$H-NMR ($CDCl_3$) δ: 1.83-2.43 (m, 8H), 3.27-3.45 (m, 1H), 6.81 (dd, J = 3.3, 2.1 Hz, 1H), 7.28-7.39 (m, 1H), 9.24 (s, 1H), 9.25 (br s, 1H). LC/MS: condition 1, retention time = 3.59 min LC/MS (ESI$^+$) m/z; 278 [M + H]$^+$ LC/MS (ESI$^-$) m/z; 276 [M − H]$^-$ |
| 65 | $^1$H-NMR ($CDCl_3$) δ: 1.23-1.87 (m, 7H), 2.46 (m, 2H), 2.57 (s, 1H), 3.22 (m, 1H), 6.80 (m, 1H), 7.29 (t, J = 3.3 Hz, 1H), 9.17 (br s, 1H), 9.22 (s, 1H). LC/MS: condition 1, retention time = 3.89 min LC/MS (ESI$^+$) m/z; 254 [M + H]$^+$ LC/MS (ESI$^-$) m/z; 252 [M − H]$^-$ |
| 66 | $^1$H-NMR ($CDCl_3$) δ: 1.67-1.75 (m, 6H), 1.92 (m, 2H), 2.06-2.14 (m, 4H), 3.40 (tt, J = 9.6, 4.8 Hz, 1H), 6.80 (m, 1H), 7.27 (t, J = 2.7 Hz, 1H), 9.03 (br s, 1H), 9.21 (s, 1H). LC/MS: condition 1, retention time = 3.94 min LC/MS (ESI$^+$) m/z; 256 [M + H]$^+$ LC/MS (ESI$^-$) m/z; 254 [M − H]$^-$ |

TABLE[a] 104

| Ex | Data |
|---|---|
| 67 | $^1$H-NMR ($CDCl_3$) δ: 2.06-2.27 (m, 2H), 2.45-2.72 (m, 4H), 4.05 (quin t, 8.4 Hz, 1H), 6.80 (dd, J = 3.3, 2.1, 1H), 7.29 (t, J = 2.7 Hz, 1H), 9.17 (br s, 1H), 9.22 (s, 1H). LC/MS: condition 1, retention time = 3.34 min LC/MS (ESI$^+$) m/z; 214 [M + H]$^+$ LC/MS (ESI$^-$) m/z; 212 [M − H]$^-$ |
| 68 | $^1$H-NMR ($CDCl_3$) δ: 1.60-2.08 (m, 8H), 3.71 (quin t, J = 9.0 Hz, 1H), 7.02 (dd, J = 3.3, 2.1, 1H), 7.34 (dd, J = 3.6, 2.4 Hz, 1H), 8.88 (s, 1H), 10.05 (br s, 1H). |
| 69 | $^1$H-NMR (DMSO-$d_6$) δ: 1.50-1.70 (m, 2H), 1.71-1.92 (m, 2H), 1.93-2.18 (m, 4H), 2.30-2.67 (m, 1H), 3.15-3.38 (m, 1H), 6.87-7.00 (m, 1H), 7.40-7.55 (m, 1H), 9.52 (s, 1H), 12.52 (br s, 1H). LC/MS: condition 1, retention time = 3.97 min LC/MS (ESI$^+$) m/z; 310 [M + H]$^+$ LC/MS (ESI$^-$) m/z; 308 [M − H]$^-$ |
| 70 | $^1$H-NMR (DMSO-$d_6$) δ: 1.49-1.70 (m, 2H), 1.72-1.93 (m, 2H), 1.95-2.15 (m, 4H), 2.36-2.66 (m, 1H), 3.14-3.39 (m, 1H), 6.93 (dd, J = 3.3, 1.8 Hz, 1H), 7.42-7.55 (m, 1H), 9.52 (s, 1H), 12.52 (br s, 1H). LC/MS: condition 1, retention time = 3.95 min LC/MS (ESI$^+$) m/z; 310 [M + H]$^+$ LC/MS (ESI$^-$) m/z; 308 [M − H]$^-$ |
| 71 | $^1$H-NMR (DMSO-$d_6$) δ: 1.10-1.43 (m, 2H), 1.49-2.17 (m, 7H), 2.36 (s, 3H), 2.87 (d, J = 6.6 Hz, 2H), 3.05-3.22 (m, 1H), 6.73-6.90 (m, 1H), 7.40-7.59 (m, 1H), 9.50 (s, 1H), 12.50 (br s, 1H). LC/MS: condition 1, retention time = 3.88 min LC/MS (ESI$^+$) m/z; 330 [M + H]$^+$ LC/MS (ESI$^-$) m/z; 328 [M − H]$^-$ |
| 72 | $^1$H-NMR ($CDCl_3$) δ: 1.17-1.40 (m, 2H), 1.71-2.28 (m, 7H), 2.10 (s, 3H), 3.10-3.27 (m, 1H), 4.00 (d, J = 6.6 Hz, 2H), 6.79 (dd, J = 3.3, 2.1 Hz, 1H), 7.21-7.35 (m, 1H), 9.12 (br s, 1H), 9.22 (s, 1H). LC/MS: condition 1, retention time = 3.55 min |

TABLE[a] 104-continued

| Ex | Data |
|---|---|
| | LC/MS (ESI$^+$) m/z; 314 [M + H]$^+$ LC/MS (ESI$^-$) m/z; 312 [M − H]$^-$ |
| 73 | $^1$H-NMR ($CDCl_3$) δ: 1.20-1.50 (m, 2H), 1.64-2.40 (m, 7H), 3.05-3.60 (m, 1H), 4.20-4.50 (m, 2H), 6.70-7.00 (m, 1H), 7.20-7.40 (m, 1H), 9.10 (br s, 1H), 9.22 (s, 1H). LC/MS: condition 1, retention time = 3.63 min LC/MS (ESI$^+$) m/z; 274 [M + H]$^+$ LC/MS (ESI$^-$) m/z; 272 [M − H]$^-$ |
| 74 | $^1$H-NMR ($CDCl_3$) δ: 1.20-1.45 (m, 2H), 1.75-2.28 (m, 7H), 3.07-3.23 (m, 1H), 3.41 (d, J = 6.0 Hz, 2H), 6.72-6.84 (m, 1H), 7.24-7.35 (m, 1H), 9.02 (br s, 1H), 9.22 (s, 1H). LC/MS: condition 1, retention time = 3.97 min LC/MS (ESI$^+$) m/z; 334, 336 [M + H]$^+$ LC/MS (ESI$^-$) m/z; 332, 334 [M − H]$^-$ |

TABLE[a] 105

| Ex | Data |
|---|---|
| 75 | $^1$H-NMR ($CDCl_3$) δ: 1.23-1.44 (m, 2H), 1.76-2.27 (m, 7H), 3.09-3.25 (m, 1H), 3.51 (d, J = 6.6 Hz, 2H), 6.79 (dd, J = 3.3, 2.1 Hz, 1H), 7.20-7.33 (m, 1H), 9.03 (br s, 1H), 9.22 (s, 1H). LC/MS: condition 2, retention time = 1.75 min LC/MS (ESI$^+$) m/z; 290, 292 [M + H]$^+$ |
| 76 | $^1$H-NMR ($CDCl_3$) δ: 1.15-1.31 (m, 2H), 1.32-1.42 (m, 1H), 1.50-1.73 (m, 1H), 1.85-2.03 (m, 2H), 2.04-2.25 (m, 4H), 2.55 (dd, J = 8.3, 6.6 Hz, 2H), 3.06-3.25 (m, 1H), 6.72-6.85 (m, 1H), 7.20-7.36 (m, 1H), 9.00 (br s, 1H), 9.21 (s, 1H). LC/MS: condition 1, retention time = 3.84 min LC/MS (ESI$^+$) m/z; 288 [M + H]$^+$ LC/MS (ESI$^-$) m/z; 286 [M − H]$^-$ |
| 77 | $^1$H-NMR ($CDCl_3$) δ: 1.32-1.50 (m, 2H), 1.90-2.09 (m, 2H), 2.01-2.36 (m, 5H), 2.97 (s, 3H), 3.04 (d, J = 5.4 Hz, 2H), 3.10-3.29 (m, 1H), 6.78 (dd, J = 2.1, 3.3 Hz, 1H), 7.29 (t, J = 3.0 Hz, 1H), 9.00 (br s, 1H), 9.21 (s, 1H). LC/MS: condition 1, retention time = 2.87 min LC/MS (ESI$^+$) m/z; 334 [M + H]$^+$ LC/MS (ESI$^-$) m/z; 332 [M − H]$^-$ |
| 78 | $^1$H-NMR ($CDCl_3$) δ: 1.41-1.69 (m, 2H), 1.89-2.10 (m, 2H), 2.16-2.32 (m, 4H), 2.36-2.54 (m, 1H), 3.09-3.27 (m, 1H), 6.70-6.80 (m, 1H), 7.27-7.35 (m, 1H), 9.03 (br s, 1H), 9.22 (s, 1H), 9.74 (d, J = 1.2 Hz, 1H). LC/MS: condition 1, retention time = 3.13 min LC/MS (ESI$^+$) m/z; 270 [M + H]$^+$ LC/MS (ESI$^-$) m/z; 268 [M − H]$^-$ |
| 79 | $^1$H-NMR ($CDCl_3$) δ: 1.35-1.60 (m, 2H), 1.80-2.40 (m, 7H), 3.10-3.60 (m, 1H), 5.40-5.90 (m, 1H), 6.72-6.85 (m, 1H), 7.20-7.40 (m, 1H), 9.02 (br s, 1H), 9.22 (s, 1H). LC/MS: condition 1, retention time = 3.74 min LC/MS (ESI$^+$) m/z; 292 [M + H]$^+$ LC/MS (ESI$^-$) m/z; 290 [M − H]$^-$ |
| 80 | $^1$H-NMR (DMSO-$d_6$) δ: 1.60 (dq, J = 12.2, 2.3 Hz, 2H), 1.78 (dq, J = 12.6, 2.3 Hz, 2H), 1.97-2.10 (m, 4H), 2.26-2.37 (m, 1H), 2.43-2.47 (m, 1H), 3.17 (tt, J = 11.6, 3.3 Hz, 1H), 6.86 (d, J = 3.3 Hz, 1H), 7.49 (d, J = 3.0 Hz, 1H), 9.52 (s, 1H), 12.53 (br s, 1H). LC/MS: condition 1, retention time = 2.70 min LC/MS (ESI$^+$) m/z; 286 [M + H]$^+$ LC/MS (ESI$^-$) m/z; 284 [M − H]$^-$ |
| 81 | $^1$H-NMR ($CD_3OD$) δ: 1.54 (q, J = 11.2 Hz, 2H), 1.91 (dq, J = 12.2, 4.0 Hz, 2H), 2.05-2.18 (m, 4H), 3.17 (dt, J = 12.9, 3.3 Hz, 1H), 3.67-3.78 (m, 1H), 6.82 (d, J = 3.0 Hz, 1H), 7.40 (d, J = 3.3 Hz, 1H), 9.30 (s, 1H). LC/MS: condition 1, retention time = 1.79 min LC/MS (ESI$^+$) m/z; 258 [M + H]$^+$ LC/MS (ESI$^-$) m/z; 256 [M − H]$^-$ |

TABLE[a] 106

| Ex | Data |
|---|---|
| 82 | $^1$H-NMR ($CDCl_3$) δ: 2.38-2.47 (m, 4H), 2.53-2.65 (m, 2H), 2.71 (dt, J = 14.5, 5.0 Hz, 2H), 3.65-3.77 (m, 1H), 6.80 (dd, J = 3.6, 2.0 Hz, 1H), 7.33 (t, J = 3.0 Hz, 1H), 9.26 (s, 2H).<br>LC/MS: condition 1, retention time = 2.55 min<br>LC/MS ($ESI^+$) m/z; 256 $[M + H]^+$<br>LC/MS ($ESI^-$) m/z; 254 $[M - H]^-$ |
| 83 | $^1$H-NMR ($CD_3OD$) δ: 1.79 (m, 4H), 1.97 (m, 2H), 2.34 (m, 2H), 3.26 (m, 1H), 4.10 (br s, 1H), 6.96 (d, J = 3.3 Hz, 1H), 7.37 (d, J = 3.0 Hz, 1H), 7.89 (s, 1H), 9.28 (s, 1H).<br>LC/MS: condition 1, retention time = 2.67 min<br>LC/MS ($ESI^+$) m/z; 258 $[M + H]^+$<br>LC/MS ($ESI^-$) m/z; 256 $[M - H]^-$ |
| 84 | $^1$H-NMR ($CDCl_3$) δ: 1.97-2.09 (m, 4H), 3.02 (br s, 2H), 3.19-3.26 (m, 1H), 4.37 (br s, 2H), 5.18 (s, 2H), 6.61 (dd, J = 3.2, 2.3 Hz, 1H), 7.09 (t, J = 3.0 Hz, 1H), 7.28-7.41 (m, 5H), 8.11 (s, 1H), 8.50 (s, 1H), 8.89 (br s, 1H).<br>LC/MS: condition 3, retention time = 2.05 min<br>LC/MS ($ESI^+$) m/z; 376 $[M + H]^+$ |
| 85 | $^1$H-NMR (DMSO-$d_6$) δ: 1.64-1.92 (m, 4H), 3.01 (br s, 2H), 3.20-3.30 (m, 1H), 4.07-4.20 (m, 2H), 5.12 (s, 2H), 6.63 (br s, 1H), 7.14-7.20 (m, 1H), 7.29-7.43 (m, 5H), 8.63 (s, 1H), 12.05 (br s, 1H), 13.14 (br s, 1H).<br>LC/MS: condition 3, retention time = 2.20 min<br>LC/MS ($ESI^+$) m/z; 408 $[M + H]^+$<br>LC/MS ($ESI^-$) m/z; 406 $[M - H]^-$ |
| 86 | $^1$H-NMR (DMSO-$d_6$) δ: 1.62-1.76 (m, 2H), 1.90-2.09 (m, 2H), 2.13-2.28 (m, 2H), 2.85-3.05 (m, 3H), 3.63 (s, 2H), 6.56 (br s, 1H), 7.14-7.21 (m, 1H), 7.69 (d, J = 8.3 Hz, 2H), 7.71 (d, J = 8.3 Hz, 2H), 8.64 (s, 1H), 12.05 (br s, 1H), 13.14 (br s, 1H).<br>LC/MS: condition 3, retention time = 1.64 min<br>LC/MS ($ESI^+$) m/z; 432 $[M + H]^+$<br>LC/MS ($ESI^-$) m/z; 430 $[M - H]^-$ |
| 87 | LC/MS: condition 3, retention time = 2.01 min<br>LC/MS ($ESI^+$) m/z; 349 $[M + H]^+$<br>LC/MS ($ESI^-$) m/z; 347 $[M - H]^-$ |
| 88 | $^1$H-NMR ($CDCl_3$) δ: 1.07-1.33 (m, 2H), 1.45-1.73 (m, 1H), 1.80-2.28 (m, 6H), 2.40 (d, J = 7.1 Hz, 2H), 2.90-3.28 (m, 9H), 6.71-6.84 (m, 1H), 7.20-7.40 (m, 1H), 9.02 (br s, 1H), 9.22 (s, 1H).<br>LC/MS: condition 1, retention time = 1.84 min<br>LC/MS ($ESI^+$) m/z; 389 $[M + H]^+$<br>LC/MS ($ESI^-$) m/z; 387 $[M - H]^-$ |
| 89 | $^1$H-NMR ($CDCl_3$) δ: 1.04-1.24 (m, 2H), 1.60-2.40 (m, 15H), 2.55-2.77 (m, 3H), 3.05-3.25 (m, 1H), 6.71-6.84 (m, 1H), 7.20-7.36 (m, 1H), 8.99 (br s, 1H), 9.21 (s, 1H).<br>LC/MS: condition 1, retention time = 0.39 min<br>LC/MS ($ESI^+$) m/z; 364 $[M + H]^+$<br>LC/MS ($ESI^-$) m/z; 362 $[M - H]^-$ |

TABLE[a] 107

| Ex | Data |
|---|---|
| 90 | $^1$H-NMR ($CDCl_3$) δ: 1.21-1.32 (m, 2H), 1.40-2.27 (m, 8H), 2.50-2.75 (m, 4H), 2.97 (t, J = 6.3 Hz, 2H), 3.10-3.25 (m, 1H), 6.71-6.87 (m, 1H), 7.20-7.35 (m, 1H), 9.00 (br s, 1H), 9.21 (s, 1H).<br>LC/MS: condition 1, retention time = 0.37 min<br>LC/MS ($ESI^+$) m/z; 324 $[M + H]^+$<br>LC/MS ($ESI^-$) m/z; 322 $[M - H]^-$ |
| 91 | $^1$H-NMR ($CDCl_3$) δ: 1.05-1.31 (m, 2H), 1.61-1.80 (m, 1H), 1.81-1.99 (m, 2H), 2.00-2.20 (m, 4H), 2.24 (d, J = 7.1 Hz, 2H), 2.39-2.53 (m, 4H), 3.10-3.25 (m, 1H), 3.65-3.81 (m, 4H), 6.71-6.85 (m, 1H), 7.20-7.35 (m, 1H), 9.00 (br s, 1H), 9.21 (s, 1H).<br>LC/MS: condition 1, retention time = 0.37 min<br>LC/MS ($ESI^+$) m/z; 341 $[M + H]^+$<br>LC/MS ($ESI^-$) m/z; 339 $[M - H]^-$ |
| 92 | $^1$H-NMR (DMSO-$d_6$) δ: 1.15-1.40 (m, 2H), 1.55-1.90 (m, 3H), 1.92-2.12 (m, 4H), 2.99-3.09 (m, 2H), 3.00-3.26 (m, 1H), 6.69 (d, J = 8.9 Hz, 2H), 6.81 (d, J = 3.3 Hz, 2H), 7.45 (d, J = 8.6 Hz, 2H), 7.50 (d, J = 3.3 Hz, 1H), 9.52 (s, 1H), 12.54 (br s, 1H).<br>LC/MS: condition 1, retention time = 3.95 min<br>LC/MS ($ESI^+$) m/z; 372 $[M + H]^+$<br>LC/MS ($ESI^-$) m/z; 370 $[M - H]^-$ |
| 93 | $^1$H-NMR ($CDCl_3$) δ: 1.10-1.31 (m, 2H), 1.50-1.77 (m, 1H), 1.82-2.20 (m, 6H), 2.56 (d, J = 6.6 Hz, 2H), 3.07-3.23 (m, 1H), 3.89 (s, 2H), 6.78 (dd, J = 3.3, 2.1 Hz, 1H), 7.21-7.32 (m, 1H), 7.48 (d, J = 8.6 Hz, 2H), 7.56-7.68 (m, 2H), 9.02 (br s, 1H), 9.21 (s, 1H).<br>LC/MS: condition 1, retention time = 2.27 min<br>LC/MS ($ESI^+$) m/z; 386 $[M + H]^+$<br>LC/MS ($ESI^-$) m/z; 384 $[M - H]^-$ |
| 94 | $^1$H-NMR ($CDCl_3$) δ: 1.10-1.30 (m, 2H), 1.50-1.75 (m, 1H), 1.82-2.30 (m, 8H), 2.33-2.60 (m, 3H), 2.63-2.97 (m, 3H), 3.05-3.40 (m, 1H), 5.02-5.33 (m, 1H), 6.72-6.84 (m, 1H), 7.20-7.34 (m, 1H), 9.15 (br s, 1H), 9.21 (s, 1H).<br>LC/MS: condition 1, retention time = 0.44 min<br>LC/MS ($ESI^+$) m/z; 343 $[M + H]^+$<br>LC/MS ($ESI^-$) m/z; 341 $[M - H]^-$ |
| 95 | $^1$H-NMR ($CDCl_3$) δ: 1.04-1.32 (m, 2H), 1.50-1.77 (m, 1H), 1.81-2.29 (m, 8H), 2.33-2.61 (m, 3H), 2.65-2.98 (m, 3H), 3.09-3.40 (m, 1H), 5.00-5.35 (m, 1H), 6.73-6.85 (m, 1H), 7.21-7.35 (m, 1H), 9.12 (br s, 1H), 9.21 (s, 1H).<br>LC/MS: condition 1, retention time = 0.42 min<br>LC/MS ($ESI^+$) m/z; 343 $[M + H]^+$<br>LC/MS ($ESI^-$) m/z; 341 $[M - H]^-$ |
| 96 | $^1$H-NMR ($CDCl_3$) δ: 1.05-1.21 (m, 2H), 1.23 (s, 6H), 1.48-1.66 (m, 1H), 1.79-2.17 (m, 8H), 2.43 (d, J = 6.8 Hz, 2H), 3.00-3.23 (m, 1H), 3.05 (s, 2H), 6.72-6.82 (m, 1H), 7.20-7.32 (m, 1H), 9.21 (s, 1H), 9.41 (br s, 1H).<br>LC/MS: condition 1, retention time = 0.79 min<br>LC/MS ($ESI^+$) m/z; 339 $[M + H]^+$<br>LC/MS ($ESI^-$) m/z; 337 $[M - H]^-$ |

TABLE[a] 108

| Ex | Data |
|---|---|
| 97 | $^1$H-NMR ($CDCl_3$) δ: 1.05-1.33 (m, 2H), 1.50-1.80 (m, 1H), 1.82-2.20 (m, 10H), 2.28 (d, J = 7.4 Hz, 2H), 2.49-2.62 (m, 4H), 3.07-3.44 (m, 1H), 6.79 (dd, J = 3.3, 2.1 Hz, 1H), 7.20-7.34 (m, 1H), 9.15 (br s, 1H), 9.22 (s, 1H).<br>LC/MS: condition 1, retention time = 0.62 min<br>LC/MS ($ESI^+$) m/z; 375 $[M + H]^+$<br>LC/MS ($ESI^-$) m/z; 373 $[M - H]^-$ |
| 98 | $^1$H-NMR (DMSO-$d_6$) δ: 1.06-1.30 (m, 2H), 1.50-1.66 (m, 1H), 1.68-1.85 (m, 2H), 1.90-2.08 (m, 4H), 2.42 (d, J = 6.6 Hz, 1H), 3.03-3.20 (m, 1H), 3.25-3.38 (m, 1H), 3.81 (s, 2H), 6.70-6.85 (m, 1H), 7.40-7.51 (m, 1H), 7.58 (d, J = 8.3 Hz, 2H), 7.67 (d, J = 8.0 Hz, 2H), 9.51 (s, 1H), 12.51 (br s, 1H).<br>LC/MS: condition 1, retention time = 2.95 min<br>LC/MS ($ESI^+$) m/z; 429 $[M + H]^+$<br>LC/MS ($ESI^-$) m/z; 427 $[M - H]^-$ |
| 99 | $^1$H-NMR (DMSO-$d_6$) δ: 1.19-1.40 (m, 2H), 1.65-1.88 (m, 3H), 1.95-2.11 (m, 4H), 2.95-3.07 (m, 2H), 3.10-3.25 (m, 1H), 6.40-6.52 (m, 1H), 6.69 (d, J = 8.6 Hz, 2H), 6.76-6.87 (m, 1H), 7.36 (d, J = 8.6 Hz, 2H), 7.45-7.55 (m, 1H), 9.51 (s, 1H), 12.52 (br s, 1H).<br>LC/MS: condition 1, retention time = 4.49 min |

TABLE[a] 108-continued

| Ex | Data |
|---|---|
| | LC/MS ($ESI^+$) m/z; 415 $[M + H]^+$<br>LC/MS ($ESI^-$) m/z; 413 $[M - H]^-$ |
| 100 | $^1$H-NMR (DMSO-$d_6$) δ: 1.16-1.40 (m, 2H), 1.61-1.88 (m, 3H), 1.94-2.10 (m, 4H), 2.85-3.00 (m, 2H), 3.10-3.25 (m, 1H), 5.52-5.65 (m, 1H), 6.50-6.63 (m, 2H), 6.76-6.82 (m, 1H), 6.85-6.98 (m, 2H), 7.49 (t, J = 3.0, 1H), 9.51 (s, 1H), 12.52 (br s, 1H).<br>LC/MS: condition 1, retention time = 3.63 min<br>LC/MS ($ESI^+$) m/z; 365 $[M + H]^+$ |
| 101 | $^1$H-NMR (DMSO-$d_6$) δ: 1.10-1.30 (m, 2H), 1.50-2.10 (m, 9H), 3.08-3.21 (m, 1H), 3.69-3.90 (m, 2H), 6.79 (d, J = 3.3 Hz, 1H), 7.10-7.25 (m, 2H), 7.38-7.56 (m, 3H), 9.51 (s, 1H), 12.52 (br s, 1H).<br>LC/MS: condition 1, retention time = 2.67 min<br>LC/MS ($ESI^+$) m/z; 379 $[M + H]^+$<br>LC/MS ($ESI^-$) m/z; 377 $[M - H]^-$ |
| 102 | $^1$H-NMR (DMSO-$d_6$) δ: 1.18-1.40 (m, 2H), 1.60-2.10 (m, 7H), 2.92 (s, 3H), 3.05-3.25 (m, 3H), 6.68 (dd, J = 9.5, 4.2 Hz, 2H), 6.76-6.83 (m, 1H), 6.94-7.08 (m, 2H), 7.41-7.54 (m, 1H), 9.50 (s, 1H), 12.52 (br s, 1H).<br>LC/MS: condition 1, retention time = 3.80 min<br>LC/MS ($ESI^+$) m/z; 379 $[M + H]^+$<br>LC/MS ($ESI^-$) m/z; 377 $[M - H]^-$ |
| 103 | $^1$H-NMR (DMSO-$d_6$) δ: 1.15-1.37 (m, 2H), 1.65-1.88 (m, 3H), 1.91-2.08 (m, 4H), 2.12 (s, 3H), 3.05-3.23 (m, 3H), 5.89-6.00 (m, 1H), 6.65 (d, J = 8.6 Hz, 1H), 6.75-6.84 (m, 1H), 7.26-7.53 (m, 3H), 9.51 (s, 1H), 12.51 (br s, 1H).<br>LC/MS: condition 1, retention time = 4.07 min<br>LC/MS ($ESI^+$) m/z; 386 $[M + H]^+$<br>LC/MS ($ESI^-$) m/z; 384 $[M - H]^-$ |

TABLE[a] 109

| Ex | Data |
|---|---|
| 104 | $^1$H-NMR (DMSO-$d_6$) δ: 1.15-1.38 (m, 2H), 1.66-1.90 (m, 3H), 1.95-2.10 (m, 4H), 2.13 (s, 3H), 2.95-3.08 (m, 2H), 3.10-3.25 (m, 1H), 6.56 (d, J = 8.3 Hz, 1H), 6.76-6.85 (m, 1H), 6.91-7.05 (m, 2H), 7.41-7.54 (m, 1H), 9.51 (s, 1H), 12.51 (br s, 1H).<br>LC/MS: condition 1, retention time = 4.67 min<br>LC/MS ($ESI^+$) m/z; 445 $[M + H]^+$<br>LC/MS ($ESI^-$) m/z; 443 $[M - H]^-$ |
| 105 | $^1$H-NMR (DMSO-$d_6$) δ: 1.15-1.40 (m, 2H), 1.65-1.88 (m, 3H), 1.95-2.10 (m, 4H), 3.01-3.25 (m, 3H), 6.75-6.95 (m, 2H), 7.01-7.12 (m, 1H), 7.27-7.39 (m, 1H), 7.43-7.53 (m, 1H), 7.66-7.77 (m, 1H), 9.51 (s, 1H), 12.52 (br s, 1H).<br>LC/MS: condition 1, retention time = 4.22 min<br>LC/MS ($ESI^+$) m/z; 440 $[M + H]^+$<br>LC/MS ($ESI^-$) m/z; 438 $[M - H]^-$ |
| 106 | $^1$H-NMR (DMSO-$d_6$) δ: 1.06-1.29 (m, 2H), 1.45-1.63 (m, 1H), 1.65-1.85 (m, 2H), 1.89-2.07 (m, 4H), 2.32-2.62 (m, 2H), 2.39 (s, 3H), 3.05-3.20 (m, 1H), 3.74-3.89 (m, 2H), 6.55-6.67 (m, 1H), 6.71 (d J = 3.3 Hz, 1H), 6.80 (d, J = 2.7 Hz, 1H), 7.42-7.54 (m, 1H), 9.50 (s, 1H), 12.51 (br s, 1H).<br>LC/MS: condition 1, retention time = 2.75 min<br>LC/MS ($ESI^+$) m/z; 381 $[M + H]^+$<br>LC/MS ($ESI^-$) m/z; 379 $[M - H]^-$ |
| 107 | $^1$H-NMR (DMSO-$d_6$) δ: 1.06-1.30 (m, 2H), 1.45-1.63 (m, 1H), 1.65-1.87 (m, 2H), 1.89-2.08 (m, 4H), 2.77 (t, J = 5.4 Hz, 1H), 2.81-2.91 (m, 1H), 3.05-3.20 (m, 1H), 4.39 (t, J = 5.1 Hz, 1H), 4.49-4.61 (m, 1H), 6.72-6.85 (m, 1H), 7.40-7.53 (m, 1H), 9.51 (s, 1H), 12.51 (br s, 1H).<br>LC/MS: condition 1, retention time = 0.39 min<br>LC/MS ($ESI^+$) m/z; 317 $[M + H]^+$<br>LC/MS ($ESI^-$) m/z; 315 $[M - H]^-$ |
| 108 | $^1$H-NMR (DMSO-$d_6$) δ: 1.19-1.42 (m, 2H), 1.60-2.10 (m, 7H), 3.05 (s, 3H), 3.07-3.22 (m, 1H), 3.25-3.41 (m, 2H), 6.70-6.90 (m, 3H), 7.40-7.60 (m, 3H), 9.50 (s, 1H), 12.51 (br s, 1H).<br>LC/MS: condition 1, retention time = 4.10 min<br>LC/MS ($ESI^+$) m/z; 386 $[M + H]^+$<br>LC/MS ($ESI^-$) m/z; 384 $[M - H]^-$ |
| 109 | $^1$H-NMR ($CDCl_3$) δ: 1.12-1.28 (m, 2H), 1.33 (d, J = 6.6 Hz, 3H), 1.37-2.16 (m, 7H), 2.30 (dd, J = 11.4, 6.9 Hz, 1H), 2.48 (dd, J = 11.7, 6.3 Hz, 1H), 3.15 (tt, J = 12.0, 3.3 Hz, 1H), 3.74 (q, J = 6.3 Hz, 1H), 6.77 (d, J = 2.4 Hz, 1H), 7.05-7.7.28 (m, 4H), 9.23 (s, 1H), 9.52 (br s, 1H).<br>LC/MS: condition 1, retention time = 2.89 min<br>LC/MS ($ESI^+$) m/z; 411 $[M + H]^+$<br>LC/MS ($ESI^-$) m/z; 409 $[M - H]^-$ |

TABLE[a] 110

| Ex | Data |
|---|---|
| 110 | $^1$H-NMR ($CDCl_3$) δ: 1.22 (m, 2H), 1.86-2.17 (m, 7H), 2.58 (d, J = 6.6 Hz, 2H), 3.18 (tt, J = 11.7, 3.6 Hz, 1H), 3.83 (s, 2H), 6.77 (m, 1H), 7.16-7.39 (m, 5H), 9.22 (s, 1H), 9.43 (br s, 1H).<br>LC/MS: condition 1, retention time = 3.03 min<br>LC/MS ($ESI^+$) m/z; 445 $[M + H]^+$<br>LC/MS ($ESI^-$) m/z; 443 $[M - H]^-$ |
| 111 | $^1$H-NMR ($CDCl_3$) δ: 1.22 (m, 2H), 1.85-2.14 (m, 7H), 2.58 (d, J = 6.6 Hz, 2H), 2.72-2.95 (m, 4H), 3.16 (tt, J = 11.7, 3.3 Hz, 1H), 6.78 (d, J = 3.9 Hz, 1H), 6.95-7.27 (m, 5H), 9.21 (s, 1H).<br>LC/MS: condition 1, retention time = 2.81 min<br>LC/MS ($ESI^+$) m/z; 393 $[M + H]^+$<br>LC/MS ($ESI^-$) m/z; 391 $[M - H]^-$ |

TABLE[a] 110-continued

| Ex | Data |
|---|---|
| 112 | $^1$H-NMR ($CDCl_3$) δ: 1.25 (m, 2H), 1.70 (m, 1H), 1.86-2.18 (m, 6H), 2.57 (d, J = 6.6 Hz, 2H), 3.17 (tt, J = 11.7, 3.6 Hz, 1H), 3.84 (s, 2H), 6.78 (m, 1H), 7.15 (t, J = 9.9 Hz, 1H), 7.29 (t, J = 2.7 Hz, 1H), 7.54 (m, 1H), 7.60 (dd, J = 6.9, 1.5 Hz, 1H), 9.25 (s, 1H), 9.60 (br s, 1H).<br>LC/MS: condition 1, retention time = 2.97 min<br>LC/MS (ESI$^+$) m/z; 447 $[M + H]^+$<br>LC/MS (ESI$^-$) m/z; 445 $[M - H]^-$ |
| 113 | $^1$H-NMR ($CDCl_3$) δ: 1.22 (m, 2H), 1.87-2.17 (m, 7H), 2.57 (d, J = 6.6 Hz, 2H), 3.06 (s, 3H), 3.16 (tt, J = 12.0, 3.3 Hz, 1H), 3.93 (s, 2H), 6.78 (m, 1H), 7.27, (m, 1H), 7.58 (d, J = 8.4 Hz, 2H), 7.90 (d, J = 8.7 Hz, 2H), 9.09 (br s, 1H), 9.21 (s, 1H).<br>LC/MS: condition 1, retention time = 0.70 min<br>LC/MS (ESI$^+$) m/z; 439 $[M + H]^+$ |
| 114 | $^1$H-NMR (DMSO-$d_6$) δ: 1.27 (q, J = 11.4 Hz, 2H), 1.68-1.85 (m, 3H), 1.96-2.09 (m, 4H), 2.94 (t, J = 5.7 Hz, 1H), 3.17 (d, J = 5.3 Hz, 2H), 5.96 (t, J = 5.7 Hz, 1H), 6.62 (d, J = 9.0 Hz, 2H), 6.80 (dd, J = 3.3, 1.2 Hz, 1H), 7.04 (d, J = 8.6 Hz, 2H), 7.48 (t, J = 2.5 Hz, 1H), 9.51 (s, 1H), 12.51 (br s, 1H).<br>LC/MS: condition 1, retention time = 4.49 min<br>LC/MS (ESI$^+$) m/z; 431 $[M + H]^+$<br>LC/MS (ESI$^-$) m/z; 429 $[M - H]^-$ |
| 115 | $^1$H-NMR (DMSO-$d_6$) δ: 1.26 (q, J = 11.4 Hz, 2H), 1.76 (q, J = 12.3 Hz, 3H), 1.92-2.07 (m, 4H), 3.10 (t, J = 6.1 Hz, 2H), 5.61 (t, J = 6.1 Hz, 1H), 6.78-6.82 (m, 2H), 7.17 (dd, J = 8.6, 2.5 Hz, 1H), 7.35 (dd, J = 2.9, 0.8 Hz, 1H), 7.48 (t, J = 2.9 Hz, 1H), 9.51 (s, 1H), 12.51 (br s, 1H).<br>LC/MS: condition 1, retention time = 4.77 min<br>LC/MS (ESI$^+$) m/z; 465 $[M + H]^+$<br>LC/MS (ESI$^-$) m/z; 463 $[M - H]^-$ |

TABLE[a] 111

| Ex | Data |
|---|---|
| 116 | $^1$H-NMR (DMSO-$d_6$) δ: 1.25 (q, J = 11.4 Hz, 2H), 1.67-1.83 (m, 3H), 1.91-2.07 (m, 4H), 3.08-3.22 (m, 3H), 6.08 (t, J = 5.7 Hz, 1H), 6.79-6.87 (m, 2H), 7.33 (td, J = 9.0, 3.3 Hz, 1H), 7.42 (dd, J = 8.6, 2.9 Hz, 1H), 7.48 (d, J = 2.9 Hz, 1H), 9.51 (s, 1H), 12.51 (br s, 1H).<br>LC/MS: condition 1, retention time = 4.15 min<br>LC/MS (ESI$^+$) m/z; 390 $[M + H]^+$<br>LC/MS (ESI$^-$) m/z; 388 $[M - H]^-$ |
| 117 | $^1$H-NMR (DMSO-$d_6$) δ: 1.25 (dq, J = 12.3, 2.5 Hz, 2H), 1.67-1.83 (m, 3H), 1.94-2.03 (m, 4H), 3.07-3.22 (m, 3H), 5.33 (t, J = 5.7 Hz, 1H), 6.80 (d, J = 2.9 Hz, 1H), 6.88 (dd, J = 9.0, 4.5 Hz, 1H), 7.28 (dd, J = 9.0, 3.3 Hz, 1H), 7.33 (dd, J = 9.0, 3.3 Hz, 1H), 7.48 (br s, 1H), 9.50 (s, 1H), 12.51 (br s, 1H).<br>LC/MS: condition 1, retention time = 4.55 min<br>LC/MS (ESI$^+$) m/z; 433 $[M + H]^+$<br>LC/MS (ESI$^-$) m/z; 431 $[M - H]^-$ |
| 118 | $^1$H-NMR (DMSO-$d_6$) δ: 1.26 (q, J = 11.9 Hz, 2H), 1.67-1.84 (m, 3H), 1.96-2.08 (m, 4H), 2.90 (br s, 5H), 3.17 (t, J = 12.3 Hz, 1H), 3.31 (s, 2H), 3.71 (t, J = 3.7 Hz, 4H), 6.55 (d, J = 7.8 Hz, 2H), 6.77 (d, J = 7.8 Hz, 2H), 6.80 (dd, J = 3.3, 2.0 Hz, 1H), 7.48 (t, J = 2.9 Hz, 1H), 9.51 (s, 1H), 12.52 (br s, 1H).<br>LC/MS: condition 1, retention time = 2.80 min<br>LC/MS (ESI$^+$) m/z; 432 $[M + H]^+$<br>LC/MS (ESI$^-$) m/z; 430 $[M - H]^-$ |
| 119 | $^1$H-NMR ($CDCl_3$) δ: 1.06-1.37 (m, 2H), 1.57-2.37 (m, 11H), 2.38-2.47 (m, 2H), 2.48-2.59 (m, 1H), 2.72-2.87 (m, 1H), 2.90-3.04 (m, 1H), 3.09-3.25 (m, 1H), 4.25-4.44 (m, 1H), 6.71-6.87 (m, 1H), 7.22-7.38 (m, 1H), 9.10 (br s, 1H), 9.21 (s, 1H).<br>LC/MS: condition 1, retention time = 0.39 min<br>LC/MS (ESI$^+$) m/z; 341 $[M + H]^+$<br>LC/MS (ESI$^-$) m/z; 339 $[M - H]^-$ |
| 120 | $^1$H-NMR ($CDCl_3$) δ: 1.11-1.33 (m, 2H), 1.42-1.81 (m, 2H), 1.83-2.23 (m, 10H), 2.51-2.83 (m, 4H), 3.07-3.25 (m, 1H), 3.70-3.94 (m, 2H), 3.99-4.14 (m, 1H), 6.72-6.83 (m, 1H), 7.21-7.35 (m, 1H), 9.05 (br s, 1H), 9.21 (s, 1H).<br>LC/MS: condition 1, retention time = 1.19 min<br>LC/MS (ESI$^+$) m/z; 355 $[M + H]^+$<br>LC/MS (ESI$^-$) m/z; 353 $[M - H]^-$ |
| 121 | LC/MS: condition 1, retention time = 3.74, 3.87 min (cis/trans mixture)<br>LC/MS (ESI$^+$) m/z; 358 $[M + H]^+$<br>LC/MS (ESI$^-$) m/z; 356 $[M - H]^-$ |

TABLE[a] 111-continued

| Ex | Data |
|---|---|
| 122 | LC/MS: condition 1, retention time = 0.36 min (cis/trans mixture)<br>LC/MS ($ESI^+$) m/z; 362 $[M + H]^+$<br>LC/MS ($ESI^-$) m/z; 360 $[M - H]^-$ |
| 123 | LC/MS: condition 1, retention time = 2.61 min (cis/trans mixture)<br>LC/MS ($ESI^+$) m/z; 361 $[M + H]^+$<br>LC/MS ($ESI^-$) m/z; 359 $[M - H]^-$ |

TABLE[a] 112

| Ex | Data |
|---|---|
| 124 | LC/MS: condition 1, retention time = 0.39 min (cis/trans mixture)<br>LC/MS ($ESI^+$) m/z; 327 $[M + H]^+$<br>LC/MS ($ESI^-$) m/z; 325 $[M - H]^-$ |
| 125 | LC/MS: condition 1, retention time = 3.04 min (cis/trans mixture)<br>LC/MS ($ESI^+$) m/z; 429 $[M + H]^+$<br>LC/MS ($ESI^-$) m/z; 427 $[M - H]^-$ |
| 126 | LC/MS: condition 1, retention time = 0.36 min (cis/trans mixture)<br>LC/MS ($ESI^+$) m/z; 370 $[M + H]^+$<br>LC/MS ($ESI^-$) m/z; 368 $[M - H]^-$ |
| 127 | LC/MS: condition 1, retention time = 0.37 min (cis/trans mixture)<br>LC/MS ($ESI^+$) m/z; 350 $[M + H]^+$<br>LC/MS ($ESI^-$) m/z; 348 $[M - H]^-$ |
| 128 | LC/MS: condition 1, retention time = 4.25, 4.39 min (cis/trans mixture)<br>LC/MS ($ESI^+$) m/z; 401 $[M + H]^+$<br>LC/MS ($ESI^-$) m/z; 399 $[M - H]^-$ |
| 129 | LC/MS: condition 1, retention time = 3.95 min (cis/trans mixture)<br>LC/MS ($ESI^+$) m/z; 376 $[M + H]^+$<br>LC/MS ($ESI^-$) m/z; 374 $[M - H]^-$ |
| 130 | LC/MS: condition 1, retention time = 2.79 min (cis/trans mixture)<br>LC/MS ($ESI^+$) m/z; 365 $[M + H]^+$<br>LC/MS ($ESI^-$) m/z; 363 $[M - H]^-$ |
| 131 | LC/MS: condition 1, retention time = 2.84, 3.24 min (cis/trans mixture)<br>LC/MS ($ESI^+$) m/z; 351 $[M + H]^+$ |

TABLE[a] 112-continued

| Ex | Data |
|---|---|
| | LC/MS ($ESI^-$) m/z; 349 $[M - H]^-$ |
| 132 | LC/MS: condition 1, retention time = 3.94, 4.02 min (cis/trans mixture)<br>LC/MS ($ESI^+$) m/z; 372 $[M + H]^+$<br>LC/MS ($ESI^-$) m/z; 370 $[M - H]^-$ |
| 133 | LC/MS: condition 1, retention time = 4.45 min (cis/trans mixture)<br>LC/MS ($ESI^+$) m/z; 431 $[M + H]^+$<br>LC/MS ($ESI^-$) m/z; 429 $[M - H]^-$ |
| 134a | $^1$H-NMR (DMSO-$d_6$) δ: 1.82-1.95 (m, 6H), 2.07-2.23 (m, 2H), 3.35-3.43 (m, 1H), 3.67 (br s, 1H), 6.77-6.73 (m, 3H), 6.86 (dd, J = 2.9, 1.2 Hz, 1H), 7.44 (d, J = 9.0 Hz, 2H), 7.50 (t, J = 2.9 Hz, 1H), 9.53 (s, 1H), 12.53 (br s, 1H).<br>LC/MS: condition 1, retention time = 3.88 min<br>LC/MS ($ESI^+$) m/z; 358 $[M + H]^+$<br>LC/MS ($ESI^-$) m/z; 356 $[M - H]^-$ |
| 134b | $^1$H-NMR (DMSO-$d_6$) δ: 1.48 (dq, J = 11.9, 3.7 Hz, 2H), 1.86-2.18 (m, 6H), 3.15-3.25 (m, 1H), 3.50 (br s, 1H), 6.64 (d, J = 8.1, 1H), 6.72 (d, J = 8.6 Hz, 2H), 6.90 (dd, J = 3.3, 1.6 Hz, 1H), 7.44 (d, J = 8.6 Hz, 2H), 7.50 (t, J = 2.9 Hz, 1H), 9.52 (s, 1H), 12.53 (br s, 1H).<br>LC/MS: condition 1, retention time = 3.74 min<br>LC/MS ($ESI^+$) m/z; 358 $[M + H]^+$<br>LC/MS ($ESI^-$) m/z; 356 $[M - H]^-$ |

TABLE[a] 113

| Ex | Data |
|---|---|
| 135a | $^1$H-NMR ($CDCl_3$) δ: 1.91 (m, 6H), 2.29 (m, 2H), 2.92 (m, 5H), 3.34 (tt, J = 9.9, 3.6 Hz, 1H), 7.10 (d, J = 3.3 Hz, 1H), 7.18-7.33 (m, 6H), 9.21 (s, 1H), 9.69 (br s, 1H).<br>LC/MS: condition 1, retention time = 2.78 min<br>LC/MS ($ESI^+$) m/z; 361 $[M + H]^+$<br>LC/MS ($ESI^-$) m/z; 359 $[M - H]^-$ |
| 135b | $^1$H-NMR ($CDCl_3$) δ: 1.30 (m, 2H), 1.88 (m, 2H), 2.07 (m, 4H), 2.62 (tt, J = 11.4, 3.3 Hz, 1H), 2.79 (t, J = 7.5 Hz, 2H), 2.95 (t, J = 7.2 Hz, 2H), 3.10 (tt, J = 12.3, 3.3 Hz, 1H), 6.68 (d, J = 2.7 Hz, 1H), 7.12-7.26 (m, 6H), 9.15 (s, 1H), 9.95 (br s, 1H).<br>LC/MS: condition 1, retention time = 2.51 min<br>LC/MS ($ESI^+$) m/z; 361 $[M + H]^+$<br>LC/MS ($ESI^-$) m/z; 359 $[M - H]^-$ |
| 136a | $^1$H-NMR ($CDCl_3$) δ: 1.31-1.94 (m, 10H), 2.30 (m, 1H), 2.72 (m, 4H), 2.92 (s, 1H), 3.30 (m, 1H), 7.14-7.34 (m, 7H), 9.21 (s, 1H), 9.48 (br s, 1H).<br>LC/MS: condition 1, retention time = 2.84 min<br>LC/MS ($ESI^+$) m/z; 375 $[M + H]^+$<br>LC/MS ($ESI^-$) m/z; 373 $[M - H]^-$ |
| 136b | $^1$H-NMR ($CDCl_3$) δ: 1.37 (m, 2H), 1.80-2.01 (m, 5H), 2.13 (m, 4H), 2.63 (m, 1H), 2.70 (t, J = 7.5 Hz, 1H), 2.76 (t, J = 7.5 Hz, 1H), 3.26 (m, 1H), 3.17 (m, 1H), 6.76 (d, J = 3.6 Hz, 1H), 7.16-7.34 (m, 6H), 9.21 (br s, 1H), 9.21 (s, 1H).<br>LC/MS: condition 1, retention time = 2.76 min<br>LC/MS ($ESI^+$) m/z; 375 $[M + H]^+$<br>LC/MS ($ESI^-$) m/z; 373 $[M - H]^-$ |
| 136b | $^1$H-NMR ($CDCl_3$) δ: 1.37 (m, 2H), 1.80-2.01 (m, 5H), 2.13 (m, 4H), 2.63 (m, 1H), 2.70 (t, J = 7.5 Hz, 1H), 2.76 (t, J = 7.5 Hz, 1H), 3.26 (m, 1H), 3.17 (m, 1H), 6.76 (d, J = 3.6 Hz, 1H), 7.16-7.34 (m, 6H), 9.21 (br s, 1H), 9.21 (s, 1H).<br>LC/MS: condition 1, retention time = 2.76 min<br>LC/MS ($ESI^+$) m/z; 375 $[M + H]^+$<br>LC/MS ($ESI^-$) m/z; 373 $[M - H]^-$ |

TABLE[a] 113-continued

| Ex | Data |
|---|---|
| 137a | $^1$H-NMR (DMSO-$d_6$) δ: 1.56-1.71 (m, 4H), 1.80-1.90 (m, 2H), 2.19-2.35 (m, 2H), 2.84 (br s, 1H), 3.19-3.26 (m, 1H), 3.84 (br s, 2H), 7.08 (d, J = 3.0 Hz, 1H), 7.43 (t, J = 2.6 Hz, 1H), 7.63 (d, J = 8.3 Hz, 2H), 7.83 (d, J = 8.3 Hz, 2H), 9.52 (s, 1H), 12.51 (br s, 1H).<br>LC/MS: condition 1, retention time = 1.03 min<br>LC/MS (ESI$^+$) m/z; 372 [M + H]$^+$ |
| 137b | $^1$H-NMR ($CDCl_3$) δ: 1.40 (dq, J = 12.6, 3.3 Hz, 2H), 1.96 (dq, J = 12.9, 4.0 Hz, 2H), 2.12-2.22 (m, 4H), 2.71 (tt, J = 11.2, 3.6 Hz, 1H), 3.19 (tt, J = 12.2, 3.3 Hz, 1H), 3.96 (s, 2H), 6.77 (dd, J = 3.6, 2.3 Hz, 1H), 7.30 (t, J = 3.0 Hz, 1H), 7.50 (d, J = 7.9 Hz, 2H), 7.64 (d, J = 8.3 Hz, 2H), 9.14 (br s, 1H), 9.23 (s, 1H).<br>LC/MS: condition 1, retention time = 0.85 min<br>LC/MS (ESI$^+$) m/z; 372 [M + H]$^+$<br>LC/MS (ESI$^-$) m/z; 370 [M − H]$^-$ |

TABLE[a] 114

| Ex | Data |
|---|---|
| 138a | $^1$H-NMR ($CDCl_3$) δ: 1.74 (t, J = 3.3 Hz, 1H), 1.76-1.87 (m, 4H), 1.95 (br s, 2H), 2.27-2.42 (m, 2H), 2.99-3.05 (m, 1H), 3.29-3.41 (m, 1H), 3.91 (s, 2H), 7.10 (dd, J = 3.3, 2.0 Hz, 1H), 7.19 (t, J = 2.6 Hz, 1H), 7.53 (d, J = 8.3 Hz, 2H), 7.61 (d, J = 8.3 Hz, 2H), 9.23 (s, 1H), 9.31 (br s, 1H).<br>LC/MS: condition 1, retention time = 2.87 min<br>LC/MS (ESI$^+$) m/z; 415 [M + H]$^+$<br>LC/MS (ESI$^-$) m/z; 413 [M − H]$^-$ |
| 138b | $^1$H-NMR (DMSO-$d_6$) δ: 1.35 (q, J = 10.6 Hz, 2H), 1.76 (q, J = 12.2 Hz, 2H), 1.95-2.14 (m, 4H), 2.19-2.32 (m, 1H), 3.15 (t, J = 12.2 Hz, 1H), 3.89 (s, 2H), 6.80 (d, J = 2.6 Hz, 1H), 7.49 (br s, 1H), 7.61 (d, J = 8.6 Hz, 2H), 7.69 (d, J = 8.3 Hz, 2H), 9.52 (d, J = 1.3 Hz, 1H), 12.53 (br s, 1H).<br>LC/MS: condition 1, retention time = 2.72 min<br>LC/MS (ESI$^+$) m/z; 415 [M + H]$^+$<br>LC/MS (ESI$^-$) m/z; 413 [M − H]$^-$ |
| 139a | $^1$H-NMR ($CDCl_3$) δ: 1.64-1.78 (m, 5H), 1.90-1.99 (m, 2H), 2.33 (dq, J = 13.2, 3.0 Hz, 2H), 2.74 (br s, 4H), 3.21 (t, J = 3.3 Hz, 1H), 3.27-3.38 (m, 1H), 3.75 (t, J = 4.6 Hz, 4H), 7.23 (dd, J = 3.6, 2.0 Hz, 1H), 7.28 (t, J = 3.0 Hz, 1H), 9.21 (br s, 1H), 9.22 (s, 1H).<br>LC/MS: condition 1, retention time = 0.79 min<br>LC/MS (ESI$^+$) m/z; 342 [M + H]$^+$ |
| 139b | $^1$H-NMR ($CDCl_3$) δ: 1.37 (dq, J = 12.9, 4.0 Hz, 2H), 1.57 (br s, 1H), 1.96 (dq, J = 12.6, 3.0 Hz, 2H), 2.08-2.19 (m, 4H), 2.69 (br s, 4H), 2.94 (tt, J = 11.2, 3.3 Hz, 1H), 3.18 (tt, J = 12.2, 4.0 Hz, 1H), 3.76 (t, J = 4.6 Hz, 4H), 6.78 (dd, J = 3.3, 2.3 Hz, 1H), 7.29 (t, J = 2.6 Hz, 1H), 9.09 (br s, 1H), 9.22 (s, 1H).<br>LC/MS: condition 1, retention time = 0.57 min<br>LC/MS (ESI$^+$) m/z; 342 [M + H]$^+$ |
| 140 | $^1$H-NMR (DMSO-$d_6$) δ: 4.59 (d, J = 5.4 Hz, 2H), 5.27 (t, J = 6.0 Hz, 1H), 6.86 (m, 1H), 7.54 (m, 3H), 7.92 (d, J = 8.1 Hz, 2H), 9.65 (s, 1H), 12.68 (br s, 1H).<br>LC/MS: condition 1, retention time = 2.77 min<br>LC/MS (ESI$^+$) m/z; 266 [M + H]$^+$<br>LC/MS (ESI$^-$) m/z; 264 [M − H]$^-$ |
| 141 | $^1$H-NMR (DMSO-$d_6$) δ: 1.25 (m, 2H), 1.66 (m, 1H), 1.87 (m, 2H), 2.00-2.15 (m, 4H), 3.18 (tt, J = 12.3 Hz, 3.6 Hz, 1H), 3.47 (d, J = 6.6 Hz, 2H), 6.81 Hz (d, J = 3.3 Hz, 1H), 7.38 (d, J = 3.3 Hz, 1H), 9.28 (s, 1H).<br>LC/MS: condition 1, retention time = 2.80 min<br>LC/MS (ESI$^+$) m/z; 272 [M + H]$^+$<br>LC/MS (ESI$^-$) m/z; 270 [M − H]$^-$ |
| 142 | $^1$H-NMR (DMSO-$d_6$) δ: 1.88-2.06 (m, 4H), 2.19-2.32 (m, 2H), 2.92-3.02 (m, 2H), 3.10-3.14 (m, 1H), 3.62 (s, 2H), 6.82 (br s, 1H), 7.13-7.25 (m, 2H), 7.27-7.40 (m, 1H), 7.45-7.53 (m, 2H), 9.52 (s, 1H), 12.52 (br s, 1H).<br>LC/MS: condition 3, retention time = 1.33 min<br>LC/MS (ESI$^+$) m/z; 351 [M + H]$^+$<br>LC/MS (ESI$^-$) m/z; 349 [M − H]$^-$ |

TABLE[a] 115

| Ex | Data |
|---|---|
| 143 | $^1$H-NMR (DMSO-$d_6$) δ: 1.88-2.05 (m, 4H), 2.21-2.35 (m, 2H), 2.94-3.03 (m, 2H), 3.10-3.24 (m, 1H), 3.68 (s, 2H), 6.58 (d, J = 3.3 Hz, 1H), 6.81 (d, J = 3.3 Hz, 1H), 7.15-7.20 (m, 1H), 7.46-7.52 (m, 1H), 9.52 (s, 1H), 12.52 (br s, 1H).<br>LC/MS: condition 3, retention time = 1.52 min<br>LC/MS ($ESI^+$) m/z; 391 $[M + H]^+$<br>LC/MS ($ESI^-$) m/z; 389 $[M - H]^-$ |
| 144 | LC/MS: condition 3, retention time = 1.22 min<br>LC/MS ($ESI^+$) m/z; 364 $[M + H]^+$<br>LC/MS ($ESI^-$) m/z; 362 $[M - H]^-$ |
| 145 | $^1$H-NMR ($CDCl_3$) δ: 1.97-2.11 (m, 2H), 2.12-2.33 (m, 4H), 2.97-3.10 (m, 2H), 3.15-3.31 (m, 1H), 3.59 (s, 2H), 6.80-6.87 (m, 1H), 6.93 (dd, J = 8.4, 2.7 Hz, 1H), 7.31 (t, J = 3.0 Hz, 1H), 7.80-7.90 (m, 1H), 8.15-8.20 (m, 1H), 9.15 (br s, 1H), 9.23 (s, 1H).<br>LC/MS: condition 3, retention time = 1.58 min<br>LC/MS ($ESI^+$) m/z; 411, 413 $[M + H]^+$ |
| 146 | $^1$H-NMR (DMSO-$d_6$) δ: 1.90-2.04 (m, 4H), 2.19-2.31 (m, 2H), 2.92-3.03 (m, 2H), 3.06-3.20 (m, 1H), 3.57 (s, 2H), 6.30-6.35 (m, 1H), 6.40-6.45 (m, 1H), 6.78-6.84 (m, 1H), 7.47-7.53 (m, 1H), 7.60 (s, 1H), 9.52 (s, 1H), 12.52 (br s, 1H).<br>LC/MS: condition 3, retention time = 1.14 min<br>LC/MS ($ESI^+$) m/z; 323 $[M + H]^+$ |
| 147 | $^1$H-NMR (DMSO-$d_6$) δ: 1.84-2.06 (m, 4H), 2.15-2.33 (m, 2H), 2.87-3.04 (m, 2H), 3.06-3.22 (m, 1H), 3.58 (s, 2H), 6.29 (d, J = 3.3 Hz, 1H), 6.63 (d, J = 3.3 Hz, 1H), 6.81 (br s, 1H), 7.44-7.51 (m, 1H), 9.51 (s, 1H), 12.52 (br s, 1H).<br>LC/MS: condition 3, retention time = 1.44 min<br>LC/MS ($ESI^+$) m/z; 449 $[M + H]^+$<br>LC/MS ($ESI^-$) m/z; 447 $[M - H]^-$ |
| 148 | $^1$H-NMR (DMSO-$d_6$) δ: 1.86-2.10 (m, 4H), 2.18-2.33 (m, 2H), 2.94-3.10 (m, 2H), 3.11-3.26 (m, 1H), 3.76 (s, 2H), 6.82 (br s, 1H), 6.91-7.03 (m, 2H), 7.40-7.46 (m, 1H), 7.46-7.53 (m, 1H), 9.52 (s, 1H), 12.52 (br s, 1H).<br>LC/MS: condition 3, retention time = 1.24 min<br>LC/MS ($ESI^+$) m/z; 339 $[M + H]^+$<br>LC/MS ($ESI^-$) m/z; 337 $[M - H]^-$ |
| 149 | $^1$H-NMR (DMSO-$d_6$) δ: 1.84-2.06 (m, 4H), 2.17-2.33 (m, 2H), 2.88-3.04 (m, 2H), 3.05-3.22 (m, 1H), 3.57 (s, 2H), 6.40 (d, J = 3.3 Hz, 1H), 6.51 (d, J = 3.3 Hz, 1H), 6.81 (br s, 1H), 7.43-7.52 (m, 1H), 9.51 (s, 1H), 12.52 (br s, 1H).<br>LC/MS: condition 3, retention time = 1.39 min<br>LC/MS ($ESI^+$) m/z; 401, 403 $[M + H]^+$ |
| 150 | $^1$H-NMR (DMSO-$d_6$) δ: 1.85-2.08 (m, 4H), 2.20-2.37 (m, 2H), 2.94-3.05 (m, 2H), 3.11-3.27 (m, 1H), 3.78 (s, 2H), 6.82 (br s, 1H), 7.46-7.53 (m, 1H), 7.58 (s, 1H), 9.52 (s, 1H), 12.52 (br s, 1H).<br>LC/MS: condition 3, retention time = 1.21 min<br>LC/MS ($ESI^+$) m/z; 374 $[M + H]^+$<br>LC/MS ($ESI^-$) m/z; 372 $[M - H]^-$ |

TABLE[a] 116

| Ex | Data |
|---|---|
| 151 | $^1$H-NMR (DMSO-$d_6$) δ: 1.82-2.08 (m, 4H), 2.12-2.28 (m, 2H), 2.86-3.05 (m, 2H), 3.05-3.20 (m, 1H), 3.46-3.65 (m, 2H), 6.09-6.23 (m, 1H), 6.81 (br s, 1H), 7.48 (br s, 1H), 9.52 (s, 1H), 12.52 (br s, 1H).<br>LC/MS: condition 3, retention time = 0.63 min<br>LC/MS ($ESI^+$) m/z; 323 $[M + H]^+$<br>LC/MS ($ESI^-$) m/z; 321 $[M - H]^-$ |
| 152 | $^1$H-NMR (DMSO-$d_6$) δ: 1.87-2.12 (m, 4H), 2.25-2.42 (m, 2H), 2.97-3.10 (m, 2H), 3.10-3.25 (m, 1H), 4.13 (s, 2H), 6.82 (br s, 1H), 7.45-7.53 (m, 1H), 9.10 (s, 1H), 9.52 (s, 1H), 12.52 (br s, 1H).<br>LC/MS: condition 3, retention time = 0.81 min<br>LC/MS ($ESI^+$) m/z; 341 $[M + H]^+$<br>LC/MS ($ESI^-$) m/z; 339 $[M - H]^-$ |
| 153 | $^1$H-NMR (DMSO-$d_6$) δ: 1.85-2.06 (m, 4H), 2.20-2.36 (m, 2H), 2.92-3.05 (m, 2H), 3.12-3.27 (m, 1H), 3.80 (s, 2H), 6.82 (br s, 1H), 7.48-7.53 (m, 1H), 7.59 (s, 1H), 9.52 (s, 1H), 12.52 (br s, 1H).<br>LC/MS: condition 3, retention time = 1.58 min<br>LC/MS ($ESI^+$) m/z; 418, 420 $[M + H]^+$<br>LC/MS ($ESI^-$) m/z; 416, 418 $[M - H]^-$ |
| 154 | $^1$H-NMR (DMSO-$d_6$) δ: 1.96-2.03 (m, 4H), 2.23-2.29 (m, 2H), 2.94 (d, J = 11.4 Hz, 2H), 3.16-3.21 (m, 1H), 3.63 (s, 2H), 6.82 (d, J = 2.4 Hz, 1H), 7.46-7.52 (m, 2H), 7.74 (d, J = 7.5 Hz, 2H), 9.52 (s, 1H), 12.55 (br s, 1H).<br>LC/MS: condition 3, retention time = 1.68 min<br>LC/MS ($ESI^+$) m/z; 419 $[M + H]^+$<br>LC/MS ($ESI^-$) m/z; 417 $[M - H]^-$ |
| 155 | $^1$H-NMR (DMSO-$d_6$) δ: 1.95-2.06 (m, 4H), 2.23-2.30 (m, 2H), 2.94 (d, J = 11.7 Hz, 2H), 3.16-3.19 (m, 1H), 3.65 (s, 2H), 6.82 (d, J = 3.3 Hz, 1H), 7.49 (d, J = 3.3 Hz, 1H), 7.71 (s, 2H), 7.84 (s, 1H), 9.52 (s, 1H).<br>LC/MS: condition 3, retention time = 1.79 min<br>LC/MS ($ESI^+$) m/z; 435, 437 $[M + H]^+$<br>LC/MS ($ESI^-$) m/z; 433, 435 $[M - H]^-$ |
| 156 | $^1$H-NMR (DMSO-$d_6$) δ: 1.96-2.04 (m, 4H), 2.23-2.30 (m, 2H), 2.96 (d, J = 10.2 Hz, 2H), 3.22 (s, 3H), 3.67 (s, 2H), 6.81 (d, J = 3.0 Hz, 1H), 7.49 (d, J = 3.3 Hz, 1H), 7.65 (d, J = 8.4 Hz, 2H), 7.91 (d, J = 8.7 Hz, 2H), 9.49 (s, 1H).<br>LC/MS: condition 3, retention time = 1.12 min<br>LC/MS ($ESI^+$) m/z; 411 $[M + H]^+$<br>LC/MS ($ESI^-$) m/z; 409 $[M - H]^-$ |
| 157 | $^1$H-NMR (DMSO-$d_6$) δ: 1.95-2.07 (m, 4H), 2.27-2.33 (m, 2H), 2.98 (d, J = 11.7 Hz, 2H), 3.15-3.18 (m, 1H), 3.70 (s, 2H), 6.82 (d, J = 3.0 Hz, 1H), 7.49 (d, J = 3.3 Hz, 1H), 7.61-7.68 (m, 2H), 7.76 (t, J = 7.7 Hz, 1H), 9.51 (s, 1H).<br>LC/MS: condition 3, retention time = 1.66 min |

TABLE[a] 116-continued

| Ex | Data |
|---|---|
| | LC/MS ($ESI^+$) m/z; 419 $[M + H]^+$<br>LC/MS ($ESI^-$) m/z; 417 $[M - H]^-$ |

TABLE[a] 117

| Ex | Data |
|---|---|
| 158 | $^1$H-NMR (DMSO-$d_6$) δ: 1.94-2.04 (m, 4H), 2.26 (td, J = 10.8, 3.5 Hz, 2H), 2.95 (d, J = 11.7 Hz, 2H), 4.12 (s, 2H), 6.82 (d, J = 3.0 Hz, 1H), 7.31 (dd, J = 8.4, 2.1 Hz, 1H), 7.41 (dd, J = 9.9, 2.1 Hz, 1H), 7.49-7.54 (m, 2H), 9.53 (s, 1H), 12.54 (br s, 1H).<br>LC/MS: condition 3, retention time = 1.54 min<br>LC/MS ($ESI^+$) m/z; 385, 387 $[M + H]^+$ |
| 159 | $^1$H-NMR (DMSO-$d_6$) δ: 1.95-2.06 (m, 4H), 2.21-2.27 (m, 2H), 2.94 (d, J = 11.4 Hz, 2H), 3.15-3.22 (m, 1H), 3.57 (s, 2H), 6.83 (d, J = 3.3 Hz, 1H), 7.25 (d, J = 7.8 Hz, 1H), 7.40 (d, J = 10.8 Hz, 1H), 7.50 (d, J = 3.3 Hz, 1H), 7.56 (t, J = 8.1 Hz, 1H), 9.53 (s, 1H), 12.54 (br s, 1H).<br>LC/MS: condition 3, retention time = 1.58 min<br>LC/MS ($ESI^+$) m/z; 385, 387 $[M + H]^+$<br>LC/MS ($ESI^-$) m/z; 383, 385 $[M - H]^-$ |
| 160 | $^1$H-NMR ($CDCl_3$) δ: 1.99-2.13 (m, 2H), 2.17-2.37 (m, 4H), 2.94-3.10 (m, 2H), 3.16-3.32 (m, 1H), 3.59 (s, 2H), 6.80-6.88 (m, 1H), 7.21-7.35 (m, 2H), 7.41 (s, 1H), 8.34 (d, J = 5.1 Hz, 1H), 9.18 (br s, 1H), 9.24 (s, 1H).<br>LC/MS: condition 3, retention time = 1.16 min<br>LC/MS ($ESI^+$) m/z; 368, 370 $[M + H]^+$<br>LC/MS ($ESI^-$) m/z; 366, 368 $[M - H]^-$ |
| 161 | $^1$H-NMR ($CDCl_3$) δ: 2.00-2.16 (m, 2H), 2.16-2.42 (m, 4H), 3.00-3.15 (m, 2H), 3.15-3.30 (m, 1H), 3.71 (s, 2H), 6.80-6.90 (m, 1H), 7.28-7.37 (m, 1H), 7.53 (t, J = 5.4 Hz, 1H), 8.38-8.50 (m, 2H), 9.11-9.30 (m, 2H).<br>LC/MS: condition 3, retention time = 0.86 min<br>LC/MS ($ESI^+$) m/z; 352 $[M + H]^+$<br>LC/MS ($ESI^-$) m/z; 350 $[M - H]^-$ |
| 162 | $^1$H-NMR ($CDCl_3$) δ: 2.00-2.10 (m, 2H), 2.16-2.42 (m, 4H), 3.01-3.15 (m, 2H), 3.16-3.32 (m, 1H), 3.74 (s, 2H), 6.80-6.89 (m, 1H), 7.29 (t, J = 3.0 Hz, 1H), 7.40 (td, J = 8.7, 3.0 Hz, 1H), 7.54 (dd, J = 8.4, 4.5 Hz, 1H), 8.42 (d, J = 2.7 Hz, 1H), 9.08 (br s, 1H), 9.22 (s, 1H).<br>LC/MS: condition 3, retention time = 1.17 min<br>LC/MS ($ESI^+$) m/z; 352 $[M + H]^+$<br>LC/MS ($ESI^-$) m/z; 350 $[M - H]^-$ |
| 163 | $^1$H-NMR ($CDCl_3$) δ: 2.00-2.15 (m, 2H), 2.19-2.50 (m, 4H), 3.02-3.14 (m, 2H), 3.18-3.33 (m, 1H), 3.70 (s, 2H), 6.82-6.91 (m, 1H), 7.29-7.38 (m, 1H), 7.59 (d, J = 4.8 Hz, 1H), 8.48 (d, J = 4.8 Hz, 1H), 8.54 (s, 1H), 9.09 (br s, 1H), 9.23 (s, 1H).<br>LC/MS: condition 3, retention time = 1.13 min<br>LC/MS ($ESI^+$) m/z; 368, 370 $[M + H]^+$ |
| 164 | $^1$H-NMR (DMSO-$d_6$) δ: 1.93-2.00 (m, 4H), 2.21-2.27 (m, 2H), 2.95 (d, J = 10.5 Hz, 2H), 3.59 (s, 2H), 6.81 (d, J = 2.4 Hz, 1H), 7.10 (t, J = 8.4 Hz, 1H), 7.21 (t, J = 9.3 Hz, 1H), 7.48-7.56 (m, 2H), 9.52 (s, 1H).<br>LC/MS: condition 3, retention time = 1.39 min<br>LC/MS ($ESI^+$) m/z; 369 $[M + H]^+$ |

TABLE[a] 118

| Ex | Data |
|---|---|
| 165 | $^1$H-NMR (DMSO-$d_6$) δ: 1.95-2.07 (m, 4H), 2.23 (td, J = 11.3, 3.0 Hz, 2H), 2.97 (d, J = 11.1 Hz, 2H), 3.62 (s, 2H), 6.83 (d, J = 3.3 Hz, 1H), 7.25 (td, J = 8.6, 2.6 Hz, 1H), 7.43 (dd, J = 8.9, 2.6 Hz, 1H), 7.50 (d, J = 3.3 Hz, 1H), 7.60 (dd, J = 8.6, 6.2 Hz, 1H), 9.52 (s, 1H).<br>LC/MS: condition 3, retention time = 1.50 min<br>LC/MS ($ESI^+$) m/z; 385, 387 $[M + H]^+$ |
| 166 | $^1$H-NMR (DMSO-$d_6$) δ: 1.91-2.06 (m, 4H), 2.23 (td, J = 11.2, 3.1 Hz, 2H), 2.94 (d, J = 11.7 Hz, 2H), 3.55 (s, 2H), 6.82 (d, J = 3.3 Hz, 1H), 7.19-7.24 (m, 1H), 7.35-7.45 (m, 2H), 7.50 (d, J = 3.3 Hz, 1H), 9.52 (s, 1H).<br>LC/MS: condition 3, retention time = 1.45 min<br>LC/MS ($ESI^+$) m/z; 369 $[M + H]^+$<br>LC/MS ($ESI^-$) m/z; 367 $[M - H]^-$ |

TABLE[a] 118-continued

| Ex | Data |
|---|---|
| 167 | $^1$H-NMR (DMSO-$d_6$) δ: 1.92-2.09 (m, 4H), 2.25-2.31 (m, 2H), 2.96 (d, J = 12.0 Hz, 2H), 3.67 (s, 2H), 6.82 (d, J = 3.3 Hz, 1H), 7.43-7.52 (m, 3H), 7.77 (t, J = 8.0 Hz, 1H), 9.51 (s, 1H).<br>LC/MS: condition 3, retention time = 1.71 min<br>LC/MS (ESI$^+$) m/z; 419 $[M + H]^+$<br>LC/MS (ESI$^-$) m/z; 417 $[M - H]^-$ |
| 168 | $^1$H-NMR (DMSO-$d_6$) δ: 1.91-2.23 (m, 8H), 2.91 (t, J = 11.6 Hz, 1H), 3.46 (s, 2H), 3.69-3.71 (m, 2H), 3.96 (br s, 2H), 6.71 (s, 1H), 6.90 (t, J = 6.8 Hz, 2H), 7.25 (t, J = 8.3 Hz, 2H), 7.43 (s, 1H), 9.37 (s, 1H).<br>LC/MS: condition 3, retention time = 1.15 min<br>LC/MS (ESI$^+$) m/z; 393 $[M + H]^+$ |
| 169 | $^1$H-NMR ($CDCl_3$) δ: 1.98-2.13 (m, 2H), 2.13-2.34 (m, 4H), 2.98-3.16 (m, 2H), 3.16-3.32 (m, 1H), 3.59 (s, 2H), 5.91 (tt, J = 56.1, 3.0 Hz, 1H), 6.81-6.90 (m, 1H), 7.18 (d, J = 8.4 Hz, 2H), 7.27-7.33 (m, 1H), 7.41 (d, J = 8.4 Hz, 2H), 9.19 (br s, 1H), 9.23 (s, 1H).<br>LC/MS: condition 3, retention time = 1.72 min<br>LC/MS (ESI$^+$) m/z; 449 $[M + H]^+$<br>LC/MS (ESI$^-$) m/z; 447 $[M - H]^-$ |
| 170 | $^1$H-NMR ($CDCl_3$) δ: 1.96-2.12 (m, 2H), 2.12-2.35 (m, 4H), 3.00-3.16 (m, 2H), 3.16-3.31 (m, 1H), 3.54 (s, 2H), 3.95 (s, 3H), 6.75 (d, J = 8.1 Hz, 1H), 6.81-6.90 (m, 1H), 7.27-7.36 (m, 1H), 7.64 (dd, J = 8.4, 2.4 Hz, 1H), 8.11 (d, J = 2.1 Hz, 1H), 9.23 (s, 1H), 9.51 (br s, 1H).<br>LC/MS: condition 3, retention time = 1.22 min<br>LC/MS (ESI$^+$) m/z; 364 $[M + H]^+$ |
| 171 | LC/MS: condition 3, retention time = 1.40 min<br>LC/MS (ESI$^+$) m/z; 386 $[M + H]^+$ |

TABLE[a] 119

| Ex | Data |
|---|---|
| 172 | $^1$H-NMR ($CDCl_3$) δ: 1.12-1.28 (m, 2H), 1.62 (m, 1H), 1.84-2.02 (m, 4H), 2.15 (m, 2H), 2.52 (dd, J = 12.0, 6.9 Hz, 1H), 2.66 (dd, J = 12.0, 6.6 Hz, 1H), 2.98 (d, J = 12.9 Hz, 1H), 3.15 (tt, J = 12.3, 3.3 Hz, 1H), 3.54 (d, J = 12.9 Hz, 1H), 6.78 (m, 1H), 7.33-7.40 (m, 4H), 7.60 (m, 2H), 9.22 (s, 1H), 9.45 (br s, 1H).<br>LC/MS: condition 1, retention time = 2.81 min<br>LC/MS (ESI$^+$) m/z; 459 $[M + H]^+$<br>LC/MS (ESI$^-$) m/z; 457 $[M - H]^-$ |
| 173 | $^1$H-NMR (DMSO-$d_6$) δ: 1.23-1.38 (m, 2H), 1.71-1.86 (m, 2H), 1.95-2.09 (m, 4H), 3.08-3.23 (m, 3H), 6.82 (dd, J = 1.7, 3.3 Hz, 1H), 6.86 (d, J = 9.2 Hz, 2H), 7.50 (t, J = 3.0 Hz, 1H), 7.59 (t, J = 5.6 Hz, 1H), 7.68 (d, J = 8.9 Hz, 2H), 9.52 (s, 1H), 12.54 (br s, 1H).<br>LC/MS: condition 1, retention time = 4.30 min<br>LC/MS (ESI$^+$) m/z; 479 $[M + H]^+$<br>LC/MS (ESI$^-$) m/z; 477 $[M - H]^-$ |
| 174 | $^1$H-NMR ($CD_3OD$) δ: 1.17-1.33 (m, 2H), 1.70-1.78 (m, 1H), 1.78-1.90 (m, 2H), 1.93-2.01 (m, 2H), 2.06-2.15 (m, 2H), 2.66 (d, J = 7.0 Hz, 2H), 2.79-3.02 (m, 5H), 3.17 (tt, J = 12.3, 3.3 Hz, 1H), 6.79 (d, J = 3.3 Hz, 1H), 7.16-7.32 (m, 6H), 7.38 (d, J = 3.3 Hz, 1H), 9.27 (br s, 1H).<br>LC/MS: condition 1, retention time = 2.75 min<br>LC/MS (ESI$^+$) m/z; 375 $[M + H]^+$<br>LC/MS (ESI$^-$) m/z; 373 $[M - H]^-$ |
| 175 | $^1$H-NMR (DMSO-$d_6$) δ: 1.24-1.39 (m, 2H), 1.71-1.87 (m, 3H), 2.01-2.09 (m, 5H), 3.00 (d, J = 5.9 Hz, 2H), 3.13-3.25 (m, 1H), 5.94 (bs, 1H), 6.57 (br s, 1H), 6.79-6.83 (m, 2H), 7.44 (d, J = 8.9 Hz, 1H), 7.50 (t, J = 3.0 Hz, 1H), 9.52 (s, 1H), 12.53 (br s, 1H).<br>LC/MS: condition 1, retention time = 3.35 min<br>LC/MS (ESI$^+$) m/z; 455 $[M + H]^+$<br>LC/MS (ESI$^-$) m/z; 453 $[M - H]^-$ |
| 176 | $^1$H-NMR (DMSO-$d_6$) δ: 1.19-1.34 (m, 2H), 1.69-1.84 (m, 3H), 1.96-2.07 (m, 4H), 2.93 (t, J = 5.6 Hz, 2H), 3.11-3.25 (m, 1H), 5.89 (t, J = 5.6 Hz, 1H), 6.56-6.62 (m, 2H), 6.81 (dd, J = 3.0, 1.7 Hz, 1H), 7.05-7.11 (m, 2H), 7.49 (t, J = 3.0 Hz, 1H), 9.52 (s, 1H), 12.53 (br s, 1H).<br>LC/MS: condition 1, retention time = 4.32 min<br>LC/MS (ESI$^+$) m/z; 381 $[M + H]^+$<br>LC/MS (ESI$^-$) m/z; 379 $[M - H]^-$ |
| 177 | $^1$H-NMR ($CDCl_3$) δ: 1.24 (m, 2H), 1.76 (m, 1H), 1.86-2.17 (m, 6H), 2.57 (d, J = 6.6 Hz, 1H), 3.16 (tt, J = 12.3, 3.6 Hz, 1H), 3.81 (s, 2H), 6.77 (d, J = 3.3 Hz, 1H), 7.26-7.29 (m, 5H), 9.22 (s, 1H), 9.70 (br s, 1H). |

TABLE[a] 119-continued

| Ex | Data |
|---|---|
| | LC/MS: condition 1, retention time = 2.84 min<br>LC/MS ($ESI^+$) m/z; 395, 397 $[M + H]^+$<br>LC/MS ($ESI^-$) m/z; 393, 395 $[M - H]^-$ |

TABLE[a] 120

| Ex | Data |
|---|---|
| 178 | $^1$H-NMR ($CDCl_3$) δ: 1.19 (m, 2H), 1.66 (m, 1H), 1.90 (m, 4H), 2.12 (m, 2H), 2.57 (d, J = 6.6 Hz, 2H), 2.70-2.97 (m, 4H), 3.16 (tt, J = 12.6, 3.3 Hz, 1H), 6.77 (d, J = 3.3 Hz, 1H), 7.15 (m, 3H), 7.27 (m, 2H), 9.21 (s, 1H), 9.33 (br s, 1H).<br>LC/MS: condition 1, retention time = 2.97 min<br>LC/MS ($ESI^+$) m/z; 409, 411 $[M + H]^+$<br>LC/MS ($ESI^-$) m/z; 407, 409 $[M - H]^-$ |
| 179 | $^1$H-NMR ($CDCl_3$) δ: 1.17-1.39 (m, 2H), 1.71-2.28 (m, 7H), 2.86-3.06 (m, 4H), 3.10-3.30 (m, 1H), 3.33-3.55 (m, 2H), 6.30-6.43 (m, 1H), 6.70-6.88 (m, 3H), 7.20-7.39 (m, 1H), 9.02 (br s, 1H), 9.22 (s, 1H).<br>LC/MS: condition 1, retention time = 4.40 min<br>LC/MS ($ESI^+$) m/z; 391 $[M + H]^+$<br>LC/MS ($ESI^-$) m/z; 389 $[M - H]^-$ |
| 180 | $^1$H-NMR ($CDCl_3$) δ: 1.04-1.28 (m, 2H), 1.46-1.73 (m, 1H), 1.82-2.02 (m, 2H), 2.04-2.23 (m, 4H), 2.39-2.60 (m, 6H), 2.84-3.00 (m, 4H), 3.09-3.28 (m, 1H), 6.72-6.83 (m, 1H), 7.27-7.37 (m, 1H), 8.99 (br s, 1H), 9.21 (s, 1H).<br>LC/MS: condition 1, retention time = 3.38 min<br>LC/MS ($ESI^+$) m/z; 377 $[M + H]^+$<br>LC/MS ($ESI^-$) m/z; 375 $[M - H]^-$ |
| 181 | $^1$H-NMR ($CDCl_3$) δ: 1.00-1.31 (m, 2H), 1.50-1.80 (m, 1H), 1.81-2.18 (m, 7H), 2.24 (s, 6H), 2.26-2.59 (m, 4H), 2.68-2.92 (m, 3H), 3.08-3.24 (m, 1H), 6.71-6.83 (m, 1H), 7.17-7.33 (m, 1H), 9.00-9.40 (m, 1H), 9.21 (s, 1H).<br>LC/MS: condition 1, retention time = 0.34 min<br>LC/MS ($ESI^+$) m/z; 368 $[M + H]^+$<br>LC/MS ($ESI^-$) m/z; 366 $[M - H]^-$ |
| 182 | $^1$H-NMR ($CDCl_3$) δ: 1.00-1.32 (m, 2H), 1.40-1.80 (m, 1H), 1.82-2.21 (m, 7H), 2.29 (s, 3H), 2.58 (d, J = 6.6 Hz, 2H), 3.08-3.25 (m, 1H), 3.76 (s, 2H), 5.89 (d, J = 2.1 Hz, 1H), 6.06 (d, J = 3.0 Hz, 1H), 6.78 (d, J = 3.0 Hz, 1H), 7.17-7.32 (m, 1H), 9.00-9.40 (m, 1H), 9.21 (s, 1H).<br>LC/MS: condition 1, retention time = 2.49 min<br>LC/MS ($ESI^+$) m/z; 365 $[M + H]^+$<br>LC/MS ($ESI^-$) m/z; 363 $[M - H]^-$ |
| 183 | $^1$H-NMR ($CDCl_3$) δ: 1.11-1.35 (m, 2H), 1.40-1.81 (m, 1H), 1.83-2.25 (m, 7H), 2.57 (s, 3H), 2.62 (d, J = 6.6 Hz, 2H), 3.07-3.27 (m, 1H), 3.96 (s, 2H), 6.70-6.85 (m, 1H), 7.10-7.37 (m, 1H), 8.35-8.46 (m, 1H), 8.49-8.59 (m, 1H), 9.00-9.40 (m, 1H), 9.21 (s, 1H).<br>LC/MS: condition 1, retention time = 0.77 min<br>LC/MS ($ESI^+$) m/z; 377 $[M + H]^+$<br>LC/MS ($ESI^-$) m/z; 375 $[M - H]^-$ |
| 184 | $^1$H-NMR ($CDCl_3$) δ: 1.11-1.38 (m, 5H), 1.55-2.35 (m, 9H), 2.40-2.85 (m, 4H), 3.09-3.27 (m, 1H), 3.72-3.92 (m, 1H), 6.80 (d, J = 3.3 Hz, 1H), 7.30 (d, J = 3.3 Hz, 1H), 8.60-10.00 (m, 1H), 9.23 (s, 1H).<br>LC/MS: condition 1, retention time = 0.39 min<br>LC/MS ($ESI^+$) m/z; 329 $[M + H]^+$<br>LC/MS ($ESI^-$) m/z; 327 [M − H] |

TABLE[a] 121

| Ex | Data |
|---|---|
| 185 | $^1$ H-NMR ($CDCl_3$) δ: 1.10-1.50 (m, 5H), 1.55-2.35 (m, 9H), 2.40-2.90 (m, 4H), 3.10-3.31 (m, 1H), 3.75-4.00 (m, 1H), 6.80 (d, J = 3.3 Hz, 1H), 7.30 (d, J = 3.3 Hz, 1H), 8.80-10.00 (m, 1H), 9.23 (s, 1H).<br>LC/MS: condition 1, retention time = 0.37 min<br>LC/MS ($ESI^+$) m/z; 329 $[M + H]^+$<br>LC/MS ($ESI^-$) m/z; 327 $[M - H]^-$ |
| 186 | $^1$H-NMR ($CD_3OD$) δ: 1.30 (m, 2H), 1.70-2.15 (m, 7H), 2.74 (t, J = 6.6 Hz, 2H), 2.92 (d, J = 6.6 Hz, 2H), 3.21 (tt, J = 12.0, 4.2 Hz, 1H), 4.92 (m, 1H), 6.82 (d, J = 3.3 Hz, 1H), 6.83-7.43 (m, 6H), 9.30 (s, 1H).<br>LC/MS: condition 1, retention time = 2.52 min<br>LC/MS ($ESI^+$) m/z; 391 $[M + H]^+$, LC/MS ($ESI^-$) m/z; 389 $[M - H]^-$ |

TABLE[a] 121-continued

| Ex | Data |
|---|---|
| 187 | $^1$H-NMR ($CDCl_3$) δ: 1.07-1.31 (m, 2H), 1.47-1.74 (m, 1H), 1.80-2.32 (m, 8H), 2.34-2.49 (m, 2H), 2.55-2.80 (m, 3H), 2.88-3.25 (m, 3H), 6.71-6.86 (m, 1H), 7.18-7.39 (m, 1H), 9.01 (br s, 1H), 9.21 (s, 1H).<br>LC/MS: condition 3, retention time = 1.14 min<br>LC/MS ($ESI^+$) m/z; 350 $[M + H]^+$<br>LC/MS ($ESI^-$) m/z; 348 $[M - H]^-$ |
| 188 | $^1$H-NMR ($CDCl_3$) δ: 1.10-1.40 (m, 3H), 1.50-1.80 (m, 1H), 1.83-2.24 (m, 6H), 2.68 (d, J = 6.0 Hz, 2H), 3.06-3.50 (m, 3H), 6.70-6.85 (m, 1H), 7.18-7.35 (m, 1H), 9.10 (br s, 1H), 9.22 (s, 1H).<br>LC/MS: condition 3, retention time = 1.30 min<br>LC/MS ($ESI^+$) m/z; 353 $[M + H]^+$ |
| 189 | $^1$H-NMR ($CDCl_3$) δ: 1.11-1.45 (m, 3H), 1.78-2.36 (m, 6H), 2.91-3.31 (m, 5H), 3.00 (s, 3H), 3.52-3.80 (m, 2H), 6.40 (d, J = 8.6 Hz, 1H), 6.70-6.90 (m, 1H), 7.20-7.38 (m, 1H), 7.50 (s, 1H), 7.54-7.73 (m, 1H), 9.22 (s, 1H), 9.30 (br s, 1H).<br>LC/MS: condition 3, retention time = 2.13 min<br>LC/MS ($ESI^+$) m/z; 451 $[M + H]^+$, LC/MS ($ESI^-$) m/z; 449 $[M - H]^-$ |
| 190 | $^1$H-NMR ($CDCl_3$) δ: 1.15-1.40 (m, 3H), 1.80-2.30 (m, 6H), 2.68 (s, 6H), 3.00-3.30 (m, 5H), 3.55-3.74 (m, 2H), 6.40 (d, J = 8.6 Hz, 1H), 6.79 (t, J = 2.4 Hz, 1H), 7.29 (t, J = 3.0 Hz, 1H), 7.34 (s, 1H), 7.50 (dd, J = 8.3, 1.2 Hz, 1H), 9.09 (br s, 1H), 9.22 (s, 1H).<br>LC/MS: condition 3, retention time = 2.35 min<br>LC/MS ($ESI^+$) m/z; 480 $[M + H]^+$, LC/MS ($ESI^-$) m/z; 478 $[M - H]^-$ |
| 191 | $^1$H-NMR ($CDCl_3$) δ: 1.00-1.40 (m, 3H), 1.50-2.40 (m, 7H), 2.51-2.93 (m, 4H), 3.00-3.23 (m, 1H), 3.25-3.68 (m, 6H), 4.50-4.89 (m, 1H), 6.67-6.84 (m, 1H), 7.20-7.42 (m, 1H), 9.20 (s, 1H), 9.97 (br s, 1H).<br>LC/MS: condition 3, retention time = 1.13 min<br>LC/MS ($ESI^+$) m/z; 383 $[M + H]^+$<br>LC/MS ($ESI^-$) m/z; 381 $[M - H]^-$ |
| 192 | $^1$H-NMR (DMSO-$d_6$) δ: 1.13-1.42 (m, 2H), 1.64-2.15 (m, 6H), 2.78-3.60 (m, 9H), 6.81 (s, 1H), 7.40-7.62 (m, 2H), 8.99 (s, 1H), 9.08 (br s, 1H), 9.52 (s, 1H), 12.56 (s, 1H), 14.44 (br s, 1H).<br>LC/MS: condition 3, retention time = 0.68 min<br>LC/MS ($ESI^+$) m/z; 365 $[M + H]^+$<br>LC/MS ($ESI^-$) m/z; 363 $[M - H]^-$ |

TABLE[a] 122

| Ex | Data |
|---|---|
| 193 | $^1$H-NMR (DMSO-$d_6$) δ: 1.10-1.26 (m, 2H), 1.51-1.63 (m, 1H), 1.75 (qd, J = 12.2, 3.3 Hz, 2H), 1.92-2.04 (m, 4H), 2.42 (d, J = 6.6 Hz, 2H), 3.13 (tt, J = 12.6, 3.3 Hz, 1H), 3.72 (s, 2H), 6.80 (d, J = 3.6 Hz, 1H), 7.22 (tt, J = 6.9, 2.0 Hz, 1H), 7.28-7.38 (m, 4H), 7.49 (d, J = 3.3 Hz, 1H), 9.51 (s, 1H), 12.52 (br s, 1H).<br>LC/MS: condition 1, retention time = 2.67 min<br>LC/MS ($ESI^+$) m/z; 361 $[M + H]^+$<br>LC/MS ($ESI^-$) m/z; 359 $[M - H]^-$ |
| 194a | $^1$H-NMR (DMSO-$d_6$) δ: 1.55-1.70 (m, 4H), 1.81-1.92 (m, 2H), 1.99-2.07 (m, 1H), 2.20-2.35 (m, 2H), 2.84-2.89 (m, 1H), 3.16-3.29 (m, 1H), 3.75 (s, 2H), 7.13 (d, J = 3.3 Hz, 1H), 7.23 (tt, J = 6.9, 1.7 Hz, 1H), 7.31-7.43 (m, 5H), 9.50 (s, 1H), 12.49 (br s, 1H).<br>LC/MS: condition 1, retention time = 2.22 min<br>LC/MS ($ESI^+$) m/z; 347 $[M + H]^+$<br>LC/MS ($ESI^-$) m/z; 345 $[M - H]^-$ |
| 194b | $^1$H-NMR (DMSO-$d_6$) δ: 1.26-1.42 (m, 2H), 1.75 (qd, J = 12.7, 3.3 Hz, 2H), 1.95-2.14 (m, 5H), 2.51-2.62 (m, 1H), 3.15 (tt, J = 12.3, 3.7 Hz, 1H), 3.79 (s, 2H), 6.79 (d, J = 3.3 Hz, 1H), 7.22 (tt, J = 7.4, 1.6 Hz, 1H), 7.28-7.39 (m, 4H), 7.48 (d, J = 3.3 Hz, 1H), 9.50 (s, 1H), 12.51 (br s, 1H).<br>LC/MS: condition 1, retention time = 1.47 min<br>LC/MS ($ESI^+$) m/z; 347 $[M + H]^+$<br>LC/MS ($ESI^-$) m/z; 345 $[M - H]^-$ |
| 195a | $^1$H-NMR (DMSO-$d_6$) δ: 1.54-1.69 (m, 4H), 1.80-1.90 (m, 2H), 2.18-2.33 (m, 2H), 2.81-2.88 (m, 1H), 3.14-3.17 (m, 1H), 3.18-3.30 (m, 1H), 3.73 (s, 2H), 7.08-7.20 (m, 3H), 7.38-7.46 (m, 3H), 9.50 (s, 1H), 12.49 (br s, 1H).<br>LC/MS: condition 1, retention time = 2.55 min<br>LC/MS ($ESI^+$) m/z; 365 $[M + H]^+$<br>LC/MS ($ESI^-$) m/z; 363 $[M - H]^-$ |
| 195b | $^1$H-NMR (DMSO-$d_6$) δ: 1.25-1.41 (m, 2H), 1.67-1.83 (m, 2H), 1.95-2.12 (m, 5H), 2.51-2.60 (m, 1H), 3.08-3.20 (m, 1H), 3.78 (s, 2H), 6.80 (d, J = 3.3 Hz, 1H), 7.10-7.18 (m, 2H), 7.37-7.44 (m, 2H), 7.49 (d, J = 3.3 Hz, 1H), 9.51 (s, 1H), 12.53 (br s, 1H).<br>LC/MS: condition 1, retention time = 1.03 min |

TABLE[a] 122-continued

| Ex | Data |
|---|---|
| | LC/MS ($ESI^+$) m/z; 365 $[M + H]^+$<br>LC/MS ($ESI^-$) m/z; 363 $[M - H]^-$ |
| 196a | $^1$H-NMR ($CDCl_3$) δ: 1.77-1.92 (m, 6H), 2.19 (m, 2H), 2.81 (m, 1H), 3.00 (d, J = 13.2 Hz, 1H), 3.35 (m, 1H), 3.55 (d, J = 13.2 Hz, 1H), 6.75 (d, J = 3.3 Hz, 1H), 7.30 (m, 1H), 7.37 (m, 3H), 7.60 (m, 2H), 9.22 (s, 1H), 9.44 (br s, 1H).<br>LC/MS: condition 1, retention time = 2.75 min<br>LC/MS ($ESI^+$) m/z; 445 $[M + H]^+$<br>LC/MS ($ESI^-$) m/z; 443 $[M - H]^-$ |

TABLE[a] 123

| Ex | Data |
|---|---|
| 196b | $^1$H-NMR ($CDCl_3$) δ: 1.26-1.38 (m, 2H), 1.92 (m, 2H), 2.15 (m, 4H), 2.62 (tt, J = 11.4, 3.6 Hz, 1H), 3.02 (d, J = 13.2 Hz, 1H), 3.15 (tt, J = 12.0, 3.3 Hz, 1H), 3.60 (d, J = 13.2 Hz, 1H), 6.74 (d, J = 3.3 Hz, 1H), 7.30 (d, J = 2.7 Hz, 1H), 7.39 (m, 3H), 7.61 (m, 2H), 9.22 (s, 1H), 9.63 (br s, 1H).<br>LC/MS: condition 1, retention time = 2.57 min<br>LC/MS ($ESI^+$) m/z; 445 $[M + H]^+$<br>LC/MS ($ESI^-$) m/z; 443 $[M - H]^-$ |
| 197a | $^1$H-NMR (DMSO-$d_6$) δ: 1.56-1.71 (m, 4H), 1.80-1.91 (m, 2H), 2.13-2.35 (m, 3H), 2.82-2.88 (m, 1H), 3.19-3.30 (m, 1H), 3.75 (s, 2H), 7.10 (d, J = 3.3 Hz, 1H), 7.39-7.47 (m, 5H), 9.52 (s, 1H), 12.51 (br s, 1H).<br>LC/MS: condition 1, retention time = 2.75 min<br>LC/MS ($ESI^+$) m/z; 381 $[M + H]^+$<br>LC/MS ($ESI^-$) m/z; 379 $[M - H]^-$ |
| 197b | $^1$H-NMR (DMSO-$d_6$) δ: 1.26-1.41 (m, 2H), 1.75 (qd, J = 12.6, 2.3 Hz, 2H), 1.95-2.12 (m, 5H), 2.54 (tt, J = 10.9, 3.3 Hz, 1H), 3.14 (tt, J = 11.9, 3.3 Hz, 1H), 3.78 (s, 2H), 6.80 (d, J = 3.3 Hz, 1H), 7.34-7.43 (m, 4H), 7.49 (d, J = 3.0 Hz, 1H), 9.51 (s, 1H), 12.53 (br s, 1H).<br>LC/MS: condition 1, retention time = 2.62 min<br>LC/MS ($ESI^+$) m/z; 381 $[M + H]^+$<br>LC/MS ($ESI^-$) m/z; 379 $[M - H]^-$ |
| 198b | $^1$H-NMR ($CDCl_3$) δ: 1.33 (m, 2H), 1.94 (m, 2H), 2.14 (m, 4H), 2.69 (m, 1H), 2.83 (t, J = 6.9 Hz, 2H), 2.99 (t, J = 6.9 Hz, 2H), 3.16 (tt, J = 12.0, 3.3 Hz, 1H), 7.75 (d, J = 3.3 Hz, 1H), 7.16 (m, 2H), 7.29 (m, 3H), 9.21 (s, 1H), 9.46 (br s, 1H).<br>LC/MS: condition 1, retention time = 2.87 min<br>LC/MS ($ESI^+$) m/z; 395, 397 $[M + H]^+$<br>LC/MS ($ESI^-$) m/z; 393, 395 $[M - H]^-$ |
| 199b | $^1$H-NMR ($CDCl_3$) δ: 1.26-1.38 (m, 2H), 1.92 (m, 2H), 2.15 (m, 4H), 2.62 (tt, J = 11.1, 3.3 Hz, 1H), 2.98 (d, J = 12.9 Hz, 1H), 3.16 (tt, J = 12.6, 3.3 Hz, 1H), 3.60 (d, J = 13.2 Hz, 1H), 6.74 (d, J = 3.3 Hz, 1H), 7.30-7.39 (m, 3H), 7.55 (m, 2H), 9.23 (s, 1H), 9.77 (br s, 1H).<br>LC/MS: condition 1, retention time = 2.97 min<br>LC/MS ($ESI^+$) m/z; 479, 481 $[M + H]^+$<br>LC/MS ($ESI^-$) m/z; 477, 479 $[M - H]^-$ |
| 200b | $^1$H-NMR ($CDCl_3$) δ: 1.26-1.43 (m, 2H), 1.92 (m, 2H), 2.15 (m, 4H), 2.63 (tt, J = 11.4, 3.3 Hz, 1H), 3.00 (d, J = 13.2 Hz, 1H), 3.17 (tt, J = 12.3, 3.3 Hz, 1H), 3.60 (d, J = 13.2 Hz, 1H), 6.74 (d, J = 3.3 Hz, 1H), 7.09 (t, J = 8.4 Hz, 2H), 7.32 (d, J = 3.0 Hz, 1H), 7.59(dd, J = 8.7, 5.7 Hz, 2H), 9.24 (s, 1H), 10.00 (br s, 1H).<br>LC/MS: condition 1, retention time = 2.79 min<br>LC/MS ($ESI^+$) m/z; 463 $[M + H]^+$<br>LC/MS ($ESI^-$) m/z; 461 $[M - H]^-$ |

TABLE[a] 124

| Ex | Data |
|---|---|
| 201b | $^1$H-NMR (DMSO-$d_6$) δ: 1.19-1.35 (m, 2H), 1.78 (qd, J = 12.6, 4.0 Hz, 2H), 1.92-2.07 (m, 4H), 2.51-2.61 (m, 1H), 2.68-2.75 (m, 2H), 2.78-2.86 (m, 2H), 3.07-3.19 (m, 2H), 6.80 (d, J = 3.6 Hz, 1H), 7.06-7.14 (m, 2H), 7.24-7.31 (m, 2H), 7.49 (d, J = 3.6 Hz, 1H), 9.51 (s, 1H), 12.52 (br s, 1H).<br>LC/MS: condition 1, retention time = 2.57 min<br>LC/MS ($ESI^+$) m/z; 379 $[M + H]^+$<br>LC/MS ($ESI^-$) m/z; 377 $[M - H]^-$ |
| 202b | $^1$H-NMR ($CD_3OD$) δ: 1.52 (m, 2H), 1.90 (m, 2H), 2.18 (m, 4H), 2.80-3.00 (m, 3H), 3.23 (m, 1H), 4.92 (m, 1H), 6.82 (d, J = 3.3 Hz, |

TABLE[a] 124-continued

| Ex | Data |
| --- | --- |
| | 1H), 6.83-7.43 (m, 6H), 9.29 (s, 1H).<br>LC/MS: condition 1, retention time = 0.94 min<br>LC/MS ($ESI^+$) m/z; 377 $[M + H]^+$<br>LC/MS ($ESI^-$) m/z; 375 $[M - H]^-$ |
| 203b | $^1$H-NMR ($CD_3OD$) δ: 1.43 (m, 2H), 1.90 (m, 2H), 2.12 (m, 4H), 2.71 (tt, J = 11.1, 3.9 Hz, 1H), 2.79-2.91 (m, 2H), 3.21 (tt, J = 12.3, 3.6 Hz, 1H), 4.79 (m, 1H), 6.81 (d, J = 3.3 Hz, 1H), 7.25-7.42 (m, 6H), 9.27 (s, 1H).<br>LC/MS: condition 1, retention time = 1.29 min<br>LC/MS ($ESI^+$) m/z; 377 $[M + H]^+$<br>LC/MS ($ESI^-$) m/z; 375 $[M - H]^-$ |
| 204b | $^1$H-NMR ($CD_3OD$) δ: 1.57 (m, 2H), 1.93 (m, 2H), 2.20 (m, 4H), 2.95-3.09 (m, 3H), 3.24 (m, 1H), 4.90 (m, 1H), 6.83 (d, J = 3.3 Hz, 1H), 7.27-7.44 (m, 6H), 9.30 (s, 1H).<br>LC/MS: condition 1, retention time = 1.29 min<br>LC/MS ($ESI^+$) m/z; 377 $[M + H]^+$<br>LC/MS ($ESI^-$) m/z; 375 $[M - H]^-$ |
| 205 | LC/MS: condition 1, retention time = 3.80, 4.15 min (cis/trans mixture)<br>LC/MS ($ESI^+$) m/z; 367 $[M + H]^+$<br>LC/MS ($ESI^-$) m/z; 365 $[M - H]^-$ |
| 206 | $^1$H-NMR (DMSO-$d_6$) δ: 1.72-1.88 (m, 4H), 1.96-2.13 (m, 4H), 3.19-3.38 (m, 2H), 6.89 (d, J = 3.3 Hz, 1H), 7.10-7.18 (m, 2H), 7.51 (d, J = 3.0 Hz, 1H), 7.63-7.70 (m, 2H), 9.54 (s, 1H), 9.98 (s, 1H), 12.55 (br s, 1H).<br>LC/MS: condition 1, retention time = 3.63 min<br>LC/MS ($ESI^+$) m/z; 379 $[M + H]^+$<br>LC/MS ($ESI^-$) m/z; 377 $[M - H]^-$ |
| 207 | $^1$H-NMR (DMSO-$d_6$) δ: 1.66-1.82 (m, 4H), 1.89-1.97 (m, 2H), 2.00-2.09 (m, 2H), 2.32-2.43 (m, 1H), 3.14-3.25 (m, 1H), 4.27 (d, J = 6.3 Hz, 2H), 6.86 (dd, J = 3.0, 1.7 Hz, 1H), 7.12-7.20 (m, 2H), 7.26-7.32 (m, 2H), 7.50 (t, J = 3.0 Hz, 1H), 8.31-8.37 (m, 1H), 9.52 (s, 1H), 12.53 (br s, 1H).<br>LC/MS: condition 1, retention time = 3.49 min<br>LC/MS ($ESI^+$) m/z; 393 $[M + H]^+$<br>LC/MS ($ESI^-$) m/z; 391 $[M - H]^-$ |

TABLE[a] 125

| Ex | Data |
| --- | --- |
| 208 | $^1$H-NMR (DMSO-$d_6$) δ: 1.60-1.88 (m, 6H), 1.98-2.06 (m, 2H), 2.20-2.31 (m, 1H), 2.72 (t, J = 6.9 Hz, 2H), 3.11-3.22 (m, 1H), 3.24-3.31 (m, 2H), 6.84 (dd, J = 3.0, 1.7 Hz, 1H), 7.07-7.16 (m, 2H), 7.21-7.28 (m, 2H), 7.50 (t, J = 3.0 Hz, 1H), 7.85 (t, J = 5.6 Hz, 1H), 9.52 (s, 1H), 12.53 (br s, 1H).<br>LC/MS: condition 1, retention time = 3.59 min<br>LC/MS ($ESI^+$) m/z; 407 $[M + H]^+$<br>LC/MS ($ESI^-$) m/z; 405 $[M - H]^-$ |
| 209 | LC/MS: condition 1, retention time = 3.00 min<br>LC/MS ($ESI^+$) m/z; 357 $[M + H]^+$<br>LC/MS ($ESI^-$) m/z; 355 $[M - H]^-$ |
| 210 | $^1$H-NMR (DMSO-$d_6$) δ: 1.78-1.98 (m, 3H), 2.21 (br s, 1H), 2.91 (br s, 3H), 3.63 (s, 2H), 6.57 (s, 1H), 7.17 (s, 1H), 7.57 (d, J = 7.5 Hz, 2H), 7.82 (d, J = 7.5 Hz, 2H), 8.31 (s, 1H), 8.83 (s, 1H), 11.94 (br s, 1H).<br>LC/MS: condition 3, retention time = 1.21 min<br>LC/MS ($ESI^+$) m/z; 357 $[M + H]^+$ |
| 211 | $^1$H-NMR ($CDCl_3$) δ: 2.46-2.63 (m, 2H), 3.58-4.09 (m, 5H), 5.18 (s, 2H), 6.76 (s, 1H), 7.31-7.40 (m, 6H), 9.19 (br s, 1H), 9.24 (s, 1H).<br>LC/MS: condition 3, retention time = 2.05 min<br>LC/MS ($ESI^+$) m/z; 363 $[M + H]^+$<br>LC/MS ($ESI^-$) m/z; 361 $[M - H]^-$ |
| 212 | $^1$H-NMR ($CDCl_3$) δ: 2.02-2.41 (m, 5H), 2.45-2.73 (m, 3H), 3.02 (d, J = 10.7 Hz, 1H), 3.21-3.36 (m, 1H), 3.37 (d, J = 9.4 Hz, 1H), 4.86 (dd, J = 10.7, 3.4 Hz, 1H), 6.82 (d, J = 3.0 Hz, 1H), 7.32 (br s, 1H), 7.54 (d, J = 8.3 Hz, 2H), 7.63 (d, J = 8.3 Hz, 2H), 9.14 (br s, 1H), 9.25 (s, 1H).<br>LC/MS: condition 1, retention time = 2.67 min<br>LC/MS ($ESI^+$) m/z; 431 $[M + H]^+$<br>LC/MS ($ESI^-$) m/z; 429 $[M - H]^-$ |

TABLE[a] 126

| Ex | Data |
|---|---|
| 213 | LC/MS: condition 3, retention time = 1.35 min<br>LC/MS ($ESI^+$) m/z; 388 $[M + H]^+$<br>LC/MS ($ESI^-$) m/z; 386 $[M - H]^-$ |
| 214 | $^1$H-NMR (DMSO-$d_6$) δ: 1.86-2.05 (m, 4H), 2.19-2.32 (m, 2H), 2.88-3.00 (m, 2H), 3.37-3.50 (m, 1H), 3.60 (s, 2H), 6.80-6.85 (m, 1H), 7.47-7.54 (m, 2H), 7.80-7.89 (m, 1H), 8.38-8.42 (m, 1H), 9.53 (s, 1H), 12.54 (br s, 1H).<br>LC/MS: condition 3, retention time = 1.21 min<br>LC/MS ($ESI^+$) m/z; 368 $[M + H]^+$<br>LC/MS ($ESI^-$) m/z; 366 $[M - H]^-$ |
| 215 | $^1$H-NMR (DMSO-$d_6$) δ: 1.88-2.08 (m, 4H), 2.13-2.29 (m, 2H), 2.94-3.07 (m, 2H), 3.10-3.22 (m, 3H), 6.10-6.22 (m, 1H), 6.37-6.53 (m, 3H), 6.81 (d, J = 3.2 Hz, 1H), 7.49 (d, J = 3.2 Hz, 1H), 7.60 (s, 1H), 9.52 (s, 1H), 12.52 (br s, 1H).<br>LC/MS: condition 3, retention time = 1.40 min<br>LC/MS ($ESI^+$) m/z; 349 $[M + H]^+$ |
| 216 | $^1$H-NMR (DMSO-$d_6$) δ: 1.84-2.05 (m, 4H), 2.05-2.18 (m, 2H), 2.24 (s, 3H), 2.86-2.96 (m, 2H), 3.15-3.18 (m, 1H), 6.80 (d, J = 3.2 Hz, 1H), 7.49 (d, J = 3.2 Hz, 1H), 9.52 (s, 1H), 12.53 (br s, 1H).<br>LC/MS: condition 3, retention time = 0.47 min<br>LC/MS ($ESI^+$) m/z; 257 $[M + H]^+$ |
| 217 | $^1$H-NMR (DMSO-$d_6$) δ: 1.85-2.06 (m, 4H), 2.18-2.32 (m, 2H), 2.70-2.76 (m, 1H), 2.90-3.03 (m, 2H), 3.68 (s, 2H), 6.82 (d, J = 3.3 Hz, 1H), 7.45-7.62 (m, 4H), 9.52 (s, 1H), 12.53 (br s, 1H), 13.22 (br s, 1H).<br>LC/MS: condition 3, retention time = 1.35 min<br>LC/MS ($ESI^+$) m/z; 407, 409 $[M + H]^+$ |
| 218 | $^1$H-NMR (DMSO-$d_6$) δ: 1.88-2.15 (m, 4H), 2.25-2.40 (m, 2H), 2.97-3.10 (m, 2H), 3.14-3.30 (m, 1H), 3.83 (s, 2H), 6.84 (d, J = 3.0 Hz, 1H), 7.50 (d, J = 3.0 Hz, 1H), 7.89-7.96 (m, 1H), 8.00-8.15 (m, 2H), 8.89-9.00 (m, 2H), 9.52 (s, 1H), 12.53 (br s, 1H).<br>LC/MS: condition 3, retention time = 1.15 min<br>LC/MS ($ESI^+$) m/z; 385 $[M + H]^+$ |
| 219 | $^1$H-NMR (DMSO-$d_6$) δ: 1.82-2.08 (m, 4H), 2.20-2.32 (m, 2H), 2.94-3.10 (m, 2H), 3.10-3.23 (m, 1H), 3.50 (s, 2H), 6.80 (d, J = 3.2 Hz, 1H), 7.48 (d, J = 3.2 Hz, 1H), 8.01 (s, 1H), 8.31 (s, 1H), 9.52 (s, 1H), 12.53 (br s, 1H).<br>LC/MS: condition 3, retention time = 0.63 min<br>LC/MS ($ESI^+$) m/z; 324 $[M + H]^+$ |
| 220 | $^1$H-NMR (DMSO-$d_6$) δ: 1.93-2.00 (m, 4H), 2.16-2.22 (m, 2H), 2.93 (d, J = 11.4 Hz, 2H), 3.16 (s, 1H), 3.53 (s, 2H), 6.78 (dd, J = 3.3, 1.2, 1H), 7.13 (d, J = 8.4 Hz, 2H), 7.20 (s, 1H), 7.39 (d, J = 7.8 Hz, 2H), 7.45-7.47 (m, 1H), 9.48 (s, 1H).<br>LC/MS: condition 3, retention time = 1.54 min<br>LC/MS ($ESI^+$) m/z; 399 $[M + H]^+$ |

TABLE[a] 127

| Ex | Data |
|---|---|
| 221 | $^1$H-NMR (DMSO-$d_6$) δ: 1.95-2.06 (m, 4H), 2.23 (t, J = 9.8 Hz, 2H), 2.97 (d, J = 10.8 Hz, 2H), 3.16 (s, 1H), 3.59 (s, 2H), 6.80 (d, J = 3.3 Hz, 1H), 7.08 (s, 1H), 7.47-7.49 (m, 3H), 7.61 (d, J = 8.4 Hz, 2H), 7.72 (s, 1H), 8.22 (s, 1H), 9.49 (s, 1H).<br>LC/MS: condition 3, retention time = 0.48 min<br>LC/MS ($ESI^+$) m/z; 399 $[M + H]^+$ |
| 222 | $^1$H-NMR (DMSO-$d_6$) δ: 1.92-2.09 (m, 4H), 2.25-2.32 (m, 2H), 2.94 (d, J = 11.1 Hz, 2H), 3.68 (s, 2H), 6.82 (d, J = 2.7 Hz, 1H), 7.43-7.54 (m, 3H), 7.91 (t, J = 7.5 Hz, 1H), 9.50 (s, 1H).<br>LC/MS: condition 3, retention time = 1.35 min<br>LC/MS ($ESI^+$) m/z; 376 $[M + H]^+$<br>LC/MS ($ESI^-$) m/z; 374 $[M - H]^-$ |
| 223 | $^1$H-NMR (DMSO-$d_6$) δ: 1.93-2.05 (m, 4H), 2.24 (td, J = 11.1, 3.3 Hz, 2H), 2.92 (d, J = 11.7 Hz, 2H), 3.58 (s, 2H), 6.81 (d, J = 2.7 Hz, 1H), 7.47-7.53 (m, 2H), 7.75-7.80 (m, 1H), 7.86 (dd, J = 6.3, 2.1 Hz, 1H), 9.51 (s, 1H), 12.51 (br s, 1H).<br>LC/MS: condition 3, retention time = 1.37 min<br>LC/MS ($ESI^+$) m/z; 376 $[M + H]^+$<br>LC/MS ($ESI^-$) m/z; 374 $[M - H]^-$ |
| 224 | LC/MS: condition 3, retention time = 1.63 min<br>LC/MS ($ESI^+$) m/z; 437 $[M + H]^+$<br>LC/MS ($ESI^-$) m/z; 435 $[M - H]^-$ |
| 225 | $^1$H-NMR (DMSO-$d_6$) δ: 1.89-2.08 (m, 4H), 2.11-2.32 (m, 2H), 2.89-3.03 (m, 2H), 3.12-3.26 (m, 1H), 3.40-3.52 (m, 2H), 4.55 (s, 2H), 6.77-7.00 (m, 4H), 7.47-7.53 (m, 1H), 9.52 (s, 1H), 10.66 (br |

TABLE[a] 127-continued

| Ex | Data |
|---|---|
| | s, 1H), 12.53 (br s, 1H).<br>LC/MS: condition 3, retention time = 1.23 min<br>LC/MS ($ESI^+$) m/z; 404 $[M + H]^+$<br>LC/MS ($ESI^-$) m/z; 402 $[M - H]^-$ |
| 226 | $^1$H-NMR (DMSO-$d_6$) δ: 1.90-1.97 (m, 4H), 2.13 (t, J = 10.7 Hz, 2H), 2.69 (t, J = 6.6 Hz, 2H), 2.91-2.96 (m, 5H), 3.41 (s, 2H), 3.64 (t, J = 6.8 Hz, 2H), 6.73 (d, J = 8.4 Hz, 2H), 6.79 (d, J = 3.3 Hz, 1H), 7.15 (d, J = 8.1 Hz, 2H), 7.48 (d, J = 3.0 Hz, 1H), 9.50 (s, 1H).<br>LC/MS: condition 3, retention time = 1.48 min<br>LC/MS ($ESI^+$) m/z; 415 $[M + H]^+$ |
| 227 | $^1$H-NMR (DMSO-$d_6$) δ: 1.87-2.08 (m, 4H), 2.15-2.30 (m, 2H), 2.90-3.00 (m, 2H), 3.10-3.26 (m, 1H), 3.57 (s, 2H), 6.82 (d, J = 3.3 Hz, 1H), 7.19 (dd, J = 1.5, 8.5 Hz, 1H), 7.36 (d, J = 8.5 Hz, 1H), 7.39 (d, J = 1.5 Hz, 1H), 7.49 (d, J = 3.3 Hz, 1H), 9.52 (s, 1H), 12.52 (br s, 1H).<br>LC/MS: condition 3, retention time = 1.66 min<br>LC/MS ($ESI^+$) m/z; 413 $[M + H]^+$<br>LC/MS ($ESI^-$) m/z; 411 $[M - H]^-$ |

TABLE[a] 128

| Ex | Data |
|---|---|
| 228 | $^1$H-NMR (DMSO-$d_6$) δ: 1.87-2.08 (m, 4H), 2.18-2.32 (m, 2H), 2.90-3.03 (m, 2H), 3.04-3.22 (m, 1H), 3.55 (s, 2H), 6.39-6.48 (m, 2H), 6.81 (d, J = 3.0 Hz, 1H), 7.48 (d, J = 3.0 Hz, 1H), 9.51 (s, 1H), 12.52 (br s, 1H).<br>LC/MS: condition 3, retention time = 1.37 min<br>LC/MS ($ESI^+$) m/z; 357, 359 $[M + H]^+$ |
| 229 | $^1$H-NMR (DMSO-$d_6$) δ: 1.86-2.06 (m, 4H), 2.20-2.34 (m, 2H), 2.92-3.02 (m, 2H), 3.10-3.24 (m, 1H), 3.67 (s, 2H), 6.80-6.85 (m, 1H), 7.14-7.33 (m, 3H), 7.44-7.50 (m, 1H), 9.52 (s, 1H), 12.52 (br s, 1H).<br>LC/MS: condition 3, retention time = 1.60 min<br>LC/MS ($ESI^+$) m/z; 413 $[M + H]^+$<br>LC/MS ($ESI^-$) m/z; 411 $[M - H]^-$ |
| 230 | $^1$H-NMR (DMSO-$d_6$) δ: 1.94-2.17 (m, 4H), 3.46-3.65 (m, 3H), 4.25-4.38 (m, 2H), 6.91 (d, J = 3.3 Hz, 1H), 7.10 (t, J = 6.9 Hz, 1H), 7.31 (t, J = 6.9 Hz, 2H), 7.51 (d, J = 7.5 Hz, 2H), 7.52 (s, 2H), 9.54 (s, 1H), 12.56 (br s, 1H).<br>LC/MS: condition 3, retention time = 2.23 min<br>LC/MS ($ESI^+$) m/z; 370 $[M + H]^+$<br>LC/MS ($ESI^-$) m/z; 368 $[M - H]^-$ |
| 231 | LC/MS: condition 3, retention time = 1.44 min<br>LC/MS ($ESI^+$) m/z; 402, 404 $[M + H]^+$<br>LC/MS ($ESI^-$) m/z; 400, 403 $[M - H]^-$ |

TABLE[a] 128-continued

| Ex | Data |
|---|---|
| 232 | LC/MS: condition 3, retention time = 1.49 min<br>LC/MS ($ESI^+$) m/z; 390 $[M + H]^+$<br>LC/MS ($ESI^-$) m/z; 388 $[M - H]^-$ |
| 233 | LC/MS: condition 3, retention time = 1.77 min<br>LC/MS ($ESI^+$) m/z; 495, 497, 499 $[M + H]^+$<br>LC/MS ($ESI^-$) m/z; 493, 495, 497 $[M - H]^-$ |
| 234 | LC/MS: condition 3, retention time = 1.20 min<br>LC/MS ($ESI^+$) m/z; 425 $[M + H]^+$<br>LC/MS ($ESI^-$) m/z; 423 $[M - H]^-$ |
| 235 | LC/MS: condition 3, retention time = 2.44 min<br>LC/MS ($ESI^+$) m/z; 404, 406 $[M + H]^+$<br>LC/MS ($ESI^-$) m/z; 402, 404 $[M - H]^-$ |
| 236 | LC/MS: condition 3, retention time = 1.46 min<br>LC/MS ($ESI^+$) m/z; 353 $[M + H]^+$<br>LC/MS ($ESI^-$) m/z; 351 $[M - H]^-$ |
| 237 | LC/MS: condition 3, retention time = 1.51 min<br>LC/MS ($ESI^+$) m/z; 417, 419 $[M + H]^+$ |
| 238 | LC/MS: condition 3, retention time = 1.55 min<br>LC/MS ($ESI^+$) m/z; 417, 419 $[M + H]^+$<br>LC/MS ($ESI^-$) m/z; 415, 417 $[M - H]^-$ |
| 239 | LC/MS: condition 3, retention time = 0.50 min<br>LC/MS ($ESI^+$) m/z; 334 $[M + H]^+$<br>LC/MS ($ESI^-$) m/z; 332 $[M - H]^-$ |

TABLE[a] 129

| Ex | Data |
|---|---|
| 240 | $^1$H-NMR (DMSO-$d_6$) δ: 1.85-2.08 (m, 4H), 2.20-2.34 (m, 2H), 2.96-3.09 (m, 2H), 3.09-3.22 (m, 1H), 3.74 (s, 2H), 6.81 (d, J = 3.2 Hz, 1H), 7.48 (d, J = 3.2 Hz, 1H), 7.55 (s, 1H), 9.06 (s, 1H), 9.52 (s, 1H), 12.52 (br s, 1H).<br>LC/MS: condition 3, retention time = 0.88 min<br>LC/MS ($ESI^+$) m/z; 340 $[M + H]^+$ |
| 241 | $^1$H-NMR (DMSO-$d_6$) δ: 1.95-2.08 (m, 4H), 2.22 (t, J = 11.1 Hz, 2H), 2.95 (d, J = 9.9 Hz, 2H), 3.28 (s, 1H), 3.60 (s, 2H), 6.82 (br s, 1H), 7.28 (br s, 1H), 7.42 (d, J = 8.1 Hz, 2H), 7.49 (t, J = 2.7 Hz, 1H), 7.84 (d, J = 8.1 Hz, 2H), 7.91 (br s, 1H), 9.51 (s, 1H), 12.52 (br s, 1H).<br>LC/MS: condition 3, retention time = 0.73 min<br>LC/MS ($ESI^+$) m/z; 376 $[M + H]^+$<br>LC/MS ($ESI^-$) m/z; 374 $[M - H]^-$ |
| 242 | $^1$H-NMR (DMSO-$d_6$) δ: 1.95-2.04 (m, 4H), 2.28 (t, J = 10.1 Hz, 2H), 2.92 (d, J = 11.7 Hz, 2H), 3.16-3.19 (m, 1H), 3.70 (s, 2H), 6.82 (dd, J = 3.3, 1.5 Hz, 1H), 7.49 (d, J = 3.3 Hz, 1H), 7.92 (d, J = 8.7 Hz, 1H), 8.11-8.13 (m, 2H), 9.51 (s, 1H).<br>LC/MS: condition 3, retention time = 1.34 min<br>LC/MS ($ESI^+$) m/z; 383 $[M + H]^+$<br>LC/MS ($ESI^-$) m/z; 381 $[M - H]^-$ |

TABLE[a] 129-continued

| Ex | Data |
|---|---|
| 243 | $^1$H-NMR (DMSO-$d_6$) δ: 1.95-2.07 (m, 4H), 2.28 (t, J = 10.1 Hz, 2H), 2.94 (d, J = 11.1 Hz, 2H), 3.71 (s, 2H), 6.83 (dd, J = 3.3, 1.2 Hz, 1H), 7.49 (d, J = 3.3 Hz, 1H), 7.97 (m, 2H), 8.13 (s, 1H), 9.52 (s, 1H).<br>LC/MS: condition 3, retention time = 1.65 min<br>LC/MS ($ESI^+$) m/z; 426 $[M + H]^+$<br>LC/MS ($ESI^-$) m/z; 424 $[M - H]^-$ |
| 244 | $^1$H-NMR (DMSO-$d_6$) δ: 1.91-2.08 (m, 4H), 2.30 (td, J = 11.3, 2.9 Hz, 2H), 2.93 (d, J = 11.7 Hz, 2H), 3.16-3.23 (m, 1H), 3.74 (s, 2H), 6.82 (d, J = 3.3 Hz, 1H), 7.48 (d, J = 3.3 Hz, 1H), 7.89 (d, J = 7.8 Hz, 1H), 7.98 (s, 1H), 8.14 (d, J = 7.8 Hz, 1H), 9.50 (s, 1H).<br>LC/MS: condition 3, retention time = 1.60 min<br>LC/MS ($ESI^+$) m/z; 426 $[M + H]^+$<br>LC/MS ($ESI^-$) m/z; 424 $[M - H]^-$ |
| 245 | $^1$H-NMR (DMSO-$d_6$) δ: 1.35 (d, J = 6.6 Hz, 3H), 1.82-2.05 (m, 4H), 2.05-2.30 (m, 2H), 2.83-2.95 (m, 1H), 3.02-3.19 (m, 1H), 3.55 (q, J = 6.6 Hz, 1H), 6.79 (d, J = 8.3 Hz, 2H), 7.18-7.28 (m, 1H), 7.28-7.40 (m, 4H), 7.48 (d, J = 3.3 Hz, 1H), 9.51 (s, 1H), 12.51 (br s, 1H).<br>LC/MS: condition 3, retention time = 1.44 min<br>LC/MS ($ESI^+$) m/z; 347 $[M + H]^+$<br>LC/MS ($ESI^-$) m/z; 345 $[M - H]^-$ |
| 246 | LC/MS: condition 3, retention time = 1.16 min<br>LC/MS ($ESI^+$) m/z; 282 $[M + H]^+$<br>LC/MS ($ESI^-$) m/z; 280 $[M - H]^-$ |

TABLE[a] 130

| Ex | Data |
|---|---|
| 247 | LC/MS: condition 3, retention time = 2.38 min<br>LC/MS ($ESI^+$) m/z; 406 $[M + H]^+$<br>LC/MS ($ESI^-$) m/z; 404 $[M - H]^-$ |
| 248 | LC/MS: condition 3, retention time = 2.48 min<br>LC/MS ($ESI^+$) m/z; 422 $[M + H]^+$<br>LC/MS ($ESI^-$) m/z; 420 $[M - H]^-$ |
| 249 | LC/MS: condition 3, retention time = 2.48 min<br>LC/MS ($ESI^+$) m/z; 383 $[M + H]^+$<br>LC/MS ($ESI^-$) m/z; 381 $[M - H]^-$ |
| 250 | LC/MS: condition 3, retention time = 2.61 min<br>LC/MS ($ESI^+$) m/z; 401 $[M + H]^+$<br>LC/MS ($ESI^-$) m/z; 399 $[M - H]^-$ |
| 251 | LC/MS: condition 3, retention time = 2.67 min<br>LC/MS ($ESI^+$) m/z; 433 $[M + H]^+$<br>LC/MS ($ESI^-$) m/z; 431 $[M - H]^-$ |
| 252 | LC/MS: condition 3, retention time = 2.36 min<br>LC/MS ($ESI^+$) m/z; 390 $[M + H]^+$<br>LC/MS ($ESI^-$) m/z; 388 $[M - H]^-$ |
| 253 | LC/MS: condition 3, retention time = 0.65 min<br>LC/MS ($ESI^+$) m/z; 371 $[M + H]^+$<br>LC/MS ($ESI^-$) m/z; 369 $[M - H]^-$ |
| 254 | LC/MS: condition 3, retention time = 1.24 min<br>LC/MS ($ESI^+$) m/z; 343 $[M + H]^+$ |
| 255 | LC/MS: condition 3, retention time = 1.18 min<br>LC/MS ($ESI^+$) m/z; 335 $[M + H]^+$<br>LC/MS ($ESI^-$) m/z; 333 $[M - H]^-$ |
| 256 | LC/MS: condition 3, retention time = 1.40 min<br>LC/MS ($ESI^+$) m/z; 367 $[M + H]^+$<br>LC/MS ($ESI^-$) m/z; 365 $[M - H]^-$ |
| 257 | LC/MS: condition 3, retention time = 1.08 min<br>LC/MS ($ESI^+$) m/z; 327 $[M + H]^+$ |
| 258 | LC/MS: condition 3, retention time = 1.48 min<br>LC/MS ($ESI^+$) m/z; 407 $[M + H]^+$<br>LC/MS ($ESI^-$) m/z; 405 $[M - H]^-$ |
| 259 | LC/MS: condition 3, retention time = 1.16 min<br>LC/MS ($ESI^+$) m/z; 310 $[M + H]^+$<br>LC/MS ($ESI^-$) m/z; 308 $[M - H]^-$ |
| 260 | LC/MS: condition 3, retention time = 0.96 min<br>LC/MS ($ESI^+$) m/z; 354 $[M + H]^+$<br>LC/MS ($ESI^-$) m/z; 352 $[M - H]^-$ |
| 261 | LC/MS: condition 3, retention time = 1.09 min<br>LC/MS ($ESI^+$) m/z; 382 $[M + H]^+$ |

TABLE[a] 130-continued

| Ex | Data |
|---|---|
| 262 | LC/MS: condition 3, retention time = 2.22 min<br>LC/MS ($ESI^+$) m/z; 397 $[M + H]^+$<br>LC/MS ($ESI^-$) m/z; 395 $[M - H]^-$ |

TABLE[a] 131

| Ex | Data |
|---|---|
| 263 | LC/MS: condition 3, retention time = 2.49 min<br>LC/MS ($ESI^+$) m/z; 406 $[M + H]^+$<br>LC/MS ($ESI^-$) m/z; 404 $[M - H]^-$ |
| 264 | LC/MS: condition 3, retention time = 2.06 min<br>LC/MS ($ESI^+$) m/z; 386 $[M + H]^+$<br>LC/MS ($ESI^-$) m/z; 384 $[M - H]^-$ |
| 265 | LC/MS: condition 3, retention time = 1.17 min<br>LC/MS ($ESI^+$) m/z; 355 $[M + H]^+$ |
| 266 | LC/MS: condition 3, retention time = 1.17 min<br>LC/MS ($ESI^+$) m/z; 355 $[M + H]^+$ |
| 267 | LC/MS: condition 3, retention time = 1.10 min<br>LC/MS ($ESI^+$) m/z; 341 $[M + H]^+$ |
| 268 | LC/MS: condition 3, retention time = 1.51 min<br>LC/MS ($ESI^+$) m/z; 405 $[M + H]^+$ |
| 269 | LC/MS: condition 3, retention time = 1.51 min<br>LC/MS ($ESI^+$) m/z; 413 $[M + H]^+$<br>LC/MS ($ESI^-$) m/z; 411 $[M - H]^-$ |
| 270 | $^1$H-NMR ($CD_3OD$) δ: 1.34 (m, 2H), 1.84-2.18 (m, 7H), 2.96 (d, J = 6.9 Hz, 2H), 3.23 (m, 1H), 3.82 (s, 3H), 4.17 (s, 2H), 6.81 (d, J = 3.3 Hz, 1H), 7.01 (d, J = 8.7 Hz, 2H), 7.40 (d, J = 3.3 Hz, 1H), 7.44 (d, J = 8.7 Hz, 2H) 9.30 (s, 1H).<br>LC/MS: condition 1, retention time = 2.72 min<br>LC/MS ($ESI^+$) m/z; 391 $[M + H]^+$<br>LC/MS ($ESI^-$) m/z; 389 $[M - H]^-$ |
| 271 | LC/MS: condition 1, retention time = 0.37 min<br>LC/MS ($ESI^+$) m/z; 355 $[M + H]^+$<br>LC/MS ($ESI^-$) m/z; 353 $[M - H]^-$ |
| 272 | LC/MS: condition 1, retention time = 1.40 min<br>LC/MS ($ESI^+$) m/z; 315 $[M + H]^+$<br>LC/MS ($ESI^-$) m/z; 313 $[M - H]^-$ |
| 273 | LC/MS: condition 1, retention time = 3.12 min<br>LC/MS ($ESI^+$) m/z; 418 $[M + H]^+$<br>LC/MS ($ESI^-$) m/z; 416 $[M - H]^-$ |

TABLE[a] 131-continued

| Ex | Data |
|---|---|
| 274 | LC/MS: condition 1, retention time = 3.05 min<br>LC/MS ($ESI^+$) m/z; 418 $[M + H]^+$<br>LC/MS ($ESI^-$) m/z; 416 $[M - H]^-$ |
| 275 | LC/MS: condition 1, retention time = 4.40 min<br>LC/MS ($ESI^+$) m/z; 427 $[M + H]^+$<br>LC/MS ($ESI^-$) m/z; 425 $[M - H]^-$ |
| 276 | LC/MS: condition 1, retention time = 2.59 min<br>LC/MS ($ESI^+$) m/z; 391 $[M + H]^+$<br>LC/MS ($ESI^-$) m/z; 389 $[M - H]^-$ |
| 277 | LC/MS: condition 1, retention time = 2.52 min<br>LC/MS ($ESI^+$) m/z; 391 $[M + H]^+$<br>LC/MS ($ESI^-$) m/z; 389 $[M - H]^-$ |

TABLE[a] 132

| Ex | Data |
|---|---|
| 278 | LC/MS: condition 1, retention time = 0.37 min<br>LC/MS ($ESI^+$) m/z; 355 $[M + H]^+$<br>LC/MS ($ESI^-$) m/z; 353 $[M - H]^-$ |
| 279 | LC/MS: condition 1, retention time = 0.39 min<br>LC/MS ($ESI^+$) m/z; 355 $[M + H]^+$<br>LC/MS ($ESI^-$) m/z; 353 $[M - H]^-$ |
| 280 | LC/MS: condition 1, retention time = 0.63 min<br>LC/MS ($ESI^+$) m/z; 311 $[M + H]^+$<br>LC/MS ($ESI^-$) m/z; 309 $[M - H]^-$ |
| 281 | LC/MS: condition 1, retention time = 0.39 min<br>LC/MS ($ESI^+$) m/z; 336 $[M + H]^+$<br>LC/MS ($ESI^-$) m/z; 334 $[M - H]^-$ |
| 282 | LC/MS: condition 1, retention time = 2.70 min<br>LC/MS ($ESI^+$) m/z; 400 $[M + H]^+$<br>LC/MS ($ESI^-$) m/z; 398 $[M - H]^-$ |
| 283 | LC/MS: condition 3, retention time = 1.36 min<br>LC/MS ($ESI^+$) m/z; 325 $[M + H]^+$ |
| 284 | LC/MS: condition 3, retention time = 1.46 min<br>LC/MS ($ESI^+$) m/z; 339 $[M + H]^+$ |
| 285 | LC/MS: condition 3, retention time = 1.36 min<br>LC/MS ($ESI^+$) m/z; 325 $[M + H]^+$ |
| 286 | LC/MS: condition 3, retention time = 1.15 min<br>LC/MS ($ESI^+$) m/z; 311 $[M + H]^+$ |
| 287 | LC/MS: condition 3, retention time = 1.22 min<br>LC/MS ($ESI^+$) m/z; 325 $[M + H]^+$ |
| 288 | LC/MS: condition 3, retention time = 1.07 min<br>LC/MS ($ESI^+$) m/z; 356 $[M + H]^+$<br>LC/MS ($ESI^-$) m/z; 354 $[M - H]^-$ |
| 289 | LC/MS: condition 3, retention time = 1.33 min<br>LC/MS ($ESI^+$) m/z; 355 $[M + H]^+$ |
| 290 | LC/MS: condition 3, retention time = 1.49 min<br>LC/MS ($ESI^+$) m/z; 339 $[M + H]^+$<br>LC/MS ($ESI^-$) m/z; 337 $[M - H]^-$ |
| 291 | LC/MS: condition 3, retention time = 1.39 min<br>LC/MS ($ESI^+$) m/z; 325 $[M + H]^+$<br>LC/MS ($ESI^-$) m/z; 323 $[M - H]^-$ |
| 292 | LC/MS: condition 3, retention time = 2.33 min<br>LC/MS ($ESI^+$) m/z; 379 $[M + H]^+$<br>LC/MS ($ESI^-$) m/z; 377 $[M - H]^-$ |
| 293 | LC/MS: condition 3, retention time = 1.37 min<br>LC/MS ($ESI^+$) m/z; 355 $[M + H]^+$<br>LC/MS ($ESI^-$) m/z; 353 $[M - H]^-$ |
| 294 | LC/MS: condition 3, retention time = 1.09 min<br>LC/MS ($ESI^+$) m/z; 327 $[M + H]^+$<br>LC/MS ($ESI^-$) m/z; 325 $[M - H]^-$ |

TABLE[a] 133

| Ex | Data |
|---|---|
| 295 | LC/MS: condition 3, retention time = 1.36 min<br>LC/MS ($ESI^+$) m/z; 325 $[M + H]^+$ |
| 296 | LC/MS: condition 3, retention time = 1.10 min<br>LC/MS ($ESI^+$) m/z; 299 $[M + H]^+$ |
| 297 | LC/MS: condition 3, retention time = 1.07 min<br>LC/MS ($ESI^+$) m/z; 329 $[M + H]^+$ |

TABLE[a] 133-continued

| Ex | Data |
|---|---|
| 298 | LC/MS: condition 3, retention time = 1.03 min<br>LC/MS ($ESI^+$) m/z; 359 $[M + H]^+$ |
| 299 | LC/MS: condition 3, retention time = 1.62 min<br>LC/MS ($ESI^+$) m/z; 440 $[M + H]^+$ |
| 300 | LC/MS: condition 3, retention time = 2.38 min<br>LC/MS ($ESI^+$) m/z; 400 $[M + H]^+$<br>LC/MS ($ESI^-$) m/z; 398 $[M - H]^-$ |
| 301 | LC/MS: condition 3, retention time = 1.16 min<br>LC/MS ($ESI^+$) m/z; 350 $[M + H]^+$ |
| 302 | LC/MS: condition 3, retention time = 1.14 min<br>LC/MS ($ESI^+$) m/z; 338 $[M + H]^+$<br>LC/MS ($ESI^-$) m/z; 336 $[M - H]^-$ |
| 303 | LC/MS: condition 3, retention time = 1.31 min<br>LC/MS ($ESI^+$) m/z; 421 $[M + H]^+$ |
| 304 | LC/MS: condition 3, retention time = 1.45 min<br>LC/MS ($ESI^+$) m/z; 421 $[M + H]^+$ |
| 305 | LC/MS: condition 3, retention time = 1.20 min<br>LC/MS ($ESI^+$) m/z; 369 $[M + H]^+$ |
| 306 | LC/MS: condition 3, retention time = 1.54 min<br>LC/MS ($ESI^+$) m/z; 397 $[M + H]^+$ |
| 307 | LC/MS: condition 3, retention time = 1.62 min<br>LC/MS ($ESI^+$) m/z; 440 $[M + H]^+$ |
| 308 | LC/MS: condition 3, retention time = 1.74 min<br>LC/MS ($ESI^+$) m/z; 437 $[M + H]^+$<br>LC/MS ($ESI^-$) m/z; 435 $[M - H]^-$ |
| 309 | LC/MS: condition 3, retention time = 2.00 min<br>LC/MS ($ESI^+$) m/z; 533 $[M + H]^+$<br>LC/MS ($ESI^-$) m/z; 531 $[M - H]^-$ |
| 310 | LC/MS: condition 3, retention time = 1.71 min<br>LC/MS ($ESI^+$) m/z; 440 $[M + H]^+$ |
| 311 | LC/MS: condition 3, retention time = 1.30 min<br>LC/MS ($ESI^+$) m/z; 397 $[M + H]^+$ |
| 312 | LC/MS: condition 3, retention time = 1.46 min<br>LC/MS ($ESI^+$) m/z; 383 $[M + H]^+$<br>LC/MS ($ESI^-$) m/z; 381 $[M - H]^-$ |
| 313 | LC/MS: condition 3, retention time = 1.46 min<br>LC/MS ($ESI^+$) m/z; 383 $[M + H]^+$ |
| 314 | LC/MS: condition 3, retention time = 1.23 min<br>LC/MS ($ESI^+$) m/z; 393 $[M + H]^+$ |

TABLE[a] 134

| Ex | Data |
|---|---|
| 315 | LC/MS: condition 3, retention time = 0.96 min<br>LC/MS ($ESI^+$) m/z; 384 $[M + H]^+$ |
| 316 | LC/MS: condition 3, retention time = 1.41 min<br>LC/MS ($ESI^+$) m/z; 337 $[M + H]^+$ |
| 317 | LC/MS: condition 3, retention time = 2.52 min<br>LC/MS ($ESI^+$) m/z; 421 $[M + H]^+$<br>LC/MS ($ESI^-$) m/z; 419 $[M - H]^-$ |
| 318 | LC/MS: condition 3, retention time = 1.13 min<br>LC/MS ($ESI^+$) m/z; 382 $[M + H]^+$ |
| 319 | LC/MS: condition 3, retention time = 1.13 min<br>LC/MS ($ESI^+$) m/z; 382 $[M + H]^+$ |
| 320 | LC/MS: condition 3, retention time = 1.41 min<br>LC/MS ($ESI^+$) m/z; 436 $[M + H]^+$<br>LC/MS ($ESI^-$) m/z; 434 $[M - H]^-$ |
| 321 | LC/MS: condition 3, retention time = 1.41 min<br>LC/MS ($ESI^+$) m/z; 436 $[M + H]^+$<br>LC/MS ($ESI^-$) m/z; 434 $[M - H]^-$ |
| 322 | LC/MS: condition 3, retention time = 1.60 min<br>LC/MS ($ESI^+$) m/z; 421 $[M + H]^+$<br>LC/MS ($ESI^-$) m/z; 419 $[M - H]^-$ |
| 323 | LC/MS: condition 3, retention time = 1.76 min<br>LC/MS ($ESI^+$) m/z; 405 $[M + H]^+$ |
| 324 | LC/MS: condition 3, retention time = 1.83 min<br>LC/MS ($ESI^+$) m/z; 419 $[M + H]^+$ |
| 325 | LC/MS: condition 3, retention time = 1.23 min<br>LC/MS ($ESI^+$) m/z; 343 $[M + H]^+$ |
| 326 | LC/MS: condition 3, retention time = 1.38 min<br>LC/MS ($ESI^+$) m/z; 387 $[M + H]^+$ |
| 327 | LC/MS: condition 3, retention time = 1.19 min<br>LC/MS ($ESI^+$) m/z; 341 $[M + H]^+$ |

TABLE[a] 134-continued

| Ex | Data |
|---|---|
| 328 | LC/MS: condition 3, retention time = 1.26 min<br>LC/MS ($ESI^+$) m/z; 361 $[M + H]^+$<br>LC/MS ($ESI^-$) m/z; 359 $[M - H]^-$ |
| 329 | LC/MS: condition 3, retention time = 1.08 min<br>LC/MS ($ESI^+$) m/z; 285 $[M + H]^+$<br>LC/MS ($ESI^-$) m/z; 283 $[M - H]^-$ |
| 330 | LC/MS: condition 3, retention time = 1.18 min<br>LC/MS ($ESI^+$) m/z; 299 $[M + H]^+$ |
| 331 | LC/MS: condition 3, retention time = 1.28 min<br>LC/MS ($ESI^+$) m/z; 313 $[M + H]^+$ |
| 332 | LC/MS: condition 3, retention time = 1.38 min<br>LC/MS ($ESI^+$) m/z; 327 $[M + H]^+$ |
| 333 | LC/MS: condition 3, retention time = 1.21 min<br>LC/MS ($ESI^+$) m/z; 309 $[M + H]^+$ |
| 334 | LC/MS: condition 1, retention time = 0.34 min<br>LC/MS ($ESI^+$) m/z; 424 $[M + H]^+$<br>LC/MS ($ESI^-$) m/z; 422 $[M - H]^-$ |

TABLE[a] 135

| Ex | Data |
|---|---|
| 335 | LC/MS: condition 1, retention time = 2.94 min<br>LC/MS ($ESI^+$) m/z; 468 $[M + H]^+$<br>LC/MS ($ESI^-$) m/z; 466 $[M - H]^-$ |
| 336 | LC/MS: condition 1, retention time = 2.75 min<br>LC/MS ($ESI^+$) m/z; 468 $[M + H]^+$<br>LC/MS ($ESI^-$) m/z; 466 $[M - H]^-$ |
| 337 | LC/MS: condition 1, retention time = 2.77 min<br>LC/MS ($ESI^+$) m/z; 440 $[M + H]^+$<br>LC/MS ($ESI^-$) m/z; 438 $[M - H]^-$ |
| 338 | LC/MS: condition 3, retention time = 1.15 min<br>LC/MS ($ESI^+$) m/z; 329 $[M + H]^+$<br>LC/MS ($ESI^-$) m/z; 327 $[M - H]^-$ |
| 339 | LC/MS: condition 3, retention time = 1.19 min<br>LC/MS ($ESI^+$) m/z; 347 $[M + H]^+$<br>LC/MS ($ESI^-$) m/z; 345 $[M - H]^-$ |
| 340 | LC/MS: condition 3, retention time = 0.81 min<br>LC/MS ($ESI^+$) m/z; 368 $[M + H]^+$ |
| 341 | LC/MS: condition 3, retention time = 1.39 min<br>LC/MS ($ESI^+$) m/z; 410 $[M + H]^+$<br>LC/MS ($ESI^-$) m/z; 408 $[M - H]^-$ |
| 342 | LC/MS: condition 3, retention time = 1.85 min<br>LC/MS ($ESI^+$) m/z; 403 $[M + H]^+$<br>LC/MS ($ESI^-$) m/z; 401 $[M - H]^-$ |
| 343 | LC/MS: condition 3, retention time = 1.38 min<br>LC/MS ($ESI^+$) m/z; 383 $[M + H]^+$<br>LC/MS ($ESI^-$) m/z; 381 $[M - H]^-$ |
| 344 | LC/MS: condition 3, retention time = 1.31 min<br>LC/MS ($ESI^+$) m/z; 343 $[M + H]^+$<br>LC/MS ($ESI^-$) m/z; 341 $[M - H]^-$ |
| 345 | LC/MS: condition 3, retention time = 1.31 min<br>LC/MS ($ESI^+$) m/z; 432 $[M + H]^+$<br>LC/MS ($ESI^-$) m/z; 430 $[M - H]^-$ |
| 346 | $^1$H-NMR ($CD_3OD$) δ: 1.39-1.74 (m, 6H), 1.95 (m, 2H), 2.19 (tt, J = 11.7, 3.3, 1H), 3.05 (tt, J = 12.6, 3.9, 1H), 3.67 (d, J = 14.4 Hz, 1H), 4.02 (d, J = 14.4 Hz, 1H), 6.70 (d, J = 3.3 Hz, 1H), 7.28 (m, 4H), 7.50 (m, 2H), 9.17 (s, 1H).<br>LC/MS: condition 1, retention time = 3.77 min<br>LC/MS ($ESI^+$) m/z; 473 $[M + H]^+$<br>LC/MS ($ESI^-$) m/z; 389 $[M - H]^-$ |
| 347 | $^1$H-NMR ($CD_3OD$) δ: 1.41-1.76 (m, 6H), 1.96 (m, 2H), 2.20 (tt, J = 12, 3.3, 1H), 3.06 (tt, J = 11.7, 3.6, 1H), 3.65 (d, J = 14.4 Hz, 1H), 4.02 (d, J = 14.4 Hz, 1H), 6.70 (d, J = 3.3 Hz, 1H), 7.02 (t, J = 8.7 Hz, 2H), 7.28 (d, J = 3.3 Hz, 1H), 7.53 (dd, J = 8.7, 5.4 Hz, 2H), 9.17 (s, 1H).<br>LC/MS: condition 1, retention time = 3.84 min<br>LC/MS ($ESI^+$) m/z; 491 $[M + H]^+$<br>LC/MS ($ESI^-$) m/z; 489 $[M - H]^-$ |

TABLE[a] 136

| Ex | Data |
|---|---|
| 348 | $^1$H-NMR (DMSO-$d_6$) δ: 1.56-1.85 (m, 4H), 1.92 (dd, J = 12.7, 2.5 Hz, 2H), 2.03 (dd, J = 13.1, 3.3 Hz, 2H), 2.28 (tt, J = 11.4, 3.3 Hz, 1H), 3.16 (tt, J = 11.9, 3.7 Hz, 1H), 6.69 (br s, 1H), 6.82-6.85 (m, 1H), 7.24 (br s, 1H), 7.49 (t, J = 2.9 Hz, 1H), 9.51 (s, 1H), 12.52 (br s, 1H).<br>LC/MS: condition 1, retention time = 1.22 min<br>LC/MS ($ESI^+$) m/z; 285 $[M + H]^+$<br>LC/MS ($ESI^-$) m/z; 283 $[M - H]^-$ |
| 349 | LC/MS: condition 1, retention time = 3.42 min<br>LC/MS ($ESI^+$) m/z; 379 $[M + H]^+$<br>LC/MS ($ESI^-$) m/z; 377 $[M - H]^-$ |
| 350 | $^1$H-NMR (DMSO-$d_6$) δ: 1.67-1.87 (m, 4H), 1.91-2.10 (m, 4H), 2.35-2.43 (m, 1H), 3.14-3.25 (m, 1H), 4.37 (d, J = 5.7 Hz, 2H), 6.84-6.87 (m, 1H), 7.44 (d, J = 7.8 Hz, 2H), 7.49 (t, J = 2.9 Hz, 1H), 7.80 (d, J = 7.8 Hz, 2H), 8.45 (t, J = 5.7 Hz, 1H), 9.51 (s, 1H), 12.52 (br s, 1H).<br>LC/MS: condition 1, retention time = 3.34 min<br>LC/MS ($ESI^+$) m/z; 400 $[M + H]^+$<br>LC/MS ($ESI^-$) m/z; 398 $[M - H]^-$ |
| 351 | $^1$H-NMR (DMSO-$d_6$) δ: 1.65-1.83 (m, 4H), 1.88-2.11 (m, 5H), 3.14-3.26 (m, 1H), 6.19 (d, J = 7.8 Hz, 1H), 6.84-6.87 (m, 1H), 7.46-7.51 (m, 6H), 9.14 (d, J = 7.8 Hz, 1H), 9.51 (s, 1H), 12.52 (br s, 1H).<br>LC/MS: condition 1, retention time = 3.34 min<br>LC/MS ($ESI^+$) m/z; 400 $[M + H]^+$<br>LC/MS ($ESI^-$) m/z; 398 $[M - H]^-$ |
| 352 | $^1$H-NMR (DMSO-$d_6$) δ: 1.60-1.88 (m, 6H), 1.98-2.06 (m, 2H), 2.19-2.32 (m, 1H), 2.69-2.76 (m, 2H), 3.12-3.22 (m, 1H), 3.25-3.33 (m, 2H), 6.83-6.86 (m, 1H), 7.24 (d, J = 8.3 Hz, 2H), 7.35 (d, J = 8.9 Hz, 2H), 7.50 (t, J = 2.6 Hz, 1H), 7.85 (t, J = 5.6 Hz, 1H), 9.52 (s, 1H), 12.53 (br s, 1H).<br>LC/MS: condition 1, retention time = 3.84 min<br>LC/MS ($ESI^+$) m/z; 423 $[M + H]^+$<br>LC/MS ($ESI^-$) m/z; 421 $[M - H]^-$ |
| 353 | $^1$H-NMR (DMSO-$d_6$) δ: 1.55-1.89 (m, 6H), 1.97-2.05 (m, 2H), 2.26-2.39 (m, 1H), 3.11-3.22 (m, 1H), 3.26-3.34 (m, 2H), 4.58-4.66 (m, 1H), 5.45 (d, J = 4.5 Hz, 1H), 6.84 (d, J = 3.3 Hz, 1H), 7.21-7.28 (m, 1H), 7.33 (d, J = 4.1 Hz, 4H), 7.49 (d, J = 3.3 Hz, 1H), 7.81 (t, J = 5.3 Hz, 1H), 9.51 (s, 1H), 12.52 (br s, 1H).<br>LC/MS: condition 1, retention time = 3.19 min<br>LC/MS ($ESI^+$) m/z; 405 $[M + H]^+$<br>LC/MS ($ESI^-$) m/z; 403 $[M - H]^-$ |

TABLE[a] 137

| Ex | Data |
|---|---|
| 354 | $^1$H-NMR (DMSO-$d_6$) δ: 1.65-1.82 (m, 4H), 1.87-1.95 (m, 2H), 2.00-2.09 (m, 2H), 2.36-2.43 (m, 1H), 3.13-3.24 (m, 1H), 3.85-3.98 (m, 2H), 6.84-6.87 (m, 1H), 7.49 (t, J = 2.9 Hz, 1H), 8.47 (t, J = 6.5 Hz, 1H), 9.51 (s, 1H), 12.52 (br s, 1H).<br>LC/MS: condition 1, retention time = 3.27 min<br>LC/MS ($ESI^+$) m/z; 367 $[M + H]^+$<br>LC/MS ($ESI^-$) m/z; 365 $[M - H]^-$ |
| 355 | $^1$H-NMR (DMSO-$d_6$) δ: 1.64-1.82 (m, 4H), 1.87-1.96 (m, 2H), 2.01-2.09 (m, 2H), 2.26-2.39 (m, 1H), 3.14-3.25 (m, 1H), 4.15 (d, J = 5.9 Hz, 2H), 6.85-6.88 (m, 1H), 7.50 (t, J = 2.6 Hz, 1H), 8.55 (t, J = 5.3 Hz, 1H), 9.52 (s, 1H), 12.53 (br s, 1H).<br>LC/MS: condition 1, retention time = 2.65 min<br>LC/MS ($ESI^+$) m/z; 324 $[M + H]^+$<br>LC/MS ($ESI^-$) m/z; 322 $[M - H]^-$ |
| 356 | $^1$H-NMR (DMSO-$d_6$) δ: 1.64-1.82 (m, 4H), 1.87-1.95 (m, 2H), 2.00-2.08 (m, 2H), 2.26-2.37 (m, 1H), 2.66 (t, J = 6.6 Hz, 2H), 3.13-3.24 (m, 1H), 3.26-3.32 (m, 2H), 6.84-6.87 (m, 1H), 1 7.50 (t, J = 3.3 Hz, H), 8.19 (t, J = 5.6 Hz, 1H), 9.52 (s, 1H), 12.53 (br s, 1H).<br>LC/MS: condition 1, retention time = 2.65 min<br>LC/MS ($ESI^+$) m/z; 338 $[M + H]^+$<br>LC/MS ($ESI^-$) m/z; 336 $[M - H]^-$ |
| 357 | LC/MS: condition 1, retention time = 2.90 min<br>LC/MS ($ESI^+$) m/z; 364 $[M + H]^+$<br>LC/MS ($ESI^-$) m/z; 362 $[M - H]^-$ |

TABLE[a] 137-continued

| Ex | Data |
|---|---|
| 358 | LC/MS: condition 1, retention time = 2.47 min<br>LC/MS ($ESI^+$) m/z; 355 $[M + H]^+$<br>LC/MS ($ESI^-$) m/z; 353 $[M - H]^-$ |
| 359 | $^1$H-NMR (DMSO-$d_6$) δ: 0.39 (dd, J = 4.3, 2.6 Hz, 2H), 0.61 (dd, J = 6.9, 2.3 Hz, 2H), 1.61-1.78 (m, 4H), 1.80-1.89 (m, 2H), 1.98-2.07 (m, 2H), 2.16-2.28 (m, 1H), 2.60-2.68 (m, 1H), 3.11-3.22 (m, 1H), 6.84 (dd, J = 3.3, 2.0 Hz, 1H), 7.50 (t, J = 3.0 Hz, 1H), 7.83 (d, J = 4.3 Hz, 1H), 9.52 (s, 1H), 12.53 (br s, 1H).<br>LC/MS: condition 1, retention time = 2.92 min<br>LC/MS ($ESI^+$) m/z; 325 $[M + H]^+$<br>LC/MS ($ESI^-$) m/z; 323 $[M - H]^-$ |
| 360 | $^1$H-NMR (DMSO-$d_6$) δ: 1.62-1.80 (m, 4H), 1.83-1.92 (m, 2H), 1.99-2.07 (m, 2H), 2.26-2.37 (m, 1H), 3.10-3.19 (m, 1H), 3.32-3.44 (m, 4H), 4.65 (t, J = 5.6 Hz, 1H), 6.83-6.87 (m, 1H), 7.48-7.52 (m, 1H), 7.76 (t, J = 5.9 Hz, 1H), 9.52 (s, 1H), 12.53 (br s, 1H).<br>LC/MS: condition 1, retention time = 2.34 min<br>LC/MS ($ESI^+$) m/z; 329 $[M + H]^+$<br>LC/MS ($ESI^-$) m/z; 327 $[M - H]^-$ |

TABLE[a] 138

| Ex | Data |
|---|---|
| 361 | $^1$H-NMR (DMSO-$d_6$) δ: 1.55-1.70 (m, 2H), 1.76-1.87 (m, 4H), 1.97-2.06 (m, 2H), 2.32-2.46 (m, 1H), 3.12-3.23 (m, 1H), 3.58 (dd, J = 10.2, 3.6 Hz, 1H), 3.89-3.96 (m, 1H), 3.99-4.07 (m, 1H), 4.41-4.49 (m, 1H), 5.68-5.73 (m, 1H), 6.88 (dd, J = 3.3, 2.0 Hz, 2H), 7.49 (t, J = 3.0 Hz, 1H), 9.51 (s, 1H), 12.52 (br s, 1H).<br>LC/MS: condition 1, retention time = 1.79 min<br>LC/MS ($ESI^+$) m/z; 341 $[M - H]^+$<br>LC/MS ($ESI^-$) m/z; 339 $[M - H]^-$ |
| 362 | $^1$H-NMR (DMSO-$d_6$) δ: 1.59-1.86 (m, 6H), 1.98-2.06 (m, 3H), 2.19-2.30 (m, 2H), 2.83 (t, J = 7.3 Hz, 2H), 3.15-3.25 (m, 1H), 6.83-6.86 (m, 1H), 7.43 (d, J = 7.9 Hz, 2H), 7.50 (t, J = 3.0 Hz, 1H), 7.78 (d, J = 7.6 Hz, 2H), 7.87 (t, J = 5.6 Hz, 1H), 9.52 (s, 1H), 12.53 (br s, 1H).<br>LC/MS: condition 1, retention time = 3.40 min<br>LC/MS ($ESI^+$) m/z; 414 $[M + H]^+$<br>LC/MS ($ESI^-$) m/z; 412 $[M - H]^-$ |
| 363 | $^1$H-NMR (DMSO-$d_6$) δ: 1.56-1.70 (m, 2H), 1.73-1.91 (m, 4H), 1.97-2.06 (m, 2H), 2.33-2.44 (m, 1H), 3.13-3.25 (m, 1H), 3.74-3.86 (m, 1H), 3.97-4.05 (m, 1H), 4.11-4.20 (m, 1H), 4.41-4.56 (m, 2H), 6.89 (dd, J = 3.3, 2.0 Hz, 1H), 7.49 (t, J = 2.6 Hz, 1H), 9.51 (s, 1H), 12.52 (br s, 1H).<br>LC/MS: condition 1, retention time = 2.88 min<br>LC/MS ($ESI^+$) m/z; 350 $[M + H]^+$<br>LC/MS ($ESI^-$) m/z; 348 $[M - H]^-$ |
| 364 | $^1$H-NMR ($CDCl_3$) δ: 1.30-1.40 (m, 2H), 1.81-2.02 (m, 2H), 2.05-2.25 (m, 5H), 3.10 (d, J = 6.0 Hz, 2H), 3.12-3.21 (m, 1H), 6.76 (dd, J = 3.6, 2.1 Hz, 1H), 7.29 (t, J = 3.0 Hz, 1H), 7.55-7.73 (m, 3H), 7.91-7.99 (m, 2H), 9.00 (br s, 1H), 9.21 (s, 1H).<br>LC/MS: condition 3, retention time = 2.00 min<br>LC/MS ($ESI^+$) m/z; 396 $[M + H]^+$<br>LC/MS ($ESI^-$) m/z; 394 $[M - H]^-$ |
| 365 | $^1$H-NMR ($CDCl_3$) δ: 1.31-1.56 (m, 2H), 1.86-2.02 (m, 2H), 2.06-2.24 (m, 5H), 3.09 (d, J = 6.0 Hz, 2H), 3.11-3.22 (m, 1H), 6.76 (dd, J = 6.0, 2.4 Hz, 1H), 7.22-7.31 (m, 3H), 7.93-8.00 (m, 2H), 9.13 (br s, 1H), 9.21 (s, 1H).<br>LC/MS: condition 3, retention time = 2.06 min<br>LC/MS ($ESI^+$) m/z; 414 $[M + H]^+$<br>LC/MS ($ESI^-$) m/z; 412 $[M - H]^-$ |
| 366 | $^1$H-NMR (DMSO-$d_6$) δ: 0.96-1.07 (m, 4H), 1.31-1.51 (m, 2H), 1.70-1.91 (m, 2H), 1.95-2.18 (m, 4H), 2.69-2.84 (m, 1H), 3.15 (d, J = 5.7 Hz, 2H), 3.65 (s, 2H), 6.81 (dd, J = 3.3, 1.8 Hz, 1H), 7.49 (t, J = 2.7 Hz, 1H), 9.51 (s, 1H), 12.52 (br s, 1H).<br>LC/MS: condition 3, retention time = 1.51 min<br>LC/MS ($ESI^+$) m/z; 360 $[M + H]^+$<br>LC/MS ($ESI^-$) m/z; 358 $[M - H]^-$ |

TABLE[a] 139

| Ex | Data |
|---|---|
| 367 | $^1$H-NMR ($CDCl_3$) δ: 1.20-1.38 (m, 2H), 1.58-1.67 (m, 1H), 1.87-2.05 (m, 2H), 2.06-2.21 (m, 4H), 3.09-3.19 (m, 1H), 3.22 (d, J = 6.0 Hz, 2H), 6.78 (dd, J = 3.0, 1.8 Hz, 1H), 7.29 (t, J = 3.0 Hz, 1H), 9.11 (br s, 1H), 9.22 (s, 1H).<br>LC/MS: condition 3, retention time = 2.42 min<br>LC/MS ($ESI^+$) m/z; 382 $[M + H]^+$ |
| 368 | $^1$H-NMR ($CDCl_3$) δ: 1.51-1.56 (m, 2H), 1.92-2.12 (m, 2H), 2.13-2.32 (m, 4H), 2.33-2.51 (m, 1H), 3.11-3.20 (m, 1H), 3.21 (d, J = 6.6 Hz, |

TABLE[a] 139-continued

| Ex | Data |
|---|---|
| | 2H), 6.77 (dd, J = 6.0, 2.1 Hz, 1H), 7.30 (t, J = 6.0 Hz, 1H), 9.11 (br s, 1H), 9.22 (s, 1H). LC/MS: condition 3, retention time = 2.16 min LC/MS ($ESI^+$) m/z; 388 $[M + H]^+$ LC/MS ($ESI^-$) m/z; 386 $[M - H]^-$ |
| 369 | $^1$H-NMR ($CDCl_3$) δ: 1.20-1.38 (m, 2H), 1.70-1.85 (m, 1H), 1.85-2.08 (m, 4H), 2.11-2.22 (m, 2H), 3.10-3.22 (m, 1H), 3.26 (d, J = 6.6 Hz, 2H), 6.78 (dd, J = 3.3, 2.4 Hz, 1H), 7.29 (t, J = 2.7 Hz, 1H), 9.14 (br s, 1H), 9.22 (s, 1H). LC/MS: condition 3, retention time = 2.09 min LC/MS ($ESI^+$) m/z; 297 $[M + H]^+$ LC/MS($ESI^-$) m/z; 295 $[M - H]^-$ |
| 370 | $^1$H-NMR (DMSO-$d_6$) δ: 1.22-1.40 (m, 2H), 1.47 (s, 6H), 1.64-1.83 (m, 3H), 1.91-2.09 (m, 3H), 2.41-2.57 (m, 1H), 3.21-3.36 (m, 1H), 3.30 (br s, 1H), 4.26 (d, J = 6.9 Hz, 1H), 5.07 (s, 1H), 6.85-6.90 (m, 1H), 7.42-7.52 (m, 1H), 7.89 (s, 1H), 9.52 (s, 1H), 12.53 (s, 1H). LC/MS: condition 3, retention time = 1.53 min LC/MS ($ESI^+$) m/z; 381 $[M + H]^+$ LC/MS ($ESI^-$) m/z; 379 $[M - H]^-$ |
| 371 | $^1$H-NMR (DMSO-$d_6$) δ: 1.06-1.24 (m, 2H), 1.29-1.45 (m, 1H), 1.66-1.84 (m, 2H), 1.87-2.07 (m, 4H), 2.40-2.54 (m, 2H), 3.05-3.20 (m, 1H), 3.30 (br s, 1H), 6.79 (d, J = 3.3 Hz, 1H), 7.48 (d, J = 3.3 Hz, 1H), 9.50 (s, 1H). LC/MS: condition 3, retention time = 0.99 min LC/MS ($ESI^+$) m/z; 271 $[M + H]^+$ |
| 372 | $^1$H-NMR (DMSO-$d_6$) δ: 1.12-1.31 (m, 2H), 1.52-1.63 (m, 1H), 1.64-1.82 (m, 2H), 1.82-2.07 (m, 4H), 3.04 (t, J = 6.6 Hz, 2H), 3.08-3.20 (m, 1H), 3.65 (s, 2H), 6.80 (dd, J = 3.0, 1.8 Hz, 1H), 7.48 (t, J = 3.0 Hz, 1H), 8.19-8.28 (m, 1H), 9.51 (s, 1H), 12.51 (br s, 1H). LC/MS: condition 3, retention time = 1.51 min LC/MS ($ESI^+$) m/z; 338 $[M + H]^+$ LC/MS ($ESI^-$) m/z; 336 $[M - H]^-$ |
| 373 | $^1$H-NMR (DMSO-$d_6$) δ: 1.12-1.32 (m, 2H), 1.46-1.64 (m, 1H), 1.65-1.82 (m, 2H), 1.82-2.07 (m, 4H), 3.05 (t, J = 6.0 Hz, 2H), 3.07-3.20 (m, 1H), 3.23 (d, J = 11.6 Hz, 1H), 3.27-3.35 (m, 1H), 6.79 (dd, J = 3.0, 1.8 Hz, 1H), 7.48 (t, J = 3.0 Hz, 1H), 8.18-8.31 (m, 1H), 9.51 (s, 1H), 12.51 (br s, 1H). LC/MS: condition 3, retention time = 1.75 min LC/MS ($ESI^+$) m/z; 381 $[M + H]^+$ LC/MS ($ESI^-$) m/z; 379 $[M - H]^-$ |

TABLE[a] 140

| Ex | Data |
|---|---|
| 374 | $^1$H-NMR (DMSO-$d_6$) δ: 1.85-2.02 (m, 4H), 2.13-2.30 (m, 2H), 2.36 (s, 3H), 2.86-2.99 (m, 2H), 3.10-3.24 (m, 1H), 3.67 (s, 2H), 5.09 (q, J = 9.0 Hz, 2H), 6.81 (d, J = 3.3 Hz, 1H), 7.49 (d, J = 3.3 Hz, 1H), 9.52 (s, 1H), 12.54 (br s, 1H). LC/MS: condition 3, retention time = 1.50 min LC/MS ($ESI^+$) m/z; 381 $[M + H]^+$ LC/MS ($ESI^-$) m/z; 379 $[M - H]^-$ |
| 375 | $^1$H-NMR (DMSO-$d_6$) δ: 1.86-2.04 (m, 4H), 2.16-2.32 (m, 2H), 2.62 (t, J = 7.5 Hz, 2H), 2.89 (t, J = 7.5 Hz, 2H), 3.01-3.12 (m, 2H), 3.12-3.24 (m, 1H), 6.76 (d, J = 3.3 Hz, 1H), 7.47 (d, J = 3.3 Hz, 1H), 7.49 (d, J = 7.8 Hz, 2H), 7.76 (d, J = 7.8 Hz, 2H), 9.52 (s, 1H), 12.53 (br s, 1H). LC/MS: condition 3, retention time = 1.38 min LC/MS ($ESI^+$) m/z; 372 $[M + H]^+$ LC/MS ($ESI^-$) m/z; 370 $[M - H]^-$ |
| 376 | $^1$H-NMR ($CDCl_3$) δ: 2.19-2.28 (m, 4H), 3.14-3.23 (m, 2H), 3.46-3.53 (m, 1H), 4.06 (d, J = 12.6 Hz, 2H), 6.67 (dd, J = 3.3, 2.4 Hz, 1H), 6.96 (d, J = 9.0 Hz, 2H), 7.53 (d, J = 9.0 Hz, 2H), 9.06 (br s, 1H), 9.24 (s, 1H). LC/MS: condition 3, retention time = 2.07 min LC/MS ($ESI^+$) m/z; 344 $[M + H]^+$ LC/MS ($ESI^-$) m/z; 342 $[M - H]^-$ |
| 377 | $^1$H-NMR (DMSO-$d_6$) δ: 1.90-2.08 (m, 4H), 2.11-2.30 (m, 2H), 2.70-2.76 (m, 1H), 2.87-3.01 (m, 2H), 3.62 (s, 2H), 7.56 (d, J = 8.3 Hz, 2H), 7.66 (s, 1H), 7.80 (d, J = 3.3 Hz, 2H), 9.51 (s, 1H), 12.51 (br s, 1H). |

TABLE[a] 140-continued

| Ex | Data |
|---|---|
| | LC/MS: condition 3, retention time = 1.45 min<br>LC/MS ($ESI^+$) m/z; 392, 394 $[M + H]^+$<br>LC/MS ($ESI^-$) m/z; 390, 392 $[M - H]^-$ |
| 378 | $^1$H-NMR ($CDCl_3$) δ: 1.56 (m, 2H), 1.94-2.07 (m, 8H), 2.20-2.33 (m, 6H), 3.01-3.26 (m, 7H), 3.41 (m, 1H), 4.26 (d, J = 5.4 Hz, 1H), 4.34 (d, J = 5.4 Hz, 1H), 4.44 (m, 2H), 6.77 (m, 1H), 6.80 (m, 1H), 7.22-7.32 (m, 10H), 9.22 (s, 2H), 10.04 (br s, 2H).<br>LC/MS: condition 1, retention time = 0.99, 1.25 min (cis/trans mixture)<br>LC/MS ($ESI^+$) m/z; 389 $[M + H]^+$<br>LC/MS ($ESI^-$) m/z; 387 $[M - H]^-$ |
| 379 | $^1$H-NMR ($CDCl_3$) δ: 1.57 (m, 2H), 1.94-2.07 (m, 8H), 2.19-2.32 (m, 6H), 3.01-3.22 (m, 7H), 3.41 (m, 1H), 4.27 (d, J = 5.4 Hz, 1H), 4.34 (d, J = 5.4 Hz, 1H), 4.44 (m, 2H), 6.76 (m, 1H), 6.80 (m, 1H), 7.22-7.30 (m, 10H), 9.22 (s, 2H), 10.28 (br s, 2H).<br>LC/MS: condition 1, retention time = 0.87, 1.03 min (cis/trans mixture)<br>LC/MS ($ESI^+$) m/z; 389 $[M + H]^+$<br>LC/MS ($ESI^-$) m/z; 387 $[M - H]^-$ |

TABLE[a] 141

| Ex | Data |
|---|---|
| 380 | $^1$H-NMR (DMSO-$d_6$) δ: 1.58 (m, 6H), 1.75-1.84 (m, 12H), 2.02 (m, 4H), 2.17 (m, 2H), 2.60 (m, 12H), 2.75 (m, 3H), 2.82 (m, 12H), 3.17 (m, 2H), 3.51 (m, 1H), 6.82 (m, 1H), 6.88 (m, 2H), 7.48 (m, 3H), 9.50 (s, 2H), 9.52 (s, 1H).<br>LC/MS: condition 1, retention time = 2.75 min<br>LC/MS ($ESI^+$) m/z; 363 $[M + H]^+$<br>LC/MS ($ESI^-$) m/z; 361 $[M - H]^-$ |
| 381a | $^1$H-NMR (DMSO-$d_6$) δ: 1.76-1.96 (m, 6H), 2.10-2.23 (m, 2H), 3.30-3.40 (m, 1H), 3.49-3.57 (m, 1H), 5.57 (d, J = 6.9 Hz, 1H), 6.61-6.68 (m, 2H), 6.86-6.94 (m, 3H), 7.50 (t, J = 2.6 Hz, 1H), 9.53 (s, 1H), 12.53 (br s, 1H).<br>LC/MS: condition 1, retention time = 3.22 min<br>LC/MS ($ESI^+$) m/z; 351 $[M + H]^+$<br>LC/MS ($ESI^-$) m/z; 349 $[M - H]^-$ |
| 381b | $^1$H-NMR (DMSO-$d_6$) δ: 1.41 (qd, J = 12.9, 3.6 Hz, 2H), 1.84-2.19 (m, 6H), 3.20 (tt, J = 11.9, 3.6 Hz, 1H), 3.31-3.39 (m, 1H), 5.37 (d, J = 8.3 Hz, 1H), 6.60-6.66 (m, 2H), 6.86-6.95 (m, 3H), 7.50 (d, J = 3.3 Hz, 1H), 9.53 (s, 1H), 12.54 (br s, 1H).<br>LC/MS: condition 1, retention time = 2.82 min<br>LC/MS ($ESI^+$) m/z; 351 $[M + H]^+$<br>LC/MS ($ESI^-$) m/z; 349 $[M - H]^-$ |
| 382a | LC/MS: condition 3, retention time = 1.51 min<br>LC/MS ($ESI^+$) m/z; 392, 399 $[M + H]^+$<br>LC/MS ($ESI^-$) m/z; 390, 397 $[M - H]^-$ |
| 382b | $^1$H-NMR ($CDCl_3$) δ: 1.26-1.46 (m, 2H), 1.87-2.05 (m, 2H), 2.08-2.23 (m, 4H), 2.76-2.91 (m, 1H), 3.10-3.24 (m, 1H), 3.44 (d, J = 12.5 Hz, 1H), 3.48 (d, J = 12.5 Hz, 1H), 6.76 (dd, J = 3.3, 1.8 Hz, 1H), 7.29 (t, J = 3.3 Hz, 1H), 9.08 (br s, 1H), 9.21 (s, 1H).<br>LC/MS: condition 3, retention time = 1.28 min<br>LC/MS ($ESI^+$) m/z; 399 $[M + H]^+$<br>LC/MS ($ESI^-$) m/z; 397 $[M - H]^-$ |
| 383a | $^1$H-NMR (DMSO-$d_6$) δ: 1.60-1.75 (m, 4H), 1.77-1.88 (m, 2H), 2.12-2.25 (m, 1H), 2.25-2.37 (m, 1H), 2.85-2.92 (m, 1H), 3.20-3.40 (m, 3H), 6.98 (dd, J = 3.3, 2.0 Hz, 1H), 7.45 (t, J = 2.6 Hz, 1H), 9.52 (s, 1H), 12.51 (br s, 1H).<br>LC/MS: condition 1, retention time = 2.90 min<br>LC/MS ($ESI^+$) m/z; 389 $[M + H]^+$<br>LC/MS ($ESI^-$) m/z; 387 $[M - H]^-$ |
| 383b | $^1$H-NMR (DMSO-$d_6$) δ: 1.23-1.39 (m, 2H), 1.70-1.86 (m, 2H), 1.96-2.09 (m, 4H), 2.17-2.28 (m, 1H), 2.54-2.65 (m, 1H), 3.14 (tt, J = 12.2, 3.0 Hz, 1H), 3.33-3.45 (m, 2H), 6.82 (d, J = 2.6 Hz, 1H), 7.49 (d, J = 2.6 Hz, 1H), 9.52 (s, 1H), 12.53 (br s, 1H).<br>LC/MS: condition 1, retention time = 1.84 min<br>LC/MS ($ESI^+$) m/z; 389 $[M + H]^+$<br>LC/MS ($ESI^-$) m/z; 387 $[M - H]^-$ |

TABLE[a] 142

| Ex | Data |
|---|---|
| 384a | $^1$H-NMR (DMSO-$d_6$) δ: 1.58-1.86 (m, 6H), 2.09-2.30 (m, 2H), 2.41-2.54 (m, 1H), 2.69-2.81 (m, 1H), 3.25 (s, 2H), 3.88-4.05 (m, 2H), 6.94-6.98 (m, 1H), 7.44 (t, J = 3.0 Hz, 1H), 8.32-8.45 (m, 1H), 9.51 (s, 1H), 12.49 (s, 1H). LC/MS: condition 3, retention time = 1.35 min LC/MS (ESI$^+$) m/z; 396 $[M + H]^+$ LC/MS (ESI$^-$) m/z; 394 $[M - H]^-$ |
| 384b | $^1$H-NMR (DMSO-$d_6$) δ: 1.25-1.41 (m, 2H), 1.67-1.84 (m, 2H), 1.94-2.05 (m, 4H), 2.44-2.57 (m, 1H), 3.06-3.20 (m, 1H), 3.26 (s, 2H), 3.87-4.02 (m, 2H), 6.78 (dd, J = 3.0, 1.5 Hz, 1H), 7.48 (t, J = 3.0 Hz, 1H), 8.41 (br s, 1H), 9.50 (s, 1H), 12.51 (s, 1 H). LC/MS: condition 3, retention time = 1.22 min LC/MS (ESI$^+$) m/z; 396 $[M + H]^+$ LC/MS (ESI$^-$) m/z; 394 $[M - H]^-$ |
| 385b | $^1$H-NMR ($CD_3OD$) δ: 1.35 (m, 2H), 1.84 (m, 2H), 2.07 (m, 4H), 2.58 (tt, J = 11.4, 3.3 Hz, 1H), 3.16 (tt, J = 12.3, 3.3 Hz, 1H), 3.36 (d, J = 13.5 Hz, 1H), 3.46 (d, J = 12.9 Hz, 1H), 6.77 (d, J = 3.3 Hz, 1H), 7.38 (d, J = 3.3 Hz, 1H), 7.50 (dd, J = 7.5, 4.2 Hz, 1H), 8.10 (d, J = 8.1 Hz, 1H), 8.55 (dd, J = 5.1, 1.2 Hz, 1H), 8.81 (d, J = 1.2 Hz, 1H), 9.27 (s, 1H). LC/MS: condition 1, retention time = 0.39 min LC/MS (ESI$^+$) m/z; 446 $[M + H]^+$ LC/MS (ESI$^-$) m/z; 444 $[M - H]^-$ |
| 386b | $^1$H-NMR ($CD_3OD$) δ: 1.43 (m, 2H), 1.84 (m, 2H), 2.09 (m, 4H), 2.49 (s, 3H), 2.69 (tt, J = 11.1, 3.6 Hz, 1H), 3.17 (tt, J = 12.3, 3.3 Hz, 1H), 3.38 (d, J = 13.2 Hz, 1H), 3.45 (d, J = 12.9 Hz, 1H), 6.77 (d, J = 3.3 Hz, 1H), 7.31 (d, J = 8.7 Hz, 2H), 7.38 (d, J = 3.3 Hz, 1H), 7.57 (d, J = 8.7 Hz, 2H), 9.27 (s, 1H). LC/MS: condition 1, retention time = 2.92 min LC/MS (ESI$^+$) m/z; 491 $[M + H]^+$ LC/MS (ESI$^-$) m/z; 489 $[M - H]^-$ |
| 387b | $^1$H-NMR ($CD_3OD$) δ: 1.40 (m, 2H), 1.85 (m, 2H), 2.10 (m, 4H), 2.65 (tt, J = 11.4, 3.6 Hz, 1H), 3.17 (tt, J = 12.3, 3.6 Hz, 1H), 3.35 (d, J = 13.5 Hz, 1H), 3.42 (d, J = 13.2 Hz, 1H), 3.93 (s, 3H), 6.77 (d, J = 3.3 Hz, 1H), 6.84 (d, J = 8.7 Hz, 1H), 7.38 (d, J = 3.3 Hz, 1H), 7.89 (s, 1H), 8.38 (d, J = 2.4 Hz, 1H), 9.27 (s, 1H). LC/MS: condition 1, retention time = 2.49 min LC/MS (ESI$^+$) m/z; 476 $[M + H]^+$ LC/MS (ESI$^-$) m/z; 474 $[M - H]^-$ |
| 388b | $^1$H-NMR ($CD_3OD$) δ: 1.42 (m, 2H), 1.82 (m, 2H), 2.10 (m, 4H), 2.68 (tt, J = 11.4, 3.6, 1H), 3.17 (tt, J = 12.6, 3.3 Hz, 1H), 3.37 (d, J = 13.2 Hz, 1H), 3.43 (d, 13.2 Hz, 1H), 3.81 (s, 3H), 6.77 (d, J = 3.3 Hz, 1H), 6.97 (d, J = 9.0 Hz, 2H), 7.38 (d, J = 3.3 Hz, 1H), 7.56 (d, J = 8.4 Hz, 2H), 9.27 (s, 1H). LC/MS: condition 1, retention time = 2.75 min LC/MS (ESI$^+$) m/z; 475 $[M + H]^+$ LC/MS (ESI$^-$) m/z; 473 $[M - H]^-$ |

TABLE[a] 143

| Ex | Data |
|---|---|
| 389b | $^1$H-NMR ($CDCl_3$) δ: 0.87 (m, 2H), 1.34 (m, 2H), 1.73 (m, 2H), 1.96 (m, 2H), 2.15 (m, 4H), 2.68-2.79 (m, 3H), 3.18 (m, 1H), 6.77 (d, J = 3.3 Hz, 1H), 6.90-7.04 (m, 4H), 7.28 (d, J = 3.3 Hz, 1H), 9.16 (br s, 1H), 9.21 (s, 1H). LC/MS: condition 1, retention time = 2.75 min LC/MS (ESI$^+$) m/z; 405 $[M + H]^+$ LC/MS (ESI$^-$) m/z; 403 $[M - H]^-$ |
| 390b | $^1$H-NMR ($CDCl_3$) δ: 1.33 (m, 2H), 1.92 (m, 2H), 2.17 (m, 4H), 2.68 (tt, J = 11.1, 3.3, 1H), 3.08 (d, J = 12.6 Hz, 1H), 3.16 (tt, J = 12.3, 3.9 Hz, 1H), 3.58 (d, J = 12 Hz, 1H), 3.89 (s, 3H), 3.60 (s, 3H), 6.73 (d, J = 3.0 Hz, 1H), 6.88 (d, J = 8.7 Hz, 1H), 7.07 (d, J = 8.4 Hz, 1H), 7.21 (m, 1H), 7.29 (m, 1H), 9.21 (s, 1H), 9.41 (br s, 1H). LC/MS: condition 1, retention time = 2.67 min LC/MS (ESI$^+$) m/z; 505 $[M + H]^+$ LC/MS (ESI$^-$) m/z; 503 $[M - H]^-$ |
| 391b | $^1$H-NMR ($CD_3OD$) δ: 1.40 (m, 2H), 1.90 (m, 2H), 2.14 (m, 4H), 2.71 (m, 1H), 2.94 (s, 4H), 3.29 (m, 1H), 6.82 (d, J = 3.3 Hz, 1H), 7.40 (d, J = 3.3 Hz, 1H), 7.46 (d, J = 8.1 Hz, 2H), 7.67 (d, J = 8.4 Hz, 2H) 9.30 (s, 1H). LC/MS: condition 1, retention time = 1.62 min LC/MS (ESI$^+$) m/z; 386 $[M + H]^+$ LC/MS (ESI$^-$) m/z; 384 $[M - H]^-$ |

TABLE[a] 143-continued

| Ex | Data |
|---|---|
| 392b | $^1$H-NMR ($CDCl_3$) δ: 0.40 (m, 2H), 0.50 (m, 2H), 1.37 (m, 2H), 1.98 (m, 2H), 2.14-2.26 (m, 5H), 2.82 (m, 1H), 3.18 (tt, J = 12.3, 3.3 Hz, 1H), 3.71, 6.78 (d, J = 3.3 Hz, 1H), 7.30 (d, J = 3.3 Hz, 1H), 9.23 (s, 1H).<br>LC/MS: condition 1, retention time = 3.55 min<br>LC/MS ($ESI^+$) m/z; 424 $[M + H]^+$<br>LC/MS ($ESI^-$) m/z; 422 $[M - H]^-$ |
| 393b | $^1$H-NMR ($CDCl_3$) δ: 1.42 (m, 2H), 1.95-2.20 (m, 6H), 2.92 (m, 1H), 3.21 (tt, J = 12.6, 3.6 Hz, 1H), 3.71 (d, J = 7.8 Hz, 2H), 6.78 (d, J = 3.3 Hz, 1H), 7.31 (d, J = 3.3 Hz, 1H), 9.23 (s, 1H).<br>LC/MS: condition 1, retention time = 0.35 min<br>LC/MS ($ESI^+$) m/z; 296 $[M + H]^+$<br>LC/MS ($ESI^-$) m/z; 294 $[M - H]^-$ |
| 394b | $^1$H-NMR ($CDCl_3$) δ: 1.37 (m, 2H), 1.96 (m, 2H), 2.16 (m, 4H), 2.56 (t, J = 6.6 Hz, 2H), 2.71 (tt, J = 11.7, 3.6 Hz, 1H), 3.04 (t, J = 6.6 Hz, 2H), 3.18 (tt, J = 11.7, 3.9 Hz, 1H), 6.77 (dd, J = 3.3, 2.1 Hz, 1H), 7.30 (t, J = 2.7 Hz, 1H), 9.22 (s, 1H), 9.36 (br s, 1H).<br>LC/MS: condition 1, retention time = 0.35 min<br>LC/MS ($ESI^+$) m/z; 310 $[M + H]^+$<br>LC/MS ($ESI^-$) m/z; 308 $[M - H]^-$ |

TABLE[a] 144

| Ex | Data |
|---|---|
| 395b | $^1$H-NMR ($CDCl_3$) δ: 1.38 (m, 2H), 1.96 (m, 2H), 2.17 (m, 4H), 2.78 (tt, J = 11.1, 3.3 Hz, 1H), 3.18 (tt, J = 12.4, 3.3 Hz, 1H), 3.29 (q, J = 9.6 Hz, 2H), 6.76 (dd, J = 3.3, 2.1 Hz, 1H), 7.30 (t, J = 2.7 Hz, 1H), 9.22 (s, 1H), 9.43 (br s, 1H).<br>LC/MS: condition 1, retention time = 0.37 min<br>LC/MS ($ESI^+$) m/z; 339 $[M + H]^+$<br>LC/MS ($ESI^-$) m/z; 337 $[M - H]^-$ |
| 396b | $^1$H-NMR ($CDCl_3$) δ: 0.16 (m, 2H), 0.51 (m, 2H), 1.01 (m, 1H), 1.42 (m, 2H), 1.98 (m, 2H), 2.17 (m, 4H), 2.60 (d, J = 6.9 Hz, 2H), 2.72 (tt, J = 11.1, 3.9 Hz, 1H), 3.19 (tt, J = 12.3, 3.3 Hz, 1H), 6.77 (d, J = 3.3 Hz, 1H), 7.31 (d, J = 3.3 Hz, 1H), 9.23 (s, 1H).<br>LC/MS: condition 1, retention time = 0.37 min<br>LC/MS ($ESI^+$) m/z; 311 $[M + H]^+$<br>LC/MS ($ESI^-$) m/z; 309 $[M - H]^-$ |
| 397b | $^1$H-NMR ($CD_3OD$) δ: 1.51 (m, 2H), 1.95 (m, 2H), 2.18 (m, 4H), 2.39 (s, 6H), 2.42 (m, 1H), 3.15 (tt, J = 11.7, 3.9 Hz, 1H), 6.79 (d, J = 3.3 Hz, 1H), 7.29 (d, J = 3.3 Hz, 1H), 9.22 (s, 1H).<br>LC/MS: condition 1, retention time = 0.35 min<br>LC/MS ($ESI^+$) m/z; 285 $[M + H]^+$<br>LC/MS ($ESI^-$) m/z; 283 $[M - H]^-$ |
| 398b | $^1$H-NMR ($CDCl_3$) δ: 1.33 (m, 2H), 1.93 (m, 2H), 2.15 (m, 4H), 2.51 (s, 3H), 2.56 (m, 1H), 3.18 (tt, J = 12.3, 3.6 Hz, 1H), 6.78 (d, J = 3.6 Hz, 1H), 7.28 (d, J = 3.3 Hz, 1H), 9.21 (s, 1H).<br>LC/MS: condition 1, retention time = 0.35 min<br>LC/MS ($ESI^+$) m/z; 271 $[M + H]^+$<br>LC/MS ($ESI^-$) m/z; 269 $[M - H]^-$ |
| 399b | $^1$H-NMR ($CDCl_3$) δ: 1.37 (m, 2H), 1.97 (m, 2H), 2.17 (m, 4H), 2.72 (tt, J = 11.4, 3.6 Hz, 1H), 3.08 (td, J = 15.3, 4.5 Hz, 2H), 3.18 (tt, J = 12.3, 3.3 Hz, 1H), 5.88 (m, 1H), 6.77 (m, 1H), 7.31 (m, 1H), 9.23 (s, 1H), 9.59 (br s, 1H).<br>LC/MS: condition 3, retention time = 0.81 min<br>LC/MS ($ESI^+$) m/z; 321 $[M + H]^+$<br>LC/MS ($ESI^-$) m/z; 319 $[M - H]^-$ |
| 400b | $^1$H-NMR ($CDCl_3$) δ: 1.45 (m, 2H), 1.96 (m, 2H), 2.16 (m, 4H), 2.97 (m, 1H), 3.18 (tt, J = 12.0, 3.6 Hz, 1H), 3.79 (m, 1H), 6.77 (m, 1H), 7.31 (m, 1H), 9.17 (br s, 1H), 9.23 (s, 1H).<br>LC/MS: condition 1, retention time = 4.04 min<br>LC/MS ($ESI^+$) m/z; 407 $[M + H]^+$<br>LC/MS ($ESI^-$) m/z; 405 $[M - H]^-$ |
| 401 | $^1$H-NMR ($CD_3OD$) δ: 1.71-2.18 (m, 9H), 3.33-3.45 (m, 1H), 3.67 (d, J = 6.6 Hz, 2H), 6.80 (d, J = 3.3 Hz, 1H), 7.39 (d, J = 3.3 Hz, 1H), 9.30 (s, 1H).<br>LC/MS: condition 3, retention time = 1.53 min<br>LC/MS ($ESI^+$) m/z; 272 $[M + H]^+$<br>LC/MS ($ESI^-$) m/z; 270 $[M - H]^-$ |

TABLE[a] 145

| Ex | Data |
|---|---|
| 402 | $^1$H-NMR ($CDCl_3$) δ: 1.76-1.91 (m, 2H), 1.95-2.06 (m, 4H), 2.32-2.44 (m, 2H), 2.54-2.64 (m, 1H), 3.26-3.38 (m, 1H), 6.78 (dd, J = 3.3, 1.8 Hz, 1H), 7.29 (t, J = 3.0 Hz, 1H), 9.19 (br s, 1H), 9.22 (s, 1H), 9.84 (s, 1H).<br>LC/MS: condition 3, retention time = 1.71 min<br>LC/MS ($ESI^+$) m/z; 270 $[M + H]^+$<br>LC/MS ($ESI^-$) m/z; 268 $[M - H]^-$ |
| 403 | $^1$H-NMR (DMSO-$d_6$) δ: 1.56-1.99 (m, 10H), 2.39 (d, J = 6.3 Hz, 2H), 2.65 (dd, J = 7.4, 6.0 Hz, 2H), 3.50 (dd, J = 7.4, 6.0 Hz, 2H), 4.14 (dd, J = 9.8, 3.3 Hz, 2H), 6.76 (d, J = 3.3 Hz, 1H), 7.47 (d, J = 3.3 Hz, 1H), 9.50 (s, 1H), 12.50 (br s, 1H).<br>LC/MS: condition 1, retention time = 0.94 min<br>LC/MS ($ESI^+$) m/z; 327 $[M + H]^+$ |
| 404 | $^1$H-NMR (DMSO-$d_6$) δ: 1.47-1.62 (m, 1H), 1.63-1.85 (m, 4H), 1.89-2.07 (m, 3H), 2.24-2.59 (m, 6H), 2.65-2.75 (m, 1H), 3.22-3.44 (m, 1H), 4.08-4.29 (m, 1H), 4.62 (d, J = 4.5 Hz, 1H), 2.86-2.98 (m, 1H), 3.29-3.39 (m, 1H), 6.77 (d, J = 3.3 Hz, 1H), 7.48 (d, J = 3.3 Hz, 1H), 9.51 (s, 1H), 12.51 (br s, 1H).<br>LC/MS: condition 3, retention time = 0.95 min<br>LC/MS ($ESI^+$) m/z; 341 $[M + H]^+$ |
| 405 | $^1$H-NMR ($CDCl_3$) δ: 1.59-1.96 (m, 7H), 2.06-2.31 (m, 5H), 2.42-2.61 (m, 3H), 2.75 (d, J = 9.8 Hz, 1H), 2.86-2.98 (m, 1H), 3.29-3.39 (m, 1H), 4.26-4.37 (m, 1H), 6.77 (d, J = 3.3 Hz, 1H), 7.28 (d, J = 3.3 Hz, 1H), 9.22 (s, 1H), 9.30 (br s, 1H).<br>LC/MS: condition 3, retention time = 1.20 min<br>LC/MS ($ESI^+$) m/z; 341 $[M + H]^+$ |
| 406 | $^1$H-NMR ($CDCl_3$) δ: 0.31-0.49 (m, 4H), 1.54-1.98 (m, 7H), 2.09-2.42 (m, 3H), 2.78 (d, J = 6.6 Hz, 2H), 3.36-3.44 (m, 1H), 6.78 (d, J = 3.0 Hz, 1H), 7.29 (d, J = 3.0 Hz, 1H), 9.23 (s, 1H), 9.27 (br s, 1H).<br>LC/MS: condition 3, retention time = 1.29 min<br>LC/MS ($ESI^+$) m/z; 311 $[M + H]^+$ |
| 407 | $^1$H-NMR (DMSO-$d_6$) δ: 1.21-1.38 (m, 2H), 1.70-1.83 (m, 4H), 1.91-2.07 (m, 3H), 3.08-3.19 (m, 1H), 3.33 (dd, J = 18.4, 7.8 Hz, 2H), 4.11 (s, 1H), 4.20-4.27 (m, 3H), 6.79-6.83 (m, 1H), 7.49 (q, J = 2.5 Hz, 1H), 9.51 (s, 1H), 12.52 (br s, 1H).<br>LC/MS: condition 1, retention time = 3.60 min<br>LC/MS ($ESI^+$) m/z; 420 $[M + H]^+$<br>LC/MS ($ESI^-$) m/z; 418 $[M - H]^-$ |
| 408 | $^1$H-NMR (DMSO-$d_6$) δ: 1.21-1.36 (m, 2H), 1.69-1.90 (m, 5H), 1.98-2.07 (m, 2H), 3.08-3.19 (m, 1H), 3.26-3.34 (m, 2H), 4.18 (s, 2H), 4.43 (s, 2H), 6.78-6.83 (m, 1H), 7.49-7.52 (m, 1H), 9.52 (s, 1H), 12.54 (br s, 1H).<br>LC/MS: condition 1, retention time = 3.09 min<br>LC/MS ($ESI^+$) m/z; 377 $[M + H]^+$<br>LC/MS ($ESI^-$) m/z; 375 $[M - H]^-$ |

TABLE[a] 146

| Ex | Data |
|---|---|
| 409 | $^1$H-NMR (DMSO-$d_6$) δ: 0.81-0.89 (m, 4H), 1.17-1.30 (m, 2H), 1.70-1.89 (m, 5H), 1.98-2.07 (m, 2H), 2.74-2.81 (m, 1H), 3.10-3.20 (m, 1H), 3.25 (d, J = 7.6 Hz, 2H), 4.16 (s, 2H), 6.81-6.85 (m, 1H), 7.47-7.52 (m, 1H), 9.52 (s, 1H), 12.53 (br s, 1H).<br>LC/MS: condition 1, retention time = 3.38 min<br>LC/MS ($ESI^+$) m/z; 378 $[M + H]^+$<br>LC/MS ($ESI^-$) m/z; 376 $[M - H]^-$ |
| 410 | LC/MS: condition 1, retention time = 3.72 min<br>LC/MS ($ESI^+$) m/z; 432 $[M + H]^+$<br>LC/MS ($ESI^-$) m/z; 430 $[M - H]^-$ |
| 411 | $^1$H-NMR (DMSO-$d_6$) δ: 1.13-1.38 (m, 2H), 1.70-1.85 (m, 4H), 1.89-2.06 (m, 4H), 3.08-3.21 (m, 1H), 3.21-3.32 (m, 1H), 3.38 (d, J = 7.3 Hz, 2H), 3.76-3.89 (m, 1H), 4.21-4.32 (m, 1H), 6.80-6.84 (m, 1H), 7.47-7.52 (m, 1H), 9.52 (s, 1H), 12.53 (br s, 1H).<br>LC/MS: condition 1, retention time = 3.97 min<br>LC/MS ($ESI^+$) m/z; 463 $[M + H]^+$<br>LC/MS ($ESI^-$) m/z; 461 $[M - H]^-$ |
| 412 | $^1$H-NMR (DMSO-$d_6$) δ: 1.22-1.41 (m, 2H), 1.69-1.96 (m, 5H), 1.98-2.08 (m, 2H), 3.10-3.22 (m, 1H), 3.37 (d, J = 7.3 Hz, 2H), 3.71-3.86 (m, 2H), 4.44 (s, 2H), 6.79-6.82 (m, 1H), 7.48-7.53 (m, 1H), 9.53 (s, 1H), 12.54 (br s, 1H).<br>LC/MS: condition 1, retention time = 3.54 min<br>LC/MS ($ESI^+$) m/z; 420 $[M + H]^+$<br>LC/MS ($ESI^-$) m/z; 418 $[M - H]^-$ |

TABLE[a] 146-continued

| Ex | Data |
|---|---|
| 413 | $^1$H-NMR ($CDCl_3$) δ: 0.15 (m, 2H), 0.55 (m, 2H), 0.90 (m, 1H), 1.48 (m, 2H), 1.90-2.04 (m, 4H), 2.18 (m, 2H), 2.61 (d, J = 6.0 Hz, 2H), 2.97 (m, 1H), 3.12 (m, 1H), 3.18 (q, J = 9.6 Hz, 2H), 6.79 (d, J = 3.3 Hz, 1H), 7.30 (m, 1H), 9.22 (s, 1H), 9.29 (br s, 1H).<br>LC/MS: condition 1, retention time = 3.85 min<br>LC/MS ($ESI^+$) m/z; 393 $[M + H]^+$<br>LC/MS ($ESI^-$) m/z; 391 $[M - H]^-$ |
| 414 | $^1$H-NMR (DMSO-$d_6$) δ: 0.12-0.19 (m, 2H), 0.48-0.55 (m, 2H), 0.78-0.90 (m, 1H), 1.08-1.25 (m, 2H), 1.69-2.05 (m, 6H), 2.33-2.39 (m, 5H), 3.09-3.21 (m, 1H), 3.87 (s, 2H), 6.83-6.86 (m, 1H), 7.49 (t, J = 3.0 Hz, 1H), 9.51 (s, 1H), 12.52 (br s, 1H).<br>LC/MS: condition 1, retention time = 3.74 min<br>LC/MS ($ESI^+$) m/z; 364 $[M + H]^+$<br>LC/MS ($ESI^-$) m/z; 362 $[M - H]^-$ |
| 415 | $^1$H-NMR (DMSO-$d_6$) δ: 0.10-0.16 (m, 2H), 0.44-0.52 (m, 2H), 0.83-0.94 (m, 1H), 1.05-1.21 (m, 2H), 1.54-1.68 (m, 1H), 1.68-1.84 (m, 2H), 1.92-2.06 (m, 4H), 2.44-2.58 (m, 4H), 3.09-3.21 (m, 1H), 3.25-3.39 (m, 2H), 6.80-6.84 (m, 1H), 7.47-7.51 (m, 1H), 9.51 (s, 1H), 12.52 (br s, 1H).<br>LC/MS: condition 1, retention time = 4.45 min<br>LC/MS ($ESI^+$) m/z; 407 $[M + H]^+$<br>LC/MS ($ESI^-$) m/z; 405 $[M - H]^-$ |

TABLE[a] 147

| Ex | Data |
|---|---|
| 416 | $^1$H-NMR (DMSO-$d_6$) δ: 1.16-1.28 (m, 3H), 1.67-1.88 (m, 3H), 1.93-2.01 (m, 2H), 2.11-2.19 (m, 2H), 2.40 (d, J = 5.7 Hz, 2H), 3.10 (tt, J = 11.9, 3.7 Hz, 1H), 6.77-6.80 (m, 1H), 7.48 (t, J = 2.9 Hz, 1H), 9.50 (s, 1H), 12.50 (br s, 1H).<br>LC/MS: condition 1, retention time = 2.75 min<br>LC/MS ($ESI^+$) m/z; 336 $[M + H]^+$<br>LC/MS ($ESI^-$) m/z; 334 $[M - H]^-$ |
| 417 | LC/MS: condition 1, retention time = 3.30 min<br>LC/MS ($ESI^+$) m/z; 375 $[M + H]^+$<br>LC/MS ($ESI^-$) m/z; 373 $[M - H]^-$ |
| 418 | $^1$H-NMR (DMSO-$d_6$) δ: 1.39 (qd, J = 12.6, 3.0 Hz, 2H), 1.72-1.87 (m, 2H), 1.97-2.15 (m, 4H), 2.71-2.80 (m, 1H), 2.79 (s, 6H), 2.99 (d, J = 6.6 Hz, 2H), 3.15 (tt, J = 12.2, 3.3 Hz, 1H), 6.81 (dd, J = 3.3, 2.0 Hz, 1H), 7.50 (t, J = 3.0 Hz, 1H), 9.52 (s, 1H), 12.54 (br s, 1H).<br>LC/MS: condition 1, retention time = 3.30 min<br>LC/MS ($ESI^+$) m/z; 363 $[M + H]^+$<br>LC/MS ($ESI^-$) m/z; 361 $[M - H]^-$ |
| 419 | LC/MS: condition 1, retention time = 3.13 min<br>LC/MS ($ESI^+$) m/z; 374 $[M + H]^+$<br>LC/MS ($ESI^-$) m/z; 372 $[M - H]^-$ |
| 420 | LC/MS: condition 3, retention time = 1.89 min<br>LC/MS ($ESI^+$) m/z; 417 $[M + H]^+$<br>LC/MS ($ESI^-$) m/z; 415 $[M - H]^-$ |
| 421 | $^1$H-NMR ($CDCl_3$) δ: 1.07-1.30 (m, 2H), 1.80-2.04 (m, 4H), 2.06-2.19 (m, 2H), 2.44 (d, J = 6.6 Hz, 2H), 2.92-3.04 (m, 2H), 3.07-3.19 (m, 1H), 3.67-3.78 (m, 2H), 3.76 (d, J = 8.3 Hz, 1H), 3.82 (d, J = 8.3 Hz, 1H), 4.20-4.32 (m, 1H), 6.75-6.80 (m, 1H), 7.23-7.29 (m, 1H), 9.10 (br s, 1H), 9.20 (s, 1H).<br>LC/MS: condition 3, retention time = 1.52 min<br>LC/MS ($ESI^+$) m/z; 409 $[M + H]^+$ |
| 422 | $^1$H-NMR ($CDCl_3$) δ: 1.12-1.30 (m, 3H), 1.51 (s, 3H), 1.84-2.18 (m, 7H), 2.43 (d, J = 6.9 Hz, 2H), 3.06 (d, J = 8.3 Hz, 2H), 3.09-3.20 (m, 1H), 3.35 (d, J = 8.3 Hz, 2H), 6.75-6.81 (m, 1H), 7.22-7.29 (m, 1H), 9.13 (br s, 1H), 9.21 (s, 1H).<br>LC/MS: condition 3, retention time = 1.12 min<br>LC/MS ($ESI^+$) m/z; 341 $[M + H]^+$ |
| 423 | $^1$H-NMR (DMSO-$d_6$) δ: 1.08-1.24 (m, 2H), 1.35-1.50 (m, 1H), 1.65-1.81 (m, 2H), 1.83-2.01 (m, 4H), 2.00 (s, 6H), 2.29 (d, J = 6.6 Hz, 2H), 2.68-2.75 (m, 3H), 3.11 (tt, J = 12.6, 3.6 Hz, 1H), 3.37-3.42 (m, 2H), 6.79 (d, J = 3.3 Hz, 1H), 7.47 (d, J = 3.3 Hz, 1H), 9.49 (s, 1H), 12.55 (br s, 1H).<br>LC/MS: condition 1, retention time = 0.34 min<br>LC/MS ($ESI^+$) m/z; 354 $[M + H]^+$<br>LC/MS ($ESI^-$) m/z; 352 $[M - H]^-$ |

TABLE[a] 148

| Ex | Data |
|---|---|
| 424 | $^1$H-NMR (DMSO-$d_6$) δ: 0.94 (t, J = 7.3 Hz, 3H), 1.15 (qd, J = 12.6, 2.6 Hz, 2H), 1.36-1.50 (m, 1H), 1.73 (qd, J = 12.6, 2.6 Hz, 2H), 1.84-2.03 (m, 4H), 1.98 (s, 3H), 2.20 (q, J = 7.3 Hz, 2H), 2.29 (d, J = 6.6 Hz, 2H), 2.69 (t, J = 6.9 Hz, 2H), 2.81-2.92 (m, 1H), 3.11 (tt, J = 11.6, 3.3 Hz, 1H), 3.43 (t, J = 6.9 Hz, 2H), 6.80 (d, J = 3.3 Hz, 1H), 7.48 (d, J = 3.3 Hz, 1H), 9.51 (s, 1H), 12.53 (br s, 1H).<br>LC/MS: condition 1, retention time = 0.34 min<br>LC/MS (ESI$^+$) m/z; 368 $[M + H]^+$<br>LC/MS (ESI$^-$) m/z; 366 $[M - H]^-$ |
| 425 | $^1$H-NMR (DMSO-$d_6$) δ: 1.05-1.27 (m, 2H), 1.27-1.45 (m, 1H), 1.54-1.82 (m, 2H), 1.83-2.04 (m, 4H), 2.38 (d, J = 6.6 Hz, 1H), 3.03-3.12 (m, 1H), 3.13 (d, J = 9.5 Hz, 2H), 3.55 (d, J = 9.5 Hz, 2H), 6.80 (dd, J = 3.0, 2.1 Hz, 2H), 6.82 (s, 1H), 7.47 (t, J = 3.0 Hz, 1H), 9.50 (s, 1H), 12.50 (s, 1H).<br>LC/MS: condition 3, retention time = 1.32 min<br>LC/MS (ESI$^+$) m/z; 395 $[M + H]^+$<br>LC/MS (ESI$^-$) m/z; 393 $[M - H]^-$ |
| 426 | LC/MS: condition 3, retention time = 1.42 min<br>LC/MS (ESI$^+$) m/z; 436 $[M + H]^+$<br>LC/MS (ESI$^-$) m/z; 434 $[M - H]^-$ |
| 427 | $^1$H-NMR (DMSO-$d_6$) δ: 1.10-1.30 (m, 2H), 1.49-1.64 (m, 1H), 1.66-1.84 (m, 2H), 1.86-2.08 (m, 4H), 2.82-2.93 (m, 5H), 3.06-3.22 (m, 1H), 6.80 (dd, J = 3.0, 2.1 Hz, 1H), 7.01 (t, J = 6.3 Hz, 1H), 7.48 (t, J = 3.0 Hz, 1H), 9.51 (s, 1H), 12.5 (s, 1H).<br>LC/MS: condition 3, retention time = 1.57 min<br>LC/MS (ESI$^+$) m/z; 349 $[M + H]^+$<br>LC/MS (ESI$^-$) m/z; 347 $[M - H]^-$ |
| 428 | $^1$H-NMR (DMSO-$d_6$) δ: 1.09-1.28 (m, 2H), 1.40 (s, 9H), 1.64-1.85 (m, 2H), 1.87-2.07 (m, 5H), 2.39-2.57 (m, 2H), 3.05-3.26 (m, 1H), 3.57 (brs, 2H), 4.32 (d, J = 10.2 Hz, 2H), 4.62 (d, J = 10.2 Hz, 2H), 6.93 (d, J = 3.3 Hz, 1H), 7.75 (d, J = 3.3 Hz, 1H), 9.62 (s, 1H).<br>LC/MS: condition 3, retention time = 2.09 min<br>LC/MS (ESI$^+$) m/z; 465 $[M + H]^+$ |
| 429 | $^1$H-NMR (DMSO-$d_6$) δ: 1.40-1.59 (m, 2H), 1.71-2.10 (m, 6H), 2.26-2.40 (m, 1H), 3.09-3.26 (m, 1H), 6.80-6.87 (m, 1H), 6.54 (d, J = 6.8 Hz, 0.2H), 7.31 (d, J = 4.8 Hz, 0.8H), 9.51 (s, 1H), 10.4 (s, 0.8H), 10.7 (s, 0.2H), 12.51 (s, 1H).<br>LC/MS: condition 3, retention time = 1.51 min<br>LC/MS (ESI$^+$) m/z; 271 $[M + H]^+$ |
| 430 | $^1$H-NMR ($CDCl_3$) δ: 1.76-2.06 (m, 4H), 2.16-2.28 (m, 2H), 2.30-2.41 (m, 2H), 2.58-2.73 (m, 1H), 3.17-3.30 (m, 1H), 6.75 (dd, J = 3.3, 1.8 Hz, 1H), 7.31 (t, J = 3.3 Hz, 1H), 9.15 (br s, 1H), 9.22 (s, 1H).<br>LC/MS: condition 3, retention time = 1.68 min<br>LC/MS (ESI$^+$) m/z; 267 $[M + H]^+$<br>LC/MS (ESI$^-$) m/z; 265 $[M - H]^-$ |

TABLE[a] 149

| Ex | Data |
|---|---|
| 431 | $^1$H-NMR ($CDCl_3$) δ: 1.48-1.65 (m, 2H), 1.95-2.13 (m, 4H), 2.19-2.33 (m, 2H), 2.85-3.02 (m, 1H), 3.15-3.29 (m, 1H), 6.76 (dd, J = 3.3, 2.1 Hz, 1H), 7.23 (d, J = 10.4 Hz, 1H), 7.31 (t, J = 3.3 Hz, 1H), 9.20 (br s, 1H), 9.23 (s, 1H).<br>LC/MS: condition 3, retention time = 1.99 min<br>LC/MS (ESI$^+$) m/z; 318 $[M + H]^+$<br>LC/MS (ESI$^-$) m/z; 316 $[M - H]^-$ |
| 432 | $^1$H-NMR (DMSO-$d_6$) δ: 1.21-1.39 (m, 2H), 1.54-1.67 (m, 1H), 1.68-1.86 (m, 2H), 1.87-2.11 (m, 6H), 3.08-3.22 (m, 1H), 4.92 (t, J = 7.4 Hz, 1H), 6.80 (dd, J = 3.0, 1.8 Hz, 1H), 7.49 (t, J = 3.0 Hz, 1H), 9.51 (s, 1H), 12.51 (s, 1H).<br>LC/MS: condition 3, retention time = 1.93 min<br>LC/MS (ESI$^+$) m/z; 320 $[M + H]^+$<br>LC/MS (ESI$^-$) m/z; 318 $[M - H]^-$ |
| 433 | $^1$H-NMR (DMSO-$d_6$) δ: 1.70-1.90 (m, 2H), 2.00-2.18 (m, 2H), 2.23-2.80 (m, 4H), 3.20-3.50 (m, 1H), 4.72 (s, 2H), 6.81 (d, J = 2.7 Hz, 1H), 7.49 (d, J = 1.8 Hz, 1H), 9.51 (s, 1H), 12.52 (br s, 1H).<br>LC/MS: condition 1, retention time = 3.79 min<br>LC/MS (ESI$^+$) m/z; 254 $[M + H]^+$<br>LC/MS (ESI$^-$) m/z; 252 $[M - H]^-$ |
| 434 | $^1$H-NMR ($CDCl_3$) δ: 2.13 (m, 2H), 2.30 (m, 2H), 2.45 (m, 2H), 2.68 (m, 1H), 3.13 (m, 1H), 3.50 (tt, J = 11.4, 3.9 Hz, 1H), 5.21 (s, 1H), 6.77 (t, J = 3.0 Hz, 1H), 7.34 (t, J = 3.0 Hz, 1H), 9.25 (s, 1H), 9.38 (br s, 1H).<br>LC/MS: condition 1, retention time = 3.37 min |

TABLE[a] 149-continued

| Ex | Data |
|---|---|
| | LC/MS ($ESI^+$) m/z; 279 $[M + H]^+$<br>LC/MS ($ESI^-$) m/z; 277 $[M - H]^-$ |
| 435a | $^1$H-NMR ($CDCl_3$) δ: 1.86 (m, 4H), 1.96 (m, 2H), 2.09 (m, 1H), 2.19 (m, 2H), 2.42 (d, J = 7.5 Hz, 2H), 3.46 (m, 1H), 6.75 (t, J = 3.0 Hz, 1H), 7.30 (t, J = 3.0 Hz, 1H), 9.23 (s, 1H), 9.25 (br s, 1H).<br>LC/MS: condition 1, retention time = 3.38 min<br>LC/MS ($ESI^+$) m/z; 281 $[M + H]^+$<br>LC/MS ($ESI^-$) m/z; 279 $[M - H]^-$ |
| 435b | $^1$H-NMR ($CDCl_3$) δ: 1.43 (m, 2H), 1.84-2.01 (m, 3H), 2.05-2.26 (m, 2H), 2.20 (m, 2H), 2.41 (m, 2H), 3.18 (tt, J = 12, 3.6 Hz, 1H), 6.78 (m, 1H), 7.31 (m, 1H), 9.23 (s, 1H), 9.47 (br s, 1H).<br>LC/MS: condition 1, retention time = 3.27 min<br>LC/MS ($ESI^+$) m/z; 281 $[M + H]^+$<br>LC/MS ($ESI^-$) m/z; 279 $[M - H]^-$ |
| 436 | $^1$H-NMR ($CDCl_3$) δ: 1.31 (t, 3H), 2.03-2.32 (m, 5H), 2.40-2.58 (m, 2H), 3.50 (tt, J = 11.1, 3.6 Hz, 1H), 3.96 (m, 1H), 4.20 (q, J = 6.9 Hz, 2H), 5.76 (s, 1H), 6.78 (dd, J = 3.3, 2.1 Hz, 1H), 7.33 (t, J = 3.3 Hz, 1H), 9.26 (s, 1H), 10.02 (br s, 1H).<br>LC/MS: condition 1, retention time = 3.80 min<br>LC/MS ($ESI^+$) m/z; 326 $[M + H]^+$<br>LC/MS ($ESI^-$) m/z; 324 $[M - H]^-$ |

TABLE[a] 150

| Ex | Data |
|---|---|
| 437 | $^1$H-NMR ($CDCl_3$) δ: 1.97 (s, 3H), 2.00-2.28 (m, 5H), 2.44 (m, 1H), 2.90 (m, 1H), 3.13 (m, 1H), 3.48 (tt, J = 10.8, 3.9 Hz, 1H), 6.76 (m, 1H), 7.31 (m, 1H), 9.17 (br s, 1H), 9.23 (s, 1H).<br>LC/MS: condition 1, retention time = 3.54 min<br>LC/MS ($ESI^+$) m/z; 293 $[M + H]^+$<br>LC/MS ($ESI^-$) m/z; 291 $[M - H]^-$ |
| 438 | $^1$H-NMR ($CDCl_3$) δ: 1.28 (m, 6H), 1.75 (m, 4H), 1.81-2.02 (m, 8H), 2.13-2.32 (m, 8H), 2.43 (d, J = 7.2 Hz, 2H), 3.17 (tt, J = 11.7, 3.6 Hz, 1H), 3.39 (m, 1H), 4.16 (m, 4H), 6.78 (m, 2H), 7.32 (m, 2H), 9.25 (s, 1H), 9.26 (s, 1H), 10.00 (br s, 2H).<br>LC/MS: condition 1, retention time = 3.80 min (cis/trans mixture)<br>LC/MS ($ESI^+$) m/z; 328 $[M + H]^+$<br>LC/MS ($ESI^-$) m/z; 326 $[M - H]^-$ |
| 439a | $^1$H-NMR ($CDCl_3$) δ: 1.34 (d, J = 7.2 Hz, 3H), 1.42-1.61 (m, 5H), 1.80 (m, 2H), 1.93 (m, 2H), 2.68 (quin, J = 7.2 Hz, 1H), 3.51 (m, 1H), 6.76 (m, 1H), 7.29 (m, 1H), 9.23 (s, 1H).<br>LC/MS: condition 1, retention time = 3.65 min<br>LC/MS ($ESI^+$) m/z; 295 $[M + H]^+$<br>LC/MS ($ESI^-$) m/z; 293 $[M - H]^-$ |
| 439b | $^1$H-NMR ($CDCl_3$) δ: 1.40 (m, 3H), 1.42-1.61 (m, 5H), 1.97 (m, 2H), 2.20 (m, 2H), 2.65 (quin, J = 6.6 Hz, 1H), 3.19 (m, 1H), 6.79 (m, 1H), 7.31 (m, 1H), 9.15 (br s, 1H), 9.23 (s, 1H).<br>LC/MS: condition 1, retention time = 3.49 min<br>LC/MS ($ESI^+$) m/z; 295 $[M + H]^+$<br>LC/MS ($ESI^-$) m/z; 293 $[M - H]^-$ |
| 440 | $^1$H-NMR ($CDCl_3$) δ: 1.42 (m, 2H), 1.91-2.04 (m, 4H), 2.20 (m, 2H), 2.36 (m, 1H), 3.16 (tt, J = 12.0, 3.6 Hz, 1H), 5.37 (dd, J = 16.5, 1.5 Hz, 1H), 6.76 (dd, J = 16.5, 6.9 Hz, 1H), 6.77 (d, J = 3.3, 1H), 7.29 (d, J = 3.3 Hz, 1H), 9.16 (br s, 1H), 9.22 (s, 1H).<br>LC/MS: condition 1, retention time = 3.54 min<br>LC/MS ($ESI^+$) m/z; 293 $[M + H]^+$<br>LC/MS ($ESI^-$) m/z; 291 $[M - H]^-$ |
| 441 | $^1$H-NMR ($CDCl_3$) δ: 1.24 (m, 2H), 1.59-1.73 (m, 5H), 1.87-2.04 (m, 2H), 2.16 (m, 2H), 2.44 (t, J = 7.2 Hz, 2H), 3.17 (tt, J = 12.3, 3.3 Hz, 1H), 6.78 (dd, J = 3.3, 2.1, 1H), 7.30 (t, J = 3.3 Hz, 1H), 9.22 (s, 1H), 9.28 (br s, 1H).<br>LC/MS: condition 1, retention time = 3.47 min<br>LC/MS ($ESI^+$) m/z; 295 $[M + H]^+$<br>LC/MS ($ESI^-$) m/z; 293 $[M - H]^-$ |
| 442a | $^1$H-NMR ($CDCl_3$) δ: 1.74 (m, 4H), 1.91-2.17 (m, 6H), 2.31 (m, 1H), 3.40 (m, 1H), 3.93 (m, 2H), 6.77 (m, 1H), 7.25 (m, 1H), 9.12 (br s, 1H), 9.22 (s, 1H).<br>LC/MS: condition 1, retention time = 3.42 min<br>LC/MS ($ESI^+$) m/z; 381 $[M + H]^+$<br>LC/MS ($ESI^-$) m/z; 379 $[M - H]^-$ |

TABLE[a] 151

| Ex | Data |
|---|---|
| 442b | $^1$H-NMR ($CDCl_3$) δ: 1.74 (m, 2H), 1.98 (m, 4H), 2.13 (m, 3H), 2.25 (m, 2H), 3.17 (m, 1H), 3.96 (m, 2H), 6.78 (m, 1H), 7.28 (m, 1H), 9.07 (br s, 1H), 9.21 (s, 1H).<br>LC/MS: condition 1, retention time = 3.30 min<br>LC/MS ($ESI^+$) m/z; 381 $[M + H]^+$<br>LC/MS ($ESI^-$) m/z; 379 $[M - H]^-$ |
| 443a | $^1$H-NMR ($CD_3OD$) 5: 1.75 (m, 4H), 1.94 (m, 3H), 2.10-2.30 (m, 4H), 3.39 (m, 1H), 4.15 (s, 2H), 6.80 (d, J = 3.3 Hz, 1H), 7.38 (d, J = 3.3 Hz, 1H), 9.29 (s, 1H).<br>LC/MS: condition 1, retention time = 3.04 min<br>LC/MS ($ESI^+$) m/z; 338 $[M + H]^+$<br>LC/MS ($ESI^-$) m/z; 336 $[M - H]^-$ |
| 443b | $^1$H-NMR ($CD_3OD$) δ: 1.75-2.33 (m, 11H), 3.54 (m, 1H), 4.16 (s, 2H), 6.83 (d, J = 3.3 Hz, 1H), 7.40 (d, J = 3.3 Hz, 1H), 9.29 (s, 1H).<br>LC/MS: condition 1, retention time = 2.85 min<br>LC/MS ($ESI^+$) m/z; 338 $[M + H]^+$<br>LC/MS ($ESI^-$) m/z; 336 $[M - H]^-$ |
| 444 | $^1$H-NMR ($CDCl_3$) δ: 1.13 (m, 3H), 1.33 (m, 2H), 2.13 (m, 6H), 3.19 (m, 1H), 6.83 (d, J = 3.3 Hz, 1H), 7.33 (d, J = 3.3 Hz, 1H), 9.24 (s, 1H), 9.35 (br s, 1H).<br>LC/MS: condition 1, retention time = 3.32 min<br>LC/MS ($ESI^+$) m/z; 293 $[M + H]^+$<br>LC/MS ($ESI^-$) m/z; 291 $[M - H]^-$ |
| 445 | $^1$H-NMR (DMSO-$d_6$) δ: 1.60-1.80 (m, 6H), 1.99-2.11 (m, 6H), 2.26-2.32 (m, 2H), 4.60 (s, 1H), 6.83 (dd, J = 3.0, 1.7 Hz, 1H), 7.52 (t, J = 3.0 Hz, 1H), 9.54 (s, 1H), 12.58 (br s, 1H).<br>LC/MS: condition 1, retention time = 3.10 min<br>LC/MS ($ESI^+$) m/z; 310 $[M + H]^+$<br>LC/MS ($ESI^-$) m/z; 308 $[M - H]^-$ |

Pharmacological Assay

Now, a pharmacological assay of the tricyclic pyrimidine compounds of the present invention will be described.

Assay Example[a] 1

Enzyme Assay

JAK1, JAK2, JAK3 and Tyk2 were purchased from Carna Biosciences, Inc. As the substrate, LANCE Ultra ULight-JAK1 Peptide (manufactured by PerkinElmer Co., Ltd. (PE)) was used. Dilute solutions of compounds and enzymes in assay buffer (50 mM HEPES pH7.5, 1 mM EGTA, 1 mM $MgCl_2$, 2 mM DTT, 0.01% Tween20) were dispensed into wells of a 384-well black plate. After 5 minutes of preincubation, dilute solutions of the substrate and ATP (adenosine triphosphate) were added at a final concentration of 100 μM, and the plate was incubated at room temperature for 2 hours. After addition of a termination reagent containing EDTA (ethylenediamine tetraacetic acid) at a final concentration of 10 mM, LANCE Eu-W1024 Anti-phosphotyrosine (PT66) (manufactured by PE) was added, and after 1 hour of incubation, the fluorescences were measured with ARVO-HTS. From the plot of logarithm of a compound concentration and inhibitory activity, the $IC_{50}$ was calculated. The results of JAK3, JAK1, JAK2 and Tyk2 enzyme assays of the compounds of Synthetic Examples[a] are shown in Tables[a] 152 to 155. "*" in the Tables indicates $IC_{50}$>1 μM.

TABLE[a] 152

| Ex[a]. No. | $IC_{50}$ (μM) JAK3 | $IC_{50}$ (μM) JAK1 |
|---|---|---|
| 1 | 1.4 | 0.23 |
| 2 | 0.061 | 0.014 |
| 3 | 1.4 | 0.057 |
| 4 | 0.29 | 0.013 |
| 5 | 0.26 | 0.020 |
| 6 | 0.15 | 0.0038 |
| 7 | 0.055 | 0.0042 |
| 8 | 0.43 | 0.020 |
| 9 | 0.43 | 0.030 |
| 10 | 0.19 | 0.0031 |

TABLE[a] 153

| EX[a]. No. | $IC_{50}$ (μM) JAK2 | $IC_{50}$ (μM) TYK2 |
|---|---|---|
| 1 | 0.31 | 0.59 |
| 2 | 0.017 | 0.059 |
| 3 | 0.13 | * |
| 4 | 0.026 | 0.23 |
| 5 | 0.13 | 0.13 |
| 6 | 0.012 | 0.046 |
| 7 | 0.012 | 0.056 |
| 8 | 0.030 | 0.036 |
| 9 | 0.046 | 0.078 |
| 10 | 0.019 | 0.037 |

TABLE[a] 154

| Ex[a]. No. | $IC_{50}$ (μM) JAK1 | $IC_{50}$ (μM) JAK2 | $IC_{50}$ (μM) JAK3 | $IC_{50}$ (μM) TYK2 |
|---|---|---|---|---|
| 11 | 0.20 | 0.34 | 0.44 | 4.1 |
| 12 | 0.021 | 0.22 | 0.40 | 0.91 |
| 13 | 0.12 | 0.25 | * | * |
| 14 | 0.021 | 0.11 | 1.0 | 2.2 |
| 15 | 0.29 | 2.5 | 4.3 | * |
| 16 | 0.28 | 0.57 | 5.3 | 2.6 |
| 17 | 0.029 | 0.076 | 2.1 | 0.57 |
| 18 | 0.21 | 0.62 | * | * |

TABLE[a] 154-continued

| Ex[a]. No. | $IC_{50}$ (μM) JAK1 | $IC_{50}$ (μM) JAK2 | $IC_{50}$ (μM) JAK3 | $IC_{50}$ (μM) TYK2 |
|---|---|---|---|---|
| 19 | 0.072 | 0.27 | 1.0 | 1.0 |
| 20 | 0.019 | 0.032 | 0.33 | 0.42 |
| 21 | 0.015 | 0.11 | 0.90 | 0.71 |
| 22 | 0.061 | 0.56 | * | 0.88 |
| 23 | 0.55 | * | * | * |
| 24 | 0.16 | 0.51 | 6.9 | 5.3 |
| 25 | 0.016 | 0.047 | 0.44 | 0.16 |
| 26 | 0.028 | 0.21 | * | * |
| 27 | 0.18 | * | * | * |
| 28 | 0.019 | 0.040 | 0.22 | 1.5 |
| 29 | 0.094 | 0.34 | * | * |
| 30 | 0.0095 | 0.064 | 0.48 | 0.20 |
| 31 | 0.023 | 0.21 | * | * |
| 32 | 0.0098 | 0.036 | 0.38 | 0.99 |
| 33 | 0.0025 | 0.019 | 0.078 | 0.63 |
| 34 | 0.0033 | 0.010 | 0.031 | 0.17 |
| 35 | 0.0049 | 0.017 | 0.26 | 0.46 |
| 36 | 0.073 | 0.18 | * | * |
| 37 | 0.0054 | 0.041 | 0.31 | * |
| 38 | 0.0046 | 0.032 | 0.22 | * |
| 39 | 0.0049 | 0.028 | 0.53 | * |
| 40 | 0.0022 | 0.0064 | 0.037 | 0.15 |
| 41 | 0.0011 | 0.0061 | 0.042 | 0.15 |
| 42 | 0.082 | 0.41 | * | * |
| 43 | 0.0027 | 0.014 | 0.054 | 0.10 |
| 44 | 0.0049 | 0.013 | 0.042 | 0.12 |
| 45 | 0.066 | 1.0 | * | * |
| 46 | 0.025 | 0.17 | * | * |
| 47 | 0.78 | * | * | * |
| 48 | 0.022 | 0.054 | 0.44 | 0.46 |
| 49 | 0.00061 | 0.0027 | 0.041 | 0.057 |
| 50 | 0.011 | * | * | * |
| 51 | 0.25 | * | * | * |
| 52 | 0.0021 | 0.018 | 0.041 | 0.36 |
| 53 | 0.00032 | 0.0015 | 0.024 | 0.047 |
| 54 | 0.0012 | 0.015 | 0.071 | 0.21 |
| 55 | 0.0061 | 0.030 | 0.22 | 0.39 |
| 56a | 0.50 | * | * | * |
| 56b | 0.035 | 0.60 | * | * |
| 57 | 0.069 | * | * | * |
| 58 | 0.18 | 0.82 | * | * |
| 59 | 0.032 | 0.18 | * | * |
| 60 | 0.0051 | 0.032 | * | 4.2 |
| 61 | 0.016 | 0.15 | 0.53 | 0.44 |
| 62 | 0.0099 | 0.031 | 0.47 | 0.14 |
| 63 | 0.011 | 0.040 | 0.78 | 0.20 |
| 64 | 0.033 | 0.12 | 0.93 | 0.31 |
| 65 | 0.0031 | 0.013 | 0.15 | 0.025 |
| 66 | 0.0033 | 0.013 | 0.086 | 0.027 |
| 67 | 0.052 | 0.20 | 0.65 | 0.41 |
| 69 | 0.0047 | 0.026 | * | 0.041 |
| 71 | 0.00094 | 0.0028 | 0.055 | 0.028 |
| 72 | 0.0021 | 0.0077 | 0.048 | 0.032 |
| 73 | 0.0019 | 0.014 | 0.065 | 0.011 |
| 74 | 0.00040 | 0.003 | 0.074 | 0.0026 |
| 75 | 0.00020 | 0.0010 | 0.032 | 0.0012 |
| 76 | 0.00033 | 0.0022 | 0.030 | 0.0097 |
| 77 | 0.0013 | 0.0054 | 0.053 | 0.044 |
| 78 | 0.0033 | 0.015 | 0.17 | 0.055 |
| 79 | 0.0030 | 0.020 | 0.39 | 0.043 |
| 81 | 0.012 | 0.053 | 0.64 | 0.15 |
| 82 | 0.041 | 0.30 | * | 0.55 |
| 83 | 0.0091 | 0.048 | 0.28 | 0.096 |
| 84 | 0.018 | 0.089 | 0.62 | 0.54 |
| 85 | 0.053 | 0.31 | * | 0.50 |
| 86 | 0.020 | 0.17 | 0.48 | * |
| 88 | 0.0055 | 0.026 | 0.21 | 0.15 |
| 89 | 0.025 | 0.20 | * | 0.61 |
| 90 | 0.0047 | 0.026 | 0.20 | 0.044 |
| 91 | 0.018 | 0.094 | 0.64 | 0.32 |
| 92 | 0.0058 | * | * | * |
| 93 | 0.0075 | 0.061 | 0.31 | 0.0059 |
| 94 | 0.0041 | 0.041 | 0.83 | 0.25 |
| 95 | 0.0099 | 0.083 | * | 0.43 |
| 96 | 0.027 | 0.21 | * | * |
| 97 | 0.021 | 0.10 | 0.97 | * |
| 98 | 0.0033 | 0.070 | 0.30 | 0.0026 |
| 99 | 0.060 | 0.42 | * | * |
| 100 | 0.0093 | 0.045 | 0.24 | 0.47 |
| 101 | 0.0026 | 0.046 | 0.22 | 0.0023 |
| 102 | 0.019 | 0.15 | * | * |
| 103 | 0.016 | 0.17 | * | 0.47 |
| 104 | 0.089 | * | * | * |
| 105 | 0.021 | 0.19 | * | 0.37 |
| 106 | 0.0019 | 0.041 | 0.28 | 0.0036 |
| 107 | 0.0028 | 0.055 | 0.28 | 0.036 |
| 108 | 0.0039 | 0.024 | 0.58 | 0.58 |
| 109 | 0.0016 | 0.011 | 0.16 | 0.072 |
| 110 | 0.0056 | 0.091 | 0.51 | 0.0049 |
| 111 | 0.0019 | 0.027 | 0.22 | 0.028 |
| 112 | 0.0049 | 0.079 | 0.25 | 0.0033 |
| 113 | 0.0078 | 0.089 | 0.71 | 0.0087 |
| 114 | 0.095 | 0.43 | * | 0.87 |
| 115 | 0.13 | 0.40 | * | * |
| 116 | 0.0033 | 0.032 | 0.56 | 0.19 |
| 117 | 0.039 | 0.36 | * | * |
| 118 | 0.015 | 0.035 | * | 0.13 |
| 119 | 0.0040 | 0.039 | 0.59 | 0.10 |
| 120 | 0.014 | 0.20 | * | 0.12 |
| 121 | 0.0039 | 0.042 | 0.46 | 0.14 |
| 122 | 0.023 | 0.47 | * | 0.34 |
| 123 | 0.0061 | 0.19 | 0.87 | 0.23 |
| 124 | 0.029 | 0.23 | * | 0.55 |
| 125 | 0.071 | * | * | * |
| 126 | 0.073 | * | * | * |
| 127 | 0.017 | 0.19 | * | 0.42 |
| 128 | 0.14 | * | * | * |
| 129 | 0.0071 | 0.078 | * | 0.18 |
| 130 | 0.011 | 0.024 | * | 0.18 |
| 131 | 0.0054 | 0.032 | 0.56 | 0.13 |
| 132 | 0.0050 | 0.034 | * | 0.11 |
| 133 | 0.12 | * | * | * |
| 134a | 0.022 | 0.095 | 1.0 | 0.37 |
| 134b | 0.0022 | 0.024 | 0.66 | 0.056 |
| 135a | 0.097 | 0.94 | * | * |
| 135b | 0.0063 | 0.094 | * | 0.18 |
| 136a | 0.14 | * | * | * |
| 136b | 0.016 | 0.29 | * | 0.45 |
| 137a | 0.032 | 0.49 | * | 0.31 |
| 137b | 0.0041 | 0.039 | 0.38 | 0.088 |
| 138a | 0.023 | 0.74 | * | 0.25 |
| 138b | 0.0043 | 0.043 | 0.40 | 0.046 |
| 139a | 0.26 | 0.40 | 0.43 | * |
| 139b | 0.021 | 0.076 | * | 0.50 |
| 140 | 0.028 | 0.039 | 0.50 | 0.13 |
| 141 | 0.0028 | 0.014 | 0.24 | 0.038 |
| 142 | 0.0080 | 0.014 | 0.36 | 0.28 |
| 143 | 0.0025 | 0.0056 | 0.18 | 0.12 |
| 144 | 0.00066 | 0.0040 | 0.054 | 0.062 |
| 145 | 0.0037 | 0.015 | 0.026 | 0.20 |
| 146 | 0.0091 | 0.020 | 0.31 | 0.17 |
| 147 | 0.0024 | 0.0049 | 0.18 | 0.16 |
| 148 | 0.0043 | 0.010 | 0.20 | 0.21 |
| 149 | 0.0014 | 0.0028 | 0.060 | 0.098 |
| 150 | 0.00098 | 0.022 | 0.0098 | 0.091 |
| 151 | 0.049 | 0.072 | 0.63 | * |
| 152 | 0.0018 | 0.0037 | 0.032 | 0.11 |
| 153 | 0.0010 | 0.0023 | 0.015 | 0.11 |
| 154 | 0.0086 | 0.024 | 0.62 | 0.70 |
| 155 | 0.011 | 0.032 | 0.95 | * |
| 156 | 0.0032 | 0.042 | 0.52 | 0.65 |
| 157 | 0.0020 | 0.020 | 0.24 | 0.31 |
| 158 | 0.00070 | 0.0044 | 0.059 | 0.097 |
| 159 | 0.0016 | 0.011 | 0.080 | 0.30 |
| 160 | 0.0053 | 0.021 | 0.35 | 0.26 |
| 161 | 0.0034 | 0.011 | 0.31 | 0.14 |
| 162 | 0.032 | 0.20 | 0.68 | * |
| 163 | 0.010 | 0.034 | 0.41 | 0.31 |
| 164 | 0.0058 | 0.030 | 0.23 | 0.29 |
| 165 | 0.0044 | 0.020 | 0.10 | 0.34 |
| 166 | 0.0053 | 0.023 | 0.17 | 0.49 |
| 167 | 0.0031 | 0.030 | 0.17 | 0.98 |
| 168 | 0.084 | 0.71 | * | * |
| 169 | 0.0050 | 0.052 | 0.58 | * |

TABLE[a] 154-continued

| Ex[a]. No. | $IC_{50}$ (μM) JAK1 | $IC_{50}$ (μM) JAK2 | $IC_{50}$ (μM) JAK3 | $IC_{50}$ (μM) TYK2 |
|---|---|---|---|---|
| 170 | 0.021 | 0.11 | 0.52 | * |
| 171 | 0.10 | 0.94 | * | * |
| 172 | 0.013 | 0.093 | * | 0.63 |
| 173 | 0.034 | 0.26 | * | 0.46 |
| 174 | 0.0057 | 0.072 | 0.61 | 0.099 |
| 175 | 0.0056 | 0.0074 | 0.34 | 0.045 |
| 176 | 0.034 | 0.19 | * | * |
| 177 | 0.0029 | 0.031 | 0.20 | 0.0028 |
| 178 | 0.0026 | 0.024 | 0.17 | 0.053 |
| 179 | 0.028 | 0.094 | * | * |
| 180 | 0.0013 | 0.0019 | 0.030 | 0.022 |
| 181 | 0.024 | 0.13 | * | 0.49 |
| 182 | 0.0054 | 0.039 | 0.28 | 0.016 |
| 183 | 0.0061 | 0.055 | 0.80 | 0.041 |
| 184 | 0.0035 | 0.042 | 0.58 | 0.087 |
| 185 | 0.0081 | 0.051 | 0.32 | 0.13 |
| 186 | 0.0027 | 0.027 | 0.099 | 0.044 |
| 187 | 0.0076 | 0.038 | 0.37 | 0.36 |
| 188 | 0.0012 | 0.0084 | 0.11 | 0.063 |
| 189 | 0.011 | 0.038 | 0.61 | 0.38 |
| 190 | 0.022 | 0.098 | * | 0.61 |
| 191 | 0.010 | 0.084 | 0.92 | 0.18 |
| 192 | 0.0039 | 0.038 | 0.32 | 0.10 |
| 193 | 0.0053 | 0.041 | 0.28 | 0.0055 |
| 194a | 0.032 | 0.74 | * | 0.33 |
| 194b | 0.0084 | 0.046 | 0.50 | 0.11 |
| 195a | 0.030 | 0.55 | * | 0.31 |
| 195b | 0.0070 | 0.042 | 0.56 | 0.12 |
| 196a | 0.060 | 0.75 | * | * |
| 196b | 0.0032 | 0.036 | 0.29 | 0.27 |
| 197a | 0.016 | 0.40 | * | 0.15 |
| 197b | 0.0054 | 0.045 | 0.52 | 0.11 |
| 198b | 0.0025 | 0.037 | 0.40 | 0.065 |
| 199b | 0.0035 | 0.035 | 0.18 | 0.44 |
| 200b | 0.0025 | 0.032 | 0.076 | 0.24 |
| 201b | 0.0039 | 0.066 | 0.41 | 0.10 |
| 202b | 0.0034 | 0.085 | 0.68 | 0.26 |
| 203b | 0.0041 | 0.16 | 1.0 | 0.33 |
| 204b | 0.0072 | 0.19 | * | 0.35 |
| 205 | 0.026 | 0.25 | * | 0.75 |
| 206 | 0.27 | * | * | * |
| 207 | 0.0090 | 0.055 | * | * |
| 208 | 0.0028 | 0.033 | 0.36 | 0.37 |
| 209 | 0.061 | 0.42 | * | * |
| 210 | 0.0047 | 0.019 | 0.077 | 0.29 |
| 211 | 0.12 | 0.74 | * | * |
| 212 | 0.0054 | 0.047 | 0.62 | 0.45 |

TABLE[a] 155

| Ex[a]. No. | $IC_{50}$ (μM) JAK1 | $IC_{50}$ (μM) JAK2 | $IC_{50}$ (μM) JAK3 | $IC_{50}$ (μM) TYK2 |
|---|---|---|---|---|
| 213 | 0.024 | 0.19 | * | * |
| 214 | 0.0026 | 0.013 | 0.040 | 0.29 |
| 215 | 0.026 | 0.25 | * | * |
| 216 | 0.38 | * | * | * |
| 217 | 0.080 | 0.18 | 0.38 | * |
| 218 | 0.028 | 0.14 | * | * |
| 219 | 0.039 | 0.081 | 0.62 | 0.97 |
| 220 | 0.013 | 0.086 | 0.62 | * |
| 221 | 0.018 | 0.090 | * | * |
| 222 | 0.0035 | 0.033 | 0.32 | 0.77 |
| 223 | 0.015 | 0.031 | 0.94 | * |
| 224 | 0.0020 | 0.012 | 0.43 | 0.95 |
| 225 | 0.021 | 0.20 | * | * |
| 226 | 0.28 | * | * | * |
| 227 | 0.0025 | 0.021 | 0.079 | 0.57 |
| 228 | 0.0016 | 0.0044 | 0.17 | 0.10 |
| 229 | 0.039 | 0.087 | * | * |
| 230 | 0.035 | 0.13 | * | * |
| 231 | 0.0043 | 0.023 | 0.23 | 0.61 |
| 232 | 0.0053 | 0.033 | * | 0.74 |
| 233 | 0.021 | 0.071 | * | * |

TABLE[a] 155-continued

| Ex[a]. No. | $IC_{50}$ (μM) JAK1 | $IC_{50}$ (μM) JAK2 | $IC_{50}$ (μM) JAK3 | $IC_{50}$ (μM) TYK2 |
|---|---|---|---|---|
| 234 | 0.36 | 0.88 | * | * |
| 235 | 0.056 | 0.37 | * | * |
| 236 | 0.0068 | 0.052 | 0.45 | * |
| 237 | 0.0015 | 0.010 | 0.41 | * |
| 238 | 0.00079 | 0.0046 | 0.055 | 0.11 |
| 239 | 0.0081 | 0.035 | 0.61 | 0.65 |
| 240 | 0.039 | 0.11 | 0.60 | * |
| 241 | 0.046 | 0.17 | * | * |
| 242 | 0.0065 | 0.052 | 0.96 | * |
| 243 | 0.044 | 0.29 | * | * |
| 244 | 0.0054 | 0.038 | 0.44 | 0.79 |
| 245 | 0.017 | 0.062 | * | * |
| 246 | 0.0053 | 0.019 | 0.28 | 0.14 |
| 247 | 0.013 | 0.090 | 0.92 | * |
| 248 | 0.041 | 0.14 | * | * |
| 249 | 0.017 | 0.056 | 0.49 | 0.86 |
| 250 | 0.031 | 0.18 | * | * |
| 251 | 0.031 | 0.20 | * | * |
| 252 | 0.017 | 0.060 | * | * |
| 253 | 0.0011 | 0.0066 | 0.14 | 0.044 |
| 254 | 0.0071 | 0.024 | 0.53 | 0.16 |
| 255 | 0.0025 | 0.015 | 0.24 | 0.14 |
| 256 | 0.015 | 0.062 | 0.99 | 0.27 |
| 257 | 0.0017 | 0.016 | 0.49 | 0.049 |
| 258 | 0.012 | 0.081 | * | 0.74 |
| 259 | 0.0021 | 0.0081 | 0.27 | 0.037 |
| 260 | 0.024 | 0.048 | * | 0.97 |
| 261 | 0.023 | 0.091 | * | 0.64 |
| 262 | 0.0047 | 0.045 | 0.59 | 0.91 |
| 263 | 0.027 | 0.22 | * | * |
| 264 | 0.011 | 0.032 | * | * |
| 265 | 0.046 | 0.18 | * | * |
| 266 | 0.025 | 0.11 | * | 0.35 |
| 267 | 0.0010 | 0.032 | 0.79 | 0.019 |
| 268 | 0.0044 | 0.036 | 0.72 | 0.12 |
| 269 | 0.0013 | 0.012 | 0.057 | 0.10 |
| 270 | 0.012 | 0.10 | 0.75 | 0.0048 |
| 271 | 0.020 | 0.063 | * | 0.43 |
| 272 | 0.0035 | 0.053 | 0.43 | 0.094 |
| 273 | 0.0046 | 0.021 | 0.57 | 0.24 |
| 274 | 0.0035 | 0.029 | * | 0.20 |
| 275 | 0.0067 | 0.065 | 0.85 | 0.52 |
| 276 | 0.0029 | 0.049 | 0.063 | 0.032 |
| 277 | 0.0015 | 0.033 | 0.27 | 0.050 |
| 278 | 0.0043 | 0.034 | 0.45 | 0.40 |
| 279 | 0.0074 | 0.044 | 0.53 | 0.20 |
| 280 | 0.0019 | 0.062 | 0.68 | 0.10 |
| 281 | 0.0077 | 0.050 | 0.15 | 0.48 |
| 282 | 0.0052 | 0.070 | 0.39 | 0.080 |
| 283 | 0.014 | 0.11 | 0.90 | 0.23 |
| 284 | 0.017 | 0.15 | * | 0.32 |
| 285 | 0.0091 | 0.12 | 0.61 | 0.068 |
| 286 | 0.0059 | 0.035 | 0.57 | 0.23 |
| 287 | 0.0065 | 0.077 | * | 0.33 |
| 288 | 0.046 | 0.15 | 0.15 | 0.37 |
| 289 | 0.021 | 0.15 | 0.85 | 0.16 |
| 290 | 0.0076 | 0.039 | 0.50 | 0.27 |
| 291 | 0.0053 | 0.10 | 0.67 | 0.14 |
| 292 | 0.0027 | 0.017 | 0.39 | 0.27 |
| 293 | 0.024 | 0.10 | 0.94 | 0.31 |
| 294 | 0.022 | 0.12 | 0.48 | 0.34 |
| 295 | 0.0069 | 0.064 | 0.84 | 0.33 |
| 296 | 0.0038 | 0.065 | 0.73 | 0.19 |
| 297 | 0.0095 | 0.10 | * | 0.32 |
| 298 | 0.019 | 0.11 | * | 0.59 |
| 299 | 0.016 | 0.17 | * | * |
| 300 | 0.025 | 0.059 | 0.75 | * |
| 301 | 0.024 | 0.072 | 0.96 | * |
| 302 | 0.012 | 0.029 | 0.49 | 0.36 |
| 303 | 0.057 | 0.35 | * | * |
| 304 | 0.049 | 0.27 | * | * |
| 305 | 0.046 | 0.29 | * | * |
| 306 | 0.015 | 0.054 | * | 0.62 |
| 307 | 0.0066 | 0.26 | * | * |
| 308 | 0.0024 | 0.012 | 0.24 | 0.79 |
| 309 | 0.0076 | 0.097 | * | 0.31 |
| 310 | 0.071 | 0.38 | * | * |

TABLE[a] 155-continued

| Ex[a]. No. | $IC_{50}$ (μM) JAK1 | $IC_{50}$ (μM) JAK2 | $IC_{50}$ (μM) JAK3 | $IC_{50}$ (μM) TYK2 |
|---|---|---|---|---|
| 311 | 0.025 | 0.16 | * | 0.94 |
| 312 | 0.012 | 0.045 | * | 0.37 |
| 313 | 0.0084 | 0.051 | * | 0.51 |
| 314 | 0.0080 | 0.19 | * | 0.75 |
| 315 | 0.010 | 0.20 | * | 0.53 |
| 316 | 0.013 | 0.099 | * | 0.59 |
| 317 | 0.0013 | 0.016 | 0.47 | 0.62 |
| 318 | 0.0048 | 0.057 | * | 0.61 |
| 319 | 0.027 | 0.23 | * | * |
| 320 | 0.0076 | 0.057 | * | 0.86 |
| 321 | 0.024 | 0.21 | * | * |
| 322 | 0.0013 | 0.0071 | 0.20 | 0.43 |
| 323 | 0.0051 | 0.034 | 0.83 | 0.78 |
| 324 | 0.0034 | 0.034 | 0.66 | 0.75 |
| 325 | 0.011 | 0.058 | * | 0.88 |
| 326 | 0.048 | 0.31 | * | * |
| 327 | 0.0070 | 0.054 | 0.79 | 0.55 |
| 328 | 0.0073 | 0.033 | 0.53 | 0.90 |
| 329 | 0.0048 | 0.029 | 0.80 | 0.21 |
| 330 | 0.0074 | 0.047 | * | 0.14 |
| 331 | 0.0088 | 0.054 | * | 0.42 |
| 332 | 0.012 | 0.045 | * | 0.49 |
| 333 | 0.0085 | 0.044 | * | 0.27 |
| 334 | 0.064 | * | * | * |
| 335 | 0.029 | 0.29 | * | 0.71 |
| 336 | 0.025 | 0.37 | * | * |
| 337 | 0.029 | 0.34 | * | 0.51 |
| 338 | 0.0069 | 0.060 | 0.48 | 0.59 |
| 339 | 0.018 | 0.052 | 0.26 | 0.86 |
| 340 | 0.021 | 0.23 | * | * |
| 341 | 0.010 | 0.059 | 0.31 | 0.32 |
| 342 | 0.0039 | 0.034 | 0.13 | 0.35 |
| 343 | 0.010 | 0.063 | 0.33 | 0.44 |
| 344 | 0.012 | 0.068 | 0.52 | 0.39 |
| 345 | 0.025 | 0.20 | * | * |
| 346 | 0.0051 | 0.060 | * | * |
| 347 | 0.0069 | 0.11 | 0.65 | * |
| 348 | 0.0099 | 0.051 | 0.75 | 0.29 |
| 349 | 0.0059 | 0.048 | * | 0.25 |
| 350 | 0.0080 | 0.047 | * | 0.54 |
| 351 | 0.012 | 0.089 | * | * |
| 352 | 0.0050 | 0.029 | * | * |
| 353 | 0.0029 | 0.031 | 0.35 | 0.46 |
| 354 | 0.0018 | 0.026 | 0.69 | 0.16 |
| 355 | 0.0042 | 0.033 | * | 0.15 |
| 356 | 0.0036 | 0.036 | * | 0.16 |
| 357 | 0.067 | 0.33 | * | 0.87 |
| 358 | 0.63 | 0.91 | * | * |
| 359 | 0.042 | 0.22 | * | 0.56 |
| 360 | 0.026 | 0.10 | * | 0.33 |
| 361 | 0.089 | 0.25 | * | * |
| 362 | 0.0074 | 0.057 | * | * |
| 363 | 0.044 | 0.29 | * | * |
| 364 | 0.0057 | 0.011 | 0.39 | 0.21 |
| 365 | 0.0054 | 0.016 | 0.74 | 0.34 |
| 366 | 0.011 | 0.028 | 0.28 | 0.26 |
| 367 | 0.00099 | 0.0043 | 0.054 | 0.0073 |
| 368 | 0.0013 | 0.0061 | 0.37 | 0.030 |
| 369 | 0.00033 | 0.0017 | 0.048 | 0.0092 |
| 370 | 0.0074 | 0.097 | 0.59 | * |
| 371 | 0.0033 | 0.035 | 0.39 | 0.18 |
| 372 | 0.0041 | 0.016 | 0.23 | 0.41 |
| 373 | 0.0015 | 0.011 | 0.035 | 0.53 |
| 374 | 0.038 | 0.18 | * | * |
| 375 | 0.047 | 0.33 | * | * |
| 376 | 0.019 | 0.19 | * | * |
| 377 | 0.0045 | 0.017 | 0.054 | * |
| 378 | 0.0040 | 0.071 | 0.41 | 0.20 |
| 379 | 0.013 | 0.11 | 0.66 | 0.29 |
| 380 | 0.0020 | 0.0025 | 0.20 | 0.028 |
| 381a | 0.069 | 0.22 | 0.26 | * |
| 381b | 0.0066 | 0.057 | 0.42 | 0.24 |
| 382a | 0.015 | 0.063 | 0.75 | 0.76 |
| 382b | 0.00031 | 0.0028 | 0.070 | 0.013 |
| 383a | 0.090 | 0.37 | * | * |
| 383b | 0.0015 | 0.013 | 0.50 | 0.17 |
| 384a | 0.087 | 0.56 | * | * |
| 384b | 0.022 | 0.080 | * | * |
| 385b | 0.0019 | 0.031 | 0.18 | 0.21 |
| 386b | 0.0017 | 0.027 | 0.28 | 0.39 |
| 387b | 0.0019 | 0.032 | 0.12 | 0.18 |
| 388b | 0.0012 | 0.025 | 0.26 | 0.21 |
| 389b | 0.0079 | 0.14 | * | 0.67 |
| 390b | 0.0024 | 0.089 | 0.52 | 0.36 |
| 391b | 0.018 | 0.39 | * | 0.58 |
| 392b | 0.014 | 0.080 | 0.61 | 0.33 |
| 393b | 0.0062 | 0.030 | 0.79 | 0.38 |
| 394b | 0.015 | 0.090 | * | * |
| 395b | 0.0022 | 0.010 | 0.61 | 0.15 |
| 396b | 0.022 | 0.19 | * | 0.71 |
| 397b | 0.023 | 0.21 | * | 0.80 |
| 398b | 0.029 | 0.11 | * | 0.75 |
| 399b | 0.0075 | 0.029 | * | 0.20 |
| 400b | 0.042 | 0.19 | * | 0.84 |
| 401 | 0.012 | 0.036 | 0.36 | 0.15 |
| 402 | 0.011 | 0.030 | 0.13 | 0.10 |
| 403 | 0.040 | 0.30 | 0.44 | 0.81 |
| 404 | 0.11 | 0.35 | 0.32 | * |
| 405 | 0.025 | 0.25 | * | 0.77 |
| 406 | 0.083 | 0.56 | * | 0.94 |
| 407 | 0.0034 | 0.0073 | 0.31 | 0.13 |
| 408 | 0.0052 | 0.013 | 0.22 | 0.31 |
| 409 | 0.019 | 0.032 | 0.92 | 0.84 |
| 410 | 0.022 | 0.040 | 0.32 | 0.58 |
| 411 | 0.0043 | 0.015 | 0.17 | 0.36 |
| 412 | 0.0026 | 0.0056 | 0.054 | 0.32 |
| 413 | 0.020 | 0.031 | * | 0.62 |
| 414 | 0.0095 | 0.13 | * | 0.11 |
| 415 | 0.030 | 0.095 | * | * |
| 416 | 0.029 | 0.047 | * | 0.68 |
| 417 | 0.0078 | 0.026 | 0.38 | 0.42 |
| 418 | 0.0043 | 0.0084 | 0.33 | 0.17 |
| 419 | 0.0035 | 0.0061 | 0.069 | 0.27 |
| 420 | 0.0057 | 0.015 | 0.41 | 0.30 |
| 421 | 0.010 | 0.17 | * | * |
| 422 | 0.0028 | 0.051 | * | 0.13 |
| 423 | 0.077 | 0.72 | * | * |
| 424 | 0.044 | 0.48 | * | * |
| 425 | 0.0025 | 0.022 | 0.082 | 0.37 |
| 426 | 0.011 | 0.062 | 0.87 | 0.58 |
| 427 | 0.00016 | 0.0012 | 0.030 | 0.016 |
| 428 | 0.19 | 0.75 | * | * |
| 429 | 0.017 | 0.035 | 0.79 | 0.52 |
| 430 | 0.0086 | 0.049 | * | 0.41 |
| 431 | 0.0048 | 0.013 | 0.29 | 0.24 |
| 432 | 0.0026 | 0.0088 | 0.17 | 0.067 |
| 433 | 0.0081 | 0.027 | 0.71 | 0.12 |
| 434 | 0.0023 | 0.014 | 0.49 | 0.034 |
| 435a | 0.0054 | 0.021 | 0.72 | 0.17 |
| 435b | 0.00011 | 0.0025 | 0.032 | 0.0029 |
| 436 | 0.035 | 0.17 | * | * |
| 437 | 0.020 | 0.055 | 0.57 | 0.45 |
| 438 | 0.017 | 0.044 | 0.34 | 0.58 |
| 439a | 0.13 | 0.34 | * | * |
| 439b | 0.0031 | 0.0067 | 0.33 | 0.025 |
| 440 | 0.0053 | 0.031 | 0.54 | 0.14 |
| 441 | 0.0016 | 0.0046 | 0.12 | 0.024 |
| 442a | 0.027 | 0.061 | 0.52 | 0.79 |
| 442b | 0.0032 | 0.014 | 0.10 | 0.88 |
| 443a | 0.026 | 0.060 | 0.73 | 0.54 |
| 443b | 0.010 | 0.030 | 0.34 | * |
| 444 | 0.0034 | 0.0090 | 0.25 | 0.045 |
| 445 | 0.031 | 0.13 | 0.22 | 0.052 |

The tricyclic pyrimidine compounds of the present invention have favorable inhibitory activity against JAKs as shown above.

Assay Example[a] 2

Signal Assay in Human Whole Blood

To be a effective pharmaceutical compound for the target diseases of the present invention, especially for rheumatoid arthritis, it is more favorable that the compounds indicate excellent inhibitory activity against JAKs in human whole blood. Inhibitory activity against JAKs in human whole blood can be assessed by, for example, STAT phosphorylation assay in human whole blood as described below.

Compounds are added at the various concentrations to human whole blood which is collected from healthy volunteers and preincubated for 30 minutes. Next, cytokine such as IL-2 or IL-6 is added to the mixture and incubated for 15 minutes. Cytokines can be purchased, for example, from PeproTech Inc. Cytokines are added to mixture at 100 ng/mL as final concentration. The mixture including the blood cells are hemolyzed, fixed, permeabilized, washed, and resuspended in stain buffer. BD Cytofix/Cytoperm® solution (manufactured by Becton, Dickinson and Company (BD)), for example, can be used to hemolyze, fix, and permeabilize. Staining buffer (manufactured by BD), for example, can be used as stain buffer according to each protocol issued by BD. Fluorescence-labeled anti-phosphorylated STAT antibody and fluorescence-labeled anti-CD3 antibody are added to the cell suspension and incubated for 30 minutes. Then, cells are washed and resuspended in stain buffer. Fluorescence-labeled anti-phosphorylated STAT antibody and fluorescence-labeled anti-CD3 antibody can be purchased, for example from BD, and final concentration of antibodies can be determined according to each protocols issued by BD. Fluorescence intensity of fluorescence-labeled cells in cell suspension is detected by flow-cytometory. Because the detected fluorescence intensity is proportional to the concentration of the phosphorylated STAT protein in CD3 positive cells, inhibitory activity against STAT phosphorylation by the compounds can be calculated from the ratio between the above mentioned fluorescence intensity and the blank fluorescence intensity which is measured simultaneously without the compounds. From the plot of logarithm of the compound concentrations and the inhibitory activities, the $IC_{50}$ value can be calculated.

Assay Example[a] 3

Inhibition of Proliferation of Erythro-Leukemic Cell Line

The inhibitory activity of the tricyclic pyrimidine compounds of the present invention on cell proliferation mediated by JAK signal can be assayed using a human erythroleukemic cell line, TF-1.

TF-1 cells can be purchased from ATCC (American Type Culture Collection). TF-1 cells can be expanded in RPMI1640 media containing 5% FBS and 1 ng/mL GM-CSF (Granulocyte Macrophage Colony-Stimulating Factor) using a $CO_2$ incubator (5% $CO_2$, 37° C.). At the assay, TF-1 cells washed by PBS (Phosphate Buffered Saline) are resuspended in RPMI1640 media containing 5% FBS, and dispensed in 96-well culture plate at $1\times10^4$ cells/well. Compounds at various concentrations are added to the cells and preincubated for 30 minutes, and then cytokine such as IL-4 or IL-6 is added to the cells. Culture plates are incubated using a $CO_2$ incubator (5% $CO_2$, 37° C.) for 3 days. Cell proliferation can be assayed using WST-8 reagent (Kishida Chemical Co., Ltd.) according to instructions by the manufacturer. The formazan pigment is generated by the addition of WST-8 reagent solution to each well of the culture plates and the subsequent incubation in a $CO_2$ incubator (5% $CO_2$, 37° C.) for 4 hours, and then detected by measuring the absorbance at 450 nm with a microplate reader. From the plot of logarithm of the compound concentrations and the inhibitory activities, the $IC_{50}$ value can be calculated.

Reference Synthetic Example[b] 1

Methyl 4-methylpyridin-3-ylcarbamate

Potassium tert-butoxide (10.3 g, 92.5 mmol) in tetrahydrofuran (25 mL) was stirred at 23 to 27° C. for 30 minutes, and dimethyl carbonate (4.67 mL, 55.5 mmol) was added while the temperature was kept at 35° C. or below. To the reaction mixture, 3-amino-4-methylpyridine (5.00 g, 46.2 mmol) in tetrahydrofuran (40 mL) stirred at 32 to 38° C. for 90 minutes was added dropwise at 20 to 35° C. over 2 hours with stirring. The resulting reaction mixture was cooled to 15 to 20° C., stirred with water (25 mL) at 25° C. or below for 1 hour and extracted with tetrahydrofuran. The organic layer was azeotropically distilled with toluene under reduced pressure to a volume of about 50 mL and stirred at 23 to 27° C. for one day. The precipitated solid was collected by filtration, washed with toluene and dried under reduced pressure to give the title compound as a brown solid (6.77 g, yield 88%).

Reference Synthetic Example[b] 2

Methyl rac-(3R,4R)-1-benzyl-4-methylpiperidin-3-ylcarbamate

Methyl 4-methylpyridin-3-ylcarbamate (30.6 g, 184 mmol) and 5% rhodium-carbon (12 g) in acetic acid (120 mL) were stirred at 72 to 78° C. under a hydrogen atmosphere (70-80 psi). After disappearance of the starting materials was confirmed by NMR, the reaction mixture was filtered, and the filtrate was concentrated under reduced pressure to give a concentrate (40.9 g). The concentrate (31.7 g) was stirred with benzaldehyde (21.5 mL, 202 mmol) in toluene (184 mL) at 20 to 30° C. for 30 minutes. The resulting toluene solution was added dropwise at 30° C. or below to a toluene (40 mL) solution of sodium triacetoxyborohydride (9.35 g, 44.0 mmol) stirred at 20 to 30° C. for 1 hour. The resulting reaction mixture was stirred for 2 hours, adjusted to pH 6-7 with 3 M aqueous sodium hydroxide at 20° C. to 30° C. and extracted with toluene. The organic layer was dried over anhydrous magnesium sulfate and concentrated under reduced pressure to give a brown oil (38.1 g) containing the title compound. The oil was used for the next step without further purification.

Reference Synthetic Example[b] 3 rac-(3R,4R)-1-Benzyl-4-methylpiperidin-3-amine

Crude methyl rac-(3R,4R)-1-benzyl-4-methylpiperidin-3-ylcarbamate (2.3 g) in concentrated hydrochloric acid (15 mL) was refluxed for one day under heating and allowed to cool to room temperature. The hydrochloric acid was removed under reduced pressure, and the reaction mixture was partitioned between chloroform and saturated aqueous sodium chloride. The aqueous layer was basified with saturated aqueous sodium carbonate and extracted with ethyl acetate twice, and the organic layers were combined, dried over anhydrous magnesium sulfate and concentrated under reduced pressure. The resulting brown oil (4.94 g) containing the title compound was used for the next step without further purification.

Reference Synthetic Example[b] 4

1H-Pyrrolo[2,3-b]pyridine 7-oxide m-Chloroperbenzoic acid (25 wt % water content, 12.7 g, 55.2 mmol) in ethyl acetate (30 mL) was gradually added dropwise to 1H-pyrrolo[2,3-b]pyridine (5.14 g, 43.5 mmol) in ethyl acetate (45 mL) cooled to 0° C., and the reaction mixture was stirred at room temperature for one day and then stirred with m-chloroperbenzoic acid (25 wt % water content, 3.93 g, 17.1 mmol) in ethyl acetate (4 mL) at room temperature for 4 hours. The reaction mixture was cooled with ice and filtered, and the resulting solid was purified by silica gel column chromatography (silica gel NH type manufactured by Fuji Silysia Chemical Ltd.: chloroform/methanol=10/1 (v/v)) to give the title compound as a yellow solid (4.95 g, yield 85%).

Reference Synthetic Example[b] 5

4-Chloro-1H-pyrrolo[2,3-b]pyridine

1H-Pyrrolo[2,3-b]pyridine 7-oxide (4.95 g, 36.9 mmol) in N,N-dimethylformamide (10 mL) was heated to 50° C., mixed with methanesulfonyl chloride (8.00 mL, 103 mmol) and stirred at 73° C. for 3 hours. The reaction mixture was cooled with ice and diluted with water (70 mL), neutralized with sodium hydroxide and stirred for 10 minutes under cooling with ice. The precipitated solid was collected by filtration, washed with water and dried under reduced pressure to give the title compound as a reddish brown solid (4.65 g, yield 83%).

Reference Synthetic Example[b] 6

4-Chloro-1-(triisopropylsilyl)-1H-pyrrolo[2,3-b]pyridine

4-Chloro-1H-pyrrolo[2,3-b]pyridine (2.84 g, 18.6 mmol) in N,N-dimethylformamide (10 mL) and tetrahydrofuran (10 mL) was stirred with sodium hydride (55 wt % dispersion in mineral oil, 1.08 g, 27.0 mmol) under cooling with ice for 1 hour. The reaction mixture was stirred with triisopropylsilyl chloride (6.0 mL, 28 mmol) at room temperature for one day. After addition of water, the reaction mixture was warmed to room temperature and extracted with hexane twice. The resulting organic layers were combined, washed with saturated aqueous sodium chloride dried over anhydrous magnesium sulfate and concentrated under reduced pressure. The residue was purified by silica gel column chromatography (hexane) to give the title compound as a reddish brown oil (5.74 mg, yield 99%).

Reference Synthetic Example[b] 7

4-Chloro-1H-pyrrolo[2,3-b]pyridine-5-carbaldehyde s-Butyllithium-hexane/cyclohexane solution (1.06 M, 27 mL, 29 mmol) was added to 4-chloro-1-(triisopropylsilyl)-1H-pyrrolo[2,3-b]pyridine (5.74 g, 18.6 mmol) in tetrahydrofuran (50 mL) cooled to −78° C., and the reaction mixture was stirred for 1 hour. The reaction mixture was stirred with N,N-dimethylformamide (7.0 mL, 90 mmol) for another 1 hour and then with 4 M hydrogen chloride-1,4-dioxane solution (20 mL) for 30 minutes, and after addition of water, extracted with ethyl acetate. The organic layer was washed with saturated aqueous sodium chloride, dried over anhydrous magnesium sulfate and concentrated under reduced pressure. The resulting residue was dissolved in dichloromethane (15 mL) and stirred with trifluoroacetic acid (15 mL) for one day. The reaction mixture was concentrated under reduced pressure, diluted with water and neutralized with saturated aqueous sodium hydrogen carbonate, and the residue was collected by filtration and dried under reduced pressure. The crude product was mixed with ethyl acetate (20 mL) and hexane (20 mL), and the solid was collected by filtration, washed with hexane and dried under reduced pressure to give the title compound as a pale yellow solid (2.72 g, yield 81%).

Reference Synthetic Example[b] 8

4-(Cyclohexylamino)-1H-pyrrolo[2,3-b]pyridine-5-carbaldehyde

4-Chloro-1H-pyrrolo[2,3-b]pyridine-5-carbaldehyde (845 mg, 4.68 mmol) and cyclohexylamine (2.5 mL, 22 mmol) in ethylene glycol (2 mL) were stirred at 170° C. for 1 hour under microwave irradiation. The reaction mixture was allowed to cool to room temperature and, after addition of water, extracted with chloroform. The organic layer was stirred with 2 M hydrochloric acid (20 mL) for 1 hour, and the organic layer was separated. The aqueous layer was adjusted to pH 9 or above with 10 M aqueous sodium hydroxide and extracted with chloroform. The organic layers were combined, washed with saturated aqueous sodium chloride, dried over anhydrous magnesium sulfate and concentrated under reduced pressure. The residue was purified by silica gel column chromatography (chloroform/methanol=10/1 (v/v)) to give the title compound as a pale yellow oil (804 mg, yield 71%).

Reference Synthetic Example[b] 9

4-(Cyclohexylamino)-1-{[2-(trimethylsilyl)ethoxy]methyl}-1H-pyrrolo[2,3-b]pyridine-5-carbaldehyde 4-(Cyclohexylamino)-1H-pyrrolo[2,3-b]pyridine-5-carbaldehyde (273 mg, 1.12 mmol) in N,N-dimethylformamide (3 mL) was stirred with sodium hydride (55 wt % dispersion in mineral oil, 61.2 mg, 1.53 mmol) for 1 hour under cooling with ice. The reaction mixture was stirred with [2-(chloromethoxy)ethyl]trimethylsilane (260 μL, 1.47 mmol) at room temperature for one day, and after addition of water, extracted with ethyl acetate. The organic layer was washed with saturated aqueous sodium chloride, dried over anhydrous magnesium sulfate and concentrated under reduced pressure. The resulting residue was purified by silica gel column chromatography (hexane/ethyl acetate=5/1 (v/v)) to give the title compound as a pale yellow oil (265 mg, yield 63%).

Reference Synthetic Example[b] 10

(4-(Cyclohexylamino)-1-{[2-(trimethylsilyl)ethoxy]methyl}-1H-pyrrolo[2,3-b]pyridin-5-yl)methanol 4-(Cyclohexylamino)-1-{[2-(trimethylsilyl)ethoxy]methyl}-1H-pyrrolo[2,3-b]pyridine-5-carbaldehyde (104 mg, 0.279 mmol) in methanol (3 mL) was stirred with sodium borohydride (15.8 mg, 0.418 mmol) at room temperature for 2 hours, after addition of water, the reaction mixture was extracted with chloroform twice, and the organic layers were combined, dried over anhydrous magnesium sulfate and concentrated under reduced pressure. The resulting pale yellow oil containing the title compound was used for the next step without further purification.

Reference Synthetic Example$^b$ 11

1-Cyclohexyl-7-{[2-(trimethylsilyl)ethoxy]methyl}-1,2,4,7-tetrahydropyrrolo[3',2':5,6]pyrido[4,3-d][1,3]oxazine

[4-(Cyclohexylamino)-1-{[2-(trimethylsilyl)ethoxy]methyl}-1H-pyrrolo[2,3-b]pyridin-5-yl)methanol (38 mg, 0.10 mmol) and aqueous formaldehyde (35 wt %, 0.6 mL, 8 mmol) in ethanol (2 mL) were stirred at 75° C. for 1 hour. The reaction mixture was then stirred with acetic acid (1 mL) at 75° C. for 1 hour, allowed to cool to room temperature, and after addition of saturated aqueous sodium hydrogen carbonate, extracted with ethyl acetate. The organic layer was dried over anhydrous sodium sulfate and concentrated under reduced pressure. The residue was purified by silica gel column chromatography (hexane/ethyl acetate=2/1 (v/v)) to give the title compound as a colorless oil (19.8 mg, yield 51%).

Reference Synthetic Example$^b$ 12

5-(Aminomethyl)-N-cyclohexyl-1-{[2-(trimethylsilyl)ethoxy]methyl}-1H-pyrrolo[2,3-b]pyridin-4-amine (4-(Cyclohexylamino)-1-{[2-(trimethylsilyl)ethoxy]methyl}-1H-pyrrolo[2,3-b]pyridin-5-yl)methanol (870 mg, 2.31 mmol) obtained in Reference Synthetic Example$^b$ 10, phthalimide (681 mg, 4.63 mmol) and triphenylphosphine (1.21, 4.63 mmol) in tetrahydrofuran (10 mL) were stirred at room temperature for 30 minutes and then stirred with diisopropyl azodicarboxylate (936 mg, 4.63 mmol) for one day. The reaction mixture was concentrated under reduced pressure, and after addition of water, extracted with ethyl acetate. The organic layer was dried over anhydrous magnesium sulfate and concentrated under reduced pressure. The residue was purified by silica gel column chromatography (hexane/ethyl acetate=10/1 (v/v)) to remove triphenylphosphine oxide. The resulting crude product was dissolved in ethanol (30 mL) and stirred with hydrazine monohydrate (1.0 mL, 12 mmol) at 80° C. for 1 hour and allowed to cool to room temperature. The precipitated solid was collected by filtration and washed with ethanol and chloroform. The filtrate and the washings were combined and concentrated under reduced pressure, and the residue was purified by silica gel column chromatography (chloroform/methanol=20/1 (v/v) to give the title compound as a colorless oil (513 mg, yield 59%).

Reference Synthetic Example$^b$ 13

1-Cyclohexyl-7-{[2-(trimethylsilyl)ethoxy]methyl}-3,4-dihydro-1H-Pyrrolo[3',2':5,6]pyrido[4,3-d]pyrimidin-2(7H)-one 5-(Aminomethyl)-N-cyclohexyl-1-{[2-(trimethylsilyl)ethoxy]methyl}-1H-pyrrolo[2,3-b]pyridin-4-amine (127 mg, 0.339 mmol) in dichloromethane was stirred with 1,1'-carbonyldiimidazole (65.9 mg, 0.407 mmol) at 60° C. for 2 hours. The reaction mixture was concentrated under reduced pressure and, after addition of water, extracted with chloroform. The organic layer was dried over anhydrous magnesium sulfate and concentrated under reduced pressure to give the title compound as a colorless oil (93.2 mg, yield 69%).

Reference Synthetic Example$^b$ 14

1-Cyclohexyl-1,4-dihydro-7-{[2-(trimethylsilyl)ethoxy]methyl}-pyrrolo[3',2':5,6]pyrido[3,4-e]pyrimidine 5-(Aminomethyl)-N-cyclohexyl-1-{[2-(trimethylsilyl)ethoxy]methyl}-1H-pyrrolo[2,3-b]pyridin-4-amine (104 mg, 0.278 mmol) obtained in Reference Synthetic Example$^b$ 12 in ethyl orthoformate (1 mL) was reacted at 180° C. for 30 minutes under microwave irradiation and allowed to cool to room temperature. After addition of water, the reaction mixture was extracted with ethyl acetate, and the organic layer was dried over anhydrous magnesium sulfate and concentrated under reduced pressure. The resulting residue was purified by silica gel column chromatography (Hi Flash column amino type manufactured by Yamazen Corporation: hexane/ethyl acetate=1/1 (v/v) to give the title compound as a pale yellow oil (48.8 mg, yield 45%).

Reference Synthetic Example$^b$ 15

2,3-Dihydro-1H-pyrrolo[2,3-b]pyridine

1H-Pyrrolo[2,3-b]pyridine (8.78 g, 74.3 mmol) and 5% palladium-carbon in a mixture of triethylamine (5 mL) and formic acid (30 mL) was stirred at 80° C. for 4 days. The reaction mixture was allowed to cool to room temperature and filtered, and the filtrate was concentrated under reduced pressure. The resulting residue was adjusted to pH 12 with 6 M aqueous sodium hydroxide and stirred at 65° C. for 5 hours. The reaction mixture was allowed to cool to room temperature and extracted with chloroform, and the organic layer was dried over anhydrous sodium sulfate and concentrated under reduced pressure. The residue was purified by silica gel column chromatography (hexane/ethyl acetate=1/2→ethyl acetate/methanol=20/1 (v/v)) to give the title compound as a pale yellow solid (2.15 g, yield 24%).

Reference Synthetic Example$^b$ 16

5-Bromo-2,3-dihydro-1H-pyrrolo[2,3-b]pyridine 2,3-Dihydro-1H-pyrrolo[2,3-b]pyridine (4.40 g, 36.6 mmol) in a mixture of pyridine (4.4 mL) and dichloromethane (20 mL) was gradually added dropwise to bromine (7.00 g, 43.8 mmol) in dichloromethane (20 mL) cooled to 0° C., and the resulting reaction mixture was stirred at 0° C. for 20 minutes, after addition of saturated aqueous sodium thiosulfate, the reaction mixture was extracted with chloroform, and the organic layer was dried over anhydrous sodium sulfate and concentrated under reduced pressure. The residue was purified by silica gel column chromatography (hexane/ethyl acetate=1/1→0/1 (v/v)) to give the title compound as a brown solid (2.83 g, yield 39%).

Reference Synthetic Example[b] 17

5-Bromo-1H-pyrrolo[2,3-b]pyridine

5-Bromo-2,3-dihydro-1H-pyrrolo[2,3-b]pyridine (2.83 g, 14.2 mol) and manganese dioxide (5.0 g, 58 mmol) in chloroform (30 mL) were stirred at 65° C. for 3 hours. The reaction mixture was allowed to cool to room temperature and filtered, and the solid was washed with chloroform, and the filtrate and the washings were combined and concentrated under reduced pressure. The residue was purified by silica gel column chromatography (hexane/ethyl acetate/chloroform=2/1/1→1/1/0 (v/v/v)) to give the title compound as a brown solid (2.14 g, yield 76%).

Reference Synthetic Example[b] 18

5-Bromo-1H-pyrrolo[2,3-b]pyridine 7-oxide m-Chloroperbenzoic acid (25 wt % water content, 322 mg, 1.40 mmol) in ethyl acetate (5 mL) was gradually added dropwise to 5-bromo-1H-pyrrolo[2,3-b]pyridine (184 mg, 0.934 mmol) in ethyl acetate (10 mL), and the reaction mixture was stirred at room temperature for 6 hours. After addition of saturated aqueous sodium hydrogen carbonate, the reaction mixture was extracted with chloroform, and the organic layer was dried over anhydrous sodium sulfate and concentrated under reduced pressure. The residue was mixed with a mixture of ethyl acetate/hexane=1/1 (v/v), and the solid was collected by filtration, washed with hexane and dried under reduced pressure to give the title compound as a light brown solid (150 mg, yield 75%).

Reference Synthetic Example[b] 19

5-Bromo-4-chloro-1-{[2-(trimethylsilyl)ethoxy]methyl}-1H-pyrrolo[2,3-b]pyridine

5-Bromo-1H-pyrrolo[2,3-b]pyridine 7-oxide (150 mg, 0.704 mmol) in N,N-dimethylformamide (2 mL) was heated to 50° C. and stirred with methanesulfonyl chloride (58 μL, 0.75 mmol) at 70° C. for 2 hours and allowed to cool to room temperature. After addition of saturated aqueous sodium chloride, the reaction mixture was extracted with ethyl acetate, and the organic layer was dried over anhydrous sodium sulfate and concentrated under reduced pressure. The resulting residue was dissolved in N,N-dimethylformamide (2 mL), cooled to 0° C., mixed with sodium hydride (55 wt % dispersion in mineral oil, 45 mg, 1.03 mmol) and [2-(chloromethoxy)ethyl]trimethylsilane (186 μL, 1.05 mmol) and stirred at room temperature for 3 hours. After addition of saturated aqueous sodium chloride, the reaction mixture was extracted with ethyl acetate, and the organic layer was dried over anhydrous sodium sulfate and concentrated under reduced pressure. The residue was purified by silica gel column chromatography (hexane/ethyl acetate=20/1 (v/v)) to give the title compound as a pale yellow oil (158 mg, yield 62%).

Reference Synthetic Example[b] 20

5-Bromo-N-cyclohexyl-1-{[2-(trimethylsilyl)ethoxy]methyl}-1H-pyrrolo[2,3-b]pyridin-4-amine 5-Bromo-4-chloro-1-{[2-(trimethylsilyl)ethoxy]methyl}-1H-pyrrolo[2,3-b]pyridine (150 mg, 0.415 mmol) and cyclohexylamine (1 mL, 9 mmol) in ethylene glycol (1 mL) were stirred at 200° C. for 2 hour under microwave irradiation. The reaction mixture was allowed to cool to room temperature and, after addition of saturated aqueous sodium chloride, extracted with ethyl acetate. The organic layer was dried over anhydrous sodium sulfate and concentrated under reduced pressure. The residue was purified by silica gel column chromatography (hexane/ethyl acetate=10/1 (v/v)) to give the title compound as an orange oil (141 mg, yield 80%).

Reference Synthetic Example[a] 21

1-(4-(Cyclohexylamino)-1-{[2-(trimethylsilyl)ethoxy]methyl}-1H-pyrrolo[2,3-b]pyridin-5-yl)ethanone 5-Bromo-N-cyclohexyl-1-{[2-(trimethylsilyl)ethoxy]methyl}-1H-pyrrolo[2,3-b]pyridin-4-amine (160 mg, 0.377 mmol) in toluene (3 mL) was stirred with bis(triphenylphosphine)palladium (II) dichloride (35 mg, 0.050 mmol) and tributyl(1-ethoxyvinyl)tin (382 μL, 1.13 mmol) at 75° C. for 3 hours. The reaction mixture was allowed to cool to room temperature and stirred with 1 M hydrochloric acid (2 mL) and potassium fluoride (100 mg, 1.73 mmol) at room temperature for 30 minutes. The reaction mixture was filtered, and the solid was washed with ethyl acetate. The filtrate and the washings were mixed with water and extracted with ethyl acetate, and the organic layer was dried over anhydrous sodium sulfate and concentrated under reduced pressure. The residue was purified by silica gel column chromatography (hexane/ethyl acetate=20/1→5/1 (v/v)) to give the title compound as a yellow oil (58 mg, yield 40%).

Reference Synthetic Example[a] 22

1-(4-(Cyclohexylamino)-1-{[2-(trimethylsilyl)ethoxy]methyl}-1H-pyrrolo[2,3-b]pyridin-5-yl)ethanol 1-(4-(Cyclohexylamino)-1-{[2-(trimethylsilyl)ethoxy]methyl}-1H-pyrrolo[2,3-b]pyridin-5-yl)ethanone (13 mg, 0.034 mmol) in methanol (1 mL) was stirred with sodium borohydride (30 mg, 0.79 mmol) at room temperature for 1 hour and at 60° C. for another 5 hours. The reaction mixture was allowed to cool to room temperature and, after addition of water, extracted with ethyl acetate, and the organic layer was dried over anhydrous sodium sulfate and concentrated under reduced pressure. The residue was purified by silica gel column chromatography (hexane/ethyl acetate=4/1→3/1 (v/v)) to give the title compound as a colorless oil (9.1 mg, yield 70%).

Reference Synthetic Example[b] 23

1-Cyclohexyl-4-methyl-7-{[2-(trimethylsilyl)ethoxy]methyl}-1,2,4,7-tetrahydropyrrolo[3',2':5,6]pyrido[4,3-d][1,3]oxazine 1-(4-(Cyclohexylamino)-1-{[2-(trimethylsilyl)ethoxy]methyl}-1H-pyrrolo[2,3-b]pyridin-5-yl)ethanol (9 mg, 0.02 mmol) and aqueous formaldehyde (35 wt %, 0.3 mL, 4 mmol) in ethanol (1 mL) were stirred at 75° C. for 1 hour. The reaction mixture was allowed to cool to room temperature and, after addition of water, extracted with ethyl acetate. The organic layer was dried over anhydrous sodium sulfate and concentrated under reduced pressure. The resulting pale yellow oil (9 mg) containing the title compound was used for the next step without further purification.

Reference Synthetic Example[b] 24

1-Cyclohexyl-7-{[2-(trimethylsilyl)ethoxy]methyl}-1H-pyrrolo[2,3-h][1,6]naphthyridin-4(7H)-one 1-(4-(Cyclohexylamino)-1-{[2-(trimethylsilyl)ethoxy]methyl}-1H-pyrrolo[2,3-b]pyridin-5-yl)ethanone (25 mg, 0.065 mmol) obtained in Reference Synthetic Example[b] 21 in N,N-dimethylformamide dimethyl acetal (0.5 mL) was stirred at 180° C. for 3 hours under microwave irradiation. The reaction mixture was allowed to cool to room temperature and concentrated under reduced pressure, and the resulting residue was dissolved in tetrahydrofuran (1 mL) and stirred with 1 M hydrochloric acid (1 mL) at 80° C. for 1 hour. The reaction mixture was allowed to cool to room temperature and, after addition of saturated aqueous sodium hydrogen carbonate, extracted with chloroform, and the organic layer was dried over anhydrous sodium sulfate and concentrated under reduced pressure. The residue was purified by silica gel column chromatography (hexane/ethyl acetate/methanol=1/1/0→0/10/1 (v/v/v)) to give the title compound as a colorless oil (13.6 mg, yield 53%).

Reference Synthetic Example[b] 25

4-Chloro-5-(methylsulfonyl)-1-(triisopropylsilyl)-1H-pyrrolo[2,3-b]pyridine s-Butyllithium-hexane/cyclohexane solution (1.06 M, 0.700 mL, 0.742 mmol) was gradually added dropwise to 4-chloro-1-(triisopropylsilyl)-1H-pyrrolo[2,3-b]pyridine (100 mg, 0.324 mmol) obtained in Reference Synthetic Example[b] 6 in tetrahydrofuran (1 mL) cooled to −78° C., and the reaction mixture was stirred at −78° C. for 30 minutes and stirred with dimethyl disulfide (30 μL, 0.33 mmol) at −78° C. for 30 minutes. After addition of 1 M aqueous sodium hydroxide, the reaction mixture was extracted with ethyl acetate, and the organic layer was dried over anhydrous sodium sulfate and concentrated under reduced pressure. The resulting residue was dissolved in ethanol (2 mL) and stirred with ammonium molybdate tetrahydrate (40 mg, 0.032 mmol) and aqueous hydrogen peroxide (30 wt %, 132 μL, 1.29 mmol) at room temperature for 5 hours. After addition of water, the reaction mixture was extracted with ethyl acetate, and the organic layer was dried over anhydrous sodium sulfate and concentrated under reduced pressure. The residue was purified by silica gel column chromatography (hexane/ethyl acetate=20/1→5/1 (v/v)) to give the title compound as a pale yellow oil (61.4 mg, yield 49%).

Reference Synthetic Example[b] 26

N-Cyclohexyl-5-(methylsulfonyl)-1H-pyrrolo[2,3-b]pyridin-4-amine

4-Chloro-5-(methylsulfonyl)-1-(triisopropylsilyl)-1H-pyrrolo[2,3-b]pyridine (61 mg, 0.16 mmol) in cyclohexylamine (200 μL, 1.74 mmol) was stirred with N,N-diisopropylethylamine (40 μL, 0.23 mmol) at 120° C. for 30 minutes The reaction mixture was allowed to cool to room temperature and, after addition of water, extracted with chloroform, and the organic layer was dried over anhydrous sodium sulfate and concentrated under reduced pressure. The residue was purified by silica gel column chromatography (hexane/ethyl acetate=20/1→5/1 (v/v)) to give the title compound as a colorless solid (7.0 mg, yield 15%).

Reference Synthetic Example[b] 27

N-Cyclohexyl-5-(methylsulfonyl)-1-{[2-(trimethylsilyl)ethoxy]methyl}-1H-pyrrolo[2,3-b]pyridin-4-amine N-Cyclohexyl-5-(methylsulfonyl)-1H-pyrrolo[2,3-b]pyridin-4-amine (7.0 mg, 0.024 mmol) in N,N-dimethylformamide (1 mL) was stirred with sodium hydride (55 wt % dispersion in mineral oil, 3.0 mg, 0.069 mmol) and [2-(chloromethoxy)ethyl]trimethylsilane (10 μL, 0.057 mmol) at room temperature for 2 hours. After addition of saturated aqueous sodium chloride, the reaction mixture was extracted with ethyl acetate, and the organic layer was dried over anhydrous sodium sulfate and concentrated under reduced pressure. The residue was purified by silica gel column chromatography (hexane/ethyl acetate=10/1→3/1 (v/v)) to give the title compound as a colorless oil (6.1 mg, yield 60%).

Reference Synthetic Example[b] 28

1-Cyclohexyl-7-{[2-(trimethylsilyl)ethoxy]methyl}-1,4-di hydropyrrolo[3',2':5,6]pyrido[3,4-b][1,4]thiazine-4,4(7H)-dione N-Cyclohexyl-5-(methylsulfonyl)-1-{[2-(trimethylsilyl)ethoxy]methyl}-1H-pyrrolo[2,3-b]pyridin-4-amine (6.1 mg, 0.014 mmol) in N,N-dimethylformamide dimethyl acetal (2.5 mL) was stirred at 170° C. for 3 hours under microwave irradiation. The reaction mixture was allowed to cool to room temperature and concentrated under reduced pressure. The resulting residue was dissolved in tetrahydrofuran (1 mL) and stirred with 1 M hydrochloric acid (1 mL) at 80° C. for 1 hour. The reaction mixture was allowed to cool to room temperature and, after addition of water, extracted with ethyl acetate, and the organic layer was dried over anhydrous sodium sulfate and concentrated under reduced pressure. The resulting pale yellow oil (8.5 mg) containing the title compound was used for the next step without further purification.

Reference Synthetic Example[b] 29

4-(Cyclohexylamino)-1-{[2-(trimethylsilyl)ethoxy]methyl}-1H-pyrrolo[2,3-b]pyridine-5-carboxylic acid 4-(Cyclohexylamino)-1-{[2-(trimethylsilyl)ethoxy]methyl}-1H-pyrrolo[2,3-b]pyridine-5-carbaldehyde (380 mg, 1.02 mmol) obtained in Reference Synthetic Example[b] 9 in acetic acid (4 mL) was stirred with sulphamic acid (150 mg, 1.54 mmol) and 2-methyl-2-butene (500 μL, 4.71 mmol) under cooling with ice, and then sodium chlorite (100 mg, 1.11 mmol) in water (0.5 mL) was added dropwise, and the resulting reaction mixture was stirred at room temperature for 1 hour. Sodium chlorite (30 mg, 0.33 mmol) in water (0.3 mL) was further added dropwise, and the resulting reaction mixture was stirred for 1 hour. After addition of water, the reaction mixture was extracted with chloroform, and the organic layer was dried over anhydrous sodium sulfate and concentrated under reduced pressure. The residue was purified by silica gel column chromatography (hexane/ethyl acetate=3/1→0/1 (v/v)) to give the title compound as a pale yellow oil (207 mg, yield 52%).

Reference Synthetic Example[b] 30

4-(Cyclohexylamino)-1-{[2-(trimethylsilyl)ethoxy]methyl}-1H-pyrrolo[2,3-b]pyridine-5-carboxamide 4-(Cyclohexylamino)-1-{[2-(trimethylsilyl)ethoxy]methyl}-1H-pyrrolo[2,3-b]pyridine-5-carboxylic acid (100 mg, 0.257 mmol) in dichloromethane (2 mL) was stirred with 1-(3-dimethylaminopropyl)-3-ethylcarbodiimide hydrochloride (10 mg, 0.052 mmol), N-hydroxybenzotriazole (50 mg, 0.37 mmol) and 7 M ammonia-methanol solution (0.2 mL, 1.4 mmol) at room temperature for one day. After addition of saturated aqueous ammonium chloride, the reaction mixture was extracted with chloroform, and the organic layer was dried over anhydrous sodium sulfate and concentrated under reduced pressure. The residue was purified by silica gel column chromatography (hexane/ethyl acetate=1/1→0/1 (v/v)) to give the title compound as a pale yellow amorphous (71.1 mg, yield 71%).

Reference Synthetic Example[b] 31

4-(Cyclohexylamino)-N-formyl-1-{[2-(trimethylsilyl)ethoxy]methyl}-1H-pyrrolo[2,3-b]pyridine-5-carboxamide 4-(Cyclohexylamino)-1-{[2-(trimethylsilyl)ethoxy]methyl}-1H-pyrrolo[2,3-b]pyridine-5-carboxamide (45 mg, 0.12 mmol) in triethyl orthoformate (2 mL) was stirred at 120° C. for one day. The reaction mixture was allowed to cool to room temperature and concentrated under reduced pressure, and the residue was purified by silica gel column chromatography (hexane/ethyl acetate=3/1→0/1 (v/v)) to give the title compound as a pale yellow amorphous (12.4 mg, yield 27%).

Reference Synthetic Example[b] 32

1-Cyclohexyl-7-{[2-(trimethylsilyl)ethoxy]methyl}-1H-pyrrolo[3',2':5,6]pyrido[4,3-d]pyrimidin-4(7H)-one 4-(Cyclohexylamino)-N-formyl-1-{[2-(trimethylsilyl)ethoxy]methyl}-1H-pyrrolo[2,3-b]pyridine-5-carboxamide (12.4 mg, 0.0311 mmol) in N-methyl-2-pyrrolidinone (0.5 mL) was stirred at 200° C. for 30 minutes under microwave irradiation. The reaction mixture was allowed to cool to room temperature and, after addition of saturated aqueous ammonium chloride, extracted with ethyl acetate, and the organic layer was dried over anhydrous sodium sulfate and concentrated under reduced pressure. The residue was purified by silica gel column chromatography (hexane/ethyl acetate=1/1 (v/v)) to give the title compound as a pale yellow amorphous (9.2 mg, yield 74%).

Reference Synthetic Example[b] 33

1-(4-Chloro-1-{[2-(trimethylsilyl)ethoxy]methyl}-1H-pyrrolo[2,3-b]pyridin-5-yl)ethanone 5-Bromo-4-chloro-1-{[2-(trimethylsilyl)ethoxy]methyl}-1H-pyrrolo[2,3-b]pyridine (47 mg, 0.13 mmol) obtained in Reference Synthetic Example[b] 19 in toluene (1 mL) was stirred with bis(triphenylphosphine)palladium (II) dichloride (10 mg, 0.014 mmol) and tributyl(1-ethoxyvinyl)tin (50 μL, 0.15 mmol) at 120° C. for 4 hours. The reaction mixture was allowed to cool to room temperature and stirred with water (2 mL) and potassium fluoride (100 mg, 1.73 mmol) at room temperature for 1 hour. The reaction mixture was filtered, and the solid was washed with ethyl acetate. The filtrate and the washings were mixed with water and extracted with ethyl acetate, and the organic layer was dried over anhydrous sodium sulfate and filtered. The filtrate was stirred with hydrogen chloride-methanol solution (10 wt %, 0.1 mL) at room temperature for 10 minutes. The reaction mixture was concentrated under reduced pressure, and the residue was purified by silica gel column chromatography (hexane/ethyl acetate=10/1→2/1 (v/v)) to give the title compound as a pale yellow oil (20 mg, yield 47%).

Reference Synthetic Example[b] 34 rac-1-(4-{[(3R,4R)-1-Benzyl-4-methylpiperidin-3-yl]amino}-1-{[2-(trimethylsilyl)ethoxy]methyl}-1H-pyrrolo[2,3-b]pyridin-5-yl)ethanone 1-(4-Chloro-1-{[2-(trimethylsilyl)ethoxy]methyl}-1H-pyrrolo[2,3-b]pyridin-5-yl)ethanone (15 mg, 0.46 mmol) and rac-(3R,4R)-1-benzyl-4-methylpiperidin-3-amine (34 mg, 0.17 mmol) obtained in Reference Synthetic Example[b] 3 in ethylene glycol (3 mL) was stirred with N,N-diisopropylethylamine (10 μL, 0.057 mmol) at 200° C. for 1 hour under microwave irradiation. The reaction mixture was allowed to cool to room temperature and stirred with methanol (2 mL) and 1 M hydrochloric acid (1 mL) at 50° C. for 30 minutes. The reaction mixture was allowed to cool to room temperature and, after addition of saturated aqueous sodium hydrogen carbonate, extracted with ethyl acetate. The organic layer was dried over anhydrous sodium sulfate and concentrated under reduced pressure. The residue was purified by silica gel column chromatography (hexane/ethyl acetate=10/1→4/1 (v/v)) to give the title compound as a yellow oil (7.0 mg, yield 31%).

Reference Synthetic Example[b] 35 rac-1-[(3R,4R)-1-Benzyl-4-methylpiperidin-3-yl]-7-{[2-(trimethylsilyl)ethoxy]methyl}-1H-pyrrolo[2,3-h][1,6]naphthyridin-4(7H)-one rac-1-(4-{[(3R,4R)-1-Benzyl-4-methylpiperidin-3-yl]amino}-1-{[2-(trimethylsilyl)ethoxy]methyl}-1H-pyrrolo[2,3-b]pyridin-5-yl)ethanone (20 mg, 0.041 mmol) in N,N-dimethylformamide dimethyl acetal (1 mL) was stirred at 170° C. for 6 hours under microwave irradiation. The reaction mixture was allowed to cool to room temperature and concentrated under reduced pressure, and the resulting residue was dissolved in tetrahydrofuran (1 mL) and stirred with 1 M hydrochloric acid (1 mL) at 80° C. for 1 hour. The reaction mixture was allowed to cool to room temperature and, after addition of saturated aqueous sodium hydrogen carbonate, extracted with chloroform, and the organic layer was dried over anhydrous sodium sulfate and concentrated under reduced pressure. The residue was purified by silica gel column chromatography (hexane/ethyl acetate/methanol=1/1/0→0/5/1 (v/v/v)) to give the title compound as a yellow oil (6.1 mg, yield 30%).

Reference Synthetic Example[b] 36 rac-1-[(3R,4R)-4-Methylpiperidin-3-yl]-7-{[2-(trimethylsilyl)ethoxy]methyl}-1H-pyrrolo[2,3-h][1,6]naphthyridin-4(7H)-one rac-1-[(3R,4R)-1-Benzyl-4-methylpiperidin-3-yl]-7-{[2-(trimethylsilyl)ethoxy]methyl}-1H-pyrrolo[2,3-h][1,6]

naphthyridin-4(7H)-one (98 mg, 0.20 mmol) and 5% palladium-carbon (65 mg) in methanol (2 mL) were stirred at room temperature for 2 hours under a hydrogen atmosphere, then at 40° C. for 5 hours and at room temperature for one day. The reaction mixture was filtered, and the filtrate was concentrated under reduced pressure to give the title compound as a pale yellow amorphous (76.8 mg, yield 95%).

Reference Synthetic Example[b] 37 rac-1-[(3R,4R)-1-(Isobutylsulfonyl)-4-methylpiperidin-3-yl]-7-{[2-(trimethylsilyl)ethoxy]methyl}-1H-pyrrolo[2,3-h][1,6]naphthyridin-4(7H)-one rac-1-[(3R,4R)-4-Methylpiperidin-3-yl]-7-{[2-(trimethylsilyl)ethoxy]methyl}-1H-pyrrolo[2,3-h][1,6]naphthyridin-4(7H)-one (23 mg, 0.056 mmol) in dichloromethane (2 mL) was mixed with N,N-diisopropylethylamine (30 μL, 0.17 mmol) and 2-methylpropane-1-sulfonyl chloride (12 μL, 0.092 mmol) under cooling with ice and stirred at room temperature for 2 hours. After addition of water, the reaction mixture was extracted with ethyl acetate, and the organic layer was dried over anhydrous sodium sulfate and concentrated under reduced pressure. The residue was purified by silica gel column chromatography (hexane/ethyl acetate/methanol=1/1/0→0/10/1 (v/v/v)) to give the title compound as a pale pink solid (18.3 mg, yield 62%).

Reference Synthetic Example[b] 38 rac-4-{[(3R,4R)-1-Benzyl-4-methylpiperidin-3-yl]amino}-1H-pyrrolo[2,3-b]pyridine-5-carbaldehyde 4-Chloro-1H-pyrrolo[2,3-b]pyridine-5-carbaldehyde (247 mg, 1.36 mmol) obtained in Reference Synthetic Example[b] 7 and rac-(3R,4R)-1-benzyl-4-methylpiperidin-3-amine (700 mg, 3.42 mmol) obtained in Reference Synthetic Example[b] 3 in ethylene glycol (3 mL) were stirred at 180° C. for 3 hours under microwave irradiation. The reaction mixture was allowed to cool to room temperature and, after addition of water and 1 M aqueous sodium hydroxide, extracted with chloroform, and the organic layer was dried over anhydrous magnesium sulfate and concentrated under reduced pressure. The resulting residue was stirred with 1,4-dioxane (5 mL), 4 M hydrogen chloride-1,4-dioxane solution (10 mL) and water (2 mL) at room temperature for one day. The reaction mixture was concentrated under reduced pressure, adjusted to pH 9 or above with 1M aqueous sodium hydroxide and extracted with chloroform and water, and the organic layer was dried over anhydrous magnesium sulfate and concentrated under reduced pressure. The residue was purified by silica gel column chromatography (Hi Flash column amino type manufactured by Yamazen Corporation: hexane/ethyl acetate=1/1 (v/v)) to give the title compound as a brown oil (154 mg, yield 33%).

Reference Synthetic Example[b] 39 rac-4-{[(3R,4R)-1-Benzyl-4-methylpiperidin-3-yl]amino}-1-{[2-(trimethylsilyl)ethoxy]methyl}-1H-pyrrolo[2,3-b]pyridine-5-carbaldehyde rac-4-{[(3R,4R)-1-Benzyl-4-methylpiperidin-3-yl]amino}-1H-pyrrolo[2,3-b]pyridine-5-carbaldehyde (118 mg, 0.338 mmol) in N,N-dimethylformamide (3 mL) was cooled to 0° C. and stirred with sodium hydride (55 wt % dispersion in mineral oil, 126 mg, 0.586 mmol) for 30 minutes and then with [2-(chloromethoxy)ethyl]trimethylsilane (104 μL. 0.586 mmol) at room temperature for one day. After addition of water, the reaction mixture was extracted with chloroform, and the organic layer was dried over anhydrous magnesium sulfate and concentrated under reduced pressure. The residue was purified by silica gel column chromatography (hexane/ethyl acetate=1/1 (v/v)) to give the title compound as a brown oil (67.5 mg, yield 42%).

Reference Synthetic Example[b] 40 rac-(4-{[(3R,4R)-1-Benzyl-4-methylpiperidin-3-yl]amino}-1-{[2-(trimethylsilyl)ethoxy]methyl}-1H-pyrrolo[2,3-b]pyridin-5-yl)methanol rac-4-{[(3R,4R)-1-Benzyl-4-methylpiperidin-3-yl]amino}-1-{[2-(trimethylsilyl)ethoxy]methyl}-1H-pyrrolo[2,3-b]pyridine-5-carbaldehyde (112 mg, 0.234 mmol) in methanol was stirred with sodium borohydride (13.3 mg, 0.351 mmol) at room temperature for 1 hour. The reaction mixture was concentrated under reduced pressure and, after addition of water, extracted with ethyl acetate, and the organic layer was dried over anhydrous magnesium sulfate and concentrated under reduced pressure. The residue was purified by silica gel column chromatography (Hi Flash column amino type manufactured by Yamazen Corporation: hexane/ethyl acetate=1/1 (v/v)) to give the title compound as a colorless oil (55 mg, yield 49%).

Reference Synthetic Example[b] 41 rac-1-[(3R,4R)-1-Benzyl-4-methylpiperidin-3-yl]-7-{[2-(trimethylsilyl)ethoxy]methyl}-1,2,4,7-tetrahydropyrrolo[3',2':5,6]pyrido[4,3-d][1,3]oxazine rac-(4-{[(3R,4R)-1-Benzyl-4-methylpiperidin-3-yl]amino}-1-{[2-(trimethylsilyl)ethoxy]methyl}-1H-pyrrolo[2,3-b]pyridin-5-yl)methanol (55 mg, 0.11 mmol) was stirred with formic acid (2 mL) and acetic acid (200 μL) at 75° C. for 4 hours. The reaction mixture was concentrated under reduced pressure and, after addition of water, extracted with chloroform, and the organic layer was dried over anhydrous magnesium sulfate and concentrated under reduced pressure. The residue was purified by silica gel column chromatography (hexane/ethyl acetate=2/1 (v/v)) to give the title compound (34.3 mg, yield 61%).

Reference Synthetic Example[b] 42

6-Bromo-3H-imidazo[4,5-b]pyridine 2,3-Diamino-5-bromopyridine (4.10 g, 21.8 mmol) in formic acid (25 mL) was stirred at 100° C. for 4 hours. The reaction mixture was allowed to cool to room temperature and concentrated under reduced pressure, and the resulting residue was mixed with water and adjusted to pH 8 or above with saturated aqueous sodium hydrogen carbonate. The precipitated solid was collected by filtration, washed with water and chloroform and dried under reduced pressure to give the title compound as a dark brown solid (4.13 g, yield 96%).

Reference Synthetic Example[b] 43

6-Bromo-3H-imidazo[4,5-b]pyridine 4-oxide m-Chloroperbenzoic acid (25 wt % water content, 2.77 g, 12.0 mmol) was gradually added dropwise to 6-bromo-3H- imidazo[4,5-b]pyridine (1.58 mg, 7.98 mmol) in ethyl acetate (15 mL), and the reaction mixture was stirred at room temperature for one day. The precipitated solid was collected by filtration and washed with ethyl acetate and diethyl ether and dried under reduced pressure to give the title compound as a pale yellow solid (1.67 g, yield 98%).

Reference Synthetic Example[b] 44

6-Bromo-7-chloro-3H-imidazo[4,5-b]pyridine

6-Bromo-3H-imidazo[4,5-b]pyridine 4-oxide (1.88 g, 8.82 mmol) in N,N-dimethylformamide (12 mL) was heated to 50° C., mixed with methanesulfonyl chloride (8.00 mL, 103 mmol) and stirred at 73° C. for 3 hours. The reaction mixture was cooled with ice and gradually poured into saturated aqueous sodium hydrogen carbonate (75 mL), and the precipitated solid was collected by filtration, washed with water and chloroform and dried under reduced pressure to give the title compound as a dark brown solid (1.07 g, yield 52%).

Reference Synthetic Example[b] 45

6-Bromo-7-chloro-3-{[2-(trimethylsilyl)ethoxy]methyl}-3H-imidazo[4,5-b]pyridine

6-Bromo-7-chloro-3H-imidazo[4,5-b]pyridine (1.07 g, 4.60 mmol) in N,N-dimethylformamide (12 mL) was cooled to 0° C., mixed with sodium hydride (55 wt % dispersion in mineral oil, 300 mg, 6.88 mmol) and [2-(chloromethoxy)ethyl]trimethylsilane (12.0 mL, 6.78 mmol) and stirred at room temperature for 3 hours. After addition of saturated aqueous sodium chloride, the reaction mixture was extracted with ethyl acetate, and the organic layer was dried over anhydrous magnesium sulfate and concentrated under reduced pressure. The resulting residue was purified by silica gel column chromatography (hexane/ethyl acetate=10/1→5/1 (v/v)) to give the title compound as a yellow oil (640 mg, yield 38%).

Reference Synthetic Example[b] 46

1-(7-Chloro-3-{[2-(trimethylsilyl)ethoxy]methyl}-3H-imidazo[4,5-b]pyridin-6-yl)ethanone 6-Bromo-7-chloro-3-{[2-(trimethylsilyl)ethoxy]methyl}-3H-imidazo[4,5-b]pyridine (379 mg, 1.05 mmol) in toluene (6 mL) was stirred with bis(triphenylphosphine)palladium (II) dichloride (106 mg, 0.151 mmol) and tributyl(1-ethoxyvinyl)tin (435 mg, 1.21 mmol) at 120° C. 4 hours. The reaction mixture was allowed to cool to room temperature and stirred with water (20 mL) and potassium fluoride (0.5 g) at room temperature for 1 hour. The reaction mixture was extracted with ethyl acetate, and the organic layer was dried over anhydrous magnesium sulfate and filtered. The filtrate was stirred with hydrogen chloride-methanol solution (10 wt %, 4 mL) at room temperature for 10 minutes. The reaction mixture was concentrated under reduced pressure, and the residue was purified by silica gel column chromatography (hexane/ethyl acetate=5/1→3/1 (v/v)) to give the title compound as a yellow solid (89.6 mg, yield 26%).

Reference Synthetic Example[b] 47

1-[7-(Cyclohexylamino)-3-{[2-(trimethylsilyl)ethoxy]methyl}-3H-imidazo[4,5-b]pyridin-6-yl]ethanone 1-[7-Chloro-3-{[2-(trimethylsilyl)ethoxy]methyl}-3H-imidazo[4,5-b]pyridin-6-yl]ethanone (89.6 mg, 0.275 mmol) and cyclohexylamine (214 mg, 2.16 mmol) in ethylene glycol (2 mL) were stirred at 180° C. for 1 hour under microwave irradiation. The reaction mixture was allowed to cool to room temperature and, after addition of saturated aqueous sodium chloride, extracted with chloroform. The organic layer was stirred with 2 M hydrochloric acid (12 mL) at room temperature for 1 hour. The reaction mixture was basified with 10 M aqueous sodium hydroxide and extracted with chloroform, and the organic layer was washed with saturated aqueous sodium chloride, dried over anhydrous magnesium sulfate and concentrated under reduced pressure. The residue was purified by silica gel column chromatography hexane/ethyl acetate=1/1 (v/v)) to give the title compound as a dark brown oil (88.9 mg, yield 83%).

Reference Synthetic Example[b] 48

9-Cyclohexyl-3-{[2-(trimethylsilyl)ethoxy]methyl}-3H-imidazo[4,5-h][1,6]naphthyridin-6(9H)-one 1-[7-(Cyclohexylamino)-3-{[2-(trimethylsilyl)ethoxy]methyl}-3H-imidazo[4,5-b]pyridin-6-yl]ethanone (88.9 mg, 0.229 mmol) in N,N-dimethylformamide dimethyl acetal (2.0 mL) was stirred at 180° C. for 5 hours. The reaction mixture was allowed to cool to room temperature and concentrated under reduced pressure, and the resulting residue was dissolved in tetrahydrofuran (5 mL) and stirred with 1 M hydrochloric acid (2 mL) at 80° C. for 1 hour. The reaction mixture was allowed to cool to room temperature and, after addition of saturated aqueous sodium hydrogen carbonate, extracted with ethyl acetate, and the organic layer was dried over anhydrous magnesium sulfate and concentrated under reduced pressure. The residue was purified by silica gel column chromatography (hexane/ethyl acetate/methanol=1/1/0→0/10/1 (v/v/v)) to give the title compound as a yellow solid (57.5 mg, yield 63%).

Reference Synthetic Example[b] 49

1-(3-Bromo-4-chloro-1-{[2-(trimethylsilyl)ethoxy]methyl}-1H-pyrrolo[2,3-b]pyridin-5-yl)ethanone 1-(4-Chloro-1-{[2-(trimethylsilyl)ethoxy]methyl}-1H-pyrrolo[2,3-b]pyridin-5-yl)ethanone (91 mg, 0.28 mmol) obtained in Reference Synthetic Example[b] 33 in dichloromethane (3 mL) was mixed with N-bromosuccinimide (75 mg, 0.42 mmol) under cooling with ice and stirred at room temperature for 2 hours. After addition of saturated aqueous sodium thiosulfate, the reaction mixture was extracted with ethyl acetate, and the organic layer was dried over anhydrous sodium sulfate and concentrated under reduced pressure. The residue was purified by silica gel column chromatography (hexane/ethyl acetate=5/1 (v/v)) to give the title compound as a colorless oil (61.0 mg, yield 54%).

Reference Synthetic Example$^b$ 50 rac-1-(4-{[(3R,4R)-1-Benzyl-4-methylpiperidin-3-yl]amino}-3-bromo-1-{[2-(trimethylsilyl)ethoxy]methyl}-1H-pyrrolo[2,3-b]pyridin-5-yl)ethanone 1-(3-Bromo-4-chloro-1-{[2-(trimethylsilyl)ethoxy]methyl}-1H-pyrrolo[2,3-b]pyridin-5-yl)ethanone (61 mg, 0.15 mmol) was stirred with rac-(3R,4R)-1-Benzyl-4-methylpiperidin-3-amine (85 mg, 0.42 mmol) obtained in Reference Synthetic Example$^b$ 3 and N,N-diisopropylethylamine (50 μL, 0.29 mmol) at 130° C. for 5 hours. The reaction mixture was allowed to cool to room temperature and purified by silica gel column chromatography (hexane/ethyl acetate=10/1 (v/v)) to give the title compound as a pale yellow oil (28.7 mg, yield 33%).

Reference Synthetic Example$^b$ 51 rac-1-[(3R,4R)-1-Benzyl-4-methylpiperidin-3-yl]-9-bromo-7-{[2-(trimethylsilyl)ethoxy]methyl}-1H-pyrrolo[2,3-h][1,6]naphthyridin-4-(7H)-one The reactions in Reference Synthetic Example$^b$ 35 were carried out in substantially the same manners except that rac-1-(4-{[(3R,4R)-1-benzyl-4-methylpiperidin-3-yl]amino}-3-bromo-1-{[2-(trimethylsilyl)ethoxy]methyl}-1H-pyrrolo[2,3-b]pyridin-5-yl)ethanone was used instead of rac-1-(4-{[(3R,4R)-1-benzyl-4-methylpiperidin-3-yl]amino}-1-{[2-(trimethylsilyl)ethoxy]methyl}-1H-pyrrolo[2,3-b]pyridin-5-yl)ethanone to give the title compound as a colorless oil (12.3 mg, yield 45%).

Reference Synthetic Example$^b$ 52

1-(3,4-Dichloro-1-{[2-(trimethylsilyl)ethoxy]methyl}-1H-pyrrolo[2,3-b]pyridin-5-yl)ethanone 1-(4-Chloro-1-{[2-(trimethylsilyl)ethoxy]methyl}-1H-pyrrolo[2,3-b]pyridin-5-yl)ethanone (80 mg, 0.25 mmol) obtained in Reference Synthetic Example$^b$ 33 in N,N-dimethylformamide (2 mL) was stirred with N-chlorosuccinimide (66 mg, 0.49 mmol) at 80° C. for 3 hours. The reaction mixture was allowed to cool to room temperature and, after addition of saturated aqueous sodium chloride, extracted with ethyl acetate, and the organic layer was dried over anhydrous sodium sulfate and concentrated under reduced pressure. The residue was purified by silica gel column chromatography (hexane/ethyl acetate=10/1→5/1 (v/v)) to give the title compound as a colorless solid (23.8 mg, yield 27%).

Reference Synthetic Example$^b$ 53 rac-1-(4-{[(3R,4R)-1-Benzyl-4-methylpiperidin-3-yl]amino}-3-chloro-1-{[2-(trimethylsilyl)ethoxy]methyl}-1H-pyrrolo[2,3-b]pyridin-5-yl)ethanone The reactions in Reference Synthetic Example$^b$ 50 were carried out in substantially the same manners except that 1-(3,4-dichloro-1-{[2-(trimethylsilyl)ethoxy]methyl}-1H-pyrrolo[2,3-b]pyridin-5-yl)ethanone was used instead of 1-(3-bromo-4-chloro-1-{[2-(trimethylsilyl)ethoxy]methyl}-1H-pyrrolo[2,3-b]pyridin-5-yl)ethanone to give the title compound as a pale yellow oil (13.4 mg, yield 39%).

Reference Synthetic Example$^b$ 54 rac-1-[(3R,4R)-1-Benzyl-4-methylpiperidin-3-yl]-9-chloro-7-{[2-(trimethylsilyl)ethoxy]methyl}-1H-pyrrolo[2,3-h][1,6]naphthyridin-4(7H)-one The reactions in Reference Synthetic Example$^b$ 35 were carried out in substantially the same manners except that rac-1-(4-{[(3R,4R)-1-benzyl-4-methylpiperidin-3-yl]amino}-3-chloro-1-{[2-(trimethylsilyl)ethoxy]methyl}-1H-pyrrolo[2,3-b]pyridin-5-yl)ethanone was used instead of rac-1-(4-{[(3R,4R)-1-benzyl-4-methylpiperidin-3-yl]amino}-1-{[2-(trimethylsilyl)ethoxy]methyl}-1H-pyrrolo[2,3-b]pyridin-5-yl)ethanone to give the title compound as a colorless oil (5.6 mg, yield 42%).

Reference Synthetic Example$^b$ 55

4-Chloro-1-{[2-(trimethylsilyl)ethoxy]methyl}-1H-pyrrolo[2,3-b]pyridine-5-carbaldehyde 4-Chloro-1H-pyrrolo[2,3-b]pyridine-5-carbaldehyde (550 mg, 3.05 mmol) obtained in Reference Synthetic Example$^b$ 7 in N,N-dimethylformamide (5 mL) was stirred with sodium hydride (60 wt % dispersion in liquid paraffin, 150 mg, 3.75 mmol) for 10 minutes under cooling with ice and then stirred with [2-(chloromethoxy)ethyl]trimethylsilane (650 μL, 3.67 mmol) at room temperature for 30 minutes. After addition of saturated aqueous ammonium chloride, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (hexane/ethyl acetate=5/1 (v/v)) to give the title compound as a colorless solid (815 mg, yield 86%).

Reference Synthetic Example$^b$ 56

1-(4-Chloro-1-{[2-(trimethylsilyl)ethoxy]methyl}-1H-pyrrolo[2,3-b]pyridin-5-yl)propan-1-ol 4-Chloro-1-{[2-(trimethylsilyl)ethoxy]methyl}-1H-pyrrolo[2,3-b]pyridine-5-carbaldehyde (117 mg, 0.360 mmol) in tetrahydrofuran (2 mL) was mixed with ethylmagnesium bromide-tetrahydrofuran solution (1.0 M, 1.0 mL, 1.0 mmol) under cooling with ice and stirred at room temperature for one day. After addition of saturated aqueous ammonium chloride, the reaction mixture was extracted with ethyl acetate, and the organic layer was dried over anhydrous sodium sulfate and concentrated under reduced pressure. The residue was purified by silica gel column chromatography (hexane/ethyl acetate=4/1 (v/v)) to give the title compound as a colorless oil (75.6 mg, yield 62%).

Reference Synthetic Example$^b$ 57

1-(4-Chloro-1-{[2-(trimethylsilyl)ethoxy]methyl}-1H-pyrrolo[2,3-b]pyridin-5-yl)propan-1-one 1-(4-Chloro-1-{[2-(trimethylsilyl)ethoxy]methyl}-1H-pyrrolo[2,3-b]pyridin-5-yl)propan-1-ol (75.6 mg, 0.222 mmol) in 1,2-dimethoxyethane (5 mL) was vigorously stirred with manganese dioxide (450 mg, 5.17 mmol) at 60° C. for 3 hours and then at 80° C. for 3 hours. The reaction mixture was filtered, the solid was washed with chloroform, and the filtrate and the washings were concentrated under reduced pressure. The residue was purified by silica gel column chromatography (hexane/ethyl acetate=10/1→5/1 (v/v)) to give the title compound as a colorless oil (39.9 mg, yield 53%).

Reference Synthetic Example[b] 58 rac-1-(4-{[(3R,4R)-1-Benzyl-4-methylpiperidin-3-yl]amino}-1-{[2-(trimethylsilyl)ethoxy]methyl}-1H-pyrrolo[2,3-b]pyridin-5-yl)propan-1-one The reactions in Reference Synthetic Example[b] 50 were carried out in substantially the same manners except that 1-(4-chloro-1-{[2-(trimethylsilyl)ethoxy]methyl}-1H-pyrrolo[2,3-b]pyridin-5-yl)propan-1-one was used instead of 1-(3-bromo-4-chloro-1-{[2-(trimethylsilyl)ethoxy]methyl}-1H-pyrrolo[2,3-b]pyridin-5-yl)ethanone to give the title compound as a pale yellow oil (40.1 mg, yield 71%).

Reference Synthetic Example[b] 59 rac-1-[(3R,4R)-1-Benzyl-4-methylpiperidin-3-yl]-3-methyl-7-{[2-(trimethylsilyl)ethoxy]methyl}-1H-pyrrolo[2,3-h][1,6]naphthyridin-4(7H)-one The reactions in Reference Synthetic Example[b] 35 were carried out in substantially the same manners except that rac-1-(4-{[(3R,4R)-1-benzyl-4-methylpiperidin-3-yl]amino}-1-{[2-(trimethylsilyl)ethoxy]methyl}-1H-pyrrolo[2,3-b]pyridin-5-yl)propan-1-one was used instead of rac-1-(4-{[(3R,4R)-1-benzyl-4-methylpiperidin-3-yl]amino}-1-{[2-(trimethylsilyl)ethoxy]methyl}-1H-pyrrolo[2,3-b]pyridin-5-yl)ethanone to give the title compound as a colorless oil (18.0 mg, yield 44%).

Reference Synthetic Example[b] 60 rac-1-[(3R,4R)-1-Benzyl-4-methylpiperidin-3-yl]-3-bromo-7-{[2-(trimethylsilyl)ethoxy]methyl}-1H-pyrrolo[2,3-h][1,6]naphthyridin-4(7H)-one rac-1-[(3R,4R)-1-Benzyl-4-methylpiperidin-3-yl]-7-{[2-(trimethylsilyl)ethoxy]methyl}-1H-pyrrolo[2,3-h][1,6]naphthyridin-4(7H)-one (70 mg, 0.14 mmol) obtained in Reference Synthetic Example[b] 35 in dichloromethane (5 mL) was mixed with N-bromosuccinimide (25 mg, 0.14 mmol) under cooling with ice and stirred at room temperature for one day and then with N-bromosuccinimide (8 mg, 0.04 mmol) for one day. After addition of saturated aqueous sodium hydrogen carbonate, the reaction mixture was extracted with ethyl acetate, and the organic layer was dried over anhydrous sodium sulfate and concentrated under reduced pressure. The residue was purified by silica gel column chromatography (hexane/ethyl acetate=5/1→2/1 (v/v)) to give a mixture (22.4 mg) containing the title compound. The mixture was used for the next step without further purification.

Reference Synthetic Example[b] 61 rac-2-{[3R,4R)-4-Methyl-3-(4-oxo-7-{[2-(trimethylsilyl)ethoxy]methyl}-4,7-dihydro-1H-pyrrolo[2,3-h][1,6]naphthyridin-1-yl)piperidin-1-yl]sulfonyl}benzonitrile rac-1-[(3R,4R)-4-Methylpiperidin-3-yl]-7-{[2-(trimethylsilyl)ethoxy]methyl}-1H-pyrrolo[2,3-h][1,6]naphthyridin-4(7H)-one (20 mg, 0.049 mmol) obtained in Reference Synthetic Example[b] 36 in dichloromethane (2 mL) was stirred with 2-cyanobenzenesulfonyl chloride (15 mg, 0.074 mmol) and N,N-diisopropylethylamine (20 μL, 0.11 mmol) at room temperature for 1 hour. The reaction mixture was purified by silica gel column chromatography (hexane/ethyl acetate/methanol=1/1/0→0/10/1 (v/v/v)) to give the title compound as a colorless solid (24.5 mg, yield 87%).

Reference Synthetic Examples[b] 62 to 71

The reactions in Reference Synthetic Example[b] 61 were carried out in substantially the same manners except that 3-cyanobenzenesulfonyl chloride, ethyl chloroformate, 1-isocyanato-2-(trifluoromethyl)benzene, 1-isocyanato-3-(trifluoromethyl)benzene, 2-(trifluoromethyl)benzoyl chloride, 3-(trifluoromethyl)benzoyl chloride, 2-(4-fluorophenyl)acetyl chloride, 3-(trifluoromethyl)benzenesulfonyl chloride, 4-(trifluoromethyl)benzoyl chloride or benzyl chloroformate was used instead of 2-cyanobenzenesulfonyl chloride to give the compounds of Reference Synthetic Examples[b] 62 to 71. The names, morphologies and yields of the compounds synthesized are shown in Tables[b] 3 to 4.

TABLE[b] 3

| Rf | Compound Name | Morphology | Yield |
|---|---|---|---|
| 62 | rac-3-{[(3R,4R)-4-methyl-3-(4-oxo-7-{[2-(trimethylsilyl)ethoxy]methyl}-4,7-dihydro-1H-pyrrolo[2,3-h][1,6]naphthyridin-1-yl)piperidin-1-yl]sulfonyl}benzonitrile | colorless solid | 65% |
| 63 | rac-(3R,4R)-ethyl 4-methyl-3-(4-oxo-7-{[2-(trimethylsilyl)ethoxy]methyl}-4,7-dihydro-1H-pyrrolo[2,3-h][1,6]naphthyridin-1-yl)piperidine-1-carboxylate | colorless oil | 85% |
| 64 | rac-(3R,4R)-4-methyl-3-(4-oxo-7-{[2-(trimethylsilyl)ethoxy]methyl}-4,7-dihydro-1H-pyrrolo[2,3-h][1,6]naphthyridin-1-yl)-N-[2-(trifluoromethyl)phenyl]piperidine-1-carboxamide | colorless oil | 87% |
| 65 | rac-(3R,4R)-4-methyl-3-(4-oxo-7-{[2-(trimethylsilyl)ethoxy]methyl}-4,7-dihydro-1H-pyrrolo[2,3-h][1,6]naphthyridin-1-yl)-N-[3-(trifluoromethyl)phenyl]piperidine-1-carboxamide | colorless oil | 98% |

TABLE[b] 3-continued

| Rf | Compound Name | Morphology | Yield |
|---|---|---|---|
| 66 | rac-1-{(3R,4R)-4-methyl-1-[2-(trifluoromethyl)benzoyl]piperidin-3-yl}-7-{[2-(trimethylsilyl)ethoxy]methyl}-1H-pyrrolo[2,3-h][1,6]naphthyridin-4(7H)-one | colorless oil | 94% |
| 67 | rac-1-{(3R,4R)-4-methyl-1-[3-(trifluoromethyl)benzoyl]piperidin-3-yl}-7-{[2-(trimethylsilyl)ethoxy]methyl}-1H-pyrrolo[2,3-h][1,6]naphthyridin-4(7H)-one | colorless oil | 92% |
| 68 | rac-1-{(3R,4R)-1-[2-(4-fluorophenyl)acetyl]-4-methylpiperidin-3-yl}-7-{[2-(trimethylsilyl)ethoxy]methyl}-1H-pyrrolo[2,3-h][1,6]naphthyridin-4(7H)-one | colorless oil | 80% |
| 69 | rac-1-((3R,4R)-4-methyl-1-{[3-(trifluoromethyl)phenyl]sulfonyl}piperidin-3-yl)-7-{[2-(trimethylsilyl)ethoxy]methyl}-1H-pyrrolo[2,3-h][1,6]naphthyridin-4(7H)-one | colorless oil | 78% |
| 70 | rac-1-{(3R,4R)-4-methyl-1-[4-(trifluoromethyl)benzoyl]piperidin-3-yl}-7-{[2-(trimethylsilyl)ethoxy]methyl}-1H-pyrrolo[2,3-h][1,6]naphthyridin-4(7H)-one | colorless oil | 69% |

TABLE[b] 4

| Rf | Compound Name | Morphology | Yield |
|---|---|---|---|
| 71 | rac-(3R,4R)-benzyl 4-methyl-3-(4-oxo-7-{[2-(trimethylsilyl)ethoxy]methyl}-4,7-dihydro-1H-pyrrolo[2,3-h][1,6]naphthyridin-1-yl)piperidine-1-carboxylate | colorless oil | 66% |

Reference Synthetic Example[b] 72

Phenyl 1,3,4-thiadiazol-2-ylcarbamate 1,3,4-Thiadiazol-2-amine (253 mg, 2.50 mmol) in N,N-dimethylacetamide (3 mL) was stirred with phenyl chloroformate (392 μL, 3.13 mmol) at room temperature for one day. Water was added to the reaction mixture, and the precipitated solid was collected by filtration, washed with water and hexane and dried under reduced pressure to give the title compound as a colorless solid (418 mg, yield 76%).

Reference Synthetic Example[b] 73 rac-(3R,4R)-4-Methyl-3-(4-oxo-7-{[2-(trimethylsilyl)ethoxy]methyl}-4,7-dihydro-1H-pyrrolo[2,3-h][1,6]naphthyridin-1-yl)-N-(1,3,4-thiadiazol-2-yl)piperidine-1-carboxamide rac-1-[(3R,4R)-4-Methylpiperidin-3-yl]-7-{[2-(trimethylsilyl)ethoxy]methyl}-1H-pyrrolo[2,3-h][1,6]naphthyridin-4(7H)-one (30.2 mg, 0.0732 mmol) obtained in Reference Synthetic Example[b] 36 in tetrahydrofuran (3 mL) was refluxed with phenyl 1,3,4-thiadiazol-2-ylcarbamate (19.6 mg, 0.0886 mmol) and triethylamine (17.9 μL, 0.128 mmol) for 3 hours under heating. The reaction mixture was concentrated under reduced pressure, and the residue was purified by silica gel column chromatography (ethyl acetate→chloroform/methanol=10/1 (v/v)) to give the title compound as a pale yellow solid (44.0 mg, quantitative yield).

Reference Synthetic Example[b] 74

Phenyl(3-methylisothiazol-5-yl)carbamate

3-Methylisothiazol-5-amine (156 mg, 1.04 mmol) in pyridine (1.2 mL) was mixed with phenyl chloroformate (260 μL, 2.07 mmol) under cooling with ice and stirred at room temperature for 3 hours. The reaction mixture was concentrated under reduced pressure, and after addition of water, extracted with chloroform twice, and the organic layer was concentrated under reduced pressure. The residue was purified by silica gel column chromatography (hexane/ethyl acetate=1/1 (v/v)) to give the title compound as a pale yellow solid (173 mg, yield 71%).

Reference Synthetic Example[b] 75 rac-(3R,4R)-4-Methyl-N-(3-methylisothiazol-5-yl)-3-(4-oxo-7-{[2-(trimethylsilyl)ethoxy]methyl}-4,7-dihydro-1H-pyrrolo[2,3-h][1,6]naphthyridin-1-yl)piperidine-1-carboxamide rac-1-[(3R,4R)-4-Methylpiperidin-3-yl]-7-{[2-(trimethylsilyl)ethoxy]methyl}-1H-pyrrolo[2,3-h][1,6]naphthyridin-4(7H)-one (29.5 mg, 0.0715 mmol) obtained in Reference Synthetic Example[b] 36 in tetrahydrofuran (3 mL) was refluxed with phenyl(3-methylthiazol-5-yl)carbamate (21.2 mg, 0.0905 mmol) and triethylamine (17.5 μL, 0.125 mmol) for 3 hours under heating. The reaction mixture was concentrated under reduced pressure, and the residue was purified by silica gel column chromatography (ethyl acetate→chloroform/methanol=10/1 (v/v)) to give the title compound as a yellow oil (38.4 mg, yield 97%).

Reference Synthetic Example[b] 76 rac-1-[(3R,4R)-1-(Cyclopentanecarbonyl)-4-methylpiperidin-3-yl]-7-{[2-(trimethylsilyl)ethoxy]methyl}-1H-pyrrolo[2,3-h][1,6]naphthyridin-4(7H)-one rac-1-[(3R,4R)-4-Methylpiperidin-3-yl]-7-{[2-(trimethylsilyl)ethoxy]methyl}-1H-pyrrolo[2,3-h][1,6]naphthyridin-4(7H)-one (31.0 mg, 0.751 mmol) obtained in Reference Synthetic Example[b] 36 and triethylamine (30.0 μL, 0.215 mmol) in tetrahydrofuran (4 mL) were stirred with cyclopentanecarbonyl chloride (20.0 μL, 0.165 mmol) at room temperature for one day. After addition of 1 M aqueous sodium hydroxide, the reaction mixture was extracted with chloroform, and the organic layer was washed with saturated aqueous sodium chloride, dried over anhydrous magnesium sulfate and concentrated under reduced pressure. The residue was purified by silica gel column chromatography (chloroform/methanol=10/1 v/v)) to give the title compound as a pale yellow oil (44.5 mg, quantitative yield).

Reference Synthetic Example[b] 77 rac-1-{(3R,4R)-4-methyl-1-[3-(trifluoromethyl)benzyl]piperidin-3-yl}-7-{[2-(trimethylsilyl)ethoxy]methyl}-1H-pyrrolo[2,3-h][1,6]naphthyridin-4(7H)-one rac-1-[(3R,4R)-4-Methylpiperidin-3-yl]-7-{[2-(trimethylsilyl)ethoxy]methyl}-1H-pyrrolo[2,3-h][1,6]naphthyridin-4(7H)-one (24.8 mg, 0.0601 mmol) obtained in Reference Synthetic Example[b] 36 in tetrahydrofuran (4 mL) was stirred sodium hydride (55 wt % dispersion in mineral oil, 49.4 mg, 1.23 mmol) and 3-(trifluoromethyl)benzyl bromide (38.2 mg, 0.160 mmol) at room temperature for one day. After addition of water under cooling with ice, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (ethyl acetate→chloroform/methanol=20/1 (v/v)) to give the title compound as a pale yellow oil (26.8 mg, quantitative yield).

Reference Synthetic Example[b] 78 rac-1-{(3R,4R)-4-methyl-1-[4-(trifluoromethyl)benzyl]piperidin-3-yl}-7-{[2-(trimethylsilyl)ethoxy]methyl}-1H-pyrrolo[2,3-h][1,6]naphthyridin-4(7H)-one The reactions in Reference Synthetic Example[b] 77 were carried out in substantially the same manners except that 4-(trifluoromethyl)benzyl bromide was used instead of 3-(trifluoromethyl)benzyl bromide to give the title compound as a pale yellow oil (32.8 mg, quantitative yield).

Reference Synthetic Example[b] 79 rac-1-{(3R,4R)-4-methyl-1-[2-(trifluoromethyl)benzyl]piperidin-3-yl}-7-{[2-(trimethylsilyl)ethoxy]methyl}-1H-pyrrolo[2,3-h][1,6]naphthyridin-4(7H)-one rac-1-[(3R,4R)-4-Methylpiperidin-3-yl]-7-{[2-(trimethylsilyl)ethoxy]methyl}-1H-pyrrolo[2,3-h][1,6]naphthyridin-4(7H)-one (13.4 mg, 0.0325 mmol) obtained in Reference Synthetic Example[b] 36 in tetrahydrofuran (4 mL) was stirred with sodium hydride (55 wt % dispersion in mineral oil, 30.6 mg, 0.765 mmol) and 2-(trifluoromethyl)benzyl bromide (27.8 mg, 0.116 mmol) at room temperature for one day. After addition of water under cooling with ice, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (ethyl acetate→chloroform/methanol=20/1 (v/v)) to give the title compound as a pale yellow oil, which was used for the next step.

Reference Synthetic Example[b] 80 rac-3-{[(3R,4R)-4-Methyl-3-(4-oxo-7-{[2-(trimethylsilyl)ethoxy]methyl}-4,7-dihydro-1H-pyrrolo[2,3-h][1,6]naphthyridin-1-yl)piperidin-1-yl]methyl}benzonitrile rac-1-[(3R,4R)-4-Methylpiperidin-3-yl]-7-{[2-(trimethylsilyl)ethoxy]methyl}-1H-pyrrolo[2,3-h][1,6]naphthyridin-4(7H)-one (25.0 mg, 0.0606 mmol) obtained in Reference Synthetic Example[b] 36 in tetrahydrofuran (3 mL) was stirred with sodium hydride (55 wt % dispersion in mineral oil, 15.4 mg, 0.385 mmol) and 3-cyanobenzyl bromide (12.8 mg, 0.0653 mmol) at room temperature for one day. The reaction mixture was further stirred with sodium hydride (55 wt % dispersion in mineral oil, 20.8 mg, 0.520 mmol) and 3-cyanobenzyl bromide (11.6 mg, 0.0592 mmol) at room temperature for one day. After addition of water, the reaction mixture was extracted with chloroform twice, and the organic layer was concentrated under reduced pressure. The residue was purified by silica gel column chromatography (ethyl acetate→chloroform/methanol=10/1 (v/v)) to give the title compound as a pale yellow oil (32.4 mg, quantitative yield).

Reference Synthetic Example[b] 81 rac-2-{[(3R,4R)-4-Methyl-3-(4-oxo-7-{[2-(trimethylsilyl)ethoxy]methyl}-4,7-dihydro-1H-pyrrolo[2,3-h][1,6]naphthyridin-1-yl)piperidin-1-yl]methyl}benzonitrile The reactions in Reference Synthetic Example[b] 77 were carried out in substantially the same manners except that 2-cyanobenzyl bromide was used instead of 3-(trifluoromethyl)benzyl bromide to give the title compound as a pale yellow oil (31.4 mg, yield 97%).

Reference Synthetic Example[b] 82 rac-4-{[(3R,4R)-4-Methyl-3-(4-oxo-7-{[2-(trimethylsilyl)ethoxy]methyl}-4,7-dihydro-1H-pyrrolo[2,3-h][1,6]naphthyridin-1-yl)piperidin-1-yl]methyl}benzonitrile The reactions in Reference Synthetic Example[b] 77 were carried out in substantially the same manners except that 4-cyanobenzyl bromide was used instead of 3-(trifluoromethyl)benzyl bromide to give the title compound as a pale yellow oil (28.5 mg, yield 89%).

Reference Synthetic Example[b] 83 tert-Butyl rac-(3R,4R)-4-methyl-3-(4-oxo-7-{[2-(trimethylsilyl)ethoxy]methyl}-4,7-dihydro-1H-pyrrolo[2,3-h][1,6]naphthyridin-1-yl)piperidin-1-carboxylate rac-1-[(3R,4R)-4-Methylpiperidin-3-yl]-7-{[2-(trimethylsilyl)ethoxy]methyl}-1H-pyrrolo[2,3-h][1,6]naphthyridin-4(7H)-one (20 mg, 0.049 mmol) obtained in Reference Synthetic Example[b] 36 in 1,4-dioxane (2 mL) was stirred with di-tert-butyl bicarbonate (40 mg, 0.18 mmol) and 1 M aqueous sodium hydroxide (200 µL. 0.200 mmol) at room temperature for 1 hour. After addition of water, the reaction mixture was extracted with ethyl acetate, and the organic layer was dried over anhydrous sodium sulfate and concentrated under reduced pressure. The residue was purified by silica gel column chromatography (ethyl acetate/methanol=1/0→10/1 (v/v)) to give the title compound as a colorless oil (21.1 mg, yield 85%).

Reference Synthetic Example[b] 84 rac-1-[(3R,4R)-1-(4-Fluorophenethyl)-4-methylpiperidin-3-yl]-7-{[2-(trimethylsilyl)ethoxy]methyl}-1H-pyrrolo[2,3-h][1,6]naphthyridin-4(7H)-one rac-1-[(3R,4R)-4-Methylpiperidin-3-yl]-7-{[2-(trimethylsilyl)ethoxy]methyl}-1H-pyrrolo[2,3-h][1,6]naphthyridin-4(7H)-one (20 mg, 0.049 mmol) obtained in Reference Synthetic Example[b] 36 in a mixture of N,N-dimethylformamide (2 mL) and dichloromethane (1 mL) was stirred with 4-fluorophenethyl bromide (22 µL, 0.16 mmol) and N,N-diisopropylethylamine (20 µL, 0.11 mmol) at 50° C. for 2 hours and then with sodium hydride (60 wt % dispersion in liquid paraffin, 10 mg, 0.24 mmol) at 70° C. for 5 hours. The reaction mixture was allowed to cool to room temperature and, after addition of saturated aqueous sodium chloride, extracted with ethyl acetate, and the organic layer was dried over anhydrous sodium sulfate and concentrated under reduced pressure. The residue was purified by silica gel column chromatography (hexane/ethyl acetate=1/1→0/1 (v/v)) to give a mixture (4.4 mg) containing the title compound. The mixture was used for the next step without further purification.

Reference Synthetic Example[b] 85 rac-1-[(3R,4R)-1-cyclopentyl-4-methylpiperidin-3-yl]-7-{[2-(trimethylsilyl)ethoxy]methyl}-1H-pyrrolo[2,3-h][1,6]naphthyridin-4(7H)-one rac-1-[(3R,4R)-4-Methylpiperidin-3-yl]-7-{[2-(trimethylsilyl)ethoxy]methyl}-1H-pyrrolo[2,3-h][1,6]naphthyridin-4(7H)-one (32 mg, 0.078 mmol) obtained in Reference Synthetic Example[b] 36 in a mixture of methanol (2 mL) and acetic acid (0.2 mL) was stirred with cyclopentanone (100 µL, 1.13 mmol) and 2-picoline borane (50 mg, 0.47 mmol) at room temperature for 1 hour. After addition of water, the reaction mixture was extracted with ethyl acetate, and the organic layer was dried over anhydrous sodium sulfate and concentrated under reduced pressure. The resulting colorless oil (38 mg) containing the title compound was used for the next step without further purification.

Reference Synthetic Example[b] 86

1-{1-[4-(tert-Butyl)cyclohexanecarbonyl]-4-methylpiperidin-3-yl}-7-{[2-(trimethylsilyl)ethoxy]methyl}-1H-pyrrolo[2,3-h][1,6]naphthyridin-4(7H)-one rac-1-[(3R,4R)-4-Methylpiperidin-3-yl]-7-{[2-(trimethylsilyl)ethoxy]methyl}-1H-pyrrolo[2,3-h][1,6]naphthyridin-4(7H)-one (20 mg, 0.049 mmol) obtained in Reference Synthetic Example[b] 36 in chloroform (2 mL) was stirred with 4-(tert-butyl)cyclohexanecarboxylic acid (20 mg, 0.11 mmol), 1-(3-dimethylaminopropyl)-3-ethylcarbodiimide hydrochloride (20 mg, 0.10 mmol) and N,N-diisopropylethylamine (50 µL, 0.29 mmol) at room temperature for 2 hours. After addition of 0.1 M aqueous sodium hydroxide, the reaction mixture was extracted with ethyl acetate, and the organic layer was washed with 0.1 M hydrochloric acid, dried over anhydrous sodium sulfate and concentrated under reduced pressure. The residue was purified by silica gel column chromatography (ethyl acetate) to give two isomers of the title compound in a less polar fraction (Reference Synthetic Example[b] 86a: colorless oil, 9.0 mg, yield 32%) and in more polar fraction (Reference Synthetic Example[b] 86 b: colorless oil, 9.3 mg, yield 33%).

Reference Synthetic Example[b] 87

4-Chloro-1-{[2-(trimethylsilyl)ethoxy]methyl}-1H-pyrrolo[2,3-b]pyridine-5-carboxylic acid 4-Chloro-1-{[2-(trimethylsilyl)ethoxy]methyl}-1H-pyrrolo[2,3-b]pyridine-5-carbaldehyde (486 mg, 1.56 mmol) obtained in Reference Synthetic Example[b] 55 in acetic acid (10 mL) was mixed with sulfamic acid (227 mg, 2.34 mmol) and 2-methyl-2-butene (486 µL, 4.58 mmol), and then sodium chlorite (254 mg, 2.81 mmol) in water (0.5 mL) was added dropwise. The resulting reaction mixture was stirred at room temperature for 2 hours, and after addition of water, adjusted to pH 7 with 1 M aqueous sodium hydroxide and extracted with chloroform. The organic layer was dried over anhydrous sodium sulfate and concentrated under reduced pressure. The residue was purified by silica gel column chromatography (ethyl acetate/methanol=10/1→1/1 (v/v)) to give the title compound as a colorless solid (484 mg, yield 95%).

Reference Synthetic Example[b] 88

4-Chloro-1-{[2-(trimethylsilyl)ethoxy]methyl}-1H-pyrrolo[2,3-b]pyridine-5-carboxamide 4-Chloro-1-{[2-(trimethylsilyl)ethoxy]methyl}-1H-pyrrolo[2,3-b]pyridine-5-carboxylic acid (480 mg, 1.47 mmol) in thionyl chloride (3 mL) was stirred at room temperature for 2 hours. After addition of toluene, the reaction mixture was concentrated under reduced pressure, and after addition of toluene, concentrated under reduced pressure. The residue was dissolved in dichloromethane (5 mL), and ammonia-methanol solution (7.0 M, 1.0 mL, 7.0 mmol) was added dropwise, and the resulting reaction mixture was stirred for 1 hour. After addition of saturated aqueous sodium chloride, the reaction mixture was extracted with ethyl acetate, and the organic layer was dried over anhydrous sodium sulfate and concentrated under reduced pressure to give the title compound as a colorless solid (461 mg, yield 96%).

Reference Synthetic Example[b] 89

4-[(1-Benzylpiperidin-4-yl)amino]-1-{[2-(trimethylsilyl)ethoxy]methyl}-1H-pyrrolo[2,3-b]pyridine-5-carboxamide 4-Chloro-1-{[2-(trimethylsilyl)ethoxy]methyl}-1H-pyrrolo[2,3-b]pyridine-5-carboxamide (456 mg, 1.40 mmol) was stirred with 1-benzyl-4-aminopiperidine (900 mg, 4.73 mmol) and N,N-diisopropylethylamine (250 µL, 1.44 mmol) at 140° C. for 3 hours. The reaction mixture was allowed to cool to room temperature and, after addition of water, extracted with ethyl acetate, and the organic layer was dried over anhydrous sodium sulfate and concentrated under reduced pressure. The residue was purified by silica gel column chromatography (chloroform→ethyl acetate/methanol=1/0→5/1 (v/v)) to give the title compound as a colorless solid (542 mg, yield 81%).

Reference Synthetic Example[b] 90

1-(1-Benzylpiperidin-4-yl)-7-{[2-(trimethylsilyl) ethoxy]methyl}-1H-pyrrolo[3',2':5,6]pyrido[4,3-d] pyrimidine-2,4(3H,7H)-dione 4-[(1-Benzylpiperidin-4-yl)amino]-1-{[2-(trimethylsilyl) ethoxy]methyl}-1H-pyrrolo[2,3-b]pyridine-5-carboxamide (484 mg, 1.01 mmol) in N,N-dimethylacetamide (5 mL) was stirred with 1,1'-carbonyldiimidazole (486 mg, 3.00 mmol) at 120° C. for 3 hours. The reaction mixture was allowed to cool to room temperature and, after addition of saturated aqueous sodium chloride, extracted with ethyl acetate, and the organic layer was dried over anhydrous sodium sulfate and concentrated under reduced pressure. The residue was purified by silica gel column chromatography (chloroform/methanol=20/1 (v/v)) to give the title compound as a colorless solid (360 mg, yield 70%).

Reference Synthetic Example[b] 91

1-(Piperidin-4-yl)-7-{[2-(trimethylsilyl)ethoxy] methyl}-1H-pyrrolo[3',2':5,6]pyrido[4,3-d]pyrimidine-2,4(3H,7H)-dione hydrochloride 1-(1-Benzylpiperidin-4-yl)-7-{[2-(trimethylsilyl)ethoxy] methyl}-1H-pyrrolo[3',2':5,6]pyrido[4,3-d]pyrimidine-2,4 (3H,7H)-dione (360 mg, 0.712 mmol) and 5% palladium-carbon (100 mg) in a mixture of methanol and 10 wt % hydrogen chloride-methanol solution (0.5 mL) were stirred with at room temperature for 2 hours under a hydrogen atmosphere, then at 40° C. for 5 hours and at room temperature for one day. The reaction mixture was filtered, and the filtrate was concentrated under reduced pressure to give the title compound as a colorless solid (324 mg, quantitative yield).

Reference Synthetic Example[b] 92

4-{[4-(2,4-Dioxo-7-{[2-(trimethylsilyl)ethoxy] methyl}-2,3,4,7-tetrahydro-1H-pyrrolo[3',2':5,6] pyrido[4,3-d]pyrimidin-1-yl)piperidin-1-yl] methyl}benzonitrile 1-(Piperidin-4-yl)-7-{[2-(trimethylsilyl)ethoxy]methyl}-1H-pyrrolo[3',2':5,6]pyrido[4,3-d]pyrimidine-2,4(3H,7H)-dione hydrochloride (50 mg, 0.111 mmol) and 4-cyanobenzaldehyde (29 mg, 0.22 mmol) in a mixture of methanol (2 ml) and acetic acid (0.2 mL) were stirred with 2-picoline borane (50 mg, 0.47 mmol) at room temperature for 2 days. After addition of 1 M aqueous sodium hydroxide, the reaction mixture was extracted with a mixture of ethyl acetate and 2-propanol, and the organic layer was dried over anhydrous sodium sulfate and concentrated under reduced pressure. The residue was purified by silica gel column chromatography (chloroform/methanol=10/1 (v/v)) to give the title compound as a colorless solid (23.4 mg, yield 40%).

Reference Synthetic Example[b] 93

1-{1-[(5-Chlorothiophen-2-yl)methyl]piperidin-4-yl}-7-{[2-(trimethylsilyl)ethoxy]methyl}-1H-pyrrolo [3',2':5,6]pyrido[4,3-d]pyrimidine-2,4(3H,7H)-dione The reactions in Reference Synthetic Example[b] 92 were carried out in substantially the same manners except that 5-chlorothiophene-2-carbaldehyde was used instead of 4-cyanobenzaldehyde to give the title compound as a colorless solid (21.1 mg, yield 58%).

Reference Synthetic Example[b] 94

1-{1-[4-(Trifluoromethyl)benzyl]piperidin-4-yl}-7-{ [2-(trimethylsilyl)ethoxy]methyl}-1H-pyrrolo[3',2':5, 6]pyrido[4,3-d]pyrimidine-2,4(3H,7H)-dione The reactions in Reference Synthetic Example[b] 92 were carried out in substantially the same manners except that 4-(trifluoromethyl)benzaldehyde was used instead of 4-cyanobenzaldehyde to give the title compound as a colorless amorphous (28.1 mg, yield 44%).

Reference Synthetic Example[b] 95

1-Cyclohexyl-7-{[2-(trimethylsilyl)ethoxy]methyl}-1H-pyrrolo[3',2':5,6]pyrido[4,3-d]pyrimidine-2,4 (3H,7H)-dione 4-(Cyclohexylamino)-1-{[2-(trimethylsilyl)ethoxy] methyl}-1H-pyrrolo[2,3-b]pyridine-5-carboxamide (26 mg, 0.067 mmol) obtained in Reference Synthetic Example[b] 30 in N,N-dimethylacetamide (1 mL) was stirred with 1,1'-carbonyldiimidazole (22 mg, 0.14 mmol) at 170° C. for 2 hours under microwave irradiation. The reaction mixture was allowed to cool to room temperature and, after addition of water, extracted with ethyl acetate, and the organic layer was dried over anhydrous sodium sulfate and concentrated under reduced pressure. The residue was purified by silica gel column chromatography (hexane/ethyl acetate=1/1 (v/v)) to give the title compound as a colorless solid (13.7 mg, yield 49%).

Reference Synthetic Example[b] 96

1-(4-Chloro-1-{[2-(trimethylsilyl)ethoxy]methyl}-1H-pyrrolo[2,3-b]pyridin-5-yl)ethanone Methylmagnesium bromide-diethyl ether solution (3.0 M, 10 mL, 30 mmol) was added dropwise to 4-chloro-1-{[2-(trimethylsilyl)ethoxy]methyl}-1H-pyrrolo[2,3-b]pyridine-5-carbaldehyde (4.89 g, 15.7 mmol) obtained in Reference Synthetic Example[b] 55 in tetrahydrofuran (50 mL) under cooling with ice, and the reaction mixture was stirred for 2 hours. After dropwise addition of water and addition of saturated aqueous ammonium chloride, the reaction mixture was extracted with ethyl acetate, and the organic layer was dried over anhydrous sodium sulfate and concentrated under reduced pressure. The residue was dissolved in 1,2-dimethoxyethane (25 mL) and vigorously stirred with manganese dioxide (9.0 g, 0.10 mol) at 80° C. for 4 hours. The reaction mixture was filtered, and the filtrate was concentrated under reduced pressure. The residue was dissolved in 1,2-dimethoxyethane (25 mL) and vigorously stirred with manganese dioxide (9.0 g, 0.10 mol) at 80° C. for 4 hours. The reaction mixture was filtered, and the filtrate was concentrated under reduced pressure. The residue was purified by silica gel column chromatography (hexane/ethyl acetate=10/1 (v/v)) to give the title compound as an orange oil (3.09 g, yield 61%). (alternative to Reference Synthetic Example[b] 33)

Reference Synthetic Example[b] 97

1-(4-[(1-Benzylpiperidin-4-yl)amino]-1-{[2-(trimethylsilyl)ethoxy]methyl}-1H-pyrrolo[2,3-b]pyridin-5-yl)ethanone 1-(4-Chloro-1-{[2-(trimethylsilyl)ethoxy]methyl}-1H-pyrrolo[2,3-b]pyridin-5-yl)ethanone (400 mg, 1.23 mmol) and 1-benzylpiperidin-4-amine (1.70 mL, 8.93 mmol) was stirred with N,N-diisopropylethylamine (251 μL. 1.47 mmol) at 140° C. for one day. The reaction mixture was purified by silica gel column chromatography (hexane/ethyl acetate=1/1 (v/v)) to give the title compound (343 mg, yield 58%).

Reference Synthetic Example[b] 98

1-(1-Benzylpiperidin-4-yl)-7-{[2-(trimethylsilyl)ethoxy]methyl}-1H-pyrrolo[2,3-h][1,6]naphthyridin-4(7H)-one 1-{4-[(1-Benzylpiperidin-4-yl)amino]-1-{[2-(trimethylsilyl)ethoxy]methyl}-1H-pyrrolo[2,3-b]pyridin-5-yl}ethanone (343 mg, 0.720 mmol) in N,N-dimethylformamide dimethyl acetal (2 mL) was stirred at 170° C. for 6 hours under microwave irradiation. The reaction mixture was allowed to cool to room temperature and concentrated under reduced pressure, and the residue was dissolved in tetrahydrofuran (5 mL) and stirred with 1 M hydrochloric acid (3 mL) at 80° C. for 1 hour. After addition of saturated aqueous sodium hydrogen carbonate, the reaction mixture was extracted with chloroform, and the organic layer was dried over anhydrous sodium sulfate and concentrated under reduced pressure. The residue was purified by silica gel column chromatography (chloroform/methanol=9/1 (v/v)) to give the title compound (299 mg, yield 85%).

Reference Synthetic Example[b] 99

1-(Piperidin-4-yl)-7-{[2-(trimethylsilyl)ethoxy]methyl}-1H-pyrrolo[2,3-h][1,6]naphthyridin-4(7H)-one 1-(1-Benzylpiperidin-4-yl)-7-{[2-(trimethylsilyl)ethoxy]methyl}-1H-pyrrolo[2,3-h][1,6]naphthyridin-4(7H)-one (341 mg, 0.697 mmol) in methanol was stirred with 5% palladium-carbon (500 mg) for one day under a hydrogen atmosphere. The reaction mixture was filtered, and the filtrate was concentrated under reduced pressure. The residue was purified by silica gel column chromatography (Hi Flash column amino type manufactured by Yamazen Corporation: chloroform/methanol=9/1/(v/v)) to give the title compound (189 mg, yield 68%).

Reference Synthetic Example[b] 100

1-{1-[(5-Chlorothiophen-2-yl)methyl]piperidin-4-yl}-7-{[2-(trimethylsilyl)ethoxy]methyl}-1H-pyrrolo[2,3-h][1,6]naphthyridin-4(7H)-one 1-(Piperidin-4-yl)-7-{[2-(trimethylsilyl)ethoxy]methyl}-1H-pyrrolo[2,3-h][1,6]naphthyridin-4(7H)-one (20 mg, 0.050 mmol) in methanol was stirred with 5-chlorothiophen-2-carbaldehyde (6.3 μL, 0.06 mmol), 2-picoline borane (6.4 mg, 0.06 mmol) and acetic acid (100 μL) for one day. The reaction mixture was concentrated under reduced pressure, and the residue was purified by silica gel column chromatography (chloroform/methanol=10/1 (v/v)) to give the title compound as a colorless oil (20 mg, yield 75%).

Reference Synthetic Example[b] 101

1-{1-[4-(Trifluoromethyl)benzyl]piperidin-4-yl}-7-{[2-(trimethylsilyl)ethoxy]methyl}-1H-pyrrolo[2,3-h][1,6]naphthyridin-4(7H)-one 1-(Piperidin-4-yl)-7-[{2-(trimethylsilyl)ethoxy}methyl]-1H-pyrrolo[2,3-h][1,6]naphthyridin-4(7H)-one (20 mg, 0.050 mmol) obtained in Reference Synthetic Example[b] 99 in dichloromethane was stirred with 4-(trifluoromethyl)benzyl bromide (14.3 mg, 0.0600 mmol) and triethylamine (10.5 μL, 0.0750 mmol) for one day. After addition of water, the reaction mixture was extracted with chloroform, and the organic layer as dried over anhydrous magnesium sulfate and concentrated under reduced pressure. The residue was purified by silica gel column chromatography (chloroform/methanol=9/1 (v/v)) to give the title compound (20 mg, yield 72%).

Reference Synthetic Example[b] 102

4-{[4-(4-Oxo-7-{[2-(trimethylsilyl)ethoxy]methyl}-4,7-dihydro-1H-pyrrolo[2,3-h][1,6]naphthyridin-1-yl)piperidin-1-yl)methyl}benzonitrile The reactions in Reference Synthetic Example[b] 101 were carried out in substantially the same manners except that 4-cyanobenzyl bromide was used instead of 4-(trifluoromethyl)benzyl bromide to give the title compound (29.7 mg, yield 77%).

Reference Synthetic Example[b] 103

3-Fluoro-4-{[4-(4-oxo-7-{[2-(trimethylsilyl)ethoxy]methyl}-4,7-dihydro-1H-pyrrolo[2,3-h][1,6]naphthyridin-1-yl)piperidin-1-yl]methyl}benzonitrile The reactions in Reference Synthetic Example[b] 101 were carried out in substantially the same manners except that 4-(bromomethyl)-3-fluorobenzonitrile was used instead of 4-(trifluoromethyl)benzyl bromide to give the title compound as a yellow oil (17.6 mg, yield 66%).

Reference Synthetic Example[b] 104

4-[(1-Benzylpiperidin-4-yl)amino]-1H-pyrrolo[2,3-b]pyridine-5-carbaldehyde

4-Chloro-1H-pyrrolo[2,3-b]pyridine-5-carbaldehyde (600 mg, 3.32 mmol) obtained in Reference Synthetic Example[b] 7 and 1-benzylpiperidin-4-amine (2.53 g, 13.3 mmol) in ethylene glycol (300 μL) were stirred at 180° C. for 2 hours under microwave irradiation. The reaction mixture was allowed to cool to room temperature and, after addition of water, extracted with chloroform, and the organic layer was dried over anhydrous magnesium sulfate and concentrated under reduced pressure. The resulting residue was dissolved in 1,4-dioxane (5 mL) and stirred with 4 M hydrogen chloride-1,4-dioxane solution (5 mL) and water (2 mL) at room temperature for one day. The reaction mixture was concentrated under reduced pressure, adjusted to pH 9 or above with 1M aqueous sodium hydroxide and extracted with chloroform and water, and the organic layer was dried over anhydrous magnesium sulfate and concentrated under reduced pressure. The residue was purified by silica gel column chromatography (Hi Flash column amino type manufactured by Yamazen Corporation: hexane/ethyl acetate=1/1 (v/v)) to give the title compound (672 mg, yield 60%).

Reference Synthetic Example[b] 105

4-[(1-Benzylpiperidin-4-yl)amino]-1-{[2-(trimethylsilyl)ethoxy]methyl}-1H-pyrrolo[2,3-b]pyridine-5-carbaldehyde 4-[(1-Benzylpiperidin-4-yl)amino]-1H-pyrrolo[2,3-b]pyridine-5-carbaldehyde (672 mg, 2.01 mmol) in N,N-dimethylformamide (5 mL) was mixed with sodium hydride (55 wt % dispersion in mineral oil, 436 mg, 10.0 mmol) under cooling with ice, and the reaction mixture was stirred for 30 minutes. The reaction mixture was stirred with [2-(chloromethoxyl)ethyl]trimethylsilane (885 μL, 5.00 mmol) at room temperature for one day. After addition of water, the reaction mixture was extracted with chloroform, and the organic layer was dried over anhydrous magnesium sulfate and concentrated under reduced pressure. The residue was purified by silica gel column chromatography (hexane/ethyl acetate=1/1 (v/v)) to give the title compound (392 mg, yield 42%).

Reference Synthetic Example[b] 106

{4-[(1-Benzylpiperidin-4-yl)amino]-1-{[2-(trimethylsilyl)ethoxy]methyl}-1H-pyrrolo[2,3-b]pyridin-5-yl}methanol 4-[(1-Benzylpiperidin-4-yl)amino]-1-{[2-(trimethylsilyl)ethoxy]methyl}-1H-pyrrolo[2,3-b]pyridine-5-carbaldehyde (289 mg, 0.620 mmol) in methanol was stirred with sodium borohydride (35.3 mg, 0.93 mmol) at room temperature for 1 hour. The reaction mixture was concentrated under reduced pressure and, after addition of water, extracted with ethyl acetate. The organic layer was dried over anhydrous magnesium sulfate and concentrated under reduced pressure. The residue was purified by silica gel column chromatography (hexane/ethyl acetate=1/1(v/v)) to give the title compound (258 mg, yield 89%).

Reference Synthetic Example[b] 107

5-(Aminomethyl)-N-(1-benzylpiperidin-4-yl)-1-{[2-(trimethylsilyl)ethoxy]methyl}-1H-pyrrolo[2,3-b]pyridin-4-amine {4-[(1-Benzylpiperidin-4-yl)amino]-1-{[2-(trimethylsilyl)ethoxy]methyl}-1H-pyrrolo[2,3-b]pyridin-5-yl}methanol (212 mg, 0.454 mmol), phthalimide (134 mg, 0.909 mmol) and triphenylphosphine (238 mg, 0.909 mmol) in tetrahydrofuran was stirred at room temperature for 30 minutes and with diisopropyl azodicarboxylate (184 mg, 0.909 mmol) for one day. The reaction mixture was concentrated under reduced pressure and, after addition of water, extracted with ethyl acetate. The residue was purified by silica gel column chromatography (hexane/ethyl acetate=1/1/(v/v)) to remove triphenylphosphine oxide. The residue was dissolved in ethanol (10 mL) and stirred with hydrazine monohydrate (1.00 mL, 11.6 mmol) at 80° C. for 1 hour. The reaction mixture was concentrated under reduced pressure and, after addition of water, extracted with chloroform, and the organic layer was dried over anhydrous magnesium sulfate and concentrated under reduced pressure. The residue was purified by silica gel column chromatography (hexane/ethyl acetate=1/1 (v/v)) to give the title compound (51.1 mg, yield 24%).

Reference Synthetic Example[b] 108

1-(1-Benzylpiperidin-4-yl)-7-{[2-(trimethylsilyl)ethoxy]methyl}-3,4-dihydro-1H-pyrrolo[3',2':5,6]pyrido[4,3-d]pyrimidin-2(7H)-one 5-(Aminomethyl)-N-(1-benzylpiperidin-4-yl)-1-{[2-(trimethylsilyl)ethoxy]methyl}-1H-pyrrolo[2,3-b]pyridin-4-amine (38 mg, 0.081 mmol) in dichloromethane was stirred with 1,1'-carbonyldiimidazole (20.0 mg, 0.123 mmol) at 80° C. for 1 hour. The reaction mixture was concentrated under reduced pressure and, after addition of water, extracted with ethyl acetate, and the organic layer was dried over anhydrous magnesium sulfate and concentrated under reduced pressure. The residue was purified by silica gel column chromatography (chloroform/methanol=10/1 (v/v)) to give the title compound (30.9 mg, yield 77%).

Reference Synthetic Example[b] 109

1-(Piperidin-4-yl)-7-{[2-(trimethylsilyl)ethoxy]methyl}-3,4-dihydro-1H-pyrrolo[3',2':5,6]pyrido[4,3-d]pyrimidin-2(7H)-one 1-(1-Benzylpiperidin-4-yl)-7-{[2-(trimethylsilyl)ethoxy]methyl}-3,4-dihydro-1H-pyrrolo[3',2':5,6]pyrido[4,3-d]pyrimidin-2(7H)-one (61 mg, 0.12 mmol) in ethanol was stirred with 5% palladium-carbon (60 mg) for one day under a hydrogen atmosphere. The reaction mixture was filtered, and the filtrate was concentrated under reduced pressure to give the title compound (48 mg, yield 100%).

Reference Synthetic Example[b] 110

1-[1-(Benzylsulfonyl)piperidin-4-yl]-7-{[2-(trimethylsilyl)ethoxy]methyl}-3,4-dihydro-1H-pyrrolo[3',2':5,6]pyrido[4,3-d]pyrimidin-2(7H)-one 1-(Piperidin-4-yl)-7-{[2-(trimethylsilyl)ethoxy]methyl}-3,4-dihydro-1H-pyrrolo[3',2':5,6]pyrido[4,3-d]pyrimidin-2(7H)-one (18.5 mg, 0.0460 mmol) in dichloromethane was mixed with phenylmethanesulfonyl chloride (17.5 mg, 0.092 mmol) and triethylamine (12.8 μL, 0.0920 mmol) for 1 hour under cooling with ice. After addition of water, the reaction mixture was extracted with chloroform, and the organic layer was dried over anhydrous magnesium sulfate and concentrated under reduced pressure. The residue was purified by silica gel column chromatography (chloroform/methanol=9/1 (v/v)) to give the title compound as a pale yellow solid (18.4 mg, yield 72%).

Reference Synthetic Example[b] 111

1-[1-(Pyridin-3-ylmethyl)piperidin-4-yl]-7-{[2-(trimethylsilyl)ethoxy]methyl}-3,4-dihydro-1H-pyrrolo[3',2':5,6]pyrido[4,3-d]pyrimidin-2(7H)-one The reactions in Reference Synthetic Example[b] 110 were carried out in substantially the same manners except that 3-picolyl bromide was used instead of phenylmethanesulfonyl chloride to give the title compound (14 mg, yield 46%).

Reference Synthetic Example[b] 112

4-{[4-(2-Oxo-7-{[2-(trimethylsilyl)ethoxy]methyl}-2,3,4,7-tetrahydro-1H-pyrrolo[3',2':5,6]pyrido[4,3-d]pyrimidin-1-yl)piperidin-1-yl]methyl}benzonitrile The reactions in Reference Synthetic Example[b] 110 were carried out in substantially the same manners except that 4-cyanobenzyl bromide was used instead of phenylmethanesulfonyl chloride to give the title compound (20.6 mg, yield 54%).

Reference Synthetic Example[b] 113

1-{1-[4-(Trifluoromethyl)benzyl]piperidin-4-yl}-7-{[2-(trimethylsilyl)ethoxy]methyl}-3,4-dihydro-1H-pyrrolo[3',2':5,6]pyrido[4,3-d]pyrimidin-2(7H)-one The reactions in Reference Synthetic Example[b] 110 were carried out in substantially the same manners except that 4-(trifluoromethyl)benzyl bromide was used instead of phenylmethanesulfonyl chloride to give the title compound (18.9 mg, yield 46%).

Reference Synthetic Example[b] 114

4-(2-Oxo-7-{[2-(trimethylsilyl)ethoxy]methyl}-2,3,4,7-tetrahydro-1H-pyrrolo[3',2':5,6]pyrido[4,3-d]pyrimidin-1-yl)-N-(1,3,4-thiadiazol-2-yl)piperidine-1-carboxamide 1-(Piperidin-4-yl)-7-{[2-(trimethylsilyl)ethoxy]methyl}-3,4-dihydro-1H-pyrrolo[3',2':5,6]pyrido[4,3-d]pyrimidin-2(7H)-one (16.3 mg, 0.0407 mmol) obtained in Reference Synthetic Example[b] 109 and phenyl 1,3,4-thiadiazol-2-ylcarbamate (10.8 mg, 0.0488 mol) obtained in Reference Synthetic Example[b] 72 in tetrahydrofuran was stirred with triethylamine (8.1 μL, 0.061 mmol) at 60° C. for 2 hours. After addition of water, the reaction mixture was extracted with ethyl acetate, and the organic layer was dried over anhydrous magnesium sulfate and concentrated under reduced pressure. The residue was purified by silica gel column chromatography (chloroform/methanol=9/1 (v/v)) to give the title compound as a colorless solid (20 mg, yield 93%).

Reference Synthetic Example[b] 115

1-[1-(3,3,3-Trifluoropropanoyl)piperidin-4-yl]-7-{[2-(trimethylsilyl)ethoxy]methyl}-3,4-dihydro-1H-pyrrolo[3',2':5,6]pyrido[4,3-d]pyrimidin-2(7H)-one 1-(Piperidin-4-yl)-7-{[2-(trimethylsilyl)ethoxy]methyl}-3,4-dihydro-1H-pyrrolo[3',2':5,6]pyrido[4,3-d]pyrimidin-2(7H)-one (25 mg, 0.062 mmol) obtained in Reference Synthetic Example[b] 109 in N,N-dimethylformamide was stirred with 3,3,3-trifluoropropionic acid (8.7 mg, 0.068 mmol), O-(7-azabenzotriazol-1-yl)-N,N,N',N'-tetramethyluronium hexafluorophosphate (28.1 mg, 0.0740 mmol) and N,N-diisopropylethylamine (21.2 μL, 0.124 mmol) at room temperature for 2 hours. After addition of water, the reaction mixture was extracted with ethyl acetate, and the organic layer was dried over anhydrous magnesium sulfate and concentrated under reduced pressure. The residue was purified by silica gel column chromatography (chloroform/methanol=10/1 (v/v)) to give the title compound as a yellow oil (15.5 mg, yield 49%).

Reference Synthetic Example[b] 116

1-[1-(Thiazol-5-ylmethyl)piperidin-4-yl]-7-{[2-(trimethylsilyl)ethoxy]methyl}-3,4-dihydro-1H-pyrrolo[3',2':5,6]pyrido[4,3-d]pyrimidin-2(7H)-one 1-(Piperidin-4-yl)-7-{[2-(trimethylsilyl)ethoxy]methyl}-3,4-dihydro-1H-pyrrolo[3',2':5,6]pyrido[4,3-d]pyrimidin-2(7H)-one (20 mg, 0.050 mmol) obtained in Reference Synthetic Example[b] 109 in methanol was stirred with thiazol-5-carbaldehyde (6.6 μL, 0.075 mmol), 2-picoline borane (8.0 mg, 0.075 mmol) and acetic acid (100 μL) for one day. The reaction mixture was concentrated under reduced pressure, and the residue was purified by silica gel column chromatography (chloroform/methanol=10/1 (v/v)) to give the title compound (12 mg, yield 48%).

Reference Synthetic Example[b] 117 rac-4-{[(3R,4R)-1-Benzyl-4-methylpiperidin-3-yl]amino}-1H-pyrrolo[2,3-b]pyridine-5-carbaldehyde The reactions in Reference Synthetic Example[b] 104 were carried out in substantially the same manners except that rac-(3R,4R)-1-benzyl-4-methylpiperidin-3-amine obtained in Reference Synthetic Example[b] 3 was used instead of 1-benzylpiperidin-4-amine to give the title compound as a brown oil (282 mg, yield 30%). (alternative to Reference Synthetic Example[b] 38)

Reference Synthetic Example[b] 118 rac-4-{[(3R,4R)-1-Benzyl-4-methylpiperidin-3-yl]amino}-1-{[2-(trimethylsilyl)ethoxy]methyl}-1H-pyrrolo[2,3-b]pyridine-5-carbaldehyde The reactions in Reference Synthetic Example[b] 105 were carried out in substantially the same manners except that rac-4-{[(3R,4R)-1-benzyl-4-methylpiperidin-3-yl]amino}-1H-pyrrolo[2,3-b]pyridine-5-carbaldehyde was used instead of 4-[(1-benzylpiperidin-4-yl)amino]-1H-pyrrolo[2,3-b]pyridine-5-carbaldehyde to give the title compound (231 mg, yield 60%). (alternative to Reference Synthetic Example[b] 39)

Reference Synthetic Example[b] 119 rac-(4-{[(3R,4R)-1-Benzyl-4-methylpiperidin-3-yl]amino}-1-{[2-(trimethylsilyl)ethoxy]methyl}-1H-pyrrolo[2,3-b]pyridin-5-yl)methanol The reactions in Reference Synthetic Example[b] 106 were carried out in substantially the same manners except that rac-4-{[(3R,4R)-1-benzyl-4-methylpiperidin-3-yl]amino}-1-{[2-(trimethylsilyl)ethoxy]methyl}-1H-pyrrolo[2,3-b]pyridine-5-carbaldehyde was used instead of 4-[(1-benzylpiperidin-4-yl)amino]-1-{[2-(trimethylsilyl)ethoxy]methyl}-1H-pyrrolo[2,3-b]pyridine-5-carbaldehyde to give the title compound as a yellow oil (105 mg, yield 84%). (alternative to Reference Synthetic Example[b] 40)

Reference Synthetic Example[b] 120 rac-5-(Aminomethyl)-N-[(3R,4R)-1-benzyl-4-methylpiperidin-3-yl]-1-{[2-(trimethylsilyl)ethoxy]methyl}-1H-pyrrolo[2,3-b]pyridin-4-amine The reactions in Reference Synthetic Example[b] 107 were carried out in substantially the same manners except that rac-(4-{[(3R,4R)-1-benzyl-4-methylpiperidin-3-yl]amino}-1-{[2-(trimethylsilyl)ethoxy]methyl}-1H-pyrrolo[2,3-b]pyridin-5-yl)methanol was used instead of {4-[(1-benzylpiperidin-4-yl)amino]-1-{[2-(trimethylsilyl)ethoxy]methyl}-1H-pyrrolo[2,3-b]pyridin-5-yl}methanol to give the title compound (20.8 mg, yield 21%).

Reference Synthetic Example[b] 121 rac-1-[(3R,4R)-1-benzyl-4-methylpiperidin-3-yl]-7-{[2-(trimethylsilyl)ethoxy]methyl}-3,4-dihydro-1H-pyrrolo[3',2':5,6]pyrido[4,3-d]pyrimidin-2(7H)-one The reactions in Reference Synthetic Example[b] 108 were carried out in substantially the same manners except that rac-5-(aminomethyl)-N-[(3R,4R)-1-benzyl-4-methylpiperidin-3-yl]-1-{[2-(trimethylsilyl)ethoxy]methyl}-1H-pyrrolo[2,3-b]pyridine-4-amine was used instead of 5-(aminomethyl)-N-(1-benzylpiperidin-4-yl)-1-{[2-(trimethylsilyl)ethoxy]methyl}-1H-pyrrolo[2,3-b]pyridine-4-amine to give the title compound (22 mg, yield 100%).

Reference Synthetic Example[b] 122

(trans-4-Aminocyclohexyl)methanol trans-4-Aminocyclohexanecarboxylic acid (314 mg, 2.19 mmol) was gradually added to sodium bis(2-methoxyethoxy)aluminum hydride-toluene solution (65 wt %, 3.0 mL) in toluene (3 mL) at 75° C., and the reaction mixture was stirred for 7 hours. The reaction mixture was allowed to cool to room temperature and stirred with 1 M aqueous sodium hydroxide (20 mL) at 80° C. for 10 minutes. The reaction mixture was allowed to cool to room temperature and partitioned between water and toluene, and the aqueous layer was extracted with chloroform three times. The organic layer was dried over anhydrous sodium sulfate and concentrated under reduced pressure to give the title compound as a colorless solid (170 mg, yield 60%).

Reference Synthetic Example[b] 123

1-(4-{[trans-4-(Hydroxymethyl)cyclohexyl]amino}-1-{[2-(trimethylsilyl)ethoxy]methyl}-1H-pyrrolo[2,3-b]pyridin-5-yl)ethanone (trans-4-Aminocyclohexyl)methanol (170 mg, 1.32 mmol) and 1-(4-chloro-1-{[2-(trimethylsilyl)ethoxy]methyl}-1H-pyrrolo[2,3-b]pyridin-5-yl)ethanone (120 mg, 0.369 mmol) obtained in Reference Synthetic Example[b] 96 in N,N-dimethylacetamide (1 mL) were stirred with N,N-diisopropylethylamine (128 μL, 0.735 mmol) at 140° C. for 7 hours. The reaction mixture was allowed to cool to room temperature and, after addition of saturated aqueous sodium chloride, extracted with ethyl acetate, and the organic layer was washed with saturated aqueous sodium chloride, dried over anhydrous sodium sulfate and concentrated under reduced pressure. The residue was purified by silica gel column chromatography (ethyl acetate) to give the title compound as a pale yellow oil (118 mg, yield 77%).

Reference Synthetic Example[b] 124

1-[trans-4-(Hydroxymethyl)cyclohexyl]-7-{[2-(trimethylsilyl)ethoxy]methyl}-1H-pyrrolo[2,3-h][1,6]naphthyridin-4(7H)-one The reactions in Reference Synthetic Example[b] 98 were carried out in substantially the same manners except that 1-(4-{[trans-4-(Hydroxymethyl)cyclohexyl]amino}-1-{[2-(trimethylsilyl)ethoxy]methyl}-1H-pyrrolo[2,3-b]pyridin-5-yl)ethanone was used instead of 1-{4-[(1-benzylpiperidin-4-yl)amino]-1-{[2-(trimethylsilyl)ethoxy]methyl}-1H-pyrrolo[2,3-b]pyridin-5-yl}ethanone to give the title compound as a pale yellow solid (35 mg, yield 29%).

Reference Synthetic Example[b] 125 tert-Butyl (trans-4-methoxycyclohexyl)carbamate tert-Butyl (trans-4-hydroxycyclohexyl)carbamate (1.0 g, 4.6 mmol) in tetrahydrofuran (20 mL) was stirred with sodium hydride (55 wt % dispersion in mineral oil, 24 mg, 6.4 mmol) and 15-crown-5 ether (965 μL) for 30 minutes under cooling with ice and then with iodomethane (289 μL) at room temperature for 1 hour. Methanol (2 mL) was added to the reaction mixture, and the precipitated solid was removed by filtration. The filtrate was concentrated under reduced pressure. The residue was purified by silica gel column chromatography (hexane/ethyl acetate=8/1 (v/v)) to give the title compound (708 mg, yield 67%).

Reference Synthetic Example[b] 126 trans-4-Methoxycyclohexanamine hydrochloride tert-Butyl (trans-4-methoxycyclohexyl)carbamate in ethanol (5 mL) was stirred with acetyl chloride (1.5 mL) for one day under cooling with ice, and the solvent was concentrated under reduced pressure to give the title compound (475 mg, yield 95%).

Reference Synthetic Example[b] 127

1-(4-[(trans-4-Methoxycyclohexyl)amino]-1-{[2-(trimethylsilyl)ethoxy]methyl}-1H-pyrrolo[2,3-b]pyridin-5-yl)ethanone 1-(4-Chloro-1-{[2-(trimethylsilyl)ethoxy]methyl}-1H-pyrrolo[2,3-b]pyridin-5-yl)ethanone (228 mg, 0.170 mmol) obtained in Reference Synthetic Example[a] 96 in ethylene glycol (1 mL) was stirred with trans-4-methoxycyclohexanamine hydrochloride and N,N-diisopropylethylamine at 180° C. for 1 hour under microwave irradiation. After addition of saturated aqueous sodium hydrogen carbonate, the reaction mixture was extracted with ethyl acetate, and the organic layer was dried over anhydrous sodium sulfate and concentrated under reduced pressure. The residue was purified by silica gel column chromatography (hexane/ethyl acetate=1/9 (v/v)) to give the title compound as a yellow oil (179 mg, yield 61%).

Reference Synthetic Example[b] 128

1-(trans-4-Methoxycyclohexyl)-7-{[2-(trimethylsilyl)ethoxy]methyl}-1H-pyrrolo[2,3-h][1,6]naphthyridin-4(7H)-one 1-(4-[(trans-4-Methoxycyclohexyl)amino]-1-{[2-(trimethylsilyl)ethoxy]methyl}-1H-pyrrolo[2,3-b]pyridin-5-yl) ethanone (179 mg, 0.428 mmol) in N,N-dimethylformamide dimethyl acetal (3 mL) was stirred at 170° C. for 6 hours under microwave irradiation. The reaction mixture was allowed to cool to room temperature and concentrated under reduced pressure, and the resulting residue was dissolved in tetrahydrofuran (3 mL) and stirred with 1 M hydrochloric acid (3 mL) at 80° C. for 1 hour. The reaction mixture was allowed to cool to room temperature and, after addition of saturated aqueous sodium hydrogen carbonate, extracted with chloroform, and the organic layer was dried over anhydrous sodium sulfate and concentrated under reduced pressure. The residue was purified by silica gel column chromatography (chloroform/methanol=9/1 (v/v)) to give the title compound (141 mg, yield 77%).

Reference Synthetic Examples[b] 129 to 134

The reactions in Reference Synthetic Example[b] 101 were carried out in substantially the same manners except that 2-(bromomethyl)-5-(trifluoromethyl)furan, 2-(bromomethyl)-5-nitrofuran, ethyl 5-(chloromethyl)furan-2-carboxylate, 4-(chloromethyl)-1,2-difluorobenzene, 1,2-dichloro-4-(chloromethyl)benzene or 5-(chloromethyl)-2-(trifluoromethyl)pyridine was used instead of 4-(trifluoromethyl)benzyl bromide to give the compounds of Reference Examples[b] 129 to 134. The names, morphologies and yields of the compounds synthesized are shown in Table[b] 5.

TABLE[b] 5

| Rf | Compound Name | Yield |
|---|---|---|
| 129 | 1-(1-{[5-(trifluoromethyl)furan-2-yl]methyl}piperidin-4-yl)-7-{[2-(trimethylsilyl)ethoxy]methyl}-1H-pyrrolo[2,3-h][1,6]naphthyridin-4(7H)-one | 74% |
| 130 | 1-{1-[(5-nitrofuran-2-yl)methyl]piperidin-4-yl}-7-{[2-(trimethylsilyl)ethoxy]methyl}-1H-pyrrolo[2,3,h][1,6]naphthyridin-4(7H)-one | 84% |
| 131 | Ethyl 5-{[4-(4-oxo-7-{[2-(trimethylsilyl)ethoxy]methyl}-4,7-dihydro-1H-pyrrolo[2,3-h][1,6]naphthyridin-1-yl)piperidin-1-yl]methyl}furan-2-carboxylate | 74% |
| 132 | 1-[1-(3,4-difluorobenzyl)piperidin-4-yl]-7-{[2-(trimethylsilyl)ethoxy]methyl}-1H-pyrrolo[2,3-h][1,6]naphthyridin-4(7H)-one | 82% |
| 133 | 1-[1-(3,4-dichlorobenzyl)piperidin-4-yl]-7-{[2-(trimethylsilyl)ethoxy]methyl}-1H-pyrrolo[2,3-h][1,6]naphthyridin-4(7H)-one | 95% |
| 134 | 1-(1-{[6-(trifluoromethyl)pyridin-3-yl]methyl}piperidin-4-yl)-7-{[2-(trimethylsilyl)ethoxy]methyl}-1H-pyrrolo[2,3-h][1,6]naphthyridin-4(7H)-one | 79% |

Reference Synthetic Example[b] 135 to 143

The reactions in Reference Synthetic Example[b] 100 were carried out in substantially the same manners except that 2-chlorothiazole-5-carbaldehyde, 4-fluoro-3-(trifluoromethyl)benzaldehyde, 5-nitrothiophene-3-carbaldehyde, 5-bromofuran-2-carbaldehyde, 5-bromothiophene-2-carbaldehyde, 4-bromothiophene-2-carbaldehyde, 2-bromothiazole-5-carbaldehyde, 2,2-difluorobenzo[d][1,3]dioxole-5-carbaldehyde or 1H-indole-5-carbaldehyde was used instead of 5-chlorothiophene-2-carbaldehyde to give the compounds of Reference Examples[b] 135 to 143. The names, morphologies and yields of the compounds synthesized are shown in Table[b] 6.

TABLE[b] 6

| Rf | Compound Name | Yield |
|---|---|---|
| 135 | 1-{1-[(2-chlorothiazol-5-yl)methyl]piperidin-4-yl}-7-{[2-(trimethylsilyl)ethoxy]methyl}-1H-pyrrolo[2,3-h][1,6]naphthyridin-4(7H)-one | 82% |
| 136 | 1-{1-[4-fluoro-3-(trifluoromethyl)benzyl]piperidin-4-yl}-7-{[2-(trimethylsilyl)ethoxy]methyl}-1H-pyrrolo[2,3-h][1,6]naphthyridin-4(7H)-one | 86% |
| 137 | 1-{1-[(5-nitrothiophen-3-yl)methyl]piperidin-4-yl}-7-{[2-(trimethylsilyl)ethoxy]methyl}-1H-pyrrolo[2,3-h][1,6]naphthyridin-4(7H)-one | 86% |
| 138 | 1-{1-[(5-bromofuran-2-yl)methyl]piperidin-4-yl}-7-{[2-(trimethylsilyl)ethoxy]methyl}-1H-pyrrolo[2,3-h][1,6]naphthyridin-4(7H)-one | 80% |
| 139 | 1-{1-[(5-bromothiophen-2-yl)methyl]piperidin-4-yl}-7-{[2-(trimethylsilyl)ethoxy]methyl}-1H-pyrrolo[2,3-h][1,6]naphthyridin-4(7H)-one | 78% |
| 140 | 1-{1-[(4-bromothiophen-2-yl)methyl]piperidin-4-yl}-7-{[2-(trimethylsilyl)ethoxy]methyl}-1H-pyrrolo[2,3-h][1,6]naphthyridin-4(7H)-one | 65% |
| 141 | 1-{1-[(2-bromothiazol-5-yl)methyl]piperidin-4-yl}-7-{[2-(trimethylsilyl)ethoxy]methyl}-1H-pyrrolo[2,3-h][1,6]naphthyridin-4(7H)-one | 80% |
| 142 | 1-{1-[(2,2-difluorobenzo[d][1,3]dioxol-5-yl)methyl]piperidin-4-yl}-7-{[2-(trimethylsilyl)ethoxy]methyl}-1H-pyrrolo[2,3-h][1,6]naphthyridin-4(7H)-one | 94% |
| 143 | 1-{1-[(1H-indol-5-yl)methyl]piperidin-4-yl}-7-{[2-(trimethylsilyl)ethoxy]methyl}-1H-pyrrolo[2,3-h][1,6]naphthyridin-4(7H)-one | 81% |

Reference Synthetic Example[b] 144

1-[1-(5-Chlorothiophene-2-carbonyl)piperidin-4-yl]-7-{[2-(trimethylsilyl)ethoxy]methyl}-1H-pyrrolo[2,3-h][1,6]naphthyridin-4(7H)-one 1-(Piperidin-4-yl)-7-{[2-(trimethylsilyl)ethoxy]methyl}-1H-pyrrolo[2,3-h][1,6]naphthyridin-4(7H)-one (20 mg, 0.050 mmol) obtained in Reference Synthetic Example[b] 99 in N,N-dimethylformamide (2 mL) was stirred with 5-chlorothiophene-2-carboxylic acid (13.4 mg, 0.0825 mmol), N,N-diisopropylethylamine (25.5 μL, 0.150 mmol) and O-(7-azabenzotriazol-1-yl)-N,N,N',N'-tetramethyluronium hexafluorophosphate (34.2 mg, 0.0899 mmol) for one day. After addition of water, the reaction mixture was extracted with ethyl acetate, and the organic layer was dried over anhydrous magnesium sulfate and concentrated under reduced pressure. The residue was purified by silica gel column chromatography (chloroform/methanol=9/1 (v/v)) to give the title compound (40.0 mg, quantitative yield).

Reference Synthetic Examples[b] 145 to 150

The reactions in Reference Synthetic Example[b] 92 were carried out in substantially the same manners except that tert-butyl(2-oxoethyl)carbamate, 5-bromothiophene-2-carbaldehyde, 2-(tetrahydro-2H-thiopyran-4-yl)acetaldehyde, cyclopropanecarbaldehyde, 2-methylbutanal or 2-(tetrahydro-2H-pyran-4-yl)acetaldehyde was used instead of 4-cyanobenzaldehyde to give the compounds of Reference Synthetic Examples[b] 145 to 150. The names, morphologies and yields of the compounds synthesized are shown in Table[b] 7.

TABLE[b] 7

| Rf | Compound Name | Morphology | Yield |
|---|---|---|---|
| 145 | tert-butyl {2-[4-(2,4-dioxo-7-{[2-(trimethylsilyl)ethoxy]methyl}-2,3,4,7-tetrahydro-1H-pyrrolo[3',2':5,6]pyrido[4,3-d]pyrimidin-1-yl)piperidin-1-yl]ethyl}carbamate | Colorless solid | 89% |
| 146 | 1-{1-[(5-bromothiophen-2-yl)methyl]piperidin-4-yl}-7-{[2-(trimethylsilyl)ethoxy]methyl}-1H-pyrrolo[3',2':5,6]pyrido[4,3-d]pyrimidine-2,4(3H,7H)-dione | Colorless solid | 70% |
| 147 | 1-{1-[2-(tetrahydro-2H-thiopyran-4-yl)ethyl]piperidin-4-yl}-7-{[2-(trimethylsilyl)ethoxy]methyl}-1H-pyrrolo[3',2':5,6]pyrido[4,3-d]pyrimidine-2,4(3H,7H)-dione | Yellow oil | 36% |
| 148 | 1-[1-(cyclopropylmethyl)piperidin-4-yl]-7-{[2-(trimethylsilyl)ethoxy]methyl}-1H-pyrrolo[3',2':5,6]pyrido[4,3-d]pyrimidine-2,4(3H,7H)-dione | Colorless solid | 51% |
| 149 | 1-[1-(2-mothylbutyl)piperidin-4-yl]-7-{[2-(trimethylsilyl)ethoxy]methyl}-1H-pyrrolo[3',2':5,6]pyrido[4,3-d]pyrimidine-2,4(3H,7H)-dione | Colorless solid | 56% |
| 150 | 1-{1-[2-(tetrahydro-2H-pyran-4-yl)ethyl]piperidin-4-yl}-7-{[2-(trimethylsilyl)ethoxy]methyl}-1H-pyrrolo[3',2':5,6]pyrido[4,3-d]pyrimidine-2,4(3H,7H)-dione | Colorless solid | 80% |

Reference Synthetic Example[b] 151

2-[4-(2,4-Dioxo-7-{[2-(trimethylsilyl)ethoxy]methyl}-2,3,4,7-tetrahydro-1H-pyrrolo[3',2':5,6]pyrido[4,3-d]pyrimidin-1-yl)piperidin-1-yl]acetonitrile 1-(Piperidin-4-yl)-7-{[2-(trimethylsilyl)ethoxy]methyl}-1H-pyrrolo[3',2':5,6]pyrido[4,3-d]pyrimidine-2,4(3H,7H)-dione hydrochloride (40.0 mg, 0.0885 mmol) obtained in Reference Synthetic Example[b] 91 in acetonitrile (1 mL) was mixed with 2-chloroacetonitrile (8.2 μL, 0.133 mmol) and N,N-diisopropylethylamine (31.0 μL, 0.177 mmol) and stirred at 60° C. for 26 hours. The reaction mixture was concentrated under reduced pressure, and the residue was purified by silica gel column chromatography (chloroform→methanol/chloroform=8/92 (v/v)) to give the title compound as a colorless solid (31.2 mg, yield 78%).

Reference Synthetic Examples[b] 152 to 156

The reactions in Reference Synthetic Example[b] 151 were carried out in substantially the same manners except that 2,2,2-trifluoroethyl trifluoromethanesulfonate, 5-bromopentanenitrile, 6-bromo-1,1,1-trifluorohexane, 4-bromobutanenitrile or 2-(bromomethyl)tetrahydrofuran was used instead of 2-chloroacetonitrile to give the compounds of Reference Synthetic Examples[b] 152 to 156. The names, morphologies and yields of the compounds synthesized are shown in Table[b] 8.

TABLE[b] 8

| Rf | Compound Name | Morphology | Yield |
|---|---|---|---|
| 152 | 1-[1-(2,2,2-trifluoroethyl)piperidin-4-yl]-7-{[2-(trimethylsilyl)ethoxy]methyl}-1H-pyrrolo[3',2':5,6]pyrido[4,3-d]pyrimidine-2,4(3H,7H)-dione | Colorless solid | 81% |
| 153 | 5-[4-(2,4-dioxo-7-{[2-(trimethylsilyl)ethoxy]methyl}-2,3,4,7-tetrahydro-1H-pyrrolo[3',2':5,6]pyrido[4,3-d]pyrimidin-1-yl)piperidin-1-yl]pentanenitrile | Colorless solid | 78% |
| 154 | 1-[1-(6,6,6-trifluorohexyl)piperidin-4-yl]-7-{[2-(trimethylsilyl)ethoxy]methyl}-1H-pyrrolo[3',2':5,6]pyrido[4,3-d]pyrimidine-2,4(3H,7H)-dione | Pale yellow solid | 83% |
| 155 | 4-[4-(2,4-dioxo-7-{[2-(trimethylsilyl)ethoxy]methyl}-2,3,4,7-tetrahydro-1H-pyrrolo[3',2':5,6]pyrido[4,3-d]pyrimidin-1-yl)piperidin-1-yl]butanenitrile | Colorless solid | 76% |
| 156 | 1-{1-[(tetrahydrofuran-2-yl)methyl]piperidin-4-yl}-7-{[2-(trimethylsilyl)ethoxy]methyl}-1H-pyrrolo[3',2':5,6]pyrido[4,3-d]pyrimidine-2,4(3H,7H)-dione | Pale orange solid | 65% |

Reference Synthetic Example[b] 157

3-[4-(2,4-Dioxo-7-{[2-(trimethylsilyl)ethoxy]methyl}-2,3,4,7-tetrahydro-1H-pyrrolo[3',2': 5,6]pyrido[4,3-d]pyrimidin-1-yl)piperidin-1-yl]propanenitrile 1-(Piperidin-4-yl)-7-{[2-(trimethylsilyl)ethoxy]methyl}-1H-pyrrolo[3',2':5,6]pyrido[4,3-d]pyrimidine-2,4(3H,7H)-dione hydrochloride (40.0 mg, 0.0885 mmol) obtained in Reference Synthetic Example[b] 91 in ethanol (1 mL) was refluxed with acrylonitrile (11.5 μL, 0.176 mmol) and N,N-diisopropylethylamine (18.9 μL, 0.110 mmol) for 8.5 hours. The reaction mixture was concentrated under reduced pressure, and the residue was purified by silica gel column chromatography (chloroform→methanol/chloroform=6/94 (v/v)) to give the title compound as a colorless solid (27.3 mg, yield 66%).

Reference Synthetic Example[b] 158

4-Aminoadamantan-1-ol

Concentrated sulfuric acid (35 mL) was mixed with concentrated nitric acid (4.5 mL) and 2-adamantylamine (5.10 g, 4.57 mmol) under cooling with ice, and the reaction mixture was stirred at room temperature for 2 hours. The reaction mixture was added to ice water and adjusted to pH 10 with 7.5 M aqueous sodium hydroxide. After addition of water, the reaction mixture was extracted with chloroform, and the organic layer was dried over anhydrous magnesium sulfate and concentrated under reduced pressure to give the title compound as a yellow solid (2.79 g, yield 61%).

Reference Synthetic Example[b] 159

159a: Benzyl [(1R,2s,3S,5s,7s)-5-hydroxyadamantan-2-yl]carbamate

159b: Benzyl [(1R,2r,3S,5s,7s)-5-hydroxyadamantan-2-yl]carbamate

4-Aminoadamantan-1-ol (2.57 g, 15.4 mmol) in tetrahydrofuran (25 mL) was mixed with benzyl chloroformate (2.30 mL, 16.1 mmol) and 1 M aqueous sodium hydroxide (16.0 mL, 16.0 mmol) under cooling with ice and then stirred at room temperature for one day. After addition of 10% aqueous potassium hydrogen sulfate, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (hexane/ethyl acetate=1/2 (v/v)) to give benzyl [(1R,2s,3S,5s,7s)-5-hydroxyadamantan-2-yl]carbamate (Reference Synthetic Example[b] 159a; yellow oil, 1.72 g, yield 37%) in a more polar fraction and benzyl [(1R,2r,3S,5s,7s)-5-hydroxyadamantan-2-yl]carbamate (Reference Synthetic Example[b] 159 b; yellow oil, 2.24 g, yield 48%) in a less polar fraction.

Reference Synthetic Example[b] 160

(1s,3R,4s,5S,7s)-4-Aminoadamantan-1-ol

Benzyl [(1R,2s,3S,5s,7s)-5-hydroxyadamantan-2-yl]carbamate (318 mg, 1.05 mmol) obtained in Reference Synthetic Example[b] 159a and 5% palladium-carbon (63 mg) in methanol (2 mL) were stirred at room temperature for one day under a hydrogen atmosphere. The reaction mixture was filtered, and the filtrate was concentrated under reduced pressure to give the title compound as a colorless solid (144 mg, yield 82%).

Reference Synthetic Example[b] 161

(1s,3R,4r,5S,7s)-4-Aminoadamantan-1-ol

Benzyl [(1R,2r,3S,5s,7s)-5-hydroxyadamantan-2-yl]carbamate (2.24 g, 7.46 mmol) obtained in Reference Synthetic Example[b] 159 b and 5% palladium-carbon (700 mg) in methanol (30 mL) were stirred at room temperature for one day under a hydrogen atmosphere. The reaction mixture was filtered, and the filtrate was concentrated under reduced pressure to give the title compound as a colorless solid (1.29 g, quantitative yield).

Reference Synthetic Example[b] 162 tert-Butyl 3-oxoazetidine-1-carboxylate tert-Butyl 3-hydroxyazetidine-1-carboxylate (4.02 g, 23.2 mmol) in dichloromethane (305 mL) was mixed with Dess-Martin Periodinane (9.55 g, 22.5 mmol) under cooling with ice and then stirred at room temperature for 3 hours. After addition of 10% aqueous sodium thiosulfate and saturated aqueous sodium hydrogen carbonate under cooling with ice, the reaction mixture was extracted with chloroform, and the organic layer was washed with saturated aqueous sodium chloride, dried over anhydrous magnesium sulfate and concentrated under reduced pressure. The residue was purified by silica gel column chromatography (hexane/ethyl acetate=2/1 (v/v)) to give the title compound as a colorless solid (3.39 g, yield 85%).

Reference Synthetic Example[b] 163 tert-Butyl 3-(cyanomethylene)azetidine-1-carboxylate

Diethyl cyanomethylphosphonate (3.54 g, 20.0 mmom) in tetrahydrofuran (20 mL) was added to potassium tert-butoxide (2.03 g, 21.1 mmol) in tetrahydrofuran (30 mL) under cooling with ice and stirred for 30 minutes. The reaction mixture was mixed with tert-butyl 3-oxoazetidine-1-carboxylate (2.96 g, 17.3 mmol) in tetrahydrofuran (15 mL) and stirred at room temperature for 1 day, and after addition of water, extracted with ethyl acetate. The organic layer was washed with saturated aqueous sodium chloride, dried over anhydrous magnesium sulfate and concentrated under reduced pressure. The resulting residue was purified by silica gel column chromatography (hexane/ethyl acetate=3/1 (v/v)) to give the title compound as a colorless solid (1.93 g, yield 58%).

Reference Synthetic Example[b] 164 tert-Butyl 3-(cyanomethyl)azetidine-1-carboxylate tert-Butyl 3-(cyanomethylene)azetidine-1-carboxylate (823 mg, 4.24 mmol) in a mixture of methanol (20 mL) and 1,4-dioxane (10 mL) was stirred with 5% palladium-carbon (129 mg) for one day under a hydrogen atmosphere. The reaction mixture was filtered, and the filtrate was concentrated under reduced pressure. The resulting residue was purified by silica gel column chromatography (hexane/ethyl acetate=1/1 (v/v)) to give the title compound as a colorless oil (657 mg, yield 79%).

Reference Synthetic Example[b] 165

2-(Azetidin-3-yl)acetonitrile hydrochloride tert-Butyl 3-(cyanomethyl)azetidine-1-carboxylate (621 mg, 3.17 mmol) in 1,4-dioxane (4 mL) was stirred with 4 M hydrogen chloride-1,4-dioxane solution (6 mL) at room temperature for 1 day. The reaction mixture was concentrated under reduced pressure to give the title compound as a colorless oil (543 mg, quantitative yield).

Reference Synthetic Example[b] 166

4-{[trans-4-(Hydroxymethyl)cyclohexyl]amino}-1-{[2-(trimethylsilyl)ethoxy]methyl}-1H-pyrrolo[2,3-b]pyridine-5-carboxamide 4-Chloro-1-{[2-(trimethylsilyl)ethoxy]methyl}-1H-pyrrolo[2,3-b]pyridine-5-carboxamide (680 mg, 2.09 mmol) obtained in Reference Synthetic Example[b] 88 in N,N-dimethylacetamide (1.1 mL) was mixed with N,N-diisopropylethylamine (1.1 mL) and (trans-4-Aminocyclohexyl)methanol (945 mg, 7.31 mmol) obtained in Reference Synthetic Example[b] 122 and stirred at 130° C. for 3 hours. The reaction mixture was allowed to cool to room temperature and, after addition of saturated aqueous ammonium chloride, extracted with ethyl acetate, and the organic layer was dried over anhydrous sodium sulfate and concentrated under reduced pressure. The residue was purified by silica gel column chromatography (ethyl acetate/hexane=5/1 (v/v)) to give the title compound as a colorless solid (781 mg, yield 89%).

Reference Synthetic Example[b] 167

1-[trans-4-(Hydroxymethyl)cyclohexyl]-7-{[2-(trimethylsilyl)ethoxy]methyl}-1H-pyrrolo[3',2':5,6]pyrido[4,3-d]pyrimidine-2,4(3H,7H)-dione 4-{[trans-4-(Hydroxymethyl)cyclohexyl]amino}-1-{[2-(trimethylsilyl)ethoxy]methyl}-1H-pyrrolo[2,3-b]pyridine-5-carboxamide (270 mg, 0.645 mmol) in N,N-dimethylacetamide (3 mL) was mixed with N,N-diisopropylethylamine (3 mL) and 1,1'-carbonyldiimidazole (1.04 g, 6.45 mmol) and stirred at 120° C. for 3 hours. The reaction mixture was allowed to cool to room temperature and stirred with 1M aqueous sodium hydroxide (3 mL) and acetonitrile (3 mL) for 5 hours. After addition of water, the reaction mixture was extracted with ethyl acetate, and the organic layer was dried over anhydrous sodium sulfate and concentrated under reduced pressure. The residue was purified by silica gel column chromatography (ethyl acetate/hexane=9/1 (v/v)) to give the title compound as a colorless solid (206 mg, yield 73%).

Reference Synthetic Example[b] 168 trans-4-(2,4-Dioxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde 1-[trans-4-(Hydroxymethyl)cyclohexyl]-7-{[2-(trimethylsilyl)ethoxy]methyl}-1H-pyrrolo[3',2':5,6]pyrido[4,3-d]pyrimidine-2,4(3H,7H)-dione (107 mg, 0.240 mmol) in a mixture of toluene (1 mL) and dimethyl sulfoxide (0.25 mL) was mixed with 2-iodoxybenzoic acid (80.9 mg, 0.288 mmol) and stirred at 50° C. for 2 hours. After addition of saturated aqueous sodium thiosulfate and saturated aqueous sodium hydrogen carbonate, the reaction mixture was stirred at room temperature for 30 minutes, and extracted with ethyl acetate, and the organic layer was dried over anhydrous sodium sulfate and concentrated under reduced pressure. The residue was purified by silica gel column chromatography (ethyl acetate/hexane=1/1→7/3 (v/v)) to give the title compound as a colorless solid (70.1 mg, yield 66%).

Reference Synthetic Example[b] 169

1-(4-{[(2,2,2-Trifluoroethyl)amino]methyl}cyclohexyl)-7-{[2-(trimethylsilyl)ethoxy]methyl}-1H-pyrrolo[3',2':5,6]pyrido[4,3-d]pyrimidine-2,4(3H,7H)-dione trans-4-(2,4-Dioxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde (30.4 mg, 0.0680 mmol) in a mixture of methanol (0.5 mL) and acetic acid (50 μL) was stirred with 2,2,2-trifluoroethanamine hydrochloride (12.1 mg, 0.089 mmol) and 2-picoline borane (9.50 mg, 0.089 mmol) at room temperature for 1 day. After addition of 1 M aqueous sodium hydroxide, the reaction mixture was extracted with ethyl acetate, and the organic layer was dried over anhydrous sodium sulfate and concentrated under reduced pressure. The residue was purified by silica gel thin layer chromatography (ethyl acetate/hexane=1/1 (v/v)) to give the title compound as a colorless solid (32.3 mg, yield 90%).

Reference Synthetic Example[b] 170

3-[trans-4-(2,4-Dioxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]acrylonitrile trans-4-(2,4-Dioxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde (34.2 mg, 0.0770 mmol) obtained in Reference Synthetic Example[b] 168 in tetrahydrofuran (2 mL) was mixed with diethyl cyanomethylphosphonate (37 μL, 0.235 mmol) and sodium hydride (55 wt % dispersion in mineral oil, 10 mg, 0.235 mmol) under cooling with ice and then stirred at room temperature for 30 minutes. After addition of water, the reaction mixture was extracted with ethyl acetate, and the organic layer was washed with saturated aqueous sodium chloride, dried over anhydrous magnesium sulfate and concentrated under reduced pressure. The residue was purified by silica gel column chromatography (ethyl acetate/hexane=1/2→1/0 (v/v)) to give the title compound as a colorless solid (32.0 mg, yield 92%).

Reference Synthetic Examples[b] 171 And 172

The reactions in Reference Synthetic Example[b] 89 were carried out in substantially the same manners except that (1s,3R,4r,5S,7s)-4-aminoadamantan-1-ol obtained in Reference Synthetic Example[b] 161 or (1s,3R,4s,5S,7s)-4-amino-adamantan-1-ol obtained in Reference Synthetic Example[b] 160 was used instead of 1-benzyl-4-aminopiperidine to give the compounds of Reference Examples[b] 171 and 172. The names, morphologies and yields of the compounds synthesized are shown in Table[b] 9.

TABLE[b] 9

| Rf | Compound Name | Morphology | Yield |
|---|---|---|---|
| 171 | 4-{[(1R,2r,3S,5s,7s)-5-hydroxyadamantan-2-yl]amino}-1-{[2-(trimethylsilyl)-ethoxy]methyl}-1H-pyrrolo[2,3-b]pyridine-5-carboxamide | Brown oil | 86% |
| 172 | 4-{[(1R,2s,3S,5s,7s)-5-hydroxyadamantan-2-yl]amino}-1-{[2-(trimethylsilyl)-ethoxy]methyl}-1H-pyrrolo[2,3-b]pyridine-5-carboxamide | Colorless oil | 58% |

Reference Synthetic Examples[b] 173 And 174

The reactions in Reference Synthetic Example[b] 90 were carried out in substantially the same manners except that 4-{[(1R,2r,3S,5s,7s)-5-hydroxyadamantan-2-yl]amino}-1-{[2-(trimethylsilyl)ethoxy]methyl}-1H-pyrrolo[2,3-b]pyridine-5-carboxamide obtained in Reference Synthetic Example[b] 171 or 4-{[(1R,2s,3S,5s,7s)-5-hydroxyadamantan-2-yl]amino}-1-{[2-(trimethylsilyl)ethoxy]methyl}-1H-pyrrolo[2,3-b]pyridine-5-carboxamide obtained in Reference Synthetic Example[b] 172 was used instead of 4-[(1-benzylpiperidin-4-yl)amino]-1-{[2-(trimethylsilyl)ethoxy]methyl}-1H-pyrrolo[2,3-b]pyridine-5-carboxamide to give the compounds of Reference Synthetic Examples[b] 173 and 174. The names, morphologies and yields of the compounds synthesized are shown in Table[b] 10.

TABLE[b] 10

| Rf | Compound Name | Morphology | Yield |
|---|---|---|---|
| 173 | 1-[(1R,2r,3S,5s,7s)-5-hydroxyadamantan-2-yl]-7-{[2-(trimethylsilyl)ethoxy]methyl}-1H-pyrrolo[3',2':5,6]pyrido[4,3-d]pyrimidine-2,4(3H,7H)-dione | Colorless solid | 95% |
| 174 | 1-[(1R,2s,3S,5s,7s)-5-hydroxyadamantan-2-yl]-7-{[2-(trimethylsilyl)ethoxy]methyl}-1H-pyrrolo[3',2':5,6]pyrido[4,3-d]pyrimidine-2,4(3H,7H)-dione | Yellow oil | 99% |

Reference Synthetic Examples[b] 175 And 176

The reactions in Reference Synthetic Example[b] 97 were carried out in substantially the same manners except that (1s,3R,4r,5S,7s)-4-aminoadamantan-1-ol obtained in Reference Synthetic Example[b] 161 or (1s,3R,4s,5S,7s)-4-aminoadamantan-1-ol obtained in Reference Synthetic Example[b] 160 was used instead of 1-benzylpiperidine-4-amine to give the compounds of Reference Synthetic Examples[b] 175 and 176. The names, morphologies and yields of the compounds synthesized are shown in Table[b] 11.

TABLE[b] 11

| Rf | Compound Name | Morphology | Yield |
|---|---|---|---|
| 175 | 1-(4-{[(1R,2r,3S,5s,7s)-5-hydroxyadamantan-2-yl]amino}-1-{[2-(trimethylsilyl)ethoxy]methyl}-1H-pyrrolo[2,3-b]pyridin-5-yl)ethanone | Yellow solid | 78% |

TABLE[b] 11-continued

| Rf | Compound Name | Morphology | Yield |
|---|---|---|---|
| 176 | 1-(4-{[(1R,2s,3S,5s,7s)-5-hydroxyadamantan-2-yl]amino}-1-{[2-(trimethylsilyl)ethoxy]methyl}-1H-pyrrolo[2,3-b]pyridin-5-yl)ethanone | Yellow solid | 91% |

Reference Synthetic Examples[b] 177 And 178

The reactions in Reference Synthetic Example[b] 98 were carried out in substantially the same manners except that 1-(4-{[(1R,2r,3S,5s,7s)-5-hydroxyadamantan-2-yl]amino}-1-{[2-(trimethylsilyl)ethoxy]methyl}-1H-pyrrolo[2,3-b]pyridin-5-yl)ethanone obtained in Reference Synthetic Example[b] 175 or 1-(4-{[(1R,2s,3S,5s,7s)-5-hydroxyadamantan-2-yl]amino}-1-{[2-(trimethylsilyl)ethoxy]methyl}-1H-pyrrolo[2,3-b]pyridin-5-yl)ethanone obtained in Reference Synthetic Example[b] 176 was used instead of 1-{4-[(1-benzylpiperidin-4-yl)amino]-1-{[2-(trimethylsilyl)ethoxy]methyl}-1H-pyrrolo[2,3-b]pyridin-5-yl}ethanone to give the compounds of Reference Synthetic Examples[b] 177 and 178. The names, morphologies and yields of the compounds synthesized are shown in Table[b] 12.

TABLE[b] 12

| Rf | Compound Name | Morphology | Yield |
|---|---|---|---|
| 177 | 1-[(1R,2r,3S,5s,7s)-5-hydroxyadamantan-2-yl]-7-{[2-(trimethylsilyl)ethoxy]methyl}-1H-pyrrolo[2,3-h][1,6]naphthyridin-4(7H)-one | Yellow solid | 82% |
| 178 | 1-[(1R,2s,3S,5s,7s)-5-hydroxyadamantan-2-yl]-7-{[2-(trimethylsilyl)ethoxy]methyl}-1H-pyrrolo[2,3-h][1,6]naphthyridin-4(7H)-one | Yellow solid | 83% |

Reference Synthetic Example[b] 179

3-Amino-1,1,1-trifluoro-2-(pyridin-3-yl)propan-2-ol

Isopropylmagnesium chloride-lithium chloride complex-tetrahydrofuran solution (1.3 M, 20.7 mL, 27.0 mmol) was added dropwise to 5-bromo-2-chloropyridine (5.20 g, 27.0 mmol) in tetrahydrofuran (40 mL) under cooling with ice, and the reaction mixture was stirred for 30 minutes and then mixed with ethyl 2,2,2-trifluoroacetate (11.5 g, 81.0 mmol) under cooling with ice and stirred at room temperature for 10 minutes. After addition of 1M hydrochloric acid, the reaction mixture was extracted with ethyl acetate, and the organic layer was dried over anhydrous sodium sulfate and concentrated under reduced pressure to give a yellow oil. The yellow oil was dissolved in nitromethane (30 mL) and stirred with potassium carbonate (3.73 g, 27.0 mmol) at room temperature for 30 minutes. The reaction mixture was added to 1M hydrochloric acid and extracted with ethyl acetate, and the organic layer was dried over anhydrous sodium sulfate and concentrated under reduced pressure. The residue was purified by silica gel column chromatography (hexane/ethyl acetate=3/1 (v/v)) to give a yellow oil. The yellow oil was dissolved in tetrahydrofuran (20 mL), mixed with 10% palladium-carbon (600 mg) and triethylamine (2.60 mL, 18.7 mmol) and then stirred at room temperature for one day under a hydrogen atmosphere. The reaction mixture was filtered, and the filtrate was concentrated under reduced pressure. The residue was purified by silica gel column chromatography (ethyl acetate→ethyl acetate/methanol/triethylamine=9/1/1 (v/v/v)) to give the title compound as a colorless solid (913 mg, yield 31% (4 steps)).

Synthetic Example$^b$ 1

1-Cyclohexyl-4-methyl-1,2,4,7-tetrahydropyrrolo[3',2':5,6]pyrido[4,3-d][1,3]oxazine Crude 1-cyclohexyl-4-methyl-7-{[2-(trimethylsilyl)ethoxy]methyl}-1,2,4,7-tetrahydropyrrolo[3',2':5,6]pyrido[4,3-d][1,3]oxazine (9 mg) obtained in Reference Synthetic Example$^b$ 23 in N,N-dimethylformamide (1 mL) was stirred with ethylenediamine (50 μL, 0.75 mmol) and tetrabutylammonium fluoride (1.0 M tetrahydrofuran solution, 100 μL, 0.100 mmol) at 80° C. for 1 hour and allowed to cool to room temperature. After addition of saturated aqueous sodium chloride, the reaction mixture was extracted with ethyl acetate, and the organic layer was dried over anhydrous sodium sulfate and concentrated under reduced pressure. The residue was purified by silica gel thin layer chromatography (hexane/ethyl acetate=1/2 (v/v)) to give the title compound as a colorless amorphous (1.8 mg, yield 29% (two steps)).

Synthetic Example$^b$ 2

1-Cyclohexyl-1,2,4,7-tetrahydropyrrolo[3',2':5,6]pyrido[4,3-d][1,3]oxazine

1-Cyclohexyl-7-{[2-(trimethylsilyl)ethoxy]methyl}-1,2,4,7-tetrahydropyrrolo[3',2':5,6]pyrido[4,3-d][1,3]oxazine (17 mg, 0.044 mmol) obtained in Reference Synthetic Example$^b$ 11 in N,N-dimethylformamide (1 mL) was stirred with ethylenediamine (50 μL, 0.75 mmol) and tetrabutylammonium fluoride (1.0 M tetrahydrofuran solution, 120 μL, 0.120 mmol) at 80° C. for 2 hours and allowed to cool to room temperature. After addition of saturated aqueous sodium chloride, the reaction mixture was extracted with ethyl acetate, and the organic layer was dried over anhydrous sodium sulfate and concentrated under reduced pressure. The residue was purified by silica gel thin layer chromatography (ethyl acetate/methanol=20/1 (v/v)) to give the title compound as a colorless solid (2.0 mg, yield 18%).

Synthetic Example$^b$ 3

1-Cyclohexyl-1H-pyrrolo[2,3-h][1,6]naphthyridin-4(7H)-one

1-Cyclohexyl-7-{[2-(trimethylsilyl)ethoxy]methyl}-1H-pyrrolo[2,3-h][1,6]naphthyridin-4(7H)-one (9 mg, 0.02 mmol) obtained in Reference Synthetic Example$^b$ 24 in N,N-dimethylformamide (1 mL) was stirred with ethylenediamine (25 μL, 0.37 mmol) and tetrabutylammonium fluoride (1.0 M tetrahydrofuran solution, 70 μL, 0.070 mmol) at 80° C. for 30 minutes and allowed to cool to room temperature. After addition of saturated aqueous sodium chloride, the reaction mixture was extracted with ethyl acetate, and the organic layer was dried over anhydrous sodium sulfate and concentrated under reduced pressure. The residue was purified by silica gel thin layer chromatography (ethyl acetate/methanol=20/1 (v/v)) to give the title compound as a colorless solid (3.3 mg, yield 54%).

Synthetic Example$^b$ 4 rac-1-[(3R,4R)-1-Benzyl-4-methylpiperidin-3-yl]-1H-pyrrolo[2,3-h][1,6]naphthyridin-4(7H)-one rac-1-[(3R,4R)-1-Benzyl-4-methylpiperidin-3-yl]-7-{[2-(trimethylsilyl)ethoxy]methyl}-1H-pyrrolo[2,3-h][1,6]naphthyridin-4(7H)-one (90 mg, 0.18 mmol) obtained in Reference Synthetic Example$^b$ 35 in N,N-dimethylformamide (3 mL) was stirred with ethylenediamine (50 μL, 0.75 mmol) and tetrabutylammonium fluoride (1.0 M tetrahydrofuran solution, 900 μL, 0.900 mmol) at 80° C. for 2 hours and allowed to cool to room temperature. After addition of water, the reaction mixture was extracted with chloroform, and the organic layer was dried over anhydrous sodium sulfate and concentrated under reduced pressure. The residue was mixed with ethyl acetate, and the solid was collected by filtration to give the title compound as a pale orange solid (46.5 mg, yield 70%).

Synthetic Example$^b$ 5 rac-1-[(3R,4R)-4-Methylpiperidin-3-yl]-1H-pyrrolo[2,3-h][1,6]naphthyridin-4(7H)-one hydrochloride rac-1-[(3R,4R)-1-Benzyl-4-methylpiperidin-3-yl]-1H-pyrrolo[2,3-h][1,6]naphthyridin-4(7H)-one (16 mg, 0.043 mmol) and 5% palladium-carbon (15 mg) in methanol (2 mL) was stirred with hydrogen chloride-methanol solution (10 wt %, 20 μL) at 40° C. for 2 hours under a hydrogen atmosphere. The reaction mixture was filtered, and the filtrate was concentrated under reduced pressure to give the title compound as a pale yellow solid (15 mg, quantitative yield).

Synthetic Example$^b$ 6 rac-1-[(3R,4R)-1-(2,3-Difluorobenzyl)-4-methylpiperidin-3-yl]-1H-pyrrolo[2,3-h][1,6]naphthyridin-4(7H)-one (Synthetic Example$^b$ 6a)

rac-1-[(3R,4R)-1,4-Dimethylpiperidin-3-yl]-1H-pyrrolo[2,3-h][1,6]naphthyridin-4(7H)-one (Synthetic Example$^b$ 6b)

rac-1-[(3R,4R)-4-methylpiperidin-3-yl]-1H-pyrrolo[2,3-h][1,6]naphthyridin-4(7H)-one hydrochloride (18 mg, 0.057 mmol) and 2,3-difluorobenzaldehyde (10 mg, 0.070 mmol) in a mixture of methanol (1 mL)/acetic acid (1 mL) was stirred with 2-picoline borane (10 mg, 0.094 mmol) at room temperature for one day. After addition of saturated aqueous sodium hydrogen carbonate and 1 M aqueous sodium hydroxide, the reaction mixture was extracted with chloroform, and the organic layer was dried over anhydrous sodium sulfate and concentrated under reduced pressure. The residue was purified by silica gel thin layer chromatography (chloroform/methanol=20/1 (v/v)) to give rac-1-[(3R,4R)-1-(2,3-difluorobenzyl)-4-methylpiperidin-3-yl]-1H-pyrrolo[2,3-h][1,6]naphthyridin-4(7H)-one (less polar fraction: 6.1 mg, yield 26%) as a pale yellow solid and rac-1-[(3R,4R)-1,4-dimethylpiperidin-3-yl]-1H-pyrrolo[2,3-h][1,6]naphthyridin-4(7H)-one (more polar fraction: 5.9 mg, yield 35%) as a colorless oil.

Synthetic Example[b] 7 rac-3-[(3R,4R)-4-Methyl-3-(4-oxo-4,7-dihydro-1H-pyrrolo[2,3-h][1,6]naphthyridin-1-yl)piperidin-1yl]-3-oxopropanenitrile rac-1-[(3R,4R)-4-Methylpiperidin-3-yl]-1H-pyrrolo[2,3-h][1,6]naphthyridin-4(7H)-one hydrochloride (15 mg, 0.040 mmol) obtained in Synthetic Example[b] 5, 1-(3-dimethylaminopropyl)-3-ethylcarbodiimide hydrochloride (10 mg, 0.052 mmol), N-hydroxybenzotriazole (6 mg, 0.04 mmol), 2-cyanoacetic acid (5 mg, 0.06 mmol) and N,N-diisopropylethylamine (30 μL, 0.017 mmol) in N,N-dimethylformamide (0.5 mL) was stirred at room temperature for 2 hours. After addition of water, the reaction mixture was extracted with chloroform, and the aqueous layer was extracted with a mixture of chloroform/2-propanol. The organic layer was dried over anhydrous sodium sulfate and concentrated under reduced pressure. The residue was purified by silica gel thin layer chromatography (ethyl acetate/methanol=20/1 (v/v)), and the crude product was further purified by silica gel thin layer chromatography (NH-PLC05 plate manufactured by Fuji Silysia Chemical Ltd.: chloroform/methanol=10/1 (v/v)) to give the title compound as a colorless solid (2.5 mg, yield 17%).

Synthetic Example[b] 8 rac-1-[(3R,4R)-1-(2-Cyclopropylacetyl)-4-methylpiperidin-3-yl]-1H-pyrrolo[2,3-h][1,6]naphthyridin-4(7H)-one rac-1-[(3R,4R)-4-Methylpiperidin-3-yl]-1H-pyrrolo[2,3-h][1,6]naphthyridin-4(7H)-one hydrochloride (20 mg, 0.054 mmol) obtained in Synthetic Example[b] 5, 1-(3-dimethylaminopropyl)-3-ethylcarbodiimide hydrochloride (20 mg, 0.10 mmol), 2-cyclopropylacetic acid (10 μL) and N,N-diisopropylethylamine (26 μL, 0.015 mmol) in N,N-dimethylformamide (1 mL) was stirred at room temperature for 6 hours. After addition of saturated aqueous sodium hydrogen carbonate, the reaction mixture was extracted with chloroform, and the organic layer was dried over anhydrous sodium sulfate and concentrated under reduced pressure. The residue was purified by silica gel thin layer chromatography (chloroform/methanol=15/1 (v/v)), and the crude product was further purified by silica gel thin layer chromatography (NH-PLC05 plate manufactured by Fuji Silysia Chemical Ltd.: chloroform/methanol=30/1 (v/v)) to give the title compound as a colorless solid (7.9 mg, yield 40%).

Synthetic Example[b] 9 rac-1-[(3R,4R)-4-Methyl-1-(3,3,3-trifluoropropanoyl)piperidin-3-yl]-1H-pyrrolo[2,3-h][1,6]naphthyridin-4(7H)-one rac-1-[(3R,4R)-4-Methylpiperidin-3-yl]-1H-pyrrolo[2,3-h][1,6]naphthyridin-4(7H)-one hydrochloride (15.6 mg, 0.0489 mmol) obtained in Synthetic Example[b] 5, 1-(3-dimethylaminopropyl)-3-ethylcarbodiimide hydrochloride (12.5 mg, 0.0978 mmol), 3,3,3-trifluoropropionic acid (13 μL, 0.098 mmol) and N,N-diisopropylethylamine (26 μL, 0.015 mmol) in N,N-dimethylformamide (1 mL) was stirred at room temperature for one day. After addition of saturated aqueous sodium hydrogen carbonate, the reaction mixture was extracted with ethyl acetate, and the organic layer was dried over anhydrous sodium sulfate and concentrated under reduced pressure. The residue was purified by silica gel thin layer chromatography (chloroform/methanol=4/1 (v/v)) to give the title compound as a colorless solid (12.2 mg, yield 64%).

Synthetic Example[b] 10 rac-1-[(3R,4R)-1-(Isobutylsulfonyl)-4-methylpiperidin-3-yl]-1H-pyrrolo[2,3-h][1,6]naphthyridin-4(7H)-one rac-1-[(3R,4R)-1-(Isobutylsulfonyl)-4-methylpiperidin-3-yl]-7-{[2-(trimethylsilyl)ethoxy]methyl}-1H-pyrrolo[2,3-h][1,6]naphthyridin-4(7H)-one (18 mg, 0.034 mmol) obtained in Reference Synthetic Example[b] 37 in dichloromethane (1 mL) was stirred with trifluoroacetic acid (1 mL) at room temperature for 3 hours. After addition of saturated aqueous sodium hydrogen carbonate, the reaction mixture was extracted with chloroform, and the organic layer was dried over anhydrous sodium sulfate and concentrated under reduced pressure. The residue was dissolved in a mixture of dichloromethane (1 mL) and methanol (1 mL) and stirred with ethylenediamine (100 μL, 1.50 mmol) and 1 M aqueous sodium hydroxide (100 μL, 0.100 mmol) at room temperature for one day. After addition of water, the reaction mixture was extracted with chloroform, and the organic layer was dried over anhydrous sodium sulfate and concentrated under reduced pressure. The residue was purified by silica gel thin layer chromatography (ethyl acetate/methanol=20/1 (v/v)) to give the title compound as a colorless solid (8.2 mg, yield 60%).

Synthetic Example[b] 11 rac-1-[(3R,4R)-4-Methyl-1-(2,2,2-trifluoroethylsulfonyl)piperidin-3-yl]-1H-pyrrolo[2,3-h][1,6]naphthyridin-4(7H)-one rac-1-[(3R,4R)-4-Methylpiperidin-3-yl]-1H-pyrrolo[2,3-h][1,6]naphthyridin-4(7H)-one hydrochloride (16 mg, 0.050 mmol) obtained in Synthetic Example[b] 5 in a mixture of dichloromethane (1 mL) and N,N-dimethylformamide (100 μL) was mixed with N,N-diisopropylethylamine (30 μL, 0.17 mmol) and 2,2,2-trifluoroethanesulfonyl chloride (20 mg, 0.11 mmol) under cooling with ice and stirred at room temperature for one day. After addition of saturated aqueous sodium hydrogen carbonate, the reaction mixture was extracted with chloroform, and the organic layer was dried over anhydrous sodium sulfate and concentrated under reduced pressure. The residue was purified by silica gel thin layer chromatography (ethyl acetate/methanol=10/1 (v/v)) to give the title compound as a colorless solid (2.5 mg, yield 12%).

Synthetic Example[b] 12

1-Cyclohexyl-1,4-dihydropyrrolo[3',2':5,6]pyrido[3,4-b][1,4]thiazine-4,4(7H)-dione Crude 1-cyclohexyl-7-{[2-(trimethylsilyl)ethoxy]methyl}-1,4-dihydropyrrolo[3',2':5,6]pyrido[3,4-b][1,4]thiazine-4,4(7H)-dione (8.5 mg) obtained in Reference Synthetic Example[b] 28 in dichloromethane (1 mL) was stirred with trifluoroacetic acid (1 mL) at room temperature for 3 hours. After addition of saturated aqueous sodium hydrogen carbonate, the reaction mixture was extracted with chloroform, and the organic layer was dried over anhydrous sodium sulfate and concentrated under reduced pressure. The resulting residue was dissolved in methanol (1 mL) and stirred with ethylenediamine (20 μL, 0.30 mmol) and 1 M aqueous sodium hydroxide (20 μL, 0.020 mmol) at room temperature for 3 hours. The precipitated solid was collected by filtration to give the title compound as a colorless solid (1.7 mg, yield 39% (two steps)).

Synthetic Example[b] 13

1-Cyclohexyl-1H-pyrrolo[3',2':5,6]pyrido[4,3-d]pyrimidin-4(7H)-one

1-Cyclohexyl-7-{[2-(trimethylsilyl)ethoxy]methyl}-1H-pyrrolo[3',2':5,6]pyrido[4,3-d]pyrimidin-4(7H)-one (9 mg, 0.02 mmol) obtained in Reference Synthetic Example[b] 32 in dichloromethane (2 mL) was stirred with trifluoroacetic acid (1 mL) at room temperature for 2 hours. After addition of saturated aqueous sodium hydrogen carbonate, the reaction mixture was extracted with chloroform, and the organic layer was dried over anhydrous sodium sulfate and concentrated under reduced pressure. The resulting residue was dissolved in methanol (2 mL) and dichloromethane (1 mL) and stirred with ethylenediamine (50 μL, 0.75 mmol) and 1 M aqueous sodium hydroxide (50 μL, 0.050 mmol) at room temperature for 3 days. After addition of water, the reaction mixture was extracted with chloroform, and the organic layer was dried over anhydrous sodium sulfate and concentrated under reduced pressure. The residue was purified by silica gel thin layer chromatography (chloroform/methanol=30/1 (v/v)) to give the title compound as a colorless solid (2.1 mg, yield 35%).

Synthetic Example[b] 14 rac-1-[(3R,4R)-1-Benzyl-4-methylpiperidin-3-yl]-1,2,4,7-tetrahydropyrrolo[3',2':5,6]pyrido[4,3-d][1,3]oxazine rac-1-[(3R,4R)-1-Benzyl-4-methylpiperidin-3-yl]-7-{[2-(trimethylsilyl)ethoxy]methyl}-1,2,4,7-tetrahydropyrrolo[3',2':5,6]pyrido[4,3-d][1,3]oxazine (64.6 mg, 0.131 mmol) obtained in Reference Synthetic Example[b] 41 in dichloromethane (2 mL) was stirred with trifluoroacetic acid (1 mL) at room temperature for 2 hours, and the reaction mixture was concentrated under reduced pressure. The resulting residue was stirred with dichloromethane (4 mL), methanol (2 mL), ethylenediamine (200 μL, 3.00 mmol) and 1 M aqueous sodium hydroxide (2 mL, 2 mmol) at room temperature for 1 hour. The reaction solution was concentrated under reduced pressure, and after addition of water, extracted with chloroform. The organic layer was dried over anhydrous sodium sulfate and concentrated under reduced pressure. The residue was purified by silica gel thin layer chromatography (chloroform/methanol=10/1 (v/v)) to give the title compound as a pale yellow amorphous (28.2 mg, yield 59%).

Synthetic Example[b] 15 rac-1-[(3R,4R)-4-Methylpiperidin-3-yl]-1,2,4,7-tetrahydropyrrolo[3',2':5,6]pyrido[4,3-d][1,3]oxazine rac-1-[(3R,4R)-1-Benzyl-4-methylpiperidin-3-yl]-1,2,4,7-tetrahydropyrrolo[3',2':5,6]pyrido[4,3-d][1,3]oxazine (28.2 mg, 0.0777 mmol) in ethanol was stirred with 5% palladium-carbon (30 mg) and concentrated hydrochloric acid (2 drops) at 50° C. for 2 hours under a hydrogen atmosphere. The reaction mixture was allowed to cool to room temperature and filtered, and the filtrate was concentrated under reduced pressure to give the title compound (21.2 mg, yield 100%).

Synthetic Example[b] 16 rac-3-[(3R,4R)-4-Methyl-3-(pyrrolo[3',2':5,6]pyrido[4,3-d][1,3]oxazin-1(2H,4H,7H)-yl)piperidin-1-yl]-3-oxopropanenitrile rac-1-[(3R,4R)-4-Methylpiperidin-3-yl]-1,2,4,7-tetrahydropyrrolo[3',2':5,6]pyrido[4,3-d][1,3]oxazine (21.2 mg, 0.0777 mmol) in N,N-dimethylformamide was stirred with cyanoacetic acid (15 mg, 0.18 mmol), O-(7-azabenzotriazol-1-yl)-N,N,N',N'-tetramethyluronium hexafluorophosphate (67 mg, 0.18 mmol), N,N-diisopropylethylamine (44.9 μL, 0.264 mmol) at room temperature for one day. After addition of water, the reaction mixture was extracted with ethyl acetate, and the organic layer was dried over anhydrous magnesium sulfate and concentrated under reduced pressure. The resulting residue was purified by silica gel column chromatography (Hi Flash column amino type manufactured by Yamazen Corporation: chloroform/methanol=20/1 (v/v)) to give the title compound as a yellow oil (3 mg, yield 10%).

Synthetic Example[b] 17

1-Cyclohexyl-3,4-dihydro-1H-pyrrolo[3',2':5,6]pyrido[4,3-d]pyrimidin-2(7H)-one 1-Cyclohexyl-7-{[2-(trimethylsilyl)ethoxy]methyl}-3,4-dihydro-1H-pyrrolo[3',2':5,6]pyrido[4,3-d]pyrimidin-2(7H)-one (46.6 mg, 0.116 mmol) obtained in Reference Synthetic Example[b] 13 in dichloromethane (3 mL) was stirred with trifluoroacetic acid (1 mL) at room temperature for 2 hours. The reaction mixture was concentrated under reduced pressure, and the resulting residue was stirred with dichloromethane (2 mL), methanol (1 mL), ethylenediamine (200 μL, 3.00 mmol) and 1 M aqueous sodium hydroxide (1 mL, 1 mmol) for one day. The reaction mixture was concentrated under reduced pressure, and after addition of water, extracted with chloroform, and the organic layer was dried over anhydrous magnesium sulfate and concentrated under reduced pressure to give the title compound as a colorless solid (22.2 mg, yield 70%).

Synthetic Example[b] 18

1-Cyclohexyl-1H-pyrrolo[3',2':5,6]pyrido[4,3-d]pyrimidin-2(7H)-one

1-Cyclohexyl-3,4-dihydro-1H-pyrrolo[3',2':5,6]pyrido[4,3-d]pyrimidin-2(7H)-one (18 mg, 0.066 mmol) in chloroform (2 mL) was stirred with manganese dioxide (100 mg, 1.15 mmol) at 50° C. for 5 hours. The reaction mixture was filtered, and the filtrate was purified by silica gel column chromatography (Hi Flash column amino type manufactured by Yamazen Corporation: chloroform/methanol=10/1 (v/v)) to give the title compound as a colorless solid (0.58 mg, yield 3.2%).

Synthetic Example[b] 19

1-Cyclohexyl-1,4-dihydro-7H-pyrrolo[3',2':5,6]pyrido[3,4-e]pyrimidine

1-Cyclohexyl-1,4-dihydro-7-{[2-(trimethylsilyl)ethoxy]methyl}-pyrrolo[3',2':5,6]pyrido[3,4-e]pyrimidine (48.8 mg, 0.127 mmol) obtained in Reference Synthetic Example[b] 14 in dichloromethane (2 mL) was stirred with trifluoroacetic acid (1 mL) for one day. The reaction mixture was concentrated under reduced pressure and stirred with dichloromethane (2 mL), methanol (1 mL), ethylenediamine (300 μL, 4.49 mmol) and 1 M aqueous sodium hydroxide (1 mL, 1 mmol) for one day. The reaction mixture was concentrated under reduced pressure and extracted with chloroform, and the organic layer was dried over anhydrous magnesium sulfate and concentrated under reduced pressure. The residue was purified by silica gel column chromatography (Hi Flash column amino type manufactured by Yamazen Corporation: chloroform/methanol=10/1 (v/v)) to give the title compound as a colorless solid (11 mg, yield 34%).

Synthetic Example[b] 20

9-Cyclohexyl-3H-imidazo[4,5-h][1,6]naphthyridin-6(9H)-one

9-Cyclohexyl-3-{[2-(trimethylsilyl)ethoxy]methyl}-3H-imidazo[4,5-h][1,6]naphthyridin-6(9H)-one (57.5 mg, 0.144 mmol) obtained in Reference Synthetic Example[b] 48 in dichloromethane (2 mL) was stirred with trifluoroacetic acid (2 mL) at room temperature for 1 hour. The reaction mixture was concentrated under reduced pressure, and the resulting residue was stirred with dichloromethane (4 mL), methanol (1 mL), ethylenediamine (200 μL, 3.00 mmol) and 1 M aqueous sodium hydroxide (1 mL, 1 mmol) at room temperature for 2 hours. The reaction mixture was concentrated under reduced pressure, and the resulting residue was purified by silica gel chromatography (chloroform/methanol=10/1 (v/v)) to give the title compound as a pale yellow solid (23.0 mg, yield 59%).

Synthetic Examples[b] 21 to 47

The reactions in Synthetic Example[b] 10 were carried out in substantially the same manners except that the compounds obtained in Reference Synthetic Examples[b] 51, 54, 59 to 71, 73 or 75 to 85 were used instead of rac-1-[(3R,4R)-1-(isobutylsulfonyl)-4-methylpiperidin-3-yl]-7-{[2-(trimethylsilyl)ethoxy]methyl}-1H-pyrrolo[2,3-h][1,6]naphthyridin-4(7H)-one to give the compounds of Synthetic Examples[b] 21 to 47. The names, morphologies and yields of the compounds synthesized are shown in Tables[b] 13 to 15.

TABLE[b] 13

| Ex | Compound Name | Morphology | Yield |
|---|---|---|---|
| 21 | rac-1-[(3R,4R)-1-benzyl-4-methylpiperidin 3-yl]-9-bromo-1H-pyrrolo[2,3-h][1,6]naphthyridin-4(7H)-one | colorless oil | 34% |
| 22 | rac-1-[(3R,4R)-1-benzyl-4-methylpiperidin-3-yl]-9-chloro-1H-pyrrolo[2,3-h][1,6]naphthyridin-4(7H)-one | colorless oil | 69% |
| 23 | rac-1-[(3R,4R)-1-benzyl-4-methylpiperidin-3-yl]-3-methyl-1H-pyrrolo[2,3-h][1,6]naphthyridin-4(7H)-one | colorless oil | 60% |
| 24 | rac-1-[(3R,4R)-1-benzyl-4-methylpiperidin-3-yl]-3-bromo-1H-pyrrolo[2,3-h][1,6]naphthyridin-4(7H)-one | colorless oil | 2.3% (two steps) |
| 25 | rac-2-{[(3R,4R)-4-methyl-3-(4-oxo-4,7-dihydro-1H-pyrrolo[2,3-h][1,6]naphthyridin-1-yl)piperidin-1-yl]sulfonyl}benzonitrile | colorless solid | 44% |
| 26 | rac-3-{[(3R,4R)-4-methyl-3-(4-oxo-4,7-dihydro-1H-pyrrolo[2,3-h][1,6]naphthyridin-1-yl)piperidin-1-yl]sulfonyl}benzonitrile | colorless solid | 52% |
| 27 | rac-(3R,4R)-ethyl 4-methyl-3-(4-oxo-4,7-dihydro-1H-pyrrolo[2,3-h][1,6]naphthyridin-1-yl)piperidine-1-carboxylate | colorless solid | 53% |
| 28 | rac-(3R,4R)-4-methyl-3-(4-oxo-4,7-dihydro-1H-pyrrolo[2,3-h][1,6]naphthyridin-1-yl)-N-[2-(trifluoromethyl)phenyl]piperidine-1-carboxamide | colorless solid | 75% |
| 29 | rac-(3R,4R)-4-methyl-3-(4-oxo-4,7-dihydro-1H-pyrrolo[2,3-h][1,6]naphthyridin-1-yl)-N-[3-(trifluoromethyl)phenyl]piperidine-1-carboxamide | colorless solid | 36% |
| 30 | rac-1-{(3R,4R)-4-methyl-1-[2-(trifluoromethyl)benzoyl]piperidin-3-yl}-1H-pyrrolo[2,3-h][1,6]naphthyridin-4(7H)-one | colorless solid | 37% |
| 31 | rac-1-{(3R,4R)-4-methyl-1-[3-(trifluoromethyl)benzoyl]piperidin-3-yl}-1H-pyrrolo[2,3-h][1,6]naphthyridin-4(7H)-one | colorless solid | 66% |
| 32 | rac-1-{(3R,4R)-1-[2-(4-fluorophenyl)acetyl]-4-methylpiperidin-3-yl}-1H-pyrrolo[2,3-h][1,6]naphthyridin-4(7H)-one | colorless solid | 79% |

TABLE[b] 13-continued

| Ex | Compound Name | Morphology | Yield |
|---|---|---|---|
| 33 | rac-1-((3R,4R)-4-methyl-1-{[3-(trifluoromethyl)phenyl]sulfonyl}piperidin-3-yl)-1H-pyrrolo[2,3-h][1,6]naphthyridin-4(7H)-one | colorless solid | 57% |

TABLE[b] 14

| Ex | Compound Name | Morphology | Yield |
|---|---|---|---|
| 34 | rac-1-{(3R,4R)-4-methyl-1-[4-(trifluoromethyl)benzoyl]piperidin-3-yl}-1H-pyrrolo[2,3-h][1,6]naphthyridin-4(7H)-one | colorless solid | 70% |
| 35 | rac-(3R,4R)-benzyl 4-methyl-3-(4-oxo-4,7-dihydro-1H-pyrrolo[2,3-h][1,6]naphthyridin-1-yl)piperidine-1-carboxylate | colorless oil | 56% |
| 36 | rac-(3R,4R)-4-methyl-3-(4-oxo-4,7-dihydro-1H-pyrrolo[2,3-h][1,6]naphthyridin-1-yl)-N-(1,3,4-thiadiazol-2-yl)piperidine-1-carboxamide | pale yellow solid | 81% |
| 37 | rac-(3R,4R)-4-methyl-N-(3-methylisothiazol-5-yl)-3-(4-oxo-4,7-dihydro-1H-pyrrolo[2,3-h][1,6]naphthyridin-1-yl)piperidine-1-carboxamide | pale yellow solid | 90% |
| 38 | rac-1-[(3R,4R)-1-(cyclopentanecarbonyl)-4-methylpiperidin-3-yl]-1H-pyrrolo[2,3-h][1,6]naphthyridin-4(7H)-one | pale yellow solid | 76% |
| 39 | rac-1-{(3R,4R)-4-methyl-1-[3-(trifluoromethyl)benzyl]piperidin-3-yl}-1H-pyrrolo[2,3-h][1,6]naphthyridin-4(7H)-one | pale yellow solid | 42% |
| 40 | rac-1-{(3R,4R)-4-methyl-1-[4-(trifluoromethyl)benzyl]piperidin-3-yl}-1H-pyrrolo[2,3-h][1,6]naphthyridin-4(7H)-one | yellow solid | 85% |
| 41 | rac-1-{(3R,4R)-4-methyl-1-[2-(trifluoromethyl)benzyl]piperidin-3-yl}-1H-pyrrolo[2,3-h][1,6]naphthyridin-4(7H)-one | yellow solid | 57% (two steps) |
| 42 | rac-3-{[(3R,4R)-4-methyl-3-(4-oxo-4,7-dihydro-1H-pyrrolo[2,3-h][1,6]naphthyridin-1-yl)piperidin-1-yl]methyl}benzonitrile | pale yellow solid | 88% |
| 43 | rac-2-{[(3R,4R)-4-methyl-3-(4-oxo-4,7-dihydro-1H-pyrrolo[2,3-h][1,6]naphthyridin-1-yl)piperidin-1-yl]methyl}benzonitrile | pale yellow solid | 88% |
| 44 | rac-4-{[(3R,4R)-4-methyl-3-(4-oxo-4,7-dihydro-1H-pyrrolo[2,3-h][1,6]naphthyridin-1-yl)piperidin-1-yl]methyl}benzonitrile | yellow solid | 41% |
| 45 | rac-(3R,4R)-tert-butyl 4-methyl-3-(4-oxo-4,7-dihydro-1H-pyrrolo[2,3-h][1,6]naphthyridin-1-yl)piperidine-1-carboxylate | colorless solid | 53% |

TABLE[b] 15

| Ex | Compound Name | Morphology | Yield |
|---|---|---|---|
| 46 | rac-1-[(3R,4R)-1-(4-fluorophenethyl)-4-methylpiperidin-3-yl]-1H-pyrrolo[2,3-h][1,6]naphthyridin-4(7H)-one | colorless oil | 12% (two steps) |
| 47 | rac-1-[(3R,4R)-1-cyclopentyl-4-methyl-piperidin-3-yl]-1H-pyrrolo[2,3-h][1,6]naphthyrdin-4(7H)-one | colorless solid | 55% (two steps) |

Synthetic Example[b] 48

1-{1-[4-(tert-Butyl)cyclohexanecarbonyl]-4-methyl-piperidin-3-yl}-1H-pyrrolo[2,3-h][1,6]naphthyridin-4(7H)-one The reactions in Synthetic Example[b] 10 were carried out in substantially the same manners except that Reference Synthetic Examples[b] 86a or 86b obtained in Reference Synthetic Example[b] 86 were used instead of rac-1-[(3R,4R)-1-(isobutylsulfonyl)-4-methylpiperidin-3-yl]-7-{[2-(trimethylsilyl)ethoxy]methyl}-1H-pyrrolo[2,3-h][1,6]naphthyridin-4(7H)-one to give the two isomers of the title compound, Synthetic Example[b] 48a (colorless amorphous, 5.0 mg, 71%) or Synthetic Example[b] 48 b (colorless amorphous, 4.1 mg, yield 56%).

Synthetic Examples[b] 49 to 53

The reactions in Synthetic Example[b] 10 were carried out in substantially the same manners except that the compounds obtained in Reference Synthetic Examples[b] 90 and 92 to 95 were used instead of rac-1-[(3R,4R)-1-(isobutylsulfonyl)-4-methylpiperidin-3-yl]-7-{[2-(trimethylsilyl)ethoxy]methyl}-1H-pyrrolo[2,3-h][1,6]naphthyridin-4(7H)-one to give the compounds of Synthetic Examples[b] 49 to 53. The names, morphologies and yields of the compounds synthesized are shown in Table[b] 16.

TABLE[b] 16

| Ex | Compound Name | Morphology | Yield |
|---|---|---|---|
| 49 | 1-(1-benzylpiperidin-4-yl)-1H-pyrrolo[3',2':5,6]pyrido[4,3-d]pyrimidine-2,4(3H,7H)-dione | colorless solid | 40% |
| 50 | 4-{[4-(2,4-dioxo-2,3,4,7-tetrahydro-1H-pyrrolo[3',2':5,6]pyrido[4,3-d]pyrimidin-1-yl)piperidin-1-yl]methyl}-benzonitrile | colorless solid | 69% |
| 51 | 1-{1-[(5-chlorothiophen-2-yl)methyl]piperidin-4-yl}-1H-pyrrolo[3',2':5,6]pyrido[4,3-d]pyrimidine-2,4(3H,7H)-dione | colorless solid | 59% |
| 52 | 1-{1-[4-(trifluoromethyl)benzyl]piperidin-4-yl}-1H-pyrrolo[3',2':5,6]pyrido[4,3-d]pyrimidine-2,4(3H,7H)-dione | colorless solid | 80% |
| 53 | 1-cyclohexyl-1H-pyrrolo[3',2':5,6]pyrido[4,3-d]pyrimidine-2,4(3H,7H)-dione | colorless solid | 21% |

Synthetic Examples[b] 54 to 58

The reactions in Synthetic Example[b] 10 were carried out in substantially the same manners except that the compounds obtained in Reference Synthetic Examples[b] 98 and 100 to 103 were used instead of rac-1-[(3R,4R)-1-(isobutylsulfonyl)-4-methylpiperidin-3-yl]-7-{[2-(trimethylsilyl)ethoxy]methyl}-1H-pyrrolo[2,3-h][1,6]naphthyridin-4(7H)-one to give the compounds of Synthetic Examples[b] 54 to 58. The names, morphologies and yields of the compounds synthesized are shown in Table[b] 17.

TABLE[b] 17

| Ex | Compound Name | Morphology | Yield |
|---|---|---|---|
| 54 | 1-(1-benzylpiperidin-4-yl)-1H-pyrrolo[2,3-h][1,6]naphthyridin-4(7H)-one | colorless solid | 53% |
| 55 | 1-{1-[(5-chlorothiophen-2-yl)methyl]piperidin-4-yl}-1H-pyrrolo[2,3-h][1,6]naphthyridin-4(7H)-one | pale yellow solid | 95% |
| 56 | 1-{1-[4-(trifluoromethyl)benzyl]piperidin-4-yl}-1H-pyrrolo[2,3-h][1,6]naphthyridin-4(7H)-one | yellow solid | 98% |
| 57 | 4-{[4-(4-oxo-4,7-dihydro-1H-pyrrolo[2,3-h][1,6]naphthyridin-1-yl)piperidin-1-yl]methyl}benzonitrile | yellow solid | 69% |
| 58 | 3-fluoro-4-{[4-(4-oxo-4,7-dihydro-1H-pyrrolo[2,3-h][1,6]naphthyridin-1-yl)piperidin-1-yl]methyl}benzonitrile | yellow solid | 98% |

Synthetic Examples[b] 59 to 67

The reactions in Synthetic Example[b] 10 were carried out in substantially the same manners except that the compounds obtained in Reference Synthetic Examples[b] 108 and 110 to 116 and 121 were used instead of rac-1-[(3R,4R)-1-(isobutylsulfonyl)-4-methylpiperidin-3-yl]-7-{[2-(trimethylsilyl)ethoxy]methyl}-1H-pyrrolo[2,3-h][1,6]naphthyridin-4(7H)-one to give the compounds of Synthetic Examples[b] 59 to 67. The names, morphologies and yields of the compounds synthesized are shown in Table[b] 18.

TABLE[b] 18

| Ex | Compound Name | Morphology | Yield |
|---|---|---|---|
| 59 | 1-(1-benzylpiperidin-4-yl)-3,4-dihydro-1H-pyrrolo[3',2':5,6]pyrido[4,3-d]pyrimidin-2(7H)-one | colorless solid | 99% |
| 60 | 1-[1-(benzylsulfonyl)piperidin-4-yl]-3,4-dihydro-1H-pyrrolo[3',2':5,6]pyrido[4,3-d]pyrimidin-2(7H)-one | colorless solid | 47% |
| 61 | 1-[1-(pyridin-3-ylmethyl)piperidin-4-yl]-3,4-dihydro-1H-pyrrolo[3',2':5,6]pyrido[4,3-d]pyrimidin-2(7H)-one | colorless solid | 43% |
| 62 | 4-{[4-(2-oxo-2,3,4,7-tetrahydro-1H-pyrrolo[3',2':5,6]pyrido[4,3-d]pyrimidin-1-yl)piperidin-1-yl]methyl}benzonitrile | brown solid | 72% |
| 63 | 1-{1-[4-(trifluoromethyl)benzyl]piperidin-4-yl}-3,4-dihydro-1H-pyrrolo[3',2':5,6]pyrido[4,3-d]pyrimidin-2(7H)-one | brown solid | 77% |
| 64 | 4-(2-oxo-2,3,4,7-tetrahydro-1H-pyrrolo[3',2':5,6]pyrido[4,3-d]primidin-1-yl)-N-(1,3,4-thiadiazol-2-yl)piperidine-1-carboxamide | brown solid | 86% |
| 65 | 1-[1-(3,3,3-trifluoropropanoyl)piperidin-4-yl]-3,4-dihydro-1H-pyrrolo[3',2':5,6]pyrido[4,3-d]pyrimidin-2(7H)-one | colorless solid | 32% |
| 66 | 1-[1-(thiazol-5-ylmethyl)piperidin-4-yl]-3,4-dihydro-1H-pyrrolo[3',2':5,6]pyrido[4,3-d]pyrimidin-2(7H)-one | colorless solid | 92% |
| 67 | rac-1-[(3R,4R)-1-benzyl-4-methylpiperidin-3-yl]-3,4-dihydro-1H-pyrrolo[3',2':5,6]pyrido[4,3-d]pyrimidin-2(7H)-one | brown solid | 56% |

Synthetic Example[b] 68

1-(Piperidin-4-yl)-3,4-dihydro-1H-pyrrolo[3',2':5,6]pyrido[4,3-d]pyrimidin-2(7H)-one 1-(1-Benzylpiperidin-4-yl)-3,4-dihydro-1H-pyrrolo[3',2':5,6]pyrido[4,3-d]pyrimidin-2(7H)-one (25.6 mg, 0.0708 mmol) obtained in Synthetic Example[b] 59 and 5% palladium-carbon (30 mg) in ethanol was stirred with 10 wt % hydrogen chloride-methanol (2 drops) at 50° C. for 2 hours under a hydrogen atmosphere. The reaction mixture was filtered, and the filtrate was concentrated under reduced pressure to give the title compound as a colorless solid (9 mg, yield 46%).

Synthetic Examples[b] 69 to 85

The reactions in Synthetic Example[b] 10 were carried out in substantially the same manners except that the compounds obtained in Reference Synthetic Examples[b] 124 and 128 to 144 were used instead of rac-1-[(3R,4R)-1-(isobutylsulfonyl)-4-methylpiperidin-3-yl]-7-{[2-(trimethylsilyl)ethoxy]methyl}-1H-pyrrolo[2,3-h][1,6]naphthyridin-4(7H)-one to give the compounds of Synthetic Examples[b] 69 to 85. The names, morphologies and yields of the compounds synthesized are shown in Tables[b] 19 and 20.

TABLE[b] 19

| Ex | Compound Name | Morphology | Yield |
|---|---|---|---|
| 69 | 1-(trans-4-(hydroxymethyl)cyclohexyl)-1H-pyrrolo[2,3-h][1,6]naphthyridin-4(7H)-one | pale yellow solid | 38% |
| 70 | 1-(trans-4-methoxycyclohexyl)-1H-pyrrolo[2,3-h][1,6]naphthyridin-4(7H)-one | brown solid | 42% |
| 71 | 1-(1-{[5-(trifluoromethyl)furan-2-yl]methyl}piperidin-4-yl)-1H-pyrrolo[2,3-h][1,6]naphthyridin-4(7H)-one | yellow solid | quant |
| 72 | 1-{1-[(5-nitrofuran-2-yl)methyl]piperidin-4-yl}-1H-pyrrolo[2,3-h][1,6]naphthyridin-4(7H)-one | Yellow oil | 33% |
| 73 | ethyl 5-{[4-(4-oxo-4,7-dihydro-1H-pyrrolo[2,3-h][1,6]naphthyridin-1-yl)piperidin-1-yl]methyl}furan-2-carboxylate | yellow amorphous | quant |
| 74 | 1-[1-(3,4-difluorobenzyl)piperidin-4-yl]-1H-pyrrolo[2,3-h][1,6]naphthyridin-4(7H)-one | Yellow oil | 80% |
| 75 | 1-[1-(3,4-dichlorobenzyl)piperidin-4-yl]-1H-pyrrolo[2,3-h][1,6]naphthyridin-4(7H)-one | yellow solid | quant |
| 76 | 1-(1-{[6-(trifluoromethyl)pyridin-3-yl]methyl}piperidin-4-yl)-1H-pyrrolo[2,3-h][1,6]naphthyridin-4(7H)-one | yellow solid | quant |
| 77 | 1-{1-[(2-chlorothiazol-5-yl)methyl]piperidin-4-yl}-1H-pyrrolo[2,3-h][1,6]naphthyridin-4(7H)-one | Yellow oil | 69% |
| 78 | 1-{1-[4-fluoro-3-(trifluoromethyl)benzyl]-piperidin-4-yl}-1H-pyrrolo[2,3-h][1,6]naphthyridin-4(7H)-one | yellow solid | 96% |
| 79 | 1-{1-[(5-nitrothiophen-3-yl)methyl]piperidin-4-yl}-1H-pyrrolo[2,3-h][1,6]naphthyridin-4(7H)-one | brown solid | 27% |
| 80 | 1-{1-[(5-bromofuran-2-yl)methyl]piperidin-4-yl}-1H-pyrrolo[2,3-h][1,6]naphthyridin-4(7H)-one | yellow solid | quant |
| 81 | 1-{1-[(5-bromothiophen-2-yl)methyl]piperidin-4-yl}-1H-pyrrolo[2,3-h][1,6]naphthyridin-4(7H)-one | yellow solid | quant |
| 82 | 1-{1-[(4-bromothiophen-2-yl)methyl]piperidin-4-yl}-1H-pyrrolo[2,3-h][1,6]naphthyridin-4(7H)-one | yellow solid | quant |

TABLE[b] 20

| Ex | Compound Name | Morphology | Yield |
|---|---|---|---|
| 83 | 1-{1-[(2-bromothiazol-5-yl)methyl]piperidin-4-yl}-1H-pyrrolo[2,3-h][1,6]naphthyridin-4(7H)-one | yellow solid | quant |
| 84 | 1-{1-[(2,2-difluorobenzo[d][1,3]dioxol-5-yl)methyl]piperidin-4-yl}-1H-pyrrolo[2,3-h][1,6]naphthyridin-4(7H)-one | yellow solid | quant |
| 85 | 1-{1-[(1H-indol-5-yl)methyl]piperidin-4-yl}-1H-pyrrolo[2,3-h][1,6]naphthyridin-4(7H)-one | yellow solid | 38% |

Synthetic Example[b] 86

1-{1-[(2-Methylthiazol-4-yl)methyl]piperidin-4-yl}-1H-pyrrolo[2,3-h][1,6]naphthyridin-4(7H)-one 1-(Piperidin-4-yl)-7-{[2-(trimethylsilyl)ethoxy]methyl}-1H-pyrrolo[2,3-h][1,6]naphthyridin-4(7H)-one (30 mg, 0.075 mmol) obtained in Reference Synthetic Example[b] 99 in dichloromethane was stirred with 4-(chloromethyl)-2-methylthiazole hydrochloride (13.3 mg, 0.0901 mmol) and triethylamine (16 μL, 0.11 mmol) at 40° C. for one day. After addition of water, the reaction mixture was extracted with chloroform, and the organic layer was dried over anhydrous magnesium sulfate and concentrated under reduced pressure. The residue was roughly purified by silica gel column chromatography (chloroform/methanol=9/1 (v/v)), and the resulting crude product was dissolved in dichloromethane (2 mL) and stirred with trifluoroacetic acid (1 mL) at room temperature for 1 hour. The reaction mixture was concentrated under reduced pressure, and the residue was dissolved in a mixture of dichloromethane (2 mL) and methanol (1 mL) and stirred with ethylenediamine (200 μL) and 1 M aqueous sodium hydroxide (1 mL) for one day. After addition of water, the reaction mixture was extracted with chloroform, and the organic layer was dried over anhydrous magnesium sulfate and concentrated under reduced pressure to give the title compound as a brown oil (6.3 mg, yield 22%).

Synthetic Example[b] 87

1-[1-(5-Chlorothiophene-2-carbonyl)piperidin-4-yl]-1H-pyrrolo[2,3-h][1,6]naphthyridin-4(7H)-one 1-[1-(5-Chlorothiophene-2-carbonyl)piperidin-4-yl]-7-{[2-(trimethylsilyl)ethoxy]methyl}-1H-pyrrolo[2,3-h][1,6]naphthyridin-4(7H)-one obtained in Reference Synthetic Example[b] 144 in dichloromethane (2 mL) was stirred with trifluoroacetic acid (1 mL) at room temperature for 1 hour. The reaction mixture was concentrated under reduced pressure, and the residue was dissolved in a mixture of dichloromethane (2 mL) and methanol (1 mL) and stirred with ethylenediamine (200 μL) and 1 M aqueous sodium hydroxide (1 mL) for one day. The precipitated solid was collected by filtration to give the title compound as a colorless solid (22.8 mg, yield 73%).

Synthetic Examples[b] 88 to 107

The reactions in Synthetic Example[b] 14 were carried out in substantially the same manners except that the compounds obtained in Reference Synthetic Examples[b] 145 to 157, 167, 169, 170, 173, 174, 177 or 178 were used instead of rac-1-[(3R,4R)-1-Benzyl-4-methylpiperidin-3-yl]-7-{[2-(trimethylsilyl)ethoxy]methyl}-1,2,4,7-tetrahydropyrrolo[3',2':5,6]pyrido[4,3-d][1,3]oxazine to give the compounds of Synthetic Examples[b] 88 to 107. The names, morphologies and yields of the compounds synthesized are shown in Tables[b] 21 and 22.

TABLE[b] 21

| Ex | Compound Name | Morphology | Yield |
|---|---|---|---|
| 88 | 1-[1-(2-aminoethyl)piperidin-4-yl]-1H-pyrrolo[3',2':5,6]pyrido[4,3-d]pyrimidine-2,4(3H,7H)-dione | brown solid | 90% |
| 89 | 1-{1-[(5-bromothiophen-2-yl)methyl]piperidin-4-yl}-1H-pyrrolo[3',2':5',6]pyrido[4,3-d]pyrimidine-2,4(3H,7H)-dione | Colorless solid | 77% |
| 90 | 1-{1-[2-(tetrahydro-2H-thiopyran-4-yl)ethyl]piperidin-4-yl}-1H-pyrrolo[3',2':5,6]pyrido[4,3-d]pyrimidine-2,4(3H,7H)-dione | Colorless solid | 26% |
| 91 | 1-[1-(cyclopropylmethyl)piperidin-4-yl]-1H-pyrrolo[3',2':5,6]pyrido[4,3-d]pyrimidine-2,4(3H,7H)-dione | Colorless solid | 24% |
| 92 | 1-[1-(2-methylbutyl)piperidin-4-yl]-1H-pyrrolo[3',2':5,6]pyrido[4,3-d]-pyrimidine-2,4(3H,7H)-dione | Colorless solid | 4% |

TABLE[b] 21-continued

| Ex | Compound Name | Morphology | Yield |
|---|---|---|---|
| 93 | 1-{1-[2-(tetrahydro-2H-pyran-4-yl)ethyl]-piperidin-4-yl}-1H-pyrrolo[3',2':5,6]pyrido[4,3-d]pyrimidine-2,4(3H,7H)-dione | Colorless solid | 13% |
| 94 | 2-[4-(2,4-dioxo-2,3,4,7-tetrahydro-1H-pyrrolo[3',2':5,6]pyrido[4,3-d]pyrimidin-1-yl)piperidin-1-yl]acetonitrile | Colorless solid | 3% |
| 95 | 1-[1-(2,2,2-trifluoroethyl)piperidin-4-yl]-1H-pyrrolo[3',2':5,6]pyrido[4,3-d]pyrimidine-2,4(3H,7H)-dione | Colorless solid | 38% |
| 96 | 5-[4-(2,4-dioxo-2,3,4,7-tetrahydro-1H-pyrrolo[3',2':5,6]pyrido[4,3-d]pyrimidin-1-yl)piperidin-1-yl]pentanenitrile | Colorless solid | 88% |
| 97 | 1-[1-(6,6,6-trifluorohexyl)piperidin-4-yl]-1H-pyrrolo[3',2':5,6]pyrido[4,3-d]pyrimidine-2,4(3H,7H)-dione | Colorless solid | 29% |
| 98 | 4-[4-(2,4-dioxo-2,3,4,7-tetrahydro-1H-pyrrolo[3',2':5,6]pyrido[4,3-d]pyrimidin-1-yl)piperidin-1-yl]butanenitrile | Colorless solid | 4% |

TABLE[b] 22

| Ex | Compound Name | Morphology | Yield |
|---|---|---|---|
| 99 | 1-{1-[(tetrahydrofuran-2-yl)methyl]piperidin-4-yl}-1H-pyrrolo[3',2':5,6]pyrido[4,3-d]pyrimidine-2,4(3H,7H)-dione | Colorless solid | 40% |
| 100 | 3-[4-(2,4-dioxo-2,3,4,7-tetrahydro-1H-pyrrolo[3',2':5,6]pyrido[4,3-d]pyrimidin-1-yl)piperidin-1-yl]propanenitrile | Colorless solid | 43% |
| 101 | 1-[trans-4-(hydroxymethyl)cyclohexyl]-1H-pyrrolo[3',2':5,6]pyrido[4,3-d]pyrimidine-2,4(3H,7H)-dione | Colorless solid | 74% |
| 102 | 1-(trans-4-{[(2,2,2-trifluoroethyl)amino]methyl}cyclohexyl)-1H-pyrrolo[3',2':5,6]pyrido[4,3-d]pyrimidine-2,4(3H,7H)-dione | Colorless solid | 75% |
| 103 | 3-[trans-4-(2,4-dioxo-2,3,4,7-tetrahydro-1H-pyrrolo[3',2':5,6]pyrido[4,3-d]pyrimidin-1-yl)cyclohexyl]acrylonitrile | Colorless solid | 53% |
| 104 | 1-((1R,2r,3S,5s,7s)-5-hydroxyadamantan-2-yl)-1H-pyrrolo[3',2':5,6]pyrido[4,3-d]pyrimidine-2,4(3H,7H)-dione | Colorless solid | 41% |
| 105 | 1-((1R,2s,3S,5s,7s)-5-hydroxyadamantan-2-yl)-1H-pyrrolo[3',2':5,6]pyrido[4,3-d]pyrimidine-2,4(3H,7H)-dione | Brown oil | 25% |
| 106 | 1-((1R,2r,3S,5s,7s)-5-hydroxyadamantan-2-yl)-1H-pyrrolo[2,3-h][1,6]naphthyridin-4(7H)-one | Colorless solid | 55% |
| 107 | 1-((1R,2s,3S,5s,7s)-5-hydroxyadamantan-2-yl)-1H-pyrrolo[2,3-h][1,6]naphthyridin-4(7H)-one | Colorless solid | 69% |

Synthetic Example[b] 108

1-[1-(2-Morpholinoethyl)piperidin-4-yl]-1H-pyrrolo[3',2':5,6]pyrido[4,3-d]pyrimidine-2,4(3H,7H)-dione 1-(Piperidin-4-yl)-7-{[2-(trimethylsilyl)ethoxy]methyl}-1H-pyrrolo[3',2':5,6]pyrido[4,3-d]pyrimidine-2,4(3H,7H)-dione hydrochloride (30.0 mg, 0.0664 mmol) obtained in Reference Synthetic Example[b] 91 and 4-(2-chloroethyl)morpholine hydrochloride (36.8 mg, 0.198 mmol) in acetonitrile (1.5 mL) were mixed with N,N-diisopropylethylamine (79.5 µL, 0.462 mmol) and stirred at 60° C. for 15 hours and then with 4-(2-chloroethyl)morpholine hydrochloride (36.8 mg, 0.198 mmol) and N,N-diisopropylethylamine (34.1 µL, 0.198 mmol) for 30.5 hours. The reaction mixture was allowed to cool to room temperature and concentrated under reduced pressure. The resulting residue was purified by silica gel column chromatography (methanol/chloroform=3/97→12/88 (v/v)). The resulting crude product was dissolved in dichloromethane (1.5 mL) and stirred with trifluoroacetic acid (0.5 mL) at room temperature for 2 hours. The reaction mixture was azeotropically distilled with toluene under reduced pressure, and the residue was dissolved in methanol (2 mL) and stirred with ethylenediamine (75 µL, 1.12 mmol) and 1 M aqueous sodium hydroxide (0.8 mL) at room temperature for 2.5 hours. The reaction mixture was concentrated under reduced pressure and, after addition of water, extracted with 1-butanol four times. The organic layer was dried over anhydrous sodium sulfate and concentrated under reduced pressure. The resulting residue was purified by silica gel column chromatography (Hi Flash column amino type manufactured by Yamazen Corporation: methanol/chloroform=0/1→9/91 (v/v)) to give the title compound as a colorless solid (1.5 mg, yield 6% (three steps)).

Synthetic Example[b] 109 tert-Butyl 4-({2-[4-(2,4-dioxo-2,3,4,7-tetrahydro-1H-pyrrolo[3',2':5,6]pyrido[4,3-d]pyrimidin-1-yl)piperidin-1-yl]ethyl}amino)piperidine-1-carboxylate 1-[1-(2-Aminoethyl)piperidin-4-yl]-1H-pyrrolo[3',2':5,6]pyrido[4,3-d]pyrimidine-2,4(3H,7H)-dione (20.0 mg, 0.0609 mmol) obtained in Synthetic Example[b] 88 and tert-butyl 4-oxopiperidine-1-carboxylate (24.3 mg, 0.122 mmol) in a mixture of methanol (1 mL) and acetic acid (100 µL) were stirred with 2-picoline borane (13.0 mg, 0.122 mmol) at room temperature for 17 hours. The reaction mixture was basified with 1 M aqueous sodium hydroxide and extracted with a mixture of chloroform and 2-propanol four times. The organic layer was dried over anhydrous sodium sulfate and concentrated under reduced pressure. The residue was purified by silica gel column chromatography (methanol/chloroform=0/1→1/0 (v/v)) to give the title compound as a colorless solid (18.0 mg, yield 57%).

Synthetic Example[b] 110

1-(1-{2-[(Cyclopropylmethyl)amino] ethyl}piperidin-4-yl)-1H-pyrrolo[3',2':5,6]pyrido[4,3-d]pyrimidine-2,4(3H,7H)-dione The reactions in Synthetic Example[b] 109 were carried out in substantially the same manners except that cyclopropanecarbaldehyde was used instead of tert-butyl 4-oxopiperidine-1-carboxylate to give the title compound as a colorless solid (5.5 mg, yield 23%).

Synthetic Example[b] 111

1-{1-[2-(Piperidin-4-ylamino)ethyl]piperidin-4-yl}-1H-pyrrolo[3',2':5,6]pyrido[4,3-d]pyrimidine-2,4(3H,7H)-dione tert-Butyl 4-({2-[4-(2,4-dioxo-2,3,4,7-tetrahydro-1H-pyrrolo[3',2':5,6]pyrido[4,3-d]pyrimidin-1-yl)piperidin-1-yl] ethyl}amino)piperidine-1-carboxylate (16.9 mg, 0.0330 mmol) obtained in Synthetic Example[b] 109 in a mixture of dichloromethane (1 mL) and methanol (1 mL) was stirred with trifluoroacetic acid (100 μL, 1.31 mmol) at room temperature for 2.5 hours and then with trifluoroacetic acid (400 μL, 5.23 mmol) at room temperature for 2.5 hours and then with trifluoroacetic acid (500 μL, 6.53 mmol) at room temperature for 4.5 hours and then with trifluoroacetic acid (2 mL, 26.1 mmol) at room temperature for 16 hours. The reaction mixture was concentrated under reduced pressure, and the resulting residue was purified by silica gel chromatography (Hi Flash column amino type manufactured by Yamazen Corporation: methanol/ethyl acetate=1/4→4/1 (v/v)) to give the title compound as a colorless solid (4.21 mg, yield 30%).

Synthetic Example[b] 112

1-{trans-4-[((R)-3-Hydroxypyrrolidin-1-yl)methyl] cyclohexyl}-1H-Pyrrolo[3',2':5,6]pyrido[4,3-d]pyrimidine-2,4(3H,7H)-dione trans-4-(2,4-Dioxo-7-{[2-(trimethylsilyl)ethoxy] methyl}-2,3,4,7-tetrahydro-1H-pyrrolo[3',2':5,6]pyrido[4,3-d]pyrimidin-1-yl)cyclohexanecarbaldehyde (30.0 mg, 0.067 mmol) obtained in Reference Synthetic Example[b] 168 in a mixture of methanol (0.5 mL) and acetic acid (50 μL) was stirred with (R)-3-hydroxy-pyrrolidine (14.3 mg, 0.088 mmol) and 2-picoline borane (9.4 mg, 0.088 mmol) at room temperature for 1 day. After addition of 1M aqueous sodium hydroxide, the reaction mixture was extracted with ethyl acetate, and the organic layer was dried over anhydrous sodium sulfate and concentrated under reduced pressure. The residue was purified by silica gel thin layer chromatography (ethyl acetate/methanol=10/1 (v/v)) to give the compound as a colorless solid. The resulting colorless solid was dissolved in dichloromethane (1.0 mL) and stirred with trifluoroacetic acid (0.4 mL) at room temperature for 5 hours. The reaction mixture was concentrated under reduced pressure, and the resulting residue was stirred with methanol (0.7 mL), ethylenediamine (30 μL) and 1 M aqueous sodium hydroxide (30 μL) at room temperature for 1 day. The reaction mixture was filtered and the resulting solid was washed with water and methanol to give the title compound as a colorless solid (20.0 mg, yield 52% (three steps)).

Synthetic Examples[b] 113 to 132

The reactions in Synthetic Example[b] 112 were carried out in substantially the same manners except that 3-hydroxyazetidine hydrochloride, thiomorpholine-1,1-dioxide, 4,4-difluoropiperidine, 3,3'-iminodipropionitrile, cyclopropylmethylamine, (R)-3-cyanopyrrolidine, 3,3-dimethylazetidine, 2-methylaminoethanol, 2-(phenylmethyl)aminoethanol, 1-trifluoromethyl-1-cyclopropylamine, N-(2-aminoethyl) morpholine, 2-(azetidin-3-yl)acetonitrile hydrochloride, 2,2-dimethylcyclopropylamine hydrochloride, 1-aminomethylcyclohexanol, aminoacetonitrile hydrochloride, 4-trifluoromethylpiperidine, 3-(trifluoromethyl)azetidin-3-ol hydrochloride, tetrahydrofurylmethylamine, 2-methoxyethanamine or 3-amino-1,1,1-trifluoro-2-(pyridin-3-yl)propan-2-ol obtained in Reference Synthetic Example[b] 179 were used instead of (R)-3-hydroxy-pyrrolidine to give the compounds of Synthetic Examples[b] 113 to 132. The names, morphologies and yields of the compounds synthesized are shown in Tables[b] 23 and 24.

TABLE[b] 23

| Ex | Compound Name | Morphology | Yield |
|---|---|---|---|
| 113 | 1-{trans-4-[(3-hydroxyazetidin-1-yl)methyl]cyclohexyl}-1H-pyrrolo[3',2':5,6]pyrido[4,3-d]pyrimidine-2,4(3H,7H)-dione | Colorless solid | 62% (3steps) |
| 114 | 1-{trans-4-[(1,1-dioxidothiomorpholino)methyl]cyclohexyl}-1H-pyrrolo[3',2':5,6]pyrido[4,3-d]pyrimidine-2,4(3H,7H)-dione | Colorless solid | 33% (3steps) |
| 115 | 1-{trans-4-[(4,4-difluoropiperidin-1-yl)methyl]cyclohexyl}-1H-pyrrolo[3',2':5,6]pyrido[4,3-d]pyrimidine-2,4(3H,7H)-dione | Colorless solid | 68% (3steps) |
| 116 | 3,3'-({[trans-4-(2,4-dioxo-2,3,4,7-tetrahydro-1H-pyrrolo[3',2': 5,6]pyrido[4,3-d]pyrimidin-1-yl)cyclohexyl]methyl}azanediyl)dipropanenitrile | Colorless solid | 63% (3steps) |
| 117 | 1-(trans-4-{[(cyclopropylmethyl)amino]methyl}cyclohexyl)-1H-1-pyrrolo[3',2':5,6]pyrido[4,3-d]pyrimidine-2,4(3H,7H)-dione | Colorless solid | 45% (3steps) |

TABLE[b] 23-continued

| Ex | Compound Name | Morphology | Yield |
|---|---|---|---|
| 118 | (R)-1-{[trans-4-(2,4-dioxo-2,3,4,7-tetrahydro-1H-pyrrolo[3',2':5,6]pyrido[4,3-d]pyrimidin-1-yl)cyclohexyl]methyl}pyrrolidine-3-carbonitrile | Colorless solid | 63% (3steps) |
| 119 | 1-{trans-4-[(3,3-dimethylazetidin-1-yl)methyl]cyclohexyl}-1H-pyrrolo[3',2':5,6]pyrido[4,3-d]pyrimidine-2,4(3H,7H)-dione | Brown oil | 47% (3steps) |
| 120 | 1-(trans-4-{[(2-hydroxyethyl)(methyl)amino]methyl}cyclohexyl)-1H-pyrrolo[3',2':5,6]pyrido[4,3-d]pyrimidine-2,4(3H,7H)-dione | Colorless solid | 52% (3steps) |
| 121 | 1-(trans-4-{[benzyl(2-hydroxyethyl)amino]methyl}cyclohexyl)-1H-pyrrolo[3',2':5,6]pyrido[4,3-d]pyrimidine-2,4(3H,7H)-dione | Colorless solid | 56% (3steps) |
| 122 | 1-[trans-4-({[1-(trifluoromethyl)cyclopropyl]amino}methyl)cyclohexyl]-1H-pyrrolo[3',2':5,6]pyrido[4,3-d]pyrimidine-2,4(3H,7H)-dione | Colorless solid | 43% (3steps) |

TABLE[b] 24

| Ex | Compound Name | Morphology | Yield |
|---|---|---|---|
| 123 | 1-(trans-4-{[(2-morpholinoethyl)amino]methyl}cyclohexyl)-1H-pyrrolo[3',2':5,6]pyrido[4,3-d]pyrimidine-2,4(3H,7H)-dione | Colorless solid | 17% (3 steps) |
| 124 | 2-(1-{[trans-4-(2,4-dioxo-2,3,4,7-tetrahydro-1H-pyrrolo[3',2':5,6]pyrido[4,3-d]pyrimidin-1-yl)cyclohexyl]methyl}azetidin-3-yl)acetonitrile | Colorless solid | 5% (3 steps) |
| 125 | 1-(trans-4-{[(2,2-dimethylcyclopropyl)amino]methyl}cyclohexyl)-1H-pyrrolo[3',2':5,6]pyrido[4,3-d]pyrimidine-2,4(3H,7H)-dione | Colorless solid | 35% (3 steps) |
| 126 | 1-[trans-4-({[(1-hydroxycyclohexyl)methyl]amino}methyl)cyclohexyl]-1H-pyrrolo[3',2':5,6]pyrido[4,3-d]pyrimidine-2,4(3H,7H)-dione | Colorless solid | 23% (3 steps) |
| 127 | 2-({[trans-4-(2,4-dioxo-2,3,4,7-tetrahydro-1H-pyrrolo[3',2':5,6]pyrido[4,3-d]pyrimidin-1-yl)cyclohexyl]methyl}amino)acetonitrile | Colorless solid | 46% (3 steps) |
| 128 | 1-(trans-4-{[4-(trifluoromethyl)piperidin-1-yl]methyl}cyclohexyl)-1H-pyrrolo[3',2':5,6]pyrido[4,3-d]pyrimidine-2,4(3H,7H)-dione | Colorless solid | 70% (3 steps) |
| 129 | 1-(trans-4-{[3-hydroxy-3-(trifluoromethyl)azetidin-1-yl]methyl}cyclohexyl)-1H-pyrrolo[3',2':5,6]pyrido[4,3-d]pyrimidine-2,4(3H,7H)-dione | Brown oil | 55% (3 steps) |
| 130 | 1-[trans-4-({[(tetrahydrofuran-2-yl)methyl]amino}methyl)cyclohexyl]-1H-pyrrolo[3',2':5,6]pyrido[4,3-d]pyrimidine-2,4(3H,7H)-dione | Colorless solid | 72% (3 steps) |
| 131 | 1-(trans-4-{[(2-methoxyethyl)amino]methyl}cyclohexyl)-1H-pyrrolo[3',2':5,6]pyrido[4,3-d]pyrimidine-2,4(3H,7H)-dione | Colorless solid | 19% (3 steps) |
| 132 | 1-[trans-4-({[3,3,3-trifluoro-2-hydroxy-2-(pyridin-3-yl)propyl]amino}methyl)cyclohexyl]-1H-pyrrolo[3',2':5,6]pyrido[4,3-d]pyrimidine-2,4(3H,7H)-dione | Colorless solid | 61% (3 steps) |

Synthetic Example[b] 133 trans-4-(2,4-Dioxo-2,3,4,7-tetrahydro-1H-pyrrolo[3',2':5,6]pyrido[4,3-d]pyrimidin-1-yl)cyclohexanecarbaldehyde 1-[trans-4-(Hydroxymethyl)cyclohexyl]-1H-pyrrolo[3',2':5,6]pyrido[4,3-d]pyrimidine-2,4(3H,7H)-dione (35.0 mg, 0.111 mmol) obtained in Synthetic Example[b] 101 in a mixture of toluene (1 mL) and dimethyl sulfoxide (0.25 mL) was mixed with 2-iodoxybenzoic acid (37.4 mg, 0.133 mmol) and stirred at 50° C. for 2 hours. The reaction mixture was allowed to cool to room temperature and stirred with saturated aqueous sodium thiosulfate and saturated aqueous sodium hydrogen carbonate at room temperature for 30 minutes. The precipitated solid was collected by filtration to give the title compound as a colorless solid (26.7 mg, yield 77%).

Synthetic Example[b] 134

3-[trans-4-(2,4-Dioxo-2,3,4,7-tetrahydro-1H-pyrrolo[3',2':5,6]pyrido[4,3-d]pyrimidin-1-yl)cyclohexyl]propanenitrile 3-[trans-4-(2,4-Dioxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]acrylonitrile (16.2 mg, 0.0347 mmol) obtained in Reference Synthetic Example[b] 170 in tetrahydrofuran (1.0 mL) was stirred with 5% palladium-carbon (10 mg) at room temperature for 1 day under a hydrogen atmosphere. The reaction mixture was filtered, and the filtrate was concentrated under reduced pressure. The resulting residue was dissolved in dichloromethane (1.0 mL) and stirred with trifluoroacetic acid (0.4 mL) at room temperature for 5 hours. The reaction mixture was concentrated under reduced pressure, and the resulting residue was stirred with methanol (0.7 mL), ethylenediamine (30 μL) and 1 M aqueous sodium hydroxide (30 μL) at room temperature for 1 day. The reaction mixture was filtered, and the resulting solid was washed with water and methanol to give the title compound as a colorless solid (2.73 mg, yield 25% (three steps)).

Synthetic Example[b] 135

2-Cyano-N-{[trans-4-(2,4-dioxo-2,3,4,7-tetrahydro-1H-pyrrolo[3',2':5,6]pyrido[4,3-d]pyrimidin-1-yl)cyclohexyl]methyl}-N-(2,2,2-trifluoroethyl)acetamide 1-(4-{[(2,2,2-Trifluoroethyl)amino]methyl}cyclohexyl)-7-{[2-(trimethylsilyl)ethoxy]methyl}-1H-pyrrolo[3',2':5,6]pyrido[4,3-d]pyrimidine-2,4(3H,7H)-dione (25.0 mg, 0.048 mmol) obtained in Reference Synthetic Example[b] 169 in N,N-dimethylformamide (1 mL) was stirred with 2-cyanoacetic acid (10 mg, 0.071 mmol), O-(7-azabenzotriazol-1-yl)-N,N,N',N'-tetramethyluronium hexafluorophosphate (27 mg, 0.071 mmol) and N,N-diisopropylethylamine (16 μL, 0.095 mmol) at room temperature for 3 days. After addition of saturated aqueous sodium hydrogen carbonate, the reaction mixture was extracted with chloroform, and the organic layer was dried over anhydrous sodium sulfate and concentrated under reduced pressure. The residue was purified by silica gel column chromatography (chloroform/methanol=19/1 (v/v)) to give the compound as a yellow oil. The resulting yellow oil was dissolved in dichloromethane (1.0 mL) and stirred with trifluoroacetic acid (150 μL) at room temperature for 1 day. The reaction mixture was concentrated under reduced pressure, and the resulting residue was stirred with methanol (1 mL), ethylenediamine (50 μL) and 1 M aqueous sodium hydroxide (50 μL) at room temperature for 1 day. The precipitated solid was collected by filtration to give the title compound as a colorless solid (2.70 mg, yield 14% (three steps)).

Synthetic Example[b] 136

1-(trans-4-{[Methyl(2,2,2-trifluoroethyl)amino]methyl}cyclohexyl)-1H-pyrrolo[3',2':5,6]pyrido[4,3-d]pyrimidine-2,4(3H,7H)-dione 1-(4-{[(2,2,2-Trifluoroethyl)amino]methyl}cyclohexyl)-7-{[2-(trimethylsilyl)ethoxy]methyl}-1H-pyrrolo[3',2':5,6]pyrido[4,3-d]pyrimidine-2,4(3H,7H)-dione (30 mg, 0.048 mol) obtained in Reference Synthetic Example[b] 169 in a mixture of methanol (1 mL) and acetic acid (100 μL) was stirred with formaldehyde solution (37%) (20 μL) and 2-picoline borane (15 mg, 0.14 mmol) at room temperature for 3 days. After addition of saturated aqueous ammonium chloride, the reaction mixture was extracted with chloroform, and the organic layer was dried over anhydrous sodium sulfate and concentrated under reduced pressure. The resulting residue was purified by silica gel column chromatography (chloroform/methanol=19/1 (v/v)) to give the compound as a colorless solid. The resulting colorless solid was dissolved in dichloromethane (1 mL) and stirred with trifluoroacetic acid (150 μL) at room temperature for 1 day. The reaction mixture was concentrated under reduced pressure, and the resulting residue was stirred with methanol (1 mL), ethylenediamine (50 μL) and 1 M aqueous sodium hydroxide (50 μL) at room temperature for 1 day. The precipitated solid was collected by filtration to give the title compound as a colorless solid (24.95 mg, quantitative yield (three steps)).

Synthetic Example[b] 137

2-(1-Cyclohexyl-2,4-dioxo-1H-pyrrolo[3',2':5,6]pyrido[4,3-d]pyrimidin-3(2H,4H,7H)-yl)acetonitrile 1-Cyclohexyl-7-{[2-(trimethylsilyl)ethoxy]methyl}-1H-pyrrolo[3',2':5,6]pyrido[4,3-d]pyrimidine-2,4(3H,7H)-dione (20 mg, 0.048 mmol) obtained in Reference Synthetic Example[b] 95 in N,N-dimethylformamide (1 mL) was mixed with potassium carbonate (10 mg, 0.072 mmol) and 2-chloroacetonitrile (5.0 μL, 0.072 mmol) and stirred at 80° C. for 1 day. After addition of saturated aqueous ammonium chloride, the reaction mixture was extracted with chloroform, and the organic layer was dried over anhydrous sodium sulfate and concentrated under reduced pressure. The residue was purified by silica gel column chromatography (ethyl acetate/hexane=1/4→1/3 (v/v)) to give the compound as a yellow oil. The resulting yellow oil was dissolved in dichloromethane (1 mL) and stirred with trifluoroacetic acid (150 μL) at room temperature for 1 day. The reaction mixture was concentrated under reduced pressure, and the resulting residue was stirred with methanol (1 mL), ethylenediamine (50 μL) and 1 M aqueous sodium hydroxide (50 μL) at room temperature for 1 day. The precipitated solid was collected by filtration to give the title compound as a colorless solid (24.5 mg, yield 79% (three steps)).

Synthetic Examples[b] 138 to 154

The reactions in Synthetic Example[b] 137 were carried out in substantially the same manners except that iodomethane, 2,2,2-trifluoroethyl trifluoromethanesulfonate, 2-bromoethanol, 3-bromopropan-1-ol, 4-(2-chloroethyl)morpholine hydrochloride, chloro(methoxy)methane, 1-bromo-4-fluorobutane, 1-bromo-2-methoxyethane, 2-bromopropanenitrile, (chloromethyl)(methyl)sulfane, bromocyclopentane, (bromomethyl)cyclopropane, 2-(bromomethyl)tetrahydrofuran, 3-(chloromethyl)-3-methyloxetane, 2-chloro-N,N-dimethylacetamide, 2-chloro-N,N-dimethylethanamine hydrochloride or tert-butyl 4-bromopiperidine-1-carboxylate were used instead of 2-chloroacetonitrile to give the compounds of Synthetic Examples[b] 138 to 154. The names, morphologies and yields of the compounds synthesized are shown in Tables[b] 25 and 26.

TABLE[b] 25

| Ex | Compound Name | Morphology | Yield |
|---|---|---|---|
| 138 | 1-cyclohexyl-3-methyl-1H-pyrrolo[3',2':5,6]pyrido[4,3-d]pyrimidine-2,4(3H, 7H)-dione | Colorless solid | 59% (3 steps) |
| 139 | 1-cyclohexyl-3-(2,2,2-trifluoroethyl)-1H-pyrrolo[3',2':5,6]pyrido[4,3-d]pyrimidine-2,4(3H,7H)-dione | Colorless solid | 49% (3 steps) |
| 140 | 1-cyclohexyl-3-(2-hydroxyethyl)-1H-pyrrolo[3',2':5,6]pyrido[4,3-d]pyrimidine-2,4(3H,7H)-dione | Colorless solid | 61% (3 steps) |
| 141 | 1-cyclohexyl-3-(3-hydroxypropyl)-1H-pyrrolo[3',2':5,6]pyrido[4,3-d]pyrimidine-2,4(3H,7H)-dione | Colorless solid | 31% (3 steps) |
| 142 | 1-cyclohexyl-3-(2-morpholinoethyl)-1H-pyrrolo[3',2':5,6]pyrido[4,3-d]pyrimidine-2,4(3H,7H)-dione | Colorless solid | 68% (3 steps) |
| 143 | 1-cyclohexyl-3-(methoxymethyl)-1H-pyrrolo[3',2':5,6]pyrido[4,3-d]pyrimidine-2,4(3H,7H)-dione | Colorless solid | 49% (3 steps) |
| 144 | 1-cyclohexyl-3-(4-fluorobutyl)-1H-pyrrolo[3',2':5,6]pyrido[4,3-d]pyrimidine-2,4(3H,7H)-dione | Colorless solid | 55% (3 steps) |
| 145 | 1-cyclohexyl-3-(2-methoxyethyl)-1H-pyrrolo[3',2':5,6]pyrido[4,3-d]pyrimidine-2,4(3H,7H)-dione | Colorless solid | 60% (3 steps) |
| 146 | 2-(1-cyclohexyl-2,4-dioxo-1H-pyrrolo[3',2':5,6]pyrido[4,3-d]pyrimidin-3(2H,4H,7H)-yl)propanenitrile | Colorless solid | 72% (3 steps) |
| 147 | 1-cyclohexyl-3-[(methylthio)methyl]-1H-pyrrolo[3',2':5,6]pyrido[4,3-d]pyrimidine-2,4(3H,7H)-dione | Colorless solid | 80% (3 steps) |

TABLE[b] 26

| Ex | Compound Name | Morphology | Yield |
|---|---|---|---|
| 148 | 1-cyclohexyl-3-cyclopentyl-1H-pyrrolo[3',2':5,6]pyrido[4,3-d]pyrimidine-2,4(3H,7H)-dione | Colorless solid | 55% (3 steps) |
| 149 | 1-cyclohexyl-3-(cyclopropylmethyl)-1H-pyrrolo[3',2':5,6]pyrido[4,3-d]pyrimidine-2,4(3H,7H)-dione | Colorless solid | 99% (3 steps) |
| 150 | 1-cyclohexyl-3-[(tetrahydrofuran-2-yl)methyl]-1H-pyrrolo[3',2':5,6]pyrido[4,3-d]pyrimidine-2,4(3H,7H)-dione | Colorless solid | 83% (3 steps) |
| 151 | 1-cyclohexyl-3-[3-hydroxy-2-(hydroxymethyl)-2-methylpropyl]-1H-pyrrolo[3', 2':5,6]pyrido[4,3-d]pyrimidine-2,4(3H,7H)-dione | Colorless solid | 56% (3 steps) |
| 152 | 2-(1-cyclohexyl-2,4-dioxo-1H-pyrrolo[3',2':5,6]pyrido[4,3-d]pyrimidin-3(2H,4H,7H)-yl)-N,N-dimethylacetamide | Colorless solid | 64% (3 steps) |
| 153 | 1-cyclohexyl-3-[2-(dimethylamino)ethyl]-1H-pyrrolo[3',2':5,6]pyrido[4,3-d]pyrimidine-2,4(3H,7H)-dione | Colorless solid | 30% (3 steps) |
| 154 | 1-cyclohexyl-3-(piperidin-4-yl)-1H-pyrrolo[3',2':5,6]pyrido[4,3-d]pyrimidine-2,4(3H,7H)-dione | Colorless solid | 15% (3 steps) |

Synthetic Example[b] 155

N-{[trans-4-(2,4-Dioxo-2,3,4,7-tetrahydro-1H-pyrrolo[3',2':5,6]pyrido[4,3-d]pyrimidin-1-yl)cyclohexyl]methyl}-3,3,3-trifluoro-N-(2,2,2-trifluoroethyl)propanamide The reactions in Synthetic Example[b] 135 were carried out in substantially the same manners except that 3,3,3-trifluoropropanoic acid was used instead of 2-cyanoacetic acid to give the title compound as a colorless solid (1.95 mg, yield 8% (three steps)).

The structural formulae of the compounds obtained the Reference Synthetic Examples[b] and Synthetic Examples[b] are shown below in Tables[b] 27 to 44. The physical property data on the compounds obtained the Reference Synthetic Examples[b] and Synthetic Examples[b] are shown below in Tables[b] 45 to 77.

TABLE[b] 27

| Rf | Structure |
|---|---|
| 1 | 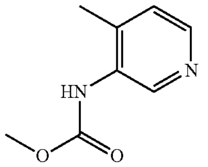 |
| 2 | 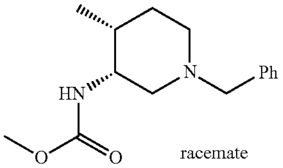 [SMILES: COC(=O)N[C@H]1CN(Cc2ccccc2)CC[C@H]1C] racemate |
| 3 | 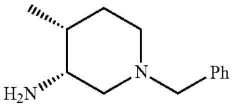 racemate |
| 4 | 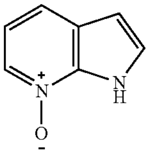 |

TABLE[b] 27-continued
| Rf | Structure |
|---|---|
| 5 | 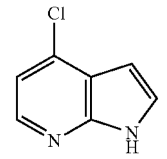 |
| 6 | 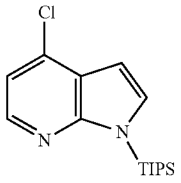 |
| 7 | 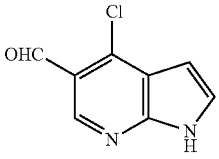 [SMILES: O=Cc1cnc2[nH]ccc2c1Cl] |
| 8 | 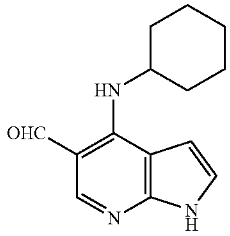 [SMILES: O=Cc1cnc2[nH]ccc2c1NC1CCCCC1] |
| 9 | 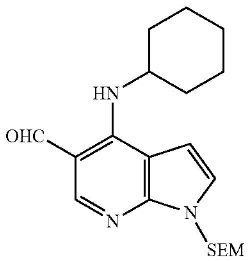 [SMILES: C[Si](C)(C)CCOCn1ccc2c(NC3CCCCC3)c(C=O)cnc21] |
| 10 | 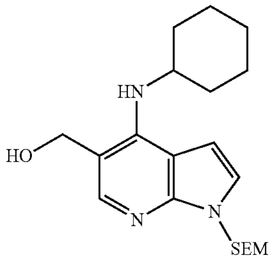 [SMILES: C[Si](C)(C)CCOCn1ccc2c(NC3CCCCC3)c(CO)cnc21] |
| 11 | 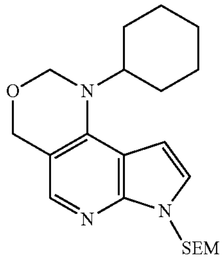 [SMILES: C[Si](C)(C)CCOCn1ccc2c3c(cnc21)COCN3C1CCCCC1] |
TABLE[b] 27-continued
| Rf | Structure |
|---|---|
| 12 | 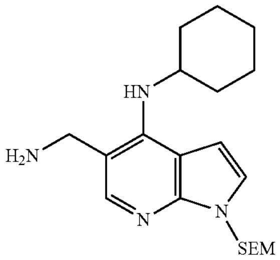 [SMILES: C[Si](C)(C)CCOCn1ccc2c(NC3CCCCC3)c(CN)cnc21] |
| 13 | 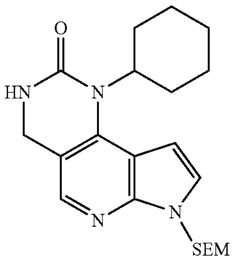 [SMILES: C[Si](C)(C)CCOCn1ccc2c3c(cnc21)CNC(=O)N3C1CCCCC1] |
| 14 | 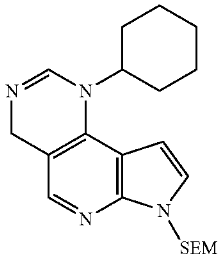 [SMILES: C[Si](C)(C)CCOCn1ccc2c3c(cnc21)CN=CN3C1CCCCC1] |
| 15 | 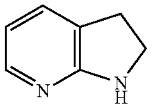 |
| 16 | 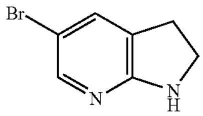 |
| 17 | 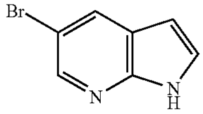 |
| 18 | 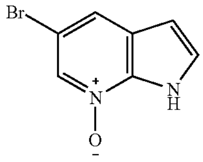 [SMILES: [O-][n+]1cc(Br)cc2cc[nH]c21] |
| 19 | 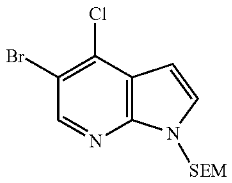 [SMILES: C[Si](C)(C)CCOCn1ccc2c(Cl)c(Br)cnc21] |

TABLE[b] 27-continued
| Rf | Structure |
|---|---|
| 20 | 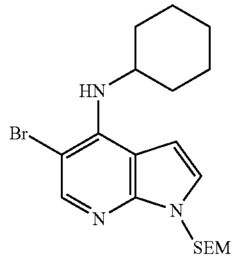 [SMILES: C[Si](C)(C)CCOCn1ccc2c(NC3CCCCC3)c(Br)cnc21] |
| 21 | 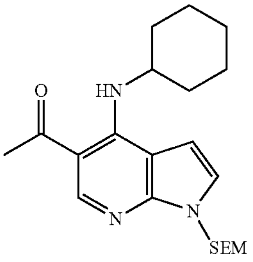 [SMILES: CC(=O)c1cnc2c(ccn2COCC[Si](C)(C)C)c1NC1CCCCC1] |
| 22 | 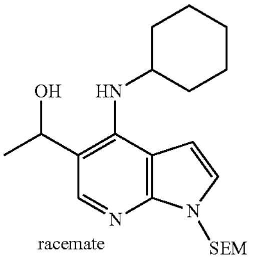 [SMILES: CC(O)c1cnc2c(ccn2COCC[Si](C)(C)C)c1NC1CCCCC1] racemate |
| 23 | 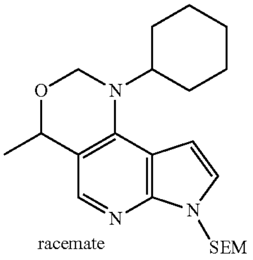 [SMILES: CC1OCN(C2CCCCC2)c2c1cnc1c2ccn1COCC[Si](C)(C)C] racemate |
| 24 | 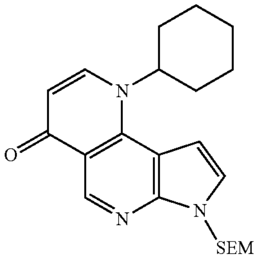 [SMILES: C[Si](C)(C)CCOCn1ccc2c1ncc1c(=O)ccn(C3CCCCC3)c12] |
TABLE[b] 28
| Rf | Structure |
|---|---|
| 25 | 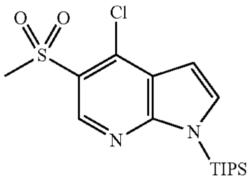 |
| 26 | 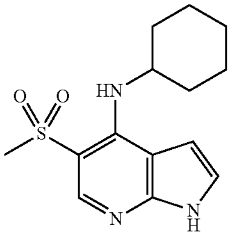 [SMILES: CS(=O)(=O)c1cnc2[nH]ccc2c1NC1CCCCC1] |
| 27 | 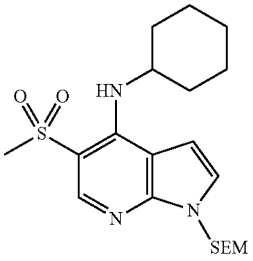 [SMILES: C[Si](C)(C)CCOCn1ccc2c(NC3CCCCC3)c(S(C)(=O)=O)cnc21] |
| 28 | 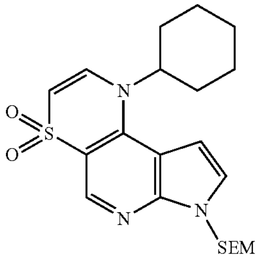 [SMILES: C[Si](C)(C)CCOCn1ccc2c3c(cnc21)S(=O)(=O)C=CN3C1CCCCC1] |
| 29 | 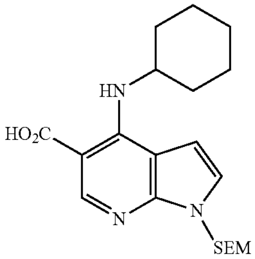 [SMILES: C[Si](C)(C)CCOCn1ccc2c(NC3CCCCC3)c(C(=O)O)cnc21] |
| 30 | 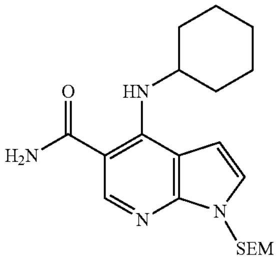 [SMILES: C[Si](C)(C)CCOCn1ccc2c(NC3CCCCC3)c(C(N)=O)cnc21] |

TABLE[b] 28-continued
| Rf | Structure |
|---|---|
| 31 | 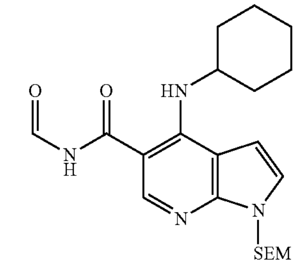 [SMILES: C[Si](C)(C)CCOCn1ccc2c(NC3CCCCC3)c(C(=O)NC=O)cnc21] |
| 32 | 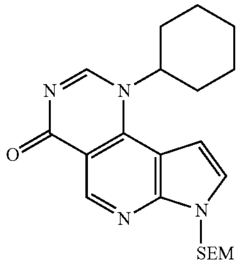 [SMILES: C[Si](C)(C)CCOCn1ccc2c1ncc1c(=O)ncn(C3CCCCC3)c12] |
| 33 | 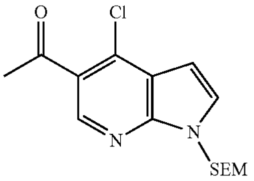 [SMILES: CC(=O)c1cnc2c(ccn2COCC[Si](C)(C)C)c1Cl] |
| 34 | 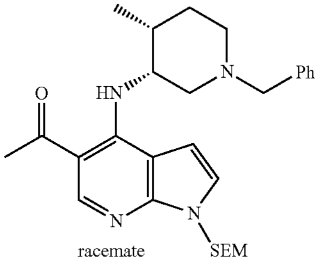 [SMILES: CC(=O)c1cnc2c(ccn2COCC[Si](C)(C)C)c1N[C@H]1CN(Cc2ccccc2)CC[C@H]1C] racemate |
| 35 | 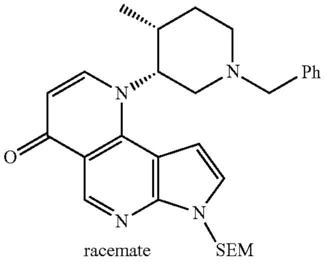 [SMILES: C[C@@H]1CCN(Cc2ccccc2)C[C@@H]1n1ccc(=O)c2cnc3c(ccn3COCC[Si](C)(C)C)c21] racemate |
| 36 | 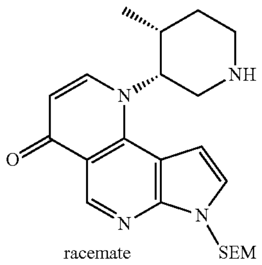 [SMILES: C[C@@H]1CCNC[C@@H]1n1ccc(=O)c2cnc3c(ccn3COCC[Si](C)(C)C)c21] racemate |
TABLE[b] 28-continued
| Rf | Structure |
|---|---|
| 37 | 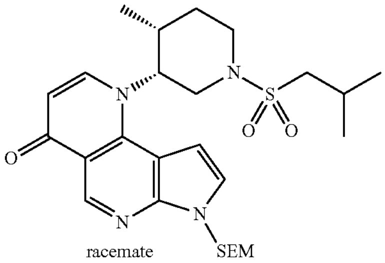 [SMILES: CC(C)CS(=O)(=O)N1CC[C@@H](C)[C@@H](n2ccc(=O)c3cnc4c(ccn4COCC[Si](C)(C)C)c32)C1] racemate |
| 38 | 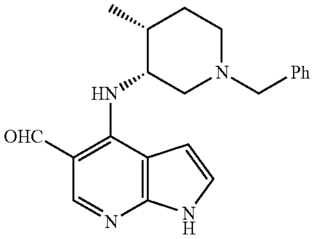 racemate |
| 39 | 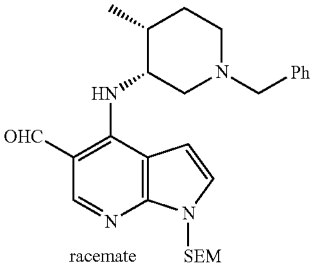 [SMILES: C[C@@H]1CCN(Cc2ccccc2)C[C@@H]1Nc1c(C=O)cnc2c1ccn2COCC[Si](C)(C)C] racemate |
| 40 | 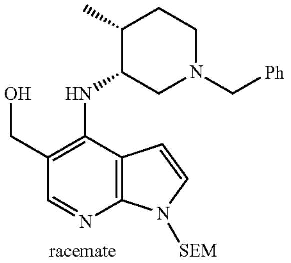 [SMILES: C[C@@H]1CCN(Cc2ccccc2)C[C@@H]1Nc1c(CO)cnc2c1ccn2COCC[Si](C)(C)C] racemate |
| 41 | 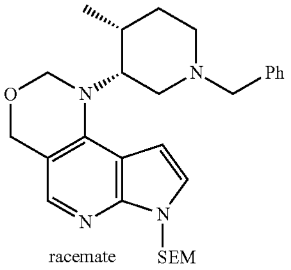 [SMILES: C[C@@H]1CCN(Cc2ccccc2)C[C@@H]1N1COCc2cnc3c(ccn3COCC[Si](C)(C)C)c21] racemate |
| 42 | 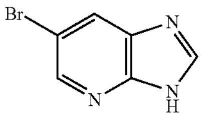 |

TABLE[b] 28-continued
| Rf | Structure |
|---|---|
| 43 | 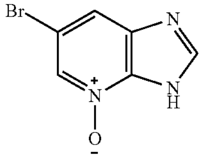 [SMILES: O[n+]1cc(Br)cc2nc[nH]c21] |
| 44 | 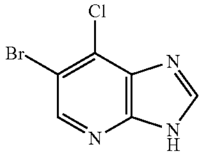 [SMILES: Clc1c(Br)cnc2[nH]cnc12] |
| 45 | 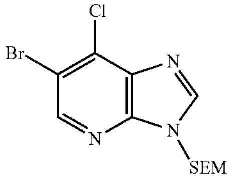 [SMILES: C[Si](C)(C)CCOCn1cnc2c(Cl)c(Br)cnc21] |
| 46 | 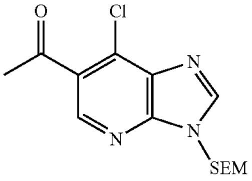 [SMILES: CC(=O)c1cnc2c(ncn2COCC[Si](C)(C)C)c1Cl] |
| 47 | 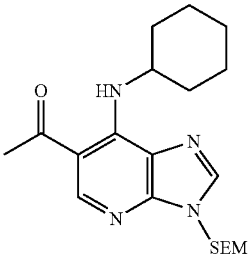 [SMILES: CC(=O)c1cnc2c(ncn2COCC[Si](C)(C)C)c1NC1CCCCC1] |
| 48 | 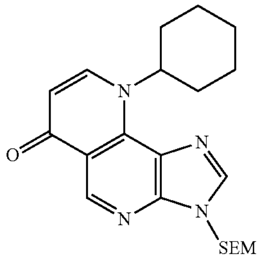 [SMILES: C[Si](C)(C)CCOCn1cnc2c1ncc1c(=O)ccn(C3CCCCC3)c12] |
TABLE[b] 29
| Rf | Structure |
|---|---|
| 49 | 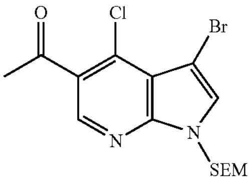 [SMILES: CC(=O)c1cnc2c(c(Br)cn2COCC[Si](C)(C)C)c1Cl] |
TABLE[b] 29-continued
| Rf | Structure |
|---|---|
| 50 | 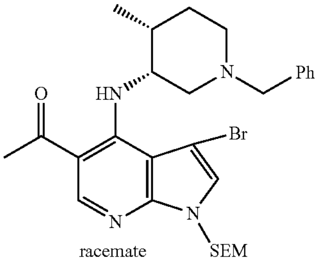 [SMILES: CC(=O)c1cnc2c(c(Br)cn2COCC[Si](C)(C)C)c1N[C@H]1CN(Cc2ccccc2)CC[C@H]1C] racemate |
| 51 | 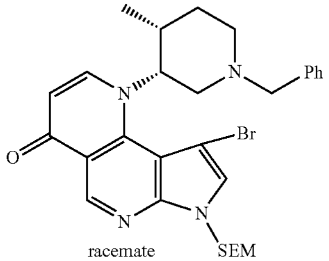 [SMILES: C[C@@H]1CCN(Cc2ccccc2)C[C@@H]1n1ccc(=O)c2cnc3c(c(Br)cn3COCC[Si](C)(C)C)c21] racemate |
| 52 | 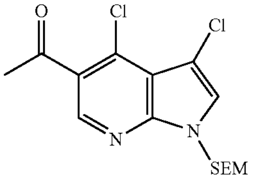 [SMILES: CC(=O)c1cnc2c(c(Cl)cn2COCC[Si](C)(C)C)c1Cl] |
| 53 | 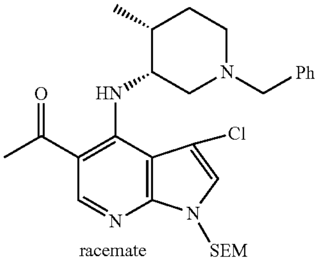 [SMILES: CC(=O)c1cnc2c(c(Cl)cn2COCC[Si](C)(C)C)c1N[C@H]1CN(Cc2ccccc2)CC[C@H]1C] racemate |
| 54 | 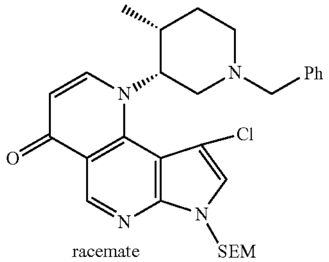 [SMILES: C[C@@H]1CCN(Cc2ccccc2)C[C@@H]1n1ccc(=O)c2cnc3c(c(Cl)cn3COCC[Si](C)(C)C)c21] racemate |
| 55 | 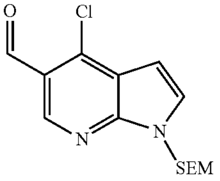 [SMILES: C[Si](C)(C)CCOCn1ccc2c(Cl)c(C=O)cnc21] |

TABLE[b] 29-continued
| Rf | Structure |
|---|---|
| 56 | 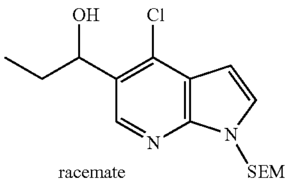 [SMILES: CCC(O)c1cnc2c(ccn2COCC[Si](C)(C)C)c1Cl] racemate |
| 57 | 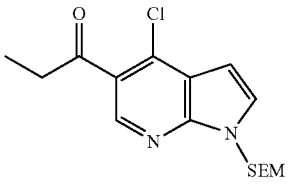 [SMILES: CCC(=O)c1cnc2c(ccn2COCC[Si](C)(C)C)c1Cl] |
| 58 | 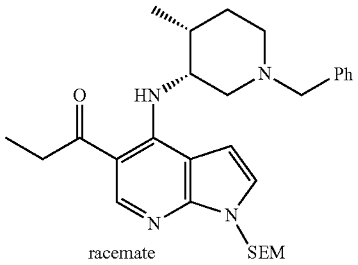 [SMILES: CCC(=O)c1cnc2c(ccn2COCC[Si](C)(C)C)c1N[C@H]1CN(Cc2ccccc2)CC[C@H]1C] racemate |
| 59 | 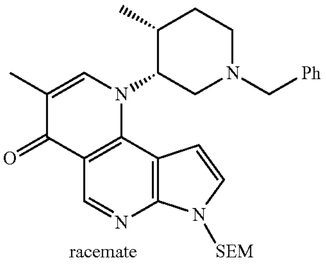 [SMILES: Cc1cn([C@H]2CN(Cc3ccccc3)CC[C@H]2C)c2c(cnc3c2ccn3COCC[Si](C)(C)C)c1=O] racemate |
| 60 | 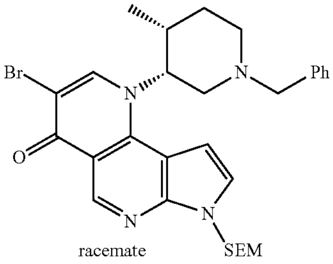 [SMILES: C[C@@H]1CCN(Cc2ccccc2)C[C@@H]1n1cc(Br)c(=O)c2cnc3c(ccn3COCC[Si](C)(C)C)c21] racemate |
| 61 | 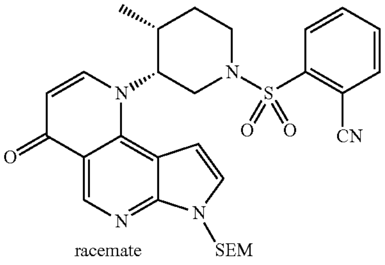 [SMILES: C[C@@H]1CCN(S(=O)(=O)c2ccccc2C#N)C[C@@H]1n1ccc(=O)c2cnc3c(ccn3COCC[Si](C)(C)C)c21] racemate |
| 62 | 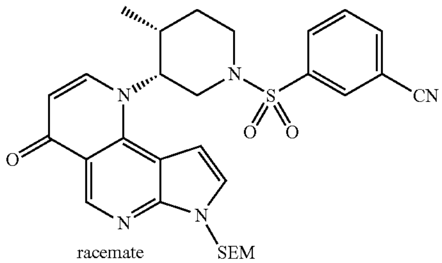 [SMILES: C[C@@H]1CCN(S(=O)(=O)c2cccc(C#N)c2)C[C@@H]1n1ccc(=O)c2cnc3c(ccn3COCC[Si](C)(C)C)c21] racemate |
| 63 | 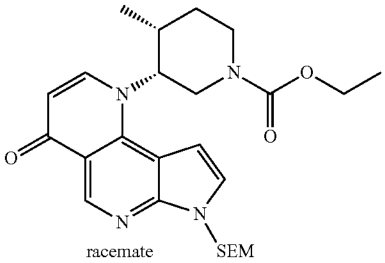 [SMILES: CCOC(=O)N1CC[C@@H](C)[C@@H](n2ccc(=O)c3cnc4c(ccn4COCC[Si](C)(C)C)c32)C1] racemate |
| 64 | 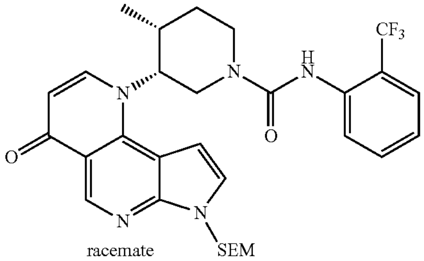 [SMILES: C[C@@H]1CCN(C(=O)Nc2ccccc2C(F)(F)F)C[C@@H]1n1ccc(=O)c2cnc3c(ccn3COCC[Si](C)(C)C)c21] racemate |
| 65 | 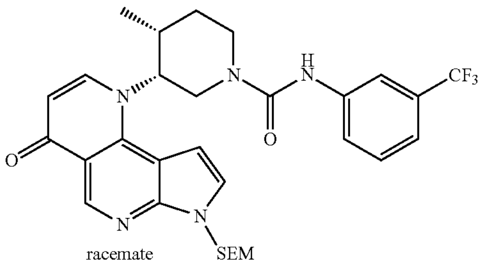 [SMILES: C[C@@H]1CCN(C(=O)Nc2cccc(C(F)(F)F)c2)C[C@@H]1n1ccc(=O)c2cnc3c(ccn3COCC[Si](C)(C)C)c21] racemate |
| 66 | 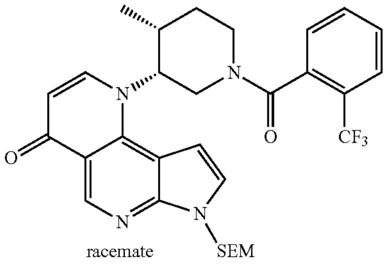 [SMILES: C[C@@H]1CCN(C(=O)c2ccccc2C(F)(F)F)C[C@@H]1n1ccc(=O)c2cnc3c(ccn3COCC[Si](C)(C)C)c21] racemate |

TABLE[b] 29-continued
| Rf | Structure |
|---|---|
| 67 | 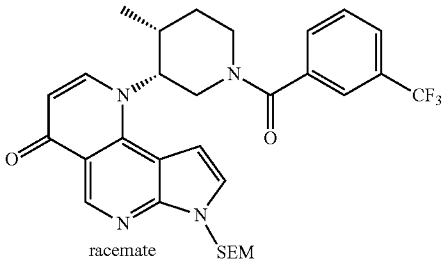 [SMILES: C[C@@H]1CCN(C(=O)c2cccc(C(F)(F)F)c2)C[C@@H]1n1ccc(=O)c2cnc3c(ccn3COCC[Si](C)(C)C)c21] racemate |
| 68 | 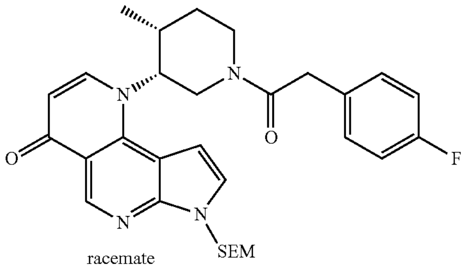 [SMILES: C[C@@H]1CCN(C(=O)Cc2ccc(F)cc2)C[C@@H]1n1ccc(=O)c2cnc3c(ccn3COCC[Si](C)(C)C)c21] racemate |
| 69 | 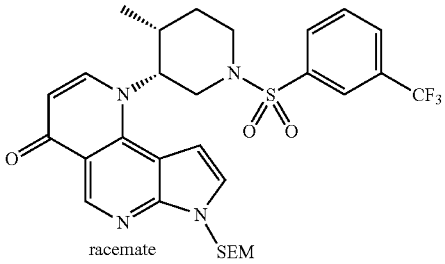 [SMILES: C[C@@H]1CCN(S(=O)(=O)c2cccc(C(F)(F)F)c2)C[C@@H]1n1ccc(=O)c2cnc3c(ccn3COCC[Si](C)(C)C)c21] racemate |
TABLE[b] 30
| Rf | Structure |
|---|---|
| 70 | 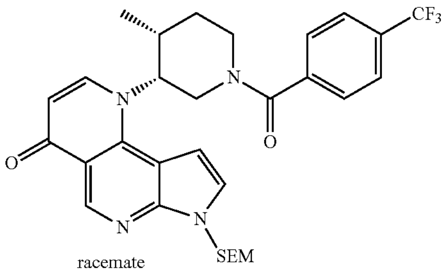 [SMILES: C[C@@H]1CCN(C(=O)c2ccc(C(F)(F)F)cc2)C[C@@H]1n1ccc(=O)c2cnc3c(ccn3COCC[Si](C)(C)C)c21] racemate |
| 71 | 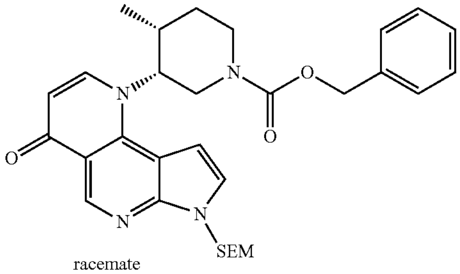 [SMILES: C[C@@H]1CCN(C(=O)OCc2ccccc2)C[C@@H]1n1ccc(=O)c2cnc3c(ccn3COCC[Si](C)(C)C)c21] racemate |
TABLE[b] 30-continued
| Rf | Structure |
|---|---|
| 72 | 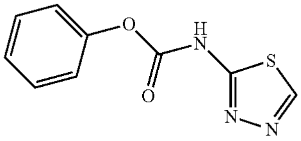 [SMILES: O=C(Nc1nncs1)Oc1ccccc1] |
| 73 | 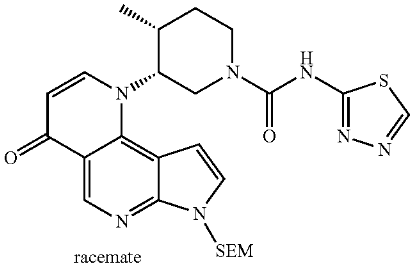 [SMILES: C[C@@H]1CCN(C(=O)Nc2nncs2)C[C@@H]1n1ccc(=O)c2cnc3c(ccn3COCC[Si](C)(C)C)c21] racemate |
| 74 | 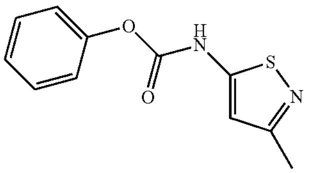 [SMILES: Cc1cc(NC(=O)Oc2ccccc2)sn1] |
| 75 | 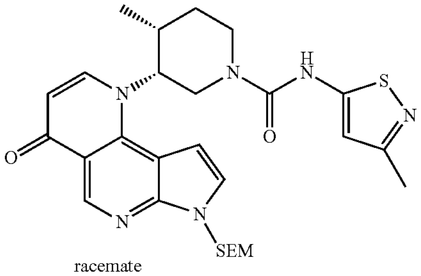 [SMILES: Cc1cc(NC(=O)N2CC[C@@H](C)[C@@H](n3ccc(=O)c4cnc5c(ccn5COCC[Si](C)(C)C)c43)C2)sn1] racemate |
| 76 | 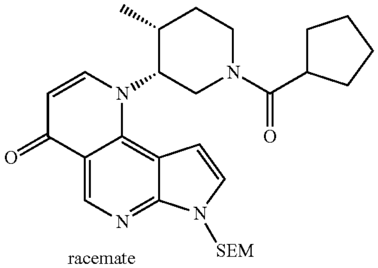 [SMILES: C[C@@H]1CCN(C(=O)C2CCCC2)C[C@@H]1n1ccc(=O)c2cnc3c(ccn3COCC[Si](C)(C)C)c21] racemate |
| 77 | 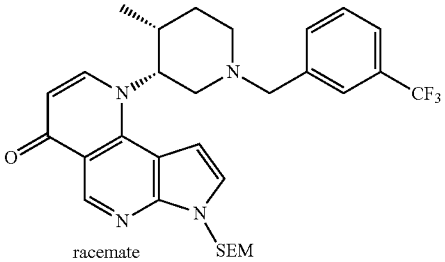 [SMILES: C[C@@H]1CCN(Cc2cccc(C(F)(F)F)c2)C[C@@H]1n1ccc(=O)c2cnc3c(ccn3COCC[Si](C)(C)C)c21] racemate |

TABLE[b] 30-continued
| Rf | Structure |
|---|---|
| 78 | 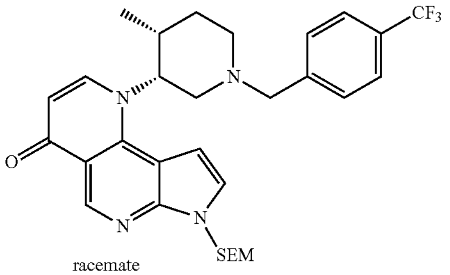 [SMILES: C[C@@H]1CCN(Cc2ccc(C(F)(F)F)cc2)C[C@@H]1n1ccc(=O)c2cnc3c(ccn3COCC[Si](C)(C)C)c21] racemate |
| 79 | 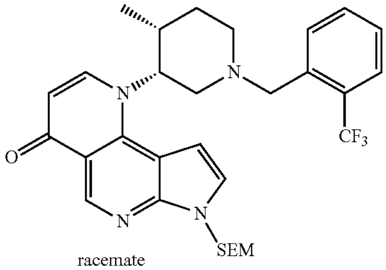 [SMILES: C[C@@H]1CCN(Cc2ccccc2C(F)(F)F)C[C@@H]1n1ccc(=O)c2cnc3c(ccn3COCC[Si](C)(C)C)c21] racemate |
| 80 | 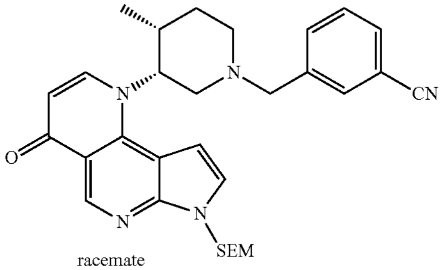 [SMILES: C[C@@H]1CCN(Cc2cccc(C#N)c2)C[C@@H]1n1ccc(=O)c2cnc3c(ccn3COCC[Si](C)(C)C)c21] racemate |
| 81 | 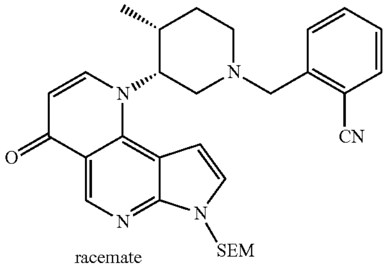 [SMILES: C[C@@H]1CCN(Cc2ccccc2C#N)C[C@@H]1n1ccc(=O)c2cnc3c(ccn3COCC[Si](C)(C)C)c21] racemate |
| 82 | 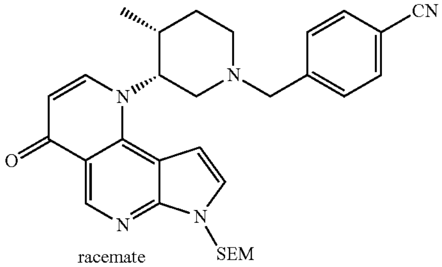 [SMILES: C[C@@H]1CCN(Cc2ccc(C#N)cc2)C[C@@H]1n1ccc(=O)c2cnc3c(ccn3COCC[Si](C)(C)C)c21] racemate |
| 83 | 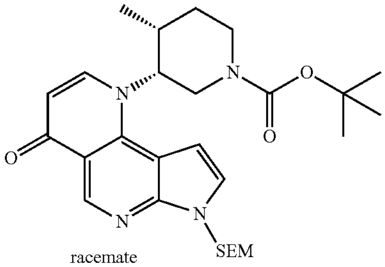 [SMILES: C[C@@H]1CCN(C(=O)OC(C)(C)C)C[C@@H]1n1ccc(=O)c2cnc3c(ccn3COCC[Si](C)(C)C)c21] racemate |
| 84 | 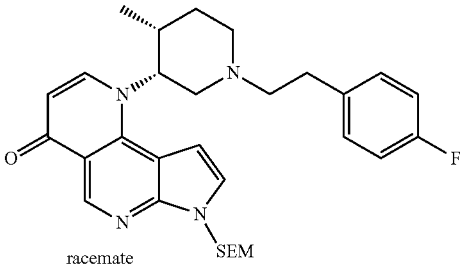 [SMILES: C[C@@H]1CCN(CCc2ccc(F)cc2)C[C@@H]1n1ccc(=O)c2cnc3c(ccn3COCC[Si](C)(C)C)c21] racemate |
| 85 | 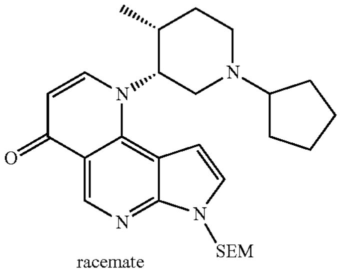 [SMILES: C[C@@H]1CCN(C2CCCC2)C[C@@H]1n1ccc(=O)c2cnc3c(ccn3COCC[Si](C)(C)C)c21] racemate |
| 86a | 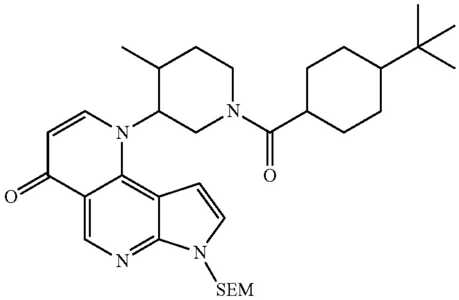 less polar fraction |
| 86b | 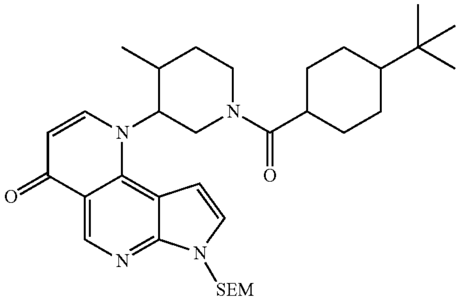 more polar fraction |

TABLE[b] 30-continued
| Rf | Structure |
|---|---|
| 87 | 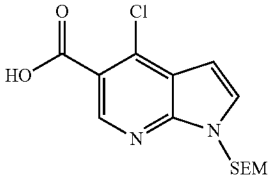 [SMILES: C[Si](C)(C)CCOCn1ccc2c(Cl)c(C(=O)O)cnc21] |
| 88 | 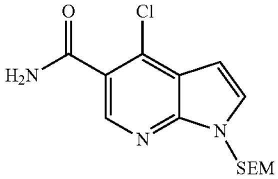 [SMILES: C[Si](C)(C)CCOCn1ccc2c(Cl)c(C(N)=O)cnc21] |
| 89 | 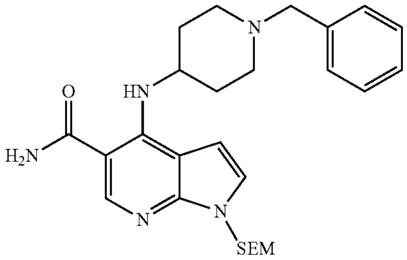 [SMILES: C[Si](C)(C)CCOCn1ccc2c(NC3CCN(Cc4ccccc4)CC3)c(C(N)=O)cnc21] |
TABLE[b] 31
| Rf | Structure |
|---|---|
| 90 | 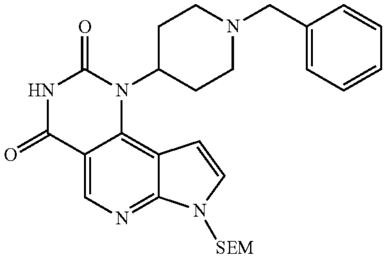 [SMILES: C[Si](C)(C)CCOCn1ccc2c1ncc1c(=O)[nH]c(=O)n(C3CCN(Cc4ccccc4)CC3)c12] |
| 91 | 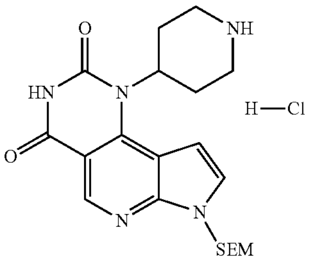 |
| 92 | 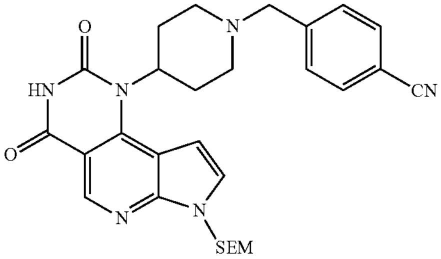 [SMILES: C[Si](C)(C)CCOCn1ccc2c1ncc1c(=O)[nH]c(=O)n(C3CCN(Cc4ccc(C#N)cc4)CC3)c12] |
TABLE[b] 31-continued
| Rf | Structure |
|---|---|
| 93 | 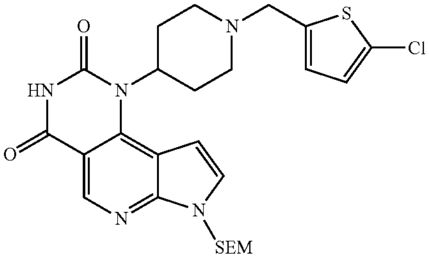 [SMILES: C[Si](C)(C)CCOCn1ccc2c1ncc1c(=O)[nH]c(=O)n(C3CCN(Cc4ccc(Cl)s4)CC3)c12] |
| 94 | 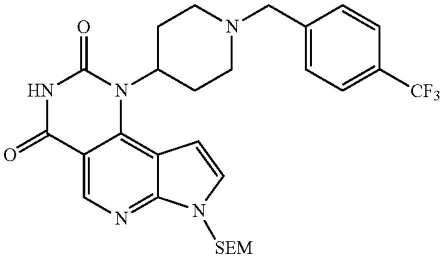 [SMILES: C[Si](C)(C)CCOCn1ccc2c1ncc1c(=O)[nH]c(=O)n(C3CCN(Cc4ccc(C(F)(F)F)cc4)CC3)c12] |
| 95 | 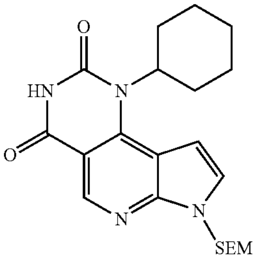 [SMILES: C[Si](C)(C)CCOCn1ccc2c1ncc1c(=O)[nH]c(=O)n(C3CCCCC3)c12] |
| 96 | 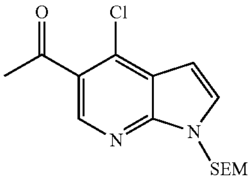 [SMILES: CC(=O)c1cnc2c(ccn2COCC[Si](C)(C)C)c1Cl] |
| 97 | 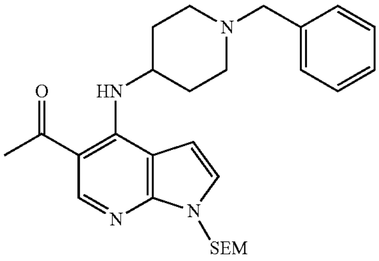 [SMILES: CC(=O)c1cnc2c(ccn2COCC[Si](C)(C)C)c1NC1CCN(Cc2ccccc2)CC1] |
| 98 | 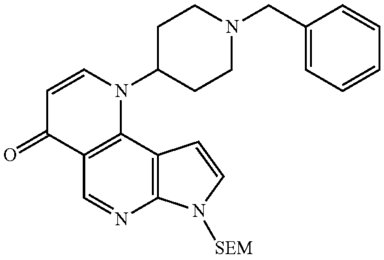 [SMILES: C[Si](C)(C)CCOCn1ccc2c1ncc1c(=O)ccn(C3CCN(Cc4ccccc4)CC3)c12] |

TABLE[b] 31-continued
| Rf | Structure |
|---|---|
| 99 | 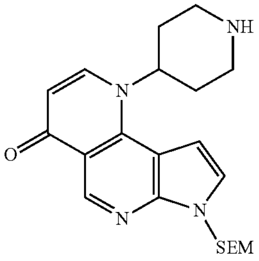 [SMILES: C[Si](C)(C)CCOCn1ccc2c1ncc1c(=O)ccn(C3CCNCC3)c12] |
| 100 | 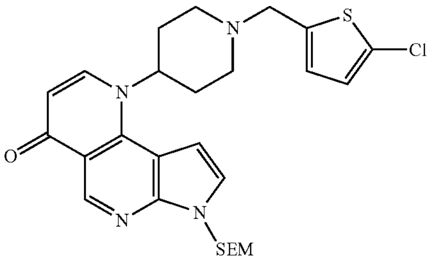 |
| 101 | 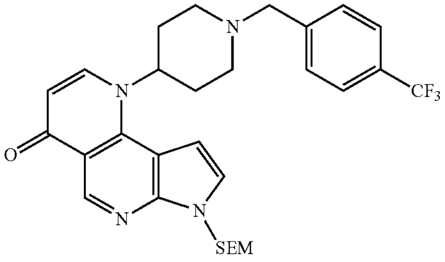 [SMILES: C[Si](C)(C)CCOCn1ccc2c1ncc1c(=O)ccn(C3CCN(Cc4ccc(C(F)(F)F)cc4)CC3)c12] |
| 102 | 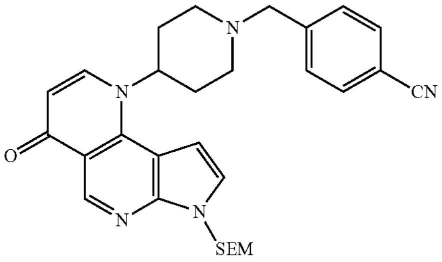 [SMILES: C[Si](C)(C)CCOCn1ccc2c1ncc1c(=O)ccn(C3CCN(Cc4ccc(C#N)cc4)CC3)c12] |
| 103 | 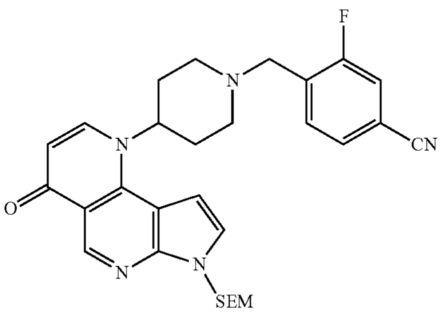 [SMILES: C[Si](C)(C)CCOCn1ccc2c1ncc1c(=O)ccn(C3CCN(Cc4ccc(C#N)cc4F)CC3)c12] |
| 104 | 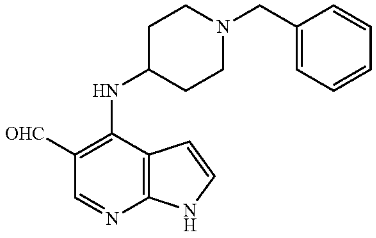 [SMILES: O=Cc1cnc2[nH]ccc2c1NC1CCN(Cc2ccccc2)CC1] |
| 105 | 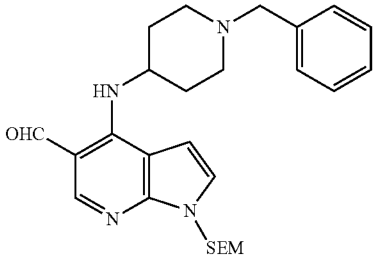 [SMILES: C[Si](C)(C)CCOCn1ccc2c(NC3CCN(Cc4ccccc4)CC3)c(C=O)cnc21] |
| 106 | 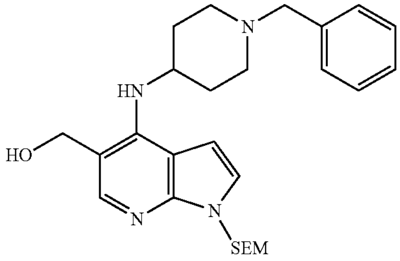 [SMILES: C[Si](C)(C)CCOCn1ccc2c(NC3CCN(Cc4ccccc4)CC3)c(CO)cnc21] |
| 107 | 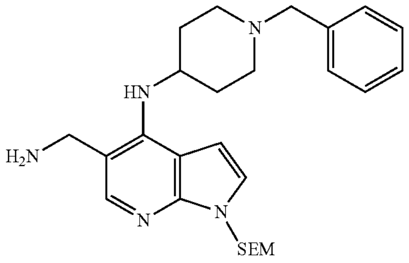 [SMILES: C[Si](C)(C)CCOCn1ccc2c(NC3CCN(Cc4ccccc4)CC3)c(CN)cnc21] |
| 108 | 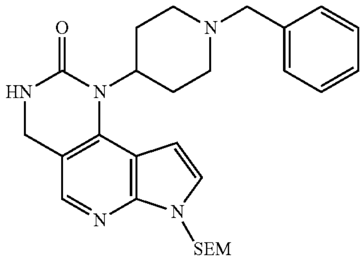 [SMILES: C[Si](C)(C)CCOCn1ccc2c3c(cnc21)CNC(=O)N3C1CCN(Cc2ccccc2)CC1] |
| 109 | 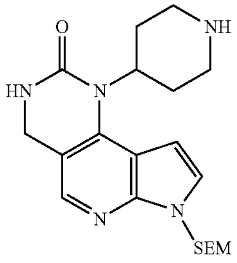 [SMILES: C[Si](C)(C)CCOCn1ccc2c3c(cnc21)CNC(=O)N3C1CCNCC1] |

TABLE[b] 31-continued
| Rf | Structure |
|---|---|
| 110 | 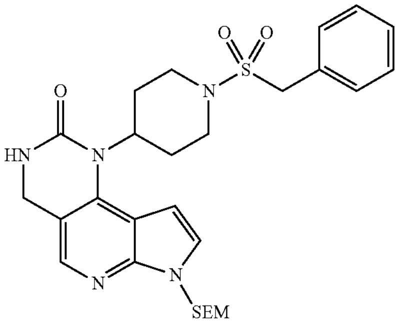 [SMILES: C[Si](C)(C)CCOCn1ccc2c3c(cnc21)CNC(=O)N3C1CCN(S(=O)(=O)Cc2ccccc2)CC1] |
TABLE[b] 32
| Rf | Structure |
|---|---|
| 111 | 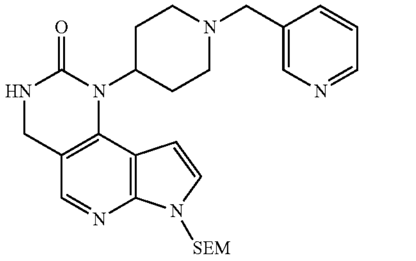 [SMILES: C[Si](C)(C)CCOCn1ccc2c3c(cnc21)CNC(=O)N3C1CCN(Cc2cccnc2)CC1] |
| 112 | 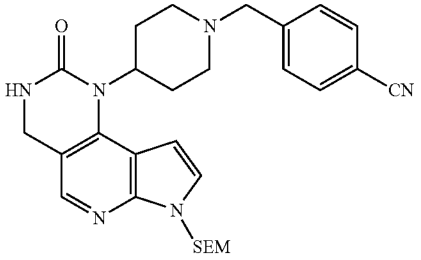 [SMILES: C[Si](C)(C)CCOCn1ccc2c3c(cnc21)CNC(=O)N3C1CCN(Cc2ccc(C#N)cc2)CC1] |
| 113 | 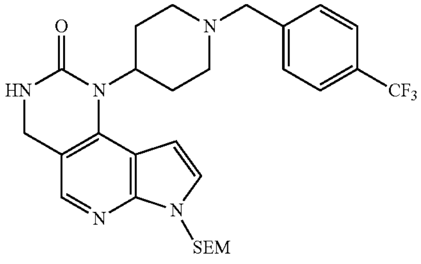 [SMILES: C[Si](C)(C)CCOCn1ccc2c3c(cnc21)CNC(=O)N3C1CCN(Cc2ccc(C(F)(F)F)cc2)CC1] |
| 114 | 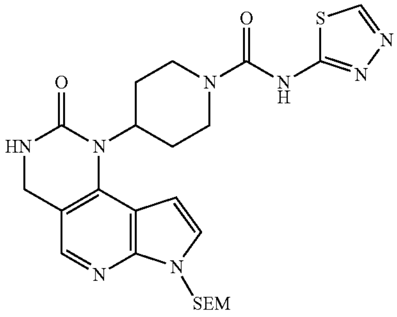 [SMILES: C[Si](C)(C)CCOCn1ccc2c3c(cnc21)CNC(=O)N3C1CCN(C(=O)Nc2nncs2)CC1] |
TABLE[b] 32-continued
| Rf | Structure |
|---|---|
| 115 | 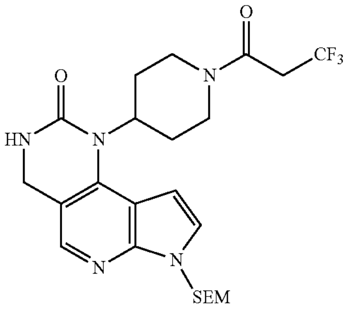 [SMILES: C[Si](C)(C)CCOCn1ccc2c3c(cnc21)CNC(=O)N3C1CCN(C(=O)CC(F)(F)F)CC1] |
| 116 | 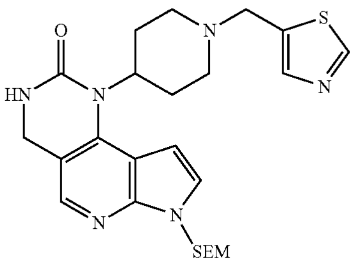 [SMILES: C[Si](C)(C)CCOCn1ccc2c3c(cnc21)CNC(=O)N3C1CCN(Cc2cncs2)CC1] |
| 117 | 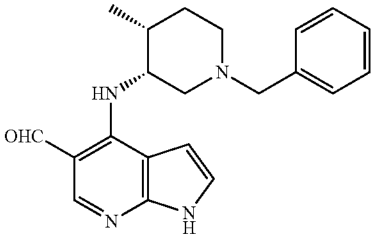 racemate |
| 118 | 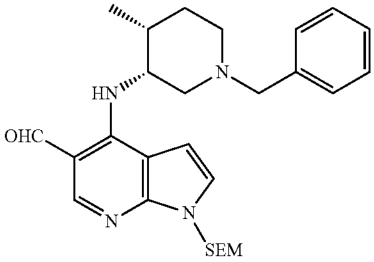 racemate |
| 119 | 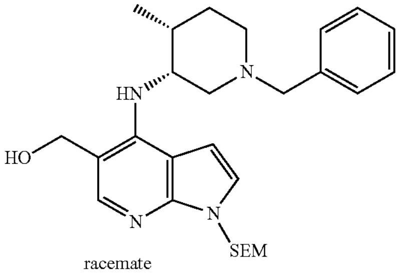 [SMILES: C[C@@H]1CCN(Cc2ccccc2)C[C@@H]1Nc1c(CO)cnc2c1ccn2COCC[Si](C)(C)C] racemate |

TABLE[b] 32-continued
| Rf | Structure |
|---|---|
| 120 | 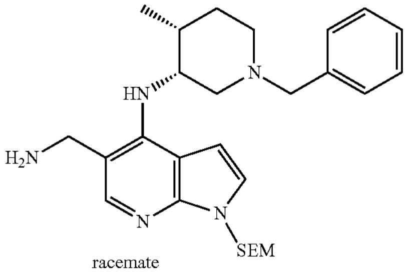 [SMILES: C[C@@H]1CCN(Cc2ccccc2)C[C@@H]1Nc1c(CN)cnc2c1ccn2COCC[Si](C)(C)C] racemate |
| 121 | 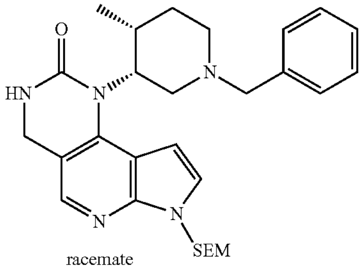 [SMILES: C[C@@H]1CCN(Cc2ccccc2)C[C@@H]1N1C(=O)NCc2cnc3c(ccn3COCC[Si](C)(C)C)c21] racemate |
| 122 | 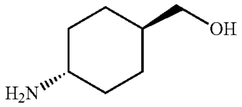 |
| 123 | 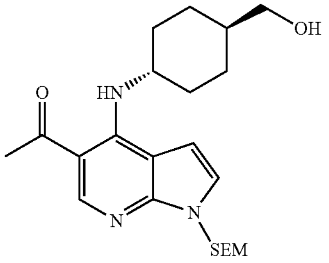 [SMILES: CC(=O)c1cnc2c(ccn2COCC[Si](C)(C)C)c1N[C@H]1CC[C@H](CO)CC1] |
| 124 | 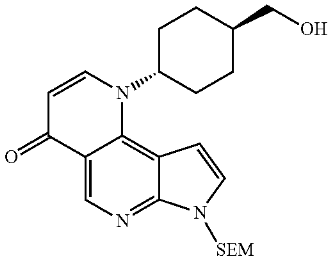 [SMILES: C[Si](C)(C)CCOCn1ccc2c1ncc1c(=O)ccn([C@H]3CC[C@H](CO)CC3)c12] |
| 125 | 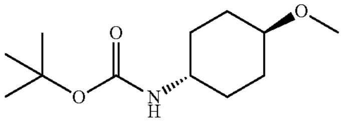 [SMILES: CO[C@H]1CC[C@H](NC(=O)OC(C)(C)C)CC1] |
| 126 | HCl 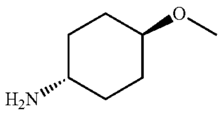 |
| 127 | 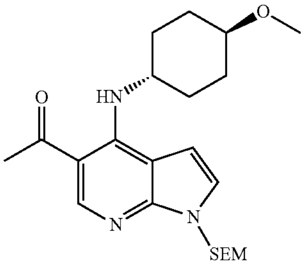 [SMILES: CO[C@H]1CC[C@H](Nc2c(C(C)=O)cnc3c2ccn3COCC[Si](C)(C)C)CC1] |
| 128 | 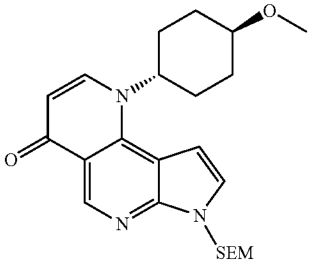 [SMILES: CO[C@H]1CC[C@H](n2ccc(=O)c3cnc4c(ccn4COCC[Si](C)(C)C)c32)CC1] |
| 129 | 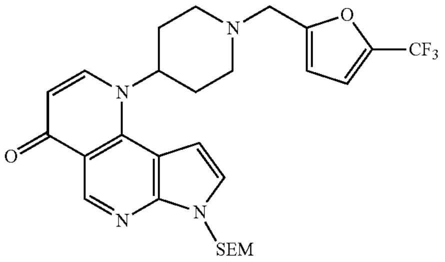 [SMILES: C[Si](C)(C)CCOCn1ccc2c1ncc1c(=O)ccn(C3CCN(Cc4ccc(C(F)(F)F)o4)CC3)c12] |
| 130 | 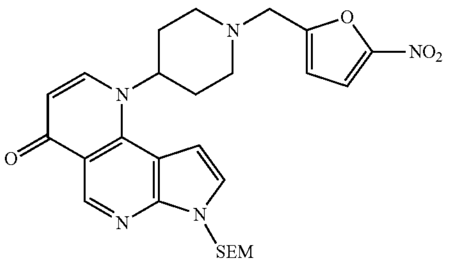 [SMILES: C[Si](C)(C)CCOCn1ccc2c1ncc1c(=O)ccn(C3CCN(Cc4ccc([N+](=O)[O-])o4)CC3)c12] |
| 131 | 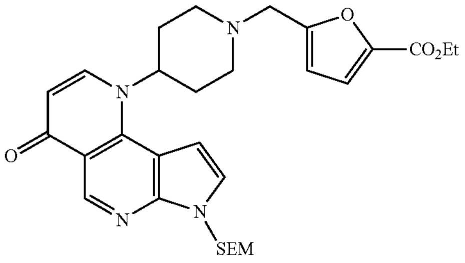 [SMILES: CCOC(=O)c1ccc(CN2CCC(n3ccc(=O)c4cnc5c(ccn5COCC[Si](C)(C)C)c43)CC2)o1] |

TABLE[b] 33
| Rf | Structure |
|---|---|
| 132 | 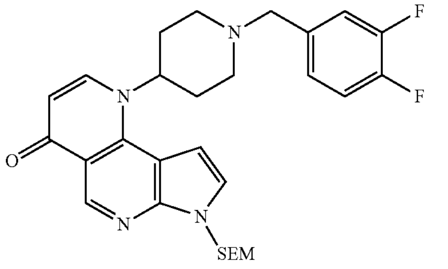 [SMILES: C[Si](C)(C)CCOCn1ccc2c1ncc1c(=O)ccn(C3CCN(Cc4ccc(F)c(F)c4)CC3)c12] |
| 133 | 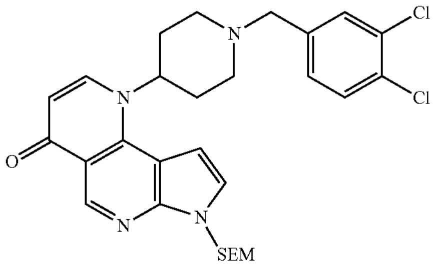 [SMILES: C[Si](C)(C)CCOCn1ccc2c1ncc1c(=O)ccn(C3CCN(Cc4ccc(Cl)c(Cl)c4)CC3)c12] |
| 134 | 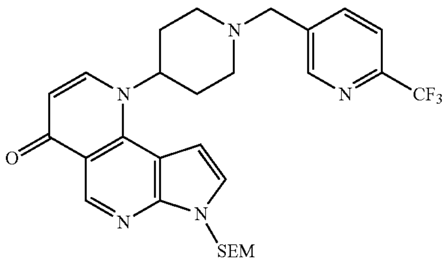 [SMILES: C[Si](C)(C)CCOCn1ccc2c1ncc1c(=O)ccn(C3CCN(Cc4ccc(C(F)(F)F)nc4)CC3)c12] |
| 135 | 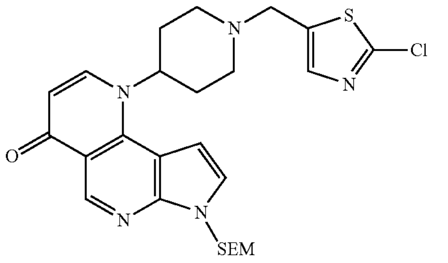 [SMILES: C[Si](C)(C)CCOCn1ccc2c1ncc1c(=O)ccn(C3CCN(Cc4cnc(Cl)s4)CC3)c12] |
| 136 | 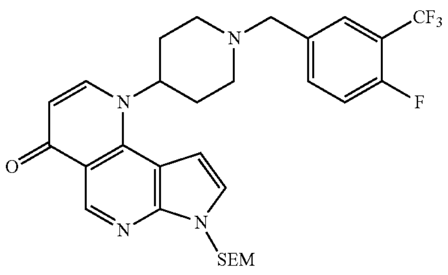 [SMILES: C[Si](C)(C)CCOCn1ccc2c1ncc1c(=O)ccn(C3CCN(Cc4ccc(F)c(C(F)(F)F)c4)CC3)c12] |
| 137 | 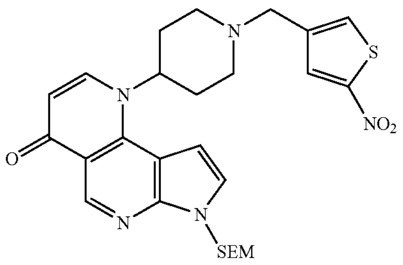 [SMILES: C[Si](C)(C)CCOCn1ccc2c1ncc1c(=O)ccn(C3CCN(Cc4csc([N+](=O)[O-])c4)CC3)c12] |
TABLE[b] 33-continued
| Rf | Structure |
|---|---|
| 138 | 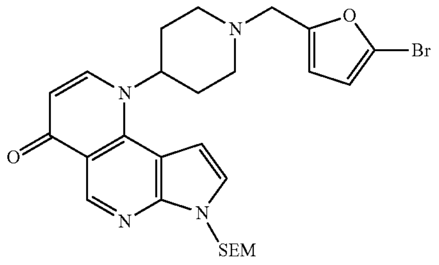 [SMILES: C[Si](C)(C)CCOCn1ccc2c1ncc1c(=O)ccn(C3CCN(Cc4ccc(Br)o4)CC3)c12] |
| 139 | 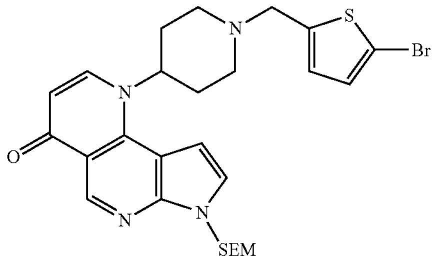 |
| 140 | 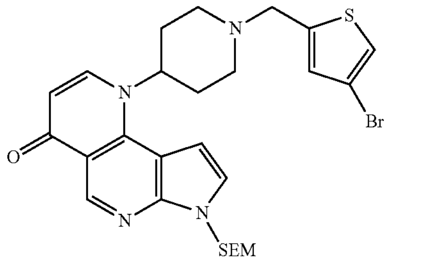 [SMILES: C[Si](C)(C)CCOCn1ccc2c1ncc1c(=O)ccn(C3CCN(Cc4cc(Br)cs4)CC3)c12] |
| 141 | 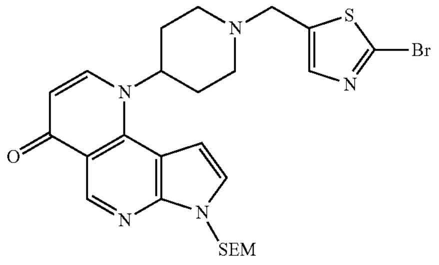 [SMILES: C[Si](C)(C)CCOCn1ccc2c1ncc1c(=O)ccn(C3CCN(Cc4cnc(Br)s4)CC3)c12] |
| 142 | 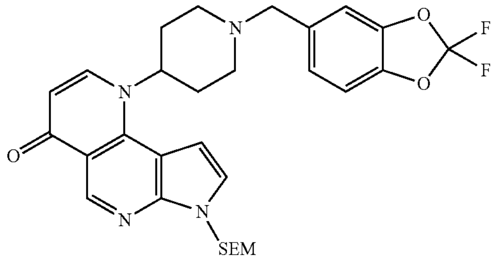 [SMILES: C[Si](C)(C)CCOCn1ccc2c1ncc1c(=O)ccn(C3CCN(Cc4ccc5c(c4)OC(F)(F)O5)CC3)c12] |

TABLE[b] 33-continued
| Rf | Structure |
|---|---|
| 143 | 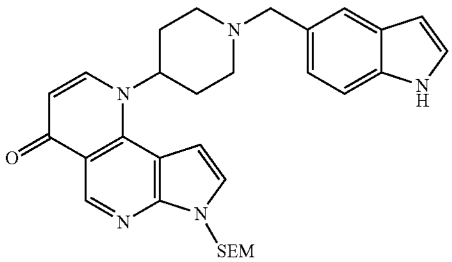 [SMILES: C[Si](C)(C)CCOCn1ccc2c1ncc1c(=O)ccn(C3CCN(Cc4ccc5[nH]ccc5c4)CC3)c12] |
| 144 | 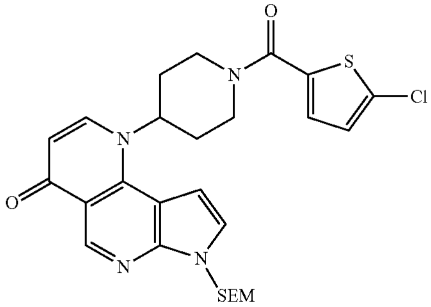 [SMILES: C[Si](C)(C)CCOCn1ccc2c1ncc1c(=O)ccn(C3CCN(C(=O)c4ccc(Cl)s4)CC3)c12] |
TABLE[b] 34
| Rf | Structure |
|---|---|
| 145 | 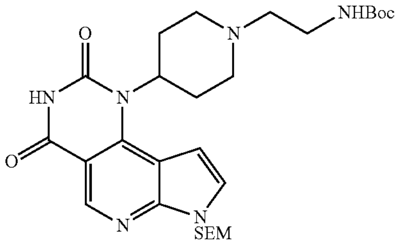 [SMILES: CC(C)(C)OC(=O)NCCN1CCC(n2c(=O)[nH]c(=O)c3cnc4c(ccn4COCC[Si](C)(C)C)c32)CC1] |
| 146 | 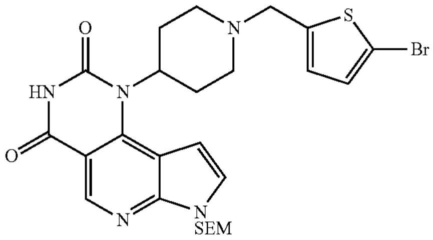 [SMILES: C[Si](C)(C)CCOCn1ccc2c1ncc1c(=O)[nH]c(=O)n(C3CCN(Cc4ccc(Br)s4)CC3)c12] |
| 147 | 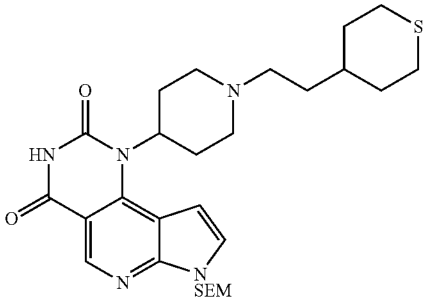 |
TABLE[b] 34-continued
| Rf | Structure |
|---|---|
| 148 | 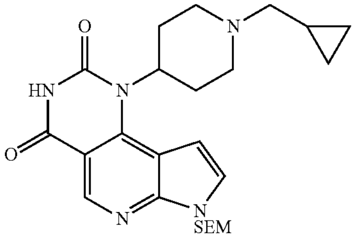 [SMILES: C[Si](C)(C)CCOCn1ccc2c1ncc1c(=O)[nH]c(=O)n(C3CCN(CC4CC4)CC3)c12] |
| 149 | 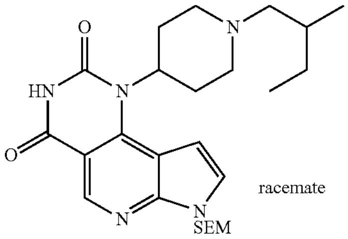 [SMILES: CCC(C)CN1CCC(n2c(=O)[nH]c(=O)c3cnc4c(ccn4COCC[Si](C)(C)C)c32)CC1] racemate |
| 150 | 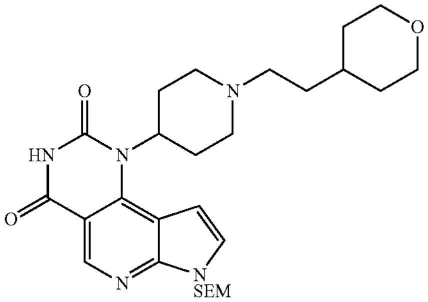 [SMILES: C[Si](C)(C)CCOCn1ccc2c1ncc1c(=O)[nH]c(=O)n(C3CCN(CCC4CCOCC4)CC3)c12] |
| 151 | 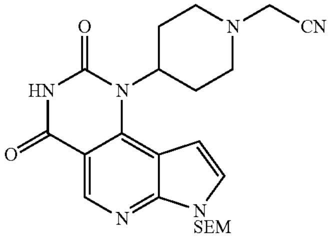 [SMILES: C[Si](C)(C)CCOCn1ccc2c1ncc1c(=O)[nH]c(=O)n(C3CCN(CC#N)CC3)c12] |
| 152 | 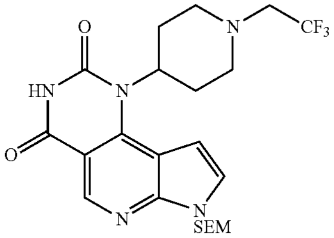 [SMILES: C[Si](C)(C)CCOCn1ccc2c1ncc1c(=O)[nH]c(=O)n(C3CCN(CC(F)(F)F)CC3)c12] |
| 153 | 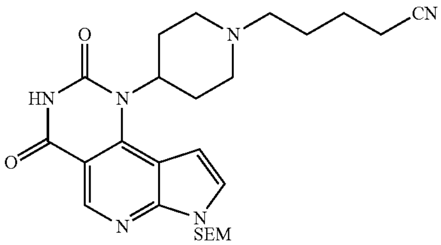 [SMILES: C[Si](C)(C)CCOCn1ccc2c1ncc1c(=O)[nH]c(=O)n(C3CCN(CCCCC#N)CC3)c12] |

TABLE[b] 34-continued
| Rf | Structure |
|---|---|
| 154 | 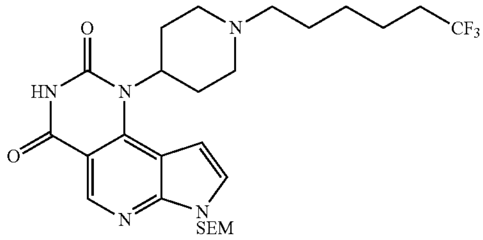 [SMILES: C[Si](C)(C)CCOCn1ccc2c1ncc1c(=O)[nH]c(=O)n(C3CCN(CCCCCC(F)(F)F)CC3)c12] |
| 155 | 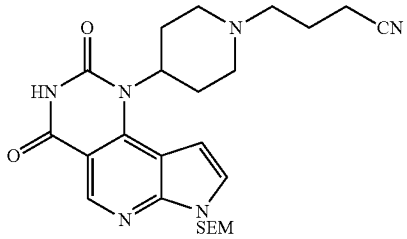 [SMILES: C[Si](C)(C)CCOCn1ccc2c1ncc1c(=O)[nH]c(=O)n(C3CCN(CCCC#N)CC3)c12] |
| 156 | 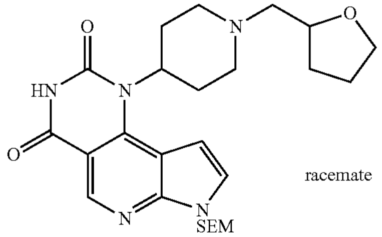 [SMILES: C[Si](C)(C)CCOCn1ccc2c1ncc1c(=O)[nH]c(=O)n(C3CCN(CC4CCCO4)CC3)c12] racemate |
| 157 | 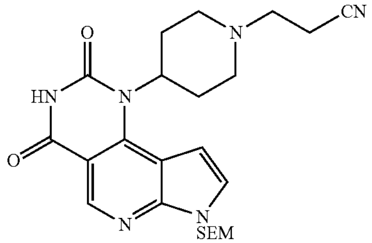 [SMILES: C[Si](C)(C)CCOCn1ccc2c1ncc1c(=O)[nH]c(=O)n(C3CCN(CCC#N)CC3)c12] |
| 158 | 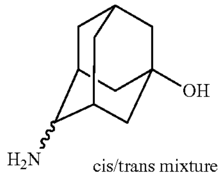 [SMILES: NC1C2CC3CC1CC(O)(C3)C2] cis/trans mixture |
| 159a | 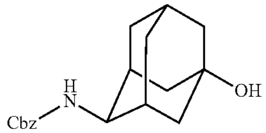 [SMILES: O=C(NC1C2CC3CC1CC(O)(C3)C2)OCc1ccccc1] |
| 159b | 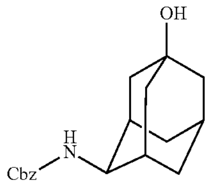 [SMILES: O=C(NC1C2CC3CC1CC(O)(C3)C2)OCc1ccccc1] |
| 160 | 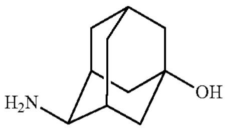 [SMILES: NC1C2CC3CC1CC(O)(C3)C2] |
| 161 | 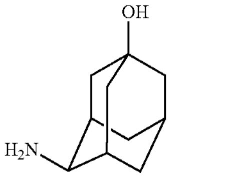 [SMILES: NC1C2CC3CC1CC(O)(C3)C2] |
| 162 | 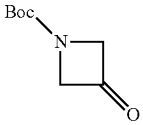 |
| 163 | 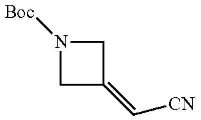 |
| 164 | 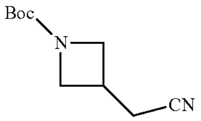 [SMILES: CC(C)(C)OC(=O)N1CC(=CC#N)C1] |
| 165 | 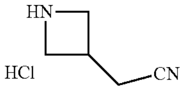 |
| 166 | 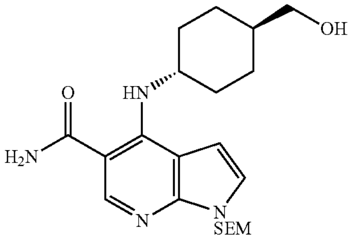 [SMILES: C[Si](C)(C)CCOCn1ccc2c(N[C@H]3CC[C@H](CO)CC3)c(C(N)=O)cnc21] |
| 167 | 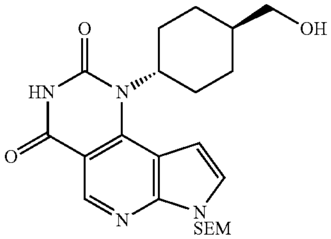 [SMILES: C[Si](C)(C)CCOCn1ccc2c1ncc1c(=O)[nH]c(=O)n([C@H]3CC[C@H](CO)CC3)c12] |
| 168 | 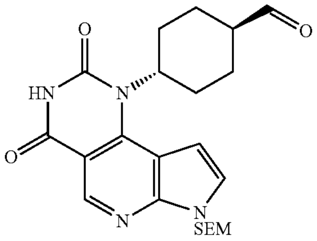 [SMILES: C[Si](C)(C)CCOCn1ccc2c1ncc1c(=O)[nH]c(=O)n([C@H]3CC[C@H](C=O)CC3)c12] |

TABLE[b] 34-continued
| Rf | Structure |
|---|---|
| 169 | 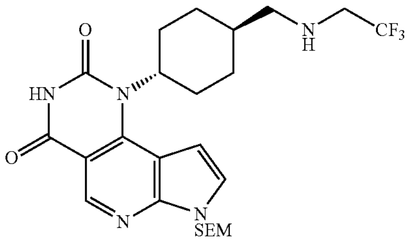 [SMILES: C[Si](C)(C)CCOCn1ccc2c1ncc1c(=O)[nH]c(=O)n([C@H]3CC[C@H](CNCC(F)(F)F)CC3)c12] |
| 170 | 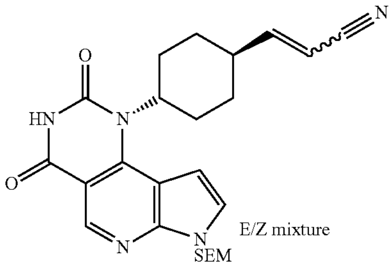 E/Z mixture |
TABLE[b] 35
| Rf | Structure |
|---|---|
| 171 | 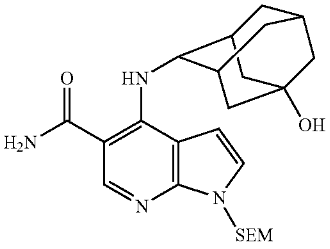 [SMILES: C[Si](C)(C)CCOCn1ccc2c(NC3C4CC5CC3CC(O)(C5)C4)c(C(N)=O)cnc21] |
| 172 | 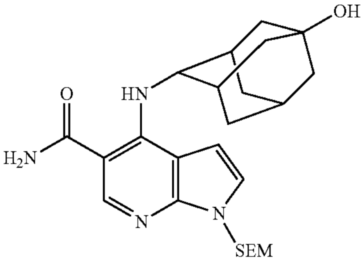 [SMILES: C[Si](C)(C)CCOCn1ccc2c(NC3C4CC5CC3CC(O)(C5)C4)c(C(N)=O)cnc21] |
| 173 | 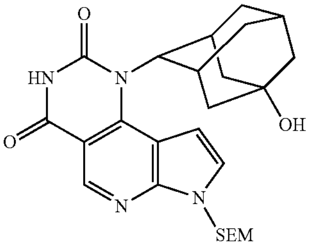 [SMILES: C[Si](C)(C)CCOCn1ccc2c1ncc1c(=O)[nH]c(=O)n(C3C4CC5CC3CC(O)(C5)C4)c12] |
TABLE[b] 35-continued
| Rf | Structure |
|---|---|
| 174 | 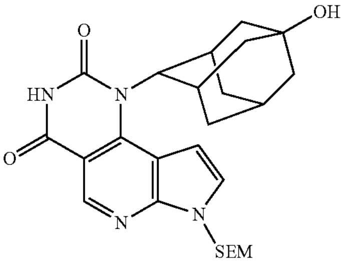 [SMILES: C[Si](C)(C)CCOCn1ccc2c1ncc1c(=O)[nH]c(=O)n(C3C4CC5CC3CC(O)(C5)C4)c12] |
| 175 | 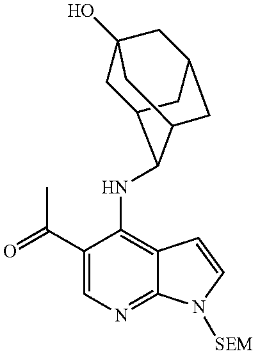 [SMILES: CC(=O)c1cnc2c(ccn2COCC[Si](C)(C)C)c1NC1C2CC3CC1CC(O)(C3)C2] |
| 176 | 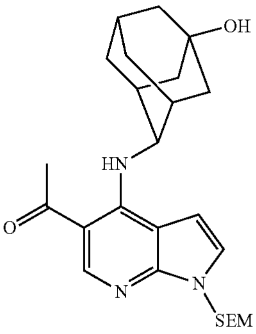 [SMILES: CC(=O)c1cnc2c(ccn2COCC[Si](C)(C)C)c1NC1C2CC3CC1CC(O)(C3)C2] |
| 177 | 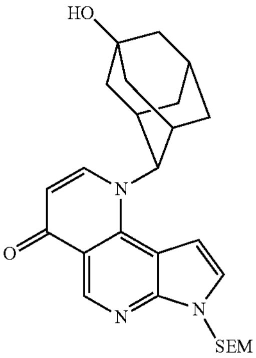 [SMILES: C[Si](C)(C)CCOCn1ccc2c1ncc1c(=O)ccn(C3C4CC5CC3CC(O)(C5)C4)c12] |

TABLE[b] 35-continued
| Rf | Structure |
|---|---|
| 178 | 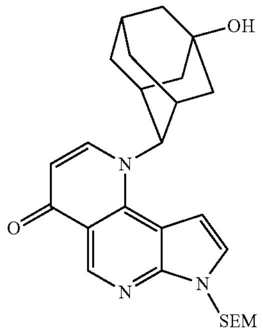 [SMILES: C[Si](C)(C)CCOCn1ccc2c1ncc1c(=O)ccn(C3C4CC5CC3CC(O)(C5)C4)c12] |
| 179 | 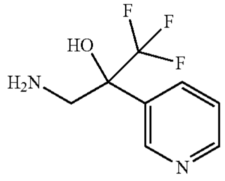 racemate |
TABLE[b] 36
| Ex | Structure |
|---|---|
| 1 | 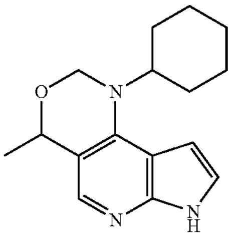 [SMILES: CC1OCN(C2CCCCC2)c2c1cnc1[nH]ccc21] |
| 2 | 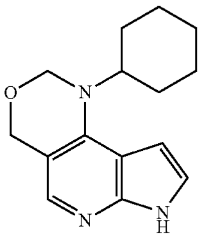 [SMILES: c1cc2c3c(cnc2[nH]1)COCN3C1CCCCC1] |
| 3 | 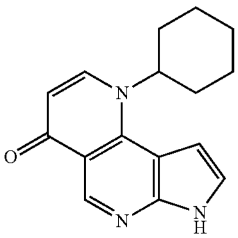 [SMILES: O=c1ccn(C2CCCCC2)c2c1cnc1[nH]ccc12] |
TABLE[b] 36-continued
| Ex | Structure |
|---|---|
| 4 | 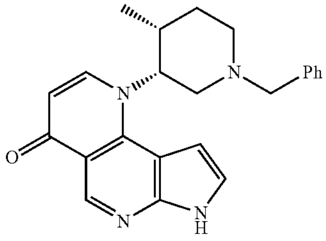 racemate |
| 5 | 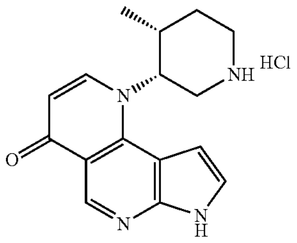 racemate |
| 6a | 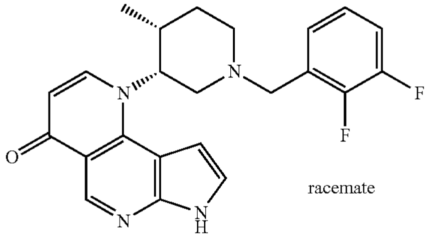 [SMILES: C[C@@H]1CCN(Cc2cccc(F)c2F)C[C@@H]1n1ccc(=O)c2cnc3[nH]ccc3c21] racemate |
| 6b | 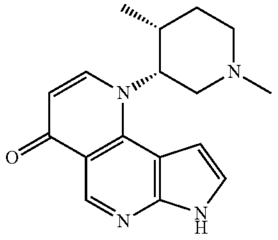 racemate |
| 7 | 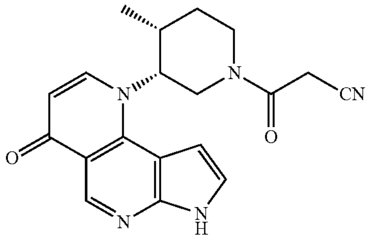 racemate |
| 8 | 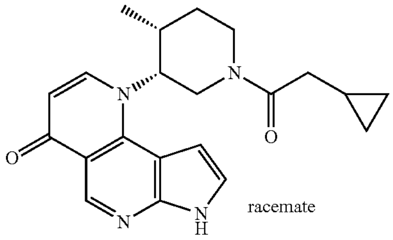 [SMILES: C[C@@H]1CCN(C(=O)CC2CC2)C[C@@H]1n1ccc(=O)c2cnc3[nH]ccc3c21] racemate |

TABLE[b] 36-continued
| Ex | Structure |
|---|---|
| 9 | 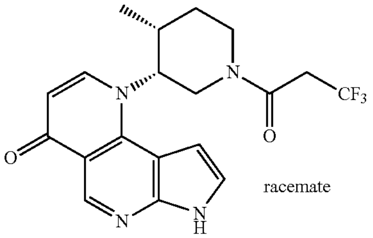 [SMILES: C[C@@H]1CCN(C(=O)CC(F)(F)F)C[C@@H]1n1ccc(=O)c2cnc3[nH]ccc3c21] racemate |
| 10 | 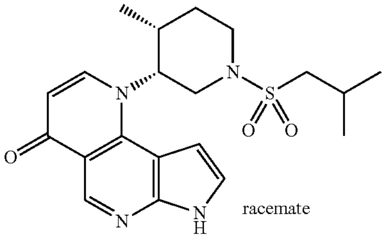 [SMILES: CC(C)CS(=O)(=O)N1CC[C@@H](C)[C@@H](n2ccc(=O)c3cnc4[nH]ccc4c32)C1] racemate |
| 11 | 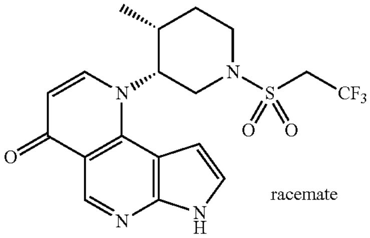 [SMILES: C[C@@H]1CCN(S(=O)(=O)CC(F)(F)F)C[C@@H]1n1ccc(=O)c2cnc3[nH]ccc3c21] racemate |
| 12 | 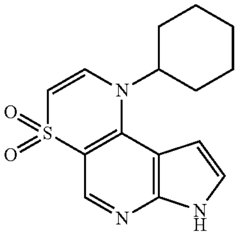 [SMILES: O=S1(=O)C=CN(C2CCCCC2)c2c1cnc1[nH]ccc21] |
| 13 | 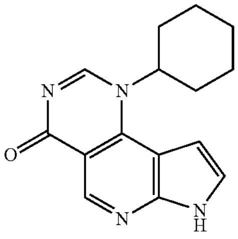 [SMILES: O=c1ncn(C2CCCCC2)c2c1cnc1[nH]ccc12] |
| 14 | 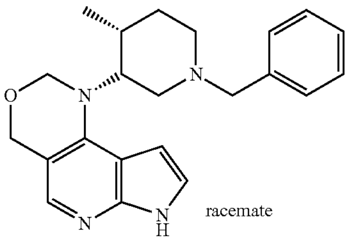 racemate |
TABLE[b] 36-continued
| Ex | Structure |
|---|---|
| 15 | 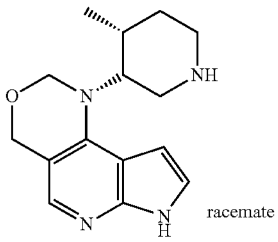 racemate |
| 16 | 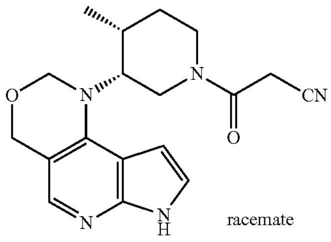 [SMILES: C[C@@H]1CCN(C(=O)CC#N)C[C@@H]1N1COCc2cnc3[nH]ccc3c21] racemate |
| 17 | 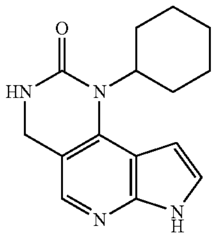 [SMILES: O=C1NCc2cnc3[nH]ccc3c2N1C1CCCCC1] |
| 18 | 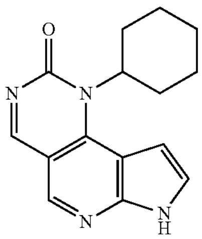 [SMILES: O=c1ncc2cnc3[nH]ccc3c2n1C1CCCCC1] |
| 19 | 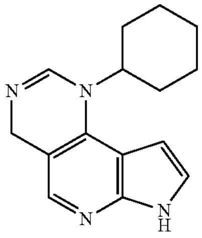 [SMILES: C1=NCc2cnc3[nH]ccc3c2N1C1CCCCC1] |
| 20 | 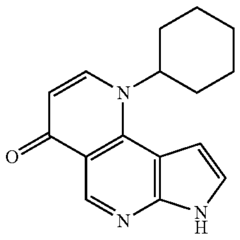 [SMILES: O=c1ccn(C2CCCCC2)c2c1cnc1[nH]ccc12] |

TABLE[b] 37
| Ex | Structure |
| --- | --- |
| 21 | 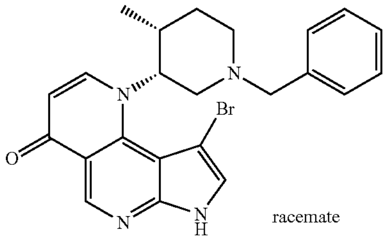 racemate |
| 22 | 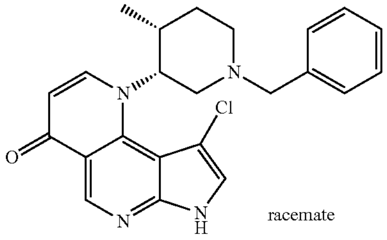 [SMILES: C[C@@H]1CCN(Cc2ccccc2)C[C@@H]1n1ccc(=O)c2cnc3[nH]cc(Cl)c3c21] racemate |
| 23 | 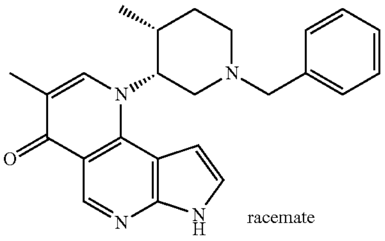 [SMILES: Cc1cn([C@H]2CN(Cc3ccccc3)CC[C@H]2C)c2c(cnc3[nH]ccc32)c1=O] racemate |
| 24 | 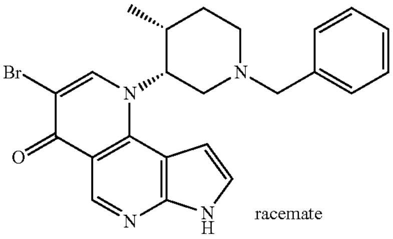 [SMILES: C[C@@H]1CCN(Cc2ccccc2)C[C@@H]1n1cc(Br)c(=O)c2cnc3[nH]ccc3c21] racemate |
| 25 | 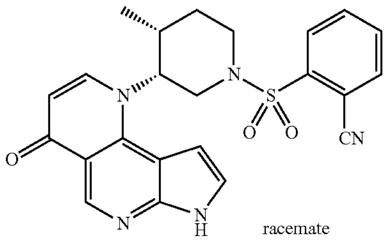 [SMILES: C[C@@H]1CCN(S(=O)(=O)c2ccccc2C#N)C[C@@H]1n1ccc(=O)c2cnc3[nH]ccc3c21] racemate |
| 26 | 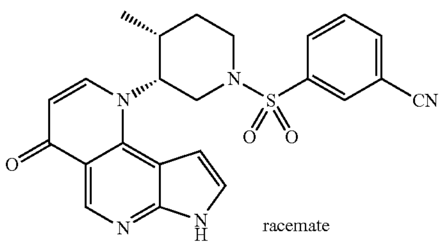 [SMILES: C[C@@H]1CCN(S(=O)(=O)c2cccc(C#N)c2)C[C@@H]1n1ccc(=O)c2cnc3[nH]ccc3c21] racemate |
TABLE[b] 37-continued
| Ex | Structure |
| --- | --- |
| 27 | 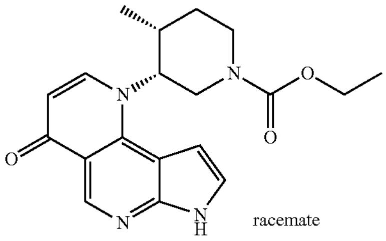 [SMILES: CCOC(=O)N1CC[C@@H](C)[C@@H](n2ccc(=O)c3cnc4[nH]ccc4c32)C1] racemate |
| 28 | 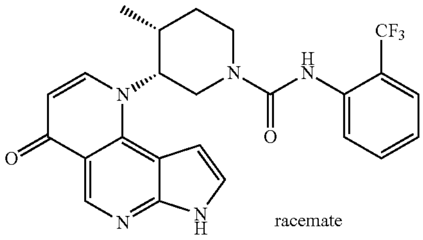 [SMILES: C[C@@H]1CCN(C(=O)Nc2ccccc2C(F)(F)F)C[C@@H]1n1ccc(=O)c2cnc3[nH]ccc3c21] racemate |
| 29 | 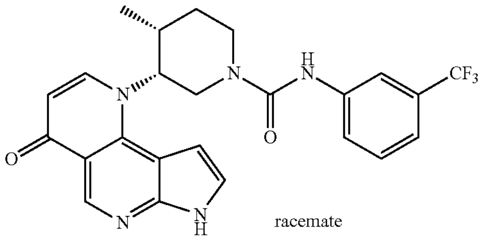 [SMILES: C[C@@H]1CCN(C(=O)Nc2cccc(C(F)(F)F)c2)C[C@@H]1n1ccc(=O)c2cnc3[nH]ccc3c21] racemate |
| 30 | 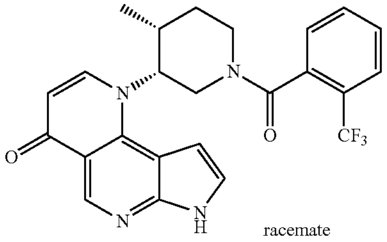 [SMILES: C[C@@H]1CCN(C(=O)c2ccccc2C(F)(F)F)C[C@@H]1n1ccc(=O)c2cnc3[nH]ccc3c21] racemate |
| 31 | 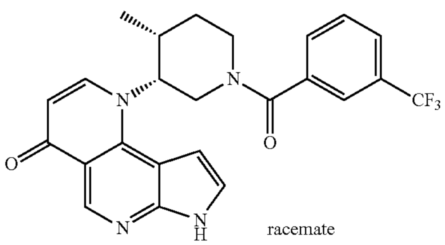 [SMILES: C[C@@H]1CCN(C(=O)c2cccc(C(F)(F)F)c2)C[C@@H]1n1ccc(=O)c2cnc3[nH]ccc3c21] racemate |
| 32 | 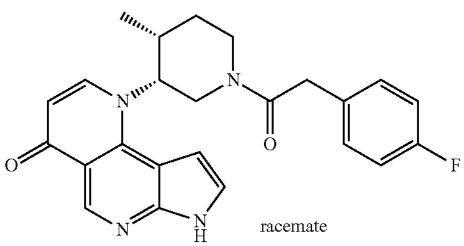 [SMILES: C[C@@H]1CCN(C(=O)Cc2ccc(F)cc2)C[C@@H]1n1ccc(=O)c2cnc3[nH]ccc3c21] racemate |

TABLE[b] 37-continued
| Ex | Structure |
|---|---|
| 33 | 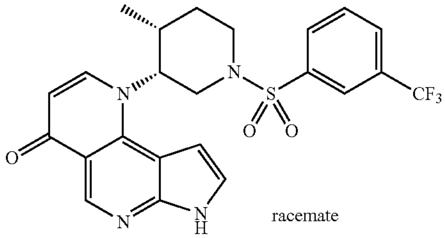 [SMILES: C[C@@H]1CCN(S(=O)(=O)c2cccc(C(F)(F)F)c2)C[C@@H]1n1ccc(=O)c2cnc3[nH]ccc3c21] racemate |
| 34 | 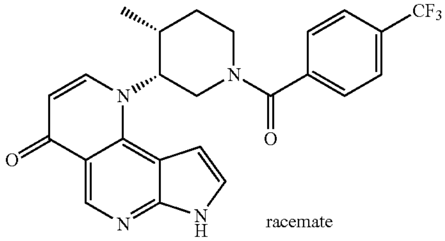 [SMILES: C[C@@H]1CCN(C(=O)c2ccc(C(F)(F)F)cc2)C[C@@H]1n1ccc(=O)c2cnc3[nH]ccc3c21] racemate |
| 35 | 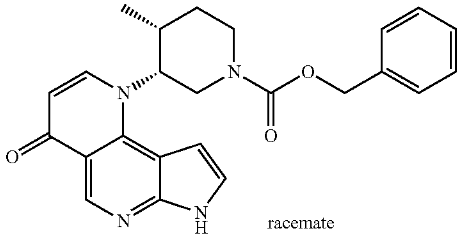 [SMILES: C[C@@H]1CCN(C(=O)OCc2ccccc2)C[C@@H]1n1ccc(=O)c2cnc3[nH]ccc3c21] racemate |
| 36 | 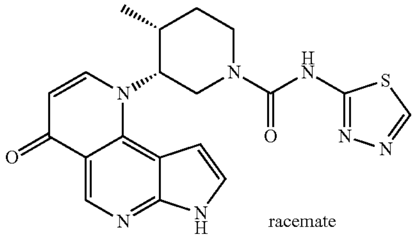 [SMILES: C[C@@H]1CCN(C(=O)Nc2nncs2)C[C@@H]1n1ccc(=O)c2cnc3[nH]ccc3c21] racemate |
| 37 | 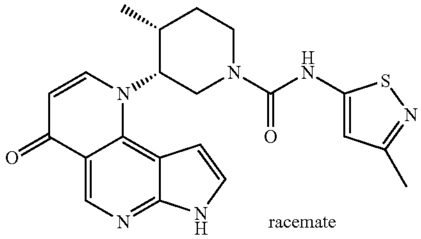 [SMILES: Cc1cc(NC(=O)N2CC[C@@H](C)[C@@H](n3ccc(=O)c4cnc5[nH]ccc5c43)C2)sn1] racemate |
| 38 | 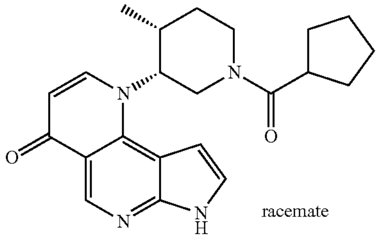 [SMILES: C[C@@H]1CCN(C(=O)C2CCCC2)C[C@@H]1n1ccc(=O)c2cnc3[nH]ccc3c21] racemate |
| 39 | 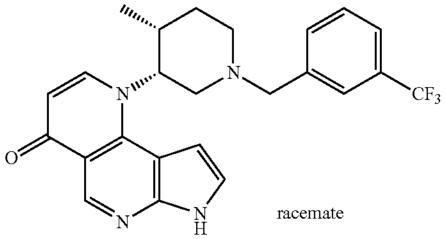 [SMILES: C[C@@H]1CCN(Cc2cccc(C(F)(F)F)c2)C[C@@H]1n1ccc(=O)c2cnc3[nH]ccc3c21] racemate |
| 40 | 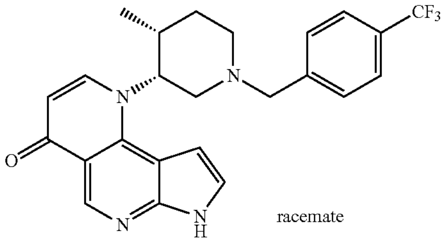 [SMILES: C[C@@H]1CCN(Cc2ccc(C(F)(F)F)cc2)C[C@@H]1n1ccc(=O)c2cnc3[nH]ccc3c21] racemate |
| 41 | 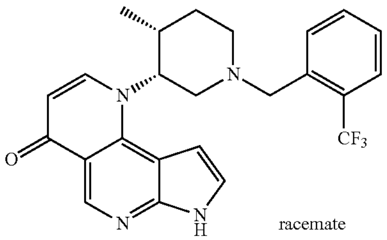 [SMILES: C[C@@H]1CCN(Cc2ccccc2C(F)(F)F)C[C@@H]1n1ccc(=O)c2cnc3[nH]ccc3c21] racemate |
TABLE[b] 38
| Ex | Structure |
|---|---|
| 42 | 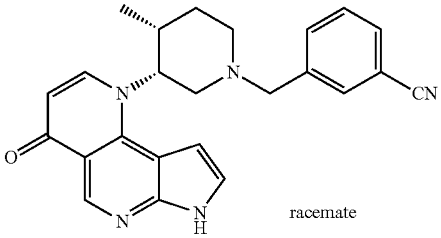 [SMILES: C[C@@H]1CCN(Cc2cccc(C#N)c2)C[C@@H]1n1ccc(=O)c2cnc3[nH]ccc3c21] racemate |
| 43 | 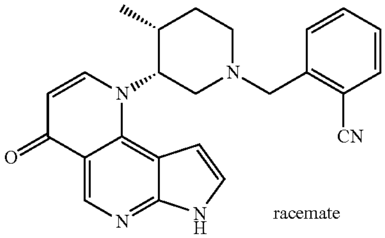 [SMILES: C[C@@H]1CCN(Cc2ccccc2C#N)C[C@@H]1n1ccc(=O)c2cnc3[nH]ccc3c21] racemate |

TABLE[b] 38-continued
| Ex | Structure |
|---|---|
| 44 | 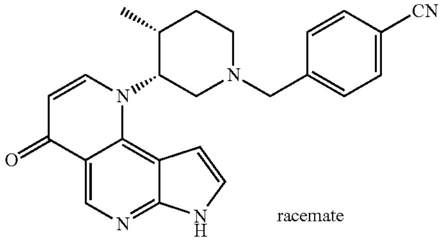 [SMILES: C[C@@H]1CCN(Cc2ccc(C#N)cc2)C[C@@H]1n1ccc(=O)c2cnc3[nH]ccc3c21] racemate |
| 45 | 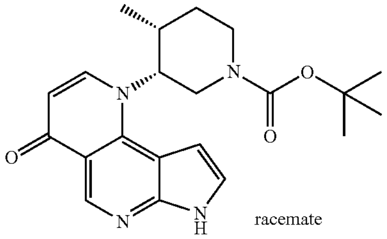 [SMILES: C[C@@H]1CCN(C(=O)OC(C)(C)C)C[C@@H]1n1ccc(=O)c2cnc3[nH]ccc3c21] racemate |
| 46 | 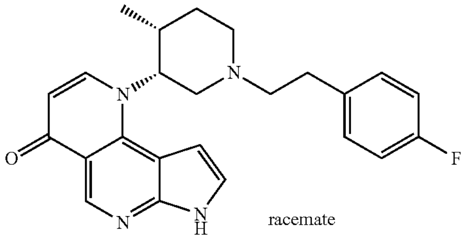 [SMILES: C[C@@H]1CCN(CCc2ccc(F)cc2)C[C@@H]1n1ccc(=O)c2cnc3[nH]ccc3c21] racemate |
| 47 | 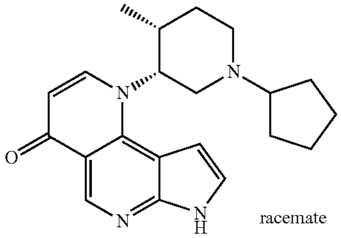 [SMILES: C[C@@H]1CCN(C2CCCC2)C[C@@H]1n1ccc(=O)c2cnc3[nH]ccc3c21] racemate |
| 48a | 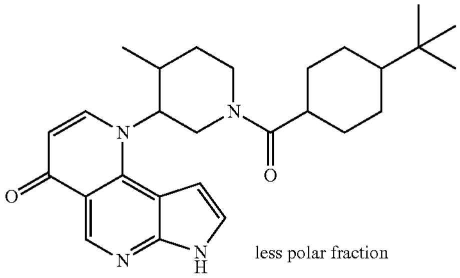 [SMILES: CC1CCN(C(=O)C2CCC(C(C)(C)C)CC2)CC1n1ccc(=O)c2cnc3[nH]ccc3c21] less polar fraction |
| 48b | 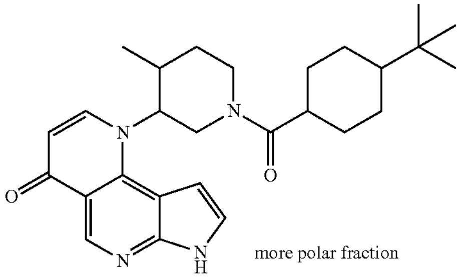 [SMILES: CC1CCN(C(=O)C2CCC(C(C)(C)C)CC2)CC1n1ccc(=O)c2cnc3[nH]ccc3c21] more polar fraction |
TABLE[b] 38-continued
| Ex | Structure |
|---|---|
| 49 | 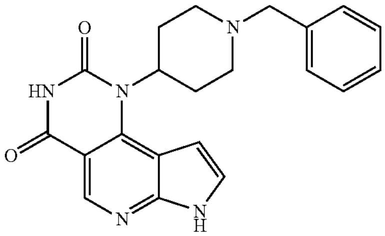 [SMILES: O=c1[nH]c(=O)n(C2CCN(Cc3ccccc3)CC2)c2c1cnc1[nH]ccc12] |
| 50 | 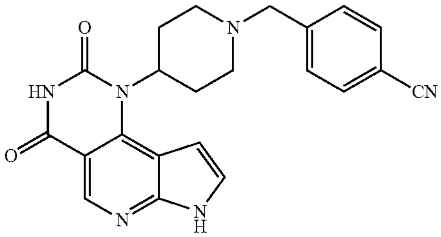 [SMILES: N#Cc1ccc(CN2CCC(n3c(=O)[nH]c(=O)c4cnc5[nH]ccc5c43)CC2)cc1] |
| 51 | 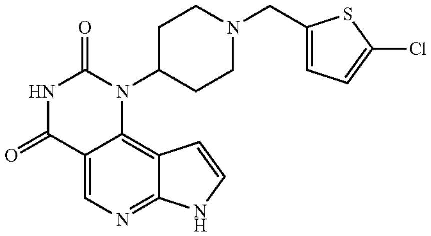 [SMILES: O=c1[nH]c(=O)n(C2CCN(Cc3ccc(Cl)s3)CC2)c2c1cnc1[nH]ccc12] |
| 52 | 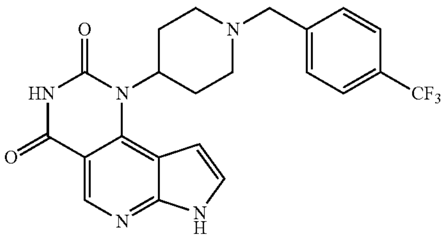 [SMILES: O=c1[nH]c(=O)n(C2CCN(Cc3ccc(C(F)(F)F)cc3)CC2)c2c1cnc1[nH]ccc12] |
| 53 | 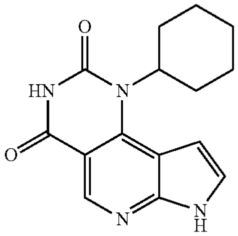 [SMILES: O=c1[nH]c(=O)n(C2CCCCC2)c2c1cnc1[nH]ccc12] |
| 54 | 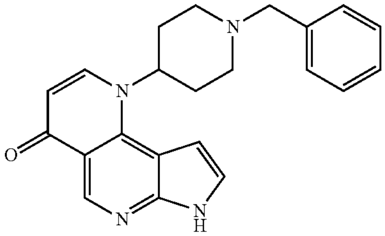 [SMILES: O=c1ccn(C2CCN(Cc3ccccc3)CC2)c2c1cnc1[nH]ccc12] |

TABLE[b] 38-continued
| Ex | Structure |
|---|---|
| 55 | 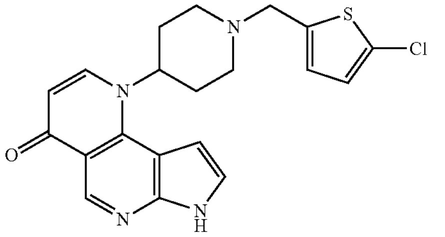 [SMILES: O=c1ccn(C2CCN(Cc3ccc(Cl)s3)CC2)c2c1cnc1[nH]ccc12] |
| 56 | 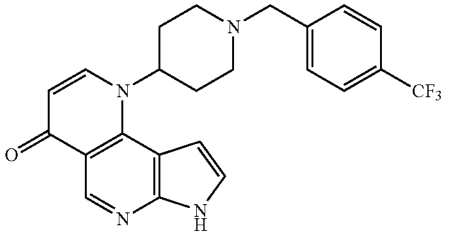 [SMILES: O=c1ccn(C2CCN(Cc3ccc(C(F)(F)F)cc3)CC2)c2c1cnc1[nH]ccc12] |
| 57 | 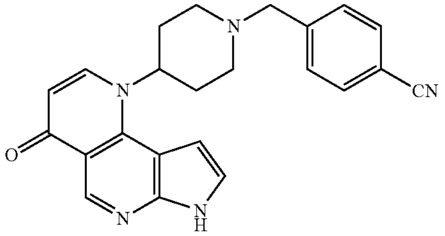 [SMILES: N#Cc1ccc(CN2CCC(n3ccc(=O)c4cnc5[nH]ccc5c43)CC2)cc1] |
| 58 | 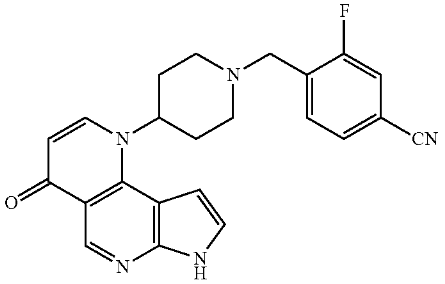 [SMILES: N#Cc1ccc(CN2CCC(n3ccc(=O)c4cnc5[nH]ccc5c43)CC2)c(F)c1] |
| 59 | 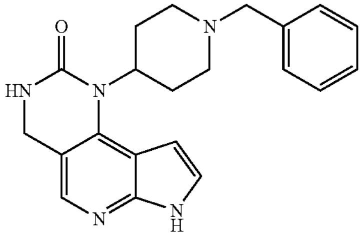 [SMILES: O=C1NCc2cnc3[nH]ccc3c2N1C1CCN(Cc2ccccc2)CC1] |
| 60 | 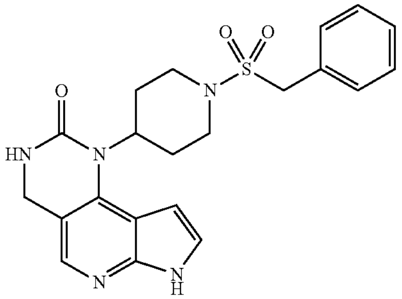 [SMILES: O=C1NCc2cnc3[nH]ccc3c2N1C1CCN(S(=O)(=O)Cc2ccccc2)CC1] |
| 61 | 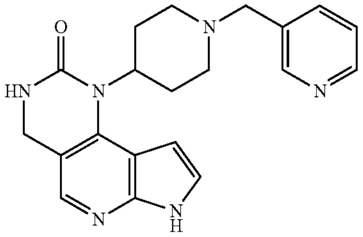 [SMILES: O=C1NCc2cnc3[nH]ccc3c2N1C1CCN(Cc2cccnc2)CC1] |
TABLE[b] 39
| Ex | Structure |
|---|---|
| 62 | 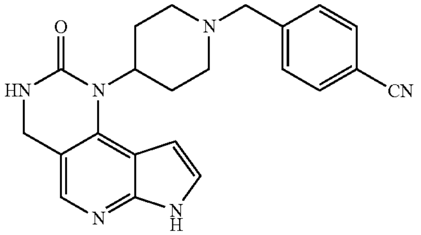 [SMILES: N#Cc1ccc(CN2CCC(N3C(=O)NCc4cnc5[nH]ccc5c43)CC2)cc1] |
| 63 | 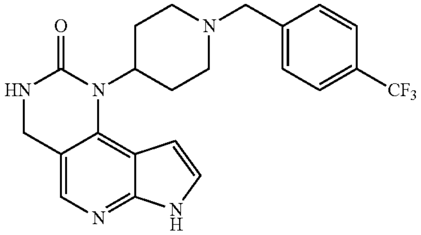 [SMILES: O=C1NCc2cnc3[nH]ccc3c2N1C1CCN(Cc2ccc(C(F)(F)F)cc2)CC1] |
| 64 | 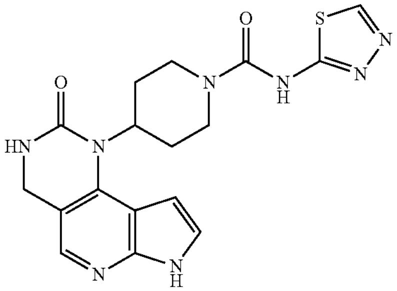 [SMILES: O=C(Nc1nncs1)N1CCC(N2C(=O)NCc3cnc4[nH]ccc4c32)CC1] |
| 65 | 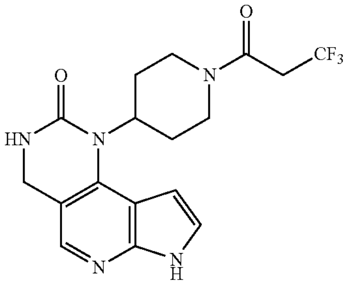 [SMILES: O=C(CC(F)(F)F)N1CCC(N2C(=O)NCc3cnc4[nH]ccc4c32)CC1] |

TABLE[b] 39-continued
| Ex | Structure |
|---|---|
| 66 | 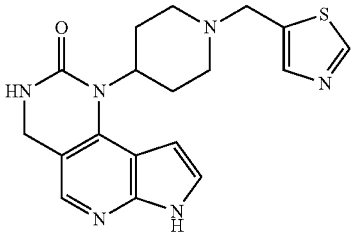 [SMILES: O=C1NCc2cnc3[nH]ccc3c2N1C1CCN(Cc2cncs2)CC1] |
| 67 | 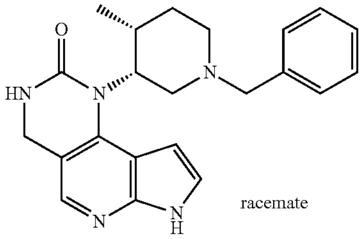 [SMILES: C[C@@H]1CCN(Cc2ccccc2)C[C@@H]1N1C(=O)NCc2cnc3[nH]ccc3c21] racemate |
| 68 | 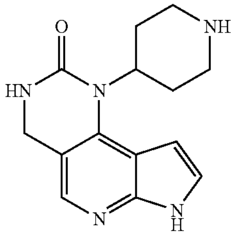 [SMILES: O=C1NCc2cnc3[nH]ccc3c2N1C1CCNCC1] |
| 69 | 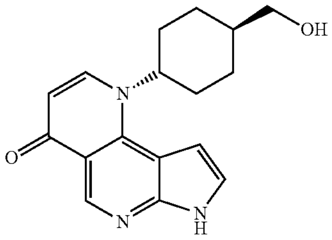 |
| 70 | 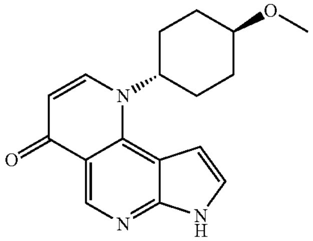 [SMILES: CO[C@H]1CC[C@H](n2ccc(=O)c3cnc4[nH]ccc4c32)CC1] |
| 71 | 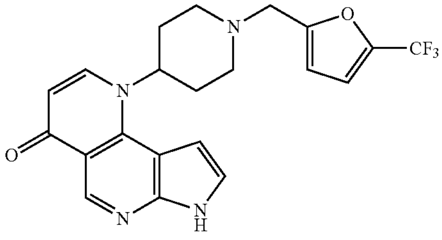 [SMILES: O=c1ccn(C2CCN(Cc3ccc(C(F)(F)F)o3)CC2)c2c1cnc1[nH]ccc12] |
TABLE[b] 39-continued
| Ex | Structure |
|---|---|
| 72 | 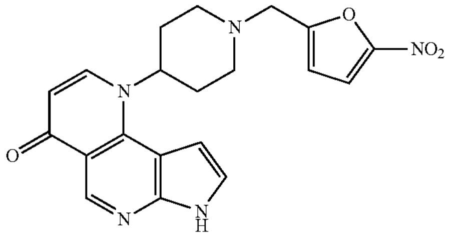 [SMILES: O=c1ccn(C2CCN(Cc3ccc([N+](=O)[O-])o3)CC2)c2c1cnc1[nH]ccc12] |
| 73 | 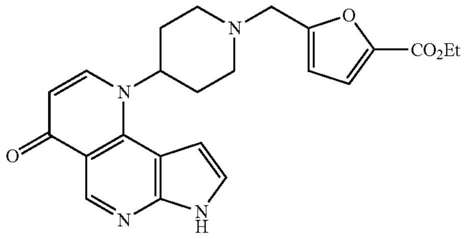 [SMILES: CCOC(=O)c1ccc(CN2CCC(n3ccc(=O)c4cnc5[nH]ccc5c43)CC2)o1] |
| 74 | 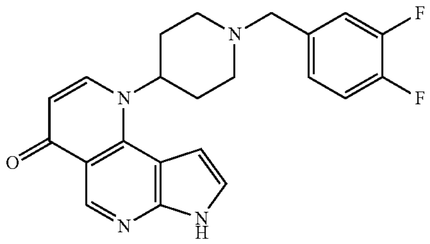 [SMILES: O=c1ccn(C2CCN(Cc3ccc(F)c(F)c3)CC2)c2c1cnc1[nH]ccc12] |
| 75 | 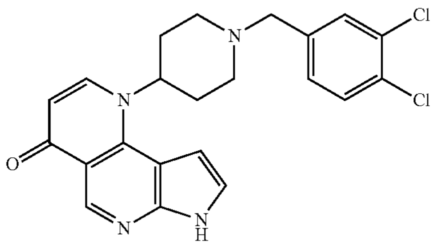 [SMILES: O=c1ccn(C2CCN(Cc3ccc(Cl)c(Cl)c3)CC2)c2c1cnc1[nH]ccc12] |
| 76 | 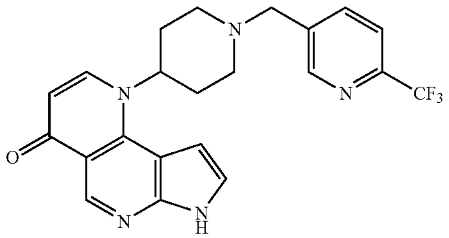 |
| 77 | 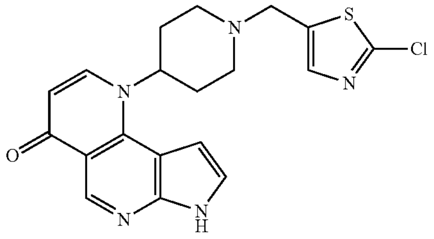 [SMILES: O=c1ccn(C2CCN(Cc3cnc(Cl)s3)CC2)c2c1cnc1[nH]ccc12] |

TABLE[b] 39-continued
| Ex | Structure |
|---|---|
| 78 | 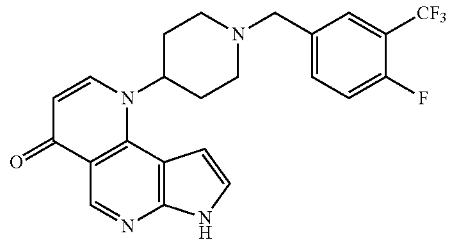 [SMILES: O=c1ccn(C2CCN(Cc3ccc(F)c(C(F)(F)F)c3)CC2)c2c1cnc1[nH]ccc12] |
| 79 | 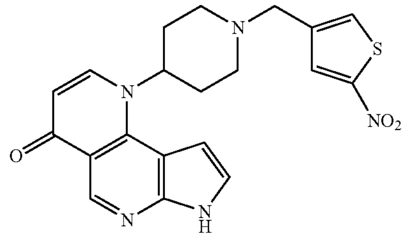 [SMILES: O=c1ccn(C2CCN(Cc3csc([N+](=O)[O-])c3)CC2)c2c1cnc1[nH]ccc12] |
| 80 | 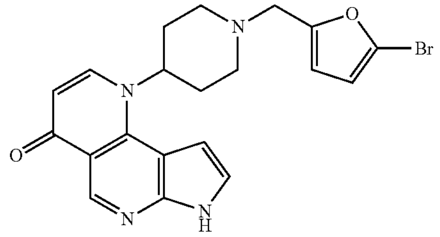 [SMILES: O=c1ccn(C2CCN(Cc3ccc(Br)o3)CC2)c2c1cnc1[nH]ccc12] |
| 81 | 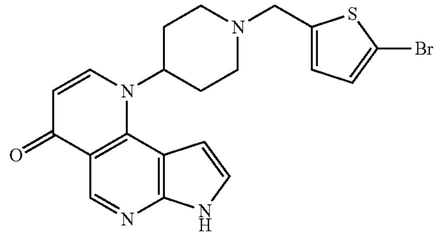 |
| 82 | 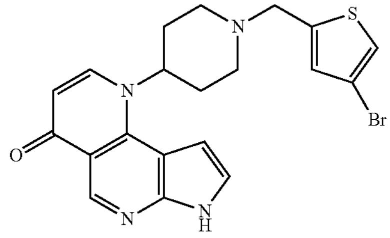 [SMILES: O=c1ccn(C2CCN(Cc3cc(Br)cs3)CC2)c2c1cnc1[nH]ccc12] |
TABLE[b] 40
| Ex | Structure |
|---|---|
| 83 | 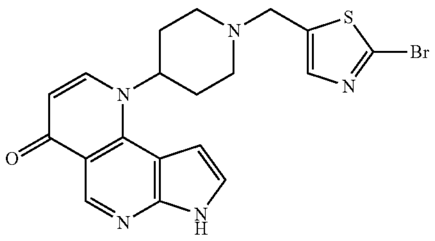 |
TABLE[b] 40-continued
| Ex | Structure |
|---|---|
| 84 | 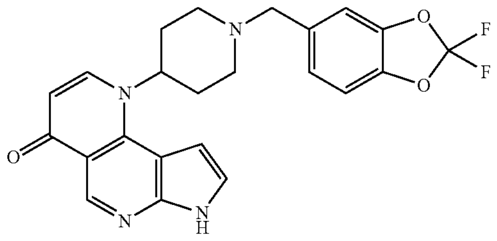 [SMILES: O=c1ccn(C2CCN(Cc3ccc4c(c3)OC(F)(F)O4)CC2)c2c1cnc1[nH]ccc12] |
| 85 | 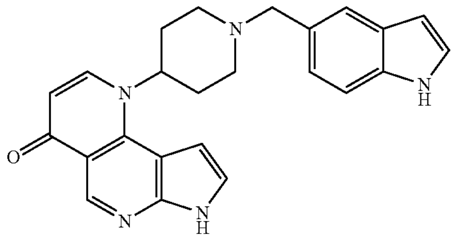 [SMILES: O=c1ccn(C2CCN(Cc3ccc4[nH]ccc4c3)CC2)c2c1cnc1[nH]ccc12] |
| 86 | 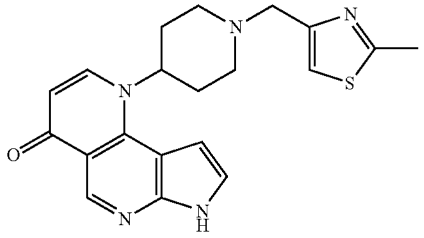 [SMILES: Cc1nc(CN2CCC(n3ccc(=O)c4cnc5[nH]ccc5c43)CC2)cs1] |
| 87 | 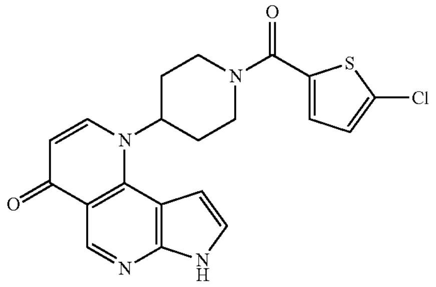 [SMILES: O=C(c1ccc(Cl)s1)N1CCC(n2ccc(=O)c3cnc4[nH]ccc4c32)CC1] |
TABLE[b] 41
| Ex | Structure |
|---|---|
| 88 | 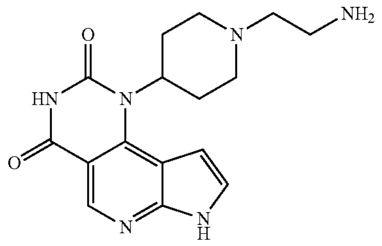 [SMILES: NCCN1CCC(n2c(=O)[nH]c(=O)c3cnc4[nH]ccc4c32)CC1] |

TABLE[b] 41-continued
| Ex | Structure |
|---|---|
| 89 | 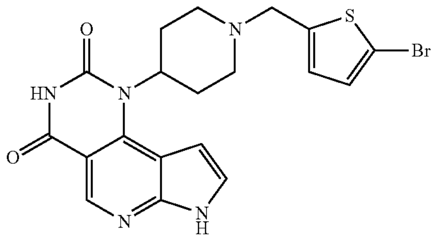 [SMILES: O=c1[nH]c(=O)n(C2CCN(Cc3ccc(Br)s3)CC2)c2c1cnc1[nH]ccc12] |
| 90 | 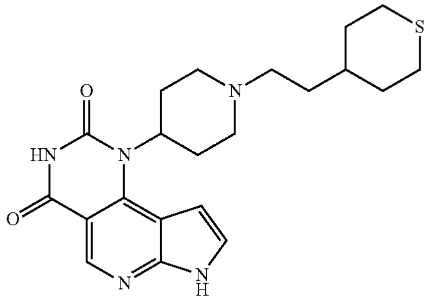 [SMILES: O=c1[nH]c(=O)n(C2CCN(CCC3CCSCC3)CC2)c2c1cnc1[nH]ccc12] |
| 91 | 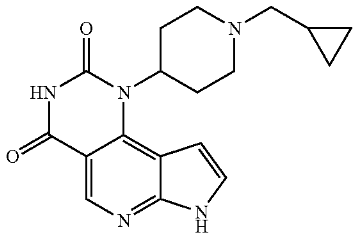 [SMILES: O=c1[nH]c(=O)n(C2CCN(CC3CC3)CC2)c2c1cnc1[nH]ccc12] |
| 92 | 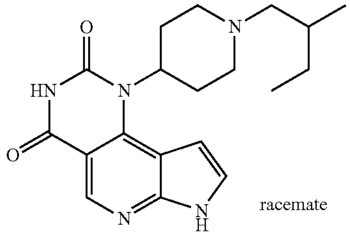 [SMILES: CCC(C)CN1CCC(n2c(=O)[nH]c(=O)c3cnc4[nH]ccc4c32)CC1] racemate |
| 93 | 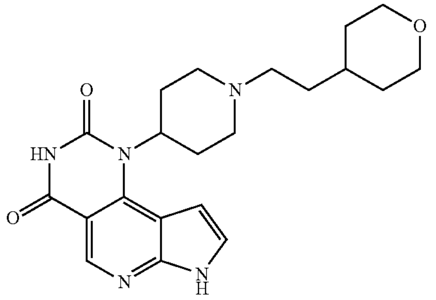 [SMILES: O=c1[nH]c(=O)n(C2CCN(CCC3CCOCC3)CC2)c2c1cnc1[nH]ccc12] |
| 94 | 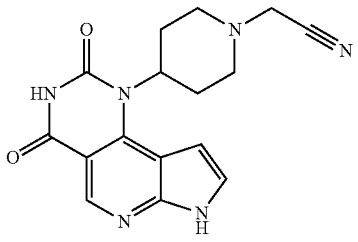 [SMILES: N#CCN1CCC(n2c(=O)[nH]c(=O)c3cnc4[nH]ccc4c32)CC1] |
TABLE[b] 41-continued
| Ex | Structure |
|---|---|
| 95 | 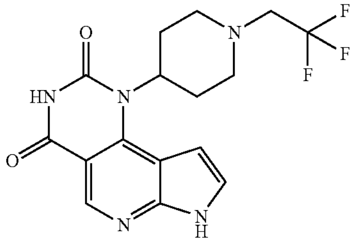 [SMILES: O=c1[nH]c(=O)n(C2CCN(CC(F)(F)F)CC2)c2c1cnc1[nH]ccc12] |
| 96 | 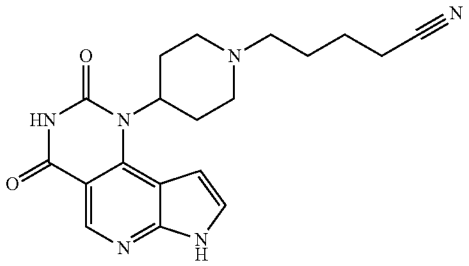 [SMILES: N#CCCCCN1CCC(n2c(=O)[nH]c(=O)c3cnc4[nH]ccc4c32)CC1] |
| 97 | 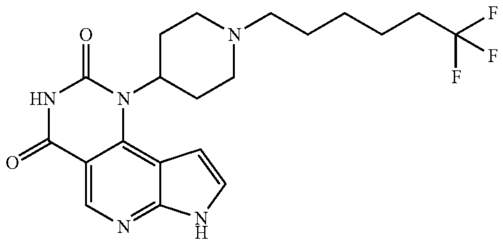 [SMILES: O=c1[nH]c(=O)n(C2CCN(CCCCCC(F)(F)F)CC2)c2c1cnc1[nH]ccc12] |
| 98 | 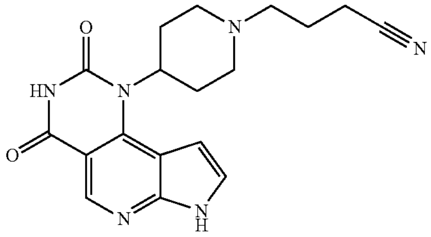 [SMILES: N#CCCCN1CCC(n2c(=O)[nH]c(=O)c3cnc4[nH]ccc4c32)CC1] |
| 99 | 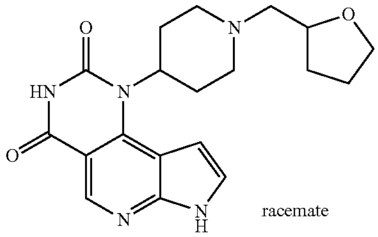 [SMILES: O=c1[nH]c(=O)n(C2CCN(CC3CCCO3)CC2)c2c1cnc1[nH]ccc12] racemate |
| 100 | 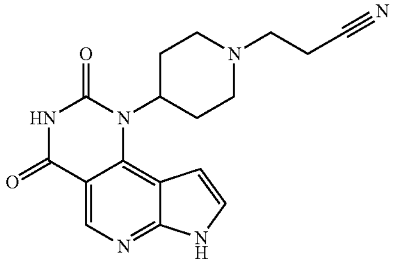 [SMILES: N#CCCN1CCC(n2c(=O)[nH]c(=O)c3cnc4[nH]ccc4c32)CC1] |

TABLE[b] 41-continued
| Ex | Structure |
|---|---|
| 101 | 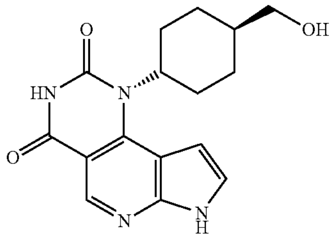 |
| 102 | 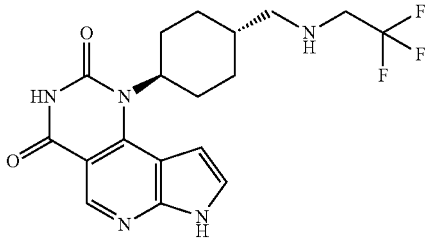 [SMILES: O=c1[nH]c(=O)n([C@H]2CC[C@H](CNCC(F)(F)F)CC2)c2c1cnc1[nH]ccc12] |
| 103 | 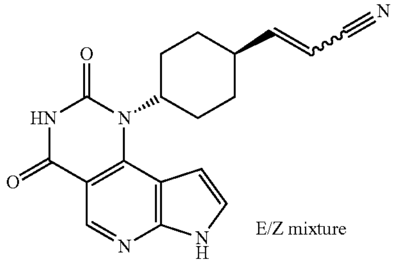 E/Z mixture |
| 104 | 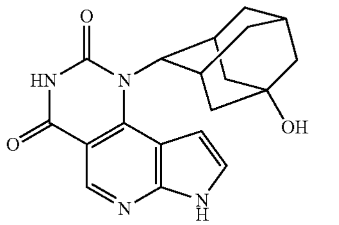 [SMILES: O=c1[nH]c(=O)n(C2C3CC4CC2CC(O)(C4)C3)c2c1cnc1[nH]ccc12] |
| 105 | 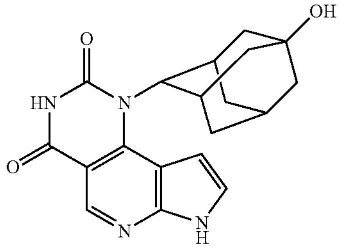 [SMILES: O=c1[nH]c(=O)n(C2C3CC4CC2CC(O)(C4)C3)c2c1cnc1[nH]ccc12] |
| 106 | 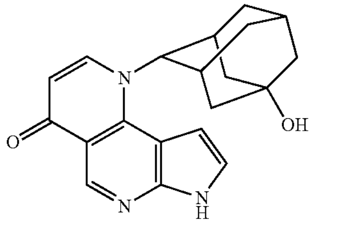 [SMILES: O=c1ccn(C2C3CC4CC2CC(O)(C4)C3)c2c1cnc1[nH]ccc12] |
| 107 | 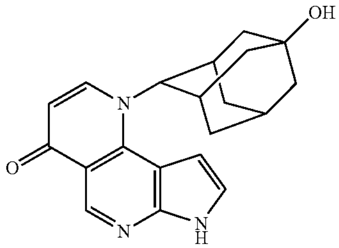 [SMILES: O=c1ccn(C2C3CC4CC2CC(O)(C4)C3)c2c1cnc1[nH]ccc12] |
| 108 | 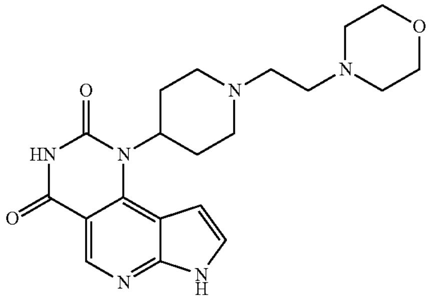 [SMILES: O=c1[nH]c(=O)n(C2CCN(CCN3CCOCC3)CC2)c2c1cnc1[nH]ccc12] |
TABLE[b] 42
| Ex | Structure |
|---|---|
| 109 | 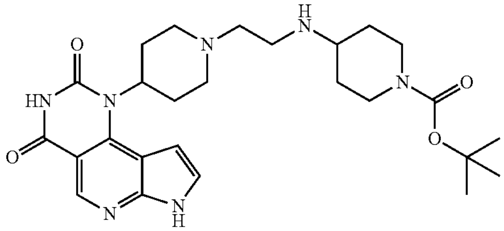 [SMILES: CC(C)(C)OC(=O)N1CCC(NCCN2CCC(n3c(=O)[nH]c(=O)c4cnc5[nH]ccc5c43)CC2)CC1] |
| 110 | 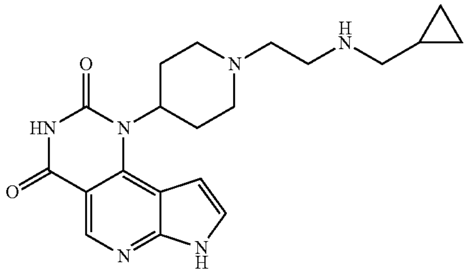 [SMILES: O=c1[nH]c(=O)n(C2CCN(CCNCC3CC3)CC2)c2c1cnc1[nH]ccc12] |
| 111 | 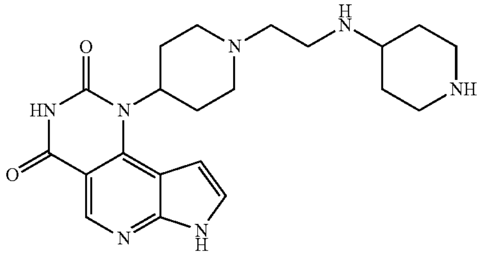 [SMILES: O=c1[nH]c(=O)n(C2CCN(CCNC3CCNCC3)CC2)c2c1cnc1[nH]ccc12] |

TABLE[b] 42-continued
| Ex | Structure |
|---|---|
| 112 | 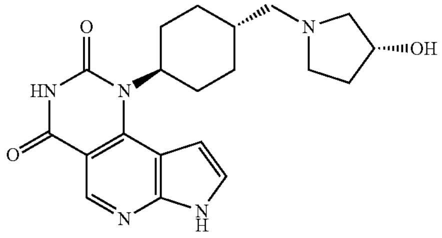 [SMILES: O=c1[nH]c(=O)n([C@H]2CC[C@H](CN3CC[C@@H](O)C3)CC2)c2c1cnc1[nH]ccc12] |
| 113 | 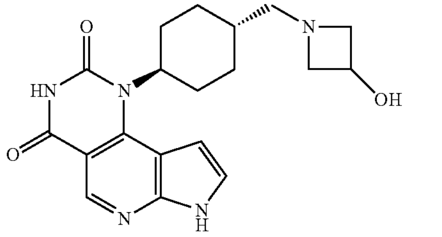 [SMILES: O=c1[nH]c(=O)n([C@H]2CC[C@H](CN3CC(O)C3)CC2)c2c1cnc1[nH]ccc12] |
| 114 | 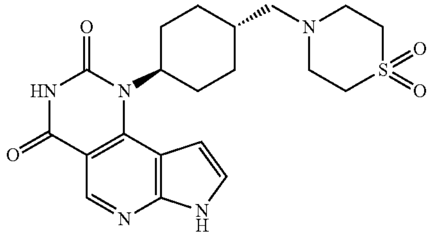 [SMILES: O=c1[nH]c(=O)n([C@H]2CC[C@H](CN3CCS(=O)(=O)CC3)CC2)c2c1cnc1[nH]ccc12] |
| 115 | 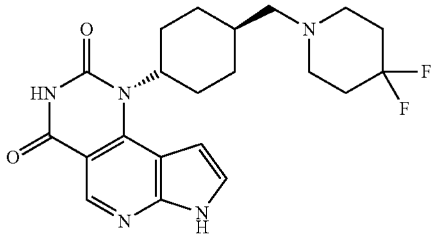 |
| 116 | 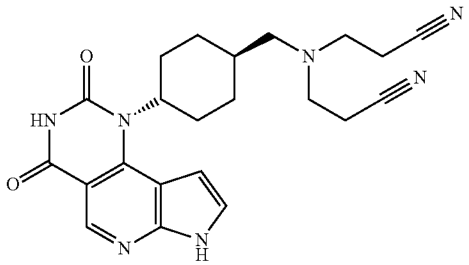 |
| 117 | 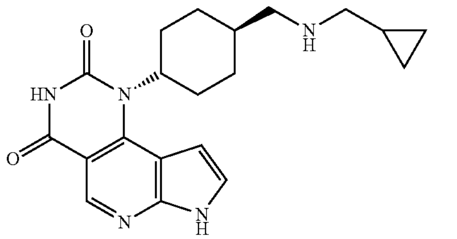 |
TABLE[b] 42-continued
| Ex | Structure |
|---|---|
| 118 | 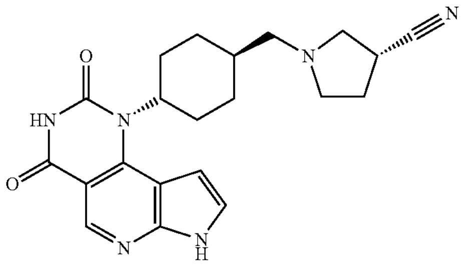 |
| 119 | 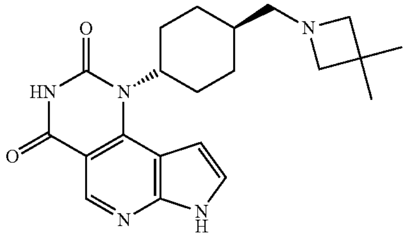 |
| 120 | 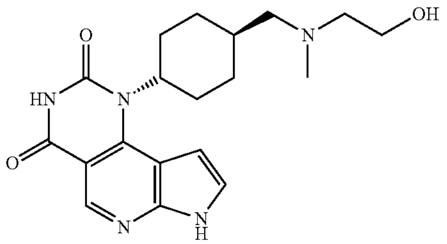 |
| 121 | 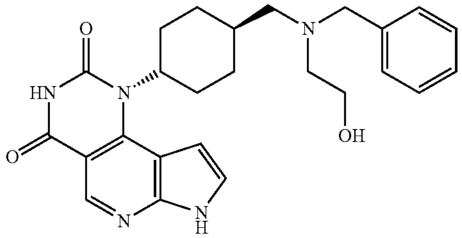 |
| 122 | 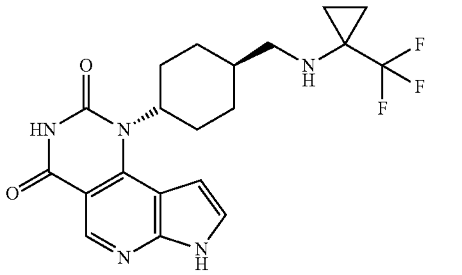 |
| 123 | 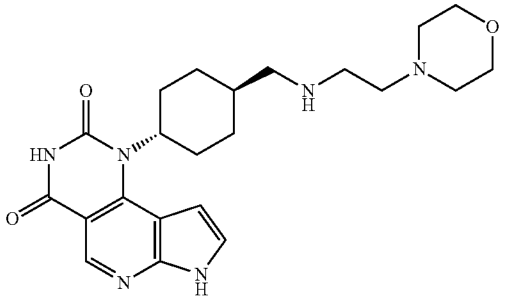 [SMILES: O=c1[nH]c(=O)n([C@H]2CC[C@H](CNCCN3CCOCC3)CC2)c2c1cnc1[nH]ccc12] |

TABLE[b] 42-continued
| Ex | Structure |
|---|---|
| 124 | 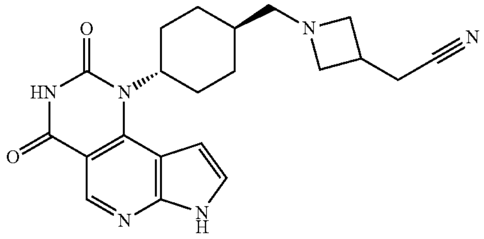 [SMILES: N#CCC1CN(C[C@H]2CC[C@H](n3c(=O)[nH]c(=O)c4cnc5[nH]ccc5c43)CC2)C1] |
| 125 | 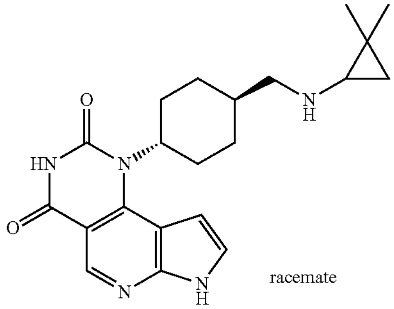 [SMILES: CC1(C)CC1NC[C@H]1CC[C@H](n2c(=O)[nH]c(=O)c3cnc4[nH]ccc4c32)CC1] racemate |
| 126 | 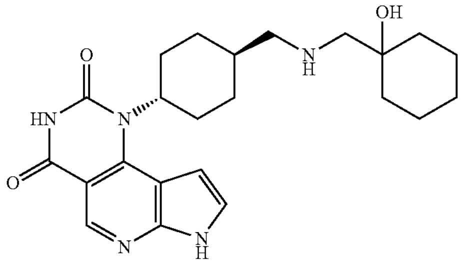 [SMILES: O=c1[nH]c(=O)n([C@H]2CC[C@H](CNCC3(O)CCCCC3)CC2)c2c1cnc1[nH]ccc12] |
| 127 | 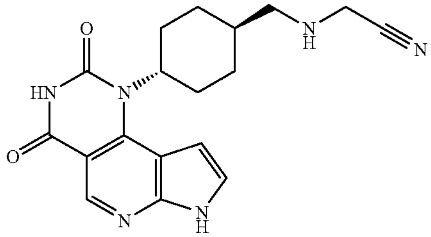 [SMILES: N#CCNC[C@H]1CC[C@H](n2c(=O)[nH]c(=O)c3cnc4[nH]ccc4c32)CC1] |
| 128 | 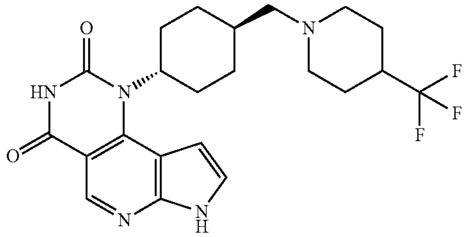 [SMILES: O=c1[nH]c(=O)n([C@H]2CC[C@H](CN3CCC(C(F)(F)F)CC3)CC2)c2c1cnc1[nH]ccc12] |
TABLE[b] 42-continued
| Ex | Structure |
|---|---|
| 129 | 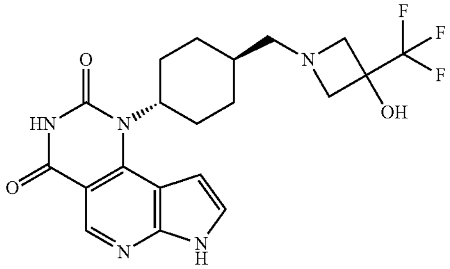 [SMILES: O=c1[nH]c(=O)n([C@H]2CC[C@H](CN3CC(O)(C(F)(F)F)C3)CC2)c2c1cnc1[nH]ccc12] |
TABLE[b] 43
| Ex | Structure |
|---|---|
| 130 | 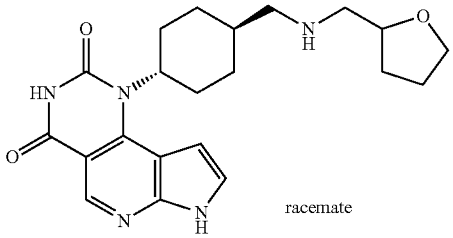 [SMILES: O=c1[nH]c(=O)n([C@H]2CC[C@H](CNCC3CCCO3)CC2)c2c1cnc1[nH]ccc12] racemate |
| 131 | 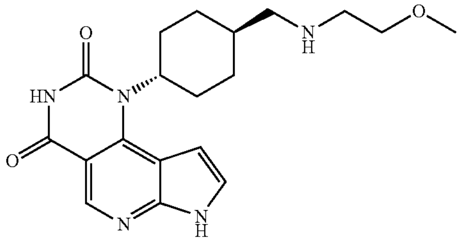 [SMILES: COCCNC[C@H]1CC[C@H](n2c(=O)[nH]c(=O)c3cnc4[nH]ccc4c32)CC1] |
| 132 | 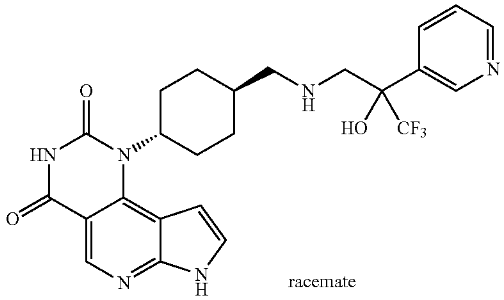 [SMILES: O=c1[nH]c(=O)n([C@H]2CC[C@H](CNCC(O)(c3cccnc3)C(F)(F)F)CC2)c2c1cnc1[nH]ccc12] racemate |
| 133 | 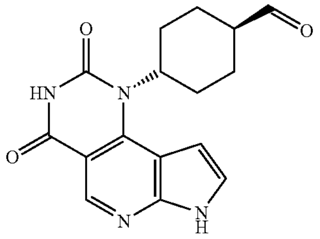 |

TABLE[b] 43-continued
| Ex | Structure |
|---|---|
| 134 | 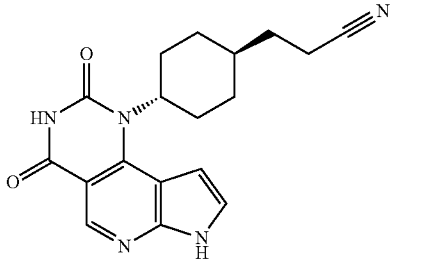 [SMILES: N#CCC[C@H]1CC[C@H](n2c(=O)[nH]c(=O)c3cnc4[nH]ccc4c32)CC1] |
| 135 | 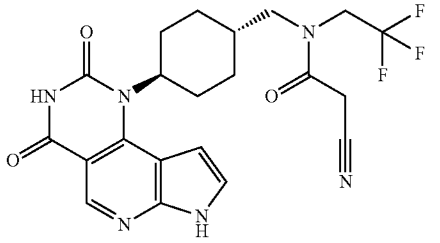 [SMILES: N#CCC(=O)N(CC(F)(F)F)C[C@H]1CC[C@H](n2c(=O)[nH]c(=O)c3cnc4[nH]ccc4c32)CC1] |
| 136 | 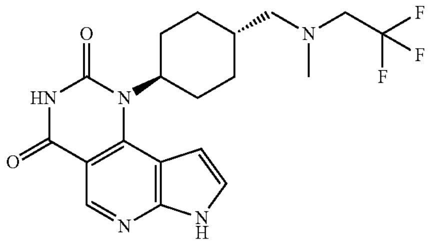 [SMILES: CN(CC(F)(F)F)C[C@H]1CC[C@H](n2c(=O)[nH]c(=O)c3cnc4[nH]ccc4c32)CC1] |
| 137 | 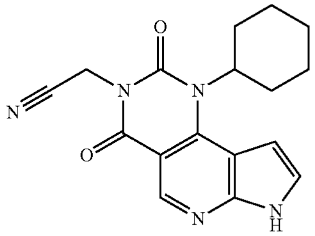 [SMILES: N#CCn1c(=O)c2cnc3[nH]ccc3c2n(C2CCCCC2)c1=O] |
| 138 | 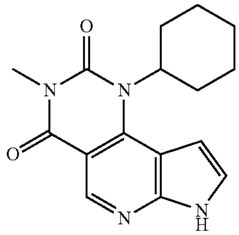 [SMILES: Cn1c(=O)c2cnc3[nH]ccc3c2n(C2CCCCC2)c1=O] |
| 139 | 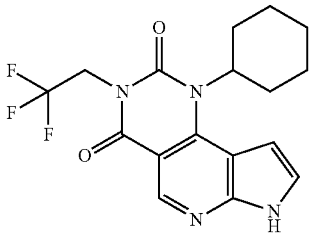 [SMILES: O=c1c2cnc3[nH]ccc3c2n(C2CCCCC2)c(=O)n1CC(F)(F)F] |
TABLE[b] 43-continued
| Ex | Structure |
|---|---|
| 140 | 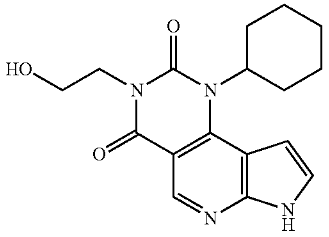 [SMILES: O=c1c2cnc3[nH]ccc3c2n(C2CCCCC2)c(=O)n1CCO] |
| 141 | 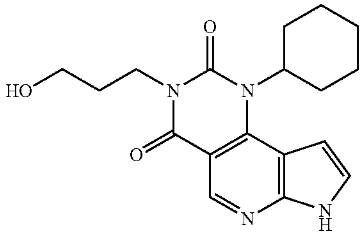 [SMILES: O=c1c2cnc3[nH]ccc3c2n(C2CCCCC2)c(=O)n1CCCO] |
| 142 | 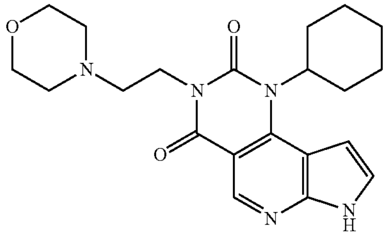 [SMILES: O=c1c2cnc3[nH]ccc3c2n(C2CCCCC2)c(=O)n1CCN1CCOCC1] |
| 143 | 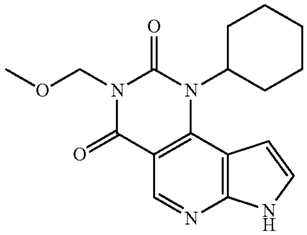 [SMILES: COCn1c(=O)c2cnc3[nH]ccc3c2n(C2CCCCC2)c1=O] |
| 144 | 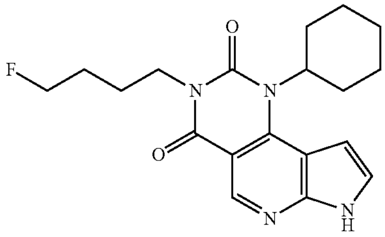 [SMILES: O=c1c2cnc3[nH]ccc3c2n(C2CCCCC2)c(=O)n1CCCCF] |
| 145 | 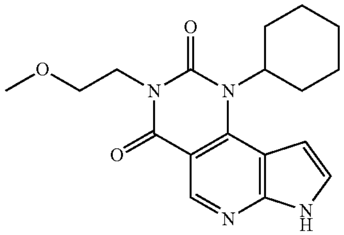 [SMILES: COCCn1c(=O)c2cnc3[nH]ccc3c2n(C2CCCCC2)c1=O] |

TABLE[b] 43-continued
| Ex | Structure |
|---|---|
| 146 | 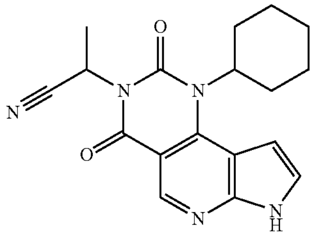 racemate |
| 147 | 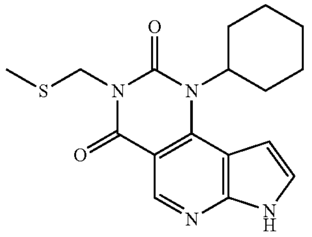 [SMILES: CSCn1c(=O)c2cnc3[nH]ccc3c2n(C2CCCCC2)c1=O] |
TABLE[b] 44
| Ex | Structure |
|---|---|
| 148 | 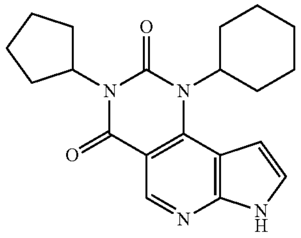 [SMILES: O=c1c2cnc3[nH]ccc3c2n(C2CCCCC2)c(=O)n1C1CCCC1] |
| 149 | 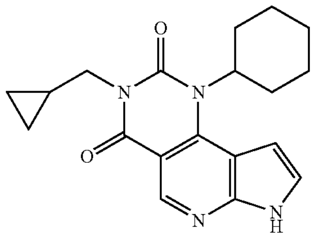 [SMILES: O=c1c2cnc3[nH]ccc3c2n(C2CCCCC2)c(=O)n1CC1CC1] |
| 150 | 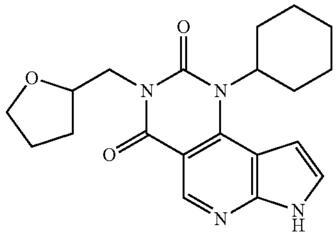 racemate |
TABLE[b] 44-continued
| Ex | Structure |
|---|---|
| 151 | 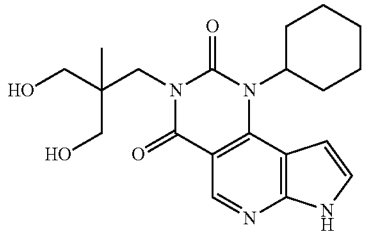 [SMILES: CC(CO)(CO)Cn1c(=O)c2cnc3[nH]ccc3c2n(C2CCCCC2)c1=O] |
| 152 | 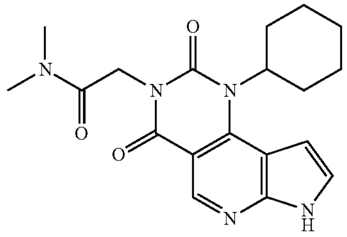 [SMILES: CN(C)C(=O)Cn1c(=O)c2cnc3[nH]ccc3c2n(C2CCCCC2)c1=O] |
| 153 | 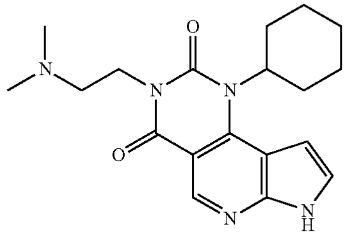 [SMILES: CN(C)CCn1c(=O)c2cnc3[nH]ccc3c2n(C2CCCCC2)c1=O] |
| 154 | 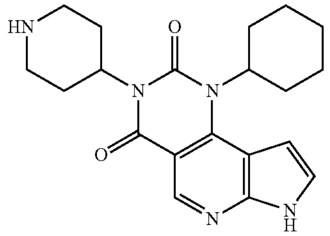 [SMILES: O=c1c2cnc3[nH]ccc3c2n(C2CCCCC2)c(=O)n1C1CCNCC1] |
| 155 | 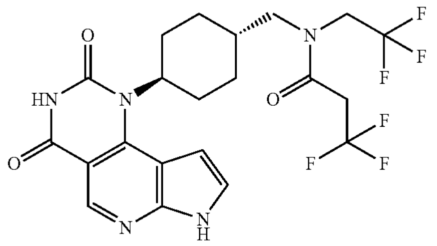 [SMILES: O=C(CC(F)(F)F)N(CC(F)(F)F)C[C@H]1CC[C@H](n2c(=O)[nH]c(=O)c3cnc4[nH]ccc4c32)CC1] |

TABLE[b] 45

| Rf | Data |
|---|---|
| 1 | $^1$H-NMR ($CD_3OD$) δ: 3.31 (s, 3H), 3.76 (s, 3H), 7.28 (d, J = 5.36 Hz, 1H), 8.18 (d, J = 4.76 Hz, 1H), 8.57 (s, 1H).<br>LC/MS: condition 1, retention time = 0.54 min<br>LC/MS (ESI$^+$) m/z; 167 [M + H]$^+$ |
| 2 | $^1$H-NMR ($CDCl_3$) δ: 0.98 (d, J = 6.5 Hz, 3H), 1.56-1.83 (m, 3H), 2.20-2.35 (m, 1H), 2.61-2.85 (m, 1H), 3.31 (d, J = 10.9 Hz, 1H), 3.53 (d, J = 14.9 Hz, 1H), 3.67 (s, 3H), 4.02 (dd, J = 13.0, 5.4, 1H), 4.13-4.26 (m, 2H), 7.47 (d, J = 2.4 Hz, 2H), 7.55 (d, J = 2.38 Hz, 3H), 12.4 (bs, 1H).<br>LC/MS: condition 1, retention time = 0.51 min<br>LC/MS (ESI$^+$) m/z; 263 [M + H]$^+$ |
| 3 | $^1$H-NMR ($CDCl_3$) δ: 0.92 (d, 3H), 1.41-1.53 (m, 3H), 1.90-2.18 (m, 2H), 2.65-2.89 (m, 3H), 3.46 (s, 2H), 7.18-7.40 (m, 5H).<br>LC/MS: condition 1, retention time = 0.47 min<br>LC/MS (ESI$^+$) m/z; 205 [M + H]$^+$ |
| 4 | $^1$H-NMR ($CDCl_3$) δ: 6.55 (d, J = 3.3 Hz, 1H), 7.06 (dd, J = 8.0, 6.3 Hz, 1H), 7.43 (d, J = 3.3 Hz, 1H), 7.70 (d, J = 8.0 Hz, 1H), 8.26 (d, J = 6.3 Hz, 1H).<br>LC/MS: condition 1, retention time = 0.64 min<br>LC/MS (ESI$^+$) m/z; 135.0 [M + H]$^+$ |
| 5 | $^1$H-NMR ($CDCl_3$) δ: 6.63 (d, J = 3.6 Hz, 1H), 7.14 (d, J = 5.2 Hz, 1H), 7.39 (d, J = 3.6 Hz, 1H), 8.22 (d, J = 5.2 Hz, 1H), 10.4 (br s, 1H).<br>LC/MS: condition 1, retention time = 3.16 min<br>LC/MS (ESI$^+$) m/z; 153, 155 [M + H]$^+$ |
| 6 | $^1$H-NMR ($CDCl_3$) δ: 1.11 (d, J = 7.5 Hz, 18H), 1.84 (septet, J = 7.5 Hz, 3H), 6.65 (d, J = 3.6 Hz, 1H), 7.06 (d, J = 5.2 Hz, 1H), 7.33 (d, J = 3.6 Hz, 1H), 7.75 (d, J = 5.2 Hz, 1H).<br>LC/MS: condition 1, retention time = 6.91 min<br>LC/MS (ESI$^+$) m/z; 309, 311 [M + H]$^+$ |
| 7 | $^1$H-NMR (DMSO-$d_6$) δ: 6.73 (dd, J = 3.6, 2.1 Hz, 1H), 7.75 (br t, J = 3.0 Hz, 1H), 8.68 (s, 1H), 10.4 (s, 1H), 12.5 (bs, 1H).<br>LC/MS: condition 1, retention time = 3.19 min<br>LC/MS (ESI$^+$) m/z; 181, 183 [M + H]$^+$<br>LC/MS (ESI) m/z; 179, 181 [M − H] |
| 8 | $^1$H-NMR ($CDCl_3$) δ: 1.29-1.56 (m, 4H), 1.60-1.75 (m, 2H), 1.78-1.92 (m, 2H), 2.07-2.20 (m, 2H), 3.94-4.06 (m, 1H), 6.59 (d, J = 3.6 Hz, 1H), 7.10 (d, J = 3.6 Hz, 1H), 8.20 (s, 1H), 9.62 (br d, J = 7.6 Hz, 1H), 9.80 (s, 1H), 11.0 (br s, 1H).<br>LC/MS: condition 1, retention time = 3.02 min<br>LC/MS (ESI$^+$) m/z; 244 [M + H]$^+$ |
| 9 | $^1$H-NMR ($CDCl_3$) δ: −0.05 (s, 9H), 0.91 (t, J = 8.5 Hz, 2H), 1.25-1.75 (m, 6H), 1.75-1.90 (m, 2H), 2.07-2.20 (m, 2H), 3.54 (t, J = 8.5 Hz, 2H), 3.90-4.05 (m, 1H), 5.61 (s, 2H), 6.60 (d, J = 3.8 Hz, 1H), 7.09 (d, J = 3.8 Hz, 1H), 8.18 (s, 1H), 9.58 (br d, J = 7.7 Hz, 1H), 9.80 (s, 1H).<br>LC/MS: condition 1, retention time = 5.22 min<br>LC/MS (ESI$^+$) m/z; 374 [M + H]$^+$ |

TABLE[b] 46

| Rf | Data |
|---|---|
| 11 | $^1$H-NMR ($CDCl_3$) δ: −0.06 (s, 9H), 0.90-1.00 (m, 2H), 1.10-1.80 (m, 6H), 1.80-1.95 (m, 2H), 1.95-2.10 (m, 2H), 3.50-3.60 (m, 2H), 3.90-4.10 (m, 1H), 4.76 (s, 2H), 4.96 (s, 2H), 5.62 (s, 2H), 6.43 (d, J = 3.6 Hz, 1H), 7.20 (d, J = 3.6 Hz, 1H), 7.82 (s, 1H).<br>LC/MS: condition 1, retention time = 3.86 min<br>LC/MS (ESI$^+$) m/z; 388 [M + H]$^+$ |
| 12 | $^1$H-NMR ($CDCl_3$)<br>δ: −0.06 (s, 9H), 0.90 (t, J = 8.3 Hz, 2H), 1.37-1.54 (m, 6H), 1.74-1.92 (m, 2H), 2.02-2.24 (m, 2H), 3.54 (t, J = 8.0 Hz, 2H), 3.83-4.04 (m, 3H), 5.58, (s, 2H), 6.52 (d, J = 3.9 Hz, 1H), 6.74-6.94 (m, 1H), 7.08 (d, J = 3.3 Hz, 1H), 7.79 (s, 1H).<br>LC/MS: condition 1, retention time = 3.02 min<br>LC/MS (ESI$^+$) m/z; 375 [M + H]$^+$ |
| 13 | $^1$H-NMR ($CDCl_3$) δ: −0.05 (s, 9H), 0.92, (t, J = 8.3 Hz, 2H), 1.23-1.50 (m, 3H), 1.57-1.84 (m, 2H), 1.84-2.02 (m, 3H), 2.63-2.67 (m, 2H), 3.54 (t, J = 8.0 Hz, 2H), 4.00-4.23 (m, 1H), 4.36 (d, J = 2.1 Hz, 2H), 5.20 (s, 1H), 5.65 (s, 2H), 6.49 (d, J = 3.6 Hz, 1H), 7.30 (d, J = 3.9 Hz 1H), 7.97 (s, 1H).<br>LC/MS: condition 1, retention time = 4.79 min<br>LC/MS (ESI$^+$) m/z; 401 [M + H]$^+$ |
| 14 | LC/MS: condition 1, retention time = 3.46 min<br>LC/MS (ESI$^+$) m/z; 385 [M + H]$^+$ |

TABLE$^b$ 46-continued

| Rf | Data |
|---|---|
| 15 | $^1$H-NMR ($CDCl_3$) δ: 3.06 (t, J = 8.1 Hz, 2H), 3.61 (t, J = 8.1 Hz, 2H), 4.48 (br s, 1H), 6.50 (dd, J = 5.4, 6.9 Hz, 1H), 7.24 (d, J = 6.9 Hz, 1H), 7.81 (d, J = 5.4 Hz, 1H).<br>LC/MS: condition 1, retention time = 0.50 min<br>LC/MS (ESI$^+$) m/z; 121 [M + H]$^+$ |
| 16 | $^1$H-NMR ($CDCl_3$) δ: 3.07 (t, J = 8.4 Hz, 2H), 3.65 (t, J = 8.1 Hz, 2H), 4.50 (br s, 1H), 7.32 (s, 1H), 7.85 (s, 1H).<br>LC/MS: condition 1, retention time = 0.52 min<br>LC/MS (ESI$^+$) m/z; 199, 201 [M + H]$^+$ |
| 17 | $^1$H-NMR ($CDCl_3$) δ: 6.40-6.50 (m, 1H), 7.30-7.40 (m, 1H), 8.07 (d, J = 2.1 Hz, 1H), 8.35 (d, J = 1.5 Hz, 1H), 9.50 (br s, 1H).<br>LC/MS: condition 1, retention time = 3.52 min<br>LC/MS (ESI$^+$) m/z; 197, 199 [M + H]$^+$ |
| 18 | LC/MS: condition 1, retention time = 1.36 min<br>LC/MS (ESI$^+$) m/z; 213, 215 [M + H]$^+$ |
| 19 | $^1$H-NMR ($CDCl_3$) δ: −0.06 (s, 9H), 0.90 (t, J = 8.1 Hz, 2H), 3.52 (t, J = 7.8 Hz, 2H), 5.63 (s, 2H), 6.60 (d, J = 3.6 Hz, 1H), 7.38 (d, J = 3.6 Hz, 1H), 8.41 (s, 1H).<br>LC/MS: condition 1, retention time = 5.54 min<br>LC/MS (ESI$^+$) m/z; 361, 363, 365 [M + H]$^+$ |
| 20 | $^1$H-NMR ($CDCl_3$) δ: −0.06 (s, 9H), 0.90 (t, J = 8.1 Hz, 2H), 1.30-1.70 (m, 6H), 1.80-1.90 (m, 2H), 2.10-2.20 (m, 2H), 3.53 (t, J = 8.1 Hz, 2H), 3.90-4.00 (m, 1H), 4.97 (d, J = 8.4 Hz, 1H), 5.58 (s, 2H), 6.51 (d, J = 3.6 Hz, 1H), 7.12 (d, J = 3.9 Hz, 1H), 8.11 (s, 1H).<br>LC/MS: condition 1, retention time = 5.42 min<br>LC/MS (ESI$^+$) m/z; 424, 426 [M + H]$^+$ |

TABLE$^b$ 47

| Rf | Data |
|---|---|
| 21 | LC/MS: condition 1, retention time = 5.01 min<br>LC/MS (ESI$^+$) m/z; 388 [M + H]$^+$ |
| 23 | LC/MS: condition 1, retention time = 4.01 min<br>LC/MS (ESI$^+$) m/z; 402 [M + H]$^+$ |
| 24 | $^1$H-NMR ($CDCl_3$) δ: −0.06 (s, 9H), 0.93 (t, J = 8.1 Hz, 2H), 1.50-1.95 (m, 6H), 2.00-2.15 (m, 2H), 2.20-2.30 (m, 2H), 3.56 (t, J = 8.1 Hz, 2H), 4.85-5.00 (m, 1H), 5.80 (s, 2H), 6.43 (d, J = 8.1 Hz, 1H), 6.81 (d, J = 3.6 Hz, 1H), 7.43 (d, J = 3.9 Hz, 1H), 7.77 (d, J = 8.1 Hz, 1H), 9.41 (s, 1H).<br>LC/MS: condition 1, retention time = 4.64 min<br>LC/MS (ESI$^+$) m/z; 398 [M + H]$^+$ |
| 25 | LC/MS: condition 1, retention time = 5.46 min<br>LC/MS (ESI$^+$) m/z; 387, 389 [M + H]$^+$ |
| 26 | $^1$H-NMR ($CDCl_3$) δ: 1.30-1.60 (m, 4H), 1.60-1.80 (m, 2H), 1.80-1.95 (m, 2H), 2.10-2.25 (m, 2H), 3.07 (s, 3H), 3.95-4.10 (m, 1H), 6.61 (d, J = 3.3 Hz, 1H), 7.15-7.25 (m, 2H), 8.54 (s, 1H), 11.82 (br s, 1H).<br>LC/MS: condition 1, retention time = 3.31 min<br>LC/MS (ESI$^+$) m/z; 294 [M + H]$^+$ |
| 28 | LC/MS: condition 1, retention time = 4.87 min<br>LC/MS (ESI$^+$) m/z; 434 [M + H]$^+$ |
| 29 | LC/MS: condition 1, retention time = 4.26 min<br>LC/MS (ESI+) m/z; 390 [M + 1]+<br>LC/MS (ESI−) m/z; 388 [M − 1]− |
| 30 | $^1$H-NMR ($CDCl_3$) δ: −0.05 (s, 9H), 0.91 (t, J = 8.1 Hz, 2H), 1.35-1.45 (m, 5H), 1.60-1.70 (m, 1H), 1.75-1.90 (m, 2H), 2.05-2.20 (m, 2H), 3.54 (t, J = 7.8 Hz, 2H), 3.90-4.05 (m, 1H), 5.58 (s, 2H), 5.55-5.70 (m, 2H), 6.59 (d, J = 3.6 Hz, 1H), 7.08 (d, J = 3.9 Hz, 1H), 8.29 (s, 1H), 9.32 (d, J = 7.5 Hz, 1H).<br>LC/MS: condition 1, retention time = 4.02 min<br>LC/MS (ESI$^+$) m/z; 389 [M + H]$^+$ |
| 31 | LC/MS: condition 1, retention time = 4.97 min<br>LC/MS (ESI$^+$) m/z; 417 [M + H]$^+$ |
| 32 | $^1$H-NMR ($CDCl_3$) δ: −0.06 (s, 9H), 0.93 (t, J = 8.1 Hz, 2H), 1.50-2.00 (m, 6H), 2.00-2.15 (m, 2H), 2.20-2.40 (m, 2H), 3.56 (t, J = 8.1 Hz, 2H), 4.70-4.85 (m, 1H), 5.79 (s, 2H), 6.77 (d, J = 4.2 Hz, 1H), 7.51 (d, J = 3.9 Hz, 1H), 8.50 (s, 1H), 9.32 (s, 1H).<br>LC/MS: condition 1, retention time = 4.42 min<br>LC/MS (ESI$^+$) m/z; 399 [M + H]$^+$ |
| 33 | $^1$H-NMR ($CDCl_3$) δ: −0.06 (s, 9H), 0.85-1.00 (m, 2H), 2.76 (s, 3H), 3.50-3.60 (m, 2H), 5.68 (s, 2H), 6.74 (d, J = 3.6 Hz, 1H), 7.44 (s, J = 3.6 Hz, 1H), 8.66 (s, 1H). |

TABLE[b] 47-continued

| Rf | Data |
|---|---|
| | LC/MS: condition 1, retention time = 4.87 min<br>LC/MS ($ESI^+$) m/z; 325, 327 $[M + H]^+$ |

TABLE[b] 48

| Rf | Data |
|---|---|
| 34 | $^1$H-NMR ($CDCl_3$) δ: −0.06 (s, 9H), 0.90 (t, J = 8.1 Hz, 2H), 0.98 (d, J = 6.6 Hz, 3H), 1.60-1.85 (m, 2H), 1.90-2.00 (m, 1H), 2.20-2.30 (m, 1H), 2.25-2.35 (m, 1H), 2.67 (s, 3H), 2.70-2.90 (m, 2H), 3.45-3.60 (m, 4H), 4.30-4.40 (m, 1H), 5.57 (s, 2H), 6.58 (d, J = 3.6 Hz, 1H), 7.00 (d, J = 3.9 Hz, 1H), 7.10-7.40 (m, 5H), 8.66 (s, 1H), 10.70 (d, J = 9.9 Hz, 1H). |
| 35 | $^1$H-NMR ($CDCl_3$) δ: −0.08 (s, 9H), 0.86 (d, J = 6.9 Hz, 3H), 0.91 (t, J = 8.1 Hz, 2H), 1.70-2.00 (m, 2H), 2.40-2.60 (m, 2H), 2.75-2.90 (m, 2H), 2.95-3.05 (m, 1H), 3.50-3.65 (m, 4H), 5.35-5.45 (m, 1H), 5.78 (dd, J = 10.5, 15.0 Hz, 2H), 6.39 (d, J = 8.1 Hz, 1H), 6.81 (d, J = 3.9 Hz, 1H), 7.25-7.40 (m, 5H), 7.41 (d, J = 3.6 Hz, 1H), 8.54 (br s, 1H), 9.41 (s, 1H).<br>LC/MS: condition 1, retention time = 3.59 min<br>LC/MS ($ESI^+$) m/z; 503 $[M + H]^+$ |
| 36 | LC/MS: condition 1, retention time = 3.06 min<br>LC/MS ($ESI^+$) m/z; 413 $[M + H]^+$ |
| 37 | $^1$H-NMR ($CDCl_3$) δ: −0.06 (s, 9H), 0.93 (t, J = 8.1 Hz, 2H), 1.02 (d, J = 7.5 Hz, 3H), 1.14 (d, J = 6.6 Hz, 6H), 1.80-1.90 (m, 1H), 2.15-2.45 (m, 2H), 2.65-2.80 (m, 1H), 2.87 (d, J = 6.6 Hz, 2H), 3.15-3.35 (m, 1H), 3.56 (t, J = 8.1 Hz, 2H), 3.55-3.75 (m, 2H), 3.85-3.95 (m, 1H), 5.35-5.45 (m, 1H), 5.80 (s, 2H), 6.40 (d, J = 7.8 Hz, 1H), 6.75 (d, J = 3.6 Hz, 1H), 7.46 (d, J = 3.9 Hz, 1H), 7.60 (d, J = 8.1 Hz, 1H), 9.42 (s, 1H).<br>LC/MS: condition 1, retention time = 4.52 min<br>LC/MS ($ESI^+$) m/z; 533 $[M + H]^+$<br>LC/MS ($ESI^-$) m/z; 577 $[M + HCOO]^-$ |
| 38 | LC/MS: condition 1, retention time = 0.54 min<br>LC/MS ($ESI^+$) m/z; 349 $[M + H]^+$ |
| 39 | $^1$H-NMR ($CDCl_3$) δ: −0.06 (s, 9H), 0.87-0.95 (m, 2H), 0.98 (d, J = 6.9 Hz, 3H), 1.59-1.80 (m, 2H), 1.87-2.04 (m, 1H), 2.14-2.24 (m, 1H), 2.38-2.41 (m, 1H), 2.85-2.89 (m, 2H), 3.47-3.62 (m, 4H), 4.28-4.39 (m, 1H), 5.59 (s, 2H), 6.59 (d, J = 3.6 Hz, 1H), 7.04 (d, J = 3.9 Hz, 1H), 7.17-7.39 (m, 5H), 8.20 (s, 1H), 9.87 (s, 1H), 10.0 (d, J = 9.5 Hz, 1H).<br>LC/MS: condition 1, retention time = 3.57 min<br>LC/MS ($ESI^+$) m/z; 479 $[M + H]^+$ |
| 40 | $^1$H-NMR ($CDCl_3$) δ: −0.07 (s, 9H), 0.86-0.92 (m, 2H), 1.01 (d, J = 6.6 Hz, 3H), 1.43-1.96 (m, 3H), 2.07-2.14 (m, 1H), 2.25-2.28 (m, 1H), 2.78-2.93 (m, 2H), 3.46-3.55 (m, 4H), 4.20-4.31 (m, 1H), 4.77 (dd, J = 20.8, 12.2 Hz, 2H), 5.57 (s, 2H), 5.95 (d, J = 9.8 Hz, 1H), 6.51 (d, J = 3.6 Hz, 1H), 7.07 (d, J = 3.6 Hz, 1H), 7.18-7.29 (m, 5H), 7.87 (s, 1H).<br>LC/MS: condition 1, retention time = 3.04 min<br>LC/MS ($ESI^+$) m/z; 481 $[M + H]^+$ |
| 41 | LC/MS: condition 1, retention time = 2.91 min<br>LC/MS ($ESI^+$) m/z; 363 $[M + H − SEM]^+$ |
| 42 | $^1$H-NMR (DMSO-$d_6$) δ: 8.30 (br s, 1H), 8.44 (s, 1H), 8.49 (s, 1H).<br>LC/MS: condition 1, retention time = 0.89 min<br>LC/MS ($ESI^+$) m/z; 198, 200 $[M + H]^+$<br>LC/MS ($ESI^-$) m/z; 196, 198 $[M − H]^-$ |

TABLE[b] 49

| Rf | Data |
|---|---|
| 43 | LC/MS: condition 1, retention time = 0.54 min<br>LC/MS ($ESI^+$) m/z; 214, 216 $[M + H]^+$ |
| 44 | $^1$H-NMR (DMSO-$d_6$) δ: 8.50 (s, 1H), 8.56 (s, 1H), 8.57 (d, J = 1.8 Hz, 1H).<br>LC/MS: condition 1, retention time = 2.74 min<br>LC/MS ($ESI^+$) m/z; 232, 234, 236 $[M + H]^+$<br>LC/MS ($ESI^-$) m/z; 230, 232, 234 $[M − H]^-$ |
| 46 | $^1$H-NMR ($CDCl_3$) δ: −0.04 (s, 9H), 0.94 (t, J = 8.4 Hz, 2H), 2.79 (s, 3H), 3.62 (t, J = 8.4 Hz, 2H), 5.69 (s, 2H), 8.30 (s, 1H), 8.73 (s, 1H). |

TABLE[b] 49-continued

| Rf | Data |
|---|---|
| | LC/MS: condition 1, retention time = 4.31 min<br>LC/MS ($ESI^+$) m/z; 326, 328 $[M + H]^+$ |
| 47 | $^1$H-NMR ($CDCl_3$) δ: −0.03 (s, 9H), 0.93 (t, J = 8.4 Hz, 2H), 1.22-1.78 (m, 6H), 1.78-1.90 (m, 2H), 2.03-2.18 (m, 2H), 2.63 (s, 3H), 3.61 (t, J = 8.4 Hz, 2H), 4.87-5.03 (m, 1H), 5.58 (s, 2H), 7.88 (s, 1H), 8.69 (s, 1H), 10.10 (br s, 1H).<br>LC/MS: condition 1, retention time = 5.19 min<br>LC/MS ($ESI^+$) m/z; 389 $[M + H]^+$ |
| 48 | $^1$H-NMR ($CDCl_3$) δ: −0.04 (s, 9H), 0.95 (t, J = 8.4 Hz, 2H), 1.20-1.38 (m, 1H), 1.58-2.24 (m, 9H), 3.65 (t, J = 8.4 Hz, 2H), 5.77 (s, 2H), 6.46 (d, J = 8.0 Hz, 1H), 6.40-6.55 (m, 1H), 7.81 (d, J = 8.0 Hz, 1H), 8.16 (s, 1H), 9.47 (s, 1H).<br>LC/MS: condition 1, retention time = 4.66 min<br>LC/MS ($ESI^+$) m/z; 399 $[M + H]^+$ |

TABLE[b] 50

| Rf | Data |
|---|---|
| 49 | $^1$H-NMR ($CDCl_3$) δ: −0.04 (s, 9H), 0.92 (t, J = 8.4 Hz, 2H), 2.74 (s, 3H), 3.53 (t, J = 8.7 Hz, 2H), 5.64 (s, 2H), 7.48 (s, 1H), 8.54 (s, 1H).<br>LC/MS: condition 1, retention time = 5.19 min<br>LC/MS ($ESI^+$) m/z; 403, 405 $[M + H]^+$ |
| 50 | $^1$H-NMR ($CDCl_3$) δ: −0.07 (s, 9H), 0.72 (d, J = 6.3 Hz, 3H), 0.96 (t, J = 8.1 Hz, 2H), 1.45-1.60 (m, 1H), 1.70-1.90 (m, 2H), 2.05-2.18 (m, 1H), 2.31-2.42 (m, 1H), 2.71 (s, 3H), 2.88-3.00 (m, 1H), 3.10-3.22 (m, 1H), 3.51-3.69 (m, 4H), 4.60-4.80 (m, 1H), 5.61 (dd, J = 10.8, 16.2 Hz, 2H), 7.21-7.43 (m, 6H), 8.65 (s, 1H).<br>LC/MS: condition 1, retention time = 3.86 min<br>LC/MS ($ESI^+$) m/z; 571, 573 $[M + H]^+$ |
| 51 | $^1$H-NMR ($CDCl_3$) δ: −0.08 (s, 9H), 0.20 (d, J = 6.9 Hz, 3H), 0.90 (t, J = 8.7 Hz, 2H), 1.40-1.52 (m, 1H), 1.62-1.72 (m, 1H), 1.82-2.00 (m, 1H), 2.05-2.20 (m, 1H), 2.70-2.82 (m, 1H), 3.02-3.17 (m, 1H), 3.50-3.60 (m, 4H), 3.60-3.71 (m, 1H), 5.40-5.50 (m, 1H), 5.74 (dd, J = 13.8, 10.5 Hz, 2H), 6.44 (d, J = 7.8 Hz, 1H), 7.20-7.45 (m, 5H), 7.47 (s, 1H), 9.34 (s, 1H), 9.49 (d, J = 7.8 Hz, 1H).<br>LC/MS: condition 1, retention time = 4.89 min<br>LC/MS ($ESI^+$) m/z; 581, 583 $[M + H]^+$ |
| 52 | $^1$H-NMR ($CDCl_3$) δ: −0.05 (s, 9H), 0.91 (t, J = 8.4 Hz, 2H), 2.74 (s, 3H), 3.52 (t, J = 8.1 Hz, 2H), 5.63 (s, 2H), 7.40 (s, 1H), 8.54 (s, 1H).<br>LC/MS: condition 1, retention time = 5.00 min<br>LC/MS ($ESI^+$) m/z; 359, 361 $[M + H]^+$ |
| 53 | LC/MS: condition 1, retention time = 3.67 min<br>LC/MS ($ESI^+$) m/z; 527, 529 $[M + H]^+$ |
| 54 | $^1$H-NMR ($CDCl_3$) δ: −0.10 (s, 9H), 0.27 (d, J = 6.9 Hz, 3H), 0.90 (t, J = 8.4 Hz, 2H), 1.41-1.56 (m, 1H), 1.60-1.80 (m, 1H), 1.86-2.03 (m, 1H), 2.06-2.20 (m, 1H), 2.68-2.80 (m, 1H), 3.05-3.20 (m, 1H), 3.50-3.70 (m, 5H), 5.35-5.42 (m, 1H), 5.74 (s, 2H), 6.44 (d, J = 8.1 Hz, 1H), 7.22-7.48 (m, 6H), 9.34 (s, 1H), 9.45 (d, J = 8.1 Hz, 1H).<br>LC/MS: condition 1, retention time = 4.60 min<br>LC/MS ($ESI^+$) m/z; 537, 539 $[M + H]^+$ |
| 55 | LC/MS: condition 1, retention time = 4.79 min<br>LC/MS ($ESI^+$) m/z; 311, 313 $[M + H]^+$ |
| 56 | $^1$H-NMR ($CDCl_3$) δ: −0.07 (s, 9H), 0.90 (t, J = 8.4 Hz, 2H), 1.00 (t, J = 7.2 Hz, 3H), 1.91 (quint, J = 7.2 Hz, 2H), 3.53 (t, J = 8.4 Hz, 2H), 5.10-5.20 (m, 1H), 5.65 (s, 2H), 6.60 (d, J = 3.6 Hz, 1H), 7.36 (d, J = 3.6 Hz, 1H), 8.45 (s, 1H).<br>LC/MS: condition 1, retention time = 4.81 min<br>LC/MS ($ESI^+$) m/z; 341, 343 $[M + H]^+$ |
| 57 | LC/MS: condition 1, retention time = 5.21 min<br>LC/MS ($ESI^+$) m/z; 339, 341 $[M + H]^+$ |

TABLE[b] 50-continued

| Rf | Data |
|---|---|
| 58 | LC/MS: condition 1, retention time = 3.71 min<br>LC/MS ($ESI^+$) m/z; 507 $[M + H]^+$ |

TABLE[b] 51

| Rf | Data |
|---|---|
| 59 | $^1$H-NMR ($CDCl_3$) δ: −0.10 (s, 9H), 0.85 (d, J = 7.2 Hz, 3H), 0.90 (t, J = 9.0 Hz, 2H), 1.70-1.85 (m, 1H), 1.85-2.00 (m, 1H), 2.19 (s, 3H), 2.35-2.58 (m, 2H), 2.75-2.90 (m, 2H), 3.00-3.12 (m, 1H), 3.50-3.70 (m, 4H), 5.33-5.41 (m, 1H), 5.77 (dd, J = 9.9, 15.0 Hz, 2H), 6.79 (d, J = 3.6 Hz, 1H), 7.20-7.40 (m, 6H), 8.51 (br s, 1H), 9.45 (s, 1H).<br>LC/MS: condition 1, retention time = 3.74 min<br>LC/MS ($ESI^+$) m/z; 517 $[M + H]^+$ |
| 60 | LC/MS: condition 1, retention time = 4.24 min<br>LC/MS ($ESI^+$) m/z; 581, 583 $[M + H]^+$ |
| 61 | $^1$H-NMR ($CDCl_3$) δ: −0.05 (s, 9H), 0.85-0.95 (m, 2H), 0.99 (d, J = 7.5 Hz, 3H), 1.85-1.95 (m, 1H), 2.25-2.35 (m, 1H), 2.65-2.75 (m, 1H), 3.35-3.45 (m, 1H), 3.58 (t, J = 8.1 Hz, 2H), 3.65-3.85 (m, 2H), 3.90-4.00 (m, 1H), 5.40-5.50 (m, 1H), 5.80 (s, 2H), 6.36 (d, J = 8.1 Hz, 1H), 6.75 (d, J = 3.6 Hz, 1H), 7.46 (d, J = 3.6 Hz, 1H), 7.53 (d, J = 8.1 Hz, 1H), 7.70-7.85 (m, 2H), 7.90-7.95 (m, 1H), 8.10-8.15 (m, 1H), 9.40 (s, 1H).<br>LC/MS: condition 3, retention time = 2.56 min<br>LC/MS ($ESI^+$) m/z; 578 $[M + H]^+$ |
| 62 | $^1$H-NMR ($CDCl_3$) δ: −0.07 (s, 9H), 0.88-0.96 (m, 5H), 1.82-1.98 (m, 1H), 2.10-2.29 (m, 1H), 2.55-2.70 (m, 1H), 3.08-3.21 (m, 1H), 3.42-3.64 (m, 4H), 3.70-3.82 (m, 1H), 5.40-5.50 (m, 1H), 5.80 (s, 2H), 6.40 (d, J = 7.8 Hz, 1H), 6.68 (d, J = 3.9 Hz, 1H), 7.46 (d, J = 3.9 Hz, 1H), 7.60 (d, J = 7.8 Hz, 1H), 7.76 (t, J = 7.8 Hz, 1H), 7.95 (d, J = 7.8 Hz, 1H), 8.06 (d, J = 7.8 Hz, 1H), 8.12 (s, 1H), 9.41 (s, 1H).<br>LC/MS: condition 3, retention time = 2.59 min<br>LC/MS ($ESI^+$) m/z; 578 $[M + H]^+$ |
| 63 | $^1$H-NMR ($CDCl_3$) δ: −0.07 (s, 9H), 0.82-0.99 (m, 2H), 1.03 (d, J = 6.9 Hz, 3H), 1.26 (t, J = 7.2 Hz, 3H), 1.70-1.85 (m, 1H), 2.65-2.80 (m, 1H), 3.24-3.42 (m, 1H), 3.57 (t, J = 8.4 Hz, 2H), 3.66-3.84 (m, 1H), 3.90-4.02 (m, 1H), 4.10-4.29 (m, 4H), 5.12-5.22 (m, 1H), 5.76-5.84 (m, 2H), 6.40 (d, J = 7.8 Hz, 1H), 6.72 (d, J = 3.9 Hz, 1H), 7.44 (d, J = 3.9 Hz, 1H), 7.54 (d, J = 3.9 Hz, 1H), 9.43 (s, 1H).<br>LC/MS: condition 1, retention time = 4.27 min<br>LC/MS ($ESI^+$) m/z; 485 $[M + H]^+$<br>LC/MS ($ESI^-$) m/z; 529 $[M + HCOO]^-$ |
| 64 | $^1$H-NMR ($CDCl_3$) δ: −0.08 (s, 9H), 0.92 (t, J = 8.4 Hz, 2H), 1.04 (d, J = 6.9 Hz, 3H), 1.80-1.95 (m, 1H), 2.08-2.25 (m, 1H), 2.70-2.88 (m, 1H), 3.42-3.60 (m, 1H), 3.56 (t, J = 8.4 Hz, 2H), 3.65-3.82 (m, 2H), 4.32-4.46 (m, 1H), 5.21-5.38 (m, 1H), 5.78 (s, 2H), 6.38 (d, J = 7.8 Hz, 1H), 6.72 (d, J = 4.2 Hz, 1H), 6.95-7.10 (m, 1H), 7.20 (t, J = 8.1 Hz, 1H), 7.44 (d, J = 3.6 Hz, 1H), 7.45-7.60 (m, 3H), 7.99 (d, J = 8.1 Hz, 1H), 9.38 (s, 1H).<br>LC/MS: condition 3, retention time = 2.60 min<br>LC/MS ($ESI^+$) m/z; 600 $[M + H]^+$<br>LC/MS ($ESI^-$) m/z; 598 $[M - H]^-$ |

TABLE[b] 52

| Rf | Data |
|---|---|
| 65 | $^1$H-NMR ($CDCl_3$) δ: −0.09 (s, 9H), 0.80-0.92 (m, 2H), 0.95 (d, J = 7.2 Hz, 3H), 1.70-1.84 (m, 1H), 2.06-2.22 (m, 1H), 2.60-2.73 (m, 1H), 3.11-3.28 (m, 1H), 3.37-3.59 (m, 2H), 3.78-3.91 (m, 1H), 4.27-4.41 (m, 1H), 4.50-4.63 (m, 1H), 5.09-5.20 (m, 1H), 5.47 (d, J = 10.8 Hz, 1H), 5.63 (d, J = 10.2 Hz, 1H), 6.04 (d, J = 7.8 Hz, 1H), 6.67 (d, J = 3.9 Hz, 1H), 7.17-7.40 (m, 3H), 7.41 (d, J = 3.6 Hz, 1H), 7.78 (d, J = 8.7 Hz, 1H), 8.07 (s, 1H), 8.74 (s, 1H), 9.66 (br s, 1H).<br>LC/MS: condition 3, retention time = 2.74 min<br>LC/MS ($ESI^+$) m/z; 600 $[M + H]^+$<br>LC/MS ($ESI^-$) m/z; 598 $[M - H]^-$ |
| 66 | LC/MS: condition 3, retention time = 2.62 min<br>LC/MS ($ESI^+$) m/z; 585 $[M + H]^+$ |

TABLE[b] 52-continued

| Rf | Data |
|---|---|
| 67 | LC/MS: condition 3, retention time = 2.68 min<br>LC/MS ($ESI^+$) m/z; 585 $[M + H]^+$ |
| 68 | LC/MS: condition 3, retention time = 2.51 min<br>LC/MS ($ESI^+$) m/z; 549 $[M + H]^+$ |
| 69 | $^1$H-NMR ($CDCl_3$) δ: −0.06 (s, 9H), 0.82-0.99 (m, 5H), 1.80-1.96 (m, 1H), 2.09-2.28 (m, 1H), 2.51-2.68 (m, 1H), 3.07-3.26 (m, 1H), 3.42-3.63 (m, 4H), 3.70-3.81 (m, 1H), 5.39-5.48 (m, 1H), 5.80 (dd, 10.5, 12.9 Hz, 2H), 6.39 (d, J = 7.8 Hz, 1H), 6.67 (d, J = 3.9 Hz, 1H), 7.45 (d, J = 4.2 Hz, 1H), 7.63 (d, J = 8.1 Hz, 1H), 7.77 (t, J = 7.8 Hz, 1H), 7.95 (d, J = 8.1 Hz, 1H), 8.03 (d, J = 7.8 Hz, 1H), 8.09 (s, 1H), 9.42 (s, 1H).<br>LC/MS: condition 3, retention time = 2.82 min<br>LC/MS ($ESI^+$) m/z; 621 $[M + H]^+$ |
| 70 | LC/MS: condition 1, retention time = 2.69 min<br>LC/MS ($ESI^+$) m/z; 585 $[M + H]^+$<br>LC/MS ($ESI^-$) m/z; 629 $[M + HCOO]^-$ |
| 71 | LC/MS: condition 3, retention time = 2.72 min<br>LC/MS ($ESI^+$) m/z; 547 $[M + H]^+$ |
| 72 | LC/MS: condition 1, retention time = 2.88 min<br>LC/MS ($ESI^+$) m/z; 222 $[M + H]^+$ |
| 73 | LC/MS: condition 1, retention time = 3.86 min<br>LC/MS ($ESI^+$) m/z; 540 $[M + H]^+$<br>LC/MS ($ESI^-$) m/z; 538 $[M - H]^-$ |
| 74 | LC/MS: condition 1, retention time = 3.52 min<br>LC/MS ($ESI^+$) m/z; 235 $[M + H]^+$<br>LC/MS ($ESI^-$) m/z; 233 $[M - H]^-$ |
| 75 | LC/MS: condition 1, retention time = 3.97 min<br>LC/MS ($ESI^+$) m/z; 553 $[M + H]^+$<br>LC/MS ($ESI^-$) m/z; 551 $[M - H]^-$ |
| 76 | LC/MS: condition 1, retention time = 4.34 min<br>LC/MS ($ESI^+$) m/z; 509 $[M + H]^+$<br>LC/MS ($ESI^-$) m/z; 553 $[M + HCOO]^-$ |
| 77 | LC/MS: condition 1, retention time = 1.26 min<br>LC/MS ($ESI^+$) m/z; 571 $[M + H]^+$ |

TABLE[b] 53

| Rf | Data |
|---|---|
| 78 | LC/MS: condition 1, retention time = 4.21 min<br>LC/MS ($ESI^+$) m/z; 571 $[M + H]^+$<br>LC/MS ($ESI^-$) m/z; 615 $[M + HCOO]^-$ |
| 79 | LC/MS: condition 1, retention time = 4.85 min<br>LC/MS ($ESI^+$) m/z; 571 $[M + H]^+$ |
| 80 | LC/MS: condition 1, retention time = 3.89 min<br>LC/MS ($ESI^+$) m/z; 528 $[M + H]^+$<br>LC/MS ($ESI^-$) m/z; 572 $[M + HCOO]^-$ |
| 81 | LC/MS: condition 1, retention time = 4.45 min<br>LC/MS ($ESI^+$) m/z; 528 $[M + H]^+$ |
| 82 | LC/MS: condition 1, retention time = 3.89 min<br>LC/MS ($ESI^+$) m/z; 528 $[M + H]^+$ |
| 83 | $^1$H-NMR ($CDCl_3$) δ: −0.15 (s, 9H), 0.93 (t, J = 8.1 Hz, 2H), 1.01 (d, J = 7.2 Hz, 3H), 1.44 (s, 9H), 1.70-1.80 (m, 1H), 1.95-2.10 (m, 1H), 2.60-2.77 (m, 1H), 3.25-3.45 (m, 1H), 3.57 (t, J = 8.1 Hz, 2H), 3.64-3.90 (m, 2H), 4.00-4.20 (m, 1H), 5.10-5.22 (m, 1H), 5.80 (dd, J = 10.8, 13.2 Hz, 2H), 6.48 (d, J = 8.1 Hz, 1H), 6.72 (d, J = 3.6 Hz, 1H), 7.44 (d, J = 4.2 Hz, 1H), 7.57 (d, J = 8.4 Hz, 1H), 9.43 (s, 1H).<br>LC/MS: condition 1, retention time = 4.55 min<br>LC/MS ($ESI^+$) m/z; 513 $[M + H]^+$<br>LC/MS ($ESI^-$) m/z; 557 $[M + HCOO]^-$ |
| 84 | $^1$H-NMR ($CDCl_3$) δ: −0.04 (s, 9H), 0.87-1.08 (m, 5H), 1.71-2.10 (m, 2H), 2.40-3.30 (m, 8H), 3.58-3.72 (m, 2H), 5.40-5.54 (m, 1H), 5.80-5.94 (m, 2H), 6.37 (d, J = 7.8 Hz, 1H), 6.87 (d, J = 3.9 Hz, 1H), 6.99-7.15 (m, 2H), 7.15-7.30 (m, 2H), 7.30-7.45 (m, 1H), 7.49 (d, J = 3.6 Hz, 1H), 8.44 (br s, 1H), 9.50 (s, 1H).<br>LC/MS: condition 3, retention time = 2.14 min<br>LC/MS ($ESI^+$) m/z; 535 $[M + H]^+$ |
| 85 | LC/MS: condition 3, retention time = 1.89 min<br>LC/MS ($ESI^+$) m/z; 481 $[M + H]^+$ |
| 86a | LC/MS: condition 3, retention time = 3.17 min<br>LC/MS ($ESI^+$) m/z; 579 $[M + H]^+$ |
| 86b | LC/MS: condition 3, retention time = 3.09 min<br>LC/MS ($ESI^+$) m/z; 579 $[M + H]^+$ |

TABLE[b] 53-continued

| Rf | Data |
|---|---|
| 87 | LC/MS: condition 3, retention time = 2.66 min<br>LC/MS ($ESI^+$) m/z; 327, 329 $[M + H]^+$<br>LC/MS ($ESI^-$) m/z; 325, 327 $[M - H]^-$ |
| 88 | $^1$H-NMR ($CDCl_3$) δ: −0.06 (s, 9H), 0.91 (t, J = 8.4 Hz, 2H), 3.53 (t, J = 8.4 Hz, 2H), 5.68 (s, 2H), 6.71 (d, J = 3.6 Hz, 1H), 7.45 (d, J = 3.9 Hz, 1H), 8.81 (s, 1H).<br>LC/MS: condition 3, retention time = 2.40 min<br>LC/MS ($ESI^+$) m/z; 326, 328 $[M + H]^+$ |

TABLE[b] 54

| Rf | Data |
|---|---|
| 89 | $^1$H-NMR ($CDCl_3$) δ: −0.06 (s, 9H), 0.90 (t, J = 7.5 Hz, 2H), 1.60-1.84 (m, 2H), 2.07-2.19 (m, 2H), 2.21-2.38 (m, 2H), 2.77-2.91 (m, 2H), 3.46 (m, 4H), 3.92-4.10 (m, 1H), 5.57 (s, 4H), 6.58 (d, J = 3.6 Hz, 1H), 7.08 (d, J = 3.9 Hz, 1H), 7.20-7.38 (m, 5H), 8.30 (s, 1H), 9.39 (d, J = 7.5 Hz, 1H).<br>LC/MS: condition 3, retention time = 1.89 min<br>LC/MS ($ESI^+$) m/z; 480 $[M + H]^+$ |
| 90 | $^1$H-NMR ($CDCl_3$) δ: −0.05 (s, 9H), 0.93 (t, J = 8.7 Hz, 2H), 1.80-1.96 (m, 2H), 2.10-2.28 (m, 1H), 2.94-3.22 (m, 4H), 3.56 (t, J = 8.7 Hz, 2H), 3.59 (s, 2H), 4.68-4.85 (m, 1H), 5.73 (s, 2H), 6.74 (d, J = 3.3 Hz, 1H), 7.22-7.48 (m, 6H), 8.03 (s, 1H), 9.04 (s, 1H).<br>LC/MS: condition 3, retention time = 2.18 min<br>LC/MS ($ESI^+$) m/z; 506 $[M + H]^+$ |
| 91 | LC/MS: condition 3, retention time = 1.90 min<br>LC/MS ($ESI^+$) m/z; 416 $[M + H]^+$ |
| 92 | $^1$H-NMR ($CDCl_3$) δ: −0.04 (s, 9H), 0.94 (t, J = 8.1 Hz, 2H), 1.84-1.98 (m, 2H), 2.18-2.32 (m, 2H), 3.00-3.18 (m, 4H), 3.57 (t, J = 8.1 Hz, 2H), 3.65 (s, 2H), 4.70-4.84 (m, 1H), 5.75 (s, 2H), 6.73 (d, J = 3.6 Hz, 1H), 7.45 (d, J = 3.9 Hz, 1H), 7.53 (d, J = 8.4 Hz, 2H), 7.64 (d, J = 8.1 Hz, 2H), 8.09 (s, 1H), 9.06 (s, 1H).<br>LC/MS: condition 3, retention time = 2.23 min<br>LC/MS ($ESI^+$) m/z; 531 $[M + H]^+$ |
| 93 | $^1$H-NMR ($CDCl_3$) δ: −0.05 (s, 9H), 0.93 (t, J = 7.5 Hz, 2H), 1.81-1.96 (m, 2H), 2.18-2.30 (m, 2H), 2.93-3.26 (m, 4H), 3.51-3.62 (m, 2H), 3.71 (s, 2H), 4.66-4.83 (m, 1H), 5.74 (s, 2H), 6.66-6.80 (m, 2H), 7.44 (d, J = 4.2 Hz, 1H), 8.03 (br s, 1H), 9.05 (s, 1H).<br>LC/MS: condition 3, retention time = 2.21 min<br>LC/MS ($ESI^+$) m/z; 546, 548 $[M + H]^+$ |
| 94 | $^1$H-NMR ($CDCl_3$) δ: −0.05 (s, 9H), 0.93 (t, J = 8.1 Hz, 2H), 1.80-1.96 (m, 2H), 2.13-2.30 (m, 2H), 2.95-3.16 (m, 4H), 3.56 (t, J = 8.1 Hz, 2H), 3.64 (s, 2H), 4.70-4.82 (m, 1H), 5.74 (s, 2H), 6.73 (d, J = 3.9 Hz, 1H), 7.40-7.68 (m, 5H), 8.14 (s, 1H), 9.05 (s, 1H).<br>LC/MS: condition 3, retention time = 2.43 min<br>LC/MS ($ESI^+$) m/z; 574 $[M + H]^+$ |
| 95 | LC/MS: condition 3, retention time = 2.87 min<br>LC/MS ($ESI^+$) m/z; 415 $[M + H]^+$ |
| 96 | $^1$H-NMR ($CDCl_3$) δ: −0.06 (s, 9H), 0.88 (t, J = 8.1 Hz, 2H), 2.76 (s, 3H), 3.48-3.62 (m, 2H), 5.67 (s, 2H), 6.74 (d, J = 3.3 Hz, 1H), 7.43 (d, J = 3.9 Hz, 1H), 8.72 (s, 1H). |
| 97 | LC/MS: condition 1, retention time = 3.32 min<br>LC/MS ($ESI^+$) m/z; 479 $[M + H]^+$ |
| 98 | LC/MS: condition 1, retention time = 3.18 min<br>LC/MS ($ESI^+$) m/z; 489 $[M + H]^+$ |
| 99 | LC/MS: condition 1, retention time = 2.88 min<br>LC/MS ($ESI^+$) m/z; 399 $[M + H]^+$ |

TABLE[b] 55

| Rf | Data |
|---|---|
| 100 | LC/MS: condition 1, retention time = 3.50 min<br>LC/MS ($ESI^+$) m/z; 529, 531 $[M + H]^+$ |
| 101 | LC/MS: condition 1, retention time = 3.50 min<br>LC/MS ($ESI^+$) m/z; 557 $[M + H]^+$ |
| 102 | LC/MS: condition 1, retention time = 3.26 min<br>LC/MS ($ESI^+$) m/z; 514 $[M + H]^+$ |

TABLE[b] 55-continued

| Rf | Data |
|---|---|
| 103 | LC/MS: condition 1, retention time = 2.98 min<br>LC/MS ($ESI^+$) m/z; 532 $[M + H]^+$ |
| 104 | LC/MS: condition 1, retention time = 0.35 min<br>LC/MS ($ESI^+$) m/z; 335 $[M + H]^+$ |
| 105 | LC/MS: condition 1, retention time = 3.30 min<br>LC/MS ($ESI^+$) m/z; 465 $[M + H]^+$ |
| 106 | $^1$H-NMR ($CDCl_3$) δ: −0.07 (s, 9H), 0.85-0.98 (m, 2H), 1.52-1.79 (m, 2H), 2.04-2.38 (m, 4H), 2.79-2.95 (m, 2H), 3.44-3.62 (m, 4H), 3.89-4.06 (m, 1H), 4.70 (s, 2H), 5.58 (s, 2H), 6.49 (d, J = 3.6 Hz, 1H), 7.11 (d, J = 3.9 Hz, 1H), 7.23-7.40 (m, 5H), 7.82 (s, 1H). |
| 107 | $^1$H-NMR ($CD_3OD$) δ: −0.03 (s, 9H), 0.92 (t, J = 8.0 Hz, 2H), 1.70-1.91 (m, 2H), 2.12-2.51 (m, 4H), 2.90-3.10 (m, 2H), 3.54-3.78 (m, 4H), 3.96 (s, 2H), 4.02-4.19 (m, 1H), 5.61 (s, 2H), 6.65 (d, J = 4.2 Hz, 1H), 7.28 (d, J = 3.6 Hz, 1H), 7.31-7.53 (m, 5H), 7.84 (s, 1H).<br>LC/MS: condition 1, retention time = 0.37 min<br>LC/MS ($ESI^+$) m/z; 466 $[M + H]^+$ |
| 108 | LC/MS: condition 1, retention time = 3.24 min<br>LC/MS ($ESI^+$) m/z; 492 $[M + H]^+$ |
| 109 | LC/MS: condition 1, retention time = 2.96 min<br>LC/MS ($ESI^+$) m/z; 402 $[M + H]^+$ |
| 110 | LC/MS: condition 1, retention time = 4.45 min<br>LC/MS ($ESI^+$) m/z; 556 $[M + H]^+$ |
| 111 | $^1$H-NMR ($CDCl_3$) δ: −0.05 (s, 9H), 0.81-1.06 (m, 2H), 1.55-2.05 (m, 3H), 2.05-2.29 (m, 1H), 2.93-3.20 (m, 4H), 3.46-3.70 (m, 4H), 4.11-4.28 (m, 1H), 4.29-4.49 (m, 2H), 5.13 (s, 1H), 5.65 (s, 2H), 6.47 (d, J = 3.6 Hz, 1H), 7.21-7.41 (m, 2H), 7.78 (d, J = 7.7 Hz, 1H), 7.98 (s, 1H), 8.45-8.67 (m, 2H).<br>LC/MS: condition 1, retention time = 2.92 min<br>LC/MS ($ESI^+$) m/z; 493 $[M + H]^+$ |
| 112 | LC/MS: condition 1, retention time = 3.26 min<br>LC/MS ($ESI^+$) m/z; 517 $[M + H]^+$ |
| 113 | LC/MS: condition 1, retention time = 3.48 min<br>LC/MS ($ESI^+$) m/z; 560 $[M + H]^+$ |
| 114 | $^1$H-NMR ($CDCl_3$) δ: −0.03 (s, 9H), 0.87-1.05 (m, 2H), 1.50-1.89 (m, 4H), 2.02-2.28 (m, 2H), 2.92-3.25 (m, 2H), 3.60 (t, J = 8.3 Hz, 2H), 4.30-3.72 (m, 3H), 5.70 (s, 2H), 6.44 (d, J = 3.6 Hz, 1H), 7.37 (d, J = 3.9 Hz, 1H), 7.79 (s, 1H), 8.07 (s, 1H), 8.69 (s, 1H).<br>LC/MS: condition 1, retention time = 3.87 min<br>LC/MS ($ESI^+$) m/z; 529 $[M + H]^+$ |

TABLE[b] 56

| Rf | Data |
|---|---|
| 115 | $^1$H-NMR ($CDCl_3$) δ: −0.05 (s, 9H), 0.80-1.03 (m, 2H), 1.53-1.77 (m, 4H), 1.93-2.13 (m, 2H), 3.10-3.40 (m, 2H), 3.55 (t, J = 8.3 Hz, 2H), 3.90-4.07 (m, 1H), 4.31-4.53 (m, 2H), 4.82-4.98 (m, 1H), 5.21 (s, 1H), 5.67 (s, 2H), 6.35-6.48 (m, 1H), 7.35 (d, J = 3.6 Hz, 1H), 8.01 (s, 1H).<br>LC/MS: condition 1, retention time = 4.17 min<br>LC/MS ($ESI^+$) m/z; 512 $[M + H]^+$ |
| 116 | LC/MS: condition 1, retention time = 2.99 min<br>LC/MS ($ESI^+$) m/z; 499 $[M + H]^+$ |
| 117 | LC/MS: condition 1, retention time = 0.52 min<br>LC/MS ($ESI^+$) m/z; 349 $[M + H]^+$ |
| 118 | LC/MS: condition 1, retention time = 3.57 min<br>LC/MS ($ESI^+$) m/z; 479 $[M + H]^+$ |
| 119 | LC/MS: condition 1, retention time = 2.91 min<br>LC/MS ($ESI^+$) m/z; 481 $[M + H]^+$ |
| 120 | LC/MS: condition 1, retention time = 3.42 min<br>LC/MS ($ESI^+$) m/z; 480 $[M + H]^+$ |
| 121 | LC/MS: condition 1, retention time = 3.36 min<br>LC/MS ($ESI^+$) m/z; 506 $[M + H]^+$ |
| 122 | $^1$H-NMR ($CDCl_3$) δ: 0.92-1.19 (m, 4H), 1.41-1.51 (m, 1H), 1.74-1.96 (m, 4H), 2.55-2.68 (m, 1H), 3.45 (d, J = 6.3 Hz, 2H).<br>LC/MS: condition 3, retention time = 0.29 min<br>LC/MS ($ESI^+$) m/z; 130 $[M + H]^+$ |
| 123 | LC/MS: condition 3, retention time = 2.33 min<br>LC/MS ($ESI^+$) m/z; 418 $[M + H]^+$ |
| 124 | LC/MS: condition 3, retention time = 2.16 min<br>LC/MS ($ESI^+$) m/z; 428 $[M + H]^+$ |

TABLE$^b$ 56-continued

| Rf | Data |
|---|---|
| 125 | LC/MS: condition 1, retention time = 3.62 min LC/MS (ESI$^+$) m/z; 230 [M + H]$^+$ |
| 126 | LC/MS: condition 1, retention time = 0.39 min LC/MS (ESI$^+$) m/z; 130 [M + H]$^+$ |
| 127 | LC/MS: condition 1, retention time = 4.43 min LC/MS (ESI$^+$) m/z; 418 [M + H]$^+$ |
| 128 | LC/MS: condition 1, retention time = 4.08 min LC/MS (ESI$^+$) m/z; 428 [M + H]$^+$ |
| 129 | LC/MS: condition 1, retention time = 3.58 min LC/MS (ESI$^+$) m/z; 547 [M + H]$^+$ |
| 130 | LC/MS: condition 1, retention time = 3.52 min LC/MS (ESI$^+$) m/z; 524 [M + H]$^+$ |
| 131 | LC/MS: condition 1, retention time = 3.38 min LC/MS (ESI$^+$) m/z; 551 [M + H]$^+$ |
| 132 | LC/MS: condition 1, retention time = 3.34 min LC/MS (ESI$^+$) m/z; 525 [M + H]$^+$ |
| 133 | LC/MS: condition 1, retention time = 3.56 min LC/MS (ESI$^+$) m/z; 557, 558, 559 [M + H]$^+$ |

TABLE$^b$ 57

| Rf | Data |
|---|---|
| 134 | LC/MS: condition 1, retention time = 3.46 min LC/MS (ESI$^+$) m/z; 558 [M + H]$^+$ |
| 135 | LC/MS: condition 1, retention time = 3.44 min LC/MS (ESI$^+$) m/z; 530, 532 [M + H]$^+$ |
| 136 | LC/MS: condition 1, retention time = 3.56 min LC/MS (ESI$^+$) m/z; 575 [M + H]$^+$ |
| 137 | LC/MS: condition 1, retention time = 3.28 min LC/MS (ESI$^+$) m/z; 540 [M + H]$^+$ |
| 138 | LC/MS: condition 1, retention time = 3.30 min LC/MS (ESI$^+$) m/z; 557, 559 [M + H]$^+$ |
| 139 | LC/MS: condition 1, retention time = 3.56 min LC/MS (ESI$^+$) m/z; 573, 575 [M + H]$^+$ |
| 140 | LC/MS: condition 1, retention time = 3.50 min LC/MS (ESI$^+$) m/z; 573, 575 [M + H]$^+$ |
| 141 | LC/MS: condition 1, retention time = 3.44 min LC/MS (ESI$^+$) m/z; 574, 576 [M + H]$^+$ |
| 142 | LC/MS: condition 1, retention time = 3.46 min LC/MS (ESI$^+$) m/z; 569 [M + H]$^+$ |
| 143 | LC/MS: condition 1, retention time = 3.19 min LC/MS (ESI$^+$) m/z; 528 [M + H]$^+$ |
| 144 | LC/MS: condition 1, retention time = 4.33 min LC/MS (ESI$^+$) m/z; 543, 545 [M + H]$^+$ |

TABLE$^b$ 58

| Rf | Data |
|---|---|
| 145 | LC/MS: condition 3, retention time = 2.21 min LC/MS (ESI$^+$) m/z; 559 [M + H]$^+$ |
| 146 | LC/MS: condition 3, retention time = 2.32 min LC/MS (ESI$^+$) m/z; 590, 592 [M + H]$^+$ |
| 147 | LC/MS: condition 3, retention time = 2.22 min LC/MS (ESI$^+$) m/z; 544 [M + H]$^+$ |
| 148 | LC/MS: condition 3, retention time = 2.05 min LC/MS (ESI$^+$) m/z; 470 [M + H]$^+$ |
| 149 | LC/MS: condition 3, retention time = 2.19 min LC/MS (ESI$^+$) m/z; 486 [M + H]$^+$ |
| 150 | LC/MS: condition 3, retention time = 2.02 min LC/MS (ESI$^+$) m/z; 528 [M + H]$^+$ |
| 151 | $^1$H-NMR ($CDCl_3$) δ: −0.04 (s, 9H), 0.91-0.97 (m, 2H), 1.98 (d, J = 12.3 Hz, 2H), 2.59 (t, J = 11.7 Hz, 2H), 3.00-3.15 (m, 4H), 3.54-3.59 (m, 2H), 3.66 (s, 2H), 4.73-4.81 (m, 1H), 5.75 (s, 2H), 6.84 (d, J = 3.9 Hz, 1H), 7.48 (d, J = 3.6 Hz, 1H), 8.32 (br s, 1H), 9.06 (s, 1H). LC/MS: condition 3, retention time = 2.35 min LC/MS (ESI$^+$) m/z; 455 [M + H]$^+$ |
| 152 | $^1$H-NMR ($CDCl_3$) δ: −0.05 (s, 9H), 0.94 (t, J = 8.3 Hz, 2H), 1.87 (d, J = 10.8 Hz, 2H), 2.67 (t, J = 12 Hz, 2H), 2.98-3.21 (m, 6H), 3.56 (t, J = 8.3 Hz, 2H), 4.71-4.79 (m, 1H), 5.74 (s, 2H), 6.71 (d, J = 3.9 Hz, 1H), 7.45 (d, |

TABLE$^b$ 58-continued

| Rf | Data |
|---|---|
| | J = 3.9 Hz, 1H), 8.08 (br s, 1H), 9.05 (s, 1H). LC/MS: condition 3, retention time = 2.71 min LC/MS (ESI$^+$) m/z; 498 [M + H]$^+$ |
| 153 | LC/MS: condition 3, retention time = 2.00 min LC/MS (ESI$^+$) m/z; 497 [M + H]$^+$ |
| 154 | LC/MS: condition 3, retention time = 2.33 min LC/MS (ESI$^+$) m/z; 554 [M + H]$^+$ |
| 155 | LC/MS: condition 3, retention time = 1.99 min LC/MS (ESI$^+$) m/z; 483 [M + H]$^+$ |
| 156 | LC/MS: condition 3, retention time = 2.05 min LC/MS (ESI$^+$) m/z; 500 [M + H]$^+$ |
| 157 | $^1$H-NMR ($CDCl_3$) δ: −0.04 (s, 9H), 0.93 (t, J = 8.4 Hz, 2H), 1.90 (d, J = 12.3 Hz, 2H), 2.32 (t, J = 11.1 Hz, 2H), 2.57 (t, J = 7.1 Hz, 2H), 2.81 (t, J = 6.9 Hz, 2H), 3.01-3.17 (m, 4H), 3.56 (t, J = 8.3 Hz, 2H), 4.71-4.79 (m, 1H), 5.74 (s, 2H), 6.72 (d, J = 3.9 Hz, 1H), 7.45 (d, J = 3.9 Hz, 1H), 8.12 (br s, 1H), 9.05 (s, 1H). LC/MS: condition 3, retention time = 1.97 min LC/MS (ESI$^+$) m/z; 469 [M + H]$^+$ |
| 158 | LC/MS: condition 1, retention time = 0.33 min LC/MS (ESI$^+$) m/z; 168 [M + H]$^+$ |

TABLE$^b$ 59

| Rf | Data |
|---|---|
| 159a | $^1$H-NMR ($CDCl_3$) δ: 1.52-1.80 (m, 9H), 2.05-2.25 (m, 3H), 3.60-3.75 (m, 1H), 4.90-5.15 (m, 1H), 5.10 (s, 2H), 7.25-7.45 (m, 5H). LC/MS: condition 1, retention time = 3.63 min LC/MS (ESI$^+$) m/z; 302 [M + H]$^+$ |
| 159b | $^1$H-NMR ($CDCl_3$) δ: 1.41-1.53 (m, 3H), 1.53-1.91 (m, 7H), 2.01-2.25 (m, 3H), 3.73-3.86 (m, 1H), 4.98-5.02 (m, 1H), 5.10 (s, 2H), 7.28-7.43 (m, 5H). LC/MS: condition 1, retention time = 3.63 min LC/MS (ESI$^+$) m/z; 302 [M + H]$^+$ |
| 160 | $^1$H-NMR (DMSO-$d_6$) δ: 1.20 (d, J = 12.3 Hz, 2H), 1.57 (m, 5H), 1.72 (s, 1H), 1.92-1.96 (m, 5H), 2.83 (s, 1H), 4.26 (br s, 1H). LC/MS: condition 1, retention time = 0.33 min LC/MS (ESI$^+$) m/z; 168 [M + H]$^+$ |
| 161 | $^1$H-NMR (DMSO-$d_6$) δ: 1.27 (d, J = 12.7 Hz, 2H), 1.41-1.63 (m, 6H), 1.76-2.02 (m, 5H), 2.75-2.80 (br s, 1H). LC/MS: condition 1, retention time = 0.33 min LC/MS (ESI$^+$) m/z; 168 [M + H]$^+$ |
| 162 | $^1$H-NMR ($CDCl_3$) δ: 1.48 (s, 9H), 4.70 (s, 4H). |
| 163 | $^1$H-NMR ($CDCl_3$) δ: 1.46 (s, 9H), 4.58-4.65 (m, 2H), 4.68-4.74 (m, 2H), 5.36-5.41 (m, 1H). LC/MS: condition 1, retention time = 3.44 min LC/MS (ESI$^+$) m/z; 195 [M + H]$^+$ |
| 164 | $^1$H-NMR ($CDCl_3$) δ: 1.44 (s, 9H), 2.64 (d, J = 7.2 Hz, 2H), 2.79-2.94 (m, 1H), 3.69 (dd, J = 8.8, 5.5 Hz, 2H), 4.13 (dd, J = 8.8, 8.3 Hz, 2H). LC/MS: condition 1, retention time = 3.20 min LC/MS (ESI$^+$) m/z; 197 [M + H]$^+$ |
| 165 | LC/MS: condition 1, retention time = 0.33 min LC/MS (ESI$^+$) m/z; 97 [M + H]$^+$ |
| 166 | $^1$H-NMR ($CDCl_3$) δ: −0.05 (s, 9H), 0.95 (t, J = 8.4 Hz, 2H), 1.23 (m, 2H), 1.47 (m, 3H), 2.00 (d, J = 8.7 Hz, 2H), 2.33 (d, J = 8.7 Hz, 2H), 3.58 (m, 4H), 5.63 (br s, 4H), 6.62 (d, J = 4.0 Hz, 1H), 7.13 (d, J = 4.0 Hz, 1H), 8.33 (s, 1H), 9.29 (d, J = 7.8 Hz, 1H). LC/MS: condition 3, retention time = 1.99 min LC/MS (ESI$^+$) m/z; 419 [M + H]$^+$ |
| 167 | $^1$H-NMR ($CDCl_3$) δ: −0.04 (s, 9H), 0.97 (t, J = 8.4 Hz, 2H), 1.28 (m, 2H), 1.43 (m, 1H), 1.74 (m, 1H), 2.09 (m, 4H), 2.80 (m, 2H), 3.60 (t, J = 8.4 Hz, 2H), 3.60 (m, 2H), 4.75 (m, 1H), 5.78 (s, 2H), 6.74 (d, J = 4.0 Hz, 1H), 7.47 (d, J = 4.0 Hz, 1H), 8.41 (s, 1H), 9.10 (s, 1H). LC/MS: condition 3, retention time = 2.33 min LC/MS (ESI$^+$) m/z; 445 [M + H]$^+$ |

TABLE[b] 60

| Rf | Data |
|---|---|
| 168 | $^1$H-NMR ($CDCl_3$) δ: −0.04 (s, 9H), 0.95 (t, J = 8.1 Hz, 2H), 1.53 (m, 2H), 2.06 (m, 4H), 2.42 (m, 1H), 2.85 (m, 2H), 3.60 (t, J = 8.1 Hz, 2H), 4.75 (m, 1H), 5.78 (br s, 2H), 6.70 (d, J = 4.0 Hz, 1H), 7.79 (d, J = 4.0 Hz, 1H), 8.67 (br s, 1H), 9.10 (s, 1H), 9.79 (s, 1H).<br>LC/MS: condition 3, retention time = 2.52 min<br>LC/MS (ESI$^+$) m/z; 443 [M + H]$^+$ |
| 169 | $^1$H-NMR ($CDCl_3$) δ: −0.06 (s, 9H), 0.96 (t, J = 8.1 Hz, 2H), 1.19 (m, 2H), 1.30 (br s, 1H), 1.67 (br s, 1H), 2.07 (m, 4H), 2.08 (m, 2H), 2.80 (m, 2H), 3.25 (m, 2H), 3.60 (t, J = 8.1 Hz, 2H), 4.74 (m, 1H), 5.78 (br s, 2H), 6.73 (d, J = 4.0 Hz, 1H), 7.47 (d, J = 4.0 Hz, 1H), 9.10 (s, 1H).<br>LC/MS: condition 3, retention time = 2.27 min<br>LC/MS (ESI$^+$) m/z; 526 [M + H]$^+$ |
| 170 | $^1$H-NMR ($CDCl_3$) δ: −0.06 (s, 9H), 0.92 (t, J = 8.1 Hz, 2H), 1.88 (m, 2H), 2.03 (m, 4H), 2.37 (m, 1H), 2.85 (m, 2H), 3.53 (t, J = 8.1 Hz, 2H), 4.70 (m, 1H), 5.34 (m, 1H), 5.72 (br s, 2H), 6.30-6.74 (m, 1H), 6.70 (d, J = 4.0 Hz, 1H), 7.44 (d, J = 4.0 Hz, 1H), 9.04 (s, 1H), 9.31 (s, 1H).<br>LC/MS: condition 3, retention time = 2.65 min<br>LC/MS (ESI$^+$) m/z; 446 [M + H]$^+$ |
| 171 | LC/MS: condition 3, retention time = 2.23 min<br>LC/MS (ESI$^+$) m/z; 457 [M + H]$^+$ |
| 172 | LC/MS: condition 3, retention time = 2.23 min<br>LC/MS (ESI$^+$) m/z; 457 [M + H]$^+$ |
| 173 | LC/MS: condition 3, retention time = 2.46 min<br>LC/MS (ESI$^+$) m/z; 483 [M + H]$^+$ |
| 174 | LC/MS: condition 3, retention time = 2.28 min<br>LC/MS (ESI$^+$) m/z; 483 [M + H]$^+$ |
| 175 | $^1$H-NMR ($CDCl_3$) δ: −0.04 (s, 9H), 0.91 (t, J = 7.3 Hz, 2H), 1.53-1.88 (m, 8H), 2.02-2.12 (m, 2H), 2.18-2.27 (m, 1H), 2.37-2.49 (m, 2H), 2.63 (s, 3H), 3.54 (d, J = 7.3 Hz, 2H), 4.05-4.20 (m, 1H), 5.61 (s, 2H), 6.53 (d, J = 3.6 Hz, 1H), 7.07 (d, J = 3.6 Hz, 1H), 8.67 (s, 1H), 10.78 (d, J = 7.6 Hz, 1H).<br>LC/MS: condition 1, retention time = 4.23 min<br>LC/MS (ESI$^+$) m/z; 456 [M + H]$^+$<br>LC/MS (ESI$^-$) m/z; 500 [M + HCOO]$^-$ |
| 176 | $^1$H-NMR ($CDCl_3$) δ: −0.05 (s, 9H), 0.91 (t, J = 8.3 Hz, 2H), 1.40-1.62 (m, 4H), 1.73-2.13 (m, 6H), 2.18-2.28 (m, 1H), 2.30-2.42 (m, 2H), 2.65 (s, 3H), 3.54 (d, J = 8.3 Hz, 2H), 4.19-4.30 (m, 1H), 5.58 (s, 2H), 6.51 (d, J = 4.0 Hz, 1H), 7.07 (d, J = 4.0 Hz, 1H), 8.66 (s, 1H), 10.75 (d, J = 8.0 Hz, 1H).<br>LC/MS: condition 1, retention time = 4.07 min<br>LC/MS (ESI$^+$) m/z; 456 [M + H]$^+$<br>LC/MS (ESI$^-$) m/z; 500 [M + HCOO]$^-$ |

TABLE[b] 61

| Rf | Data |
|---|---|
| 177 | LC/MS: condition 3, retention time = 2.33 min<br>LC/MS (ESI$^+$) m/z; 466 [M + H]$^+$ |
| 178 | LC/MS: condition 3, retention time = 2.15 min<br>LC/MS (ESI$^+$) m/z; 466 [M + H]$^+$ |
| 179 | $^1$H-NMR ($CDCl_3$) δ: 3.01 (d, J = 13.2 Hz, 1H), 3.62 (d, J = 13.2 Hz, 1H), 7.35 (m, 1H), 7.93 (m, 1H), 8.60 (m, 1H), 8.78 (s, 1H).<br>LC/MS: condition 3, retention time = 0.39 min<br>LC/MS (ESI$^+$) m/z; 207 [M + H]$^+$ |

TABLE[b] 62

| Ex | Data |
|---|---|
| 1 | $^1$H-NMR ($CDCl_3$) δ: 1.10-2.00 (m, 10H), 1.58 (d, J = 6.3 Hz, 3H), 3.90-4.10 (m, 1H), 4.67 (d, J = 10.2 Hz, 1H), 4.83 (d, J = 10.2 Hz, 1H), 5.13 (q, J = 6.6 Hz, 1H), 6.43 (.d, J = 3.6 Hz, 1H), 7.17 (d, J = 3.3 Hz, 1H), 7.89 (s, 1H), 9.29 (br s, 1H).<br>LC/MS: condition 1, retention time = 2.82 min<br>LC/MS (ESI$^+$) m/z; 272 [M + H]$^+$ |
| 2 | $^1$H-NMR ($CDCl_3$) δ: 1.10-1.90 (m, 8H), 1.95-2.10 (m, 2H), 3.95-4.10 (m, 1H), 4.78 (s, 2H), 4.96 (s, 2H), 6.43 (d, J = 3.6 Hz, 1H), 7.17 (d, J = 3.3 Hz, 1H), 7.81 (s, 1H), 9.45 (br s, 1H).<br>LC/MS: condition 1, retention time = 2.37 min<br>LC/MS (ESI$^+$) m/z; 258 [M + H]$^+$ |

TABLE[b] 62-continued

| Ex | Data |
|---|---|
| 3 | $^1$H-NMR ($CDCl_3$) δ: 1.50-2.00 (m, 6H), 2.00-2.15 (m, 2H), 2.20-2.35 (m, 2H), 4.90-5.05 (m, 1H), 6.46 (d, J = 7.8 Hz, 1H), 6.80-6.85 (m, 1H), 7.40-7.50 (m, 1H), 7.80 (d, J = 8.1 Hz, 1H), 9.46 (s, 1H), 11.25 (br s, 1H).<br>LC/MS: condition 1, retention time = 3.32 min<br>LC/MS (ESI$^+$) m/z; 268 [M + H]$^+$ |
| 4 | LC/MS: condition 1, retention time = 0.79 min<br>LC/MS (ESI$^+$) m/z; 373 [M + H]$^+$ |
| 5 | LC/MS: condition 1, retention time = 0.50 min<br>LC/MS (ESI$^+$) m/z; 283 [M + H]$^+$ |
| 6a | $^1$H-NMR ($CDCl_3$) δ: 0.87 (d, J = 7.2 Hz, 3H), 1.60-2.00 (m, 2H), 2.40-2.60 (m, 2H), 2.75-3.00 (m, 2H), 3.00-3.20 (m, 1H), 3.70 (s, 2H), 5.40-5.50 (m, 1H), 6.42 (d, J = 7.8 Hz, 1H), 6.80-6.85 (m, 1H), 7.00-7.20 (m, 3H), 7.45-7.50 (m, 1H), 8.51 (br s, 1H), 9.46 (s, 1H), 11.77 (br s, 1H).<br>LC/MS: condition 1, retention time = 2.86 min<br>LC/MS (ESI$^+$) m/z; 409 [M + H]$^+$ |
| 6b | $^1$H-NMR ($CDCl_3$) δ: 0.88 (d, J = 7.2 Hz, 3H), 1.60-2.00 (m, 2H), 2.37 (s, 3H), 2.40-2.55 (m, 2H), 2.55-2.70 (m, 1H), 2.80-2.90 (m, 1H), 2.95-3.05 (m, 1H), 5.40-5.50 (m, 1H), 6.42 (d, J = 8.4 Hz, 1H), 6.83 (d, J = 3.3 Hz, 1H), 7.40-7.50 (m, 1H), 8.30-8.50 (m, 1H), 9.48 (s, 1H), 11.85 (br s, 1H).<br>LC/MS: condition 1, retention time = 0.50 min<br>LC/MS (ESI$^+$) m/z; 297 [M + H]$^+$ |
| 7 | $^1$H-NMR ($CD_3OD$) δ: 1.00-1.10 (m, 3H), 1.80-1.95 (m, 1H), 2.10-2.20 (m, 1H), 2.70-2.90 (m, 1H), 3.20-3.30 (m, 1H), 3.35 (s, 2H), 3.60-3.75 (m, 1H), 3.90-4.25 (m, 1H), 4.25-4.55 (m, 1H), 5.25-5.50 (m, 1H), 6.40-6.55 (m, 1H), 6.85-7.00 (m, 1H), 7.50-7.60 (m, 1H), 8.00-8.10 (m, 1H), 9.21 (s, 1H).<br>LC/MS: condition 1, retention time = 1.92 min<br>LC/MS (ESI$^+$) m/z; 350 [M + H]$^+$ |
| 8 | LC/MS: condition 1, retention time = 3.09 min<br>LC/MS (ESI$^+$) m/z; 365 [M + H]$^+$<br>LC/MS (ESI$^-$) m/z; 363 [M − H]$^-$ |

TABLE[b] 63

| Ex | Data |
|---|---|
| 9 | $^1$H-NMR ($CD_3OD$) δ: 1.01-1.08 (m, 3H), 1.77-1.91 (m, 1H), 2.11-2.19 (m, 1H), 2.74-2.85 (m, 1H), 3.11-3.18 (m, 1H), 3.59-3.82 (m, 3H), 4.00 (dd, J = 9.1, 12.7 Hz, 1H), 4.17 (d, J = 6.8 Hz, 1H), 4.35-4.49 (m, 1H), 5.30-5.44 (m, 1H), 6.40-6.45 (m, 1H), 6.86-6.88 (m, 1H), 7.53-7.55 (m, 1H), 8.00-8.05 (m, 1H), 9.21 (s, 1H).<br>LC/MS: condition 2, retention time = 3.29 min<br>LC/MS (ESI$^+$) m/z; 393 [M + 1]$^+$<br>LC/MS (ESI$^-$) m/z; 391 [M − 1]$^-$ |
| 10 | $^1$H-NMR ($CDCl_3$) δ: 1.02 (d, J = 7.5 Hz, 3H), 1.15 (d, J = 7.2 Hz, 6H), 1.80-1.95 (m, 1H), 2.10-2.40 (m, 2H), 2.70-2.80 (m, 1H), 2.91 (d, J = 6.3 Hz, 2H), 3.25-3.40 (m, 1H), 3.50-3.70 (m, 1H), 3.70-3.80 (m, 1H), 3.85-4.00 (m, 1H), 5.40-5.55 (m, 1H), 6.41 (d, J = 7.8 Hz, 1H), 6.70-6.80 (m, 1H), 7.40-7.50 (m, 1H), 7.67 (d, J = 7.8 Hz, 1H), 9.39 (s, 1H), 11.91 (br s, 1H).<br>LC/MS: condition 1, retention time = 3.44 min<br>LC/MS (ESI$^+$) m/z; 403 [M + H]$^+$<br>LC/MS (ESI$^-$) m/z; 401 [M − H]$^-$ |
| 11 | $^1$H-NMR ($CD_3OD$) δ: 1.00 (d, J = 6.9 Hz, 3H), 1.85-2.00 (m, 1H), 2.10-2.25 (m, 1H), 2.65-2.80 (m, 1H), 3.50-3.70 (m, 2H), 3.90-4.10 (m, 2H), 4.31 (q, J = 9.6 Hz, 2H), 5.50-5.60 (m, 1H), 6.43 (d, J = 8.1 Hz, 1H), 6.92 (d, J = 3.9 Hz, 1H), 7.57 (d, J = 3.6 Hz, 1H), 8.15 (d, J = 8.1 Hz, 1H), 9.22 (s, 1H).<br>LC/MS: condition 1, retention time = 3.37 min<br>LC/MS (ESI$^+$) m/z; 429 [M + H]$^+$<br>LC/MS (ESI$^-$) m/z; 427 [M − H]$^-$ |
| 12 | LC/MS: condition 1, retention time = 3.51 min<br>LC/MS (ESI$^+$) m/z; 304 [M + H]$^+$<br>LC/MS (ESI$^-$) m/z; 302 [M − H]$^-$ |
| 13 | LC/MS: condition 1, retention time = 2.94 min<br>LC/MS (ESI$^+$) m/z; 269 [M + H]$^+$ |
| 14 | $^1$H-NMR ($CDCl_3$) δ: 1.01 (d, J = 7.2 Hz, 3H), 1.53-1.92 (m, 4H), 2.09-2.38 (m, 2H), 2.48-2.73 (m, 2H), 2.75-2.99 (m, 1H), 3.37-2.58 (m, 2H), 4.45-4.62 (m, 1H), 4.88-5.01 (m, 2H), 6.41 |

TABLE[b] 63-continued

| Ex | Data |
|---|---|
| | (d, J = 3.6 Hz, 1H), 7.12 (d, J = 3.6 Hz, 1H), 7.30-7.35 (m, 5H), 7.75 (s, 1H), 9.40 (br s, 1H). |
| 15 | LC/MS: condition 1, retention time = 0.50 min<br>LC/MS ($ESI^+$) m/z; 273 $[M + H]^+$ |
| 16 | $^1$H-NMR ($CDCl_3$) δ: 1.15-1.27 (m, 3H), 1.70-2.05 (m, 2H), 2.44-2.55 (m, 1H), 3.48-3.94 (m, 5H), 4.32-4.36 (m, 1H), 4.65-4.85 (m, 2H), 4.95-5.07 (m, 2H), 6.32-6.38 (m, 1H), 7.19-7.29 (m, 2H), 7.83-7.88 (m, 1H), 9.60-9.49 (m, 1H).<br>LC/MS: condition 1, retention time = 0.54 min<br>LC/MS ($ESI^+$) m/z; 340 $[M + H]^+$ |
| 17 | LC/MS: condition 1, retention time = 2.27 min<br>LC/MS ($ESI^+$) m/z; 271 $[M + H]^+$ |
| 18 | LC/MS: condition 1, retention time = 3.27 min<br>LC/MS ($ESI^+$) m/z; 269 $[M + H]^+$ |
| 19 | LC/MS: condition 1, retention time = 0.54 min<br>LC/MS ($ESI^+$) m/z; 255 $[M + H]^+$ |

TABLE[b] 64

| Ex | Data |
|---|---|
| 20 | $^1$H-NMR (DMSO-$d_6$) δ: 1.20-2.10 (m, 10H), 6.25 (d, J = 8.0 Hz, 1H), 6.42-6.58 (m, 1H), 8.22 (d, J = 8.0 Hz, 1H), 8.49 (s, 1H), 9.10 (s, 1H).<br>LC/MS: condition 1, retention time = 3.24 min<br>LC/MS ($ESI^+$) m/z; 269 $[M + 1]^+$<br>LC/MS ($ESI^-$) m/z; 267 $[M - 1]^-$ |

TABLE[b] 65

| Ex | Data |
|---|---|
| 21 | $^1$H-NMR ($CDCl_3$) δ: 0.23 (d, J = 6.9 Hz, 3H), 1.42-1.56 (m, 1H), 1.60-1.80 (m, 1H), 1.86-2.01 (m, 1H), 2.08-2.21 (m, 1H), 2.72-2.82 (m, 1H), 3.05-3.18 (m, 1H), 3.60 (s, 2H), 3.68 (d, J = 11.4 Hz, 1H), 5.50-5.58 (m, 1H), 6.48 (d, J = 7.8 Hz, 1H), 7.25-7.42 (m, 5H), 7.48 (s, 1H), 9.38 (s, 1H), 9.54 (d, J = 7.8 Hz, 1H).<br>LC/MS: condition 1, retention time = 3.31 min<br>LC/MS ($ESI^+$) m/z; 451, 453 $[M + H]^+$ |
| 22 | $^1$H-NMR ($CDCl_3$) δ: 0.31 (d, J = 6.6 Hz, 3H), 1.40-1.55 (m, 1H), 1.60-1.85 (m, 1H), 1.90-2.05 (m, 1H), 2.10-2.25 (m, 1H), 2.70-2.80 (m, 1H), 3.05-3.20 (m, 1H), 3.50-3.65 (m, 1H), 3.59 (s, 2H), 5.45-5.50 (m, 1H), 6.48 (d, J = 8.1 Hz, 1H), 7.25-7.50 (m, 6H), 9.39 (s, 1H), 9.49 (d, J = 8.4 Hz, 1H), 11.9 (br s, 1H).<br>LC/MS: condition 1, retention time = 3.09 min<br>LC/MS ($ESI^+$) m/z; 407, 409 $[M + H]^+$<br>LC/MS ($ESI^-$) m/z; 405, 407 $[M - H]^-$ |
| 23 | $^1$H-NMR ($CDCl_3$) δ: 0.86 (d, J = 6.9 Hz, 3H), 1.60-1.80 (m, 1H), 1.85-2.00 (m, 1H), 2.22 (s, 3H), 2.40-2.60 (m, 2H), 2.75-2.90 (m, 2H), 3.00-3.10 (m, 1H), 3.65 (dd, J = 22.2, 9.6 Hz, 2H), 5.40-5.50 (m, 1H), 6.80 (s, 1H), 7.20-7.50 (m, 6H), 8.58 (br s, 1H), 9.49 (s, 1H), 11.93 (br s, 1H).<br>LC/MS: condition 1, retention time = 1.00 min<br>LC/MS ($ESI^+$) m/z; 387 $[M + H]^+$<br>LC/MS ($ESI^-$) m/z; 385 $[M - H]^-$ |
| 24 | LC/MS: condition 1, retention time = 2.74 min<br>LC/MS ($ESI^+$) m/z; 451, 453 $[M + H]^+$<br>LC/MS ($ESI^-$) m/z; 449, 451 $[M - H]^-$ |
| 25 | $^1$H-NMR ($CD_3OD$) δ: 0.95 (d, J = 7.2 Hz, 3H), 1.90-2.00 (m, 1H), 2.10-2.25 (m, 1H), 2.60-2.70 (m, 1H), 3.50-3.60 (m, 2H), 3.85-4.05 (m, 2H), 5.45-5.60 (m, 1H), 6.40 (d, J = 8.1 Hz, 1H), 6.82 (d, J = 3.9 Hz, 1H), 7.54 (d, J = 3.6 Hz, 1H), 7.80-7.90 (m, 2H), 8.00-8.05 (m, 1H), 8.10-8.15 (m, 1H), 8.16 (d, J = 7.8 Hz, 1H), 9.20 (s, 1H).<br>LC/MS: condition 3, retention time = 1.73 min<br>LC/MS ($ESI^+$) m/z; 448 $[M + H]^+$<br>LC/MS ($ESI^-$) m/z; 446 $[M - H]^-$ |
| 26 | LC/MS: condition 3, retention time = 1.78 min<br>LC/MS ($ESI^+$) m/z; 448 $[M + H]^+$<br>LC/MS (ESI) m/z; 446 [M − H] |
| 27 | $^1$H-NMR ($CDCl_3$) δ: 1.04 (d, J = 6.9 Hz, 3H), 1.26 (t, J = 6.9 Hz, 3H), 1.70-1.86 (m, 1H), 2.00-2.18 (m, 1H), 2.68-2.84 (m, 1H), |

TABLE[b] 65-continued

| Ex | Data |
|---|---|
| | 3.28-3.50 (m, 1H), 3.68-3.88 (m, 1H), 3.88-4.02 (m, 1H), 4.05-4.38 (m, 3H), 5.15-5.25 (m, 1H), 6.43 (d, J = 7.8 Hz, 1H), 6.73 (br s, 1H), 7.32 (br s, 1H), 7.58 (d, J = 8.1 Hz, 1H), 9.47 (s, 1H), 11.51 (br s, 1H).<br>LC/MS: condition 3, retention time = 1.59 min<br>LC/MS ($ESI^+$) m/z; 355 $[M + H]^+$ |

TABLE[b] 66

| Ex | Data |
|---|---|
| 28 | $^1$H-NMR ($CDCl_3$) δ: 0.98 (d, J = 6.9 Hz, 3H), 1.77-1.88 (m, 1H), 2.16-2.31 (m, 1H), 2.68-2.82 (m, 1H), 3.26-3.42 (m, 1H), 3.90-4.05 (m, 1H), 4.10-4.28 (m, 1H), 4.44-4.59 (m, 1H), 5.38-5.50 (m, 1H), 6.18 (d, J = 7.8 Hz, 1H), 6.89 (br s, 1H), 7.31 (t, J = 7.5 Hz, 1H), 7.49-7.62 (m, 3H), 7.66 (d, J = 7.8 Hz, 1H), 7.75 (d, J = 7.8 Hz, 1H), 8.54 (br s, 1H).<br>LC/MS: condition 3, retention time = 1.78 min<br>LC/MS ($ESI^+$) m/z; 470 $[M + H]^+$<br>LC/MS ($ESI^-$) m/z; 468 $[M - H]^-$ |
| 29 | LC/MS: condition 3, retention time = 1.98 min<br>LC/MS ($ESI^+$) m/z; 470 $[M + H]^+$<br>LC/MS ($ESI^-$) m/z; 468 $[M - H]^-$ |
| 30 | LC/MS: condition 3, retention time = 1.78 min<br>LC/MS ($ESI^+$) m/z; 455 $[M + H]^+$<br>LC/MS (ESI) m/z; 453 [M − H] |
| 31 | $^1$H-NMR ($CDCl_3$) δ: 1.10 (d, J = 7.2 Hz, 3H), 1.75-1.90 (m, 1H), 2.00-2.20 (m, 1H), 2.79-2.99 (m, 1H), 3.41-4.03 (m, 3H), 4.60-5.08 (m, 1H), 5.20-5.40 (m, 1H), 6.45 (d, J = 7.8 Hz, 1H), 6.70 (s, 1H), 7.42-7.86 (m, 6H), 9.46 (s, 1H), 12.14 (s, 1H).<br>LC/MS: condition 3, retention time = 1.87 min<br>LC/MS ($ESI^+$) m/z; 455 $[M + H]^+$<br>LC/MS ($ESI^-$) m/z; 453 $[M - H]^-$ |
| 32 | LC/MS: condition 3, retention time = 1.66 min<br>LC/MS ($ESI^+$) m/z; 419 $[M + H]^+$ |
| 33 | $^1$H-NMR ($CDCl_3$) δ: 0.90 (s, 3H), 1.81-1.98 (m, 1H), 2.10-2.26 (m, 1H), 2.51-2.69 (m, 1H), 3.18-3.33 (m, 1H), 3.34-3.52 (m, 1H), 3.52-3.69 (m, 1H), 3.69-3.81 (m, 1H), 5.40-5.52 (m, 1H), 6.42 (d, J = 7.8 Hz, 1H), 6.67 (s, 1H), 7.46 (s, 1H), 7.65-7.86 (m, 2H), 7.95 (d, J = 7.5 Hz, 1H), 8.05 (d, J = 7.2 Hz, 1H), 8.10 (s, 1H), 9.43 (s, 1H), 11.40 (s, 1H).<br>LC/MS: condition 3, retention time = 2.07 min<br>LC/MS ($ESI^+$) m/z; 491 $[M + H]^+$<br>LC/MS ($ESI^-$) m/z; 489 $[M - H]^-$ |
| 34 | LC/MS: condition 3, retention time = 1.89 min<br>LC/MS ($ESI^+$) m/z; 455 $[M + H]^+$<br>LC/MS ($ESI^-$) m/z; 453 $[M - H]^-$ |
| 35 | LC/MS: condition 3, retention time = 1.88 min<br>LC/MS ($ESI^+$) m/z; 417 $[M + H]^+$ |
| 36 | LC/MS: condition 1, retention time = 2.57 min<br>LC/MS ($ESI^+$) m/z; 410 $[M + H]^+$<br>LC/MS ($ESI^-$) m/z; 408 $[M - H]^-$ |
| 37 | LC/MS: condition 1, retention time = 2.57 min<br>LC/MS ($ESI^+$) m/z; 423 $[M + H]^+$<br>LC/MS ($ESI^-$) m/z; 421 $[M - H]^-$ |
| 38 | LC/MS: condition 1, retention time = 3.20 min<br>LC/MS ($ESI^+$) m/z; 379 $[M + H]^+$<br>LC/MS ($ESI^-$) m/z; 377 $[M - H]^-$ |

TABLE[b] 67

| Ex | Data |
|---|---|
| 39 | LC/MS: condition 1, retention time = 3.00 min<br>LC/MS ($ESI^+$) m/z; 441 $[M + H]^+$<br>LC/MS ($ESI^-$) m/z; 439 $[M - H]^-$ |
| 40 | LC/MS: condition 1, retention time = 3.02 min<br>LC/MS ($ESI^+$) m/z; 441 $[M + H]^+$<br>LC/MS ($ESI^-$) m/z; 439 $[M - H]^-$ |
| 41 | LC/MS: condition 1, retention time = 3.50 min<br>LC/MS ($ESI^+$) m/z; 441 $[M + H]^+$<br>LC/MS ($ESI^-$) m/z; 439 $[M - H]^-$ |

TABLE[b] 67-continued

| Ex | Data |
|---|---|
| 42 | LC/MS: condition 1, retention time = 2.40 min<br>LC/MS ($ESI^+$) m/z; 398 $[M + H]^+$<br>LC/MS ($ESI^-$) m/z; 396 $[M - H]^-$ |
| 43 | LC/MS: condition 1, retention time = 3.07 min<br>LC/MS ($ESI^+$) m/z; 398 $[M + H]^+$<br>LC/MS ($ESI^-$) m/z; 396 $[M - H]^-$ |
| 44 | LC/MS: condition 1, retention time = 1.67 min<br>LC/MS ($ESI^+$) m/z; 398 $[M + H]^+$<br>LC/MS ($ESI^-$) m/z; 396 $[M - H]^-$ |
| 45 | LC/MS: condition 3, retention time = 1.84 min<br>LC/MS ($ESI^+$) m/z; 383 $[M + H]^+$ |
| 46 | LC/MS: condition 3, retention time = 1.34 min<br>LC/MS ($ESI^+$) m/z; 405 $[M + H]^+$ |
| 47 | $^1$H-NMR ($CDCl_3$) δ: 0.88 (d, J = 7.2 Hz, 3H), 1.33-2.08 (m, 10H), 2.40-2.79 (m, 4H), 2.86-3.12 (m, 2H), 5.38-5.49 (m, 1H), 6.41 (d, J = 8.4 Hz, 1H), 6.80-6.90 (m, 1H), 7.40-7.48 (m, 1H), 8.38 (br s, 1H), 9.48 (s, 1H), 11.33 (s, 1H).<br>LC/MS: condition 3, retention time = 1.06 min<br>LC/MS ($ESI^+$) m/z; 351 $[M + H]^+$ |
| 48a | $^1$H-NMR ($CDCl_3$) δ: 0.83 (s, 9H), 1.04 (d, J = 6.6 Hz, 3H), 1.36-2.17 (m, 12H), 2.70-3.00 (m, 2H), 3.38-3.90 (m, 2H), 4.55-4.85 (m, 1H), 5.10-5.30 (m, 1H), 6.41 (d, J = 7.8 Hz, 1H), 6.52 (s, 1H), 7.46 (s, 1H), 7.57 (d, J = 8.4 Hz, 1H), 9.46 (s, 1H), 11.74 (br s, 1H).<br>LC/MS: condition 3, retention time = 2.37 min<br>LC/MS ($ESI^+$) m/z; 449 $[M + H]^+$ |
| 48b | LC/MS: condition 3, retention time = 2.28 min<br>LC/MS ($ESI^+$) m/z; 449 $[M + H]^+$ |
| 49 | LC/MS: condition 3, retention time = 1.22 min<br>LC/MS ($ESI^+$) m/z; 376 $[M + H]^+$<br>LC/MS ($ESI^-$) m/z; 374 $[M - H]^-$ |
| 50 | $^1$H-NMR (DMSO-$d_6$) δ: 1.79-1.90 (m, 2H), 2.12-2.28 (m, 2H), 2.70-2.90 (m, 2H), 2.90-3.04 (m, 2H), 3.63 (s, 2H), 4.62-4.87 (m, 1H), 6.64 (d, J = 3.6 Hz, 1H), 7.56 (d, J = 8.1 Hz, 2H), 7.61 (d, J = 3.6 Hz, 1H), 7.82 (d, J = 8.4 Hz, 2H), 8.74 (s, 1H).<br>LC/MS: condition 3, retention time = 1.37 min<br>LC/MS ($ESI^+$) m/z; 401 $[M + H]^+$<br>LC/MS ($ESI^-$) m/z; 399 $[M - H]^-$ |

TABLE[b] 68

| Ex | Data |
|---|---|
| 51 | $^1$H-NMR (DMSO-$d_6$) δ: 1.77-1.93 (m, 2H), 2.08-2.30 (m, 2H), 2.66-2.89 (m, 2H), 2.98-3.14 (m, 2H), 3.69 (s, 2H), 4.60-4.80 (m, 1H), 6.60-6.70 (m, 1H), 6.86 (d, J = 3.6 Hz, 1H), 6.96 (d, J = 3.3 Hz, 1H), 7.61 (d, J = 3.0 Hz, 1H), 8.74 (s, 1H), 12.36 (br s, 1H).<br>LC/MS: condition 3, retention time = 1.43 min<br>LC/MS ($ESI^+$) m/z; 416, 418 $[M + H]^+$<br>LC/MS ($ESI^-$) m/z; 414, 416 $[M - H]^-$ |
| 52 | $^1$H-NMR (DMSO-$d_6$) δ: 1.78-1.90 (m, 2H), 2.10-2.28 (m, 2H), 2.70-2.90 (m, 2H), 2.90-3.05 (m, 2H), 3.63 (s, 2H), 4.61-4.79 (m, 1H), 6.65 (d, J = 3.3 Hz, 1H), 7.52-7.64 (m, 3H), 7.71 (d, J = 8.1 Hz, 2H), 8.74 (s, 1H).<br>LC/MS: condition 3, retention time = 1.75 min<br>LC/MS ($ESI^+$) m/z; 444 $[M + H]^+$<br>LC/MS ($ESI^-$) m/z; 442 $[M - H]^-$ |
| 53 | LC/MS: condition 3, retention time = 1.79 min<br>LC/MS ($ESI^+$) m/z; 285 $[M + H]^+$ |
| 54 | $^1$H-NMR ($CDCl_3$) δ: 2.05-2.48 (m, 6H), 3.10-3.30 (m, 2H), 3.64 (s, 2H), 4.91-5.10 (m, 1H), 6.46 (d, J = 8.3 Hz, 1H), 6.76-6.89 (m, 1H), 7.21-7.41 (m, 5H), 7.42-7.53 (m, 1H), 7.82 (d, J = 8.0 Hz, 1H), 9.44 (s, 1H), 12.1 (s, 1H).<br>LC/MS: condition 1, retention time = 0.37 min<br>LC/MS ($ESI^+$) m/z; 359 $[M + H]^+$ |
| 55 | $^1$H-NMR (DMSO-$d_6$) δ: 1.98-2.22 (m, 4H), 2.30-2.68 (m, 2H), 3.00-3.18 (m, 2H), 3.76 (s, 2H), 4.83-5.02 (m, 1H), 6.19 (d, J = 7.7 Hz, 1H), 6.80 (d, J = 3.6 Hz, 1H), 6.90 (d, J = 3.6 Hz, 1H), 6.92-7.03 (m, 1H), 7.60 (d, J = 3.3 Hz, 1H), 8.21 (d, J = 8.0 Hz, 1H), 8.32 (s, 1H), 9.02 (s, 1H).<br>LC/MS: condition 1, retention time = 0.94 min<br>LC/MS ($ESI^+$) m/z; 399 $[M + H]^+$ |
| 56 | $^1$H-NMR ($CD_3OD$) δ: 2.12-2.32 (m, 4H), 2.39-2.57 (m, 2H), 3.08-3.23 (m, 2H), 3.75 (s, 2H), 5.09-5.25 (m, 1H), 6.47 (d, |

TABLE[b] 68-continued

| Ex | Data |
|---|---|
| | J = 8.04 Hz, 1H), 6.95 (d, J = 4.2 Hz, 1H), 7.50-7.70 (m, 5H), 8.28 (d, J = 8.0 Hz, 1H), 9.19 (s, 1H).<br>LC/MS: condition 1, retention time = 1.65 min<br>LC/MS ($ESI^+$) m/z; 427 $[M + H]^+$ |
| 57 | $^1$H-NMR (DMSO-$d_6$) δ: 1.98-2.43 (m, 6H), 2.95-3.09 (m, 2H), 3.69 (s, 2H), 4.86-5.01 (m, 1H), 6.19 (d, J = 8.0 Hz, 1H), 7.81 (d, J = 3.9 Hz, 1H), 7.50-7.68 (m, 3H), 7.83 (d, J = 8.3 Hz, 2H), 8.21 (d, J = 8.9 Hz, 1H), 9.02 (s, 1H).<br>LC/MS: condition 1, retention time = 0.37 min<br>LC/MS ($ESI^+$) m/z; 384 $[M + H]^+$ |
| 58 | $^1$H-NMR (DMSO-$d_6$) δ: 1.97-2.24 (m, 4H), 2.35-2.60 (m, 2H), 2.92-3.11 (m, 2H), 3.73 (s, 2H), 4.85-5.03 (m, 1H), 6.01 (d, J = 8.0 Hz, 1H), 6.81 (d, J = 3.6 Hz, 1H), 6.60 (d, J = 3.6 Hz, 1H), 7.64-7.79 (m, 2H), 7.86 (d, J = 9.2 Hz, 1H), 8.20 (d, J = 8.0 Hz, 1H), 8.32 (s, 1H).<br>LC/MS: condition 1, retention time = 0.45 min<br>LC/MS ($ESI^+$) m/z; 402 $[M + H]^+$ |

TABLE[b] 69

| Ex | Data |
|---|---|
| 59 | $^1$H-NMR (DMSO-$d_6$) δ: 1.74-1.90 (m, 2H), 1.98-2.19 (m, 2H), 2.70-3.15 (m, 4H), 3.50 (s, 2H), 3.98-4.14 (m, 1H), 4.18 (s, 2H), 6.31 (d, J = 3.0 Hz, 1H), 7.18 (br s, 1H), 7.22-7.29 (m, 1H), 7.31-7.38 (m, 5H), 7.4 (br s, 1H), 7.93 (s, 1H).<br>LC/MS: condition 1, retention time = 0.35 min<br>LC/MS ($ESI^+$) m/z; 362 $[M + H]^+$ |
| 60 | $^1$H-NMR (DMSO-$d_6$) δ: 1.80-1.98 (m, 2H), 2.68-3.00 (m, 4H), 3.63-3.60 (m, 2H), 4.11-4.31 (m, 3H), 4.43 (s, 2H), 6.29 (br s, 1H), 7.27 (s, 1H), 7.32-7.50 (m, 5H), 7.95 (s, 1H), 11.7 (s, 1H).<br>LC/MS: condition 1, retention time = 2.78 min<br>LC/MS ($ESI^+$) m/z; 426 $[M + H]^+$ |
| 61 | $^1$H-NMR (DMSO-$d_6$) δ: 1.71-1.90 (m, 2H), 2.00-2.20 (m, 2H), 2.68-3.03 (m, 4H), 3.54 (s, 2H), 3.98-4.26 (m, 3H), 6.31 (s, 1H), 7.19 (s, 1H), 7.32-7.49 (m, 2H), 7.68-7.80 (m, 1H), 7.93 (s, 1H), 8.40-8.61 (m, 2H), 11.7 (s, 1H).<br>LC/MS: condition 1, retention time = 0.33 min<br>LC/MS ($ESI^+$) m/z; 363 $[M + H]^+$ |
| 62 | $^1$H-NMR (DMSO-$d_6$) δ: 1.80-1.92 (m, 2H), 2.02-2.20 (m, 2H), 2.68-3.09 (m, 4H), 3.60 (s, 2H), 4.00-4.29 (m, 3H), 6.31 (s, 1H), 7.21 (s, 1H), 7.42 (s, 1H), 7.55 (d, J = 7.7 Hz, 2H), 7.81 (d, J = 7.4 Hz, 2H), 7.94 (s, 1H), 11.7 (s, 1H).<br>LC/MS: condition 1, retention time = 0.35 min<br>LC/MS ($ESI^+$) m/z; 387 $[M + H]^+$ |
| 63 | $^1$H-NMR (DMSO-$d_6$) δ: 1.70-1.92 (m, 2H), 2.01-2.20 (m, 2H), 2.71-3.12 (m, 4H), 3.60 (s, 2H), 4.00-4.33 (m, 3H), 6.32 (d, J = 3.6 Hz, 1H), 7.21 (s, 1H), 7.42 (d, J = 3.6 Hz, 1H), 7.58 (s, J = 7.7 Hz, 2H), 7.71 (d, J = 8.0 Hz, 2H), 7.94 (s, 1H), 11.7 (s, 1H).<br>LC/MS: condition 1, retention time = 0.64 min<br>LC/MS ($ESI^+$) m/z; 430 $[M + H]^+$ |
| 64 | $^1$H-NMR (DMSO-$d_6$) δ: 1.80-2.00 (m, 2H), 2.55-2.79 (m, 2H), 2.85-3.10 (m, 2H), 4.20 (s, 2H), 4.25-4.51 (m, 3H), 6.39 (d, J = 2.4, 1H), 7.24 (s, 1H), 7.43 (s, 1H), 7.95 (s, 1H), 8.94 (s, 1H), 11.7 (s, 1H).<br>LC/MS: condition 1, retention time = 0.39 min<br>LC/MS ($ESI^+$) m/z; 399 $[M + H]^+$ |
| 65 | $^1$H-NMR ($CDCl_3$) δ: 1.95-2.13 (m, 2H), 2.80-3.10 (m, 4H), 3.48-3.62 (m, 2H), 4.02-4.18 (m, 1H), 4.40 (s, 2H), 4.80-4.98 (m, 1H), 5.66 (s, 1H), 6.33-6.51 (m, 1H), 7.15-7.45 (m, 1H), 7.99 (s, 1H), 9.31 (s, 1H). |
| 66 | $^1$H-NMR ($CDCl_3$) δ: 1.89-2.00 (m, 2H), 2.11-2.28 (m, 2H), 2.91-3.24 (m, 4H), 3.84 (s, 2H), 4.14-4.30 (m, 1H), 4.39 (s, 2H), 5.32 (s, 1H), 6.45 (d, J = 3.9 Hz, 1H), 7.30 (d, J = 3.9 Hz, 1H), 7.73 (s, 1H), 7.97 (s, 1H), 8.77 (s, 1H), 9.62 (s, 1H).<br>LC/MS: condition 1, retention time = 0.33 min<br>LC/MS ($ESI^+$) m/z; 369 $[M + H]^+$ |
| 67 | $^1$H-NMR ($CD_3OD$) δ: 0.90-1.05 (m, 3H), 1.53-2.87 (m, 7H), 3.39-3.53 (m, 2H), 4.20-4.56 (m, 3H), 6.48 (d, J = 2.4 Hz, 1H), 7.00-7.35 (m, 5H), 7.67 (s, 1H), 7.90 (s, 1H). |

TABLE$^b$ 70

| Ex | Data |
|---|---|
| 68 | $^1$H-NMR ($CD_3OD$) δ: 2.11-2.22 (m, 2H), 2.92-3.18 (m, 4H), 3.41-3.52 (m, 2H), 4.33 (d, J = 3.9 Hz, 2H), 4.42-4.65 (m, 1H), 6.44-6.49 (m, 1H), 7.36-7.43 (m, 1H), 7.92 (d, J = 4.5 Hz, 1H).<br>LC/MS: condition 1, retention time = 0.35 min<br>LC/MS (ESI$^+$) m/z; 272 $[M + H]^+$ |
| 69 | LC/MS: condition 3, retention time = 1.22 min<br>LC/MS (ESI$^+$) m/z; 298 $[M + H]^+$ |
| 70 | $^1$H-NMR ($CDCl_3$) δ: 1.40-2.10 (m, 4H), 2.15-2.60 (m, 4H), 3.22-3.62 (m, 4H), 4.88-5.21 (m, 1H), 6.45 (d, J = 7.7 Hz, 1H), 6.81 (s, 1H), 7.49 (s, 1H), 7.74 (d, J = 7.7 Hz, 1H), 9.43 (s, 1H), 12.1 (s, 1H).<br>LC/MS: condition 1, retention time = 2.62 min<br>LC/MS (ESI$^+$) m/z; 298 $[M + H]^+$ |
| 71 | $^1$H-NMR ($CDCl_3$) δ: 2.08-2.31 (m, 4H), 2.32-2.53 (m, 2H), 3.12-3.32 (m, 2H), 3.73 (s, 2H), 4.90-5.11 (m 1H), 6.36 (d, J = 3.6 Hz, 1H), 6.46 (d, J = 8.3 Hz, 1H), 6.78 (d, J = 3.9 Hz, 2H), 7.47 (d, J = 3.9 Hz, 1H), 7.79 (d, J = 8.3 Hz, 1H), 9.43 (s, 1H), 11.6 (s, 1H).<br>LC/MS: condition 1, retention time = 0.89 min<br>LC/MS (ESI$^+$) m/z; 417 $[M + H]^+$ |
| 72 | LC/MS: condition 1, retention time = 0.55 min<br>LC/MS (ESI$^+$) m/z; 394 $[M + H]^+$ |
| 73 | LC/MS: condition 1, retention time = 0.62 min<br>LC/MS (ESI$^+$) m/z; 421 $[M + H]^+$ |
| 74 | $^1$H-NMR ($CDCl_3$) δ: 2.02-2.49 (m, 6H), 3.06-3.26 (m, 2H), 3.57 (d, J = 4.5 Hz, 2H), 4.83-5.13 (m, 1H), 5.87 (s, 1H), 6.43 (dd, J = 14.0, 8.0 Hz, 1H), 6.76 (dd, J = 18.8, 3.3 Hz, 1H), 7.02-7.35 (m, 3H), 7.42-7.56 (m, 1H), 7.79 (dd, J = 12.8, 8.0 Hz, 1H), 11.3 (s, 1H).<br>LC/MS: condition 1, retention time = 0.40 min<br>LC/MS (ESI$^+$) m/z; 395 $[M + H]^+$ |
| 75 | $^1$H-NMR (DMSO-$d_6$) δ: 1.95-2.42 (m, 6H), 2.92-3.10 (m, 2H), 3.61 (s, 2H), 4.86-5.04 (m, 1H), 6.19 (d, J = 7.7 Hz, 1H), 6.81 (d, J = 3.6 Hz, 1H), 7.37 (d, J = 8.9 Hz, 1H), 7.52-7.68 (m, 3H), 8.22 (d, J = 8.3 Hz, 1H), 9.02 (s, 1H).<br>LC/MS: condition 1, retention time = 2.42 min<br>LC/MS (ESI$^+$) m/z; 427, 428, 429 $[M + H]^+$ |
| 76 | LC/MS: condition 1, retention time = 0.87 min<br>LC/MS (ESI$^+$) m/z; 428 $[M + H]^+$ |
| 77 | $^1$H-NMR ($CDCl_3$) δ: 1.79-2.60 (m, 6H), 3.15-3.38 (m, 2H), 3.80 (s, 2H), 4.92-5.17 (m, 1H), 6.46 (d, J = 8.3 Hz, 1H), 6.78 (d, J = 3.6 Hz, 1H), 7.41 (s, 1H), 7.49 (d, J = 3.3 Hz, 1H), 7.79 (d, J = 8.3 Hz, 1H), 9.39 (s, 1H), 12.2 (s, 1H).<br>LC/MS: condition 1, retention time = 0.37 min<br>LC/MS (ESI$^+$) m/z; 400, 402 $[M + H]^+$ |

TABLE$^b$ 71

| | |
|---|---|
| 78 | $^1$H-NMR (DMSO-$d_6$) δ: 1.98-2.70 (m, 6H), 2.92-3.10 (m, 2H), 3.67 (s, 2H), 4.84-5.03 (m, 1H), 6.18 (d, J = 7.7 Hz, 1H), 6.81 (d, J = 3.3 Hz, 1H), 7.43-7.62 (m, 2H), 7.75 (d, J = 6.9 Hz, 2H), 8.22 (d, J = 7.7 Hz, 1H), 9.02 (s, 1H).<br>LC/MS: condition 1, retention time = 2.49 min<br>LC/MS (ESI$^+$) m/z; 445 $[M + H]^+$ |
| 79 | LC/MS: condition 1, retention time = 0.37 min<br>LC/MS (ESI$^+$) m/z; 410 $[M + H]^+$ |
| 80 | $^1$H-NMR ($CDCl_3$) δ: 2.09-2.56 (m, 6H), 3.13-3.36 (m, 2H), 3.66 (s, 2H), 4.90-5.11 (m, 1H), 6.28 (dd, J = 9.5, 3.3 Hz, 2H), 6.40-6.55 (d, J = 8.3 Hz, 1H), 6.78 (d, J = 3.9 Hz, 1H), 7.49 (d, J = 3.6 Hz, 1H), 7.79 (d, J = 8.3 Hz, 1H), 9.41 (s, 1H).<br>LC/MS: condition 1, retention time = 0.62 min<br>LC/MS (ESI$^+$) m/z; 427, 429 $[M + H]^+$ |
| 81 | $^1$H-NMR ($CDCl_3$) δ: 2.06-2.51 (m, 6H), 3.15-3.33 (m, 2H), 3.80 (s, 2H), 4.90-5.11 (m, 1H), 6.47 (d, J = 8.3 Hz, 1H), 6.79 (d, J = 3.9 Hz, 1H), 6.89 (d, J = 0.9 Hz, 1H), 8.18 (d, J = 1.5 Hz, 1H), 7.47 (d, J = 3.9 Hz, 1H), 7.81 (d, J = 8.3 Hz, 1H), 9.44 (s, 1H).<br>LC/MS: condition 1, retention time = 0.87 min<br>LC/MS (ESI$^+$) m/z; 443, 445 $[M + H]^+$ |
| 82 | LC/MS: condition 1, retention time = 0.84 min<br>LC/MS (ESI$^+$) m/z; 443, 445 $[M + H]^+$ |
| 83 | $^1$H-NMR ($CDCl_3$) δ: 2.05-2.52 (m, 6H), 3.18-3.30 (m, 2H), 3.82 (s, 2H), 4.93-5.12 (m, 1H), 6.46 (d, J = 7.7 Hz, 1H), 6.78 (d, J = 3.9 Hz, 1H), 7.44 (s, 1H), 7.48 (d, J = 3.9 Hz, 1H), 7.79 (d, J = 8.0 Hz, 1H), 9.42 (s, 1H).<br>LC/MS: condition 1, retention time = 0.50 min<br>LC/MS (ESI$^+$) m/z; 443, 445 $[M + H]^+$ |
| 84 | $^1$H-NMR ($CDCl_3$) δ: 2.05-2.43 (m, 6H), 3.09-3.25 (m, 2H), 3.60 (s, 2H), 4.91-5.11 (m, 1H), 6.46 (d, J = 8.2 Hz, 1H), 6.80 (d, J = 3.8 Hz, 1H), 6.95-7.11 (m, 2H), 7.15 (s, 1H), 7.46 (d, J = 3.4 Hz, 1H), 7.81 (d, J = 8.2 Hz, 1H), 9.43 (s, 1H).<br>LC/MS: condition 1, retention time = 1.37 min<br>LC/MS (ESI$^+$) m/z; 439 $[M + H]^+$ |
| 85 | LC/MS: condition 1, retention time = 0.37 min<br>LC/MS (ESI$^+$) m/z; 398 $[M + H]^+$ |
| 86 | LC/MS: condition 1, retention time = 0.35 min<br>LC/MS (ESI$^+$) m/z; 380 $[M + H]^+$ |
| 87 | LC/MS: condition 1, retention time = 3.32 min<br>LC/MS (ESI$^+$) m/z; 413, 415 $[M + H]^+$<br>LC/MS (ESI$^-$) m/z; 411, 413 $[M - H]^-$ |

TABLE$^b$ 72

| | |
|---|---|
| 88 | LC/MS: condition 3, retention time = 0.37 min<br>LC/MS (ESI$^+$) m/z; 329 $[M + H]^+$<br>LC/MS (ESI$^-$) m/z; 327 $[M - H]^-$ |
| 89 | LC/MS: condition 3, retention time = 1.43 min<br>LC/MS (ESI$^+$) m/z; 460, 462 $[M + H]^+$<br>LC/MS (ESI$^-$) m/z; 458, 460 $[M - H]^-$ |
| 90 | LC/MS: condition 3, retention time = 1.33 min<br>LC/MS (ESI$^+$) m/z; 414 $[M + H]^+$ |
| 91 | LC/MS: condition 3, retention time = 0.75 min<br>LC/MS (ESI$^+$) m/z; 340 $[M + H]^+$ |
| 92 | LC/MS: condition 3, retention time = 1.22 min<br>LC/MS (ESI$^+$) m/z; 356 $[M + H]^+$ |
| 93 | LC/MS: condition 3, retention time = 1.03 min<br>LC/MS (ESI$^+$) m/z; 398 $[M + H]^+$ |
| 94 | LC/MS: condition 3, retention time = 1.16 min<br>LC/MS (ESI$^+$) m/z; 325 $[M + H]^+$ |
| 95 | LC/MS: condition 3, retention time = 1.51 min<br>LC/MS (ESI$^+$) m/z; 368 $[M + H]^+$<br>LC/MS (ESI$^-$) m/z; 366 $[M - H]^-$ |
| 96 | LC/MS: condition 3, retention time = 0.61 min<br>LC/MS (ESI$^+$) m/z; 367 $[M + H]^+$ |
| 97 | LC/MS: condition 3, retention time = 1.49 min<br>LC/MS (ESI$^+$) m/z; 424 $[M + H]^+$<br>LC/MS (ESI$^-$) m/z; 422 $[M - H]^-$ |
| 98 | LC/MS: condition 3, retention time = 0.48 min<br>LC/MS (ESI$^+$) m/z; 353 $[M + H]^+$<br>LC/MS (ESI) m/z; 351 [M − H] |
| 99 | LC/MS: condition 3, retention time = 0.85 min<br>LC/MS (ESI$^+$) m/z; 370 $[M + H]^+$ |
| 100 | $^1$H-NMR (DMSO-$d_6$) δ: 1.82 (d, J = 11.7 Hz, 2H), 2.18 (t, J = 11.3 Hz, 2H), 2.61-2.78 (m, 6H), 3.05 (d, J = 11.4 Hz, 2H), 4.66 (t, J = 11.7 Hz, 1H), 6.64 (d, J = 3.3 Hz, 1H), 7.60 (d, J = 3.3 Hz, 1H), 8.73 (s, 1H), 11.48 (br s, 1H), 12.36 (br s, 1H).<br>LC/MS: condition 3, retention time = 0.43 min<br>LC/MS (ESI$^+$) m/z; 339 $[M + H]^+$<br>LC/MS (ESI$^-$) m/z; 337 $[M - H]^-$ |
| 101 | $^1$H-NMR (DMSO-$d_6$) δ: 1.13 (m, 2H), 1.43 (br s, 1H), 1.90 (m, 4H), 2.52 (m, 2H), 3.30 (m, 2H), 4.43 (t, J = 8.1 Hz, 1H), 4.62 (m, 1H), 6.61 (d, J = 3.9 Hz, 1H), 7.60 (d, J = 3.9 Hz, 1H), 8.73 (s, 1H), 11.42 (br s, 1H), 12.34 (br s, 1H).<br>LC/MS: condition 3, retention time = 1.28 min<br>LC/MS (ESI$^+$) m/z; 315 $[M + H]^+$ |
| 102 | $^1$H-NMR (DMSO-$d_6$) δ: 1.10 (m, 2H), 1.45 (br s, 1H), 1.93 (m, 4H), 2.31 (m, 1H), 3.23 (m, 6H), 4.64 (m, 1H), 6.62 (d, J = 3.3 Hz, 1H), 7.60 (d, J = 3.3 Hz, 1H), 8.74 (s, 1H), 11.42 (br s, 1H), 12.35 (br s, 1H).<br>LC/MS: condition 3, retention time = 1.20 min<br>LC/MS (ESI$^+$) m/z; 396 $[M + H]^+$ |

TABLE$^b$ 73

| | |
|---|---|
| 103 | $^1$H-NMR (DMSO-$d_6$) δ: 1.23-1.60 (m, 2H), 1.81-1.92 (m, 4H), 2.16 (br s, 1H), 2.60 (m, 2H), 4.66 (m, 1H), 5.64-5.77 (m, 1H), 6.56-6.92 (m, 2H), 7.60 (d, J = 3.6 Hz, 1H), 8.73 (s, 1H).<br>LC/MS: condition 3, retention time = 1.70 min<br>LC/MS (ESI$^+$) m/z; 336 $[M + H]^+$ |

TABLE[b] 73-continued

| | |
|---|---|
| 104 | LC/MS: condition 3, retention time = 1.45 min<br>LC/MS ($ESI^+$) m/z; 353 $[M + H]^+$<br>LC/MS ($ESI^-$) m/z; 351 $[M - H]^-$ |
| 105 | LC/MS: condition 3, retention time = 1.27 min<br>LC/MS ($ESI^+$) m/z; 353 $[M + H]^+$ |
| 106 | $^1$H-NMR (DMSO-$d_6$) δ: 1.43-1.84 (m, 7H), 2.00-2.23 (m, 4H), 2.63-2.77 (m, 2H), 4.57 (br s, 1H), 4.91-4.98 (m, 1H), 6.21 (d, J = 8.3 Hz, 1H), 6.90 (d, J = 3.6 Hz, 1H), 7.58 (d, J = 3.6 Hz, 1H), 8.17 (d, J = 8.3 Hz, 1H), 9.05 (s, 1H), 12.06 (br s, 1H).<br>LC/MS: condition 3, retention time = 1.39 min<br>LC/MS ($ESI^+$) m/z; 336 $[M + H]^+$ |
| 107 | $^1$H-NMR (DMSO-$d_6$) δ: 1.40-1.54 (m, 2H), 1.60-1.84 (m, 5H), 2.03-2.18 (m, 4H), 2.63 (br s, 2H), 4.65 (br s, 1H), 5.06 (br s, 1H), 6.19 (d, J = 8.3 Hz, 1H), 6.85 (s, 1H), 7.57-7.63 (m, 1H), 8.20 (d, J = 8.3 Hz, 1H), 9.03 (s, 1H), 12.26 (br s, 1H).<br>LC/MS: condition 3, retention time = 1.24 min<br>LC/MS ($ESI^+$) m/z; 336 $[M + H]^+$ |
| 108 | LC/MS: condition 3, retention time = 0.62 min<br>LC/MS ($ESI^+$) m/z; 399 $[M + H]^+$ |
| 109 | LC/MS: condition 3, retention time = 2.16 min<br>LC/MS ($ESI^+$) m/z; 512 $[M + H]^+$ |
| 110 | LC/MS: condition 3, retention time = 0.74 min<br>LC/MS ($ESI^+$) m/z; 383 $[M + H]^+$ |
| 111 | LC/MS: condition 3, retention time = 0.47 min<br>LC/MS ($ESI^+$) m/z; 412 $[M + H]^+$ |
| 112 | $^1$H-NMR (DMSO-$d_6$) δ: 1.07 (m, 2H), 1.51 (m, 2H), 1.96 (m, 5H), 2.27 (m, 3H), 2.40 (dd, J = 13.5, 7.8 Hz, 1H), 2.50-2.57 (m, 3H), 2.68 (dd, J = 9.6, 6.3 Hz, 1H), 4.17 (br s, 1H), 4.63, (d, J = 1.5 Hz, 2H), 6.62 (d, J = 4.0 Hz, 1H), 7.59 (d, J = 4.0 Hz, 1H), 8.73 (s, 1H), 11.44 (br s, 1H), 12.34 (br s, 1H).<br>LC/MS: condition 3, retention time = 0.81 min<br>LC/MS ($ESI^+$) m/z; 384 $[M + H]^+$ |
| 113 | $^1$H-NMR (DMSO-$d_6$) δ: 1.04 (m, 2H), 1.27 (br s, 1H), 1.86 (d, J = 8.7 Hz, 4H), 2.22 (d, J = 6.9 Hz, 2H), 2.50 (m, 2H), 2.62 (dd, J = 7.5, 6.6 Hz, 2H), 3.48 (dd, J = 7.5, 6.3 Hz, 2H), 4.11 (br s, 1H), 4.58 (m, 1H), 5.18 (br s, 1H), 6.57 (d, J = 3.3 Hz, 1H), 7.56 (d, J = 3.3 Hz, 1H), 8.70 (s, 1H).<br>LC/MS: condition 3, retention time = 0.74 min<br>LC/MS ($ESI^+$) m/z; 370 $[M + H]^+$ |

TABLE[b] 74

| | |
|---|---|
| 114 | $^1$H-NMR (DMSO-$d_6$) δ: 1.04 (m, 2H), 1.51 (br s, 1H), 1.90 (m, 4H), 2.30 (d, J = 7.5 Hz, 2H), 2.50 (m, 2H), 2.86 (br s, 4H), 3.14 (br s, 4H), 4.61 (m, 1H), 6.57 (d, J = 3.3 Hz, 1H), 7.56 (d, J = 3.3 Hz, 1H), 8.71 (s, 1H), 11.40 (br s, 1H), 12.32 (br s, 1H).<br>LC/MS: condition 3, retention time = 1.17 min<br>LC/MS ($ESI^+$) m/z; 432 $[M + H]^+$ |
| 115 | $^1$H-NMR (DMSO-$d_6$) δ: 1.18 (m, 2H), 1.56 (br s, 1H), 1.93 (m, 8H), 2.21 (d, J = 7.8 Hz, 2H), 2.50 (m, 6H), 4.64 (m, 1H), 6.62 (d, J = 3.9 Hz, 1H), 7.59 (d, J = 3.9 Hz, 1H), 8.74 (d, J = 2.7 Hz, 1H), 11.39 (br s, 1H), 12.35 (br s, 1H).<br>LC/MS: condition 3, retention time = 1.19 min<br>LC/MS ($ESI^+$) m/z; 418 $[M + H]^+$ |
| 116 | $^1$H-NMR (DMSO-$d_6$) δ: 1.09 (m, 2H), 1.53 (br s, 1H), 1.90 (d, J = 12.0 Hz, 2H), 2.01 (d, J = 12.0 Hz, 2H), 2.33 (d, J = 7.2 Hz, 2H), 2.55 (m, 2H), 2.61 (m, 4H), 2.76 (m, 4H), 4.64 (m, 1H), 6.62 (d, J = 3.6 Hz, 1H), 7.60 (d, J = 3.6 Hz, 1H), 8.75 (s, 1H), 11.33 (br s, 1H), 12.34 (br s, 1H).<br>LC/MS: condition 3, retention time = 1.62 min<br>LC/MS ($ESI^+$) m/z; 420 $[M + H]^+$ |
| 117 | $^1$H-NMR (DMSO-$d_6$) δ: 0.09 (m, 2H), 0.39 (m, 2H), 0.87 (m, 1H), 1.11 (m, 2H), 1.45 (br s, 1H), 1.92 (m, 4H), 2.40 (d, J = 6.6 Hz, 2H), 2.43 (d, J = 6.6 Hz, 2H), 2.51 (m, 3H), 4.64 (m, 1H), 6.61 (d, J = 3.9 Hz, 1H), 7.59 (d, J = 3.3 Hz, 1H), 8.73 (s, 1H), 11.40 (br s, 1H), 12.32 (br s, 1H).<br>LC/MS: condition 3, retention time = 1.23 min<br>LC/MS ($ESI^+$) m/z; 368 $[M + H]^+$ |
| 118 | $^1$H-NMR (DMSO-$d_6$) δ: 1.09 (m, 2H), 1.52 (br s, 1H), 1.93 (m, 4H), 2.29 (m, 4H), 2.58-2.68 (m, 7H), 4.64 (m, 1H), 6.61 (d, J = 3.6 Hz, 1H), 7.58 (d, J = 3.6 Hz, 1H), 8.74 (s, 1H), 11.31 (br s, 1H), 12.32 (br s, 1H).<br>LC/MS: condition 3, retention time = 0.97 min<br>LC/MS ($ESI^+$) m/z; 393 $[M + H]^+$ |
| 119 | $^1$H-NMR (DMSO-$d_6$) δ: 1.04 (m, 2H), 1.16 (s, 6H), 1.28 (br s, 1H), 1.89 (m, 4H), 2.24 (d, J = 5.4 Hz, 2H), 2.51 (m, 2H), 2.84 (m, 4H), 4.61 (m, 1H), 6.59 (d, J = 3.3 Hz, 1H), 7.59 (d, J = 3.3 |

TABLE[b] 74-continued

| | |
|---|---|
| | Hz, 1H), 8.73 (s, 1H), 11.42 (br s, 1H), 12.34 (br s, 1H).<br>LC/MS: condition 3, retention time = 1.23 min<br>LC/MS ($ESI^+$) m/z; 382 $[M + H]^+$ |
| 120 | $^1$H-NMR (DMSO-$d_6$) δ: 1.05 (m, 2H), 1.51 (br s, 1H), 1.92 (m, 4H), 2.18 (m, 5H), 2.39 (t, J = 6.3 Hz, 2H), 2.55 (m, 2H), 3.47 (dd, J = 12.0, 5.4 Hz, 2H), 4.28 (t, J = 5.4 Hz, 1H), 4.64 (m, 1H), 6.62 (d, J = 3.6 Hz, 1H), 7.59 (d, J = 3.6 Hz, 1H), 8.73 (s, 1H), 11.37 (br s, 1H), 12.34 (br s, 1H).<br>LC/MS: condition 3, retention time = 0.75 min<br>LC/MS ($ESI^+$) m/z; 372 $[M + H]^+$ |

TABLE[b] 75

| | |
|---|---|
| 121 | $^1$H-NMR (DMSO-$d_6$) δ: 0.99 (m, 2H), 1.56 (br s, 1H), 1.89 (d, J = 10.8 Hz, 2H), 2.00 (d, J = 10.8 Hz, 2H), 2.30 (d, J = 3.9 Hz, 2H), 2.60 (m, 4H), 3.47 (dd, J = 12.0, 6.6 Hz, 2H), 3.59 (s, 2H), 4.31 (t, J = 5.4 Hz, 1H), 4.61 (m, 1H), 6.58 (d, J = 3.6 Hz, 1H), 7.21-7.35 (m, 5H), 7.57 (d, J = 3.6 Hz, 1H), 8.73 (s, 1H), 11.41 (br s, 1H), 12.33 (br s, 1H).<br>LC/MS: condition 3, retention time = 1.14 min<br>LC/MS ($ESI^+$) m/z; 448 $[M + H]^+$ |
| 122 | $^1$H-NMR (DMSO-$d_6$) δ: 0.85 (s, 2H), 0.92 (s, 2H), 1.13 (m, 2H), 1.28 (br s, 1H), 1.90 (m, 4H), 2.26 (m, 1H), 2.56 (m, 4H), 4.61 (m, 1H), 6.61 (d, J = 3.6 Hz, 1H), 7.59 (d, J = 3.6 Hz, 1H), 8.73 (s, 1H), 11.45 (br s, 1H), 12.32 (br s, 1H).<br>LC/MS: condition 3, retention time = 1.88 min<br>LC/MS ($ESI^+$) m/z; 422 $[M + H]^+$ |
| 123 | $^1$H-NMR (DMSO-$d_6$) δ: 1.09 (m, 2H), 1.46 (br s, 1H), 1.92 (m, 4H), 2.35-2.43 (m, 9H), 2.60 (m, 4H), 3.56 (m, 4H), 4.63 (m, 1H), 6.61 (d, J = 3.6 Hz, 1H), 7.59 (d, J = 3.6 Hz, 1H), 8.73 (s, 1H).<br>LC/MS: condition 3, retention time = 1.40 min<br>LC/MS ($ESI^+$) m/z; 427 $[M + H]^+$ |
| 124 | LC/MS: condition 3, retention time = 1.05 min<br>LC/MS ($ESI^+$) m/z; 393 $[M + H]^+$ |
| 125 | $^1$H-NMR (DMSO-$d_6$) δ: 0.04 (t, J = 4.2 Hz, 1H), 0.35 (dd, J = 7.2, 4.2 Hz, 1H), 0.98 (s, 3H), 1.11 (s, 3H), 1.13 (m, 2H), 1.46 (br s, 1H), 1.82 (dd, J = 7.2, 3.6 Hz, 1H), 1.93 (m, 5H), 2.41 (m, 2H), 2.55 (m, 2H), 4.64 (m, 1H), 6.62 (d, J = 3.6 Hz, 1H), 7.59 (d, J = 3.6 Hz, 1H), 8.73 (s, 1H), 11.37 (br s, 1H), 12.34 (br s, 1H).<br>LC/MS: condition 3, retention time = 1.37 min<br>LC/MS ($ESI^+$) m/z; 382 $[M + H]^+$ |
| 126 | $^1$H-NMR (DMSO-$d_6$) δ: 1.05-1.27 (m, 3H), 1.36-1.58 (m, 6H), 1.94 (m, 4H), 2.41 (s, 1H), 2.42 (d, J = 6.6 Hz, 2H), 2.55 (m, 6H), 3.93 (br s, 2H), 4.65 (m, 2H), 6.63 (d, J = 3.6 Hz, 1H), 7.60 (d, J = 3.6 Hz, 1H), 8.73 (s, 1H).<br>LC/MS: condition 3, retention time = 1.35 min<br>LC/MS ($ESI^+$) m/z; 426 $[M + H]^+$ |
| 127 | $^1$H-NMR (DMSO-$d_6$) δ: 1.16 (m, 2H), 1.48 (br s, 1H), 1.92 (m, 4H), 2.55 (m, 5H), 3.61 (d, J = 6.0 Hz, 2H), 4.65 (m, 1H), 6.62 (d, J = 3.6 Hz, 1H), 7.59 (d, J = 3.6 Hz, 1H), 8.73 (s, 1H), 11.34 (br s, 1H), 12.34 (br s, 1H).<br>LC/MS: condition 3, retention time = 1.02 min<br>LC/MS ($ESI^+$) m/z; 353 $[M + H]^+$ |
| 128 | $^1$H-NMR (DMSO-$d_6$) δ: 1.07 (m, 2H), 1.47 (m, 2H), 1.56 (br s, 1H), 1.78 (d, J = 17.4 Hz, 2H), 1.95 (m, 6H), 2.15 (d, J = 6.9 Hz, 2H), 2.21 (m, 1H), 2.55 (m, 2H), 2.92 (d, J = 17.4 Hz, 2H), 4.64 (m, 1H), 6.62 (d, J = 3.6 Hz, 1H), 7.59 (d, J = 3.6 Hz, 1H), 8.73 (s, 1H), 11.42 (br s, 1H), 12.34 (br s, 1H).<br>LC/MS: condition 3, retention time = 1.36 min<br>LC/MS ($ESI^+$) m/z; 450 $[M + H]^+$ |

TABLE[b] 76

| | |
|---|---|
| 129 | $^1$H-NMR (DMSO-$d_6$) δ: 1.10 (m, 2H), 1.34 (br s, 1H), 1.89 (m, 4H), 2.35 (d, J = 6.6 Hz, 2H), 2.55 (m, 2H), 3.11 (d, J = 8.4 Hz, 2H), 3.53 (d, J = 8.4 Hz, 2H), 4.61 (m, 1H), 6.60 (d, J = 3.6 Hz, 1H), 6.82 (s, 1H), 7.59 (d, J = 3.6 Hz, 1H), 8.70 (s, 1H), 11.37 (br s, 1H), 12.34 (br s, 1H).<br>LC/MS: condition 3, retention time = 1.20 min<br>LC/MS ($ESI^+$) m/z; 438 $[M + H]^+$<br>LC/MS ($ESI^-$) m/z; 436 $[M - H]^-$ |
| 130 | $^1$H-NMR (DMSO-$d_6$) δ: 1.09 (m, 2H), 1.51 (m, 2H), 1.74-1.84 (m, 4H), 1.92 (m, 4H), 2.43 (d, J = 6.6 Hz, 2H), 2.55 (m, 4H), 3.59 (ddd, J = 14.4, 7.8, 1.2 Hz, 1H), 3.72 (ddd, J = 14.4, 7.8, |

TABLE[b] 76-continued

| | |
|---|---|
| | 1.2 Hz, 1H), 3.85 (m, 1H), 4.64 (m, 1H), 6.62 (d, J = 3.6 Hz, 1H), 7.59 (d, J = 3.6 Hz, 1H), 8.73 (s, 1H).<br>LC/MS: condition 3, retention time = 1.21 min<br>LC/MS ($ESI^+$) m/z; 398 $[M + H]^+$ |
| 131 | LC/MS: condition 3, retention time = 1.10 min<br>LC/MS ($ESI^+$) m/z; 372 $[M + H]^+$ |
| 132 | LC/MS: condition 3, retention time = 1.25 min<br>LC/MS ($ESI^+$) m/z; 503 $[M + H]^+$<br>LC/MS ($ESI^-$) m/z; 501 $[M - H]^-$ |
| 133 | LC/MS: condition 3, retention time = 1.39 min<br>LC/MS ($ESI^+$) m/z; 313 $[M + H]^+$ |
| 134 | $^1$H-NMR (DMSO-$d_6$) δ: 1.19 (m, 2H), 1.42 (br s, 1H), 1.56 (dd, J = 14.1, 7.5 Hz, 2H), 1.80 (m, 2H), 1.92 (m, 4H), 2.55 (m, 2H), 4.64 (m, 1H), 6.62 (d, J = 3.6 Hz, 1H), 7.59 (d, J = 3.6 Hz, 1H), 8.73 (s, 1H).<br>LC/MS: condition 3, retention time = 1.66 min<br>LC/MS ($ESI^+$) m/z; 338 $[M + H]^+$ |
| 135 | LC/MS: condition 3, retention time = 1.80 min<br>LC/MS ($ESI^+$) m/z; 463 $[M + H]^+$<br>LC/MS (ESI) m/z; 461 [M − H] |
| 136 | LC/MS: condition 3, retention time = 1.85 min<br>LC/MS ($ESI^+$) m/z; 410 $[M + H]^+$<br>LC/MS ($ESI^-$) m/z; 408 $[M - H]^-$ |
| 137 | LC/MS: condition 3, retention time = 2.13 min<br>LC/MS ($ESI^+$) m/z; 324 $[M + H]^+$<br>LC/MS ($ESI^-$) m/z; 322 $[M - H]^-$ |
| 138 | LC/MS: condition 3, retention time = 2.13 min<br>LC/MS ($ESI^+$) m/z; 299 $[M + H]^+$<br>LC/MS ($ESI^-$) m/z; 297 $[M - H]^-$ |
| 139 | LC/MS: condition 3, retention time = 2.49 min<br>LC/MS ($ESI^+$) m/z; 367 $[M + H]^+$<br>LC/MS ($ESI^-$) m/z; 365 $[M - H]^-$ |
| 140 | LC/MS: condition 3, retention time = 1.86 min<br>LC/MS ($ESI^+$) m/z; 329 $[M + H]^+$<br>LC/MS ($ESI^-$) m/z; 327 $[M - H]^-$ |

TABLE[b] 77

| | |
|---|---|
| 141 | LC/MS: condition 3, retention time = 1.93 min<br>LC/MS ($ESI^+$) m/z; 343 $[M + H]^+$<br>LC/MS ($ESI^-$) m/z; 341 $[M - H]^-$ |
| 142 | LC/MS: condition 3, retention time = 1.61 min<br>LC/MS ($ESI^+$) m/z; 398 $[M + H]^+$<br>LC/MS ($ESI^-$) m/z; 396 $[M - H]^-$ |
| 143 | LC/MS: condition 3, retention time = 2.13 min<br>LC/MS ($ESI^+$) m/z; 329 $[M + H]^+$<br>LC/MS ($ESI^-$) m/z; 327 $[M - H]^-$ |
| 144 | LC/MS: condition 3, retention time = 2.45 min<br>LC/MS ($ESI^+$) m/z; 359 $[M + H]^+$<br>LC/MS ($ESI^-$) m/z; 357 $[M - H]^-$ |
| 145 | LC/MS: condition 3, retention time = 2.19 min<br>LC/MS ($ESI^+$) m/z; 343 $[M + H]^+$<br>LC/MS ($ESI^-$) m/z; 341 $[M - H]^-$ |
| 146 | LC/MS: condition 3, retention time = 2.26 min<br>LC/MS ($ESI^+$) m/z; 338 $[M + H]^+$<br>LC/MS ($ESI^-$) m/z; 336 $[M - H]^-$ |
| 147 | LC/MS: condition 3, retention time = 2.41 min<br>LC/MS ($ESI^+$) m/z; 345 $[M + H]^+$<br>LC/MS ($ESI^-$) m/z; 343 $[M - H]^-$ |
| 148 | LC/MS: condition 3, retention time = 2.83 min<br>LC/MS ($ESI^+$) m/z; 353 $[M + H]^+$<br>LC/MS ($ESI^-$) m/z; 351 $[M - H]^-$ |
| 149 | LC/MS: condition 3, retention time = 2.58 min<br>LC/MS ($ESI^+$) m/z; 339 $[M + H]^+$ |
| 150 | LC/MS: condition 3, retention time = 2.31 min<br>LC/MS ($ESI^+$) m/z; 369 $[M + H]^+$<br>LC/MS ($ESI^-$) m/z; 367 $[M - H]^-$ |
| 151 | LC/MS: condition 3, retention time = 1.95 min<br>LC/MS ($ESI^+$) m/z; 387 $[M + H]^+$<br>LC/MS ($ESI^-$) m/z; 385 $[M - H]^-$ |
| 152 | LC/MS: condition 3, retention time = 1.94 min<br>LC/MS ($ESI^+$) m/z; 370 $[M + H]^+$ |
| 153 | LC/MS: condition 3, retention time = 1.62 min<br>LC/MS ($ESI^+$) m/z; 356 $[M + H]^+$<br>LC/MS (ESI) m/z; 354 [M − H] |
| 154 | LC/MS: condition 3, retention time = 1.64 min<br>LC/MS ($ESI^+$) m/z; 368 $[M + H]^+$ |

TABLE[b] 77-continued

| | |
|---|---|
| 155 | LC/MS: condition 3, retention time = 2.07 min<br>LC/MS ($ESI^+$) m/z; 506 $[M + H]^+$<br>LC/MS ($ESI^-$) m/z; 504 $[M - H]^-$ |

Pharmacological Assay

Now, a pharmacological assay of the tricyclic pyridine compounds of the present invention will be described.

Assay Example[b] 1

Enzyme Assay

JAK1, JAK2, JAK3 and Tyk2 were purchased from Carna Biosciences, Inc. As the substrate, LANCE Ultra ULight-JAK1 Peptide (manufactured by PerkinElmer Co., Ltd. (PE)) was used. Dilute solutions of compounds and enzymes in assay buffer (50 mM HEPES pH7.5, 1 mM EGTA, 1 mM $MgCl_2$, 2 mM DTT, 0.01% Tween20) were dispensed into wells of a 384-well black plate. After 5 minutes of preincubation, dilute solutions of the substrate and ATP (adenosine triphosphate) were added at a final concentration of 100 μM, and the plate was incubated at room temperature for 2 hours. After addition of a termination reagent containing EDTA (ehylenediamine tetraacetic acid) at a final concentration of 10 mM, LANCE Eu-W1024 Anti-phosphotyrosine (PT66) (manufactured by PE) was added, and after 1 hour of incubation, the fluorescences were measured with ARVO-HTS. From the plot of logarithm of a compound concentration and inhibitory activity, the $IC_{50}$ was calculated. The results of JAK3, JAK1, JAK2 and Tyk2 enzyme assays of the compounds of Synthetic Examples[b] are shown in Tables[b] 78 to 81. "*" in the Tables indicates $IC_{50}$>1 μM.

TABLE[b] 78

| Ex[b]. No. | $IC_{50}$ (μM) JAK3 | $IC_{50}$ (μM) JAK1 |
|---|---|---|
| 1 | 2.0 | 0.38 |
| 2 | 1.2 | 0.33 |
| 3 | 0.22 | 0.017 |
| 4 | 0.065 | 0.030 |
| 6a | 0.031 | 0.027 |
| 6b | 0.25 | 0.19 |
| 7 | 0.0032 | 0.0017 |
| 8 | 0.041 | 0.026 |
| 9 | 0.010 | 0.0040 |
| 10 | 0.034 | 0.0081 |
| 11 | 0.034 | 0.012 |
| 12 | 1.3 | 0.13 |
| 13 | 1.3 | 0.042 |
| 16 | 0.11 | 0.038 |
| 17 | 0.69 | 0.027 |
| 18 | 1.2 | 0.045 |
| 19 | 2.2 | 0.29 |
| 20 | 0.51 | 0.28 |

TABLE[b] 79

| Ex[b]. No. | $IC_{50}$ (μM) JAK2 | $IC_{50}$ (μM) TYK2 |
|---|---|---|
| 1 | 2.2 | 4.1 |
| 2 | 1.9 | 3.1 |
| 3 | 0.15 | 0.13 |
| 4 | 0.10 | * |
| 6a | 0.046 | 0.63 |
| 6b | 0.38 | 3.9 |
| 7 | 0.0040 | 0.060 |

TABLE$^b$ 79-continued

| Ex$^b$. No. | $IC_{50}$ (μM) JAK2 | $IC_{50}$ (μM) TYK2 |
|---|---|---|
| 8 | 0.075 | 1.5 |
| 9 | 0.0094 | 0.15 |
| 10 | 0.039 | 1.6 |
| 11 | 0.033 | 0.44 |
| 12 | 0.46 | * |
| 13 | 0.56 | * |
| 16 | 0.088 | 0.57 |
| 17 | 0.020 | 0.093 |
| 18 | 0.12 | 0.25 |
| 19 | 1.3 | 1.5 |
| 20 | 1.6 | 0.76 |

TABLE$^b$ 80

| Ex$^b$. No. | $IC_{50}$ (μM) JAK1 | $IC_{50}$ (μM) JAK2 | $IC_{50}$ (μM) JAK3 | $IC_{50}$ (μM) TYK2 |
|---|---|---|---|---|
| 21 | 0.56 | 1.3 | 0.82 | * |
| 22 | 0.33 | 0.28 | 0.37 | * |
| 23 | 0.035 | 0.22 | 0.10 | * |
| 24 | 0.025 | 0.74 | 0.56 | * |
| 25 | 0.055 | 0.23 | 0.070 | 0.70 |
| 26 | 0.0066 | 0.048 | 0.10 | 0.41 |
| 27 | 0.018 | 0.040 | 0.042 | 0.43 |
| 28 | 0.31 | 2.0 | 2.3 | 7.9 |
| 29 | 0.015 | 0.19 | 0.20 | 0.41 |
| 30 | 0.18 | * | * | * |
| 31 | 0.24 | * | * | * |
| 32 | 0.081 | 0.77 | 0.55 | * |
| 33 | 0.0098 | 0.12 | 0.096 | 0.40 |
| 34 | 0.16 | 0.86 | * | * |
| 35 | 0.018 | 0.089 | 0.11 | 0.99 |
| 36 | 0.00058 | 0.0032 | 0.0038 | 0.051 |
| 37 | 0.0015 | 0.0061 | 0.0028 | 0.062 |
| 38 | 0.0046 | 0.028 | 0.031 | 0.27 |
| 39 | 0.048 | 0.15 | 0.18 | * |
| 40 | 0.088 | 0.50 | 0.26 | * |
| 41 | 0.20 | 0.29 | 0.32 | * |
| 42 | 0.016 | 0.15 | 0.093 | * |
| 43 | 0.030 | 0.16 | 0.15 | 0.51 |
| 44 | 0.014 | 0.15 | 0.057 | 0.84 |
| 45 | 0.012 | 0.038 | 0.040 | 0.44 |
| 46 | 0.033 | 0.21 | 0.046 | * |
| 47 | 0.11 | 0.23 | 0.11 | * |
| 48a | 0.14 | 1.0 | * | * |
| 48b | 0.094 | 0.46 | 0.36 | * |
| 49 | 0.0079 | 0.10 | * | * |
| 50 | 0.0087 | * | * | * |
| 51 | 0.0050 | 0.36 | * | * |
| 52 | 0.021 | * | * | * |
| 53 | 0.0074 | 0.048 | 0.047 | 0.040 |
| 54 | 0.0030 | 0.032 | 0.47 | 0.32 |
| 55 | 0.0012 | 0.020 | 0.21 | 0.22 |
| 56 | 0.019 | 0.24 | * | * |
| 57 | 0.013 | 0.25 | * | 0.86 |
| 58 | 0.037 | 0.57 | * | * |
| 59 | 0.042 | 0.16 | 2.1 | 4.3 |
| 60 | 0.35 | 0.48 | * | * |
| 61 | 0.077 | 0.22 | 5.4 | 3.6 |
| 62 | 0.054 | 0.36 | * | * |
| 63 | 0.12 | * | * | * |
| 64 | 0.012 | 0.020 | 0.22 | 0.17 |
| 65 | 0.19 | 0.11 | 9.5 | 2.9 |
| 66 | 0.080 | 0.14 | * | 0.99 |
| 68 | 0.50 | 2.4 | 9.1 | * |
| 69 | 0.036 | 0.46 | * | 0.30 |
| 70 | 0.16 | * | * | * |
| 71 | 0.0019 | 0.036 | 0.46 | 0.38 |
| 72 | 0.0098 | 0.33 | * | 0.88 |
| 73 | 0.053 | * | * | * |
| 74 | 0.0050 | 0.069 | 0.86 | 0.84 |
| 75 | 0.0089 | 0.062 | * | * |
| 76 | 0.028 | 0.45 | * | * |

TABLE$^b$ 80-continued

| Ex$^b$. No. | $IC_{50}$ (μM) JAK1 | $IC_{50}$ (μM) JAK2 | $IC_{50}$ (μM) JAK3 | $IC_{50}$ (μM) TYK2 |
|---|---|---|---|---|
| 77 | 0.0079 | 0.077 | 1.0 | * |
| 78 | 0.0039 | 0.066 | * | * |
| 79 | 0.00040 | 0.0063 | 0.094 | 0.12 |
| 80 | 0.0016 | 0.020 | 0.34 | 0.24 |
| 81 | 0.000084 | 0.0016 | 0.031 | 0.034 |
| 82 | 0.0021 | 0.021 | 0.32 | 0.32 |
| 83 | 0.0052 | 0.043 | 0.62 | 0.81 |
| 84 | 0.00075 | 0.017 | 0.13 | 0.33 |
| 85 | 0.075 | 0.68 | * | * |
| 86 | 0.043 | * | * | * |
| 87 | 0.025 | 0.38 | * | * |

TABLE$^b$ 81

| Ex$^b$. No. | $IC_{50}$ (μM) JAK1 | $IC_{50}$ (μM) JAK2 | $IC_{50}$ (μM) JAK3 | $IC_{50}$ (μM) TYK2 |
|---|---|---|---|---|
| 88 | 0.082 | * | * | * |
| 89 | 0.011 | * | * | * |
| 90 | 0.22 | * | * | * |
| 91 | 0.083 | * | * | * |
| 92 | 0.097 | * | * | * |
| 93 | 0.37 | * | * | * |
| 94 | 0.034 | * | * | 0.93 |
| 95 | 0.017 | 0.34 | * | * |
| 96 | 0.019 | * | * | * |
| 97 | 0.23 | * | * | * |
| 98 | 0.021 | 0.67 | * | * |
| 99 | 0.069 | * | * | * |
| 100 | 0.0066 | 0.046 | * | 0.45 |
| 101 | 0.015 | 0.40 | * | 0.46 |
| 102 | 0.0028 | 0.080 | 0.32 | 0.091 |
| 103 | 0.0043 | 0.083 | * | 0.12 |
| 104 | 0.034 | 0.046 | 0.38 | 0.38 |
| 105 | 3.2 | * | * | * |
| 106 | 0.047 | 0.25 | 0.61 | 0.38 |
| 107 | 0.31 | 0.60 | 0.41 | * |
| 108 | 0.37 | * | * | * |
| 109 | 0.92 | * | * | * |
| 110 | 0.42 | * | * | * |
| 111 | 0.44 | * | * | * |
| 112 | 0.0026 | 0.25 | * | 0.032 |
| 113 | 0.0033 | 0.22 | * | 0.19 |
| 114 | 0.010 | 0.23 | 0.52 | 0.25 |
| 115 | 0.030 | * | * | * |
| 116 | 0.0012 | 0.012 | 0.036 | 0.039 |
| 117 | 0.030 | 0.85 | * | 0.80 |
| 118 | 0.027 | 0.34 | * | * |
| 119 | 0.039 | * | * | * |
| 120 | 0.029 | 0.73 | * | * |
| 121 | 0.0074 | 0.21 | * | * |
| 122 | 0.0032 | 0.49 | * | * |
| 123 | 0.15 | * | * | * |
| 124 | 0.025 | 0.61 | * | * |
| 125 | 0.020 | 0.43 | * | * |
| 126 | 0.028 | 0.36 | * | * |
| 127 | 0.0055 | 0.19 | * | 0.12 |
| 128 | 0.067 | * | * | * |
| 129 | 0.0079 | 0.18 | 0.81 | 0.36 |
| 130 | 0.048 | * | * | * |
| 131 | 0.036 | * | * | 0.78 |
| 132 | 0.0092 | 0.32 | * | * |
| 133 | 0.012 | 0.27 | * | 0.41 |
| 134 | 0.0020 | 0.025 | 0.81 | 0.032 |
| 135 | 0.0049 | 0.060 | 0.50 | 0.33 |
| 136 | 0.0032 | 0.051 | 0.75 | 0.32 |
| 137 | 0.057 | * | 0.91 | * |
| 138 | 0.040 | 0.42 | 0.51 | * |
| 139 | 0.10 | 0.77 | * | * |
| 140 | 0.018 | 0.25 | 0.78 | 0.36 |
| 141 | 0.046 | 0.23 | 0.80 | 0.60 |
| 142 | 0.34 | * | * | * |
| 143 | 0.073 | 0.85 | * | * |

TABLE[b] 81-continued

| $Ex^b$. No. | $IC_{50}$ (μM) JAK1 | $IC_{50}$ (μM) JAK2 | $IC_{50}$ (μM) JAK3 | $IC_{50}$ (μM) TYK2 |
|---|---|---|---|---|
| 144 | 0.053 | 0.70 | * | * |
| 145 | 0.047 | 0.69 | * | * |
| 146 | 0.21 | * | * | * |
| 147 | 0.098 | 0.82 | * | * |
| 148 | 0.44 | * | * | * |
| 149 | 0.27 | * | * | * |
| 150 | 0.092 | 0.23 | 0.64 | * |
| 151 | 0.21 | * | * | * |
| 152 | 0.067 | 0.21 | 0.48 | * |
| 153 | 0.33 | * | * | * |
| 154 | 0.29 | * | * | * |
| 155 | 0.0021 | 0.055 | 0.20 | 0.14 |

The tricyclic pyridine compounds of the present invention have favorable inhibitory activity against JAKs as shown above.

Assay Example[b] 2

Signal Assay in Human Whole Blood

To be a effective pharmaceutical compound for the target diseases of the present invention, especially for rheumatoid arthritis, it is more favorable that the compounds indicate excellent inhibitory activity against JAKs in human whole blood. Inhibitory activity against JAKs in human whole blood can be assessed by, for example, STAT phosphorylation assay in human whole blood as described below.

Compounds are added at the various concentrations to human whole blood which is collected from healthy volunteers and preincubated for 30 minutes. Next, cytokine such as IL-2 or IL-6 is added to the mixture and incubated for 15 minutes. Cytokines can be purchased, for example, from PeproTech Inc. Cytokines are added to mixture at 100 ng/mL as final concentration. The mixture including the blood cells are hemolyzed, fixed, permeabilized, washed, and resuspended in stain buffer. BD Cytofix/Cytoperm® solution (manufactured by Becton, Dickinson and Company (BD)), for example, can be used to hemolyze, fix, and permeabilize. Staining buffer (manufactured by BD), for example, can be used as stain buffer according to each protocol issued by BD. Fluorescence-labeled anti-phosphorylated STAT antibody and fluorescence-labeled anti-CD3 antibody are added to the cell suspension and incubated for 30 minutes. Then, cells are washed and resuspended in stain buffer. Fluorescence-labeled anti-phosphorylated STAT antibody and fluorescence-labeled anti-CD3 antibody can be purchased, for example from BD, and final concentration of antibodies can be determined according to each protocols issued by BD. Fluorescence intensity of fluorescence-labeled cells in cell suspension is detected by flow-cytometory. Because the detected fluorescence intensity is proportional to the concentration of the phosphorylated STAT protein in CD3 positive cells, inhibitory activity against STAT phosphorylation by the compounds can be calculated from the ratio between the above mentioned fluorescence intensity and the blank fluorescence intensity which is measured simultaneously without the compounds. From the plot of logarithm of the compound concentrations and the inhibitory activities, the $IC_{50}$ value can be calculated.

Assay Example[b] 3

Inhibition of Proliferation of Erythro-Leukemic Cell Line

The inhibitory activity of the tricyclic pyridine compounds of the present invention on cell proliferation mediated by JAK signal can be assayed using a human erythroleukemic cell line, TF-1.

TF-1 cells can be purchased from ATCC (American Type Culture Collection). TF-1 cells can be expanded in RPMI1640 media containing 5% FBS and 1 ng/mL GM-CSF (Granulocyte Macrophage Colony-Stimulating Factor) using a $CO_2$ incubator (5% $CO_2$, 37° C.). At the assay, TF-1 cells washed by PBS (Phosphate Buffered Saline) are resuspended in RPMI1640 media containing 5% FBS, and dispensed in 96-well culture plate at $1\times10^4$ cells/well. Compounds at various concentrations are added to the cells and preincubated for 30 minutes, and then cytokine such as IL-4 or IL-6 is added to the cells. Culture plates are incubated using a $CO_2$ incubator (5% $CO_2$, 37° C.) for 3 days. Cell proliferation can be assayed using WST-8 reagent (Kishida Chemical Co., Ltd.) according to instructions by the manufacturer. The formazan pigment is generated by the addition of WST-8 reagent solution to each well of the culture plates and the subsequent incubation in a $CO_2$ incubator (5% $CO_2$, 37° C.) for 4 hours, and then detected by measuring the absorbance at 450 nm with a microplate reader. From the plot of logarithm of the compound concentrations and the inhibitory activities, the $IC_{50}$ value can be calculated.

Now, examples of formulations of tricyclic pyrimidine compounds represented by the formula ($I^a$) and tricyclic pyridine compounds represented by the formula ($I^b$) of the present invention (hereinafter referred to collectively as compounds represented by the formula (I)) will be shown.

Formulation Example 1

A granule preparation containing the following ingredients is prepared.

| Ingredients | |
|---|---|
| Compound represented by the formula (I) | 10 mg |
| Lactose | 700 mg |
| Corn Starch | 274 mg |
| HPC-L | 16 mg |
| Total | 1000 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
|---|---|
| Compound represented by the formula (I) | 10 mg |
| Lactose | 79 mg |
| Corn Starch | 10 mg |
| Magnesium Stearate | 1 mg |
| Total | 100 mg |

A compound represented by the formula (I) and lactose are sifted through a 60-mesh sieve. Corn starch is sifted though a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.

| Ingredients | |
|---|---|
| Compound represented by the formula (1) | 15 mg |
| Lactose | 90 mg |
| Corn Starch | 42 mg |
| HPC-L | 3 mg |
| Total | 150 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard gelatin capsules No. 4, 150 mg each.

Formulation Example 4

A tablet preparation containing the following ingredients is prepared.

| Ingredients | |
|---|---|
| Compound represented by the formula (I) | 10 mg |
| Lactose | 90 mg |
| Microcrystalline cellulose | 30 mg |
| Magnesium Stearate | 5 mg |
| CMC-Na | 15 mg |
| Total | 150 mg |

A compound represented by the formula (I), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| | |
|---|---|
| Compound represented by the formula (I) | 100 mg |
| Saturated Fatty Acid Glyceride | 1000 ml |

Solutions having the above-mentioned composition are usually administered to a patient intravenously at a rate of 1 ml per 1 minute.

INDUSTRIAL APPLICABILITY

The compounds of the present invention have excellent JAK inhibitory activities and are useful for prevention or treatment of autoimmune diseases, especially rheumatoid arthritis, inflammatory diseases and allergic diseases.

The invention claimed is:

1. A compound represented by the formula ($I^b$):

($I^b$)

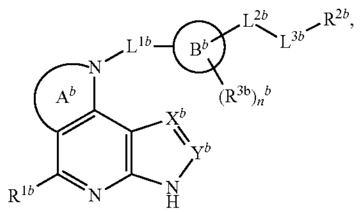

wherein:

the ring $A^b$ is represented by the formula ($IV^b$):

($IV^b$)

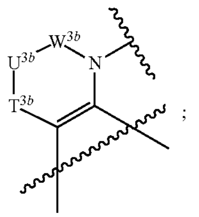

$T^{3b}$ is C(═O); $U^{3b}$ is NH; $W^{3b}$ is C(═O);

$X^b$ is CH;

$Y^b$ is CH;

$R^{1b}$ is a hydrogen atom, a halogen atom, a $C_{1-6}$ alkyl group or a $C_{1-6}$ haloalkyl group;

the ring $B^b$ is a $C_{3-11}$ cycloalkane, a $C_{3-11}$ cycloalkene, a 3 to 11-membered non-aromatic heterocycle, a $C_{6-14}$ aromatic carbocycle or a 5 to 10-membered aromatic heterocycle;

$L^{1b}$ is a single bond, a $C_{1-6}$ alkylene group, a $C_{2-6}$ alkenylene group or a $C_{2-6}$ alkynylene group (the $C_{1-6}$ alkylene group, the $C_{2-6}$ alkenylene group and the $C_{2-6}$ alkynylene group are unsubstituted or substituted with one or more identical or different substituents independently selected from the group consisting of halogen atoms, hydroxy groups, amino groups, cyano groups and nitro groups);

$L^{2b}$ is a single bond, a $C_{1-6}$ alkylene group, a $C_{2-6}$ alkenylene group or a $C_{2-6}$ alkynylene group (the $C_{1-6}$ alkylene group, the $C_{2-6}$ alkenylene group and the $C_{2-6}$ alkynylene group are unsubstituted or substituted with one or more identical or different substituents independently selected from the group consisting of halogen atoms, hydroxy groups, amino groups, cyano groups and nitro groups);

$L^{3b}$ is a single bond or is represented by any of the following formulae ($V^b$-1) to ($V^b$-20):

($V^b$)

($V^b$-1)

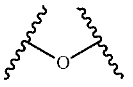

($V^b$-2)

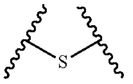

($V^b$-3)

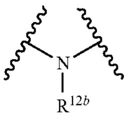

($V^b$-4)

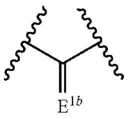

($V^b$-5)

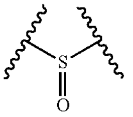

($V^b$-6)

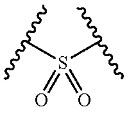

($V^b$-7)

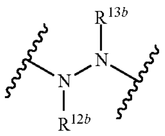

($V^b$-8)

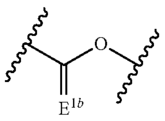

($V^b$-9)

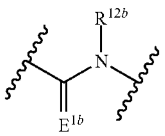

($V^b$-10)

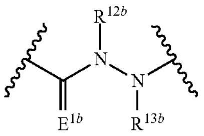

-continued ($V^b$-11)

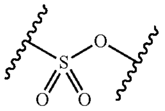

($V^b$-12)

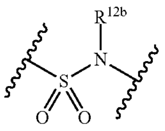

($V^b$-13)

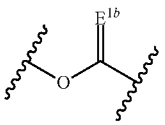

($V^b$-14)

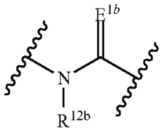

($V^b$-15)

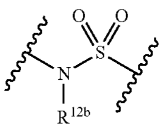

($V^b$-16)

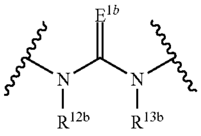

($V^b$-17)

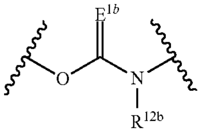

($V^b$-18)

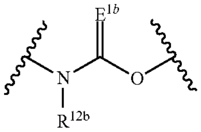

($V^b$-19)

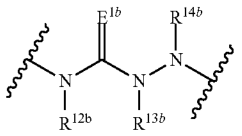

($V^b$-20)

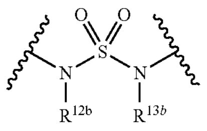, $E^{1b}$ is an oxygen atom, a sulfur atom or $NR^{18b}$;

when $L^{3b}$ is a single bond, $R^{2b}$ is a hydrogen atom, a halogen atom, a $C_{3-11}$ cycloalkyl group, a 3 to 14-membered non-aromatic heterocyclyl group, a $C_{6-14}$ aryl group, a 5 to 10-membered aromatic heterocyclyl group, an 8 to 14-membered partially saturated aromatic cyclic group or an 8 to 14-membered aromatic ring-condensed alicyclic hydrocarbon group (the $C_{3-11}$ cycloalkyl group, the 3 to 14-membered non-aromatic heterocyclyl group, the $C_{6-14}$ aryl group, the 5 to 10-membered aromatic heterocyclyl group, the 8 to 14-membered partially saturated aromatic cyclic group and the 8 to 14-membered aromatic ring-condensed alicyclic hydrocarbon group are unsubstituted or substituted with one or more identical or different substituents independently selected from a substituent set $V^{4b}$ and a substituent set $V^{9b}$);

when $L^{3b}$ is not a single bond, $R^{2b}$ is a hydrogen atom, a $C_{1-6}$ alkyl group, a $C_{2-6}$ alkenyl group (the $C_{1-6}$ alkyl group and the $C_{2-6}$ alkenyl group are unsubstituted or substituted with one or more identical or different substituents independently selected from a substituent set $V^{6b}$ and the substituent set $V^{9b}$), a $C_{3-11}$ cycloalkyl group, a 3 to 14-membered non-aromatic heterocyclyl group, a $C_{6-14}$ aryl group, a 5 to 10-membered aromatic heterocyclyl group, an 8 to 14-membered partially saturated aromatic cyclic group or an 8 to 14-membered aromatic ring-condensed alicyclic hydrocarbon group (the $C_{3-11}$ cycloalkyl group, the 3 to 14-membered non-aromatic heterocyclyl group, the $C_{6-14}$ aryl group, the 5 to 10-membered aromatic heterocyclyl group, the 8 to 14-membered partially saturated aromatic cyclic group and the 8 to 14-membered aromatic ring-condensed alicyclic hydrocarbon group are unsubstituted or substituted with one or more identical or different substituents independently selected from the substituent set $V^{4b}$ and the substituent set $V^{9b}$);

$n^b$ is 0, 1 or 2;

$R^{3b}$ is a hydroxy group, an amino group, a carboxy group, a carbamoyl group, a sulfamoyl group, a phosphono group, a phosphonooxy group, a sulfo group, a sulfoxy group, a tetrazolyl group, a halogen atom, a cyano group, a nitro group, a $C_{1-6}$ alkyl group, a $C_{1-6}$ haloalkyl group, a $C_{3-11}$ cycloalkyl group, a $C_{2-6}$ alkenyl group, a $C_{2-6}$ haloalkenyl group, a $C_{1-6}$ alkoxy group, a $C_{1-6}$ haloalkoxy group, a $C_{1-6}$ alkylthio group, a $C_{1-6}$ haloalkylthio group, a $C_{1-6}$ alkylcarbonyl group, a $C_{1-6}$ haloalkylcarbonyl group, a $C_{1-6}$ alkylsulfonyl group, a $C_{1-6}$ haloalkylsulfonyl group, a $C_{1-6}$ alkoxycarbonyl group, a mono-$C_{1-6}$ alkylamino group, a di-$C_{1-6}$ alkylamino group, a mono-$C_{1-6}$ alkylaminocarbonyl group, a di-$C_{1-6}$ alkylaminocarbonyl group or a $C_{1-6}$ alkylcarbonylamino group (when $n^b$ is 2, $R^{3b}$'s may be identical or different);

each of $R^{12b}$, $R^{13b}$ and $R^{14b}$ is independently a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or more identical or different substituents independently selected from a substituent set $V^{3b}$, a substituent set $V^{8b}$ and the substituent set $V^{9b}$);

$R^{18b}$ is a hydrogen atom, a hydroxy group, a cyano group, a nitro group, a $C_{1-6}$ alkyl group or a $C_{1-6}$ alkoxy group;

a substituent set $V^{1b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkyl groups, $C_{1-6}$ haloalkyl groups, $C_{3-11}$ cycloalkyl groups, $C_{2-6}$ alkenyl groups, $C_{2-6}$ haloalkenyl groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, $C_{1-6}$ alkoxycarbonyl groups, 3 to 11-membered non-aromatic heterocyclyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups and $C_{1-6}$ alkylcarbonylamino groups;

a substituent set $V^{2b}$ consists of the groups in the substituent set $V^{1b}$, and $C_{6-14}$ aryl groups and 5 to 10-membered aromatic heterocyclyl groups (the $C_{6-14}$ aryl groups and the 5 to 10-membered aromatic heterocyclyl groups are unsubstituted or substituted with one or more identical or different substituents independently selected from the substituent set $V^{1b}$), the substituent set $V^{3b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkoxy groups, $C_{1-6}$ haloalkoxy groups, $C_{1-6}$ alkylthio groups, $C_{1-6}$ haloalkylthio groups, $C_{1-6}$ alkylcarbonyl groups, $C_{1-6}$ haloalkylcarbonyl groups, $C_{1-6}$ alkylsulfonyl groups, $C_{1-6}$ haloalkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{3-11}$ cycloalkyl groups, 3 to 11-membered non-aromatic heterocyclyl groups, $C_{6-14}$ aryl groups and 5 to 10-membered aromatic heterocyclyl groups (the $C_{3-11}$ cycloalkyl groups, the 3 to 11-membered non-aromatic heterocyclyl groups, the $C_{6-14}$ aryl groups and the 5 to 10-membered aromatic heterocyclyl groups are unsubstituted or substituted with one or more identical or different substituents independently selected from the substituent set $V^{1b}$);

the substituent set $V^{4b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkyl groups, $C_{2-6}$ alkenyl groups, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups (the $C_{1-6}$ alkyl groups, the $C_{2-6}$ alkenyl groups, the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups and the $C_{1-6}$ alkylcarbonylamino groups are unsubstituted or substituted with one or more identical or different substituents independently selected from the substituent set $V^{3b}$), $C_{3-11}$ cycloalkyl groups, 3 to 11-membered non-aromatic heterocyclyl groups, $C_{6-14}$ aryl groups and 5 to 10-membered aromatic heterocyclyl groups (the $C_{3-11}$ cycloalkyl groups, the 3 to 11-membered non-aromatic heterocyclyl groups, the $C_{6-14}$ aryl groups and the 5 to 10-membered aromatic heterocyclyl groups are unsubstituted or substituted with one or more identical or different substituents independently selected from the substituent set $V^{1b}$);

the substituent set $V^{6b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups (the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups and the $C_{1-6}$ alkylcarbonylamino groups are unsubstituted or substituted with one or more identical or different substituents independently selected from the substituent set $V^{3b}$), $C_{3-11}$ cycloalkyl groups, 3 to 11-membered non-aromatic heterocyclyl groups, $C_{6-14}$ aryl groups, 5 to 10-membered aromatic heterocyclyl groups, 8 to 14-membered partially saturated aromatic cyclic groups and 8 to 14-membered aromatic ring-condensed alicyclic hydrocarbon groups (the $C_{3-11}$ cycloalkyl groups, the 3 to 11-membered non-aromatic heterocyclyl groups, the $C_{6-14}$ aryl groups, the 5 to 10-membered aromatic heterocyclyl groups, the 8 to 14-membered partially saturated aromatic cyclic groups and the 8 to 14-membered aromatic ring-condensed alicyclic hydrocarbon groups are unsubstituted or substituted with one or more identical or different substituents independently selected from the substituent set $V^{4b}$ and the substituent set $V^{9b}$), the substituent set $V^{8b}$ consists of 8 to 14-membered partially saturated aromatic cyclic groups and 8 to 14-membered aromatic ring-condensed alicyclic hydrocarbon groups (the 8 to 14-membered partially saturated aromatic cyclic groups and the 8 to 14-membered aromatic ring-condensed alicyclic hydrocarbon groups are unsubstituted or substituted with one or more identical or different substituents independently selected from the substituent set $V^{2b}$); and the substituent set $V^{9b}$ consists of, mono-$C_{1-6}$ alkylaminosulfonyl groups, di-$C_{1-6}$ alkylaminosulfonyl groups, $C_{1-6}$ alkylsulfonylamino groups (the mono-$C_{1-6}$ alkylaminosulfonyl groups, di-$C_{1-6}$ alkylaminosulfonyl groups and $C_{1-6}$ alkylsulfonylamino groups are unsubstituted or substituted with one or more identical or different substituents independently selected from the substituent set $V^{3b}$), $C_{3-6}$ cycloalkoxy groups, $C_{3-6}$ cycloalkylamino groups, $C_{3-6}$ cycloalkylthio groups, $C_{3-6}$ cycloalkylcarbonyl groups and $C_{3-6}$ cycloalkylsulfonyl groups (the $C_{3-6}$ cycloalkoxy groups, the $C_{3-6}$ cycloalkylamino groups, the $C_{3-6}$ cycloalkylthio groups, the $C_{3-6}$ cycloalkylcarbonyl groups and the $C_{3-6}$ cycloalkylsulfonyl groups unsubstituted or substituted with one or more identical or different substituents independently selected from the substituent set $V^{2b}$), or a tautomer or pharmaceutically acceptable salt thereof.

2. The compound of claim 1, wherein $L^{2b}$ is a single bond or a $C_{1-3}$ alkylene group; and the ring $B^b$ is cyclohexyl or piperdinyl, or a tautomer or pharmaceutically acceptable salt thereof.

3. The compound of claim 1, wherein $n^b$ is 0 or 1; and $R^{3b}$ is a $C_{1-3}$ alkyl group, or a tautomer or pharmaceutically acceptable salt thereof.

4. The compound of claim 1, wherein $L^{1b}$ is a single bond;

$L^{2b}$ is a single bond, a $C_{1-6}$ alkylene group, a $C_{2-6}$ alkenylene group or a $C_{1-6}$ haloalkylene group (the $C_{1-6}$ alkylene group and the $C_{2-6}$ alkenylene group are unsubstituted or substituted with a hydroxy group or a cyano group), the ring $B^b$ is a $C_{3-11}$ cycloalkane or a 4 to 7-membered non-aromatic heterocycle;

$n^b$ is 0 or 1; and $R^{3b}$ is a hydroxy group, a $C_{1-3}$ alkyl group or a $C_{1-3}$ alkoxy group, or a tautomer or pharmaceutically acceptable salt thereof.

5. The compound of claim 1, wherein $R^{1b}$ is a hydrogen atom;

the ring $B^b$ is a $C_{3-11}$ cycloalkane, a 3 to 11-membered non-aromatic heterocycle, a $C_{6-14}$ aromatic carbocycle or a 5 to 10-membered aromatic heterocycle;

$L^{1b}$ is single bond or a $C_{1-3}$ alkylene group;

$L^{2b}$ is a single bond, a $C_{1-6}$ alkylene group or a $C_{2-6}$ alkenylene group (the $C_{1-6}$ alkylene group and the $C_{2-6}$ alkenylene group are unsubstituted or substituted with one or more identical or different substituents independently selected from the group consisting of halogen atoms, hydroxy groups, amino groups, cyano groups and nitro groups);

$n^b$ is 0 or 1, $R^{3b}$ is a hydroxy group, an amino group, a carboxy group, a carbamoyl group, a tetrazolyl group, a halogen atom, a cyano group, a nitro group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkyl sulfonyl group;

$L^{3b}$ is a single bond or is represented by any of the following formulae ($XXII^b$-1) to ($XXII^b$-15):

($XXII^b$)

($XXII^b$-1)

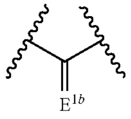

($XXII^b$-2)

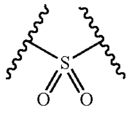

($XXII^b$-3)

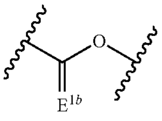

($XXII^b$-4)

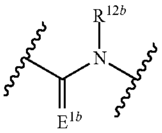

($XXII^b$-5)

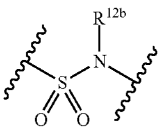

-continued (XXII$^b$-6)
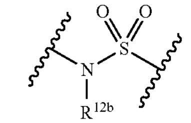

(XXII$^b$-7)
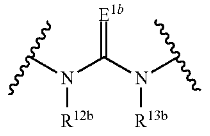

(XXII$^b$-8)
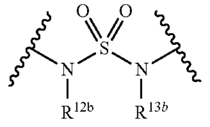

(XXII$^b$-9)
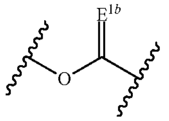

(XXII$^b$-10)
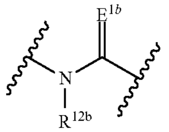

(XXII$^b$-11)
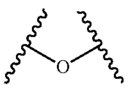

(XXII$^b$-12)
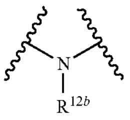

(XXII$^b$-13)
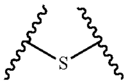

(XXII$^b$-14)
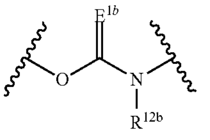

(XXII$^b$-15)
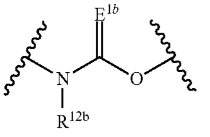

$E^{1b}$ is an oxygen atom or a sulfur atom;

each of $R^{12b}$ and $R^{13b}$ is independently a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or more identical or different substituents independently selected from the group consisting of halogen atoms, cyano groups, hydroxy groups, $C_{1-6}$ alkoxy groups, $C_{1-6}$ alkylthio groups, $C_{1-6}$ alkylsulfonyl groups, $C_{3-6}$ cycloalkyl groups, 4 to 7-membered non-aromatic heterocyclyl groups, phenyl groups and 5 to 6-membered aromatic heterocyclyl groups (the phenyl groups and 5 to 6-membered aromatic heterocyclyl groups are unsubstituted or substituted with a substituent selected from the group consisting of a halogen atom, a cyano group, a $C_{1-3}$ alkyl group and a $C_{1-3}$ haloalkyl group));

when $L^{3b}$ is a single bond, $R^{2b}$ is a hydrogen atom, a halogen atom, a $C_{3-11}$ cycloalkyl group, a 3 to 11-membered non-aromatic heterocyclyl group, a phenyl group, a naphthyl group, a 5 to 10-membered aromatic heterocyclyl group, an 8 to 11-membered partially saturated aromatic cyclic group or an 8 to 11-membered aromatic ring-condensed alicyclic hydrocarbon group (the $C_{3-11}$ cycloalkyl group, the 3 to 11-membered non-aromatic heterocyclyl group, the phenyl group, the naphthyl group, the 5 to 10-membered aromatic heterocyclyl group, the 8 to 11-membered partially saturated aromatic cyclic group and the 8 to 11-membered aromatic ring-condensed alicyclic hydrocarbon group are unsubstituted or substituted with one or more identical or different substituents independently selected from the substituent set $V^{4b}$ and the substituent set $V^{9b}$); and when $L^{3b}$ is not a single bond, $R^{2b}$ is a hydrogen atom, a $C_{1-6}$ alkyl group, a $C_{2-6}$ alkenyl group (the $C_{1-6}$ alkyl group and the $C_{2-6}$ alkenyl group are unsubstituted or substituted with one or more identical or different substituents independently selected from the substituent set $V^{6b}$ and the substituent set $V^{9b}$), a $C_{3-11}$ cycloalkyl group, a 3 to 11-membered non-aromatic heterocyclyl group, a $C_{6-14}$ aryl group, a 5 to 10-membered aromatic heterocyclyl group, an 8 to 11-membered partially saturated aromatic cyclic group or an 8 to 11-membered aromatic ring-condensed alicyclic hydrocarbon group (the $C_{3-11}$ cycloalkyl group, the 3 to 11-membered non-aromatic heterocyclyl group, the $C_{6-14}$ aryl group, the 5 to 10-membered aromatic heterocyclyl group, the 8 to 11-membered partially saturated aromatic cyclic group or the 8 to 11-membered aromatic ring-condensed alicyclic hydrocarbon group are unsubstituted or substituted with one or more identical or different substituents independently selected from the substituent set $V^{4b}$ and the substituent set $V^{9b}$), or a tautomer or pharmaceutically acceptable salt thereof.

6. The compound of claim 1, wherein $L^{3b}$ is represented by any of the following formulae (XIX$^b$-1) to (XIX$^b$-7):

(XIX$^b$)

(XIX$^b$-1)
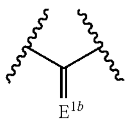

(XIX$^b$-2)
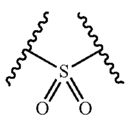

(XIX$^b$-3)
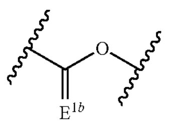

-continued (XIX$^b$-4)

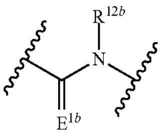

(XIX$^b$-5)

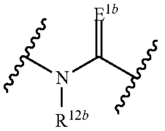

(XIX$^b$-6)

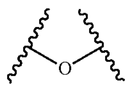

(XIX$^b$-7)

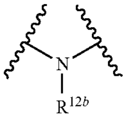

, $E^{1b}$ is an oxygen atom;

$R^{12b}$ is a hydrogen atom or a $C_{1-6}$ alkyl group (the $C_{1-6}$ alkyl group is unsubstituted or substituted with one or more identical or different substituents independently selected from the group consisting of halogen atoms, cyano groups, hydroxy groups, $C_{1-3}$ alkoxy groups, $C_{3-6}$ cycloalkyl groups, 4 to 7-membered non-aromatic heterocyclyl groups, phenyl groups and 5 to 6-membered aromatic heterocyclyl groups); and $R^{2b}$ is a hydrogen atom, a $C_{1-6}$ alkyl group, a $C_{1-6}$ haloalkyl group (the $C_{1-6}$ alkyl group and the $C_{1-6}$ haloalkyl group are unsubstituted or substituted with one or two identical or different substituents independently selected from the group consisting of cyano groups, hydroxy groups, $C_{1-6}$ alkoxy groups, $C_{1-6}$ alkylthio groups, $C_{1-6}$ alkylsulfonyl groups, $C_{3-6}$ cycloalkyl groups, 4 to 7-membered non-aromatic heterocyclyl groups, phenyl groups and 5 to 6-membered aromatic heterocyclyl groups (the $C_{3-6}$ cycloalkyl groups, the 4 to 7-membered non-aromatic heterocyclyl groups, the phenyl groups and the 5 to 6-membered aromatic heterocyclyl groups are unsubstituted or substituted with one, two or three identical or different substituents independently selected from the group consisting of the substituent set $V^{2b}$, mono-$C_{1-6}$ alkylaminosulfonyl groups and di-$C_{1-6}$ alkylaminosulfonyl groups)), a $C_{3-6}$ cycloalkyl group, a 4 to 7-membered non-aromatic heterocyclyl group, a phenyl group, a 5 to 6-membered aromatic heterocyclyl group or an 8 to 11-membered partially saturated aromatic cyclic group (the $C_{3-6}$ cycloalkyl group, the 4 to 7-membered non-aromatic heterocyclyl group, the phenyl group, the 5 to 6-membered aromatic heterocyclyl group and the 8 to 11-membered partially saturated aromatic cyclic group are unsubstituted or substituted with one, two or three identical or different substituents independently selected from the group consisting of the substituent set $V^{2b}$, mono-$C_{1-6}$ alkylaminosulfonyl groups and di-$C_{1-6}$ alkylaminosulfonyl groups), or a tautomer or pharmaceutically acceptable salt thereof.

7. The compound of claim 6, wherein $L^{3b}$ is represented by the formula (XXXII$^b$):

(XXXII$^b$)

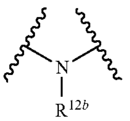

$R^{12b}$ is a hydrogen atom, a $C_{1-3}$ alkyl group (the $C_{1-3}$ alkyl group is unsubstituted or substituted with a substituent selected from the group consisting of a cyano group, a hydroxy group, a $C_{1-3}$ alkoxy group, a $C_{3-6}$ cycloalkyl group and a phenyl group), or a $C_{1-3}$ haloalkyl group; and $R^{2b}$ is a hydrogen atom, a $C_{1-3}$ alkyl group, a $C_{1-3}$ haloalkyl group (the $C_{1-3}$ alkyl group and the $C_{1-3}$ haloalkyl group are unsubstituted or substituted with one or two identical or different substituent selected from the group consisting of hydroxy groups, cyano groups, $C_{1-3}$ alkoxy groups, $C_{3-6}$ cycloalkyl groups (the $C_{3-6}$ cycloalkyl groups are unsubstituted or substituted with a hydroxy groups), 4 to 7-membered non-aromatic heterocyclyl groups, phenyl groups and 5 to 6-membered aromatic heterocyclyl groups), a $C_{3-6}$ cycloalkyl group or a 4 to 7-membered non-aromatic heterocyclyl group (the $C_{3-6}$ cycloalkyl group and the 4 to 7-membered non-aromatic heterocyclyl group are unsubstituted or substituted with one or two identical or different substituents independently selected from the group consisting of $C_{1-3}$ alkyl groups, $C_{1-3}$ haloalkyl groups and $C_{1-6}$ alkoxycarbonyl groups), or a tautomer or pharmaceutically acceptable salt thereof.

8. The compound of claim 1, wherein $R^{1b}$ is a hydrogen atom;

$R^{2b}$ is a $C_{1-6}$ alkyl group (the $C_{1-6}$ alkyl group is unsubstituted or substituted with one or more identical or different substituents independently selected from the substituent set $V^{6b}$ and the substituent set $V^{9b}$);

the ring $B^b$ is cyclohexyl;

$L^{1b}$ is a single bond;

$L^{2b}$ is a methylene group;

$L^3$b is the formula (V$^b$-1)

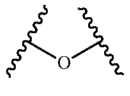

or the formula (V$^b$-3)

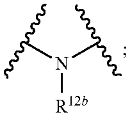

;

$R^{12b}$ is a hydrogen atom; and $n^b$ is 0, or a tautomer or pharmaceutically acceptable salt thereof.

9. The compound of claim 8, wherein $L^{3b}$ is the formula ($V^b$-3)

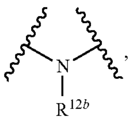

or a tautomer or pharmaceutically acceptable salt thereof.

10. The compound of claim 1, wherein when $L^{3b}$ is a single bond, $R^{2b}$ is a hydrogen atom, a halogen atom, a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{4b}$);

when $L^{3b}$ is not a single bond, $R^{2b}$ is a hydrogen atom, a $C_{1-6}$ alkyl group, a $C_{2-6}$ alkenyl group (the $C_{1-6}$ alkyl group and the $C_{2-6}$ alkenyl group are unsubstituted or substituted with one or more identical or different substituents independently selected from a substituent set $V^{5b}$), a $C_{3-11}$ cycloalkyl group, a 3 to 11-membered non-aromatic heterocyclyl group, a $C_{6-14}$ aryl group or a 5 to 10-membered aromatic heterocyclyl group (the $C_{3-11}$ cycloalkyl group, the 3 to 11-membered non-aromatic heterocyclyl group, the $C_{6-14}$ aryl group and the 5 to 10-membered aromatic heterocyclyl group are unsubstituted or substituted with one or more identical or different substituents independently selected from the substituent set $V^{4b}$);

each of $R^{12b}$, $R^{13b}$ and $R^{14b}$ is independently a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or more identical or different substituents independently selected from the substituent set $V^{3b}$); and the substituent set $V^{5b}$ consists of hydroxy groups, amino groups, carboxy groups, carbamoyl groups, sulfamoyl groups, phosphono groups, phosphonooxy groups, sulfo groups, sulfoxy groups, tetrazolyl groups, halogen atoms, cyano groups, nitro groups, $C_{1-6}$ alkoxy groups, $C_{1-6}$ alkylthio groups, $C_{1-6}$ alkylcarbonyl groups, $C_{1-6}$ alkylsulfonyl groups, $C_{1-6}$ alkoxycarbonyl groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{3-11}$ cycloalkyl groups, 3 to 11-membered non-aromatic heterocyclyl groups, $C_{6-14}$ aryl groups and 5 to 10-membered aromatic heterocyclyl groups (the $C_{1-6}$ alkoxy groups, the $C_{1-6}$ alkylthio groups, the $C_{1-6}$ alkylcarbonyl groups, the $C_{1-6}$ alkylsulfonyl groups, the $C_{1-6}$ alkoxycarbonyl groups, the mono-$C_{1-6}$ alkylamino groups, the di-$C_{1-6}$ alkylamino groups, the mono-$C_{1-6}$ alkylaminocarbonyl groups, the di-$C_{1-6}$ alkylaminocarbonyl groups, the $C_{1-6}$ alkylcarbonylamino groups, the $C_{3-11}$ cycloalkyl groups, the 3 to 11-membered non-aromatic heterocyclyl groups, the $C_{6-14}$ aryl groups and the 5 to 10-membered aromatic heterocyclyl groups are unsubstituted or substituted with one or more identical or different substituents independently selected from the substituent set $V^{3b}$), or a tautomer or pharmaceutically acceptable salt thereof.

11. The compound of claim 10, wherein $R^{1b}$ is a hydrogen atom, or a tautomer or pharmaceutically acceptable salt thereof.

12. The compound of claim 10, wherein the ring $B^b$ is cyclohexyl or piperdinyl, or a tautomer or pharmaceutically acceptable salt thereof.

13. The compound of claim 10, wherein $L^{1b}$ is a single bond or a $C_{1-3}$ alkylene group;

$L^{2b}$ is a single bond, a $C_{1-3}$ alkylene group (the $C_{1-3}$ alkylene group is unsubstituted or substituted with a cyano group), or a $C_{1-3}$ haloalkyl group;

the ring $B^b$ is a $C_{3-11}$ cycloalkane, a $C_{3-11}$ cycloalkene, a 3 to 11-membered non-aromatic heterocycle, benzene or a 5 to 6-membered aromatic heterocycle;

$n^b$ is 0 or 1;

$R^{3b}$ is a hydroxy group, an amino group, a carbamoyl group, a halogen atom, a cyano group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkylsulfonyl group;

$L^{3b}$ is represented by any of the following formulae ($VI^b$-1) to ($VI^b$-11):

($VI^b$)

($VI^b$-1)

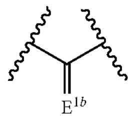

($VI^b$-2)

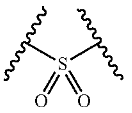

($VI^b$-3)

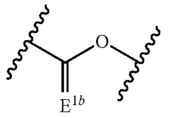

($VI^b$-4)

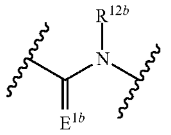

($VI^b$-5)

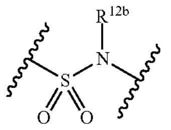

($VI^b$-6)

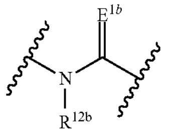

-continued (VI$^b$-7)

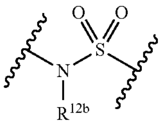

(VI$^b$-8)

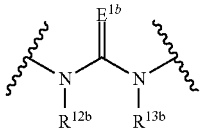

(VI$^b$-9)

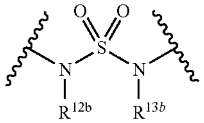

(VI$^b$-10)

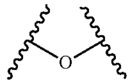

(VI$^b$-11)

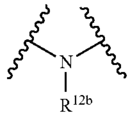

$E^{1b}$ is an oxygen atom;

each of $R^{12b}$ and $R^{13b}$ is independently a hydrogen atom, a $C_{1-6}$ alkyl group or a $C_{1-6}$ haloalkyl group); and $R^{2b}$ is a hydrogen atom, a $C_{1-6}$ alkyl group, or a $C_{2-6}$ alkenyl group (the $C_{1-6}$ alkyl group and the $C_{2-6}$ alkenyl group are unsubstituted or substituted with one or more identical or different substituents independently selected from the substituent set $V^{5b}$), or a tautomer or pharmaceutically acceptable salt thereof.

14. The compound of claim 10, wherein $L^{1b}$ is a single bond;

$L^{2b}$ is a single bond, a $C_{1-6}$ alkylene group or a $C_{2-6}$ alkenylene group (the $C_{1-6}$ alkylene group and the $C_{2-6}$ alkenylene group are unsubstituted or substituted with one or more identical or different substituents independently selected from the group consisting of halogen atoms, hydroxy groups, amino groups, cyano groups and nitro groups);

the ring $B^b$ is a $C_{3-11}$ cycloalkane, a $C_{3-11}$ cycloalkene, a 3 to 11-membered non-aromatic heterocycle, a $C_{6-14}$ awl group or a 5 to 10-membered aromatic heterocycle;

$n^b$ is 0 or 1;

$R^{3b}$ is a hydroxy group, an amino group, a halogen atom, a cyano group, a $C_{1-3}$ alkyl group, a $C_{1-3}$ haloalkyl group, a $C_{3-6}$ cycloalkyl group, a $C_{1-3}$ alkoxy group or a $C_{1-3}$ haloalkoxy group;

$L^{3b}$ is represented by any of the following formulae (VI$^b$-1) to (VI$^b$-11):

(VI$^b$)

(VI$^b$-1)

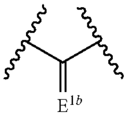

-continued (VI$^b$-2)

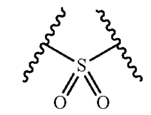

(VI$^b$-3)

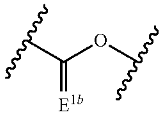

(VI$^b$-4)

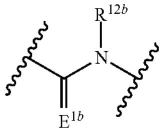

(VI$^b$-5)

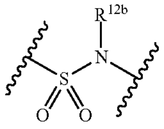

(VI$^b$-6)

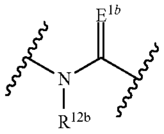

(VI$^b$-7)

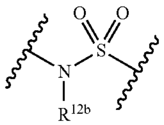

(VI$^b$-8)

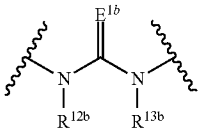

(VI$^b$-9)

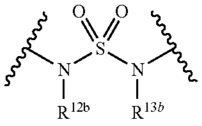

(VI$^b$-10)

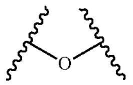

(VI$^b$-11)

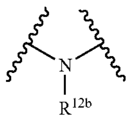

$E^{1b}$ is an oxygen atom or a sulfur atom;

each of $R^{12b}$ and $R^{13b}$ is independently a hydrogen atom, a $C_{1-6}$ alkyl group or a $C_{1-6}$ haloalkyl group (the $C_{1-6}$ alkyl group and the $C_{1-6}$ haloalkyl group are unsubstituted or substituted with one or more identical or different substituents independently selected from the group consisting of halogen atoms, cyano groups, hydroxy groups, $C_{1-6}$ alkoxy groups, $C_{1-6}$ alkylthio groups, $C_{1-6}$ alkylsulfonyl groups, $C_{3-6}$ cycloalkyl groups, 4 to 7-membered non-aromatic heterocyclyl groups, phenyl groups and 5 to 6-membered aromatic heterocyclyl groups (the phenyl groups and the 5 to 6-membered aromatic heterocyclyl groups are unsubstituted or substituted with a substituent selected from the group consisting of a halogen atom, a cyano group, a $C_{1-3}$ alkyl group and a $C_{1-3}$ haloalkyl group); and $R^{2b}$ is a hydrogen atom, a $C_{1-6}$ alkyl group, or a $C_{2-6}$ alkenyl group (the $C_{1-6}$ alkyl group and the $C_{2-6}$ alkenyl group are unsubstituted or substituted with one or more identical or different substituents independently selected from the substituent set $V^{5b}$), or a tautomer or pharmaceutically acceptable salt thereof.

15. The compound of claim 14, wherein the ring $B^b$ is a $C_{3-11}$ cycloalkane or a 4 to 7-membered non-aromatic heterocycle; and $L^{3b}$ is represented by any of the following formulae ($XIX^b$-1) to ($XIX^b$-7):

($XIX^b$)

($XIX^b$-1)

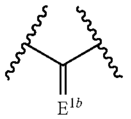

($XIX^b$-2)

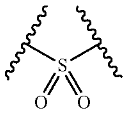

($XIX^b$-3)

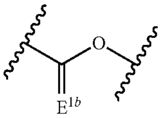

($XIX^b$-4)

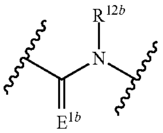

($XIX^b$-5)

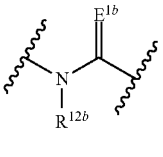

($XIX^b$-6)

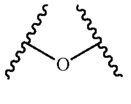

($XIX^b$-7)

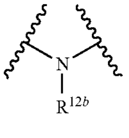

, $E^{1b}$ is an oxygen atom, and $R^{12b}$ is a hydrogen atom, a $C_{1-6}$ alkyl group (the $C_{1-6}$ alkyl group is unsubstituted or substituted with one or more identical or different substituents independently selected from the group consisting of cyano groups, hydroxy groups, $C_{1-3}$ alkoxy groups, $C_{3-6}$ cycloalkyl groups and phenyl groups) or a $C_{1-6}$ haloalkyl group, or a tautomer or pharmaceutically acceptable salt thereof.

16. The compound of claim 10, wherein $L^{1b}$ is a single bond or a $C_{1-3}$ alkylene group;

$L^{2b}$ is a single bond, a $C_{1-3}$ alkylene group (the $C_{1-3}$ alkylene group is unsubstituted or substituted with a cyano group), or a $C_{1-3}$ haloalkyl group;

the ring $B^b$ is a $C_{3-11}$ cycloalkane, a $C_{3-11}$ cycloalkene, a 3 to 11-membered non-aromatic heterocycle, benzene or a 5 to 6-membered aromatic heterocycle;

$n^b$ is 0 or 1;

$R^{3b}$ is a hydroxy group, an amino group, a carboxy group, a carbamoyl group, a tetrazolyl group, a halogen atom, a cyano group, a nitro group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkyl sulfonyl group;

$L^{3b}$ is represented by any of the following formulae ($V^b$-1) to ($V^b$-6):

($V^b$-1)

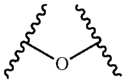

($V^b$-2)

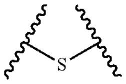

($V^b$-3)

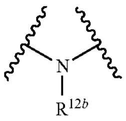

($V^b$-4)

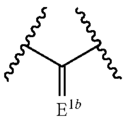

($V^b$-5)

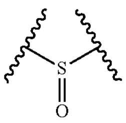

($V^b$-6)

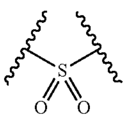

;

$R^{2b}$ is a hydrogen atom, a $C_{1-6}$ alkyl group, or a $C_{2-6}$ alkenyl group (the $C_{1-6}$ alkyl group and the $C_{2-6}$ alkenyl group are unsubstituted or substituted with one or more identical or different substituents independently selected from the substituent set $V^{5b}$), or a tautomer or pharmaceutically acceptable salt thereof.

17. The compound of claim 10, wherein $L^{1b}$ is a single bond;

$L^{2b}$ is a single bond, a $C_{1-6}$ alkylene group or a $C_{2-6}$ alkenylene group (the $C_{1-6}$ alkylene group and the $C_{2-6}$ alkenylene group are unsubstituted or substituted with one or more identical or different substituents independently selected from the group consisting of halogen atoms, hydroxy groups, amino groups, cyano groups and nitro groups);

$n^b$ is 0 or 1;

$R^{3b}$ is a hydroxy group, an amino group, a halogen atom, a cyano group, a $C_{1-3}$ alkyl group, a $C_{1-3}$ haloalkyl group, a $C_{3-6}$ cycloalkyl group, a $C_{1-3}$ alkoxy group, a $C_{1-3}$ haloalkoxy group or a $C_{1-3}$ alkylsulfonyl group;

$L^{3b}$ is represented by any of the following formulae ($V^b$-1) to ($V^b$-20):

($V^b$)

($V^b$-1)

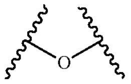

($V^b$-2)

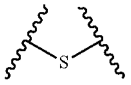

($V^b$-3)

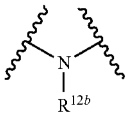

($V^b$-4)

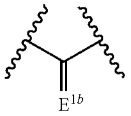

($V^b$-5)

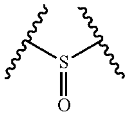

($V^b$-6)

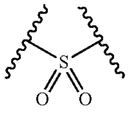

($V^b$-7)

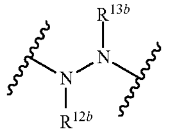

($V^b$-8)

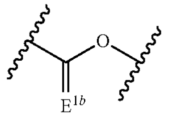

($V^b$-9)

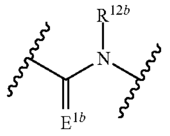

($V^b$-10)

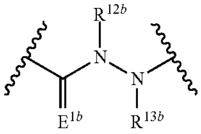

-continued ($V^b$-11)

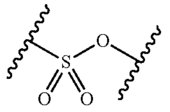

($V^b$-12)

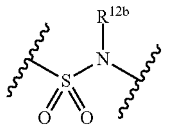

($V^b$-13)

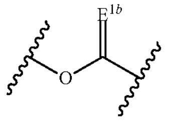

($V^b$-14)

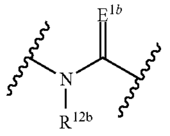

($V^b$-15)

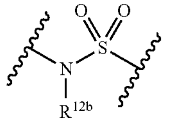

($V^b$-16)

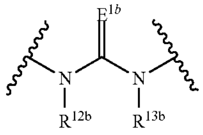

($V^b$-17)

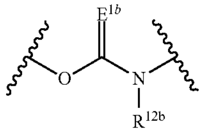

($V^b$-18)

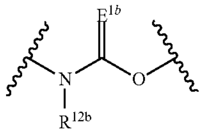

($V^b$-19)

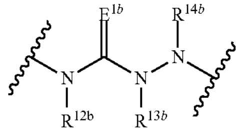

($V^b$-20)

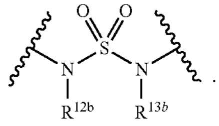

.

$R^{2b}$ is a hydrogen atom, a $C_{1-6}$ alkyl group or a $C_{2-6}$ alkenyl group (the $C_{1-6}$ alkyl group and the $C_{2-6}$ alkenyl group are unsubstituted or substituted with one or more identical or different substituents independently selected from the substituent set $V^{5b}$); and or a tautomer or pharmaceutically acceptable salt thereof.

18. The compound of claim 17, wherein $L^{2b}$ is a $C_{1-6}$ alkylene group, a $C_{2-3}$ alkenylene group (the $C_{1-6}$ alkylene group and the $C_{2-3}$ alkenylene group are unsubstituted or substituted with a cyano group) or $C_{1-6}$ haloalkylene group, or a tautomer or pharmaceutically acceptable salt thereof.

19. The compound of claim 17, wherein $L^{2b}$ is a single bond or a $C_{1-3}$ alkylene group, or a tautomer or pharmaceutically acceptable salt thereof.

20. The compound of claim 17, wherein the ring $B^b$ is a $C_{3-11}$ cycloalkane or a 4 to 7-membered non-aromatic heterocycle; and $L^{3b}$ is represented by any of the following formulae ($V^b$-1) to ($V^b$-6):

($V^b$-1)

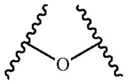

($V^b$-2)

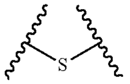

($V^b$-3)

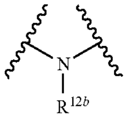

($V^b$-4)

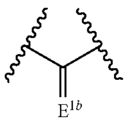

($V^b$-5)

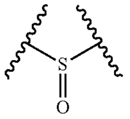

($V^b$-6)

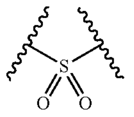

or a tautomer or pharmaceutically acceptable salt thereof.

21. The compound of claim 17, wherein the ring $B^b$ is a $C_{3-11}$ cycloalkane;

$L^{2b}$ is a $C_{1-6}$ alkylene group; and $L^{3b}$ is represented by any of the following formulae ($V^b$-1) to ($V^b$-6):

($V^b$-1)

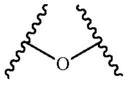

-continued ($V^b$-2)

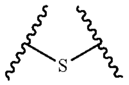

($V^b$-3)

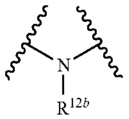

($V^b$-4)

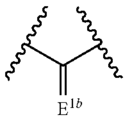

($V^b$-5)

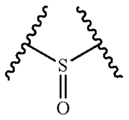

($V^b$-6)

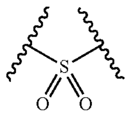

or a tautomer or pharmaceutically acceptable salt thereof.

22. A pharmaceutical composition, comprising:

a JAK inhibitor comprising the compound of claim 1, or a tautomer or pharmaceutically acceptable salt thereof; and a pharmacologically and pharmaceutically acceptable additive selected from the group consisting of an excipient, a lubricant, a binder, a disintegrant, a humectant, a plasticizer, a coating agent, a suspending agent, a perfume, a diluent, an emulsifier, cacao butter, laurin tallow, Macrogol, glycerogelatin, sodium stearate, a preservative, a solvent, a solubilizing agent, a pH regulator, an isotonizing agent, and a stabilizer.

23. The pharmaceutical composition of claim 22, wherein the pharmaceutical composition is a liquid preparation in a form of an aqueous or oily suspension, a solution, an emulsions, a syrup, or an elixir.

24. A method for treating articular rheumatism, comprising:

administering the compound of claim 1, or a tautomer or pharmaceutically acceptable salt thereof, to a patient in need thereof.

25. A method for treating articular rheumatism, comprising:

administering the pharmaceutical composition of claim 22 to a patient in need thereof.

* * * * *

UNITED STATES PATENT AND TRADEMARK OFFICE

CERTIFICATE OF CORRECTION

| | | |
|---|---|---|
| PATENT NO. | : 9,556,187 B2 | Page 1 of 1 |
| APPLICATION NO. | : 14/873897 | |
| DATED | : January 31, 2017 | |
| INVENTOR(S) | : Watanabe et al. | |

It is certified that error appears in the above-identified patent and that said Letters Patent is hereby corrected as shown below:

On the Title Page

Item (12), "Hayashi et al." should read:
--Watanabe et al.--

Item (72), Inventors should read:
--Tsuneo Watanabe, Funabashi (JP);
Koji Toyama, Funabashi (JP);
Junji Kamon, Minamisaitama-gun (JP)--

Signed and Sealed this
Fifth Day of June, 2018

Andrei Iancu
*Director of the United States Patent and Trademark Office*